United States Patent
Du et al.

(10) Patent No.: US 10,253,019 B2
(45) Date of Patent: Apr. 9, 2019

(54) TANK-BINDING KINASE INHIBITOR COMPOUNDS

(71) Applicant: Gilead Sciences, Inc., Foster City, CA (US)

(72) Inventors: Zhimin Du, Belmont, CA (US); Juan A. Guerrero, Concord, CA (US); Joshua A. Kaplan, Foster City, CA (US); John E. Knox, Jr., San Carlos, CA (US); Jennifer R. Lo, Branford, CT (US); Scott A. Mitchell, East Haven, CT (US); Devan Naduthambi, San Bruno, CA (US); Barton W. Phillips, San Mateo, CA (US); Chandrasekar Venkataramani, Redwood City, CA (US); Peiyuan Wang, San Mateo, CA (US); William J. Watkins, Saratoga, CA (US); Zhongdong Zhao, Guilford, CT (US)

(73) Assignee: Gilead Sciences, Inc., Foster City, CA (US)

( * ) Notice: Subject to any disclaimer, the term of this patent is extended or adjusted under 35 U.S.C. 154(b) by 0 days.

(21) Appl. No.: 16/020,777

(22) Filed: Jun. 27, 2018

(65) Prior Publication Data
US 2018/0370955 A1    Dec. 27, 2018

Related U.S. Application Data

(63) Continuation of application No. 14/863,108, filed on Sep. 23, 2015, now Pat. No. 10,040,781.
(Continued)

(51) Int. Cl.

| | | |
|---|---|---|
| *C07D 405/12* | (2006.01) | |
| *C07D 401/14* | (2006.01) | |
| *C07D 403/12* | (2006.01) | |
| *C07D 403/14* | (2006.01) | |
| *C07D 405/14* | (2006.01) | |
| *C07D 409/14* | (2006.01) | |
| *C07D 413/14* | (2006.01) | |
| *C07D 417/14* | (2006.01) | |
| *C07D 471/08* | (2006.01) | |
| *C07D 471/10* | (2006.01) | |
| *C07D 487/04* | (2006.01) | |
| *C07D 491/107* | (2006.01) | |
| *C07D 491/113* | (2006.01) | |
| *C07D 498/04* | (2006.01) | |
| *A61K 31/53* | (2006.01) | |
| *A61K 31/5377* | (2006.01) | |
| *A61K 31/5383* | (2006.01) | |
| *A61K 31/541* | (2006.01) | |

(52) U.S. Cl.
CPC ............ *C07D 405/12* (2013.01); *A61K 31/53* (2013.01); *A61K 31/5377* (2013.01); *A61K 31/5383* (2013.01); *A61K 31/541* (2013.01); *C07D 401/14* (2013.01); *C07D 403/12* (2013.01); *C07D 403/14* (2013.01); *C07D 405/14* (2013.01); *C07D 409/14* (2013.01); *C07D 413/14* (2013.01); *C07D 417/14* (2013.01); *C07D 471/08* (2013.01); *C07D 471/10* (2013.01); *C07D 487/04* (2013.01); *C07D 491/107* (2013.01); *C07D 491/113* (2013.01); *C07D 498/04* (2013.01)

(58) Field of Classification Search
CPC .. C07D 405/12; C07D 401/14; C07D 403/12; C07D 403/14; C07D 405/14; C07D 409/14; C07D 413/14; C07D 417/14; C07D 471/08; C07D 471/10; C07D 487/04; C07D 491/107; C07D 491/113; C07D 498/04

See application file for complete search history.

(56) References Cited

U.S. PATENT DOCUMENTS

| | | |
|---|---|---|
| 8,969,335 B2 | 3/2015 | Hoelzemann et al. |
| 10,040,781 B2 | 8/2018 | Du et al. |

(Continued)

FOREIGN PATENT DOCUMENTS

| | | |
|---|---|---|
| CN | 103251600 A | 8/2013 |
| WO | WO-2005/075465 A1 | 8/2005 |

(Continued)

OTHER PUBLICATIONS

International Preliminary Report on Patentability dated Jun. 28, 2018 for PCT/US2016/067022, 8 pages.

(Continued)

*Primary Examiner* — Rebecca L Anderson
(74) *Attorney, Agent, or Firm* — Morrison & Foerster LLP

(57) ABSTRACT

Compounds having the following formula (I) and methods of their use and preparation are disclosed:

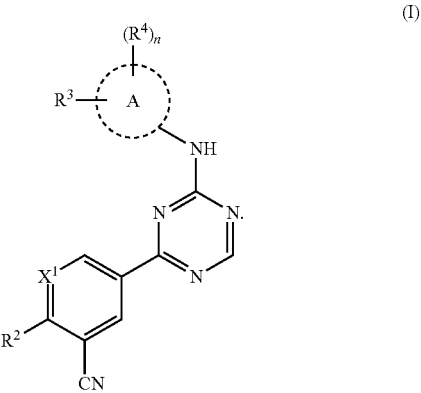

13 Claims, No Drawings

Related U.S. Application Data

(60) Provisional application No. 62/165,005, filed on May 21, 2015, provisional application No. 62/056,358, filed on Sep. 26, 2014.

(56) References Cited

U.S. PATENT DOCUMENTS

| | | | |
|---|---|---|---|
| 10,072,001 | B2 | 9/2018 | Du et al. |
| 2012/0238540 | A1 | 9/2012 | Holcomb et al. |
| 2013/0217951 | A1 | 8/2013 | Dorsch et al. |
| 2013/0289017 | A1 | 10/2013 | Dorsch et al. |
| 2014/0275027 | A1 | 9/2014 | Gong et al. |
| 2014/0323481 | A1 | 10/2014 | Dorsch et al. |
| 2015/0005284 | A1 | 1/2015 | Eggenweiler et al. |
| 2015/0344473 | A1 | 12/2015 | Du et al. |
| 2015/0352108 | A1 | 12/2015 | Holcomb et al. |
| 2016/0096827 | A1 | 4/2016 | Du et al. |
| 2016/0289684 | A1 | 10/2016 | Feng et al. |
| 2016/0376283 | A1 | 12/2016 | Sherer et al. |
| 2017/0174713 | A1 | 6/2017 | Du et al. |

FOREIGN PATENT DOCUMENTS

| | | |
|---|---|---|
| WO | WO-2007/002433 A1 | 1/2007 |
| WO | WO-2008/090181 A1 | 7/2008 |
| WO | WO-2009/030890 A1 | 3/2009 |
| WO | WO-2009/087225 A2 | 7/2009 |
| WO | WO-2009/091388 A2 | 7/2009 |
| WO | WO-2009/118567 A2 | 10/2009 |
| WO | WO-2009/122180 A1 | 10/2009 |
| WO | WO-2010/100431 A1 | 9/2010 |
| WO | WO-2010/127754 A1 | 11/2010 |
| WO | WO-2011/046970 A1 | 4/2011 |
| WO | WO-2011/048082 A1 | 4/2011 |
| WO | WO-2012/010826 A1 | 1/2012 |
| WO | WO-2012/104007 A2 | 8/2012 |
| WO | WO-2012/142329 A1 | 10/2012 |
| WO | WO-2012/161877 A1 | 11/2012 |
| WO | WO-2012/161879 A1 | 11/2012 |
| WO | WO-2012/171337 A1 | 12/2012 |
| WO | WO-2013/024282 A2 | 2/2013 |
| WO | WO-2013/026516 A1 | 2/2013 |
| WO | WO-2013/026890 A1 | 2/2013 |
| WO | WO-2013/034238 A1 | 3/2013 |
| WO | WO-2013/075785 A1 | 5/2013 |
| WO | WO-2013/085802 A1 | 6/2013 |
| WO | WO-2013/117285 A1 | 8/2013 |
| WO | WO-2014/004863 A2 | 1/2014 |
| WO | WO-2014/128486 A1 | 8/2014 |
| WO | WO-2014/139328 A1 | 9/2014 |
| WO | WO-2015/089327 A1 | 6/2015 |
| WO | WO-2015/134171 A1 | 9/2015 |
| WO | WO-2016/049211 A1 | 3/2016 |
| WO | WO-2016/057338 A1 | 4/2016 |
| WO | WO-2017/003995 A1 | 1/2017 |

OTHER PUBLICATIONS

Bamborough et al., (2006) "5-(1 H-Benzimidazol-1-yl)-3-alkoxy-2-thiophenecarbonitriles as Potent, Selective, Inhibitors of IKK-ε Kinase," *Bioorganic & Medicinal Chemistry Letters* 16: 6236-6240.
Chinese Office Action dated Jul. 19, 2018, for Patent Application No. 201580052292.6, filed Sep. 23, 2015, (English translation only).
Corrected Notice of Allowance dated Jul. 3, 2018, for U.S. Appl. No. 14/863,108, filed Sep. 23, 2015, 2 pages.
Hideshima, T. et al. (Dec. 1, 2003). "Antitumor Activity of Lysophosphatidic Acid Acyltransferase-βInhibitors, a Novel Class of Agents, in Multiple Myeloma," *Cancer Research* 63(23):8428-8436.
International Preliminary Report on Patentability dated Dec. 6, 2016 for PCT/US2015/033769, 9 pages.
International Preliminary Report on Patentability dated Mar. 28, 2017 for PCT/US2015/051757, 6 pages.
International Search Report—Written Opinion dated Feb. 3, 2017 for PCT/US2016/067022, 9 pages.
International Search Report—Written Opinion dated Aug. 20, 2015 for PCT/US2015/033769, 14 pages.
International Search Report—Written Opinion dated Nov. 13, 2015 for PCT/US2015/051757, 8 pages.
Korean Office Action dated Jun. 19, 2018, for Patent Application No. 10-2017-7010833, filed Sep. 23, 2015, 9 pages. (including English translation).
Liu, S. et al. (2013, e-pub. Jun. 21, 2013), "Crystal Structure of a Human IκB Kinase β Asymmetric Dimer," *J. Biol. Chem.* 288(31):22758-22767.
McLver, E.G. et al., (2012) "Synthesis and Structure-activity Relationships of a Novel Series of Pyrimidines as Potent Inhibitors of TBK1/IKKε Kinases," *Bioorganic & Medicinal Chemistry Letters* 22:7169-7173.
Final Office Action dated Nov. 27, 2017, for U.S. Appl. No. 14/863,108, filed Sep. 23, 2015, 8 pages.
Notice of Allowance dated Apr. 27, 2018 for U.S. Appl. No. 14/863,108, filed Sep. 23, 2015, 2 pages.
Notice of Allowance dated Mar. 28, 2018 for U.S. Appl. No. 14/863,108, filed Sep. 23, 2015, 8 pages.
Office Action dated Jan. 31, 2018, for Canadian Patent Application No. 2,962,578, filed Sep. 23, 2015, 5 pages.
Office Action dated Jan. 23, 2018, for Gulf Co-Operation Council Patent Application No. 2015-30109, filed Oct. 4, 2015, 5 pages.
Office Action dated Mar. 23, 2018, for Japanese Patent Application No. 2017-516318, filed Sep. 23, 2015, 5 pages.
Office Action dated May 18, 2017 for U.S. Appl. No. 14/863,108.
Office Action dated Jul. 13, 2017 for Pakistan Application No. 609/2015.
Office Action dated Jul. 21, 2017 for New Zealand Application No. 729618.
Office Action dated Nov. 1, 2017, for Australian Patent Application No. 2015320675, filed on Sep. 23, 2015, 2 pages.
Office Action dated Dec. 3, 2017, for Eurasian Patent Application No. 201790395/28, filed Sep. 23, 2015, 6 pages (including translation).
Office Action dated Jan. 25, 2018, for European Patent Application No. 15775054.8, filed Sep. 23, 2015, 3 pages.
Restriction Requirement dated Nov. 7, 2016, for U.S. Appl. No. 14/863,108, filed Sep. 23, 2015, 8 pages.
Wang et al. (2012, e-pub. Jan. 14, 2012). "Discovery of Azabenzimidazole Derivatives as Potent, Selective Inhibitors of TBK1/IKKε Kinases," *Bioorganic & Medicinal Chemistry Letters* 22:2063-2069.
Yu et al. (2015) "Regulation of T-Cell Activation and Migration by the Kinase TBK1 During Neuroinflammation," *Nature Communications* 6:6074; 1-13.
Zhang et al. (2016). "IkB Kinase ε Is an NFATc1 Kinase That Inhibits T Cell Immune Response" *Cell Reports* 16:1-27.
Japanese Office Action dated Nov. 7, 2018, for Patent Application No. 2017-516318, filed Sep. 23, 2015, 4 pages (including English translation).

TANK-BINDING KINASE INHIBITOR COMPOUNDS

CROSS REFERENCE TO RELATED APPLICATIONS

This application is a continuation of U.S. application Ser. No. 14/863,108, filed on Sep. 23, 2015, which claims priority to U.S. Provisional Application Ser. No. 62/056,358, filed Sep. 26, 2014, and to U.S. Provisional Application Ser. No. 62/165,005, filed May 21, 2015, the disclosures of each of which are incorporated herein by reference in their entireties.

FIELD OF THE INVENTION

This application relates to chemical compounds which may inhibit or otherwise modulate the activity of TANK-binding kinase (TBK1) and I-Kappa-B kinase (IKKε, IKBKE), and to compositions and formulations containing such compounds, and methods of using and making such compounds.

BACKGROUND OF THE INVENTION

TBK1 is a serine/threonine kinase with diverse roles in cancer, inflammation, and the host-pathogen response. Shen, R. R. and W. C. Hahn (2011) Oncogene 30(6): 631-641. TBK1 activates its substrates IRF3 and IRF7 transcription factors by direct phosphorylation of specific sites that induces their localization to the nucleus to drive transcription of type I IFN genes (Sankar, S., H. Chan, et al., (2006) Cell Signal 18(7): 982-993). In addition, NFkB activation can be bolstered by the kinase activity of TBK1 by phosphorylating the inhibitors of NFkB, which enables activation of the canonical or non-canonical NFkB transcription factors.

TBK1 has been implicated as being a key gene required for KRAS-dependent cancers, required for HER2+ breast cancers, and contributing to the acquisition of resistance to erlotinib. Depletion of TBK1 by shRNA results in synthetic lethality with KRAS-dependent cancer cell lines and xenograft models (Barbie, D. A., P. Tamayo, et al. (2009) Nature 462(7269): 108-112) and TBK1 is required for RAS-mediated transformation of murine embryonic fibroblasts (Ou, Y. H., M. Torres, et al. (2011) Mol Cell 41(4): 458-470). TBK1 is downstream of RAS and elicits its oncogenic properties via the RALB-NFkB and AKT pathways (Chien, Y., S. Kim, et al. (2006) Cell 127(1): 157-170). In addition, TBK1 directly phosphorylates AKT at S473 and results in the downstream activation of the mTORC1/2 pathway (Ou, Y. H., M. Torres, et al. (2011) Mol Cell 41(4): 458-470). TBK1 was also identified as being important for the survival of HER2+ breast cancer cell lines via an shRNA kinome screen and showed combination effects with the EGFR/HER2 kinase inhibitor, lapatinib (Deng, T., J. C. Liu, et al. (2014) Cancer Res 74(7): 2119-2130). Additionally, integrin alphaVbeta3 was identified as a marker of cells that are resistant to EGFR therapies and have stem-like properties. The signaling cascade required for the survival of these cells was attributed to KRAS-TALB-TBK1-NFkB axis and inhibiting TBK1 was sufficient to block the survival of these cells. Seguin, L., S. Kato, et al. (2014), Nat Cell Biol 16(5): 457-468.

IKKε is a serine/threonine kinase and its gene amplifications have been identified in up to 30% of breast cancers. Depleting IKKε in cell lines with shRNA that have these amplifications results in their decreased viability (Boehm, J. S., J. J. Zhao, et al. (2007) Cell 129(6): 1065-1079). Overexpression of IKKε in ovarian cancer has been demonstrated to mediate resistance to cisplatin and is a poor prognostic factor (Guo, J. P., S. K. Shu, et al. (2009) Am J Pathol 175(1): 324-333).

TBK1 and IKKε are also both implicated in inflammatory responses and associated disorders. IKKε has been shown to be involved in manifestations of rheumatoid arthritis (RA) that include extracellular matrix destruction, synovial inflammation, and activation of the innate immune response (Sweeney, S. E., D. Hammaker, et al. (2005) J Immunol 174(10): 6424-6430). IKKε and IRF3 protein levels are increased in the synovium of RA patients and mice deficient in IKKε show reduced clinical signs of arthritis in a collagen-induced arthritis model as well as associated reduction of inflammation and erosion. Corr, M., D. L. Boyle, et al. (2009), *Ann Rheum Dis* 68(2): 257-263. Other inflammatory disorders that manifest as a result of Type I IFN response and upstream activation of TLR3/TLR4 or cytosolic nucleic acid sensors are likely to also rely on a TBK1/IKKε signaling axis to initiate and maintain their pathogenic state such as Sjogrens syndrome, inflammatory bowel disease (IBD), chronic obstructive pulmonary disease (COPD), systemic lupus erythematosus (SLE), dermatomyositis, polymyositis, systemic sclerosis. Baccala, R., K. Hoebe, et al. (2007), Nat Med 13(5): 543-551. Furthermore, both TBK1 and IKKε have been shown to play a role in maintaining macrophages in an activated state in response to IFN. Solis, M., R. Romieu-Mourez, et al. (2007) Eur J Immunol 37(2): 528-539.

In addition to inflammation and cancer, IKKε is implicated in obesity, type 2 diabetes, and insulin resistance. Mice deficient for IKKε are protected from obesity induced by a high-fat diet, hepatic steatosis, insulin resistance, and chronic inflammation of the liver and fat. Chiang, S. H., M. Bazuine, et al. (2009) Cell 138(5): 961-975. Consistent with this, high levels of NFkB activation have been seen in the liver, adipocytes, and adipose tissue resident macrophages as well as increase levels of IKKε over healthy mice. Treatment with a kinase inhibitor to TBK1/IKKε improved obesity-related metabolic dysfunction in mice fed a high fat diet (Reilly, S. M., S. H. Chiang, et al. (2013) Nat Med 19(3): 313-321).

Accordingly, there is a need for inhibitors of the kinase activity of TBK1 and/or IKKε for treating cancers, inflammatory, and metabolic disorders that may have an active TBK1 and/or IKKε pathway.

SUMMARY OF THE INVENTION

One embodiment provides a compound of formula (I):

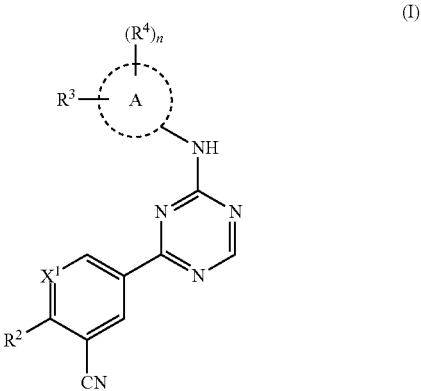

wherein,

A is $C_{6-10}$ aryl or 5-10 membered heteroaryl;

$X^1$ is $CR^1$ or N;

$R^1$ is selected from the group consisting of H, $C_{1-6}$ alkyl, $C_{1-6}$ haloalkyl, —$NR^aR^b$, halogen, —CN, and —$OR^a$;

$R^2$ is selected from the group consisting of H, hydroxyl, $C_{1-6}$ alkyl, $C_{1-6}$ heteroalkyl, —$NR^aR^b$, halogen, —$C(O)R^a$, —$C(O)OR^a$, —$C(O)NR^aR^b$, —$OC(O)NR^aR^b$, —$NR^aC(O)R^b$, —$NR^aC(O)OR^b$, —$S(O)_{0-2}R^c$, —$S(O)_2NR^aR^b$, —$NR^aS(O)_2R^b$, $C_{6-10}$ aryl, $C_{3-10}$ cycloalkyl, 5-10 membered heteroaryl, 3-12 membered heterocyclyl and —O—$R^5$, wherein each $C_{1-6}$ alkyl, $C_{1-6}$ heteroalkyl, $C_{6-10}$ aryl, $C_{3-10}$ cycloalkyl, 5-10 membered heteroaryl and 3-12 membered heterocyclyl is optionally substituted with from one to five $R^{20}$ groups;

or $R^1$ and $R^2$ are taken together to form a fused $C_6$ aryl, 5-6 membered heteroaryl, 5-6 membered heterocyclyl or $C_{5-6}$ cycloalkyl each optionally substituted with one to five $R^{20}$ groups;

$R^3$ is selected from the group consisting of H, $C_{1-6}$ alkyl, $C_{1-6}$ heteroalkyl, —$NR^aR^b$, halogen, —$C(O)R^a$, —$C(O)OR^a$, —$C(O)NR^aR^b$, —$OC(O)NR^aR^b$, —$NR^aC(O)R^b$, —$NR^aC(O)OR^b$, —$S(O)_{0-2}R^c$, —$S(O)(R^c)=NR^b$, —$S(O)_2F$, —$S(O)_2NR^2R^b$, —$NR^aS(O)_2R^b$, —$N_3$, —CN, —$NO_2$, —$OR^a$, $C_{6-10}$ aryl, $C_{3-10}$ cycloalkyl, 5-10 membered heteroaryl and 3-12 membered heterocyclyl wherein each $C_{1-6}$ alkyl, $C_{1-6}$ heteroalkyl, $C_{6-10}$ aryl, $C_{3-10}$ cycloalkyl, 5-10 membered heteroaryl and 3-12 membered heterocyclyl is optionally substituted with 1-5 $R^{20}$ groups;

each $R^4$ is independently selected from the group consisting of H, $C_{1-6}$ alkyl, $C_{1-6}$ heteroalkyl, $C_{1-6}$ haloalkyl, $C_{1-6}$ hydroxyalkyl, $C_{2-6}$ alkenyl, $C_{2-6}$ alkynyl, —$NR^aR^b$, halogen, —$C(O)R^a$, —$C(O)OR^a$, —$C(O)NR^aR^b$, —$OC(O)NR^aR^b$, —$NR^aC(O)R^b$, —$NR^aC(O)OR^b$, —$S(O)_{0-2}R^c$, —$S(O)_2NR^aR^b$, —$NR^aS(O)_2R^b$, —$N_3$, —CN, —$NO_2$ and —$OR^a$;

$R^5$ is H; or $C_{1-6}$ alkyl, $C_{1-6}$ haloalkyl, $C_{6-10}$ aryl, 5-10 membered heteroaryl, $C_{3-10}$ cycloalkyl, or 3-12 membered heterocyclyl, each of which is optionally substituted with from one to five $R^{20}$ groups;

n is 0-2;

each $R^{20}$ is independently $C_{1-6}$ alkyl, $C_{3-10}$ cycloalkyl, $C_{1-6}$ heteroalkyl, 3-12 membered heterocyclyl, $C_{6-10}$ aryl, 5-10 membered heteroaryl, halogen, oxo, —$OR^a$, —$C(O)R^a$, —$C(O)OR^a$, —$C(O)NR^aR^b$, —$OC(O)NR^aR^b$, —$NR^aR^b$, —$NR^aC(O)R^b$, —$NR^aC(O)OR^b$, —$S(O)_{0-2}R^c$, —$S(O)(R^a)=NR^b$, —$S(O)_2NR^aR^b$, —$NR^aS(O)_2R^b$, —$N_3$, —CN, or —$NO_2$, or two $R^{20}$ groups can join together to form a fused, spiro or bridged $C_{3-10}$ cylcloalkyl or 3-12 membered heterocyclyl; wherein each $C_{1-6}$ alkyl, $C_{3-10}$ cycloalkyl, $C_{1-6}$ heteroalkyl, 3-12 membered heterocyclyl, $C_{6-10}$ aryl, 5-10 membered heteroaryl is optionally substituted with from one to five halogen, $C_{1-6}$ alkyl, $C_{1-6}$ heteroalkyl, $C_{1-6}$ haloalkyl, oxo, imino, —$OR^a$, —$C(O)R^a$, —$C(O)OR^a$, —$C(O)NR^aR^b$, —$OC(O)NR^aR^b$, —$NR^aR^b$, —$NR^aC(O)R^b$, —$NR^a(O)OR^b$, —$S(O)_{0-2}R^a$, —$S(O)_2NR^aR^b$, —$NR^aS(O)_2R^b$, —$N_3$, —CN, or —$NO_2$;

each $R^{21}$ is independently $C_{1-6}$ alkyl, $C_{3-10}$ cycloalkyl, $C_{1-6}$ heteroalkyl, 3-12 membered heterocyclyl, $C_6$-$C_{10}$ aryl, 5-10 membered heteroaryl, hydroxyl, $C_{1-6}$ alkoxy, amino, —CN, —C(O)H, —$C(O)NH_2$, —$C(O)NH(C_{1-6}$ alkyl), —$C(O)N(C_{1-6}$ alkyl$)_2$, —COOH, —$C(O)C_{1-6}$ alkyl, —$C(O)OC_{1-6}$ alkyl, or halogen; and each $R^a$ and each $R^b$ are independently H; or $C_{1-6}$ alkyl, $C_{2-6}$ alkenyl, $C_{3-10}$ cycloalkyl, $C_{1-6}$ heteroalkyl, 3-12 membered heterocyclyl, $C_{6-10}$ aryl, 5-10 membered heteroaryl, each of which is optionally substituted with from one to five $R^{21}$; or $R^a$ and $R^b$ together with the atoms to which they are attached form a 3-12 membered heterocyclyl optionally substituted with one to five $R^{21}$ groups;

each $R^c$ is independently $C_{1-6}$ alkyl, $C_{2-6}$ alkenyl, $C_{3-10}$ cycloalkyl, $C_{1-6}$ heteroalkyl, 3-12 membered heterocyclyl, $C_{6-10}$ aryl, 5-10 membered heteroaryl, each of which is optionally substituted with from one to five $R^{21}$;

or a pharmaceutically acceptable salt thereof.

Another embodiment provides a compound having the following formula (Ia):

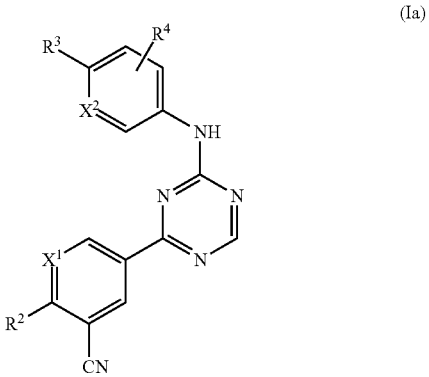

(Ia)

wherein $X^2$ is N or $CR^4$.

or a pharmaceutically acceptable salt thereof.

Another embodiment provides a compound having the following formula (Ib):

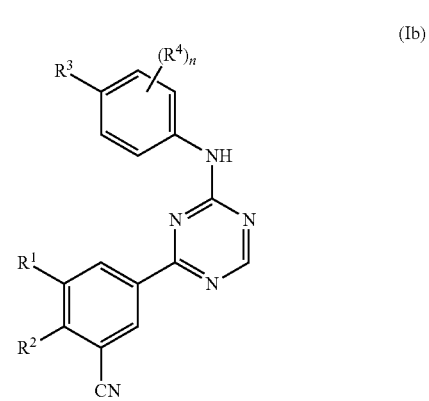

(Ib)

or a pharmaceutically acceptable salt thereof.

Another embodiment provides a compound having the following formula (Ic):

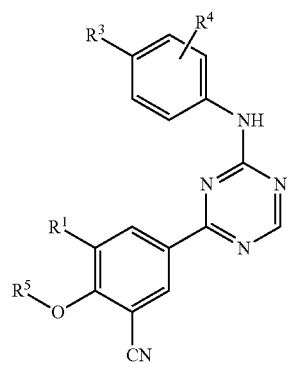

(Ic)

or a pharmaceutically acceptable salt thereof.

In another embodiment, $X^1$ is $CR^1$. In another embodiment, X is N. In another embodiment, $X^2$ is $CR^1$. in another embodiment, $X^2$ is N.

In another embodiment, A is a 5-6 membered heteroaryl. In another embodiment, A is phenyl.

In another embodiment, $R^3$ comprises a piperazinyl group. In another embodiment, piperazinyl group is substituted with an oxetanyl group.

In another embodiment, $R^3$ is:

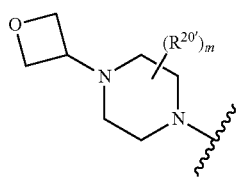

wherein,
m is 0-2; and
$R^{20'}$ is H, $C_{1-6}$ alkyl, $C_{1-6}$ heteroalkyl and $C_{1-6}$ hydroxyalkyl.

In another embodiment, $R^3$ is:

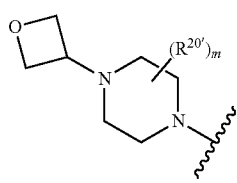

wherein,
m is 0-2; and
$R^{20'}$ is H, CN, oxo, $CONR^{ax}R^{bx}$, $C_{1-6}$ alkyl, $C_{1-6}$ heteroalkyl and $C_{1-6}$ hydroxyalkyl; wherein $R^{ax}$ and $R^{bx}$ are independently H; or $C_{1-6}$ alkyl, $C_{2-6}$ alkenyl, $C_{3-10}$ cycloalkyl, $C_{1-6}$ heteroalkyl, 3-12 membered heterocyclyl, $C_{6-10}$ aryl, 5-10 membered heteroaryl, each of which is optionally substituted with from one to five groups selected from $C_{1-6}$ alkyl, $C_{3-10}$ cycloalkyl, $C_{1-6}$ heteroalkyl, 3-12 membered heterocyclyl, $C_6$-$C_{10}$ aryl, 5-10 membered heteroaryl, hydroxyl, $C_{1-6}$ alkoxy, amino, —CN, —C(O)H, —C(O)NH$_2$, —C(O)NH(C$_{1-6}$ alkyl), —C(O)N(C$_{1-6}$ alkyl)$_2$, —COOH, —C(O)C$_{1-6}$ alkyl, —C(O)OC$_{1-6}$ alkyl, or halogen.

In another embodiment, m is 0.

In another embodiment, the following substituent

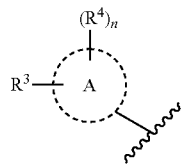

in Formula (I) is selected from the group consisting of:

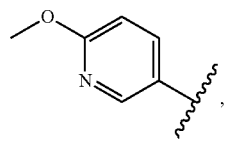

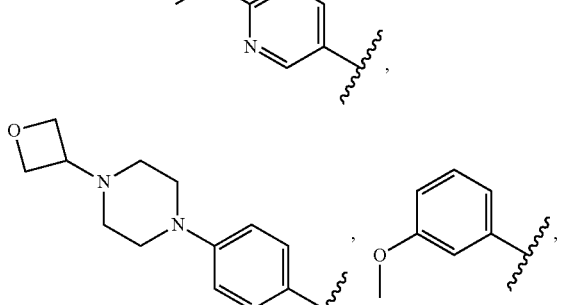

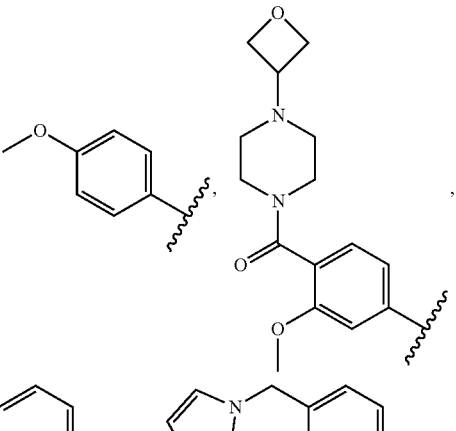

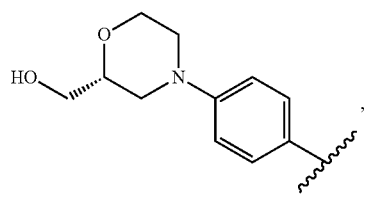

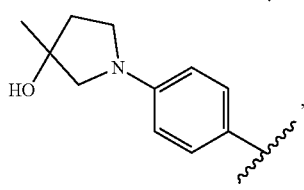

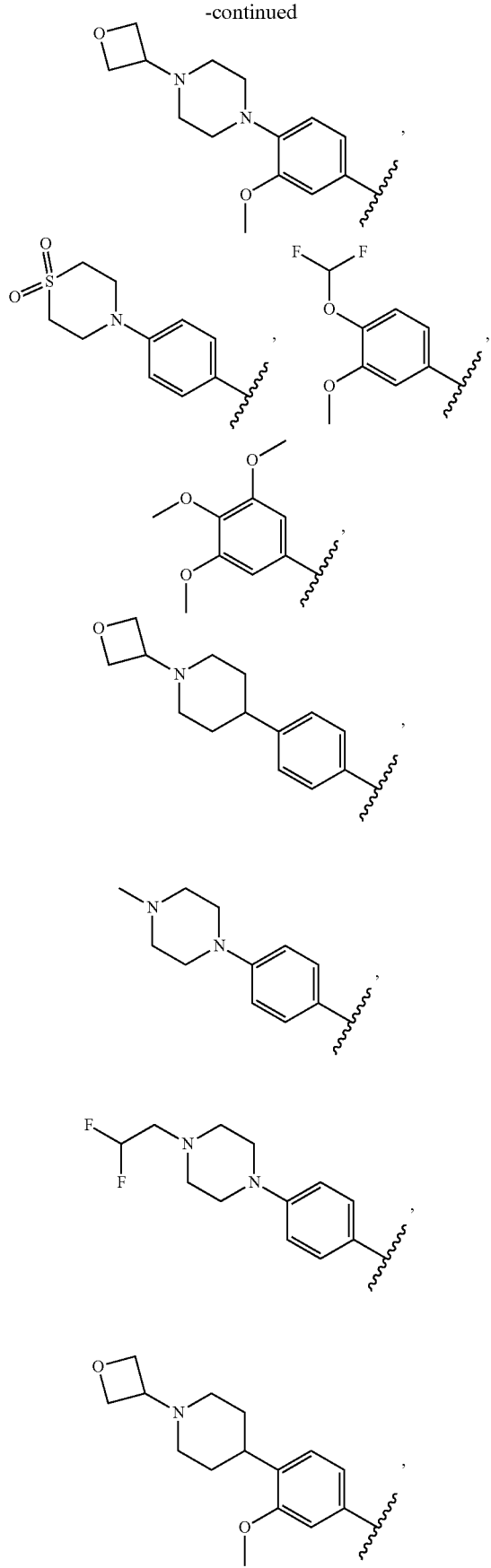
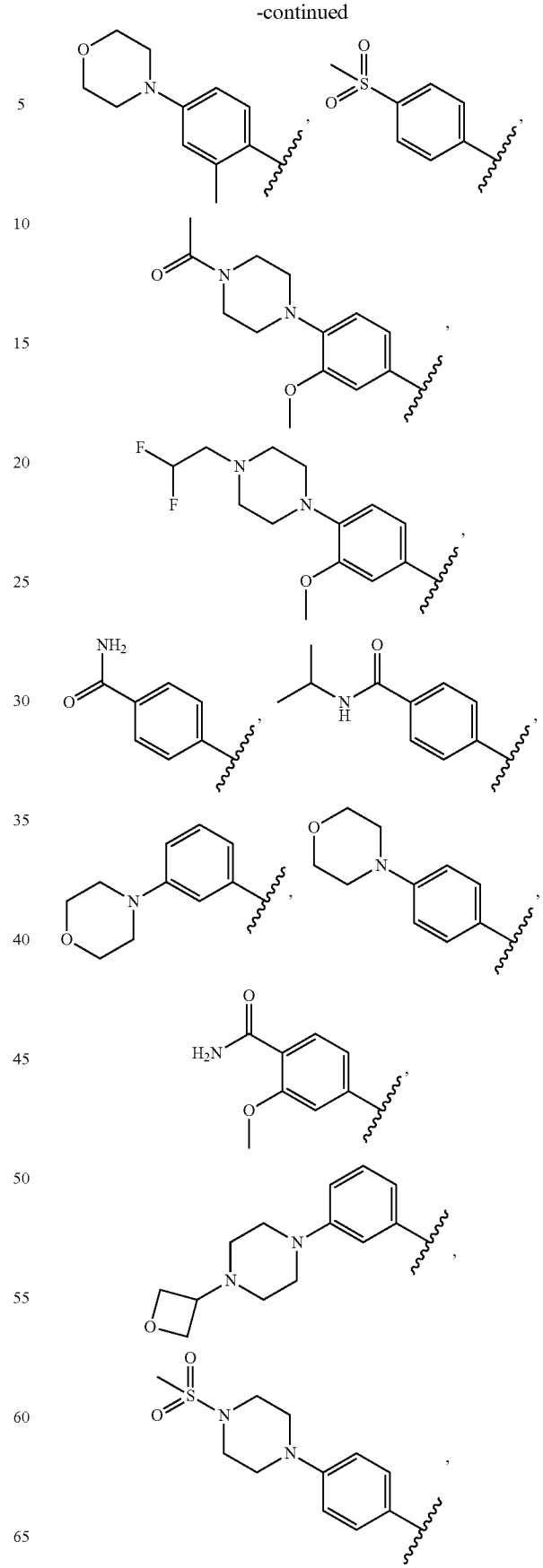

-continued
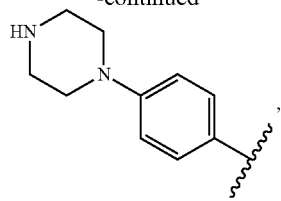
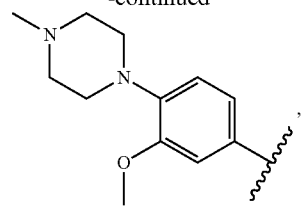
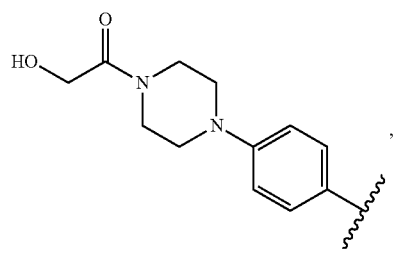
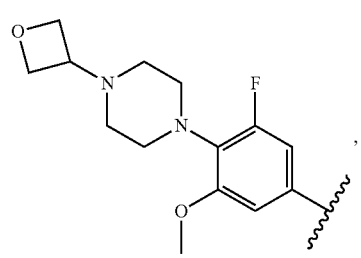
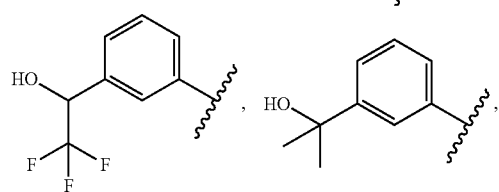
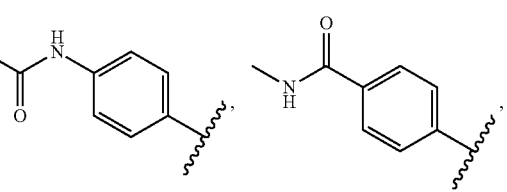
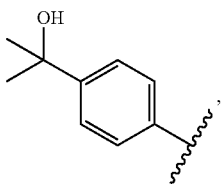
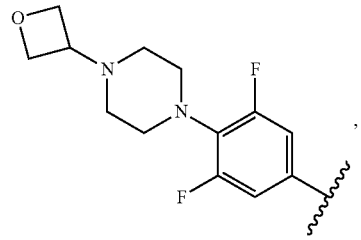
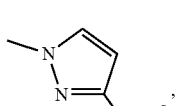 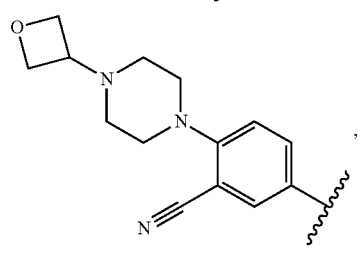
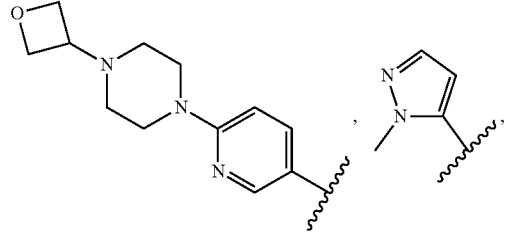

11
-continued
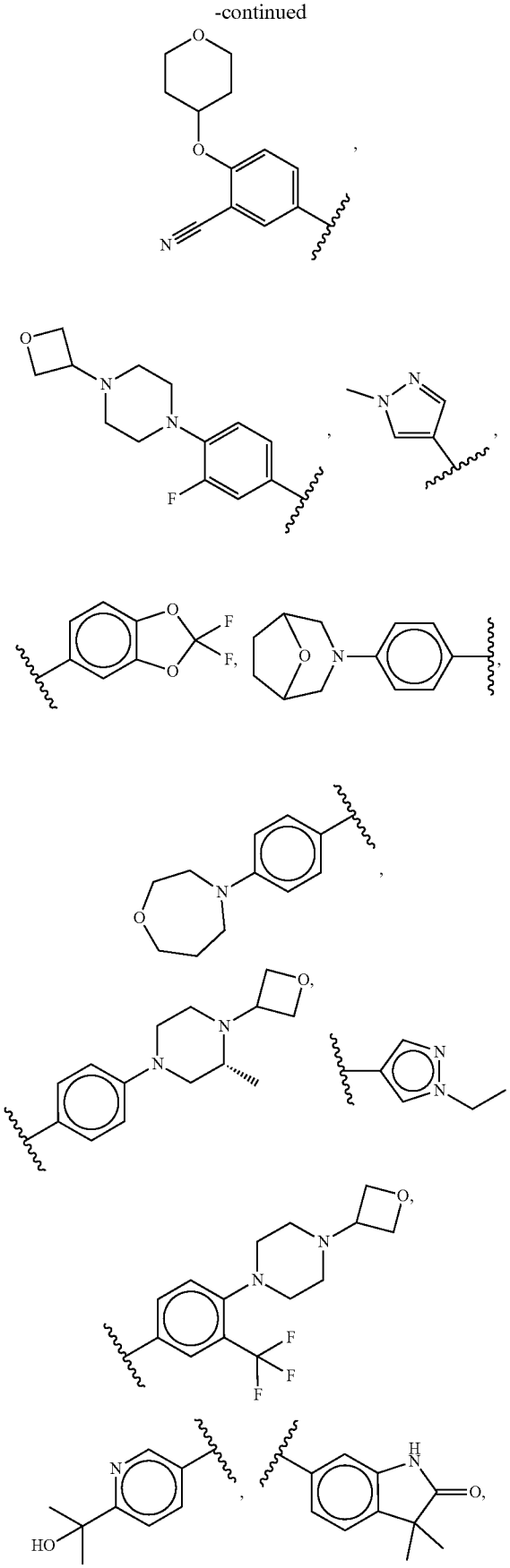
12
-continued
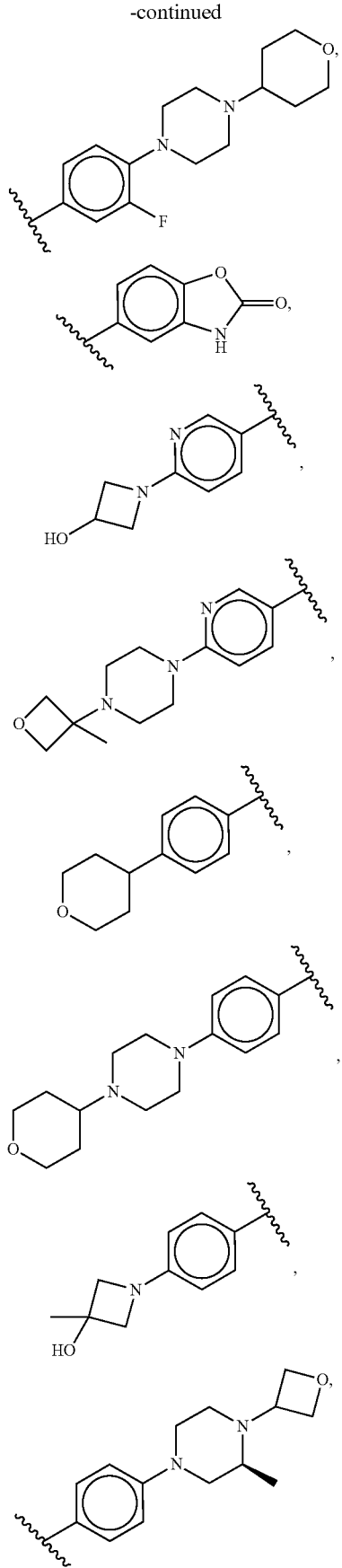

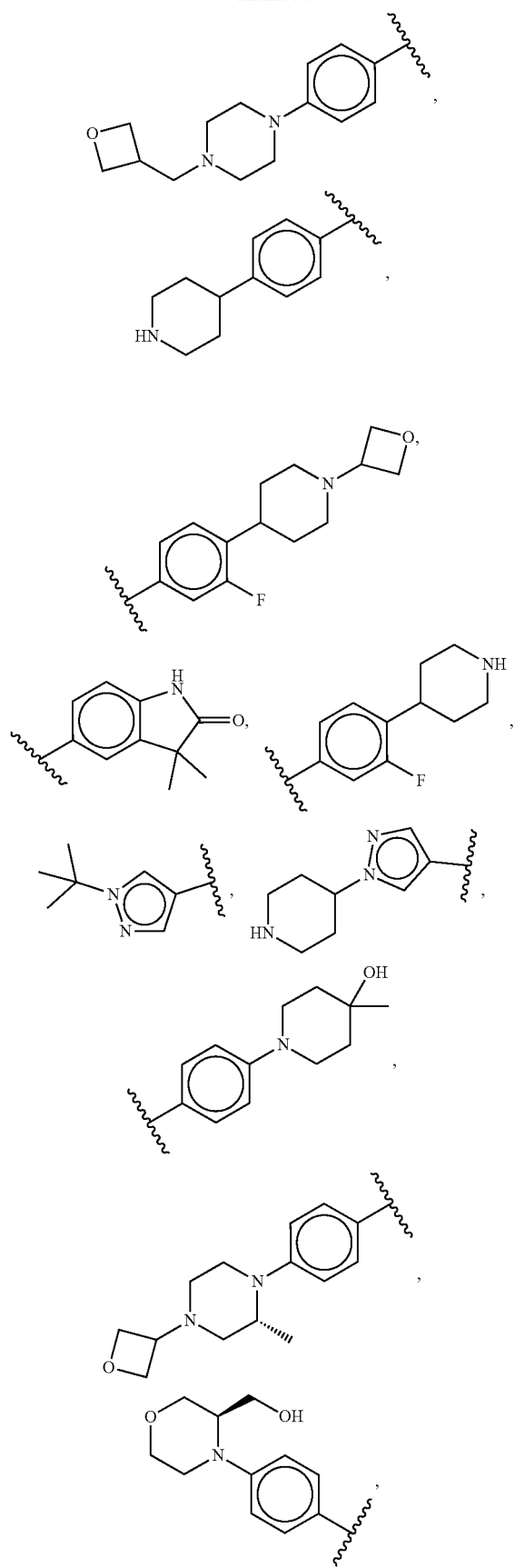
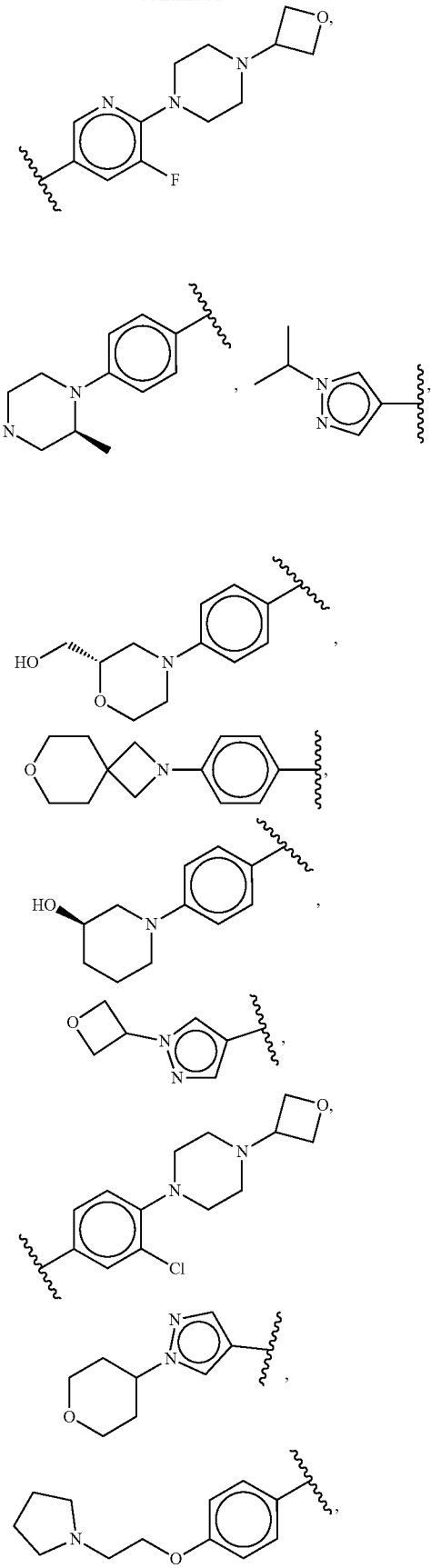

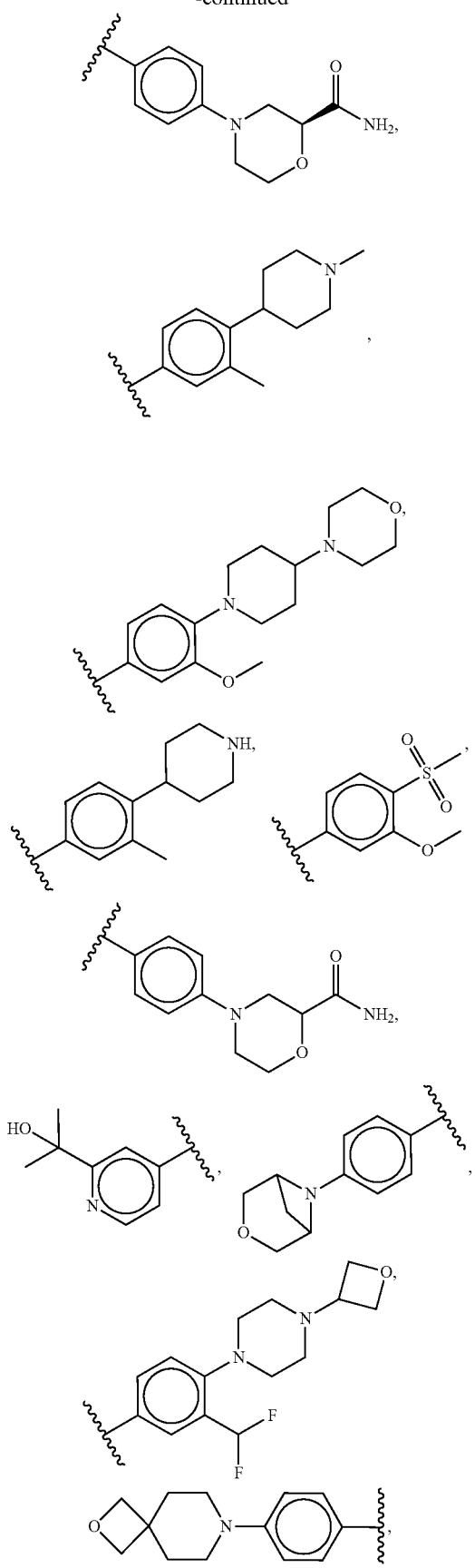
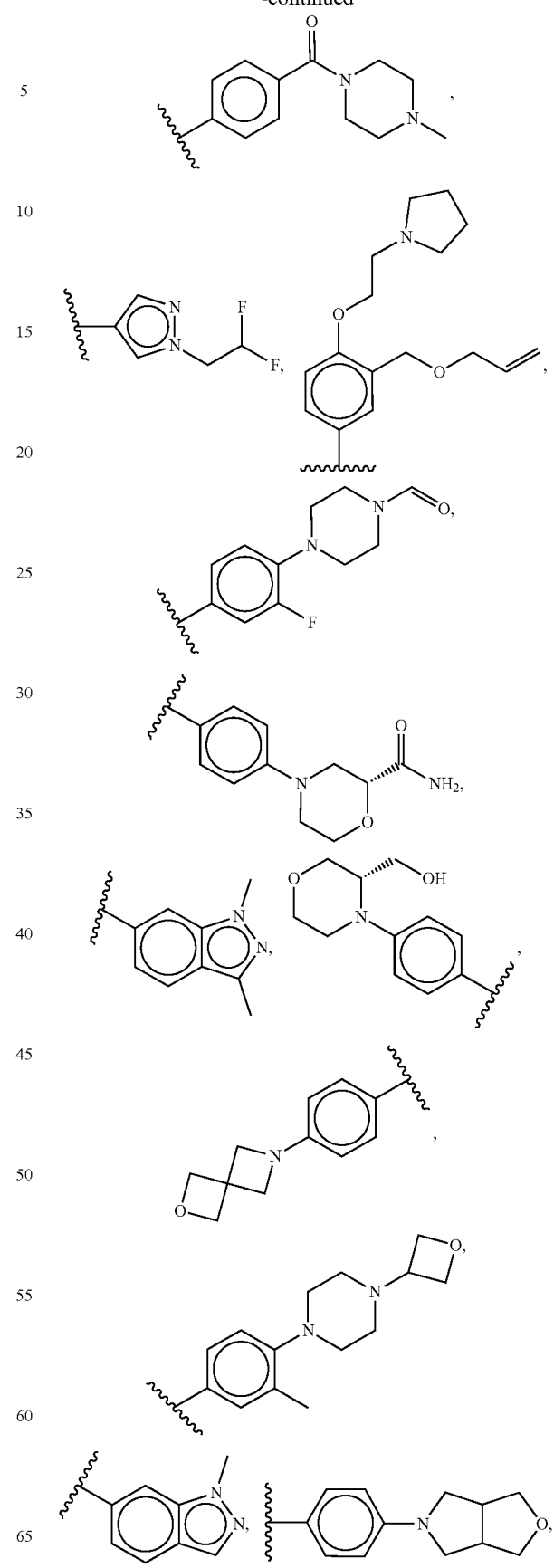

-continued

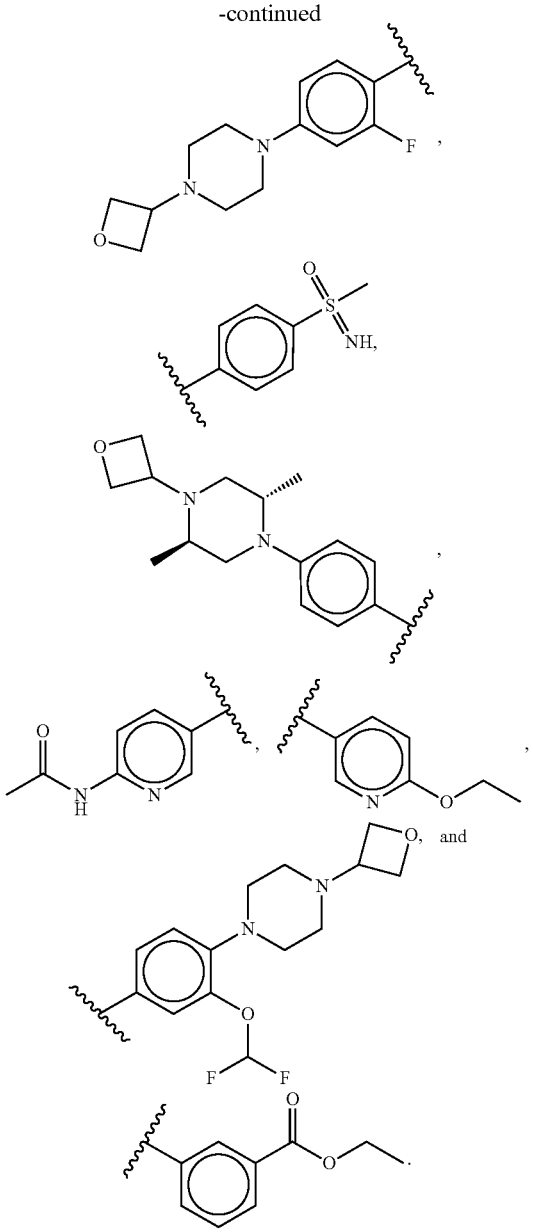

In another embodiment, $R^3$ is not H. In another embodiment, $R^4$ is H. In another embodiment, $R^1$ is H.

In another embodiment, $R^2$ is —$NR^aR^b$. In another embodiment, $R^a$ and $R^b$ on $R^5$ join together with the atoms to which they are attached form a 3-12 membered heterocyclyl which is optionally substituted with one to three of halo, hydroxyl, oxo, $C_{1-6}$ alkyl, $C_{1-6}$ alkoxy, $C_{1-6}$ haloalkyl, $C_{1-6}$ haloalkoxy, CN, amino, or $C_{1-6}$ alkylamino.

In another embodiment, $R^2$ is —O—$R^5$. In another embodiment, $R^5$ is selected from the group consisting of tetrahydropyranyl, tetrahydrofuranyl, pyrrolidinyl, oxetanylmethyl, 1-(oxetan-3-yl)pyrrolidinyl, oxo-propanylnitrilepyrrolinyl and piperidinyl. In another embodiment, $R^5$ is unsubstituted tetrahydropyranyl. In another embodiment, $R^2$ is N-pyrrolidinyloxy or N-piperidinyloxy substituted with $C_{1-6}$ alkoxycarbonyl, hydroxyl $C_{1-6}$ alkylcarbonyl, hydroxyl 3-6 membered heterocyclyl, halo 3-6 membered heterocyclyl, $C_{1-6}$ alkoxycarbonyl, cyano $C_{1-6}$ alkylcabonyl or $C_{3-6}$ cycloalkyl-$C_{1-6}$alkoxy. In another embodiment, $R^5$ is substituted with one $R^{20}$ group selected from $C_{1-6}$ alkoxycarbonyl, hydroxyl $C_{1-6}$ alkylcarbonyl, $C_{1-6}$ alkoxycarbonyl, cyano $C_{1-6}$ alkylcabonyl or $C_{3-6}$ cycloalkyl-$C_{1-6}$ alkoxy.

In another embodiment, the $R^5$ group is substituted with one or two fluoro groups. More particularly, the fluoro groups are substituted at the ortho position with respect to the point of attachment of the $R^5$ group.

In another embodiment, $R^5$ is:

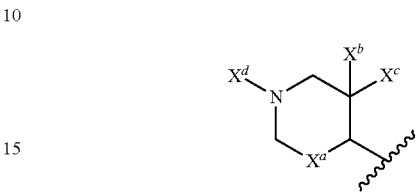

$X^a$ is a bond or $C(R^x)(R^y)$, wherein $R^x$ and $R^y$ are independently selected from the group consisting of H, halo or methyl;

$X^b$ and $X^c$ are independently selected from the group consisting of H, halo or methyl;

$X^d$ is selected from the group consisting of H; or $C_{1-6}$ alkyl, $C_{2-6}$ alkenyl, $C_{3-10}$ cycloalkyl, $C_{1-6}$ heteroalkyl, 3-12 membered heterocyclyl, $C_{6-10}$ aryl, 5-10 membered heteroaryl, each of which is optionally substituted with from one to five groups selected from $C_{1-6}$ alkyl, $C_{3-10}$ cycloalkyl, $C_{1-6}$ heteroalkyl, 3-12 membered heterocyclyl, $C_6$-$C_{10}$ aryl, 5-10 membered heteroaryl, hydroxyl, $C_{1-}$ alkoxy, amino, —CN, —C(O)H, —C(O)NH$_2$, —C(O)NH($C_{1-6}$ alkyl), —C(O)N($C_{1-6}$ alkyl)$_2$, —COOH, —C(O)$C_{1-6}$ alkyl, —C(O)OC$_{1-6}$ alkyl, or halogen.

In another embodiment, $X^d$ is $C_{1-6}$ alkyl substituted with hydroxyl. In another embodiment, $X^a$ is CH$_2$. In another embodiment, $X^b$ is fluoro. In another embodiment, $X^c$ is H.

In another embodiment, $R^2$ is selected from the group consisting of:

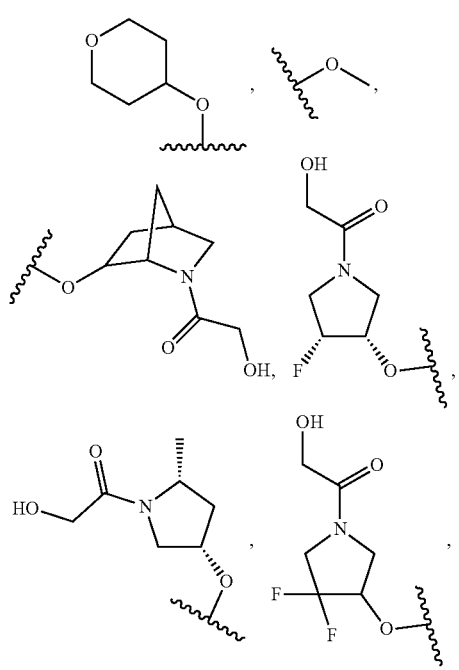

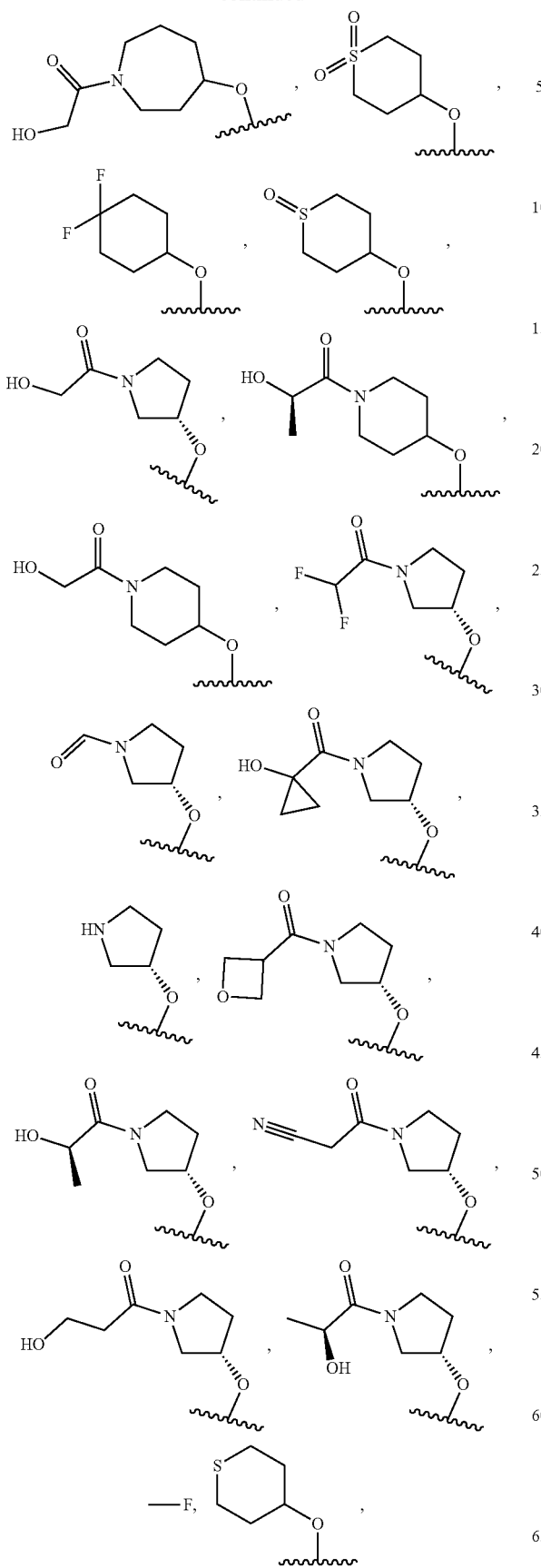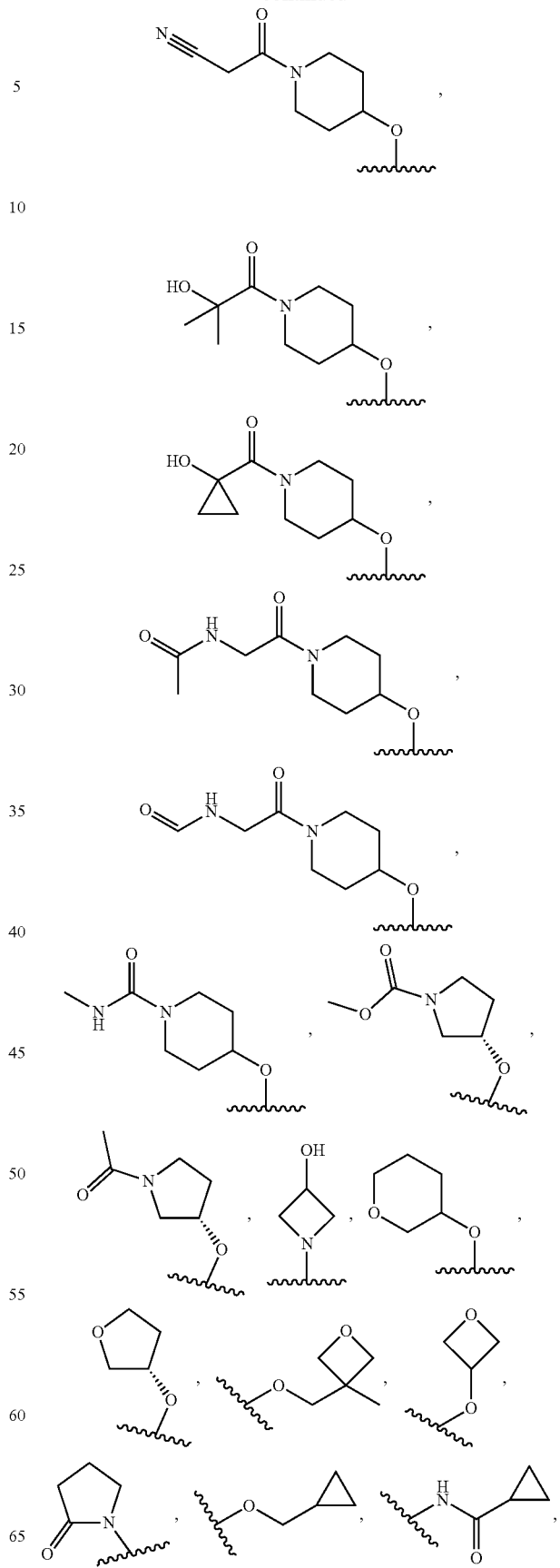

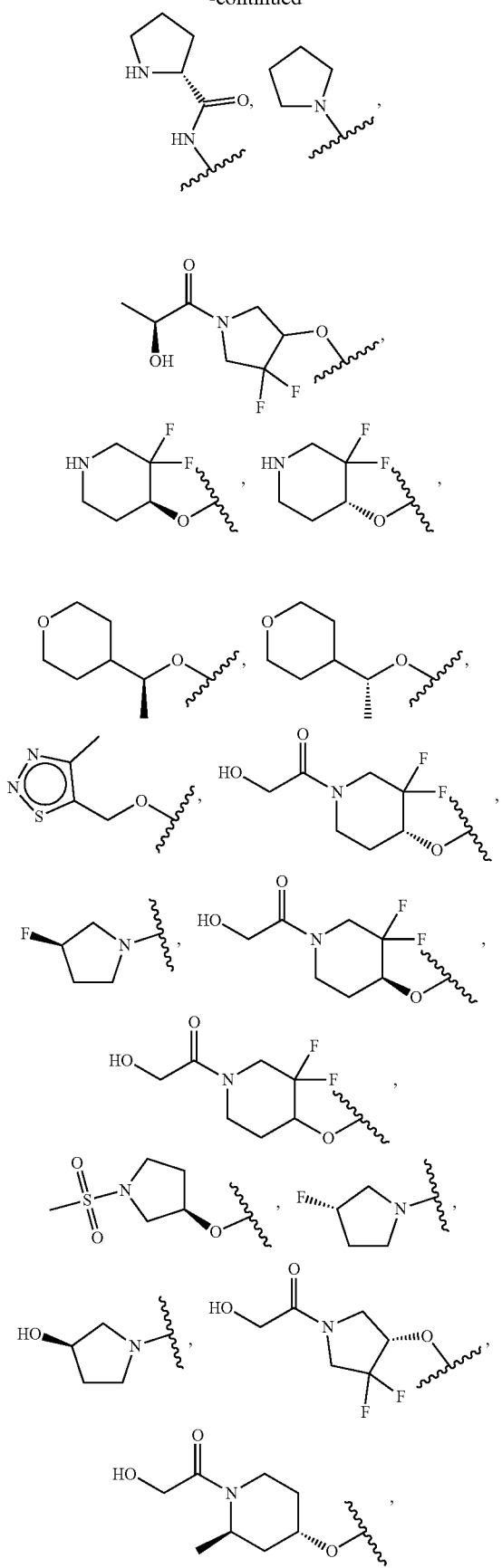
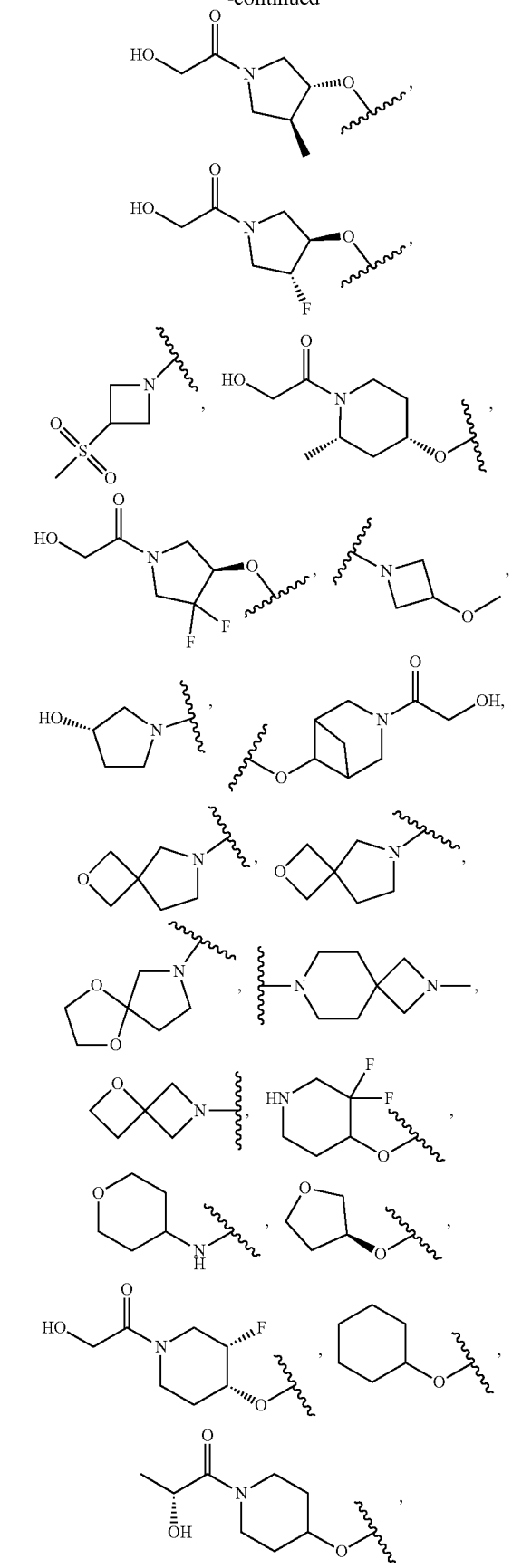

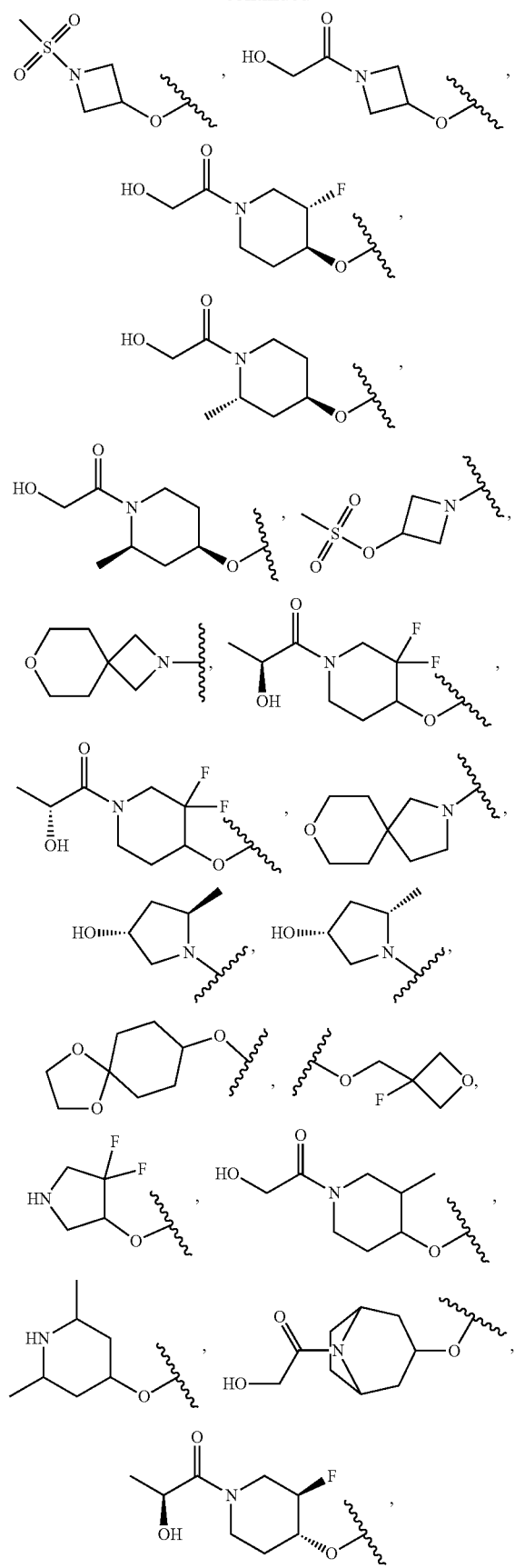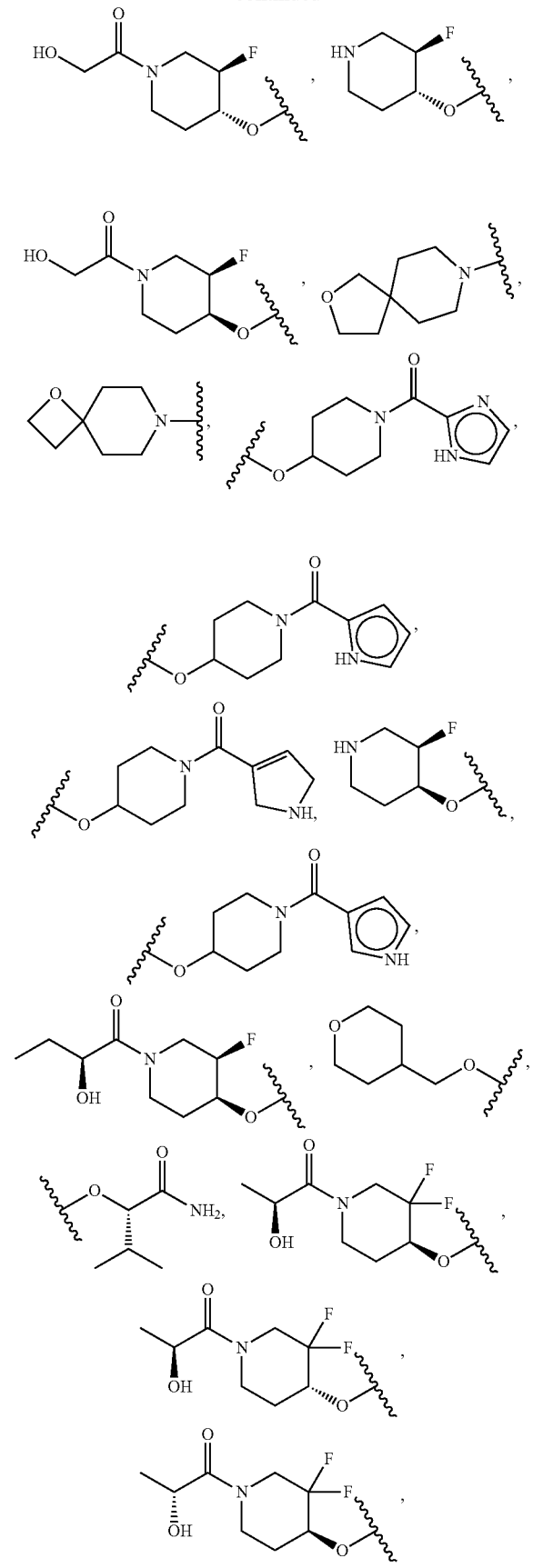

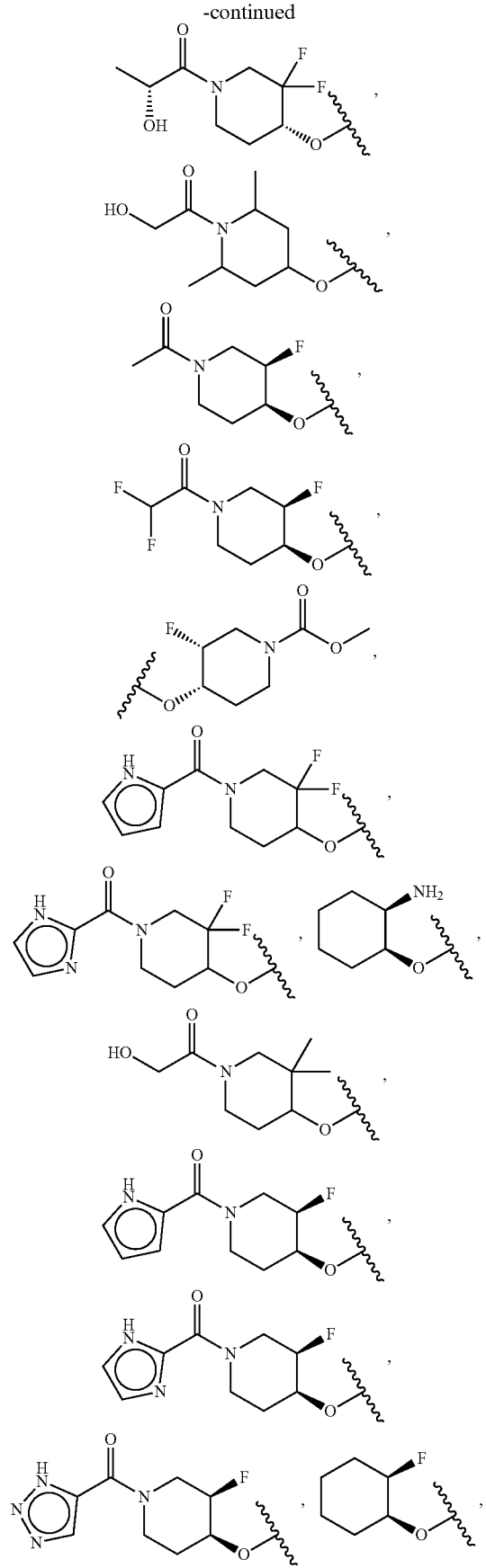
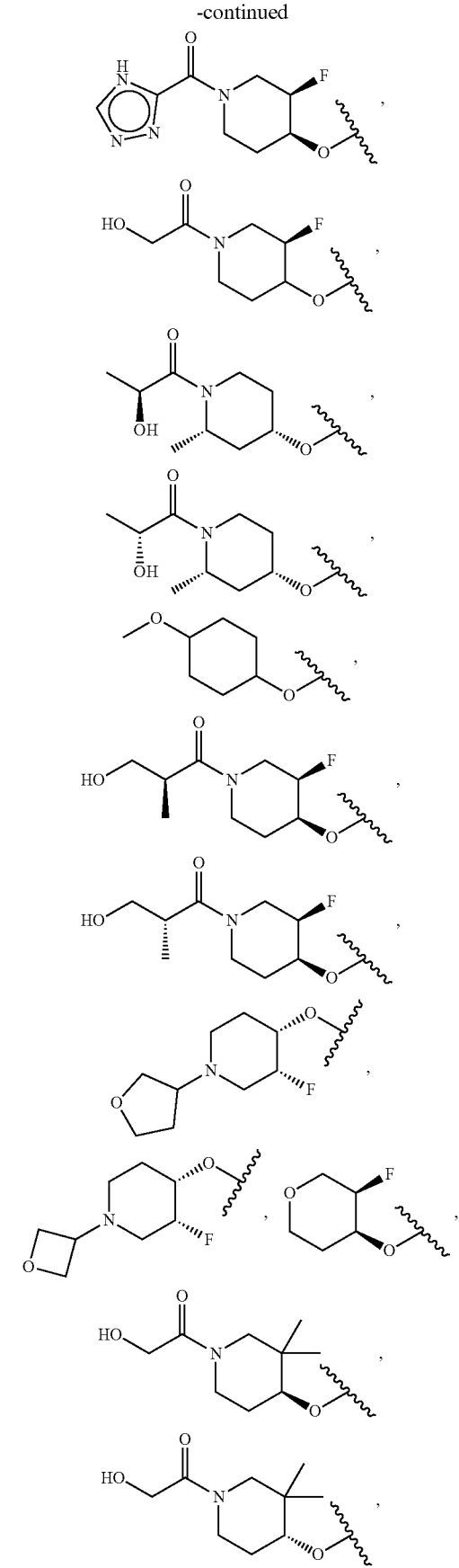

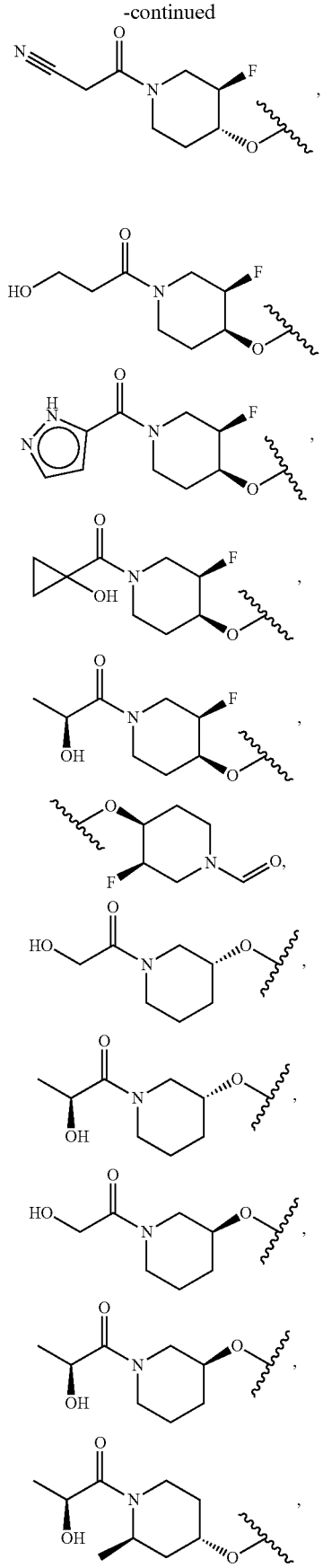
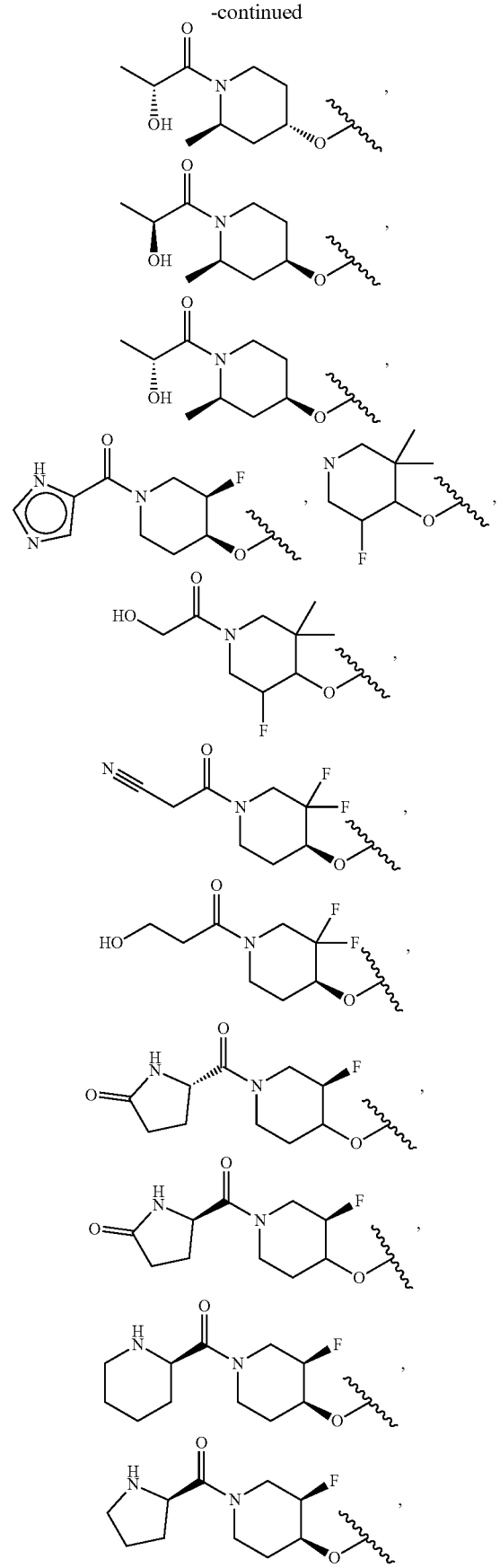

-continued
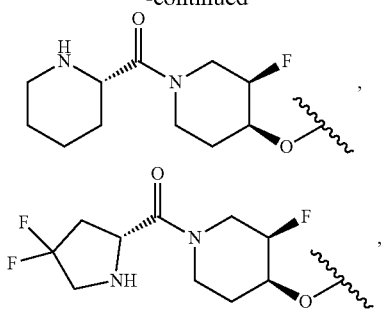
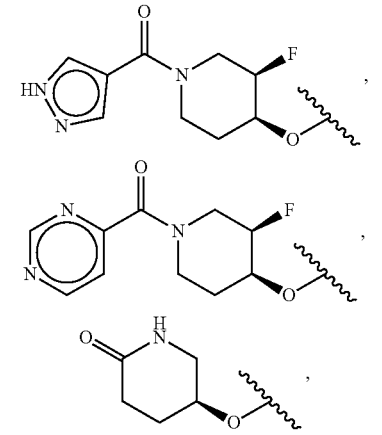
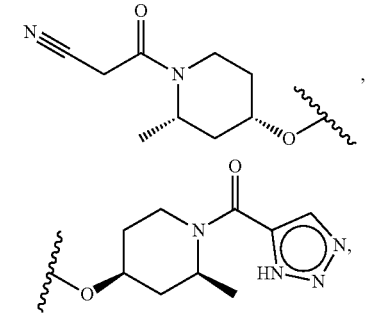
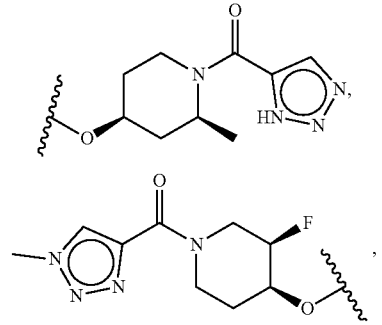
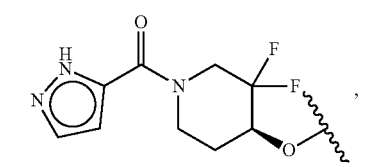
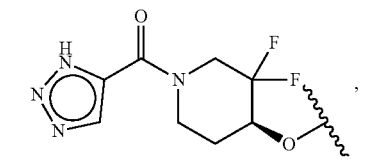
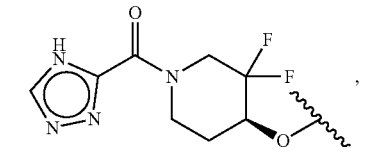
-continued
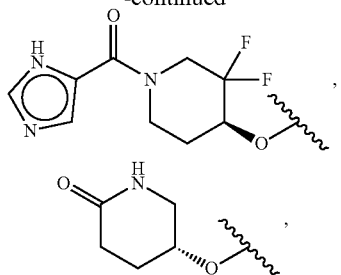
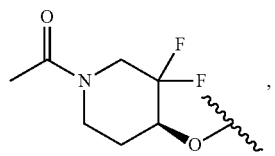
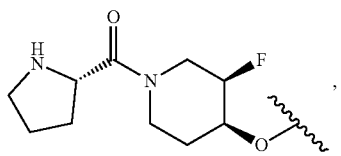
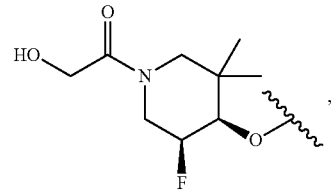
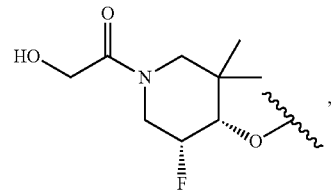
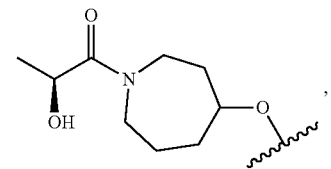
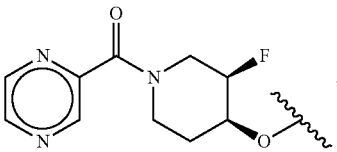
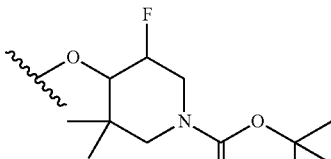
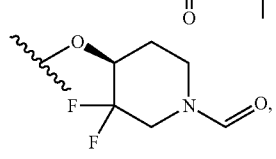

31
-continued
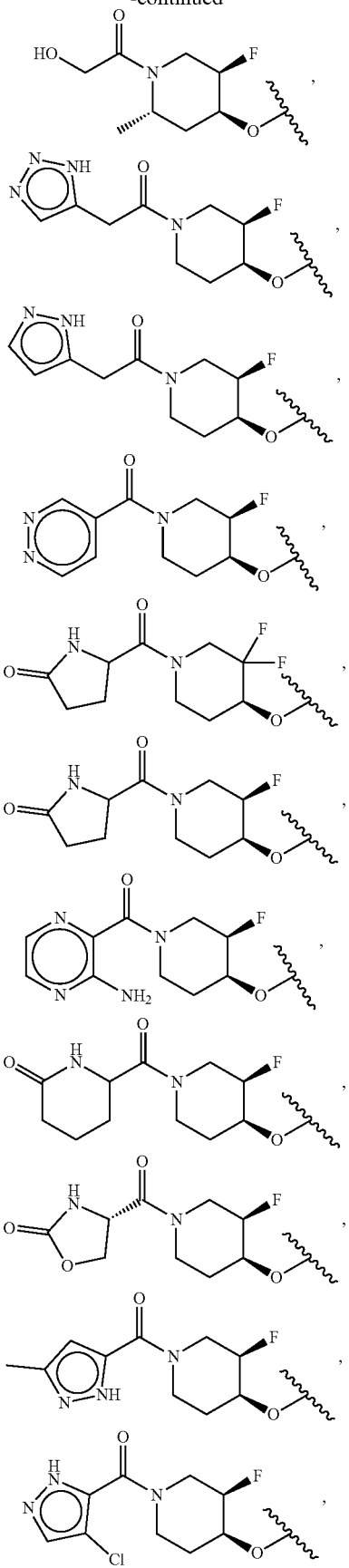
32
-continued
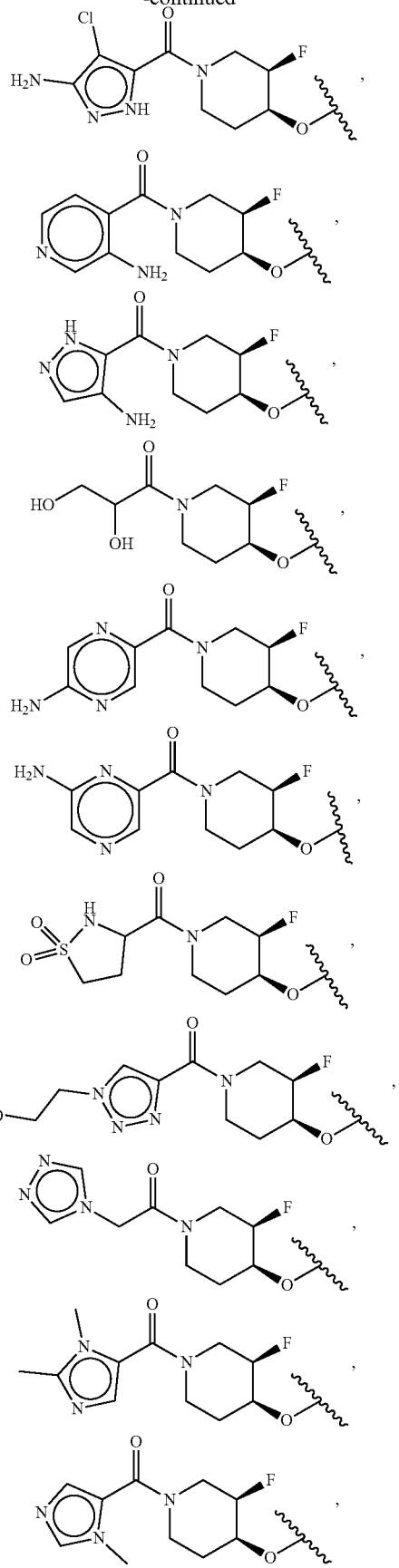

Another embodiment provides a compound selected from the group consisting of:

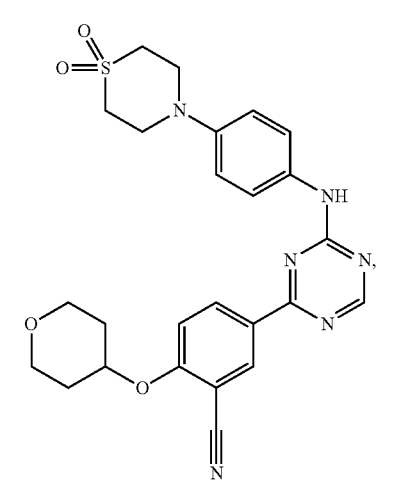
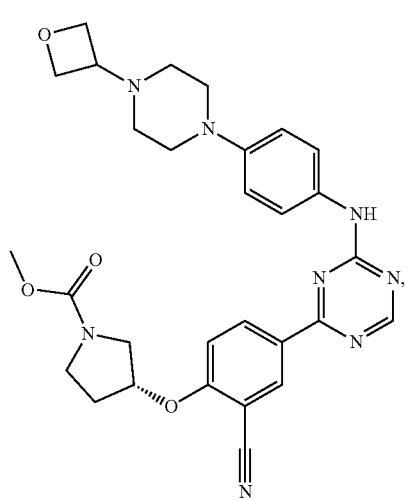
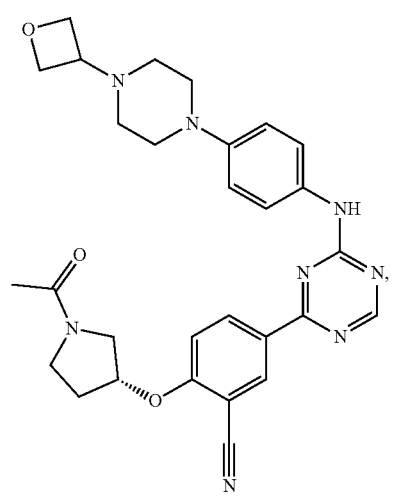
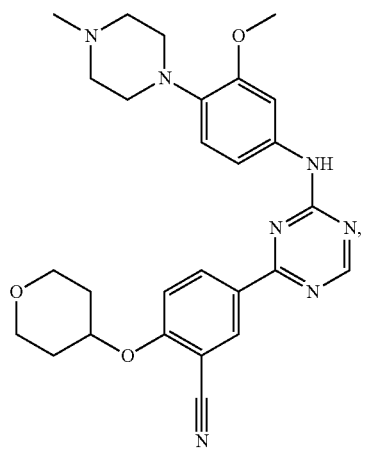
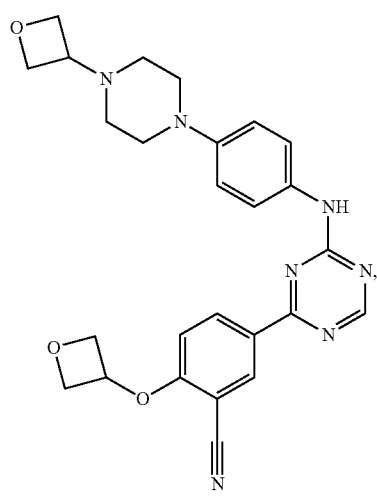
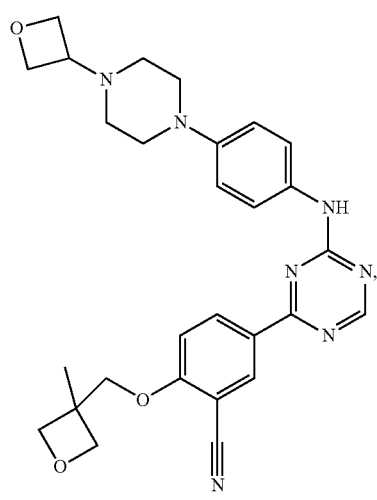

37
-continued
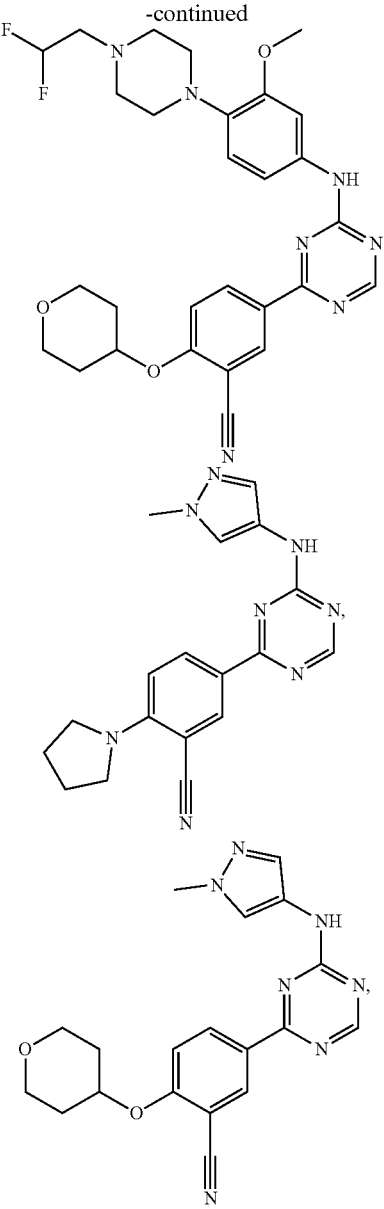
38
-continued
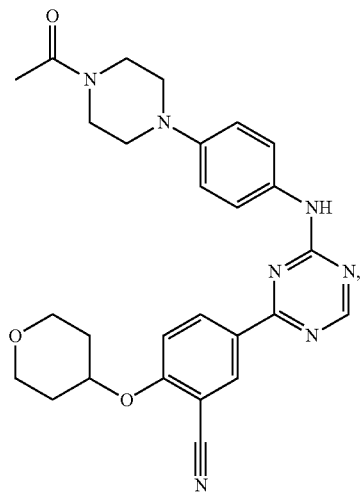
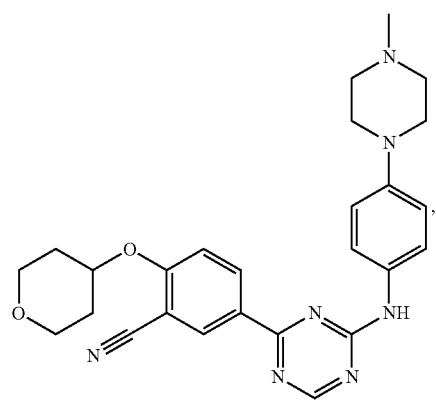
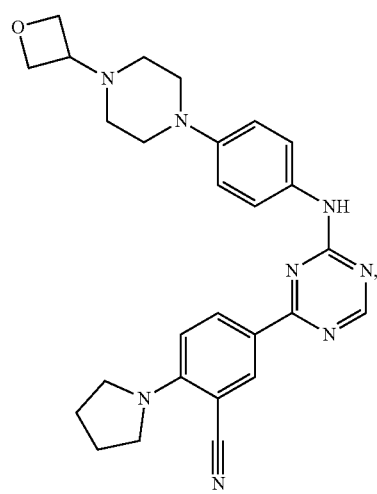
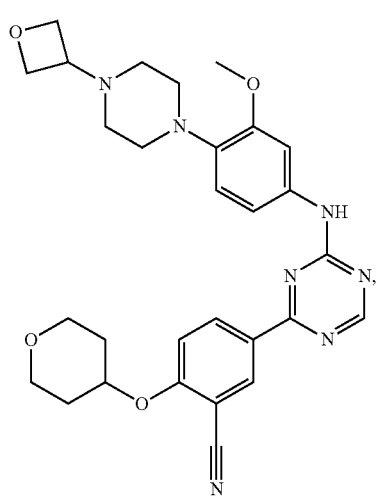

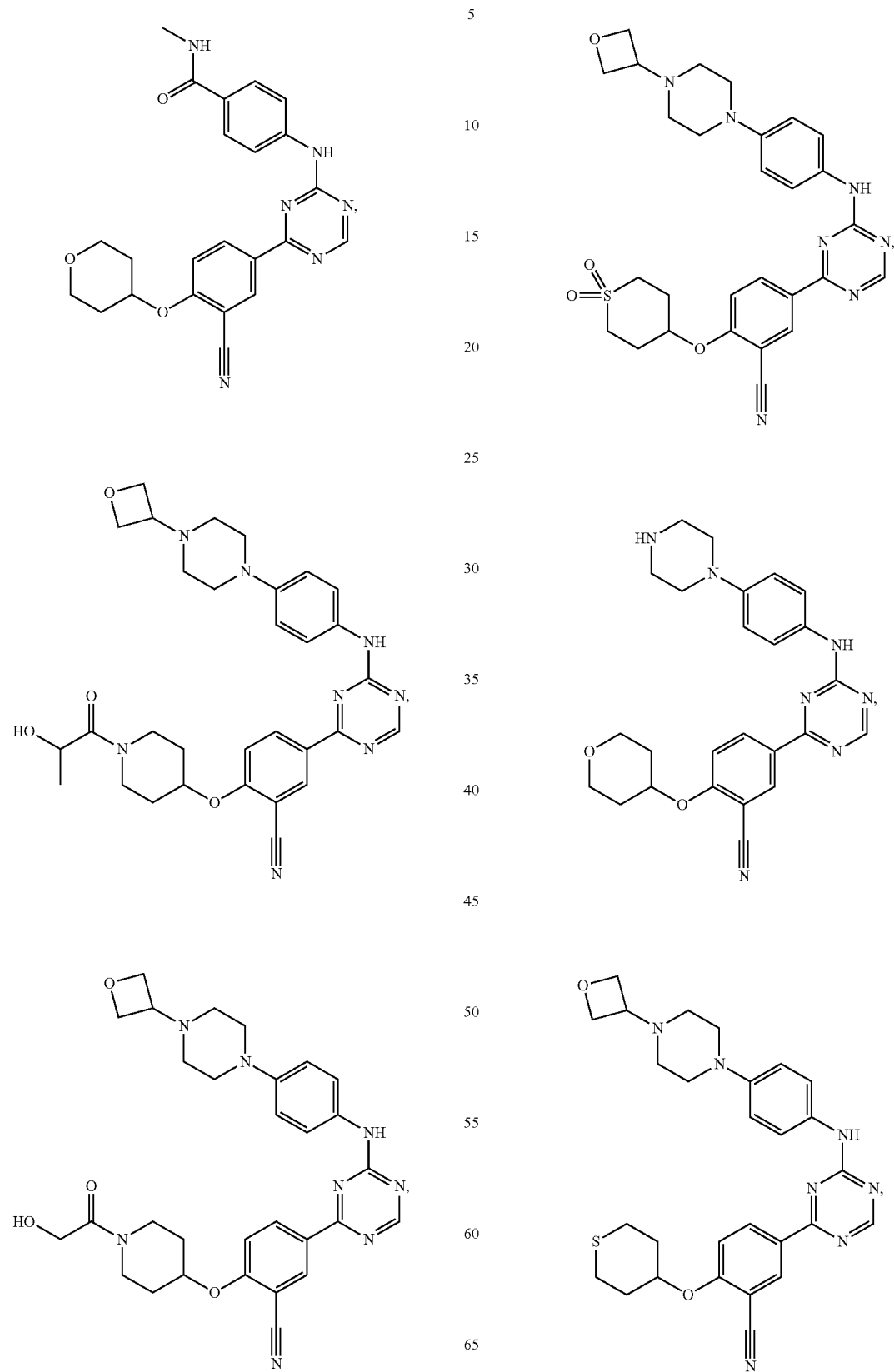

41
-continued
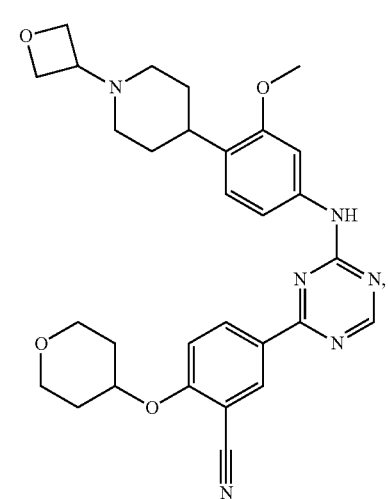
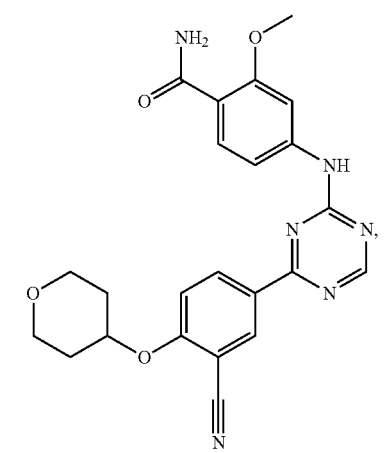
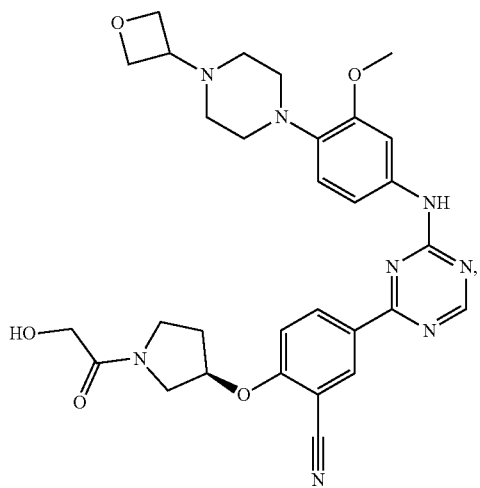
42
-continued
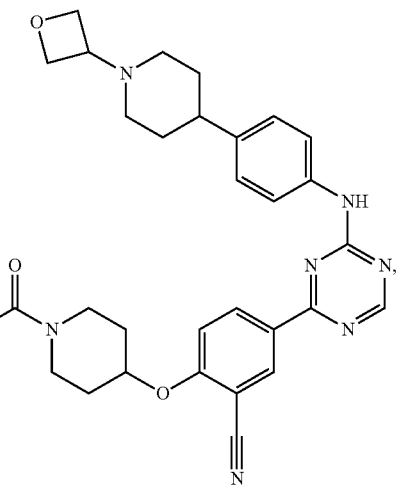
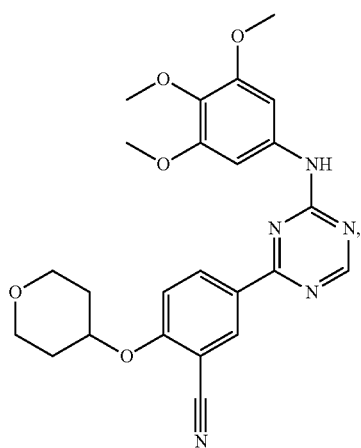
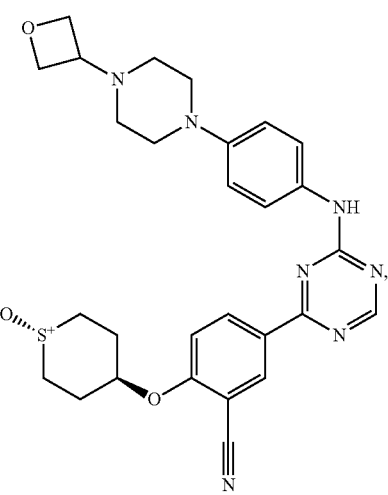

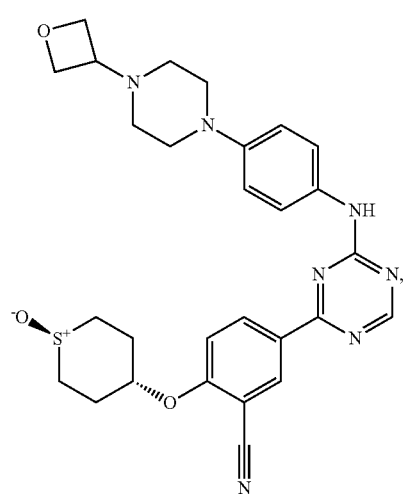
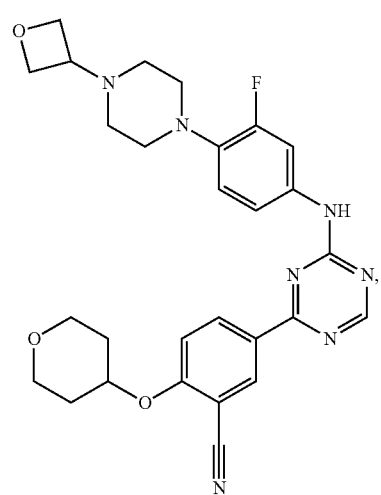
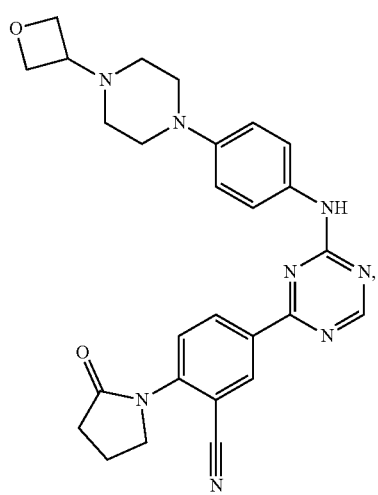
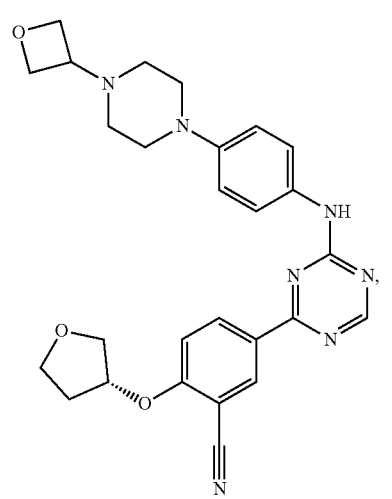
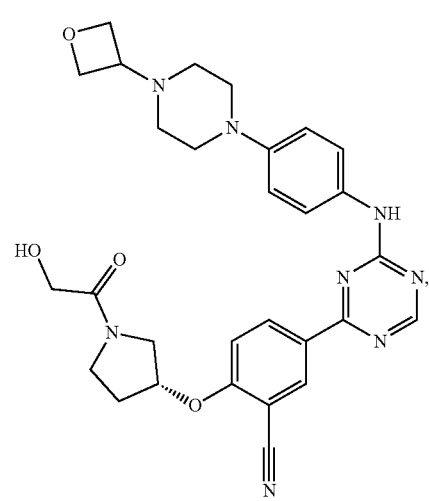
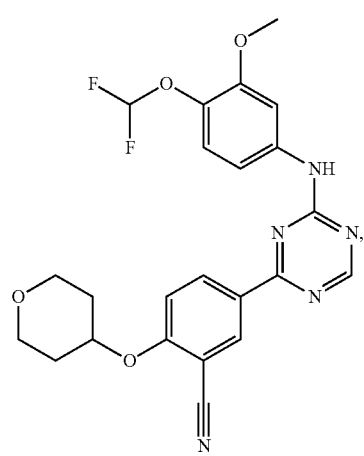

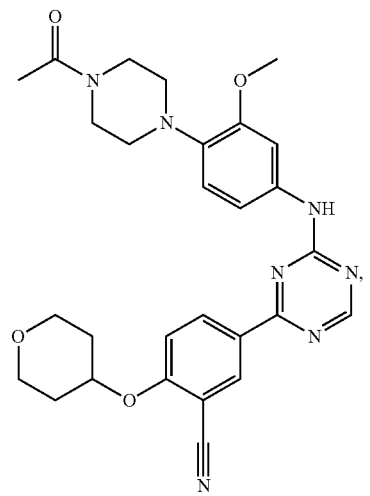
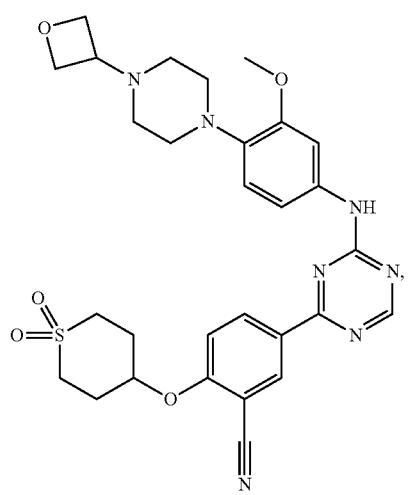
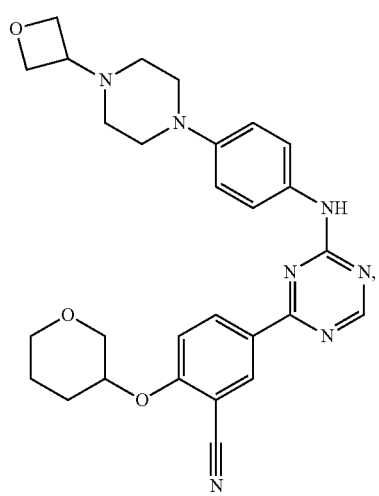
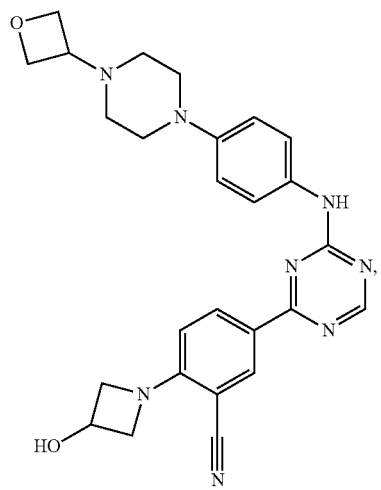
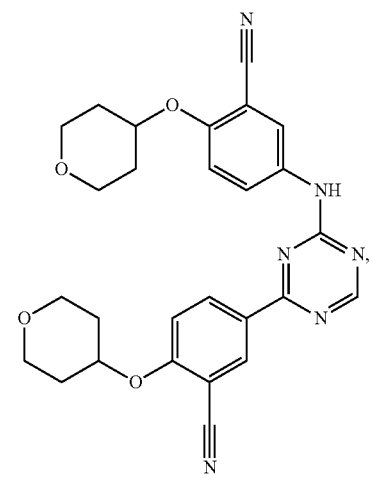
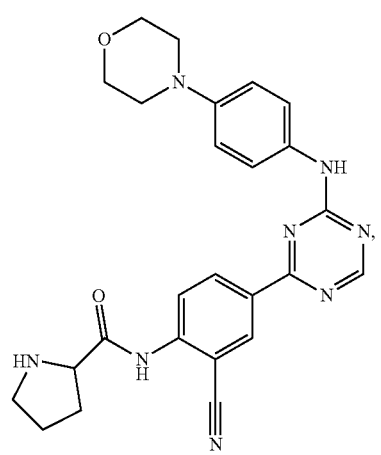

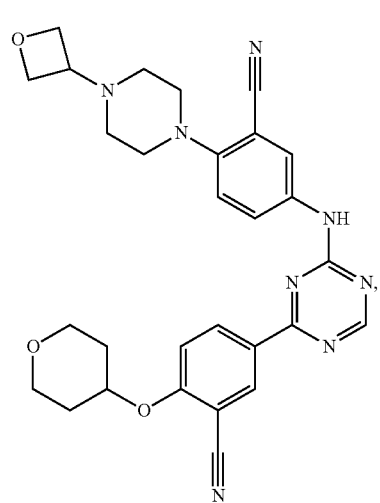
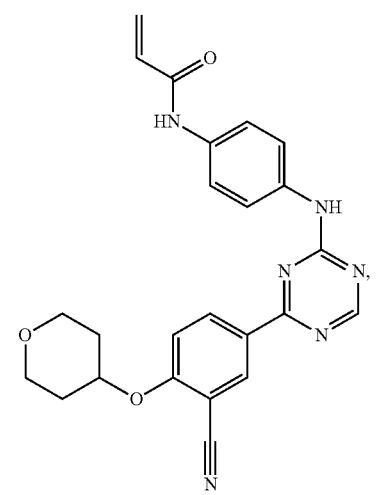
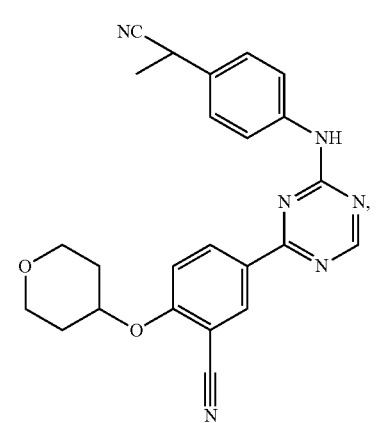
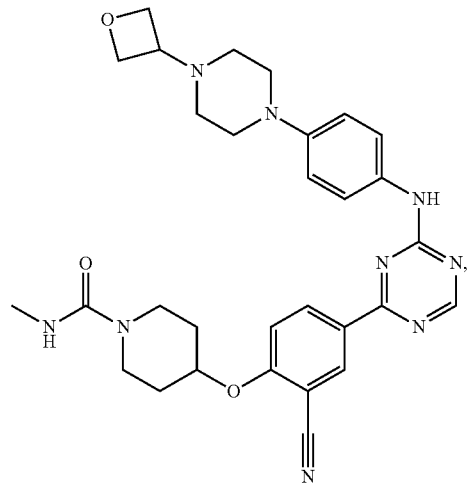
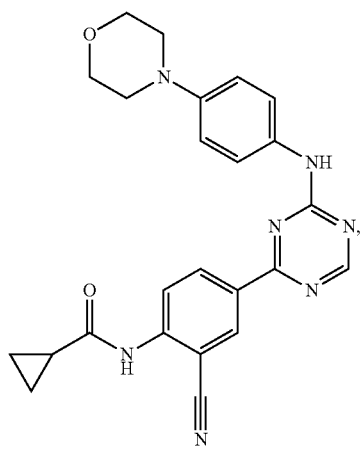
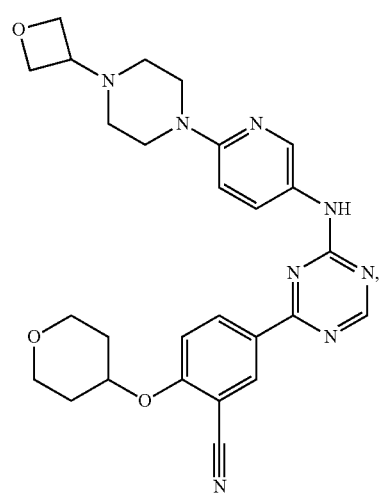

-continued
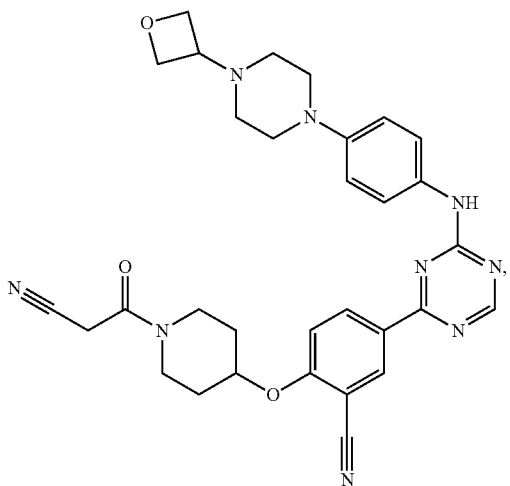
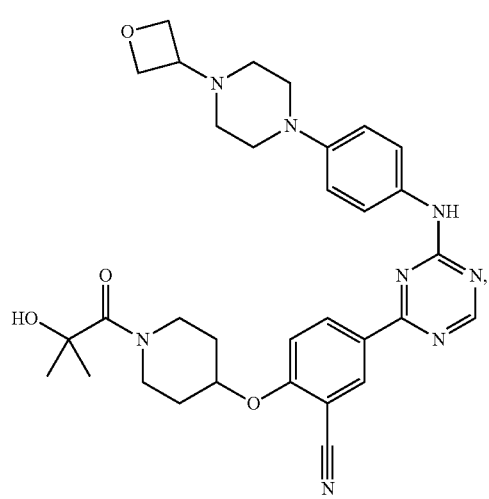
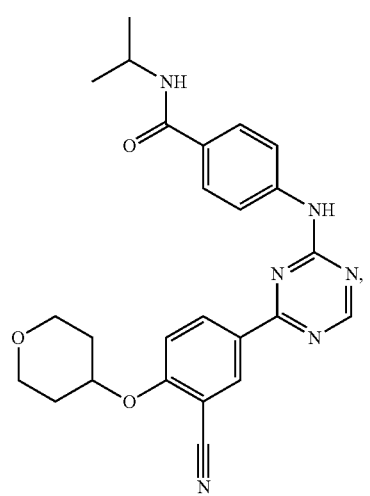
-continued
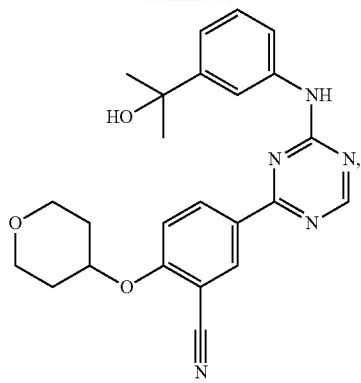
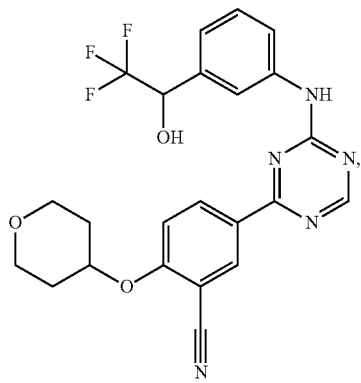
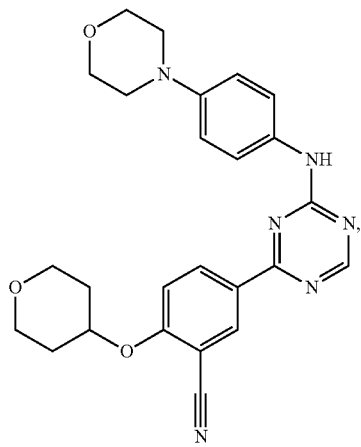
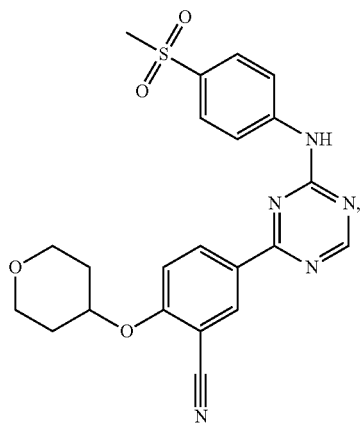

51
-continued
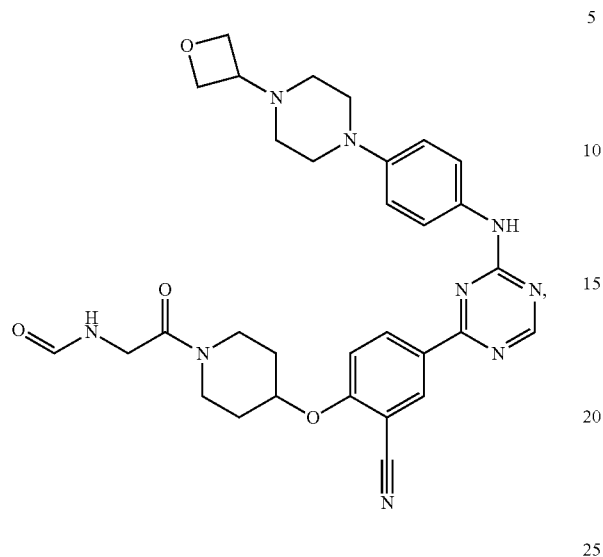
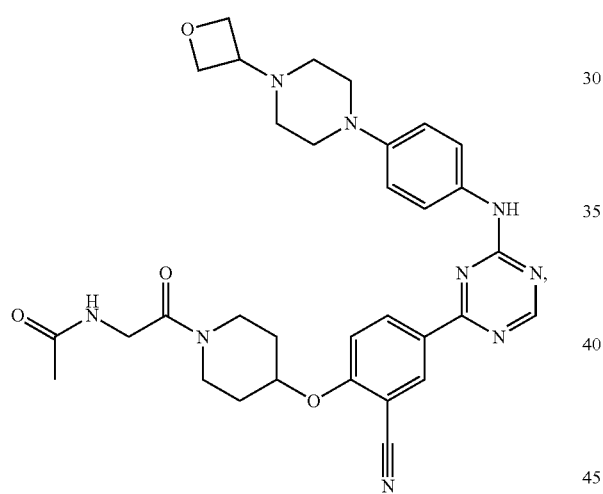
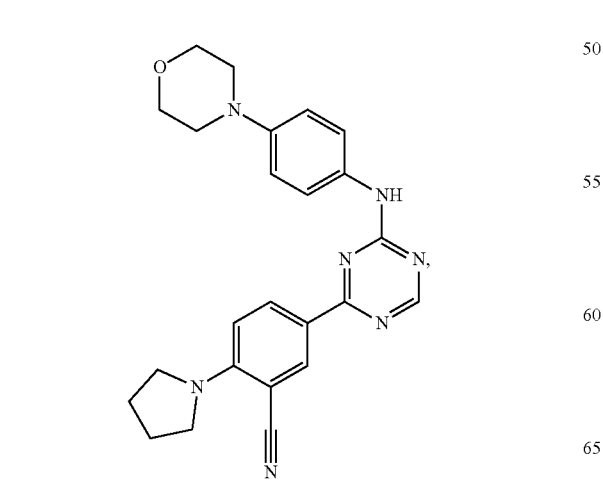
52
-continued
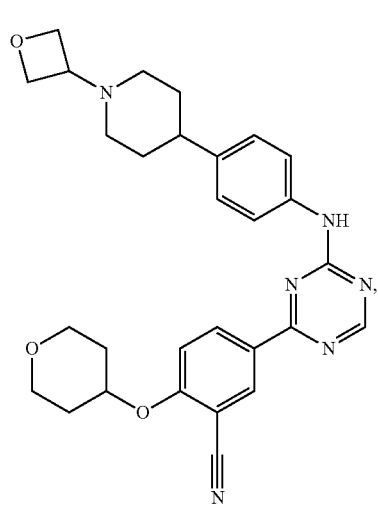
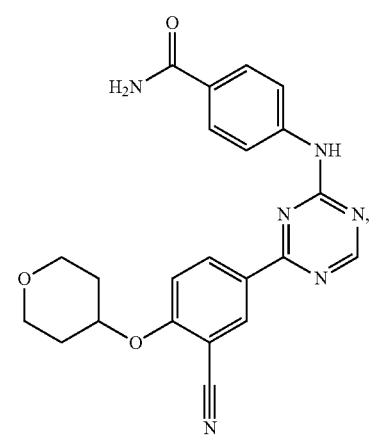
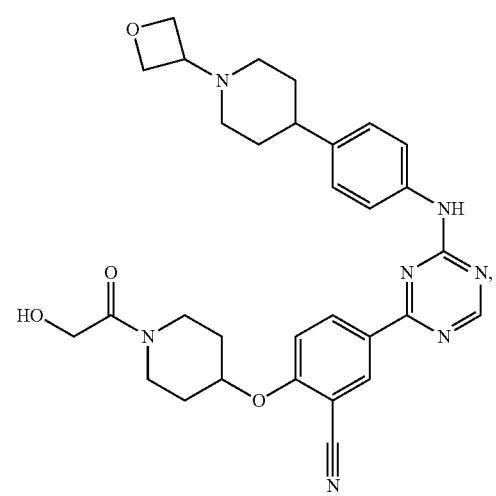

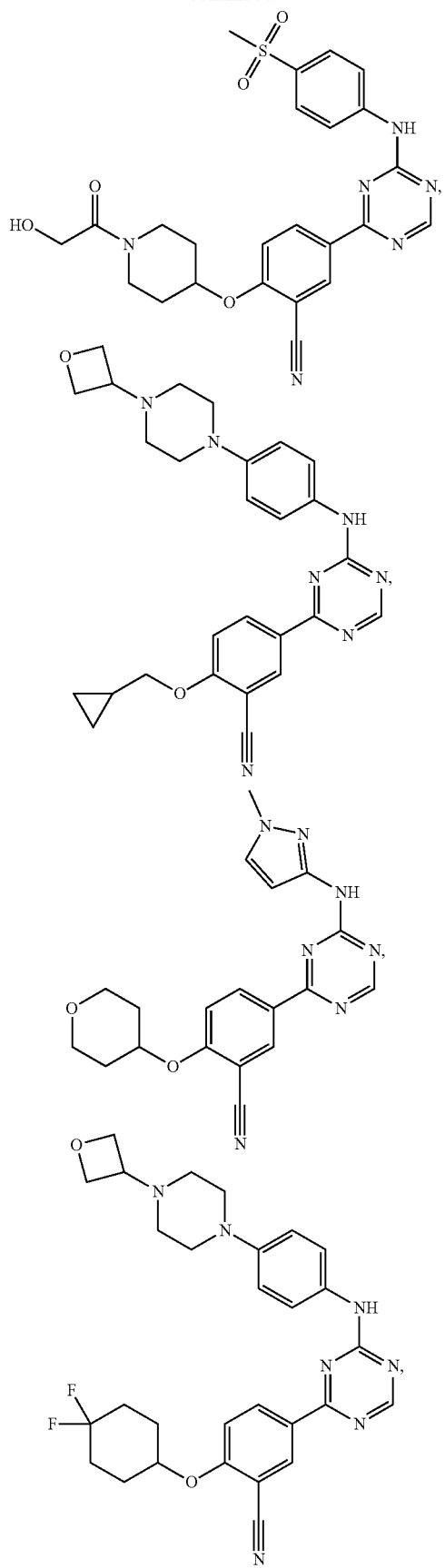
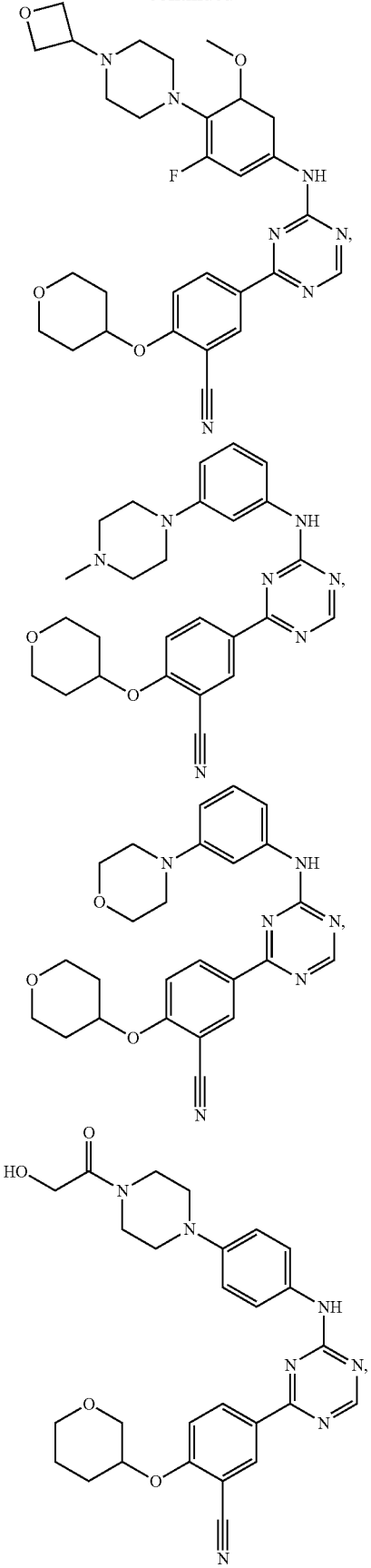

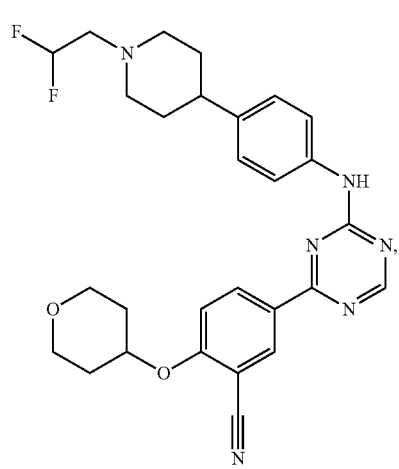
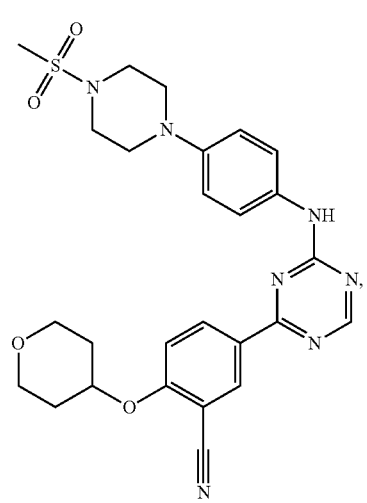
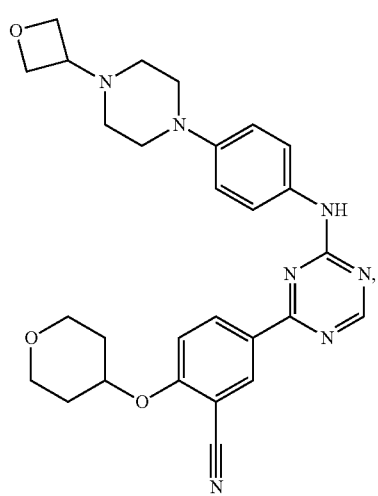
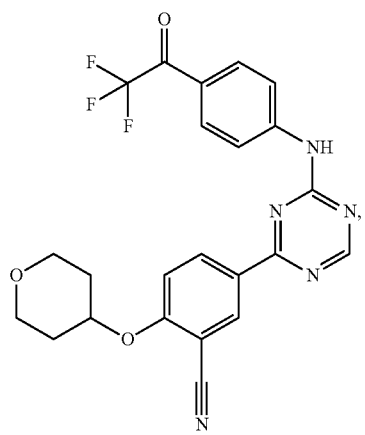
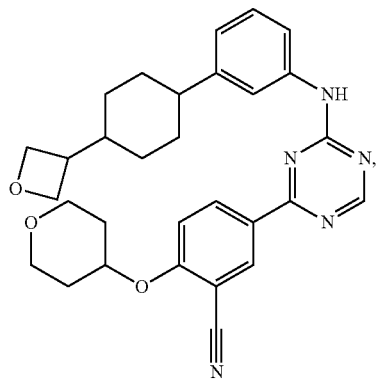
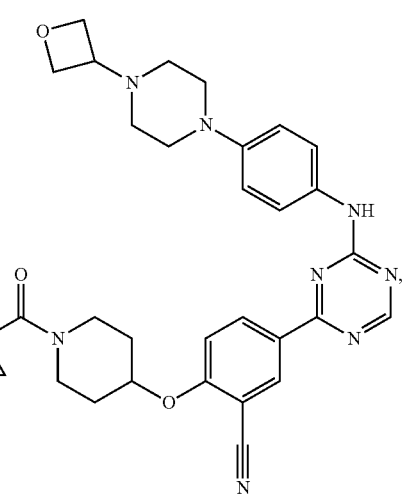

57
-continued
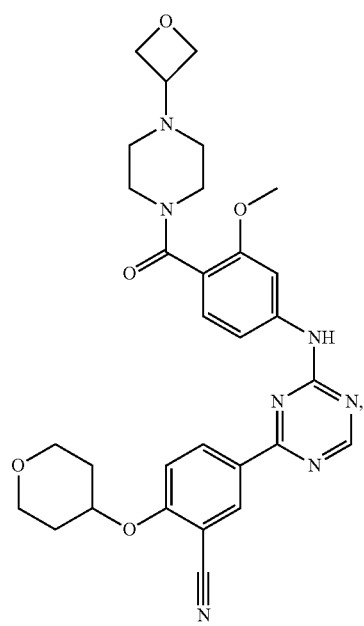
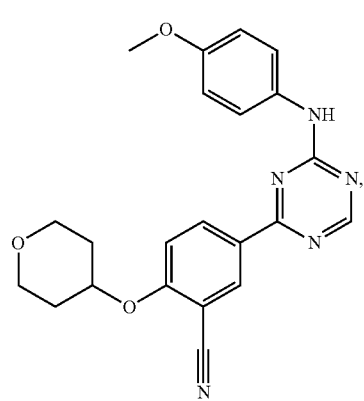
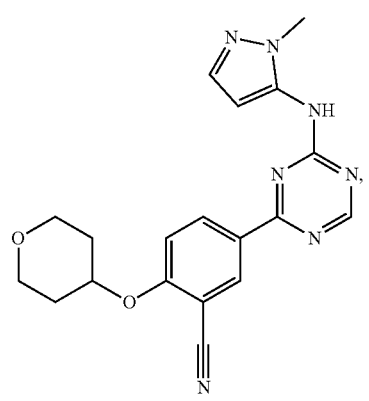
58
-continued
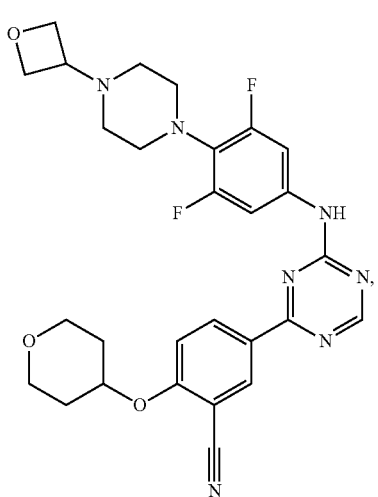
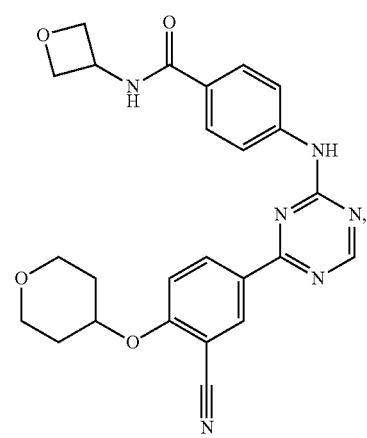
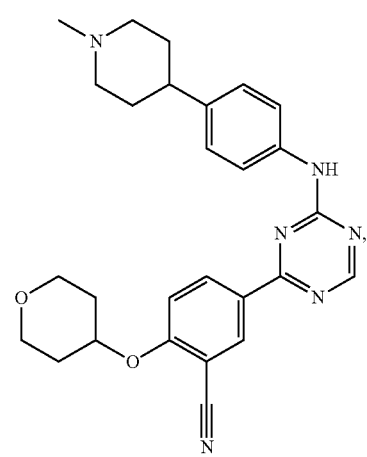

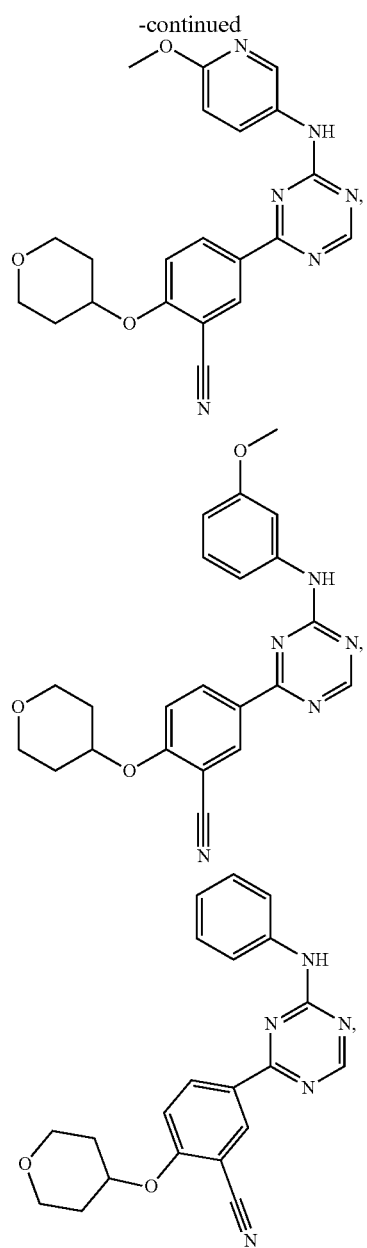
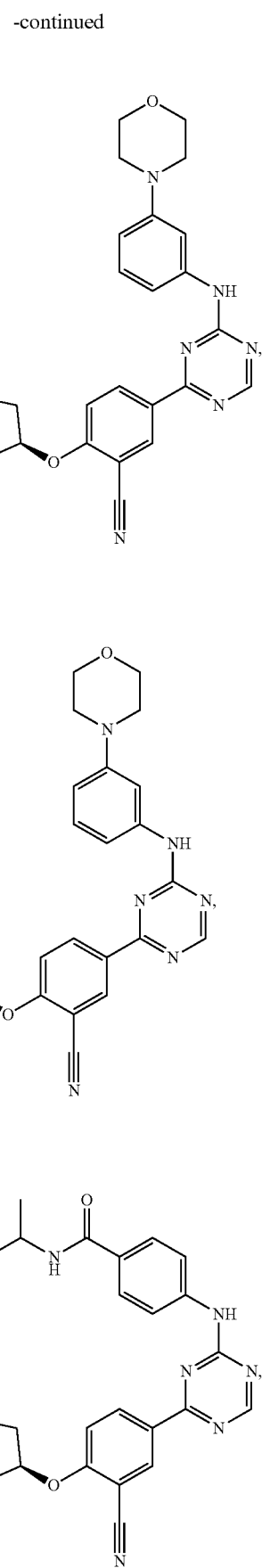

61
-continued
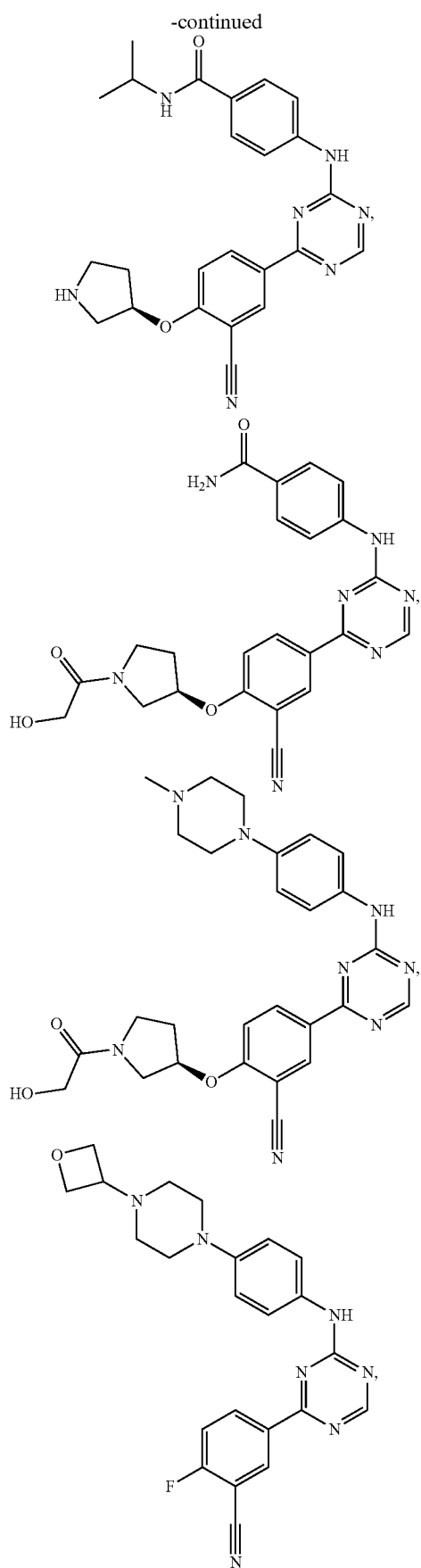
62
-continued
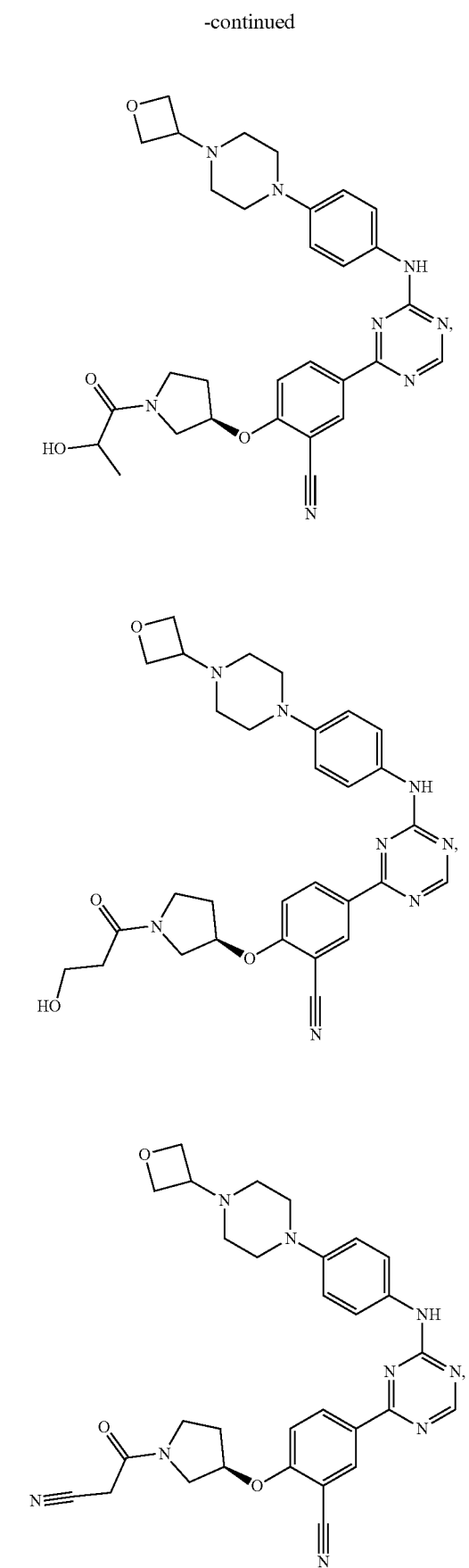

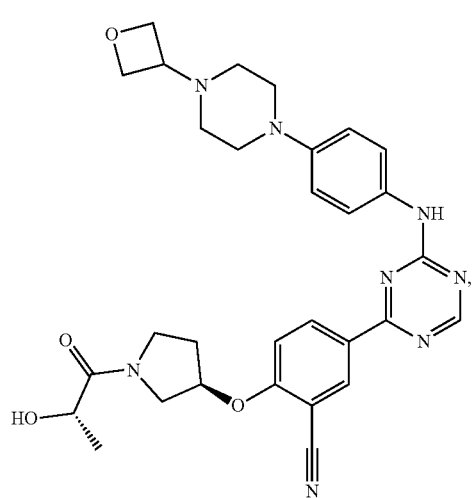
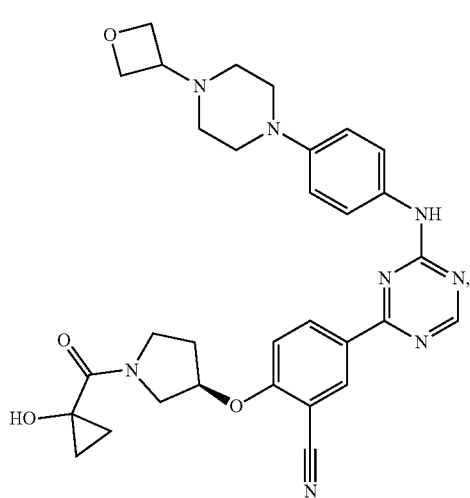
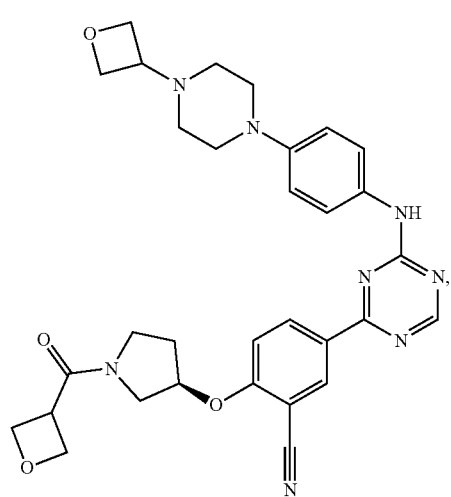
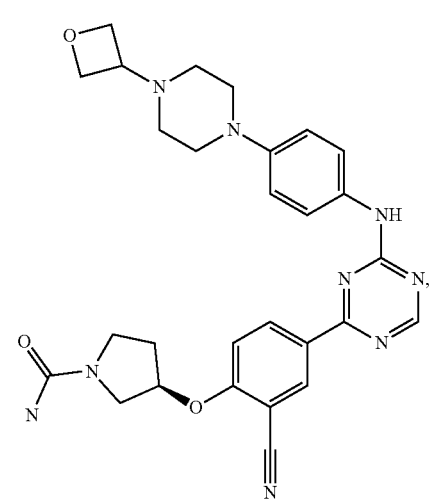
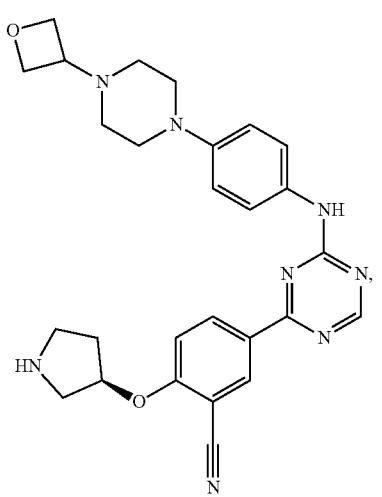
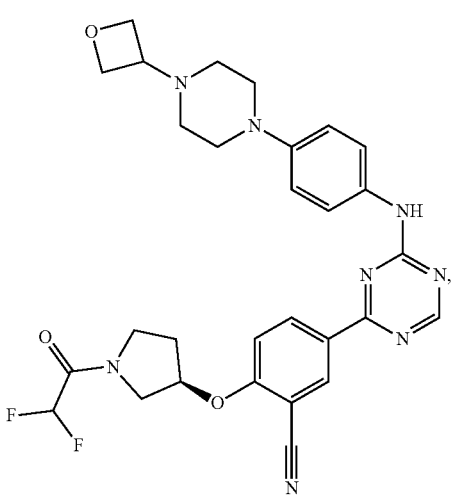

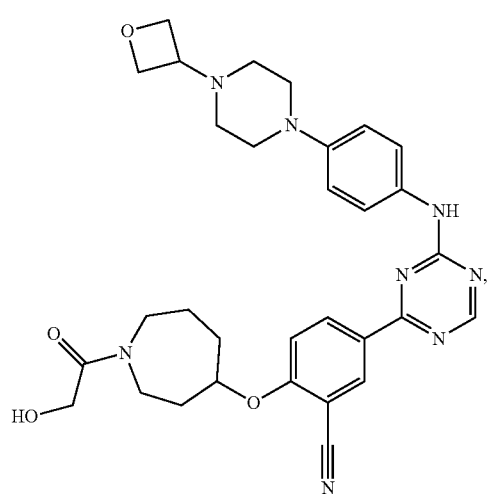
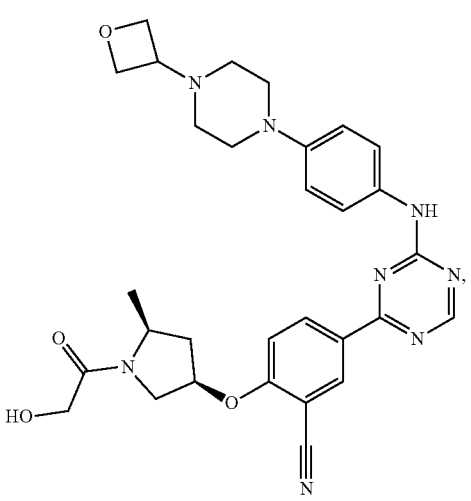
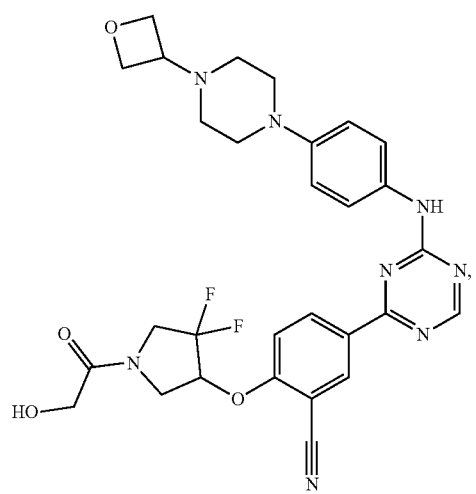
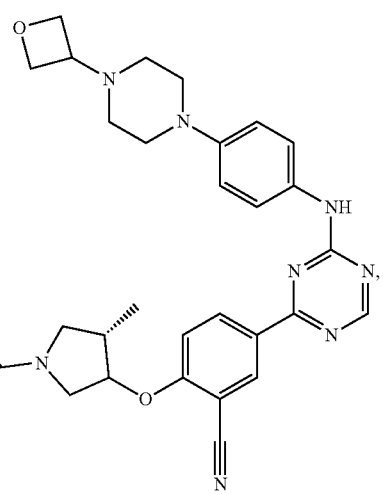
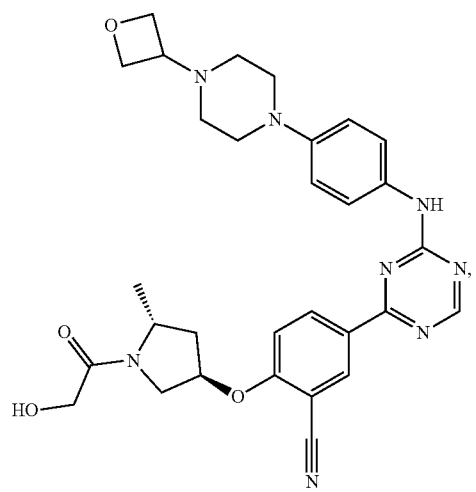
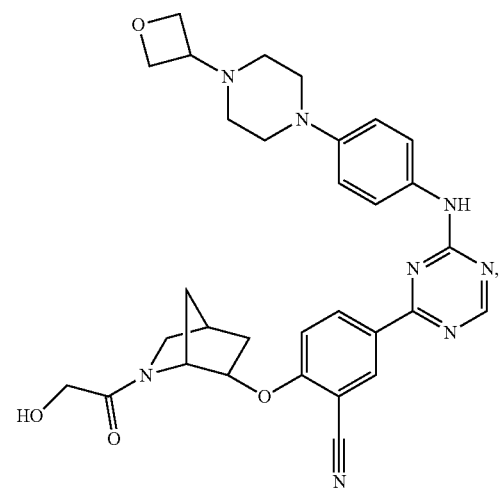

67
-continued
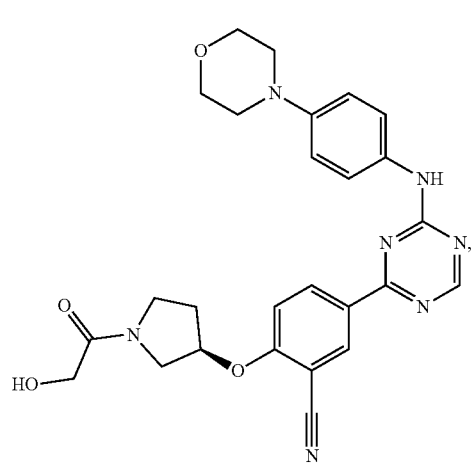
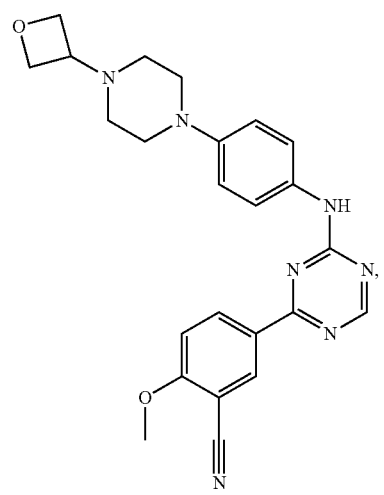
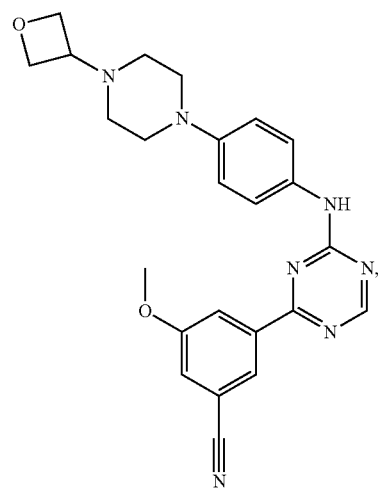
68
-continued
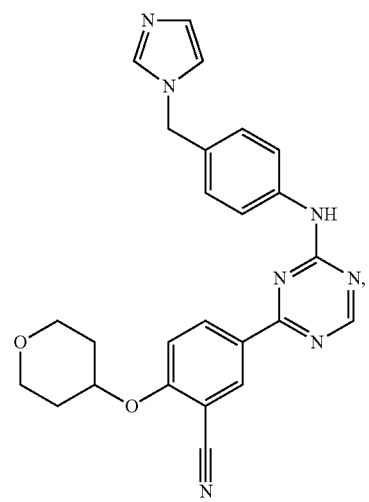
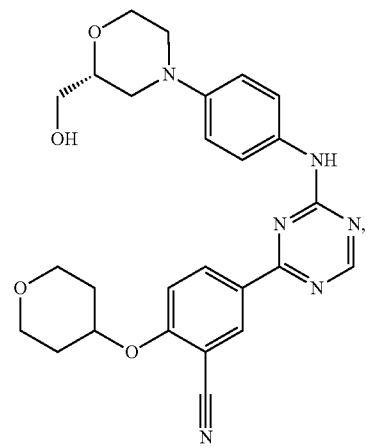
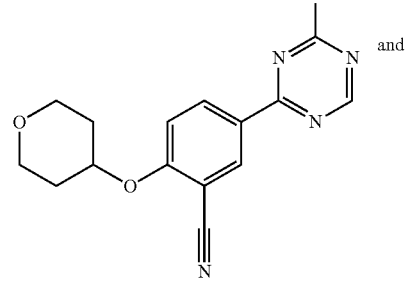
and

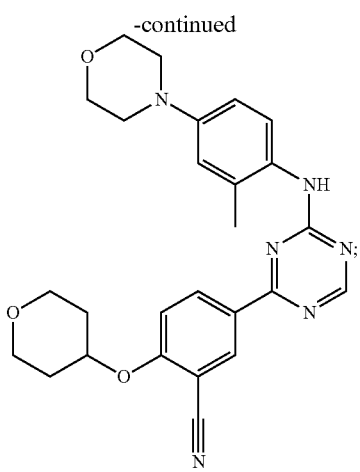

or a pharmaceutically acceptable salt thereof.

Another embodiment provides a pharmaceutical composition comprising a compound as described herein, or a pharmaceutically acceptable salt thereof, and a pharmaceutically acceptable carrier.

Another embodiment provides a method of treating a subject having a disease or condition responsive to the inhibition of TBK1, comprising administering to the subject a therapeutically effective amount of a compound as described herein, or a pharmaceutically acceptable salt thereof. In another embodiment, the disease is cancer. Another embodiment provides a method of treating a subject having a disease or condition responsive to the inhibition of IKKε, comprising administering to the subject a therapeutically effective amount of a compound as described herein, or a pharmaceutically acceptable salt thereof.

Another embodiment provides a method of treating a subject suffering from a RAS-dependent/mutant cancer, comprising administering to the subject a therapeutically effective amount of a compound as described herein. In another embodiment, the RAS-dependent/mutant cancer is selected from the group consisting of non-small cell lung cancer, colorectal cancer, pancreatic cancer, AML, and melanoma.

Another embodiment provides a method of treating a subject suffering from breast or ovarian cancer, comprising administering to the subject a therapeutically effective amount of a compound as described herein. Another embodiment provides a method of treating a subject suffering from cancer resistant to HER2 and EGFR targeted therapies comprising administering to the subject a therapeutically effective amount of a compound as described herein.

Another embodiment provides a method of treating a subject suffering from a disease selected from the group consisting of Rheumatoid arthritis (RA), Inflammatory bowel disease (IBD), Chronic obstructive pulmonary disease (COPD), Systemic lupus erythematosus (SLE), Polymositis, Systemic sclerosis, Type 2 diabetes, Obesity and Hepatic steatosis.

Another embodiment provides a method of inhibiting TBK1 in a subject, comprising administering a compound of a compound described herein, or a pharmaceutically acceptable salt thereof. Another embodiment provides a method of inhibiting IKKε in a subject, comprising administering a compound as described herein, or a pharmaceutically acceptable salt thereof. In another embodiment, the compound is selective against JAK2 or does not substantially inhibit JAK2.

Another embodiment provides a compound as described herein, or a pharmaceutically acceptable salt thereof, for use in therapy.

Another embodiment provides a compound as described herein, or a pharmaceutically acceptable salt thereof, for use in a method of treating a subject having a disease or condition responsive to the inhibition of TBK1. In an embodiment, the disease is cancer. Another embodiment provides a compound as described herein, or a pharmaceutically acceptable salt thereof for use in a method of treating a subject having a disease or condition responsive to the inhibition of IKKε.

Another embodiment provides a compound as described herein, or a pharmaceutically acceptable salt thereof, for use in a method of treating a subject suffering from a RAS-dependent/mutant cancer. In an embodiment, the RAS-dependent/mutant cancer is selected from the group consisting of non-small cell lung cancer, colorectal cancer, pancreatic cancer, AML, and melanoma.

Another embodiment provides a compound as described herein, or a pharmaceutically acceptable salt thereof, for use in a method of treating a subject suffering from breast or ovarian cancer. Another embodiment provides a compound as described herein, or a pharmaceutically acceptable salt thereof, for use in a method of treating a subject suffering from cancer resistant to HER2 and EGFR targeted therapies.

Another embodiment provides a compound as described herein, or a pharmaceutically acceptable salt thereof, for use in a method of treating a subject suffering from a disease selected from the group consisting of Rheumatoid arthritis (RA), Inflammatory bowel disease (IBD), Chronic obstructive pulmonary disease (COPD), Systemic lupus erythematosus (SLE), Polymositis, Systemic sclerosis, Type 2 diabetes, Obesity and Hepatic steatosis.

Another embodiment provides a compound as described herein, or a pharmaceutically acceptable salt thereof, for use in a method of treating a subject suffering from cancer.

Another embodiment provides a compound as described herein, or a pharmaceutically acceptable salt thereof, for use in a method of inhibiting TBK1 in a subject. Another embodiment provides a compound as described herein, or a pharmaceutically acceptable salt thereof, for use in a method of inhibiting IKKε in a subject.

Another embodiment provides the use of a compound as described herein, or a pharmaceutically acceptable salt thereof, in the manufacture of a medicament for treating a subject having a disease or condition responsive to the inhibition of TBK1. In an embodiment, the disease is cancer. Another embodiment the use of a compound as described herein, or a pharmaceutically acceptable salt thereof, in the manufacture of a medicament for treating a subject having a disease or condition responsive to the inhibition of IKKε.

Another embodiment provides the use of a compound as described herein, or a pharmaceutically acceptable salt thereof, in the manufacture of a medicament for treating a subject suffering from a RAS-dependent/mutant cancer. In an embodiment, the RAS-dependent/mutant cancer is selected from the group consisting of non-small cell lung cancer, colorectal cancer, pancreatic cancer, AML, and melanoma.

Another embodiment provides the use of a compound as described herein, or a pharmaceutically acceptable salt thereof, in the manufacture of a medicament for treating a subject suffering from breast or ovarian cancer. Another embodiment provides the use of a compound as described herein, or a pharmaceutically acceptable salt thereof, in the manufacture of a medicament for treating a subject suffering from cancer resistant to HER2 and EGFR targeted therapies.

Another embodiment provides the use of a compound as described herein, or a pharmaceutically acceptable salt thereof, in the manufacture of a medicament for treating a subject suffering from a disease selected from the group consisting of Rheumatoid arthritis (RA), Inflammatory bowel disease (IBD), Chronic obstructive pulmonary disease (COPD), Systemic lupus erythematosus (SLE), Polymositis, Systemic sclerosis, Type 2 diabetes, Obesity and Hepatic steatosis.

Another embodiment provides the use of a compound as described herein, or a pharmaceutically acceptable salt thereof, in the manufacture of a medicament for inhibiting TBK1 in a subject. Another embodiment provides the use of a compound as described herein, or a pharmaceutically acceptable salt thereof, in the manufacture of a medicament for inhibiting IKKε in a subject.

Another embodiment provides further administering to the subject an additional therapeutic agent, a list of which is provided in the following Detailed Description.

DETAILED DESCRIPTION OF THE INVENTION

The following is a list of abbreviations and acronyms used throughout the application:

| Abbreviation | Meaning |
| --- | --- |
| ° C. | Degree Celsius |
| ATP | Adenosine-5'-triphosphate |
| AcOH | Acetic acid |
| ACN | Acetonitrile |
| CAN | Ceric ammonium nitrate |
| CDI | 1,1'-carbonyldiimidazole |
| conc. | Concentrated |
| d | Doublet |
| DABCO | 1,4-Diazabicyclo[2.2.2]octane |
| DAST | (Diethylamino)sulfur trifluoride |
| dd | Doublet of doublets |
| DCE | 1,2-dichloroethane |
| DCM | Dichloromethane |
| DEAD | Diethyl azodicarboxylate |
| DIAD | Diisopropyl azodicarboxylate |
| DIPEA/DIEA | N,N-diisopropylethylamine |
| DMAP | 4-dimethylaminopyridine |
| DME | 1,2-dimethoxyethane |
| DMF | Dimethylformamide |
| DMSO | Dimethylsulfoxide |
| dppf | 1,1'-Bis(diphenylphosphino)ferrocene |
| EA | Ethyl alcohol |
| ECF | Extracellular fluid |
| EDTA | Ethylenediaminetetraacetic acid |
| EGTA | Ethylene glycol tetraacetic acid |
| ETOAC | Ethyl acetate |
| equiv/eq | Equivalents |
| ESI | Electrospray ionization |
| Ac | Acetate |
| Et | Ethyl |
| g | Grams |
| HATU | 2-(7-Aza-1H-Benzotriazole-1-yl)-1,1,3,3-tetramethyluronium hexafluorophosphate |
| hERG | human Ether-à-go-go Related Gene |
| HMDS | hexamethyldisilazane(azide) |
| HPLC | High-performance liquid chromatography |
| h/hr | Hours |
| Hz | Hertz |
| $IC_{50}$ | The half maximal inhibitory concentration |
| J | Coupling constant |
| Kg | Kilogram |

-continued

| Abbreviation | Meaning |
| --- | --- |
| LAH | Lithium ammonium hydride |
| LCMS/LC-MS | Liquid chromatography-mass spectrometry |
| LDA | Lithium diisopropylamide |
| M | Molar |
| m | multiplet |
| m/z | mass-to-charge ratio |
| M+ | Mass peak |
| M + H | Mass peak plus hydrogen |
| mCPBA | 3-chloroperoxybenzoic acid |
| Me | Methyl |
| MeOH | Methyl alcohol/methanol |
| mg | Milligram |
| MHz | Megahertz |
| min/m | Minute |
| ml/mL | Milliliter |
| mM | Millimolar |
| mmol | Millimole |
| MS | Mass spectroscopy |
| mw | Microwave |
| N | Normal |
| mol | Mole |
| NMP | N-methylpyrrolidinone |
| NMR | Nuclear magnetic resonance |
| Ph | Phenyl |
| $Pd(PPh_3)_4$ | Tetrakis(triphenylphosphine)palladium(0) |
| PEPPS ™-IPr | [1,3-Bis(2,6-Diisopropylphenyl)irnidazol-2-ylidene](3-chloropyridyl)palladium(II) dichloride |
| ppm | Parts per million |
| prep | Preparative |
| Rf | Retention factor |
| RP | Reverse phase |
| RT/rt | Hoorn temperature |
| s | Second |
| s | Singlet |
| SEM | 2-(Trimethylsilyl)ethoxymethyl |
| t | Triplet |
| TEA | Triethylamine |
| TFA | Trifluoroacetic acid |
| THF | Tetrahydrofuran |
| 2-MeTHF/Me-THF | 2-Methyl Tetrahydrofuran |
| TLC | Thin layer chromatography |
| TMS | trimethylsilyl |
| WT | Wild type |
| δ | Chemical shift |
| μg | Microgram |
| μL/μl | Microliter |
| μM | Micromolar |
| μm | Micrometer |
| μmol | Micromole |

Unless defined otherwise, all technical and scientific terms used herein have the same meaning as commonly understood by one of ordinary skill in the art. It must be noted that as used herein and in the appended claims, the singular forms "a", "and", and "the" include plural referents unless the context clearly dictates otherwise. Thus, e.g., reference to "the compound" includes a plurality of such compounds and reference to "the assay" includes reference to one or more assays and equivalents thereof known to those skilled in the art, and so forth.

A wavy line drawn through a line in a structure indicates a point of attachment of a group, e.g.:

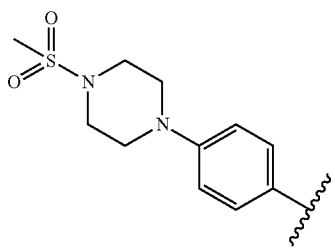 [SMILES: *c1ccc(N2CCN(S(C)(=O)=O)CC2)cc1]

A dashed line indicates an optional bond. A dash at the front or end of a chemical group is a matter of convenience; chemical groups may be depicted with or without one or more dashes without losing their ordinary meaning. When used, a dash indicates the point of attachment, e.g. —S(O)(R$^c$)=NR$^b$ indicates the following structure with point of attachment at the S:

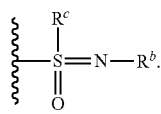

Where multiple substituent groups are identified the point of attachment is at the terminal substituent (e.g. for "alkylaminocarbonyl" the point of attachment is at the carbonyl substituent).

The prefix "C$_{x-y}$" indicates that the following group has from x (e.g. 1) to y (e.g. 6) carbon atoms, one or more of which, in certain groups (e.g. heteroalkyl, heteroaryl, heteroarylalkyl, etc.), may be replaced with one or more heteroatoms or heteroatomic groups. For example, "C$_{1-6}$ alkyl" indicates that the alkyl group has from 1 to 6 carbon atoms. Likewise, the term "x-y membered" rings, wherein x and y are numerical ranges, such as "3-12 membered heterocyclyl", refers to a ring containing x-y atoms (e.g. 3-12), of which up to half may be heteroatoms, such as N, O, S, P, and the remaining atoms are carbon.

Also, certain commonly used alternative chemical names may or may not be used. For example, a divalent group such as a divalent "alkyl" group, a divalent "aryl" group, etc., may also be referred to as an "alkylene" group or an "alkylenyl" group, or alkylyl group, an "arylene" group or an "arylenyl" group, or arylyl group, respectively.

"Alkyl" refers to any group derived from a linear or branched saturated hydrocarbon. Alkyl groups include, but are not limited to, methyl, ethyl, propyl such as propan-1-yl, propan-2-yl (iso-propyl), butyls such as butan-1-yl, butan-2-yl (sec-butyl), 2-methyl-propan-1-yl (iso-butyl), 2-methyl-propan-2-yl (t-butyl), pentyls, hexyls, octyls, dectyls, and the like. Unless otherwise specified, an alkyl group has from 1 to 10 carbon atoms, for example from 1 to 6 carbon atoms, for example from 1 to 4 carbon atoms.

"Alkenyl" refers to any group derived from a straight or branched hydrocarbon with at least one carbon-carbon double bond. Alkenyl groups include, but are not limited to, ethenyl (vinyl), propenyl (allyl), 1-butenyl, 1,3-butadienyl, and the like. Unless otherwise specified, an alkenyl group has from 2 to 10 carbon atoms, for example from 2 to 6 carbon atoms, for example from 2 to 4 carbon atoms.

"Alkynyl" refers to any group derived from a straight or branched hydrocarbon with at least one carbon-carbon triple bond and includes those groups having one triple bond and one double bond. Examples of alkynyl groups include, but are not limited to, ethynyl (—CH≡CH), propargyl (—CH$_2$C≡CH), (E)-pent-3-en-1-ynyl, and the like. Unless otherwise specified, an alkynyl group has from 2 to 10 carbon atoms, for example from 2 to 6 carbon atoms, for example from 2 to 4 carbon atoms.

"Amino" refers to —NH$_2$. Amino groups may also be substituted as described herein, such as with alkyl, carbonyl or other amino groups. The term "alkylamino" refers to an amino group substituted with one or two alkyl substituents (e.g. dimethylamino or propylamino).

"Aryl" refers to any group derived from one or more aromatic rings, that is, a single aromatic ring, a bicyclic or a multicyclic ring system. Aryl groups include, but are not limited to, those groups derived from acenaphthylene, anthracene, azulene, benzene, chrysene, a cyclopentadienyl anion, naphthalene, fluoranthene, fluorene, indane, perylene, phenalene, phenanthrene, pyrene and the like.

"Arylalkyl" (also "aralkyl") refers to any combination aryl group and an alkyl group. Arylalkyl groups include, but are not limited to, those groups derived from benzyl, tolyl, dimethylphenyl, 2-phenylethan-1-yl, 2-naphthylmethyl, and the like. An arylalkyl group comprises from 6 to 30 carbon atoms, for example the alkyl group can comprise from 1 to 10 carbon atoms and the aryl group can comprise from 5 to 20 carbon atoms.

"Bridged" refers to a ring fusion wherein non-adjacent atoms on a ring are joined by a divalent substituent, such as an alkylenyl or heteroalkylenyl group or a single heteroatom. Quinuclidinyl and admantanyl are examples of bridged ring systems.

"Cycloalkyl" refers to a cyclic alkyl and alkenyl groups. A cycloalkyl group can have one or more cyclic rings and includes fused and bridged groups that are fully saturated or partially unsaturated. Examples include, but are not limited to, cyclopropyl, cyclobutyl, cyclopentyl, cyclohexyl, adamantyl, methylcycloproyl (cyclopropylmethyl), ethylcyclopropyl, cyclohexenyl and the like. Another example includes C$_{5-7}$ cycloakenyl.

"Halo" and "halogen" refer to fluoro, chloro, bromo and iodo.

"Haloalkyl" refers to an alkyl wherein one or more hydrogen atoms are each replaced by a halogen. Examples include, but are not limited to, —CH$_2$Cl, —CH$_2$F, —CH$_2$Br, —CFClBr, —CH$_2$CH$_2$Cl, —CH$_2$CH$_2$F, —CF$_3$, —CH$_2$CF$_3$, —CH$_2$CCl$_3$, and the like, as well as alkyl groups such as perfluoroalkyl in which all hydrogen atoms are replaced by fluorine atoms.

"Hydroxyalkyl" refers to an alkyl wherein one or more hydrogen atoms are each replaced by a hydroxyl group. Examples include, but are not limited to, —CH$_2$OH, —CH$_2$CH$_2$OH, —C(CH$_3$)$_2$OH, and the like.

"Halo 3-6 membered heterocyclyl" refers to a heterocyclyl group substituted at a carbon atom with at least one halogen atom, and may include multiple halogen atoms, such as 3,3-difluoroazetidinyl.

"Heteroalkyl" refers to an alkyl in which one or more of the carbon atoms (and any associated hydrogen atoms) are each independently replaced with the same or different heteroatom or heteroatomic group. Heteroatoms include, but are not limited to, N, P, O, S, etc. Heteroatomic groups include, but are not limited to, —NR—, —O—, —S—, —PH—, —P(O)$_2$—, —S(O)—, —S(O)$_2$—, and the like, where R is H, alkyl, aryl, cycloalkyl, heteroalkyl, heteroaryl or cycloheteroalkyl. Heteroalkyl groups include, but are not limited to, —OCH$_3$, —CH$_2$OCH$_3$, —SCH$_3$, —CH$_2$SCH$_3$, —NRCH$_3$, —CH$_2$NRCH$_3$, —CH$_2$OH and the like, where R is hydrogen, alkyl, aryl, arylalkyl, heteroalkyl, or heteroaryl, each of which may be optionally substituted. A heteroalkyl group comprises from 1 to 10 carbon and up to three hetero atoms, e.g., from 1 to 6 carbon and from 1 to 2 hetero atoms.

"Heteroaryl" refers to mono or multicyclic aryl group in which one or more of the aromatic carbon atoms (and any associated hydrogen atoms) are independently replaced with the same or different heteroatom or heteroatomic group, as defined above. Multicyclic ring systems are included in heteroaryl and may be attached at the ring with the heteroatom or the aryl ring. Heteroaryl groups include, but are not limited to, groups derived from acridine, benzoimidazole, benzothiophene, benzofuran, benzoxazole, benzothiazole, carbazole, carboline, cinnoline, furan, imidazole, imidazopyridine, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. Heteroaryl groups may have 5-14 members, 5-10 members, or 5-6 members.

"Heterocycle," "heterocyclic," and "heterocyclyl" refer to a saturated or partially unsaturated non-aromatic ring or a partially non-aromatic multiple-ring system with at least one heteroatom or heteroatomic group, as defined above. Heterocycles include, but are not limited to, groups derived from azetidine, aziridine, imidazolidine, morpholine, thiomorpholine, tetrahydro-2H-thiopyran, 1-iminotetrahydro-2H-thiopyran 1-oxide, oxirane (epoxide), oxetane, piperazine, piperidine, pyrazolidine, piperidine, pyrrolidine, pyrrolidinone, tetrahydrofuran, tetrahydrothiophene, dihydropyridine, tetrahydropyridine, quinuclidine, N-bromopyrrolidine, N-chloropiperidine, and the like. Heterocyclyl groups also include partially unsaturated ring systems containing one or more double bonds, including fused ring systems with one aromatic ring and one non-aromatic ring, but not fully aromatic ring systems. Examples include dihydroquinolines, e.g. 3,4-dihydroquinoline, dihydroisoquinolines, e.g. 1,2-dihydroisoquinoline, dihydroimidazole, tetrahydroimidazole, etc., indoline, isoindoline, isoindolones (e.g. isoindolin-1-one), isatin, dihydrophthalazine, quinolinone, spiro[cyclopropane-1,1'-isoindolin]-3'-one, and the like. Heterocycle groups may have 3-12 members, or 3-10 members, or 3-7 members, or 5-6 members.

"Hydroxyl" and "hydroxy" are used interchangeably and refer to —OH. "Oxo" refers to =O, or oxide where N-oxide or S-oxide exist. Where tautomeric forms of the compound exist, hydroxyl and oxo groups are interchangeable.

It is understood that combinations of chemical groups may be used and will be recognized by persons of ordinary skill in the art. For instance, the group "hydroxyalkyl" would refer to a hydroxyl group attached to an alkyl group. A great number of such combinations may be readily envisaged. Additional examples of substituent combinations used herein include: $C_{1-6}$ alkylamiocarbonyl (e.g. $CH_3CH_2NHC(O)$—) $C_{1-6}$ alkoxycarbonyl (e.g. $CH_3O$—C(O)—), 5-7 membered heterocyclyl-$C_{1-6}$ alkyl (e.g. piperazinyl-$CH_2$—), $C_{1-6}$ alkylsulfonyl- 5-7 membered heterocyclyl (e.g. $CH_3S(O)_2$-morpholinyl-), 5-7 membered heterocyclyl $C_{1-6}$ alkoxy (e.g. pyrrolidinyl-O—), 5-7 membered heterocyclyloxy, (4-7 membered heterocyclyl)- 4-7 membered heterocyclyl (e.g. oxetanyl-pyrrolidinyl-), $C_{3-6}$ cycloalkylaminocarbonyl (e.g. cyclopropyl-NH—C(O)—), 5-7 membered heterocyclyl-$C_{2-6}$ alkynyl (e.g. N-piperazinyl-$CH_2C\equiv CCH_2$—), and $C_{6-10}$ arylaminocarbonyl (e.g. phenyl-NH—C(O)—).

"Spiro" refers to a ring substituent which is joined by two bonds at the same carbon atom. Examples of spiro groups include 1,1-diethylcyclopentane, dimethyl-dioxolane, and 4-benzyl-4-methylpiperidine, wherein the cyclopentane and piperidine, respectively, are the spiro substituents.

The term "pharmaceutically acceptable" with respect to a substance refers to that substance which is generally regarded as safe and suitable for use without undue toxicity, irritation, allergic response, and the like, commensurate with a reasonable benefit/risk ratio.

The compounds described herein include isomers, stereoisomers and the like. As used herein, the term "isomers" refers to different compounds that have the same molecular formula but differ in arrangement and configuration of the atoms. Also as used herein, the term "an optical isomer" or "a stereoisomer" refers to any of the various stereo isomeric configurations which may exist for a given compound of the present invention and includes geometric isomers. It is understood that a substituent may be attached at a chiral center of a carbon atom. Therefore, the invention includes enantiomers, diastereomers or racemates of the compound.

The term "fused" refers to a ring which is bound to an adjacent ring.

"Enantiomers" are a pair of stereoisomers that are non-superimposable mirror images of each other. A 1:1 mixture of a pair of enantiomers is a "racemic" mixture.

The phrase ortho, refers to the position on the ring where the substituent is adjoined with respect to the point of attachment of the ring, and is shown below with an arrow, wherein z represents a carbon atom or nitrogen:

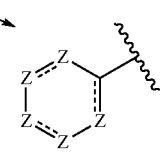

Similarly, "para" refers to attachment of a substituent at the 4-position with respect to the point of attachment of the ring and "meta" refers to attachment of a substituent at the 3-position with respect to the point of attachment of the ring.

The term is used to designate a racemic mixture where appropriate. "Diastereoisomers" are stereoisomers that have at least two asymmetric atoms, but which are not mirror-images of each other.

The absolute stereochemistry is specified according to the Cahn-Ingold-Prelog R-S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers and may thus give rise to enantiomers, diastereomers, and other stereoisomeric forms that may be defined, in terms of absolute stereochemistry, as (R)- or (S)-. The present invention is meant to include all such possible isomers, including racemic mixtures, optically pure forms and intermediate mixtures. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included.

"Pharmaceutically acceptable salt" refers to a salt of a compound that is pharmaceutically acceptable and that possesses (or can be converted to a form that possesses) the desired pharmacological activity of the parent compound. Such salts include acid addition salts formed with inorganic acids such as hydrochloric acid, hydrobromic acid, sulfuric acid, nitric acid, phosphoric acid, and the like; or formed with organic acids such as acetic acid, benzenesulfonic acid, benzoic acid, camphorsulfonic acid, citric acid, ethanesulfonic acid, fumaric acid, glucoheptonic acid, gluconic acid, lactic acid, maleic acid, malonic acid, mandelic acid, methanesulfonic acid, 2-napththalenesulfonic acid, oleic acid, palmitic acid, propionic acid, stearic acid, succinic acid, tartaric acid, p-toluenesulfonic acid, trimethylacetic acid, and the like, and salts formed when an acidic proton present in the parent compound is replaced by either a metal ion, e.g., an alkali metal ion, an alkaline earth ion, or an aluminum ion; or coordinates with an organic base such as diethanolamine, triethanolamine, N-methylglucamine and the like. Also included in this definition are ammonium and substituted or quaternized ammonium salts. Representative non-limiting lists of pharmaceutically acceptable salts can be found in S. M. Berge et al., J. Pharma Sci., 66(1), 1-19 (1977), and Remington: The Science and Practice of Pharmacy, R. Hendrickson, ed., 21st edition, Lippincott, Williams & Wilkins, Philadelphia, Pa., (2005), at p. 732, Table 38-5, both of which are hereby incorporated by reference herein.

"Subject" and "subjects" refers to humans, domestic animals (e.g., dogs and cats), farm animals (e.g., cattle, horses, sheep, goats and pigs), laboratory animals (e.g., mice, rats, hamsters, guinea pigs, pigs, pocket pets, rabbits, dogs, and monkeys), and the like.

"Treating" and "treatment" of a disease include the following:
  (1) preventing or reducing the risk of developing the disease, i.e., causing the clinical symptoms of the disease not to develop in a subject that may be exposed to or predisposed to the disease but does not yet experience or display symptoms of the disease,
  (2) inhibiting the disease, i.e., arresting or reducing the development of the disease or its clinical symptoms, or
  (3) relieving the disease, i.e., causing regression of the disease or its clinical symptoms.

"Effective amount" refers to an amount that may be effective to elicit the desired biological, clinical, or medical response, including the amount of a compound that, when administered to a subject for treating a disease, is sufficient to effect such treatment. The effective amount will vary depending on the compound, the disease and its severity and the age, weight, etc., of the subject to be treated. The effective amount can include a range of amounts.

Reference to a compound that is "selective" against an enzyme, such as JAK2, indicates relative activity versus a target ezyme, such as TBK1 or IKKε. For example a compound that has 2-10 fold greater inhibitory activity—as measured by $IC_{50}$ values—for a desired enzyme(s), such as TBK1 and/or IKKε, as compared to the enzyme for which the compound is selective against, such as JAK2, is selective against the referenced enzyme.

The compounds of the invention include solvates, hydrates, tautomers, stereoisomers and salt forms thereof.

Provided are also compounds in which from 1 to n hydrogen atoms attached to a carbon atom may be replaced by a deuterium atom, or tritiated with a tritium atom, in which n is the number of hydrogen atoms in the molecule. As known in the art, the deuterium atom is a non-radioactive isotope of the hydrogen atom and tritium is a radioactive isotope. Such compounds, particularly deuterated compounds, may increase resistance to metabolism, and thus may be useful for increasing the half-life of the compounds when administered to a mammal. See, e.g., Foster, "Deuterium Isotope Effects in Studies of Drug Metabolism," Trends Pharmacol. Sci., 5(12):524-527 (1984). Such compounds are synthesized by means well known in the art, for example by employing starting materials in which one or more hydrogen atoms have been replaced by deuterium.

The pharmaceutical compositions of compounds of Formual (I) (including compounds of Formulae (Ia)-(Ic)) may be administered in either single or multiple doses by any of the accepted modes of administration of agents having similar utilities, for example as described in those patents and patent applications incorporated by reference, including rectal, buccal, intranasal and transdermal routes, by intraarterial injection, intravenously, intraperitoneally, parenterally, intramuscularly, subcutaneously, orally, topically, as an inhalant, or via an impregnated or coated device such as a stent, for example, or an artery-inserted cylindrical polymer.

In one aspect, the compounds described herein may be administered orally. Oral administration may be via, for example, capsule or enteric coated tablets. In making the pharmaceutical compositions that include at least one compound of Formula (I), or a pharmaceutically acceptable salt, is usually diluted by an excipient and/or enclosed within such a carrier that can be in the form of a capsule, sachet, paper or other container. When the excipient serves as a diluent, it can be in the form of a solid, semi-solid, or liquid material (as above), which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl and propylhydroxy-benzoates; sweetening agents; and flavoring agents.

The compositions that include at least one compound of Formula (I), or a pharmaceutically acceptable salt, can be formulated so as to provide quick, sustained or delayed release of the active ingredient after administration to the subject by employing procedures known in the art. Controlled release drug delivery systems for oral administration include osmotic pump systems and dissolutional systems containing polymer-coated reservoirs or drug-polymer matrix formulations. Examples of controlled release systems are given in U.S. Pat. Nos. 3,845,770; 4,326,525; 4,902,514; and 5,616,345. Another formulation for use in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. Nos. 5,023,252, 4,992,445 and 5,001,139. The compositions may, in some embodiments, be formulated in a unit dosage form. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient (e.g., a tablet, capsule, ampoule). The compounds are generally administered in a pharmaceutically effective amount. In some embodiments, for oral administration, each dosage unit contains from about 10 mg to about 1000 mg of a compound described herein, for example from about 50 mg to about 500 mg, for example about 50 mg, about 75 mg, about 100 mg, about 150 mg, about 200 mg, about 250 mg, or about 300 mg. In other embodiments, for parenteral administration, each dosage unit contains from 0.1 to 700 mg of a compound a compound described herein. It will be understood, however, that the amount of the compound actually administered usually will be determined by a physician, in the light of the relevant circumstances, including the condition to be treated, the chosen route of administration, the actual compound administered and its relative activity, the age, weight, and response of the individual subject, and the severity of the subject's symptoms.

In certain embodiments, dosage levels may be from 0.1 mg to 100 mg per kilogram of body weight per day, for example from about 1 mg to about 50 mg per kilogram, for example from about 5 mg to about 30 mg per kilogram. Such dosage levels may, in certain instances, be useful in the treatment of the above-indicated conditions. In other embodiments, dosage levels may be from about 10 mg to about 2000 mg per subject per day. The amount of active ingredient that may be combined with the vehicle to produce a single dosage form will vary depending upon the host treated and the particular mode of administration. Dosage unit forms may contain from 1 mg to 500 mg of an active ingredient.

Frequency of dosage may also vary depending on the compound used and the particular disease or condition treated. In some embodiments, for example, for the treatment of an autoimmune and/or inflammatory disease, a dosage regimen of 4 times daily or less is used. In some embodiments, a dosage regimen of 1 or 2 or 3 times daily is used. It will be understood, however, that the specific dose level for any particular subject will depend upon a variety of factors including the activity of the specific compound employed, the age, body weight, general health, sex, diet, time of administration, route of administration, and rate of excretion, drug combination and the severity of the particular disease in the subject undergoing therapy.

For preparing solid compositions such as tablets, the principal active ingredient may be mixed with a pharmaceutical excipient to form a solid preformulation composition containing a homogeneous mixture of a compound of Formula (I), or a pharmaceutically acceptable salt, thereof. When referring to these preformulation compositions as homogeneous, the active ingredient may be dispersed evenly throughout the composition so that the composition may be readily subdivided into equally effective unit dosage forms such as tablets, pills and capsules.

The tablets or pills of the compounds described herein may be coated or otherwise compounded to provide a dosage form affording the advantage of prolonged action, or to protect from the acid conditions of the stomach. For example, the tablet or pill can comprise an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Kits that include a compound of Formula (I), or a pharmaceutically acceptable salt, thereof, and suitable packaging are provided. In one embodiment, a kit further includes instructions for use. In one aspect, a kit includes a compound of Formula (I), or a pharmaceutically acceptable salt thereof, and instructions for use of the compounds in the treatment of the diseases or conditions described herein.

Articles of manufacture that include a compound of Formula (I), or a pharmaceutically acceptable salt thereof, in a suitable container are provided. The container may be a vial, jar, ampoule, preloaded syringe, and intravenous bag.

Compounds of Formula (I) may be combined with one or more additional therapeutic agents. The present application provides methods, compositions, kits and articles of manufacture thereof that use or include one or more therapeutic agents inhibiting one or more targets that relate to, directly or indirectly, to cell growth, proliferation, or apoptosis for treating hyperproliferative disorders such as cancers or myeloproliferative neoplasms. The one or more therapeutic agents are compounds or molecules that is an Abl inhibitor, an ACK inhibitor, an A2B inhibitor, an ASK inhibitor, an Auroa kinase inhibitor, a BTK inhibitor, a BRD inhibitor, a c-Kit inhibitor, a c-Met inhibitor, a CAK inhibitor, a CaMK inhibitor, a CDK inhibitor, a CK inhibitor, a DDR inhibitor, an EGFR inhibitor, a FAK inhibitor, a Flt-3 inhibitor, a FYN inhibitor, a GSK inhibitor, a HCK inhibitor, a HDAC inhibitor, an IKK inhibitor, an IDH inhibitor, an IKK inhibitor, a JAK inhibitor, a KDR inhibitor, a LCK hibitor, a LOX inhibitor, a LOXL inhibitor, a LYN inhibitor, a MMP inhibitor, a MEK inhibitor, a MAPK inhibitor, a NEK9 inhibitor, a NPM-ALK inhibitor, a p38 kinase inhibitor, a PDGF inhibitor, a PI3 kinase (PI3K), a PK inhibitor, a PLK inhibitor, a PK inhibitor, a PYK inhibitor, a SYK inhibitor, a TPL2 inhibitor, a STK inhibitor, a STAT inhibitor, a SRC inhibitor, a TBK inhibitor, a TIE inhibitor, a TK inhibitor, a VEGF inhibitor, a YES inhibitor, a chemotherapeutic agent, an immunotherapeutic agent, a radiotherapeutic agent, an anti-neoplastic agent, an anti-cancer agent, an anti-proliferation agent, an anti-fibrotic agent, an anti-angiogenic agent, a therapeutic antibody, or any combination thereof. In some embodiment, the therapeutic agents are compounds or molecules that target a PI3 kinase (PI3K), a spleen tyrosine kinase (SYK), a Janus kinase (JAK), a Bruton's tyrosine kinase (BTK), or any combination thereof, resulting in the inhibition of one or more targets. In certain embodiments, the therapeutic agent is a PI3Kδ inhibitor that selectively inhibits PI3K p110 delta isoform (PI3Kδ). In some embodiments, the therapeutic agents are a PI3Kδ inhibitor and a JAK1/2 inhibitor.

The JAK inhibitor binds and inhibits one or more members of JAK family, including JAK1, JAK2, and/or JAK3.

In one embodiment, the JAK inhibitor is Compound A having the structure:

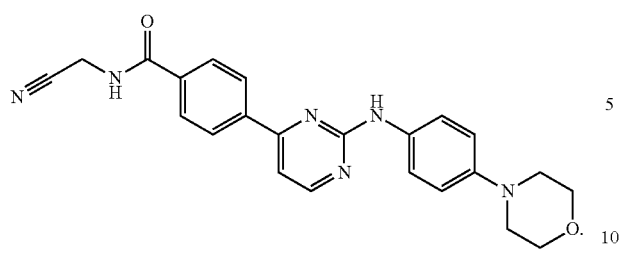

Compound A may be referred to by its compound name: N-(cyanomethyl)-4-[2-(4-morpholinoanilino)pyrimidin-4-yl]benzamide using ChemDraw. Compound A, also referred to as CYT0387 or momelotinib, is a selective inhibitor to JAK2 and JAK1, relative to JAK3. Methods for synthesizing compounds of formula I and Compound A are previously described in U.S. Pat. No. 8,486,941. This reference is hereby incorporated herein by reference in its entirety.

Additional JAK inhibitors include, but are not limited to, ruxolitinib (INCB018424), fedratinib (SAR302503, TG101348), tofacitinib, baricitinib, lestaurtinib, pacritinib (SB1518), XL019, AZD1480, INCB039110, LY2784544, BMS911543, and NS018.

The PI3K inhibitors inhibit one or more isoforms of Class I PI3K, including PI3Kα, PI3Kβ, PI3Kδ, PI3Kγ, or any combination thereof.

In some embodiments, the PI3Kδ inhibitor is Compound B having the structure:

(B)

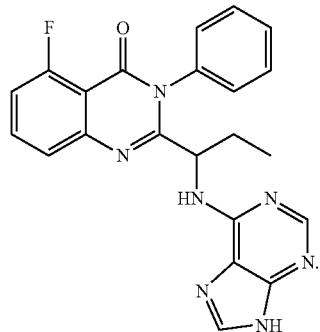

In other embodiments, Compound B is predominantly the S-enantiomer, having the structure:

(B)S

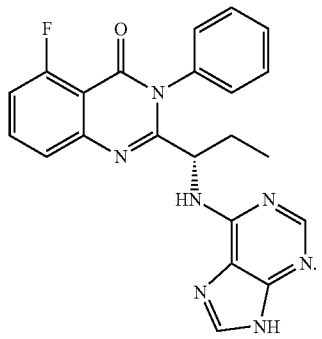

The (S)-enantiomer of Compound B may also be referred to by its compound name: (S)-2-(1-((9H-purin-6-yl)amino)propyl)-5-fluoro-3-phenylquinazolin-4(3H)-one using Chem Draw.

In certain embodiments, the PI3Kδ inhibitor is Compound C having the structure:

(C)

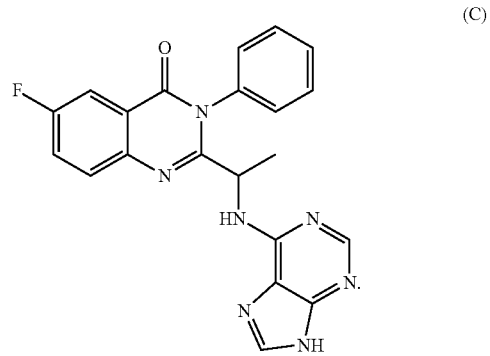 [SMILES: CC(Nc1ncnc2[nH]cnc12)c1nc2ccc(F)cc2c(=O)n1-c1ccccc1]

In additional embodiments, Compound C is predominantly the S-enantiomer, having the structure:

(C)S

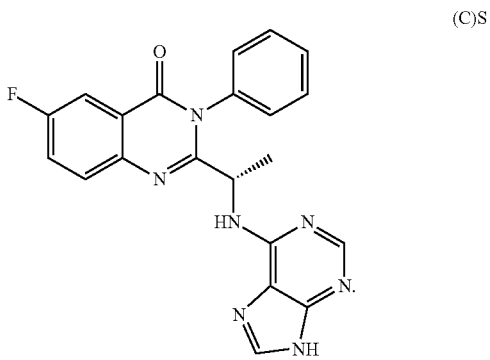 [SMILES: C[C@H](Nc1ncnc2[nH]cnc12)c1nc2ccc(F)cc2c(=O)n1-c1ccccc1]

The (S)-enantiomer of Compound C may also be referred to by its compound name: (S)-2-(1-((9H-purin-6-yl)amino)ethyl)-6-fluoro-3-phenylquinazolin-4(3H)-one using ChemDraw.

In another embodiment, the PI3K inhibitor is Compound D, having the structure:

(D)

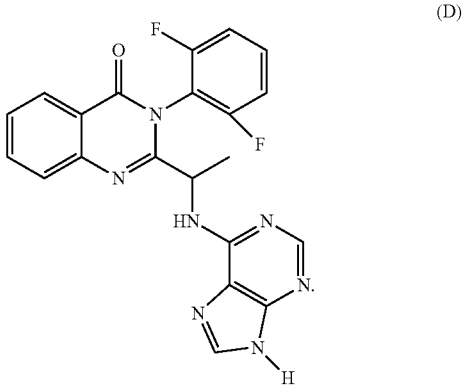 [SMILES: CC(Nc1ncnc2[nH]cnc12)c1nc2ccccc2c(=O)n1-c1c(F)cccc1F]

In one embodiment, Compound D is predominantly the S-enantiomer, having the structure:

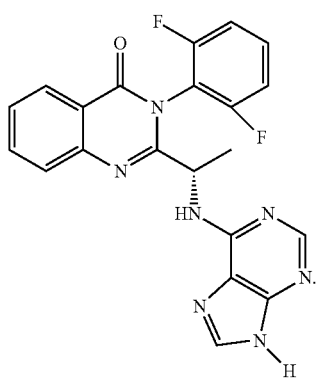

(D)S

The (S)-enantiomer of Compound D may also be referred to by its compound name: (S)-2-(1((9H-purin-6-yl)amino)ethyl)-3-(2,6-difluorophenyl)quinazolin-4(3H)-one using Chem Draw.

In yet other embodiment, the PI3K inhibitor is Compound E which is named by its compound name: (S)-4-amino-6-((1-(5-chloro-4-oxo-3-phenyl-3,4-dihydroquinazolin-2-yl)ethyl)amino)pyrimidine-5-carbonitrile using ChemDraw. In some other embodiment, the PI3K inhibitor includes the compounds described in U.S. Provisional Application Nos. 61/543,176; 61/581,528; 61/745,429; 61/745,437; and 61/835,333. The references are hereby incorporated herein by reference in their entirety.

Compounds B, C, D, and E are PI3Kδ inhibitors, selectively inhibiting PI3K p110δ compared to other PI3K isoforms. Methods for synthesizing the compounds of formula II, Compounds B, C, D, and E are previously described in U.S. Pat. No. 7,932,260 or U.S. Provisional Application No. 61/581,528. The references are hereby incorporated herein by reference in their entirety.

Additional PI3K inhibitors include but are not limited to XL147, BKM120, GDC-0941, BAY80-6946, PX-866, CH5132799, XL756, BEZ235, and GDC-0980, wortmannin, LY294002, PI3K II, TGR-1202, AMG-319, GSK2269557, X-339, X-414, RP5090, KAR4141, XL499, OXY111A, IPI-145, IPI-443, GSK2636771, BAY 10824391, buparlisib, BYL719, RG7604, MLN1117, WX-037, AEZS-129, PA799, AS252424, TGX221, TG100115, IC87114, and ZSTK474.

The SYK inhibitor includes but is not limited to 6-(1H-indazol-6-yl)-N-(4-morpholinophenyl)imidazo[1,2-a]pyrazin-8-amine, R406 (tamatinib), R788 (fostamatinib), PRT062607, BAY-61-3606, NVP-QAB 205 AA, R112, or R343, or a pharmaceutically acceptable salt thereof. See Kaur et al., European Journal of Medicinal Chemistry 67 (2013) 434-446. In one embodiment, the Syk inhibitor is 6-(1H-indazol-6-yl)-N-(4-morpholinophenyl)imidazo[1,2-a]pyrazin-8-amine as described in U.S. Pat. No. 8,450,321.

In various embodiments, compounds of Formula (I) may be combined with one or more therapeutic agents, which are IDO1 inhibitors. In one embodiment, the IDO1 inhibitor is INCB24360 having the structure:

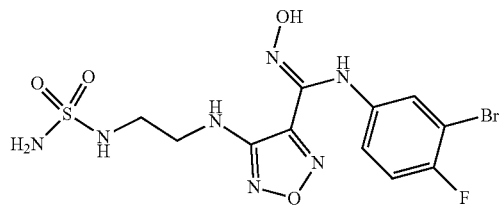 [SMILES: NS(=O)(=O)NCCNc1nonc1/C(=N/O)Nc1ccc(F)c(Br)c1]

In another embodiment, the IDO1 inhibitor is NLG-919 having the following structure:

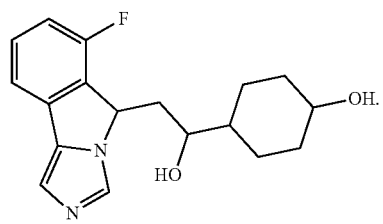 [SMILES: OC1CCC(C(O)CC2c3c(F)cccc3-c3cncn32)CC1]

In another embodiment, the IDO1 inhibitor is indoximod having the following structure:

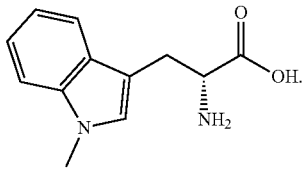 [SMILES: Cn1cc(C[C@@H](N)C(=O)O)c2ccccc21]

Another embodiment provides a compound of formula (I), or a pharmaceutically acceptable salt thereof, in combination with a one or more additional therapeutic agents, for example one or more additional therapeutic agents from the above list of additional therapeutic agents, for use in: therapy; a method of treating a subject having a disease or condition responsive to the inhibition of TBK1, such as cancer; a method of treating a subject having a disease or condition responsive to the inhibition of IKKε; a method of treating a subject suffering from a RAS-dependent/mutant cancer, such as non-small cell lung cancer, colorectal cancer, pancreatic cancer, AML, and melanoma; a method of treating a subject suffering from breast or ovarian cancer; a method of treating a subject suffering from cancer resistant to HER2 and EGFR targeted therapies; a method of treating a subject suffering from a disease selected from the group consisting of Rheumatoid arthritis (RA), Inflammatory bowel disease (IBD), Chronic obstructive pulmonary disease (COPD), Systemic lupus erythematosus (SLE), Polymositis, Systemic sclerosis, Type 2 diabetes, Obesity and Hepatic steatosis; or a method of treating a subject suffering from cancer.

Another embodiment provides the use of a compound of formula (I), or a pharmaceutically acceptable salt thereof, in combination with a one or more additional therapeutic agents, for example one or more additional therapeutic agents from the above list of additional therapeutic agents, in the manufacture of a medicament for: therapy; treating a subject having a disease or condition responsive to the inhibition of TBK1, such as cancer; treating a subject having a disease or condition responsive to the inhibition of IKKε;

treating a subject suffering from a RAS-dependent/mutant cancer, such as non-small cell lung cancer, colorectal cancer, pancreatic cancer, AML, and melanoma; treating a subject suffering from breast or ovarian cancer; treating a subject suffering from cancer resistant to HER2 and EGFR targeted therapies; treating a subject suffering from a disease selected from the group consisting of Rheumatoid arthritis (RA), Inflammatory bowel disease (IBD), Chronic obstructive pulmonary disease (COPD), Systemic lupus erythematosus (SLE), Polymositis, Systemic sclerosis, Type 2 diabetes, Obesity and Hepatic steatosis; or treating a subject suffering from cancer.

In an embodiment, the above combinations comprise one additional therapeutic agent, for example one additional therapeutic agent selected from the additional therapeutic agents listed above.

Another embodiment of the invention provides a product comprising a compound of formula (I), or a pharmaceutically acceptable salt thereof, and one or more additional therapeutic agents, such as one or more of the additional therapeutic agents listed above, as a combined preparation for simultaneous, separate or sequential use in therapy.

Synthesis of certain compounds, and intermediates used to prepare compounds, are detailed in the following sections. Example numbers are listed for convenience.

All operations involving moisture and/or oxygen sensitive materials were conducted under an atmosphere of dry nitrogen in pre-dried glassware. Unless noted otherwise, materials were obtained from commercially available sources and used without further purification.

Nuclear magnetic resonance ("NMR") spectra were recorded on a Varian 400 MHz resonance spectrometer. 1H NMR chemical shifts are given in parts per million (δ) downfield from tetramethylsilane ("TMS") using TMS or the residual solvent signal (CHCl3=δ 7.24, DMSO=δ 2.50) as internal standard. 1H NMR information is tabulated in the following format: multiplicity (s, singlet; d, doublet; t, triplet; q, quartet; m, multiplet), coupling constant(s) (J) in Hertz, number of protons. The prefix app is occasionally applied in cases where the true signal multiplicity was unresolved and br indicates the signal in question was broadened.

The compounds were named using ChemBioDraw Ultra Version 12.0.

When production of starting materials is not particularly described, the compounds are known or may be prepared analogously to methods known in the art or as disclosed in the Examples. One of skill in the art will appreciate that synthetic methodologies described herein are only representative of methods for preparation of the compounds described herein, and that other known methods and variants of methods described herein may be used. Compounds containing —SO$_2$F substituents are prepared according to Sulfur(VI) Fluoride Exchange (SuFEx): Another Good Reaction for Click Chemistry, Angew et al., Chem. Int. Ed. 2014, 53, 2-21. The methods or features described in various Examples may be combined or adapted in various ways to provide additional ways of making the compounds described herein.

EXAMPLES

Methods for obtaining the novel compounds described herein will be apparent to those of ordinary skill in the art, with suitable procedures being described, for example, in the reaction schemes and examples below, and in the references cited herein.

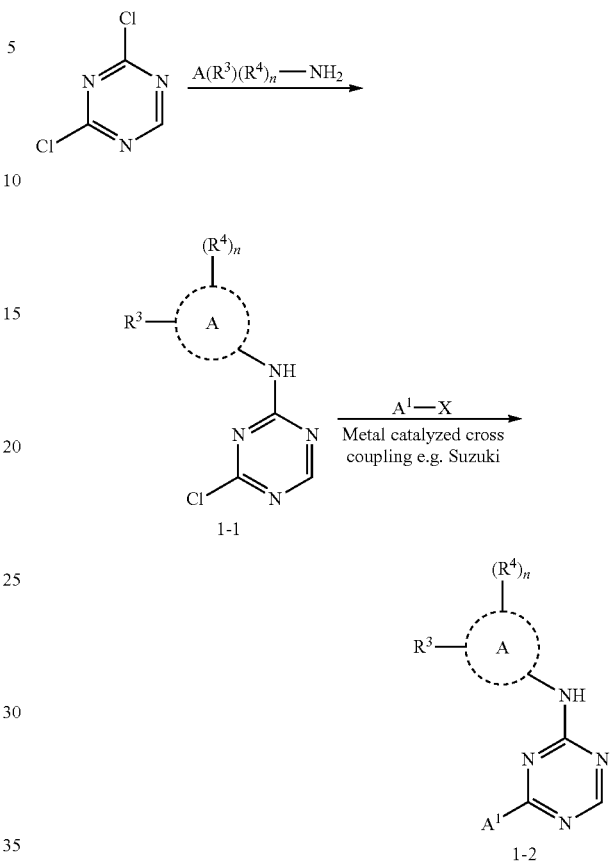

Scheme 1 shows a general synthesis of compounds of the invention beginning with the displacement of the one chloro from 2,4-Dichloro-1,3,5-triazine with anilines either at rt or at elevated temperature in the presence of an inert solvent such as DMF, DME or acetonitrile or mixture of such solvents in the presence or absence of a base such as DIPEA, or TEA to yield intermediate 1-1 which undergoes metal catalyzed cross coupling reactions (e.g. Suzuki) of A$^1$ groups to yield final compounds of the type 1-2. A$^1$ is preferably:

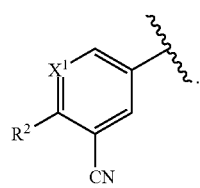

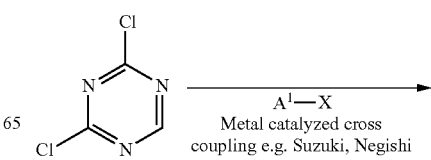

-continued

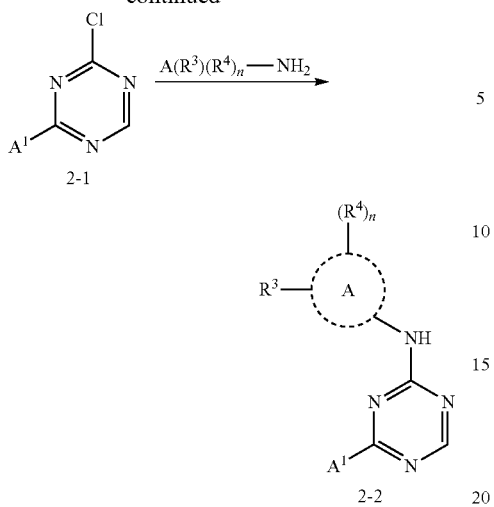

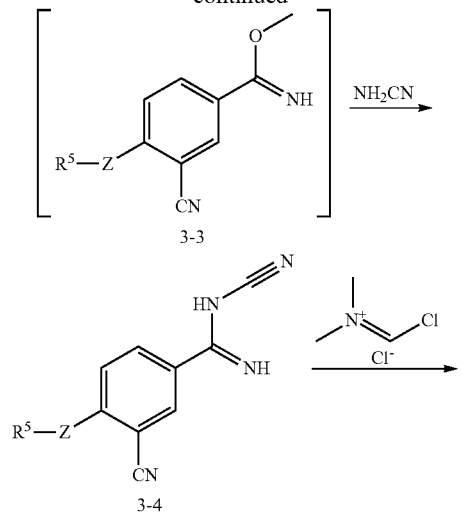

Scheme 2 shows a general synthesis of compounds of the invention beginning with the Metal catalyzed cross coupling reactions (ex: Suzuki, Negishi) to yield intermediate 2-1 which undergoes displacement of the chloro from 2-1 with anilines as in general scheme 1 (at rt or at elevated temperature in the presence of an inert solvent such as DMF, DME or acetonitrile or mixture of such solvents in the presence or absence of a base such as DIPEA, or TEA) to yield final compounds of the type 2-2. $A^1$ is preferably:

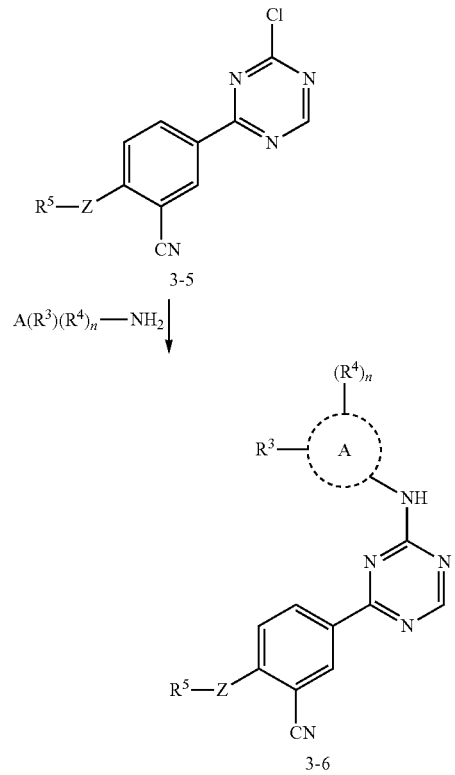

Z: O, N, S

General Scheme 3

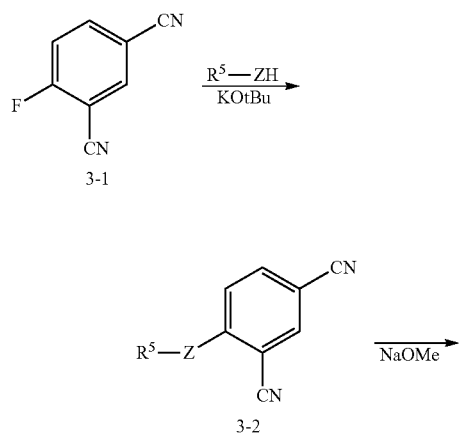

Scheme 3 shows a general synthesis of compounds of the invention beginning with the benzonitrile (3-1), where the Fluorine displacement with nucleophiles (where Z equals Oxygen, Nitrogen or Sulfur) yield 3-2 which on with sodium methoxide gave methyl 3-cyano-4-substituted benzimidate 3-3 which was not isolated and subsequently treated with cyanamide and N-(chloromethylene)-N-methylmethanaminium chloride to give 1,3,5-triazine (3-5). Chlorotrizine (3-5) then undergoes displacement of the chloro with anilines as in general scheme 1 (at rt or at elevated temperature in the presence of an inert solvent such as DMF, DME or acetonitrile or mixture of such solvents in the presence or absence of a base such as DIPEA, or TEA) to yield final compounds of the type 3-6.

Intermediates tert-butyl 4-(2-cyano-4-(4,4,5,5-tetramethyl-1,3,2-dioxaborolan-2-yl)phenoxy)piperidine-1-carboxylate

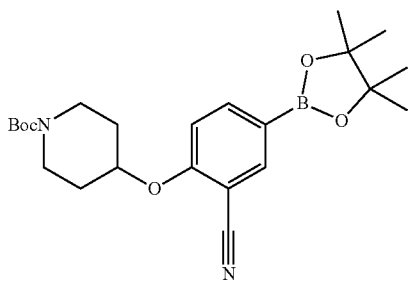 [SMILES: CC(C)(C)OC(=O)N1CCC(Oc2ccc(B3OC(C)(C)C(C)(C)O3)cc2C#N)CC1]

Step 1: 5-bromo-2-hydroxybenzonitrile (45 g, 0.23 mol) in anhydrous THF (1000 mL) was combined with tert-butyl 4-hydroxypiperidine-1-carboxylate (55 g, 0.27 mol), PPh₃ (70.7 g, 0.27 mol), followed by addition of DEAD (47.7 g, 0.27 mol) at r.t. The mixture was stirred at r.t. for 18 h. The reaction mixture was concentrated under reduced pressure. The residue was purified by silica gel chromatography (PE/EA=20/1 to 10/1) to give tert-butyl 4-(4-bromo-2-cyanophenoxy)piperidine-1-carboxylate. ¹H NMR: (CDCl₃, 400 MHz): δ 7.67 (s, 1H), 7.62-7.59 (m, 1H), 6.88 (d, J=9.2 Hz, 1H), 4.62-4.61 (m, 1H), 3.63-3.47 (m, 4H), 1.91-1.85 (m, 4H), 1.47 (s, 9H)

Step 2: To a solution of tert-butyl 4-(4-bromo-2-cyanophenoxy)piperidine-1-carboxylate (46.7 g, 0.12 mol) in dioxane (1000 mL) was added Pd(dppf)Cl₂ (4.4 g, 6 mmol), (Bpin)₂ (37.5 g, 0.14 mol), and KOAc (35.3 g, 0.36 mol). After stirring at 80° C. for 20 h under N₂, the mixture was filtered to remove KOAc, and the filtrate was concentrated under reduced pressure. The residue was purified by twice column chromatography (PE/EA=20/1 to 10/1) to give the title compound. ¹H NMR: (CDCl₃, 400 MHz): δ 8.03 (s, 1H), 7.92 (d, J=8.8 Hz, 1H), 6.95 (d, J=8.8 Hz, 1H), 4.70 (m, 1H), 3.64 (m, 2H), 3.52-3.48 (m, 2H), 1.90-1.84 (m, 4H), 1.59 (s, 9H),1.47-1.34 (m, 12H).

(R)-tert-butyl 3-(2-cyano-4-(4,4,5,5-tetramethyl-1,3,2-dioxaborolan-2-yl)phenoxy)pyrrolidine-1-carboxylate

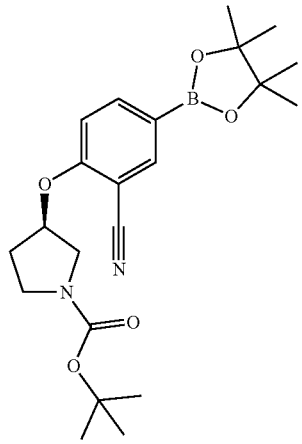 [SMILES: CC(C)(C)OC(=O)N1CC[C@@H](Oc2ccc(B3OC(C)(C)C(C)(C)O3)cc2C#N)C1]

The title compound was prepared following similar procedure to prepare Intermediate B using (S)-tert-butyl 3-hydroxypyrrolidine-1-carboxylate instead of tert-butyl 4-hydroxypiperidine-1-carboxylate in step 1. ¹H NMR: (CDCl₃, 400 MHz): δ 8.03 (s, 1H), 7.92 (d, J=7.6 Hz, 1H), 6.89 (d, J=8.4 Hz, 1H), 5.02 (s, 1H), 3.71-3.57 (m, 4H), 2.27-2.15 (m, 2H), 1.58 (s, 9H),1.34 (s, 12H).

(S)-tert-butyl 3-(2-cyano-4-(4,4,5,5-tetramethyl-1,3,2-dioxaborolan-2-yl)phenoxy)pyrrolidine-1-carboxylate

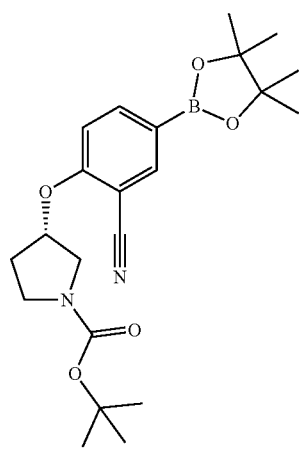 [SMILES: CC(C)(C)OC(=O)N1CC[C@H](Oc2ccc(B3OC(C)(C)C(C)(C)O3)cc2C#N)C1]

The title compound was prepared following similar procedure to prepare Intermediate B using (R)-tert-butyl 3-hydroxypyrrolidine-1-carboxylate instead of tert-butyl 4-hydroxypiperidine-1-carboxylate in step 1. ¹H NMR: (CDCl₃, 400 MHz): δ 8.04 (s, 1H), 7.94 (d, J=7.2 Hz, 1H), 6.91 (d, J=8.4 Hz, 1H), 5.04 (s, 1H), 3.73-3.59 (m, 4H), 2.29-2.16 (m, 2H), 1.59 (s, 9H), 1.36 (s, 12H).

2-(cyclopropylmethoxy)-5-(4,4,5,5-tetramethyl-1,3,2-dioxaborolan-2-yl)benzonitrile

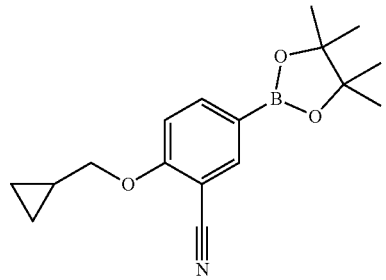 [SMILES: CC1(C)OB(c2ccc(OCC3CC3)c(C#N)c2)OC1(C)C]

Step 1: To a solution of cyclopropylmethanol (2.7 g, 38 mmol, 1.52 equiv.) in dry DMF (100 mL), sodium hydride, 60% suspension in oil (1.5 g, 38 mmol, 1.52 equiv.) at 0° C. under nitrogen. After 30 minutes at 0° C., 5-bromo-2-fluorobenzonitrile (5 g, 25 mmol, 1 equiv.) in dry DMF (20 mL) was added and the reaction mixture was heated to 50° C. for 16 h. The reaction mixture is mixed with ice water and ethyl acetate. The organic phases are washed with water and saturated sodium chloride solution and dried with sodium sulfate. After removal of the solvent the crude product was purified by column by chromatography (PE: EA=30:1) to obtain 5-bromo-2-(cyclopropylmethoxy)benzonitrile. $^1$H NMR: (CDCl$_3$): δ 7.65 (d, J=1.6 Hz, 1H), 7.59 (dd, J=8.0, 1.6 Hz, 1H) 6.84 (d, J=8.0 Hz, 1H), 3.92 (d, J=6.8 Hz, 2H), 1.26-1.33 (m, 1H), 0.65-0.69 (m, 2H), 0.37-0.41 (m, 2H).

Step 2: A solution of 5-bromo-2-(cyclopropylmethoxy) benzonitrile (36 g, 0.144 mol, 1 equiv.) in 1,4-Dioxane (600 mL) was degassed for 10 min, then (Bpin)$_2$ (40.2 g, 0.156 mol, 1.08 equiv.), [1,1'-bis(diphenylphosphino)ferrocene] dichloropalladium (II) (2.64 g, 3.6 mmol, 0.025 equiv.), 1,1' bis(diphenylphosphino)ferrocene (1.98 g, 3.6 mmol, 0.025 equiv.) and potassium acetate (28.2 g, 0.288 mol) are added at room temperature and refluxed for 18 h. The reaction mixture is mixed with ice water (200 mL) and ethyl acetate extracted. The organic phases are washed with water and saturated sodium chloride solution and dried with sodium sulfate. After removal of the solvent the crude product was purified by column by chromatography to obtain the title compound. $^1$H NMR: (CDCl$_3$): δ 8.01 (d, J=1.6 Hz, 1H), 7.91 (dd, J=8.4, 1.6 Hz, 1H), 6.91 (d, J=8.4 Hz, 1H), 3.96 (d, J=6.8 Hz, 2H), 1.33 (s, 12H), 1.28-1.34 (m, 1H), 0.65-0.69 (m, 2H), 0.38-0.42 (m, 2H).

2-((tetrahydro-2H-pyran-4-yl)oxy)-5-(4,4,5,5-tetramethyl-1,3,2-dioxaborolan-2-yl)benzonitrile

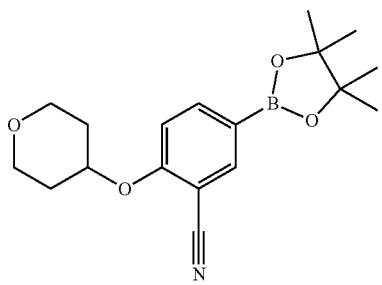 [SMILES: CC1(C)OB(c2ccc(OC3CCOCC3)c(C#N)c2)OC1(C)C]

Step 1: To tetrahyropyranol (30.0 g, 294 mmol) in DMF (400 mL) at 0° C. was added NaH (19.6 g, 294 mmol). 5-bromo-2-fluorobenzonitrile (49.0 g, 245 mmol) was added drop wise as a solution in DMF (100 mL). The reaction was stirred at 45° C. for 16 h. The reaction was cooled to rt and quenched by pouring the reaction into H$_2$O. The precipitate was filtered and dried under vacuum to 5-bromo-2-((tetrahydro-2H-pyran-4-yl)oxy)benzonitrile which was used further without purification.

Step 2: To 5-Bromo-2-tetrahydropyran-4-yloxy-benzonitrile (57 g, 202 mmol) in dioxane (550 mL) was added bis(pinacolato)diboron (65 g, 256 mmol), KOAc (50.4 g, 606 mmol), and Pd(dppf)Cl$_2$ (6.3 g, 10 mmol). The reaction was heated to 90° C. for 16 h. The solvent was removed and the residual was quenched with H$_2$O (500 mL), followed by extraction with EtOAc (3×1000 mL). The aqueous and organic layers were separated. The organic layer was washed with aq. saturated NaCl and dried (Na$_2$SO$_4$). Purification by silica gel chromatography (0-100%, EtOAc in Hexanes) provided the title compound. $^1$H NMR: (CDCl$_3$): δ 8.02 (d, 1H), 7.92-7.89 (m, 1H), 6.95-6.93 (d, 1H), 4.71-4.69 (m, 1H), 4.00-3.98 (m, 2H), 3.63-3.60(m, 2H), 2.04-2.01 (m, 2H), 1.90-1.85 (m, 2H), 1.33 (s, 12H).

Example 1

5-(4-((4(4-(1,1-dioxidothiomorpholino)phenyl) amino)-1,3,5-triazin-2-yl)-2-((tetrahydro-2H-pyran-4-yl)oxy)benzonitrile

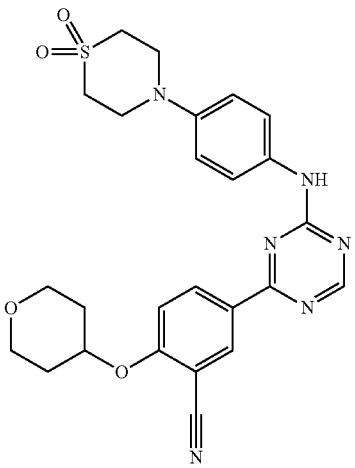 [SMILES: N#Cc1cc(-c2ncnc(Nc3ccc(N4CCS(=O)(=O)CC4)cc3)n2)ccc1OC1CCOCC1]

A suspension of 5-(4-chloro-1,3,5-triazin-2-yl)-2-((tetrahydro-2H-pyran-4-yl)oxy)benzonitrile (100 mg, 0.32 mmol) and 4-(4-aminophenyl)thiomorpholine-1,1-dioxide (TCI, 86 mg, 0.38 mmol) in acetonitrile (3 mL) was treated with N,N-diisopropylethylamine (0.28 mL, 1.6 mmol). The mixture was heated in a microwave reactor for 20 minutes at 80° C. The reaction mixture was subjected to flash chromatography (silica gel) to give a semi-pure material, which was taken up as a suspension in aqueous acetonitrile and extracted three times with dichloromethane. The combined extracts were washed once with dilute citric acid, dried over anhydrous magnesium sulfate, filtered, and concentrated under reduced pressure. The residue was recrystallized from hexanes/ethyl acetate to provide the desired material.

LCMS-ESI$^+$ (m/z): [M+H]$^+$ calcd for C$_{25}$H$_{27}$N$_6$O$_4$S: 507.2; found: 507.2

$^1$H NMR (400 MHz, DMSO-d$_6$) δ 10.21 (m, 1H), 8.79 (s, 1H), 8.60 (m, 2H), 7.67 (m, 2H), 7.59 (d, J=9.2 Hz, 1H), 7.10 (m, 2H), 4.98 (m, 1H), 3.91 (m, 2H), 3.79 (m, 4H), 3.59 (m, 2H), 3.18 (m, 4H), 2.09 (m, 2H), 1.73 (m, 2H).

Example 2

(R)-methyl 3-(2-cyano-4-(4-((4-(4-(oxetan-3-yl) piperazin-1-yl)phenyl)amino)-1,3,5-triazin-2-yl) phenoxy)pyrrolidine-1-carboxylate

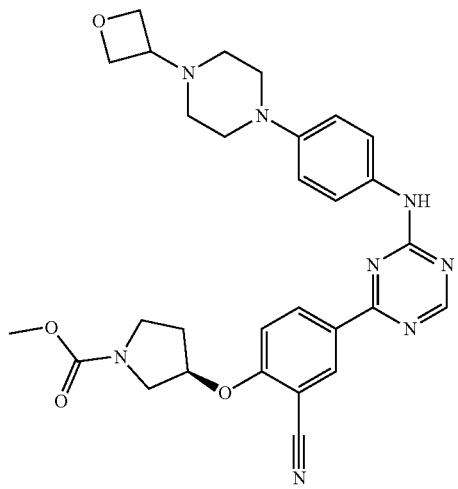 [SMILES: COC(=O)N1CC[C@@H](Oc2ccc(-c3ncnc(Nc4ccc(N5CCN(C6COC6)CC5)cc4)n3)cc2C#N)C1]

(R)-5-(4-((4-(4-(oxetan-3-yl)piperazin-1-yl)phenyl)amino)-1,3,5-triazin-2-yl)-2-(pyrrolidin-3-yloxy)benzonitrile (50 mg, 0.10 mmol) was taken up as suspension in dichloromethane (1 mL) and treated successively with N,N-diisopropylethylamine (37 µL, 0.20 mmol) and methyl chloroformate (12 µL, 0.15 mmol). The mixture was stirred for five minutes at room temperature and then purified by flash chromatography (silica gel) to provide (R)-methyl 3-(2-cyano-4-((4-(4-(oxetan-3-yl)piperazin-1-yl)phenyl)amino)-1,3,5-triazin-2-yl)phenoxy)pyrrolidine-1-carboxylate.

LCMS-ESI$^+$ (m/z): [M+H]$^+$ calcd for $C_{29}H_{33}N_8O_4$: 557.3; found: 557.3

$^1$H NMR (400 MHz, DMSO-d$_6$) δ 10.17 (m, 1H), 8.78 (d, J=2.7 Hz, 1H), 8.60 (m, 2H), 7.58 (m, 3H), 7.01 (br, 2H), 5.37 (br, 1H), 4.61 (m, 2H), 4.51 (m, 3H), 3.71 (m, 1H), 3.64 (d, J=7.8 Hz, 3H), 3.49 (m, 2H), 3.19 (m, 4H), 2.45 (m, 4H), 2.26 (m, 2H).

Example 3

(R)-2-((1-acetylpyrrolidin-3-yl)oxy)-5-(4-((4-(4-(oxetan-3-yl)piperazin-1-yl)phenyl)amino)-1,3,5-triazin-2-yl)benzonitrile

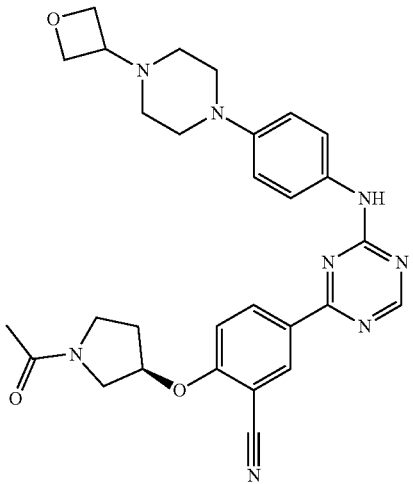 [SMILES: CC(=O)N1CC[C@@H](Oc2ccc(-c3ncnc(Nc4ccc(N5CCN(C6COC6)CC5)cc4)n3)cc2C#N)C1]

(R)-5-(4-((4-(4-(oxetan-3-yl)piperazin-1-yl)phenyl)amino)-1,3,5-triazin-2-yl)-2-(pyrrolidin-3-yloxy)benzonitrile (50 mg, 0.10 mmol) was taken up as suspension in dichloromethane (1 mL) and treated successively with N,N-diisopropylethylamine (37 µL, 0.20 mmol) and acetyl chloride (11 µL, 0.15 mmol). The mixture was stirred for five minutes at room temperature and then purified by flash chromatography (silica gel) to provide (R)-2-((1-acetylpyrrolidin-3-yl)oxy)-5-(4-((4-(4-(oxetan-3-yl)piperazin-1-yl)phenyl)amino)-1,3,5-triazin-2-yl)benzonitrile.

LCMS-ESI$^+$ (m/z): [M+H]$^+$ calcd for $C_{29}H_{33}N_8O_3$: 541.3; found: 541.4

$^1$H NMR (400 MHz, DMSO-d$_6$) δ 10.17 (m, 1H), 8.78 (s, 1H), 8.61 (m, 2H), 7.58 (m, 3H), 7.01 (br, 2H), 5.39 (m, 1H), 4.61 (m, 2H), 4.51 (m, 2H), 3.66 (m, 3H), 3.49 (m, 1H), 3.19 (m, 4H), 2.45 (m, 4H), 2.28 (m, 2H), 2.03 (s, 2H), 1.99 (s, 1H).

Example 4

5-(4-((3-methoxy-4-(4-methylpiperazin-1-yl)phenyl)amino)-1,3,5-triazin-2-yl)-2-((tetrahydro-2H-pyran-4-yl)oxy)benzonitrile

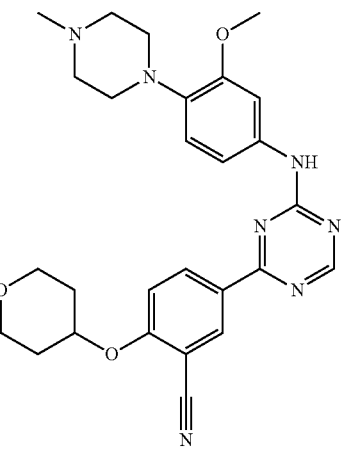

A suspension of 5-(4-chloro-1,3,5-triazin-2-yl)-2-((tetrahydro-2H-pyran-4-yl)oxy)benzonitrile (53 mg, 0.17 mmol) and 3-methoxy-4-(4-methylpiperazin-1-yl)aniline (44 mg, 0.20 mmol) in acetonitrile (2.5 mL) was treated with N,N-diisopropylethylamine (0.12 mL, 0.67 mmol). The mixture was heated on a 90° C. block for 60 minutes. The cooled reaction mixture was purified by flash chromatography (silica gel), followed by prep HPLC (10-80% acetonitrile in water, 0.1% trifluoroacetic acid buffer) to provide 5-(4-((3-methoxy-4-(4-methylpiperazin-1-yl)phenyl)amino)-1,3,5-triazin-2-yl)-2-((tetrahydro-2H-pyran-4-yl)oxy)benzonitrile. LCMS-ESI$^+$ (m/z): [M+H]$^+$ calcd for $C_{27}H_{32}N_7O_3$: 502.3; found: 502.3 $^1$H NMR (400 MHz, DMSO-d$_6$) δ 10.53 (bs, 1H), 10.34 (m, 1H), 8.83 (s, 1H), 8.64 (d, J=2.1 Hz, 1H), 8.62 (dd, J=8.9, 2.2 Hz, 1H), 7.61 (d, J=9.0 Hz, 1H), 7.29 (m, 1H), 7.00 (d, J=8.5 Hz, 1H), 4.99 (m, 1H), 4.03-3.78 (m, 4H), 3.59 (m, 2H), 3.47 (m, 5H), 3.13 (m, 4H), 2.85 (s, 3H), 2.09 (m, 2H), (m 2H).

Example 5

5-(4-((4-(4-(oxetan-3-yl)piperazin-1-yl)phenyl) amino)-1,3,5-triazin-2-yl)-2-(oxetan-3-yloxy)benzonitrile

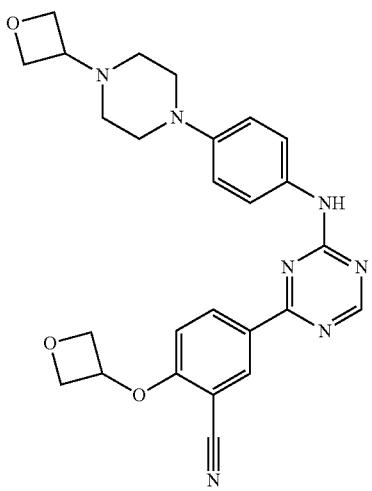 [SMILES: N#Cc1cc(-c2ncnc(Nc3ccc(N4CCN(C5COC5)CC4)cc3)n2)ccc1OC1COC1]

A solution of 3-hydroxyoxetane (1.33 g, 18 mmol) in N,N-dimethylformamide (36 mL) was stirred in an ice-water bath under an atmosphere of Argon. Sodium hydride (60% dispersion in mineral oil, 0.72 g, 18 mmol) was added in a single portion and the mixture was stirred at 0° C. for 10 minutes, and then the bath was removed. After 30 minutes of stirring at room temperature, to the mixture was added 5-bromo-2-fluorobenzonitrile (3.0 g, 18 mmol) via syringe as a solution in N,N-dimethylformamide (15 mL). The mixture was stirred overnight at 50° C. After the mixture cooled to room temperature, water was added, giving a granular precipitate. It was collected by filtration, washed with water and dried in a vacuum oven over $P_2O_5$ to provide 5-bromo-2-(oxetan-3-yloxy)benzonitrile. $^1$H NMR (400 MHz, DMSO-$d_6$) δ 8.11 (d, J=2.5 Hz, 1H), 7.84 (dd, J=9.0, 2.5 Hz, 1H), 6.90 (d, J=9.0 Hz, 1H), 5.48 (tt, J=5.9, 4.7 Hz, 1H), 4.99 (ddd, J=7.2, 6.0, 1.0 Hz, 2H), 4.61 (ddd, J=7.6, 4.7, 1.0 Hz, 2H).

A mixture of 5-bromo-2-(oxetan-3-yloxy)benzonitrile (0.22 g, 0.88 mmol), bis(pinacolato)diboron (0.45 g, 1.8 mmol), potassium acetate (0.26 g, 2.6 mmol), and [1,1'-bis (diphenylphosphino)ferrocene]dichloropalladium(II) (0.065 g, 10 mol %) in 1,4-dioxane (5 mL) was heated at 90° C. overnight. LC/MS analysis indicated the consumption of the bromide starting material. The mixture was filtered through a pad of Celite diatomaceous earth and concentrated to dryness under reduced pressure to provide the putative 2-(oxetan-3-yloxy)-5-(4,4,5,5-tetramethyl-1,3,2-dioxaborolan-2-yl)benzonitrile.

A mixture of 4-chloro-N-(4-(4-(oxetan-3-yl)piperazin-1-yl)phenyl)-1,3,5-triazin-2-amine (Prepared by treating 2,4-dichloro-1,3,5-triazine and 4-(4-(oxetan-3-yl)piperazin-1-yl)aniline (WO2013188856) in DMF at 0° C. in the presence of added DIEA at 0° C. for 30 minutes and then allowed to warm to r.t. where it remained till the reaction goes to completion. The mixture was diluted with ethyl acetate and washed with water and brine and dried. The crude mixture was purified by flash chromatography on silica gel to provide of 4-chloro-N-(4-(4-(oxetan-3-yl)piperazin-1-yl) phenyl)-1,3,5-triazin-2-amine) (0.15 g, 0.44 mmol), 2-(oxetan-3-yloxy)-5-(4,4,5,5-tetramethyl-1,3,2-dioxaborolan-2-yl)benzonitrile (0.27 g, 0.88 mmol), and tetrakis (triphenylphosphine)palladium(0) (0.025 g, 5 mol %) in 1,2-dimethoxyethane (DME, 6 mL) was treated with 2M aqueous sodium carbonate solution (1 mL). The mixture was irradiated for 1 hour in a microwave reactor at 130° C. The crude mixture was purified by flash chromatography on silica gel to provide 5-(4-((4-(4-(oxetan-3-yl)piperazin-1-yl) phenyl)amino)-1,3,5-triazin-2-yl)-2-(oxetan-3-yloxy)benzonitrile. LCMS-ESI$^+$ (m/z): [M+H]$^+$ calcd for $C_{26}H_{28}N_7O_3$: 486.2; found: 486.3

$^1$H NMR (400 MHz, DMSO-$d_6$) δ 10.15 (m, 1H), 8.78 (s, 1H), 8.60 (m, 2H), 7.63 (d, J=9.1 Hz, 1H), 7.13 (d, J=8.9 Hz, 1H), 7.01 (t, J=7.4 Hz, 2H), 5.58 (p, J=5.4 Hz, 1H), 5.04 (t, J=6.8 Hz, 2H), 4.67 (m, 2H), 4.61 (t, J=6.5 Hz, 2H), 4.52 (t, J=6.0 Hz, 2H), 3.49 (p, J=6.3 Hz, 1H), 3.19 (m, 4H), 2.45 (m, 4H).

Example 6

2-((3-methyloxetan-3-yl)methoxy)-5-(4-((4-(4-(oxetan-3-yl)piperazin-1-yl)phenyl)amino)-1,3,5-triazin-2-yl)benzonitrile

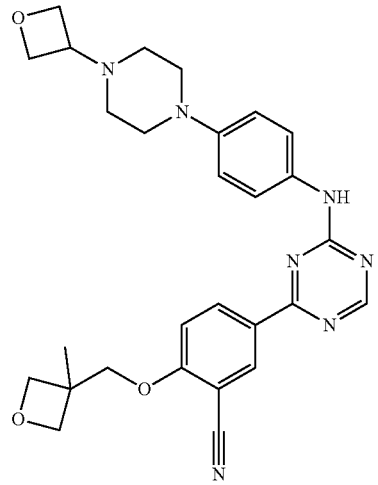 [SMILES: CC1(COc2ccc(-c3ncnc(Nc4ccc(N5CCN(C6COC6)CC5)cc4)n3)cc2C#N)COC1]

Step 1: Preparation of 5-bromo-2-((3-methyloxetan-3-yl) methoxy)benzonitrile:

A solution of 3-methyl-3-oxetanemethanol (Aldrich, 2.0 g, 20 mmol) in N,N-dimethylformamide (40 mL) was stirred in an ice-water bath under an atmosphere of Argon. Sodium hydride (60% in mineral oil, 0.78 g, 20 mmol) was added in a single portion. Mixture was stirred at 0° C. for 10 minutes and then the cooling bath was removed. The mixture was stirred overnight at room temperature. To the mixture was added via syringe 5-bromo-2-fluorobenzonitrile (Matrix Scientific, 4.7 g, 24 mmol) as a solution in N,N-dimethylformamide (20 mL) at room temperature. Mixture was stirred for 8 hours at 50° C. block and then allowed to cool to room temperature. Water was added and the resulting suspension was extracted three times with ethyl acetate. The combined extracts were washed once each with water and saturated aqueous sodium chloride solution, dried over anhydrous magnesium sulfate, filtered, and concentrated to dryness under reduced pressure. The crude material was purified via flash chromatography on silica gel to give the desired material. LCMS-ESI⁺ (m/z): [M+H]⁺ calcd for $C_{12}H_{12}BrNO_2$: 282.0; found: 281.9

Step 2: Preparation of 2-((3-methyloxetan-3-yl)methoxy)-5-(4,4,5,5-tetramethyl-1,3,2-dioxaborolan-2-yl)benzonitrile:

A mixture of 5-bromo-2-((3-methyloxetan-3-yl)methoxy)benzonitrile (0.25 g, 0.89 mmol), bis(pinacolato)diboron (0.45 g, 1.8 mmol), potassium acetate (0.26 g, 2.7 mmol), and [1,1'-bis(diphenylphosphino)ferrocene]dichloropalladium(II) complex with dichloromethane (0.066 g, 0.09 mmol) in 1,4-dioxane (8 mL) was heated for 60 minutes at 85° C. The reaction mixture was filtered through a pad of Celite diatomaceous earth, and the filtrate was concentrated to dryness under reduced pressure to provide 2-((3-methyloxetan-3-yl)methoxy)-5-(4,4,5,5-tetramethyl-1,3,2-dioxaborolan-2-yl)benzonitrile. LCMS-ESI⁺ (m/z): [M+H]⁺ calcd for $C_{18}H_{24}BNO_4$: 330.2; found: 330.0

Step 3: A mixture of 4-chloro-N-(4-(4-(oxetan-3-yl)piperazin-1-yl)phenyl)-1,3,5-triazin-2-amine (0.15 g, 0.44 mmol), 2-((3-methyloxetan-3-yl)methoxy)-5-(4,4,5,5-tetramethyl-1,3,2-dioxaborolan-2-yl)benzonitrile (0.29 g, 0.88 mmol), and tetrakis(triphenylphosphine)palladium(0) (0.025 g, 5 mol %) in 1,2-dimethoxyethane (DME, 4 mL) was treated with 2M aqueous sodium carbonate solution (1 mL). The mixture was irradiated for 1 hour in a microwave reactor at 130° C. The crude mixture was purified by flash chromatography on silica gel to provide 2-((3-methyloxetan-3-yl)methoxy)-5-(4-((4-(4-(oxetan-3-yl)piperazin-1-yl)phenyl)amino)-1,3,5-triazin-2-yl)benzonitrile LCMS-ESI⁺ (m/z): [M+H]⁺ calcd for $C_{28}H_{31}N_7O_3$: 514.3; found: 514.3

¹H NMR (400 MHz, DMSO-d₆) δ 10.13 (m, 1H), 8.76 (s, 1H), 8.70-8.44 (m, 2H), 7.75-7.56 (m, 2H), 7.52 (d, J=9.0 Hz, 1 H), 6.99 (m, 2H), 4.64-4.53 (m, 4H), 4.50 (t, J=6.0 Hz, 2H), 4.37 (m, 4H), 3.47 (p, J=6.3 Hz, 1H), 3.17 (m, 4H), 2.44 (m, 4H), 1.44 (s, 3H).

Example 7

5-(4-((4-(4-(2,2-difluoroethyl)piperazin-1-yl)-3-methoxyphenyl)amino)-1,3,5-triazin-2-yl)-2-((tetrahydro-2H-pyran-4-yl)oxy)benzonitrile

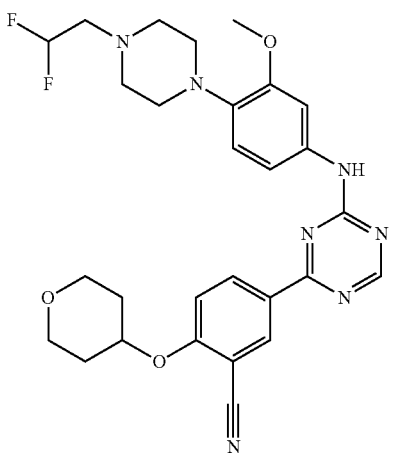 [SMILES: COc1cc(Nc2ncnc(-c3ccc(OC4CCOCC4)c(C#N)c3)n2)ccc1N1CCN(CC(F)F)CC1]

Step 1: Preparation of 1-(2,2-difluoroethyl)-4-(2-methoxy-4-nitrophenyl)piperazine:

A mixture of 1-fluoro-2-methoxy-4-nitrobenzene (0.83 g, 4.9 mmol), 1-(2,2-difluoroethyl)piperazine hydrochloride (Ryan Scientific, 1.0 g, 5.3 mmol), and potassium carbonate (2.0 g, 15 mmol) in N,N-dimethylformamide (9 mL) was stirred at 100° C. for 20 hours. After cooling to room temperature, the mixture was partitioned between ethyl acetate and saturated aqueous sodium hydrogen carbonate solution. The mixture was filtered through a pad of Celite diatomaceous earth. The collected solid was discarded, while the aqueous phase was extracted three times with ethyl acetate. The combined extracts were washed once with saturated aqueous sodium chloride solution, dried over anhydrous magnesium sulfate, filtered, and concentrated under reduced pressure. The crude residue was purified by flash chromatography (silica gel) to provide the desired material. LCMS-ESI⁺ (m/z): [M+H]⁺ calcd for $C_{13}H_{18}F_2N_3O_3$: 302.1; found: 302.1

Step 2: Preparation of 4-(4-(2,2-difluoroethyl)piperazin-1-yl)-3-methoxyaniline:

A degassed mixture of 1-(2,2-difluoroethyl)-4-(2-methoxy-4-nitrophenyl)piperazine (1.5 g, 4.9 mmol) in methanol (30 mL) was treated with 10% palladium on charcoal (250 mg). Mixture was stirred under a balloon of hydrogen overnight. The catalyst was removed by filtration through a pad of Celite diatomaceous earth. The filtrate was concentrated to dryness under reduced pressure to provide the desired material. LCMS-ESI⁺ (m/z): [M+H]⁺ calcd for $C_{13}H_{20}F_2N_3O$: 272.2; found: 272.1

Step 3: Preparation of 5-(4-((4-(4-(2,2-difluoroethyl)piperazin-1-yl)-3-methoxyphenyl)amino)-1,3,5-triazin-2-yl)-2-((tetrahydro-2H-pyran-4-yl)oxy)benzonitrile:

A suspension of 5-(4-chloro-1,3,5-triazin-2-yl)-2-((tetrahydro-2H-pyran-4-yl)oxy)benzonitrile (53 mg, 0.17 mmol) and 4-(4-(2,2-difluoroethyl)piperazin-1-yl)-3-methoxyaniline (54 mg, 0.20 mmol) in acetonitrile (3 mL) was treated with N,N-diisopropylethylamine (0.12 mL, 0.67 mmol). The mixture was heated in a microwave reactor for 20 minutes at 80° C. The cooled reaction mixture was purified by flash chromatography (silica gel) and then recrystallized from acetonitrile to provide 5-(4-((4-(4-(2,2-difluoroethyl)piperazin-1-yl)-3-methoxyphenyl)amino)-1,3,5-triazin-2-yl)-2-((tetrahydro-2H-pyran-4-yl)oxy)benzonitrile. LCMS-ESI⁺ (m/z): [M+H]⁺ calcd for $C_{28}H_{32}F_2N_7O_3$: 552.3; found: 552.3

¹H NMR (400 MHz, DMSO-d₆) δ 10.22 (m, 1H), 8.81 (s, 1H), 8.67-8.58 (m, 2H), 7.66 (bs, 1H), 7.60 (d, J=90 Hz, 1H), 7.44-7.20 (br, 1H), 6.93 (d, J=8.5 Hz, 1H), 6.21 (tt, J=55.8, 4.3 Hz, 1H), 4.98 (m, 1H), 3.92 (m, 5H), 3.59 (m, 2H), 3.00 (m, 4H), 2.82 (td, J=15.7, 4.3 Hz, 2H), 2.72 (m, 4H), 2.09 (m, 2H), 1.73 (m, 2H).

Example 8

5-(4-((1-methyl-1H-pyrazol-4-yl)amino)-1,3,5-triazin-2-yl)-2-(pyrrolidin-1-yl)benzonitrile

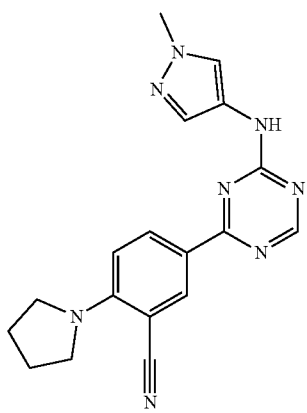 [SMILES: Cn1cc(Nc2ncnc(-c3ccc(N4CCCC4)c(C#N)c3)n2)cn1]

To a solution of 2,4-dichloro-1,3,5-triazine (0.83 g, 5.6 mmol) in N,N-dimethylformamide (DMF, 3 mL) at 0° C. were added sequentially N,N-diisopropylethylamine (DIEA, 1.0 mL, 5.8 mmol) and a solution of 4-amino-1-methylpyrazole (0.49 g, 5.0 mmol) in DMF (1 mL). The mixture was stirred at 0° C. for 30 minutes and then allowed to warm to room temperature. The mixture was diluted with ethyl acetate and water and filtered through a pad of Celite diatomaceous earth. The filtered aqueous phase was extracted once with ethyl acetate. The combined extracts were washed once each with water and a saturated aqueous solution of sodium chloride, then dried over anhydrous magnesium sulfate, filtered, and concentrated under reduced pressure to give 4-chloro-N-(1-methyl-1H-pyrazol-4-yl)-1,3,5-triazin-2-amine, which carried forward without further purification. LCMS-ESI$^+$ (m/z): [M+H]$^+$ calcd for $C_7H_8ClN_6$: 211.0; found: 211.1

A mixture of 4-chloro-N-(1-methyl-1H-pyrazol-4-yl)-1,3,5-triazin-2-amine (0.15 g, 0.71 mmol) and 2-(pyrrolidin-1-yl)-5-(4,4,5,5-tetramethyl-1,3,2-dioxaborolan-2-yl)benzonitrile (0.23 g, 0.78 mmol) in 1,2-dimethoxyethane (DME, 2 mL) was treated successively with palladium (II) acetate (0.016 g, 10 mol %), triphenylphosphine (0.056 g, 0.21 mmol), and 2M aqueous sodium carbonate solution (1.6 mL). The mixture was irradiated for 1 hour in a microwave reactor at 130° C. The crude mixture was purified by flash chromatography on silica gel to furnish 5-(4-((1-methyl-1H-pyrazol-4-yl)amino)-1,3,5-triazin-2-yl)-2-(pyrrolidin-1-yl)benzonitrile. LCMS-ESI$^+$ (m/z): [M+H]$^+$ calcd for $C_{18}H_{19}N_8$: 347.2; found: 347.3

$^1$H NMR (400 MHz, DMSO-d$_6$) δ 10.16 (d, J=5.4 Hz, 1H), 8.74 (s, 0.5H), 8.65 (s, 0.5H), 8.46 (dd, J=5.3, 2.2 Hz, 1H), 8.35 (ddd, J=25.3, 9.2, 2.2 Hz, 1H), 8.01-7.93 (m, 1H), 7.69 (s, 0.5H), 7.57 (s, 0.5H), 6.94 (t, J=9.0 Hz, 1H), 3.91 (s, 1.5H), 3.86 (s, 1.5H), 3.79-3.55 (m, 4H), 2.02 (m, 4H).

Example 9

5-(4-((1-methyl-1H-pyrazol-4-yl)amino)-1,3,5-triazin-2-yl)-2-((tetrahydro-2H-pyran-4-yl)oxy)benzonitrile

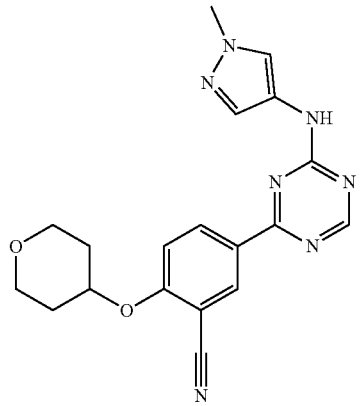 [SMILES: Cn1cc(Nc2ncnc(-c3ccc(OC4CCOCC4)c(C#N)c3)n2)cn1]

A suspension of 4-chloro-N-(1-methyl-1H-pyrazol-4-yl)-1,3,5-triazin-2-amine (0.13 g, 0.59 mmol) and 2-((tetrahydro-2H-pyran-4-yl)oxy)-5-(4,4,5,5-tetramethyl-1,3,2-dioxaborolan-2-yl)benzonitrile (0.21 g, 0.65 mmol) in 1,2-dimethoxyethane (DME, 2 mL) was treated successively with palladium (II) acetate (0.013 g, 10 mol %), triphenylphosphine (0.047 g, 0.18 mmol), and 2M aqueous sodium carbonate solution (1.3 mL). The mixture was irradiated for 1 hour in a microwave reactor at 125° C. The crude mixture was purified by flash chromatography on silica gel to furnish 5-(4-((1-methyl-1H-pyrazol-4-yl)amino)-1,3,5-triazin-2-yl)-2-((tetrahydro-2H-pyran-4-yl)oxy)benzonitrile.

LCMS-ESI$^+$ (m/z): [M+H]$^+$ calcd for $C_{19}H_{20}N_7O_2$: 378.2; found: 378.2

$^1$H NMR (400 MHz, DMSO-d$_6$) δ 10.33 (d, J=5.1 Hz, 1H), 8.83 (s, 0.5H), 8.74 (s, 0.5H), 8.70-8.55 (m, 2H), 8.00 (d, J=6.2 Hz, 1H), 7.70 (s, 0.5H), 7.64-7.56 (m, 1.5H), 4.99 (m, 1H), 4.00-3.82 (m, 5H), 3.70-3.52 (m, 2H), 2.09 (m, 2H), 1.74 (m, 2H).

Example 10

5-(4-((4-(4-(oxetan-3-yl)piperazin-1-yl)phenyl)amino)-1,3,5-triazin-2-yl)-2-(pyrrolidin-1-yl)benzonitrile

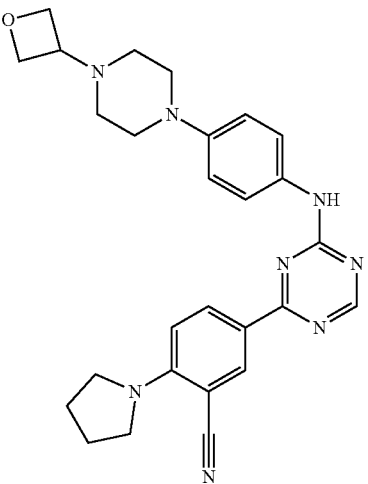 [SMILES: N#Cc1cc(-c2ncnc(Nc3ccc(N4CCN(C5COC5)CC4)cc3)n2)ccc1N1CCCC1]

To a solution of 2,4-dichloro-1,3,5-triazine (0.11 g, 0.71 mmol) in DMF (1 mL) at 0° C. were added DIEA (0.13 mL, 0.73 mmol), followed by 4-(4-(oxetan-3-yl)piperazin-1-yl) aniline (0.15 g, 0.64 mmol) and the mixture was stirred at 0° C. for 30 minutes and then allowed to stir overnight at room temperature. The mixture was concentrated to dryness under reduced pressure to provide 4-chloro-N-(4-(4-(oxetan-3-yl) piperazin-1-yl)phenyl)-1,3,5-triazin-2-amine, which was carried forward without further purification as a solution in 1,2-dimethoxyethane/N,N-dimethylformamide (1:1). LCMS-ESI$^+$ (m/z): [M+H]$^+$ calcd for $C_{16}H_{20}ClN_6O$: 347.1; found: 347.3

A mixture of 4-chloro-N-(4-(4-(oxetan-3-yl)piperazin-1-yl)phenyl)-1,3,5-triazin-2-amine (0.11 g, 0.32 mmol) and 2-(pyrrolidin-1-yl)-5-(4,4,5,5-tetramethyl-1,3,2-dioxaborolan-2-yl)benzonitrile (0.10 g, 0.35 mmol) in 1,2-dimethoxyethane (DME, 2 mL)/N,N-dimethylformamide (DMF, 1 mL) was treated successively with palladium (II) acetate (0.007 g, 10 mol %), triphenylphosphine (0.025 g, 0.21 mmol), and 2M aqueous sodium carbonate solution (0.7 mL). The mixture was irradiated for 1 hour in a microwave reactor at 130° C. The crude mixture was purified by flash chromatography on silica gel to furnish 5-(4-((4-(4-(oxetan-3-yl) piperazin-1-yl)phenyl)amino)-1,3,5-triazin-2-yl)-2-(pyrrolidin-1-yl)benzonitrile.

LCMS-ESI$^+$ (m/z): [M+H]$^+$ calcd for $C_{28}H_{31}N_8O$: 483.3; found: 483.4

$^1$H NMR (400 MHz, DMSO-d$_6$) δ 10.09 (s, 1H), 8.71 (s, 1H), 8.44 (s, 1H), 8.34 (dd, J=9.2, 2.1 Hz, 1H), 7.65 (d, J=24.3 Hz, 2H), 7.09 (s, 2H), 6.94 (d, J=9.3 Hz, 1H), 4.81 (m, 4H), 4.50 (m, 1H), 3.70 (m, 4H), 3.40-2.80 (m, 8H), 2.02 (m, 4H).

Example 11

5-(4-((4-(4-acetylpiperazin-1-yl)phenyl)amino)-1,3,5-triazin-2-yl)-2-((tetrahydro-2H-pyran-4-yl)oxy) benzonitrile

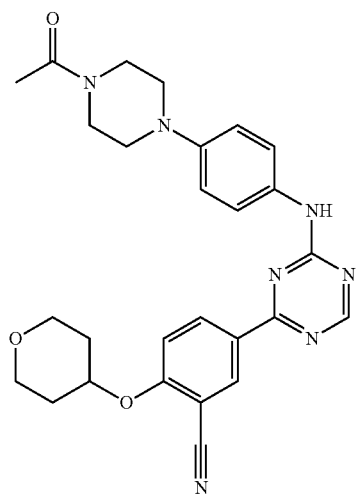 [SMILES: CC(=O)N1CCN(c2ccc(Nc3ncnc(-c4ccc(OC5CCOCC5)c(C#N)c4)n3)cc2)CC1]

A suspension of 5-(4-chloro-1,3,5-triazin-2-yl)-2-((tetrahydro-2H-pyran-4-yl)oxy)benzonitrile (53 mg, 0.16 mmol) and 1-(4-(4-aminophenyl)piperazin-1-yl)ethanone (44 mg, 0.20 mmol) in acetonitrile (2.5 mL) was treated with N,N-diisopropylethylamine (0.12 mL, 0.67 mmol). The mixture was heated in a microwave reactor for 60 minutes at 100° C. The cooled reaction mixture was purified by prep HPLC (10-80% acetonitrile in water, 0.1% trifluoroacetic acid buffer) to provide 5-(4-((4-(4-acetylpiperazin-1-yl)phenyl) amino)-1,3,5-triazin-2-yl)-2-((tetrahydro-2H-pyran-4-yl) oxy)benzonitrile. LCMS-ESI$^+$ (m/z): [M+H]$^+$ calcd for $C_{27}H_{30}N_7O_3$: 500.2; found: 500.2

$^1$H NMR (400 MHz, DMSO-d$_6$) δ 10.22 (m, 1H), 8.79 (s, 1H), 8.60 (m, 2H), 7.66 (bs, 2H), 7.60 (d, J=9.3 Hz, 1H), 7.06 (bs, 2H), 4.98 (m, 1H), 3.99-3.83 (m, 2H), 3.63 (m, 4H), 3.60 (m, 2H), 3.16 (m, 4H), 2.09 (m, 5H), 1.73 (m, 2H).

Example 12

5-(4-((4-(4-methylpiperazin-1-yl)phenyl)amino)-1,3,5-triazin-2-yl)-2-((tetrahydro-2H-pyran-4-yl)oxy) benzonitrile

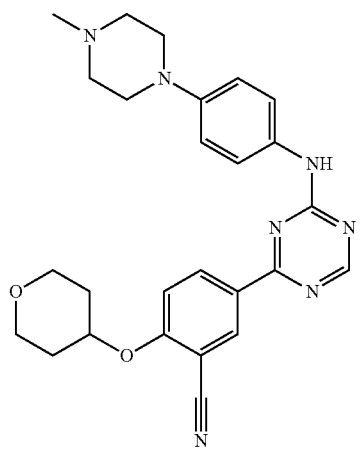 [SMILES: CN1CCN(c2ccc(Nc3ncnc(-c4ccc(OC5CCOCC5)c(C#N)c4)n3)cc2)CC1]

4-hydroxytetrahydropyran (14 g, 140 mmol) was taken up in tetrahydrofuran (300 mL) and cooled in an ice-water bath. Potassium tert-butoxide (17 g, 150 mmol) was added, and the reaction mixture was stirred for 20 minutes in the bath before the addition of 4-fluoroisophthalonitrile (10 g, 68 mmol). The mixture continued to stir in the bath for 5 minutes before the removal of the bath. The mixture was stirred at room temperature overnight and then concentrated almost to dryness under reduced pressure. The residue was partitioned between ethyl acetate and water. The aqueous phase was extracted three times with ethyl acetate. The combined organics were washed once with saturated aqueous sodium chloride solution, dried over anhydrous magnesium sulfate, filtered, concentrated to dryness under reduced pressure. The residue was recrystallized from methanol to provide 4-((tetrahydro-2H-pyran-4-yl)oxy)isophthalonitrile.

$^1$H NMR (400 MHz, DMSO-d6) δ 8.42 (d, J=2.1 Hz, 1H), 8.16 (dd, J=8.9, 2.1 Hz, 1H), 7.60 (d, J=9.0 Hz, 1H), 5.01 (m, 1H), 3.88 (m, 2H), 3.57 (m, 2H), 2.05 (m, 2H), 1.70 (m, 2H).

A suspension of 4-((tetrahydro-2H-pyran-4-yl)oxy) isophthalonitrile (1.0 g, 4.4 mmol) in methanol (15 mL) was treated with sodium methoxide (24 mg, 0.44 mmol). The suspension was stirred at room temperature for two days. Cyanamide (0.28 g, 6.6 mmol) was added and the mixture was allowed to stir for 20 days before the addition of saturated aqueous sodium chloride solution (approximately 5 mL). The solid was collected by vacuum filtration, washed with water, and dried in a vacuum oven over $P_2O_5$ to provide N,3-dicyano-4-((tetrahydro-2H-pyran-4-yl)oxy)benzirnidamide. LCMS-ESI+ (m/z): [M+H]+ calcd for $C_{14}H_{15}N_4O_2$: 271.1; found: 270.9

N,3-dicyano-4-((tetrahydro-2H-pyran-4-yl)oxy)benzimidamide (0.26 g, 0.96 mmol) was taken up as a suspension in MeCN (3 mL) and treated with (chloromethylene)dimethyliminium chloride (0.15 g, 1.1 mmol), followed by dichloromethane (2 mL). After warming the mixture to 45° C., an additional volume of dichloromethane (1 mL) was added. The mixture was stirred for 15 minutes at room temperature, and then the white precipitate was collected by vacuum filtration.

The solid and filtrate were combined in dichloromethane and washed with saturated aqueous sodium hydrogen carbonate solution. The aqueous layer was extracted three times with dichloromethane. The combined organics were washed with water, precipitating a solid. The aqueous washings were back-extracted 3 times with dichloromethane. The organics were dried over anhydrous magnesium sulfate, filtered, and concentrated under reduced pressure to provide 5-(4-chloro-1,3,5-triazin-2-yl)-2-((tetrahydro-2H-pyran-4-yl)oxy)benzonitrile.

$^1$H NMR (400 MHz, Chloroform-d) δ 9.01 (s, 1H), 8.78 (d, J=2.2 Hz, 1H), 8.67 (dd, J=9.0, 2.2 Hz, 1H), 7.09 (d, J=9.0 Hz, 1H), 4.80 (tt, J=7.2, 3.7 Hz, 1H), 4.04 (ddd, J=11.2, 7.1, 3.6 Hz, 2H), 3.67 (ddd, J=11.4, 7.2, 3.6 Hz, 2H), 2.27-2.02 (m, 2H), 2.02-1.84 (m, 2H).

A suspension of 5-(4-chloro-1,3,5-triazin-2-yl)-2-((tetrahydro-2H-pyran-4-yl)oxy)benzonitrile (0.22 g, 0.70 mmol) in acetonitrile (4 mL) was treated with 4-(4-methylpiperazin-1-yl)aniline (0.13 g, 0.70 mmol) and N,N-diisopropylethylamine (0.24 mL, 1.4 mmol). The suspension was warmed with a heat gun until homogeneous. The mixture was purified by flash chromatography (silica gel) to provide the impure desired material, which was recrystallized from methanol to provide 5-(4-((4-(4-methylpiperazin-1-yl)phenyl)amino)-1,3,5-triazin-2-yl)-2-((tetrahydro-2H-pyran-4-yl)oxy)benzonitrile. LCMS-ESI+ (m/z): [M+H]+ calcd for $C_{26}H_{30}N_7O_2$: 472.2; found: 472.3. $^1$H NMR (400 MHz, DMSO-d$_6$) δ 10.15 (m, 1H), 8.77 (s, 1H), 8.60 (m, 2H), 7.59 (m, 3H), 7.00 (dd, J=11.0, 6.9 Hz, 2H), 4.98 (m, 1H), 3.91 (m, 2H), 3.59 (m, 2H), 3.15 (m, 4H), 2.50 (m, 4H), 2.26 (s, 3H), 2.09 (m, 2H), 1.74 (m, 2H).

Example 13

5-(4-((3-methoxy-4-(4-(oxetan-3-yl)piperazin-1-yl)phenyl)amino)-1,3,5-triazin-2-yl)-2-((tetrahydro-2H-pyran-4-yl)oxy)benzonitrile

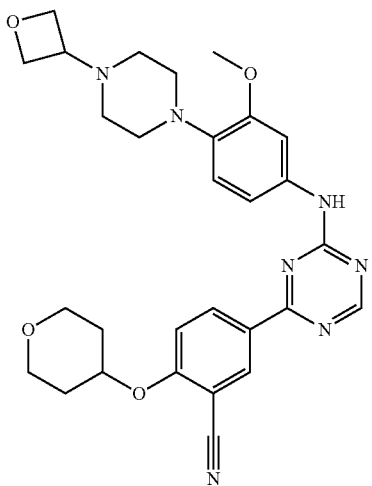 [SMILES: COc1cc(Nc2ncnc(-c3ccc(OC4CCOCC4)c(C#N)c3)n2)ccc1N1CCN(C2COC2)CC1]

A mixture of 1-fluoro-2-methoxy-4-nitrobenzene (1.0 g, 5.8 mmol), 1-(oxetan-3-yl)piperazine (0.91 g, 6.4 mmol), and potassium carbonate (1.6 g, 12 mmol) in N,N-dimethylformamide (9 mL) was stirred at 100° C. for 16 hours. The mixture was allowed to cool to room temperature. The supernatant was removed by pipette and concentrated under reduced pressure. This residue was combined with the solids and partitioned between ethyl acetate and water. The aqueous phase was extracted three times with ethyl acetate. The combined extracts were washed twice with water, once with saturated aqueous sodium chloride solution, dried over anhydrous magnesium sulfate, filtered, and concentrated to give 1-(2-methoxy-4-nitrophenyl)-4-(oxetan-3-yl)piperazine. LCMS-ESI+ (m/z): [M+H]+ calcd for $C_{14}H_{20}N_3O_4$: 294.1; found: 294.2

1-(2-methoxy-4-nitrophenyl)-4-(oxetan-3-yl)piperazine (1.6 g, 5.5 mmol) was taken up in a mixture of 2-methyltetrahydrofuran/methanol (1:1, 60 mL). The suspension was warmed until nearly homogeneous. After cooling to room temperature, the mixture was degassed before the addition of 10% palladium on charcoal (250 mg). The mixture was stirred under a balloon of hydrogen for three days, then filtered through a pad of Celite diatomaceous earth. The filtrate was concentrated under reduced pressure to provide 3-methoxy-4-(4-(oxetan-3-yl)piperazin-1-yl)aniline.
LCMS-ESI+ (m/z): [M+H]+ calcd for $C_{14}H_{22}N_3O_2$: 264.2; found: 264.2

To a solution of 2,4-dichloro-1,3,5-triazine (0.41 g, 2.7 mmol) in N,N-dimethylformamide (DMF, 6 mL) at 0° C. were added sequentially N,N-diisopropylethylamine (DIEA, 0.49 mL, 2.8 mmol) and 3-methoxy-4-(4-(oxetan-3-yl)piperazin-1-yl)aniline (0.65 g, 2.5 mmol). The mixture was stirred at 0° C. for 30 minutes and then allowed to warm to room temperature. The mixture was diluted with ethyl acetate and water. The aqueous phase was extracted twice with ethyl acetate. The combined extracts were washed once each with water and a saturated aqueous sodium chloride solution, then dried over anhydrous magnesium sulfate, filtered, and concentrated under reduced pressure. The residue was purified via flash chromatography on silica gel to provide 4-chloro-N-(3-methoxy-4-(4-(oxetan-3-yl)piperazin-1-yl)phenyl)-1,3,5-triazin-2-amine. LCMS-ESI+ (m/z): [M+H]+ calcd for $C_{17}H_{22}ClN_6O_2$: 377.1; found: 377.4 A mixture of 4-chloro-N-(3-methoxy-4-(4-(oxetan-3-yl)piperazin-1-yl)phenyl)-1,3,5-triazin-2-amine (0.15 g, 0.40 mmol), 2-((tetrahydro-2H-pyran-4-yl)oxy)-5-(4,4,5,5-tetramethyl-1,3,2-dioxaborolan-2-yl)benzonitrile (0.14 g, 0.44 mmol), and tetrakis(triphenylphosphine)palladium(0) (0.023 9, 5 mol %) in 1,2-dimethoxyethane (DME, 6 mL) was treated with 2M aqueous sodium carbonate solution (0.90 mL). The mixture was irradiated for 1 hour in a microwave reactor at 130° C. The crude mixture was purified by flash chromatography on silica gel, followed by prep HPLC (10-70% acetonitrile in water, 0.1% trifluoroacetic acid buffer). The concentrated residue was partitioned between ethyl acetate and saturated aqueous sodium hydrogen carbonate solution. The aqueous phase was extracted twice with ethyl acetate. The combined extracts were washed once with saturated aqueous sodium chloride solution, dried over anhydrous magnesium sulfate, filtered, and concentrated under reduced pressure to provide 5-(4-((3-methoxy-4-(4-(oxetan-3-yl)piperazin-1-yl)phenyl)amino)-1,3,5-triazin-2-yl)-2-((tetrahydro-2H-pyran-4-yl)oxy)benzonitrile. LCMS-ESI+ (m/z): [M+H]+ calcd for $C_{29}H_{34}N_7O_4$: 544.3; found: 544.2 .
$^1$H NMR (400 MHz, DMSO-d$_6$) δ 10.23 (br, 1H), 8.81 (s, 1H), 8.64 (d, J=2.1 Hz, 1H), 8.61 (dd, J=8.9, 2.2 Hz, 1H), 7.67 (bs, 1H), 7.61 (d, J=9.0 Hz, 1H), 7.45-7.18 (br, 1H), 6.94 (d, J=8.5 Hz, 1H), 4.98 (m, 1H), 4.60 (t, J=6.5 Hz, 2H), 4.50 (t, J=6.1 Hz, 2H), 3.99-3.76 (m, 5H), 3.59 (m, 2H), 3.51 (m, 1H), 3.36 (s, 3H), 3.02 (br, 4H), 2.45 (br, 4H), 2.18-2.03 (m, 2H), 1.73 (m, 2H).

Example 14

4-((4-(3-cyano-4-((tetrahydro-2H-pyran-4-yl)oxy)phenyl)-1,3,5-triazin-2-yl)amino)-N-methylbenzamide

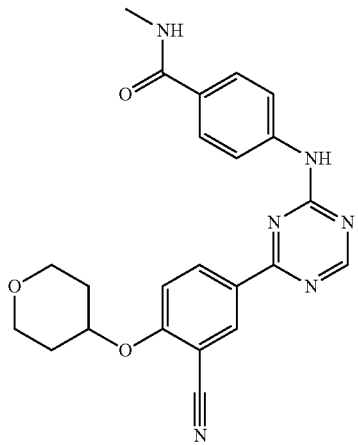 [SMILES: CNC(=O)c1ccc(Nc2ncnc(-c3ccc(OC4CCOCC4)c(C#N)c3)n2)cc1]

A suspension of 5-(4-chloro-1,3,5-triazin-2-yl)-2-((tetrahydro-2H-pyran-4-yl)oxy)benzonitrile (53 mg, 0.17 mmol) and 4-amino-N-methylbenzamide (30 mg, 0.20 mmol) in acetonitrile (2.5 mL) was treated with N,N-diisopropylethylamine (0.12 mL, 0.67 mmol). The mixture was heated in a microwave reactor for 120 minutes at 120° C. After cooling to room temperature, the solid was collected by filtration, washed with acetonitrile, and dried under house vacuum and then in a vacuum oven (60° C.) over $P_2O_5$ to provide 4-((4-(3-cyano-4-((tetrahydro-2H-pyran-4-yl)oxy)phenyl)-1,3,5-triazin-2-yl)amino)-N-methylbenzamide.
LCMS-ESI$^+$ (m/z): [M+H]$^+$ calcd for $C_{23}H_{23}N_6O_3$: 431.2; found: 431.0 $^1$H NMR (400 MHz, DMSO-d$_6$) δ 10.61 (s, 1H), 8.91 (s, 1H), 8.64 (m, 2H), 8.40 (m, 1H), 7.90 (m, 4H), 7.61 (d, J=9.5 Hz, 1H), 4.99 (m, 1H), 3.91 (m, 2H), 3.59 (m, 2H), 2.83 (d, J=4.4 Hz, 3H), 2.10 (m, 2H), 1.74 (m, 2H).

Example 15

(S)-2-((1-(2-hydroxypropanoyl)piperidin-4-yl)oxy)-5-(4-((4-(4-(oxetan-3-yl)piperazin-1-yl)phenyl)amino)-1,3,5-triazin-2-yl)benzonitrile

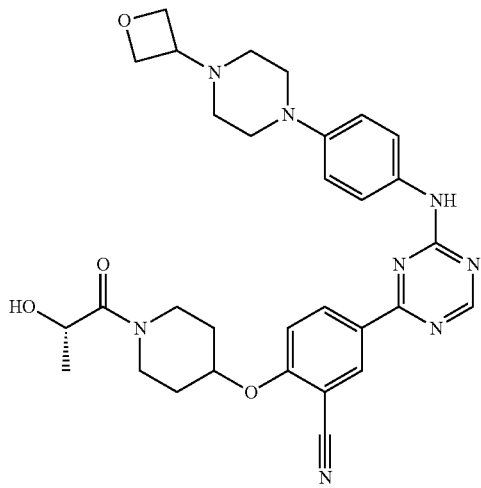

5-(4-((4-(4-(oxetan-3-yl)piperazin-1-yl)phenyl)amino)-1,3,5-triazin-2-yl)-2-(piperidin-4-yloxy)benzonitrile (78 mg, 0.15 mmol) and L-(−)-lactic acid (Sigma Aldrich, 21 mg, 0.23 mmol) were taken up as suspension in acetonitrile (3 mL). The mixture was treated successively with N,N-diisopropylethylamine (80 μL, 0.46 mmol) and N-[(dimethylamino)-1H-1,2,3-triazolo-[4,5-b]pyridin-1-ylmethylene]-N-methylmethanaminiumhexafluorophosphate N-oxide (HATU, 87 mg, 0.23 mmol). The mixture was stirred for two hours at room temperature and then purified by flash chromatography (silica gel) to provide (S)-2-((1-(2-hydroxypropanoyl)piperidin-4-yl)oxy)-5-(4-((4-(4-(oxetan-3-yl)piperazin-1-yl)phenyl)amino)-1,3,5-triazin-2-yl)benzonitrile.
LCMS-ESI $^+$ (m/z): [M+H]$^+$ calcd for $C_{31}H_{37}N_8O_4$: 585.3; found: 585.4
$^1$H NMR (400 MHz, DMSO-d$_6$) δ 10.16 (m, 1H), 8.77 (s, 1H), 8.70-8.45 (m, 2H), 7.60 (d, J=9.3 Hz, 2H), 6.99 (m, 2H), 5.07 (m, 1H), 4.97 (m, 1H), 4.61 (m, 2H), 4.56-4.46 (m, 3H), 3.94-3.68 (m, 2H), 3.68-3.43 (m, 3H), 3.17 (m, 4H), 2.51-2.39 (m, 4H), 2.12-1.94 (m, 2H), 1.84-1.63 (m, 2H), 1.24 (d, J=6.5 Hz, 3H).

Example 16

2-((1-(2-hydroxyacetyl)piperidin-4-yl)oxy)-5-(4-((4-(4-(oxetan-3-yl)piperazin-1-yl)phenyl)amino)-1,3,5-triazin-2-yl)benzonitrile

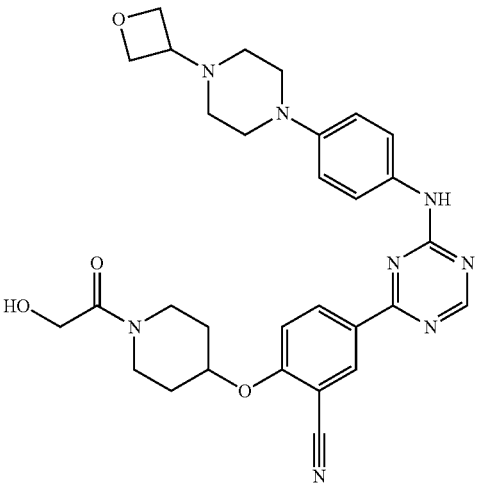

5-(4-((4-(4-(oxetan-3-yl)piperazin-1-yl)phenyl)amino)-1,3,5-triazin-2-yl)-2-(piperidin-4-yloxy)benzonitrile (57 g, 0.11 mmol), and glycolic acid (13 mg, 0.17 mmol) were take up as suspension in dichloromethane (3 mL). The mixture was treated successively with N,N-diisopropylethylamine (39 μL, 0.22 mmol) and N-[(dimethylamino)-1H-1,2,3-triazolo-[4,5-b]pyridin-1-ylmethylene]-N-methylmethanaminiumhexafluorophosphate N-oxide (HATU, 63 mg, 0.17 mmol). The suspension was stirred for three hours at room temperature and then purified by flash chromatography (silica gel) to provide 2-((1-(2-hydroxyacetyl)piperidin-4-yl)oxy)-5-(4-((4-(4-(oxetan-3-yl)piperazin-1-yl)phenyl)amino)-1,3,5-triazin-2-yl)benzonitrile.
LCMS-ESI$^+$ (m/z): [M+H]$^+$ calcd for $C_{30}H_{35}N_8O_4$: 571.3; found: 571.4
$^1$H NMR (400 MHz, DMSO-d$_6$) δ 10.18 (m, 1H), 8.77 (s, 1H), 8.60 (m, 2H), 7.61 (m, 2H), 7.01 (s, 2H), 5.04 (m, 1H), 4.60 (m, 3H), 4.52 (m, 2H), 4.17 (d, J=5.4 Hz, 2H), 3.75 (m, 1H), 3.61 (m, 1H), 3.49 (m, 2H), 3.38 (m, 1H), 3.18 (m, 4H), 2.45 (m, 4H), 2.06 (m, 2H), 1.76 (m, 2H).

Example 17

2-((1,1-dioxidotetrahydro-2H-thiopyran-4-yl)oxy)-5-(4-((4-(4-(oxetan-3-yl)piperazin-1-yl)phenyl)amino)-1,3,5-triazin-2-yl)benzonitrile

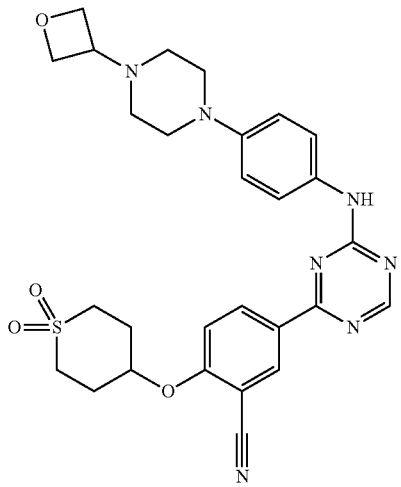 [SMILES: N#Cc1cc(-c2ncnc(Nc3ccc(N4CCN(C5COC5)CC4)cc3)n2)ccc1OC1CCS(=O)(=O)CC1]

Preparation of 5-bromo-2-((1,1-dioxidotetrahydro-2H-thiopyran-4-yl)oxy)benzonitrile:

A solution of 5-bromo-2-((tetrahydro-2H-thiopyran-4-yl)oxy)benzonitrile (1.2 g, 4.0 mmol) in dichloromethane (50 mL) was treated with calcium carbonate (1.6 g, 16 mmol). The resulting suspension was cooled in an ice-water bath. Meta-chloroperbenzoic acid (mCPBA, Sigma Aldrich, ≤77%, 2.3 g, 10 mmol) was added in a single portion. The mixture was stirred overnight while ice-water bath gradually regained room temperature. The mixture was filtered through a fritted funnel, eluting with dichloromethane. The filtrate was washed twice each with aqueous solutions of 5% sodium bisulfite and saturated sodium hydrogen carbonate. The organics were dried over anhydrous magnesium sulfate, filtered, and concentrated under reduced pressure to provide the desired material. LCMS-ESI$^+$ (m/z): [M+H]$^+$ calcd for $C_{12}H_{13}BrNO_3S$: 330.0; found: 329.9

Preparation of 2-((1,1-dioxidotetrahydro-2H-thiopyran-4-yl)oxy)-5-(4,4,5,5-tetramethyl-1,3,2-dioxaborolan-2-yl)benzonitrile:

A mixture of 5-bromo-2-((1,1-dioxidotetrahydro-2H-thiopyran-4-yl)oxy)benzonitrile (0.55 g, 1.7 mmol), bis(pinacolato)diboron (0.84 g, 3.3 mmol), potassium acetate (0.49 g, 5.0 mmol), and [1,1'-bis(diphenylphosphino)ferrocene]dichloropalladium(II) (0.12 g, 10 mol %) in 1,4-dioxane (6 mL) was heated at 90° C. overnight. LC/MS analysis indicated the consumption of the bromide starting material. The mixture was filtered through a pad of Celite diatomaceous earth and concentrated to dryness under reduced pressure to provide the desired material, which was carried forward without further purification. LCMS-ESI$^+$ (m/z): [M+H]$^+$ calcd for $C_{18}H_{25}BNO_5S$: 378.2; found: 378.1

Preparation of 2-((1,1-dioxidotetrahydro-2H-thiopyran-4-yl)oxy)-5-(4-((4-(4-(oxetan-3-yl)piperazin-1-yl)phenyl)amino)-1,3,5-triazin-2-yl)benzonitrile:

A mixture of 4-chloro-N-(4-(4-(oxetan-3-yl)piperazin-1-yl)phenyl)-1,3,5-triazin-2-amine (0.17 g, 0.49 mmol), crude 2-((1,1-dioxidotetrahydro-2H-thiopyran-4-yl)oxy)-5-(4,4,5,5-tetramethyl-1,3,2-dioxaborolan-2-yl)benzonitrile (1.6 mmol assumed), and tetrakis(triphenylphosphine)palladium (0) (0.042 g, 7.5 mol %) in 1,2-dimethoxyethane (DME, 6 mL) was treated with 2M aqueous sodium carbonate solution (1.1 mL). The mixture was irradiated for 1 hour in a microwave reactor at 130° C. The crude mixture was purified by flash chromatography on silica gel, followed by trituration with methanol, to provide 2-((1,1-dioxidotetrahydro-2H-thiopyran-4-yl)oxy)-5-(4-((4-(4-(oxetan-3-yl)piperazin-1-yl)phenyl)amino)-1,3,5-triazin-2-yl)benzonitrile. LCMS-ESI$^+$ (m/z): [M+H]$^+$ calcd for $C_{28}H_{31}N_7O_4S$: 562.2; found: 562.5. $^1$H NMR (400 MHz, DMSO-d$_6$) δ 10.16 (m, 1H), 8.78 (s, 1H), 8.61 (m, 2H), 7.60 (m, 2H), 7.01 (m, 2H), 5.11 (m, 1H), 4.61 (m, 2H), 4.52 (m, 2H), 3.49 (m, 1H), 3.27 (m, 4H), 3.19 (s, 4H), 2.46 (m, 4H), 2.36 (m, 4H).

Example 18

5-(4-((4-(piperazin-1-yl)phenyl)amino)-1,3,5-triazin-2-yl)-2-((tetrahydro-2H-pyran-4-yl)oxy)benzonitrile, trifluoroacetic acid salt

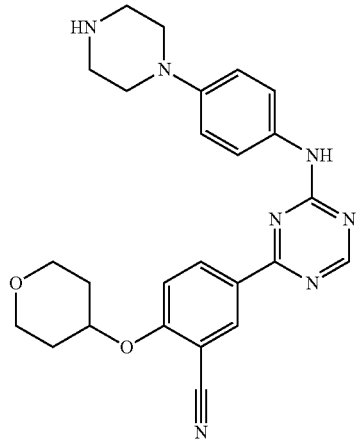 [SMILES: N#Cc1cc(-c2ncnc(Nc3ccc(N4CCNCC4)cc3)n2)ccc1OC1CCOCC1]

tert-butyl 4-(4-((4-(3-cyano-4-((tetrahydro-2H-pyran-4-yl)oxy)phenyl)-1,3,5-triazin-2-yl)amino)phenyl)piperazine-1-carboxylate (0.15 g, 0.27 mmol assumed) was taken up in dichloromethane (5 mL) and treated with trifluoroacetic acid (0.9 mL). After standing overnight at room temperature, the mixture was purified by prep HPLC (10-60% acetonitrile in water, 0.1% trifluoroacetic acid buffer) to provide 5-(4-((4-(piperazin-1-yl)phenyl)amino)-1,3,5-triazin-2-yl)-2-((tetrahydro-2H-pyran-4-yl)oxy)benzonitrile, trifluoroacetic acid salt. LCMS-ESI$^+$ (m/z): [M+H]$^+$ calcd for $C_{25}H_{28}N_7O_2$: 458.2; found: 458.3 $^1$H NMR (400 MHz, DMSO-d$_6$) δ 10.23 (m, 1H), 8.81 (m, 3H), 8.60 (m, 2H), 7.68 (m, 2H), 7.60 (d, J=9.1 Hz, 1H), 7.07 (s, 2H), 4.99 (m, 1H), 3.91 (m, 2H), 3.59 (m, 2H), 3.33 (m, 8H), 2.09 (m, 2H), 1.73 (m, 2H).

Example 19

5-(4-((4-(4-(oxetan-3-yl)piperazin-1-yl)phenyl)amino)-1,3,5-triazin-2-yl)-2-((tetrahydro-2H-thiopyran-4-yl)oxy)benzonitrile

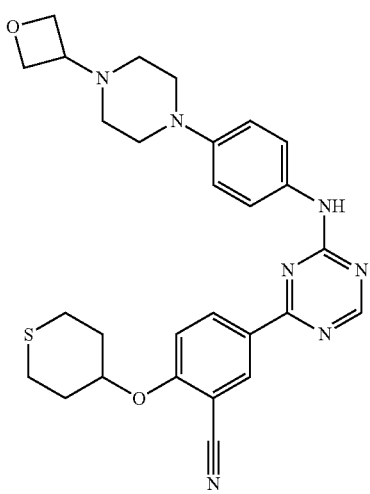

Preparation of 5-bromo-2-((tetrahydro-2H-thiopyran-4-yl)oxy)benzonitrile:

A solution of tetrahydrothiopyran-4-ol (Sigma Aldrich, 2.0 g, 17 mmol) in N,N-dimethylformamide (DMF, 30 mL) was treated with sodium hydride (60% in mineral oil, 0.68 g, 17 mmol) in a single portion at room temperature. The mixture was stirred for one hour at room temperature before 5-bromo-2-fluorobenzonitrile (2.8 g, 14 mmol) was added in a single portion. An additional volume of DMF (20 mL) was added. The mixture was stirred on a 50° C. heating block for two hours before it was poured onto ice (approximately 100 g), precipitating a solid that was then collected by vacuum filtration and dried in a vacuum oven over phosphorus pentoxide to provide the desired product. $^1$H NMR (400 MHz, DMSO-$d_6$) δ 8.03 (d, J=2.5 Hz, 1H), 7.82 (dd, J=9.1, 2.6 Hz, 1H), 7.31 (d, J=9.1 Hz, 1H), 4.74 (m, 1H), 2.83 (m, 2H), 2.63 (m, 2H), 2.16 (m, 2H), 1.90 (m, 2H).

Preparation of 2-((tetrahydro-2H-thiopyran-4-yl)oxy)-5-(4,4,5,5-tetramethyl-1,3,2-dioxaborolan-2-yl)benzonitrile:

A mixture of 5-bromo-2-((tetrahydro-2H-thiopyran-4-yl)oxy)benzonitrile (0.38 g, 1.3 mmol), bis(pinacolato)diboron (0.65 g, 2.5 mmol), potassium acetate (0.38 g, 3.8 mmol), and [1,1'-bis(diphenylphosphino)ferrocene]dichloropalladium(II) (0.095 g, 10 mol %) in 1,4-dioxane (6 mL) was heated at 90° C. overnight. LC/MS analysis indicated the consumption of the bromide starting material. The mixture was filtered through a pad of Celite diatomaceous earth and concentrated to dryness under reduced pressure to provide the putative desired material.

Preparation of 5-(4-((4-(4-(oxetan-3-yl)piperazin-1-yl)phenyl)amino)-1,3,5-triazin-2-yl)-2-((tetrahydro-2H-thiopyran-4-yl)oxy)benzonitrile:

A mixture of 4-chloro-N-(4-(4-(oxetan-3-yl)piperazin-1-yl)phenyl)-1,3,5-triazin-2-amine (0.13 g, 0.38 mmol), crude 2-((tetrahydro-2H-thiopyran-4-yl)oxy)-5-(4,4,5,5-tetramethyl-1,3,2-dioxaborolan-2-yl)benzonitrile (1.3 mmol assumed), and tetrakis(triphenylphosphine)palladium(0) (0.033 g, 7.5 mol %) in 1,2-dimethoxyethane (DME, 6 mL) was treated with 2M aqueous sodium carbonate solution (0.86 mL). The mixture was irradiated for 1 hour in a microwave reactor at 130° C. The crude mixture was purified by flash chromatography on silica gel, followed by recrystallization from methanol, to provide 5-(4-((4-(4-(oxetan-3-yl)piperazin-1-yl)phenyl)amino)-1,3,5-triazin-2-yl)-2-((tetrahydro-2H-thiopyran-4-yl)oxy)benzonitrile. LCMS-ESI$^+$ (m/z): [M+H]$^+$ calcd for $C_{28}H_{32}N_7O_2S$: 530.2; found: 530.3 $^1$H NMR (400 MHz, DMSO-$d_6$) δ 10.15 (m, 1H), 8.77 (s, 1H), 8.58 (m, 2H), 7.62 (m, 2H), 7.55 (d, J=9.2 Hz, 1H), 6.99 (d, J=10.7 Hz, 2H), 4.89 (m, 1H), 4.61 (m, 2H), 4.52 (m, 2H), 3.49 (m, 1H), 3.19 (m, 4H), 2.88 (m, 2H), 2.70 (m, 2H), 2.45 (m, 4H), 2.25 (m, 2H), 1.98 (m, 2H).

Example 20

5-(4-((3-methoxy-4-(1-(oxetan-3-yl)piperidin-4-yl)phenyl)amino)-1,3,5-triazin-2-yl)-2-((tetrahydro-2H-pyran-4-yl)oxy)benzonitrile

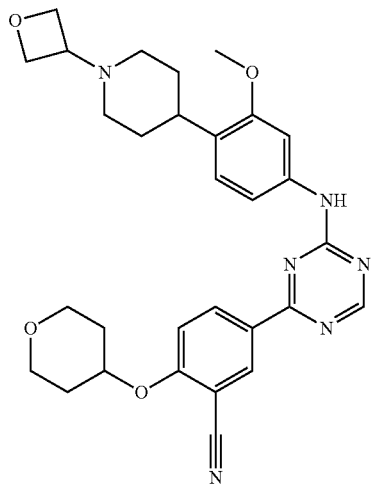

Preparation of tert-butyl 4-(2-methoxy-4-nitrophenyl)-5,6-dihydropyridine-1(2H)-carboxylate:

2-bromo-5-nitroanisole (5.0 g, 22 mmol), 4-(4,4,5,5-tetramethyl-[1,3,2]dioxaborolan-2-yl)-3,6-dihydro-2H-pyridine-1-carboxylic acid tert-butyl ester (Boron Molecular, 7.0 g, 23 mmol), tetrakis(triphenylphosphine)palladium(0) (1.5 g, 1.3 mmol), sodium carbonate aqueous solution (2M, 32 mL, 65 mmol), and 1,4-dioxane (75 mL) were combined in a sealed tube, and the mixture was heated at 80° C. for 3 days. After cooling to room temperature, the mixture was diluted with ethyl acetate and water. The aqueous phase was extracted three times with ethyl acetate. The combined extracts were washed once with a saturated aqueous sodium chloride solution, dried over anhydrous magnesium sulfate, filtered, and concentrated under reduced pressure. The crude residue was purified by flash chromatography (silica gel) to provide the desired material. LCMS-ESI$^+$ (m/z): [M−tBu.+H]$^+$ calcd for $C_{13}H_{15}N_2O_5$: 279.1; found: 279.0.

Preparation of 4-(2-methoxy-4-nitrophenyl)-1,2,3,6-tetrahydropyridin-1-ium 2,2,2-trifluoroacetate:

tert-butyl 4-(2-methoxy-4-nitrophenyl)-5,6-dihydropyridine-1(2H)-carboxylate (1.3 g, 3.8 mmol) was taken up in dichloromethane (6 mL) and treated with trifluoroacetic acid (5.8 mL, 75 mmol). The mixture was allowed to stand at room temperature for 3 hours and then concentrated under reduced pressure. The residue was reconstituted in dichloromethane and concentrated. This cycle was repeated three times with dichloromethane, then once with diethyl ether, to provide the desired material, which was carried forward without further purification. LCMS-ESI+ (m/z): [M+H]+ calcd for $C_{12}H_{15}N_2O_3$: 235.1; found: 234.9.

Preparation of 4-(2-methoxy-4-nitrophenyl)-1-(oxetan-3-yl)-1,2,3,6-tetrahydropyridine:

3-iodooxetane (0.66 mL, 7.5 mmol) was added via syringe to a suspension of 4-(2-methoxy-4-nitrophenyl)-1,2,3,6-tetrahydropyridin-1-ium 2,2,2-trifluoroacetate (3.8 mmol assumed) and potassium carbonate (2.6 g, 19 mmol) in acetonitrile. Mixture stirred overnight with heating on a 130° C. block. After cooling to room temperature, the mixture was filtered though a pad of Celite diatomaceous earth, eluting with dichloromethane and acetonitrile. The filtrate was concentrated to dryness under reduced pressure and then purified by flash chromatography (silica gel) to provide the desired material. LCMS-ESI+ (m/z): [M+H]+ calcd for $C_{15}H_{19}N_2O_4$: 291.1; found: 291.1.

Preparation of 3-methoxy-4-(1-(oxetan-3-yl)piperidin-4-yl)aniline:

4-(2-methoxy-4-nitrophenyl)-1-(oxetan-3-yl)-1,2,3,6-tetrahydropyridine (0.64 g, 2.2 mmol) was taken up in methanol (~50 mL) in a Parr bottle. After being degassed, the mixture was treated with 10% palladium on charcoal (150 mg) and shaken overnight under hydrogen (55 psi). The mixture was filtered through a pad of Celite diatomaceous earth, and the filtrate was concentrated under reduced pressure to provide the desired material. LCMS-ESI+ (m/z): [M+H]+ calcd for $C_{15}H_{23}N_2O_2$: 263.2; found: 263.1

Preparation of 5-(4-((3-methoxy-4-(1-(oxetan-3-yl)piperidin-4-yl)phenyl)amino)-1,3,5-triazin-2-yl)-2-((tetrahydro-2H-pyran-4-yl)oxy)benzonitrile:

A suspension of 5-(4-chloro-1,3,5-triazin-2-yl)-2-((tetrahydro-2H-pyran-4-yl)oxy)benzonitrile (100 mg, 0.32 mmol) and 3-methoxy-4-(1-(oxetan-3-yl)piperidin-4-yl)aniline (110 mg, 0.41 mmol) in acetonitrile (3 mL) was treated with N,N-diisopropylethylamine (0.22 mL, 1.3 mmol). The mixture was heated in a microwave reactor for 20 minutes at 80° C. The cooled reaction mixture was purified by flash chromatography (silica gel) and then triturated with methanol to provide 5-(4-((3-methoxy-4-(1-(oxetan-3-yl)piperidin-4-yl)phenyl)amino)-1,3,5-triazin-2-yl)-2-((tetrahydro-2H-pyran-4-yl)oxy)benzonitrile. LCMS-ESI+ (m/z): [M+H]+ calcd for $C_{30}H_{35}N_6O_4$: 543.3; found: 543.4

$^1$H NMR (400 MHz, DMSO-$d_6$) δ 10.34 (bs, 1H), 8.84 (s, 1H), 8.63 (m, 2H), 7.74 (br, 1H), 7.62 (m, 1H), 7.42 (m, 1H), 7.25 (m, 1H), 5.00 (m, 1H), 4.58 (m, 2H), 4.49 (m, 2H), 4.00-3.78 (m, 5H), 3.59 (m, 2H), 3.44 (m, 1H), 3.02-2.74 (m, 3H), 2.09 (m, 2H), 1.89 (m, 2H), 1.73 (m, 6H).

Example 21

4-((4-(3-cyano-4-((tetrahydro-2H-pyran-4-yl)oxy)phenyl)-1,3,5-triazin-2-yl)amino)-2-methoxybenzamide

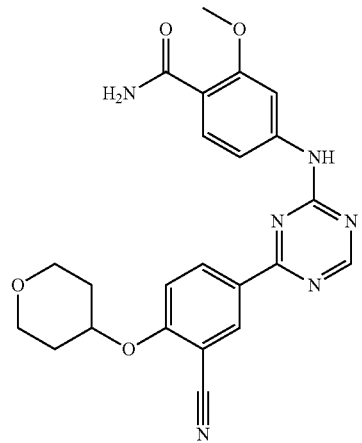 [SMILES: COc1cc(Nc2ncnc(-c3ccc(OC4CCOCC4)c(C#N)c3)n2)ccc1C(N)=O]

Preparation of 4-amino-2-methoxybenzamide: 2-methoxy-4-nitrobenzonitrile (1.0 g, 5.6 mmol) was taken up as a suspension in ethanol/water (3:1, 15 mL). Hydrido (dimethylphosphinous acid-kP)[hydrogen bis(dimethylphosphinito-kP)]platinum(II) (Strem Chemicals, Inc., 24 mg, 56 µmol) was added. The mixture was stirred overnight in a sealed vessel at 120° C. After cooling to room temperature, the suspension was concentrated to dryness under reduced pressure to provide the desired carboxamide, which was carried forward without further purification.

The concentrated residue was diluted with methanol and 2-methyltetrahydrofuran. The suspension was warmed with a heat gun and was then allowed to cool to room temperature. The mixture was degassed and then treated with 10% palladium on carbon (catalytic). The mixture was shaken under 50 psi hydrogen for 3 days. The catalyst was removed by filtration through a pad of Celite diatomaceous earth. The filtrate was concentrated under reduced pressure to provide 4-amino-2-methoxybenzamide. LCMS-ESI+ (m/z): [M+H]+ calcd for $C_8H_{11}N_2O_2$: 167.1; found: 167.0.

Preparation of 4-((4-chloro-1,3,5-triazin-2-yl)amino)-2-methoxybenzamide:

To a solution of 2,4-dichloro-1,3,5-triazine (0.40 g, 2.6 mmol) in N,N-dimethylformamide (DMF, 6 mL) at 0° C. were added sequentially N,N-diisopropylethylamine (DIEA, 0.48 mL, 2.7 mmol) 4-amino-2-methoxybenzamide (0.40 g, 2.4 mmol), and the mixture was stirred at 0° C. and then allowed to warm to room temperature. The mixture was diluted with ethyl acetate and water. A small volume of tetrahydrofuran was added. The biphasic mixture was filtered, providing 4-((4-chloro-1,3,5-triazin-2-yl)amino)-2-methoxybenzamide. Additional desired material was obtained by separation of the filtered mixture and extraction of the aqueous phase twice with ethyl acetate. The combined organics were filtered, washed once with saturated aqueous sodium chloride solution, and dried over anhydrous magnesium sulfate, filtered, and concentrated under reduced pressure to provide 4-((4-chloro-1,3,5-triazin-2-yl)amino)-2-methoxybenzamide. LCMS-ESI+ (m/z): [M+H]+ calcd for $C_{11}H_{11}ClN_6O_2$: 280.1; found: 280.0.

Preparation of 4-((4-(3-cyano-4-((tetrahydro-2H-pyran-4-yl)oxy)phenyl)-1,3,5-triazin-2-yl)amino)-2-methoxybenzamide:

A mixture of 4-((4-chloro-1,3,5-triazin-2-yl)amino)-2-methoxybenzamide (0.33 g, 1.2 mmol), 2-((tetrahydro-2H-pyran-4-yl)oxy)-5-(4,4,5,5-tetramethyl-1,3,2-dioxaborolan-2-yl)benzonitrile (0.31 g, 0.94 mmol), tetrakis(triphenylphosphine)palladium(0) (0.10 g, 7.5 mol %) in 1,2-dimethoxyethane (DME, 3 mL) was treated with 2M aqueous sodium carbonate solution (2.6 mL). The mixture was irradiated for 1 hour in a microwave reactor at 130° C. The crude mixture was purified by flash chromatography on silica gel to provide 4-((4-(3-cyano-4-((tetrahydro-2H-pyran-4-yl)oxy)phenyl)-1,3,5-triazin-2-yl)amino)-2-methoxybenzamide. LCMS-ESI$^+$ (m/z): [M+H]$^+$ calcd for $C_{23}H_{23}N_6O_4$: 447.2; found: 447.1 $^1$H NMR (400 MHz, DMSO-d$_6$) δ 10.62 (s, 1H), 8.93 (s, 1H), 8.65 (m, 2H), 7.92 (d, J=8.5 Hz, 1H), 7.62 (m, 2H), 7.46 (m, 2H), 4.99 (m, 1H), 4.02 (s, 3H), 3.92 (m, 2H), 3.60 (m, 2H), 2.09 (m, 2H), 1.74 (m, 2H).

Example 22

(R)-2-((1-(2-hydroxyacetyl)pyrrolidin-3-yl)oxy)-5-(4-((3-methoxy-4-(4-(oxetan-3-yl)piperazin-1-yl)phenyl)amino)-1,3,5-triazin-2-yl)benzonitrile

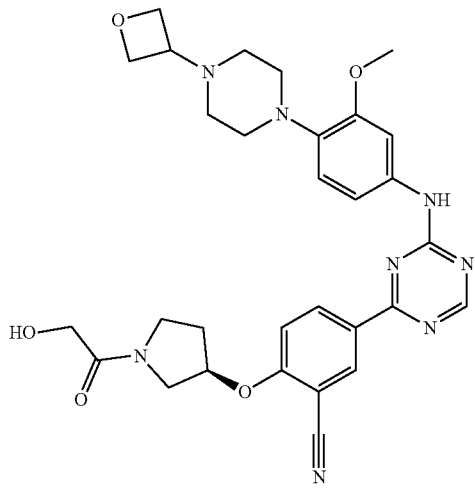 [SMILES: COc1cc(Nc2ncnc(-c3ccc(O[C@@H]4CCN(C(=O)CO)C4)c(C#N)c3)n2)ccc1N1CCN(C2COC2)CC1]

Preparation of (R)-tert-butyl 3-(2-cyano-4-(4-((3-methoxy-4-(4-(oxetan-3-yl)piperazin-1-yl)phenyl)amino)-1,3,5-triazin-2-yl)phenoxy)pyrrolidine-1-carboxylate:

A mixture of 4-chloro-N-(3-methoxy-4-(4-(oxetan-3-yl)piperazin-1-yl)phenyl)-1,3,5-triazin-2-amine (0.20 g, 0.53 mmol), (R)-tert-butyl 3-(2-cyano-4-(4,4,5,5-tetramethyl-1,3,2-dioxaborolan-2-yl)phenoxy)pyrrolidine-1-carboxylate (0.24 g, 0.58 mmol), and tetrakis(triphenylphosphine)palladium(0) (0.046 g, 7.5 mol %) in 1,2-dimethoxyethane (DME, 3 mL) was treated with 2M aqueous sodium carbonate solution (1.2 mL). The mixture was irradiated for 1 hour in a microwave reactor at 130° C. The layers of the crude mixture were separated. The aqueous phase was extracted three times with dichloromethane. The combined organics were dried over anhydrous magnesium sulfate, filtered, and concentrated under reduced pressure to provide the desired material, which was carried forward without further purification.

LCMS-ESI$^+$ (m/z): [M+H]$^+$ calcd for $C_{33}H_{41}N_8O_5$: 629.3; found: 629.2.

Preparation of (R)-5-(4-((3-methoxy-4-(4-(oxetan-3-yl)piperazin-1-yl)phenyl)amino)-1,3,5-triazin-2-yl)-2-(pyrrolidin-3-yloxy)benzonitrile:

Crude (R)-tert-butyl 3-(2-cyano-4-(4-((3-methoxy-4-(4-(oxetan-3-yl)piperazin-1-yl)phenyl)amino)-1,3,5-triazin-2-yl)phenoxy)pyrrolidine-1-carboxylate (0.53 mmol assumed) was taken up in dichloromethane (8 mL) and treated with trifluoroacetic acid (2 mL). After 30 minutes, the mixture was concentrated under reduced pressure, and the residue was purified by flash chromatography (silica gel) to provide the desired material. LCMS-ESI$^+$ (m/z): [M+H]$^+$ calcd for $C_{28}H_{33}N_8O_3$: 529.3; found: 529.3.

Preparation of (R)-2-((1-(2-hydroxyacetyl)pyrrolidin-3-yl)oxy)-5-(4-((3-methoxy-4-(4-(oxetan-3-yl)piperazin-1-yl)phenyl)amino)-1,3,5-triazin-2-yl)benzonitrile:

(R)-5-(4-((3-methoxy-4-(4-(oxetan-3-yl)piperazin-1-yl)phenyl)amino)-1,3,5-triazin-2-yl)-2-(pyrrolidin-3-yloxy)benzonitrile (60 mg, 0.11 mmol) and glycolic acid (13 mg, 0.17 mmol) were taken up as suspension in dichloromethane (3 mL). The mixture was treated successively with N,N-diisopropylethylamine (59 μL, 0.34 mmol) and N-[(dimethylamino)-1H-1,2,3-triazolo-[4,5-b]pyridin-1-ylmethylene]-N-methylmethanaminiumhexafluorophosphate N-oxide (HATU, 65 mg, 0.17 mmol). The mixture stood overnight at room temperature before being purified by flash chromatography (silica gel) to provide (R)-2-((1-(2-hydroxyacetyl)pyrrolidin-3-yl)oxy)-5-(4-((3-methoxy-4-(4-(oxetan-3-yl)piperazin-1-yl)phenyl)amino)-1,3,5-triazin-2-yl)benzonitrile. LCMS-ESI$^+$ (m/z): [M+H]$^+$ calcd for $C_{30}H_{35}N_8O_5$: 587.3; found: 587.4 $^1$H NMR (400 MHz, DMSO-d$_6$) δ 10.25 (m, 1H), 8.81 (d, J=3.9 Hz, 1H), 8.64 (m, 2H), 7.78-7.51 (m, 2H), 7.33 (br, 1H), 6.99 (m, 1H), 5.41 (m, 1H), 4.68 (m, 2H), 4.60 (m, 2H), 4.51 (m, 2H), 4.07 (m, 1H), 3.86 (m, 4H), 3.70 (m, 2H), 3.49 (m, 1H), 3.35 (m, 1H), 3.02 (m, 4H), 2.45 (m, 4H), 2.41-2.10 (m, 2H).

Example 23

(S)-2-((1-(2-hydroxypropanoyl)piperidin-4-yl)oxy)-5-(4-((4-(1-(oxetan-3-yl)piperidin-4-yl)phenyl)amino)-1,3,5-triazin-2-yl)benzonitrile

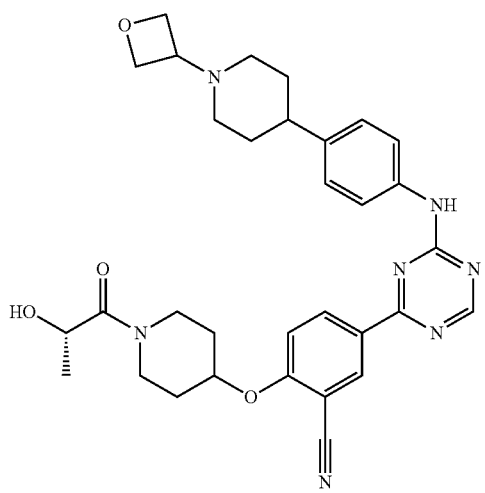 [SMILES: C[C@H](O)C(=O)N1CCC(Oc2ccc(-c3ncnc(Nc4ccc(C5CCN(C6COC6)CC5)cc4)n3)cc2C#N)CC1]

5-(4-((4-(1-(oxetan-3-yl)piperidin-4-yl)phenyl)amino)-1,3,5-triazin-2-yl)-2-(piperidin-4-yloxy)benzonitrile (60 mg, 0.12 mmol) and L-(−)-lactic acid (Sigma Aldrich, 16 mg, 0.18 mmol) were taken up as suspension in acetonitrile (3 mL). The mixture was treated successively with N,N-diisopropylethylamine (61 μL, 0.35 mmol) and N-[(dimethylamino)-1H-1,2,3-triazolo-[4,5-b]pyridin-1-ylmethylene]-N-methylmethanaminiumhexafluorophosphate N-oxide (HATU, 67 mg, 0.18 mmol). The suspension was sonicated for a few minutes and diluted with dichloromethane (2 mL). The mixture stood overnight at room temperature before being purified by flash chromatography (silica gel) to provide (S)-2-((1-(2-hydroxypropanoyl)piperidin-4-yl)oxy)-5-(4-((4-(1-(oxetan-3-yl)piperidin-4-yl)phenyl)amino)-1,3,5-triazin-2-yl)benzonitrile. LCMS-ESI+ (m/z): [M+H]+ calcd for $C_{32}H_{38}N_7O_4$: 584.3; found: 584.4.

$^1$H NMR (400 MHz, DMSO-d$_6$) δ 10.33 (s, 1H), 8.81 (m, 1H), 8.60 (m, 2H), 7.72 (m, 2H), 7.60 (m, 1H), 7.31 (m, 2H), 5.18-4.91 (m, 3H), 4.85 (t, J=7.2 Hz, 1H), 4.60 (t, J=6.5 Hz, 2H), 4.51 (m, 3H), 3.80 (m, 2H), 3.59 (m, 3H), 2.91 (m, 2H), 2.33 (m, 1H), 2.04 (m, 4H), 1.89-1.61 (m, 4H), 1.24 (dd, J=6.6, 1.9 Hz, 3H).

Example 24

2-((tetrahydro-2H-pyran-4-yl)oxy)-5-(4-((3,4,5-trimethoxyphenyl)amino)-1,3,5-triazin-2-yl)benzonitrile

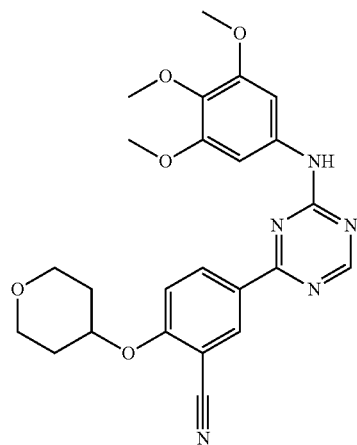 [SMILES: COc1cc(Nc2ncnc(-c3ccc(OC4CCOCC4)c(C#N)c3)n2)cc(OC)c1OC]

A suspension of 5-(4-chloro-1,3,5-triazin-2-yl)-2-((tetrahydro-2H-pyran-4-yl)oxy)benzonitrile (100 mg, 0.32 mmol) and 3,4,5-trimethoxyaniline (69 mg, 0.38 mmol) in acetonitrile (3 mL) was treated with N,N-diisopropylethylamine (0.22 mL, 1.3 mmol). The mixture was heated in a microwave reactor for 20 minutes at 80° C. The precipitated solid was collected by filtration, washed with methanol, and dried under vacuum to provide the desired material. LCMS-ESI+ (m/z): [M+H]+ calcd for $C_{24}H_{26}N_5O_5$: 464.2; found: 464.1

$^1$H NMR (400 MHz, DMSO-d$_6$) δ 10.29 (bs, 1H), 8.84 (s, 1H), 8.66 (d, J=2.2 Hz, 1H), 8.62 (dd, J=9.0, 2.2 Hz, 1H), 7.61 (d, J=9.1 Hz, 1H), 7.28 (br, 2H), 4.99 (m, 1H), 4.03-3.77 (m, 8H), 3.70 (s, 3H), 3.59 (m, 2H), 2.09 (m, 2H), 1.74 (m, 2H).

Example 25 and Example 26

5-(4-((4-(4-(oxetan-3-yl)piperazin-1-yl)phenyl)amino)-1,3,5-triazin-2-yl)-2-((1-oxidotetrahydro-2H-thiopyran-4-yl)oxy)benzonitrile, (non-polar diastereomer 1) and 5-(4-((4-(4-(oxetan-3-yl)piperazin-1-yl)phenyl)amino)-1,3,5-triazin-2-yl)-2-((1-oxidotetrahydro-2H-thiopyran-4-yl)oxy)benzonitrile, (polar diastereomer 2)

5-(4-((4-(4-(oxetan-3-yl)piperazin-1-yl)phenyl)amino)-1,3,5-triazin-2-yl)-2-((1-oxidotetrahydro-2H-thiopyran-4-yl)oxy)benzonitrile, diastereomer 1

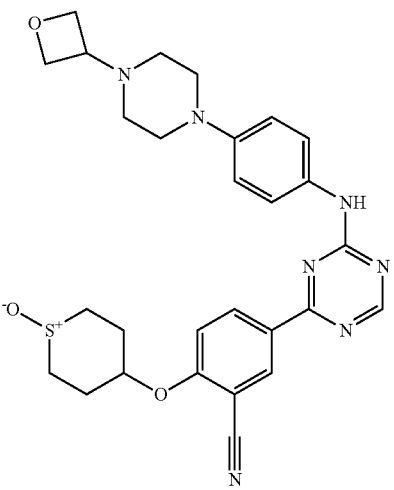

Preparation of 2-((1-oxidotetrahydro-2H-thiopyran-4-yl)oxy)-5-(4,4,5,5-tetramethyl-1,3,2-dioxaborolan-2-yl)benzonitrile (1:1 mixture of disastereomers): 5-bromo-2-((tetrahydro-2H-thiopyran-4-yl)oxy)benzonitrile (0.59 g, 2.0 mmol) was taken up in acetonitrile (5 mL) by warming with a heat gun. After cooling, the mixture was treated with iron (III) chloride (10 mg, 3 mol %). The mixture was stirred for about 5 minutes at room temperature before the addition of periodic acid (0.50 g, 2.2 mmol) in a single portion. After 15 minutes of stirring, the mixture was quenched by the addition of 25% wt/wt aqueous sodium thiosulfate solution (Na$_2$S$_2$O$_3$, ~10 mL). The suspension was allowed to stir for 10 minutes, then was extracted three times with dichloromethane. After first extraction, the mixture was filtered through a pad of Celite diatomaceous earth. The combined extracts were dried over anhydrous magnesium sulfate, filtered, concentrated to dryness under reduced pressure to give the desired product as a 1:1 mixture of diasteromers. LCMS-ESI+ (m/z): [M+H]+ calcd for $C_{12}H_{13}BrNO_2S$: 314.0; found: 314.0.

Preparation of 2-((1-oxidotetrahydro-2H-thiopyran-4-yl)oxy)-5-(4,4,5,5-tetramethyl-1,3,2-dioxaborolan-2-yl)benzonitrile (1:1 mixture of diastereomers):

A mixture of 2-((1-oxidotetrahydro-2H-thiopyran-4-yl)oxy)-5-(4,4,5,5-tetramethyl-1,3,2-dioxaborolan-2-yl)benzonitrile (1:1 mixture of disastereomers, 0.60 g, 1.9 mmol), bis(pinacolato)diboron (0.97 g, 3.8 mmol), potassium acetate (0.56 g, 5.7 mmol), and [1,1'-bis(diphenylphosphino)ferrocene]dichloropalladium(II) (0.14 g, 10 mol %) in 1,4-dioxane (6 mL) was heated at 90° C. overnight. LC/MS analysis indicated an incomplete conversion. To the mixture was added additional and [1,1'-bis(diphenylphosphino)ferrocene]dichloropalladium(II) (1.3 g, 90 mol %) The mixture continued to heat for another 4 hours, at which time LC/MS analysis indicated a complete conversion. The mixture was filtered through a pad of Celite diatomaceous earth, and the filtrate was concentrated under reduced pressure to provide the desired product as a 1:1 mixture of diasteromers, which was carried forward without further purification. LCMS-ESI$^+$ (m/z): [M+H]$^+$ calcd for C$_{18}$H$_{25}$BNO$_4$S: 362.2; found: 362.2

Preparation of 5-(4-((4-(4-(oxetan-3-yl)piperazin-1-yl)phenyl)amino)-1,3,5-triazin-2-yl)-2-((1-oxidotetrahydro-2H-thiopyran-4-yl)oxy)benzonitrile, diastereomer 1:

A mixture of 4-chloro-N-(4-(4-(oxetan-3-yl)piperazin-1-yl)phenyl)-1,3,5-triazin-2-amine (0.40 g, 1.2 mmol), crude 2-((1-oxidotetrahydro-2H-thiopyran-4-yl)oxy)-5-(4,4,5,5-tetramethyl-1,3,2-dioxaborolan-2-yl)benzonitrile (1:1 mixture of diastereomers, 1.9 mmol assumed), and tetrakis(triphenylphosphine)palladium(0) (0.10 g, 7.5 mol %) in 1,2-dimethoxyethane (DME, 8 mL) was treated with 2M aqueous sodium carbonate solution (2.6 mL). The mixture was irradiated for 1 hour in a microwave reactor at 130° C. The crude mixture was purified by flash chromatography on silica gel to provide two separable diastereomers of unknown relative configuration. Each component was separately flash chromatographed a second time and then triturated with methanol to provide 5-(4-((4-(4-(oxetan-3-yl)piperazin-1-yl)phenyl)amino)-1,3,5-triazin-2-yl)-2-((1-oxidotetrahydro-2H-thiopyran-4-yl)oxy)benzonitrile, non-polar diastereomer 1 and 5-(4-((4-(4-(oxetan-3-yl)piperazin-1-yl)phenyl)amino)-1,3,5-triazin-2-yl)-2-((1-oxidotetrahydro-2H-thiopyran-4-yl)oxy)benzonitrile, polar diastereomer 2. 5-(4-((4-(4-(oxetan-3-yl)piperazin-1-yl)phenyl)amino)-1,3,5-triazin-2-yl)-2-((1-oxidotetrahydro-2H-thiopyran-4-yl)oxy)benzonitrile, non-polar diastereomer 1: 5-(4-((4-(4-(oxetan-3-yl)piperazin-1-yl)phenyl)amino)-1,3,5-triazin-2-yl)-2-((1-oxidotetrahydro-2H-thiopyran-4-yl)oxy)benzonitrile, non-polar diastereomer 1: LCMS-ESI$^+$ (m/z): [M+H]$^+$ calcd for C$_{28}$H$_{32}$N$_7$O$_3$S: 546.3; found: 546.3 $^1$H NMR (400 MHz, DMSO-d$_6$) δ 10.16 (m, 1H), 8.78 (s, 1H), 8.61 (m, 2H), 7.61 (m, 3H), 7.02 (d, J=10.4 Hz, 2H), 5.09 (m, 1H), 4.61 (m, 2H), 4.52 (m, 2H), 3.49 (m, 1H), 3.18 (m, 4H), 2.90 (m, 4H), 2.46 (m, 6H), 2.04 (m, 2H). 5-(4-((4-(4-(oxetan-3-yl)piperazin-1-yl)phenyl)amino)-1,3,5-triazin-2-yl)-2-((1-oxidotetrahydro-2H-thiopyran-4-yl)oxy)benzonitrile, polar diastereomer 2: LCMS-ESI$^+$ (m/z): [M+H]$^+$ calcd for C$_{28}$H$_{32}$N$_7$O$_3$S: 546.3; found: 546.3 $^1$H NMR (400 MHz, DMSO-d$_6$) δ 10.16 (m, 1H), 8.78 (s, 1H), 8.60 (m, 2H), 7.62 (m, 3H), 6.99 (d, J=11.6 Hz, 2H), 4.88 (m, 1H), 4.61 (m, 2H), 4.52 (m, 2H), 3.49 (m, 1H), 3.19 (m, 4H), 3.10-2.87 (m, 4H), 2.45 (m, 4H), 2.31 (m, 2H), 2.14 (m, 2H).

Example 27

5-(4-((3-fluoro-4-(4-(oxetan-3-yl)piperazin-1-yl)phenyl)amino)-1,3,5-triazin-2-yl)-2-((tetrahydro-2H-pyran-4-yl)oxy)benzonitrile

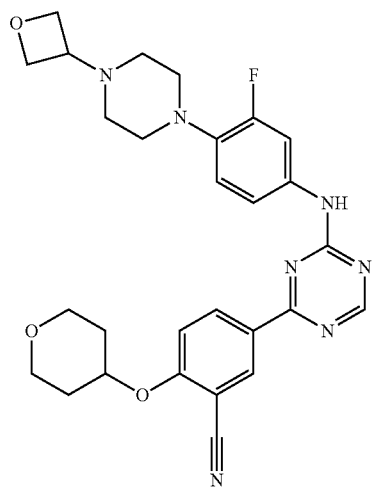 [SMILES: N#Cc1cc(-c2ncnc(Nc3ccc(N4CCN(C5COC5)CC4)c(F)c3)n2)ccc1OC1CCOCC1]

A mixture of 3,4-difluoronitrobenzene (1.0 g, 6.3 mmol) and 1-(oxetan-3-yl)piperazine (1.1 g, 7.5 mmol) in acetonitrile (100 mL) was refluxed (95° C. heating block) with stirring for 16 hours. Reaction mixture was concentrated to dryness under reduced pressure. The resulting solid was collected by filtration, washed with acetonitrile, and dried under vacuum to provide 1-(2-fluoro-4-nitrophenyl)-4-(oxetan-3-yl)piperazine. LCMS-ESI$^+$ (m/z): [M+H]$^+$ calcd for C$_{13}$H$_{17}$FN$_3$O$_3$: 282.1; found: 282.1

1-(2-fluoro-4-nitrophenyl)-4-(oxetan-3-yl)piperazine (1.6 g, 5.7 mmol) was taken up in a mixture of 2-methyltetrahydrofuran and methanol. The mixture was degassed, treated with 10% palladium on carbon (250 mg), and shaken for three days under hydrogen (30 psi). The suspension was filtered through a pad of Celite diatomaceous earth and concentrated under reduced pressure to provide 3-fluoro-4-(4-(oxetan-3-yl)piperazin-1-yl)aniline. LCMS-ESI$^+$ (m/z): [M+H]$^+$ calcd for C$_{13}$H$_{19}$FN$_3$O: 252.1; found: 252.1. To a solution of 2,4-dichloro-1,3,5-triazine (0.44 g, 2.9 mmol) in N,N-dimethylformamide (DMF, 5 mL) at 0° C. were added N,N-diisopropylethylamine (DIEA, 0.53 mL, 3.0 mmol), followed by a solution of 3-fluoro-4-(4-(oxetan-3-yl)piperazin-1-yl)aniline in DMF (10 mL). The mixture was stirred at 0° C. for 30 minutes and then allowed to warm to room temperature. The mixture was partitioned between ethyl acetate and water. The layers were separated and aqueous phase was extracted twice with ethyl acetate. The combined extracts were washed once each with water and saturated aqueous sodium chloride solution, and then dried over anhydrous magnesium sulfate, filtered, and concentrated under reduced pressure. The residue was purified by flash chromatography on silica gel to provide 4-chloro-N-(3-fluoro-4-(4-(oxetan-3-yl)piperazin-1-yl)phenyl)-1,3,5-triazin-2-amine. LCMS-ESI$^+$ (m/z): [M+H]$^+$ calcd for C$_{16}$H$_{19}$ClFN$_6$O: 365.1; found: 365.3.

A mixture of 4-chloro-N-(3-fluoro-4-(4-(oxetan-3-yl)piperazin-1-yl)phenyl)-1,3,5-triazin-2-amine (0.16 g, 0.44 mmol), 2-((tetrahydro-2H-pyran-4-yl)oxy)-5-(4,4,5,5-tetramethyl-1,3,2-dioxaborolan-2-yl)benzonitrile (0.16 g, 0.49 mmol), palladium (II) acetate (0.01 g, 10 mol %), and triphenylphosphine (0.035 g, 0.13 mmol) in 1,2-dimethoxyethane (DME, 6 mL) was treated with 2M aqueous sodium carbonate solution (1.0 mL). The mixture was irradiated for 1 hour in a microwave reactor at 130° C. The crude mixture was purified by flash chromatography on silica gel to furnish 5-(4-((3-fluoro-4-(4-(oxetan-3-yl)piperazin-1-yl)phenyl) amino)-1,3,5-triazin-2-yl)-2-((tetrahydro-2H-pyran-4-yl) oxy)benzonitrile. LCMS-ESI$^+$ (m/z): [M+H]$^+$ calcd for $C_{28}H_{31}FN_7O_3$: 532.2; found: 532.5 $^1$H NMR (400 MHz, DMSO-d$_6$) δ 10.47 (s, 1H), 8.87 (s, 1H), 8.78-8.47 (m, 2H), 7.79 (m, 1H), 7.62 (d, J=9.4 Hz, 1H), 7.53 (s, 1H), 7.31-7.07 (m, 1H), 5.00 (tt, J=8.0, 4.0 Hz, 1H), 4.92-4.69 (m, 4H), 4.53 (m, 1H), 3.91 (m, 2H), 3.60 (m, 2H), 3.55-3.00 (m, 8H), 2.09 (m, 2H), 1.74 (m, 2H).

Example 28

5-[4-[4-[4-(oxetan-3-yl)piperazin-1-yl]anilino]-1,3,5-triazin-2-yl]-2-(2-oxopyrrolidin-1-yl)benzonitrile

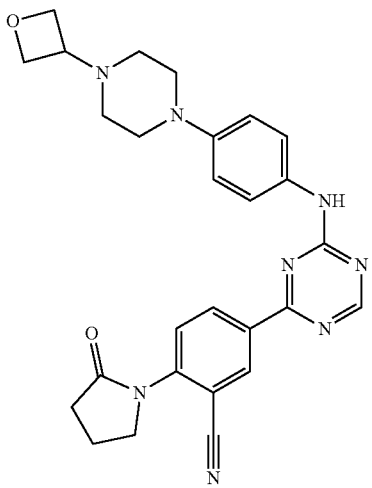 [SMILES: N#Cc1cc(-c2ncnc(Nc3ccc(N4CCN(C5COC5)CC4)cc3)n2)ccc1N1CCCC1=O]

Preparation of N-(4-bromo-2-cyanophenyl)-4-chlorobutanamide:

To a solution of 2-amino-5-bromobenzonitrile (1.5 g, 7.6 mmol) in pyridine (15 mL) was added dropwise 4-chlorobutanoyl chloride (Sigma Aldrich 1.0 mL, 9.1 mmol) at 0° C. The ice-water bath was allowed to slowly regain room temperature and the mixture was allowed to stir overnight at room temperature. The reaction mixture was poured into water, and the mixture was extracted thrice with ethyl acetate. The organic layers were combined, and the mixture was washed with saturated aqueous sodium chloride solution, dried over anhydrous magnesium sulfate, filtered, and concentrated to dryness under reduced pressure to provide the desired material, which carried forward without further purification. LCMS-ESI$^+$ (m/z): [M+H]$^+$ calcd for $C_{11}H_{11}BrClN_2O$: 303.0; found: 303.0

Preparation of 5-bromo-2-(2-oxopyrrolidin-1-yl)benzonitrile:

To a solution of crude N-(4-bromo-2-cyanophenyl)-4-chlorobutanamide (7.6 mmol assumed) in 2-methyltetrahydrofuran (30 mL) was added sodium hydride (60% dispersion in mineral oil) at 0° C., and the mixture was warmed to room temperature and stirred overnight. The reaction mixture was quenched with glacial acetic acid (approximately 5 mL) and poured into water. The mixture was extracted twice with ethyl acetate. The organic layers were combined, washed with saturated aqueous sodium chloride solution, dried over anhydrous magnesium sulfate, filtered, and concentrated to dryness under reduced pressure. The residue was purified by flash chromatography (silica gel) to provide the desired material. LCMS-ESI$^+$ (m/z): [M+H]$^+$ calcd for $C_{11}H_{10}BrN_2O$: 265.0; found: 265.1.

Preparation of (3-cyano-4-(2-oxopyrrolidin-1-yl)phenyl) boronic acid:

A mixture of 5-bromo-2-(2-oxopyrrolidin-1-yl)benzonitrile (0.23 g, 0.87 mmol), bis(pinacolato)diboron (0.44 g, 1.7 mmol), potassium acetate (0.26 g, 2.6 mmol), and [1,1'-bis (diphenylphosphino)ferrocene]dichloropalladium(II) (0.064 g, 10 mol %) in 1,4-dioxane (4 mL) was heated at 90° C. overnight. The mixture was allowed to cool to room temperature, filtered through a pad of Celite diatomaceous earth, and concentrated to dryness under reduced pressure to provide the desired product, which was carried forward without further purification.

LCMS-ESI$^+$ (m/z): [M+H]$^+$ calcd for $C_{11}H_{12}BN_2O_3$: 231.1; found: 231.2.

Preparation of 5-(4-((4-(4-(oxetan-3-yl)piperazin-1-yl) phenyl)amino)-1,3,5-triazin-2-yl)-2-(2-oxopyrrolidin-1-yl) benzonitrile: A mixture of 4-chloro-N-(4-(4-(oxetan-3-yl) piperazin-1-yl)phenyl)-1,3,5-triazin-2-amine (0.15 g, 0.43 mmol), crude (3-cyano-4-(2-oxopyrrolidin-1-yl)phenyl)boronic acid (0.20 g, 0.87 mmol), and tetrakis(triphenylphosphine)palladium(0) (0.025 g, 5 mol %) in 1,2-dimethoxyethane (DME, 6 mL) was treated with 2M aqueous sodium carbonate solution (0.98 mL). The mixture was irradiated for 1 hour in a microwave reactor at 130° C. The crude mixture was purified by flash chromatography on silica gel to provide the desired material. LCMS-ESI$^+$ (m/z): [M+H]$^+$ calcd for $C_{27}H_{29}N_8O_2$: 497.2; found: 497.2

Example 29

(R)-5-(4-((4-(4-(oxetan-3-yl)piperazin-1-yl)phenyl) amino)-1,3,5-triazin-2-yl)-2-((tetrahydrofuran-3-yl) oxy)benzonitrile

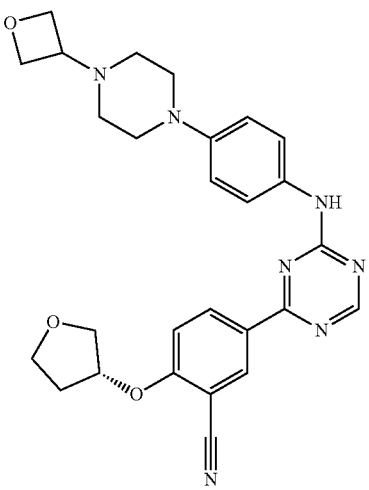 [SMILES: N#Cc1cc(-c2ncnc(Nc3ccc(N4CCN(C5COC5)CC4)cc3)n2)ccc1O[C@@H]1CCOC1]

Preparation of (R)-5-bromo-2-((tetrahydrofuran-3-yl)oxy)benzonitrile:

A solution of (R)-(−)-3-hydroxytetrahydrofuran (Sigma Aldrich, 2.0 g, 22 mmol) in N,N-dimethylformamide (40 mL) was stirred in an ice-water bath under an atmosphere of Argon. Sodium hydride (60% in mineral oil, 0.91 g, 23 mmol) was added in a single portion. The mixture was stirred at 0° C. for 10 minutes and then the cooling bath was removed. The mixture was stirred overnight at room temperature. To the mixture was added via syringe 5-bromo-2-fluorobenzonitrile (Matrix Scientific, 3.8 g, 19 mmol) as a solution in N,N-dimethylformamide (20 mL) at room temperature. Mixture was stirred for 2 hours on a 50° C. block and then allowed to cool to room temperature. Water was added and the resulting precipitate was collected by filtration, washed with water, dried under house vacuum and then in vacuum oven over $P_2O_5$ to provide the desired material. $^1$H NMR (400 MHz, DMSO-$d_6$) δ 8.06 (d, J=2.5 Hz, 1H), 7.87 (dd, J=9.1, 2.5 Hz, 1H), 7.26 (d, J=9.1 Hz, 1H), 5.24 (m, 1H), 3.87 (m, 4H), 2.31 (m, 1H), 2.02 (m, 1H).

Preparation of (R)-2-((tetrahydrofuran-3-yl)oxy)-5-(4,4,5,5-tetramethyl-1,3,2-dioxaborolan-2-yl)benzonitrile:

A mixture of (R)-5-bromo-2-((tetrahydrofuran-3-yl)oxy)benzonitrile (1.4 g, 5.2 mmol), bis(pinacolato)diboron (2.6 g, 10 mmol), potassium acetate (1.5 g, 16 mmol), and [1,1'-bis(diphenylphosphino)ferrocene]dichloropalladium (II) complex with dichloromethane (0.22 g, 5 mol %) in 1,4-dioxane (20 mL) was heated for 5 hours at 90° C. The reaction mixture was filtered through a pad of Celite diatomaceous earth, and the filtrate was concentrated to dryness under reduced pressure. The residue was purified by flash chromatography (silica gel) to provide (R)-2-((tetrahydrofuran-3-yl)oxy)-5-(4,4,5,5-tetramethyl-1,3,2-dioxaborolan-2-yl)benzonitrile. $^1$H NMR (400 MHz, DMSO-$d_6$) δ 7.99-7.88 (m, 2H), 7.31 (d, J=8.5 Hz, 1H), 5.29 (m, 1H), 4.02-3.74 (m, 4H), 2.33 (m, 1H), 2.13-1.91 (m, 1H), 1.33 (s, 12H).

A mixture of 4-chloro-N-(4-(4-(oxetan-3-yl)piperazin-1-yl)phenyl)-1,3,5-triazin-2-amine (0.12 g, 0.35 mmol), (R)-2-((tetrahydrofuran-3-yl)oxy)-5-(4,4,5,5-tetramethyl-1,3,2-dioxaborolan-2-yl)benzonitrile (0.14 g, 0.43 mmol), and tetrakis(triphenylphosphine)palladium(0) (0.030 g, 7.5 mol %) in 1,2-dimethoxyethane (DME, 2.5 mL) was treated with 2M aqueous sodium carbonate solution (0.78 mL). The mixture was irradiated for 1 hour in a microwave reactor at 130° C. The crude mixture was purified by flash chromatography on silica gel to provide (R)-5-(4-((4-(4-(oxetan-3-yl)piperazin-1-yl)phenyl)amino)-1,3,5-triazin-2-yl)-2-((tetrahydrofuran-3-yl)oxy)benzonitrile. LCMS-ESI$^+$ (m/z): [M+H]$^+$ calcd for $C_{27}H_{30}N_7O_3$: 500.2; found: 500.3 $^1$H NMR (400 MHz, DMSO-$d_6$) δ 10.16 (m, 1H), 8.78 (s, 1H), 8.71-8.50 (m, 2H), 7.61 (m, 2H), 7.49 (d, J=9.0 Hz, 1H), 7.01 (m, 2H), 5.36 (m, 1H), 4.61 (m, 2H), 4.52 (m, 2H), 4.07-3.89 (m, 3H), 3.85 (m, 1H), 3.49 (m, 1H), 3.19 (m, 4H), 2.45 (m, 4H), 2.36 (m, 1H), 2.09 (m, 1H).

Example 30

(R)-2-((1-(2-hydroxyacetyl)pyrrolidin-3-yl)oxy)-5-(4-((4-(4-(oxetan-3-yl)piperazin-1-yl)phenyl)amino)-1,3,5-triazin-2-yl)benzonitrile

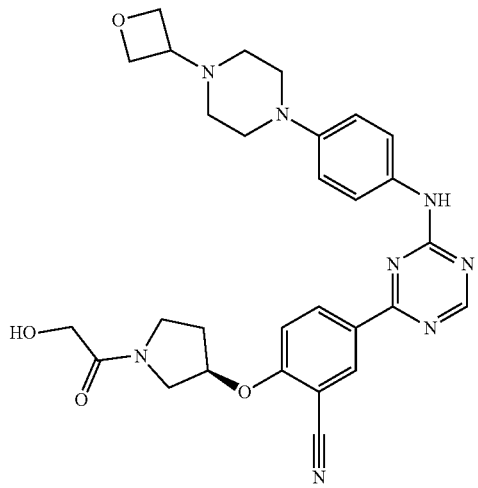 [SMILES: N#Cc1cc(-c2ncnc(Nc3ccc(N4CCN(C5COC5)CC4)cc3)n2)ccc1O[C@@H]1CCN(C(=O)CO)C1]

Preparation of (R)-tert-butyl 3-(2-cyano-4-(4-((4-(4-(oxetan-3-yl)piperazin-1-yl)phenyl)amino)-1,3,5-triazin-2-yl)phenoxy)pyrrolidine-1-carboxylate A mixture of 4-chloro-N-(4-(4-(oxetan-3-yl)piperazin-1-yl)phenyl)-1,3,5-triazin-2-amine (0.25 g, 0.72 mmol), (R)-tert-butyl 3-(2-cyano-4-(4,4,5,5-tetramethyl-1,3,2-dioxaborolan-2-yl)phenoxy)pyrrolidine-1-carboxylate (0.37 g, 0.90 mmol), and tetrakis(triphenylphosphine)palladium(0) (0.054 g, 7.5 mol %) in 1,2-dimethoxyethane (DME, 4 mL) was treated with 2M aqueous sodium carbonate solution (1.6 mL). The mixture was irradiated for 1 hour in a microwave reactor at 130° C. The crude mixture was purified by flash chromatography on silica gel to provide the desired product.

LCMS-ESI$^+$ (m/z): [M+H]$^+$ calcd for $C_{32}H_{39}N_8O_4$: 599.3; found: 599.1

Preparation of (R)-5-(4-((4-(4-(oxetan-3-yl)piperazin-1-yl)phenyl)amino)-1,3,5-triazin-2-yl)-2-(pyrrolidin-3-yloxy)benzonitrile(R)-tert-butyl 3-(2-cyano-4-(4-((4-(4-(oxetan-3-yl)piperazin-1-yl)phenyl)amino)-1,3,5-triazin-2-yl)phenoxy)pyrrolidine-1-carboxylate (0.72 mmol assumed) was taken up in dichloromethane (8 mL) and treated with trifluoroacetic acid (2 mL). After one hour, the mixture was pipetted into saturated aqueous sodium hydrogen carbonate solution. The aqueous layer was extracted three times with approximately 10% MeOH/dichloromethane. The combined organics were washed once with saturated aqueous sodium chloride solution, dried over anhydrous magnesium sulfate, filtered, and concentrated under reduced pressure to provide the desired material.

LCMS-ESI$^+$ (m/z): [M+H]$^+$ calcd for $C_{27}H_{31}N_8O_2$: 499.3; found: 499.3

Preparation of (R)-2-((1-(2-hydroxyacetyl)pyrrolidin-3-yl)oxy)-5-(4-((4-(4-(oxetan-3-yl)piperazin-1-yl)phenyl)amino)-1,3,5-triazin-2-yl)benzonitrile (R)-5-(4-((4-(4-(oxetan-3-yl)piperazin-1-yl)phenyl)amino)-1,3,5-triazin-2-yl)-2-(pyrrolidin-3-yloxy)benzonitrile (50 mg, 0.10 mmol) and glycolic acid (11 mg, 0.15 mmol) were taken up as suspension in dichloromethane (1 mL). The mixture was treated successively with N,N-diisopropylethylamine (35 μL, 0.20 mmol) and N-[(dimethylamino)-1H-1,2,3-triazolo-[4,5-b]pyridin-1-ylmethylene]-N-methylmethanaminiumhexafluorophosphate N-oxide (HATU, 57 mg, 0.15 mmol). The suspension was stirred for three hours at room temperature and then purified by flash chromatography (silica gel) to provide (R)-2-((1-(2-hydroxyacetyl)pyrrolidin-3-yl)oxy)-5-(4-((4-(4-(oxetan-3-yl)piperazin-1-yl)phenyl)amino)-1,3,5-triazin-2-yl)benzonitrile. LCMS-ESI$^+$ (m/z): [M+H]$^+$ calcd for $C_{29}H_{33}N_8O_4$: 557.3; found: 557.3 $^1$H NMR (400 MHz, DMSO-$d_6$) δ 10.17 (m, 1H), 8.78 (s, 1H), 8.61 (m, 2H), 7.59 (m, 3H), 7.01 (br, 2H), 5.41 (m, 1H), 4.70 (m, 1H), 4.61 (m, 2H), 4.52 (m, 2H), 4.09 (m, 2H), 3.74 (m, 3H), 3.51 (m, 1H), 3.18 (m, 4H), 2.45 (m, 4H), 2.28 (m, 2H).

Example 31

5-(4-((4-(difluoromethoxy)-3-methoxyphenyl)amino)-1,3,5-triazin-2-yl)-2-((tetrahydro-2H-pyran-4-yl)oxy)benzonitrile

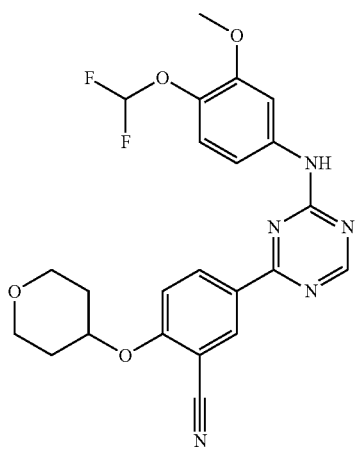 [SMILES: COc1cc(Nc2ncnc(-c3ccc(OC4CCOCC4)c(C#N)c3)n2)ccc1OC(F)F]

A suspension of 5-(4-chloro-1,3,5-triazin-2-yl)-2-((tetrahydro-2H-pyran-4-yl)oxy)benzonitrile (100 mg, 0.32 mmol) and 4-difluoromethyoxy-3-methoxyaniline hydrochloride (Princeton Biomolecular Research, 85 mg, 0.38 mmol) in acetonitrile (3 mL) was treated with N,N-diisopropylethylamine (0.28 mL, 1.6 mmol). The mixture was heated in a microwave reactor for 20 minutes at 80° C. The reaction mixture was purified by flash chromatography (silica gel) to provide the desired material. LCMS-ESI$^+$ (m/z): [M+H]$^+$ calcd for $C_{23}H_{22}F_2N_5O_4$: 470.2; found: 470.1 $^1$H NMR (400 MHz, DMSO-$d_6$) δ 10.46 (bs, 1H), 8.88 (s, 1H), 8.65 (d, J=2.2 Hz, 1H), 8.62 (dd, J=8.9, 2.2 Hz, 1H), 7.90 (bs, 1H), 7.61 (d, J=9.0 Hz, 1H), 7.31 (bs, 1H), 7.24 (m, 1H), 7.05 (m, 1H), 4.99 (m, 1H), 3.91 (m, 5H), 3.60 (m, 2H), 2.08 (m, 2H), 1.74 (m, 2H).

Example 32

5-(4-((4-(4-acetylpiperazin-1-yl)-3-methoxyphenyl)amino)-1,3,5-triazin-2-yl)-2-((tetrahydro-2H-pyran-4-yl)oxy)benzonitrile

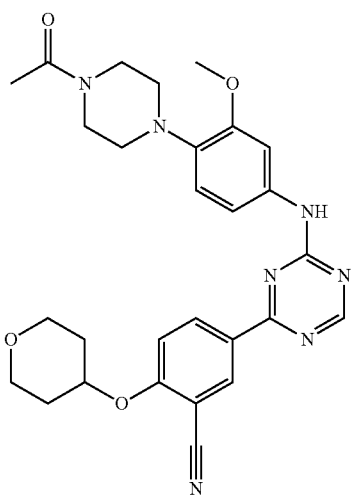 [SMILES: COc1cc(Nc2ncnc(-c3ccc(OC4CCOCC4)c(C#N)c3)n2)ccc1N1CCN(C(C)=O)CC1]

Preparation of 1-(4-(2-methoxy-4-nitrophenyl)piperazin-1-yl)ethanone:

A mixture of 1-fluoro-2-methoxy-4-nitrobenzene (0.83 g, 4.9 mmol), 1-acetylpiperazine (0.68 g, 5.3 mmol), and potassium carbonate (1.3 g, 9.7 mmol) in N,N-dimethylformamide (9 mL) was stirred at 100° C. for 20 hours. The mixture was allowed to cool to room temperature and was partitioned between ethyl acetate and water. The aqueous phase was extracted three times with ethyl acetate. The combined extracts were washed twice with water, once with saturated aqueous sodium chloride solution, dried over anhydrous magnesium sulfate, filtered, and concentrated to provide the desired material. LCMS-ESI$^+$ (m/z): [M+H]$^+$ calcd for $C_{13}H_{18}N_3O_4$: 280.1; found: 280.1

Preparation of 1-(4-(4-amino-2-methoxyphenyl)piperazin-1-yl)ethanone:

A degassed mixture of 1-(4-(2-methoxy-4-nitrophenyl)piperazin-1-yl)ethanone (approximately 4.9 mmol) in methanol/2-methyltetrahydrofuran (1:1, 60 mL) was treated with 10% palladium on charcoal (250 mg). The mixture was stirred under a balloon of hydrogen overnight. The catalyst was removed by filtration through a pad of Celite diatomaceous earth. The filtrate was concentrated to dryness under reduced pressure to provide the desired material.

LCMS-ESI$^+$ (m/z): [M+H]$^+$ calcd for $C_{13}H_{20}N_3O_2$: 250.2; found: 250.1

Preparation of 5-(4-((4-(4-acetylpiperazin-1-yl)-3-methoxyphenyl)amino)-1,3,5-triazin-2-yl)-2-((tetrahydro-2H-pyran-4-yl)oxy)benzonitrile:

A suspension of 5-(4-chloro-1,3,5-triazin-2-yl)-2-((tetrahydro-2H-pyran-4-yl)oxy)benzonitrile (57 mg, 0.18 mmol) and 1-(4-(4-amino-2-methoxyphenyl)piperazin-1-yl)ethanone (54 mg, 0.22 mmol) in acetonitrile (3 mL) was treated with N,N-diisopropylethylamine (0.13 mL, 0.72 mmol). The mixture was heated in a microwave reactor for 20 minutes at 80° C. The cooled reaction mixture was purified by flash chromatography (silica gel) and then recrystallized from methanol to provide 5-(4-((4-(4-acetylpiperazin-1-yl)-3-methoxyphenyl)amino)-1,3,5-triazin-2-yl)-2-((tetrahydro-2H-pyran-4-yl)oxy)benzonitrile. LCMS-ESI⁺ (m/z): [M+H]⁺ calcd for $C_{28}H_{32}N_7O_4$: 530.2; found: 530.3

¹H NMR (400 MHz, DMSC-d₆) δ 10.28 (s, 1H), 8.82 (s, 1H), 8.64 (d, J=2.1 Hz, 1H), 8.61 (dd, J=8.9, 2.2 Hz, 1H), 7.69 (bs, 1H), 7.60 (d, J=9.0 Hz, 1H), 7.54-7.17 (br, 1H), 6.93 (d, J=8.5 Hz, 1H), 4.98 (m, 1H), 3.92 (m, 5H), 3.60 (m, 6H), 2.94 (m, 4H), 2.07 (m, 5H), 1.73 (m, 2H).

Example 33

2-((1,1-dioxidotetrahydro-2H-thiopyran-4-yl)oxy)-5-(4-((3-methoxy-4-(4-(oxetan-3-yl)piperazin-1-yl)phenyl)amino)-1,3,5-triazin-2-yl)benzonitrile

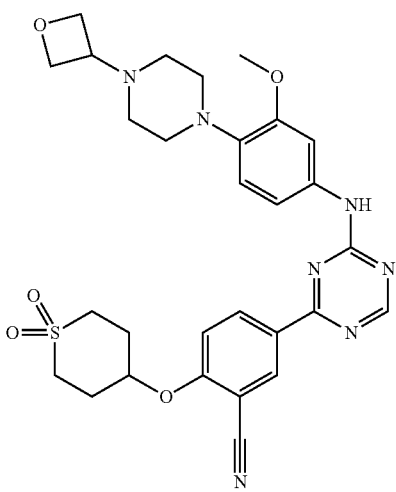 [SMILES: COc1cc(Nc2ncnc(-c3ccc(OC4CCS(=O)(=O)CC4)c(C#N)c3)n2)ccc1N1CCN(C2COC2)CC1]

A mixture of 4-chloro-N-(3-methoxy-4-(4-(oxetan-3-yl)piperazin-1-yl)phenyl)-1,3,5-triazin-2-amine (0.10 g, 0.27 mmol), crude 2-((1,1-dioxidotetrahydro-2H-thiopyran-4-yl)oxy)-5-(4,4,5,5-tetramethyl-1,3,2-dioxaborolan-2-yl)benzonitrile (1.0 assumed), and tetrakis(triphenylphosphine)palladium(0) (0.023 g, 7.5 mol %) in 1,2-dimethoxyethane (DME, 6 mL) was treated with 2M aqueous sodium carbonate solution (0.60 mL). The mixture was irradiated for 1 hour in a microwave reactor at 130° C. The crude mixture was purified by flash chromatography on silica gel, followed by precipitation from isopropanol/dichloromethane, to provide the desired material. LCMS-ESI⁺ (m/z): [M+H]⁺ calcd for $C_{29}H_{34}N_7O_5S$: 592.2; found: 592.3 ¹H NMR (400 MHz, DMSO-d₆) δ 10.29 (m, 1H), 8.82 (s, 1H), 8.65 (m, 2H), 7.67 (s, 1H), 7.61 (d, J=8.9 Hz, 1H), 7.33 (m, 1H), 6.94 (d, J=8.5 Hz, 1H), 5.12 (m, 1H), 4.60 (m, 2H), 4.51 (m, 2H), 3.51 (m, 1H), 3.35 (s, 3H), 3.27 (m, 4H), 3.01 (m, 4H), 2.49-2.32 (m, 8H).

Example 34

5-(4-((4-(4-(oxetan-3-yl)piperazin-1-yl)phenyl)amino)-1,3,5-triazin-2-yl)-2-((tetrahydro-2H-pyran-3-yl)oxy)benzonitrile

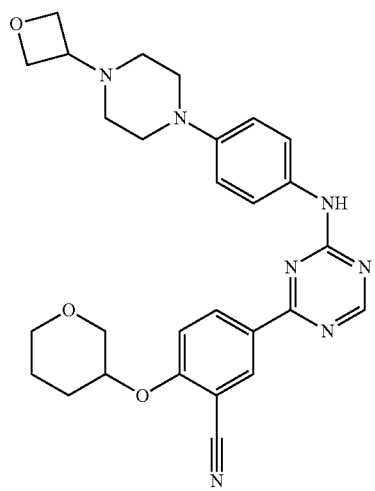 [SMILES: N#Cc1cc(-c2ncnc(Nc3ccc(N4CCN(C5COC5)CC4)cc3)n2)ccc1OC1CCCOC1]

Preparation of 5-bromo-2-((tetrahydro-2H-pyran-3-yl)oxy)benzonitrile:

A solution of 3-hydroxytetrahydropyran (Astatech, 2.0 g, 20 mmol) in N,N-dimethylformamide (40 mL) was stirred in an ice-water bath under an atmosphere of Argon. Sodium hydride (60% in mineral oil, 0.79 g, 20 mmol) was added in a single portion. Mixture was stirred at 0° C. for one hour and then the cooling bath was removed. To the mixture was added via syringe 5-bromo-2-fluorobenzonitrile (Matrix Scientific, 3.3 g, 17 mmol) as a solution in N,N-dimethylformamide (20 mL) at room temperature. Mixture was stirred for 3 hours at 50° C. block and then allowed to cool to room temperature. Water was added and the resulting precipitate was collected by filtration, washed with water, dried under house vacuum and then in vacuum oven over $P_2O_5$ to provide the desired material. ¹H NMR (400 MHz, DMSO-d₆) δ 8.04 (d, J=2.5 Hz, 1H), 7.84 (dd, J=9.1, 2.6 Hz, 1H), 7.35 (d, J=9.1 Hz, 1H), 4.64 (m, 1H), 3.82 (m, 1H), 3.63 (m, 3H), 2.05 (m, 1H), 1.83 (m, 2H), 1.57 (m, 1H).

Preparation of 2-((tetrahydro-2H-pyran-3-yl)oxy)-5-(4,4,5,5-tetramethyl-1,3,2-dioxaborolan-2-yl)benzonitrile:

A mixture of 5-bromo-2-((tetrahydro-2H-pyran-3-yl)oxy)benzonitrile (0.29 g, 1.0 mmol), bis(pinacolato)diboron (0.53 g, 2.1 mmol), potassium acetate (0.31 g, 3.1 mmol), and [1,1'-bis(diphenylphosphino)ferrocene]dichloropalladium(II) complex with dichloromethane (77 mg, 10 mol %) in 1,4-dioxane (5 mL) was heated for 2.5 hours at 90° C. The reaction mixture was filtered through a pad of Celite diatomaceous earth, and the filtrate was concentrated to dryness under reduced pressure. The crude 2-((tetrahydro-2H-pyran-3-yl)oxy)-5-(4,4,5,5-tetramethyl-1,3,2-dioxaborolan-2-yl)benzonitrile was carried forward without further purification. LCMS-ESI⁺ (m/z): [M+OH+H]⁺ calcd for $C_{18}H_{26}BNO_5$: 347.2; found: 347.1

Step 3: A mixture of 4-chloro-N-(4-(4-(oxetan-3-yl)piperazin-1-yl)phenyl)-1,3,5-triazin-2-amine (0.12 g, 0.35 mmol), crude 2-((tetrahydro-2H-pyran-3-yl)oxy)-5-(4,4,5,5-tetramethyl-1,3,2-dioxaborolan-2-yl)benzonitrile (0.34 g, 1.0 mmol), and tetrakis(triphenylphosphine)palladium(0)

(0.030 g, 7.5 mol %) in 1,2-dimethoxyethane (DME, 4 mL) was treated with 2M aqueous sodium carbonate solution (0.78 mL). The mixture was irradiated for 1 hour in a microwave reactor at 130° C. The crude mixture was purified by flash chromatography on silica gel to provide 5-(4-((4-(4-(oxetan-3-yl)piperazin-1-yl)phenyl)amino)-1,3,5-triazin-2-yl)-2-((tetrahydro-2H-pyran-3-yl)oxy)benzonitrile. LCMS-ESI+ (m/z): [M+H]+ calcd for $C_{28}H_{32}N_7O_3$: 514.3; found: 514.2.

$^1$H NMR (400 MHz, DMSO-$d_6$) δ 10.15 (m, 1H), 8.92-8.72 (m, 1H), 8.58 (m, 2H), 7.58 (m, 3H), 7.00 (m, 2H), 4.77 (m, 1H), 4.61 (m, 2H), 4.51 (m, 2H), 3.88 (m, 1H), 3.68 (m, 3H), 3.49 (p, J=6.3 Hz, 1H), 3.18 (m, 4H), 2.45 (m, 4H), 2.12 (m, 1H), 1.89 (m, 2H), 1.61 (m, 1H).

Example 35

2-(3-hydroxyazetidin-1-yl)-5-(4-((4-(4-(oxetan-3-yl)piperazin-1-yl)phenyl)amino)-1,3,5-triazin-2-yl)benzonitrile

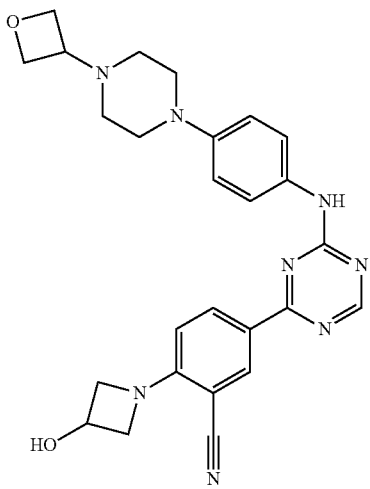 [SMILES: N#Cc1cc(-c2ncnc(Nc3ccc(N4CCN(C5COC5)CC4)cc3)n2)ccc1N1CC(O)C1]

Preparation of 2-(3-hydroxyazetidin-1-yl)-5-(4,4,5,5-tetramethyl-1,3,2-dioxaborolan-2-yl)benzonitrile:

2-Fluoro-5-(4,4,5,5-tetramethyl[1,3,2]dioxaborolan-2-yl)benzonitrile (2.0 g, 8.1 mmol), potassium carbonate (2.2 g, 16 mmol), and 3-hydroxyazetidine hydrochloride (0.89 g, 8.1 mmol) were taken up as a suspension in N,N-dimethylacetamide (20 mL) and heated on a 120° C. block overnight. The mixture was allowed to cool to room temperature and then was filtered. The filtrate was concentrated under reduced pressure. The residue was purified by flash chromatography (silica gel) to provide 2-(3-hydroxyazetidin-1-yl)-5-(4,4,5,5-tetramethyl-1,3,2-dioxaborolan-2-yl)benzonitrile. LCMS-ESI+ (m/z): [M+H]+ calcd for $C_{16}H_{22}BN_2O_3$: 301.2; found: 301.1

A mixture of 4-chloro-N-(4-(4-(oxetan-3-yl)piperazin-1-yl)phenyl)-1,3,5-triazin-2-amine (0.12 g, 0.35 mmol), 2-(3-hydroxyazetidin-1-yl)-5-(4,4,5,5-tetramethyl-1,3,2-dioxaborolan-2-yl)benzonitrile (0.16 g, 0.53 mmol), and tetrakis(triphenylphosphine)palladium(0) (0.030 g, 7.5 mol %) in 1,2-dimethoxyethane (DME, 2.5 mL) was treated with 2M aqueous sodium carbonate solution (0.78 mL). The mixture was irradiated for 1 hour in a microwave reactor at 130° C. The crude mixture was purified by flash chromatography on silica gel to provide 2-(3-hydroxyazetidin-1-yl)-5-(4-((4-(4-(oxetan-3-yl)piperazin-1-yl)phenyl)amino)-1,3,5-triazin-2-yl)benzonitrile. LCMS-ESI+ (m/z): [M+H]+ calcd for $C_{26}H_{29}N_8O_2$: 485.2; found: 485.3 $^1$H NMR (400 MHz, DMSO-$d_6$) δ 10.01 (m, 1H), 8.69 (s, 1H), 8.53-8.25 (m, 2H), 7.60 (br, 2H), 6.99 (br, 2H), 6.71 (d, J=9.0 Hz, 1H), 5.86 (d, J=6.1 Hz, 1H), 4.62 (m, 3H), 4.52 (m, 4H), 4.02 (m, 2H), 3.48 (p, J=6.3 Hz, 1H), 3.17 (m, 4H), 2.45 (m, 4H).

Example 36

5-((4-(3-cyano-4-((tetrahydro-2H-pyran-4-yl)oxy)phenyl)-1,3,5-triazin-2-yl)amino)-2-((tetrahydro-2H-pyran-4-yl)oxy)benzonitrile

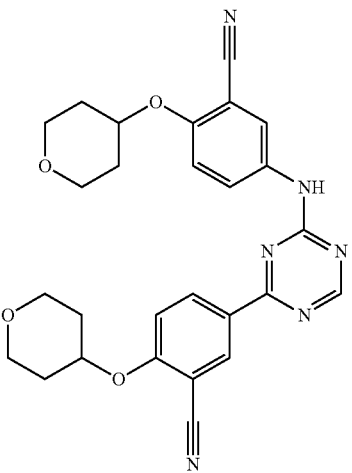 [SMILES: N#Cc1cc(Nc2ncnc(-c3ccc(OC4CCOCC4)c(C#N)c3)n2)ccc1OC1CCOCC1]

Potassium tert-butoxide (0.62 g, 5.5 mmol) was added in one portion to a solution of 4-hydroxytetrahydropyran (0.51 g, 5.0 mmol) in 2-methyltetrahydrofuran (15 mL), cooled in an ice-water bath. The reaction mixture was stirred for 20 minutes before the addition of 2-fluoro-5-nitrobenzonitrile (0.42 g, 2.5 mmol). The mixture continued to stir in the bath for about 15 minutes before the removal of the bath. The mixture was allowed to remain at room temperature. The aqueous phase was extracted twice with dichloromethane. The combined organics were washed twice with water, dried over anhydrous magnesium sulfate, filtered, concentrated to dryness under reduced pressure to provide 5-amino-2-(tetrahydro-2H-pyran-4-yloxy)benzonitrile. The crude product was carried forward without further purification.

To a solution of 2,4-dichloro-1,3,5-triazine (0.27 g, 1.8 mmol) in N,N-dimethylformamide (DMF, 2 mL) at 0° C. were added N,N-diisopropylethylamine (DIEA, 0.32 mL, 1.9 mmol), followed by a solution of 5-amino-2-(tetrahydro-2H-pyran-4-yloxy)benzonitrile (0.36 g, 1.6 mmol) in DMF (6 mL). The mixture was stirred at 0° C. for 30 minutes and then allowed to warm to room temperature where it remained overnight.

The mixture was partitioned between ethyl acetate and water. The layers were separated and aqueous phase was extracted twice with ethyl acetate. The combined extracts were washed once each with water and saturated aqueous sodium chloride solution, and then dried over anhydrous magnesium sulfate, filtered, and concentrated under reduced pressure. The residue was purified by flash chromatography on silica gel to provide 5-((4-chloro-1,3,5-triazin-2-yl)

amino)-2-((tetrahydro-2H-pyran-4-yl)oxy)benzonitrile. LCMS-ESI⁺ (m/z): [M+H]⁺ calcd for $C_{15}H_{15}ClN_5O_2$: 332.1; found: 332.1

A mixture of 5-((4-chloro-1,3,5-triazin-2-yl)amino)-2-((tetrahydro-2H-pyran-4-yl)oxy)benzonitrile (0.16 g, 0.48 mmol), 2-((tetrahydro-2H-pyran-4-yl)oxy)-5-(4,4,5,5-tetramethyl-1,3,2-dioxaborolan-2-yl)benzonitrile (0.17 g, 0.53 mmol), palladium (II) acetate (0.01 g, 10 mol %), and triphenylphosphine (0.038 g, 0.14 mmol) in 1,2-dimethoxyethane (DME, 6 mL) was treated with 2M aqueous sodium carbonate solution (1.1 mL). The mixture was irradiated for 1 hour in a microwave reactor at 130°. The crude mixture was filtered through a pad of Celite diatomaceous earth. The aqueous phase was extracted twice with ethyl acetate. The combined extracts were washed once with saturated aqueous sodium chloride solution, dried over anhydrous magnesium sulfate, filtered, concentrated to dryness under reduced pressure. The residue was purified via prep HPLC (10-95% acetonitrile in water, 0.1% trifluoroacetic acid buffer) to furnish 5-((4-(3-cyano-4-((tetrahydro-2H-pyran-4-yl)oxy)phenyl)-1,3,5-triazin-2-yl)amino)-2-((tetrahydro-2H-pyran-4-yl)oxy)benzonitrile. LCMS-ESI⁺ (m/z): [M+H]⁺ calcd for $C_{27}H_{27}N_6O_4$: 499.2; found: 499.1 ¹H NMR (400 MHz, DMSO-d₆) δ 10.46 (s, 1H), 8.87 (s, 1H), 8.59 (d, J=9.2 Hz, 2H), 8.13 (s, 1H), 7.94 (br, 1H), 7.60 (m, 1H), 7.45 (m, 1H), 5.00 (m, 1H), 4.81 (m, 1H), 3.91 (m, 4H), 3.58 (m, 4H), 2.21-1.97 (m, 4H), 1.72 (m, 4H).

Example 37

(S)-N-(2-cyano-4-(4-((4-morpholinophenyl)amino)-1,3,5-triazin-2-yl)phenyl)pyrrolidine-2-carboxamide

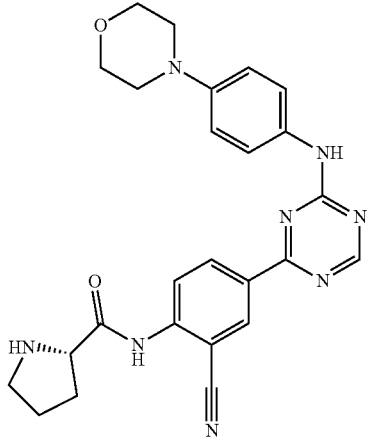 [SMILES: N#Cc1cc(-c2ncnc(Nc3ccc(N4CCOCC4)cc3)n2)ccc1NC(=O)[C@@H]1CCCN1]

Preparation of 2-amino-5-(4,4,5,5-tetramethyl-1,3,2-dioxaborolan-2-yl)benzonitrile:

A mixture of 2-amino-5-bromobenzonitrile (1.5 g, 7.6 mmol), bis(pinacolato)diboron (2.9 g, 11 mmol), potassium acetate (2.2 g, 23 mmol), and [1,1'-bis(diphenylphosphino)ferrocene]dichloropalladium(II) (0.28 g, 5 mol %) in 1,4-dioxane (23 mL) was heated at 80° C. for two days. The mixture was partitioned between water and ethyl acetate. The aqueous phase was extracted three times with ethyl acetate. The combined extracts were washed once each with water and saturated aqueous sodium chloride solutions. A portion of the combined extracts was filtered through a pad of Celite diatomaceous earth. The extracts were dried over anhydrous magnesium sulfate, filtered, and concentrated under reduced pressure to give a solid mass, which was purified by flash chromatography (silica gel) to provide the desired product. LCMS-ESI⁺ (m/z): [M+H]⁺ calcd for $C_{13}H_{18}B N_2O_2$: 245.1; found: 245.4

Preparation of (S)-tert-butyl 2-((2-cyano-4-(4,4,5,5-tetramethyl-1,3,2-dioxaborolan-2-yl)phenyl)carbamoyl)pyrrolidine-1-carboxylate:

A mixture of 2-amino-5-(4,4,5,5-tetramethyl-1,3,2-dioxaborolan-2-yl)benzonitrile (0.37 g, 1.5 mmol) and Boc-L-proline (0.33 g, 1.5 mmol) in chloroform (15 mL) was treated successively with triethylamine (0.32 mL, 2.3 mmol) and 2-ethoxy-1-ethoxycarbonyl-1,2-dihydroquinoline (EEDQ, 0.45 g, 1.8 mmol). The mixture was heated with magnetic stirring overnight at 70° C., then concentrated under reduced pressure and purified by flash chromatography (silica gel) to provide the desired material.

LCMS-ESI⁺ (m/z): [M+H]⁺ calcd for $C_{23}H_{33}BN_3O_5$: 442.2; found: 442.0.

Preparation of (S)-tert-butyl 2-((2-cyano-4-(4-((4-morpholinophenyl)amino)-1,3,5-triazin-2-yl)phenyl)carbamoyl)pyrrolidine-1-carboxylate:

A suspension of 4-chloro-N-(4-morpholinophenyl)-1,3,5-triazin-2-amine (0.10 g, 0.34 mmol) and (S)-tert-butyl 2-((2-cyano-4-(4,4,5,5-tetramethyl-1,3,2-dioxaborolan-2-yl)phenyl)carbamoyl)pyrrolidine-1-carboxylate (0.17 g, 0.38 mmol) in 1,2-dimethoxyethane (DME, 2 mL) was treated successively with palladium (II) acetate (0.008 g, 10 mol %), triphenylphosphine (0.027 g, 0.1 mmol), and 2M aqueous sodium carbonate solution (0.78 mL). The mixture was irradiated for 1 hour in a microwave reactor at 125° C. The crude mixture was purified first by flash chromatography on silica gel to furnish the desired material. LCMS-ESI⁺ (m/z): [M+H]⁺ calcd for $C_{30}H_{35}N_8O_4$: 571.3; found: 571.5.

Preparation of (S)-N-(2-cyano-4-(4-((4-morpholinophenyl)amino)-1,3,5-triazin-2-yl)phenyl)pyrrolidine-2-carboxamide, trifluoroacetic acid salt:

A solution of (S)-tert-butyl 2-((2-cyano-4-(4-((4-morpholinophenyl)amino)-1,3,5-triazin-2-yl)phenyl)carbamoyl)pyrrolidine-1-carboxylate (0.16 g, 0.28 mmol) in dichloromethane (2 mL) was treated with trifluoroacetic acid (0.86 mL, 11 mmol) and allowed to stand overnight at room temperature. The mixture was then concentrated to dryness under reduced pressure, and the residue was purified by prep HPLC (10-36% acetonitrile in water, 0.1% trifluoroacetic acid buffer) to furnish the desired material as its TFA salt. LCMS-ESI⁺ (m/z): [M+H]⁺ calcd for $C_{25}H_{27}N_8O_2$: 471.2; found: 471.3.

Example 38

5-((4-(3-cyano-4-((tetrahydro-2H-pyran-4-yl)oxy)phenyl)-1,3,5-triazin-2-yl)amino)-2-(4-(oxetan-3-yl)piperazin-1-yl)benzonitrile

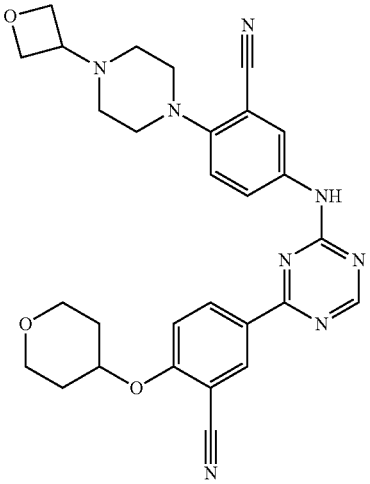 [SMILES: N#Cc1cc(-c2ncnc(Nc3ccc(N4CCN(C5COC5)CC4)c(C#N)c3)n2)ccc1OC1CCOCC1]

A mixture of 1-(oxetan-3-yl)piperazine (0.86 g, 6.0 mmol) and 2-fluoro-5-nitrobenzonitrile (1.0 g, 6.0 mmol) in acetonitrile (10 mL) was treated with potassium carbonate (0.83 g, 6.0 mmol). The mixture was allowed to stand overnight at room temperature. The supernatant was decanted and the remaining insoluble material was taken up in water, collected by vacuum filtration, washed with diethyl ether, and dried under vacuum to provide 5-nitro-2-(4-(oxetan-3-yl)piperazin-1-yl)benzonitrile. LCMS-ESI+ (m/z): [M+H]+ calcd for $C_{14}H_{17}N_4O_3$: 289.1; found: 289.1

5-nitro-2-(4-(oxetan-3-yl)piperazin-1-yl)benzonitrile (1.4 g, 4.9 mmol) was taken up as a suspension in methanol/2-methyltetrahydrofuran (1:1, 40 mL). The suspension was heated to homogeneity, and then allowed to cool to room temperature. After being degassed, to the mixture was introduced 10% palladium on charcoal (approximately 200 mg). The suspension was stirred under balloon of hydrogen for one hour. The mixture was filtered through a pad of Celite diatomaceous earth, and the filtrate was concentrated to dryness under reduced pressure to give 5-amino-2-(4-(oxetan-3-yl)piperazin-1-yl)benzonitrile. LCMS-ESI+ (m/z): [M+H]+ calcd for $C_{14}H_{19}N_4O$: 259.2; found: 259.2.

To a solution of 2,4-dichloro-1,3,5-triazine (0.42 g, 2.8 mmol) in N,N-dimethylformamide (DMF, 6 mL) at 0° C. were added sequentially N,N-diisopropylethylamine (DIEA, 0.50 mL, 2.9 mmol) and 5-amino-2-(4-(oxetan-3-yl)piperazin-1-yl)benzonitrile (0.65 g, 2.5 mmol). The mixture was stirred at 0° C. for 30 minutes and then allowed to warm to room temperature. The mixture was diluted with ethyl acetate and water. The aqueous phase was extracted twice with ethyl acetate. The combined extracts were washed once each with water and a saturated aqueous sodium chloride solution, then dried over anhydrous magnesium sulfate, filtered, and concentrated under reduced pressure. The residue was purified via flash chromatography on silica gel to provide 5-((4-chloro-1,3,5-triazin-2-yl)amino)-2-(4-(oxetan-3-yl)piperazin-1-yl)benzonitrile. LCMS-ESI+ (m/z): [M+H]+ calcd for $C_{17}H_{19}CN_7O$: 372.1; found: 372.4.

A mixture of 5-((4-chloro-1,3,5-triazin-2-yl)amino)-2-(4-(oxetan-3-yl)piperazin-1-yl)benzonitrile (0.15 g, 0.40 mmol), 2-((tetrahydro-2H-pyran-4-yl)oxy)-5-(4,4,5,5-tetramethyl-1,3,2-dioxaborolan-2-yl)benzonitrile (0.15 g, 0.44 mmol), tetrakis(triphenylphosphine)palladium(0) (0.023 g, 5 mol %) in 1,2-dimethoxyethane (DME, 6 mL) was treated with 2M aqueous sodium carbonate solution (0.91 mL). The mixture was irradiated for 1 hour in a microwave reactor at 130° C. The crude mixture was purified by flash chromatography on silica gel to furnish 5-((4-(3-cyano-4-((tetrahydro-2H-pyran-4-yl)oxy)phenyl)-1,3,5-triazin-2-yl)amino)-2-(4-(oxetan-3-yl)piperazin-1-yl) benzonitrile.

LCMS-ESI+ (m/z): [M+H]+ calcd for $C_{29}H_{31}N_8O_3$: 539.2; found: 539.3 1H NMR (400 MHz, DMSO-$d_6$) δ 10.58 (s, 1H), 8.90 (s, 1H), 8.62 (m, 2H), 8.21 (m, 1H), 8.00 (m, 1H), 7.61 (d, J=9.4 Hz, 1H), 7.38 (m, 1H), 5.01 (tt, J=8.0, 4.0 Hz, 1H), 4.82 (m, 4H), 4.60 (m, 1H), 3.91 (m, 2H), 3.60 (ddd, J=11.6, 8.5, 3.1 Hz, 2H), 3.55-2.91 (m, 8H), 2.09 (m, 2H), 1.73 (dtd, J=12.5, 8.3, 3.9 Hz, 2H).

Example 39

N-(4-((4-(3-cyano-4-((tetrahydro-2H-pyran-4-yl)oxy)phenyl)-1,3,5-triazin-2-yl)amino)phenyl)acrylamide

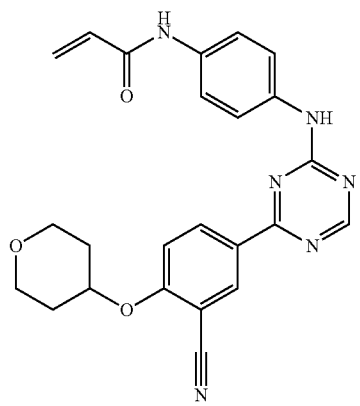 [SMILES: C=CC(=O)Nc1ccc(Nc2ncnc(-c3ccc(OC4CCOCC4)c(C#N)c3)n2)cc1]

Preparation of N-(4-aminophenyl)acrylamide:

A nearly homogeneous mixture of p-nitroaniline (2.5 g, 18 mmol) and triethylamine (5.0 mL, 36 mmol) in dichloromethane (40 mL) was stirred in an ice-water bath while acryloyl chloride (1.8 mL, 22 mmol) was added dropwise. At the end of the addition, the mixture was allowed to regain room temperature. The resulting suspension was diluted with water and filtered. The collected solid (assumed 18 mmol) was washed successively with water and dichloromethane and then taken up as a suspension in ethanol/water (5:1, 100 mL). Iron powder (2.0 g, 36 mmol) was added, followed by saturated aqueous ammonium chloride solution (10 mL). The mixture was heated on a 90° C. block for three hours and then filtered through a pad of Celite diatomaceous earth. The filtrate was concentrated to dryness under reduced pressure. The residue was partitioned between dichloromethane and water. The aqueous phase was extracted twice with dichloromethane. The combined extracts were washed once each with water and saturated aqueous sodium chloride solution, dried over anhydrous magnesium sulfate, filtered, concentrated under reduced pressure to give N-(4-aminophenyl)acrylamide. LCMS-ESI+ (m/z): [M+H]+ calcd for $C_9H_{11}N_2O$: 163.1; found: 163.1.

Preparation of N-(4-((4-chloro-1,3,5-triazin-2-yl)amino)phenyl)acrylamide:

To a solution of 2,4-dichloro-1,3,5-triazine (0.52 g, 3.4 mmol) in N,N-dimethylformamide (DMF, 4 mL) at 0° C. were added sequentially N,N-diisopropylethylamine (DIEA, 0.69 mL, 4.0 mmol) and N-(4-aminophenyl)acrylamide (0.51 g, 3.1 mmol) and the mixture was stirred at 0° C. for 30 minutes and then allowed to warm to room temperature. The mixture was partitioned between ethyl acetate and water. The aqueous phase was extracted twice with ethyl acetate. The combined organics were washed once each with water and a solution of saturated aqueous sodium chloride. The combined extracts were dried over anhydrous magnesium sulfate, filtered, and concentrated under reduced pressure to provide N-(4-((4-chloro-1,3,5-triazin-2-yl)amino) phenyl)acrylamide.

LCMS-ESI+ (m/z): [M+H]+ calcd for $C_{12}H_{11}ClN_5O$: 276.1; found: 276.2.

Preparation of N-(4-((4-(3-cyano-4-((tetrahydro-2H-pyran-4-yl)oxy)phenyl)-1,3,5-triazin-2-yl)amino)phenyl)acrylamide:

A suspension of N-(4-((4-chloro-1,3,5-triazin-2-yl)amino)phenyl)acrylamide (0.14 g, 0.49 mmol), 2-((tetrahydro-2H-pyran-4-yl)oxy)-5-(4,4,5,5-tetramethyl-1,3,2-dioxaborolan-2-yl)benzonitrile (0.19 g, 0.59 mmol), palladium (II) acetate (0.005 g, 10 mol %), and triphenylphosphine (0.039 g, 0.15 mmol) in 1,4-dioxane (3 mL) was treated with 2M aqueous sodium carbonate solution (1.1 mL). The mixture was irradiated for 1 hour in a microwave reactor at 130° C. The crude mixture was purified first by flash chromatography on silica gel and then by prep HPLC (10-90% acetonitrile in water, 0.1% trifluoroacetic acid buffer) to provide N-(4-((4-(3-cyano-4-((tetrahydro-2H-pyran-4-yl)oxy)phenyl)-1,3,5-triazin-2-yl)amino)phenyl)acrylamide. LCMS-ESI$^+$ (m/z): [M+H]$^+$ calcd for $C_{24}H_{23}N_6O_3$: 443.2; found: 443.1 $^1$H NMR (400 MHz, DMSO-$d_6$) δ 10.35 (s, 1H), 10.19 (s, 1H), 8.83 (s, 1H), 8.62 (m, 2H), 7.74 (m, 3H), 7.63 (m, 2H), 6.48 (dd, J=17.0, 10.1 Hz, 1H), 6.30 (dd, J=17.0, 2.0 Hz, 1H), 5.79 (dd, J=10.1, 2.1 Hz, 1H), 4.98 (tt, J=8.0, 4.0 Hz, 1H), 3.91 (m, 2H), 3.59 (m 2H), 2.09 (m, 2H), 1.73 (m, 2H).

Example 40

5-(4-((4-(2-hydroxypropan-2-yl)phenyl)amino)-1,3,5-triazin-2-yl)-2-((tetrahydro-2H-pyran-4-yl)oxy)benzonitrile

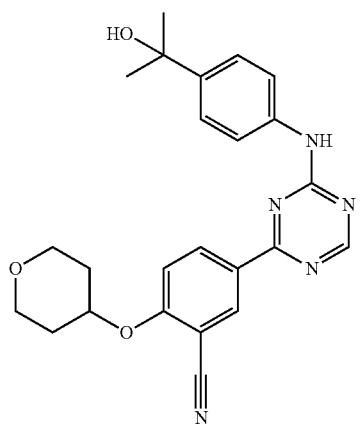 [SMILES: CC(C)(O)c1ccc(Nc2ncnc(-c3ccc(OC4CCOCC4)c(C#N)c3)n2)cc1]

Step 1: A solution of 2-(4-nitrophenyl)propan-2-ol (Sigma Aldrich, 0.25 g, 1.4 mmol) in methanol (1 mL) was added to a stirred suspension of 10% palladium on carbon in methanol (5 mL). Ammonium formate (0.44 g, 6.9 mmol) was added in a single portion. The mixture was stirred for two hours at room temperature before filtration of the mixture through a pad of Celite diatomaceous earth and concentration of the filtration under reduced pressure. The residue was taken up in ethyl acetate, washed with a saturated aqueous sodium hydrogen carbonate solution, dried over anhydrous magnesium sulfate, and concentrated to dryness under reduced pressure to provide 2-(4-aminophenyl)propan-2-ol, which was carried forward without further purification.
LCMS-ESI$^+$ (m/z): [M+H]$^+$ calcd for $C_9H_{14}NO$: 152.1; found: 152.0

Step 2: A sample of crude 2-(4-aminophenyl)propan-2-ol (50 mg, 0.33 mmol) in acetonitrile (0.5 mL) was added to a suspension of 5-(4-chloro-1,3,5-triazin-2-yl)-2-((tetrahydro-2H-pyran-4-yl)oxy)benzonitrile (46 mg, 0.15 mmol) in acetonitrile (1 mL). The suspension was treated with N,N-diisopropylethylamine (100 μL, 0.58 mmol) and then warmed with a heat gun for approximately one minute until homogeneous. Another portion crude 2-(4-aminophenyl)propan-2-ol (approximately 50 mg) was taken up in acetonitrile (approximately 0.5 mL) and added to the mixture, which was warmed with a heat gun for approximately one minute and then heated on a 70° C. block for 20 minutes. The reaction mixture was concentrated to dryness under reduced pressure and purified by prep HPLC (10-85% acetonitrile in water, 0.1% trifluoroacetic acid buffer) to furnish 5-(4-((4-(2-hydroxypropan-2-yl)phenyl)amino)-1,3,5-triazin-2-yl)-2-((tetrahydro-2H-pyran-4-yl)oxy)benzonitrile. LCMS-ESI$^+$ (m/z): [M+H]$^+$ calcd for $C_{24}H_{26}N_5O_3$: 432.2; found: 432.1 $^1$H NMR (400 MHz, DMSO-$d_6$) δ 10.39 (m, 1H), 8.85 (m, 1H), 8.69-8.56 (m, 2H), 7.81 (m, 2H), 7.71 (s, 1H), 7.59 (m, 2H), 4.99 (m, 1H), 3.91 (m, 2H), 3.59 (m, 2H), 2.10 (m, 2H), 1.74 (m, 2H), 1.47 (s, 6H).

Example 41

4-(2-cyano-4-(4-((4-(4-(oxetan-3-yl)piperazin-1-yl)phenyl)amino)-1,3,5-triazin-2-yl)phenoxy)-N-methylpiperidine-1-carboxamide

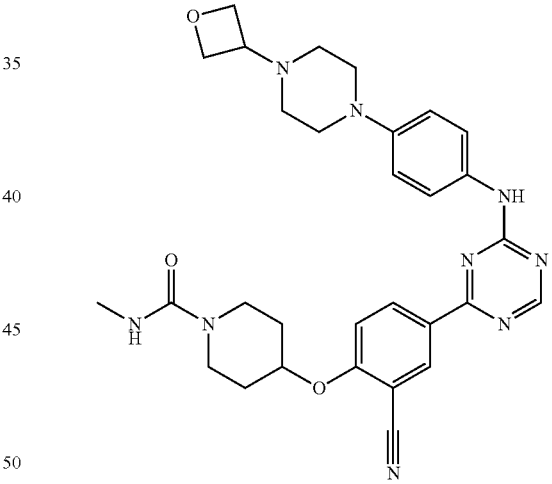

Preparation of tert-butyl 4-(2-cyano-4-(4-((4-(4-(oxetan-3-yl)piperazin-1-yl)phenyl)amino)-1,3,5-triazin-2-yl)phenoxy)piperidine-1-carboxylate:

A mixture of 4-chloro-N-(4-(4-(oxetan-3-yl)piperazin-1-yl)phenyl)-1,3,5-triazin-2-amine (0.31 g, 0.88 mmol), tert-butyl 4-(2-cyano-4-(4,4,5,5-tetramethyl-1,3,2-dioxaborolan-2-yl)phenoxy)piperidine-1-carboxylate (0.47 g, 1.1 mmol), and tetrakis(triphenylphosphine)palladium(0) (0.076 g, 7.5 mol %) in 1,2-dimethoxyethane (DME, 4 mL) was treated with 2M aqueous sodium carbonate solution (2.0 mL). The mixture was irradiated for 1 hour in a microwave reactor at 130° C. The crude mixture was purified by flash chromatography on silica gel to provide the desired product.
LCMS-ESI$^+$ (m/z): [M+H]$^+$ calcd for $C_{33}H_{41}N_8O_4$: 613.3; found: 613.1

Preparation of 5-(4-((4-(4-(oxetan-3-yl)piperazin-1-yl)phenyl)amino)-1,3,5-triazin-2-yl)-2-(piperidin-4-yloxy)benzonitrile:

tert-butyl 4-(2-cyano-4-(4-((4-(4-(oxetan-3-yl)piperazin-1-yl)phenyl)amino)-1,3,5-triazin-2-yl)phenoxy)piperidine-1-carboxylate (0.88 mmol assumed) was taken up in dichloromethane (8 mL) and treated with trifluoroacetic acid (2 mL). After one hour, the mixture was pipetted into saturated aqueous sodium hydrogen carbonate solution. The aqueous layer was extracted three times with dichloromethane. The combined organics were washed once with saturated aqueous sodium chloride solution, dried over anhydrous magnesium sulfate, filtered, and concentrated under reduced pressure to provide the desired material.
LCMS-ESI$^+$ (m/z): [M+H]$^+$ calcd for $C_{28}H_{33}N_8O_2$: 513.3; found: 513.3.

Preparation of 4-(2-cyano-4-(4-((4-(4-(oxetan-3-yl)piperazin-1-yl)phenyl)amino)-1,3,5-triazin-2-yl)phenoxy)-N-methylpiperidine-1-carboxamide:

5-(4-((4-(4-(oxetan-3-yl)piperazin-1-yl)phenyl)amino)-1,3,5-triazin-2-yl)-2-(piperidin-4-yloxy)benzonitrile (35 mg, 0.07 mmol), as a suspension in dichloromethane (1 mL), was treated with first with N,N-diisopropylethylamine (DIEA, 130 µL, 0.68 mmol), then (methylimino)(oxo)methane (Matrix Scientific, 21 µL, 0.34 mmol). After 5 minutes of stirring, the mixture was concentrated to dryness under reduced pressure. The residual solid was triturated with hot acetonitrile, filtered, and dried to provide 4-(2-cyano-4-(4-((4-(4-(oxetan-3-yl)piperazin-1-yl)phenyl)amino)-1,3,5-triazin-2-yl)phenoxy)-N-methylpiperidine-1-carboxamide. LCMS-ESI$^+$ (m/z): [M+H]$^+$ calcd for $C_{30}H_{36}N_9O_3$: 570.3; found: 570.4 $^1$H NMR (400 MHz, DMSO-d$_6$) δ 10.16 (m, 1H), 8.77 (s, 1H), 8.59 (m, 2H), 7.60 (m, 3H), 6.99 (m, 2H), 6.53 (m, 1H), 4.95 (m, 1H), 4.61 (m, 2H), 4.52 (m, 2H), 3.64 (m, 2H), 3.49 (m, 1H), 3.28 (m, 2H), 3.18 (m, 4H), 2.62 (d, J=4.2 Hz, 3H), 2.46 (m, 4H), 1.98 (m, 2H), 1.66 (m, 2H).

Example 42

N-(2-cyano-4-(4-((4-morpholinophenyl)amino)-1,3,5-triazin-2-yl)phenyl)cyclopropanecarboxamide

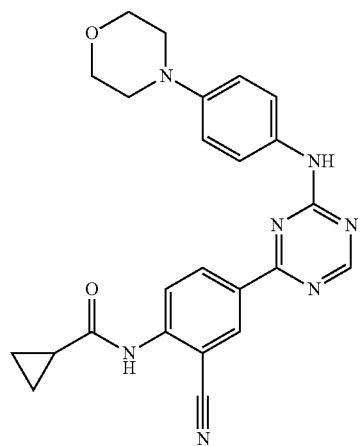 [SMILES: N#Cc1cc(-c2ncnc(Nc3ccc(N4CCOCC4)cc3)n2)ccc1NC(=O)C1CC1]

A solution of 2-amino-5-bromo-benzonitrile) 2.5 g, 13 mmol) in pyridine (25 mL) was treated with cyclopropanecarbonyl chloride (1.3 mL, 14 mmol) dropwise over a 30 minute period. The reaction was left for 3 days at room temperature, then concentrated under vacuum. The residue was partitioned between ethyl acetate and water, giving a suspension, which was then concentrated to dryness under reduced pressure. The residue was taken up in 1:1 pyridine/MeOH (60 mL) and treated with 2 M aqueous sodium hydroxide solution (12 mL) The mixture was stirred at room temperature for 90 minutes before concentration almost to dryness under reduced pressure. The residue was partitioned between ethyl acetate and water. The aqueous phase was extracted once with water. The combined organics were washed successively with water, 1% aqueous hydrochloric acid, saturated aqueous sodium hydrogen carbonate solution, and saturated aqueous sodium chloride solution. The organic layer was dried over anhydrous magnesium sulfate, filtered, and concentrated under reduced pressure to leave N-(4-bromo-2-cyanophenyl)cyclopropanecarboxamide as a solid. LCMS-ESI$^+$ (m/z): [M+H]$^+$ calcd for $C_{11}H_{10}BrN_2O$: 265.0; found: 265.1.

To a solution of N-(4-bromo-2-cyanophenyl)cyclopropanecarboxamide (3.4 g, 13 mmol) in 1,4-dioxane (60 mL), bis(pinacolato)diborane (4.0 g, 16 mmol), potassium acetate (3.7 g, 38 mmol), and [1,1'-bis(diphenylphosphino)ferrocene]dichloropalladium(II) (0.47 g, 5 mol %) were added. The resulting mixture was stirred for 3 days at 80° C. The cooled reaction mixture was diluted with ethyl acetate and water. Layers were separated. Aqueous phase was extracted once with ethyl acetate. The organics were combined, washed successively with water and saturated aqueous sodium chloride solution, dried over anhydrous magnesium sulfate, filtered, and concentrated under reduced pressure. The residue was purified by flash chromatography to provide N-(2-cyano-4-(4,4,5,5-tetramethyl-1,3,2-dioxaborolan-2-yl)phenyl)cyclopropanecarboxamide. LCMS-ESI$^+$ (m/z): [M+H]$^+$ calcd for $C_{17}H_{22}BN_2O_3$: 313.2; found: 313.3.

A suspension of 4-chloro-N-(4-morpholinophenyl)-1,3,5-triazin-2-amine (0.11 g, 0.37 mmol) and N-(2-cyano-4-(4,4,5,5-tetramethyl-1,3,2-dioxaborolan-2-yl)phenyl)cyclopropanecarboxamide (0.14 g, 0.44 mmol) in 1,2-dimethoxyethane (DME, 3 mL) was treated successively with palladium (II) acetate (0.008 g, 10 mol %), triphenylphosphine (0.029 g, 0.11 mmol), and 2M aqueous sodium carbonate solution (0.8 mL). The mixture was irradiated for 1 hour in a microwave reactor at 125° C. The crude mixture was purified by flash chromatography on silica gel to furnish N-(2-cyano-4-(4-((4-morpholinophenyl)amino)-1,3,5-triazin-2-yl)phenyl)cyclopropanecarboxamide. LCMS-ESI$^+$ (m/z): [M+H]$^+$ calcd for $C_{24}H_{24}N_7O_2$: 442.2; found: 442.5 $^1$H NMR (400 MHz, DMSO-d$_6$) δ 10.69 (s, 1H), 10.22 (d, J=13.2 Hz, 1H), 8.81 (s, 1H), 8.74-8.52 (m, 2H), 7.93 (d, J=8.8 Hz, 1H), 7.63 (m, 2H), 7.00 (m, 2H), 3.79 (m, 4H), 3.13 (s, 4H), 2.02 (m, 1H), 0.93 (m, 4H).

Example 43

5-(4-((6-(4-(oxetan-3-yl)piperazin-1-yl)pyridin-3-yl)amino)-1,3,5-triazin-2-yl)-2-((tetrahydro-2H-pyran-4-yl)oxy)benzonitrile

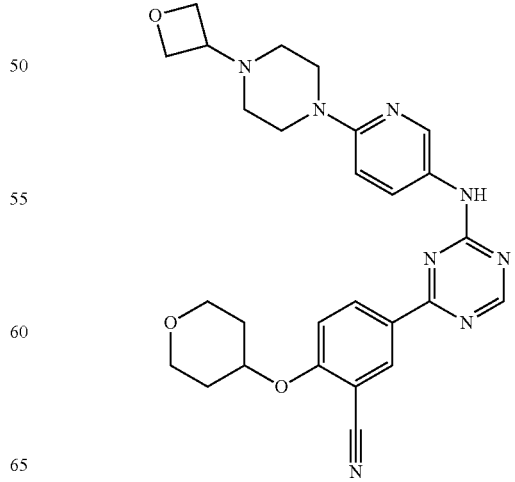

To a solution of 2-chloro-5-nitropyridine (1.0 g, 6.3 mmol) in 2-methyltetrahydrofuran (60 mL) was added 1-(oxetan-3-yl)piperazine (0.99 g, 6.9 mmol), followed by triethylamine (1.3 mL, 9.5 mmol), and the reaction mixture was stirred at room temperature overnight. After the mixture was concentrated under reduced pressure, the residue was partitioned between dichloromethane and water. The aqueous phase was extracted three times with dichloromethane. The combined extracts were washed with saturated aqueous sodium chloride solution, dried over anhydrous magnesium sulfate, filtered, and concentrated to give 1-(5-nitropyridin-2-yl)-4-(oxetan-3-yl)piperazine. LCMS-ESI$^+$ (m/z): [M+H]$^+$ calcd for $C_{12}H_{17}N_4O_3$: 265.1; found: 265.1.

A suspension of 1-(5-nitropyridin-2-yl)-4-(oxetan-3-yl) piperazine (1.7 g, 6.3 mmol) was taken up as a suspension in tetrahydrofuran/methanol/ethyl acetate (approximately 1:1:1, 100 mL) was degassed and then charged with 10% wt. palladium on charcoal (300 mg). The suspension was stirred overnight under a balloon of hydrogen. The reaction mixture was filtered over Celite diatomaceous earth, and the filtrate was concentrated under reduced pressure to provide 6-(4-(oxetan-3-yl)piperazin-1-yl)pyridin-3-amine. LCMS-ESI$^+$ (m/z): [M+H]$^+$ calcd for $C_{12}H_{19}N_4O$: 235.2; found: 235.2.

To a solution of 2,4-dichloro-1,3,5-triazine (0.35 g, 2.3 mmol) in N,N-dimethylformamide (6 mL) at 0° C. were added N,N-diisopropylethylamine, followed by 6-(4-(oxetan-3-yl)piperazin-1-yl)pyridin-3-amine (0.50 g, 2.1 mmol) and the mixture was stirred at 0° C. for 30 minutes and then allowed to warm to room temperature. The mixture was concentrated under reduced pressure and purified by flash chromatography (silica gel) to provide 4-chloro-N-(6-(4-(oxetan-3-yl)piperazin-1-yl)pyridin-3-yl)-1,3,5-triazin-2-amine. LCMS-ESI$^+$ (m/z): [M+H]$^+$ calcd for $C_{15}H_{19}ClN_7O$: 348.1; found: 348.3.

A mixture of 4-chloro-N-(6-(4-(oxetan-3-yl)piperazin-1-yl)pyridin-3-yl)-1,3,5-triazin-2-amine (0.12 g, 0.35 mmol), 2-((tetrahydro-2H-pyran-4-yl)oxy)-5-(4,4,5,5-tetramethyl-1,3,2-dioxaborolan-2-yl)benzonitrile (0.12 g, 0.38 mmol), tetrakis(triphenylphosphine)palladium(0) (0.020 g, 5 mol %) in 1,2-dimethoxyethane (DME, 3 mL) was treated with 2M aqueous sodium carbonate solution (0.78 mL). The mixture was irradiated for 1 hour in a microwave reactor at 130° C. The crude mixture was purified by flash chromatography on silica gel to furnish 5-(4-((6-(4-(oxetan-3-yl) piperazin-1-yl)pyridin-3-yl)amino)-1,3,5-triazin-2-yl)-2-((tetrahydro-2H-pyran-4-yl)oxy)benzonitrile. LCMS-ESI$^+$ (m/z): [M+H]$^+$ calcd for $C_{27}H_{31}N_8O_3$: 515.2; found: 515.3 $^1$H NMR (400 MHz, DMSO-d$_6$) δ 10.24 (br, 1H), 8.80 (s, 1H), 8.58 (m, 2H), 8.46 (s, 1H), 8.02 (br, 1H), 7.60 (d, J=9.2 Hz, 1 H), 7.08 (br, 1H), 4.99 (tt, J=7.8, 4.0 Hz, 1H), 4.77 (m, 4H), 4.40 (m, 1H), 3.91 (m, 2H), 3.59 (m, 2H), 3.50-2.80 (m, 8H), 2.09 (m, 2H), 1.73 (m, 2H).

Example 44

2-((1-(2-cyanoacetyl)piperidin-4-yl)oxy)-5-(4-((4-(4-(oxetan-3-yl)piperazin-1-yl)phenyl)amino)-1,3,5-triazin-2-yl)benzonitrile

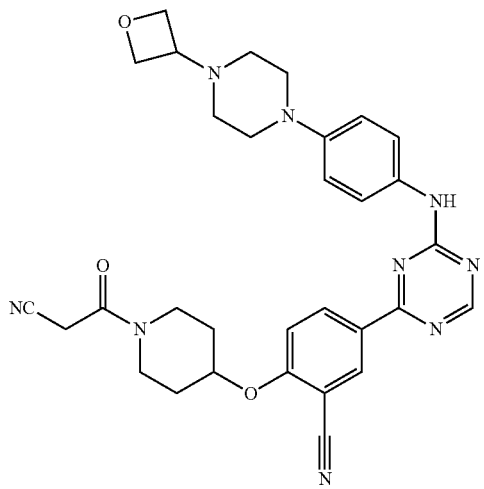

5-(4-((4-(4-(oxetan-3-yl)piperazin-1-yl)phenyl)amino)-1,3,5-triazin-2-yl)-2-(piperidin-4-yloxy)benzonitrile (78 mg, 0.15 mmol), and cyanoacetic acid (19 mg, 0.23 mmol) were taken up as suspension in acetonitrile (3 mL). The mixture was treated successively with N,N-diisopropylethylamine (80 μL, 0.46 mmol) and N-[(dimethylamino)-1H-1,2,3-triazolo-[4,5-b]pyridin-1-ylmethylene]-N-methylmethanaminiumhexafluorophosphate N-oxide (HATU, 87 mg, 0.23 mmol). The mixture was stirred for one hour at room temperature and then purified by flash chromatography (silica gel) to provide 2-((1-(2-cyanoacetyl)piperidin-4-yl) oxy)-5-(4-((4-(4-(oxetan-3-yl)piperazin-1-yl)phenyl) amino)-1,3,5-triazin-2-yl)benzonitrile. LCMS-ESI$^+$ (m/z): [M+H]$^+$ calcd for $C_{31}H_{34}N_9O_3$: 580.3; found: 580.3 $^1$H NMR (400 MHz, DMSO-d$_6$) δ 10.16 (m, 1H), 8.78 (s, 1H), 8.61 (m, 2H), 8.10 (br, 1H), 7.61 (m, 2H), 7.01 (m, 2H), 5.05 (m, 1H), 4.61 (m, 2H), 4.52 (m, 2H), 4.13 (s, 2H), 3.82-3.39 (m, 5H), 3.18 (m, 4H), 2.46 (m, 4H), 2.03 (m, 2H), 1.76 (m, 2H).

Example 45

2-((1-(2-hydroxy-2-methylpropanoyl)piperidin-4-yl) oxy)-5-(4-((4-(4-(oxetan-3-yl)piperazin-1-yl)phenyl) amino)-1,3,5-triazin-2-yl)benzonitrile

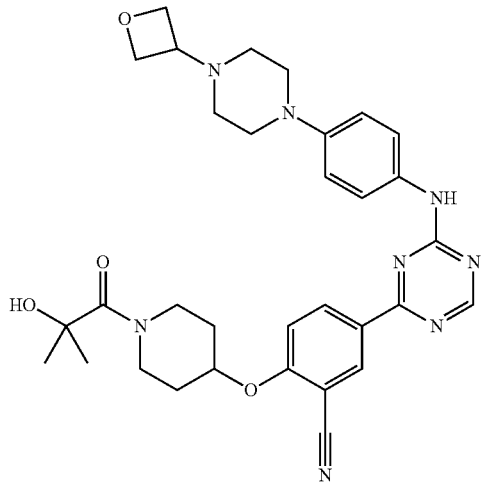 [SMILES: CC(C)(O)C(=O)N1CCC(Oc2ccc(-c3ncnc(Nc4ccc(N5CCN(C6COC6)CC5)cc4)n3)cc2C#N)CC1]

5-(4-((4-(4-(oxetan-3-yl)piperazin-1-yl)phenyl)amino)-1,3,5-triazin-2-yl)-2-(piperidin-4-yloxy)benzonitrile (52 mg, 0.10 mmol), and 2-hydroxyisobutyric acid (16 mg, 0.15 mmol) were taken up as suspension in dichloromethane (3 mL). The mixture was treated successively with N,N-diisopropylethylamine (35 µL, 0.20 mmol) and N-[(dimethylamino)-1H-1,2,3-triazolo-[4,5-b]pyridin-1-ylmethylene]-N-methylmethanaminiumhexafluorophosphate N-oxide (HATU, 58 mg, 0.15 mmol). The mixture was stirred for 20 minutes at room temperature and then purified by flash chromatography (silica gel) to provide 2-((1-(2-hydroxy-2-methylpropanoyl)piperidin-4-yl)oxy)-5-(4-((4-(4-(oxetan-3-yl)piperazin-1-yl)phenyl)amino)-1,3,5-triazin-2-yl)benzonitrile.

LCMS-ESI$^+$ (m/z): [M+H]$^+$ calcd for $C_{32}H_{38}N_8O_4$: 599.3; found: 599.3 $^1$H NMR (400 MHz, DMSO-d$_6$) δ 10.16 (m, 1H), 8.77 (s, 1H), 8.60 (m, 2H), 7.60 (m, 2H), 7.01 (m, 2H), 5.48 (s, 1H), 5.06 (m, 1H), 4.61 (m, 2H), 4.52 (m, 2H), 3.64 (m, 2H), 3.52 (m, 3H), 3.19 (m, 4H), 2.46 (m, 4H), 2.06 (m, 2H), 1.74 (m, 2H), 1.37 (s, 6H).

Example 46

4-((4-(3-cyano-4-((tetrahydro-2H-pyran-4-yl)oxy)phenyl)-1,3,5-triazin-2-yl)amino)-N-isopropylbenzamide

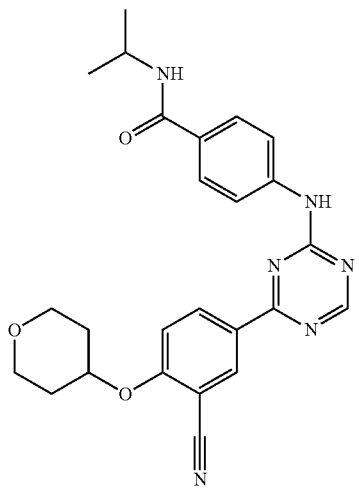 [SMILES: CC(C)NC(=O)c1ccc(Nc2ncnc(-c3ccc(OC4CCOCC4)c(C#N)c3)n2)cc1]

A suspension of 5-(4-chloro-1,3,5-triazin-2-yl)-2-((tetrahydro-2H-pyran-4-yl)oxy)benzonitrile (46 mg, 0.15 mmol) and 4-amino-N-isopropylbenzamide (31 mg, 0.17 mmol) in acetonitrile (4 mL) was treated with N,N-diisopropylethylamine (0.10 mL, 0.58 mmol). The mixture was heated in a microwave reactor in the following successive intervals: 15 minutes at 85° C., 30 minutes at 120° C. and 120 minutes at 120° C. After cooling to room temperature, the solid was collected by filtration, washed with acetonitrile, and dried under house vacuum and then in a vacuum oven (60° C.) over P$_2$O$_5$ to provide 4-((4-(3-cyano-4-((tetrahydro-2H-pyran-4-yl)oxy)phenyl)-1,3,5-triazin-2-yl)amino)-N-isopropylbenzamide. LCMS-ESI$^+$ (m/z): [M+H]$^+$ calcd for $C_{25}H_{27}N_6O_3$: 459.2; found: 459.2

$^1$H NMR (400 MHz, DMSO-d$_6$) δ 10.59 (s, 1H), 8.91 (s, 1H), 8.64 (m, 2H), 8.16 (m, 1H), 7.91 (m, 4H), 7.61 (d, J=9.4 Hz, 1H), 4.99 (m, 1H), 4.15 (m, 1H), 3.91 (m, 2H), 3.59 (m, 2H), 2.09 (m, 2H), 1.74 (m, 2H), 1.21 (d, J=6.6 Hz, 6H).

Example 47

5-(4-((3-(2-hydroxypropan-2-yl)phenyl)amino)-1,3,5-triazin-2-yl)-2-((tetrahydro-2H-pyran-4-yl)oxy)benzonitrile

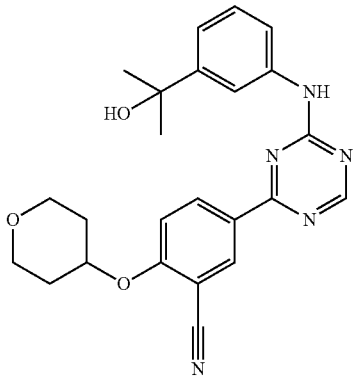 [SMILES: CC(C)(O)c1cccc(Nc2ncnc(-c3ccc(OC4CCOCC4)c(C#N)c3)n2)c1]

A suspension of 5-(4-chloro-1,3,5-triazin-2-yl)-2-((tetrahydro-2H-pyran-4-yl)oxy)benzonitrile (53 mg, 0.16 mmol) and 2-(3-aminophenyl)propan-2-ol (Enamine, 30 mg, 0.20 mmol) in acetonitrile (2.5 mL) was treated with N,N-diisopropylethylamine (0.12 mL, 0.67 mmol). The mixture was heated in a microwave reactor for 60 minutes at 85° C. The cooled reaction mixture was purified by flash chromatography (silica gel) to provide 5-(4-((3-(2-hydroxypropan-2-yl)phenyl)amino)-1,3,5-triazin-2-yl)-2-((tetrahydro-2H-pyran-4-yl)oxy)benzonitrile. LCMS-ESI$^+$ (m/z): [M+H]$^+$ calcd for $C_{24}H_{26}N_5O_3$: 432.2; found: 432.1 $^1$H NMR (400 MHz, DMSO-d$_6$) δ 10.33 (s, 1H), 8.84 (s, 1H), 8.65 (m, 2H), 8.13 (s, 1H), 7.59 (m, 1H), 7.50 (br, 1H), 7.34 (m, 1H), 7.26 (m, 1H), 5.07 (s, 1H), 5.00 (m, 1H), 3.91 (m, 2H), 3.60 (m, 2H), 2.09 (m, 2H), 1.73 (m, 2H), 1.51 (s, 6H).

Example 48

2-((tetrahydro-2H-pyran-4-yl)oxy)-5-(4-((3-(2,2,2-trifluoro-1-hydroxyethyl)phenyl)amino)-1,3,5-triazin-2-yl)benzonitrile

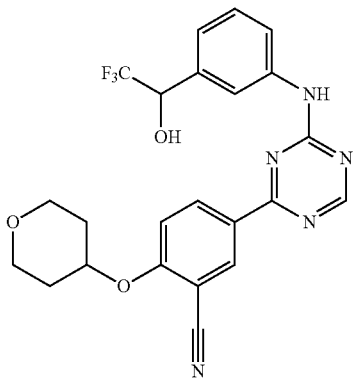 [SMILES: N#Cc1cc(-c2ncnc(Nc3cccc(C(O)C(F)(F)F)c3)n2)ccc1OC1CCOCC1]

Preparation of 1-(3-aminophenyl)-2,2,2-trifluoroethanol:
A solution of 1-(3-aminophenyl)-2,2,2-trifluoroethanone (Enamine, 0.20 g, 0.91 mmol) in methanol (5 mL) was degassed before the introduction of 10% palladium on carbon (40 mg). The mixture was stirred overnight under a balloon of hydrogen gas. The catalyst was removed by filtration through pad of Celite diatomaceous earth. The filtrate was concentrated under reduced pressure to provide 1-(3-aminophenyl)-2,2,2-trifluoroethanol. LCMS-ESI+ (m/z): [M+H]+ calcd for $C_8H_9F_3NO$: 192.1; found: 192.0.

Preparation of 2-((tetrahydro-2H-pyran-4-yl)oxy)-5-(4-((3-(2,2,2-trifluoro-1-hydroxyethyl)phenyl)amino)-1,3,5-triazin-2-yl)benzonitrile:

A suspension of 5-(4-chloro-1,3,5-triazin-2-yl)-2-((tetrahydro-2H-pyran-4-yl)oxy)benzonitrile (100 mg, 0.32 mmol) and 1-(3-aminophenyl)-2,2,2-trifluoroethanol (170 mg, 0.9 mmol) in isopropanol (2.5 mL) was treated with N,N-diisopropylethylamine (0.22 mL, 1.3 mmol). The mixture was heated in a microwave reactor for 30 minutes at 85° C. The cooled reaction mixture was purified by flash chromatography (silica gel), followed by prep HPLC (10-85% acetonitrile in water, 0.1% trifluoroacetic acid buffer), to provide 2-((tetrahydro-2H-pyran-4-yl)oxy)-5-(4-((3-(2,2,2-trifluoro-1-hydroxyethyl)phenyl)amino)-1,3,5-triazin-2-yl) benzonitrile. LCMS-ESI+ (m/z): [M+H]+ calcd for $C_{23}H_{21}F_3N_5O_3$: 472.2; found: 472.1 $^1$H NMR (400 MHz, DMSO-d6) δ 10.47 (s, 1H), 8.87 (s, 1H), 8.65 (m, 2H), 8.17 (br, 1H), 7.68 (m, 1H), 7.58 (d, J=8.8 Hz, 1H), 7.45 (t, J=7.9 Hz 1H), 7.27 (d, J=7.6 Hz 1H), 6.90 (m, 1H), 5.21 (m, 1H), 5.00 (m, 1H), 3.91 (m, 2H), 3.60 (m, 2H), 2.09 (m, 2H), 1.74 (m, 2H).

Example 49

5-(4-((4-morpholinophenyl)amino)-1,3,5-triazin-2-yl)-2-((tetrahydro-2H-pyran-4-yl)oxy)benzonitrile

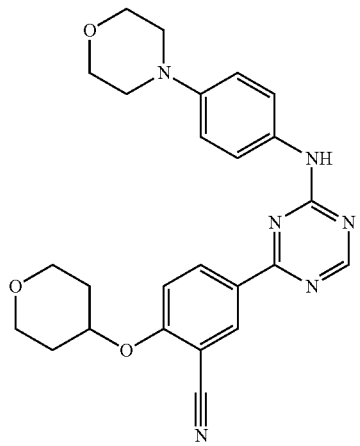 [SMILES: N#Cc1cc(-c2ncnc(Nc3ccc(N4CCOCC4)cc3)n2)ccc1OC1CCOCC1]

A suspension of 4-chloro-N-(4-morpholinophenyl)-1,3,5-triazin-2-amine (0.15 g, 0.51 mmol) and 2-((tetrahydro-2H-pyran-4-yl)oxy)-5-(4,4,5,5-tetramethyl-1,3,2-dioxaborolan-2-yl)benzonitrile (0.19 g, 0.57 mmol) in 1,2-dimethoxyethane (DME, 2 mL) was treated successively with palladium (II) acetate (0.012 g, 10 mol %), triphenylphosphine (0.049 g, 0.15 mmol), and 2M aqueous sodium carbonate solution (1.2 mL). The mixture was irradiated for 1 hour in a microwave reactor at 125° C. The crude mixture was purified first by flash chromatography on silica gel and then by prep HPLC (10-95% acetonitrile in water, 0.1% trifluoroacetic acid buffer) to furnish 5-(4-((4-morpholinophenyl)amino)-1,3,5-triazin-2-yl)-2-((tetrahydro-2H-pyran-4-yl)oxy)benzonitrile. LCMS-ESI+ (m/z): [M+H]+ calcd for $C_{25}H_{27}N_6O_3$: 459.2; found: 459.4 $^1$H NMR (400 MHz, DMSO-d6) δ 10.19 (br, 1H), 8.79 (s, 1H), 8.60 (d, J=9.5 Hz, 2H), 7.65 (br, 2H), 7.60 (d, J=9.3 Hz, 1H), 7.05 (br, 2H), 4.98 (m, 1H), 3.91 (m, 2H), 3.85-3.77 (m, 4H), 3.59 (m, 2H), 3.16 (m, 4H), 2.18-2.02 (m, 2H), 1.74 (m, 2H).

Example 50

5-(4-((4-(methylsulfonyl)phenyl)amino)-1,3,5-triazin-2-yl)-2-((tetrahydro-2H-pyran-4-yl)oxy)benzonitrile

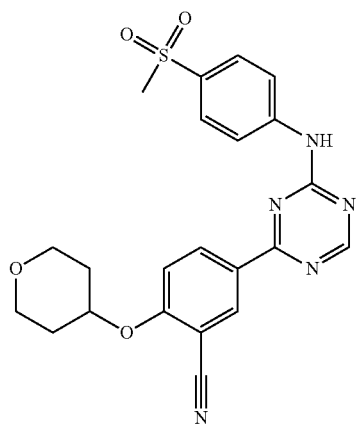 [SMILES: CS(=O)(=O)c1ccc(Nc2ncnc(-c3ccc(OC4CCOCC4)c(C#N)c3)n2)cc1]

Preparation of 4-chloro-N-(4-(methylsulfonyl)phenyl)-1,3,5-triazin-2-amine:

To a solution of 2,4-dichloro-1,3,5-triazine (0.50 g, 3.3 mmol) in N,N-dimethylformamide (DMF, 6 mL) at 0° C. were added sequentially N,N-diisopropylethylamine (DIEA, 0.60 mL, 3.5 mmol) and 4-(methylsulfonyl)aniline (0.52 g, 3.0 mmol), and the mixture was stirred at 0° C. for 30 minutes and then allowed to warm to room temperature. The mixture was diluted with ethyl acetate and water. A small volume of tetrahydrofuran was added. The layers were separated and the aqueous phase was extracted twice with ethyl acetate. The combined organics were filtered, washed once with saturated aqueous sodium chloride solution, dried over anhydrous magnesium sulfate, filtered, and concentrated under reduced pressure to provide 4-chloro-N-(4-(methylsulfonyl)phenyl)-1,3,5-triazin-2-amine. An aliquot of desired material in acetonitrile was treated with one drop of pyrrolidine to indirectly confirm the presence of the desired material.

LCMS-ESI+ (m/z): [M+pyrrolidine−HCl+H]+ calcd for $C_{14}H_{18}N_5O_2S$: 320.1; found: 320.2.

Preparation of 5-(4-((4-(methylsulfonyl)phenyl)amino)-1,3,5-triazin-2-yl)-2-((tetrahydro-2H-pyran-4-yl)oxy)benzonitrile:

A mixture of 4-chloro-N-(4-(methylsulfonyl)phenyl)-1,3,5-triazin-2-amine (0.15 g, 0.53 mmol), 2-((tetrahydro-2H-pyran-4-yl)oxy)-5-(4,4,5,5-tetramethyl-1,3,2-dioxaborolan-2-yl)benzonitrile (0.19 g, 0.58 mmol), tetrakis(triphenylphosphine)palladium(0) (0.046 g, 7.5 mol %) in 1,2-dimethoxyethane (DME, 3 mL) was treated with 2M aqueous sodium carbonate solution (1.2 mL). The mixture was irradiated for 1 hour in a microwave reactor at 130° C.

The crude mixture was purified by flash chromatography on silica gel to provide 5-(4-((4-(methylsulfonyl)phenyl)amino)-1,3,5-triazin-2-yl)-2-((tetrahydro-2H-pyran-4-yl)oxy)benzonitrile. LCMS-ESI⁺ (m/z): [M+H]⁺ calcd for $C_{22}H_{22}N_5O_4S$: 452.1; found: 452.1.

¹H NMR (400 MHz, DMSO-$d_6$) δ 10.85 (s, 1H), 8.97 (s, 1H), 8.66 (m, 2H), 8.10 (m, 2H), 7.97 (d, J=8.7 Hz, 2H), 7.62 (d, J=9.6 Hz, 1H), 5.00 (m, 1H), 3.92 (m, 2H), 3.60 (m, 2H), 3.24 (s, 3H), 2.10 (m, 2H), 1.74 (m, 2H).

Example 51

N-(2-(4-(2-cyano-4-(4-((4-(4-(oxetan-3-yl)piperazin-1-yl)phenyl)amino)-1,3,5-triazin-2-yl)phenoxy)piperidin-1-yl)-2-oxoethyl)formamide

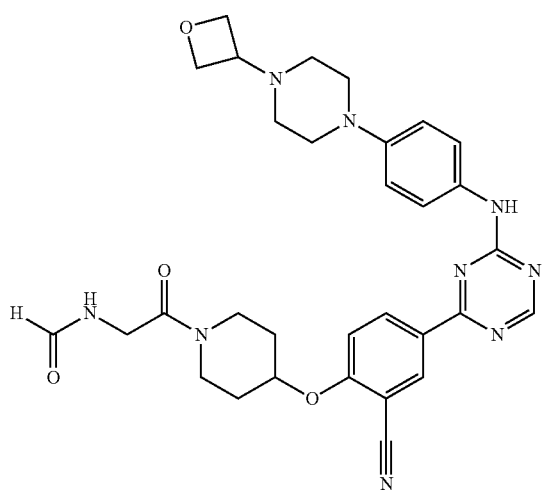 [SMILES: N#Cc1cc(-c2ncnc(Nc3ccc(N4CCN(C5COC5)CC4)cc3)n2)ccc1OC1CCN(C(=O)CNC=O)CC1]

5-(4-((4-(4-(oxetan-3-yl)piperazin-1-yl)phenyl)amino)-1,3,5-triazin-2-yl)-2-(piperidin-4-yloxy)benzonitrile (60 mg, 0.12 mmol), and N-formylglycine (Sigma Aldrich, 18 mg, 0.18 mmol) were taken up as suspension in dichloromethane (3 mL). The mixture was treated successively with N,N-diisopropylethylamine (41 μL, 0.23 mmol) and N-[(dimethylamino)-1H-1,2,3-triazolo-[4,5-b]pyridin-1-ylmethylene]-N-methylmethanaminiumhexafluorophosphate N-oxide (HATU, 67 mg, 0.18 mmol). The mixture was stirred for three days at room temperature and then purified by flash chromatography (silica gel) to provide N-(2-(4-(2-cyano-4-(4-((4-(4-(oxetan-3-yl)piperazin-1-yl)phenyl)amino)-1,3,5-triazin-2-yl)phenoxy)piperidin-1-yl)-2-oxoethyl)formamide. LCMS-ESI⁺ (m/z): [M+H]⁺ calcd for $C_{31}H_{36}N_9O_4$: 598.3; found: 598.3

¹H NMR (400 MHz, DMSO-$d_6$) δ 10.16 (m, 1H), 8.78 (s, 1H), 8.60 (m, 2H), 8.20 (m, 1H), 8.14 (s, 1H), 7.61 (m, 2H), 7.02 (m, 2H), 5.12-5.00 (m, 2H), 4.61 (m, 3H), 4.52 (m, 2H), 4.10 (t, J=4.8 Hz, 2H), 3.79 (m, 1H), 3.74-3.42 (m, 3H), 3.18 (m, 4H), 2.46 (m, 4H), 2.05 (m, 2H), 1.76 (m, 2H).

Example 52

N-(2-(4-(2-cyano-4-(4-((4-(4-(oxetan-3-yl)piperazin-1-yl)phenyl)amino)-1,3,5-triazin-2-yl)phenoxy)piperidin-1-yl)-2-oxoethyl)acetamide

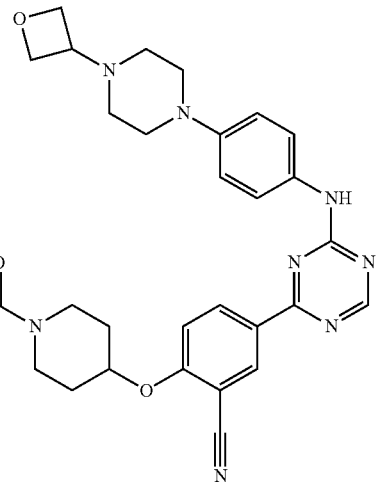

5-(4-((4-(4-(oxetan-3-yl)piperazin-1-yl)phenyl)amino)-1,3,5-triazin-2-yl)-2-(piperidin-4-yloxy)benzonitrile (55 mg, 0.11 mmol), and N-acetylglycine (Sigma Aldrich, 19 mg, 0.16 mmol) were taken up as suspension in dichloromethane (3 mL). The mixture was treated successively with N,N-diisopropylethylamine (38 μL, 0.22 mmol) and N-[(dimethylamino)-1H-1,2,3-triazolo-[4,5-b]pyridin-1-ylmethylene]-N-methylmethanaminiumhexafluorophosphate N-oxide (HATU, 61 mg, 0.16 mmol). The mixture was stirred for three days at room temperature and then purified by flash chromatography (silica gel) to provide N-(2-(4-(2-cyano-4-(4-((4-(4-(oxetan-3-yl)piperazin-1-yl)phenyl)amino)-1,3,5-triazin-2-yl)phenoxy)piperidin-1-yl)-2-oxoethyl)acetamide. LCMS-ESI⁺ (m/z): [M+H]⁺ calcd for $C_{32}H_{38}N_9O_4$: 612.3; found: 612.4.

¹H NMR (400 MHz, DMSO-$d_6$) δ 10.17 (m, 1H), 8.78 (s, 1H), 8.61 (m, 2H), 8.19 (bs, 1H), 8.01 (t, J=5.5 Hz, 1H), 7.61 (m, 2H), 7.02 (m, 2H), 5.04 (m, 1H), 4.61 (m, 2H), 4.52 (m, 2H), 4.02 (t, J=5.0 Hz, 2H), 3.80 (m, 1H), 3.65 (m, 2H), 3.48 (m, 2H), 3.18 (m, 4H), 2.46 (m, 4H), 2.05 (m, 2H), 1.91 (s, 3H), 1.76 (m, 2H).

Example 53

5-(4-((4-morpholinophenyl)amino)-1,3,5-triazin-2-yl)-2-(pyrrolidin-1-yl)benzonitrile

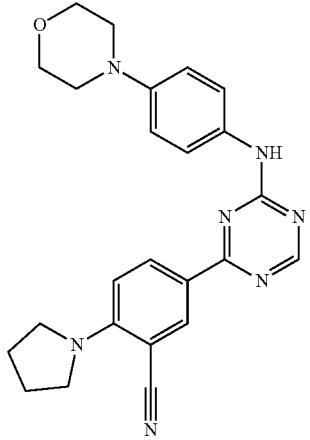 [SMILES: N#Cc1cc(-c2ncnc(Nc3ccc(N4CCOCC4)cc3)n2)ccc1N1CCCC1]

To a solution of 2,4-dichloro-1,3,5-triazine (0.65 g, 4.3 mmol) in N,N-dimethylformamide (DMF, 3 mL) at 0° C. were added sequentially N,N-diisopropylethylamine (DIEA, 0.78 mL, 4.5 mmol) and 4-morpholinoaniline (0.70 g, 3.9 mmol) and the mixture was stirred at 0° C. for 30 minutes and then allowed to warm to room temperature. The mixture was diluted with ethyl acetate and washed once each with water and a solution of saturated aqueous sodium chloride. The combined extracts were dried over anhydrous magnesium sulfate, filtered, and concentrated under reduced pressure and then purified by flash chromatography on silica gel to provide 4-chloro-N-(4-morpholinophenyl)-1,3,5-triazin-2-amine. LCMS-ESI$^+$ (m/z): [M+H]$^+$ calcd for $C_{13}H_{15}ClN_5O$: 292.1; found: 292.2.

A suspension of 4-chloro-N-(4-morpholinophenyl)-1,3,5-triazin-2-amine (0.15 g, 0.51 mmol) and 2-(pyrrolidin-1-yl)-5-(4,4,5,5-tetramethyl-1,3,2-dioxaborolan-2-yl)benzonitrile (0.17 g, 0.57 mmol) in 1,2-dimethoxyethane (DME, 2 mL) was treated successively with palladium (II) acetate (0.012 g, 10 mol %), triphenylphosphine (0.049 g, 0.15 mmol), and 2M aqueous sodium carbonate solution (1.2 mL). The mixture was irradiated for 1 hour in a microwave reactor at 125° C. The crude mixture was purified first by flash chromatography on silica gel and then by prep HPLC (10-95% acetonitrile in water, 0.1% trifluoroacetic acid buffer) to furnish 5-(4-((4-morpholinophenyl)amino)-1,3,5-triazin-2-yl)-2-(pyrrolidin-1-yl)benzonitrile. LCMS-ESI$^+$ (m/z): [M+H]$^+$ calcd for $C_{24}H_{25}N_7O$: 428.2; found: 428.3 $^1$H NMR (400 MHz, DMSO-d$_6$) δ 10.01 (bs, 1H), 8.69 (s, 1H), 8.46 (br, 1H), 8.33 (d, J=9.0 Hz, 1H), 7.63 (br, 2H), 7.00 (br, 2H), 6.94 (d, J=9.2 Hz, 1H), 3.84-3.75 (m, 4H), 3.75-3.64 (m, 4H), 3.12 (m, 4H), 2.10-1.96 (m, 4H).

Example 54

5-(4-((4-(1-(oxetan-3-yl)piperidin-4-yl)phenyl)amino)-1,3,5-triazin-2-yl)-2-((tetrahydro-2H-pyran-4-yl)oxy)benzonitrile

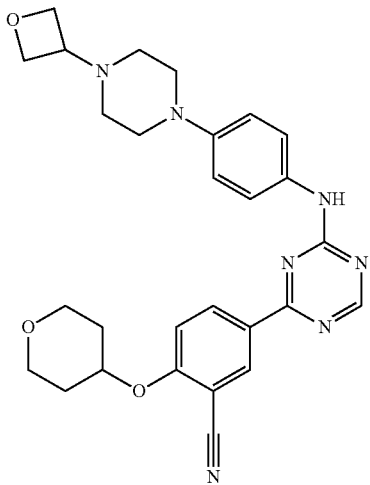 [SMILES: N#Cc1cc(-c2ncnc(Nc3ccc(N4CCN(C5COC5)CC4)cc3)n2)ccc1OC1CCOCC1]

Preparation of 4-(4-nitrophenyl)piperidine: 4-Phenylpiperidine (5.5 g, 34 mmol) was dissolved in glacial acetic acid (28 mL) and stirred in an ice-water bath (internal temp <20° C.) while a solution of 1.8 mL concentrated sulfuric acid (1.8 mL) in glacial acetic acid (28 mL) was added, followed by a solution of 90% nitric acid (1.6 mL) in acetic acid (14 mL). The cooling bath was removed and sulfuric acid (28 mL) was added without cooling, causing the internal temperature to reach a maximum of 50° C. The mixture was allowed to stir at room temperature for about 2 hours before it was added to ice-water (~200 g) and basified with small additions of solid sodium hydrogen carbonate to ~pH 5. The mixture was then brought to pH 14 with 50/50 (w/w) sodium hydroxide solution in an exothermic reaction. The mixture was extracted three times with dichloromethane, washed once each with 1% aqueous sodium hydroxide solution and saturated with sodium chloride, dried over anhydrous magnesium sulfate, filtered, and concentrated under reduced pressure. The gummy residue was triturated with refluxing cyclohexane. The resulting powder was collected by vacuum filtration to provide 4-(4-nitrophenyl)piperidine.

Preparation of 4-(4-nitrophenyl)-1-(oxetan-3-yl)piperidine:

3-iodooxetane (Astatech, 1.9 g, 10 mmol) was added via syringe to a suspension of 4-(4-nitrophenyl)piperidine (1.1 g, 5.2 mmol) and potassium carbonate (0.72 g, 5.2 mmol) in acetonitrile. Vial was sealed. The mixture was stirred with heating in a sealed vessel on a 125° C. After five hours, an additional quantity of potassium carbonate (0.72 g, 5.2 mmol) was added. The mixture was heated overnight. After cooling to room temperature, the mixture was filtered through a pad of Celite diatomaceous earth, eluting with dichloromethane and acetonitrile. The filtrate was concentrated to dryness under reduced pressure to provide 4-(4-nitrophenyl)-1-(oxetan-3-yl)piperidine, which was carried forward without further purification. LCMS-ESI$^+$ (m/z): [M+H]$^+$ calcd for $C_{14}H_{19}N_2O_3$: 263.1; found: 263.2

Preparation of 4-(1-(oxetan-3-yl)piperidin-4-yl)aniline:

Crude 4-(4-nitrophenyl)-1-(oxetan-3-yl)piperidine (5.2 mmol assumed) was taken up in methanol (10 mL) with a heat gun. After cooling, the mixture was degassed, then treated with 10% palladium on carbon (150 mg). The mixture was stirred for 5 hours under a balloon of hydrogen. The mixture was filtered through a pad of Celite diatomaceous earth. The filtrate was concentrated under reduced pressure. The residue was re-dissolved in methanol (approximately 50 mL). After the mixture was degassed, it was treated with 10% palladium on carbon (150 mg). The mixture was shaken overnight under 45 psi hydrogen. The mixture was filtered through a pad of Celite diatomaceous earth. The filtrate was concentrated under reduced pressure to provide the desired product.

LCMS-ESI$^+$ (m/z): [M+H]$^+$ calcd for $C_{14}H_{21}N_2O$: 233.2; found: 233.1.

Preparation of 4-chloro-N-(4-(1-(oxetan-3-yl)piperidin-4-yl)phenyl)-1,3,5-triazin-2-amine:

To a solution of 2,4-dichloro-1,3,5-triazine (0.36 g, 2.4 mmol) in N,N-dimethylformamide (DMF, 6 mL) at 0° C. were added sequentially N,N-diisopropylethylamine (DIEA, 0.39 mL, 2.3 mmol) and 4-(1-(oxetan-3-yl)piperidin-4-yl) aniline (0.46 g, 2.0 mmol) and the mixture was stirred at 0° C. for 30 minutes and then allowed to warm to room temperature. After one hour, the mixture was partitioned between ethyl acetate and saturated aqueous sodium hydrogen carbonate solution. A solid was collected by filtration and discarded. The aqueous phase was extracted three times with ethyl acetate. The combined organics were washed once each with water and saturated aqueous sodium chloride solution, dried over anhydrous magnesium sulfate, filtered, concentrated under reduced pressure and then purified by flash chromatography on silica gel to provide 4-chloro-N-(4-(1-(oxetan-3-yl)piperidin-4-yl)phenyl)-1,3,5-triazin-2-amine.

LCMS-ESI+ (m/z): [M+H]+ calcd for $C_{17}H_{21}ClN_5O$: 346.1; found: 346.2

Preparation of 5-(4-((4-(1-(oxetan-3-yl)piperidin-4-yl)phenyl)amino)-1,3,5-triazin-2-yl)-2-((tetrahydro-2H-pyran-4-yl)oxy)benzonitrile:

A mixture of 4-chloro-N-(4-(1-(oxetan-3-yl)piperidin-4-yl)phenyl)-1,3,5-triazin-2-amine (0.10 g, 0.29 mmol), 2-((tetrahydro-2H-pyran-4-yl)oxy)-5-(4,4,5,5-tetramethyl-1,3,2-dioxaborolan-2-yl)benzonitrile (0.10 g, 0.32 mmol), tetrakis(triphenylphosphine)palladium(0) (0.025 g, 7.5 mol %) in 1,2-dimethoxyethane (DME, 3 mL) was treated with 2M aqueous sodium carbonate solution (0.66 mL). The mixture was irradiated for 1 hour in a microwave reactor at 130° C. The crude mixture was purified by flash chromatography on silica gel to provide 5-(4-((4-(1-(oxetan-3-yl)piperidin-4-yl)phenyl)amino)-1,3,5-triazin-2-yl)-2-((tetrahydro-2H-pyran-4-yl)oxy)benzonitrile. LCMS-ESI+ (m/z): [M+H]+ calcd for $C_{29}H_{33}N_6O_3$: 513.3; found: 513.4 $^1$H NMR (400 MHz, DMSO-$d_6$) δ 10.32 (m, 1H), 8.83 (s, 1H), 8.62 (dd, J=9.0, 1.9 Hz, 2H), 7.70 (m, 2H), 7.61 (d, J=9.4 Hz, 1H), 7.30 (d, J=8.0 Hz, 2H), 4.99 (m, 1H), 4.59 (m, 2H), 4.49 (m, 2H), 3.98-3.88 (m, 3H), 3.59 (m, 2H), 3.44 (m, 1H), 2.84 (d, J=11.1 Hz, 2H), 2.09 (m, 2H), 1.90 (m, 2H), 1.85-1.60 (m, 6H).

Example 55

5-((4-chloro-1,3,5-triazin-2-yl)amino)-2-((tetrahydro-2H-pyran-4-yl)oxy)benzonitrile

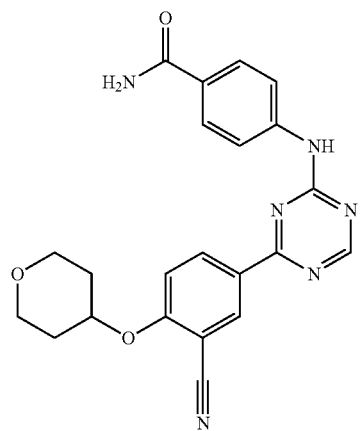 [SMILES: N#Cc1cc(-c2ncnc(Nc3ccc(C(N)=O)cc3)n2)ccc1OC1CCOCC1]

To a solution of 2,4-dichloro-1,3,5-triazine (0.41 g, 2.7 mmol) in N,N-dimethylformamide (DMF, 6 mL) at 0° C. were added sequentially N,N-diisopropylethylamine (DIEA, 0.49 mL, 2.8 mmol) and 4-aminobenzamide (0.34 g, 2.5 mmol). The mixture was stirred at 0° C. for 30 minutes and then allowed to warm to room temperature. The mixture was diluted with ethyl acetate and water. The aqueous phase was extracted twice with ethyl acetate. The combined extracts were washed once each with water and a saturated aqueous sodium chloride solution, then dried over anhydrous magnesium sulfate, filtered, and concentrated under reduced pressure to provide 4-((4-chloro-1,3,5-triazin-2-yl)amino)benzamide. LCMS-ESI+ (m/z): [M+H]+ calcd for $C_{10}H_9ClN_5O$: 250.0; found: 250.1.

A mixture of 4-((4-chloro-1,3,5-triazin-2-yl)amino)benzamide (0.19 g, 0.57 mmol), 2-((tetrahydro-2H-pyran-4-yl)oxy)-5-(4,4,5,5-tetramethyl-1,3,2-dioxaborolan-2-yl)benzonitrile (0.19 g, 0.57 mmol), and tetrakis(triphenylphosphine)palladium(0) (0.026 g, 5 mol %) in 1,2-dimethoxyethane (DME, 3 mL) was treated with 2M aqueous sodium carbonate solution (1.2 mL). The mixture was irradiated for 1 hour in a microwave reactor at 130° C. The crude mixture was purified by flash chromatography on silica gel to provide 5-((4-chloro-1,3,5-triazin-2-yl)amino)-2-((tetrahydro-2H-pyran-4-yl)oxy)benzonitrile. LCMS-ESI+ (m/z): [M+H]+ calcd for $C_{22}H_{21}N_6O_3$: 417.2; found: 417.1 $^1$H NMR (400 MHz, DMSO-$d_6$) δ 10.61 (s, 1H), 8.92 (s, 1H), 8.64 (m, 2H), 8.03-7.81 (m, 5H), 7.62 (d, J=9.6 Hz, 1H), 7.30 (s, 1H), 4.99 (tt, J=8.0, 3.9 Hz, 1H), 3.92 (m, 2H), 3.60 (m, 2H), 2.10 (m, 2H), 1.74 (m, 2H).

Example 56

2-((1-(2-hydroxyacetyl)piperidin-4-yl)oxy)-5-(4-((4-(1-(oxetan-3-yl)piperidin-4-yl)phenyl)amino)-1,3,5-triazin-2-yl)benzonitrile

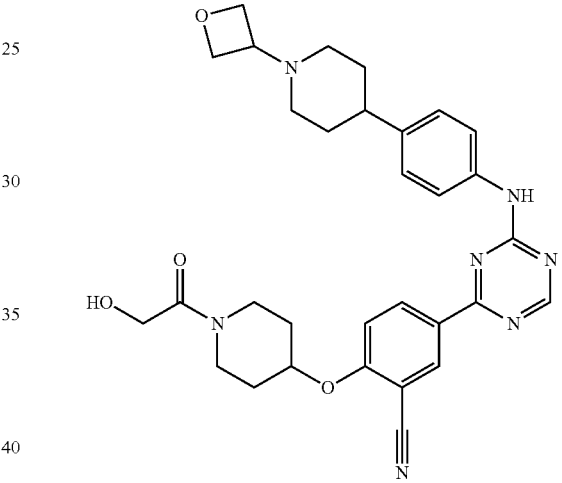

Preparation of tert-butyl 4-(2-cyano-4-(4-((4-(1-(oxetan-3-yl)piperidin-4-yl)phenyl)amino)-1,3,5-triazin-2-yl)phenoxy)piperidine-1-carboxylate:

A mixture of 4-chloro-N-(4-(1-(oxetan-3-yl)piperidin-4-yl)phenyl)-1,3,5-triazin-2-amine (0.20 g, 0.58 mmol), tert-butyl 4-(2-cyano-4-(4,4,5,5-tetramethyl-1,3,2-dioxaborolan-2-yl)phenoxy)piperidine-1-carboxylate (0.27 g, 1.1 mmol), and tetrakis(triphenylphosphine)palladium(0) (0.050 g, 7.5 mol %) in 1,2-dimethoxyethane (DME, 3 mL) was treated with 2M aqueous sodium carbonate solution (1.3 mL).The mixture was irradiated for 1 hour in a microwave reactor at 130° C. The crude mixture was purified by flash chromatography on silica gel to provide the desired product. LCMS-ESI+ (m/z): [M+H]+ calcd for $C_{34}H_{42}N_7O_4$: 612.3; found: 612.1

Preparation of 5-(4-((4-(1-(oxetan-3-yl)piperidin-4-yl)phenyl)amino)-1,3,5-triazin-2-yl)-2-(piperidin-4-yloxy)benzonitrile:

tert-butyl 4-(2-cyano-4-(4-((4-(1-(oxetan-3-yl)piperidin-4-yl)phenyl)amino)-1,3,5-triazin-2-yl)phenoxy)piperidine-1-carboxylate (0.58 mmol assumed) was taken up in dichloromethane (8 mL) and treated with trifluoroacetic acid (2 mL). After 30 minutes, the mixture was concentrated under reduced pressure, and the residue was purified by flash chromatography (silica gel) to provide the desired material. LCMS-ESI$^+$ (m/z): [M+H]$^+$ calcd for $C_{28}H_{33}N_8O_2$: 512.3; found: 512.3.

Preparation of 2-((1-(2-hydroxyacetyl)piperidin-4-yl)oxy)-5-(4-((4-(1-(oxetan-3-yl)piperidin-4-yl)phenyl)amino)-1,3,5-triazin-2-yl)benzonitrile:

5-(4-((4-(1-(oxetan-3-yl)piperidin-4-yl)phenyl)amino)-1,3,5-triazin-2-yl)-2-(piperidin-4-yloxy)benzonitrile (60 mg, 0.12 mmol) and glycolic acid (13 mg, 0.18 mmol) were taken up as suspension in dichloromethane (3 mL). The mixture was treated successively with N,N-diisopropylethylamine (61 µL, 0.35 mmol) and N-[(dimethylamino)-1H-1,2,3-triazolo-[4,5-b]pyridin-1-ylmethylene]-N-methylmethanaminiumhexafluorophosphate N-oxide (HATU, 67 mg, 0.18 mmol). The suspension was stirred for three hours at room temperature and then purified by flash chromatography (silica gel) to provide 2-((1-(2-hydroxyacetyl)piperidin-4-yl)oxy)-5-(4-((4-(1-(oxetan-3-yl)piperidin-4-yl)phenyl)amino)-1,3,5-triazin-2-yl)benzonitrile. LCMS-ESI$^+$ (m/z): [M+H]$^+$ calcd for $C_{31}H_{36}N_7O_4$: 570.3; found: 570.4 $^1$H NMR (400 MHz, DMSO-d$_6$) δ 10.33 (s, 1H), 8.84 (s, 1H), 8.62 (m, 2H), 7.72 (m, 2H), 7.60 (m, 1H), 7.30 (d, J=8.3 Hz, 2H), 5.05 (m, 1H), 4.59 (m, 3H), 4.50 (m, 2H), 4.17 (m, 2H), 3.82 (m, 1H), 3.74-3.45 (m, 5H), 2.87 (m, 2H), 2.02 (m, 2H), 1.94 (m, 2H), 1.87-1.61 (m, 6H).

Example 57

2-((1-(2-hydroxyacetyl)piperidin-4-yl)oxy)-5-(4-((4-(methylsulfonyl)phenyl)amino)-1,3,5-triazin-2-yl)benzonitrile

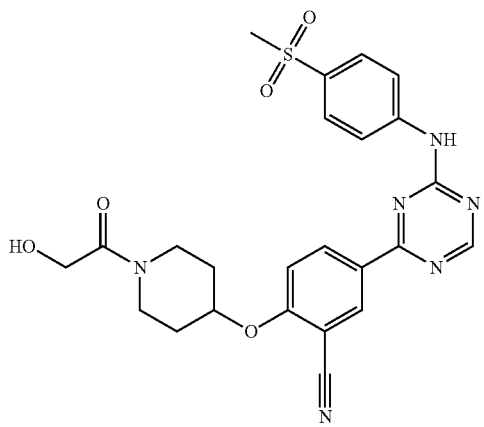 [SMILES: CS(=O)(=O)c1ccc(Nc2ncnc(-c3ccc(OC4CCN(C(=O)CO)CC4)c(C#N)c3)n2)cc1]

Preparation of tert-butyl 4-(2-cyano-4-(4-((4-(methylsulfonyl)phenyl)amino)-1,3,5-triazin-2-yl)phenoxy)piperidine-1-carboxylate:

A mixture of 4-chloro-N-(4-(methylsulfonyl)phenyl)-1,3,5-triazin-2-amine (0.27 g, 0.95 mmol), tert-butyl 4-(2-cyano-4-(4,4,5,5-tetramethyl-1,3,2-dioxaborolan-2-yl)phenoxy)piperidine-1-carboxylate (0.45 g, 1.0 mmol), and tetrakis(triphenylphosphine)palladium(0) (0.082 g, 7.5 mol %) in 1,2-dimethoxyethane (DME, 43 mL) was treated with 2M aqueous sodium carbonate solution (2.1 mL). The mixture was irradiated for 1 hour in a microwave reactor at 130° C. The crude mixture was purified by flash chromatography on silica gel to provide the desired product. LCMS-ESI$^+$ (m/z): [M–tBu+H]$^+$ calcd for $C_{23}H_{23}N_6O_5S$: 495.1; found: 495.2.

Preparation of 5-(4-((4-(methylsulfonyl)phenyl)amino)-1,3,5-triazin-2-yl)-2-(piperidin-4-yloxy)benzonitrile:

tert-butyl 4-(2-cyano-4-(4-((4-(methylsulfonyl)phenyl)amino)-1,3,5-triazin-2-yl)phenoxy)piperidine-1-carboxylate (0.25 g, 0.45 mmol) was taken up in dichloromethane (3 mL) and treated with trifluoroacetic acid (1 mL). After stirring for four hours at room temperature, the mixture was added to a separatory funnel containing 10% aqueous hydrochloric acid and dichloromethane. The thick slurry that resulted was basified with concentrated ammonium hydroxide solution and then extracted three times with dichloromethane. The combined extracts were washed once with saturated aqueous sodium chloride solution, dried over anhydrous magnesium sulfate, filtered, and concentrated under reduced pressure to provide the desired material. LCMS-ESI$^+$ (m/z): [M+H]$^+$ calcd for $C_{22}H_{23}N_6O_3S$: 451.2; found: 451.2

Preparation of 2-((1-(2-hydroxyacetyl)piperidin-4-yl)oxy)-5-(4-((4-(methylsulfonyl)phenyl)amino)-1,3,5-triazin-2-yl)benzonitrile:

5-(4-((4-(methylsulfonyl)phenyl)amino)-1,3,5-triazin-2-yl)-2-(piperidin-4-yloxy)benzonitrile (0.20 g, 0.45 mmol), and glycolic acid (52 mg, 0.68 mmol) were taken up as suspension in dichloromethane (3 mL). The mixture was treated successively with N,N-diisopropylethylamine (160 µL, 0.91 mmol) and N-[(dimethylamino)-1H-1,2,3-triazolo-[4,5-b]pyridin-1-ylmethylene]-N-methylmethanaminiumhexafluorophosphate N-oxide (HATU, 260 mg, 0.68 mmol). The suspension was stirred for three days at room temperature and then was purified by flash chromatography (silica gel) to provide 2-((1-(2-hydroxyacetyl)piperidin-4-yl)oxy)-5-(4-((4-(methylsulfonyl)phenyl)amino)-1,3,5-triazin-2-yl)benzonitrile. LCMS-ESI$^+$ (m/z): [M+H]$^+$ calcd for $C_{24}H_{25}N_6O_5S$: 509.2; found: 509.2 $^1$H NMR (400 MHz, DMSO-d$_6$) δ 10.84 (s, 1H), 8.98 (s, 1H), 8.71-8.65 (m, 2H), 8.16-8.07 (m, 2H), 8.02-7.92 (m, 2H), 7.63 (d, J=9.6 Hz, 1H), 5.06 (m, 1H), 4.60 (t, J=5.5 Hz, 1H), 4.17 (d, J=5.3 Hz, 2H), 3.79 (m, 1H), 3.61 (m, 1H), 3.51 (m, 1H), 3.42 (m, 1H), 3.24 (s, 3H), 2.07 (m, 2H), 1.77 (m, 2H).

Example 58

2-(cyclopropylmethoxy)-5-(4-((4-(4-(oxetan-3-yl)piperazin-1-yl)phenyl)amino)-1,3,5-triazin-2-yl)benzonitrile

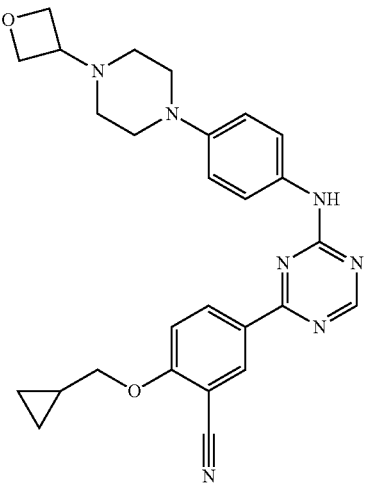 [SMILES: N#Cc1cc(-c2ncnc(Nc3ccc(N4CCN(C5COC5)CC4)cc3)n2)ccc1OCC1CC1]

A mixture of 4-chloro-N-(4-(4-(oxetan-3-yl)piperazin-1-yl)phenyl)-1,3,5-triazin-2-amine (0.15 g, 0.43 mmol), 2-(cyclopropylmethoxy)-5-(4,4,5,5-tetramethyl-1,3,2-dioxaborolan-2-yl)benzonitrile (0.14 g, 0.48 mmol), and tetrakis(triphenylphosphine)palladium(0) (0.025 g, 5 mol %) in 1,2-dimethoxyethane (DME, 3 mL) was treated with 2M aqueous sodium carbonate solution (1 mL). The mixture was irradiated for 1 hour in a microwave reactor at 130° C. The crude mixture was purified by flash chromatography on silica gel to provide 2-(cyclopropylmethoxy)-5-(4-((4-(4-(oxetan-3-yl)piperazin-1-yl)phenyl)amino)-1,3,5-triazin-2-yl)benzonitrile. LCMS-ESI$^+$ (m/z): [M+H]$^+$ calcd for C$_{27}$H$_{30}$N$_7$O$_2$: 484.2; found: 484.3 $^1$H NMR (400 MHz, DMSO-d$_6$) δ 10.28 (m, 1H), 8.80 (s, 1H), 8.71-8.47 (m, 2H), 7.67 (bs, 2H), 7.47 (d, J=9.1 Hz, 1H), 7.10 (br, 2H), 5.01 (t, J=6.8 Hz, 2H), 4.73 (t, J=7.4 Hz, 2H), 4.64-4.46 (m, 1H), 4.16 (d, J=7.0 Hz, 2H), 3.84 (m, 2H), 3.49 (m, 2H), 3.33-3.01 (m, 4H), 1.35 (m, 1H), 0.85-0.55 (m, 2H), 0.57-0.26 (m, 2H).

Example 59

5-(4-((1-methyl-1H-pyrazol-3-yl)amino)-1,3,5-triazin-2-yl)-2-((tetrahydro-2H-pyran-4-yl)oxy)benzonitrile

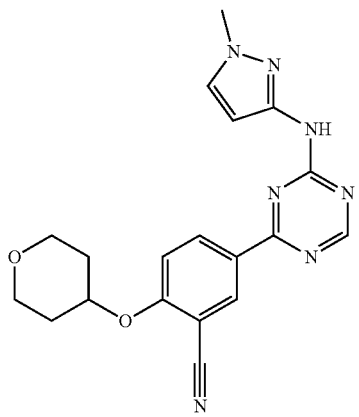 [SMILES: Cn1ccc(Nc2ncnc(-c3ccc(OC4CCOCC4)c(C#N)c3)n2)n1]

To a solution of 2,4-dichloro-1,3,5-triazine (0.90 g, 6.0 mmol) in N,N-dimethylformamide (DMF, 6 mL) at 0° C. were added sequentially N,N-diisopropylethylamine (DIEA, 1.1 mL, 6.2 mmol) and 1-methyl-1H-pyrazol-3-amine (0.53 g, 5.5 mmol). The mixture was stirred at 0° C. for 30 minutes and then allowed to warm to room temperature. The mixture was diluted with ethyl acetate and water and filtered through a pad of Celite diatomaceous earth. The aqueous phase was extracted twice with ethyl acetate. The combined extracts were washed once each with water and a saturated aqueous sodium chloride solution, then dried over anhydrous magnesium sulfate, filtered, and concentrated under reduced pressure. The residue was purified by flash chromatography (silica gel) to provide 4-chloro-N-(1-methyl-1H-pyrazol-3-yl)-1,3,5-triazin-2-amine. LCMS-ESI$^+$ (m/z): [M+H]$^+$ calcd for C$_7$H$_8$ClN$_6$: 211.0; found: 211.1.

A mixture of 4-chloro-N-(1-methyl-1H-pyrazol-3-yl)-1,3,5-triazin-2-amine (0.12 g, 0.56 mmol), 2-((tetrahydro-2H-pyran-4-yl)oxy)-5-(4,4,5,5-tetramethyl-1,3,2-dioxaborolan-2-yl)benzonitrile (0.20 g, 0.62 mmol), and tetrakis(triphenylphosphine)palladium(0) (0.032 g, 5 mol %) in 1,2-dimethoxyethane (DME, 3 mL) was treated with 2M aqueous sodium carbonate solution (1.3 mL). The mixture was irradiated for 1 hour in a microwave reactor at 130° C. The crude mixture was purified by flash chromatography on silica gel, followed by prep HPLC (10-65% acetonitrile in water, 0.1% trifluoroacetic acid buffer) to provide 5-(4-((1-methyl-1H-pyrazol-3-yl)amino)-1,3,5-triazin-2-yl)-2-((tetrahydro-2H-pyran-4-yl)oxy)benzonitrile. LCMS-ESI$^+$ (m/z): [M+H]$^+$ calcd for C$_{19}$H$_{20}$N$_7$O$_2$: 378.2; found: 378.1 $^1$H NMR (400 MHz, DMSO-d$_6$) δ 10.65 (m, 1H), 8.81 (s, 1H), 8.72-8.54 (m, 2H), 7.74 (m, 1H), 7.61 (d, J=9.1 Hz, 1H), 6.68 (m, 1H), 4.98 (m, 1H), 3.91 (m, 2H), 3.83 (s, 3H), 3.59 (m, 2H), 2.08 (m, 2H), 1.73 (m, 2H).

Example 60

2-((4,4-difluorocyclohexyl)oxy)-5-(4-((4-(4-(oxetan-3-yl)piperazin-1-yl)phenyl)amino)-1,3,5-triazin-2-yl)benzonitrile

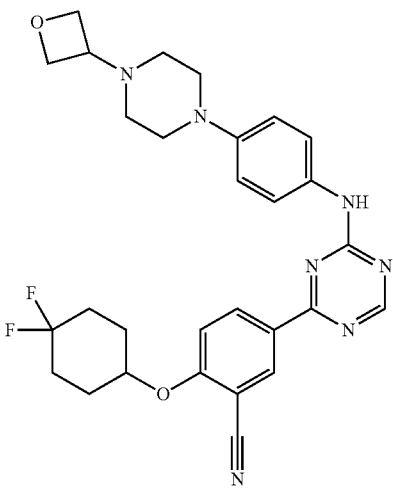 [SMILES: N#Cc1cc(-c2ncnc(Nc3ccc(N4CCN(C5COC5)CC4)cc3)n2)ccc1OC1CCC(F)(F)CC1]

Preparation of 5-bromo-2-((4,4-difluorocyclohexyl)oxy)benzonitrile:

A solution of 4,4-difluorocyclohexanol (Sigma Aldrich, 1.0 g, 7.3 mmol) in N,N-dimethylformamide (DMF, 17 mL) was treated with sodium hydride (60% dispersion in mineral oil, 0.29, 7.3 mmol) in a single portion at room temperature. The mixture was stirred for two hours at room temperature before 5-bromo-2-fluorobenzonitrile (1.3 g, 6.7 mmol) was added in a single portion at room temperature. The mixture was stirred on a 50° C. block for 1 hour. Ice-water was added to the mixture, which was then partitioned with ethyl acetate. The aqueous phase was extracted three times with ethyl acetate. The combined extracts were washed twice with water and once with saturated aqueous sodium chloride solution, then dried over anhydrous magnesium sulfate, filtered, and concentrated under reduced pressure. The residue was purified by flash chromatography (silica gel) to provide the desired material. $^1$H NMR (400 MHz, DMSO-d$_6$) δ 8.06 (d, J=2.5 Hz, 1H), 7.87 (dd, J=9.1, 2.6 Hz, 1H), 7.38 (d, J=9.1 Hz, 1 H), 4.89 (m, 1H), 2.23-1.98 (m, 4H), 1.98-1.90 (m, 4H).

Preparation of 2-((4,4-difluorocyclohexyl)oxy)-5-(4,4,5,5-tetramethyl-1,3,2-dioxaborolan-2-yl)benzonitrile:

A mixture of 5-bromo-2-((4,4-difluorocyclohexyl)oxy)benzonitrile (0.42 g, 1.3 mmol), bis(pinacolato)diboron (0.67 g, 2.6 mmol), potassium acetate (0.39 g, 4.0 mmol), and [1,1'-bis(diphenylphosphino)ferrocene]dichloropalladium(II) (0.10 g, 10 mol %) in 1,4-dioxane (8 mL) was heated at 90° C. overnight. LC/MS analysis indicated the complete consumption of the bromide starting material. The mixture was filtered through a pad of Celite diatomaceous earth, and the filtrate was concentrated under reduced pressure to provide the desired product, which was carried forward without further purification.

Preparation of 2-((4,4-difluorocyclohexyl)oxy)-5-(4-((4-(4-(oxetan-3-yl)piperazin-1-yl)phenyl)amino)-1,3,5-triazin-2-yl)benzonitrile:

A mixture of 4-chloro-N-(4-(4-(oxetan-3-yl)piperazin-1-yl)phenyl)-1,3,5-triazin-2-amine (0.15 g, 0.43 mmol), crude 2-((4,4-difluorocyclohexyl)oxy)-5-(4,4,5,5-tetramethyl-1,3,2-dioxaborolan-2-yl)benzonitrile (1.3 mmol assumed), and tetrakis(triphenylphosphine)palladium(0) (0.037 g, 7.5 mol %) in 1,2-dimethoxyethane (DME, 6 mL) was treated with 2M aqueous sodium carbonate solution (0.97 mL). The mixture was irradiated for 1 hour in a microwave reactor at 130° C. The crude mixture was purified by flash chromatography on silica gel to provide 2-((4,4-difluorocyclohexyl) oxy)-5-(4-((4-(4-(oxetan-3-yl)piperazin-1-yl)phenyl) amino)-1,3,5-triazin-2-yl)benzonitrile. LCMS-ESI+ (m/z): [M+H]+ calcd for $C_{29}H_{32}F_2N_7O_2$: 548.3; found: 548.4 $^1$H NMR (400 MHz, DMSO-$d_6$) δ 10.16 (m, 1H), 8.78 (s, 1H), 8.60 (m, 2H), 7.61 (m, 3H), 7.01 (m, 2H), 5.02 (m, 1H), 4.61 (m, 2H), 4.52 (m, 2H), 3.49 (m, 1H), 3.18 (m, 4H), 2.46 (m, 4H), 2.27-1.87 (m, 8H).

Example 61

5-(4-((3-fluoro-5-methoxy-4-(4-(oxetan-3-yl)piperazin-1-yl)phenyl)amino)-1,3,5-triazin-2-yl)-2-((tetrahydro-2H-pyran-4-yl)oxy)benzonitrile

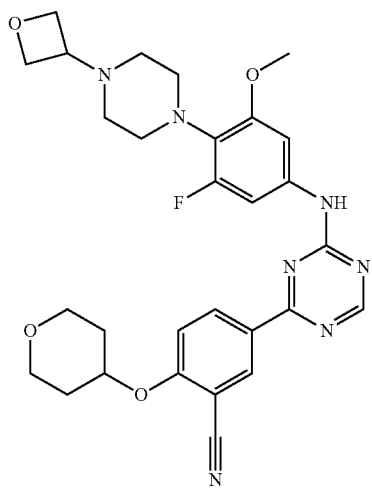 [SMILES: COc1cc(Nc2ncnc(-c3ccc(OC4CCOCC4)c(C#N)c3)n2)cc(F)c1N1CCN(C2COC2)CC1]

Preparation of 1-(2-fluoro-6-methoxy-4-nitrophenyl)-4-(oxetan-3-yl)piperazine:

1-(2,6-difluoro-4-nitrophenyl)-4-(oxetan-3-yl)piperazine (1.8 g, 5.9 mmol) was taken up as a suspension in dimethylsulfoxide (10 mL) and treated with suspension of sodium methoxide in methanol (2 mL). The mixture was heated with magnetic stirring on an 80° C. block. After 20 minutes, an additional portion of solid sodium methoxide (300 mg) was added. The mixture was stirred with heating overnight on the 80° C. block. After cooling to room temperature, the mixture was quenched by the addition of ice and water, precipitating a powder, which was collected by filtration. The solid was washed with water, dried under house vacuum and then in a vacuum oven (60° C.) to provide 1-(2-fluoro-6-methoxy-4-nitrophenyl)-4-(oxetan-3-yl)piperazine.

1-(2-fluoro-6-methoxy-4-nitrophenyl)-4-(oxetan-3-yl) piperazine (0.20 g, 0.64 mmol) was taken up in a mixture of 2-methyltetrahydrofuran and methanol (1:1, 6 mL). The mixture was degassed, treated with 10% palladium on carbon (45 mg), and stirred overnight under a balloon of hydrogen. The suspension was filtered through a pad of Celite diatomaceous earth and concentrated under reduced pressure to provide 3-fluoro-5-methoxy-4-(4-(oxetan-3-yl) piperazin-1-yl)aniline. LCMS-ESI+ (m/z): [M+H]+ calcd for $C_{14}H_{21}FN_3O_2$: 282.2; found: 282.1.

Preparation of 5-(4-((3-fluoro-5-methoxy-4-(4-(oxetan-3-yl)piperazin-1-yl)phenyl)amino)-1,3,5-triazin-2-yl)-2-((tetrahydro-2H-pyran-4-yl)oxy)benzonitrile:

A suspension of 5-(4-chloro-1,3,5-triazin-2-yl)-2-((tetrahydro-2H-pyran-4-yl)oxy)benzonitrile (50 mg, 0.16 mmol) and 3-fluoro-5-methoxy-4-(4-(oxetan-3-yl)piperazin-1-yl) aniline (140 mg, 0.50 mmol) in acetonitrile (2.5 mL) was treated with N,N-diisopropylethylamine (0.11 mL, 0.63 mmol). The mixture was heated in a microwave reactor for 60 minutes at 100° C. The cooled reaction mixture was purified by flash chromatography (silica gel), followed by trituration with ethyl acetate, to provide 5-(4-((3-fluoro-5-methoxy-4-(4-(oxetan-3-yl)piperazin-1-yl)phenyl)amino)-1,3,5-triazin-2-yl)-2-((tetrahydro-2H-pyran-4-yl)oxy)benzonitrile. LCMS-ESI+ (m/z): [M+H]+ calcd for $C_{29}H_{33}FN_7O_4$: 562.3; found: 562.3 $^1$H NMR (400 MHz, DMSO-$d_6$) δ 10.43 (bs, 1H), 8.88 (bs, 1H), 6 8.64 (d, J=2.2 Hz, 1H), 8.61 (dd, J=9.0, 2.2 Hz, 1H), 7.63 (d, J=9.0 Hz, 1H), 7.55-7.15 (br, 2H), 4.99 (m, 1H), 4.59 (m, 2H), 4.49 (m, 2H), 3.91 (m, 2H), 3.61 (m, 5H), 3.48 (m, 1H), 3.11 (m, 4H), 2.37 (m, 4H), 2.09 (m, 2H), 1.73 (m, 2H).

Example 62

5-(4-((3-(4-methylpiperazin-1-yl)phenyl)amino)-1,3,5-triazin-2-yl)-2-((tetrahydro-2H-pyran-4-yl)oxy) benzonitrile

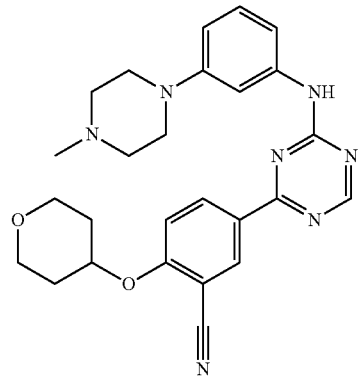 [SMILES: CN1CCN(c2cccc(Nc3ncnc(-c4ccc(OC5CCOCC5)c(C#N)c4)n3)c2)CC1]

A suspension of 5-(4-chloro-1,3,5-triazin-2-yl)-2-((tetrahydro-2H-pyran-4-yl)oxy)benzonitrile (53 mg, 0.16 mmol) and 3-(4-methylpiperazin-1-yl)aniline (38 mg, 0.20 mmol) in isopropanol (2.5 mL) was treated with N,N-diisopropylethylamine (0.12 mL, 0.67 mmol). The mixture was heated in a microwave reactor for 30 minutes at 80° C. The cooled reaction mixture was purified by prep HPLC (10-80% acetonitrile in water, 0.1% trifluoroacetic acid buffer), followed by flash chromatography (silica gel) to provide 5-(4-((3-(4-methylpiperazin-1-yl)phenyl)amino)-1,3,5-triazin-2-yl)-2-((tetrahydro-2H-pyran-4-yl)oxy)benzonitrile. LCMS-ESI+ (m/z): [M+H]+ calcd for $C_{26}H_{30}N_7O_2$: 472.2; found: 472.3 $^1$H NMR (400 MHz, DMSO-$d_6$) δ 10.22 (s, 1H), 8.84 (s, 1H), 8.62 (m, 2H), 7.60 (d, J=9.4 Hz, 1H), 7.45 (br, 1H), 7.24 (m, 1H), 7.16 (br, 1H), 6.74 (d, J=7.3 Hz, 1H), 5.00 (m, 1H), 3.91 (m, 2H), 3.60 (m, 2H), 3.21 (m, 4H), 2.53 (m, 4H), 2.27 (s, 3H), 2.08 (m, 2H), 1.74 (m, 2H).

Example 63

5-(4-((3-morpholinophenyl)amino)-1,3,5-triazin-2-yl)-2-((tetrahydro-2H-pyran-4-yl)oxy)benzonitrile

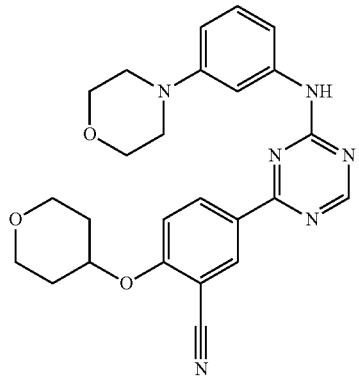 [SMILES: N#Cc1cc(-c2ncnc(Nc3cccc(N4CCOCC4)c3)n2)ccc1OC1CCOCC1]

To a solution of 2,4-dichloro-1,3,5-triazine (0.50 g, 3.3 mmol) in N,N-dimethylformamide (DMF, 6 mL) at 0° C. were added sequentially N,N-diisopropylethylamine (DIEA, 0.60 mL, 3.4 mmol) and 3-morpholin-4-ylaniline (0.54 g, 3.0 mmol). The mixture was stirred at 0° C. for 30 minutes and then allowed to warm to room temperature. The mixture was diluted with ethyl acetate and water. The aqueous phase was extracted twice with ethyl acetate. The combined extracts were washed once each with water and a saturated aqueous sodium chloride solution, then dried over anhydrous magnesium sulfate, filtered, and concentrated under reduced pressure to provide 4-chloro-N-(3-morpholinophenyl)-1,3,5-triazin-2-amine. LCMS-ESI+ (m/z): [M+H]+ calcd for $C_{13}H_{15}ClN_5$: 292.1; found: 292.3.

A mixture of 4-chloro-N-(3-morpholinophenyl)-1,3,5-triazin-2-amine (0.15 g, 0.52 mmol), 2-((tetrahydro-2H-pyran-4-yl)oxy)-5-(4,4,5,5-tetramethyl-1,3,2-dioxaborolan-2-yl)benzonitrile (0.19 g, 0.58 mmol), and tetrakis(triphenylphosphine)palladium(0) (0.026 g, 5 mol %) in 1,2-dimethoxyethane (DME, 3 mL) was treated with 2M aqueous sodium carbonate solution (1.2 mL). The mixture was irradiated for 1 hour in a microwave reactor at 130° C. The crude mixture was purified by flash chromatography on silica gel, followed by prep HPLC (10-85% acetonitrile in water, 0.1% trifluoroacetic acid buffer) to provide 5-(4-((3-morpholinophenyl)amino)-1,3,5-triazin-2-yl)-2-((tetrahydro-2H-pyran-4-yl)oxy)benzonitrile. LCMS-ESI+ (m/z): [M+H]+ calcd for $C_{25}H_{27}N_6O_3$: 459.2; found: 459.3 $^1$H NMR (400 MHz, DMSO-$d_6$) δ 10.27 (bs, 1H), 8.84 (s, 1H), 8.62 (m, 2H), 7.66 (m, 1H), 7.59 (m, 1H), 7.19 (bs, 1H), 6.77 (m. 1H), 4.99 (tt, J=8.0, 3.8 Hz, 1H), 4.02-3.87 (m, 2H), 3.82 (m, 4H), 3.59 (ddd, J=11.5. 8.5, 3.1 Hz, 2H), 3.19 (m, 4H), 2.09 (m, 2H), 1.73 (m, 2H).

Example 64

5-(4-((4-(4-(2-hydroxyacetyl)piperazin-1-yl)phenyl)amino)-1,3,5-triazin-2-yl)-2-((tetrahydro-2H-pyran-4-yl)oxy)benzonitrile

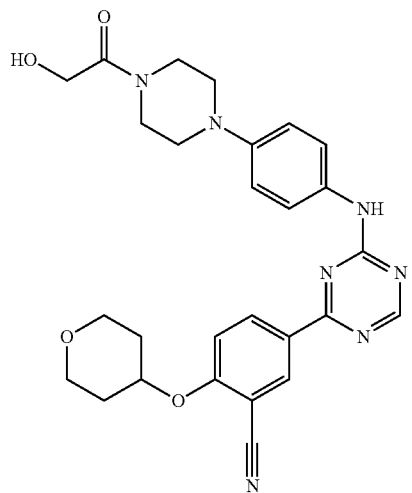 [SMILES: N#Cc1cc(-c2ncnc(Nc3ccc(N4CCN(C(=O)CO)CC4)cc3)n2)ccc1OC1CCOCC1]

Preparation of tert-butyl 4-(4-((4-(3-cyano-4-((tetrahydro-2H-pyran-4-yl)oxy)phenyl)-1,3,5-triazin-2-yl)amino)phenyl)piperazine-1-carboxylate:

A suspension of 5-(4-chloro-1,3,5-triazin-2-yl)-2-((tetrahydro-2H-pyran-4-yl)oxy)benzonitrile (50 mg, 0.16 mmol) and tert-butyl 4-(4-aminophenyl)piperazine-1-carboxylate (52 mg, 0.19 mmol) in acetonitrile (2.5 mL) was treated with N,N-diisopropylethylamine (0.11 mL, 0.63 mmol). The mixture was heated in a microwave reactor for 30 minutes at 85° C. and then concentrated to dryness under reduced pressure to provide tert-butyl 4-(4-((4-(3-cyano-4-((tetrahydro-2H-pyran-4-yl)oxy)phenyl)-1,3,5-triazin-2-yl)amino)phenyl)piperazine-1-carboxylate, which was carried forward without further purification. LCMS-ESI+ (m/z): [M+H]+ calcd for $C_{30}H_{36}N_7O_4$: 558.3; found: 558.0.

Preparation of 5-(4-((4-(piperazin-1-yl)phenyl)amino)-1,3,5-triazin-2-yl)-2-((tetrahydro-2H-pyran-4-yl)oxy)benzonitrile:

Crude tert-butyl 4-(4-((4-(3-cyano-4-((tetrahydro-2H-pyran-4-yl)oxy)phenyl)-1,3,5-triazin-2-yl)amino)phenyl)piperazine-1-carboxylate (0.16 mmol assumed) was taken up in dichloromethane (3 mL) and treated with trifluoroacetic acid (0.5 mL). After one hour of standing at room temperature, the mixture was purified by flash chromatography (silica gel) to provide 5-(4-((4-(piperazin-1-yl)phenyl)amino)-1,3,5-triazin-2-yl)-2-((tetrahydro-2H-pyran-4-yl)oxy)benzonitrile. LCMS-ESI+ (m/z): [M+H]+ calcd for $C_{25}H_{28}N_7O_2$: 458.2; found: 458.2.

Preparation of 5-(4-((4-(4-(2-hydroxyacetyl)piperazin-1-yl)phenyl)amino)-1,3,5-triazin-2-yl)-2-((tetrahydro-2H-pyran-4-yl)oxy)benzonitrile:

5-(4-((4-(piperazin-1-yl)phenyl)amino)-1,3,5-triazin-2-yl)-2-((tetrahydro-2H-pyran-4-yl)oxy)benzonitrile (110 mg, 0.24 mmol) and glycolic acid (27 mg, 0.36 mmol) were taken up as suspension in dichloromethane (2 mL). The mixture was treated successively with N,N-diisopropylethylamine (170 µL, 0.92 mmol) and N-[(dimethylamino)-1H-1,2,3-triazolo-[4,5-b]pyridin-1-ylmethylene]-N-methylmethanaminiumhexafluorophosphate N-oxide (HATU, 180 mg, 0.48 mmol). The mixture was stirred overnight at room temperature and then purified by flash chromatography (silica gel) to provide 5-(4-((4-(4-(2-hydroxyacetyl)piperazin-1-yl)phenyl)amino)-1,3,5-triazin-2-yl)-2-((tetrahydro-2H-pyran-4-yl)oxy)benzonitrile. LCMS-ESI$^+$ (m/z): [M+H]$^+$ calcd for $C_{27}H_{30}N_7O_4$: 516.2; found: 516.2 $^1$H NMR (400 MHz, DMSO-d$_6$) δ10.21 (s, 1H), 8.73 (m, 1H), 8.55 (m, 2H), 7.56 (m, 3H), 7.02 (m, 2H), 4.98 (m, 1H), 4.66 (t, J=5.5 Hz, 1H), 4.18 (d, J=5.5 Hz, 2H), 3.91 (m, 2H), 3.61 (m, 2H), 3.53 (m, 4H), 3.16 (m, 4H), 2.08 (m, 2H), 1.74 (m, 2H).

Example 65

5-(4-((4-(1-(2,2-difluoroethyl)piperidin-4-yl)phenyl)amino)-1,3,5-triazin-2-yl)-2-((tetrahydro-2H-pyran-4-yl)oxy)benzonitrile

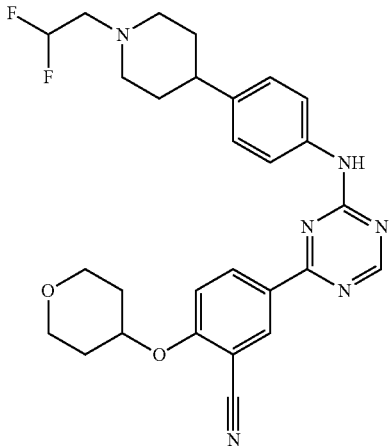 [SMILES: N#Cc1cc(-c2ncnc(Nc3ccc(C4CCN(CC(F)F)CC4)cc3)n2)ccc1OC1CCOCC1]

Preparation of 1-(2,2-difluoroethyl)-4-(4-nitrophenyl)piperidine:

A solution of 4-(4-nitrophenyl)piperidine (0.77 g, 3.7 mmol) in 2-methyltetrahydrofuran/acetonitrile (1;10, 16.5 mL) was treated with potassium carbonate (3.1 g, 22 mmol), followed by 2,2-difluoroethyl triflate (0.65 mL, 4.9 mmol). The mixture was heated for 4 hrs on a 65° C. block, then allowed to cool to room temperature. Insoluble material was removed by filtration. The filtrate was concentrated to provide the desired material, which was carried forward without further purification. LCMS-ESI$^+$ (m/z): [M+H]$^+$ calcd for $C_{13}H_{17}F_2N_2O_2$: 271.1; found: 271.1.

Preparation of 4-(1-(2,2-difluoroethyl)piperidin-4-yl)aniline:

Crude 1-(2,2-difluoroethyl)-4-(4-nitrophenyl)piperidine (3.3 mmol assumed) was taken up in methanol (approximately 25 mL) in a Parr bottle. After the mixture was degassed, it was treated with 10% palladium on charcoal (150 mg) and shaken overnight under hydrogen (55 psi). The mixture was filtered through a pad of Celite diatomaceous earth, and the filtrate was concentrated under reduced pressure to provide the desired material, which was carried forward without further purification. LCMS-ESI$^+$ (m/z): [M+H]$^+$ calcd for $C_{13}H_{19}F_2N_2$: 241.1; found: 241.1.

Preparation 5-(4-((4-(1-(2,2-difluoroethyl)piperidin-4-yl)phenyl)amino)-1,3,5-triazin-2-yl)-2-((tetrahydro-2H-pyran-4-yl)oxy)benzonitrile:

A suspension of 5-(4-chloro-1,3,5-triazin-2-yl)-2-((tetrahydro-2H-pyran-4-yl)oxy)benzonitrile (100 mg, 0.32 mmol) and 4-(1-(2,2-difluoroethyl)piperidin-4-yl)aniline (91 mg, 0.38 mmol) in acetonitrile (3 mL) was treated with N,N-disopropylethylamine (0.22 mL, 1.3 mmol). The mixture was heated in a microwave reactor for 20 minutes at 80° C. The cooled reaction mixture was purified by flash chromatography (silica gel) to provide 5-(4-((4-(1-(2,2-difluoroethyl)piperidin-4-yl)phenyl)amino)-1,3,5-triazin-2-yl)-2-((tetrahydro-2H-pyran-4-yl)oxy)benzonitrile. LCMS-ESI$^+$ (m/z): [M+H]$^+$ calcd for $C_{28}H_{31}F_2N_6O_2$: 521.2; found: 521.4 $^1$H NMR (400 MHz, DMSO-d$_6$) δ 10.31 (s, 1H), 8.83 (s, 1H), 8.61 (m, 2H), 7.70 (d, J=7.9 Hz, 2H), 7.60 (d, J=9.4 Hz, 1H), 7.29 (d, J=8.2 Hz, 2H), 6.19 (tt, J=55.8, 4.3 Hz, 1H), 4.99 (m, 1H), 3.91 (m, 2H), 3.59 (m, 3H), 3.04 (m, 2H), 2.79 (td, J=15.7, 4.4 Hz, 2H), 2.30 (m, 2H), 2.09 (m, 2H), 1.91-1.59 (m, 6H).

Example 66

5-(4-((4-(4-(methylsulfonyl)piperazin-1-yl)phenyl)amino)-1,3,5-triazin-2-yl)-2-((tetrahydro-2H-pyran-4-yl)oxy)benzonitrile

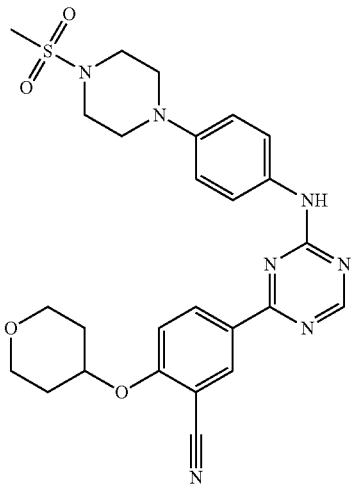 [SMILES: CS(=O)(=O)N1CCN(c2ccc(Nc3ncnc(-c4ccc(OC5CCOCC5)c(C#N)c4)n3)cc2)CC1]

5-(4-((4-(piperazin-1-yl)phenyl)amino)-1,3,5-triazin-2-yl)-2-((tetrahydro-2H-pyran-4-yl)oxy)benzonitrile, trifluoroacetic acid salt (approximately 0.14 mmol) was taken up in dichloromethane (5 mL) and treated with N,N-diisopropylethylamine (0.47 mL, 2.7 mmol). Mixture was stirred while cooling in an ice-water bath while methanesulfonyl chloride (31 µL, 0.41 mmol) was added via syringe. The cooling bath was removed, and the mixture was allowed to regain room temperature. After 15 minutes, the mixture was quenched with methanol and concentrated under reduced pressure. The residue was purified by prep HPLC (10-70% acetonitrile in water, 0.1% trifluoroacetic acid buffer) to provide 5-(4-((4-(4-(methylsulfonyl)piperazin-1-yl)phenyl)amino)-1,3,5-triazin-2-yl)-2-((tetrahydro-2H-pyran-4-yl)oxy)benzonitrile. LCMS-ESI$^+$ (m/z): [M+H]$^+$ calcd for $C_{26}H_{30}N_7O_4S$: 536.2; found: 536.2.
$^1$H NMR (400 MHz, DMSO-d$_6$) δ 10.20 (m, 1H), 8.79 (s, 1H), 8.61 (m, 2H), 7.62 (m, 3H), 7.06 (s, 2H), 4.98 (m, 1H), 3.91 (m, 2H), 3.59 (m, 2H), 3.29 (m, 8H), 2.97 (s, 3H), 2.09 (m, 2H), 1.74 (m, 2H).

Example 67

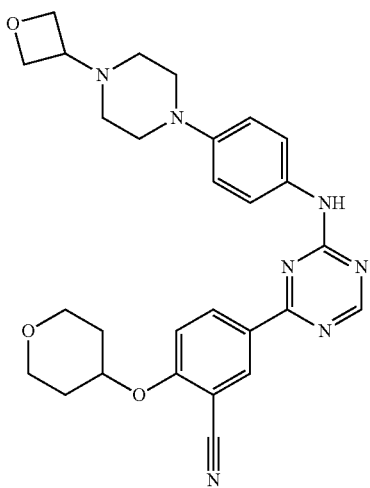 [SMILES: N#Cc1cc(-c2ncnc(Nc3ccc(N4CCN(C5COC5)CC4)cc3)n2)ccc1OC1CCOCC1]

5-(4-((4-(4-(oxetan-3-yl)piperazin-1-yl)phenyl)amino)-1,3,5-triazin-2-yl)-2-((tetrahydro-2H-pyran-4-yl)oxy)benzonitrile A mixture of 4-chloro-N-(4-(4-(oxetan-3-yl)piperazin-1-yl)phenyl)-1,3,5-triazin-2-amine (0.11 g, 0.32 mmol) and 2-((tetrahydro-2H-pyran-4-yl)oxy)-5-(4,4,5,5-tetramethyl-1,3,2-dioxaborolan-2-yl)benzonitrile (0.12 g, 0.35 mmol) in 1,2-dimethoxyethane (DME, 2 mL)/N,N-dimethylformamide (DMF, 1 mL) was treated successively with palladium (II) acetate (0.007 g, 10 mol %), triphenylphosphine (0.025 g, 0.21 mmol), and 2M aqueous sodium carbonate solution (0.7 mL). The mixture was irradiated for 1 hour in a microwave reactor at 130° C. The crude mixture was purified by flash chromatography on silica gel to furnish 5-(4-((4-(4-(oxetan-3-yl)piperazin-1-yl)phenyl)amino)-1,3,5-triazin-2-yl)-2-((tetrahydro-2H-pyran-4-yl)oxy)benzonitrile. LCMS-ESI$^+$ (m/z): [M+H]$^+$ calcd for $C_{28}H_{32}N_7O_3$: 514.3; found: 514.5 $^1$H NMR (400 MHz, DMSO-d$_6$) δ 10.23 (d, J=19.4 Hz, 1H), 8.80 (s, 1H), 8.74-8.50 (m, 2H), 7.68 (br, 2H), 7.60 (d, J=9.0 Hz, 1H), 7.11 (br, 2H), 4.99 (m, 1H), 4.91-4.74 (m, 4H), 4.52 (m, 1H), 3.91 (m, 2H), 3.59 (ddd, J=11.6, 8.5, 3.0 Hz, 2H), 3.80-3.30 (m, 4H), 3.30-2.90 (m, 4H), 2.09 (m, 2H), 1.87-1.64 (m, 2H).

Example 68

2-((tetrahydro-2H-pyran-4-yl)oxy)-5-(4-((4-(2,2,2-trifluoroacetyl)phenyl)amino)-1,3,5-triazin-2-yl)benzonitrile

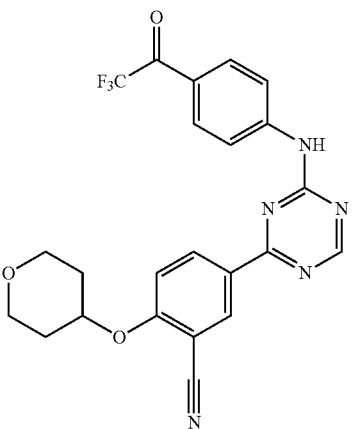 [SMILES: N#Cc1cc(-c2ncnc(Nc3ccc(C(=O)C(F)(F)F)cc3)n2)ccc1OC1CCOCC1]

Preparation of 1-(4-((4-chloro-1,3,5-triazin-2-yl)amino)phenyl)-2,2,2-trifluoroethanone:

To a solution of 2,4-dichloro-1,3,5-triazine (0.26 g, 1.7 mmol) in N,N-dimethylformamide (DMF, 2 mL) at 0° C. were added sequentially N,N-diisopropylethylamine (DIEA, 0.78 mL, 4.5 mmol) and 1-(4-aminophenyl)-2,2,2-trifluoroethanone (Key Organics, 0.30 g, 1.6 mmol) and the mixture was stirred at 0° C. for 30 minutes before the addition of more 2,4-dichloro-1,3,5-triazine (50 mg). After another 10 minutes of stirring at room temperature, additional quantities of 2,4-dichloro-1,3,5-triazine (50 mg) and DIEA (0.20 mL) were added. After stirring overnight at room temperature, the mixture was purified by flash chromatography on silica gel to provide 1-(4-((4-chloro-1,3,5-triazin-2-yl)amino)phenyl)-2,2,2-trifluoroethanone. LCMS-ESI$^+$ (m/z): [M+H$_2$O+H]$^+$ calcd for $C_{11}H_9ClF_3N_4O_2$: 321.0; found: 321.1.

Preparation of 2-((tetrahydro-2H-pyran-4-yl)oxy)-5-(4-((4-(2,2,2-trifluoroacetyl)phenyl)amino)-1,3,5-triazin-2-yl)benzonitrile:

A mixture of 1-(4-((4-chloro-1,3,5-triazin-2-yl)amino)phenyl)-2,2,2-trifluoroethanone (0.13 g, 0.43 mmol), 2-((tetrahydro-2H-pyran-4-yl)oxy)-5-(4,4,5,5-tetramethyl-1,3,2-dioxaborolan-2-yl)benzonitrile (0.18 g, 0.56 mmol), and tetrakis(triphenylphosphine)palladium(0) (0.037 g, 7.5 mol %) in 1,2-dimethoxyethane (DME, 3 mL) was treated with 2M aqueous sodium carbonate solution (0.97 mL). The mixture was irradiated for 1 hour in a microwave reactor at 130° C. The crude mixture was purified by flash chromatography on silica gel to provide 2-((tetrahydro-2H-pyran-4-yl)oxy)-5-(4-((4-(2,2,2-trifluoroacetyl)phenyl)amino)-1,3,5-triazin-2-yl)benzonitrile. LCMS-ESI$^+$ (m/z): [M+H$_2$O+H]$^+$ calcd for $C_{23}H_{21}F_3N_5O_4$: 488.2; found: 488.1 $^1$H NMR (400 MHz, DMSO-d$_6$) δ 11.04 (s, 1H), 9.02 (s, 1H), 8.67 (m, 2H), 8.16 (m, 3H), 7.63 (m, 1H), 5.00 (m, 1H), 3.92 (m, 2H), 3.60 (m, 2H), 2.10 (m, 2H), 1.75 (m, 2H).

Example 69

5-(4-((3-(4-(oxetan-3-yl)piperazin-1-yl)phenyl)amino)-1,3,5-triazin-2-yl)-2-((tetrahydro-2H-pyran-4-yl)oxy)benzonitrile

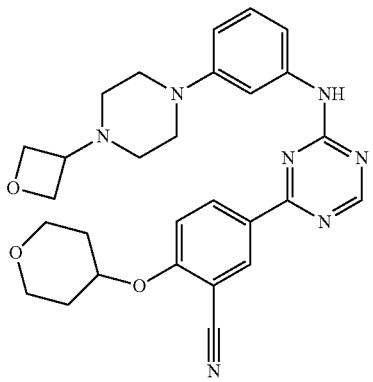 [SMILES: N#Cc1cc(-c2ncnc(Nc3cccc(N4CCN(C5COC5)CC4)c3)n2)ccc1OC1CCOCC1]

Preparation of 1-(3-nitrophenyl)-4-(oxetan-3-yl)piperazine:

To a suspension of 1-fluoro-3-nitrobenzene (1.0 g, 7.1 mmol) and potassium carbonate (2.0 g, 14 mmol) in dimethylsulfoxide (DMSO, 5 mL) was added 1-(oxetan-3-yl)piperazine (1.5 g, 11 mmol) and a DMSO rinsate (2 mL).

The mixture was stirred overnight on a 125° C. block. After cooling to room temperature, the mixture was poured into water (approximately 50 mL). The solid was collected by filtration and dried under vacuum to provide the desired material. LCMS-ESI+ (m/z): [M+H]+ calcd for $C_{13}H_{18}N_3O_3$: 264.1; found: 264.1

Preparation of 3-(4-(oxetan-3-yl)piperazin-1-yl)aniline:

1-(3-nitrophenyl)-4-(oxetan-3-yl)piperazine (0.20 g, 0.76 mmol) was taken up in a methanol/tetrahydrofuran mixture (4:1, 10 mL). After degassing the mixture, 10% palladium on charcoal (40 mg) was added. The suspension was left stirring overnight under a balloon of hydrogen gas. The catalyst was removed by filtration through pad of Celite diatomaceous earth. The filtrate concentrated under reduced pressure to provide the desired material. LCMS-ESI+ (m/z): [M+H]+ calcd for $C_{13}H_{20}N_3O$: 234.2; found: 234.1.

Preparation of 5-(4-((3-(4-(oxetan-3-yl)piperazin-1-yl) phenyl)amino)-1,3,5-triazin-2-yl)-2-((tetrahydro-2H-pyran-4-yl)oxy)benzonitrile:

A suspension of 5-(4-chloro-1,3,5-triazin-2-yl)-2-((tetrahydro-2H-pyran-4-yl)oxy)benzonitrile (57 mg, 0.18 mmol) and 3-(4-(oxetan-3-yl)piperazin-1-yl)aniline (74 mg, 0.32 mmol) in acetonitrile (3 mL) was treated with N,N-diisopropylethylamine (0.13 mL, 0.72 mmol). The mixture was heated in a microwave reactor for 20 minutes at 85° C. The cooled reaction mixture was purified by flash chromatography (silica gel) to provide 5-(4-((3-(4-(oxetan-3-yl)piperazin-1-yl)phenyl)amino)-1,3,5-triazin-2-yl)-2-((tetrahydro-2H-pyran-4-yl)oxy)benzonitrile. LCMS-ESI+ (m/z): [M+H]+ calcd for $C_{28}H_{32}N_7O_3$: 514.3; found: 514.3 1H NMR (400 MHz, DMSO-$d_6$) δ 10.26 (s, 1H), 8.84 (s, 1H), 8.62 (m, 2H), 7.66 (bs, 1H), 7.60 (m, 1H), 7.24 (m, 1H), 7.13 (bs, 1H), 6.75 (m, 1H), 4.99 (m, 1H), 4.60 (m, 2H), 4.51 (m, 2H), 3.92 (m, 2H), 3.60 (m, 2H), 3.49 (m, 1H), 3.25 (m, 4H), 2.48 (m, 4H), 2.08 (m, 2H), 1.73 (m, 2H).

Example 70

2-((1-(1-hydroxycyclopropanecarbonyl)piperidin-4-yl)oxy)-5-(4-((4-(4-(oxetan-3-yl)piperazin-1-yl)phenyl)amino)-1,3,5-triazin-2-yl)benzonitrile

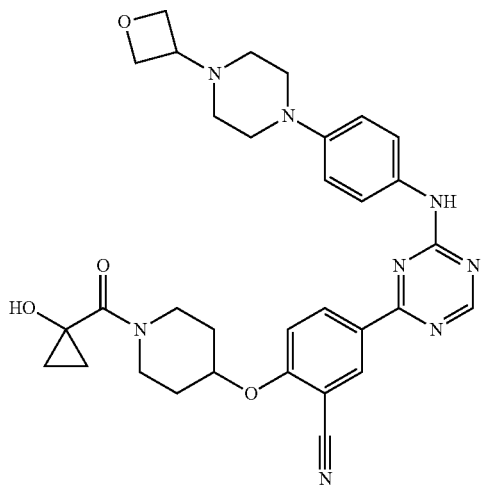 [SMILES: N#Cc1cc(-c2ncnc(Nc3ccc(N4CCN(C5COC5)CC4)cc3)n2)ccc1OC1CCN(C(=O)C2(O)CC2)CC1]

5-(4-((4-(4-(oxetan-3-yl)piperazin-1-yl)phenyl)amino)-1,3,5-triazin-2-yl)-2-(piperidin-4-yloxy)benzonitrile (52 mg, 0.10 mmol), and 1-hydroxy-1-cyclopropanecarboxylic acid (Acros Organics, 16 mg, 0.15 mmol) were taken up as suspension in dichloromethane (3 mL). The mixture was treated successively with N,N-diisopropylethylamine (35 µL, 0.20 mmol) and N-[(dimethylamino)-1H-1,2,3-triazolo-[4,5-b]pyridin-1-ylmethylene]-N-methylmethanaminium-hexafluorophosphate N-oxide (HATU, 58 mg, 0.15 mmol). The mixture was stirred overnight at room temperature and then purified by flash chromatography (silica gel) to provide 2-((1-(1-hydroxycyclopropanecarbonyl)piperidin-4-yl) oxy)-5-(4-((4-(4-(oxetan-3-yl)piperazin-1-yl)phenyl) amino)-1,3,5-triazin-2-yl)benzonitrile.

LCMS-ESI+ (m/z): [M+H]+ calcd for $C_{32}H_{37}N_8O_4$: 597.3; found: 597.3 1H NMR (400 MHz, DMSO-$d_6$) δ 10.16 (m, 1H), 8.78 (s, 1H), 8.63 (m, 2H), 7.62 (m, 2H), 7.01 (m, 2H), 6.38 (s, 1H), 5.05 (m, 1H), 4.61 (m, 2H), 4.52 (m, 2H), 4.35-3.45 (m, 4H), 3.49 (m, 1H), 3.19 (m, 4H), 2.46 (m, 4H), 2.08 (m, 2H), 1.76 (m, 2H), 0.98 (dd, J=4.7, 4.3 Hz, 2H), 0.81 (dd, J=4.6 Hz, 2H).

Example 71

5-(4-((3-methoxy-4-(4-(oxetan-3-yl)piperazine-1-carbonyl)phenyl)amino)-1,3,5-triazin-2-yl)-2-((tetrahydro-2H-pyran-4-yl)oxy)benzonitrile

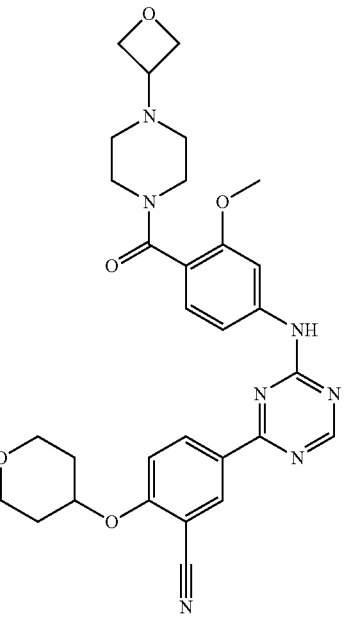

Preparation of (2-methoxy-4-nitrophenyl)(4-(oxetan-3-yl)piperazin-1-yl)methanone:

A mixture of 2-methoxy-4-nitrobenzoic acid (1.0 g, 5.0 mmol) and 1-(oxetan-3-yl)piperazine (0.79 g, 5.6 mmol) in N,N-dimethylformamide (DMF, 15 mL) was treated with N,N-diisopropylethylamine, followed by 50% propylphosphonic anhydride solution in DMF (Sigma Aldrich, 5 mL). The mixture was left to stir for one hour at room temperature before it was concentrated under reduced pressure. The residue was diluted with ethyl acetate (~100 mL) and washed successively with saturated aqueous sodium hydrogen carbonate solution (twice) and once with saturated aqueous sodium chloride solution. The organics were dried over anhydrous magnesium sulfate, filtered, concentrated to provide the desired material. LCMS-ESI⁺ (m/z): [M+H]⁺ calcd for $C_{15}H_{20}N_3O_5$: 322.1; found: 322.1.

Preparation of (4-amino-2-methoxyphenyl)(4-(oxetan-3-yl)piperazin-1-yl)methanone:

(2-methoxy-4-nitrophenyl)(4-(oxetan-3-yl)piperazin-1-yl)methanone (5.1 mmol assumed) was taken up as a suspension in methanol/tetrahydrofuran/ethyl acetate (5:2:1, 80 mL) in a Parr bottle. After mixture was de-gassed, 10% palladium on charcoal (200 mg) was introduced. The mixture was shaken under 50 psi hydrogen overnight and then filtered through pad of Celite diatomaceous earth. The filtrate was concentrated under reduced pressure to provide the desired material. LCMS-ESI⁺ (m/z): [M+H]⁺ calcd for $C_{15}H_{22}N_3O_3$: 292.2; found: 291.9.

Preparation of 5-(4-((3-methoxy-4-(4-(oxetan-3-yl)piperazine-1-carbonyl)phenyl)amino)-1,3,5-triazin-2-yl)-2-((tetrahydro-2H-pyran-4-yl)oxy)benzonitrile:

A suspension of 5-(4-chloro-1,3,5-triazin-2-yl)-2-((tetrahydro-2H-pyran-4-yl)oxy)benzonitrile (100 mg, 0.32 mmol) (4-amino-2-methoxyphenyl)(4-(oxetan-3-yl)piperazin-1-yl)methanone (92 mg, 0.32 mmol) in acetonitrile (3 mL) was treated with N,N-diisopropylethylamine (0.22 mL, 1.3 mmol). The mixture was heated in a microwave reactor for 20 minutes at 80° C. The reaction mixture was purified by flash chromatography (silica gel), followed by recrystallization from acetonitrile, to provide the desired material. LCMS-ESI⁺ (m/z): [M+H]⁺ calcd for $C_{30}H_{34}N_7O_5$: 572.3; found: 572.1.

¹H NMR (400 MHz, DMSO-d₆) δ 10.53 (s, 1H), 8.90 (s, 1H), 8.66 (d, J=2.2 Hz, 1H), 8.63 (dd, J=9.0, 2.2 Hz, 1H), 7.86 (br, 1H), 7.61 (d, J=9.0 Hz, 1H), 7.36 (br, 1H), 7.22 (d, J=8.1 Hz, 1H), 4.99 (m, 1H), 4.57 (m, 2H), 4.47 (m, 2H), 3.92 (m, 5H), 3.70 (m, 2H), 3.60 (m, 2H), 3.47 (m, 1H), 3.25 (m, 2H), 2.34 (m, 2H), 2.24 (m, 2H), 2.09 (m, 2H), 1.74 (m, 2H).

Example 72

5-(4-((4-methoxyphenyl)amino)-1,3,5-triazin-2-yl)-2-((tetrahydro-2H-pyran-4-yl)oxy)benzonitrile

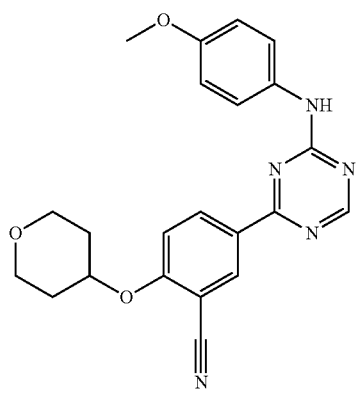 [SMILES: COc1ccc(Nc2ncnc(-c3ccc(OC4CCOCC4)c(C#N)c3)n2)cc1]

A suspension of 5-(4-chloro-1,3,5-triazin-2-yl)-2-((tetrahydro-2H-pyran-4-yl)oxy)benzonitrile (80 mg, 0.25 mmol) and para-anisidine (37 mg, 0.30 mmol) in acetonitrile (3 mL) was treated with N,N-diisopropylethylamine (0.13 mL, 0.76 mmol). The mixture was heated in a microwave reactor for 20 minutes at 80° C. The solid was collected from the mixture by filtration, washed with acetonitrile and dried in a vacuum oven to provide the desired material. LCMS-ESI⁺ (m/z): [M+H]⁺ calcd for $C_{22}H_{22}N_5O_3$: 404.2; found: 404.1 ¹H NMR (400 MHz, DMSO-d₆) δ 10.21 (m, 1H), 8.79 (s, 1H), 8.60 (m, 2H), 7.72 (m, 2H), 7.60 (d, J=9.2 Hz, 1H), 7.00 (m, 2H), 4.98 (m, 1H), 3.91 (m, 2H), 3.80 (s, 3H), 3.59 (m, 2H), 2.09 (m, 2H), 1.73 (m, 2H).

Example 73

5-(4-((1-methyl-1H-pyrazol-5-yl)amino)-1,3,5-triazin-2-yl)-2-((tetrahydro-2H-pyran-4-yl)oxy)benzonitrile

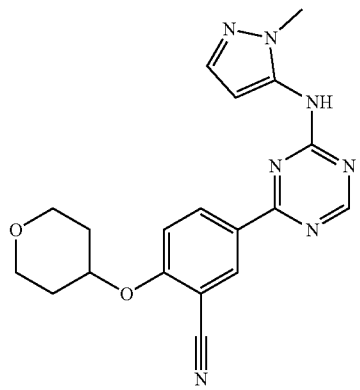 [SMILES: Cn1nccc1Nc1ncnc(-c2ccc(OC3CCOCC3)c(C#N)c2)n1]

To a solution of 2,4-dichloro-1,3,5-triazine (0.74 g, 4.9 mmol) in N,N-dimethylformamide (DMF, 6 mL) at 0° C. were added sequentially N,N-diisopropylethylamine (DIEA, 0.89 mL, 5.1 mmol) and 1-methyl-5-aminopyrazole (0.44 g, 4.5 mmol). The mixture was stirred at 0° C. for 30 minutes and then allowed to warm to room temperature. The mixture was diluted with ethyl acetate and water. The aqueous phase was extracted twice with ethyl acetate. The combined extracts were washed once each with water and a saturated aqueous sodium chloride solution, then dried over anhydrous magnesium sulfate, filtered, and concentrated under reduced pressure. The residue was purified via flash chromatography on silica gel to provide 4-chloro-N-(1-methyl-1H-pyrazol-5-yl)-1,3,5-triazin-2-amine. LCMS-ESI⁺ (m/z): [M+H]⁺ calcd for $C_7H_8ClN_6$: 211.0; found: 211.1.

A mixture of 4-chloro-N-(1-methyl-1H-pyrazol-5-yl)-1,3,5-triazin-2-amine (0.12 g, 0.55 mmol), 2-((tetrahydro-2H-pyran-4-yl)oxy)-5-(4,4,5,5-tetramethyl-1,3,2-dioxaborolan-2-yl)benzonitrile (0.20 g, 0.60 mmol), palladium (II) acetate (0.012 g, 10 mol %), and triphenylphosphine (0.043 g, 0.16 mmol) in 1,2-dimethoxyethane (DME, 6 mL) was treated with 2M aqueous sodium carbonate solution (1.2 mL). The mixture was irradiated for 1 hour in a microwave reactor at 130° C. The crude mixture was filtered through a pad of Celite diatomaceous earth. The aqueous phase was extracted twice with ethyl acetate. The combined extracts were washed once with saturated aqueous sodium chloride solution, dried over anhydrous magnesium sulfate, filtered, concentrated to dryness under reduced pressure. The residue was purified via prep HPLC (10-85% acetonitrile in water, 0.1% trifluoroacetic acid buffer) to furnish 5-(4-((1-methyl-1H-pyrazol-5-yl)amino)-1,3,5-triazin-2-yl)-2-((tetrahydro-2H-pyran-4-yl)oxy)benzonitrile. LCMS-ESI⁺ (m/z): [M+H]⁺ calcd for $C_{19}H_{19}N_7O_2$: 378.2; found: 378.3 ¹H NMR (400 MHz, DMSO-d₆) δ 10.30 (br, 1H), 8.86 (s, 1H), 8.57 (br, 2H), 7.60 (d, J=9.6 Hz, 1H), 7.48 (s, 1H), 6.40 (m, 1H), 4.97 (m, 1H), 3.91 (m, 2H), 3.75 (s, 3H), 3.59 (ddd, J =11.7, 8.4 3.1 Hz, 2H), 2.08 (m, 2H), 1.73 (m, 2H).

Example 74

5-(4-((3,5-difluoro-4-(4-(oxetan-3-yl)piperazin-1-yl)phenyl)amino)-1,3,5-triazin-2-yl)-2-((tetrahydro-2H-pyran-4-yl)oxy)benzonitrile

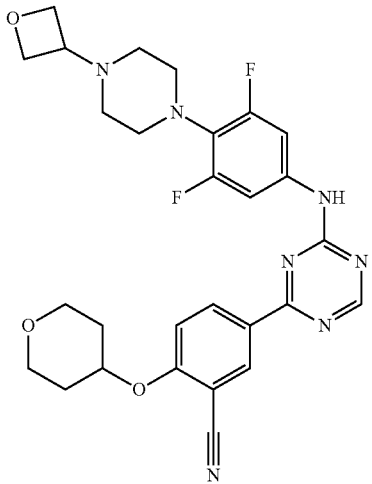 [SMILES: N#Cc1cc(-c2ncnc(Nc3cc(F)c(N4CCN(C5COC5)CC4)c(F)c3)n2)ccc1OC1CCOCC1]

Preparation of 1-(2,6-difluoro-4-nitrophenyl)-4-(oxetan-3-yl)piperazine:

A stirred mixture of 1-(oxetan-3-yl)piperazine (0.88 g, 6.2 mmol) and potassium carbonate (1.6 g, 11 mol) in N,N-dimethylformamide (9 mL) was treated via syringe with 3,4,5-trifluoronitrobenzene (1.0 g, 5.6 mmol). The reaction mixture was stirred at 85° C. overnight. The cooled reaction mixture was partitioned between ethyl acetate and water. A small volume of methanol was added to the ethyl acetate. The pH of the aqueous phase was brought basic via the addition of solid sodium carbonate. The aqueous phase was extracted three times with ethyl acetate. The combined extracts were washed once each with water and saturated aqueous sodium chloride solution, dried over anhydrous magnesium sulfate, filtered, and concentrated to give 1-(2,6-difluoro-4-nitrophenyl)-4-(oxetan-3-yl)piperazine.
LCMS-ESI⁺ (m/z): [M+H]⁺ calcd for $C_{13}H_{16}F_2N_3O_3$: 300.1; found: 300.1

Preparation of 3,5-difluoro-4-(4-(oxetan-3-yl)piperazin-1-yl)aniline:

1-(2,6-difluoro-4-nitrophenyl)-4-(oxetan-3-yl)piperazine (1.7 g, 5.6 mmol) was taken up in a mixture of tetrahydrofuran/methanol/ethyl acetate (1:3:2, 60 mL). The mixture was degassed before the addition of 10% palladium on charcoal (250 mg). The mixture was stirred under a balloon of hydrogen overnight, then filtered through a pad of Celite diatomaceous earth. The filtrate was concentrated under reduced pressure to provide 3,5-difluoro-4-(4-(oxetan-3-yl)piperazin-1-yl)aniline. LCMS-ESI⁺ (m/z): [M+H]⁺ calcd for $C_{13}H_{18}F_7N_3O$: 270.1; found: 270.2.

Preparation of 4-chloro-N-(3,5-difluoro-4-(4-(oxetan-3-yl)piperazin-1-yl)phenyl)-1,3,5-triazin-2-amine:

To a solution of 2,4-dichloro-1,3,5-triazine (0.33 g, 2.3 mmol) in N,N-dimethylformamide (DMF, 6 mL) at 0° C. were added sequentially N,N-diisopropylethylamine (DIEA, 0.41 mL, 2.4 mmol) and 3,5-difluoro-4-(4-(oxetan-3-yl)piperazin-1-yl)aniline (0.56 g, 2.1 mmol). The mixture was stirred at 0° C. for 30 minutes and then allowed to warm to room temperature. The mixture was diluted with ethyl acetate and water. The suspension was filtered through a plastic frit to provide 4-chloro-N-(3,5-difluoro-4-(4-(oxetan-3-yl)piperazin-1-yl)phenyl)-1,3,5-triazin-2-amine. The aqueous phase was extracted twice with ethyl acetate containing a small amount of methanol. The combined extracts were washed once each with water and a saturated aqueous sodium chloride solution, then dried over anhydrous magnesium sulfate, filtered, and concentrated under reduced pressure to provide additional 4-chloro-N-(3,5-difluoro-4-(4-(oxetan-3-yl)piperazin-1-yl)phenyl)-1,3,5-triazin-2-amine.
LCMS-ESI⁺ (m/z): [M+H]⁺ calcd for $C_{16}H_{18}ClF_2N_6O$: 383.1; found: 383.4.

Preparation of 5-(4-((3,5-difluoro-4-(4-(oxetan-3-yl)piperazin-1-yl)phenyl)amino)-1,3,5-triazin-2-yl)-2-((tetrahydro-2H-pyran-4-yl)oxy)benzonitrile A mixture of 4-chloro-N-(3,5-difluoro-4-(4-(oxetan-3-yl)piperazin-1-yl)phenyl)-1,3,5-triazin-2-amine (0.13 g, 0.33 mmol), 2-((tetrahydro-2H-pyran-4-yl)oxy)-5-(4,4,5,5-tetramethyl-1,3,2-dioxaborolan-2-yl)benzonitrile (0.12 g, 0.36 mmol), and tetrakis(triphenylphosphine)palladium(0) (0.019 g, 5 mol %) in 1,2-dimethoxyethane (DME, 3 mL) was treated with 2M aqueous sodium carbonate solution (0.74 mL). The mixture was irradiated for 1 hour in a microwave reactor at 130° C. The crude mixture was purified by flash chromatography on silica gel to provide 5-(4-((3,5-difluoro-4-(4-(oxetan-3-yl)piperazin-1-yl)phenyl)amino)-1,3,5-triazin-2-yl)-2-((tetrahydro-2H-pyran-4-yl)oxy)benzonitrile. LCMS-ESI⁺ (m/z): [M+H]⁺ calcd for $C_{28}H_{30}F_2N_7O_3$: 550.2; found: 550.3 ¹H NMR (400 MHz, DMSO-d₆) δ 10.58 (s, 1H), 8.91 (s, 1H), 8.60 (m, 2H), 7.62 (m, 1H), 7.59-7.50 (m, 2H), 5.00 (tt, J=8.0, 4.2 Hz, 1H), 4.59 (t, J=6.5 Hz, 2H), 4.50 (t, J=6.1 Hz, 2H), 3.91 (m, 2H), 3.59 (ddd, J=11.6, 8.5, 3.0 Hz, 2H), 3.52 (m, 1H), 3.14 (m, 4H), 2.41 (m, 4H), 2.09 (m, 2H), 1.73 (m, 2H).

Example 75

4-((4-(3-cyano-4-((tetrahydro-2H-pyran-4-yl)oxy)phenyl)-1,3,5-triazin-2-yl)amino)-N-(oxetan-3-yl)benzamide

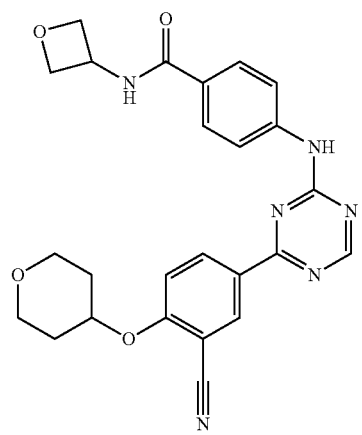

Preparation of 4-nitro-N-(oxetan-3-yl)benzamide:

To a mixture of 3-aminooxetane (Sigma Aldrich, 0.47 g, 6.5 mmol) and N,N-diisopropylethylamine (2.3 mL, 13 mmol) in 2-methyltetrahydrofuran (20 mL) at 0° C. was added dropwise via syringe a solution of 4-nitrobenzoyl chloride (1.0 g, 5.4 mmol) in 2-methyltetrahydrofuran (15 mL), immediately giving a precipitate. At the end of the addition, the cooling bath was removed. The suspension stirred at room temperature for about 2 hours and was then allowed to stand for two weeks. The suspension was concentrated under reduced pressure and then diluted with ethyl acetate and water. Collection of the solid by vacuum filtration and drying under vacuum provided the desired material. Additional desired material was obtained by the evaporation of the organic phase and the collection of the residual solid, as above. LCMS-ESI$^+$ (m/z): [M+H]$^+$ calcd for $C_{10}H_{11}N_2O_4$: 223.1; found: 223.2.

Preparation of 4-amino-N-(oxetan-3-yl)benzamide:

4-nitro-N-(oxetan-3-yl)benzamide (0.14 g, 0.63 mmol) and 10% Pd/C taken up in 1:1 methanol/2-methyltetrahydrofuran (1:1, 4 mL). After degassing of the mixture, 10% palladium on charcoal (30 mg) was introduced. The mixture was stirred for 3 hours under a balloon of hydrogen gas. The mixture was filtered through a pad of Celite diatomaceous earth, and the filtrate was concentrated under reduced pressure to provide the desired material. LCMS-ESI$^+$ (m/z): [M+H]$^+$ calcd for $C_{10}H_{13}N_2O_2$: 193.1; found: 193.0.

Preparation of 4-((4-(3-cyano-4-((tetrahydro-2H-pyran-4-yl)oxy)phenyl)-1,3,5-triazin-2-yl)amino)-N-(oxetan-3-yl) benzamide:

A suspension of 5-(4-chloro-1,3,5-triazin-2-yl)-2-((tetrahydro-2H-pyran-4-yl)oxy)benzonitrile (53 mg, 0.17 mmol) and 4-amino-N-(oxetan-3-yl)benzamide (39 mg, 0.20 mmol) in acetonitrile (2.5 mL) was treated with N,N-diisopropylethylamine (0.12 mL, 0.67 mmol). The mixture was heated in a microwave reactor for 30 minutes at 85° C., and then for 2 hours at 120° C. The precipitated solid was collected by vacuum filtration, washed with acetonitrile, and dried in a vacuum oven to provide 4-((4-(3-cyano-4-((tetrahydro-2H-pyran-4-yl)oxy)phenyl)-1,3,5-triazin-2-yl) amino)-N-(oxetan-3-yl)benzamide. LCMS-ESI$^+$ (m/z): [M+H]$^+$ calcd for $C_{25}H_{25}N_6O_4$: 473.2; found: 473.2.

$^1$H NMR (400 MHz, DMSO-d$_6$) δ 10.64 (s, 1H), 9.05 (d, J=6.5 Hz, 1H), 8.93 (s, 1H), 8.65 (m, 2H), 7.94 (m, 4H), 7.63 (m, 1H), 5.17-4.94 (m, 2H), 4.82 (t, J=6.5 Hz, 2H), 4.65 (t, J=6.4 Hz, 2H), 3.92 (m, 2H), 3.60 (m, 2H), 2.10 (m, 2H), 1.74 (m, 2H).

Example 76

5-(4-((4-(1-methylpiperidin-4-yl)phenyl)amino)-1,3,5-triazin-2-yl)-2-((tetrahydro-2H-pyran-4-yl)oxy) benzonitrile

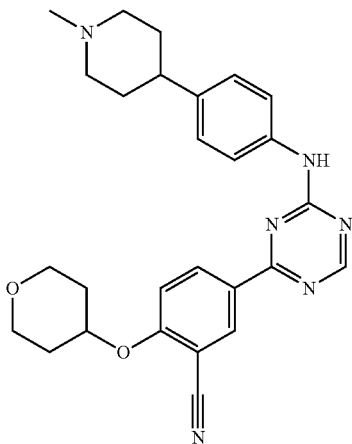

A suspension of 5-(4-chloro-1,3,5-triazin-2-yl)-2-((tetrahydro-2H-pyran-4-yl)oxy)benzonitrile (53 mg, 0.16 mmol) and 4-(1-methylpiperidin-4-yl)aniline (ChemShuttle, 38 mg, 0.20 mmol) in acetonitrile (2.5 mL) was treated with N,N-diisopropylethylamine (0.12 mL, 0.67 mmol). The mixture was heated in a microwave reactor for 30 minutes at 85° C. The cooled reaction mixture was purified by prep HPLC (10-80% acetonitrile in water, 0.1% trifluoroacetic acid buffer), followed by flash chromatography (silica gel) to provide 5-(4-((4-(1-methylpiperidin-4-yl)phenyl)amino)-1,3,5-triazin-2-yl)-2-((tetrahydro-2H-pyran-4-yl)oxy)benzonitrile. LCMS-ESI$^+$ (m/z): [M+H]$^+$ calcd for $C_{27}H_{31}N_6O_2$: 471.2; found: 471.3 $^1$H NMR (400 MHz, DMSO-d$_6$) δ 10.32 (bs, 1H), 8.83 (s, 1H), 8.62 (m, 2H), 7.71 (m, 2H), 7.61 (d, J=9.4 Hz, 1H), 7.29 (d, J=8.4 Hz, 2H), 4.99 (m, 1H), 3.91 (m, 2H), 3.59 (m, 2H), 3.35 (bs, 3H), 2.99 (d, J=11.2 Hz, 2H), 2.32 (s, 3H), 2.11 (m, 4H), 1.74 (m, 4H).

Example 77

5-(4-((6-methoxypyridin-3-yl)amino)-1,3,5-triazin-2-yl)-2-((tetrahydro-2H-pyran-4-yl)oxy)benzonitrile

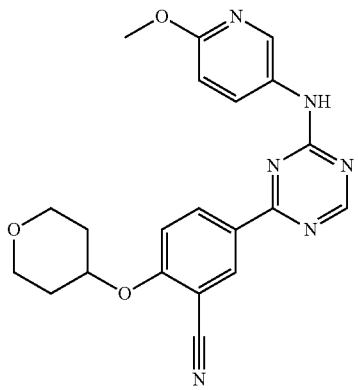

A suspension of 5-(4-chloro-1,3,5-triazin-2-yl)-2-((tetrahydro-2H-pyran-4-yl)oxy)benzonitrile (80 mg, 0.25 mmol) and 5-methoxy-2-aminopyridine (38 mg, 0.30 mmol) in acetonitrile (3 mL) was treated with N,N-diisopropylethylamine (0.13 mL, 0.76 mmol). The mixture was heated in a microwave reactor for 20 minutes at 80° C. The reaction mixture was purified by flash chromatography (silica gel), followed by recrystallization from acetonitrile, to provide the desired product. LCMS-ESI$^+$ (m/z): [M+H]$^+$ calcd for $C_{21}H_{21}N_6O_3$: 405.2; found: 405.2 $^1$H NMR (400 MHz, DMSO-d$_6$) δ 10.32 (s, 1H), 8.82 (s, 1H), 8.51 (m, 2H), 8.05 (dd, J=8.9, 2.7 Hz, 1H), 7.61 (d, J=9.4 Hz, 1H), 6.91 (m, 1H), 4.98 (m, 1H), 3.90 (m, 5H), 3.59 (m, 2H), 2.08 (m, 2H), 1.73 (m, 2H).

Example 78

5-(4-((3-methoxyphenyl)amino)-1,3,5-triazin-2-yl)-2-((tetrahydro-2H-pyran-4-yl)oxy)benzonitrile

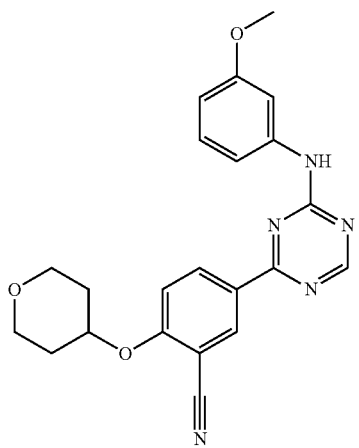

A suspension of 5-(4-chloro-1,3,5-triazin-2-yl)-2-((tetrahydro-2H-pyran-4-yl)oxy)benzonitrile (93 mg, 0.29 mmol) and meta-anisidine (43 mg, 0.35 mmol) in acetonitrile (3 mL) was treated with N,N-diisopropylethylamine (0.15 mL, 0.88 mmol). The mixture was heated in a microwave reactor for 20 minutes at 80° C. The reaction mixture was concentrated to dryness under reduced pressure. The residue was taken up in acetonitrile, and water was added to precipitate a solid. The solid was collected by filtration, washed with aqueous methanol, and dried in a vacuum oven to provide the desired material. LCMS-ESI+ (m/z): [M+H]+ calcd for $C_{22}H_{22}N_5O_3$: 404.2; found: 404.1 $^1$H NMR (400 MHz, DMSO-d$_6$) δ 10.38 (s, 1H), 8.87 (s, 1H), 8.62 (m, 2H), 7.62 (m, 2H), 7.32 (m, 2H), 6.73 (m, 1H), 5.00 (m, 1H), 3.91 (m, 2H), 3.84 (s, 3H), 3.59 (m, 2H), 2.09 (m, 2H), 1.73 (m, 2H).

Example 79

5-(4-(phenylamino)-1,3,5-triazin-2-yl)-2-((tetrahydro-2H-pyran-4-yl)oxy)benzonitrile

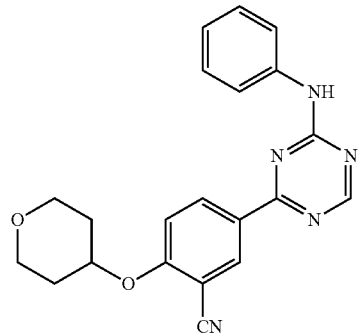 [SMILES: N#Cc1cc(-c2ncnc(Nc3ccccc3)n2)ccc1OC1CCOCC1]

Step 1: To a solution of 2,4-dichloro-1,3,5-triazine (530 mg, 3.54 mmol) in DMF (6 mL) at 0° C. were added DIEA (475 mg, 3.67 mmol), followed by a solution of aniline (300 mg, 3.22 mmol) in DMF (9 mL). The clear, golden mixture was stirred at 0° C. for 30 minutes and then allowed to warm to r.t. where it remained. The mixture was partitioned between ethyl acetate and water. Layers were separated and aqueous phase was extracted twice with EtOAc. The combined extracts were washed once each with water and brine, then dried over anhydrous MgSO$_4$, filtered, and concentrated under reduced pressure. Crude material was purified by silica gel column chromatography eluted 10-20 of % EtOAc in hexanes to give the product.

Step 2: A sealed tube containing a suspension of 4-chloro-N-phenyl-1,3,5-triazin-2-amine (150 mg, 0.73 mmol) and Pd(PPh$_3$)$_4$ (38 mg, 0.033 mmol) in a degassed mixture of dioxane/H$_2$O (3 mL, 4/1), was preheated at 85° C. for 5 min. Next, K$_2$CO$_3$ (227 mg, 2 mmol) and 2-((tetrahydro-2H-pyran-4-yl)oxy)-5-(4,4,5,5-tetramethyl-1,3,2-dioxaborolan-2-yl)benzonitrile (263 mg, 0.8 mmol), were added to the mixture and the reaction was additionally heated at 100° C. in the sealed tube for 15 h. The clear was partitioned between ethyl acetate and water. Layers were separated and aqueous phase was extracted twice with EtOAc. The combined extracts were washed once each with water and brine, then dried over anhydrous MgSO$_4$, filtered, and concentrated under reduced pressure. The residue was then purified via HPLC (20 mL/min, 20-90percent MeCN/H$_2$O (0.1% TFA v/v) gradient over 30 min) to give the title compound as a solid. $^1$H NMR (400 MHz, DMSO-d6) δ 10.33 (s, 1H), 8.80 (s, 1H), 8.67-8.45 (m, 2H), 7.75 (d, J=8.0 Hz, 2H), 7.56 (d, J=9.5 Hz, 1H), 7.37 (t, J=7.8 Hz, 2H), 7.10 (t, J=7.4 Hz, 1H), 4.93 (dt, J=8.2, 4.2 Hz, 1H), 3.97-3.76 (m, 2H), 3.54 (m, 2H), 2.04 (m, 2H), 1.68 (m, 2H).

LCMS-ESI+ (m/z): [M+H]+ calcd for $C_{21}H_{19}N_5O_2$: 374.2; found: 374.1.

Example 80

(R)-5-(4-((4-morpholinophenyl)amino)-1,3,5-triazin-2-yl)-2-(pyrrolidin-3-yloxy)benzonitrile

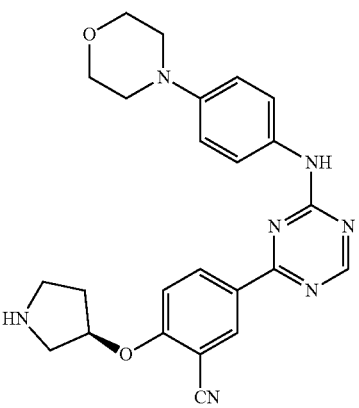 [SMILES: N#Cc1cc(-c2ncnc(Nc3ccc(N4CCOCC4)cc3)n2)ccc1O[C@@H]1CCNC1]

Step 1: To solution of 2,4-dichloro-1,3,5-triazine (500 mg, 3.33 mmol) in DMF (10 mL) at 0° C. under argon atmosphere were added DIEA (0.602 mL, 3.45 mmol), followed by 4-amino phenyl morpholine (535 mg, 3.0 mmol) at once. The reaction mixture was stirred at 0° C. for 1 h. The solvent was concentrated to dryness under reduced pressure. The crude product was purified by flash column chromatography on silica gel to afford 4-chloro-N-(4-morpholinophenyl)-1,3,5-triazin-2-amine. LCMS-ESI+ (m/z): [M+H]+ calcd for $C_{13}H_{14}ClN_5O$: 292.12 found:292.3

Step 2: To a mixture of 4-chloro-N-(4-morpholinophenyl)-1,3,5-triazin-2-amine (0.25 g, 0.86 mmol), 4-(4-(4,4,5,5-tetramethyl-1,3,2-dioxaborolan-2-yl)phenyl)morpholine (0.39 g, 0.94 mmol), and Pd(PPh$_3$)$_4$ (74 mg, 0.06 mmol) in a 20 mL microwave vial was added DME (6 mL). To well stirred mixture was added a solution of sodium carbonate (409 mg, 3.85 mmol) in water (3 mL)). The mixture was microwaved for one hour at 130° C. The reaction mixture was diluted with DCM and filtered through short pad of silica gel and washed with 10% MeOH/DCM. The solvent was concentrated to dryness under reduced pressure. The crude product was purified by flash column chromatography on silica gel to afford (R)-tert-butyl 3-(2-cyano-4-(4-((4-morpholinophenyl)amino)-1,3,5-triazin-2-yl)phenoxy)pyrrolidine-1-carboxylate. LCMS-ESI$^+$ (m/z): [M+H]$^+$ calcd for C$_{29}$H$_{33}$N$_7$O$_4$: 544.2.12 found:544.2.

Step 3: (R)-tert-butyl 3-(2-cyano-4-(4-((4-morpholinophenyl)amino)-1,3,5-triazin-2-yl)phenoxy)pyrrolidine-1-carboxylate (431 mg, 0.79 mmol) was dissolved in 20% TFA/DCM (10 mL) and stirred at room temperature for 1 h. The solvent was concentrated under reduced pressure and the residue was purified via prep HPLC (5-95% acetonitrile in water, 0.1% trifluoroacetic acid buffer) to isolate (R)-5-(4-((4-morpholinophenyl)amino)-1,3,5-triazin-2-yl)-2-(pyrrolidin-3-yloxy)benzonitrile. LCMS-ESI$^+$ (m/z): [M+H]$^+$ calcd for C$_{24}$H$_{25}$N$_7$O$_2$: 444.2.2; found:444.3 $^1$H NMR (400 MHz, DMSO-d$_6$) δ 10.13 (d, J=30.2 Hz, 1H), 9.11 (br s, 1H), 8.74 (s, 1H), 8.67-8.44 (m, 2H), 7.607.48 (m, 3H), 6.95 (t, J=9.5 Hz, 2H), 5.41 (t, J=4.8 Hz, 1H), 3.84-3.68 (m, 4H), 3.59 (dd, J=13.5, 4.8 Hz, 1H), 3.50-3.35 (m, 3H), 3.07 (d, J=6.4 Hz, 4H), 2.39-2.17 (m, 2H).

Example 81

(R)-2-((1-(2-hydroxyacetyl)pyrrolidin-3-yl)oxy)-5-(4-((3-morpholinophenyl)amino)-1,3,5-triazin-2-yl)benzonitrile

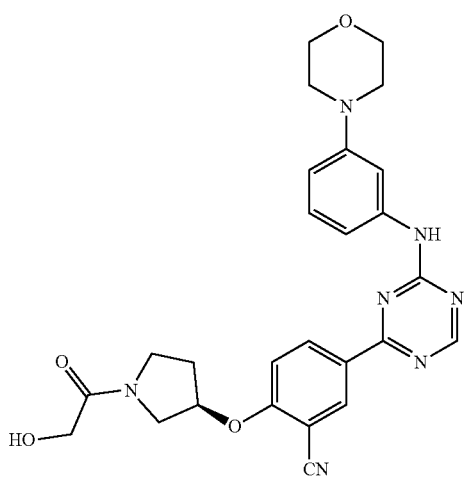 [SMILES: N#Cc1cc(-c2ncnc(Nc3cccc(N4CCOCC4)c3)n2)ccc1O[C@@H]1CCN(C(=O)CO)C1]

The title compound was prepared by glycolic acid coupling to (R)-5-(4-((3-morpholinophenyl)amino)-1,3,5-triazin-2-yl)-2-(pyrrolidin-3-yloxy)benzonitrile using the same procedure reported in Example 103. LCMS-ESI$^+$ (m/z): [M+H]$^+$ calcd for C$_{26}$H$_{27}$N$_7$O$_4$: 502.2; found:502.3 $^1$H NMR (400 MHz, DMSO-d$_6$) δ 10.22 (s, 1H), 8.79 (s, 1H), 8.69-8.43 (m, 2H), 7.51 (d, J=9.0 Hz, 2H), 7.20 (d, J=7.9 Hz, 2H), 6.82-6.56 (m, 1H), 5.36 (d, J=32.9 Hz, 1H), 4.75 (s, 1H), 4.18-3.91 (m, 2H), 3.86-3.33 (m, 8H), 3.13 (s, 4H), 2.35-2.06 (m, 3H).

Example 82

(R)-5-(4-((3-morpholinophenyl)amino)-1,3,5-triazin-2-yl)-2-(pyrrolidin-3-yloxy)benzonitrile

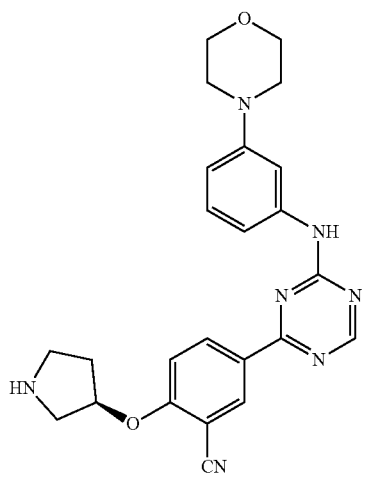 [SMILES: N#Cc1cc(-c2ncnc(Nc3cccc(N4CCOCC4)c3)n2)ccc1O[C@@H]1CCNC1]

The title compound was prepared following a similar procedure reported in Example-80 using 3-morpholinoaniline instead of 4-morpholineaniline.

LCMS-ESI$^+$ (m/z): [M+H]$^+$ calcd for C$_{24}$H$_{25}$N$_7$O$_2$: 444.2; found:444.3 $^1$H NMR (400 MHz, DMSO-d$_6$) δ 10.24 (s, 1H), 9.13 (br s, 2H), 8.80 (s, 1H), 8.69-8.48 (m, 2H), 7.66-7.42 (m, 2H), 7.29-6.97 (m, 2H), 6.79-6.60 (m, 1H), 5.43 (t, J=4.9 Hz, 1H), 3.76 (s, 4H), 3.59 (dd, J=13.5, 4.9 Hz, 1H), 3.54-3.18 (m, 5H), 3.13 (s, 4H), 2.38-2.19 (m, 2H).

Example 83

(R)-4-((4-(3-cyano-4-((1-(2-hydroxyacetyl)pyrrolidin-3-yl)oxy)phenyl)-1,3,5-triazin-2-yl)amino)-N-isopropylbenzamide

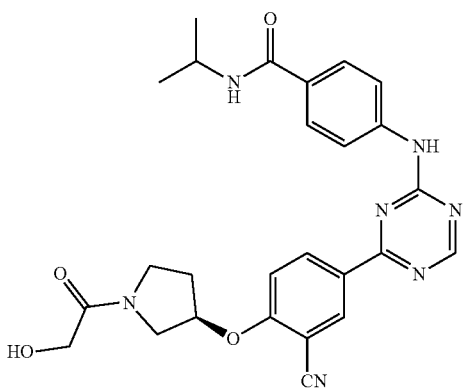 [SMILES: CC(C)NC(=O)c1ccc(Nc2ncnc(-c3ccc(O[C@@H]4CCN(C(=O)CO)C4)c(C#N)c3)n2)cc1]

The title compound was prepared by glycolic acid coupling to (R)-4-((4-(3-cyano-4-(pyrrolidin-3-yloxy)phenyl)-1,3,5-triazin-2-yl)amino)-N-isopropylbenzamide (Example 84) using the same procedure reported in Example 103. LCMS-ESI⁺ (m/z): [M+H]⁺ calcd for $C_{26}H_{27}N_7O_4$: 502.2; found:502.3

¹H NMR (400 MHz, DMSO-d₆) δ 10.55 (s, 1H), 8.87 (s, 1H), 8.72-8.50 (m, 2H), 8.11 (d, J=7.7 Hz, 1H), 7.85 (m, 4H), 7.53 (dd, J=9.1, 2.4 Hz, 1H), 5.36 (dd, J=33.4, 4.4 Hz, 1H), 4.64 (d, J=6.2 Hz, 1H), 4.17-3.90 (m, 2H), 3.85-3.35 (m, 4H), 3.12 (m, 1H), 2.38-2.04 (m, 2H), 1.16 (d, J=6.5 Hz, 6H).

Example 84

(R)-4-((4-(3-cyano-4-(pyrrolidin-3-yloxy)phenyl)-1,3,5-triazin-2-yl)amino)-N-isopropylbenzamide

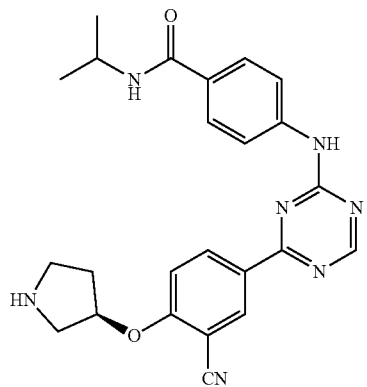 [SMILES: CC(C)NC(=O)c1ccc(Nc2ncnc(-c3ccc(O[C@@H]4CCNC4)c(C#N)c3)n2)cc1]

The title compound was prepared following the similar procedure reported in Example-80 using 4-amino-N-isopropylbenzamide instead of 4-Phenylmorpholine. LCMS-ESI⁺ (m/z): [M+H]⁺ calcd for $C_{24}H25N_7O_2$: 444.2.2; found:444.3

Example 85

(R)-4-((4-(3-cyano-4-((1-(2-hydroxyacetyl)pyrrolidin-3-yl)oxy)phenyl)-1,3,5-triazin-2-yl)amino)benzamide

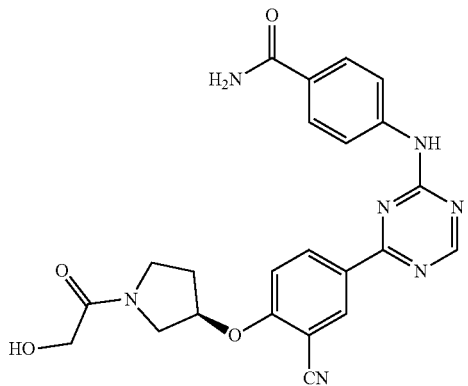 [SMILES: N#Cc1cc(-c2ncnc(Nc3ccc(C(N)=O)cc3)n2)ccc1O[C@@H]1CCN(C(=O)CO)C1]

The title compound was prepared following the similar procedure reported in Example-80 using 4-aminobenzamide instead of 4-Phenylmorpholine followed by glycolic acid coupling to (R)-4-((4-(3-cyano-4-(pyrrolidin-3-yloxy)phenyl)-1,3,5-triazin-2-yl)amino)benzamide as shown in Example-103. LCMS-ESI⁺ (m/z): [M+H]⁺ calcd for $C_{23}H_{21}N_7O_4$: 460.2; found:460.2 ¹H NMR (400 MHz, DMSO-d₆) δ 10.58 (s, 1H), 8.88 (s, 1H), 8.74 (dd, J=4.4, 1.4 Hz, 1H), 8.67-8.56 (m, 2H), 8.51 (dd, J=8.4, 1.4 Hz, 1H), 7.91-7.84 (m, 3H), 7.55-7.48 (m, 2H), 5.37 (d, J=32.3 Hz, 3H), 4.05-3.97 (m, 2H), 3.82-3.64 (m, 3H), 3.48-3.41 (m, 2H), 2.31-2.15 (m, 2H).

Example 86

(R)-2-((1-(2-hydroxyacetyl)pyrrolidin-3-yl)oxy)-5-(4-((4-(4-methylpiperazin-1-yl)phenyl)amino)-1,3,5-triazin-²-yl)benzonitrile

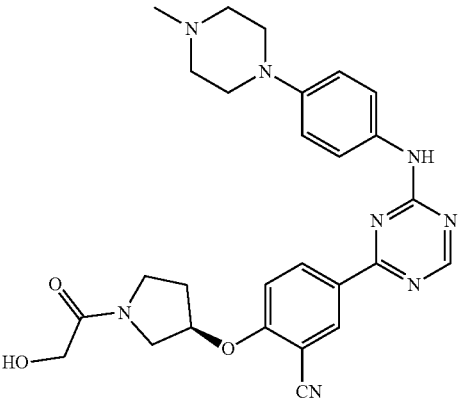 [SMILES: CN1CCN(c2ccc(Nc3ncnc(-c4ccc(O[C@@H]5CCN(C(=O)CO)C5)c(C#N)c4)n3)cc2)CC1]

The title compound was prepared following the similar procedure reported in Example-80 using 4-(4-methylpiperazin-1-yl)aniline instead of 4-Phenylmorpholine followed by glycolic acid coupling to (R)-5-(4-((4-(4-methylpiperazin-1-yl)phenyl)amino)-1,3,5-triazin-2-yl)-2-(pyrrolidin-3-yloxy)benzonitrile as shown in Example 103. LCMS-ESI⁺ (m/z): [M+H]⁺ calcd for $C_{23}H_{21}N_7O_4$: 515.2; found: 515.4
¹H NMR (400 MHz, Acetonitrile-d₃) δ 9.96 (s, 1H), 8.73 (s, 1H), 8.54-8.45 (m, 2H), 7.82-7.51 (m, 3H), 7.20 (s, 2H), 5.38 (d, J=33.1 Hz, 1H), 4.88-4.52 (m, 2H), 4.32-4.02 (m, 3H), 3.97-3.85 (m, 4H), 3.48-3.07 (m, 6H), 2.93 (s, 3H), 2.47-2.23 (m, 2H).

Example 87

2-Fluoro-5-(4-((4-(4-(oxetan-3-yl)piperazin-1-yl)phenyl)amino)-1,3,5-triazin-2-yl)benzonitrile

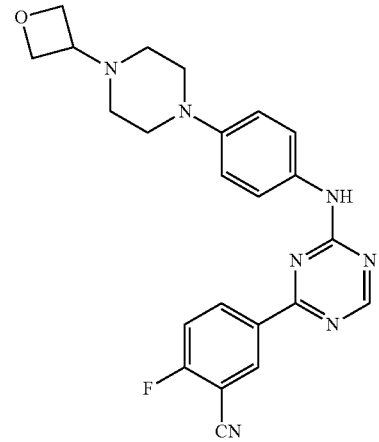 [SMILES: N#Cc1cc(-c2ncnc(Nc3ccc(N4CCN(C5COC5)CC4)cc3)n2)ccc1F]

To solution of 2,4-dichloro-1,3,5-triazine (2.5 g, 16.67 mmol) in DMF (100 mL) at 0° C. under nitrogen atmosphere was added solution of 4-(4-(oxetan-3-yl)piperazin-1-yl)aniline (3.5 g, 15.1 mmol) in DMF (120 mL) over 5 minutes. The reaction mixture was stirred at 0° C. for 1 h and the solvent concentrated to dryness under reduced pressure. The crude product was added 40% MeOH\DCM and sonicated for 2 minutes to bring solid particles in to the solution and left at RT for 5 minutes. The solid particles was filtered, washed with DCM twice and dried to afford creamy solid product. LCMS-ESI$^+$ (m/z): [M+H]$^+$ calcd for C$_{16}$H$_{19}$ClN$_6$O: 347.1 found:347.3.

A mixture of 4-chloro-N-(4-(4-(oxetan-3-yl)piperazin-1-yl)phenyl)-1,3,5-triazin-2-amine (1 g, 2.88 mmol), 2-fluoro-5-(4,4,5,5-tetramethyl-1,3,2-dioxaborolan-2-yl)benzonitrile (0.783 g, 3.17 mmol) and Pd(PPh$_3$)$_4$ (0.25 g, 0.21 mmol) was taken up in 1,2-DME (24 mL) in a 100 mL round bottom flask. To well stirred mixture was added solution of sodium carbonate (1.375 g 12.98 mmol) in water (12 mL). The mixture heated at 95° C. for 4 h. The reaction mixture was diluted with 30% MeOH/DCM (50 mL) and filtered through short pad of silica gel and washed twice with 30% MeOH/DCM. The filtrate was adsorbed on silica gel and solvent was concentrated under reduced pressure. The crude product was purified by flash column chromatography on silica gel to afford 2-fluoro-5-(4-((4-(4-(oxetan-3-yl)piperazin-1-yl)phenyl)amino)-1,3,5-triazin-2-yl)benzonitrile. LCMS-ESI$^+$ (m/z): [M+H]$^+$ calcd for C$_{23}$H$_{22}$FN$_7$O: 432.2; found:432.3 $^1$H NMR (400 MHz, DMSO-d$_6$) δ 10.20 (d, J=21.0 Hz, 1H), 8.77 (s, 1H), 8.65 (d, J=10.8 Hz, 2H), 7.72 (s, 1H), 7.64-7.43 (m, 2H), 6.96 (t, J=10.8 Hz, 2H), 4.55 (t, J=6.5 Hz, 2H), 4.46 (t, J=6.0 Hz, 2H), 3.47-3.40 (m, 1H), 3.13 (d, J=6.6 Hz, 4H), 2.46-2.32 (m, 4H).

Example 88

2-(((R)-1-((S)-2-hydroxypropanoyl)pyrrolidin-3-yl)oxy)-5-(4-((4-(4-(oxetan-3-yl)piperazin-1-yl)phenyl)amino)-1,3,5-triazin-2-yl)benzonitrile

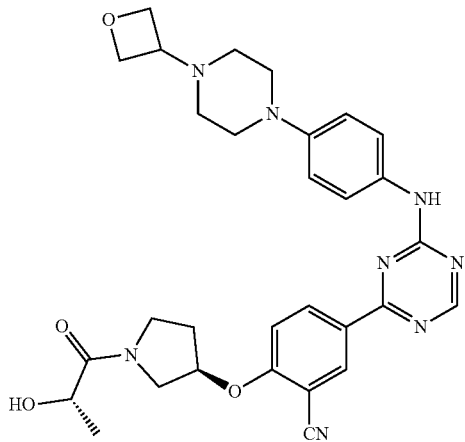 [SMILES: C[C@H](O)C(=O)N1CC[C@@H](Oc2ccc(-c3ncnc(Nc4ccc(N5CCN(C6COC6)CC5)cc4)n3)cc2C#N)C1]

Step 1: (R)-tert-butyl 3-hydroxypyrrolidine-1-carboxylate (430 mg, 2.29 mmol) was added Me-THF (20 mL) under argon atmosphere and cooled at 0° C. To well stirred solution was added potassium tert-butoxide at one portion and stirred for 30 minutes. To well stirred solution was added 2-fluoro-5-(4-((4-(4-(oxetan-3-yl)piperazin-1-yl)phenyl)amino)-1,3,5-triazin-2-yl)benzonitrile (900 mg, 2.09 mmol) and warmed to room temperature over 10 min. The reaction was heated at 60° C. overnight. The solvent was concentrated under reduced pressure. The crude product was purified by flash column chromatography on silica gel to afford (R)-tert-butyl 3-(2-cyano-4-(4-((4-(4-(oxetan-3-yl)piperazin-1-yl)phenyl)amino)-1,3,5-triazin-2-yl)phenoxy)pyrrolidine-1-carboxylate. LCMS-ESI$^+$ (m/z): [M+H]$^+$ calcd for C$_{32}$H$_{38}$FN$_8$O$_4$: 599.3; found: 599.2

Step 2: (R)-tert-butyl 3-(2-cyano-4-(4-((4-(4-(oxetan-3-yl)piperazin-1-yl)phenyl)amino)-1,3,5-triazin-2-yl)phenoxy)pyrrolidine-1-carboxylate (90 mg, 0.15 mmol) was dissolved in 20% TFA/DCM (5 mL) and stirred at room temperature for 1 h. The solvent was concentrated under reduced pressure to afford (R)-5-(4-((4-(4-(oxetan-3-yl)piperazin-1-yl)phenyl)amino)-1,3,5-triazin-2-yl)-2-(pyrrolidin-3-yloxy)benzonitrile. The dried residue was used for next step without purification. LCMS-ESI$^+$ (m/z): [M+H]$^+$ calcd for C$_{27}$H$_{30}$N$_8$O$_2$: 499.2; found: 499.3.

$^1$H NMR (400 MHz, DMSO-d$_6$) δ 10.30-10.01 (m, 1H), 9.13 (d, J=37.7 Hz, 1H), 8.75 (s, 1H), 8.64-8.55 (m, 2H), 7.75-7.39 (m, 3H), 7.03 (d, J=8.5 Hz, 2H), 5.52-5.28 (m, 1H), 4.73 (d, J=5.9 Hz, 4H), 4.39-4.36 (m, 1H) 4.00-3.53 (m, 7H), 3.27-2.91 (m, 5H), 2.44-1.81 (m, 2H).

Step 3: To solution of (R)-5-(4-((4-(4-(oxetan-3-yl)piperazin-1-yl)phenyl)amino)-1,3,5-triazin-2-yl)-2-(pyrrolidin-3-yloxy)benzonitrile (60 mg, 0.09 mmol), (S)-2-hydroxypropanoic acid (13 mg, 0.15 mmol), HATU (74 mg, 0.19 mmol) in DMF (3 mL) was added DIPEA (0.205 mL, 1.17 mmol) in a 10 mL microwave vial and sealed. This reaction mixture was stirred at room temperature overnight. The solvent was concentrated and the crude product purified via prep HPLC (5-95% acetonitrile in water, 0.1% trifluoroacetic acid buffer) to isolate 2-(((R)-1-((S)-2-hydroxypropanoyl)pyrrolidin-3-yl)oxy)-5-(4-((4-(4-(oxetan-3-yl)piperazin-1-yl)phenyl)amino)-1,3,5-triazin-2-yl)benzonitrile. LCMS-ESI$^+$ (m/z): [M+H]$^+$ calcd for C$_{30}$H$_{34}$N$_8$O$_4$: 571.2; found: 571.4 $^1$H NMR (400 MHz, DMSO-d$_6$) δ 10.17 (dd, J=23.9, 10.4 Hz, 1H), 8.75 (s, 1H), 8.66-8.42 (m, 2H), 7.62 (s, 2H), 7.51 (d, J=8.8 Hz, 1H), 7.04 (s, 2H), 5.36 (d, J=19.8 Hz, 1H), 4.77-4.75 (m, 5H), 4.42-4.20 (m, 4H), 3.98-3.76 (m, 4H), 3.73-3.36 (m, 6H), 2.31-2.12 (m, 2H), 1.17 (dd, J=12.3, 6.5 Hz, 3H).

Example 89

(R)-2-((1-(3-hydroxypropanoyl)pyrrolidin-3-yl)oxy)-5-(4-((4-(4-(oxetan-3-yl)piperazin-1-yl)phenyl)amino)-1,3,5-triazin-2-yl)benzonitrile

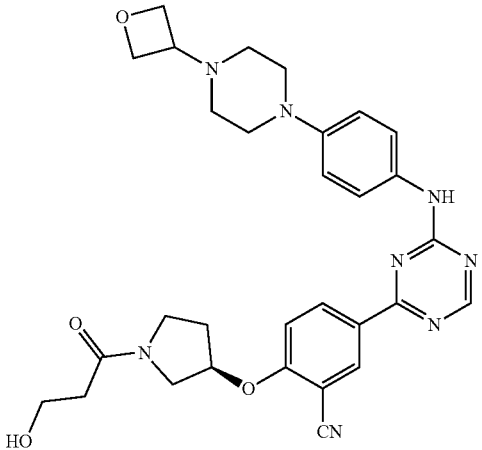 [SMILES: N#Cc1cc(-c2ncnc(Nc3ccc(N4CCN(C5COC5)CC4)cc3)n2)ccc1O[C@@H]1CCN(C(=O)CCO)C1]

The title compound was prepared following the same procedure reported in Example 88 by coupling 3-hydroxypropanoic acid to (R)-5-(4-((4-(4-(oxetan-3-yl)piperazin-1-yl)phenyl)amino)-1,3,5-triazin-2-yl)-2-(pyrrolidin-3-yloxy)benzonitrile instead of (S)-2-hydroxypropanoic acid.

LCMS-ESI⁺ (m/z): [M+H]⁺ calcd for $C_{30}H_{34}N_8O_4$: 571.2 found: 571.4.

¹H NMR (400 MHz, DMSO-d₆) δ 10.13 (d, J=19.5 Hz, 1H), 8.73 (s, 1H), 8.63-8.46 (m, 2H), 7.68-7.41 (m, 3H), 6.97 (s, 2H), 5.34 (d, J=27.8 Hz, 1H), 4.59-4.50 (m, 4H), 3.70-3.60 (m, 2H), 3.59-3.56 (m, 8H), 3.15-3.09 (m, 7H), 2.37-2.12 (m, 4H).

Example 90

(R)-2-((1-(2-cyanoacetyl)pyrrolidin-3-yl)oxy)-5-(4-((4-(4-(oxetan-3-yl)piperazin-1-yl)phenyl)amino)-1,3,5-triazin-2-yl)benzonitrile

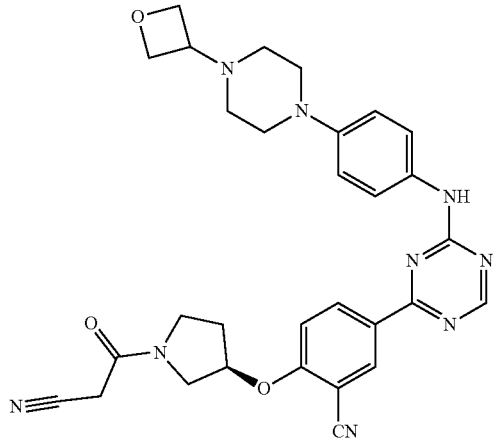 [SMILES: N#CCC(=O)N1CC[C@@H](Oc2ccc(-c3ncnc(Nc4ccc(N5CCN(C6COC6)CC5)cc4)n3)cc2C#N)C1]

The title compound was prepared following the same procedure reported in Example 88 by coupling 2-cyanoacetic acid to (R)-5-(4-((4-(4-(oxetan-3-yl)piperazin-1-yl)phenyl)amino)-1,3,5-triazin-2-yl)-2-(pyrrolidin-3-yloxy)benzonitrile instead of (S)-2-hydroxypropanoic acid.

LCMS-ESI⁺ (m/z): [M+H]⁺ calcd for $C_{30}H_{31}N_9O_3$: 566.2 found: 566.3.

¹H NMR (400 MHz, DMSO-d₆) δ 10.12 (d, J=21.2 Hz, 1H), 8.73 (s, 1H), 8.65-8.46 (m, 2H), 7.70-7.38 (m, 3H), 6.96 (s, 2H), 5.42-5.36 (m, 1H), 4.57-4.49 (m, 4H), 4.00 (d, J=10.1 Hz, 1H), 3.96-3.76 (m, 1H), 3.68-3.57 (m, 6H), 3.45-3.40 (m, 1H), 3.15-3.09 (m, 6H), 2.31-2.08 (m, 2H).

Example 91

2-(((R)-1-((R)-2-hydroxypropanoyl)pyrrolidin-3-yl)oxy)-5-(4-((4-(4-(oxetan-3-yl)piperazin-1-yl)phenyl)amino)-1,3,5-triazin-2-yl)benzonitrile

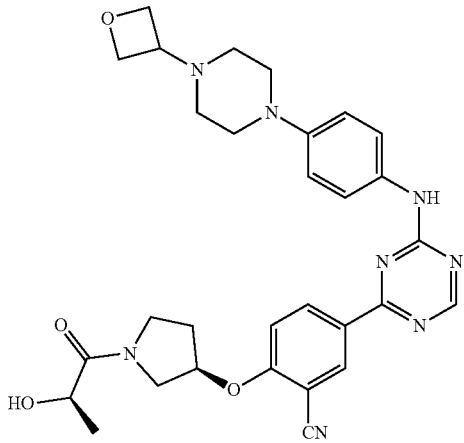 [SMILES: C[C@@H](O)C(=O)N1CC[C@@H](Oc2ccc(-c3ncnc(Nc4ccc(N5CCN(C6COC6)CC5)cc4)n3)cc2C#N)C1]

The title compound was prepared following the same procedure reported in Example 88 by coupling (R)-2-hydroxypropanoic acid to (R)-5-(4-((4-(4-(oxetan-3-yl)piperazin-1-yl)phenyl)amino)-1,3,5-triazin-2-yl)-2-(pyrrolidin-3-yloxy)benzonitrile instead of (S)-2-hydroxypropanoic acid.

LCMS-ESI⁺ (m/z): [M+H]⁺ calcd for $C_{30}H_{34}N_8O_4$: 571.2; found: 571.4.

¹H NMR (400 MHz, DMSO-d₆) δ 10.12 (d, J=20.3 Hz, 1H), 8.73 (s, 1H), 8.57 (d, J=7.8 Hz, 1H), 8.36 (s, 1H), 7.68-7.41 (m, 3H), 6.97 (d, J=10.5 Hz, 2H), 5.34 (d, J=30.1 Hz, 1H), 4.93 (d, J=28.9 Hz, 1H), 4.67-4.38 (m, 3H), 4.36-4.10 (m, 2H), 4.02-3.65 (m, 1H), 3.67-3.60 (m, 4H), 3.52-3.34 (m, 2H), 3.15-3.09 (m, 6H), 2.35-2.05 (m, 2H), 1.21-1.10 (m, 3H).

Example 92

(R)-5-(4-((4-(4-(oxetan-3-yl)piperazin-1-yl)phenyl)amino)-1,3,5-triazin-2-yl)-2-((1-(oxetane-3-carbonyl)pyrrolidin-3-yl)oxy)benzonitrile

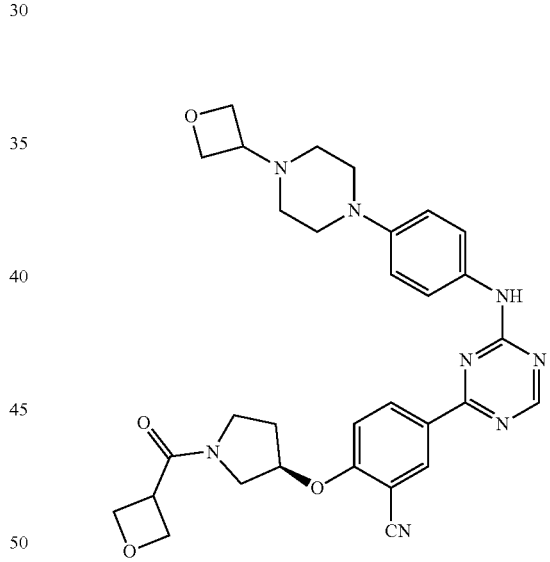

The title compound was prepared following the same procedure reported in Example 88 by coupling oxetane-3-carboxylic acid to (R)-5-(4-((4-(4-(oxetan-3-yl)piperazin-1-yl)phenyl)amino)-1,3,5-triazin-2-yl)-2-(pyrrolidin-3-yloxy)benzonitrile instead of (S)-2-hydroxypropanoic acid.

LCMS-ESI⁺ (m/z): [M+H]⁺ calcd for $C_{31}H_{34}N_8O_4$: 583.3 found: 583.3.

¹H NMR (400 MHz, DMSO-d₆) δ 10.19 (s, 1H), 8.75 (s, 1H), 8.59-8.57 (m, 2H), 7.75-7.43 (m, 3H), 7.04 (s, 2H), 5.33-5.30 (m, 1H), 4.91-4.56 (m, 8H), 4.10-3.81 (m, 4H), 3.65-3.47 (m, 5H), 3.21-2.91 (m, 4H), 2.35-2.31 (m, 4H).

Example 93

(R)-5-(4-((4-(4-(oxetan-3-yl)piperazin-1-yl)phenyl)amino)-1,3,5-triazin-2-yl)-2-(pyrrolidin-3-yloxy)benzonitrile

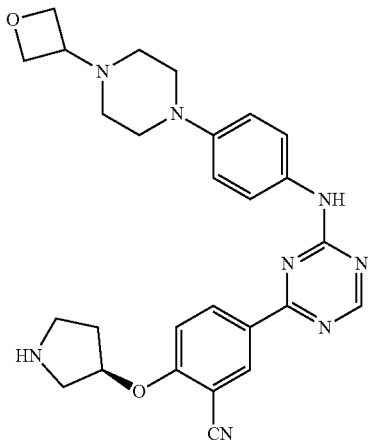 [SMILES: N#Cc1cc(-c2ncnc(Nc3ccc(N4CCN(C5COC5)CC4)cc3)n2)ccc1O[C@@H]1CCNC1]

Step 1: (R)-tert-butyl 3-hydroxypyrrolidine-1-carboxylate (430 mg, 2.29 mmol) was added Me-THF (20 mL) under argon atmosphere and cooled at 0° C. To well stirred solution was added potassium tert-butoxide at one portion and stirred for 30 minutes. To well stirred solution was added 2-fluoro-5-(4-((4-(4-(oxetan-3-yl)piperazin-1-yl)phenyl)amino)-1,3,5-triazin-2-yl)benzonitrile (900 mg, 2.09 mmol) and warmed to room temperature over 10 min. The reaction was heated at 60° C. overnight. The solvent was concentrated under reduced pressure. The crude product was purified by flash column chromatography on silica gel to afford (R)-tert-butyl 3-(2-cyano-4-(4-((4-(4-(oxetan-3-yl)piperazin-1-yl)phenyl)amino)-1,3,5-triazin-2-yl)phenoxy)pyrrolidine-1-carboxylate. LCMS-ESI$^+$ (m/z): [M+H]$^+$ calcd for $C_{37}H_{38}FN_8O_4$: 599.3; found: 599.2

Step 2: (R)-tert-butyl 3-(2-cyano-4-(4-((4-(4-(oxetan-3-yl)piperazin-1-yl)phenyl)amino)-1,3,5-triazin-2-yl)phenoxy)pyrrolidine-1-carboxylate (90 mg, 0.15 mmol) was dissolved in 20% TFA/DCM (5 mL) and stirred at room temperature for 1 h. The solvent was concentrated under reduced pressure to afford (R)-5-(4-((4-(4-(oxetan-3-yl)piperazin-1-yl)phenyl)amino)-1,3,5-triazin-2-yl)-2-(pyrrolidin-3-yloxy)benzonitrile. The dried residue was used for next step without purification. LCMS-ESI$^+$ (m/z): [M+H]$^+$ calcd for $C_{27}H_{30}N_8O_2$: 499.2; found: 499.3.

$^1$H NMR (400 MHz, DMSO-d$_6$) δ 10.30-10.01 (m, 1H), 9.13 (d, J=37.7 Hz, 1H), 8.75 (s, 1H), 8.64-8.55 (m, 2H), 7.75-7.39 (m, 3H), 7.03 (d, J=8.5 Hz, 2H), 5.52-5.28 (m, 1H), 4.73 (d, J=5.9 Hz, 4H), 4.39-4.36 (m, 1H) 4.00-3.53 (m, 7H), 3.27-2.91 (m, 5H), 2.44-1.81 (m, 2H).

Example 94

(R)-2-((1-(1-hydroxycyclopropanecarbonyl)pyrrolidin-3-yl)oxy)-5-(4-((4-(4-(oxetan-3-yl)piperazin-1-yl)phenyl)amino)-1,3,5-triazin-2-yl)benzonitrile

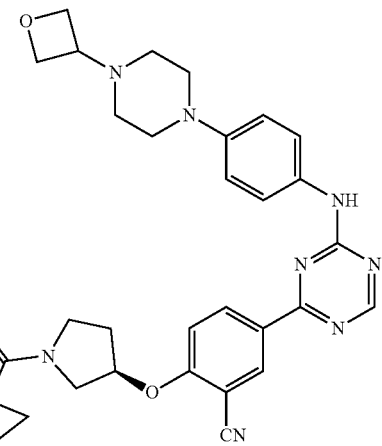

The title compound was prepared following the same procedure reported in Example 88 by coupling 1-hydroxycyclopropanecarboxylic acid to (R)-5-(4-((4-(4-(oxetan-3-yl)piperazin-1-yl)phenyl)amino)-1,3,5-triazin-2-yl)-2-(pyrrolidin-3-yloxy)benzonitrile instead of (S)-2-hydroxypropanoic acid.

LCMS-ESI$^+$ (m/z): [M+H]$^+$ calcd for $C_{31}H_{34}N_8O_4$: 583.2 found: 583.5.

$^1$H NMR (400 MHz, DMSO-d$_6$) δ 10.17 (d, J=18.3 Hz, 1H), 8.75 (s, 1H), 8.68-8.44 (m, 2H), 7.62 (s, 2H), 7.52 (d, J=8.5 Hz, 1H), 7.05 (s, 2H), 6.16 (s, 1H), 5.34 (d, J=32.5 Hz, 2H), 4.75 (d, J=6.2 Hz, 4H), 4.41 (br s, 2H), 4.27-3.81 (m, 5H), 3.21-2.98 (m, 5H), 2.43-1.97 (m, 2H), 1.17-0.64 (m, 4H).

Example 95

(R)-2-((1-formylpyrrolidin-3-yl)oxy)-5-(4-((4-(4-(oxetan-3-yl)piperazin-1-yl)phenyl)amino)-1,3,5-triazin-2-yl)benzonitrile

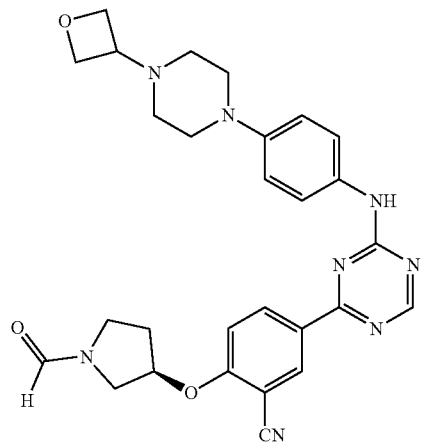 [SMILES: N#Cc1cc(-c2ncnc(Nc3ccc(N4CCN(C5COC5)CC4)cc3)n2)ccc1O[C@@H]1CCN(C=O)C1]

The title compound was prepared following the same procedure reported in Example 88 by coupling formic acid to (R)-5-(4-((4-(4-(oxetan-3-yl)piperazin-1-yl)phenyl)amino)-1,3,5-triazin-2-yl)-2-(pyrrolidin-3-yloxy)benzonitrile instead of (S)-2-hydroxypropanoic acid. LCMS-ESI$^+$ (m/z): [M+H]$^+$ calcd for $C_{28}H_{30}N_8O_3$: 527.2 found: 527.4 $^1$H NMR (400 MHz, DMSO-d$_6$) δ 10.17 (d, J=20.0 Hz, 1H), 8.75 (s, 1H), 8.65-8.43 (m, 2H), 8.21 (d, J=19.5 Hz, 1H), 7.72-7.42 (m, 3H), 7.04 (s, 2H), 5.37-5.33 (m, 1H), 4.75-4.72 (m, 4H), 4.50-4.29 (m, 1H), 3.81-3.48 (m, 7H), 3.16-2.85 (m, 5H), 2.31-2.13 (m, 2H).

Example 96

(R)-2-((1-(2,2-difluoroacetyl)pyrrolidin-3-yl)oxy)-5-(4-((4-(4-(oxetan-3-yl)piperazin-1-yl)phenyl)amino)-1,3,5-triazin-2-yl)benzonitrile

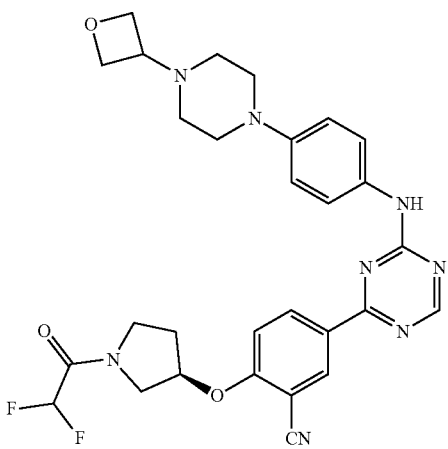 [SMILES: N#Cc1cc(-c2ncnc(Nc3ccc(N4CCN(C5COC5)CC4)cc3)n2)ccc1O[C@@H]1CCN(C(=O)C(F)F)C1]

The title compound was prepared following the same procedure reported in Example 88 by coupling 2,2-difluoroacetic acid to (R)-5-(4-((4-(4-(oxetan-3-yl)piperazin-1-yl)phenyl)amino)-1,3,5-triazin-2-yl)-2-(pyrrolidin-3-yloxy)benzonitrile instead of (S)-2-hydroxypropanoic acid.

LCMS-ESI$^+$ (m/z): [M+H]$^+$ calcd for $C_{29}H_{30}N_8O_5$: 577.2 found: 577.4 $^1$H NMR (400 MHz, DMSO-d$_6$) δ 10.18 (d, J=19.9 Hz, 1H), 8.75 (s, 1H), 8.70-8.45 (m, 2H), 7.76-7.46 (m, 3H), 7.03 (d, J=9.5 Hz, 2H), 6.57 (td, J=52.9, 27.6 Hz, 1H), 5.41 (d, J=30.9 Hz, 1H), 4.75 (d, J=6.0 Hz, 4H), 4.39 (br s, 1H), 4.01-3.59 (m, 7H), 3.27-2.79 (m, 5H), 2.35-2.15 (m, 2H).

Example 97

2-((1-(2-hydroxyacetyl)azepan-4-yl)oxy)-5-(4-((4-(4-(oxetan-3-yl)piperazin-1-yl)phenyl)amino)-1,3,5-triazin-2-yl)benzonitrile

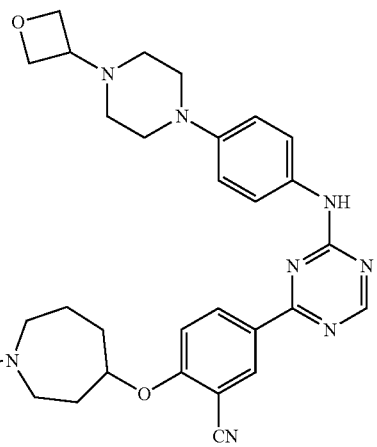

The title compound was prepared by substituting intermediate 2-fluoro-5-(4-((4-(4-(oxetan-3-yl)piperazin-1-yl)phenyl)amino)-1,3,5-triazin-2-yl)benzonitrile (Example 87) with tert-butyl 4-hydroxyazepane-1-carboxylate, followed by Boc-deprotection and coupling with glycolic acid as shown in Example-88 LCMS-ESI$^+$ (m/z): [M+H]$^+$ calcd for $C_{31}H_{36}N_8O_4$: 585.3; found: 585.2.
$^1$H NMR (400 MHz, DMSO-d$_6$) δ 10.13 (d, J=18.1 Hz, 1H), 8.72 (s, 1H), 8.63-8.45 (m, 2H), 7.70-7.36 (m, 3H), 6.99 (s, 2H), 4.90 (s, 1H), 4.65-4.61 (m, 2H), 4.17-3.95 (m, 2H), 3.64-3.41 (m, 8H), 3.22-3.09 (m, 8H), 2.19-1.42 (m, 6H).

Example 98

2-((4,4-difluoro-1-(2-hydroxyacetyl)pyrrolidin-3-yl)oxy)-5-(4-((4-(4-(oxetan-3-yl)piperazin-1-yl)phenyl)amino)-1,3,5-triazin-2-yl)benzonitrile

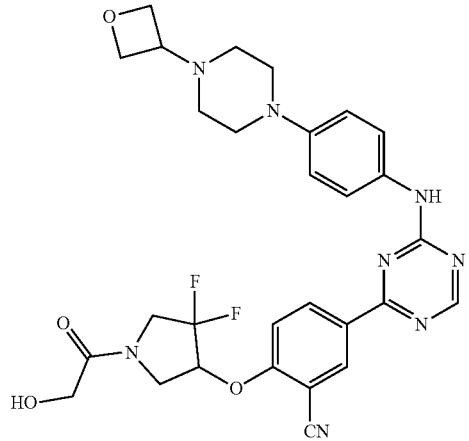 [SMILES: N#Cc1cc(-c2ncnc(Nc3ccc(N4CCN(C5COC5)CC4)cc3)n2)ccc1OC1CN(C(=O)CO)CC1(F)F]

The title compound was prepared by substituting intermediate 2-fluoro-5-(4-((4-(4-(oxetan-3-yl)piperazin-1-yl)phenyl)amino)-1,3,5-triazin-2-yl)benzonitrile (Example 87) with tert-butyl 3,3-difluoro-4-hydroxypyrrolidine-1-carboxylate, followed by Boc-deprotection and coupling with glycolic acid as shown in Example-88 LCMS-ESI⁺ (m/z): [M+H]⁺ calcd for $C_{29}H_{30}F_2N_8O_4$: 593.2; found:593.3 ¹H NMR (400 MHz, DMSO-d₆) δ 10.15 (d, J=23.3 Hz, 1H), 8.74 (s, 1H), 8.68-8.47 (m, 2H), 7.71-7.44 (m, 3H), 6.97 (d, J=11.3 Hz, 2H), 5.60 (d, J=34.2 Hz, 1H), 4.96 (d, J=23.5 Hz, 1H), 4.57-4.48 (m, 4H), 4.18-4.07 (m, 5H), 3.90-3.53 (m, 4H), 3.16-3.09 (m, 5H), 2.42 (br s, 1H).

Example 99

2-(((3R,5R)-1-(2-hydroxyacetyl)-5-methylpyrrolidin-3-yl)oxy)-5-(4-((4-(4-(oxetan-3-yl)piperazin-1-yl)phenyl)amino)-1,3,5-triazin-2-yl)benzonitrile

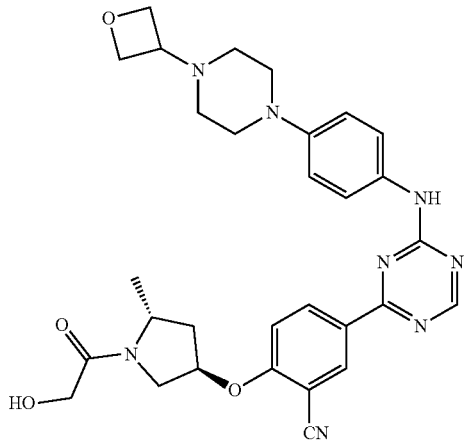 [SMILES: C[C@@H]1C[C@@H](Oc2ccc(-c3ncnc(Nc4ccc(N5CCN(C6COC6)CC5)cc4)n3)cc2C#N)CN1C(=O)CO]

The title compound was prepared by substituting intermediate 2-fluoro-5-(4-((4-(4-(oxetan-3-yl)piperazin-1-yl)phenyl)amino)-1,3,5-triazin-2-yl)benzonitrile (Example 87) with (2R,4R)-tert-butyl 4-hydroxy-2-methylpyrrolidine-1-carboxylate, followed by Boc-deprotection and coupling with glycolic acid as shown in Example-88. LCMS-ESI⁺ (m/z): [M+H]⁺ calcd for $C_{30}H_{34}N_8O_4$: 571.2; found: 571.3 ¹H NMR (400 MHz, DMSO-d₆) δ 10.13 (d, J=19.9 Hz, 1H), 8.73 (s, 1H), 8.65-8.46 (m, 2H), 7.72-7.39 (m, 2H), 6.99 (d, J=10.2 Hz, 2H), 5.34 (s, 1H), 4.77-4.36 (m, 4H), 4.19-4.14 (m, 2H), 4.07-3.74 (m, 4H), 3.69-3.56 (m, 5H), 3.30-3.02 (m, 4H), 2.47-2.31 (m, 3H), 2.19-1.94 (m, 2H).

Example 100

2-(((3R,5S)-1-(2-hydroxyacetyl)-5-methylpyrrolidin-3-yl)oxy)-5-(4-((4-(4-(oxetan-3-yl)piperazin-1-yl)phenyl)amino)-1,3,5-triazin-2-yl)benzonitrile

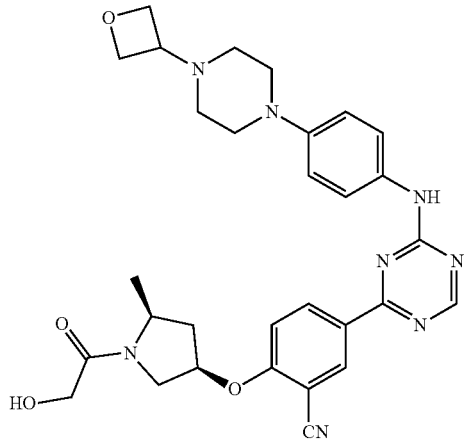 [SMILES: C[C@H]1C[C@@H](Oc2ccc(-c3ncnc(Nc4ccc(N5CCN(C6COC6)CC5)cc4)n3)cc2C#N)CN1C(=O)CO]

The title compound was prepared by substituting intermediate 2-fluoro-5-(4-((4-(4-(oxetan-3-yl)piperazin-1-yl)phenyl)amino)-1,3,5-triazin-2-yl)benzonitrile (Example 87) with (2S,4R)-tert-butyl 4-hydroxy-2-methylpyrrolidine-1-carboxylate, followed by Boc-deprotection and coupling with glycolic acid as shown in Example-88. LCMS-ESI⁺ (m/z): [M+H]⁺ calcd for $C_{30}H_{34}N_8O_4$: 571.2; found: 571.3 ¹H NMR (400 MHz, DMSO-d₆) δ 10.12 (d, J=20.8 Hz, 1H), 8.73 (s, 1H), 8.65-8.43 (m, 2H), 7.69-7.40 (m, 3H), 6.97 (brs, 2H), 5.34 (s, 1H), 4.70-4.52 (m, 4H), 4.19-4.17 (m, 1H), 3.94-3.81 (m, 3H), 3.64-3.57 (m, 5H), 3.16-3.09 (m, 6H), 2.47-2.31 (m, 3H), 2.21-1.92 (m, 2H).

Example 101

2-(((3R,4S)-4-fluoro-1-(2-hydroxyacetyl)pyrrolidin-3-yl)oxy)-5-(4-((4-(4-(oxetan-3-yl)piperazin-1-yl)phenyl)amino)-1,3,5-triazin-2-yl)benzonitrile

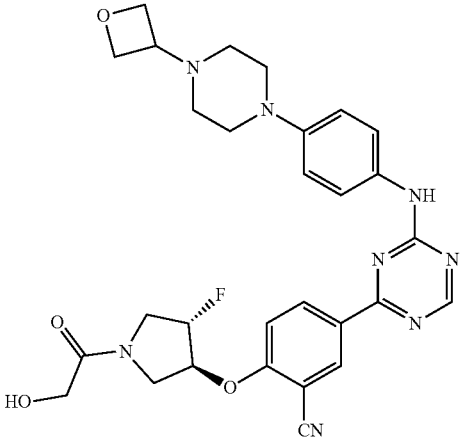 [SMILES: N#Cc1cc(-c2ncnc(Nc3ccc(N4CCN(C5COC5)CC4)cc3)n2)ccc1O[C@H]1CN(C(=O)CO)C[C@@H]1F]

The title compound was prepared by substituting intermediate 2-fluoro-5-(4-((4-(4-(oxetan-3-yl)piperazin-1-yl)phenyl)amino)-1,3,5-triazin-2-yl)benzonitrile (Example 87) with (3S,4S)-tert-butyl 3-fluoro-4-hydroxypyrrolidine-1-carboxylate, followed by Boc-deprotection and coupling with glycolic acid as shown in Example-88. LCMS-ESI⁺ (m/z): [M+H]⁺ calcd for $C_{29}H_{31}FN_8O_4$: 575.2; found: 575.4 ¹H NMR (400 MHz, DMSO-d₆) δ 10.20 (d, J=20.8 Hz, 1H), 8.76 (s, 1H), 8.68-8.34 (m, 2H), 7.63-7.61 (m, 3H), 7.07-7.02 (m, 2H), 5.77-5.26 (m, 3H), 4.81-4.46 (m, 4H), 4.44 (s, 2H), 4.22-3.67 (m, 8H), 3.66-3.60 (m, 2H), 3.40-3.25 (m, 2H).

Example 102

2-(((1R,4S,6S)-2-(2-hydroxyacetyl)-2-azabicyclo[2.2.1]heptan-6-yl)oxy)-5-(4-((4-(4-(oxetan-3-yl)piperazin-1-yl)phenyl)amino)-1,3,5-triazin-2-yl)benzonitrile

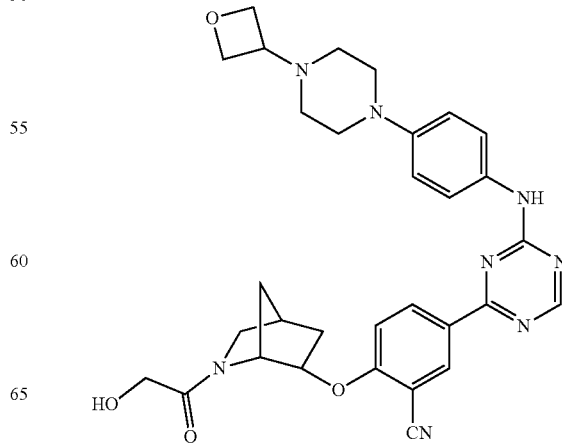

The title compound was prepared by substituting intermediate 2-fluoro-5-(4-((4-(4-(oxetan-3-yl)piperazin-1-yl)phenyl)amino)-1,3,5-triazin-2-yl)benzonitrile (Example 87) with (1R,4S,6S)-tert-butyl 6-hydroxy-2-azabicyclo[2.2.1]heptane-2-carboxylate, followed by Boc-deprotection and coupling with glycolic acid as shown in Example 88. LCMS-ESI$^+$ (m/z): [M+H]$^+$ calcd for $C_{31}H_{34}N_8O_4$: 583.2; found: 583.3 $^1$H NMR (400 MHz, DMSO-d$_6$) δ 10.17 (d, J=22.7 Hz, 1H), 8.74 (s, 1H), 8.56 (m, 2H), 7.61 (m, 3H), 7.05 (s, 2H), 4.97-4.64 (m, 4H), 4.64-4.35 (m, 3H), 4.12 (d, J=4.0 Hz, 1H), 4.04-3.91 (m, 3H), 3.38-3.16 (m, 4H), 3.07-2.85 (m, 2H), 2.69 (d, J=26.3 Hz, 2H), 2.21-1.98 (m, 1H), 1.86-1.48 (m, 4H).

Example 103

(R)-2-((1-(2-hydroxyacetyl)pyrrolidin-3-yl)oxy)-5-(4-((4-morpholinophenyl)amino)-1,3,5-triazin-2-yl)benzonitrile

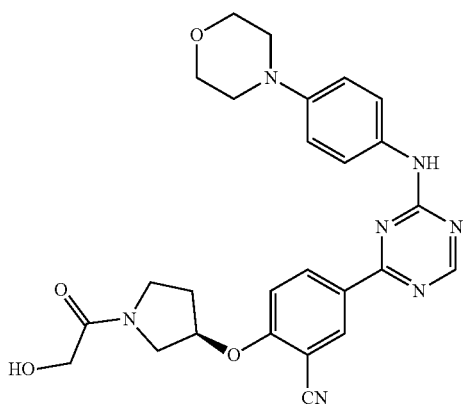 [SMILES: N#Cc1cc(-c2ncnc(Nc3ccc(N4CCOCC4)cc3)n2)ccc1O[C@@H]1CCN(C(=O)CO)C1]

To solution of (R)-5-(4-((4-morpholinophenyl)amino)-1,3,5-triazin-2-yl)-2-(pyrrolidin-3-yloxy)benzonitrile (100 mg, 0.23 mmol), glycolic acid (34 mg, 0.45 mmol), HATU (171 mg, 0.45 mmol) in dichloromethane (6 mL) was added DIPEA (0.471 mL, 2.7 mmol) in a 10 mL microwave vial and sealed. This reaction mixture was stirred at room temperature overnight. The solvent was concentrated and the crude product purified by flash column chromatography on silica gel to afford (R)-2-((1-(2-hydroxyacetyl)pyrrolidin-3-yl)oxy)-5-(4-((4-morpholinophenyl)amino)-1,3,5-triazin-2-yl)benzonitrile. LCMS-ESI$^+$ (m/z): [M+H]$^+$ calcd for $C_{26}H_{27}N_7O_4$: 502.2; found:502.3 $^1$H NMR (400 MHz, DMSO-d$_6$) δ 10.17 (s, 1H), 8.74 (s, 1H), 8.58-8.52 (m, 2H), 7.75-7.41 (m, 3H), 6.99 (br s, 2H), 5.47-5.25 (m, 1H), 4.87-4.75 (m, 1H), 4.14-3.91 (m, 2H), 3.88-3.55 (m, 7H), 3.55-3.33 (m, 1H), 3.10 (d, J=5.5 Hz, 4H), 2.37-2.06 (m, 2H).

Example 104

2-methoxy-5-(4-((4-(4-(oxetan-3-yl)piperazin-1-yl)phenyl)amino)-1,3,5-triazin-2-yl)benzonitrile

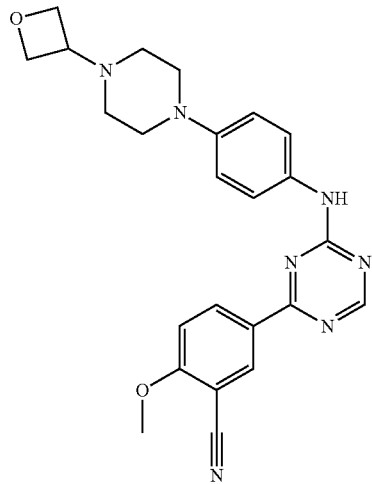 [SMILES: COc1ccc(-c2ncnc(Nc3ccc(N4CCN(C5COC5)CC4)cc3)n2)cc1C#N]

To an appropriate sized microwave vial, 4-chloro-N-(4-(4-(oxetan-3-yl)piperazin-1-yl)phenyl)-1,3,5-triazin-2-amine (50 mgs, 0.144 mmol), 2-methoxy-5-(4,4,5,5-tetramethyl-1,3,2-dioxaborolan-2-yl)benzonitrile (41 mgs, 0.159 mmol), and sodium carbonate (69 mgs, 0.66 mmol), 1,4-dioxane and water were added. The mixture was degassed with nitrogen for 10 minutes. Tetrakis(triphenylphosphine)palladium (0) (8 mgs) was added and the solution was heated at 95° C. for 2 h. After cooling to room temperature, the mixture was poured into water, and extracted with dichloromethane. The combined organic layers were washed with brine, dried with magnesium sulfate, filtered and concentrated under reduced pressure. Solids were purified via preparative HPLC (10-95% acetonitrile in water, 0.1% trifluoroacteic acid buffer) to yield the compound 2-methoxy-5-(4-((4-(4-(oxetan-3-yl)piperazin-1-yl)phenyl)amino)-1,3,5-triazin-2-yl)benzonitrile. $^1$H NMR (400 MHz, DMSO-d6) δ 10.18 (d, J=20 Hz, 1H), 8.74 (s, 1H), 8.66-8.45 (m, 2H), 7.68-7.55 (m, 2H), 7.48-7.4 (m, 1H), 7.12-7.00 (m, 2H), 4.76 (d, J=6.4 Hz, 4H), 4.48-4.38 (m, 1H), 4.01 (s, 3H), 3.82-2.85 (m, 8H). LCMS-ESI$^+$ (m/z): [M+H]$^+$ calcd for $C_{24}H_{25}N_7O_2$: 444.2; found: 444.2

Example 105

3-methoxy-5-(4-((4-(4-(oxetan-3-yl)piperazin-1-yl)phenyl)amino)-1,3,5-triazin-2-yl)benzonitrile

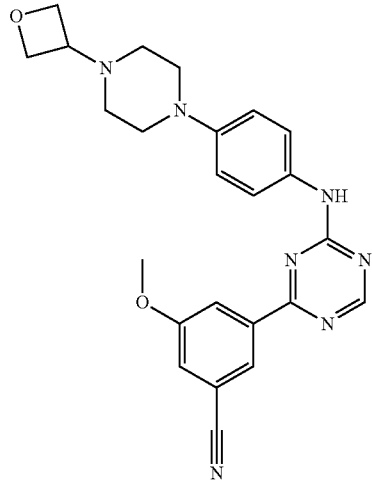 [SMILES: COc1cc(C#N)cc(-c2ncnc(Nc3ccc(N4CCN(C5COC5)CC4)cc3)n2)c1]

To an appropriate sized microwave vial, 4-chloro-N-(4-(4-(oxetan-3-yl)piperazin-1-yl)phenyl)-1,3,5-triazin-2-amine (50 mgs, 0.144mmol), 3-methoxy-5-(4,4,5,5-tetramethyl-1,3,2-dioxborolan-2-yl)benzonitrile (41 mgs, 0.159 mmol), and sodium carbonate (69 mgs, 0.66 mmol), 1,4-dioxane and water were added. The mixture was degassed with nitrogen for 10 minutes. Tetrakis(triphenylphosphine)palladium (0) (8 mgs) was added and the solution was heated at 95° C. for 2h. After cooling to room temperature, the mixture was poured into water, and extracted with dichloromethane. The combined organic layers were washed with brine, dried with magnesium sulfate, filtered and concentrated under reduced pressure. Solids were purified via preparative HPLC (10-95% acetonitrile in water, 0.1% trifluoroacteic acid buffer) to yield the compound 3-methoxy-5-(4-(4-((4-(oxetan-3-yl)piperazin-1-yl)phenyl)amino)-1,3,5-triazin-2-yl)benzonitrile. $^1$H NMR (400 MHz, DMSO-d6) δ 10.22 (d, J =21.8 Hz, 1H), 8.75 (s, 1H), 8.26-8.01 (m, 2H), 7.66 (dd, J=2.7, 1.4 Hz, 1H), 7.62-7.53 (m, 2H), 7.05-6.95 (m, 2H), 4.70 (d, J=6.9 Hz, 4H), 4.49-4.28 (m, 1H), 3.85 (s, 3H), 3.80-2.85 (m, 8H). LCMS-ESI$^+$ (m/z): [M+H]$^+$ calcd for $C_{24}H_{25}N_7O_2$: 444.2; found: 444.1

Example 106

5-(4-((4-((1H-imidazol-1-yl)methyl)phenyl)amino)-1,3,5-triazin-2-yl)-2-((tetrahydro-2H-pyran-4-yl)oxy)benzonitrile

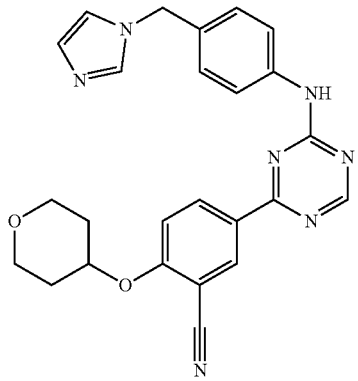 [SMILES: N#Cc1cc(-c2ncnc(Nc3ccc(Cn4ccnc4)cc3)n2)ccc1OC1CCOCC1]

To an appropriate sized microwave vial, 5-(4-chloro-1,3,5-triazin-2-yl)-2-((tetrahydro-2H-pyran-4-yl)oxy)benzonitrile (50 mg, 0.158 mmol) and 4-((1H-imidazol-1-yl)methyl)aniline (33 mg, 0.189 mmol) were dissolved in acetonitrile (1.5 ml) and N,N-dimethylformamide (1.5 ml) and stirred at room temperature for 24 hr. The mixture was purified via preparative HPLC (10-95% acetonitrile in water, 0.1% trifluoroacteic acid buffer). Clean fractions poured into a saturated solution of sodium bicarbonate in water and extracted with dichloromethane. Organic layer was dried over $Mg_2SO_4$ and evaporate under reduces pressure to yield 5-(4-((4-((1H-imidazol-1-yl)methyl)phenyl)amino)-1,3,5-triazin-2-yl)-2-((tetrahydro-2H-pyran-4-yl)oxy)benzonitrile. $^1$H NMR (400 MHz, DMSO-d6) δ 10.37 (s, 1H), 8.80 (s, 1H), 8.62-8.50 (m, 2H), 7.82-7.68 (m, 3H), 7.56 (d, J=9.6 Hz, 1H), 7.27 (d, J=8.2 Hz, 2H), 7.17 (s, 1H), 6.88 (s, 1H), 5.15 (s, 2H), 4.97-4.9 (m, 1H), 3.91-3.83 (m, 2H), 3.61-3.50 (m, 2H), 2.08-1.96 (m, 2H), 1.74-1.62 (m, 2H). LCMS-ESI$^+$ (m/z): [M+H]$^+$ calcd for $C_{25}H_{23}N_7O_2$: 454.19; found: 454.1.

Example 107

(R)-5-(4-((4-(2-(hydroxymethyl)morpholino)phenyl)amino)-1,3,5-triazin-2-yl)-2-((tetrahydro-2H-pyran-4-yl)oxy)benzonitrile

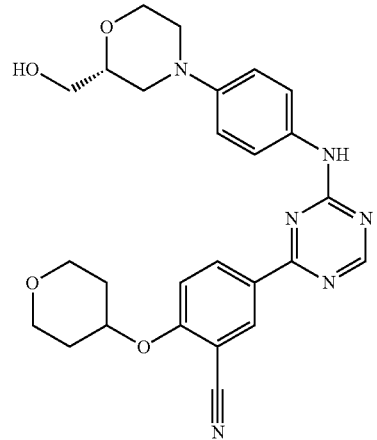 [SMILES: N#Cc1cc(-c2ncnc(Nc3ccc(N4CCO[C@@H](CO)C4)cc3)n2)ccc1OC1CCOCC1]

To an appropriate sized microwave vial, 5-(4-chloro-1,3,5-triazin-2-yl)-2-((tetrahydro-2H-pyran-4-yl)oxy)benzonitrile (50 mg, 0.158 mmol), (R)-(4-(4-aminophenyl)morpholin-2-yl)methanol (39 mg, 0.189 mmol) and N-ethyl-N-isopropylpropan-2-amine (0.137 ml, 0.789 mmol) were dissolved in acetonitrile (3 mL) and heated at 80° C. for 20 min. After cooling to room temperature, solids were collected by filtration. Solids were suspended and stirred with acetonitrile for 1 hr and then filtered off to yield the residue (R)-5-(4-((4-(2-(hydroxymethyl)morpholino)phenyl)amino)-1,3,5-triazin-2-yl)-2-((tetrahydro-2H-pyran-4-yl)oxy)benzonitrile. $^1$H NMR (400 MHz, DMSO-d6) δ 10.22-9.97 (m, 1H), 8.72 (s, 1H), 8.54 (q, J=8.2 Hz, 2H), 7.63-7.51 (m, 3H), 7.0-6.89 (m, 2H), 4.94-4.88 (m, 1H), 4.75 (d, J=5.9 Hz, 1H), 3.99-3.89 (m, 1H), 3.88-3.81 (m, 2H), 3.69-3.35 (m, 10H), 2.05-1.97 (m, 2H), 1.71-1.62 (m, 2H). LCMS-ESI$^+$ (m/z): [M+H]$^+$ calcd for $C_{26}H_{28}N_6O_4$: 489.22; found: 489.1.

Example 108

5-(4-((4-(3-hydroxy-3-methylpyrrolidin-1-yl)phenyl)amino)-1,3,5-triazin-2-yl)-2-((tetrahydro-2H-pyran-4-yl)oxy)benzonitrile

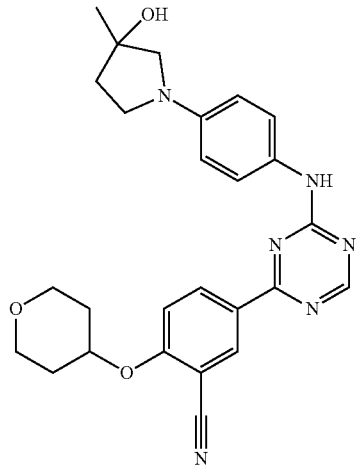 [SMILES: CC1(O)CCN(c2ccc(Nc3ncnc(-c4ccc(OC5CCOCC5)c(C#N)c4)n3)cc2)C1]

To an appropriate sized microwave vial, 5-(4-chloro-1,3,5-triazin-2-yl)-2-((tetrahydro-2H-pyran-4-yl)oxy)benzonitrile (50 mg, 0.158 mmol), 1-(4-aminophenyl)-3-methylpyrrolidin-3-ol (36 mg, 0.189 mmol) and N-ethyl-N-isopropylpropan-2-amine (0.137 ml, 0.789 mmol) were dissolved in acetonitrile (3 mL) and heated at 80° C. for 20 min. After cooling to room temperature, solids were collected by filtration. The residue was purified via preparative HPLC (10-95% acetonitrile in water, 0.1% trifluoroacteic acid buffer). Clean fractions poured into a saturated solution of sodium bicarbonate in water and extracted with dichloromethane. Organic layer was dried over Mg$_2$SO$_4$ and evaporate under reduces pressure to yield 5-(4-((4-(3-hydroxy-3-methylpyrrolidin-1-yl)phenyl)amino)-1,3,5-triazin-2-yl)-2-((tetrahydro-2H-pyran-4-yl)oxy)benzonitrile. $^1$H NMR (400 MHz, DMSO-d6) δ 10.1-9.92 (m, 1H), 8.66 (s, 1H), 8.58-8.47 (m, 2H), 7.53 (d, J=9.0 Hz, 1H), 7.5-7.4 (m, 2H), 6.4-6.52 (m, 2H), 4.92-4.88 (m, 1H), 4.76 (s, 1H), 3.89-3.83 (m, 2H), 3.57-3.47 (m, 2H), 3.39-3.22 (m, 2H), 3.22-3.14 (m, 2H), 2.11-1.98 (m, 2H), 1.9-1.85 (m, 2H), 1.72-1.62 (m, 2H), 1.34 (s, 3H). LCMS-ESI$^+$ (m/z): [M+H]$^+$ calcd for C$_{26}$H$_{28}$N$_6$O$_3$: 473.2; found: 473.2.

Example 109

5-(4-((2-methyl-4-morpholinophenyl)amino)-1,3,5-triazin-2-yl)-2-((tetrahydro-2H-pyran-4-yl)oxy)benzonitrile

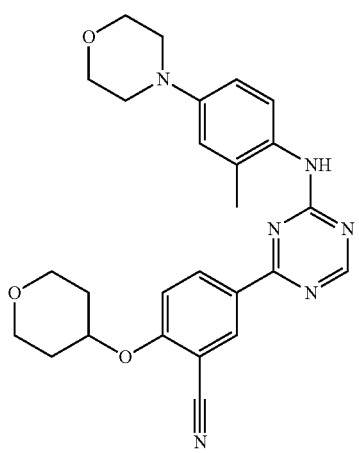 [SMILES: Cc1cc(N2CCOCC2)ccc1Nc1ncnc(-c2ccc(OC3CCOCC3)c(C#N)c2)n1]

To an 5 mL microwave vial, 5-(4-chloro-1,3,5-triazin-2-yl)-2-((tetrahydro-2H-pyran-4-yl)oxy)benzonitrile (53 mgs, 0.167 mmol), 2-methyl-4-morpholinoaniline (32 mgs, 0.167 mmol) and DIPEA (0.12 mL, 0.789 mmol) were dissolved in acetonitrile (2 mL) and heated in microwave at 80° C. for 20 min. The residue was purified via preparative HPLC (10-95% acetonitrile in water, 0.1% trifluoroacteic acid buffer). Clean fractions were then lyophilized to yield the title compound. LCMS-ESI$^+$ (m/z): [M+H]$^+$ calcd for C$_{26}$H$_{28}$N$_6$O$_3$: 473.2; found: 473.2 $^1$H NMR (400 MHz, DMSO-d$_6$) δ 9.59 (br, 1H), 8.67 (s, 1H), 8.57 (s, 1H), 8.34 (brs, 1H), 7.52 (m, 1H), 7.23 (m, 1H), 6.54 (m, 2H), 4.91 (m, 1H), 3.84 (m, 2H), 3.73-3.70 (m, 4H), 3.53 (m, 2H), 3.10 (m, 4H), 2.15 (s, 3H), 2.01 (m, 2H), 1.66 (m, 2H).

Example 110

2-(((3R,4S)-3-fluoro-1-(tetrahydrofuran-3-yl)piperidin-4-yl)oxy)-5-(4-((4-(4-(oxetan-3-yl)piperazin-1-yl)phenyl)amino)-1,3,5-triazin-2-yl)benzonitrile

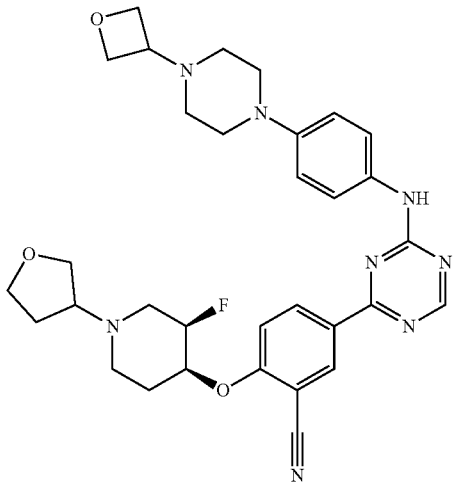 [SMILES: N#Cc1cc(-c2ncnc(Nc3ccc(N4CCN(C5COC5)CC4)cc3)n2)ccc1O[C@H]1CCN(C2CCOC2)C[C@H]1F]

A solution of 2-(((3R,4S)-3-fluoropiperidin-4-yl)oxy)-5-(4-((4-(4-(oxetan-3-yl)piperazin-1-yl)phenyl)amino)-1,3,5-triazin-2-yl)benzonitrile (100 mg, 0.188 mmol) and dihydrofuran-3(2H)-one (16 mg, 0.188 mmol) in 1 mL DCM was treated with and AcOH (14 mg, 0.226 mmol). After 5 min of stirring sodium triacetoxyborohydride (60 mg, 0.283 mmol) was added and the mixture stirred at rt overnight. The reaction was diluted with EtOAc and neutralized with sat. NaHCO$_3$ solution. The organic layer was concentrated and the residue purified HPLC eluting with 5%-95% water/acetonitrile (0.1% v/v trifluoroacetic acid). The appropriate fractions were ponied and lyophilized to provide 2-(((3R,4S)-3-fluoro-1-(tetrahydrofuran-3-yl)piperidin-4-yl)oxy)-5-(4-((4-(4-(oxetan-3-yl)piperazin-1-yl)phenyl)amino)-1,3,5-triazin-2-yl)benzonitrile as mixture of diastereorners. $^1$H NMR (400 MHz, DMSO) δ 10.11 (d, J=11 Hz, 1H), 8.72 (s, 1H), 8.54 (m, 2H), 7.56 (m, 3H), 6.95 (m, 2H), 4.95-5.03 (m, 2H), 4.55 (t, J=6 Hz, 2H), 4.45 (t, J=6 Hz, 2H), 3.70-3.82 (m, 2H), 3.35-3.65 (m, 7H), 3.14 (s, 4H), 3.05-3.11 (m, 1H), 2.40 (s, 4H), 1.94-2.03 (m, 2H), 1.80-1.89 (m, 1H), 1.70-1.80 (m, 1H). ES/MS 601.4 (M+H$^+$).

Example 111

2-(((3R,4S)-3-fluoro-1-(oxetan-3-yl)piperidin-4-yl)oxy)-5-(4-((4-(4-(oxetan-3-yl)piperazin-1-yl)phenyl)amino)-1,3,5-triazin-2-yl)benzonitrile

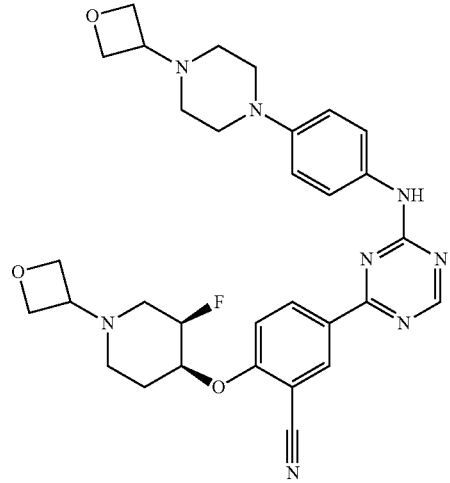 [SMILES: N#Cc1cc(-c2ncnc(Nc3ccc(N4CCN(C5COC5)CC4)cc3)n2)ccc1O[C@H]1CCN(C2COC2)C[C@H]1F]

A solution of 2-(((3R,4S)-3-fluoropiperidin-4-yl)oxy)-5-(4-((4-(4-(oxetan-3-yl)piperazin-1-yl)phenyl)amino)-1,3,5-triazin-2-yl)benzonitrile (290 mg, 0.547 mmol) and oxetan-3-one (39 mg, 0.547 mmol) in ² mL DCM was treated with and AcOH (38 uL, 0.656 mmol). After 5 min of stirring sodium triacetoxyborohydride (173 mg, 0.82 mmol) was added and the mixture stirred at rt overnight. The reaction was diluted with EtOAc and neutralized with sat. NaHCO₃ solution. The organic layer was concentrated and the residue purified HPLC eluting with 5%-95% water/acetonitrile (0.1% v/v trifluoroacetic acid). The appropriate fractions were pooled and lyophilized to provide 2-(((3R,4S)-3-fluoro-1-(oxetan-3-yl)piperidin-4-yl)oxy)-5-(4-((4-(4-(oxetan-3-yl)piperazin-1-yl)phenyl)amino)-1,3,5-triazin-2-yl)benzonitrile. ES/MS 587.3 (M+H⁺).

Example 112

2-(((3R)-3-fluoro-1-((S)-5-oxopyrrolidine-2-carbonyl)piperidin-4-yl)oxy)-5-(4-((4-(4-(oxetan-3-yl)piperazin-1-yl)phenyl)amino)-1,3,5-triazin-2-yl)benzonitrile

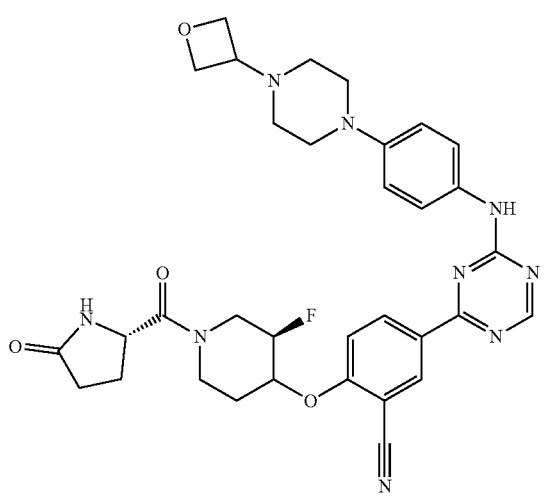 [SMILES: N#Cc1cc(-c2ncnc(Nc3ccc(N4CCN(C5COC5)CC4)cc3)n2)ccc1OC1CCN(C(=O)[C@@H]2CCC(=O)N2)C[C@H]1F]

l-Pyroglutamic acid (26 mg, 0.20 mmol) was taken up in 1 mL DMF and treated with HATU (84 mg, 0.221 mmol). After stirring for 30 sec, 2-(((3R,4S)-3-fluoropiperidin-4-yl)oxy)-5-(4-((4-(4-(oxetan-3-yl)piperazin-1-yl)phenyl)amino)-1,3,5-triazin-2-yl)benzonitrile (110 mg, 0.20 mmol) and DIEA (51 uL, 0.30 mmol) were added and the reaction stirred at rt for 45 min. The reaction was diluted with DCM and 2M Na₂CO₃ solution. The organic layer was concentrated and the residue purified by silica gel chromatography gave 2-(((3R)-3-fluoro-1-((S)-5-oxopyrrolidine-2-carbonyl)piperidin-4-yl)oxy)-5-(4-((4-(4-(oxetan-3-yl)piperazin-1-yl)phenyl)amino)-1,3,5-triazin-2-yl)benzonitrile. ¹H NMR (400 MHz, DMSO-d⁶) δ 10.11 (d, J=26.0 Hz, 1H), 8.73 (s, 1H), 8.65-8.48 (m, 2H), 7.72 (d, J=21.2 Hz, 1H), 7.63 (d, J=9.0 Hz, 1H), 7.55 (d, J=13.8 Hz, 2H), 6.95 (s, 2H), 5.13 (s, 1H), 5.04 (d, J=24.9 Hz, 1H), 4.65-4.58 (m, 1 H), 4.55 (t, J=6.5 Hz, 3H), 4.46 (t, J=6.0 Hz, 2H), 4.39 (m, 1H), 4.25-4.06 (m, 1H), 3.44 (t, J=6.3 Hz, 1H), 3.13 (s, 4H), 2.40 (s, 4H), 2.31 (d, J=9.9 Hz, 1H), 2.10 (q, J=9.2 Hz, 2H), 1.99 (s, 1H). ES/MS 642.4 (M+H⁺).

Example 113

2-(((3R)-3-fluoro-1-((R)-5-oxopyrrolidine-2-carbonyl)piperidin-4-yl)oxy)-5-(4-((4-(4-(oxetan-3-yl)piperazin-1-yl)phenyl)amino)-1,3,5-triazin-2-yl)benzonitrile

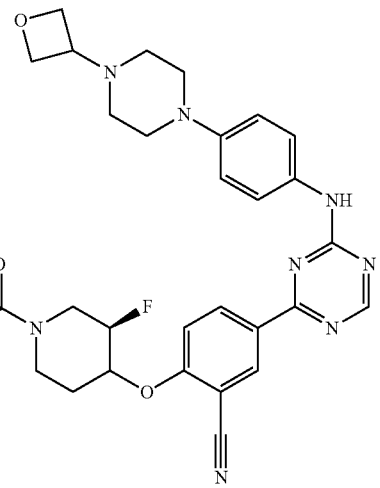

(R)-5-oxopyrrolidine-2-carboxylic acid (17 mg, 0.13 mmol) was taken up in 1 mL DMF and treated with HATU (53 mg, 0.14 mmol). After stirring for 30 sec, 2-(((3R,4S)-3-fluoropiperidin-4-yl)oxy)-5-(4-((4-(4-(oxetan-3-yl)piperazin-1-yl)phenyl)amino)-1,3,5-triazin-2-yl)benzonitrile (71 mg, 0.13 mmol) and DIEA (47 uL, 0.27 mmol) were added and the reaction stirred at rt for 45 min. The reaction was diluted with DCM and 2M Na₂CO₃ solution. The organic layer was concentrated and the residue purified by HPLC eluting with 5%-95% water/acetonitrile (0.1% v/v trifluoroacetic acid). The appropriate fractions were pooled and lyophilized to provide 2-(((3R)-3-fluoro-1-((R)-5-oxopyrrolidine-2-carbonyl)piperidin-4-yl)oxy)-5-(4-((4-(4-(oxetan-3-yl)piperazin-1-yl)phenyl)amino)-1,3,5-triazin-2-yl)benzonitrile. ES/MS 642.4 (M+H⁺).

Example 114

(S)-5-(4-((4-(4-(oxetan-3-yl)piperazin-1-yl)phenyl)amino)-1,3,5-triazin-2-yl)-2-((6-oxopiperidin-3-yl)oxy)benzonitrile

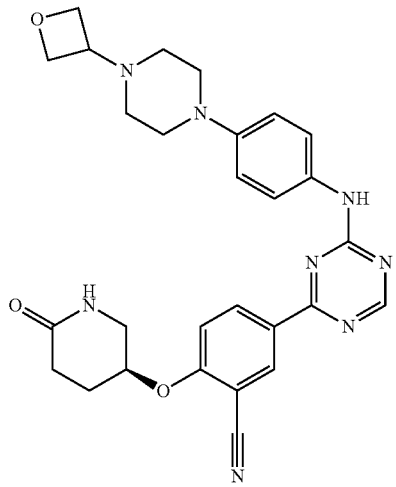 [SMILES: N#Cc1cc(-c2ncnc(Nc3ccc(N4CCN(C5COC5)CC4)cc3)n2)ccc1O[C@H]1CCC(=O)NC1]

Potassium tert-butoxide (58 mg, 0.52 mmol) was added to a solution of (S)-5-hydroxypiperidin-2-one (68 mg, 0.52 mmol) in THF (3 mL) and stirred at rt for 30 min. 2-Fluoro-5-(4-((4-(4-(oxetan-3-yl)piperazin-1-yl)phenyl)amino)-1,3,5-triazin-2-yl)benzonitrile (0.15 g, 0.35 mmol) was added and the reaction heated to 60° C. for 16 h. Mixture diluted with MeCN and neutralized to pH 7 with AcOH. The filtrate was loaded onto silica gel and purified by silica gel chromatography to give (S)-5-(4-((4-(4-(oxetan-3-yl)piperazin-1-yl)phenyl)amino)-1,3,5-triazin-2-yl)-2-((6-oxopiperidin-3-yl)oxy)benzonitrile. $^1$H NMR (400 MHz, DMSO-d$^6$) δ 10.17 (d, J=17.1 Hz, 1H), 8.74 (s, 1H), 8.63-8.48 (m, 2H), 7.70-7.51 (m, 3H), 7.46 (s, 1H), 7.03 (s, 2H), 5.17-5.06 (m, 1H), 4.85 (m, 2H), 4.69 (t, J=7.2 Hz, 2H), 3.80 (s, 2H), 3.69-3.29 (m, 5H), 3.26-2.93 (m, 3H), 2.41-2.14 (m, 2H), 2.11 (m, 1H), 1.19 (m, 2H). ES/MS 527.29 (M+H$^+$).

Example 115

2-(((2S,4S,5R)-5-fluoro-1-(2-hydroxyacetyl)-2-methylpiperidin-4-yl)oxy)-5-(4-((4-(4-(oxetan-3-yl)piperazin-1-yl)phenyl)amino)-1,3,5-triazin-2-yl)benzonitrile

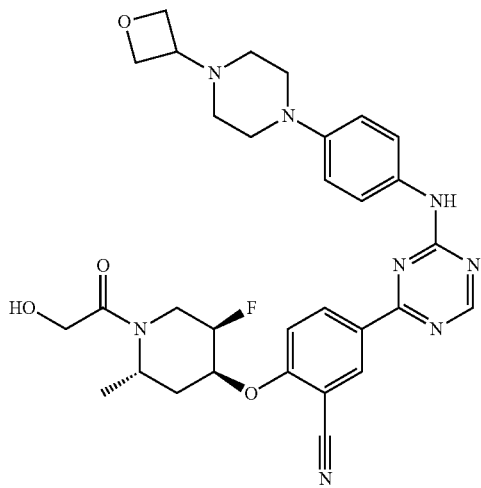 [SMILES: C[C@H]1C[C@H](Oc2ccc(-c3ncnc(Nc4ccc(N5CCN(C6COC6)CC5)cc4)n3)cc2C#N)[C@H](F)CN1C(=O)CO]

Glycolic acid (10 mg, 0.138 mmol) was taken up in 1 mL DMF and treated with HATU (58 mg, 0.151 mmol). After stirring for 30 sec, 2-(((2S,4S,5R)-5-fluoro-2-methylpiperidin-4-yl)oxy)-5-(4-((4-(4-(oxetan-3-yl)piperazin-1-yl)phenyl)amino)-1,3,5-triazin-2-yl)benzonitrile (75 mg, 0.138 mmol) and DIEA (35 uL, 0.207 mmol) were added and the reaction stirred at rt for 45 min. The reaction was diluted with DCM and 2M Na2CO3 solution. The organic layer was concentrated and the residue purified by silica gel chromatography gave 2-(((2S,4S,5R)-5-fluoro-1-(2-hydroxyacetyl)-2-methylpiperidin-4-yl)oxy)-5-(4-((4-(4-(oxetan-3-yl)piperazin-1-yl)phenyl)amino)-1,3,5-triazin-2-yl)benzonitrile. $^1$H NMR (400 MHz, DMSO-d$^6$) δ 10.18 (d, J=28.7 Hz, 1H), 8.79 (s, 1H), 8.69-8.55 (m, 2H), 7.71 (d, J=9.2 Hz, 1H), 7.66-7.55 (m, 3H), 7.06-6.96 (m, 2H), 5.35-4.93 (m, 2H), 4.66 (s, 1H), 4.61 (t, J=6.5 Hz, 2H), 4.52 (t, J=6.1 Hz, 2H), 4.35-4.26 (m, 1H), 4.16-4.08 (m, 1H), 3.72-3.58 (m, 1H), 3.49 (t, J=6.3 Hz, 1H), 3.22-3.13 (m, 5H), 2.46 (s, 4H), 2.24-2.15 (m, 1H), 2.07-1.89 (m, 1H), 1.41-1.34 (m, 2H), 1.34-1.25 (m, J=11 Hz, 6H). ES/MS 603.3 (M+H$^+$).

Example 116

2-(((S)-3,3-difluoro-1-((S)-5-oxopyrrolidine-2-carbonyl)piperidin-4-yl)oxy)-5-(4-((4-(4-(oxetan-3-yl)piperazin-1-yl)phenyl)amino)-1,3,5-triazin-2-yl)benzonitrile

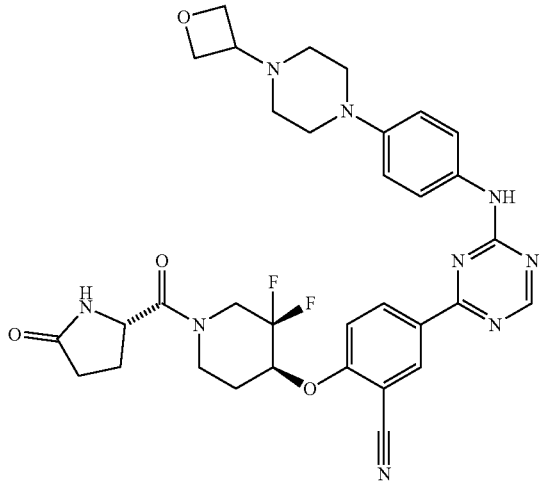

l-Pyroglutamic acid (26 mg, 0.20 mmol) was taken up in 1 mL DMF and treated with HATU (84 mg, 0.221 mmol). After stirring for 30 sec, 2-(((3R,4S)-3,3-difluoropiperidin-4-yl)oxy)-5-(4-((4-(4-(oxetan-3-yl)piperazin-1-yl)phenyl)amino)-1,3,5-triazin-2-yl)benzonitrile (110 mg, 0.20 mmol) and DIEA (51 uL, 0.30 mmol) were added and the reaction stirred at rt for 45 min. The reaction was diluted with DCM and 2M Na2CO3 solution. The organic layer was concentrated and the residue purified by silica gel chromatography gave 2-(((3R)-3-fluoro-1-((S)-5-oxopyrrolidine-2-carbonyl)piperidin-4-yl)oxy)-5-(4-((4-(4-(oxetan-3-yl)piperazin-1-yl)phenyl)amino)-1,3,5-triazin-2-yl)benzonitrile. $^1$H NMR (400 MHz, DMSO-d6) δ 10.13 (d, J=23.3 Hz, 1H), 8.73 (s, 1H), 8.57 (m, 1H), 7.76 (d, J=23.7 Hz, 1H), 7.65 (dd, J=9.2, 6.3 Hz, 1H), 7.62-7.44 (m, 2H), 6.96 (s, 2H), 5.37 (s, 1H), 4.63 (dd, J=7.1, 2.8 Hz, 1H), 4.55 (t, J=6.5 Hz, 2H), 4.46 (t, J=6.0 Hz, 2H), 4.25-4.05 (m, 1H), 3.95-3.84 (m, 1H), 3.83-3.71 (m, 1H), 3.44 (q, J=5.8, 5.0 Hz, 1H), 3.12 (s, 5H), 2.46-2.27 (m, 5H), 2.11 (m, 3H), 2.07-1.76 (m, 2H). ES/MS 660.42 (M+H$^+$).

Example 117

2-(((3R,4S)-3-fluoro-1-((S)-6-oxopiperidine-2-carbonyl)piperidin-4-yl)oxy)-5-(4-((4-(4-(oxetan-3-yl)piperazin-1-yl)phenyl)amino)-1,3,5-triazin-2-yl)benzonitrile

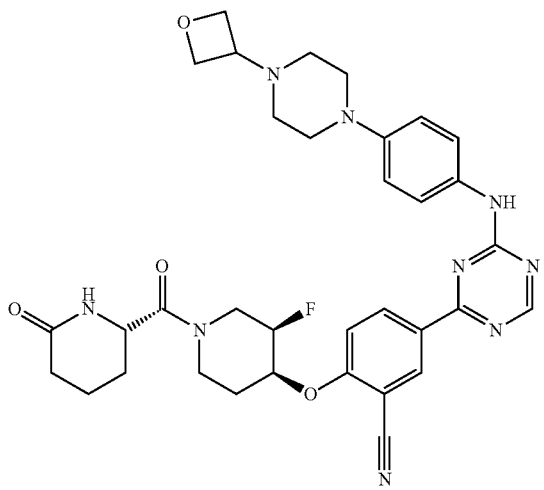

(S)-6-Oxopiperidine-2-carboxylic acid (30 mg, 0.21 mmol) was taken up in 2 mL DMF and treated with HATU (86 mg, 0.23 mmol). After stirring for 30 sec, 2-(((3R,4S)-3,3-difluoropiperidin-4-yl)oxy)-5-(4-((4-(4-(oxetan-3-yl)piperazin-1-yl)phenyl)amino)-1,3,5-triazin-2-yl)benzonitrile (100 mg, 0.19 mmol) and DIEA (48 mg, 0.38 mmol) were added and the reaction stirred at rt for 45 min. The reaction was diluted with DCM and 2M Na2CO3 solution. The organic layer was concentrated and the residue purified by silica gel chromatography gave 2-(((3R,4S)-3-fluoro-1-((S)-6-oxopiperidine-2-carbonyl)piperidin-4-yl)oxy)-5-(4-((4-(4-(oxetan-3-yl)piperazin-1-yl)phenyl)amino)-1,3,5-triazin-2-yl)benzonitrile. $^1$H NMR (400 MHz, DMSO-d6) δ 10.12 (d, J=26.4 Hz, 1H), 8.73 (s, 1H), 8.67-8.46 (m, 2H), 7.63 (d, J=9.1 Hz, 1H), 7.61-7.50 (m, 2H), 6.95 (s, 2H), 5.13 (s, 1H), 4.56 (t, J=6.5 Hz, 2H), 4.46 (t, J=6.0 Hz, 2H), 4.55-4.23 (m, 1H), 3.51-3.32 (m, 2H), 3.13 (s, 4H), 2.98-3.10 (m, 1H), 2.41 (s, 3H), 2.14-2.08 (m, 2H), 1.95-2.04 (m, 1H), 1.91-1.56 (m, 4H). ES/MS 656.3 (M+H$^+$).

Example 118

2-(((3R,4S)-1-(1,1-dioxidoisothiazolidine-3-carbonyl)-3-fluoropiperidin--4-yl)oxy)-5-(4-((4-(4-(oxetan-3-yl)piperazin-1-yl)phenyl)amino)-1,3,5-triazin-2-yl)benzonitrile

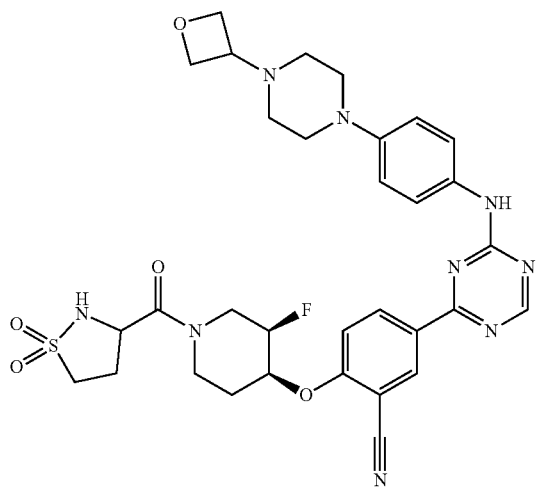 [SMILES: N#Cc1cc(-c2ncnc(Nc3ccc(N4CCN(C5COC5)CC4)cc3)n2)ccc1O[C@H]1CCN(C(=O)C2CCS(=O)(=O)N2)C[C@H]1F]

(+/−)-Isothiazolidine-3-carboxylic acid 1,1-dioxide (34 mg, 0.21 mmol) was taken up in 2 mL DMF and treated with HATU (84 mg, 0.23 mmol). After stirring for 30 sec, 2-(((3R,4S)-3,3-difluoropiperidin-4-yl)oxy)-5-(4-((4-(4-(oxetan-3-yl)piperazin-1-yl)phenyl)amino)-1,3,5-triazin-2-yl)benzonitrile (100 mg, 0.19 mmol) and DIEA (48 uL, 0.2.8 mmol) were added and the reaction stirred at rt for 45 min. The reaction was diluted with DCM and 2M Na2CO3 solution. The organic layer was concentrated and the residue purified by silica gel chromatography gave 2-(((3R,4S)-1-(1,1-dioxidoisothiazolidine-3-carbonyl)-3-fluoropiperidin-4-yl)oxy)-5-(4-((4-(4-(oxetan-3-yl)piperazin-1-yl)phenyl)amino)-1,3,5-triazin-2-yl)benzonitrile as a mixture of epimers. δ $^1$H NMR (400 MHz, DMSO-d$^6$) δ 10.12 (d, J=26.4 Hz, 1H), 8.67-8.46 (m, 2H), 7.63 (d, J=9.1 Hz, 1H), 7.61-7.50 (m, 2H), 7.24 (d, J=40.0 Hz, 1H), 6.95 (s, 2H), 5.17-4.96 (m, 1H), 4.56 (t, J=6.5 Hz, 2H), 4.46 (t, J=6.0 Hz, 2H), 4.46-4.11 (m, 1H), 3.64-3.56 (m, 0H), 3.51-3.32 (m, 2H), 3.13 (s, 5H), 2.41 (m, 3H), 2.13-2.07 (m, 2H), 1.98 (s, 1H), 1.91-1.56 (m, 4H). ES/MS 678.37 (M+H$^+$).

Example 119

2-(((3R,4S)-3-fluoro-1-(2-hydroxyacetyl)piperidin-4-yl)oxy)-5-(4-((4-(4-methylpiperazine-1-carbonyl)phenyl)amino)-1,3,5-triazin-2-yl)benzonitrile

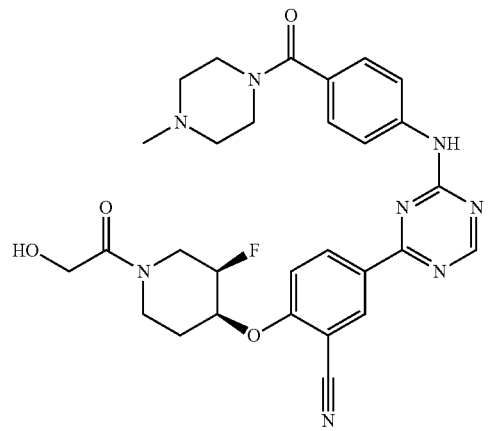 [SMILES: CN1CCN(C(=O)c2ccc(Nc3ncnc(-c4ccc(O[C@H]5CCN(C(=O)CO)C[C@H]5F)c(C#N)c4)n3)cc2)CC1]

A solution of glycolic acid (12 mg, 0.16 mmol) in 2 mL DMF was treated w/ HATU (61 mg, 0.16 mmol) and stirred for 30 sec. DIEA (37 mL, 0.218 mmol) was added, followed by 2-(((3R,4S)-3-fluoropiperidin-4-yl)oxy)-5-(4-((4-(4-methylpiperazine-1-carbonyl)phenyl)amino)-1,3,5-triazin-2-yl)benzonitrile (75 mg, 1.45 mmol) and the mixture was stirred for 1 h. The reaction was concentrated and the residue taken up in THF and loaded on silica gel. Purification by silica gel chromatography provided the desired glycolamide. $^1$H NMR (400 MHz, DMSO) δ 10.55 (s, 1H), 8.86 (m, 1H), 8.60 (dd, J=6.5, 2.8 Hz, 2H), 7.84 (d, J=8.7, 2H), 7.64 (d, J=9.5 Hz, 1H), 7.43 (d, J=8.6 Hz, 2H), 5.20-4.93 (m, 2H), 4.75-4.60 (m, 1H), 4.18-4.04 (m, 3H), 3.89 (s, 1H), 3.74-3.07 (m, 4H), 2.52 (s, 5H), 2.52 (s, 3H), 2.33 (m, 3H), 2.01-1.94 (m, 1H). ES/MS 575.1(M+H$^+$).

Example 120

2-(((3R,4S)-3-fluoro-1-((S)-2-hydroxypropanoyl)piperidin-4-yl)oxy)-5-(4-((4-(4-methylpiperazine-1-carbonyl)phenyl)amino)-1,3,5-triazin-2-yl)benzonitrile

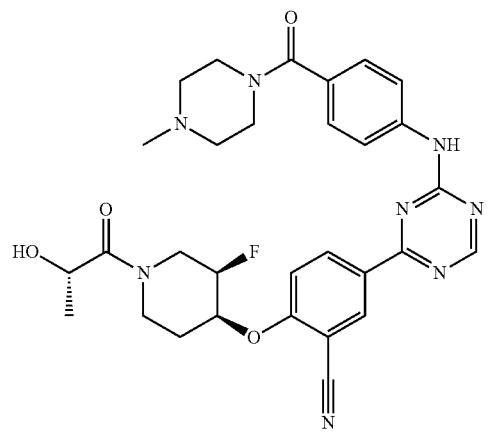 [SMILES: C[C@H](O)C(=O)N1CC[C@H](Oc2ccc(-c3ncnc(Nc4ccc(C(=O)N5CCN(C)CC5)cc4)n3)cc2C#N)[C@H](F)C1]

Title compound was prepared via the same procedure as Example 119. ¹H NMR (400 MHz, DMSO) δ 10.54 (s, 1H), 8.86 (s, 1H), 8.68-8.52 (m, 2H), 7.84 (d, J=8.4 Hz, 2H), 7.64 (d, J=9.5 Hz, 1H), 7.47-7.33 (m, 2H), 5.13 (d, J=21.8 Hz, 2H), 5.05-4.97 (m, 1H), 4.52-4.29 (m, 1H), 4.23-3.83 (m, 2H), 3.49 (s, 4H), 2.33 (s, 5H), 1.97 (s, 1H), 1.41-1.24 (m, 1H), 1.24-1.12 (m, 4H). ES/MS 589.1 (M+H⁺).

Example 121

5-(4-((4-(4-(oxetan-3-yl)piperazin-1-yl)phenyl)amino)-1,3,5-triazin-2-yl)-2-((tetrahydro-2H-pyran-4-yl)amino)benzonitrile

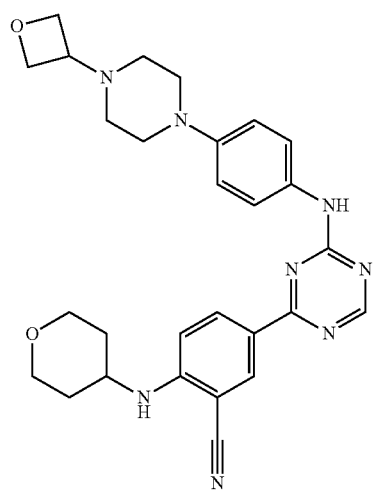 [SMILES: N#Cc1cc(-c2ncnc(Nc3ccc(N4CCN(C5COC5)CC4)cc3)n2)ccc1NC1CCOCC1]

To a solution of 2-fluoro-5-(4-((4-(4-(oxetan-3-yl)piperazin-1-yl)phenyl)amino)-1,3,5-triazin-2-yl)benzonitrile (60 mgs, 0.14 mmol) in 2-propanol (2.0 mL) was added tetrahydro-2H-pyran-4-amine (38 mgs, 0.28 mmol) in 5 mL microwave vial and sealed. This reaction mixture was stirred at 150° C. After 2 h, tetrahydro-2H-pyran-4-amine (3.0 equiv) in NMP (1 mL) was added and heated at 150° C. for 3 h. The reaction mixture was cooled to rt, evaporated under reduced pressure and purified via preparative HPLC (5-65% acetonitrile in water, 0.1% trifluoroacteic acid buffer) to yield the title compound. LCMS-ESI⁺ (m/z): [M+H]⁺ calcd for C₂₈H₃₂N₈O₂: 513.6; found: 513.2.

¹H NMR (400 MHz, DMSO-d₆) δ 10.01 (brs, 1H), 8.65 (s, 1H), 8.32 (dd, J=9.1, 2.0 Hz, 2H), 7.81 (s, 2H), 7.61 (m, 1H), 7.13-6.96 (m, 2H), 6.54 (d, J=8.0 Hz, NH), 4.74 (m, 4H), 4.03-3.88 (m, 2H), 3.60-3.40 (m, 4H), 3.20-3.00(m, 4H), 1.90-1.82 (m, 4H), 1.70-1.64 (m, 4H).

Example 122

2-((4-methoxycyclohexyl)oxy)-5-(4-((4-(4-(oxetan-3-yl)piperazin-1-yl)phenyl)amino)-1,3,5-triazin-2-yl)benzonitrile

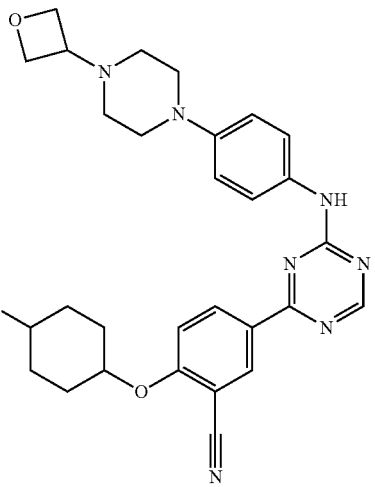

To a solution of 4-methoxycyclohexanol (45 mgs, 0.35 mmol) in Me-THF (5.0 mL) at 0° C. was added potassium tert-butoxide solution (1.0 M, 0.35 mL, 0.35 mmol). After 45 minutes at 0° C., 2-fluoro-5-(4-((4-(4-(oxetan-3-yl)piperazin-1-yl)phenyl)amino)-1,3,5-triazin-2-yl)benzonitrile (100 mgs, 0.232 mmol) was added and heated at 60° C. After 16 h, the mixture cooled to room temperature, water (1.0 mL) was added, and the mixture was then evaporated under reduced pressure and purified via preparative HPLC (5-65% acetonitrile in water, 0.1% trifluoroacteic acid buffer) to yield the title compound as mixture of isomers. LCMS-ESI⁺ (m/z): [M+H]⁺ calcd for C₃₀H₃₅N₇O₃: 542.6; found: 542.2.

Example 123

2-(((3R,4S)-3-fluoro-1-((S)-3-hydroxy-2-methylpropanoyl)piperidin-4-yl)oxy)-5-(4-((4-(4-(oxetan-3-yl)piperazin-1-yl)phenyl)amino)-1,3,5-triazin-2-yl)benzonitrile

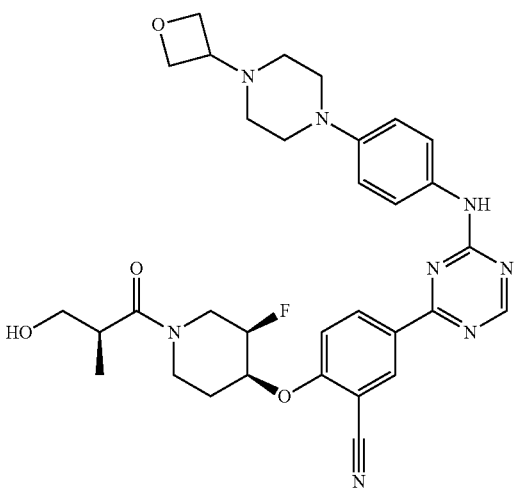 [SMILES: C[C@@H](CO)C(=O)N1CC[C@H](Oc2ccc(-c3ncnc(Nc4ccc(N5CCN(C6COC6)CC5)cc4)n3)cc2C#N)[C@H](F)C1]

To a solution of 2-(((3R,4S)-3-fluoropiperidin-4-yl)oxy)-5-(4-((4-(4-(oxetan-3-yl)piperazin-1-yl)phenyl)amino)-1,3,5-triazin-2-yl)benzonitrile (50 mgs, 0.09 mmol) in DMF (3.0 mL) was added (S)-3-hydroxy-2-methylpropanoic acid sodium salt (24 mgs, 0.18 mmol), HATU (72 mgs, 0.19 mmol) and TEA (0.02 mL, 0.18 mmol). The above reaction mixture was stirred at room temperature for 16 h. The mixture was then evaporated under reduced pressure and purified via preparative HPLC (5-65% acetonitrile in water, 0.1% trifluoroacteic acid buffer) to yield the title compound. LCMS-ESI$^+$ (m/z): [M+H]$^+$ calcd for $C_{32}H_{37}FN_8O_4$: 617.7; found: 617.3

Example 124

2-(((3R,4S)-3-fluoro-1-((R)-3-hydroxy-2-methylpropanoyl)piperidin-4-yl)oxy)-5-(4-((4-(4-(oxetan-3-yl)piperazin-1-yl)phenyl)amino)-1,3,5-triazin-2-yl)benzonitrile

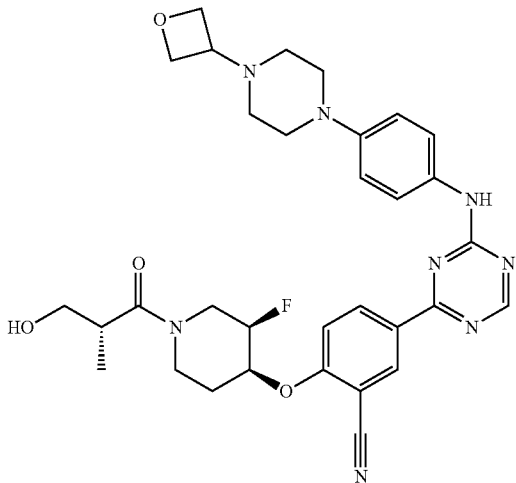 [SMILES: C[C@H](CO)C(=O)N1CC[C@H](Oc2ccc(-c3ncnc(Nc4ccc(N5CCN(C6COC6)CC5)cc4)n3)cc2C#N)[C@H](F)C1]

To a solution of 2-(((3R,4S)-3-fluoropiperidin-4-yl)oxy)-5-(4-((4-(4-(oxetan-3-yl)piperazin-1-yl)phenyl)amino)-1,3,5-triazin-2-yl)benzonitrile (50 mgs, 0.09 mmol) in DMF (3 mL) was added (R)-3-hydroxy-2-methylpropanoic acid sodium salt (24 mgs, 0.18 mmol), HATU (72 mgs, 0.19 mmol) and TEA (0.02 mL, 0.18 mmol). The above reaction mixture was stirred at room temperature for 16 h. The mixture was then evaporated under reduced pressure and purified via preparative HPLC (5-65% acetonitrile in water, 0.1% trifluoroacteic acid buffer) to yield the title compound. LCMS-ESI$^+$ (m/z): [M+H]$^+$ calcd for $C_{32}H_{37}FN_8O_4$: 617.7; found: 617.3

Example 125

(R)-2-((1-(2-hydroxyacetyl)piperidin-3-yl)oxy)-5-(4-((4-(4-(oxetan-3-yl)piperazin-1-yl)phenyl)amino)-1,3,5-triazin-2-yl)benzonitrile Step 1: To a solution of (R)-tert-butyl 3-hydroxypiperidine-1-carboxylate (51 mgs, 0.26 mmol) in Me-THF (2.0 mL) at 0° C. was added potassium tert-butoxide solution (1.0 M, 0.4 mL, 0.4 mmol). After 45 minutes at 0° C., 2-fluoro-5-(4-((4-(4-(oxetan-3-yl)piperazin-1-yl)phenyl)amino)-1,3,5-triazin-2-yl)benzonitrile (100 mgs, 0.23 mmol) was added and heated at 60° C. After 16 h, the mixture cooled to room temperature, water (0.6 mL) was added, and mixture evaporated under reduced pressure to yield (R)-5-(4-((4-(4-(oxetan-3-yl)piperazin-1-yl)phenyl)amino)-1,3,5-triazin-2-yl)-2-((1-pivaloylpiperidin-3-yl)oxy)benzonitrile which was used further without purification.

Step 2: The crude solids from previous step was diluted with DCM/TFA (6.0 mL, 1:1) and stirred at rt for 1 h. The reaction mixture was evaporated under reduced pressure and residue was suspended in a saturated aqueous solution of NaHCO$_3$ and extracted with DCM. The combined organic layers were then dried over magnesium sulfate and evaporated under reduced pressure to give (R)-5-(4-((4-(4-(oxetan-3-yl)piperazin-1-yl)phenyl)amino)-1,3,5-triazin-2-yl)-2-(piperidin-3-yloxy)benzonitrile which was further used without purification.

Step 3: To the above crude amine (from step 2, 45 mgs, 0.09 mmol) in DMF (1.0 mL) was added glycolic acid (13 mgs, 0.18 mmol), HATU (67 mgs, 0.18 mmol) and DIPEA (0.07 mL, 0.4 mmol). The above reaction mixture was stirred at room temperature for 16 h, evaporated under reduced pressure and purified via preparative HPLC (5-65% acetonitrile in water, 0.1% trifluoroacteic acid buffer) to yield the title compound. LCMS-ESI$^+$ (m/z): [M+H]$^+$ calcd for $C_{30}H_{34}N_8O_4$: 571.6; found: 571.4

Example 126

2-(((R)-1-((S)-2-hydroxypropanoyl)piperidin-3-yl)oxy)-5-(4-((4-(4-(oxetan-3-yl)piperazin-1-yl)phenyl)amino)-1,3,5-triazin-2-yl)benzonitrile

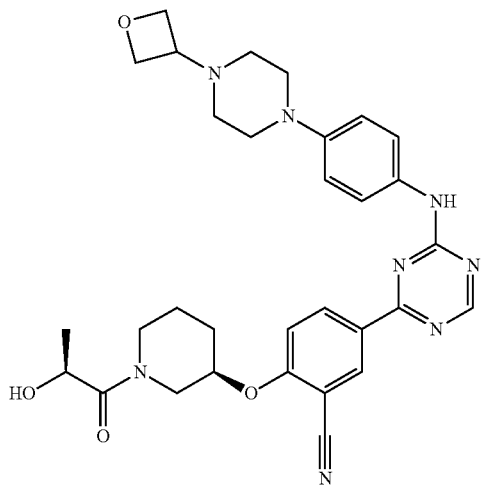 [SMILES: C[C@H](O)C(=O)N1CCC[C@@H](Oc2ccc(-c3ncnc(Nc4ccc(N5CCN(C6COC6)CC5)cc4)n3)cc2C#N)C1]

The title compound was prepared following a similar procedure reported in Example-125 (step 3) using (S)-2-hydroxypropanoic acid instead of glycolc acid. LCMS-ESI⁺ (m/z): [M+H]⁺ calcd for $C_{31}H_{36}N_8O_4$: 585.7; found: 585.3

Example 127

(S)-2-((1-(2-hydroxyacetyl)piperidin-3-yl)oxy)-5-(4-((4-(4-(oxetan-3-yl)piperazin-1-yl)phenyl)amino)-1,3,5-triazin-2-yl)benzonitrile

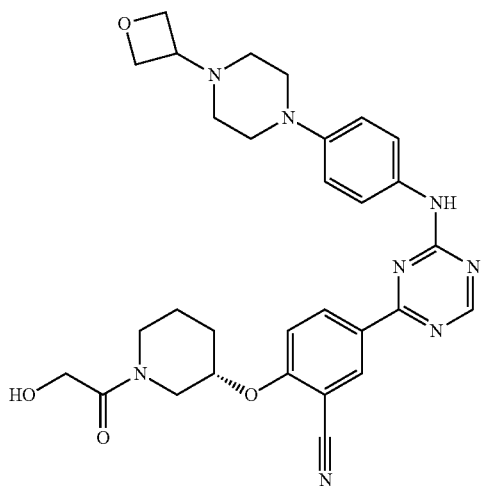 [SMILES: N#Cc1cc(-c2ncnc(Nc3ccc(N4CCN(C5COC5)CC4)cc3)n2)ccc1O[C@H]1CCCN(C(=O)CO)C1]

The title compound was prepared following a similar procedure reported in Example-125 (step 1) using (S)-tert-butyl 3-hydroxypiperidine-1-carboxylate instead of (R)-tert-butyl 3-hydroxypiperidine-1-carboxylate. LCMS-ESI⁺ (m/z): [M+H]⁺ calcd for $C_{30}H_{34}N_8O_4$: 571.6; found: 571.3

Example 128

2-(((S)-1-((S)-2-hydroxypropanoyl)piperidin-3-yl)oxy)-5-(4-((4-(4-(oxetan-3-yl)piperazin-1-yl)phenyl)amino)-1,3,5-triazin-2-yl)benzonitrile

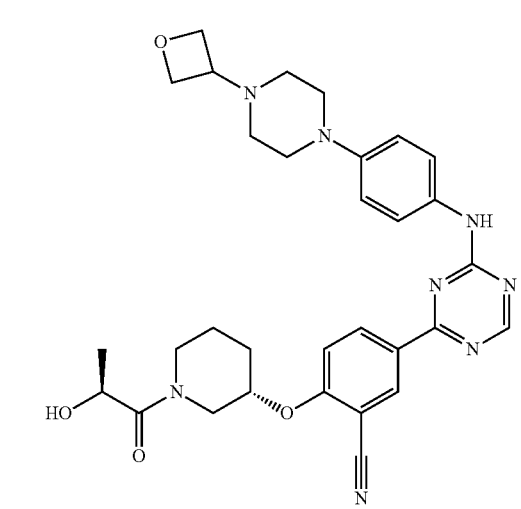 [SMILES: C[C@H](O)C(=O)N1CCC[C@H](Oc2ccc(-c3ncnc(Nc4ccc(N5CCN(C6COC6)CC5)cc4)n3)cc2C#N)C1]

The title compound was prepared following a similar procedure reported in Example-125 (step 1) using (S)-tert-butyl 3-hydroxypiperidine-1-carboxylate instead of (R)-tert-butyl 3-hydroxypiperidine-1-carboxylate and using (S)-2-hydroxypropanoic acid instead of glycolc acid. LCMS-ESI⁺ (m/z): [M+H]⁺ calcd for $C_{31}H_{36}N_8O_4$: 585.7; found: 585.3

Example 129

2-(((3R,4S)-3-fluoro-1-((R)-piperidine-2-carbonyl)piperidin-4-yl)oxy)-5-(4-((4-(4-(oxetan-3-yl)piperazin-1-yl)phenyl)amino)-1,3,5-triazin-2-yl)benzonitrile

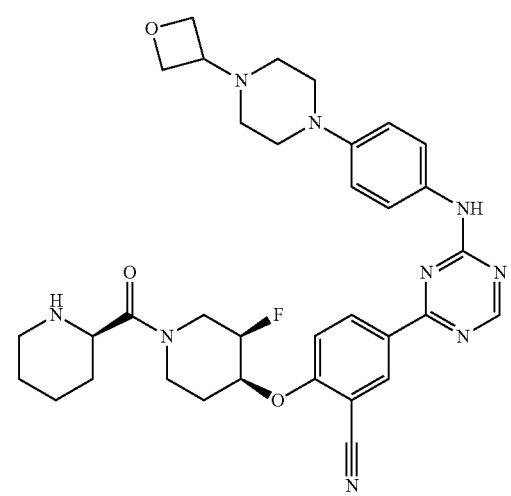 [SMILES: N#Cc1cc(-c2ncnc(Nc3ccc(N4CCN(C5COC5)CC4)cc3)n2)ccc1O[C@H]1CCN(C(=O)[C@H]2CCCCN2)C[C@H]1F]

To a solution of 2-(((3R,4S)-3-fluoropiperidin-4-yl)oxy)-5-(4-((4-(4-(oxetan-3-yl)piperazin-1-yl)phenyl)amino)-1,3,5-triazin-2-yl)benzonitrile (35 mgs, 0.07 mmol) in DMF (1.0 mL) was added (S)-1-(tert-butoxycarbonyl)piperidine-2-carboxylic acid (30 mgs, 0.13 mmol), HATU (50 mgs, 0.13 mmol) and TEA (0.02 mL, 0.13 mmol). The above reaction mixture was stirred at room temperature for 16 h, evaporated under reduced pressure. The residue was dissolved in DCM/TFA (3 mL, 2:1) and stirred at rt for 1 h. The mixture was then evaporated under reduced pressure and purified via preparative HPLC (5-65% acetonitrile in water, 0.1% trifluoroacteic acid buffer) to yield the title compound. LCMS-ESI⁺ (m/z): [M+H]⁺ calcd for $C_{34}H_{40}FN_9O_3$: 642.7; found: 642.2

Example 130

2-(((3R,4S)-3-fluoro-1-((R)-pyrrolidine-2-carbonyl)piperidin-4-yl)oxy)-5-(4-((4-(4-(oxetan-3-yl)piperazin-1-yl)phenyl)amino)-1,3,5-triazin-2-yl)benzonitrile

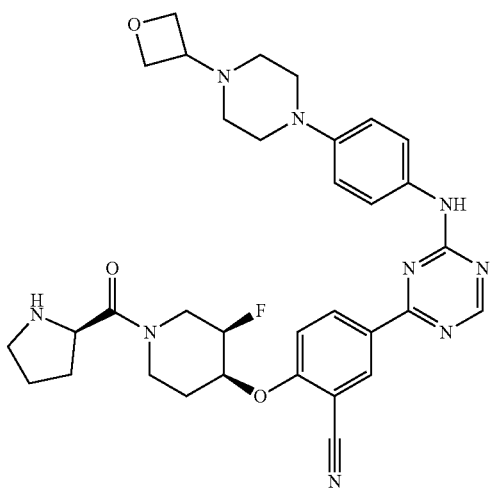 [SMILES: N#Cc1cc(-c2ncnc(Nc3ccc(N4CCN(C5COC5)CC4)cc3)n2)ccc1O[C@H]1CCN(C(=O)[C@H]2CCCN2)C[C@H]1F]

To a solution of 2-(((3R,4S)-3-fluoropiperidin-4-yl)oxy)-5-(4-((4-(4-(oxetan-3-yl)piperazin-1-yl)phenyl)amino)-1,3,5-triazin-2-yl)benzonitrile (35 mgs, 0.07 mmol) in DMF (1 mL) was added N-Boc-D-proline (28 mgs, 0.13 mmol), HATU (50 mgs, 0.13 mmol) and TEA (0.02 mL, 0.13 mmol). The above reaction mixture was stirred at room temperature for 2 h, evaporated under reduced pressure. The residue was dissolved in DCM/TFA (3 mL, 2:1) and stirred at rt for 1 h. The mixture was then evaporated under reduced pressure and purified via preparative HPLC (5-65% acetonitrile in water, 0.1% trifluoroacteic acid buffer) to yield the title compound. LCMS-ESI⁺ (m/z): [M+H]⁺ calcd for $C_{33}H_{38}FN_9O_3$: 628.7; found: 628.2

Example 131

2-(((3R,4S)-3-fluoro-1-((S)-piperidine-2-carbonyl)piperidin-4-yl)oxy)-5-(4-((4-(4-(oxetan-3-yl)piperazin-1-yl)phenyl)amino)-1,3,5-triazin-2-yl)benzonitrile

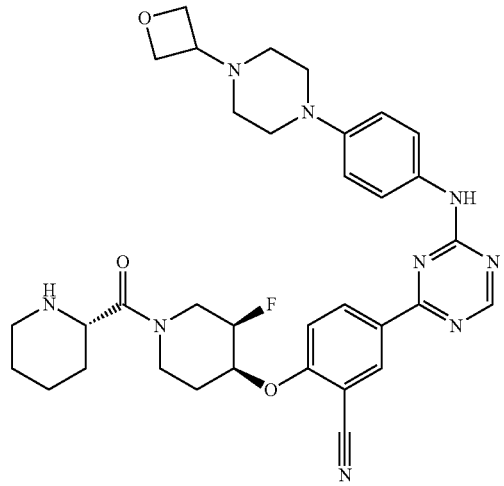 [SMILES: N#Cc1cc(-c2ncnc(Nc3ccc(N4CCN(C5COC5)CC4)cc3)n2)ccc1O[C@H]1CCN(C(=O)[C@@H]2CCCCN2)C[C@H]1F]

To a solution of 2-(((3R,4S)-3-fluoropiperidin-4-yl)oxy)-5-(4-((4-(4-(oxetan-3-yl)piperazin-1-yl)phenyl)amino)-1,3,5-triazin-2-yl)benzonitrile (35 mgs, 0.07 mmol) in DMF (1.0 mL) was added (S)-1-(tert-butoxycarbonyl)piperidine-2-carboxylic acid (30 mgs, 0.13 mmol), HATU (50 mgs, 0.13 mmol) and TEA (0.02 mL, 0.13 mmol). The above reaction mixture was stirred at room temperature for 16 h, evaporated under reduced pressure. The residue was dissolved in DCM/TFA (3 mL, 2:1) and stirred at rt for 1 h. The mixture was then evaporated under reduced pressure and purified via preparative HPLC (5-65% acetonitrile in water, 0.1% trifluoroacteic acid buffer) to yield the title compound. LCMS-ESI⁺ (m/z): [M+H]⁺ calcd for $C_{34}H_{40}FN_9O_3$: 642.7; found: 642.2

Example 132

2-(((3R,4S)-1-((R)-4,4-difluoropyrrolidine-2-carbonyl)-3-fluoropiperidin-4-yl)oxy)-5-(4-((4-(4-(oxetan-3-yl)piperazin-1-yl)phenyl)amino)-1,3,5-triazin-2-yl)benzonitrile

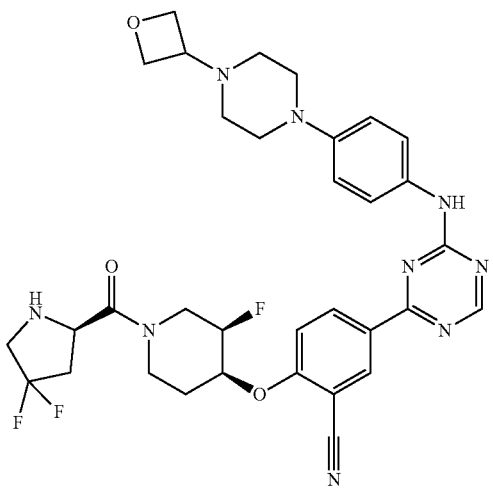 [SMILES: N#Cc1cc(-c2ncnc(Nc3ccc(N4CCN(C5COC5)CC4)cc3)n2)ccc1O[C@H]1CCN(C(=O)[C@H]2CC(F)(F)CN2)C[C@H]1F]

To a solution of 2-(((3R,4S)-3-fluoropiperidin-4-yl)oxy)-5-(4-((4-(4-(oxetan-3-yl)piperazin-1-yl)phenyl)amino)-1,3,5-triazin-2-yl)benzonitrile (35 mgs, 0.07 mmol) in DMF (1 mL) was added N-Boc-4,4-difluoro-L-proline (33 mgs, 0.13 mmol), HATU (50 mgs, 0.13 mmol) and TEA (0.02 mL, 0.13 mmol). The above reaction mixture was stirred at room temperature for 16 h, evaporated under reduced pressure. The residue was dissolved in DCM/TFA (3 mL. 2:1) and stirred at rt for 1 h. The mixture was then evaporated under reduced pressure and purified via preparative HPLC (5-65% acetonitrile in water, 0.1% trifluoroacteic acid buffer) to yield the title compound. LCMS-ESI$^+$ (m/z): [M+H]$^+$ calcd for $C_{33}H_{36}F_3N_9O_3$: 664.7; found: 664.2

Example 133

2-(((3R,4S)-3-fluoro-1-((S)-pyrrolidine-2-carbonyl)piperidin-4-yl)oxy)-5-(4-((4-(4-(oxetan-3-yl)piperazin-1-yl)phenyl)amino)-1,3,5-triazin-2-yl)benzonitrile

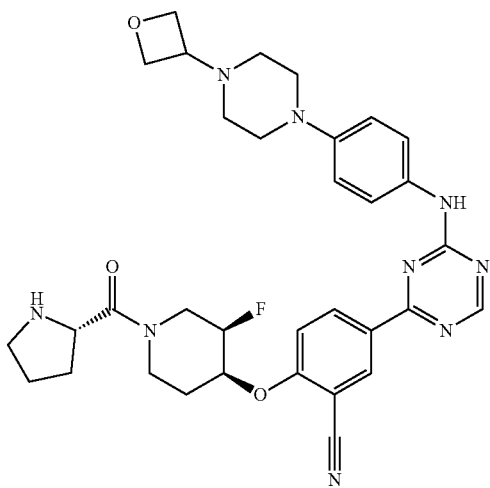 [SMILES: N#Cc1cc(-c2ncnc(Nc3ccc(N4CCN(C5COC5)CC4)cc3)n2)ccc1O[C@H]1CCN(C(=O)[C@@H]2CCCN2)C[C@H]1F]

To a solution of 2-(((3R,4S)-3-fluoropiperidin-4-yl)oxy)-5-(4-((4-(4-(oxetan-3-yl)piperazin-1-yl)phenyl)amino)-1,3,5-triazin-2-yl)benzonitrile (35 mgs, 0.07 mmol) in DMF (1 mL) was added N-Boc-D-proline (28 mg, 0.13 mmol), HATU (50 mgs, 0.13 mmol) and TEA (0.02 mL, 0.13 mmol). The above reaction mixture was stirred at room temperature for 2 h, evaporated under reduced pressure. The residue was dissolved in DCM/TFA (3 mL. 2:1) and stirred at rt for 1 h. The mixture was then evaporated under reduced pressure and purified via preparative HPLC (5-65% acetonitrile in water, 0.1% trifluoroacteic acid buffer) to yield the title compound. LCMS-ESI$^+$ (m/z): [M+H]$^+$ calcd for $C_{33}H_{38}FN_9O_3$: 628.7; found: 628.3

Example 134

(S)-3-((1-(2-hydroxypropanoyl)piperidin-4-yl)oxy)-5-(4-((4-(4-(oxetan-3-yl)piperazin-1-yl)phenyl)amino)-1,3,5-triazin-2-yl)benzonitrile

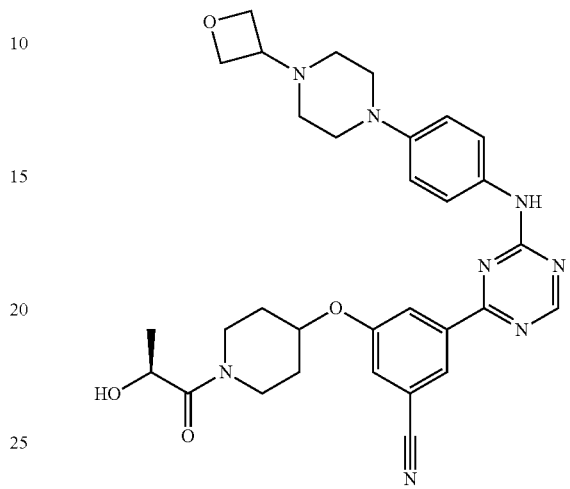

Step 1: To a suspension of triphenylphosphine resin (1.7 g) in THF (6 mL), 3-hydroxy-5-(4,4,5,5-tetramethyl-1,3,2-dioxaborolan-2-yl)benzonitrile (400 mgs, 1.632 mmol) in THF (10 mL) and Diisopropyl azodicarboxylate (0.41 mL, 2.2 mmol) was added and the mixture was stirred at rt. After 30 min, tert-butyl 4-hydroxypiperidine-1-carboxylate (411 mgs, 2.04 mmol) in THF (10 mL) was added and the mixture was stirred at rt. After 16 h, the reaction mixture was filtered and washed with THF and the filtrate was concentrated under reduced pressure. The residue was purified by flash chromatography on silica gel (5-50% EtOAc/Hexanes) to provide tert-butyl-4-(3-cyano-5-(4,4,5,5-tetramethyl-1,3,2-dioxaborolan-2-yl)phenoxy)piperidine-1-carboxylate.

Step 2: A mixture of 4-chloro-N-(4-(4-(oxetan-3-yl)piperazin-1-yl)phenyl)-1,3,5-triazin-2-amine (135 mgs, 0.39 mmol), tert-butyl 4-(3-cyano-5-(4,4,5,5-tetramethyl-1,3,2-dioxaborolan-2-yl)phenoxy)piperidine-1-carboxylate (167 mgs, 0.39 mmol), potassium carbonate (48 mgs, 0.78 mmol) and Pd(dppf)Cl$_2$ (36 mgs) in dioxane/water (9 mL, 2:1) was heated for 1 hour at 105° C. The crude mixture was then diluted with ethyl acetate and the organic layer was washed with 1N HCl. The aqueous layer was then basified to pH ~7-8 with saturated aqueous solution of NaHCO$_3$ and extracted with ethyl acetate and dried (MgSO$_4$). Filtration, followed by concentration of the organic layer gave tert-butyl 4-(3-(4-chloro-6-((4-(4-(oxetan-3-yl)piperazin-1-yl)phenyl)amino)-1,3,5-triazin-2-yl)-5-cyanophenoxy)piperidine-1-carboxylate which was further used without purification.

Step 3: To tert-butyl 4-(3-(4-chloro-6-((4-(4-(oxetan-3-yl)piperazin-1-yl)phenyl)amino)-1,3,5-triazin-2-yl)-5-cyanophenoxy)piperidine-1-carboxylate in DCM (3.0 mL), TFA (1.0 mL) was added and the mixture was stirred at rt for 1 h. The reaction mixture was evaporated under reduced pressure and residue was suspended in a saturated aqueous solution of NaHCO$_3$ and extracted with DCM. The combined organic layers were then dried over magnesium sulfate and evaporated under reduced pressure to give 3-(4-chloro-6-((4-(4-(oxetan-3-yl)piperazin-1-yl)phenyl)amino)-1,3,5- triazin-2-yl)-5-(piperidin-4-yloxy)benzonitrile which was further used without purification.

Step 4: To a solution of 3-(4-chloro-6-((4-(4-(oxetan-3-yl)piperazin-1-yl)phenyl)amino)-1,3,5-triazin-2-yl)-5-(piperidin-4-yloxy)benzonitrile (35 mgs, 0.07 mmol) in DMF (1 mL) was added L-lactic acid (12 mgs, 0.14 mmol), HATU (52 mgs, 0.14 mmol) and DIPEA (0.06 mL, 0.30 mmol). The above reaction mixture was stirred at room temperature for 16 h, evaporated under reduced pressure and purified via preparative HPLC (5-65% acetonitrile in water, 0.1% trifluoroacetic acid buffer) to yield the title compound. LCMS-ESI$^+$ (m/z): [M+H]$^+$ calcd for $C_{31}H_{36}N_8O_4$: 585.7; found: 585.3

Example 135

2-(((3R,4S)-1-(3,5-dimethyl-1H-pyrazole-4-carbonyl)-3-fluoropiperidin-4-yl)oxy)-5-(4-((4-(4-(oxetan-3-yl)piperazin-1-yl)phenyl)amino)-1,3,5-triazin-2-yl)benzonitrile

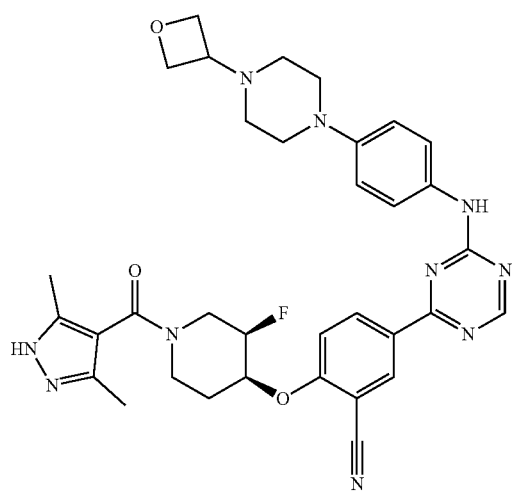 [SMILES: Cc1n[nH]c(C)c1C(=O)N1CC[C@H](Oc2ccc(-c3ncnc(Nc4ccc(N5CCN(C6COC6)CC5)cc4)n3)cc2C#N)[C@H](F)C1]

To a solution of 2-(((3R,4S)-3-fluoropiperidin-4-yl)oxy)-5-(4-((4-(4-(oxetan-3-yl)piperazin-1-yl)phenyl)amino)-1,3,5-triazin-2-yl)benzonitrile (35 mgs, 0.07 mmol) in DMF (1.0 mL) was added 3,5-Dimethyl-1H-pyrazole-4-carboxylic acid (19 mgs, 0.13 mmol), HATU (50 mgs, 0.13 mmol) and TEA (0.02 mL, 0.13 mmol). The above reaction mixture was stirred at room temperature for 2 h, evaporated under reduced pressure and purified via preparative HPLC (5-65% acetonitrile in water, 0.1% trifluoroacetic acid buffer) to yield the title compound. LCMS-ESI$^+$ (m/z): [M+H]$^+$ calcd for $C_{34}H_{37}FN_{10}O_3$: 652.7; found: 653.3 $^1$H NMR (400 MHz, DMSO-d$_6$) δ 10.74 (brs, 1H), 10.24-10.09 (m, 1H), 8.75 (s, 1H), 8.57 (m, 2H), 7.67-7.43 (m, 3H), 7.06 (d, J=9.6 Hz, 2H), 5.26-5.01 (m, 3H), 4.76 (m, 4H), 4.44 (m, 1H), 4.27-3.61 (m, 5H), 3.59-3.40 (m, 2H), 3.10-2.88 (m, 4H), 2.50 (s, 6H), 2.02-1.97 (m, 2H).

Example 136

2-(((3R,4S)-1-(5-chloro-1H-pyrazole-4-carbonyl)-3-fluoropiperidin-4-yl)oxy)-5-(4-((4-(4-(oxetan-3-yl)piperazin-1-yl)phenyl)amino)-1,3,5-triazin-2-yl)benzonitrile

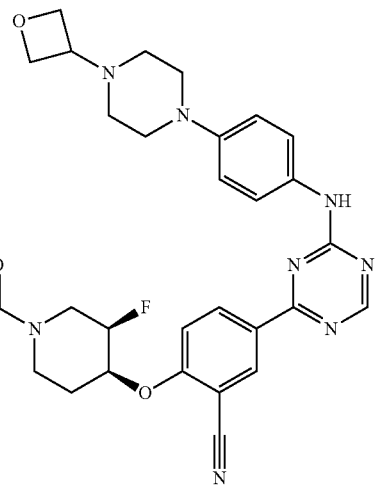

To a solution of 2-(((3R,4S)-3-fluoropiperidin-4-yl)oxy)-5-(4-((4-(4-(oxetan-3-yl)piperazin-1-yl)phenyl)amino)-1,3,5-triazin-2-yl)benzonitrile (35 mgs, 0.07 mmol) in DMF (1 mL) was added 5-chloro-1H-pyrazole-4-carboxylic acid (19 mgs, 0.13 mmol), HATU (50 mgs, 0.13 mmol) and TEA (0.02 mL, 0.13 mmol). The above reaction mixture was stirred at room temperature for 2 h, evaporated under reduced pressure and purified via preparative HPLC (5-65% acetonitrile in water, 0.1% trifluoroacteic acid buffer) to yield the title compound. LCMS-ESI$^+$ (m/z): [M+H]$^+$ calcd for $C_{32}H_{32}ClFN_{10}O_3$: 659.1; found: 659.3

Example 137

2-(((3R,4S)-3-fluoro-1-(2-oxo-1,2-dihydropyridine-4-carbonyl)piperidin-4-yl)oxy)-5-(4-((4-(4-(oxetan-3-yl)piperazin-1-yl)phenyl)amino)-1,3,5-triazin-2-yl)benzonitrile

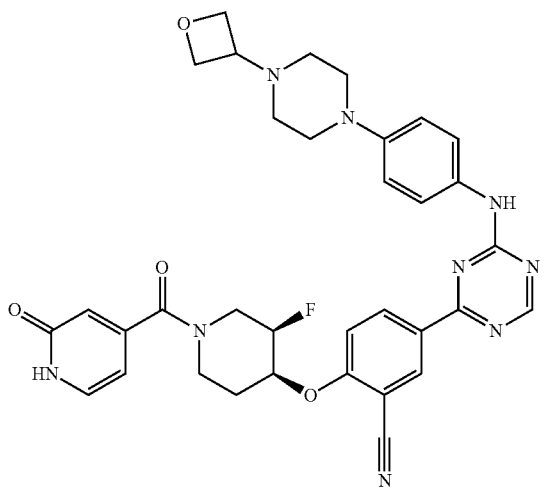 [SMILES: N#Cc1cc(-c2ncnc(Nc3ccc(N4CCN(C5COC5)CC4)cc3)n2)ccc1O[C@H]1CCN(C(=O)c2cc[nH]c(=O)c2)C[C@H]1F]

To a solution of 2-(((3R,4S)-3-fluoropiperidin-4-yl)oxy)-5-(4-((4-(4-(oxetan-3-yl)piperazin-1-yl)phenyl)amino)-1,3, 5-triazin-2-yl)benzonitrile (35 mgs, 0.07 mmol) in DMF (1 mL) was added 2-hydroxyisonicotinic acid (18 mgs, 0.13 mmol), HATU (50 mgs, 0.13 mmol) and TEA (0.02 mL, 0.13 mmol). The above reaction mixture was stirred at room temperature for 2 h, evaporated under reduced pressure and purified via preparative HPLC (5-65% acetonitrile in water, 0.1% trifluoroacteic acid buffer) to yield the title compound. LCMS-ESI$^+$ (m/z): [M+H]$^+$ calcd for $C_{34}H_{34}FN_9O_4$: 652.7; found: 652.3 $^1$H NMR (400 MHz, DMSO-$d_6$) δ 10.71 (brs, 1H), 10.19 (d, J=24.4 Hz, 1H), 8.75 (s, 1H), 8.59-8.57 (m, 2H), 7.63 (d, J=8.8 Hz, 2H), 7.45 (d, J=6.6 Hz, 1H), 7.10-7.05 (m, 3H), 6.23 (s, 1H), 6.12 (t, J=7.5 Hz, 1H), 5.26-5.03 (m, 3H), 4.82-4.72 (m, 4H), 4.42-4.35 (m, 2H), 3.63-3.41 (m, 4H), 3.3-3.30 (m, 2H), (m, 4H), 2.15-1.85 (m, 2H).

Example 138

2-(((3R,4S)-1-(2-cyanoacetyl)-3-fluoropiperidin-4-yl)oxy)-5-(4-((4-(4-(oxetan-3-yl)piperazin-1-yl)phenyl)amino)-1,3,5-triazin-2-yl)benzonitrile

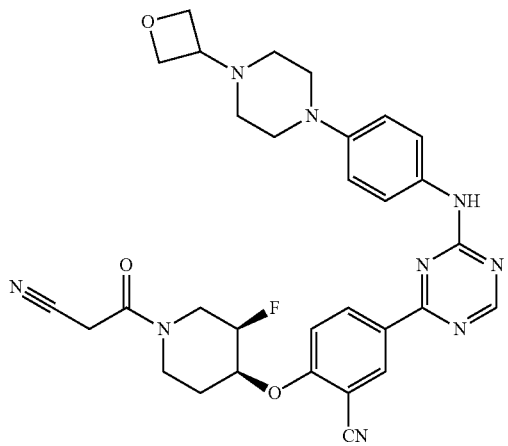 [SMILES: N#CCC(=O)N1CC[C@H](Oc2ccc(-c3ncnc(Nc4ccc(N5CCN(C6COC6)CC5)cc4)n3)cc2C#N)[C@H](F)C1]

To solution of 2-(((3R,4S)-3-fluoropiperidin-4-yl)oxy)-5-(4-((4-(4-(oxetan-3-yl)piperazin-1-yl)phenyl)amino)-1,3,5-triazin-2-yl)benzonitrile (65 mg, 0.12 mmol), 2-cyanoacetic acid (20 mg, 0.24 mmol), HATU (58 mg, 0.24 mmol) in DMF (3 mL) was added DIPEA (0.26 mL) in a 10 mL microwave vial and sealed. This reaction mixture was stirred at room temperature overnight. The solvent was concentrated and the crude product purified via prep HPLC (5-95% acetonitrile in water, 0.1% trifluoroacetic acid buffer) to isolate 2-(((3R,4S)-1-(2-cyanoacetyl)-3-fluoropiperidin-4-yl)oxy)-5-(4-((4-(4-(oxetan-3-yl)piperazin-1-yl)phenyl)amino)-1,3,5-triazin-2-yl)benzonitrile. LCMS-ESI$^+$ (m/z): [M+H]$^+$ calcd for $C_{31}H_{32}FN_9O_3$: 598.3: found:598.4 $^1$H NMR (400 MHz, DMSO-$d_6$) δ 10.19 (d, J=20.3 Hz, 1H), 8.75 (s, 1H), 8.63-8.46 (m, 2H), 7.63 (t, J=8.8 Hz, 3H), 7.14-6.90 (m, 2H), 5.24-4.92 (m, 3H), 4.75 (d, J=6.6 Hz, 5H), 4.55-4.26 (m, 2H), 4.25-3.81 (m, 4H), 3.74-3.49 (m, 1H), 3.31 (ddt, J=24.2, 18.0, 12.8 Hz, 2H), 3.19-2.83 (m, 4H), 2.10-1.79 (m, 2H).

Example 139

2-(((3R,4S)-3-fluoro-1-(3-hydroxypropanoyl)piperidin-4-yl)oxy)-5-(4-((4-(4-(oxetan-3-yl)piperazin-1-yl)phenyl)amino)-1,3,5-triazin-2-yl)benzonitrile

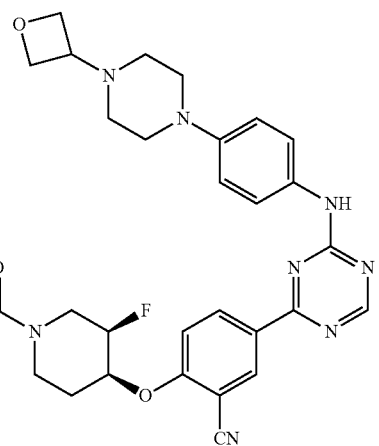

The title compound was prepared following the same procedure reported in Example 138 by coupling 3-hydroxypropanoic acid to 2-(((3R,4S)-3-fluoropiperidin-4-yl)oxy)-5-(4-((4-(4-(oxetan-3-yl)piperazin-1-yl)phenyl)amino)-1,3,5-triazin-2-yl)benzonitrile instead of 2-cyanoacetic acid. LCMS-ESI$^+$ (m/z): [M+H]$^+$ calcd for $C_{31}H_{35}FN_8O_4$: 603.3: found:603.5 $^1$H NMR (400 MHz, DMSO-$d_6$) δ 10.18 (d, J=19.3 Hz, 1H), 8.75 (s, 1H), 8.69-8.39 (m, 2H), 7.63 (t, J=8.2 Hz, 3H), 7.03 (d, J=10.5 Hz, 2H), 5.22-4.87 (m, 3H), 4.75 (d, J=6.3 Hz, 5H), 4.49-4.23 (m, 1H), 4.09 (td, J=13.9, 6.7 Hz, 1H), 3.91-3.70 (m, 1H), 3.62 (q, J=10.1, 8.4 Hz, 3H), 3.49-3.27 (m, 1H), 3.24-2.81 (m, 5H), 2.67-2.36 (m, 4H), 2.05-1.68 (m, 2H).

Example 140

2-(((3R,4S)-3-fluoro-1-(1-hydroxycyclopropanecarbonyl)piperidin-4-yl)oxy)-5-(4-((4-(4-(oxetan-3-yl)piperazin-1-yl)phenyl)amino)-1,3,5-triazin-2-yl)benzonitrile

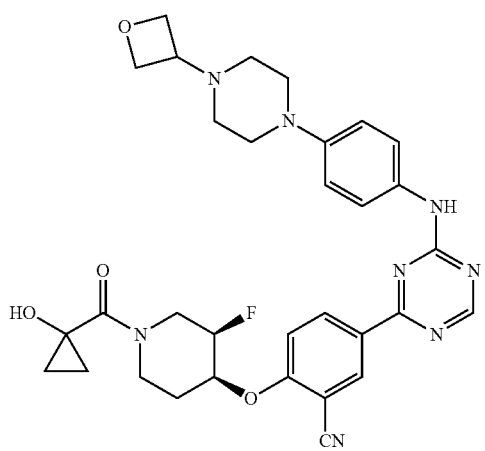 [SMILES: N#Cc1cc(-c2ncnc(Nc3ccc(N4CCN(C5COC5)CC4)cc3)n2)ccc1O[C@H]1CCN(C(=O)C2(O)CC2)C[C@H]1F]

The title compound was prepared following the same procedure reported in Example 138 by coupling 1-hydroxycyclopropanecarboxylic acid to 2-(((3R,4S)-3-fluoropiperidin-4-yl)oxy)-5-(4-((4-(4-(oxetan-3-yl)piperazin-1-yl)phenyl)amino)-1,3,5-triazin-2-yl)benzonitrile instead of 2-cyanoacetic acid. LCMS-ESI$^+$ (m/z): [M+H]$^+$ calcd for $C_{32}H_{35}FN_8O_4$: 615.3: found:615.4 $^1$H NMR (400 MHz, DMSO-d$_6$) δ 10.18 (d, J=21.8 Hz, 1H), 8.75 (s, 1H), 8.66-8.40 (m, 2H), 7.62 (d, J=9.2 Hz, 3H), 7.05 (d, J=11.2 Hz, 2H), 6.39 (s, 1H), 5.25-4.88 (m, 2H), 4.75 (d, J=6.3 Hz, 5H), 4.41 (s, 2H), 3.79 (s, 1H), 3.46 (s, 4H), 3.04 (s, 5H), 1.96 (s, 2H), 1.14-0.61 (m, 4H).

Example 141

2-(((3R,4S)-3-fluoro-1-(1H-pyrrole-2-carbonyl)piperidin-4-yl)oxy)-5-(4-((4-(4-(oxetan-3-yl)piperazin-1-yl)phenyl)amino)-1,3,5-triazin-2-yl)benzonitrile

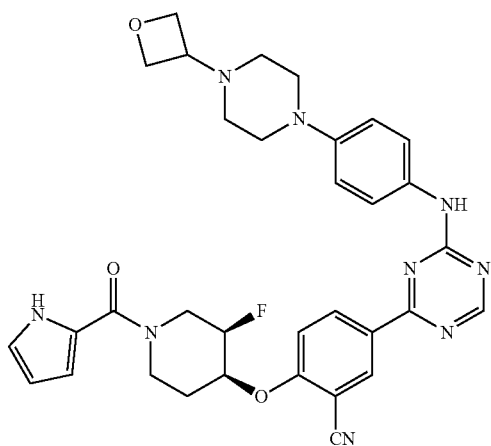 [SMILES: N#Cc1cc(-c2ncnc(Nc3ccc(N4CCN(C5COC5)CC4)cc3)n2)ccc1O[C@H]1CCN(C(=O)c2ccc[nH]2)C[C@H]1F]

The title compound was prepared following the same procedure reported in Example 138 by coupling 1-(tert-butoxycarbonyl)-1H-pyrrole-2-carboxylic acid to 2-(((3R,4S)-3-fluoropiperidin-4-yl)oxy)-5-(4-((4-(4-(oxetan-3-yl)piperazin-1-yl)phenyl)amino)-1,3,5-triazin-2-yl)benzonitrile instead of 2-cyanoacetic acid. LCMS-ESI$^+$ (m/z): [M+H]$^+$ calcd for $C_{33}H_{34}FN_9O_3$: 624.3: found:624.4 $^1$H NMR (400 MHz, DMSO-d$_6$) δ 11.49 (d, J=3.4 Hz, 1H), 10.31-10.06 (m, 1H), 8.75 (s, 1H), 8.69-8.45 (m, 2H), 7.64 (d, J=9.2 Hz, 3H), 7.06 (d, J =10.8 Hz, 2H), 6.89 (td, J=2.8, 1.4 Hz, 1H), 6.53 (t, J=2.6 Hz, 1H), 6.12 (q, J=2.7 Hz, 1H), 5.26-5.07 (m, 2H), 4.77 (d, J=6.5 Hz, 5H), 4.48 (t, J=15.0 Hz, 3H), 4.37-4.08 (m, 2H), 3.63 (dd, J=31.2, 14.1 Hz, 1H), 3.35 (s, 1H), 3.13-2.91 (m, 5H), 2.14-1.87 (m, 2H).

Example 142

2-(((3R,4S)-3-fluoro-1-(1H-imidazole-2-carbonyl)piperidin-4-yl)oxy)-5-(4-((4-(4-(oxetan-3-yl)piperazin-1-yl)phenyl)amino)-1,3,5-triazin-2-yl)benzonitrile

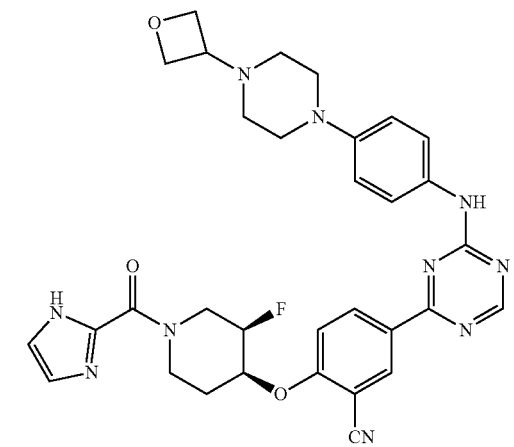 [SMILES: N#Cc1cc(-c2ncnc(Nc3ccc(N4CCN(C5COC5)CC4)cc3)n2)ccc1O[C@H]1CCN(C(=O)c2ncc[nH]2)C[C@H]1F]

The title compound was prepared following the same procedure reported in Example 138 by coupling 1H-imidazole-2-carboxylic acid to 2-(((3R,4S)-3-fluoropiperidin-4-yl)oxy)-5-(4-((4-(4-(oxetan-3-yl)piperazin-1-yl)phenyl)amino)-1,3,5-triazin-2-yl)benzonitrile instead of 2-cyanoacetic acid. LCMS-ESI$^+$ (m/z): [M+H]$^+$ calcd for $C_{37}H_{33}FN_{10}O_3$: 625.3: found:625.4 $^1$H NMR (400 MHz, DMSO-d$_6$) δ 10.19 (d, J=20.4 Hz, 1H), 8.75 (s, 1H), 8.66-8.46 (m, 2H), 7.63 (t, J=11.3 Hz, 3H), 7.31-7.15 (m, 2H), 7.05 (s, 2H), 5.71 (d, J=17.7 Hz, 1H), 5.17 (td, J=46.5, 45.7, 12.7 Hz, 3H), 4.91-4.70 (m, 5H), 4.49 (d, J=37.3 Hz, 3H), 4.30 (d, J=13.0 Hz, 1H), 4.06 (dd, J=31.3, 14.4 Hz, 1H), 3.90 (d, J=37.2 Hz, 1H), 3.67-3.42 (m, 1H), 3.28 (t, J=11.5 Hz, 1H), 3.15 (s, 2H), 2.19-1.83 (m, 3H), 1.23 (q, J=7.1, 6.6 Hz, 1H).

Example 143

2-(((3R,4S)-3-fluoro-1-(1H-1,2,3-triazole-5-carbonyl)piperidin-4-yl)oxy)-5-(4-((4-(4-(oxetan-3-yl)piperazin-1-yl)phenyl)amino)-1,3,5-triazin-2-yl)benzonitrile

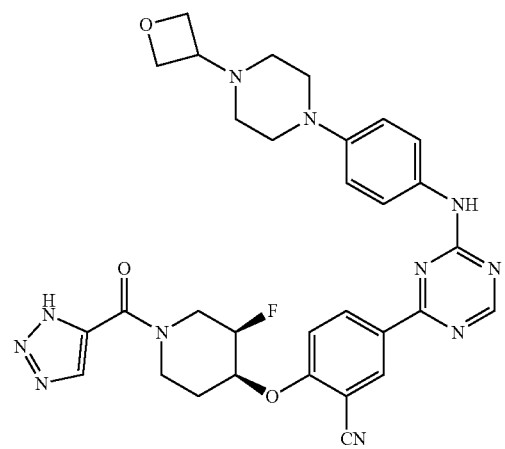 [SMILES: N#Cc1cc(-c2ncnc(Nc3ccc(N4CCN(C5COC5)CC4)cc3)n2)ccc1O[C@H]1CCN(C(=O)c2cnn[nH]2)C[C@H]1F]

The title compound was prepared following the same procedure reported in Example 138 by coupling 1H-1,2,3-triazole-5-carboxylic acid to 2-(((3R,4S)-3-fluoropiperidin-4-yl)oxy)-5-(4-((4-(4-(oxetan-3-yl)piperazin-1-yl)phenyl)amino)-1,3,5-triazin-2-yl)benzonitrile instead of 2-cyanoacetic acid. LCMS-ESI$^+$ (m/z): calcd for $C_{31}H_{32}FN_{11}O_3$: 626.3: found:626.5 $^1$H NMR (400 MHz, DMSO-d$_6$) δ 10.18 (d, J=21.7 Hz, 1H), 8.75 (s, 1H), 8.68-8.41 (m, 3H), 7.62 (t, J=12.4 Hz, 4H), 7.19-6.91 (m, 2H), 5.30-4.94 (m, 3H), 4.87-4.65 (m, 5H), 4.65-4.21 (m, 3H), 3.81 (s, 1H), 3.53 (dd, J=31.0, 14.3 Hz, 1H), 3.30 (t, J=12.4 Hz, 1H), 3.08 (s, 5H), 2.17-1.83 (m, 2H).

Example 144

2-(((3R,4S)-3-fluoro-1-(4H-1,2,4-triazole-3-carbonyl)piperidin-4-yl)oxy)-5-(4-((4-(4-(oxetan-3-yl)piperazin-1-yl)phenyl)amino)-1,3,5-triazin-2-yl)benzonitrile

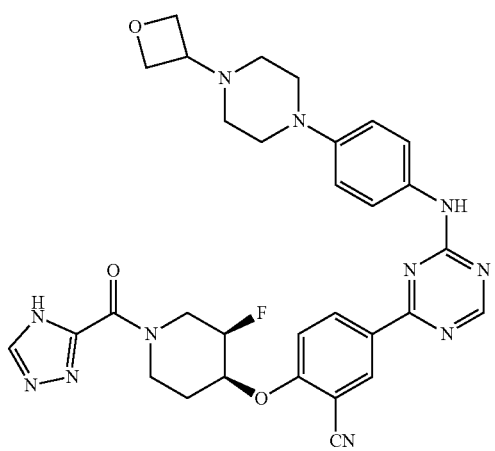 [SMILES: N#Cc1cc(-c2ncnc(Nc3ccc(N4CCN(C5COC5)CC4)cc3)n2)ccc1O[C@H]1CCN(C(=O)c2nnc[nH]2)C[C@H]1F]

The title compound was prepared following the same procedure reported in Example 138 by coupling 4H-1,2,4-triazole-3-carboxylic acid to 2-(((3R,4S)-3-fluoropiperidin-4-yl)oxy)-5-(4-((4-(4-(oxetan-3-yl)piperazin-1-yl)phenyl)amino)-1,3,5-triazin-2-yl)benzonitrile instead of 2-cyanoacetic acid. LCMS-ESI$^+$ (m/z): [M+H]$^+$ calcd for $C_{31}H_{32}FN_{11}O_3$: 626.3: found:626.4 $^1$H NMR (400 MHz, DMSO-d$_6$) δ 10.18 (d, J=21.1 Hz, 1H), 8.75 (s, 1H), 8.67-8.44 (m, 2H), 8.37 (s, 1H), 7.63 (t, J=10.0 Hz, 4H), 7.04 (s, 2H), 5.11 (dd, J=50.3, 23.7 Hz, 3H), 4.75 (d, J=6.7 Hz, 5H), 4.62-4.24 (m, 3H), 3.96-3.73 (m, 2H), 3.54 (dd, J=34.4, 17.7 Hz, 2H), 3.35-3.18 (m, 2H), 3.02 (d, J=36.8 Hz, 2H), 2.17-1.82 (m, 2H).

Example 145

2-(((3R,4S)-3-fluoro-1-(1H-pyrazole-5-carbonyl)piperidin-4-yl)oxy)-5-(4-((4-(4-(oxetan-3-yl)piperazin-1-yl)phenyl)amino)-1,3,5-triazin-2-yl)benzonitrile

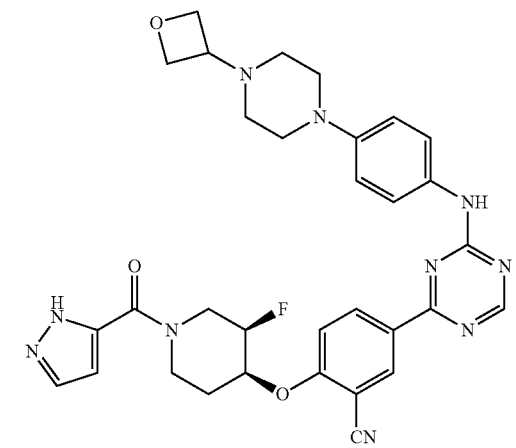 [SMILES: N#Cc1cc(-c2ncnc(Nc3ccc(N4CCN(C5COC5)CC4)cc3)n2)ccc1O[C@H]1CCN(C(=O)c2ccn[nH]2)C[C@H]1F]

The title compound was prepared following the same procedure reported in Example 138 by coupling 1H-pyrazole-5-carboxylic acid to 2-(((3R,4S)-3-fluoropiperidin-4-yl)oxy)-5-(4-((4-(4-(oxetan-3-yl)piperazin-1-yl)phenyl)amino)-1,3,5-triazin-2-yl)benzonitrile instead of 2-cyanoacetic acid. LCMS-ESI$^+$ (m/z): [M+H]$^+$ calcd for $C_{32}H_{33}FN_{10}O_3$: 625.3: found:625.5 $^1$H NMR (400 MHz, DMSO-d$_6$) δ 10.18 (d, J=21.0 Hz, 1H), 8.75 (s, 1H), 8.69-8.42 (m, 2H), 7.79 (s, 1H), 7.62 (t, J=11.2 Hz, 4H), 7.04 (s, 2H), 6.60 (d, J=2.3 Hz, 1H), 5.28-4.92 (m, 3H), 4.75 (d, J=6.3 Hz, 5H), 4.61-4.17 (m, 2H), 3.94-3.37 (m, 4H), 3.15 (s, 5H), 1.98 (d, J=36.7 Hz, 2H).

Example 146

2-(((3R,4S)-3-fluoro-1-(1H-imidazole-5-carbonyl)piperidin-4-yl)oxy)-5-(4-((4-(4-(oxetan-3-yl)piperazin-1-yl)phenyl)amino)-1,3,5-triazin-2-yl)benzonitrile

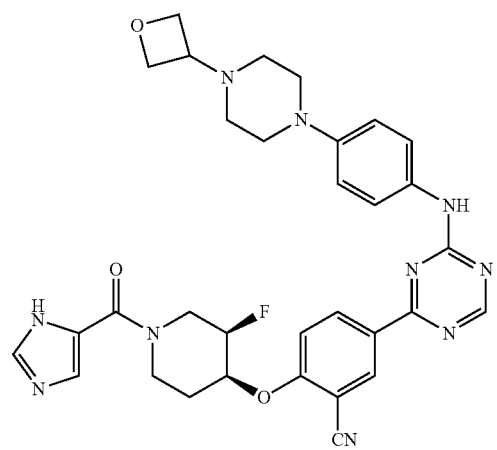 [SMILES: N#Cc1cc(-c2ncnc(Nc3ccc(N4CCN(C5COC5)CC4)cc3)n2)ccc1O[C@H]1CCN(C(=O)c2cnc[nH]2)C[C@H]1F]

The title compound was prepared following the same procedure reported in Example 138 by coupling 1H-imidazole-5-carboxylic acid to 2-(((3R,4S)-3-fluoropiperidin-4-yl)oxy)-5-(4-((4-(4-(oxetan-3-yl)piperazin-1-yl)phenyl)amino)-1,3,5-triazin-2-yl)benzonitrile instead of 2-cyanoacetic acid. LCMS-ESI$^+$ (m/z): [M+H]$^+$ calcd for $C_{32}H_{33}FN_{10}O_3$: 625.3: found:625.4

$^1$H NMR (400 MHz, DMSO-d$_6$) δ 10.18 (d, J=19.9 Hz, 1H), 8.75 (s, 1H), 8.65-8.30 (m, 3H), 7.88 (s, 1H), 7.63 (t, J=9.2 Hz, 4H), 7.04 (s, 3H), 5.31-4.94 (m, 3H), 4.76 (d, J=6.6 Hz, 5H), 4.41 (t, J=6.8 Hz, 3H), 3.24 (s, 8H), 2.05 (t, J=7.4 Hz, 2H).

Example 147

2-(((3R,4S)-3-fluoro-1-(1-methyl-1H-1,2,3-triazole-4-carbonyl)piperidin-4-yl)oxy)-5-(4-((4-(4-(oxetan-3-yl)piperazin-1-yl)phenyl)amino)-1,3,5-triazin-2-yl)benzonitrile

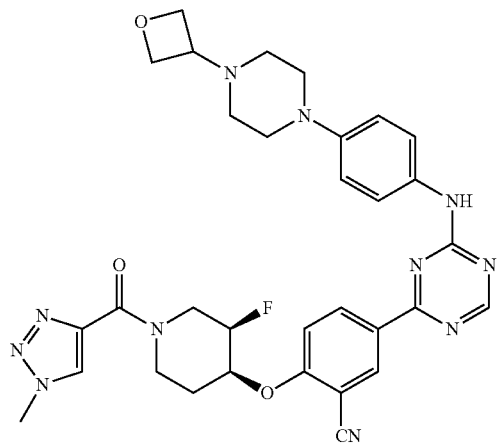 [SMILES: Cn1cc(C(=O)N2CC[C@H](Oc3ccc(-c4ncnc(Nc5ccc(N6CCN(C7COC7)CC6)cc5)n4)cc3C#N)[C@H](F)C2)nn1]

The title compound was prepared following the same procedure reported in Example 138 by coupling 1-methyl-1H-1,2,3-triazole-4-carboxylic acid to 2-(((3R,4S)-3-fluoropiperidin-4-yl)oxy)-5-(4-((4-(4-(oxetan-3-yl)piperazin-1-yl)phenyl)amino)-1,3,5-triazin-2-yl)benzonitrile instead of 2-cyanoacetic acid. LCMS-ESI$^+$ (m/z): [M+H]$^+$ calcd for $C_{32}H_{34}FN_{11}O_3$: 640.3: found:640.4 $^1$H NMR (400 MHz, DMSO-d$_6$) δ 10.28-10.09 (m, 1H), 8.75 (s, 1H), 8.66-8.55 (m, 2H), 8.52 (s, 2H), 7.74-7.49 (m, 2H), 7.04 (s, 2H), 5.10 (dd, J=49.4, 20.3 Hz, 3H), 4.76 (d, J=6.6 Hz, 4H), 4.68-4.25 (m, 2H), 4.08 (s, 3H), 3.98-3.61 (m, 5H), 3.18 (dt, J=47.1, 25.8 Hz, 5H), 2.18-1.81 (m, 2H).

Example 148

2-((3,3-difluoropiperidin-4-yl)oxy)-5-(4-((4-(4-(oxetan-3-yl)piperazin-1-yl)phenyl)amino)-1,3,5-triazin-2-yl)benzonitrile

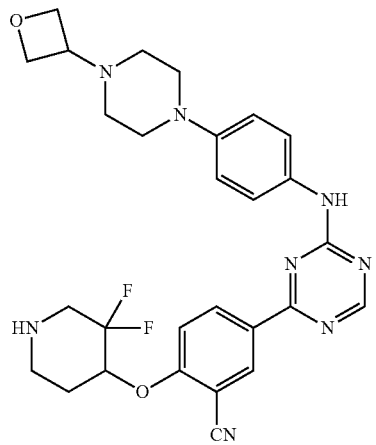

Step-1: tert-butyl 3,3-difluoro-4-hydroxypiperidine-1-carboxylate (154 mg, 0.46 mmol) was added Me-THF (9 mL) under argon atmosphere and cooled at 0° C. To well stirred solution was added potassium tert-butoxide (73 mg) at one portion and stirred for 30 minutes. To well stirred solution was added 2-fluoro-5-(4-((4-(4-(oxetan-3-yl)piperazin-1-yl)phenyl)amino)-1,3,5-triazin-2-yl)benzonitrile (200 mg, 0.46 mmol) and warmed to room temperature over 10 min. The reaction was heated at 80° C. overnight. The reaction was cooled to RT and diluted with DCM, quenched with water (5-8 mL) and the mixture was adsorbed on silica gel, the solvent concentrated to dryness. The crude product was purified by flash column chromatography on silica gel to afford tert-butyl 4-(2-cyano-4-(4-((4-(4-(oxetan-3-yl)piperazin-1-yl)phenyl)amino)-1,3,5-triazin-2-yl)phenoxy)-3,3-difluoropiperidine-1-carboxylate. LCMS-ESI$^+$ (m/z): [M+H]$^+$ calcd for $C_{33}H_{38}F_2N_8O_4$: 649.3; found: 649.2.

Step-2: tert-butyl 4-(2-cyano-4-(4-((4-(4-(oxetan-3-yl)piperazin-1-yl)phenyl)amino)-1,3,5-triazin-2-yl)phenoxy)-3,3-difluoropiperidine-1-carboxylate (90 mg) was dissolved in 20% TFA/DCM (5 mL) and stirred at room temperature for 1 h. The solvent was concentrated under reduced pressure to afford 2-((3,3-difluoropiperidin-4-yl)oxy)-5-(4-((4-(4-(oxetan-3-yl)piperazin-1-yl)phenyl)amino)-1,3,5-triazin-2-yl)benzonitrile. LCMS-ESI$^+$ (m/z): [M+H]$^+$ calcd for $C_{28}H_{30}F_2N_8O_2$: 549.2: found:549.4 $^1$H NMR (400 MHz, DMSO-d$_6$) δ 10.24 (s, 1H), 9.62 (s, 1H), 8.76 (s, 1H), 8.68-8.46 (m, 2H), 7.64 (d, J=9.2 Hz, 3H), 7.04 (s, 2H), 5.42 (ddt, J=12.8, 7.9, 3.8 Hz, 1H), 4.74 (d, J=6.3 Hz, 4H), 3.75 (qq, J=13.4, 6.5, 5.6 Hz, 6H), 3.39-2.99 (m, 7H), 2.27 (ddd, J=78.6, 13.0, 7.2 Hz, 2H).

Example 149 and Example 150

(S)-2-((3,3-difluoropiperidin-4-yl)oxy)-5-(4-((4-(4-(oxetan-3-yl)piperazin-1-yl)phenyl)amino)-1,3,5-triazin-2-yl)benzonitrile and (R)-2-((3,3-difluoropiperidin-4-yl)oxy)-5-(4-((4-(4-(oxetan-3-yl)piperazin-1-yl)phenyl)amino)-1,3,5-triazin-2-yl)benzonitrile

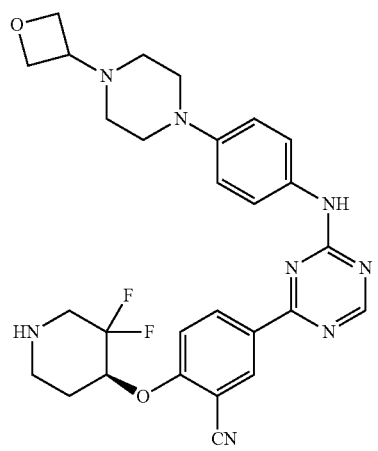

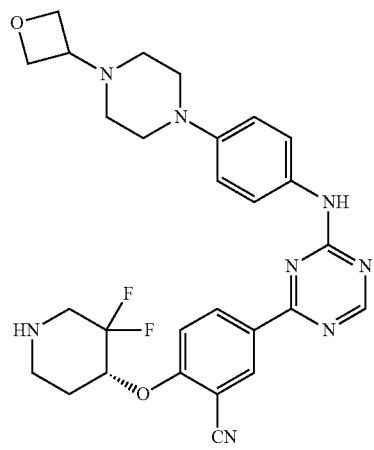 [SMILES: N#Cc1cc(-c2ncnc(Nc3ccc(N4CCN(C5COC5)CC4)cc3)n2)ccc1OC1CCNCC1(F)F]

Racemic mixtures Example 148 was separated by chiral separation using chiral column to afford title compounds and the stereochemistry were assigned tentatively. Peak A: LCMS-ESI⁺ (m/z): [M+H]⁺ calcd for $C_{28}H_{30}F_2N_8O_2$ 549.2.2: found:549.4 ¹H NMR (400 MHz, DMSO-d₆) δ 10.24 (s, 1H), 9.62 (s, 1H), 8.76 (s, 1H), 8.68-8.46 (m, 2H), 7.64 (d, J=9.2 Hz, 3H), 7.04 (s, 2H), 5.42 (ddt, J=12.8, 7.9, 3.8 Hz, 1H), 4.74 (d, J=6.3 Hz, 4H), 3.75 (qq, J=13.4, 6.5, 5.6 Hz, 6H), 3.39-2.99 (m, 7H), 2.27 (ddd, J=78.6, 13.0, 7.2 Hz, 2H). Peak B: LCMS-ESI⁺ (m/z): [M+H]⁺ calcd for $C_{28}H_{30}F_2N_8O_2$ 549.2.2: found:549.4

Example 151

2-((3,3-difluoro-1-(2-hydroxyacetyl)piperidin-4-yl)oxy)-5-(4-((4-(4-(oxetan-3-yl)piperazin-1-yl)phenyl)amino)-1,3,5-triazin-2-yl)benzonitrile

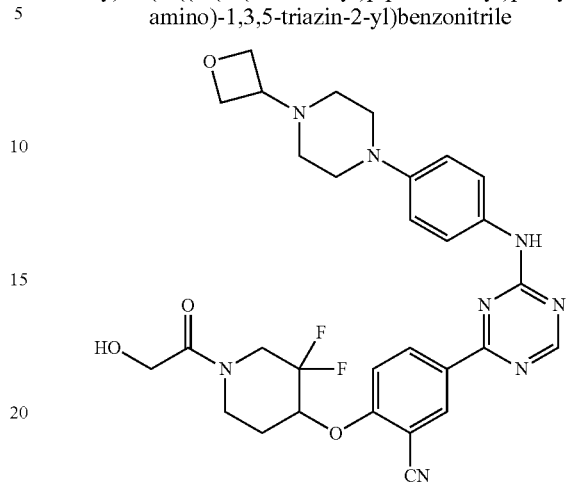

To solution of 2-((3,3-difluoropiperidin-4-yl)oxy)-5-(4-((4-(4-(oxetan-3-yl)piperazin-1-yl)phenyl)amino)-1,3,5-triazin-2-yl)benzonitrile (75 mg, 0.14 mmol), 2-hydroxyacetic acid (21 mg, 0.27 mmol), HATU (103 mg, 0.27 mmol) in DMF (4 mL) was added DIPEA (0.28 mL) in a 25 mL round bottom flask. This reaction mixture was stirred at room temperature overnight. The solvent was concentrated and the crude product purified via prep HPLC (5-95% acetonitrile in water, 0.1% trifluoroacetic acid buffer) to isolate 2-((3,3-difluoro-1-(2-hydroxyacetyl)piperidin-4-yl)oxy)-5-(4-((4-(4-(oxetan-3-yl)piperazin-1-yl)phenyl)amino)-1,3,5-triazin-2-yl)benzonitrile. LCMS-ESI⁺ (m/z): [M+H]⁺ calcd for $C_{30}H_{32}F_2N_8O_4$: 607.2: found:607.4 ¹H NMR (400 MHz, DMSO-d₆) δ 10.20 (d, J=20.9 Hz, 1H), 8.76 (s, 1H), 8.67-8.41 (m, 2H), 7.66 (d, J=9.3 Hz, 2H), 7.05 (d, J=10.4 Hz, 3H), 5.36 (ddd, J=12.7, 8.3, 4.1 Hz, 1H), 4.76 (d, J=6.6 Hz, 5H), 4.42 (s, 1H), 4.16 (d, J=14.5 Hz, 3H), 3.96-3.31 (m, 6H), 3.15 (s, 5H), 2.06 (d, J=64.9 Hz, 2H).

Example 152 and 153

(S)-2-((3,3-difluoro-1-(2-hydroxyacetyl)piperidin-4-yl)oxy)-5-(4-((4-(4-(oxetan-3-yl)piperazin-1-yl)phenyl)amino)-1,3,5-triazin-2-yl)benzonitrile and (R)-2-((3,3-difluoro-1-(2-hydroxyacetyl)piperidin-4-yl)oxy)-5-(4-((4-(4-(oxetan-3-yl)piperazin-1-yl)phenyl)amino)-1,3,5-triazin-2-yl)benzonitrile

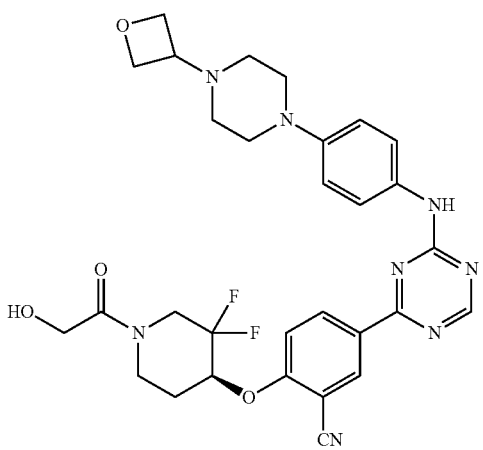 [SMILES: N#Cc1cc(-c2ncnc(Nc3ccc(N4CCN(C5COC5)CC4)cc3)n2)ccc1OC1CCN(C(=O)CO)CC1(F)F]

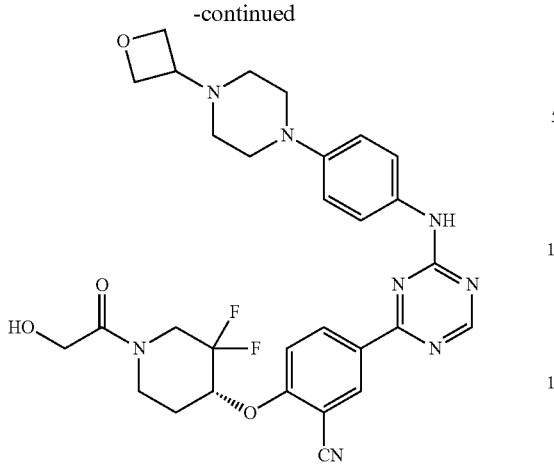

Racemic mixtures Example 151 was separated by chiral separation using chiral column to afford title compounds and the stereochemistry were assigned tentatively Peak A: LCMS-ESI+ (m/z): [M+H]+ calcd for $C_{30}H_{32}F_2N_8O_4$: 607.2: found:607.4. Peak B LCMS-ESI+ (m/z): [M+H]+ calcd for $C_{30}H_{32}F_2N_8O_4$: 607.2: found:607.4

Example 154

2-((3,3-difluoro-1-((S)-2-hydroxypropanoyl)piperidin-4-yl)oxy)-5-(4-((4-(4-(oxetan-3-yl)piperazin-1-yl)phenyl)amino)-1,3,5-triazin-2-yl)benzonitrile

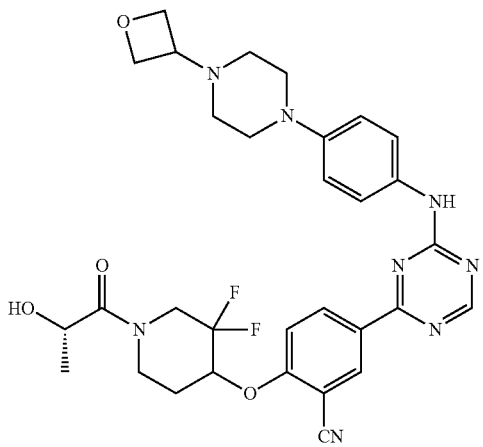 [SMILES: C[C@H](O)C(=O)N1CCC(Oc2ccc(-c3ncnc(Nc4ccc(N5CCN(C6COC6)CC5)cc4)n3)cc2C#N)C(F)(F)C1]

The title compound was prepared following the same procedure reported in Example 151 by coupling (S)-2-hydroxypropanoic acid to 2-((3,3-difluoropiperidin-4-yl)oxy)-5-(4-((4-(4-(oxetan-3-yl)piperazin-1-yl)phenyl)amino)-1,3,5-triazin-2-yl)benzonitrile. LCMS-ESI+ (m/z): [M+H]+ calcd for $C_{31}H_{34}F_2N_8O_4$: 621.2: found:621.4 1H NMR (400 MHz, DMSO-d6) δ 10.20 (d, J=20.7 Hz, 1H), 8.76 (s, 1H), 8.68-8.45 (m, 2H), 7.75-7.49 (m, 3H), 7.05 (d, J=10.3 Hz, 2H), 5.45-5.29 (m, 1H), 4.76 (d, J=6.8 Hz, 4H), 4.57-4.32 (m, 3H), 4.17-3.61 (m, 8H) 3.15-2.92 (m, 3H), 2.23-1.80 (m, 3H), 1.21 (d, J=6.5 Hz, 3H).

Example 155 and Example 156

2-(((S)-3,3-difluoro-1-((S)-2-hydroxypropanoyl)piperidin-4-yl)oxy)-5-(4-((4-(4-(oxetan-3-yl)piperazin-1-yl)phenyl)amino)-1,3,5-triazin-2-yl)benzonitrile and 2-(((R)-3,3-difluoro-1-((S)-2-hydroxypropanoyl)piperidin-4-yl)oxy)-5-(4-((4-(4-(oxetan-3-yl)piperazin-1-yl)phenyl)amino)-1,3,5-triazin-2-yl)benzonitrile

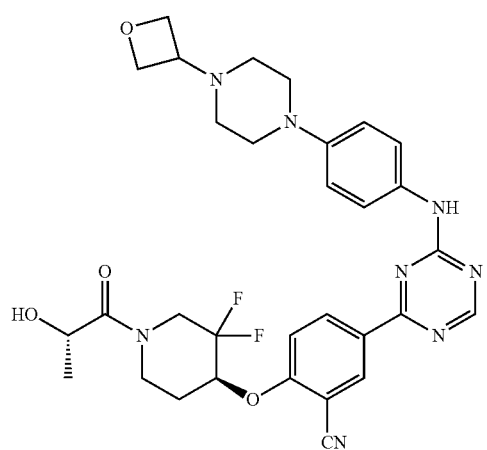

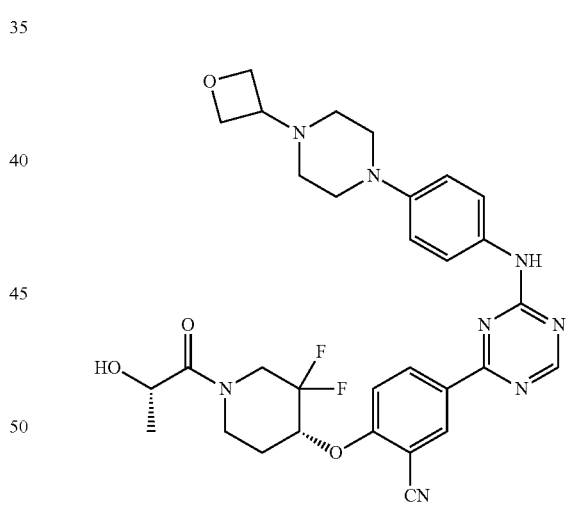

Racemic mixtures Example 154 was separated by chiral separation using chiral column to afford title compounds and the stereochemistry were assigned tentatively Peak A: LCMS-ESI+ (m/z): [M+H]+ calcd for $C_{31}H_{34}F_2N_9O_3$ 620.3: found:620.4 1H NMR (400 MHz, DMSO-d6) δ 10.20 (d, J=20.7 Hz, 1H), 8.76 (s, 1H), 8.66-8.45 (m, 2H), 7.75-7.49 (m, 3H), 7.05 (d, J=10.3 Hz, 2H), 5.45-5.29 (m, 1H), 4.76 (d, J=6.8 Hz, 4H), 4.57-4.32 (m, 3H), 4.24-3.49 (m, 8H), 3.15-2.92 (m, 3H), 2.23-1.80 (m, 2H), 1.21 (d, J=6.5 Hz, 3H). Peak B: LCMS-ESI+ (m/z): [M+H]+ calcd for $C_{31}H_{34}F_2N_9O_3$ 621.3: found:621.4

Example 157

2-((3,3-difluoro-1-((R)-2-hydroxypropanoyl)piperidin-4-yl)oxy)-5-(4-((4-(4-(oxetan-3-yl)piperazin-1-yl)phenyl)amino)-1,3,5-triazin-2-yl)benzonitrile

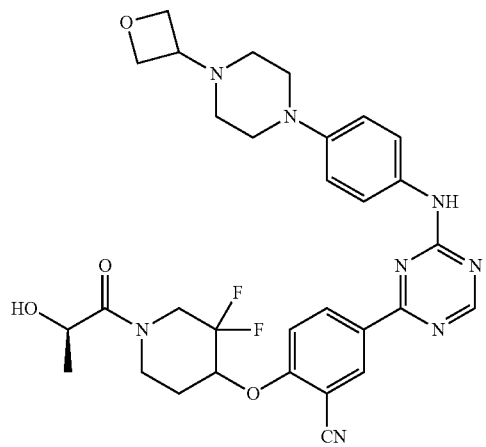 [SMILES: C[C@@H](O)C(=O)N1CCC(Oc2ccc(-c3ncnc(Nc4ccc(N5CCN(C6COC6)CC5)cc4)n3)cc2C#N)C(F)(F)C1]

The title compound was prepared as mixture of isomers following the same procedure reported in Example 151 by coupling (R)-2-hydroxypropanoic acid to 2-((3,3-difluoropiperidin-4-yl)oxy)-5-(4-((4-(4-(oxetan-3-yl)piperazin-1-yl)phenyl)amino)-1,3,5-triazin-2-yl)benzonitrile. LCMS-ESI⁺ (m/z): [M+H]⁺ calcd for $C_{31}H_{34}F_2N_8O_4$: 621.2: found:621.4 ¹H NMR (400 MHz, DMSO-d₆) δ 10.20 (d, J=21.3 Hz, 1H), 8.76 (s, 1H), 8.66-8.46 (m, 2H), 7.76-7.51 (m, 3H), 7.06 (d, J=8.9 Hz, 2H), 5.49-5.26 (m, 2H), 4.77 (dd, J=6.4, 2.1 Hz, 5H), 4.49 (q, J=9.1, 7.7 Hz, 3H), 4.18 (d, J=15.8 Hz, 2H), 4.16-3.45 (m, 5H) 3.07 (s, 2H), 2.25-1.78 (m, 3H), 1.21 (d, J=6.5 Hz, 3H).

Example 158 and Example 159

2-(((S)-3,3-difluoro-1-((R)-2-hydroxypropanoyl)piperidin-4-yl)oxy)-5-(4-((4-(4-(oxetan-3-yl)piperazin-1-yl)phenyl)amino)-1,3,5-triazin-2-yl)benzonitrile and 2-(((R)-3,3-difluoro-1-((R)-2-hydroxypropanoyl)piperidin-4-yl)oxy)-5-(4-((4-(4-(oxetan-3-yl)piperazin-1-yl)phenyl)amino)-1,3,5-triazin-2-yl)benzonitrile

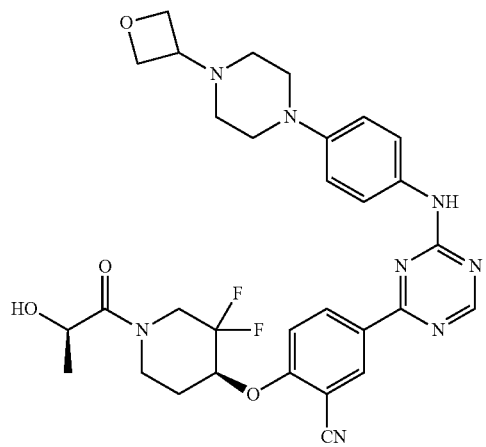

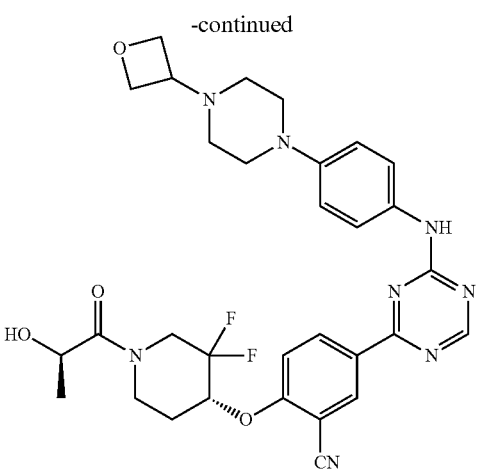

Racemic mixtures Example 154 was separated by chiral separation using chiral column to afford title compounds and the stereochemistry were assigned tentatively Peak A: LCMS-ESI⁺ (m/z): [M+H]⁺ calcd for $C_{31}H_{34}F_2N_9O_3$ 621.2: found:621.4 ¹H NMR (400 MHz, DMSO-d₆) δ 10.20 (d, J=21.3 Hz, 1H), 8.76 (s, 1H), 8.66-8.46 (m, 2H), 7.76-7.51 (m, 3H), 7.06 (d, J=8.9 Hz, 2H), 5.49-5.26 (m, 2H), 4.77 (dd, J=6.4, 2.1 Hz, 5H), 4.49 (q, J=9.1, 7.7 Hz, 3H), 4.18 (d, J=15.8 Hz, 2H), 3.89 (d, J=45.9 Hz, 3H), 3.54 (d, J=70.9 Hz, 3H), 3.07 (s, 2H), 2.25-1.78 (m, 2H), 1.21 (d, J=6.5 Hz, 3H). Peak B: LCMS-ESI⁺ (m/z): [M+H]⁺ calcd for $C_{31}H_{34}F_2N_9O_3$ 621.3: found:621.4

Example 160

(S)-2-((1-(2-cyanoacetyl)-3,3-difluoropiperidin-4-yl)oxy)-5-(4-((4-(4-(oxetan-3-yl)piperazin-1-yl)phenyl)amino)-1,3,5-triazin-2-yl)benzonitrile

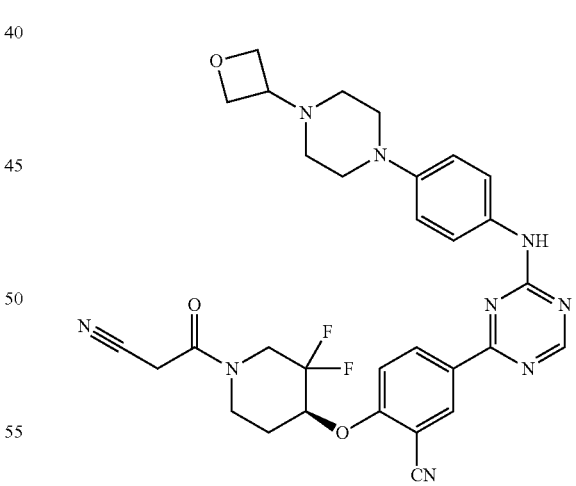

The title compound was prepared following the same procedure reported in Example 151 by coupling 2-cyanoacetic acid to (S)-2-((3,3-difluoropiperidin-4-yl)oxy)-5-(4-((4-(4-(oxetan-3-yl)piperazin-1-yl)phenyl)amino)-1,3,5-triazin-2-yl)benzonitrile. LCMS-ESI⁺ (m/z): [M+H]⁺ calcd for $C_{31}H_{31}F_2N_9O_3$: 616.3: found:616.4 ¹H NMR (400 MHz, DMSO-d₆) δ 10.21 (d, J=23.4 Hz, 1H), 8.76 (s, 1H), 8.70-8.46 (m, 2H), 7.63 (dd, J=20.9, 10.5 Hz, 3H), 7.03 (d, J=10.8 Hz, 2H), 5.37 (ddd, J=12.6, 8.4, 4.2 Hz, 1H), 4.75 (d, J=6.3 Hz, 5H), 4.40 (s, 1H), 4.16 (d, J=38.0 Hz, 3H), 3.96-3.40 (m, 5H), 3.09 (d, J=44.1 Hz, 5H), 2.28-1.79 (m, 2H).

Example 161

(S)-2-((3,3-difluoro-1-(3-hydroxypropanoyl)piperidin-4-yl)oxy)-5-(4-((4-(4-(oxetan-3-yl)piperazin-1-yl)phenyl)amino)-1,3,5-triazin-2-yl)benzonitrile

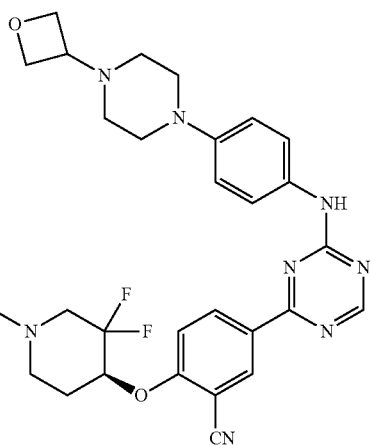

The title compound was prepared following the same procedure reported in Example 151 by coupling 2-hydroxypropionic acid to (S)-2-((3,3-difluoropiperidin-4-yl)oxy)-5-(4-((4-(4-(oxetan-3-yl)piperazin-1-yl)phenyl)amino)-1,3,5-triazin-2-yl)benzonitrile. LCMS-ESI⁺ (m/z): [M+H]⁺ calcd for $C_{31}H_{34}F_2N_8O_4$: 621.3: found:621.4 ¹H NMR (400 MHz, DMSO-$d_6$) δ 10.21 (dd, J=19.7, 6.4 Hz, 1H), 8.76 (s, 1H), 8.69-8.45 (m, 2H), 7.79-7.51 (m, 3H), 7.04 (t, J=9.6 Hz, 2H), 5.46-5.26 (m, 1H), 4.74 (d, J=6.3 Hz, 5H), 4.39 (s, 1H), 4.10 (td, J=15.7, 7.7 Hz, 1H), 3.96-3.67 (m, 3H), 3.64 (t, J=6.5 Hz, 2H), 3.60-3.40 (m, 3H), 3.12-2.90 (m, 3H), 2.56 (dt, J=11.3, 6.4 Hz, 3H), 2.25-1.75 (m, 3H).

Example 162

2-((3,3-difluoro-1-(1H-pyrrole-2-carbonyl)piperidin-4-yl)oxy)-5-(4-((4-(4-(oxetan-3-yl)piperazin-1-yl)phenyl)amino)-1,3,5-triazin-2-yl)benzonitrile

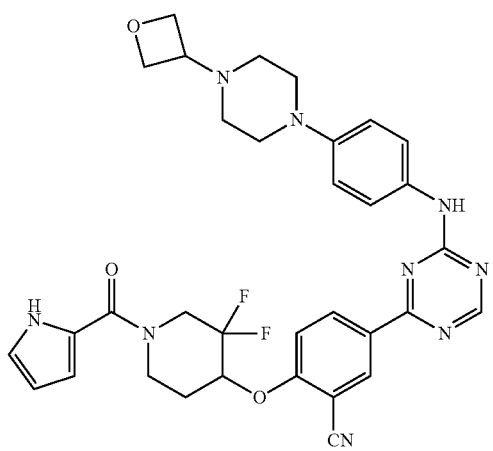 [SMILES: N#Cc1cc(-c2ncnc(Nc3ccc(N4CCN(C5COC5)CC4)cc3)n2)ccc1OC1CCN(C(=O)c2ccc[nH]2)CC1(F)F]

The title compound was prepared following the same procedure reported in Example 151 by coupling 1-(tert-butoxycarbonyl)-1H-pyrrole-2-carboxylic acid to 2-((3,3-difluoropiperidin-4-yl)oxy)-5-(4-((4-(4-(oxetan-3-yl)piperazin-1-yl)phenyl)amino)-1,3,5-triazin-2-yl)benzonitrile. LCMS-ESI⁺ (m/z): [M+H]⁺ calcd for $C_{33}H_{33}F_2N_9O_3$: 642.3: found:642.4 ¹H NMR (400 MHz, DMSO-$d_6$) δ 10.19 (d, J=19.4 Hz, 1H), 8.76 (s, 1H), 8.68-8.34 (m, 2H), 8.23-8.01 (m, 1H), 7.75-7.41 (m, 2H), 7.05 (ddd, J=13.6, 6.6, 3.0 Hz, 3H), 6.93 (td, J=2.7, 1.3 Hz, 1H), 6.59 (ddd, J=3.9, 2.6, 1.4 Hz, 1H), 6.14 (dt, J=3.7. 2.4 Hz, 1H), 5.42 (ddt, J=12.7, 8.3, 4.3 Hz, 1H) 4.74 (d, J=6.3 Hz, 5H), 4.30 (td, J=15.2, 6.6 Hz, 1H), 4.13-3.37 (m, 7H), 3.03 (s, 4H), 2.21 (d, J=13.5 Hz, 1H), 1.98 (d, J=15.2 Hz, 1H).

Example 163

2-((3,3-difluoro-1-(1H-imidazole-2-carbonyl)piperidin-4-yl)oxy)-5-(4-((4-(4-(oxetan-3-yl)piperazin-1-yl)phenyl)amino)-1,3,5-triazin-2-yl)benzonitrile

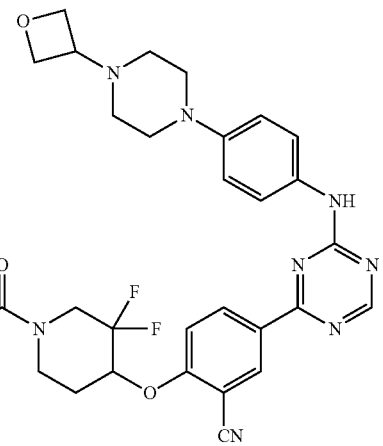

The title compound was prepared following the same procedure reported in Example 16 by coupling 1H-imidazole-2-carboxylic acid to 2-((3,3-difluoropiperidin-4-yl)oxy)-5-(4-((4-(4-(oxetan-3-yl)piperazin-1-yl)phenyl)amino)-1,3,5-triazin-2-yl)benzonitrile. ESI⁺ (m/z): [M+H]⁺ calcd for $C_{32}H_{32}F_2N_{10}O_3$: 643.3: found:643.4 ¹H NMR (400 MHz, DMSO-$d_6$) δ 10.32-10.06 (m, 1H), 8.76 (s, 1H), 8.70-8.44 (m, 2H), 7.65 (dd, J=28.2, 10.3 Hz, 3H), 7.21 (s, 2H), 7.11-6.91 (m, 3H), 5.45 (d, J=19.6 Hz, 2H), 4.89 (d, J=18.3 Hz, 1H), 4.76 (d, J=6.4 Hz, 5H), 4.36 (d, J=47.4 Hz, 2H), 4.02 (dd, J=19.6, 12.1 Hz, 1H), 3.92-3.57 (m, 2H), 3.17 (d, J=101.5 Hz, 4H), 2.78 (s, 1H), 2.27 (d, J=32.5 Hz, 1H), 2.13-1.85 (m, 1H).

Example 164

(S)-2-((3,3-difluoro-1-(1H-pyrazole-5-carbonyl)piperidin-4-yl)oxy)-5-(4-((4-(4-(oxetan-3-yl)piperazin-1-yl)phenyl)amino)-1,3,5-triazin-2-yl)benzonitrile

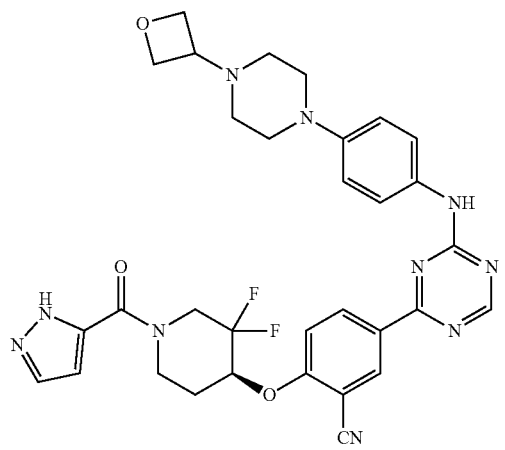 [SMILES: N#Cc1cc(-c2ncnc(Nc3ccc(N4CCN(C5COC5)CC4)cc3)n2)ccc1O[C@H]1CCN(C(=O)c2ccn[nH]2)CC1(F)F]

The title compound was prepared following the same procedure reported in Example 151 by coupling 1H-pyrazole-5-carboxylic acid to (S)-2-((3,3-difluoropiperidin-4-yl)oxy)-5-(4-((4-(4-(oxetan-3-yl)piperazin-1-yl)phenyl)amino)-1,3,5-triazin-2-yl)benzonitrile. LCMS-ESI+ (m/z): [M+H]+ calcd for $C_{32}H_{32}F_2N_{10}O_3$: 643.3: found:643.4 $^1$H NMR (400 MHz, DMSO-$d_6$) δ 13.30 (s, 1H), 10.20 (d, J=20.9 Hz, 1H), 8.76 (s, 1H), 8.67-8.41 (m, 2H), 7.83 (d, J=2.4 Hz, 1H), 7.76-7.50 (m, 3H), 7.04 (s, 2H), 6.68 (d, J=13.5 Hz, 1H), 5.41 (s, 1H), 4.75 (d, J=6.3 Hz, 5H), 4.35 (d, J=52.6 Hz, 3H), 4.10-3.55 (m, 4H), 3.09 (d, J=48.5 Hz, 5H), 2.25 (d, J=45.3 Hz, 1H), 2.02 (d, J=37.2 Hz, 1H).

Example 165

(S)-2-((3,3-difluoro-1-(1H-1,2,3-triazole-5-carbonyl)piperidin-4-yl)oxy)-5-(4-((4-(4-(oxetan-3-yl)piperazin-1-yl)phenyl)amino)-1,3,5-triazin-2-yl)benzonitrile

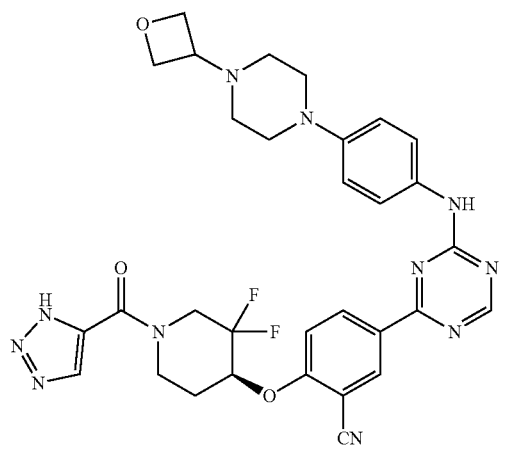 [SMILES: N#Cc1cc(-c2ncnc(Nc3ccc(N4CCN(C5COC5)CC4)cc3)n2)ccc1O[C@H]1CCN(C(=O)c2cnn[nH]2)CC1(F)F]

The title compound was prepared following the same procedure reported in Example 151 by coupling 1H-1,2,3-triazole-5-carboxylic acid to (S)-2-((3,3-difluoropiperidin-4-yl)oxy)-5-(4-((4-(4-(oxetan-3-yl)piperazin-1-yl)phenyl)amino)-1,3,5-triazin-2-yl)benzonitrile. LCMS-ESI+ (m/z): [M+H]+ calcd for $C_{31}H_{31}F_2N_{11}O_3$: 644.3: found:644.4 $^1$H NMR (400 MHz, DMSO-$d_6$) δ 10.32-10.05 (m, 1H), 8.76 (s, 1H), 8.69-8.46 (m, 2H), 7.76-7.49 (m, 4H), 7.16-6.93 (m, 3H), 5.44 (t, J=11.5 Hz, 1H), 4.75 (d, J=6.5 Hz, 5H), 4.57-4.19 (m, 3H), 3.98 (d, J=25.7 Hz, 2H), 3.91-3.58 (m, 1H), 3.43 (s, 1H), 3.05 (s, 5H), 2.23 (s, 1H), 2.13-1.88 (m, 1H).

Example 166

(S)-2-((3,3-difluoro-1-(4H-1,2,4-triazole-3-carbonyl)piperidin-4-yl)oxy)-5-(4-((4-(4-(oxetan-3-yl)piperazin-1-yl)phenyl)amino)-1,3,5-triazin-2-yl)benzonitrile

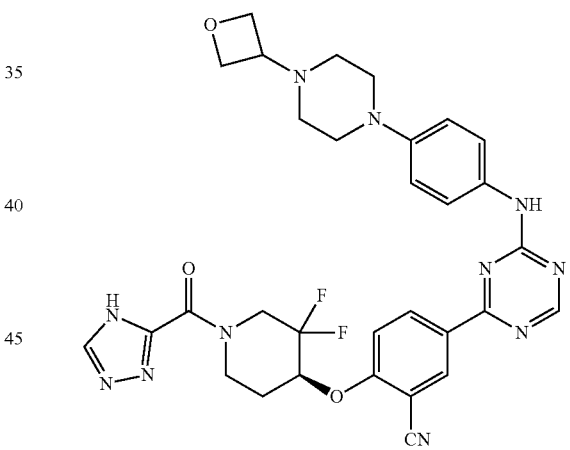

The title compound was prepared following the same procedure reported in Example 151 by coupling 4H-1,2,4-triazole-3-carboxylic acid to (S)-2-((3,3-difluoropiperidin-4-yl)oxy)-5-(4-((4-(4-(oxetan-3-yl)piperazin-1-yl)phenyl)amino)-1,3,5-triazin-2-yl)benzonitrile. LCMS-ESI+ (m/z): [M+H]+ calcd for $C_{31}H_{31}F_2N_{11}O_3$: 644.3: found:644.4 $^1$H NMR (400 MHz, DMSO-$d_6$) δ 10.16 (d, J=21.6 Hz, 1H), 8.71 (s, 1H), 8.64-8.40 (m, 2H), 7.59 (dd, J=26.9, 10.9 Hz, 4H), 7.01 (d, J=10.9 Hz, 3H), 5.38 (d, J=12.8 Hz, 1H), 4.71 (d, J=6.3 Hz, 5H), 4.46-4.16 (m, 2H), 3.97 (d, J=15.4 Hz, 1H), 3.83-3.28 (m, 3H), 3.04 (d, J=45.8 Hz, 6H), 2.17 (dd, J=12.9, 6.7 Hz, 1H), 1.94 (d, J=10.3 Hz, 1H).

Example 167

(S)-2-((3,3-difluoro-1-(1H-imidazole-5-carbonyl)piperidin-4-yl)oxy)-5-(4-((4-(4-(oxetan-3-yl)piperazin-1-yl)phenyl)amino)-1,3,5-triazin-2-yl)benzonitrile

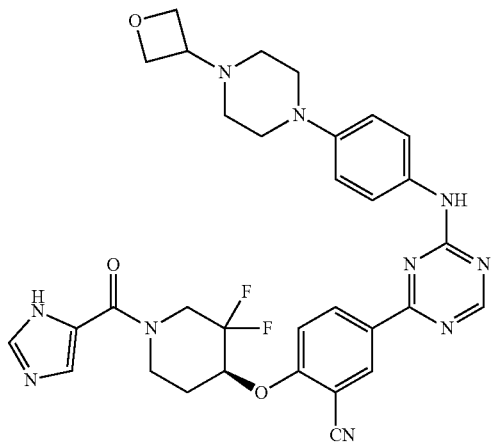 [SMILES: N#Cc1cc(-c2ncnc(Nc3ccc(N4CCN(C5COC5)CC4)cc3)n2)ccc1O[C@H]1CCN(C(=O)c2cnc[nH]2)CC1(F)F]

The title compound was prepared following the same procedure reported in Example 151 by coupling 1H-imidazole-5-carboxylic acid to (S)-2-((3,3-difluoropiperidin-4-yl)oxy)-5-(4-((4-(4-(oxetan-3-yl)piperazin-1-yl)phenyl)amino)-1,3,5-triazin-2-yl)benzonitrile. LCMS-ESI$^+$ (m/z): [M+H]$^+$ calcd for $C_{31}H_{31}F_2N_{11}O_3$: 643.3: found:643.4 $^1$H NMR (400 MHz, DMSO-d$_6$) δ 10.21 (d, J=22.2 Hz, 1H), 8.76 (s, 1H), 8.68-8.48 (m, 2H), 8.31 (s, 1H), 7.91 (s, 1H), 7.65 (dd, J =24.6, 11.0 Hz, 4H), 7.06 (d, J=11.1 Hz, 2H), 5.41 (d, J=13.9 Hz, 1H), 4.77 (dd, J=6.5, 2.1 Hz, 5H), 4.46 (q, J=6.3 Hz, 1H), 4.31-3.62 (m, 5H), 3.43-2.98 (s, 6H), 2.21 (s, 1H), 2.01 (d, J=14.6 Hz, 1H).

Example 168

2-(((2R,4S)-1-(2-hydroxyacetyl)-2-methylpiperidin-4-yl)oxy)-5-(4-((4-(4-(oxetan-3-yl)piperazin-1-yl)phenyl)amino)-1,3,5-triazin-2-yl)benzonitrile.

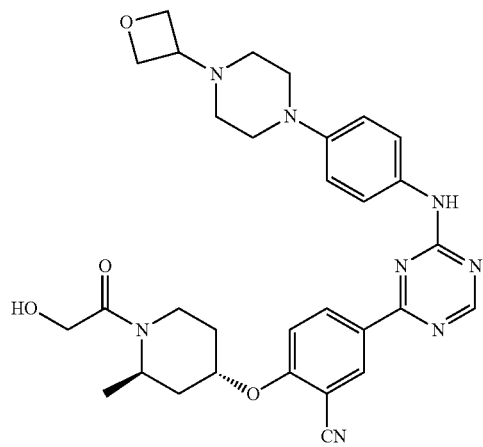 [SMILES: C[C@@H]1C[C@@H](Oc2ccc(-c3ncnc(Nc4ccc(N5CCN(C6COC6)CC5)cc4)n3)cc2C#N)CCN1C(=O)CO]

(2R,4S)-tert-butyl 4-hydroxy-2-methylpiperidine-1-carboxylate (55 mg, 0.25 mmol) was added Me-THF (4.6 mL) under argon atmosphere and cooled at 0° C. To well stirred solution was added potassium tert-butoxide (31 mg, 0.28 mmol) at one portion and stirred for 30 minutes. To well stirred solution was added 2-fluoro-5-(4-((4-(4-(oxetan-3-yl)piperazin-1-yl)phenyl)amino)-1,3,5-triazin-2-yl)benzonitrile (100 mg, 0.23 mmol) and warmed to room temperature over 10 min. The reaction was heated at 60° C. overnight. The reaction was cooled to RT and diluted with DCM and quenched with water (5 mL). The mixture was adsorbed on silica gel, the solvent concentrated to dryness. The crude product was purified by flash column chromatography on silica gel to afford (2R,4S)-tert-butyl 4-(2-cyano-4-(4-((4-(4-(oxetan-3-yl)piperazin-1-yl)phenyl)amino)-1,3,5-triazin-2-yl)phenoxy)-2-methylpiperidine-1-carboxylate. LCMS-ESI$^+$ (m/z): [M+H]$^+$ calcd for $C_{34}H_{42}N_8O_4$: 627.3; found: 627.4

(2R,4S)-tert-butyl 4-(2-cyano-4-(4-((4-(4-(oxetan-3-yl)piperazin-1-yl)phenyl)amino)-1,3,5-triazin-2-yl)phenoxy)-2-methylpiperidine-1-carboxylate (98 mg, 0.15 mmol) was dissolved in 20% TFA/DCM (5 mL) and stirred at room temperature for 1 h. The solvent was concentrated under reduced pressure to afford 2-(((2R,4S)-2-methylpiperidin-4-yl)oxy)-5-(4-((4-(4-(oxetan-3-yl)piperazin-1-yl)phenyl)amino)-1,3,5-triazin-2-yl)benzonitrile. The dried residue was used for next step LCMS-ESI$^+$ (m/z): [M+H]$^+$ calcd for $C_{29}H_{34}N_8O_2$: 527.2; found: 527.4

To solution of 2-(((2R,4S)-2-methylpiperidin-4-yl)oxy)-5-(4-((4-(4-(oxetan-3-yl)piperazin-1-yl)phenyl)amino)-1,3,5-triazin-2-yl)benzonitrile (75 mg, 0.14 mmol), (2-hydroxyacetic acid (22 mg, 0.28 mmol), HATU (108 mg, 0.28 mmol) in DMF (4 mL) was added DIPEA (0.29 mL) in a 10 mL microwave vial and sealed. This reaction mixture was stirred at room temperature overnight. The solvent was concentrated and the crude product purified via prep HPLC (5-95% acetonitrile in water, 0.1% trifluoroacetic acid buffer) to isolate 2-(((2R,4S)-1-(2-hydroxyacetyl)-2-methylpiperidin-4-yl)oxy)-5-(4-((4-(4-(oxetan-3-yl)piperazin-1-yl)phenyl)amino)-1,3,5-triazin-2-yl)benzonitrile. LCMS-ESI$^+$ (m/z): [M+H]$^+$ calcd for $C_{31}H_{36}N_8O_4$: 585.3: found:585.5 $^1$H NMR (400 MHz, DMSO-d$_6$) δ 10.17 (d, J=23.9 Hz, 1H), 8.74 (s, 1H), 8.62-8.41 (m, 2H), 7.60 (d, J=9.3 Hz, 3H), 7.04 (s, 2H), 5.08 (tt, J=10.7, 4.5 Hz, 1H), 4.87-4.64 (m, 6H), 4.44 (s, 1H), 4.25-3.96 (m, 2H), 3.94-3.33 (m, 4H), 3.16-3.04 (m, 6H), 2.27-1.96 (m, 2H), 1.49 (d, J=196.6 Hz, 5H).

Example 169

2-(((2S,4S)-1-(2-hydroxyacetyl)-2-methylpiperidin-4-yl)oxy)-5-(4-((4-(4-(oxetan-3-yl)piperazin-1-yl)phenyl)amino)-1,3,5-triazin-2-yl)benzonitrile

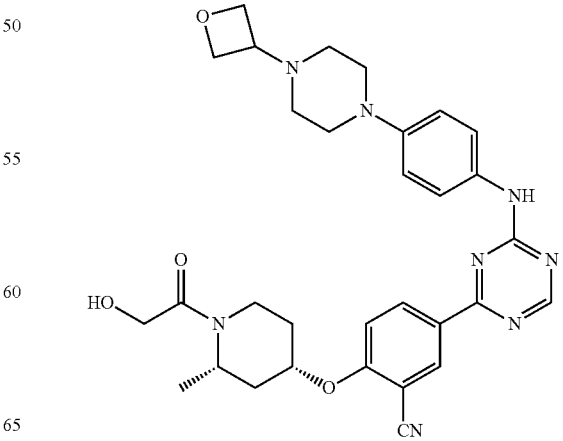

The title compound was prepared following the similar procedure reported in Example 168 by substituting (2S,4S)-tert-butyl 4-hydroxy-2-methylpiperidine-1-carboxylate to 2-fluoro-5-(4-((4-(4-(oxetan-3-yl)piperazin-1-yl)phenyl)amino)-1,3,5-triazin-2-yl)benzonitril followed by Boc deprotection and glycolic acid coupling. LCMS-ESI$^+$ (m/z): [M+H]$^+$ calcd for $C_{31}H_{36}N_8O_4$: 585.3: found:585.4.4 $^1$H NMR (400 MHz, DMSO-d$_6$) δ 10.17 (d, J=18.9 Hz, 1H), 8.75 (s, 1H), 8.66-8.42 (m, 2H), 7.62 (s, 2H), 7.48 (d, J=8.7 Hz, 1H), 7.06 (d, J=9.8 Hz, 2H), 5.19-5.05 (m, 1H), 4.76 (d, J=6.3 Hz, 5H), 4.43 (s, 2H), 4.08 (s, 6H), 3.05 (s, 6H), 1.94 (s, 4H), 1.30 (s, 3H).

Example 170

2-((1-(2-hydroxyacetyl)-3-methylpiperidin-4-yl)oxy)-5-(4-((4-(4-(oxetan-3-yl)piperazin-1-yl)phenyl)amino)-1,3,5-triazin-2-yl)benzonitrile

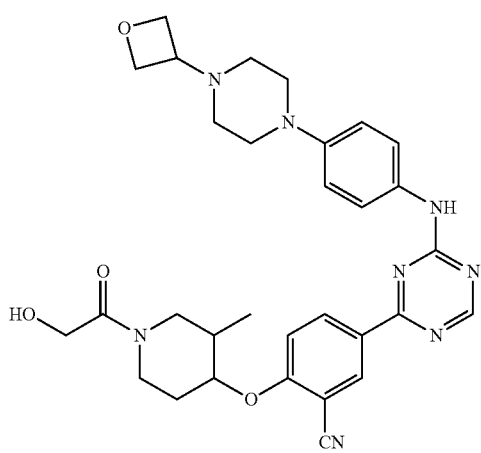 [SMILES: CC1CN(C(=O)CO)CCC1Oc1ccc(-c2ncnc(Nc3ccc(N4CCN(C5COC5)CC4)cc3)n2)cc1C#N]

The title compound was prepared following the similar procedure reported in Example 168 by substituting tert-butyl 4-hydroxy-3-methylpiperidine-1-carboxylate to 2-fluoro-5-(4-((4-(4-(oxetan-3-yl)piperazin-1-yl)phenyl)amino)-1,3,5-triazin-2-yl)benzonitrile followed by Boc deprotection and glycolic acid coupling. LCMS-ESI$^+$ (m/z): [M+H]$^+$ calcd for $C_{31}H_{36}N_8O_4$: 585.3: found:585.4 $^1$H NMR (400 MHz, DMSO-d$_6$) δ 10.17 (d, J=20.7 Hz, 1H), 8.74 (s, 1H), 8.66-8.45 (m, 2H), 7.74-7.47 (m, 3H), 7.04 (s, 2H), 4.91 (d, J=24.7 Hz, 1H), 4.74 (d, J=6.0 Hz, 4H), 4.57 (s, 1H), 4.24-4.01 (m, 3H), 3.95-3.57 (m, 4H), 3.35-2.78 (m, 8H), 2.21-2.03 (m, 1H), 2.01-1.77 (m, 1H), 1.65-1.36 (m, 1H), 0.97 (dd, J=12.1, 5.8 Hz, 3H).

Example 171

2-((1-(2-hydroxyacetyl)-2,6-dimethylpiperidin-4-yl)oxy)-5-(4-((4-(4-(oxetan-3-yl)piperazin-1-yl)phenyl)amino)-1,3,5-triazin-2-yl)benzonitrile

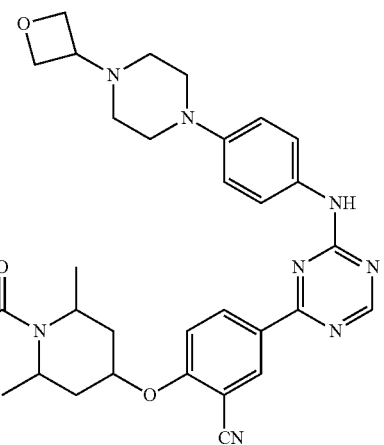

The title compound was prepared following the similar procedure reported in Example 168 by substituting tert-butyl 4-hydroxy-2,6-dimethylpiperidine-1-carboxylate to 2-fluoro-5-(4-((4-(4-(oxetan-3-yl)piperazin-1-yl)phenyl)amino)-1,3,5-triazin-2-yl)benzonitrile followed by Boc deprotection and glycolic acid coupling. LCMS-ESI$^+$ (m/z): [M+H]$^+$ calcd for $C_{32}H_{38}N_8O_4$: 599.3: found:599.4 $^1$H NMR (400 MHz, DMSO-d$_6$) δ 10.18 (d, J=30.3 Hz, 1H), 8.75 (s, 1H), 8.69 (s, 3H), 8.61-8.46 (m, 2H), 7.58 (t, J=9.6 Hz, 3H), 7.03 (d, J=8.8 Hz, 2H), 5.11 (t, J=7.7 Hz, 1H), 4.95-4.81 (m, 1H), 4.75 (d, J=6.5 Hz, 5H), 4.39 (s, 1H), 3.78 (s, 1H), 3.71-3.55 (m, 1H), 3.35 (s, 1H), 3.05 (s, 4H), 2.41-2.16 (m, 2H), 2.12-1.88 (m, 2H), 1.78-1.43 (m, 2H), 1.35 (d, J=6.7 Hz, 3H), 1.25 (dd, J=15.2, 7.1 Hz, 3H).

Example 172

2-((3-(2-hydroxyacetyl)-3-azabicyclo[3.1.1]heptan-6-yl)oxy)-5-(4-((4-(4-(oxetan-3-yl)piperazin-1-yl)phenyl)amino)-1,3,5-triazin-2-yl)benzonitrile

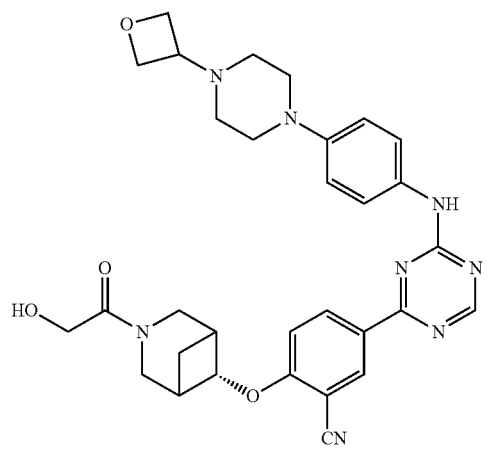

The title compound was prepared following the similar procedure reported in Example 168 by substituting tert-butyl 6-hydroxy-3-azabicyclo[3.1.1]heptane-3-carboxylate to 2-fluoro-5-(4-((4-(4-(oxetan-3-yl)piperazin-1-yl)phenyl)amino)-1,3,5-triazin-2-yl)benzonitrile, followed by Boc deprotection and glycolic acid coupling. LCMS-ESI$^+$ (m/z): [M+H]$^+$ calcd for $C_{31}H_{34}N_8O_4$: 583.3: found:583.5 $^1$H NMR (400 MHz, DMSO-d$_6$) δ 10.13 (d, J=17.6 Hz, 1H), 8.80-8.64 (m, 1H), 8.61-8.46 (m, 2H), 7.70-7.39 (m, 3H), 6.99 (d, J=19.0. Hz, 2H), 4.92 (t, J=5.7 Hz, 1H), 4.66-4.44 (m, 4H), 4.22-3.85 (m, 2H), 3.61 (dtq, J=10.4, 6.6, 3.4 Hz, 6H), 3.16-3.06 (m, 7H), 2.99-2.88 (m, 2H), 1.81 (dt, J=11.1, 6.2 Hz, 1H), 1.54-1.30 (m, 1H), 1.18-0.96 (m, 1H).

Example 173

2-((8-(2-hydroxyacetyl)-8-azabicyclo[3.2.1]octan-3-yl)oxy)-5-(4-((4-(4-(oxetan-3-yl)piperazin-1-yl)phenyl)amino)-1,3,5-triazin-2-yl)benzonitrile

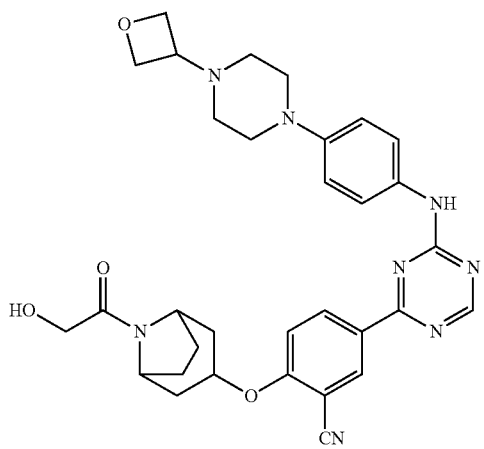 [SMILES: N#Cc1cc(-c2ncnc(Nc3ccc(N4CCN(C5COC5)CC4)cc3)n2)ccc1OC1CC2CCC(C1)N2C(=O)CO]

The title compound was prepared following the similar procedure reported in Example 168 by substituting tert-butyl 3-hydroxy-8-azabicyclo[3.2.1]octane-8-carboxylate to 2-fluoro-5-(4-((4-(4-(oxetan-3-yl)piperazin-1-yl)phenyl)amino)-1,3,5-triazin-2-yl)benzonitrile, followed by Boc deprotection and glycolic acid coupling. LCMS-ESI$^+$ (m/z): calcd for $C_{32}H_{36}N_8O_4$ 597.3: found:597.4 $^1$H NMR (400 MHz, DMSO-d$_6$) δ 10.19 (s, 1H), 8.74 (s, 1H), 8.65-8.46 (m, 2H), 7.62 (s, 2H), 7.35 (d, J=8.9 Hz, 1H), 7.04 (s, 2H), 5.01 (t, J=4.6 Hz, 1H), 4.73 (s, 5H), 4.51 (d, J=7.5 Hz, 1 H), 4.26 (s, 1H), 4.05 (q, J=14.9 Hz, 2H), 3.51 (s, 6H), 3.18-2.80 (m, 3H), 2.24-2.03 (m, 4H), 2.03-1.89 (m, 3H), 1.82 (d, J=11.6 Hz, 1H).

Example 174

2-((1-(2-hydroxyacetyl)-3,3-dimethylpiperidin-4-yl)oxy)-5-(4-((4-(4-(oxetan-3-yl)piperazin-1-yl)phenyl)amino)-1,3,5-triazin-2-yl)benzonitrile

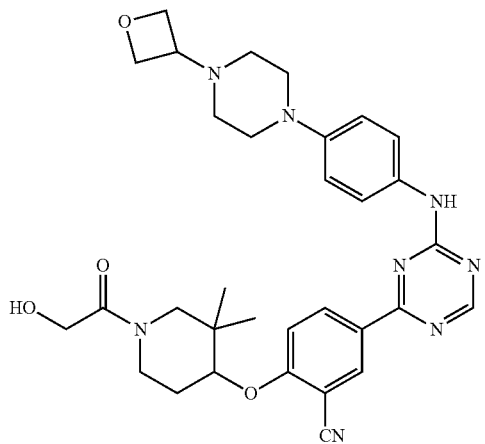 [SMILES: CC1(C)CN(C(=O)CO)CCC1Oc1ccc(-c2ncnc(Nc3ccc(N4CCN(C5COC5)CC4)cc3)n2)cc1C#N]

The title compound was prepared following the similar procedure reported in Example 168 by substituting tert-butyl 4-hydroxy-3,3-dimethylpiperidine-1-carboxylate to 2-fluoro-5-(4-((4-(4-(oxetan-3-yl)piperazin-1-yl)phenyl)amino)-1,3,5-triazin-2-yl)benzonitrile followed by Boc deprotection and glycolic acid coupling. LCMS-ESI$^+$ (m/z): [M+H]$^+$ calcd for $C_{32}H_{38}N_8O_4$: 599.3: found:599.4 $^1$H NMR (400 MHz, DMSO-d$_6$) δ 10.17 (d, J=19.7 Hz, 1H), 8.74 (s, 1H), 8.64-8.52 (m, 2H), 7.75-7.47 (m, 3H), 7.04 (d, J=8.8 Hz, 2H), 4.75 (d, J=6.6 Hz, 5H), 4.59 (d, J=8.2 Hz, 1H), 4.39 (s, 1H), 4.22-4.03 (m, 3H), 3.85 (d, J=13.6 Hz, 1H), 3.69 (d, J=13.0 Hz, 1H), 3.53 (dt, J=11.9, 5.0 Hz, 1H), 3.44-3.22 (m, 3H), 3.19-2.95 (m, 5H), 2.07-1.86 (m, 1H), 1.82-1.53 (m, 1H), 1.09-0.89 (m, 6H).

Example 175 and Example 176

(S)-2-((1-(2-hydroxyacetyl)-3,3-dimethylpiperidin-4-yl)oxy)-5-(4-((4-(4-(oxetan-3-yl)piperazin-1-yl)phenyl)amino)-1,3,5-triazin-2-yl)benzonitrile and (R)-2-((1-(2-hydroxyacetyl)-3,3-dimethylpiperidin-4-yl)oxy)-5-(4-((4-(4-(oxetan-3-yl)piperazin-1-yl)phenyl)amino)-1,3,5-triazin-2-yl)benzonitrile

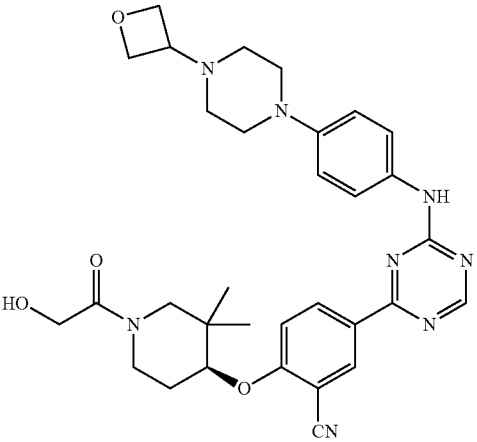

-continued

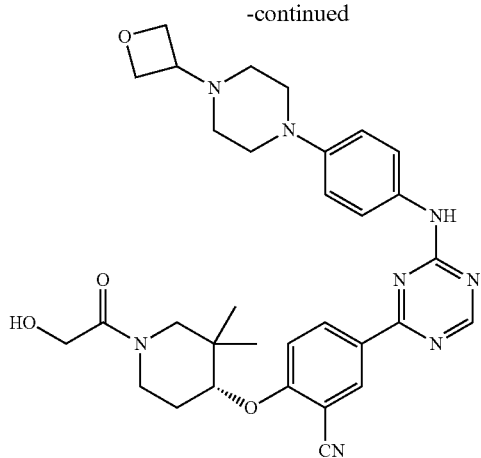

Racemic mixtures Example 174 was separated by chiral separation using chiral column to afford title compounds and the stereochemistry were assigned tentatively Peak A: LCMS-ESI⁺ (m/z): [M+H]⁺ calcd for $C_{32}H_{38}N_8O_4$: 599.3: found:599.4 ¹H NMR (400 MHz, DMSO-d₆) δ 10.17 (d, J=19.7 Hz, 1H), 8.74 (s, 1H), 8.64-8.52 (m, 1H), 8.50 (s, 1H), 7.75-7.47 (m, 3H), 7.04 (d, J=8.8 Hz, 2H), 4.75 (d, J=6.6 Hz, 5H), 4.59 (d, J=8.2 Hz, 1H), 4.39 (s, 1H), 4.22-4.03 (m, 3H), 3.85 (d, J=13.6 Hz, 1H), 3.69 (d, J=13.0 Hz, 1H), 3.53 (dt, J=11.9, 5.0 Hz, 1H), 3.44-3.22 (m, 4H), 3.19-2.95 (m, 2H), 2.07-1.86 (m, 1H), 1.82-1.53 (m, 1H), 1.09-0.89 (m, 7H). Peak B: LCMS-ESI⁺ (m/z): [M+H]⁺ calcd for $C_{32}H_{38}N_8O_4$: 599.3: found:599.4

Example 177

2-((5-fluoro-1-(2-hydroxyacetyl)-3,3-dimethylpiperidin-4-yl)oxy)-5-(4-((4-(4-(oxetan-3-yl)piperazin-1-yl)phenyl)amino)-1,3,5-triazin-2-yl)benzonitrile

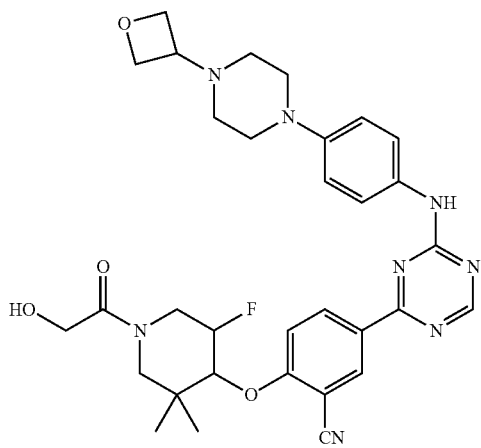 [SMILES: CC1(C)CN(C(=O)CO)CC(F)C1Oc1ccc(-c2ncnc(Nc3ccc(N4CCN(C5COC5)CC4)cc3)n2)cc1C#N]

The title compound was prepared following the similar procedure reported in Example 168 by substituting tert-butyl 5-fluoro-4-hydroxy-3,3-dimethylpiperidine-1-carboxylate to 2-fluoro-5-(4-((4-(4-(oxetan-3-yl)piperazin-1-yl)phenyl) amino)-1,3,5-triazin-2-yl)benzonitrile, followed by Boc deprotection and glycolic acid coupling. LCMS-ESI⁺ (m/z): [M+H]⁺ calcd for $C_{32}H_{37}FN_8O_4$: 617.3: found:617.4 ¹H NMR (400 MHz, DMSO-d₆) δ 10.19 (d, J=21.2 Hz, 1H), 8.75 (s, 1H), 8.66-8.43 (m, 2H), 7.64 (dd, J=9.6, 3.3 Hz, 3H), 7.04 (s, 2H), 5.09 (d, J=51.6 Hz, 1H), 4.88 (dd, J=20.4, 9.5 Hz, 1H), 4.76 (d, J=6.5 Hz, 5H), 4.44 (s, 1H), 4.28-4.07 (m, 2H), 3.72 (s, 7H), 3.66-3.52 (m, 2H), 3.32 (dd, J=50.9, 13.3 Hz, 1H), 3.18-2.76 (m, 2H), 1.12-0.93 (m, 6H).

Example 178 and Example 179

2-(((4R,5S)-5-fluoro-1-(2-hydroxyacetyl)-3,3-dimethylpiperidin-4-yl)oxy)-5-(4-((4-(4-(oxetan-3-yl)piperazin-1-yl)phenyl)amino)-1,3,5-triazin-2-yl)benzonitrile and 2-(((4S,5R)-5-fluoro-1-(2-hydroxyacetyl)-3,3-dimethylpiperidin-4-yl)oxy)-5-(4-((4-(4-(oxetan-3-yl)piperazin-1-yl)phenyl)amino)-1,3,5-triazin-2-yl)benzonitrile

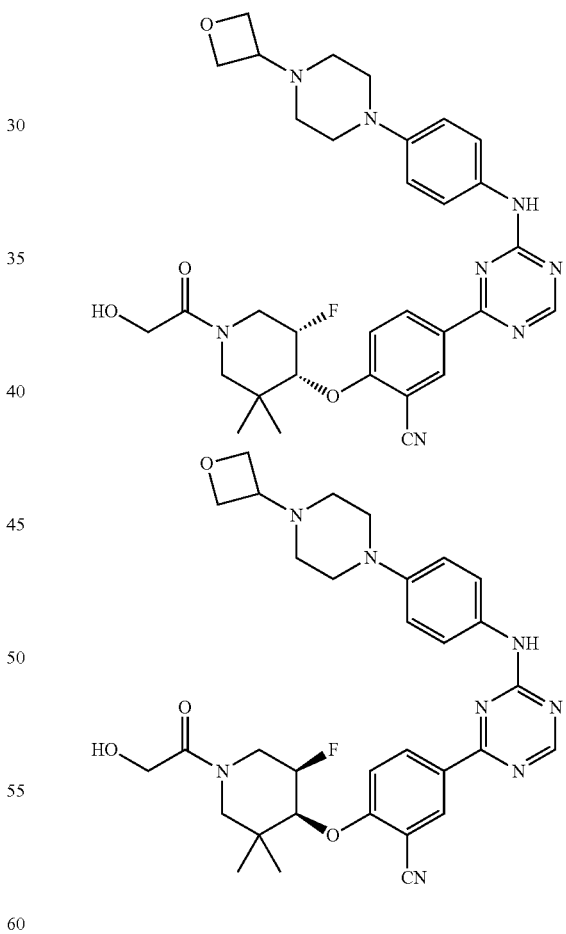

Racemic mixtures Example 174 was separated by chiral separation using chiral column to afford title compounds and the stereochemistry were assigned tentatively Peak A:. LCMS-ESI⁺ (m/z): [M+H]⁺ calcd for $C_{32}H_{37}FN_8O_4$: 617.3: found:617.4 Peak B: LCMS-ESI⁺ (m/z): [M+H]⁺ calcd for $C_{32}H_{37}FN_8O_4$: 617.3: found:617.4

Example 180

2-((5-fluoro-1-((S)-2-hydroxypropanoyl)-3,3-dimethylpiperidin-4-yl)oxy)-5-(4-((4-(4-(oxetan-3-yl)piperazin-1-yl)phenyl)amino)-1,3,5-triazin-2-yl)benzonitrile

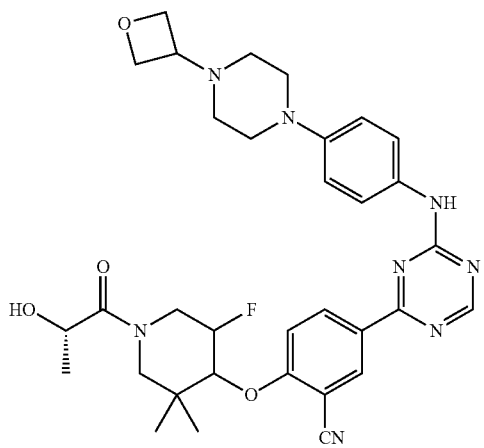 [SMILES: C[C@H](O)C(=O)N1CC(F)C(Oc2ccc(-c3ncnc(Nc4ccc(N5CCN(C6COC6)CC5)cc4)n3)cc2C#N)C(C)(C)C1]

The title compound was prepared following the similar procedure reported in Example 168 by substituting tert-butyl 5-fluoro-4-hydroxy-3,3-dimethylpiperidine-1-carboxylate to 2-fluoro-5-(4-((4-(4-(oxetan-3-yl)piperazin-1-yl)phenyl)amino)-1,3,5-triazin-2-yl)benzonitrile, followed by Boc deprotection and (S)-2-hydroxypropanoic acid coupling. LCMS-ESI$^+$ (m/z): [M+H]$^+$ calcd for $C_{33}H_{39}FN_8O_4$: 631.3: found:631.4 $^1$H NMR (400 MHz, DMSO-d$_6$) δ 10.19 (d, J=21.9 Hz, 1H), 8.75 (s, 1H), 8.67-8.46 (m, 2H), 7.63 (t, J=10.3 Hz, 3H), 7.05 (s, 2H), 5.23-4.97 (m, 2H), 4.96-4.83 (m, 1H), 4.83-4.71 (m, 5H), 4.49 (dd, J=14.8, 8.9 Hz, 4H), 3.98-3.71 (m, 1H), 3.65-3.38 (m, 1H), 3.27 (s, 1H), 3.06 (s, 6H), 1.49-1.16 (m, 3H), 1.13-0.93 (m, 6H).

Example 181

2-(((2S,4S)-1-((S)2-hydroxypropanoyl)-2-methylpiperidin-4-yl)oxy)-5-(4-((4-(4-(oxetan-3-yl)piperazin-1-yl)phenyl)amino)-1,3,5-triazin-2-yl)benzonitrile

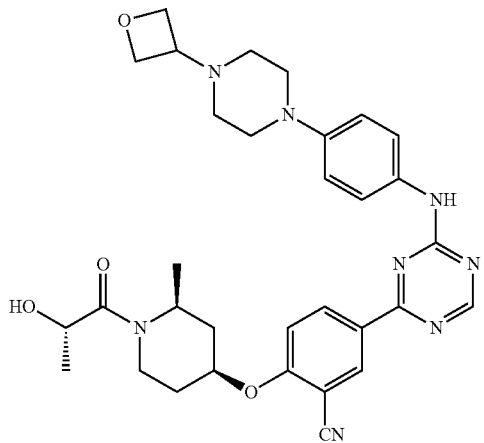 [SMILES: C[C@H](O)C(=O)N1CC[C@H](Oc2ccc(-c3ncnc(Nc4ccc(N5CCN(C6COC6)CC5)cc4)n3)cc2C#N)C[C@@H]1C]

The title compound was prepared following the similar procedure reported in Example 168 by substituting (2S,4S)-tert-butyl 4-hydroxy-2-methylpiperidine-1-carboxylate to 2-fluoro-5-(4-((4-(4-(oxetan-3-yl)piperazin-1-yl)phenyl)amino)-1,3,5-triazin-2-yl)benzonitrile, followed by Boc deprotection and (S)-2-hydroxypropanoic acid coupling. LCMS-ESI$^+$ (m/z): [M+H]$^+$ calcd for $C_{33}H_{38}N_8O_4$: 599.3: found:599.4 $^1$H NMR (400 MHz, DMSO-d$_6$) δ 10.16 (d, J=17.0 Hz, 1H), 8.74 (s, 1H), 8.67-8.43 (m, 2H), 7.62 (s, 2H), 7.53-7.38 (m, 1H), 7.03 (d, J=10.2 Hz, 2H), 5.11 (s, 1H), 4.87-4.65 (m, 5H), 4.42 (q, J=6.5 Hz, 3H), 3.62 (d, J=163.6 Hz, 6H), 3.11 (d, J=55.0 Hz, 4H), 1.96 (d, J=12.0 Hz, 3H), 1.88-1.23 (m, 4H), 1.19 (d, J=6.4 Hz, 3H).

Example 182

2-(((2S,4S)-1-((R)-2-hydroxypropanoyl)-2-methylpiperidin-4-yl)oxy)-5-(4-((4-(4-(oxetan-3-yl)piperazin-1-yl)phenyl)amino)-1,3,5-triazin-2-yl)benzonitrile

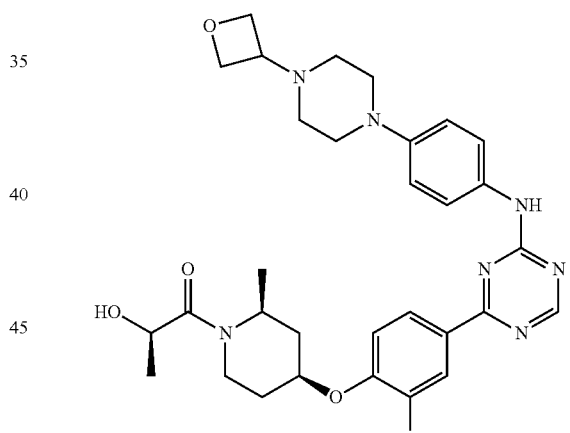

The title compound was prepared following the similar procedure reported in Example 168 by substituting (2S,4S)-tert-butyl 4-hydroxy-2-methylpiperidine-1-carboxylate to 2-fluoro-5-(4-((4-(4-(oxetan-3-yl)piperazin-1-yl)phenyl)amino)-1,3,5-triazin-2-yl)benzonitrile, followed by Boc deprotection and (R)-2-hydroxypropanoic acid coupling. LCMS-ESI$^+$ (m/z): [M+H]$^+$ calcd for $C_{33}H_{38}N_8O_4$: 599.3: found:599.4 $^1$H NMR (400 MHz, DMSO-d$_6$) δ 10.16 (d, J=17.2 Hz, 1H), 8.74 (s, 1H), 8.62-8.44 (m, 2H), 7.62 (s, 2H), 7.48 (d, J=8.9 Hz, 1H), 7.03 (d, J=10.8 Hz, 3H), 5.20-5.01 (m, 1H), 4.75 (d, J=6.4 Hz, 5H), 4.58-4.19 (m, 3H), 3.81 (s, 3H), 3.39 (s, 1H), 3.24-2.77 (m, 4H), 1.95 (d, J=12.8 Hz, 3H), 1.52-1.32 (m, 2H), 1.30-1.10 (m, 6H).

Example 183

2-(((2R,4S)-1-((S)-2-hydroxypropanoyl)-2-methylpiperidin-4-yl)oxy)-5-(4-((4-(4-(oxetan-3-yl)piperazin-1-yl)phenyl)amino)-1,3,5-triazin-2-yl)benzonitrile

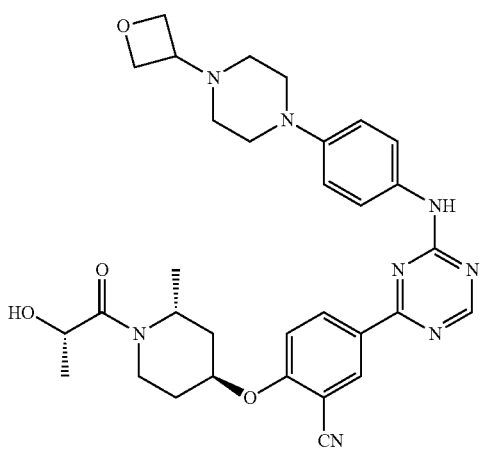 [SMILES: C[C@H](O)C(=O)N1CC[C@H](Oc2ccc(-c3ncnc(Nc4ccc(N5CCN(C6COC6)CC5)cc4)n3)cc2C#N)C[C@H]1C]

The title compound was prepared following the similar procedure reported in Example 168 by substituting (2R,4S)-tert-butyl 4-hydroxy-2-methylpiperidine-1-carboxylate to 2-fluoro-5-(4-((4-(4-(oxetan-3-yl)piperazin-1-yl)phenyl)amino)-1,3,5-triazin-2-yl)benzonitrile, followed by Boc deprotection and (S)-2-hydroxypropanoic acid coupling. LCMS-ESI$^+$ (m/z): [M+H]$^+$ calcd for $C_{32}H_{38}N_8O_4$: 599.3: found:599.4

Example 184

2-(((2R,4S)-1-((R)-2-hydroxypropanoyl)-2-methylpiperidin-4-yl)oxy)-5-(4-((4-(4-(oxetan-3-yl)piperazin-1-yl)phenyl)amino)-1,3,5-triazin-2-yl)benzonitrile

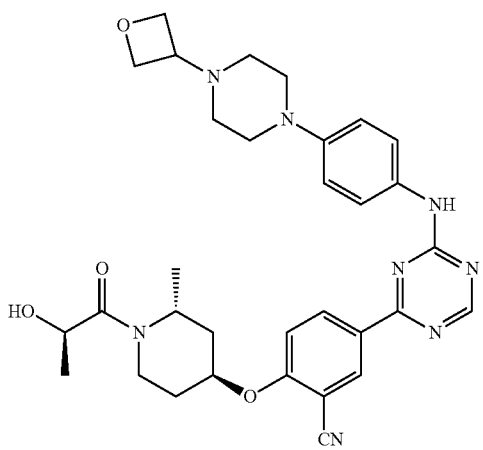 [SMILES: C[C@@H]1C[C@@H](Oc2ccc(-c3ncnc(Nc4ccc(N5CCN(C6COC6)CC5)cc4)n3)cc2C#N)CCN1C(=O)[C@@H](C)O]

The title compound was prepared following the similar procedure reported in Example 168 by substituting (2R,4S)-tert-butyl 4-hydroxy-2-methylpiperidine-1-carboxylate to 2-fluoro-5-(4-((4-(4-(oxetan-3-yl)piperazin-1-yl)phenyl)amino)-1,3,5-triazin-2-yl)benzonitrile, followed by Boc deprotection and (R)-2-hydroxypropanoic acid coupling. LCMS-ESI$^+$ (m/z): [M+H]$^+$ calcd for $C_{32}H_{38}N_8O_4$: 599.3: found:599.4

Example 185

2-(((2R,4R)-1-((S)-2-hydroxypropanoyl)-2-methylpiperidin-4-yl)oxy)-5-(4-((4-(4-(oxetan-3-yl)piperazin-1-yl)phenyl)amino)-1,3,5-triazin-2-yl)benzonitrile

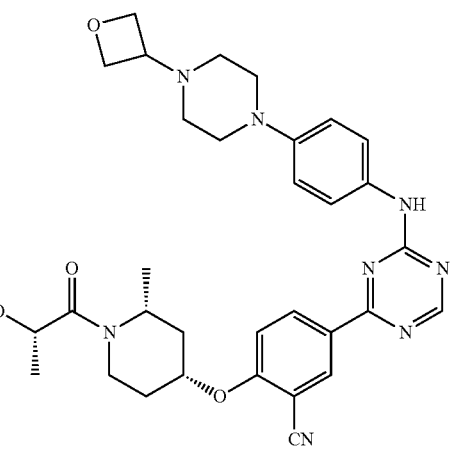

The title compound was prepared following the similar procedure reported in Example 168 by substituting (2R,4R)-tert-butyl 4-hydroxy-2-methylpiperidine-1-carboxylate to 2-fluoro-5-(4-((4-(4-(oxetan-3-yl)piperazin-1-yl)phenyl)amino)-1,3,5-triazin-2-yl)benzonitrile, followed by Boc deprotection and (S)-2-hydroxypropanoic acid coupling. LCMS-ESI$^+$ (m/z): [M+H]$^+$ calcd for $C_{32}H_{38}N_8O_4$: 599.3: found:599.4

Example 186

2-(((2R,4R)-1-((R)-2-hydroxypropanoyl)-2-methylpiperidin-4-yl)oxy)-5(4-((4-(4-(oxetan-3-yl)piperazin-1-yl)phenyl)amino)-1,3,5-triazin-2-yl)benzonitrile

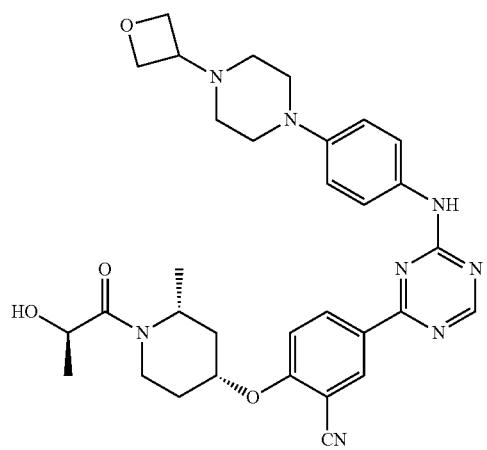 [SMILES: C[C@@H]1C[C@H](Oc2ccc(-c3ncnc(Nc4ccc(N5CCN(C6COC6)CC5)cc4)n3)cc2C#N)CCN1C(=O)[C@@H](C)O]

The title compound was prepared following the similar procedure reported in Example 168 by substituting (2R,4R)-tert-butyl 4-hydroxy-2-methylpiperidine-1-carboxylate to 2-fluoro-5-(4-((4-(4-(oxetan-3-yl)piperazin-1-yl)phenyl)amino)-1,3,5-triazin-2-yl)benzonitrile, followed by Boc deprotection and (R)-2-hydroxypropanoic acid coupling. LCMS-ESI$^+$ (m/z): [M+H]$^+$ calcd for $C_{32}H_{38}N_8O_4$: 599.3: found:599.4

Example 187

2-(((2S,4S)-1-(2-cyanoacetyl)-2-methylpiperidin-4-yl)oxy)-5-(4-((4-(4-(oxetan-3-yl)piperazin-1-yl)phenyl)amino)-1,3,5-triazin-2-yl)benzonitrile

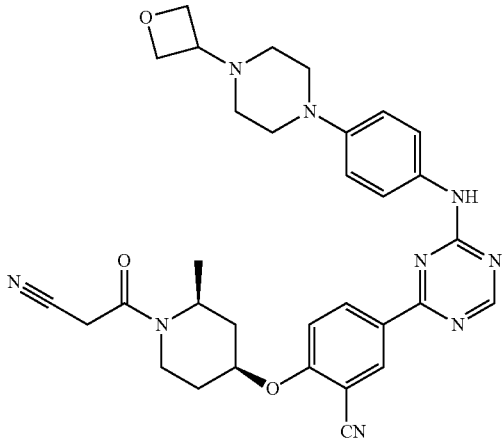 [SMILES: C[C@H]1C[C@@H](Oc2ccc(-c3ncnc(Nc4ccc(N5CCN(C6COC6)CC5)cc4)n3)cc2C#N)CCN1C(=O)CC#N]

The title compound was prepared following the similar procedure reported in Example 168 by substituting (2S,4S)-tert-butyl 4-hydroxy-2-methylpiperidine-1-carboxylate to 2-fluoro-5-(4-((4-(4-(oxetan-3-yl)piperazin-1-yl)phenyl)amino)-1,3,5-triazin-2-yl)benzonitrile, followed by Boc deprotection and 2-cyanoacetic acid coupling. LCMS-ESI$^+$ (m/z): [M+H]$^+$ calcd for $C_{32}H_{35}N_9O_3$: 594.3: found:594.4 $^1$H NMR (400 MHz, DMSO-d$_6$) δ 10.17 (d, J=19.3 Hz, 1H), 8.74 (s, 1H), 8.68-8.44 (m, 2H), 7.64 (d, J=11.9 Hz, 2H), 7.49 (d, J=8.9 Hz, 1H), 7.05 (d, J=9.7 Hz, 2H), 5.10 (s, 1H), 4.75 (d, J=6.2 Hz, 5H), 4.54-3.92 (m, 4H), 3.81 (d, J=4.9 Hz, 1H), 3.46 (s, 3H), 3.09 (d, J=44.2 Hz, 5H), 1.83 (d, J=78.8 Hz, 4H), 1.30 (dd, J=54.1, 8.1 Hz, 3H).

Example 188

2-(((2S,4S)-2-methyl-1-(1H-1,2,3-triazole-5-carbonyl)piperidin-4-yl)oxy)-5-(4-((4-(4-(oxetan-3-yl)piperazin-1-yl)phenyl)amino)-1,3,5-triazin-2-yl)benzonitrile

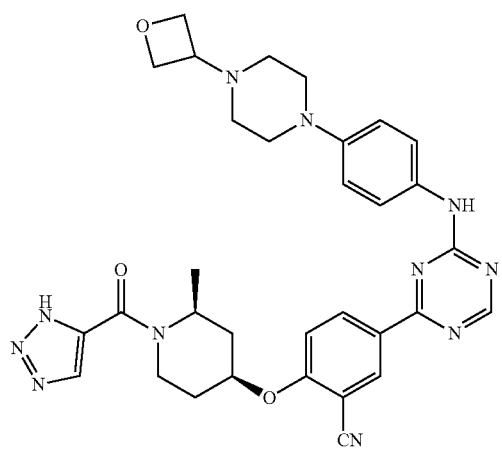 [SMILES: C[C@H]1C[C@@H](Oc2ccc(-c3ncnc(Nc4ccc(N5CCN(C6COC6)CC5)cc4)n3)cc2C#N)CCN1C(=O)c1cnn[nH]1]

The title compound was prepared following the similar procedure reported in Example 168 by substituting (2S,4S)-tert-butyl 4-hydroxy-2-methylpiperidine-1-carboxylate to 2-fluoro-5-(4-((4-(4-(oxetan-3-yl)piperazin-1-yl)phenyl)amino)-1,3,5-triazin-2-yl)benzonitrile, followed by Boc deprotection and 1H-1,2,3-triazole-5-carboxylic acid coupling. LCMS-ESI$^+$ (m/z): [M+H]$^+$ calcd for $C_{32}H_{35}N_{11}O_3$: 622.3: found:622.4 $^1$H NMR (400 MHz, DMSO-d$_6$) δ 10.17 (d, J=17.1 Hz, 1H), 8.74 (s, 1H), 8.67-8.44 (m, 2H), 8.15-7.78 (m, 1H), 7.63 (d, J=12.8 Hz, 2H), 7.50 (dd, J=7.8, 3.9 Hz, 1H), 7.04 (s, 2H), 5.14 (dd, J=5.6, 2.8 Hz, 1H), 4.75 (d, J=6.2 Hz, 6H), 4.41 (s, 2H), 3.80 (s, 3H), 3.15 (s, 5H), 2.14-1.79 (m, 4H), 1.39 (t, J=8.7 Hz, 3H).

Example 189

2-((1-(1H-imidazole-2-carbonyl)piperidin-4-yl)oxy)-5-(4-((4-(4-(oxetan-3-yl)piperazin-1-yl)phenyl)amino)-1,3,5-triazin-2-yl)benzonitrile

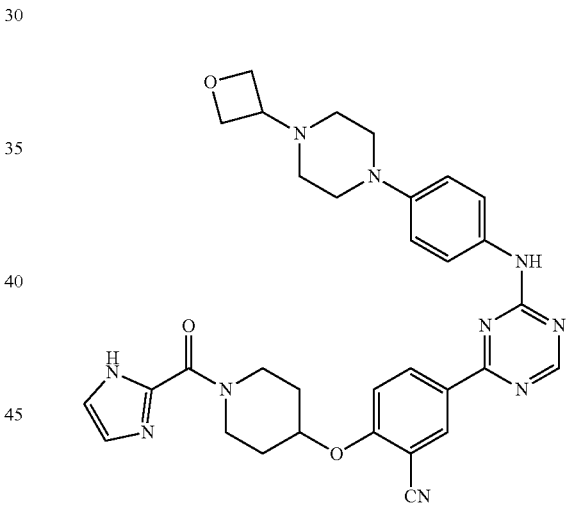

The title compound was prepared following the similar procedure reported in Example 168 by substituting tert-butyl 4-hydroxypiperidine-1-carboxylate to 2-fluoro-5-(4-((4-(4-(oxetan-3-yl)piperazin-1-yl)phenyl)amino)-1,3,5-triazin-2-yl)benzonitrile, followed by Boc deprotection and 1H-imidazole-2-carboxylic acid coupling. LCMS-ESI$^+$ (m/z): [M+H]$^+$ calcd for $C_{32}H_{34}N_{10}O_3$ 607.3: found:607.4 $^1$H NMR (400 MHz, DMSO-d$_6$) δ 10.18 (d, J=19.7 Hz, 1H), 8.75 (s, 1H), 8.58 (dd, J=8.9, 2.0 Hz, 1H), 8.52 (s, 1H), 7.73-7.47 (m, 4H), 7.22 (s, 2H), 7.06 (d, J=11.0 Hz, 2H), 5.05 (dp, J=7.3, 3.3 Hz, 1H), 4.87-4.71 (m, 5H), 4.62 (d, J=13.4 Hz, 1H), 4.45 (t, J=6.7 Hz, 1H), 4.29 (d, J=13.8 Hz, 1H), 3.90 (d, J=13.4 Hz, 2H), 3.64 (s, 1H), 3.10 (s, 6H), 2.07 (s, 2H), 1.77 (d, J=12.9 Hz, 2H).

Example 190

2-((1-(1H-pyrrole-2-carbonyl)piperidin-4-yl)oxy)-5-(4-((4-(4-(oxetan-3-yl)piperazin-1-yl)phenyl)amino)-1,3,5-triazin-2-yl)benzonitrile

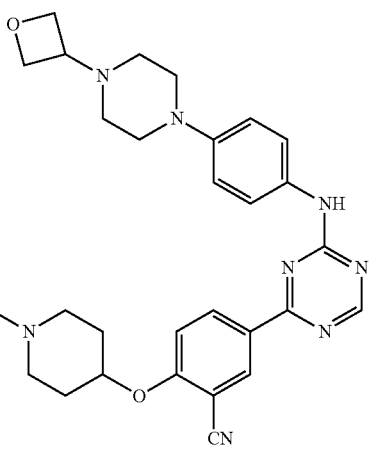

The title compound was prepared following the similar procedure reported in Example 168 by substituting tert-butyl 4-hydroxypiperidine-1-carboxylate to 2-fluoro-5-(4-((4-(4-(oxetan-3-yl)piperazin-1-yl)phenyl)amino)-1,3,5-triazin-2-yl)benzonitrile, followed by Boc deprotection and 1H-pyrrole-2-carboxylic acid coupling. LCMS-ESI$^+$ (m/z): [M+H]$^+$ calcd for $C_{33}H_{35}N_9O_3$ 606.3: found:606.4 $^1$H NMR (400 MHz, Chloroform-d) δ 9.63 (s, 1H), 9.19 (s, 1H), 8.69 (s, 1H), 8.62 (dd, J=8.9, 2.2 Hz, 1H), 7.51 (d, J=17.2 Hz, 2H), 7.09 (d, J=9.0 Hz, 1H), 7.06-6.86 (m, 3H), 6.56 (t, J=3.2 Hz, 1H), 6.35-6.21 (m, 2H), 4.89 (t, J=4.6 Hz, 1H), 4.78-4.60 (m, 4H), 4.09 (d, J=13.6 Hz, 2H), 3.96 (s, 2H), 3.67-3.51 (m, 1H), 3.27 (s, 4H), 2.05 (dd, J=8.9, 3.9 Hz, 4H), 1.28 (s, 2H), 0.95-0.73 (m, 2H).

Example 191

2-((1-(1H-pyrrole-3-carbonyl)piperidin-4-yl)oxy)-5-(4-((4-(4-(oxetan-3-yl)piperazin-1-yl)phenyl)amino)-1,3,5-triazin-2-yl)benzonitrile

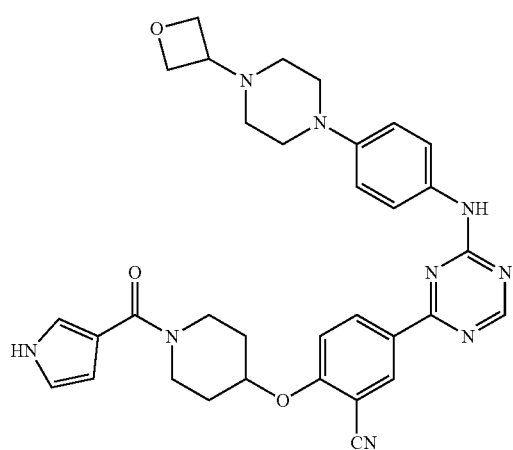 [SMILES: N#Cc1cc(-c2ncnc(Nc3ccc(N4CCN(C5COC5)CC4)cc3)n2)ccc1OC1CCN(C(=O)c2cc[nH]c2)CC1]

The title compound was prepared following the similar procedure reported in Example 168 by substituting tert-butyl 4-hydroxypiperidine-1-carboxylate to 2-fluoro-5-(4-((4-(4-(oxetan-3-yl)piperazin-1-yl)phenyl)amino)-1,3,5-triazin-2-yl)benzonitrile, followed by Boc deprotection and 1H-pyrrole-3-carboxylic acid coupling. LCMS-ESI$^+$ (m/z): [M+H]$^+$ calcd for $C_{33}H_{35}N_9O_3$ 606.3: found:606.4 $^1$H NMR (400 MHz, DMSO-d$_6$) δ 10.18 (d, J=24.5 Hz, 2H), 8.75 (s, 1H), 8.66-8.46 (m, 2H), 7.99 (s, 1H), 7.57 (d, J=9.2 Hz, 4H), 7.04 (s, 3H), 5.06 (td, J=6.8, 6.4, 3.1 Hz, 1H), 4.74 (q, J=7.9, 6.1 Hz, 5H), 4.38 (s, 1H), 3.96-3.53 (m, 6H), 3.24 (s, 3H), 2.17 (ddt, J=12.3, 7.7, 3.8 Hz, 2H), 1.93 (ddq, J=14.1, 7.2, 3.6 Hz, 2H), 1.84-1.70 (m, 1H), 1.47-1.30 (m, 1H).

Example 192

2-(((3R,4S)-1-(2-hydroxyacetyl)-4-methylpyrrolidin-3-yl)oxy)-5-(4-((4-(4-(oxetan-3-yl)piperazin-1-yl)phenyl)amino)-1,3,5-triazin-2-yl)benzonitrile

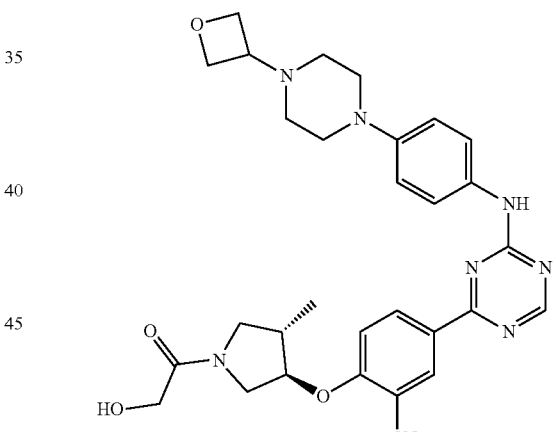

The title compound was prepared following the similar procedure reported in Example 168 by substituting (3R,4S)-tert-butyl 3-hydroxy-4-methylpyrrolidine-1-carboxylate to 2-fluoro-5-(4-((4-(4-(oxetan-3-yl)piperazin-1-yl)phenyl)amino)-1,3,5-triazin-2-yl)benzonitrile, followed by BOC deprotection and glycolic acid coupling. LCMS-ESI$^+$ (m/z): [M+H]$^+$ calcd for $C_{30}H_{34}N_8O_4$: 571.2: found:571.4 $^1$H NMR (400 MHz, DMSO-d$_6$) δ 10.18 (d, J=21.2 Hz, 1H), 8.75 (s, 1H), 8.64-8.44 (m, 2H), 7.62 (s, 2H), 7.48 (d, J=8.9 Hz, 1H), 7.04 (d, J=11.1 Hz, 2H), 5.07-4.89 (m, 1H), 4.87-4.68 (m, 5H), 4.45 (s, 2H), 4.09-3.80 (m, 4H), 3.71-3.41 (m, 4H), 3.38-2.80 (m, 5H), 2.70-2.52 (m, 1H), 1.06 (dd, J=7.1, 5.4 Hz, 3H).

Example 193

2-(((3R,4R)-4-fluoro-1-(2-hydroxyacetyl)pyrrolidin-3-yl)oxy)-5-(4-((4-(4-(oxetan-3-yl)piperazin-1-yl)phenyl)amino)-1,3,5-triazin-2-yl)benzonitrile

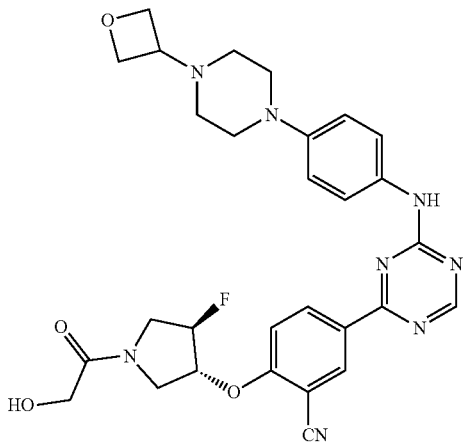 [SMILES: N#Cc1cc(-c2ncnc(Nc3ccc(N4CCN(C5COC5)CC4)cc3)n2)ccc1O[C@@H]1CN(C(=O)CO)C[C@H]1F]

The title compound was prepared following the similar procedure reported in Example 168 by substituting (3R,4R)-tert-butyl 3-fluoro-4-hydroxypyrrolidine-1-carboxylate to 2-fluoro-5-(4-((4-(4-(oxetan-3-yl)piperazin-1-yl)phenyl)amino)-1,3,5-triazin-2-yl)benzonitrile, followed by Boc deprotection and glycolic acid coupling. LCMS-ESI$^+$ (m/z): [M+H]$^+$ calcd for $C_{29}H_{31}FN_8O_4$: 575.2: found:575.4 $^1$H NMR (400 MHz, DMSO-d$_6$) δ 10.20 (d, J=21.9 Hz, 1H), 8.76 (s, 1H), 8.66-8.45 (m, 2H), 7.63 (d, J=14.5 Hz, 3H), 7.05 (s, 2H), 5.62-5.27 (m, 2H), 4.76 (d, J=6.6 Hz, 5H), 4.43 (s, 1H), 4.16-3.98 (m, 3H), 3.96-3.65 (m, 6H), 3.15 (s, 5H).

Example 194

2-((4,4-difluoropyrrolidin-3-yl)oxy)-5-(4-((4-(4-(oxetan-3-yl)piperazin-1-yl)phenyl)amino)-1,3,5-triazin-2-yl)benzonitrile

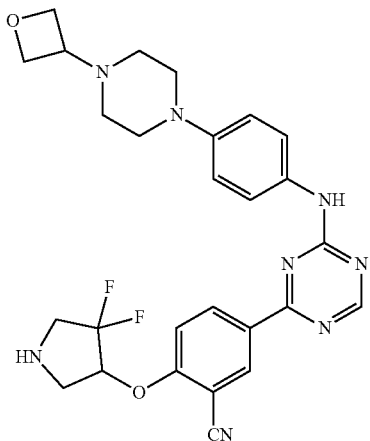 [SMILES: N#Cc1cc(-c2ncnc(Nc3ccc(N4CCN(C5COC5)CC4)cc3)n2)ccc1OC1CNCC1(F)F]

The title compound was prepared following the similar procedure reported in Example 168 by substituting tert-butyl 3,3-difluoro-4-hydroxypyrrolidine-1-carboxylate to 2-fluoro-5-(4-((4-(4-(oxetan-3-yl)piperazin-1-yl)phenyl)amino)-1,3,5-triazin-2-yl)benzonitrile, followed by Boc deprotection. LCMS-ESI$^+$ (m/z): [M+H]$^+$ calcd for $C_{27}H_{28}F_2N_8O_2$: 535.2: found:535.4 $^1$H NMR (400 MHz, DMSO-d$_6$) δ 10.21 (d, J=27.2 Hz, 1H), 8.77 (s, 1H), 8.70-8.46 (m, 2H), 7.74-7.43 (m, 3H), 7.02 (d, J=10.6 Hz, 2H), 5.64 (d, J=3.6 Hz, 1H), 4.86-4.62 (m, 4H), 4.32 (s, 2H), 4.02-3.86 (m, 3H), 3.86-3.63 (m, 4H), 3.15 (s, 4H).

Example 195 and Example 196

(S)-2-((4,4-difluoro-1-(2-hydroxyacetyl)pyrrolidin-3-yl)oxy)-5-(4-((4-(4-(oxetan-3-yl)piperazin-1-yl)phenyl)amino)-1,3,5-triazin-2-yl)benzonitrile and (R)-2-((4,4-difluoro-1-(2-hydroxyacetyl)pyrrolidin-3-yl)oxy)-5-(4-((4-(4-(oxetan-3-yl)piperazin-1-yl)phenyl)amino)-1,3,5-triazin-2-yl)benzonitrile

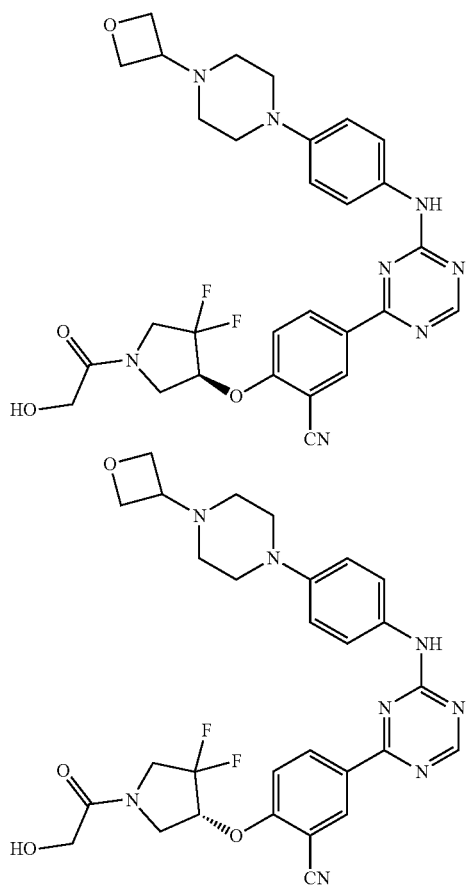

The title compound was prepared by substituting intermediate 2-fluoro-5-(4-((4-(4-(oxetan-3-yl)piperazin-1-yl)phenyl)amino)-1,3,5-triazin-2-yl)benzonitrile with tert-butyl 3,3-difluoro-4-hydroxypyrroldine-1-carboxylate, followed by Boc-deprotection and coupling with glycolic acid as shown in Example 168. Racemic mixtures were then separated by chiral separation using chiral column to afford title compounds and the stereochemistry were assigned tentatively Peak A: LCMS-ESI$^+$ (m/z): [M+H]$^+$ calcd for $C_{29}H_{30}F_2N_8O_4$: 593.2; found:593.3 $^1$H NMR (400 MHz, DMSO-d$_6$) δ 10.15 (d, J=23.3 Hz, 1H), 8.74 (s, 1H), 8.68-8.47 (m, 2H), 7.71-7.44 (m, 3H), 6.97 (d, J=11.3 Hz, 2H), 5.60 (d, J=34.2 Hz, 1H), 4.96 (d, J=23.5 Hz, 1H), 4.57-4.48 (m, 4H), 4.18-4.07 (m, 5H), 3.90-3.53 (m, 4H), 3.16-3.09 (m, 5H), 2.42 (br s, 1H). Peak B: LCMS-ESI$^+$ (m/z): [M+H]$^+$ calcd for $C_{29}H_{30}F_2N_8O_4$: 593.2; found:593.3

Example 197

(R)-2-((1-(methylsulfonyl)pyrrolidin-3-yl)oxy)-5-(4-((4-(4-(oxetan-3-yl)piperazin-1-yl)phenyl)amino)-1,3,5-triazin-2-yl)benzonitrile

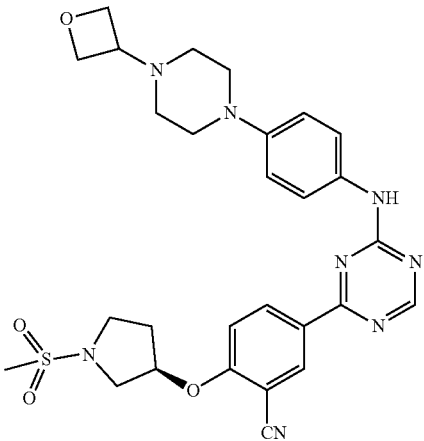 [SMILES: CS(=O)(=O)N1CC[C@@H](Oc2ccc(-c3ncnc(Nc4ccc(N5CCN(C6COC6)CC5)cc4)n3)cc2C#N)C1]

The title compound was prepared following the similar procedure reported in Example 168 by substituting (R)-tert-butyl 3-hydroxypyrrolidine-1-carboxylate to 2-fluoro-5-(4-((4-(4-(oxetan-3-yl)piperazin-1-yl)phenyl)amino)-1,3,5-triazin-2-yl)benzonitrile, followed by Boc deprotection and methanesulfonyl chloride coupling. LCMS-ESI$^+$ (m/z): [M+H]$^+$ calcd for $C_{28}H_{32}N_8O_4S$: 577.2: found:577.4 $^1$H NMR (400 MHz, DMSO-d$_6$) δ 10.20 (s, 1H), 8.75 (s, 1H), 8.65-8.43 (m, 2H), 7.61 (s, 2H), 7.50 (d, J=8.9 Hz, 1H), 7.02 (d, J=11.6 Hz, 2H), 5.34 (s, 1H), 4.73 (s, 4H), 3.86-3.64 (m, 4H), 3.55-3.36 (m, 6H), 3.04 (s, 3H), 2.95 (s, 3H), 2.35-2.14 (m, 2H).

Example 198

2-((4,4-difluoro-1-((S)-2-hydroxypropanoyl)pyrrolidin-3-yl)oxy)-5-(4-((4-(4-(oxetan-3-yl)piperazin-1-yl)phenyl)amino)-1,3,5-triazin-2-yl)benzonitrile

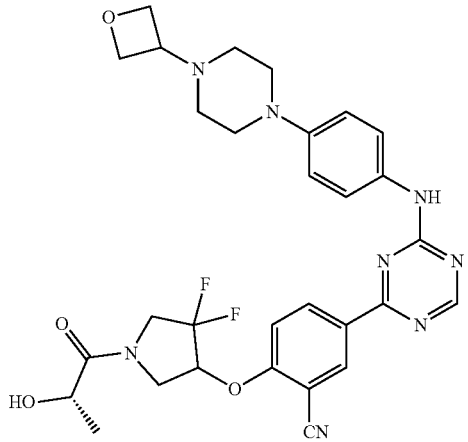 [SMILES: C[C@H](O)C(=O)N1CC(Oc2ccc(-c3ncnc(Nc4ccc(N5CCN(C6COC6)CC5)cc4)n3)cc2C#N)C(F)(F)C1]

The title compound was prepared following the similar procedure reported in Example 168 by substituting tert-butyl 3,3-difluoro-4-hydroxypyrrolidine-1-carboxylate to 2-fluoro-5-(4-((4-(4-(oxetan-3-yl)piperazin-1-yl)phenyl)amino)-1,3,5-triazin-2-yl)benzonitrile, followed by Boc deprotection and (S)-2-hydroxypropanoic acid coupling. LCMS-ESI$^+$ (m/z): [M+H]$^+$ calcd for $C_{30}H_{32}F_2N_8O_4$ 607.2: found:607.4 $^1$H NMR (400 MHz, DMSO-d$_6$) δ 10.21 (d, J=21.4 Hz, 1H), 8.76 (s, 1H), 8.70-8.50 (m, 2H), 7.63 (d, J=8.3 Hz, 3H), 7.04 (t, J=9.2 Hz, 2H), 5.62 (d, J=29.2 Hz, 1H), 4.75 (d, J=6.6 Hz, 5H), 4.51-4.24 (m, 3H), 4.24-3.59 (m, 6H), 3.09 (s, 5H), 1.19 (dd, J=8.2, 6.5 Hz, 3H).

Example 199

(R)-5-(4-((4-(4-(oxetan-3-yl)piperazin-1-yl)phenyl)amino)-1,3,5-triazin-2-yl)-2-((6-oxopiperidin-3-yl)oxy)benzonitrile

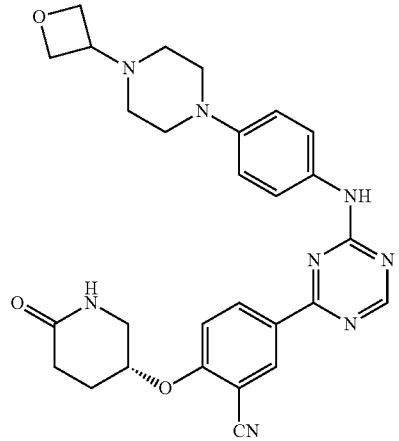 [SMILES: N#Cc1cc(-c2ncnc(Nc3ccc(N4CCN(C5COC5)CC4)cc3)n2)ccc1O[C@@H]1CCC(=O)NC1]

The title compound was prepared following the similar procedure reported in Example 168 by substituting (R)-5-hydroxypiperidin-2-one to 2-fluoro-5-(4-((4-(4-(oxetan-3-yl)piperazin-1-yl)phenyl)amino)-1,3,5-triazin-2-yl)benzonitrile. LCMS-ESI$^+$ (m/z): [M+H]$^+$ calcd for $C_{28}H_{30}N_8O_3$: 527.3: found:527.4.4 $^1$H NMR (400 MHz, DMSO-d$_6$) δ 10.29-10.07 (m, 1H), 8.75 (s, 1H), 8.67-8.44 (m, 2H), 7.74-7.50 (m, 3H), 7.46 (d, J=2.9 Hz, 1H), 7.05 (s, 2H), 5.19-5.05 (m, 1H), 4.77 (d, J=6.6 Hz, 5H), 4.45 (s, 1H), 3.82 (s, 2H), 3.60-3.30 (m, 2H), 3.06 (s, 5H), 2.43-2.18 (m, 2H), 2.17-2.02 (m, 2H).

Example 200

(R)-2-(3-fluoropyrrolidin-1-yl)-5-(4-((4-(4-(oxetan-3-yl)piperazin-1-yl)phenyl)amino)-1,3,5-triazin-2-yl)benzonitrile

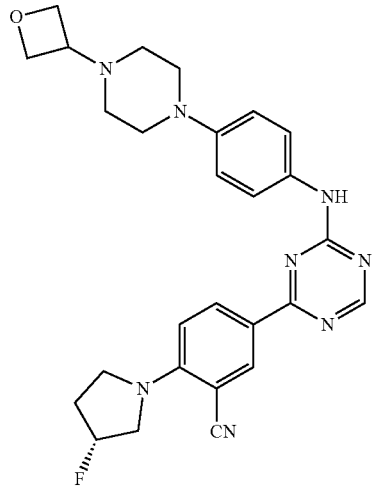 [SMILES: N#Cc1cc(-c2ncnc(Nc3ccc(N4CCN(C5COC5)CC4)cc3)n2)ccc1N1CC[C@@H](F)C1]

To the mixture of (R)-3-fluoropyrrolidine (35 mg, 0.27 mmol) and 2-fluoro-5-(4-((4-(4-(oxetan-3-yl)piperazin-1-yl)phenyl)amino)-1,3,5-triazin-2-yl)benzonitrile (60 mg, 0.14 mmol) were added IPA (2 mL) followed by DIPEA (0.15 mL) in a 10 mL microwave vial and sealed. The mixture was irradiated at 150° C. for 3 h. The reaction mixture was transferred in to 25 mL round bottom-flask and the solvent concentrated. The crude product purified via prep HPLC (5-95% acetonitrile in water, 0.1% trifluoroacetic acid buffer) to isolate (R)-2-(3-fluoropyrrolidin-1-yl)-5-(4-((4-(4-(oxetan-3-yl)piperazin-1-yl)phenyl)amino)-1,3,5-triazin-2-yl)benzonitrile. LCMS-ESI⁺ (m/z): [M+H]⁺ calcd for $C_{27}H_{29}FN_8O$: 501.2; found:501.3 ¹H NMR (400 MHz, DMSO-d₆) δ 10.05 (s, 1H), 8.67 (s, 1H), 8.43 (d, J=27.3 Hz, 1H), 8.32 (dd, J=9.2, 2.2 Hz, 1H), 7.62 (s, 2H), 7.04 (s, 2H), 6.94 (d, J=9.2 Hz, 1H), 5.49 (dt, J=53.0, 3.4 Hz, 1H), 4.87-4.65 (m, 5H), 4.44 (s, 1H), 4.08-3.66 (m, 6H), 3.07 (s, 5H), 2.40-2.05 (m, 2H).

Example 201

(S)-2-(3-fluoropyrrolidin-1-yl)-5-(4-((4-(4-(oxetan-3-yl)piperazin-1-yl)phenyl)amino)-1,3,5-triazin-2-yl)benzonitrile

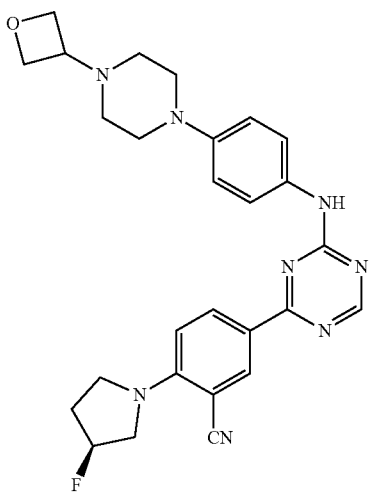 [SMILES: N#Cc1cc(-c2ncnc(Nc3ccc(N4CCN(C5COC5)CC4)cc3)n2)ccc1N1CC[C@H](F)C1]

The title compound was prepared following the similar procedure reported in Example 200 by substituting (S)-3-fluoropyrrolidine to 2-fluoro-5-(4-((4-(4-(oxetan-3-yl)piperazin-1-yl)phenyl)amino)-1,3,5-triazin-2-yl)benzonitrile instead of (R)-3-fluoropyrrolidine. LCMS-ESI⁺ (m/z): [M+H]⁺ calcd for $C_{27}H_{29}FN_8O$: 501.2; found:501.3 ¹H NMR (400 MHz, DMSO-d₆) δ 9.98 (s, 1H), 8.64 (s, 1H), 8.43 (d, J=29.4 Hz, 1H), 8.31 (d, J=8.7 Hz, 1 H), 7.70-7.43 (m, 3H), 6.94 (d, J=9.3 Hz, 2H), 5.61-5.35 (m, 1H), 4.50 (dt, J=37.5, 6.3 Hz, 4H), 4.07-3.68 (m, 4H), 3.43 (p, J=6.3 Hz, 1H), 3.13 (d, J=6.3 Hz, 4H), 2.39 (dd, J=6.5, 3.4 Hz, 4H), 2.34-2.06 (m, 2H).

Example 202

(R)-2-(3-hydroxypyrrolidin-1-yl)-5-(4-((4-(4-(oxetan-3-yl)piperazin-1-yl)phenyl)amino)-1,3,5-triazin-2-yl)benzonitrile

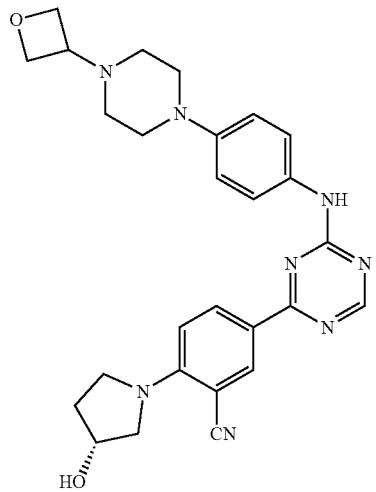 [SMILES: N#Cc1cc(-c2ncnc(Nc3ccc(N4CCN(C5COC5)CC4)cc3)n2)ccc1N1CC[C@@H](O)C1]

The title compound was prepared following the similar procedure reported in Example 200 by substituting (R)-3-hydroxypyrrolidine to 2-fluoro-5-(4-((4-(4-(oxetan-3-yl)piperazin-1-yl)phenyl)amino)-1,3,5-triazin-2-yl)benzonitrile instead of (R)-3-fluoropyrrolidine. LCMS-ESI⁺ (m/z): [M+H]⁺ calcd for $C_{27}H_{30}N_8O_2$: 499.2: found:499.4 ¹H NMR (400 MHz, DMSO-d₆) δ 11.90 (s, 1H), 10.08 (s, 1H), 8.66 (s, 1H), 8.39 (s, 1H), 8.28 (dd, J=9.3, 2.2 Hz, 1H), 7.63 (d, J=10.4 Hz, 2H), 7.03 (s, 2H), 6.89 (d, J=9.3 Hz, 1H), 4.91 (dd, J=7.7, 6.0 Hz, 2H), 4.70 (t, J=7.5 Hz, 2H), 4.62-4.33 (m, 4H), 3.93-3.59 (m, 5H), 3.57-3.37 (m, 3H), 3.12 (dd, J=33.2, 20.0 Hz, 3H), 2.14-1.83 (m, 2H).

Example 203

(S)-2-(3-hydroxypyrrolidin-1-yl)-5-(4-((4-(4-(oxetan-3-yl)piperazin-1-yl)phenyl)amino)-1,3,5-triazin-2-yl)benzonitrile

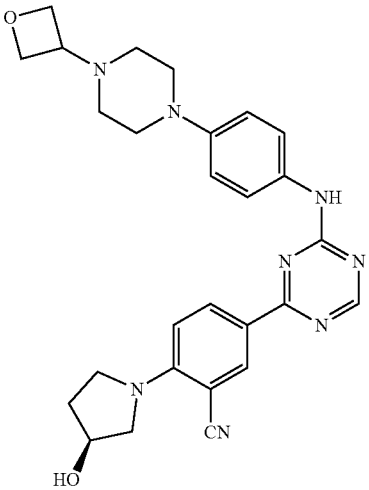 [SMILES: N#Cc1cc(-c2ncnc(Nc3ccc(N4CCN(C5COC5)CC4)cc3)n2)ccc1N1CC[C@H](O)C1]

The title compound was prepared following the similar procedure reported in Example 200 by substituting (S)-3-hydroxypyrrolidine to 2-fluoro-5-(4-((4-(4-(oxetan-3-yl)piperazin-1-yl)phenyl)amino)-1,3,5-triazin-2-yl)benzonitrile instead of (R)-3-fluoropyrrolidine. LCMS-ESI⁺ (m/z): [M+H]⁺ calcd for $C_{27}H_{30}N_8O_2$: 499.2: found:499.4 ¹H NMR (400 MHz, DMSO-d₆) δ 10.03 (s, 1H), 8.65 (s, 1H), 8.38 (s, 1H), 8.29 (dd, J=9.2, 2.2 Hz, 1H), 7.62 (s, 2H), 7.03 (s, 2H), 6.88 (d, J=9.2 Hz, 1H), 4.92-4.66 (m, 4H), 4.55-4.33 (m, 2H), 3.89-3.40 (m, 8H), 3.03 (d, J=40.8 Hz, 6H), 2.17-1.85 (m, 2H).

Example 204

2-((2R,4R)-4-hydroxy-2-methylpyrrolidin-1-yl)-5-(4-((4-(4-(oxetan-3-yl)piperazin-1-yl)phenyl)amino)-1,3,5-triazin-2-yl)benzonitrile

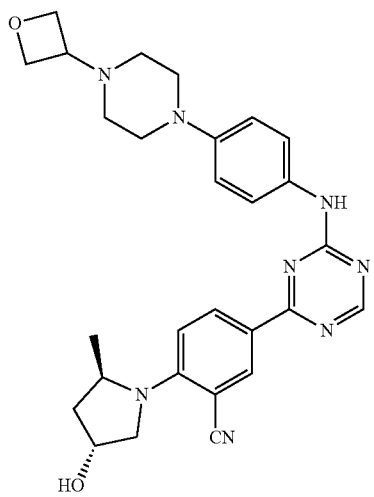 [SMILES: C[C@@H]1C[C@@H](O)CN1c1ccc(-c2ncnc(Nc3ccc(N4CCN(C5COC5)CC4)cc3)n2)cc1C#N]

The title compound was prepared following the similar procedure reported in Example 200 by substituting (3R,5R)-5-methylpyrrolidin-3-ol to 2-fluoro-5-(4-((4-(4-(oxetan-3-yl)piperazin-1-yl)phenyl)amino)-1,3,5-triazin-2-yl)benzonitrile instead of (R)-3-fluoropyrrolidine. LCMS-ESI⁺ (m/z): [M+H]⁺ calcd for $C_{28}H_{32}N_8O_2$: 513.3: found:513.4 ¹H NMR (400 MHz, DMSO-d₆) δ 10.06-9.89 (m, 1H), 8.64 (s, 1H), 8.44-8.37 (m, 1H) 8.35-8.24 (m, 1H), 7.58 (d, J=9.2 Hz, 2H), 7.01 (d, J=9.3 Hz, 1H), 6.94 (s, 2H), 4.99 (d, J=3.1 Hz, 1H), 4.55 (t, J=6.5 Hz, 2H), 4.46 (t, J=6.1 Hz, 2H), 4.35 (dd, J=13.4, 6.4 Hz, 2H), 4.01 (dd, J=10.9, 4.1 Hz, 1H), 3.51-3.37 (m, 2H), 3.12 (d, J=5.8 Hz, 4H), 2.39 (t, J=4.9 Hz, 4H), 2.12 (dd, J=13.0, 6.8 Hz, 1H), 1.78 (ddd, J=12.6, 8.0, 4.4 Hz, 1H), 1.21 (d, J=5.9 Hz, 3H).

Example 205

2-((2S,4R)-4-hydroxy-2-methylpyrrolidin-1-yl)-5-(4-((4-(4-(oxetan-3-yl)piperazin-1-yl)phenyl)amino)-1,3,5-triazin-2-yl)benzonitrile

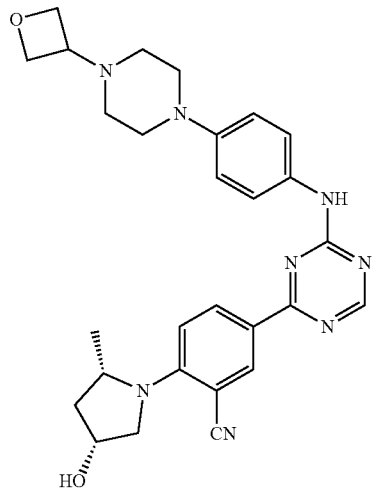 [SMILES: C[C@H]1C[C@@H](O)CN1c1ccc(-c2ncnc(Nc3ccc(N4CCN(C5COC5)CC4)cc3)n2)cc1C#N]

The title compound was prepared following the similar procedure reported in Example 200 by substituting (3R,5S)-5-methylpyrrolidin-3-ol to 2-fluoro-5-(4-((4-(4-(oxetan-3-yl)piperazin-1-yl)phenyl)amino)-1,3,5-triazin-2-yl)benzonitrile instead of (R)-3-fluoropyrrolidine LCMS-ESI⁺ (m/z): [M+H]⁺ calcd for $C_{28}H_{32}N_8O_2$: 513.3: found:513.4 ¹H NMR (400 MHz, DMSO-d₆) δ 9.95 (d, J=15.6 Hz, 1H), 8.64 (s, 1H), 8.46-8.39 (m, 1H) 8.35-8.23 (m, 1H), 7.58 (d, J=12.0 Hz, 2H), 7.01 (d, J=9.3 Hz, 1H), 6.94 (s, 2H), 4.99 (d, J=3.3 Hz, 1H), 4.55 (t, J=6.5 Hz, 2H), 4.46 (t, J=6.0 Hz, 2H), 4.35 (dt, J=13.2, 3.6 Hz, 2H), 4.01 (dd, J=10.9, 4.1 Hz, 1H), 3.53-3.37 (m, 2H), 3.12 (d, J=6.1 Hz, 4H), 2.44-2.32 (m, 4H), 2.12 (dd, J=12.9, 7.0 Hz, 1H), 1.78 (ddd, J=12.6, 8.1, 4.5 Hz, 1H), 1.21 (d, J=5.9 Hz, 3H).

Example 206

5-(4-((4-(4-(oxetan-3-yl)piperazin-1-yl)phenyl)amino)-1,3,5-triazin-2-yl)-2-(2-oxa-6-azaspiro[3.4]octan-6-yl)benzonitrile

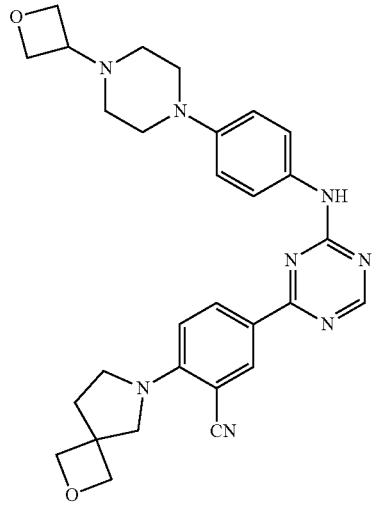 [SMILES: N#Cc1cc(-c2ncnc(Nc3ccc(N4CCN(C5COC5)CC4)cc3)n2)ccc1N1CCC2(COC2)C1]

The title compound was prepared following the similar procedure reported in Example 200 by substituting 2-oxa-6-azaspiro[3.4]octane to 2-fluoro-5-(4-((4-(4-(oxetan-3-yl)piperazin-1-yl)phenyl)amino)-1,3,5-triazin-2-yl)benzonitrile instead of (R)-3-fluoropyrrolidine. LCMS-ESI⁺ (m/z): [M+H]⁺ calcd for $C_{29}H_{32}N_8O_2$: 525.2: found:525.4 ¹H NMR (400 MHz, DMSO-$d_6$) δ 9.97 (s, 1H), 8.63 (s, 1H), 8.40 (d, J=29.1 Hz, 1H), 8.33-8.18 (m, 1H), 7.56 (s, 2H), 7.09-6.77 (m, 3H), 4.58 (dd, J=15.2, 6.3 Hz, 3H), 4.52 (dd, J=7.4, 3.9 Hz, 2H), 4.50-4.42 (m, 3H), 3.89 (s, 2H), 3.72-3.60 (m, 2H), 3.50-3.37 (m, 2H), 3.12 (s, 3H), 2.39 (t, J=4.8 Hz, 3H), 2.27 (t, J=6.9 Hz, 2H), 2.10 (td, J=7.0, 2.1 Hz, 1H).

Example 207

5-(4-((4-(4-(oxetan-3-yl)piperazin-1-yl)phenyl)amino)-1,3,5-triazin-2-yl)-2-(1-oxa-6-azaspiro[3.4]octan-6-yl)benzonitrile

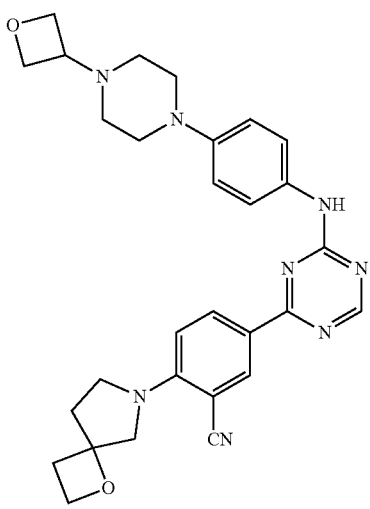 [SMILES: N#Cc1cc(-c2ncnc(Nc3ccc(N4CCN(C5COC5)CC4)cc3)n2)ccc1N1CCC2(CCO2)C1]

The title compound was prepared following the similar procedure reported in Example 200 by substituting 1-oxa-6-azaspiro[3.4]octane to 2-fluoro-5-(4-((4-(4-(oxetan-3-yl)piperazin-1-yl)phenyl)amino)-1,3,5-triazin-2-yl)benzonitrile instead of (R)-3-fluoropyrrolidine. LCMS-ESI⁺ (m/z): [M+H]⁺ calcd for $C_{29}H_{32}N_8O_2$: 525.2: found:525.4 ¹H NMR (400 MHz, DMSO-$d_6$) δ 10.04 (s, 1H), 8.66 (s, 1H), 8.41 (d, J=25.7 Hz, 1H), 8.30 (dd, J=9.2, 2.2 Hz, 1H), 7.62 (s, 2H), 7.03 (s, 2H), 6.87 (dd, J=15.4, 9.1 Hz, 1H), 4.76 (d, J=6.8 Hz, 4H), 4.54-4.34 (m, 4H), 3.96-3.77 (m, 4H), 3.77-3.54 (m, 4H), 3.05 (s, 3H), 2.85-2.59 (m, 2H), 2.36 (ddd, J=10.8, 6.7, 3.3 Hz, 1H), 2.15 (dt, J=12.6, 9.0 Hz, 1H).

Example 208

5-(4-((4-(4-(oxetan-3-yl)piperazin-1-yl)phenyl)amino)-1,3,5-triazin-2-yl)-2-(1,4-dioxa-7-azaspiro[4.4]nonan-7-yl)benzonitrile

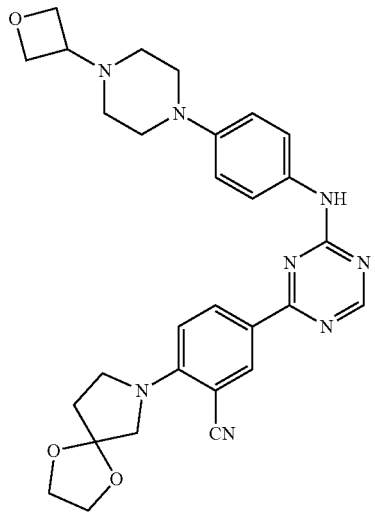 [SMILES: N#Cc1cc(-c2ncnc(Nc3ccc(N4CCN(C5COC5)CC4)cc3)n2)ccc1N1CCC2(C1)OCCO2]

The title compound was prepared following the similar procedure reported in Example 200 by substituting 1,4-dioxa-7-azaspiro[4.4]nonane to 2-fluoro-5-(4-((4-(4-(oxetan-3-yl)piperazin-1-yl)phenyl)amino)-1,3,5-triazin-2-yl)benzonitrile instead of (R)-3-fluoropyrrolidine LCMS-ESI⁺ (m/z): [M+H]⁺ calcd for $C_{29}H_{32}N_8O_3$: 541.2: found:541.4 ¹H NMR (400 MHz, DMSO-$d_6$) δ 10.05 (s, 1H), 8.66 (s, 1H), 8.38 (s, 1H), 8.31 (dd, J=9.2, 2.2 Hz, 1H), 7.62 (s, 2H), 7.03 (s, 2H), 6.90 (d, J=9.2 Hz, 1H), 4.76 (dd, J=6.4, 2.7 Hz, 4H), 4.43 (s, 2H), 3.96 (s, 4H), 3.81-3.64 (m, 4H), 3.5-3.40 (m, 3H) 3.06 (s, 4H), 2.15 (t, J=7.2 Hz, 2H).

Example 209

2-(2-methyl-2,7-diazaspiro[3.5]nonan-7-yl)-5-(4-((4-(4-(oxetan-3-yl)piperazin-1-yl)phenyl)amino)-1,3,5-triazin-2-yl)benzonitrile

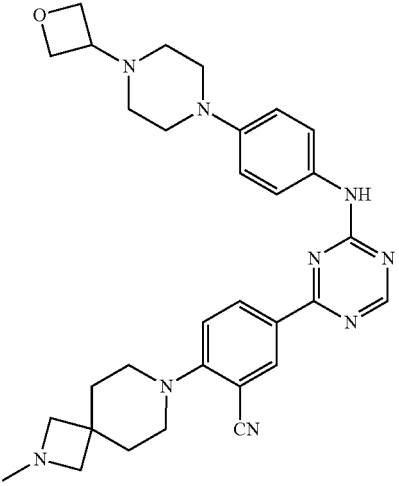 [SMILES: CN1CC2(CCN(c3ccc(-c4ncnc(Nc5ccc(N6CCN(C7COC7)CC6)cc5)n4)cc3C#N)CC2)C1]

The title compound was prepared following the similar procedure reported in Example 200 by substituting 2-methyl-2,7-diazaspiro[3.5]nonane to 2-fluoro-5-(4-((4-(4-(oxetan-3-yl)piperazin-1-yl)phenyl)amino)-1,3,5-triazin-2- yl)benzonitrile instead of (R)-3-fluoropyrrolidine LCMS-ESI+ (m/z): [M+H]+ calcd for $C_{31}H_{37}N_9O$: 552.2.3: found: 552.4 $^1$H NMR (400 MHz, DMSO-$d_6$) δ 9.95 (d, J=15.6 Hz, 1H), 8.63 (s, 1H), 8.36 (s, 1H), 8.32-8.20 (m, 1H), 7.55 (s, 2H), 6.93 (s, 2H), 6.87 (d, J=9.3 Hz, 1H), 4.55 (t, J=6.5 Hz, 2H), 4.46 (t, J=6.0 Hz, 2H), 3.67 (q, J=6.8 Hz, 2H), 3.63-3.48 (m, 2H), 3.43 (p, J=6.3 Hz, 1H), 3.11 (d, J=5.7 Hz, 4H), 2.67-2.52 (m, 2H), 2.45-2.29 (m, 6H), 2.22 (s, 3H), 1.95 (ddq, J=19.0, 12.1, 6.8 Hz, 2H), 1.77 (td, J=6.7, 2.5 Hz, 2H).

Example 210

5-(4-((4-(4-(oxetan-3-yl)piperazin-1-yl)phenyl)amino)-1,3,5-triazin-2-yl)-2-(1-oxa-6-azaspiro[3.3]heptan-6-yl)benzonitrile

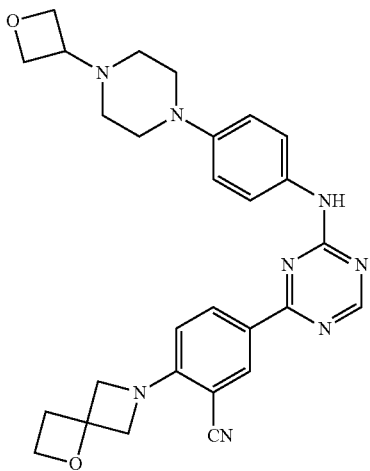 [SMILES: N#Cc1cc(-c2ncnc(Nc3ccc(N4CCN(C5COC5)CC4)cc3)n2)ccc1N1CC2(CCO2)C1]

The title compound was prepared following the similar procedure reported in Example 200 by substituting 1-oxa-6-azaspiro[3.3]heptane to 2-fluoro-5-(4-((4-(4-(oxetan-3-yl)piperazin-1-yl)phenyl)amino)-1,3,5-triazin-2-yl)benzonitrile instead of (R)-3-fluoropyrrolidine. LCMS-ESI+ (m/z): [M+H]+ calcd for $C_{28}H_{30}N_8O_2$: 511.2: found:511.4 $^1$H NMR (400 MHz, DMSO-$d_6$) δ 10.06 (s, 1H), 8.66 (s, 1H), 8.47-8.22 (m, 2H), 7.61 (s, 2H), 7.04 (s, 2H), 6.67 (d, J=9.0 Hz, 1H), 4.87-4.69 (m, 4H), 4.60-4.39 (m, 6H), 4.33 (dd, J=10.1, 1.6 Hz, 4H), 3.80-3.46 (m, 2H) 3.23-2.95 (m, 3H), 2.90 (t, J=7.5 Hz, 2H).

Example 211

5-(4-((4-(4-(oxetan-3-yl)piperazin-1-yl)phenyl)amino)-1,3,5-triazin-2-yl)-2-(7-oxa-2-azaspiro[3.5]nonan-2-yl)benzonitrile

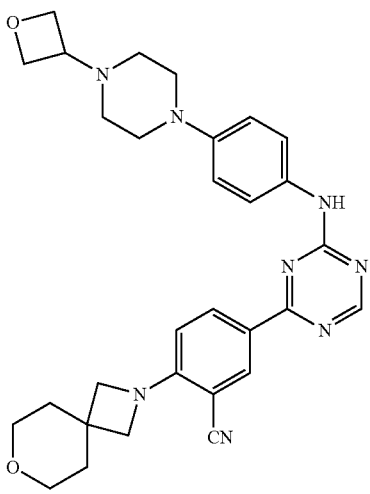 [SMILES: N#Cc1cc(-c2ncnc(Nc3ccc(N4CCN(C5COC5)CC4)cc3)n2)ccc1N1CC2(CCOCC2)C1]

The title compound was prepared following the similar procedure reported in Example 200 by substituting 7-oxa-2-azaspiro[3.5]nonane to 2-fluoro-5-(4-((4-(4-(oxetan-3-yl)piperazin-1-yl)phenyl)amino)-1,3,5-triazin-2-yl)benzonitrile instead of (R)-3-fluoropyrrolidine. LCMS-ESI+ (m/z): [M+H]+ calcd for $C_{30}H_{34}N_8O_2$: 539.2: found:549.4 $^1$H NMR (400 MHz, DMSO-$d_6$) δ 10.02 (d, J=14.9 Hz, 1H), 8.65 (s, 1H), 8.48-8.19 (m, 2H), 7.61 (s, 2H), 7.02 (s, 2H), 6.65 (d, J=9.0 Hz, 1H), 4.88 (s, 2H), 4.70 (t, J=7.4 Hz, 2H), 4.47 (s, 1H), 4.03 (s, 4H), 3.54 (t, J=5.2 Hz, 8H), 3.11 (s, 4H), 1.77 (t, J=5.2 Hz, 4H).

Example 212

5-(4-((4-(4-(oxetan-3-yl)piperazin-1-yl)phenyl)amino)-1,3,5-triazin-2-yl)-2-(8-oxa-2-azaspiro[4.5]decan-2-yl)benzonitrile

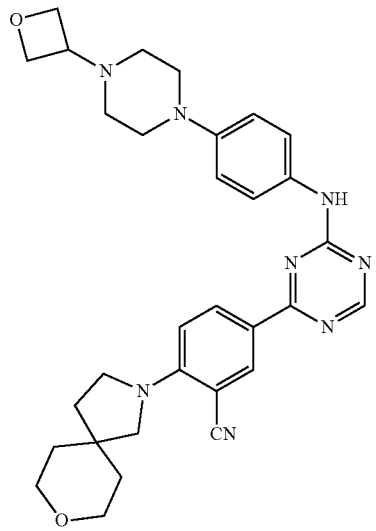 [SMILES: N#Cc1cc(-c2ncnc(Nc3ccc(N4CCN(C5COC5)CC4)cc3)n2)ccc1N1CCC2(CCOCC2)C1]

The title compound was prepared following the similar procedure reported in Example 200 by substituting 8-oxa-2-azaspiro[4.5]decane to 2-fluoro-5-(4-((4-(4-(oxetan-3-yl)piperazin-1-yl)phenyl)amino)-1,3,5-triazin-2-yl)benzonitrile instead of (R)-3-fluoropyrrolidine. LCMS-ESI+ (m/z): [M+H]+ calcd for $C_{31}H_{36}N_8O_2$: 553.3: found:553.4 $^1$H NMR (400 MHz, DMSO-$d_6$) δ 10.02 (s, 1H), 8.65 (s, 1H), 8.38 (d, J=16.6 Hz, 1H), 8.28 (dd, J=9.2, 2.1 Hz, 1H), 7.61 (s, 2H), 7.02 (d, J=8.5 Hz, 2H), 6.90 (d, J=9.3 Hz, 1H), 4.75 (d, J=6.4 Hz, 4H), 4.41 (s, 1H), 3.75 (t, J=7.0 Hz, 6H), 3.68-3.47 (m, 6H), 3.03 (s, 4H). 1.93 (t, J=7.0 Hz, 2H), 1.55 (td, J=6.8, 5.8, 3.9 Hz, 4H).

Example 213

5-(4-((4-(4-(oxetan-3-yl)piperazin-1-yl)phenyl)amino)-1,3,5-triazin-2-yl)-2-(2-oxa-8-azaspiro[4.5]decan-8-yl)benzonitrile

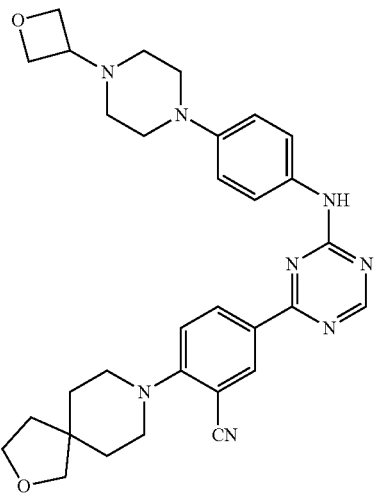 [SMILES: N#Cc1cc(-c2ncnc(Nc3ccc(N4CCN(C5COC5)CC4)cc3)n2)ccc1N1CCC2(CCOC2)CC1]

The title compound was prepared following the similar procedure reported in Example 200 by substituting 2-oxa-8-azaspiro[4.5]decane to 2-fluoro-5-(4-((4-(4-(oxetan-3-yl)piperazin-1-yl)phenyl)amino)-1,3,5-triazin-2-yl)benzonitrile instead of (R)-3-fluoropyrrolidine. LCMS-ESI⁺ (m/z): [M+H]⁺ calcd for $C_{31}H_{36}N_8O_2$ 553.3: found:553.4 ¹H NMR (400 MHz, DMSO-d₆) δ 10.10 (d, J=16.8 Hz, 1H), 8.71 (s, 1H), 8.59-8.34 (m, 2H), 7.62 (d, J=9.5 Hz, 2H), 7.27 (d, J=8.9 Hz, 1H), 7.03 (s, 2H), 4.72 (d, J=6.0 Hz, 5H), 3.76 (t, J=7.1 Hz, 2H), 3.55-3.29 (m, 8H), 3.09 (d, J=46.4 Hz, 6H), 1.77 (t, J=7.1 Hz, 2H), 1.69 (t, J=5.6 Hz, 4H).

Example 214

5-(4-((4-(4-(oxetan-3-yl)piperazin-1-yl)phenyl)amino)-1,3,5-triazin-2-yl)-2-(1-oxa-7-azaspiro[3.5]nonan-7-yl)benzonitrile

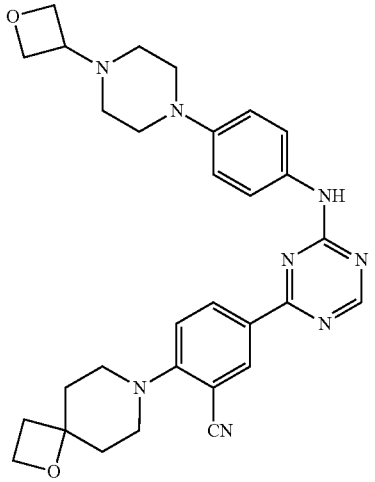 [SMILES: N#Cc1cc(-c2ncnc(Nc3ccc(N4CCN(C5COC5)CC4)cc3)n2)ccc1N1CCC2(CCO2)CC1]

The title compound was prepared following the similar procedure reported in Example 200 by substituting 1-oxa-7-azaspiro[3.5]nonane to 2-fluoro-5-(4-((4-(4-(oxetan-3-yl)piperazin-1-yl)phenyl)amino)-1,3,5-triazin-2-yl)benzonitrile instead of (R)-3-fluoropyrrolidine. LCMS-ESI⁺ (m/z): [M+H]⁺ calcd for $C_{30}H_{34}N_8O_2$ 539.3: found:539.4 ¹H NMR (400 MHz, DMSO-d₆) δ 10.37-10.00 (m, 1H), 8.84-8.61 (m, 1H), 8.57-8.35 (m, 1H), 7.67 (d, J=40.5 Hz, 2H), 7.35-7.17 (m, 1H), 7.05 (s, 2H), 4.90-4.67 (m, 4H), 4.61-4.39 (m, 2H), 4.06-3.77 (m, 12H), 3.68-3.43 (m, 2H), 3.38-3.23 (m, 1H), 3.08-2.65 (m, 1H), 2.36-2.12 (m, 1H), 1.79-1.57 (m, 3H).

Example 215

3-(4-((4-(4-(oxetan-3-yl)piperazin-1-yl)phenyl)amino)-1,3,5-triazin-2-yl)benzonitrile

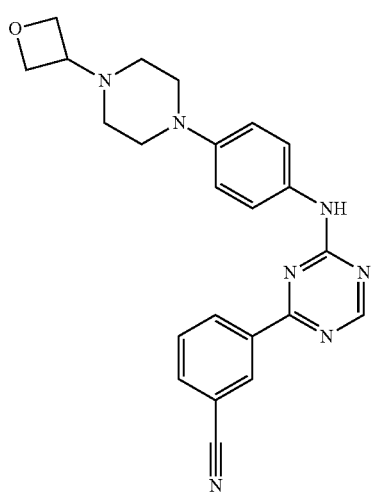 [SMILES: N#Cc1cccc(-c2ncnc(Nc3ccc(N4CCN(C5COC5)CC4)cc3)n2)c1]

To 4-chloro- N-(4-(4-(oxetan-3-yl)piperazin-1-yl)phenyl)-1,3,5-triazin-2-amine (50 mgs, 0.14 mmol), 3-(4,4,5,5-tetramethyl-1,3,2-dioxaborolan-2-yl)benzonitrile (36 mgs, 0.15 mmol), Tetrakis(triphenylphosphine)Palladium(0) (9 mg) and a de-gassed saturated aqueous solution of sodium carbonate (0.3 ml) mixture in argon atmosphere was added a mixture of de-gassed solvents (1,4-dioxane and water 2:1). The mixture was heated under argon atmosphere at 95° C. for 2 hr in a heating block. After cooling at room temperature, water was poured into the reaction mixture and desired product was extracted with DCM. Organic layer was dried over Mg₂SO₄ and evaporated to dryness. Solids re-dissolved in acetonitrile and purified via preparative HPLC (5-65% acetonitrile in water, 0.1% trifluoroacteic acid buffer). Fractions containing desired product were collected and combined with a saturated aqueous solution of NaHCO₃ to be extracted with DCM. Organic layer was collected, dried over magnesium sulfate and evaporated under reduced pressure to yield 3-(4-((4-(4-(oxetan-3-yl)piperazin-1-yl)phenyl)amino)-1,3,5-triazin-2-yl)benzonitrile. ¹H NMR (400 MHz, DMSO-d₆) δ 10.21 (d, J=13.6 Hz, 1H), 8.78 (s, 1H), 8.68-8.55 (m, 2H), 8.08 (dt, J=7.8, 1.4 Hz, 1H), 7.78 (t, J=7.9 Hz, 1H), 7.67-7.45 (m, 2H), 7.02-6.94 (m, 2H), 4.56 (t, J=6.5 Hz, 2H), 4.46 (t, J=6.0 Hz, 2H), 3.43 (p, J=6.3 Hz, 1H), 3.22-3.09 (m, 4H), 2.40 (t, J=4.9 Hz, 4H). LCMS-ESI⁺ (m/z): [M+H]⁺ calcd for $C_{23}H_{23}N_7O$: 414.2; found 414.0.

Example 216

(S)-5-(4-((4-(4-(oxetan-3-yl)piperazin-1-yl)phenyl)amino)-1,3,5-triazin-2-yl)-2-((tetrahydrofuran-3-yl)oxy)benzonitrile

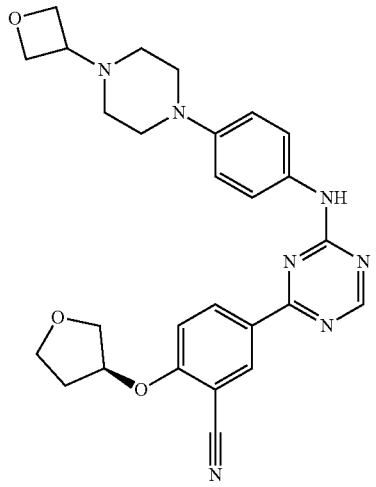 [SMILES: N#Cc1cc(-c2ncnc(Nc3ccc(N4CCN(C5COC5)CC4)cc3)n2)ccc1O[C@H]1CCOC1]

A solution of (S)-tetrahydrofuran-3-ol (22 mgs, 0.23 mmol) in THF (3 mL) was stirred in an ice-water bath under an atmosphere of Argon. Potassium tert-butoxide (1.0 M, 0.28 ml, 0.29 mmol) was added in a single portion and the mixture was stirred at 0° C. for 30 minutes, and then 2-fluoro-5-(4-((4-(4-(oxetan-3-yl)piperazin-1-yl)phenyl)amino)-1,3,5-triazin-2-yl)benzonitrile was added (100 mgs, 0.23 mmol). The mixture was stirred for 1 hr at 60° C. After the mixture cooled to room temperature, water was added, and mixture evaporated under reduced pressure. Solids were purified via preparative HPLC (5-65% acetonitrile in water, 0.1% trifluoroacetic acid buffer) to yield the compound (S)-5-(4-((4-(4-(oxetan-3-yl)piperazin-1-yl)phenyl)amino)-1,3,5-triazin-2-yl)-2-((tetrahydrofuran-3-yl)oxy)benzonitrile. $^1$H NMR (400 MHz, DMSO-d$_6$) δ 10.1 (s, 1H), 8.69 (s, 1H), 8.56-8.41 (m, 2H), 7.61-7.52 (m, 2H), 7.43-7.33 (m, 1H), 7.00 (t, J=10.0 Hz, 2H), 5.26 (ddt, J=6.1, 4.2, 1.8 Hz, 1H), 4.78-4.64 (m, 4H), 4.41 (q, J=7.3, 6.5 Hz, 1H), 3.93-3.65 (m, 5H), 3.02-2.89 (m, 7H), 2.28 (dtd, J=14.1, 8.1, 6.1 Hz, 1H), 2.03-1.90 (m, 1H). LCMS-ESI$^+$ (m/z): [M+H]$^+$ calcd for C$_{27}$H$_{29}$N$_7$O$_3$: 500.2; found: 500.3

Example 217

2-(cyclohexyloxy)-5-(4-((4-(4-(oxetan-3-yl)piperazin-1-yl)phenyl)amino)-1,3,5-triazin-2-yl)benzonitrile

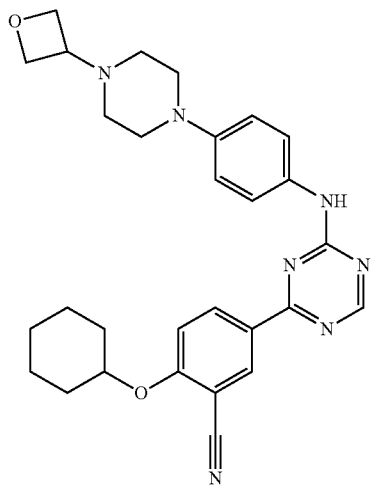 [SMILES: N#Cc1cc(-c2ncnc(Nc3ccc(N4CCN(C5COC5)CC4)cc3)n2)ccc1OC1CCCCC1]

The title compound was prepared following a similar procedure reported in Example-216 using cyclohexanol. $^1$H NMR (400 MHz, DMSO-d$_6$) δ 10.23-10.03 (m, 1H), 8.69 (s, 1H), 8.59-8.37 (m, 2H), 7.70-7.48 (m, 2H), (d, J=9.1 Hz, 1H) 7.00 (dd, J=9.4, 4.9 Hz, 2H), 4.81-4.58 (m, 5H), 4.43-4.32 (m, 2H), 4.12-2.8 (m, 7H), 1.88 (ddd, J=11.7, 7.5, 4.0 Hz, 2H), 1.68 (dp, J=12.7, 5.5, 4.4 Hz, 2H), 1.57-1.20 (m, 6H). LCMS-ESI$^+$ (m/z): [M+H]$^+$ calcd for C$_{29}$H$_{33}$N$_7$O$_2$: 512.3; found:512.3

Example 218

2-((cis-3-fluoro-1-(2-hydroxyacetyl)piperidin-4-yl)oxy)-5-(4-((4-(4-(oxetan-3-yl)piperazin-1-yl)phenyl)amino)-1,3,5-triazin-2-yl)benzonitrile

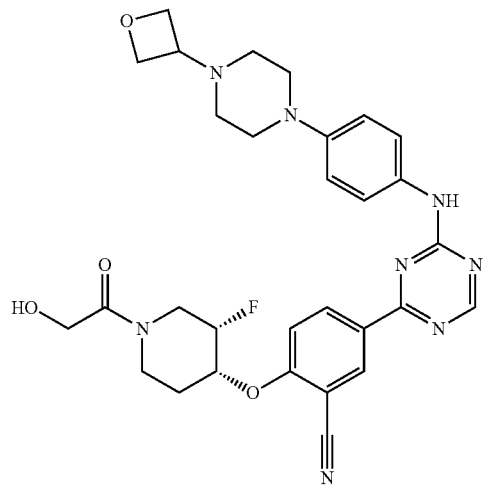 [SMILES: N#Cc1cc(-c2ncnc(Nc3ccc(N4CCN(C5COC5)CC4)cc3)n2)ccc1O[C@@H]1CCN(C(=O)CO)C[C@@H]1F]

To a solution of 2,4-dichloro-1,3,5-triazine (9.5 g, 63.3 mmol) in DMF at 0° C. (flushed with Argon) was added a solution of 4-(4-(oxetan-3-yl)piperazin-1-yl)aniline (14 g, 60.2 mmol) in DMF over 15 min and stirred in an ice-bath for 1 h. A solution of 40% MeOH/DCM was added to the reaction mixture and stirred for 1 hr. The insoluble particles were filtered off and washed with di-ethyl-ether twice. Solids were separated by filtration. $^1$H NMR (400 MHz, DMSO-d6) δ 10.58 (s, 1H), 8.54 (d, J=7.2 Hz, 1H), 7.49 (t, J=9.6 Hz, 2H), 7.01 (t, J=8.0 Hz, 2H), 4.93 (t, J=6.9 Hz, 2H), 4.67 (t, J=7.4 Hz, 2H), 4.46 (q, J=7.0, 6.0 Hz, 1H), 3.86-3.70 (m, 4H), 3.24-3.01 (m, 4H). LCMS-ESI$^+$ (m/z): [M+H]$^+$ calcd for C$_{16}$H$_{19}$ClN$_6$O: 347.1: found: 347.0.

To 4-chloro-N-(4-(4-(oxetan-3-yl)piperazin-1-yl)phenyl)-1,3,5-triazin-2-amine (4.1 g, 11.7 mmol), 2-fluoro-5-(4,4,5,5-tetramethyl-1,3,2-dioxaborolan-2-yl)benzonitrile (3.2 gr, 12.8 mmol), Pd(dppf)Cl$_2$CH$_2$Cl$_2$ (854 mg) and potassium carbonate (3.2 g, 23.4 mmol) mixture in argon atmosphere was added a mixture of de-gassed solvents (DME:water=2:1). The mixture was heated under argon atmosphere at 104° C. for 40 min in a heating block. After cooling at room temperature, water was poured into the reaction mixture and it was stirred for 20 min. Solids were filtered off and washed out with diethyl-ether. The formed solids were re-suspended in ACN and heated to boiling point and then stirred at room temperature for 2 hr. To this suspension di-ethyl ether was added and stirred at room temperature overnight. Solids were taken by filtration to yield desired product.

A solution of a racemic mixture of Cis-tert-butyl 3-fluoro-4-hydroxypiperidine-1-carboxylate (56 mgs, 0.26 mmol) in THF (5 mL) was stirred in an ice-water bath under an atmosphere of Argon. Potassium tert-butoxide (1.0 M, 0.28 ml, 0.28 mmol) was added in a single portion and the mixture was stirred at 0° C. for 40 minutes, and then 2-fluoro-5-(4-((4-(4-(oxetan-3-yl)piperazin-1-yl)phenyl) amino)-1,3,5-triazin-2-yl)benzonitrile was added (100 mgs, 0.23 mmol). The mixture was stirred for 1 hr at 60° C. After the mixture cooled to room temperature, water was added, and mixture evaporated under reduced pressure to yield the crude Cis-tert-butyl 4-(2-cyano-4-(4-((4-(4-(oxetan-3-yl) piperazin-1-yl)phenyl)amino)-1,3,5-triazin-2-yl)phenoxy)-3-fluoropiperidine-1-carboxylate.

Solids were dissolved with DCM and TFA. Reaction mixture was stirred at room temperature for 1 hr. Reaction mixture was evaporated under reduced pressure and solids were suspended in a saturated aqueous solution of NaHCO$_3$ and extracted with DCM. Organic phase was collected dried over magnesium sulfate and evaporated under reduced pressure to yield 2-((Cis-3-fluoropiperidin-4-yl)oxy)-5-(4-((4-(4-(oxetan-3-yl)piperazin-1-yl)phenyl)amino)-1,3,5-triazin-2-yl)benzonitrile.

To a solution of 2-((Cis-3-fluoropiperidin-4-yl)oxy)-5-(4-((4-(4-(oxetan-3-yl)piperazin-1-yl)phenyl)amino)-1,3,5-triazin-2-yl)benzonitrile (70 mg, 0.013 mmol), glycolic acid (20 mg, 0.026 mmol), HATU (100 mgs, 0.026 mmol) in DMF (3 mL) was added TEA (0.02 mL, 0.026 mmol) in a 10 mL microwave vial and sealed. This reaction mixture was stirred at room temperature for 2 hrs. Water was added and it was extracted with DCM. Organic layer was dried over Mg$_2$SO$_4$ and evaporated to dryness. Solids re-dissolved in acetonitrile and purified via preparative HPLC (5-65% acetonitrile in water, 0.1% trifluoroacteic acid buffer). Fractions containing desired product were collected and combined with a saturated aqueous solution of NaHCO$_3$ to be extracted with DCM. Organic layer was collected, dried over magnesium sulfate and evaporated under reduced pressure to yield 2-((Cis-3-fluoro-1-(2-hydroxyacetyl)piperidin-4-yl)oxy)-5-(4-((4-(4-(oxetan-3-yl)piperazin-1-yl)phenyl) amino)-1,3,5-triazin-2-yl)benzonitrile. $^1$H NMR (400 MHz, DMSO-d$_6$) δ 10.14 (s, 1H), 8.73 (s, 1H), 8.56 (q, J=9.0 Hz, 2H), 7.65-7.49 (m, 3H), 7.04-6.84 (m, 2H), 5.19-4.95 (m, 2H), 4.84-4.6 (m, 1H), 4.55 (t, J=6.5 Hz, 2H), 4.46 (t, J=6.0 Hz, 2H), 4.39-3.86 (m, 4H), 3.71-3.35 (m, 3H), 3.13 (d, J=6.4 Hz, 4H), 2.40 (t, J=4.9 Hz, 4H), 2.03-1.68 (m, 2H). LCMS-ESI$^+$ (m/z): [M+H]$^+$ calcd for C$_{30}$H$_{33}$FN$_8$O$_4$: 589.3; found:589.2.

Example 219

(R)-2-((1-(2-hydroxypropanoyl)piperidin-4-yl)oxy)-5-(4-((4-(4-(oxetan-3-yl)piperazin-1-yl)phenyl) amino)-1,3,5-triazin-2-yl)benzonitrile

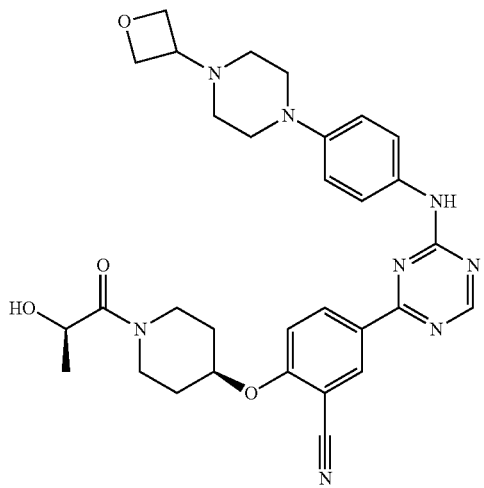

To solution of 5-(4-((4-(4-(oxetan-3-yl)piperazin-1-yl) phenyl)amino)-1,3,5-triazin-2-yl)-2-(piperidin-4-yloxy) benzonitrile (50 mg, 0.09 mmol), (R)-2-hydroxypropanoic acid (17 mg, 0.19 mmol), HATU (74 mgs, 0.19 mmol) in DMF (3 mL) was added 4-methylmorpholine (0.021 mL, 0.19 mmol) in a 10 mL microwave vial and sealed. This reaction mixture was stirred at room temperature for 2 hrs. Water was added and it was extracted with DCM. Organic layer was dried over Mg$_2$SO$_4$ and evaporated to dryness. Solids re-dissolved in acetonitrile and purified via preparative HPLC (5-65% acetonitrile in water, 0.1% trifluoroacteic acid buffer) to yield (R)-2-((1-(2-hydroxypropanoyl)piperidin-4-yl)oxy)-5-(4-((4-(4-(oxetan-3-yl)piperazin-1-yl)phenyl)amino)-1,3,5-triazin-2-yl)benzonitrile. $^1$H NMR (400 MHz, DMSO-d$_6$) δ 10.18 (d, J=21.0 Hz, 1H), 8.74 (s, 1H), 8.66-8.44 (m, 2H), 7.71-7.42 (m, 3H), 7.05-6.95 (m, 2H), 5.05-4.95 (m, 1H), 4.82-4.75 (m, 4H), 4.45 (q, J=6.5 Hz, 2H), 3.98-2.77 (m, 13H), 2.12-1.9 (m, 2H), 1.8-1.59 (m, 2H), 1.18 (d, J=6.5 Hz, 3H). LCMS-ESI$^+$ (m/z): [M+H]$^+$ calcd for C$_{31}$H$_{36}$N$_8$O$_4$: 585.3; found:585.4.

Example 220

2-((trans-3-fluoro-1-(2-hydroxyacetyl)piperidin-4-yl) oxy)-5-(4-((4-(4-(oxetan-3-yl)piperazin-1-yl)phenyl) amino)-1,3,5-triazin-2-yl)benzonitrile

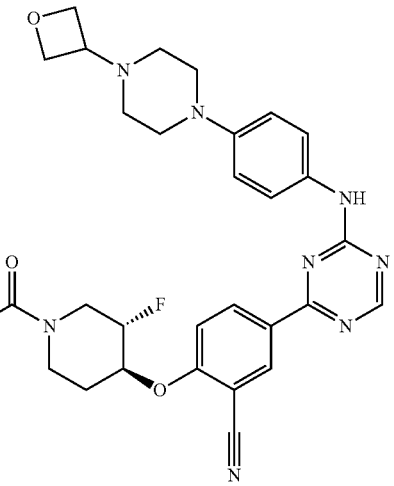

The title compound was prepared following a similar procedure reported in Example-218 using a racemic mixture of trans-tert-butyl 3-fluoro-4-hydroxypiperidine-1-carboxylate. $^1$H NMR (400 MHz, DMSO-d$_6$) δ 10.12 (d, J=23.5 Hz, 1H), 8.72 (s, 1H), 8.62-8.46 (m, 2H), 7.65-7.45 (m, 3H), 6.96 (d, J=9.5 Hz, 2H), 5.18-5.05 (m, 1H), 4.94-4.61 (m, 2H), 4.55 (t, J=6.5 Hz, 2H), 4.46 (t, J=6.0 Hz, 2H), 4.29-3.74 (m, 4H), 3.60-3.25 (m, 4H), 2.45-2.33 (m, 4H), 2.21-2.05 (m, 4H), 1.87-1.53 (m, 1H). LCMS-ESI$^+$ (m/z): [M+H]$^+$ calcd for C$_{36}$H$_{33}$FN$_8$O$_4$: 589.3; found:589.2.

Example 221

2-(((2S,4R)-1-(2-hydroxyacetyl)-2-methylpiperidin-4-yl)oxy)-5-(4-((4-(4-(oxetan-3-yl)piperazin-1-yl)phenyl)amino)-1,3,5-triazin-2-yl)benzonitrile

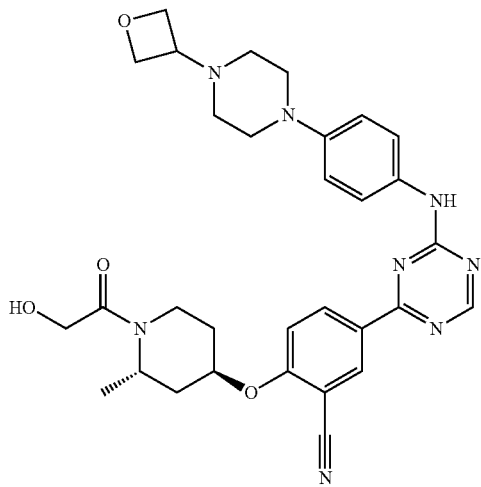 [SMILES: C[C@H]1C[C@H](Oc2ccc(-c3ncnc(Nc4ccc(N5CCN(C6COC6)CC5)cc4)n3)cc2C#N)CCN1C(=O)CO]

The title compound was prepared following a similar procedure reported in Example 218 using (2S,4R)-tert-butyl 4-hydroxy-2-methylpiperidine-1-carboxylate. $^1$H NMR (400 MHz, DMSO-d$_6$) δ 10.10 (d, J=26.9 Hz, 1H), 8.72 (s, 1H), 8.61-8.43 (m, 2H), 7.62-7.51 (m, 3H), 7.00-6.91 (m, 2H), 5.19-4.97 (m, 1H), 4.55 (t, J=6.5 Hz, 2H), 4.49-4.41 (m, 3H), 4.31-3.95 (m, 3H), 3.64 (s, 1H), 3.43 (p, J=6.4 Hz, 1H), 3.28-3.12 (m, 5H), 2.44-2.38 (m, 4H), 2.25-2.1 (m, 1H), 2.08-1.99 (m, 1H), 1.92-1.19 (m, 5H). LCMS-ESI$^+$ (m/z): [M+H]$^+$ calcd for C$_{31}$H$_{36}$N$_8$O$_4$: 585.3; found: 585.3.

Example 222

2-(((2R,4R)-1-(2-hydroxyacetyl)-2-methylpiperidin-4-yl)oxy)-5-(4-((4-(4-(oxetan-3-yl)piperazin-1-yl)phenyl)amino)-1,3,5-triazin-2-yl)benzonitrile

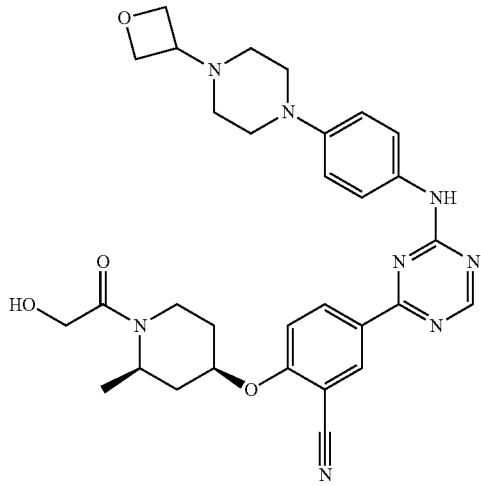 [SMILES: C[C@@H]1C[C@H](Oc2ccc(-c3ncnc(Nc4ccc(N5CCN(C6COC6)CC5)cc4)n3)cc2C#N)CCN1C(=O)CO]

The title compound was prepared following a similar procedure reported in Example 218 using (2R,4R)-tert-butyl 4-hydroxy-2-methylpiperidine-1-carboxylate. $^1$H NMR (400 MHz, DMSO-d$_6$) δ 10.08 (s, 1H), 8.72 (s, 1H), 8.62-8.47 (m, 2H), 7.67-7.35 (m, 3H), 7.03-6.84 (m, 2H), 5.18-5.04 (m, 1H), 4.55 (t, J=6.5 Hz, 2H), 4.50-4.41 (m, 3H), 4.2-4.01 (m, 3H), 3.43 (p, J=6.3 Hz, 1H), 3.20-2.99 (m, 4H), 2.44-2.32 (m, 5H), 2.00-1.65 (m, 4H), 1.41-1.2 (m, 4H). LCMS-ESI$^+$ (m/z): [M+H]$^+$ calcd for C$_{31}$H$_{36}$N$_8$O$_4$: 585.3; found: 585.2

Example 223

2-(((3S,4S)-3-fluoro-1-(2-hydroxyacetyl)piperidin-4-yl)oxy)-5-(4-((4-(4-(oxetan-3-yl)piperazin-1-yl)phenyl)amino)-1,3,5-triazin-2-yl)benzonitrile

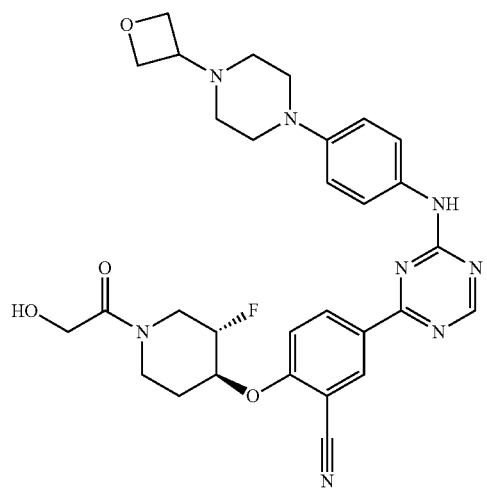 [SMILES: N#Cc1cc(-c2ncnc(Nc3ccc(N4CCN(C5COC5)CC4)cc3)n2)ccc1O[C@H]1CCN(C(=O)CO)C[C@@H]1F]

The title compound was prepared following a similar procedure reported in Example 218 using (3S,4S)-tert-butyl 3-fluoro-4-hydroxypiperidine-1-carboxylate. $^1$H NMR (400 MHz, DMSO-d$_6$) δ 10.12 (d, J=23.7 Hz, 1H), 8.73 (s, 1H), 8.64-8.47 (m, 2H), 7.65-7.5 (m, 3H), 7.0-6.85 (m, 2H), 5.15-5.05 (m, 1H), 4.83-4.61 (m, 2H), 4.55 (t, J=6.5 Hz, 2H), 4.46 (t, J=6.0 Hz, 2H), 4.25-3.98 (m, 3H), 3.92-3.75 (m, 1H), 3.6-3.4 (m, 2H), 3.38-3.3 (m, 1H), 3.2-3.09 (m, 4H), 2.43-2.30 (m, 4H), 2.2-2.05 (m, 1H), 1.85-1.55 (m, 1H). LCMS-ESI$^+$ (m/z): [M+H]$^+$ calcd for C$_{30}$H$_{33}$FN$_8$O$_4$: 589.3; found: 589.2.

Example 224

2-(((3S,4R)-3-fluoro-1-(2-hydroxyacetyl)piperidin-4-yl)oxy)-5-(4-((4-(4-(oxetan-3-yl)piperazin-1-yl)phenyl)amino)-1,3,5-triazin-2-yl)benzonitrile

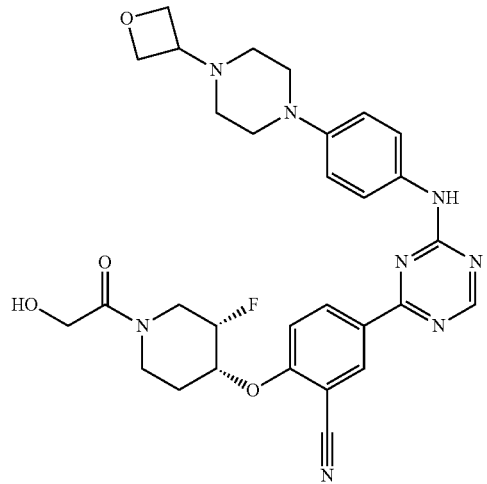 [SMILES: N#Cc1cc(-c2ncnc(Nc3ccc(N4CCN(C5COC5)CC4)cc3)n2)ccc1O[C@@H]1CCN(C(=O)CO)C[C@@H]1F]

The title compound was prepared following a similar procedure reported in Example 218 using (3S,4R)-tert-butyl 3-fluoro-4-hydroxypiperidine-1-carboxylate. $^1$H NMR (400 MHz, DMSO-d$_6$) δ 10.12 (d, J=25.2 Hz, 1H), 8.73 (s, 1H), 8.65-8.45 (m, 2H), 7.78-7.36 (m, 3H), 7.0-6.85 (m, 2H), 5.18-4.95 (m, 2H), 4.66 (dt, J=10.6, 5.7 Hz, 1H), 4.55 (t, J=6.5 Hz, 2H), 4.46 (t, J=6.0 Hz, 2H), 4.40-3.86 (m, 4H), 3.67 (d, J=13.9 Hz, 1H), 3.60-3.35 (m, 2H), 3.13 (d, J=6.4 Hz, 4H), 2.44-2.32 (m, 4H), 2.02-1.70 (m, 2H). LCMS-ESI$^+$ (m/z): [M+H]$^+$ calcd for C$_{30}$H$_{33}$FN$_8$O$_4$: 589.3; found: 589.2.

Example 225

5-(4-((4-((R)-2-(hydroxymethyl)morpholino)phenyl) amino)-1,3,5-triazin-2-yl)-2-((1-((S)-2-hydroxypropanoyl)piperidin-4-yl)oxy)benzonitrile

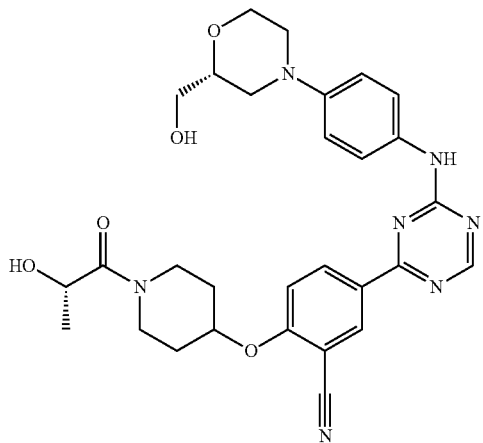 [SMILES: C[C@H](O)C(=O)N1CCC(Oc2ccc(-c3ncnc(Nc4ccc(N5CCO[C@@H](CO)C5)cc4)n3)cc2C#N)CC1]

Step 1: (R)-(4-(4-aminophenyl)morpholin-2-yl)methanol:
To a stirred solution of 1-fluoro-4-nitrobenzene (1084 mgs, 7.7 mmol) in DMSO under a nitrogen atmosphere was added (R)-morpholin-2-ylmethanol (1000 mgs, 8.5 mmol) followed by DIPEA (1.9 ml, 17 mmol). The mixture was stirred at 120° C. for 4 h, and then cooled to room temperature. The mixture was then poured into water and extracted with DCM. The combined organic layers were washed with brine, dried over magnesium sulfate, concentrated in vacuo to obtain (R)-(4-(4-nitrophenyl)morpholin-2-yl)methanol.

Step 2: To a stirred solution (R)-(4-(4-nitrophenyl)morpholin-2-yl)methanol (1410 mgs, 5.9 mmol) in ethanol was added Fe (1657 mgs, 29.64 mmol) followed by a saturated aqueous solution of ammonium chloride (5 ml). The mixture was stirred at 60° C. for 3 hrs then cooled to room temperature. The mixture was then poured into water and extracted with DCM. The combined organic layers were evaporated and concentrated in vacuo to obtain (R)-(4-(4-aminophenyl)morpholin-2-yl)methanol.

Step 3: The title compound was prepared following a similar procedure reported in Example 218 using (R)-(4-(4-aminophenyl)morpholin-2-yl)methanol, tert-butyl 4-hydroxypiperidine-1-carboxylate and (S)-2-hydroxypropanoic acid. $^1$H NMR (400 MHz, DMSO-d$_6$) δ 10.17 (s, 1H), 8.73 (s, 1H), 8.63-8.45 (m, 2H), 7.65-5.49 (m, 3H), 6.97 (d, J=9.8 Hz, 2H), 4.99 (s, 2H), 4.44 (q, J=6.5 Hz, 2H), 4.17-3.25 (m, 9H), 2.79 (d, J=4.0 Hz, 1H), 2.69-2.57 (m, 2H), 2.41 (d, J=14.8 Hz, 1H), 2.15-1.92 (m, 2H), 1.68 (d, J=36.0 Hz, 2H), 1.18 (d, J=6.5 Hz, 3H). LCMS-ESI$^+$ (m/z): [M+H]$^+$ calcd for C$_{29}$H$_{33}$FN$_7$O$_5$: 560.3; found: 560.2.

Example 226

2-((3,3-difluoropiperidin-4-yl)oxy)-5-(4-((R)-2-(hydroxymethyl)morpholino)phenyl)amino)-1,3,5-triazin-2-yl)benzonitrile

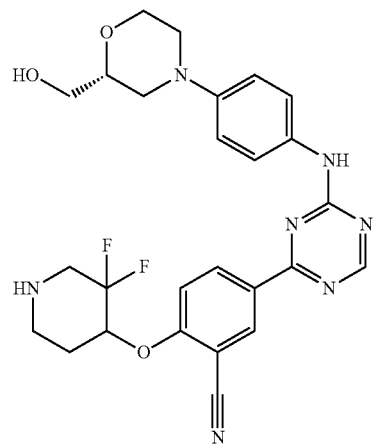 [SMILES: N#Cc1cc(-c2ncnc(Nc3ccc(N4CCO[C@@H](CO)C4)cc3)n2)ccc1OC1CCNCC1(F)F]

The title compound was prepared following a similar procedure reported in Example 225 using a racemic mixture of tert-butyl 3,3-difluoro-4-hydroxypiperidine-1-carboxylate. $^1$H NMR (400 MHz, DMSO-d$_6$) δ 10.22 (d, J=25.2 Hz, 1H), 8.76 (s, 1H), 8.61 (d, J=9.4 Hz, 2H), 7.63 (d, J=9.3 Hz, 3H), 7.02 (d, J=8.4 Hz, 2H), 5.42 (d, J=11.4 Hz, 1H), 4.00-3.90 (m, 2H), 3.85-3.71 (m, 2H), 3.70-3.53 (m, 2H), 3.52-3.38 (m, 2H), 3.34-3.15 (m, 2H), 2.87 (s, 1H), 2.82-2.61 (m, 2H), 2.6-2.45 (m, 2H), 2.41-2.26 (m, 1H), 2.17 (s, 1H). LCMS-ESI$^+$ (m/z): [M+H]$^+$ calcd for C$_{26}$H$_{27}$F$_2$N$_7$O$_3$: 524.3; found: 524.2.

Example 227

(R)-2-((1-(2-hydroxyacetyl)piperidin-4-yl)oxy)-5-(4-((4-(2-(hydroxymethyl)morpholino)phenyl)amino)-1,3,5-triazin-2-yl)benzonitrile

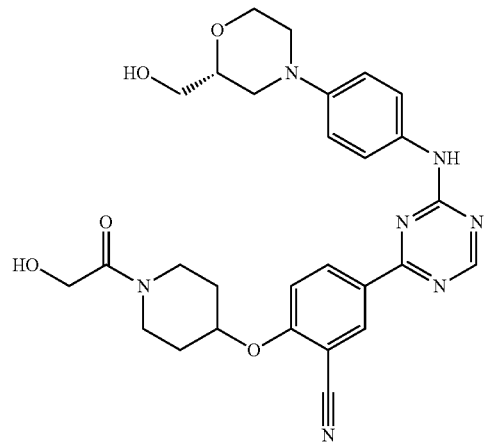 [SMILES: N#Cc1cc(-c2ncnc(Nc3ccc(N4CCO[C@@H](CO)C4)cc3)n2)ccc1OC1CCN(C(=O)CO)CC1]

The title compound was prepared following a similar procedure reported in Example 225 using tert-butyl 4-hydroxypiperidine-1-carboxylate and glycolic acid. $^1$H NMR (400 MHz, DMSO-d$_6$) δ 10.20-9.97 (m, 1H), 8.72 (d, J=2.9 Hz, 1H), 8.65-8.49 (m, 2H), 7.68-7.48 (m, 3H), 7.05-6.80 (m, 2H), 5.74 (s, 1H), 4.99 (d, J=6.8 Hz, 1H), 4.78-4.5 (m, 2H), 4.18-4.09 (m, 1H), 3.93 (d, J=12.1 Hz, 1H), 3.80-3.69 (m, 1H), 3.66-3.37 (m, 8H), 2.65 (d, J=13.2 Hz, 1H), 2.39 (s, 1H), 2.00 (q, J=16.6, 11.9 Hz, 2H), 1.70 (d, J=31.9 Hz, 2H). LCMS-ESI$^+$ (m/z): [M+H]$^+$ calcd for C$_{28}$H$_{31}$H$_7$O$_5$: 546.24; found:546.4.

Example 228

2-((3,3-difluoro-1-((S)-2-hydroxypropanoyl)piperidin-4-yl)oxy)-5-(4-((4-((R)-2-(hydroxymethyl)morpholino)phenyl)amino)-1,3,5-triazin-2-yl)benzonitrile

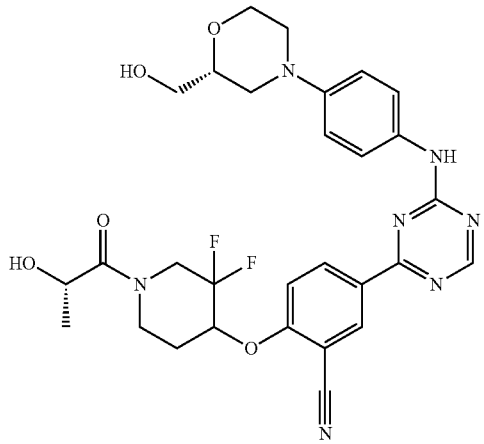 [SMILES: C[C@H](O)C(=O)N1CCC(Oc2ccc(-c3ncnc(Nc4ccc(N5CCO[C@@H](CO)C5)cc4)n3)cc2C#N)C(F)(F)C1]

The title compound was prepared following a similar procedure reported in Example 225 using a racemic mixture of tert-butyl 3,3-difluoro-4-hydroxypiperidine-1-carboxylate. $^1$H NMR (400 MHz, DMSO-d$_6$) δ 10.25-10.10 (m, 1H), 8.75 (s, 1H), 8.68-8.45 (m, 2H), 7.77-7.5 (m. 3H), 6.98-6.89 (m, 2H), 5.38 (d, J=11.9 Hz, 1H), 5.22 (d, J=6.9 Hz, 1H), 4.76 (t, J=5.7 Hz, 1H), 4.48 (d, J=6.9 Hz, 1H), 4.17 (s, 1H), 3.88 (dd, J=36.2, 10.4 Hz, 3H), 3.68-3.35 (m, 5H), 2.66 (d, J=11.9 Hz, 1H), 2.39 (qd, J=9.8, 8.4, 4.4 Hz, 1H), 2.26-1.67 (m, 2H), 1.20 (d, J=6.5 Hz, 3H), 0.98-0.84 (m, 2H). LCMS-ESI$^+$ (m/z): [M+H]$^+$ calcd for C$_{29}$H$_{31}$F$_2$N$_7$O$_5$: 596.2; found: 596.4

Example 229

2-(((3R,4S)-3-fluoro-1-(2-hydroxyacetyl)piperidin-4-yl)oxy)-5-(4-((4-((R)-2-(hydroxymethyl)morpholino)phenyl)amino)-1,3,5-triazin-2-yl)benzonitrile

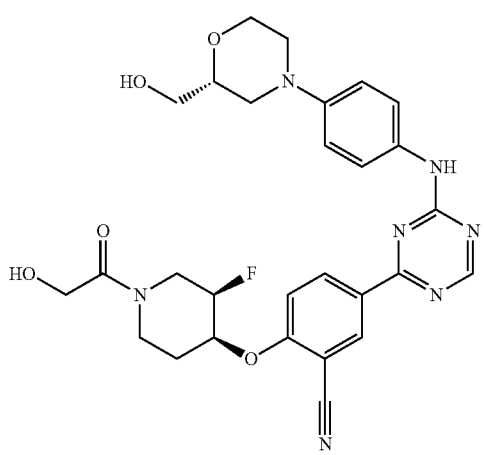 [SMILES: N#Cc1cc(-c2ncnc(Nc3ccc(N4CCO[C@@H](CO)C4)cc3)n2)ccc1O[C@H]1CCN(C(=O)CO)C[C@H]1F]

The title compound was prepared following a similar procedure reported in Example 225 using (3R,4S)-tert-butyl 3-fluoro-4-hydroxypiperidine-1-carboxylate and 2-hydroxyacetic acid. $^1$H NMR (400 MHz, DMSO-d$_6$) δ 10.14 (s, 1H), 8.73 (s, 1H), 8.56 (q, J=8.4, 7.8 Hz, 2H), 7.60 (dd, J=19.8, 11.2 Hz, 3H), 6.95 (t, J=10.5 Hz, 2H), 5.25-4.91 (m, 2H), 4.74 (s, 2H), 4.40-4.29 (m, 1H), 4.21-3.83 (m, 5H), 3.76-3.03 (m, 7H), 2.64 (t, J=11.4 Hz, 1H), 2.39 (t, J=10.9 Hz, 1H), 2.07-1.68 (m, 2H). LCMS-ESI$^+$ (m/z): [M+H]$^+$ calcd for C$_{28}$H$_{30}$FN$_7$O$_5$: 564.2; found:563.5

Example 230

2-(((S)-1-acetyl-3,3-difluoropiperidin-4-yl)oxy)-5-(4-((4-((R)-2-(hydroxymethyl)morpholino)phenyl)amino)-1,3,5-triazin-2-yl)benzonitrile

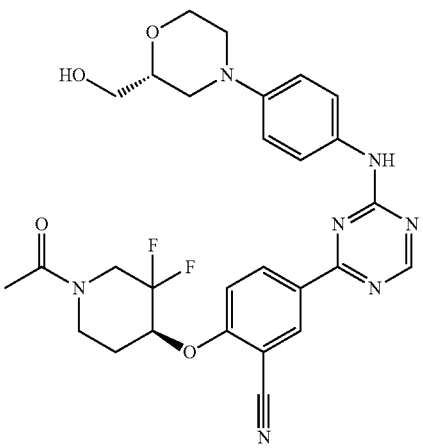 [SMILES: CC(=O)N1CC[C@H](Oc2ccc(-c3ncnc(Nc4ccc(N5CCO[C@@H](CO)C5)cc4)n3)cc2C#N)C(F)(F)C1]

The title compound was prepared following a similar procedure reported in Example 225 using (S)-tert-butyl 3,3-difluoro-4-hydroxypiperidine-1-carboxylate and acetic acid. $^1$H NMR (400 MHz, DMSO-d$_6$) δ 10.14 (s, 1H), 8.73 (s, 1H), 8.56 (q, J=8.4, 7.8 Hz, 2H), 7.60 (dd, J=19.8, 11.2 Hz, 3H), 6.95 (t, J=10.5 Hz, 2H), 5.25-4.91 (m, 2H), 4.82-4.69 (m, 2H), 4.40-4.29 (m, 1H), 4.21-3.83 (m, 5H), 3.76-3.03 (m, 6H), 2.64 (t, J=11.4 Hz, 1H), 2.39 (t, J=10.9 Hz, 1H), 2.07-1.68 (m, 2H). LCMS-ESI$^+$ (m/z): [M+H]$^+$ calcd for C$_{28}$H$_{29}$F$_2$N$_7$O$_4$: 566.2; found:565.5

Example 231

2-(((3R,4S)-3-fluoro-1-((S)-2-hydroxypropanoyl)piperidin-4-yl)oxy)-5-(4-((4-((R)-2-(hydroxymethyl)morpholino)phenyl)amino)-1,3,5-triazin-2-yl)benzonitrile

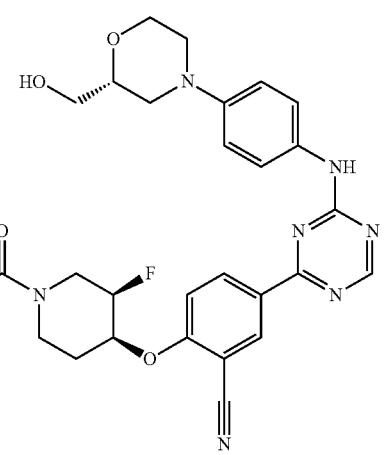

The title compound was prepared following a similar procedure reported in Example 225 using (3R,4S)-tert-butyl 3-fluoro-4-hydroxypiperidine-1-carboxylate. $^1$H NMR (400 MHz, DMSO-d$_6$) δ 10.13 (d, J=24.8 Hz, 1H), 8.74 (d, J=4.7 Hz, 1H), 8.64-8.46 (m, 2H), 7.60 (dd, J=17.3, 10.6 Hz, 3H), 6.95 (t, J=10.6 Hz, 2H), 5.25-4.89 (m, 2H), 4.55-4.30 (m, 2H), 4.24-4.02 (m, 1H), 3.98-3.84 (m, 2H), 3.76-3.25 (m, 6H), 3.14 (s, 1H), 2.71-2.58 (m, 1H), 2.39 (t, J=11.4 Hz, 1H), 2.05-1.68 (m, 2H), 1.48-1.38 (m, 1H), 1.26(d, J=6.9 Hz, 1H), 1.19 (dd, J=6.5, 4.1 Hz, 3H). LCMS-ESI$^+$ (m/z): [M+H]$^+$ calcd for C$_{29}$H$_{32}$FN$_7$O$_5$: 578.2; found:577.5.

Example 232

2-(((3R,4S)-3-fluoro-1-(2-hydroxyacetyl)piperidin-4-yl)oxy)-5-(4-((S)-2-(hydroxymethyl)morpholino)phenyl)amino)-1,3,5-triazin-2-yl)benzonitrile

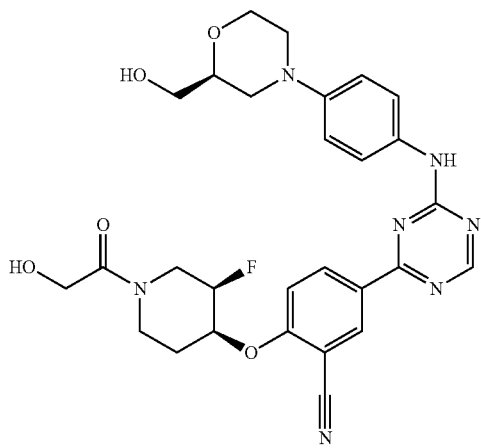 [SMILES: N#Cc1cc(-c2ncnc(Nc3ccc(N4CCO[C@H](CO)C4)cc3)n2)ccc1O[C@H]1CCN(C(=O)CO)C[C@H]1F]

The title compound was prepared following a similar procedure reported in Example 225 using (S)-morpholin-2-ylmethanol, (3R,4S)-tert-butyl 3-fluoro-4-hydroxypiperidine-1-carboxylate and 2-hydroxyacetic acid. $^1$H NMR (400 MHz, DMSO-d$_6$) δ 10.14 (s, 1H), 8.73 (s, 1H), 8.56 (q, J=8.3, 7.0 Hz, 2H), 7.71-7.44 (m, 3H), 6.95 (t, J=10.4 Hz, 2H), 5.25-4.93 (m, 2H), 4.78 (d, J=16.7 Hz, 2H), 4.33 (d, J=14.0 Hz, 1H), 4.22-4.00 (m, 3H), 3.99-3.84 (m, 2H), 3.75-3.03 (m, 7H), 2.64 (t, J=12.1 Hz, 1H), 2.44-2.30 (m, 1H), 2.04-1.71 (m, 2H). LCMS-ESI$^+$ (m/z): [M+H]$^+$ calcd for C$_{28}$H$_{30}$FN$_7$O$_5$: 564.2; found:563.5

Example 233

2-(((3R,4S)-3-fluoro-1-((S)-2-hydroxypropanoyl)piperidin-4-yl)oxy)-5-(4-((4-((S)-2-(hydroxymethyl)morpholino)phenyl)amino)-1,3,5-triazin-2-yl)benzonitrile

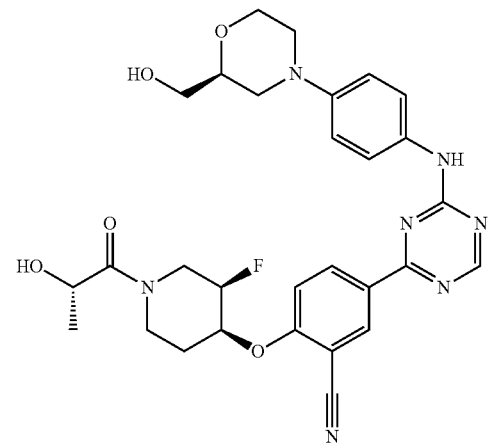 [SMILES: C[C@H](O)C(=O)N1CC[C@H](Oc2ccc(-c3ncnc(Nc4ccc(N5CCO[C@H](CO)C5)cc4)n3)cc2C#N)[C@H](F)C1]

The title compound was prepared following a similar procedure reported in Example 225 using (S)-morpholin-2-ylmethanol and (3R,4S)-tert-butyl 3-fluoro-4-hydroxypiperidine-1-carboxylate. $^1$H NMR (400 MHz, DMSO-d$_6$) δ 10.13 (d, J=24.5 Hz, 1H), 8.73 (s, 1H), 8.57 (d, J=10.4 Hz, 2H), 7.60 (dd, J=20.2, 11.7 Hz, 3H), 7.20-6.89 (m, 2H), 5.23-4.87 (m, 3H), 4.76 (t, J=5.7 Hz, 1H), 4.46 (dt, J=13.8, 6.8 Hz, 2H), 4.23-3.82 (m, 3H), 3.70-3.05 (m, 7H), 2.64 (s, 1H), 2.40 (d, J=11.9 Hz, 1H), 1.90 (d, J=59.1 Hz, 2H), 1.24-1.15 (m, 3H). LCMS-ESI$^+$ (m/z): [M+H]$^+$ calcd for C$_{29}$H$_{32}$FN$_7$O$_5$: 578.2: found:577.5

Example 234

2-(((3R,4R)-3-fluoro-1-((S)-2-hydroxypropanoyl)piperidin-4-yl)oxy)-5-(4-((4-(4-(oxetan-3-yl)piperazin-1-yl)phenyl)amino)-1,3,5-triazin-2-yl)benzonitrile

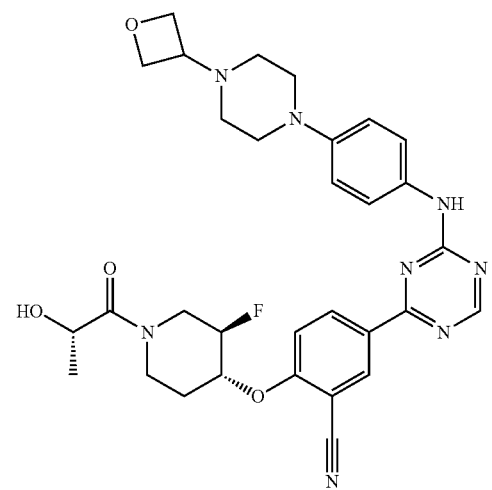 [SMILES: C[C@H](O)C(=O)N1CC[C@@H](Oc2ccc(-c3ncnc(Nc4ccc(N5CCN(C6COC6)CC5)cc4)n3)cc2C#N)[C@H](F)C1]

The title compound was prepared following a similar procedure reported in Example 218 using (3R,4R)-tert-butyl 3-fluoro-4-hydroxypiperidine-1-carboxylate and (S)-2-hydroxypropanoic acid. $^1$H NMR (400 MHz, DMSO-d$_6$) δ 10.17 (s, 1H), 8.74 (s, 1H), 8.63-8.41 (m, 2H), 7.65-7.48 (m, 3H), 7.08-6.9 (m, 2H), 5.20-5.10 (m, 2H), 4.92-4.34 (m, 7H), 4.21-3.95 (m, 1H), 3.87 (s, 1H), 3.66-3.38 (m, 2H), 3.22-3.09 (m, 4H), 2.52-2.35 (m, 4H), 2.13 (d, J=14.0 Hz, 1H), 1.8-1.55 (m, 1H), 1.19 (d, J=6.5 Hz, 3H). LCMS-ESI$^+$ (m/z): [M+H]$^+$ calcd for C$_{31}$H$_{35}$FN$_8$O$_4$: 603.3; found:603.4.

Example 235

2-(((3R,4R)-3-fluoro-1-(2-hydroxyacetyl)piperidin-4-yl)oxy)-5-(4-((4-(4-(oxetan-3-yl)piperazin-1-yl)phenyl)amino)-1,3,5-triazin-2-yl)benzonitrile

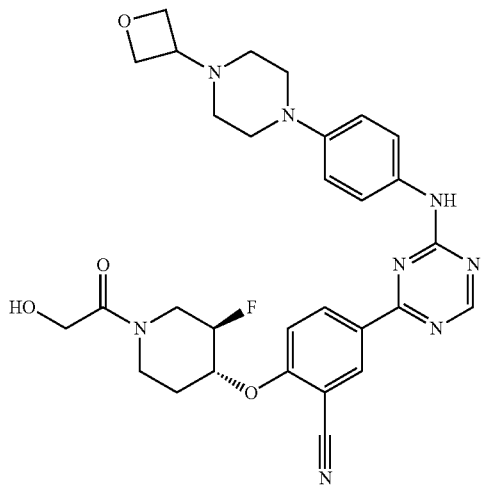 [SMILES: N#Cc1cc(-c2ncnc(Nc3ccc(N4CCN(C5COC5)CC4)cc3)n2)ccc1O[C@@H]1CCN(C(=O)CO)C[C@H]1F]

The title compound was prepared following a similar procedure reported in Example 218 using (3R,4R)-tert-butyl 3-fluoro-4-hydroxypiperidine-1-carboxylate. $^1$H NMR (400 MHz, DMSO-d$_6$) δ 10.21 (d, J=12.3 Hz, 1H), 8.81 (s, 1H), 8.68-8.58 (m, 2H), 7.81-7.51 (m, 3H), 7.08-6.98 (m, 2H), 5.25-5.12 (m, 1H), 5.08-4.7 (m, 2H), 4.64 (t, J=6.5 Hz, 2H), 4.54 (t, J=6.0 Hz, 2H), 4.36-4.06 (m, 3H), 4.05-3.85 (m, 1H), 3.71-3.46 (m, 3H), 3.22 (d, J=6.5 Hz, 4H), 2.48 (t, J=4.9 Hz, 4H), 2.25-2.15 (m, 1H), 1.95-1.65 (m, 1H). LCMS-ESI$^+$ (m/z): [M+H]$^+$ calcd for C$_{30}$H$_{33}$FN$_8$O$_4$: 589.3; found:589.4.

Example 236

2-(((3R,4R)-3-fluoropiperidin-4-yl)oxy)-5-(4-((4-(4-(oxetan-3-yl)piperazin-1-yl)phenyl)amino)-1,3,5-triazin-2-yl)benzonitrile

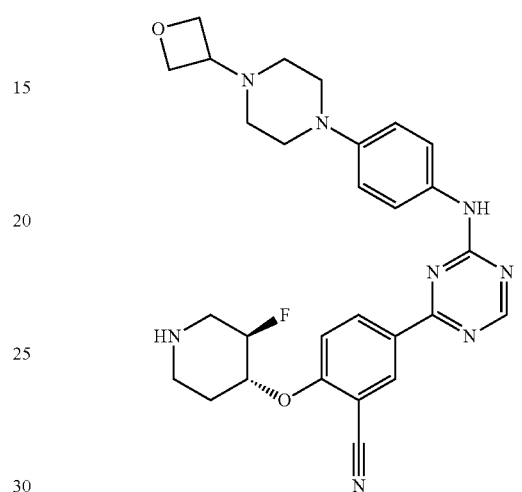

A solution of a racemic mixture of (3R,4R)-tert-butyl 3-fluoro-4-hydroxypiperidine-1-carboxylate (76 mgs, 0.35 mmol) in THF (5 mL) was stirred in an ice-water bath under an atmosphere of Argon. Potassium tert-butoxide (1.0 M, 0.35 ml, 0.35 mmol) was added in a single portion and the mixture was stirred at 0° C. for 40 minutes, and then 2-fluoro-5-(4-((4-(4-(oxetan-3-yl)piperazin-1-yl)phenyl)amino)-1,3,5-triazin-2-yl)benzonitrile was added (100 mgs, 0.23 mmol). The mixture was stirred for 1 hr at 60° C. After the mixture cooled to room temperature, water was added, and mixture evaporated under reduced pressure to yield the crude (3R,4R)-tert-butyl 4-(2-cyano-4-(4-((4-(4-(oxetan-3-yl)piperazin-1-yl)phenyl)amino)-1,3,5-triazin-2-yl)phenoxy)-3-fluoropiperidine-1-carboxylate.

Solids were dissolved with DCM and TFA. Reaction mixture was stirred at room temperature for 1 hr. Reaction mixture was evaporated under reduced pressure and solids were re-dissolved in DCM and a saturated aqueous solution of NaHCO$_3$ was added. Organics were collected and evaporated under reduced pressure. Solids were purified via preparative HPLC (5-65% acetonitrile in water, 0.1% trifluoroacteic acid buffer). Fractions containing desired product were collected and DCM and a saturated aqueous solution of NaHCO$_3$ were added. Organics were collected dried over magnesium sulfate and evaporated under reduced pressure to yield 2-(((3R,4R)-3-fluoropiperidin-4-yl)oxy)-5-(4-((4-(4-(oxetan-3-yl)piperazin-1-yl)phenyl)amino)-1,3,5-triazin-2-yl)benzonitrile. $^1$H NMR (400 MHz, DMSO-d$_6$) δ 10.2 (s, 1H), 8.72 (s, 1H), 8.54 (q, J=9.3 Hz, 2H), 7.65-8.45 (m, 3H), 6.97 (d, J=10.7 Hz, 2H), 4.92-4.82 (m, 1H), 4.65-4.42 (m, 5H), 3.43 (p, J=6.3 Hz, 1H), 3.26-3.18 (m, 1H), 3.18-3.06 (m, 4H), 2.65-2.54 (m, 3H), 2.48-2.35 (m, 4H), 2.34-2.24 (m, 1H), 2.13 (d, J=12.2 Hz, 1H), 1.55-1.43 (m, 1H). LCMS-ESI$^+$ (m/z): [M+H]$^+$ calcd for C$_{28}$H$_{31}$FN$_8$O$_2$: 531.3; found:531.4.

Example 237

2-(((3R,4S)-3-fluoro-1-(2-hydroxyacetyl)piperidin-4-yl)oxy)-5-(4-((4-(4-(oxetan-3-yl)piperazin-1-yl)phenyl)amino)-1,3,5-triazin-2-yl)benzonitrile

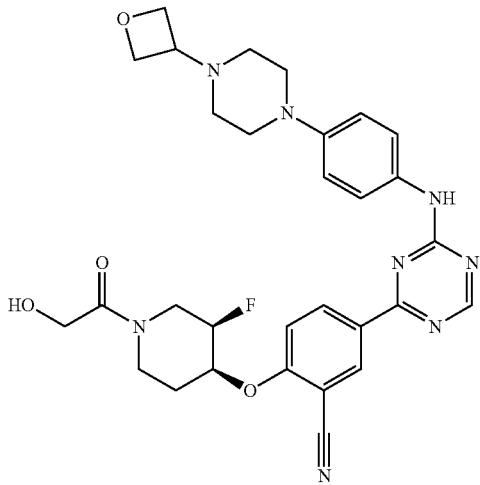

The title compound was prepared following a similar procedure reported in Example 218 using (3R,4S)-tert-butyl 3-fluoro-4-hydroxypiperidine-1-carboxylate. $^1$H NMR (400 MHz, DMSO-d$_6$) δ 10.13 (s, 1H), 8.72 (s, 1H), 8.6-8.5 (m, 2H), 7.7-7.50 (m, 3H), 6.98-6.8 (m, 2H), 5.22-4.93 (m, 2H), 4.68 (s, 1H), 4.55 (t, J=6.5 Hz, 2H), 4.46 (t, J=6.0 Hz, 2H), 4.39-3.84 (m, 4H), 3.74-3.21 (m, 3H), 3.12 (d, J=7.0 Hz, 4H), 2.44-2.34 (m, 4H), 2.06-1.73 (m, 2H). LCMS-ESI$^+$ (m/z): [M+H]$^+$ calcd for C$_{30}$H$_{33}$FN$_8$O$_4$: 589.3; found:589.4.

Example 238

2-(((3R,4S)-3-fluoro-1-((S)-2-hydroxypropanoyl)piperidin-4-yl)oxy)-5-(4-((4-(4-(oxetan-3-yl)piperazin-1-yl)phenyl)amino)-1,3,5-triazin-2-yl)benzonitrile

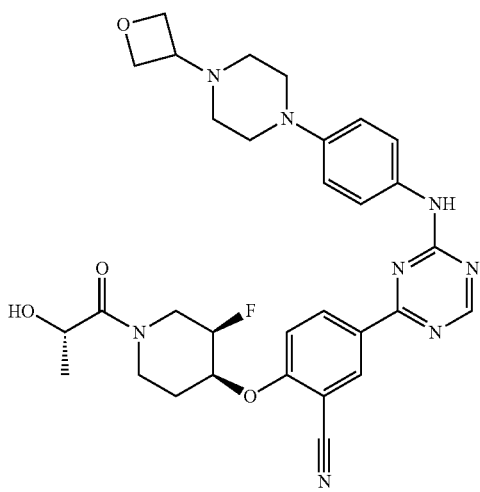 [SMILES: C[C@H](O)C(=O)N1CC[C@H](Oc2ccc(-c3ncnc(Nc4ccc(N5CCN(C6COC6)CC5)cc4)n3)cc2C#N)[C@H](F)C1]

A solution of (3R,4S)-tert-butyl 3-fluoro-4-hydroxypiperidine-1-carboxylate (PharmaBlock) (400 mgs, 0.93 mmol) in 2-methyl-tetrahydrofuran (5 mL) was stirred in an ice-water bath under an atmosphere of Argon. Potassium tert-butoxide (1.0 M, 1.9 ml, 1.9 mmol) was added in a single portion and the mixture was stirred at 0° C. for 40 minutes, and then 2-fluoro-5-(4-((4-(4-(oxetan-3-yl)piperazin-1-yl)phenyl)amino)-1,3,5-triazin-2-yl)benzonitrile was added (406 mgs, 1.9 mmol). The mixture was stirred at 60° C. for one hour. After the mixture cooled to room temperature, water was added, and mixture evaporated under reduced pressure to yield the crude (3R,4S)-tert-butyl 4-(2-cyano-4-(4-((4-(4-(oxetan-3-yl)piperazin-1-yl)phenyl)amino)-1,3,5-triazin-2-yl)phenoxy)-3-fluoropiperidine-1-carboxylate.

(3R,4S)-tert-butyl 4-(2-cyano-4-(4-((4-(4-(oxetan-3-yl)piperazin-1-yl)phenyl)amino)-1,3,5-triazin-2-yl)phenoxy)-3-fluoropiperidine-1-carboxylate was dissolved with a 1:1 mixture of DCM and TFA (6 mL). Reaction mixture was stirred at room temperature for 30 min and then evaporated under reduced pressure. Solids were suspended in a saturated aqueous solution of NaHCO$_3$ and extracted with DCM. Organic phase was dried over magnesium sulfate and evaporated under reduced pressure to yield 2-(((3R,4S)-3-fluoropiperidin-4-yl)oxy)-5-(4-((4-(4-(oxetan-3-yl)piperazin-1-yl)phenyl)amino)-1,3,5-triazin-2-yl)benzonitrile.

To solution of 2-(((3R,4S)-3-fluoropiperidin-4-yl)oxy)-5-(4-((4-(4-(oxetan-3-yl)piperazin-1-yl)phenyl)amino)-1,3,5-triazin-2-yl)benzonitrile (100 mgs, 0.19 mmol), (S)-2-hydroxypropanoic acid (34 mgs, 0.38 mmol), HATU (144 mgs, 0.38 mmol) in DMF (3 mL) was added triethylamine (0.043 mL, 0.38 mmol) in a 10 mL microwave vial and sealed. This reaction mixture was stirred at room temperature for 2 hrs. Water was added and it was extracted with dichloromethane. Organic layer was dried over Mg$_2$SO$_4$ and evaporated to dryness. Solids re-dissolved in acetonitrile and purified via preparative HPLC (5-65% acetonitrile in water, 0.1% trifluoroacteic acid buffer) to yield 2-(((3R,4S)-3-fluoro-1-((S)-2-hydroxypropanoyl)piperidin-4-yl)oxy)-5-(4-((4-(4-(oxetan-3-yl)piperazin-1-yl)phenyl)amino)-1,3,5-triazin-2-yl)benzonitrile. $^1$H NMR (400 MHz, DMSO-d$_6$) δ 10.13 (d, J=7.5 Hz, 1H), 8.73 (s, 1H), 8.63-8.44 (m, 2H), 7.65-7.44 (m, 3H), 7.0-6.88 (m, 2H), 5.22-4.94 (m, 3H), 4.55 (t, J=6.5 Hz, 2H), 4.48-4.30 (m, 3H), 4.23-3.88 (m, 2H), 3.72-3.51 (m, 1H), 3.49-3.33 (m, 2H), 3.13 (dd, J=10.3, 5.4 Hz, 4H), 2.39 (t, J=5.0 Hz, 4H), 2.06-1.70 (m, 2H), 1.19 (dd, J=6.5, 4.3 Hz, 3H). LCMS-ESI$^+$ (m/z): [M+H]$^+$ calcd for C$_{31}$H$_{35}$FN$_8$O$_4$: 603.3; found:603.2

Example 239

2-(((3R,4S)-3-fluoropiperidin-4-yl)oxy)-5-(4-((4-(4-(oxetan-3-yl)piperazin-1-yl)phenyl)amino)-1,3,5-triazin-2-yl)benzonitrile

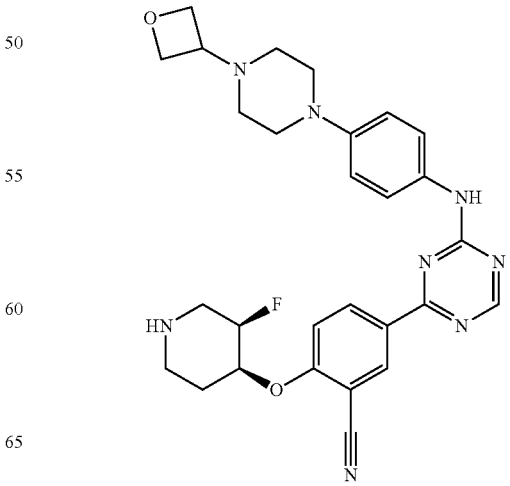

The title compound was prepared following a similar procedure reported in Example 236 using (3R,4S)-tert-butyl 3-fluoro-4-hydroxypiperidine-1-carboxylate. $^1$H NMR (400 MHz, DMSO-d$_6$) δ 10.19 (d, J=19.4 Hz, 1H), 8.80 (s, 1H), 8.69-8.55 (m, 2H), 7.74-7.56 (m, 3H), 7.08-6.95 (m, 2H), 5.18-5.02 (m, 1H), 4.98-4.82 (m, 1H), 4.64 (t, J=6.5 Hz, 2H), 4.54 (t, J=6.1 Hz, 2H), 3.52 (p, J=6.3 Hz, 1H), 3.24-3.18 (m, 4H), 2.98-2.82 (m, 3H), 2.73-2.61 (m, 1H), 2.48 (t, J=4.9 Hz, 4H), 2.22-2.07 (m, 1H), 2.00-1.87 (d, J=6.6 Hz, 2H). LCMS-ESI$^+$ (m/z): [M+H]$^+$ calcd for C$_{28}$H$_{31}$FN$_8$O$_2$: 531.3; found:531.4

Example 240

2-(((3R,4S)-3-fluoro-1-(2-hydroxyacetyl)piperidin-4-yl)oxy)-5-(4-((3-fluoro-4-(4-(oxetan-3-yl)piperazin-1-yl)phenyl)amino)-1,3,5-triazin-2-yl)benzonitrile

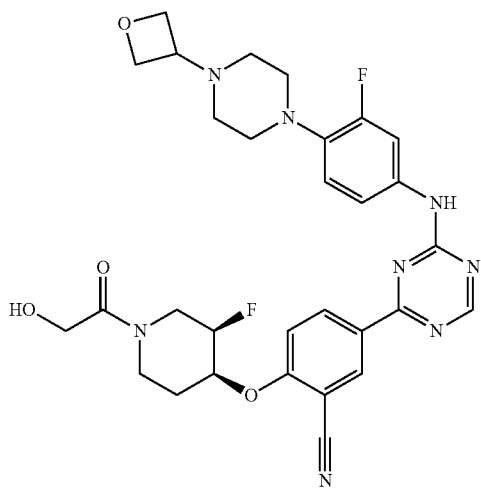

The title compound was prepared following a similar procedure reported in Example 218 using 2-fluoro-5-(4-((3-fluoro-4-(4-(oxetan-3-yl)piperazin-1-yl)phenyl)amino)-1,3,5-triazin-2-yl)benzonitrile, (3R,4S)-tert-butyl 3-fluoro-4-hydroxypiperidine-1-carboxylate and glycolic acid. $^1$H NMR (400 MHz, DMSO-d$_6$) δ 10.36 (s, 1H), 8.79 (s, 1H), 8.66-8.43 (m, 2H), 7.73-7.57 (m, 2H), 7.41 (s, 1H), 7.04 (t, J=9.3 Hz, 1H), 5.19-4.92 (m, 2H), 4.89-4.6 (m, 1H), 4.55 (t, J=6.5 Hz, 2H), 4.45 (t, J=6.1 Hz, 2H), 4.40-3.81 (m, 3H), 3.77-3.60 (m, 1H), 3.54-3.34 (m, 2H), 3.00 (d, J=4.9 Hz, 4H), 2.41 (t, J=4.8 Hz, 4H), 2.03-1.70 (m, 3H). LCMS-ESI$^+$ (m/z): [M+H]$^+$ calcd for C$_{30}$H$_{32}$F$_2$N$_8$O$_4$: 607.3; found:607.2

Example 241

2-(((3R,4S)-3-fluoro-1-(2-hydroxyacetyl)piperidin-4-yl)oxy)-5-(4-((4-((S)-3-methyl-4-(oxetan-3-yl)piperazin-1-yl)phenyl)amino)-1,3,5-triazin-2-yl)benzonitrile

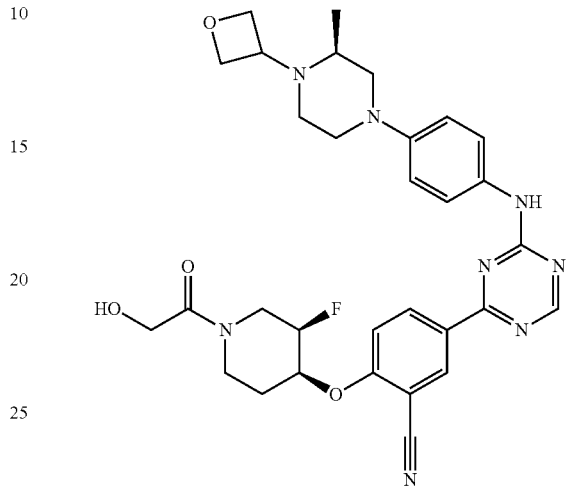

To a stirred solution of 1-fluoro-4-nitrobenzene (634 mg, 4.5 mmol) in DMSO was added (S)-tert-butyl 2-methylpiperazine-1-carboxylate (1000 mg, 5 mmol) followed by DIPEA (1.2 mL, 10 mmol). The mixture was heated at 160° C. for 4 hrs, and then cooled to room temperature. The mixture was then poured into water and extracted with DCM. The combined organic layers were concentrated in vacuo to obtain (S)-tert-butyl 2-methyl-4-(4-nitrophenyl)piperazine-1-carboxylate.

(S)-tert-butyl 2-methyl-4-(4-nitrophenyl)piperazine-1-carboxylate was dissolved with a mixture of DCM and TFA and stirred at room temperature for 1 hr. Reaction mixture was evaporated under reduced pressure and solids were re-dissolved in DCM and then poured slowly into a stirred saturated aqueous solution of NaHCO$_3$ and extracted three times with DCM. The organic layer was evaporated and concentrated in vacuo to obtain (S)-3-methyl-1-(4-nitrophenyl)piperazine.

To a mixture of (S)-3-methyl-1-(4-nitrophenyl)piperazine (620 mg, 3 mmol), zinc chloride (495 mg, 4 mmol), oxetan-3-one (2.0 g, 28 mmol) in methanol was added NaBH$_3$CN (434 mg, 7 mmol). The mixture was stirred at 75° C. for 2 hours. Reaction mixture was diluted with 1N HCl in water. It was extracted with dichloromethane three times and the combined organic layer was discharged. To aqueous layer a saturated aqueous solution of NaHCO3 was added in portions. It was extracted with DCM three times and the combined organic layer was evaporated under reduced pressure to obtain (S)-2-methyl-4-(4-nitrophenyl)-1-(oxetan-3-yl)piperazine.

To a stirred solution of (S)-2-methyl-4-(4-nitrophenyl)-1-(oxetan-3-yl)piperazine (610 mg, 2.2 mmol) in ethanol was added Fe (615 mg, 11 mmol) followed by an saturated aqueous solution of ammonium chloride (3.1 ml). The mixture was stirred at 60° C. for 3 hrs then cooled to room temperature and filtered thought celite. The filtrate was poured into a saturated aqueous solution of NaHCO$_3$ and extracted with DCM three times. The combined organic layers were evaporated and concentrated in vacuo to obtain (S)-4-(3-methyl-4-(oxetan-3-yl)piperazin-1-yl)aniline.

To a solution of 2,4-dichloro-1,3,5-triazine (109 mg, 0.7 mmol) in DMF at 0° C. (flushed with Argon) was added a solution of (S)-4-(3-methyl-4-(oxetan-3-yl)piperazin-1-yl) aniline (200 mg, 0.8 mmol) in DMF over 15 min and stirred in an ice-bath for 1 h.

Reaction mixture was poured into a saturated aqueous solution of NaHCO₃ and extracted with DCM three times. The combined organic layers were evaporated and concentrated in vacuo to obtain (S)-4-chloro-N-(4-(3-methyl-4-(oxetan-3-yl)piperazin-1-yl)phenyl)-1,3,5-triazin-2-amine.

To (S)-4-chloro-N-(4-(3-methyl-4-(oxetan-3-yl)piperazin-1-yl)phenyl)-1,3,5-triazin-2-amine (120 mg, 0.33 mmol), 2-fluoro-5-(4,4,5,5-tetramethyl-1,3,2-dioxaborolan-2-yl)benzonitrile (90 mg, 0.36 mmol), Pd(dppf)Cl₂CH₂Cl₂ (30 mg) and potassium carbonate (92 mgs, 0.67 mmol) mixture in argon atmosphere was added a mixture of degassed solvents (DME and water 2:1). The mixture was stirred under argon atmosphere at 104° C. for 40 min. After cooling at room temperature; reaction mixture was poured into water and extracted with DCM. The combined organic layers were evaporated and concentrated in vacuo to obtain (S)-2-fluoro-5-(4-((4-(3-methyl-4-(oxetan-3-yl)piperazin-1-yl)phenyl)amino)-1,3,5-triazin-2-yl)benzonitrile.

A solution of a (3R,4S)-tert-butyl 3-fluoro-4-hydroxypiperidine-1-carboxylate (81 mg, 0.3 mmol) in THF (5 mL) was stirred in an ice-water bath under an atmosphere of Argon. Potassium tert-butoxide (1.0 M, 0.37 ml, 0.38 mmol) was added in a single portion and the mixture was stirred at 0° C. for 40 minutes, and then (S)-2-fluoro-5-(4-((4-(3-methyl-4-(oxetan-3-yl)piperazin-1-yl)phenyl)amino)-1,3,5-triazin-2-yl)benzonitrile was added (83 mgs, 0.19 mmol). The mixture was stirred for 1 hr at 60° C. After the mixture cooled to room temperature, water was added, and mixture evaporated under reduced pressure to yield the crude (3R, 4S)-tert-butyl 4-(2-cyano-4-(4-((4-((S)-3-methyl-4-(oxetan-3-yl)piperazin-1-yl)phenyl)amino)-1,3,5-triazin-2-yl)phenoxy)-3-fluoropiperidine-1-carboxylate.

(3R,4S)-tert-butyl-4-(2-cyano-4-(4-((4-((S)-3-methyl-4-(oxetan-3-yl)piperazin-1-yl)phenyl)amino)-1,3,5-triazin-2-yl)phenoxy)-3-fluoropiperidine-1-carboxylate was dissolved with DCM and TFA. Reaction mixture was stirred at room temperature for 1 hr. Reaction mixture was evaporated under reduced pressure and solids were re-dissolved in DCM and a saturated aqueous solution of NaHCO₃ was added. Organics were collected dried over magnesium sulfate and evaporated under reduced pressure to yield 2-(((3R,4S)-3-fluoropiperidin-4-yl)oxy)-5-(4-((4-((S)-3-methyl-4-(oxetan-3-yl)piperazin-1-yl)phenyl)amino)-1,3,5-triazin-2-yl)benzonitrile.

To a solution of 2-(((3R,4S)-3-fluoropiperidin-4-yl)oxy)-5-(4-((4-((S)-3-methyl-4-(oxetan-3-yl)piperazin-1-yl)phenyl)amino)-1,3,5-triazin-2-yl)benzonitrile (75 mg, 0.013 mmol), glycolic acid (10 mg, 0.026 mmol), HATU (105 mgs, 0.027 mmol) in DMF (3 mL) was added TEA (56 mg, 0.05 mmol) in a 10 mL microwave vial and sealed. This reaction mixture was stirred at room temperature for 2 hrs. DCM and water were added to this crude reaction mixture. Organic layer was extracted and evaporated to dryness. Solids were purified via preparative HPLC (5-65% acetonitrile in water, 0.1% trifluoroacetic acid buffer). Fractions containing desired product were collected and DCM and a saturated aqueous solution of NaHCO₃ were added. Organics were collected dried over magnesium sulfate and evaporated under reduced pressure to yield 2-(((3R,4S)-3-fluoro-1-(2-hydroxyacetyl)piperidin-4-yl)oxy)-5-(4-((4-((S)-3-methyl-4-(oxetan-3-yl)piperazin-1-yl)phenyl)amino)-1,3,5-triazin-2-yl)benzonitrile. ¹H NMR (400 MHz, DMSO-d₆) δ 10.11 (d, J=25.9 Hz, 1H), 8.72 (s, 1H), 8.64-8.45 (m, 2H), 7.62-7.45 (m, 3H), 7.00-6.85 (m, 2H), 5.17-4.93 (m, 2H), 4.66 (dt, J=10.5, 5.6 Hz, 1H), 4.55 (td, J=6.4, 3.3 Hz, 2H), 4.49 (q, J=6.3 Hz, 2H), 4.4-4.3.9 (m, 3H), 3.71-3.65 (m, 2H), 3.42-3.2 (m, 2H), 3.2-3.12 (m, 1H), 2.82 (t, J=10.7 Hz, 1H), 2.69 (dd, J=11.5, 3.9 Hz, 1H), 2.60-2.49 (m, 2H), 2.42-2.35 (m, 1H), 2.19-2.07 (m, 1H), 2.04-1.72 (m, 2H), 0.89 (d, J=6.3 Hz, 3H).

LCMS-ESI⁺ (m/z): [M+H]⁺ calcd for $C_{31}H_{35}FN_8O_4$: 603.3; found:603.4.

Example 242

2-(((3R,4S)-3-fluoro-1-(2-hydroxyacetyl)piperidin-4-yl)oxy)-5-(4-((4-((R)-2-methyl-4-(oxetan-3-yl)piperazin-1-yl)phenyl)amino)-1,3,5-triazin-2-yl)benzonitrile

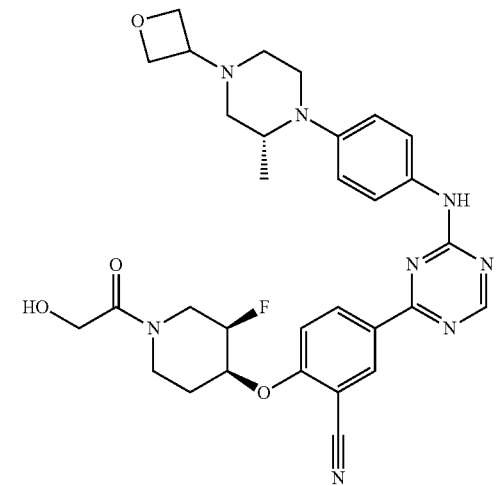 [SMILES: C[C@@H]1CN(C2COC2)CCN1c1ccc(Nc2ncnc(-c3ccc(O[C@H]4CCN(C(=O)CO)C[C@H]4F)c(C#N)c3)n2)cc1]

The title compound was prepared following a similar procedure reported in Example 241 using (R)-tert-butyl 3-methylpiperazine-1-carboxylate. ¹H NMR (400 MHz, DMSO-d₆) 6 10.11 (d, J=24.3 Hz, 1H), 8.72 (s, 1H), 8.66-8.39 (m, 2H), 7.68-7.42 (m, 3H), 6.99-6.83 (m, 2H), 5.19-4.82 (m, 2H), 4.66 (dt, J=10.6, 5.7 Hz, 1H), 4.55 (tt, J=6.7, 3.3 Hz, 2H), 4.47 (t, J=6.0 Hz, 2H), 4.41 (t, J=6.0 Hz, 2H), 4.42-4.02 (m, 3H), 4.02-3.85 (m, 1H), 3.73-3.59 (m, 1H), 3.43-3.1 (m, 3H), 3.12-2.92 (m, 1H), 2.72-2.65 (m, 1H), 2.24 (dd, J=10.8, 3.4 Hz, 1H), 2.07 (td, J=10.7, 3.4 Hz, 1H), 2.01-1.73 (m, 2H), 1.02 (s, 3H). LCMS-ESI⁺ (m/z): [M+H]⁺ calcd for $C_{31}H_{35}FN_8O_{4:\ 603.2;}$ found:603.4

Example 243

2-(((3R,4S)-3-fluoro-1-(2-hydroxyacetyl)piperidin-4-yl)oxy)-5-(4-((4-((R)-3-methyl-4-(oxetan-3-yl)piperazin-1-yl)phenyl)amino)-1,3,5-triazin-2-yl)benzonitrile

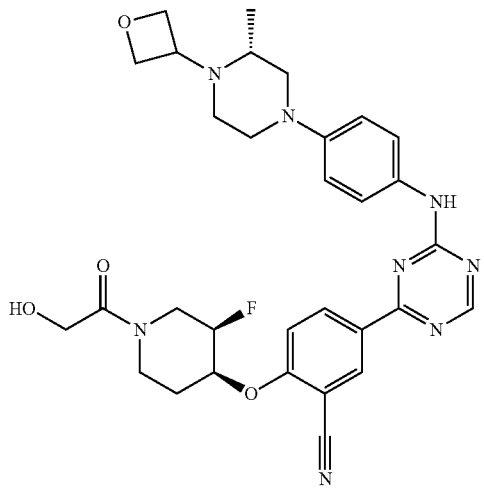 [SMILES: C[C@@H]1CN(c2ccc(Nc3ncnc(-c4ccc(O[C@H]5CCN(C(=O)CO)C[C@H]5F)c(C#N)c4)n3)cc2)CCN1C1COC1]

The title compound was prepared following a similar procedure reported in Example 241 using (R)-tert-butyl 2-methylpiperazine-1-carboxylate. $^1$H NMR (400 MHz, DMSO-d$_6$) δ 10.11 (d, J=23.9 Hz, 1H), 8.73 (s, 1H), 8.63-8.46 (m, 2H), 7.58 (dd, J=30.4, 11.9 Hz, 3H), 6.95 (d, J=10.0 Hz, 2H), 5.3-4.95 (m, 2H), 4.75-4.6 (m, 1H), 4.55 (td, J=6.5, 3.2 Hz, 2H), 4.52-4.43 (m, 2H), 4.40-3.9 (m, 3H), 3.66-3.21 (m, 6H), 2.81 (t, J=10.5 Hz, 1H), 2.69 (dd, J=11.5, 3.9 Hz, 1H), 2.59-2.50 (m, 1H), 2.42-2.33 (m, 1H), 2.13 (td, J=11.0, 9.9, 3.0 Hz, 1H), 2.02-1.73 (m, 2H), 0.89 (d, J=6.3 Hz, 3H). LCMS-ESI$^+$ (m/z): [M+H]$^+$ calcd for C$_{31}$H$_{35}$FN$_8$O$_4$: 603.2; found:603.2

Example 244

2-(((3R,4S)-3-fluoro-1-(2-hydroxyacetyl)piperidin-4-yl)oxy)-5-(4-((4-((S)-2-methyl-4-(oxetan-3-yl)piperazin-1-yl)phenyl)amino)-1,3,5-triazin-2-yl)benzonitrile

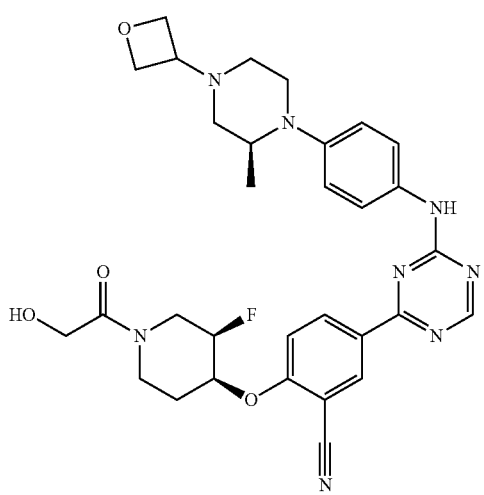 [SMILES: C[C@H]1CN(C2COC2)CCN1c1ccc(Nc2ncnc(-c3ccc(O[C@H]4CCN(C(=O)CO)C[C@H]4F)c(C#N)c3)n2)cc1]

The title compound was prepared following a similar procedure reported in Example 241 using (S)-tert-butyl 3-methylpiperazine-1-carboxylate. $^1$H NMR (400 MHz, DMSO-d$_6$) δ 10.11 (d, J=23.5 Hz, 1H), 8.73 (s, 1H), 8.67-8.60-8.45 (m, 2H), 7.64-4.48 (m, 3H), 6.92 (m, 2H), 5.19-4.95 (m, 2H), 4.7-4.6 (m, 1H), 4.58-4.51 (m, 2H), 4.47 (t, J=6.1 Hz, 2H), 4.41 (t, J=6.0 Hz, 2H), 4.21-3.35 (m, 8H), 3.05-2.9 (m, 1H), 2.75-2.62 (m, 1H), 2.24 (dd, J=10.9, 3.4 Hz, 1H), 2.07 (td, J=10.6, 3.3 Hz, 1H), 1.90-1.78 (m, 2H), 1.22 (s, 3H). LCMS-ESI$^+$ (m/z): [M+H]$^+$ calcd for C$_{31}$H$_{35}$FN$_8$O$_4$: 603.2; found:603.2

Example 245

2-(((R)-3,3-difluoro-1-((S)-2-hydroxypropanoyl)piperidin-4-yl)oxy)-5-(4-((4-((R)-3-methyl-4-(oxetan-3-yl)piperazin-1-yl)phenyl)amino)-1,3,5-triazin-2-yl)benzonitrile

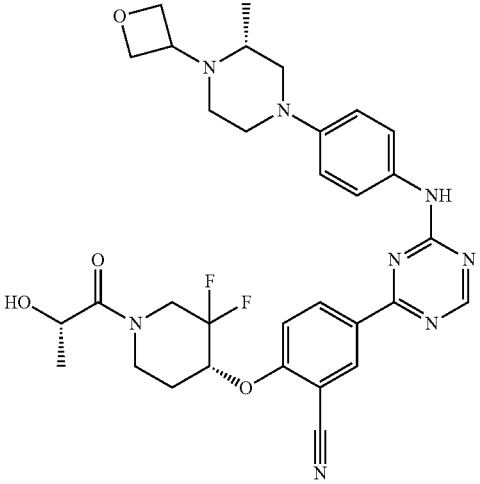 [SMILES: C[C@H](O)C(=O)N1CC[C@@H](Oc2ccc(-c3ncnc(Nc4ccc(N5CCN(C6COC6)[C@H](C)C5)cc4)n3)cc2C#N)C(F)(F)C1]

The title compound was prepared following a similar procedure reported in Example 241 using (R)-tert-butyl 2-methylpiperazine-1-carboxylate, (R)-tert-butyl 3,3-difluoro-4-hydroxypiperidine-1-carboxylate and (S)-2-hydroxypropanoic acid. $^1$H NMR (400 MHz, DMSO-d$_6$) δ 10.19 (d, J=23.4 Hz, 1H), 8.76 (s, 1H), 8.67-8.45 (m, 2H), 7.71-7.47 (m, 3H), 7.14-6.76 (m, 2H), 5.42-5.35 (m, 1H), 4.98-4.37 (m, 6H), 4.31-2.55 (m, 12H), 2.22-1.8 (m, 2H), 1.3-1.02 (m, 6H). LCMS-ESI$^+$ (m/z): [M+H]$^+$ calcd for C$_{32}$H$_6$F$_2$N$_8$O$_4$: 635.3; found:635.3

Example 246

2-(((S)-3,3-difluoro-1-((S)-2-hydroxypropanoyl)piperidin-4-yl)oxy)-5- (4-((4((R)-3-methyl-4-(oxetan-3-yl)piperazin-1-yl)phenyl)amino)-1,3,5-triazin-2-yl)benzonitrile

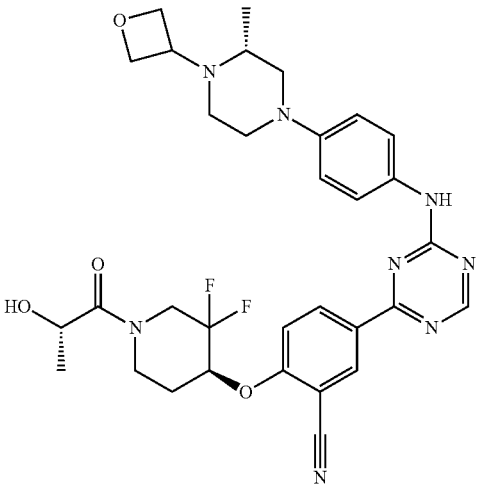 [SMILES: C[C@H](O)C(=O)N1CC[C@H](Oc2ccc(-c3ncnc(Nc4ccc(N5CCN(C6COC6)[C@H](C)C5)cc4)n3)cc2C#N)C(F)(F)C1]

The title compound was prepared following a similar procedure reported in Example 241 using (R)-tert-butyl 2-methylpiperazine-1-carboxylate, (S)-tert-butyl 3,3-difluoro-4-hydroxypiperidine-1-carboxylate and (S)-2-hydroxypropanoic acid. $^1$H NMR (400 MHz, DMSO-d$_6$) δ 10.17 (d, J=22.9 Hz, 1H), 8.75 (s, 1H), 8.66-8.44 (m, 2H), 7.75-7.48 (m, 3H), 7.14-6.77 (m, 2H), 5.49-5.02 (m, 2H), 4.98-4.34 (m, 7H), 4.25-4.15 (m, 1H), 4.06-3.39 (m, 6H), 3.05-2.58 (m, 3H), 2.20-1.69 (m, 2H), 1.32-0.8 (m, 6H). LCMS-ESI$^+$ (m/z): [M+H]$^+$ calcd for C$_{32}$H$_{36}$F$_2$N$_8$O$_4$: 635.3; found:635.3

Example 247

2-(((R)-3,3-difluoro-1-((R)-2-hydroxypropanoyl)piperidin-4-yl)oxy)-5-(4-((4-((R)-3-methyl-4-(oxetan-3-yl)piperazin-1-yl)phenyl)amino)-1,3,5-triazin-2-yl)benzonitrile

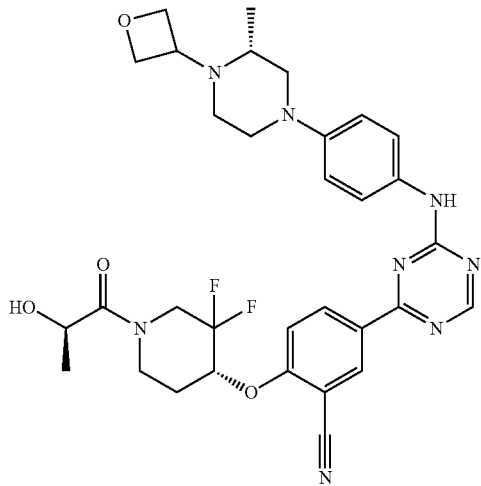 [SMILES: C[C@@H]1CN(c2ccc(Nc3ncnc(-c4ccc(O[C@@H]5CCN(C(=O)[C@@H](C)O)CC5(F)F)c(C#N)c4)n3)cc2)CCN1C1COC1]

The title compound was prepared following a similar procedure reported in Example 241 using (R)-tert-butyl 2-methylpiperazine-1-carboxylate, (R)-tert-butyl 3,3-difluoro-4-hydroxypiperidine-1-carboxylate and (R)-2-hydroxypropanoic acid. LCMS-ESI$^+$ (m/z): [M+H]$^+$ calcd for C$_{32}$H$_{36}$F$_2$N$_8$O$_4$: 635.3; found:635.3

Example 248

2-(((S)-3,3-difluoro-1-((R)-2-hydroxypropanoyl)piperidin-4-yl)oxy)-5-(4-((4-((R)-3-methyl-4-(oxetan-3-yl)piperazin-1-yl)phenyl)amino)-1,3,5-triazin-2-yl)benzonitrile

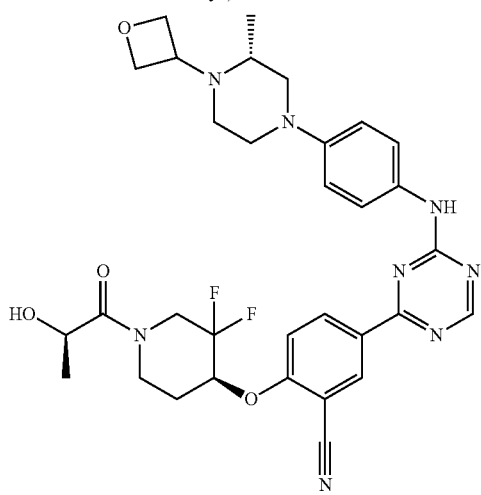

The title compound was prepared following a similar procedure reported in Example 241 using (R)-tert-butyl 2-methylpiperazine-1-carboxylate, (S)-tert-butyl 3,3-difluoro-4-hydroxypiperidine-1-carboxylate and (R)-2-hydroxypropanoic acid. $^1$H NMR (400 MHz, DMSO-d$_6$) δ 10.17 (d, J=22.9 Hz, 1H), 8.75 (s, 1H), 8.66-8.44 (m, 2H), 7.75-7.48 (m, 3H), 7.14-6.77 (m, 2H), 5.49-5.02 (m, 2H), 4.98-4.34 (m, 7H), 4.25-4.15 (m, 1H), 4.06-3.39 (m, 6H), 3.05-2.58 (m, 3H), 2.20-1.69 (m, 2H), 1.32-0.8 (m, 6H). LCMS-ESI$^+$ (m/z): [M+H]$^+$ calcd for C$_{32}$H$_{36}$F$_2$N$_8$O$_4$: 635.3; found:635.3 LCMS-ESI$^+$ (m/z): [M+H]$^+$ calcd for C$_{32}$H$_{36}$F$_2$N$_8$O$_4$: 635.3; found:635.3

Example 249

2-(((3R,4S)-3-fluoro-1-((S)-2-hydroxypropanoyl)piperidin-4-yl)oxy)-5-(4-((4-((S)-2-methyl-4-(oxetan-3-yl)piperazin-1-yl)phenyl)amino)-1,3,5-triazin-2-yl)benzonitrile

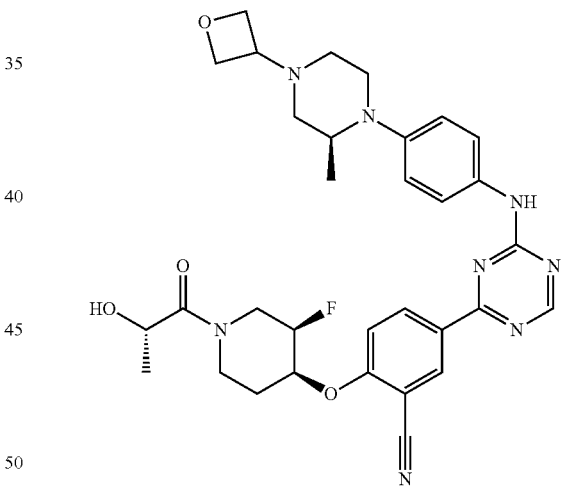

The title compound was prepared following a similar procedure reported in Example 241 using (3R,4S)-tert-butyl 3-fluoro-4-hydroxypiperidine-1-carboxylate and (S)-2-hydroxypropanoic acid. $^1$H NMR (400 MHz, DMSO-d$_6$) δ 10.11 (d, J=22.9 Hz, 1H), 8.73 (s, 1H), 8.65-8.46 (m, 2H), 7.75-7.49 (m, 3H), 6.75-6.85 (m, 2H), 5.21-4.91 (m, 3H), 4.56 (td, J=6.5, 3.0 Hz, 2H), 4.48-4.38 (m, 4H), 4.21-4.00 (m, 1H), 3.99-3.84 (m, 1H), 3.45-3.33 (m, 1H), 3.30-3.11 (m, 4H), 2.98 (d, J=12.2 Hz, 1H), 2.68 (d, J=10.4 Hz, 1H), 2.24 (dd, J=10.8, 3.4 Hz, 1H), 2.07 (td, J=10.5, 3.3 Hz, 1H), 1.95-1.78 (m, 2H), 1.2 (s, 3H), 1.00 (s, 3H). LCMS-ESI$^+$ (m/z): [M+H]$^+$ calcd for C$_{32}$H$_{37}$FN$_8$O$_4$: 617.3; found:617.4

Example 250

2-(((3R,4S)-1-(2-cyanoacetyl)-3-fluoropiperidin-4-yl)oxy)-5-(4-((4-((S)-2-methyl-4-(oxetan-3-yl)piperazin-1-yl)phenyl)amino)-1,3,5-triazin-2-yl)benzonitrile

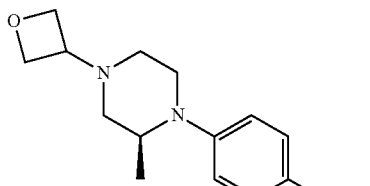

The title compound was prepared following a similar procedure reported in Example 241 using (3R,4S)-tert-butyl 3-fluoro-4-hydroxypiperidine-1-carboxylate and 2-cyanoacetic acid. $^1$H NMR (400 MHz, DMSO-$d_6$) δ 10.11 (d, J=23.8 Hz, 1H), 8.73 (s, 1H), 8.64-8.47 (m, 2H), 7.70-7.44 (m, 3H), 6.95-6.87 (m, 2H), 5.2-4.92 (m, 2H), 4.56 (td, J=6.5, 3.0 Hz, 2H), 4.47 (t, J=6.0 Hz, 1H), 4.41 (t, J=6.0 Hz, 1H), 4.27-4.03 (m, 1H), 3.94-3.82 (m, 2H), 3.72-3.5 (m, 3H), 3.4-3.32 (m, 1H), 3.35-3.15 (m, 3H), 3.1-2.92 (m, 1H), 2.72-2.65 (m, 1H), 2.24 dd, J=10.7, 3.3 Hz, 1H), 2.10-1.92 (m, 3H), 1.00 (s, 3H). LCMS-ESI$^+$ (m/z): [M+H]$^+$ calcd for $C_{32}H_{34}FN_9O_3$: 612.3; found:612.3

Example 251

2-(((3R,4S)-3-fluoro-1-(3-hydroxypropanoyl)piperidin-4-yl)oxy)-5-(4-((4-((S)-2-methyl-4-(oxetan-3-yl)piperazin-1-yl)phenyl)amino)-1,3,5-triazin-2-yl)benzonitrile

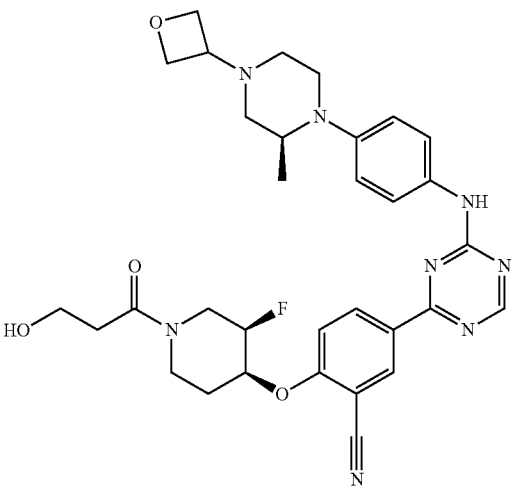 [SMILES: C[C@H]1CN(C2COC2)CCN1c1ccc(Nc2ncnc(-c3ccc(O[C@H]4CCN(C(=O)CCO)C[C@H]4F)c(C#N)c3)n2)cc1]

The title compound was prepared following a similar procedure reported in Example 241 using (3R,4S)-tert-butyl 3-fluoro-4-hydroxypiperidine-1-carboxylate and 3-hydroxypropanoic acid. $^1$H NMR (400 MHz, DMSO-$d_6$) δ 10.08 (s, 1H), 8.73 (s, 1H), 8.56 (d, J=11.2 Hz, 2H), 7.74-7.38 (m, 3H), 6.97-6.85 (m, 2H), 5.18-4.9 (m, 2H), 4.60-4.44 (m, 4H), 4.41 (t, J=6.0 Hz, 1H), 4.35-4.02 (m, 2H), 3.98-3.74 (m. 2H), 3.69-3.57 (m, 2H), 3.38 (h, J=5.6, 5.2 Hz, 2H), 3.32-3.15 (m, 2H), 3.1-2.92 (m, 2H), 2.75-2.65 (m, 1H), 2.61-2.52 (m, 1H), 2.24 (dd, J=10.8, 3.5 Hz, 1H), 2.12-2.02 (m, 1H), 1.99-1.9 (m, 2H), 1.00 (s, 3H). LCMS-ESI$^+$ (m/z): [M+H]$^+$ calcd for $C_{32}H_{37}FN_8O_4$: 617.3; found:617.3

Example 252

2-(((S)-3,3-difluoro-1-((S)-2-hydroxypropanoyl)piperidin-4-yl)oxy)-5-(4-((4-((S)-2-methyl-4-(oxetan-3-yl)piperazin-1-yl)phenyl)amino)-1,3,5-triazin-2-yl)benzonitrile

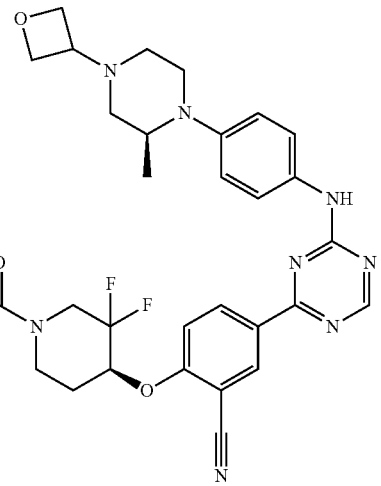

The title compound was prepared following a similar procedure reported in Example 241 using (S)-tert-butyl 3,3-difluoro-4-hydroxypiperidine-1-carboxylate and (S)-2-hydroxypropanoic acid. $^1$H NMR (400 MHz, DMSO-$d_6$) δ 10.13 (d, J=22.4 Hz, 1H), 8.74 (s, 1H), 8.65-8.51 (m, 2H), 7.66 (d, J=9.2 Hz, 1H), 7.65-7.51 (m, 2H), 7.01-6.85 (m, 2H), 5.45-5.32 (m, 1H), 5.21 (d, J=6.9 Hz, 1H), 4.56 (td, J=6.5, 3.0 Hz, 2H), 4.48 (q, J=5.7 Hz, 2H), 4.41 (t, J=6.0 Hz, 1H), 4.25-4.06 (m, 1H), 4.05-3.69 (m, 3H), 3.64-3.16 (m, 3H), 3.09-2.91 (m, 1H), 2.67 (s, 1H), 2.26-1.73 (m, 5H), 1.20 (d, J=9.0 Hz, 3H), 1.00 (s, 3H). LCMS-ESI$^+$ (m/z): [M+H]$^+$ calcd for $C_{32}H_{36}F_2N_8O_4$: 635.3; found:635.2

Example 253

2-(((S)-1-(2-cyanoacetyl)-3,3-difluoropiperidin-4-yl)oxy)-5-(4-((4-((S)-2-methyl-4-(oxetan-3-yl)piperazin-1-yl)phenyl)amino)-1,3,5-triazin-2-yl)benzonitrile

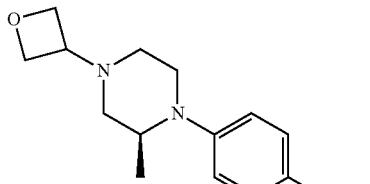

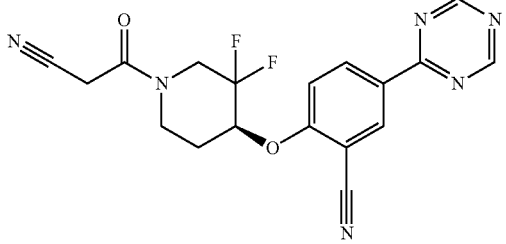

The title compound was prepared following a similar procedure reported in Example 241 using (S)-tert-butyl 3,3-difluoro-4-hydroxypiperidine-1-carboxylate and 2-cyanoacetic acid. $^1$H NMR (400 MHz, DMSO-$d_6$) δ 10.13 (d, J=23.8 Hz, 1H), 8.74 (s, 1H), 8.65-8.45 (m, 2H), 7.65 (d, J=9.2 Hz, 1H), 7.69-7.49 (m, 2H), 6.92 (s, 2H), 5.44-5.32 (m, 1H), 4.56 (td, J=6.5, 3.0 Hz, 2H), 4.47 (t, J=6.0 Hz, 1H), 4.41 (t, J=6.0 Hz, 1H), 4.21 (s, 1H), 4.16-3.72 (m, 2H), 3.65-3.36 (m, 2H), 3.25-3.07 (m, 2H), 2.97 (s, 1H), 2.67 (s, 1H), 2.29-1.96 (m, 4H), 1.22 (s, 3H), 1.09-0.93 (m, 3H). LCMS-ESI$^+$ (m/z): [M+H]$^+$ calcd for $C_{32}H_{33}F_2N_9O_3$: 630.3; found:630.3

Example 254

2-(((S)-3,3-difluoro-1-(3-hydroxypropanoyl)piperidin-4-yl)oxy)-5-(4-((4-((S)-2-methyl-4-(oxetan-3-yl)piperazin-1-yl)phenyl)amino)-1,3,5-triazin-2-yl)benzonitrile

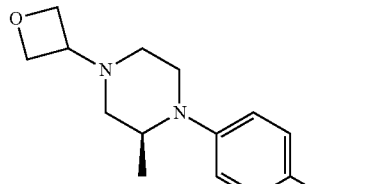

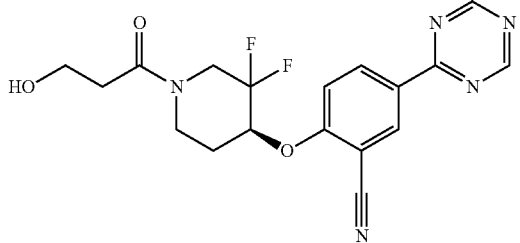

The title compound was prepared following a similar procedure reported in Example 241 using (S)-tert-butyl 3,3-difluoro-4-hydroxypiperidine-1-carboxylate and 3-hydroxypropanoic acid. $^1$H NMR (400 MHz, DMSO-$d_6$) δ 10.10 (s, 1H), 8.74 (s, 1H), 8.65-8.47 (m, 2H), 7.71-7.62 (m, 1H), 7.56 (d, J=15.1 Hz, 2H), 6.91 (d, J=10.2 Hz, 2H), 5.35 (s, 1H), 4.56 (td, J=6.5, 2.9 Hz, 3H), 4.47 (t, J=6.0 Hz, 1H), 4.41 (t, J=6.0 Hz, 1H), 4.18-3.99 (m, 1H), 3.95-3.68 (m, 2H), 3.64 (q, J=6.2 Hz, 3H), 3.39 (p, J=6.3 Hz, 1H), 3.25-2.64 (m, 4H), 2.56 (dt, J=10.7, 6.3 Hz, 2H), 2.25-1.64 (m, 5H), 1.00 (s, 3H). LCMS-ESI$^+$ (m/z): [M+H]$^+$ calcd for $C_{32}H_{36}F_2N_3O_4$: 635.3; found:635.2

Example 255

2-(((3R,4S)-3-fluoro-1-(1H-1,2,3-triazole-5-carbonyl)piperidin-4-yl)oxy)-5-(4-((4-((S)-2-methyl-4-(oxetan-3-yl)piperazin-1-yl)phenyl)amino)-1,3,5-triazin-2-yl)benzonitrile

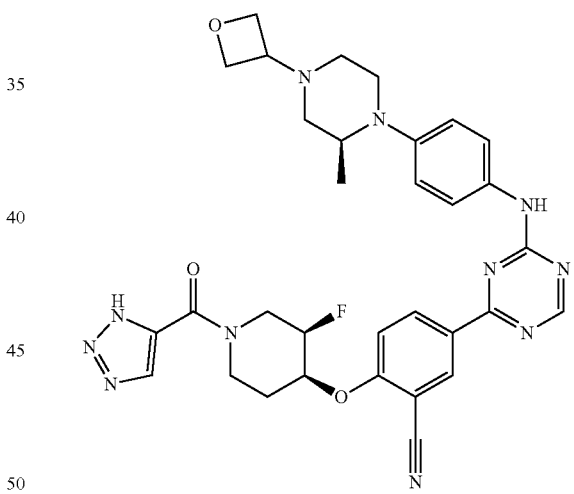

The title compound was prepared following a similar procedure reported in Example 241 using (3R,4S)-tert-butyl 3-fluoro-4-hydroxypiperidine-1-carboxylate and 1H-1,2,3-triazole-5-carboxylic acid. $^1$H NMR (400 MHz, DMSO-$d_6$) δ 10.12 (s, 1H), 8.73 (s, 1H), 8.60-8.5 (m, 2H), 7.92 (s, 1H), 7.65-7.5 (m, 4H), 6.95-6.85 (m, 2H), 5.26-4.85 (m, 2H), 4.56 (td, J=6.4, 2.9 Hz, 2H), 4.48 (t, J=6.0 Hz, 1H), 4.41 (t, J=6.0 Hz, 1H), 4.21-3.97 (m, 1H), 3.98-3.85 (m, 1H), 3.40 (q, J=6.3 Hz, 1H), 3.25-3.08 (m, 3H), 3.05-2.92 (m, 1H), 2.71-2.65 (m, 2H), 2.27-2.17 (m, 1H), 2.14-2.02 (m, 2H), 2.01-1.88 (m, 2H), 1.01 (d, J=6.3 Hz, 3H). LCMS-ESI$^+$ (m/z): [M+H]$^+$ calcd for $C_{32}H_{34}FN_{11}O_3$: 640.3; found: 640.2.

Example 256

2-(((3R,4S)-3-fluoro-1-(1H-imidazole-5-carbonyl)piperidin-4-yl)oxy)-5-(4-((4-((S)-2-methyl-4-(oxetan-3-yl)piperazin-1-yl)phenyl)amino)-1,3,5-triazin-2-yl)benzonitrile

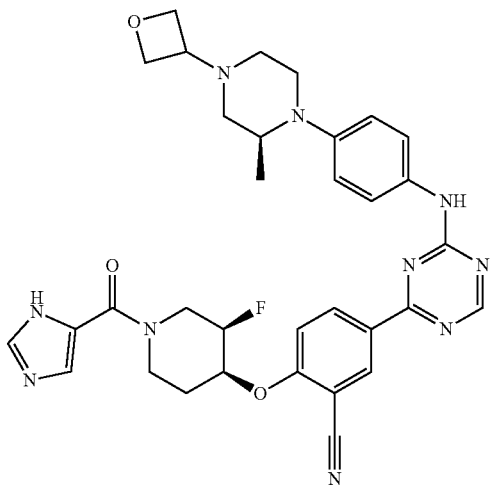 [SMILES: C[C@H]1CN(C2COC2)CCN1c1ccc(Nc2ncnc(-c3ccc(O[C@H]4CCN(C(=O)c5cnc[nH]5)C[C@H]4F)c(C#N)c3)n2)cc1]

The title compound was prepared following a similar procedure reported in Example-G using (3R,4S)-tert-butyl 3-fluoro-4-hydroxypiperidine-1-carboxylate and 1H-imidazole-5-carboxylic acid. $^1$H NMR (400 MHz, DMSO-d$_6$) δ 10.32-10.12 (m, 1H), 8.83-8.65 (m, 1H), 8.65-8.22 (m, 3H), 7.84 (s, 1H), 7.61 (dd, J=11.3, 7.1 Hz, 3H), 7.22-6.95 (m, 2H), 5.13 (d, J=22.7 Hz, 3H), 4.82-4.58 (m, 5H), 4.46-3.00 (m, 11H), 2.16-1.70 (m, 2H), 0.95 (d, J=15.0 Hz, $^3$H). LCMS-ESI$^+$ (m/z): [M+H]$^+$ calcd for C$_{33}$H$_{35}$FN$_{10}$O$_3$: 639.3; found:639.3

Example 257

2-(((3R,4S)-3-fluoro-1-(1H-pyrazole-5-carbonyl)piperidin-4-yl)oxy)-5-(4-((4-((S)-2-methyl-4-(oxetan-3-yl)piperazin-1-yl)phenyl)amino)-1,3,5-triazin-2-yl)benzonitrile

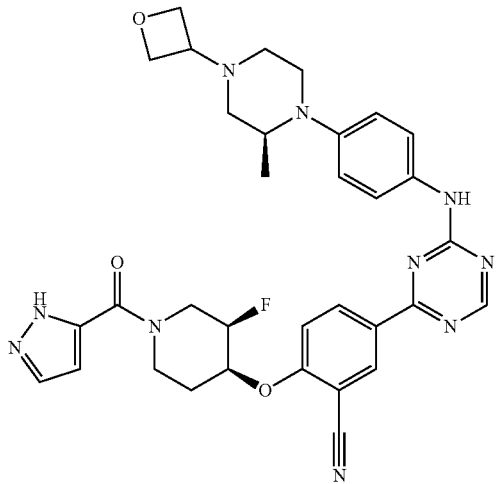 [SMILES: C[C@H]1CN(C2COC2)CCN1c1ccc(Nc2ncnc(-c3ccc(O[C@H]4CCN(C(=O)c5ccn[nH]5)C[C@H]4F)c(C#N)c3)n2)cc1]

The title compound was prepared following a similar procedure reported in Example 241 using (3R,4S)-tert-butyl 3-fluoro-4-hydroxypiperidine-1-carboxylate and 1H-pyrazole-5-carboxylic acid. $^1$H NMR (400 MHz, DMSO-d$_6$) δ 10.21 (d, J=56.9 Hz, 1H), 8.72 (d, J=7.6 Hz, 1H), 8.60-8.45 (m, 2H), 7.8-7.5 (m, 4H), 7.2-6.85 (m, 2H), 6.55 (d, J=2.3 Hz, 1H), 5.2-5.0 (m, 1H), 4.85-4.6 (m, 3H), 4.51-4.08 (m, 3H), 3.32-2.66 (m, 11H), 2.05-1.8 (m, 2H) 0.96 (d, J=65.4 Hz, 3H). LCMS-ESI$^+$ (m/z): [M+H]$^+$ calcd for C$_{33}$H$_{35}$FN$_{10}$O$_3$: 639.3; found:639.3

Example 258

2-(((S)-3,3-difluoro-1-(1H-1,2,3-triazole-5-carbonyl)piperidin-4-yl)oxy)-5-(4-((4-((S)-2-methyl-4-(oxetan-3-yl)piperazin-1-yl)phenyl)amino)-1,3,5-triazin-2-yl)benzonitrile

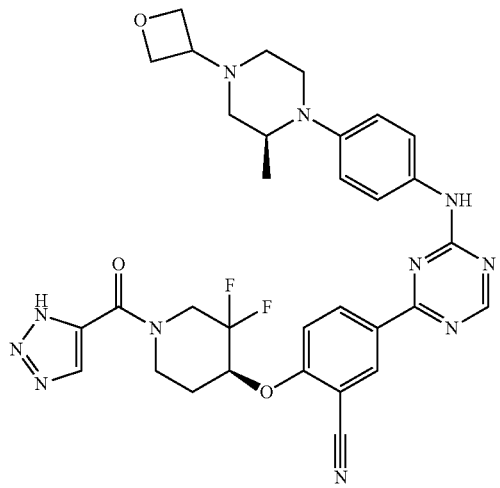 [SMILES: C[C@H]1CN(C2COC2)CCN1c1ccc(Nc2ncnc(-c3ccc(O[C@H]4CCN(C(=O)c5cnn[nH]5)CC4(F)F)c(C#N)c3)n2)cc1]

The title compound was prepared following a similar procedure reported in Example 242 using (S)-tert-butyl 3,3-difluoro-4-hydroxypiperidine-1-carboxylate and 1H-1,2,3-triazole-5-carboxylic acid. $^1$H NMR (400 MHz, DMSO-d$_6$) δ 10.59-9.84 (m, 2H), 8.74 (s, 1H), 8.65-8.42 (m, 2H), 8.12-8.01 (m, 1H), 7.63 (t, J=8.5 Hz, 2H), 7.3-6.92 (m, 2H), 5.39 (s, 1H), 4.96-4.50 (m, 3H), 4.33-3.0 (m, 15H), 2.29-1.58 (m, 2H), 1.44-0.59 (m, 3H). LCMS-ESI$^+$ (m/z): [M+H]$^+$ calcd for C$_{32}$H$_{33}$F$_2$N$_{11}$O$_3$: 658.3; found:658.3

Example 259

2-(((S)-3,3-difluoro-1-(1H-imidazole-5-carbonyl)piperidin-4-yl)oxy)-5-(4-((4-((S)-2-methyl-4-(oxetan-3-yl)piperazin-1-yl)phenyl)amino)-1,3,5-triazin-2-yl)benzonitrile

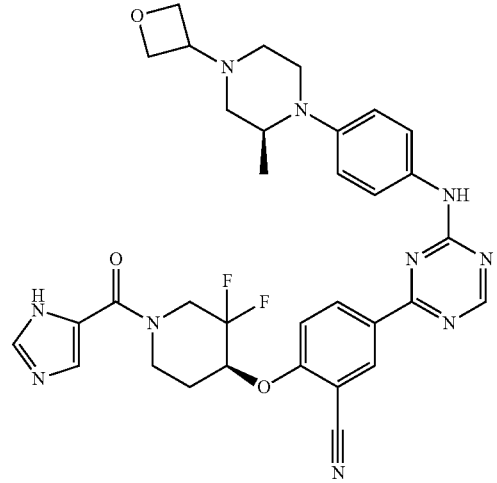

The title compound was prepared following a similar procedure reported in Example 241 using (S)-tert-butyl 3,3-difluoro-4-hydroxypiperidine-1-carboxylate and 1H-imidazole-5-carboxylic acid. $^1$H NMR (400 MHz, DMSO-$d_6$) δ 10.21 (s, 1H), 8.74 (s, 1H), 8.55 (dt, J=15.0, 7.5 Hz, 2H), 8.11 (s, 1H), 7.81 (s, 1H), 7.62 (t, J=11.2 Hz, 3H), 7.14-6.99 (m, 2H), 5.50-5.26 (m, 1H), 4.81-4.52 (m, 5H), 4.4-2.6 (m, 10H), 2.05 (d, J=84.1 Hz, 4H), 1.25-0.59 (m, 3H). LCMS-ESI$^+$ (m/z): [M+H]$^+$ calcd for $C_{33}H_{34}F_2N_{10}O_3$: 657.3; found:657.2

Example 260

2-(((S)-3,3-difluoro-1-(4H-1,2,4-triazole-3-carbonyl)piperidin-4-yl)oxy)-5-(4-((4-((S)-2-methyl-4-(oxetan-3-yl)piperazin-1-yl)phenyl)amino)-1,3,5-triazin-2-yl)benzonitrile

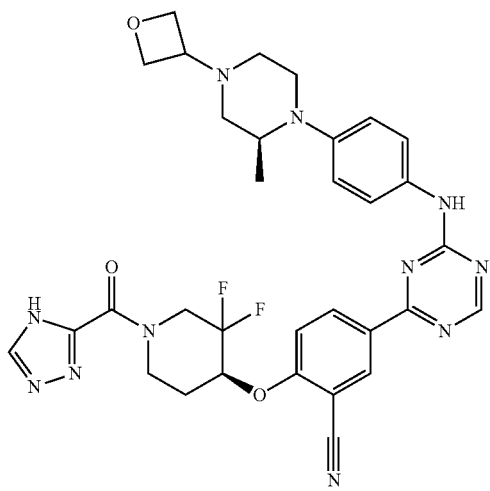 [SMILES: C[C@H]1CN(C2COC2)CCN1c1ccc(Nc2ncnc(-c3ccc(O[C@H]4CCN(C(=O)c5nnc[nH]5)CC4(F)F)c(C#N)c3)n2)cc1]

The title compound was prepared following a similar procedure reported in Example 241 using (S)-tert-butyl 3,3-difluoro-4-hydroxypiperidine-1-carboxylate and 4H-1,2,4-triazole-3-carboxylic acid. $^1$H NMR (400 MHz, DMSO-$d_6$) δ 10.4-10.1 (m, 2H), 8.83-8.65 (m, 1H), 8.56 (d, J=8.9 Hz, 2H), 7.63 (d, J=9.2 Hz, 3H), 7.05 (d, J=81.4 Hz, 3H), 5.39 (s, 1H), 4.88-3.85 (m, 8H), 3.6-2.65 (m, 7H), 2.28-1.75 (m, 3H), 1.25-0.57 (m, 3H). LCMS-ESI$^+$ (m/z): [M+H]$^+$ calcd for $C_{32}H_{33}F_2N_{11}O_3$: 658.3; found:658.2

Example 261

2-(((S)-3,3-difluoro-1-(2-hydroxyacetyl)piperidin-4-yl)oxy)-5-(4-((4-((S)-3-methyl-4-(oxetan-3-yl)piperazin-1-yl)phenyl)amino)-1,3,5-triazin-2-yl)benzonitrile

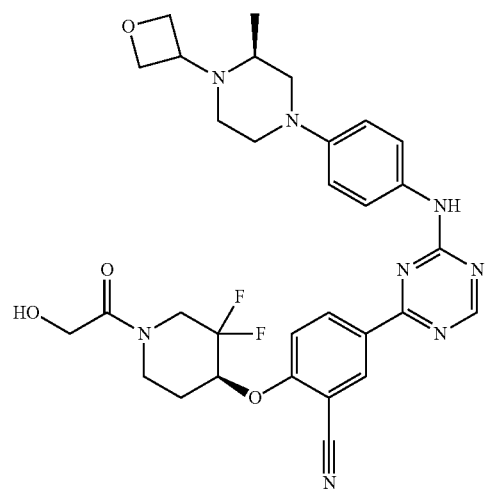 [SMILES: C[C@H]1CN(c2ccc(Nc3ncnc(-c4ccc(O[C@H]5CCN(C(=O)CO)CC5(F)F)c(C#N)c4)n3)cc2)CCN1C1COC1]

The title compound was prepared following a similar procedure reported in Example 241 using (S)-tert-butyl 2-methylpiperazine-1-carboxylate, (S)-tert-butyl 3,3-difluoro-4-hydroxypiperidine-1-carboxylate and 2-hydroxyacetic acid. $^1$H NMR (400 MHz, DMSO-$d_6$) δ 10.21-10.00 (m, 1H), 8.73 (s, 1H), 8.64-8.50 (m, 2H), 7.71-7.62 (m, 1H), 7.62-7.44 (m, 2H), 6.95 (d, J=9.4 Hz, 2H), 5.41-5.32 (m, 1H), 4.93-4.84 (m, 1H), 4.62-4.42 (m, 4H), 4.23-3.93 (m, 3H), 3.95-3.82 (m, 1H), 3.72-3.55 (m, 3H), 3.50-3.32 (m, 2H), 2.88-2.60 (m, 2H), 2.60-2.34 (m, 2H), 2.22-2.03 (m, 2H), 1.98 (d, J=11.3 Hz, 1H), 0.89 (d, J=6.3 Hz, 3H). LCMS-ESI$^+$ (m/z): [M+H]$^+$ calcd for $C_{31}H_{34}F_2N_8O_4$: 621.3; found:621.7

Example 262

2-(((S)-3,3-difluoro-1-((S)-2-hydroxypropanoyl)piperidin-4-yl)oxy)-5-(4-((4-((S)-3-methyl-4-(oxetan-3-yl)piperazin-1-yl)phenyl)amino)-1,3,5-triazin-2-yl)benzonitrile

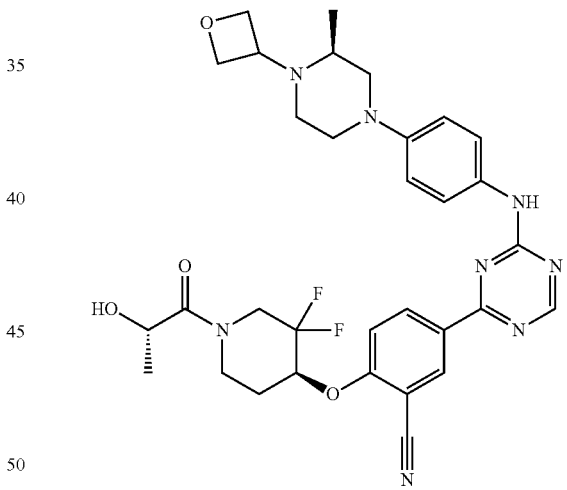

The title compound was prepared following a similar procedure reported in Example 241 using (S)-tert-butyl 2-methylpiperazine-1-carboxylate, (S)-tert-butyl 3,3-difluoro-4-hydroxypiperidine-1-carboxylate and (S)-2-hydroxypropanoic acid. $^1$H NMR (400 MHz, DMSO-$d_6$) δ 10.13 (d, J=22.7 Hz, 1H), 8.73 (d, J=2.3 Hz, 1H), 8.62-8.49 (m, 2H), 7.66 (d, J=9.2 Hz, 1H), 7.62-7.48 (m, 2H), 6.93 (d, J=8.3 Hz, 2H), 5.32-5.26 (m, 2H), 4.59-4.35 (m, 5H), 4.13 (s, 1H), 3.88-3.54 (m, 4H), 3.42-3.25 (m, 3H), 2.89-2.59 (m, 2H), 2.59-2.32 (m, 2H), 2.14 (td, J=10.0, 9.1, 5.3 Hz, 2H), 1.21 (t, J=5.1 Hz, 3H), 0.89 (d, J=6.3 Hz, 3H). LCMS-ESI$^+$ (m/z): [M+H]$^+$ calcd for $C_{32}H_{36}F_2N_8O_4$: 635.3; found:635.2

Example 263

2-(((3R,4S)-3-fluoro-1-(1H-1,2,3-triazole-5-carbonyl)piperidin-4-yl)oxy)-5-(4-((4-((S)-3-methyl-4-(oxetan-3-yl)piperazin-1-yl)phenyl)amino)-1,3,5-triazin-2-yl)benzonitrile

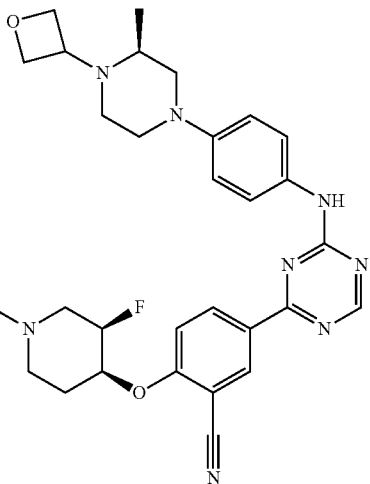

The title compound was prepared following a similar procedure reported in Example 241 using (S)-tert-butyl 2-methylpiperazine-1-carboxylate, (3R,4S)-tert-butyl 3-fluoro-4-hydroxypiperidine-1-carboxylate and 1H-1,2,3-triazole-5-carboxylic acid. $^1$H NMR (400 MHz, DMSO-$d_6$) δ 10.14 (s, 1H), 8.73 (s, 1H), 8.64-8.48 (m, 2H), 8.05 (d, J=43.5 Hz, 1H), 7.71-7.52 (m, 4H), 6.93 (d, J=7.2 Hz, 2H), 5.07 (d, J=52.8 Hz, 2H), 4.59-4.38 (m, 4H), 4.23 (s, 1H), 3.72-3.59 (m, 2H), 3.39-3.25 (m, 5H), 3.09-2.59 (m, 4H), 2.20-1.72 (m, 2H), 0.89 (d, J=6.3 Hz, 3H). LCMS-ESI$^+$ (m/z): [M+H]$^+$ calcd for $C_{32}H_{34}FN_{11}O_3$: 640.3; found: 640.2

Example 264

2-(((3R,4S)-3-fluoro-1-((S)-2-hydroxypropanoyl)piperidin-4-yl)oxy)-5-(4-((4-((S)-3-methyl-4-(oxetan-3-yl)piperazin-1-yl)phenyl)amino)-1,3,5-triazin-2-yl)benzonitrile

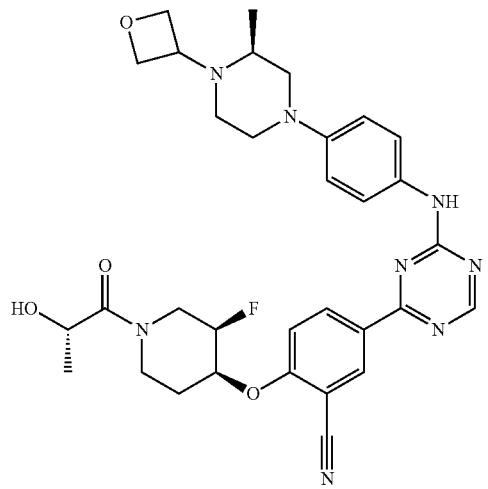 [SMILES: C[C@H](O)C(=O)N1CC[C@H](Oc2ccc(-c3ncnc(Nc4ccc(N5CCN(C6COC6)[C@@H](C)C5)cc4)n3)cc2C#N)[C@H](F)C1]

The title compound was prepared following a similar procedure reported in Example 241 using (S)-tert-butyl 2-methylpiperazine-1-carboxylate, (3R,4S)-tert-butyl 3-fluoro-4-hydroxypiperidine-1-carboxylate and (S)-2-hydroxypropanoic acid. $^1$H NMR (400 MHz, DMSO-$d_6$) δ 10.11 (d, J=25.3 Hz, 1H), 8.73 (s, 1H), 8.63-8.47 (m, 2H), 7.70-7.41 (m, 3H), 7.02-6.89 (m, 2H), 5.21-4.82 (m, 3H), 4.66-4.29 (m, 2H), 4.24-3.84 (m, 2H), 3.75-3.53 (m, 3H), 3.36 (d, J=12.6 Hz, 3H), 3.13 (s, 2H), 2.82 (t, J=10.6 Hz, 1H), 2.69 (d, J=11.2 Hz. 1H), 2.53-2.40 (m, 2H), 2.13 (t, J=10.3 Hz, 1H), 2.04-1.69 (m, 2H), 1.25-1.19 (m, 3H), 0.89 (d, J=6.3 Hz, 3H). LCMS-ESI$^+$ (m/z): [M+H]$^+$ calcd for $C_{32}H_{37}FN_8O_4$ Exact Mass: 617.3 found:617.2

Example 265

5-(4-((4-((2S,5R)-2,5-dimethyl-4-(oxetan-3-yl)piperazin-1-yl)phenyl)amino)-1,3,5-triazin-2-yl)-2-(((3R,4S)-3-fluoro-1-((S)-2-hydroxypropanoyl)piperidin-4-yl)oxy)benzonitrile

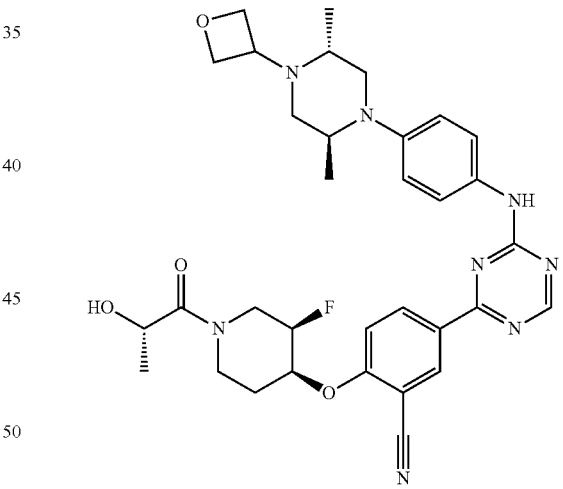

The title compound was prepared following a similar procedure reported in Example 241 using (2R,5S)-tert-butyl 2,5-dimethylpiperazine-1-carboxylate, (3R,4S)-tert-butyl 3-fluoro-4-hydroxypiperidine-1-carboxylate and (S)-2-hydroxypropanoic acid. $^1$H NMR (400 MHz, DMSO-$d_6$) δ 10.2 (s, 1H), 8.75 (s, 1H), 8.65-8.51 (m, 2H), 7.70-7.45 (m, 3H), 6.95-6.82 (m, 2H), 5.21-4.82 (m, 3H), 4.66-4.29 (m, 2H), 4.26-3.91 (m, 2H), 3.79-3.42 (m, 2H), 3.39-2.92 (m, 3H), 2.88-2.65 (m, 4H), 2.25-1.92 (m, 5H), 1.52-1.39 (m, 3H), 0.88-0.79 (m, 6H). LCMS-ESI$^+$ (m/z): [M+H]$^+$ calcd for $C_{33}H_{39}FN_8O_4$ Exact Mass: 631.3 found:631.2

Example 266

2-(((3R,4S)-1-(1,2-dimethyl-1H-imidazole-5-carbonyl)-3-fluoropiperidin-4-yl)oxy)-5-(4-((4-(4-(oxetan-3-yl)piperazin-1-yl)phenyl)amino)-1,3,5-triazin-2-yl)benzonitrile

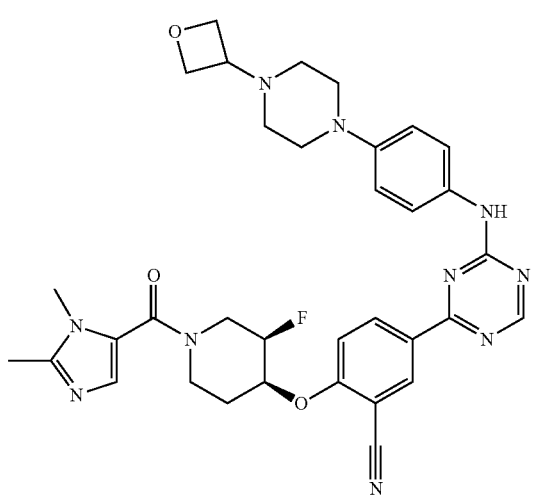 [SMILES: Cc1ncc(C(=O)N2CC[C@H](Oc3ccc(-c4ncnc(Nc5ccc(N6CCN(C7COC7)CC6)cc5)n4)cc3C#N)[C@H](F)C2)n1C]

The title compound was prepared following a similar procedure reported in Example 241 using (3R,4S)-tert-butyl 3-fluoro-4-hydroxypiperidine-1-carboxylate and 1,2-dimethyl-1H-imidazole-5-carboxylic acid. LCMS-ESI$^+$ (m/z): [M+H]$^+$ calcd for $C_{34}H_{37}FN_{10}O_3$ Exact Mass: 653.3 found: 653.2

Example 267

2-(((3R,4S)-3-fluoro-1-(1-methyl-1H-imidazole-5-carbonyl)piperidin-4-yl)oxy)-5-(4-((4-(4-(oxetan-3-yl)piperazin-1-yl)phenyl)amino)-1,3,5-triazin-2-yl)benzonitrile

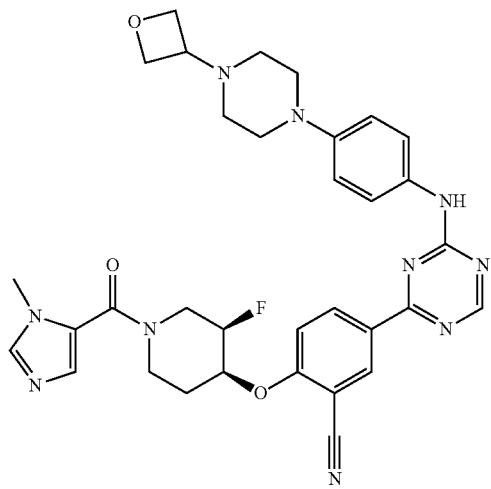 [SMILES: Cn1cncc1C(=O)N1CC[C@H](Oc2ccc(-c3ncnc(Nc4ccc(N5CCN(C6COC6)CC5)cc4)n3)cc2C#N)[C@H](F)C1]

The title compound was prepared following a similar procedure reported in Example 241 using (3R,4S)-tert-butyl 3-fluoro-4-hydroxypiperidine-1-carboxylate and 1-methyl-1H-imidazole-5-carboxylic acid LCMS-ESI$^+$ (m/z): [M+H]$^+$ calcd for $C_{33}H_{35}FN_{10}O_3$ Exact Mass: 639.3 found: 639.2

Example 268

2-((1,1-dioxidotetrahydro-2H-thiopyran-4-yl)oxy)-5-(4-((3-fluoro-4-(4-(oxetan-3-yl)piperazin-1-yl)phenyl)amino)-1,3,5-triazin-2-yl)benzonitrile

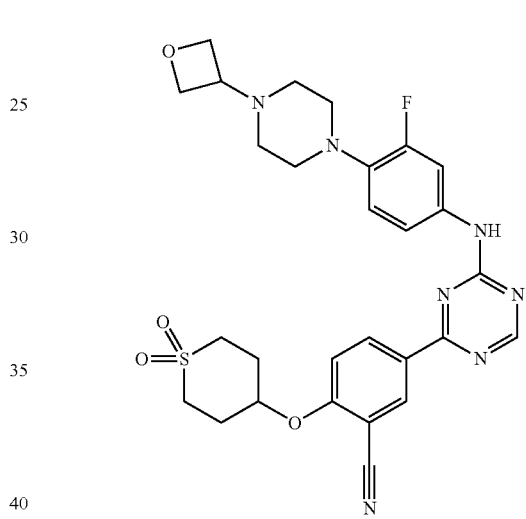

A mixture of 4-chloro-N-(3-fluoro-4-(4-(oxetan-3-yl)piperazin-1-yl)phenyl)-1,3,5-triazin-2-amine (0.10 g, 0.27 mmol), crude 2-((1,1-dioxidotetrahydro-2H-thiopyran-4-yl)oxy)-5-(4,4,5,5-tetramethyl-1,3,2-dioxaborolan-2-yl)benzonitrile (0.53 mmol assumed), and tetrakis(triphenylphosphine)palladium(0) (0.024 g, 7.5 mol %) in 1,2-dimethoxyethane (DME, 6 mL) was treated with 2M aqueous sodium carbonate solution (0.62 mL). The mixture was irradiated for 1 hour in a microwave reactor at 130° C. The crude mixture was purified by flash chromatography on silica gel to provide 2-((1,1-dioxidotetrahydro-2H-thiopyran-4-yl)oxy)-5-(4-((3-fluoro-4-(4-(oxetan-3-yl)piperazin-1-yl)phenyl)amino)-1,3,5-triazin-2-yl)benzonitrile.

LCMS-ESI$^+$ (m/z): [M+H]$^+$ calcd for $C_{28}H_{31}FN_7O_4S$: 580.2; found: 580.3 $^1$H NMR (400 MHz, DMSO-d$_6$) δ 10.40 (bs, 1H), 8.85 (s, 1H), 8.63 (m, 2H), 7.72 (dd, J=15.0, 2.4 Hz, 1H), 7.62 (m, 1H), 7.48 (bs, 1H), 7.09 (t, J=9.4 Hz, 1H), 5.12 (p, J=4.7 Hz, 1H), 4.60 (t, J=6.5 Hz, 2H), 4.51 (t, J=6.0 Hz, 2H), 3.51 (p, J=6.2 Hz, 1H), 3.27 (m, 4H), 3.06 (m, 4H), 2.47 (m, 4H), 2.36 (m, 4H).

Example 269

2-(3-methoxyazetidin-1-yl)-5-(4-((4-(4-(oxetan-3-yl)piperazin-1-yl)phenyl)amino)-1,3,5-triazin-2-yl)benzonitrile

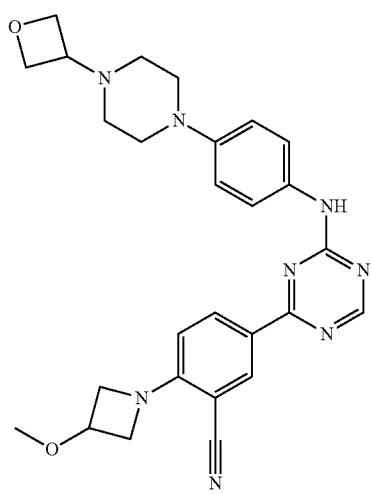 [SMILES: COC1CN(c2ccc(-c3ncnc(Nc4ccc(N5CCN(C6COC6)CC5)cc4)n3)cc2C#N)C1]

Step 1: Preparation of 2-(3-methoxyazetidin-1-yl)-5-(4,4,5,5-tetramethyl-1,3,2-dioxaborolan-2-yl)benzonitrile:

2-Fluoro-5-(4,4,5,5-tetramethyl[1,3,2]dioxaborolan-2-yl)benzonitrile (Combi-Blocks, 2.0 g, 8.1 mmol), potassium carbonate (2.2 g 16 mmol), and 3-methoxyazetidine hydrochloride (Chem-Impex, 1.0 g, 8.1 mmol) were taken up as a suspension in N,N-dimethylacetamide (20 mL) and heated on at 120° C. overnight. After the mixture had cooled to room temperature, it was filtered, and the filtrate was concentrated under reduced pressure. The residue was purified by flash chromatography on silica gel to provide 2-(3-methoxyazetidin-1-yl)-5-(4,4,5,5-tetramethyl-1,3,2-dioxaborolan-2-yl)benzonitrile.

LCMS-ESI$^+$ (m/z): [M+H]$^+$ calcd for $C_{17}H_{24}BN_2O_3$: 315.2; found: 315.1

Step 2: Preparation of 2-(3-methoxyazetidin-1-yl)-5-(4-((4-(4-(oxetan-3-yl)piperazin-1-yl)phenyl)amino)-1,3,5-triazin-2-yl)benzonitrile:

A mixture of 4-chloro-N-(4-(4-(oxetan-3-yl)piperazin-1-yl)phenyl)-1,3,5-triazin-2-amine (0.12 g, 0.35 mmol), 2-(3-methoxyazetidin-1-yl)-5-(4,4,5,5-tetramethyl-1,3,2-dioxaborolan-2-yl)benzonitrile (0.14 g, 0.43 mmol), and tetrakis(triphenylphosphine)palladium(0) (0.030 g, 7.5 mol %) in 1,2-dimethoxyethane (DME, 2.5 mL) was treated with 2M aqueous sodium carbonate solution (0.80 mL). The mixture was irradiated for 1 hour in a microwave reactor at 130° C. The crude mixture was purified by flash chromatography on silica gel, followed by precipitation with isopropanol, to provide 2-(3-methoxyazetidin-1-yl)-5-(4-((4-(4-(oxetan-3-yl)piperazin-1-yl)phenyl)amino)-1,3,5-triazin-2-yl)benzonitrile. LCMS-ESI$^+$ (m/z): [M+H]$^+$ calcd for $C_{27}H_{31}N_8O_2$: 499.3; found: 499.3 $^1$H NMR (400 MHz, DMSO-d$_6$) δ 10.02 (d, J=17.7 Hz, 1H), 8.79-8.63 (m, 1H), 8.53-8.30 (m, 2H), 7.61 (m, 2H), 6.99 (m, 2H), 6.73 (d, J=9.0 Hz, 1H), 4.61 (t, J=6.5 Hz, 2H), 4.52 (m, 4H), 4.39 (m, 1H), 4.10 (m, 2H), 3.50 (m, 1H), 3.32 (s, 3H), 3.17 (m, 4H), 2.45 (m, 4H).

Example 270

2-((1,1-dioxidotetrahydro-2H-thiopyran-4-yl)oxy)-5-(4-((4-(1-(oxetan-3-yl)piperidin-4-yl)phenyl)amino)-1,3,5-triazin-2-yl)benzonitrile

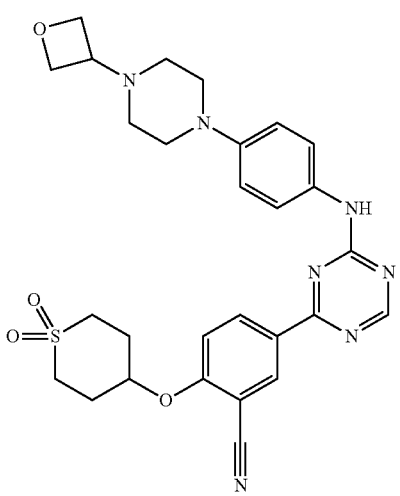

A mixture of 4-chloro-N-(4-(4-(oxetan-3-yl)piperazin-1-yl)phenyl)-1,3,5-triazin-2-amine (0.10 g, 0.29 mmol), crude 2-((1,1-dioxidotetrahydro-2H-thiopyran-4-yl)oxy)-5-(4,4,5,5-tetramethyl-1,3,2-dioxaborolan-2-yl)benzonitrile (assumed 0.61 mmol), and tetrakis(triphenylphosphine)palladium(0) (0.025 g, 7.5 mol %) in 1,2-dimethoxyethane (DME, 4 mL) was treated with 2M aqueous sodium carbonate solution (0.66 mL). The mixture was irradiated for 1 hour in a microwave reactor at 130° C. The crude mixture was purified by flash chromatography on silica gel, followed by precipitation with isopropanol, to provide (0.12 g, 0.35 mmol), 2-(3-methoxyazetidin-1-yl)-5-(4,4,5,5-tetramethyl-1,3,2-dioxaborolan-2-yl)benzonitrile. (0.14 g, 0.43 mmol), and tetrakis(triphenylphosphine)pailadium(0) (0.030 g, 7.5 mol %) in 1,2-dimethoxyethane (DME, 2.5 mL) was treated with 2M aqueous sodium carbonate solution (0.80 mL). The mixture was irradiated for 1 hour in a microwave reactor at 130° C. The crude mixture was purified by flash chromatography on silica gel, followed by precipitation with isopropanol, to provide 2-((1,1-dioxidotetrahydro-2H-thiopyran-4-yl)oxy)-5-(4-((4-(1-(oxetan-3-yl)piperidin-4-yl)phenyl)amino)-1,3,5-triazin-2-yl)benzonitrile. LCMS-ESI $^+$(m/z): [M+H]$^+$ calcd for $C_{29}H_{33}N_6O_4S$: 561.2; found: 561.4 $^1$H NMR (400 MHz, DMSO-d$_6$) δ 10.33 (bs, 1H), 8.84 (s, 1H), 8.64 (dd, J=8.8, 1.8 Hz, 2H), 7.70 (m, 2H), 7.62 (d, J=9.4 Hz, 1H), 7.30 (d, J=8.0 Hz, 2H), 5.12 (p, J=4.9 Hz, 1H), 4.59 (t, J=6.5 Hz, 2H), 4.49 (t, J=6.1 Hz, 2H), 3.44 (p, J=6.4 Hz, 1H), 3.34-3.18 (m, 4H), 2.84 (d, J=11.3 Hz, 2H), 2.37 (m, 4H), 1.96-1.85 (m, 2H), 1.80 (m, 2H), 1.72 (m, 2H).

Example 271

2-((1,1-dioxidotetrahydro-2H-thiopyran-4-yl)oxy)-3-fluoro-5-(4-((4-(4-(oxetan-3-yl)piperazin-1-yl)phenyl)amino)-1,3,5-triazin-2-yl)benzonitrile

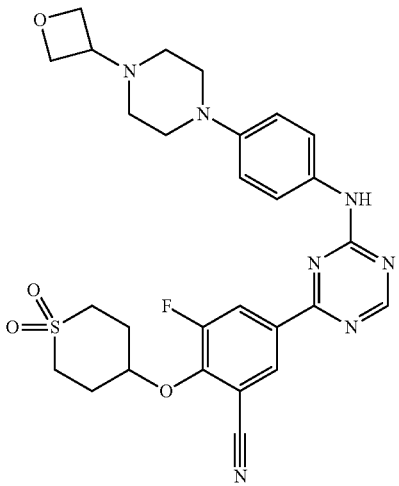 [SMILES: N#Cc1cc(-c2ncnc(Nc3ccc(N4CCN(C5COC5)CC4)cc3)n2)cc(F)c1OC1CCS(=O)(=O)CC1]

Step 1: Preparation of 5-bromo-3-fluoro-2-hydroxybenzonitrile:

N-Bromosuccinimide (3.9 g, 22 mmol) was added in a single portion to a stirred solution of 3-fluoro-2-hydroxybenzonitrile (Matrix Scientific, 3.0 g, 22 mmol) in acetonitrile (100 mL). The mixture was stirred for one hour at room temperature, then concentrated to dryness under reduced pressure. The residue was taken up in saturated aqueous sodium carbonate solution (approximately 100 mL) and extracted twice with diethyl ether. The aqueous phase was acidified to pH 2 with concentrated hydrochloric acid, then extracted three times with diethyl ether. These combined extracts were washed once with saturated aqueous sodium chloride solution, dried over anhydrous magnesium sulfate, filtered, concentrated to dryness under reduced pressure to provide 5-bromo-3-fluoro-2-hydroxybenzonitrile. LCMS-ESI$^+$ (m/z): [M+H$_2$O+H]$^+$ calcd for C$_7$H$_6$BrNO$_2$: 234.0; found: 233.9

Step 2: Preparation of 5-bromo-3-fluoro-2-((tetrahydro-2H-thiopyran-4-yl)oxy)benzonitrile:

5-bromo-3-fluoro-2-hydroxybenzonitrile (1.2 g, 5.6 mmol), tetrahydrothiopyran-4-ol (0.79 g, 6.7 mmol), and 1,1'-(azodicarbonyl)dipiperidine (ADDP, 2.8 g, 11 mmol)) were taken up in anhydrous toluene. The stirred mixture was cooled in an ice-water bath while tributylphosphine (4.1 g, 5.0 mL, 20 mmol) was added via syringe. The mixture was stirred in the ice-water bath for 10 minutes after the addition. The bath was then removed. After stirring at room temperature for 2 hours, mixture was heated for 4 hours at 120° C. and was left to stir overnight at room temperature. The mixture was concentrated to under reduced pressure and purified by flash chromatography on silica gel to provide 5-bromo-3-fluoro-2-((tetrahydro-2H-thiopyran-4-yl)oxy) benzonitrile. LCMS-ESI$^+$ (m/z): [M+H]$^+$ calcd for C$_{12}$H$_{12}$BrFNOS: 316.0; found: 316.0

Step 3: Preparation of 5-bromo-2-((1,1-dioxidotetrahydro-2H-thiopyran-4-yl)oxy)-3-fluorobenzonitrile:

A solution of 5-bromo-3-fluoro-2-((tetrahydro-2H-thiopyran-4-yl)oxy)benzonitrile (1.4 g, 4.3 mmol) in dichloromethane was treated with calcium carbonate (1.7 g, 17 mmol). The resulting suspension was cooled in an ice-water bath. 3-chloroperbenzoic acid (≤77%, 2.4 g, 11 mmol) was added in a single portion, and the mixture was allowed to stir overnight, gradually regaining room temperature. The suspension was filtered, and the filtrate was washed twice each with aqueous solutions of 5% sodium bisulfite and saturated sodium hydrogen carbonate. The organics were dried over anhydrous magnesium sulfate, filtered, concentrated under reduced pressure to provide 5-bromo-2-((1,1-dioxidotetrahydro-2H-thiopyran-4-yl)oxy)-3-fluorobenzonitrile. LCMS-ESI$^+$ (m/z): [M+H]$^+$ calcd for C$_{12}$H$_{12}$BrFNO$_3$S: 348.0; found: 347.9

Step 4: Preparation of (3-cyano-4-((1,1-dioxidotetrahydro-2H-thiopyran-4-yl)oxy)-5-fluorophenyl)boronic acid A mixture of 5-bromo-2-((1,1-dioxidotetrahydro-2H-thiopyran-4-yl)oxy)-3-fluorobenzonitrile (0.18 g, 0.52 mmol), bis(pinacolato)diboron (0.26 g, 1.0 mmol), potassium acetate (0.15 g, 1.6 mmol), and [1,1'-bis(diphenylphosphino)ferrocene]dichloropalladium(II) complex with dichloromethane (39 mg, 10 mol %) in 1,4-dioxane (6 mL) was heated overnight at 90° C. The reaction mixture was filtered through a pad of Celite diatomaceous earth, and the filtrate was concentrated to dryness under reduced pressure. The crude (3-cyano-4-((1,1-dioxidotetrahydro-2H-thiopyran-4-yl)oxy)-5-fluorophenyl)boronic acid was carried forward without further purification. LCMS-ESI$^+$ (m/z): [M+H]$^+$ calcd for C$_{12}$H$_{14}$BFNO$_5$S: 314.1; found: 314.0

Step 5: Preparation of 2-((1,1-dioxidotetrahydro-2H-thiopyran-4-yl)oxy)-3-fluoro-5-(4-((4-(4-(oxetan-3-yl)piperazin-1-yl)phenyl)amino)-1,3,5-triazin-2-yl)benzonitrile A mixture of 4-chloro-N-(4-(4-(oxetan-3-yl)piperazin-1-yl)phenyl)-1,3,5-triazin-2-amine (0.12 g, 0.35 mmol), crude (3-cyano-4-((1,1-dioxidotetrahydro-2H-thiopyran-4-yl)oxy)-5-fluorophenyl)boronic acid (assumed 0.52 mmol), and tetrakis(triphenylphosphine)palladium(0) (0.030 g, 7.5 mol %) in 1,2-dimethoxyethane (DME, 8 mL) was treated with 2M aqueous sodium carbonate solution (2.0 mL). The mixture was irradiated for 1 hour in a microwave reactor at 130° C. The crude mixture was purified by flash chromatography on silica gel to provide 2-((1,1-dioxidotetrahydro-2H-thiopyran-4-yl)oxy)-3-fluoro-5-(4-((4-(4-(oxetan-3-yl)piperazin-1-yl)phenyl)amino)-1,3,5-triazin-2-yl)benzonitrile. LCMS-ESI$^+$ (m/z): [M+H]$^+$ calcd for C$_{28}$H$_{31}$FN$_7$O$_4$S: 580.2; found: 580.3

$^1$H NMR (400 MHz, DMSO-d$_6$) δ 10.27 (d, J=28.9 Hz, 1H), 8.82 (s, 1H), 8.60-8.33 (m, 2H), 7.60 (m, 2H), 7.01 (dd, J=16.0, 8.4 Hz, 2H), 4.94 (m, 1H), 4.61 (t, J=6.5 Hz, 2H), 4.52 (t, J=6.0 Hz, 2H), 3.49 (p, J=6.5 Hz, 1H), 3.31 (m, 4H), 3.19 (m, 4H), 2.45 (m, 4H), 2.38 (m, 4H).

Example 272

2-(3-(methylsulfonyl)azetidin-1-yl)-5-(4-((4-(4-(oxetan-3-yl)piperazin-1-yl)phenyl)amino)-1,3,5-triazin-2-yl)benzonitrile

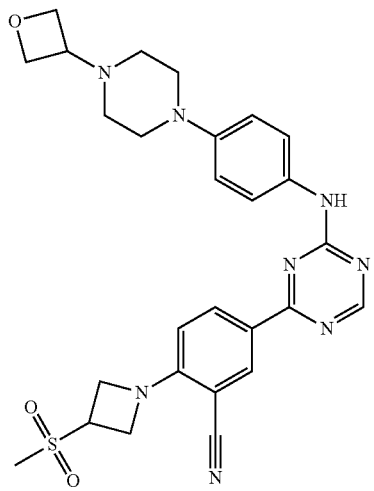 [SMILES: CS(=O)(=O)C1CN(c2ccc(-c3ncnc(Nc4ccc(N5CCN(C6COC6)CC5)cc4)n3)cc2C#N)C1]

Step 1: Preparation of 2-(3-(methylsulfonyl)azetidin-1-yl)-5-(4,4,5,5-tetramethyl-1,3,2-dioxaborolan-2-yl)benzonitrile 2-Fluoro-5-(4,4,5,5-tetramethyl[1,3,2]dioxaborolan-2-yl)benzonitrile (1.4 g, 5.8 mmol), potassium carbonate (1.6 g 12 mmol), and 3-methylsulfonylazetidine hydrochloride (Synnovator, 1.0 g, 5.8 mmol) were taken up as a suspension in N,N-dimethylacetamide (14 mL) and heated on at 120° C. overnight. After the mixture had cooled to room temperature it was filtered, and the filtrate was concentrated under reduced pressure. The residue was purified by flash chromatography on silica gel to provide 2-(3-(methylsulfonyl)azetidin-1-yl)-5-(4,4,5,5-tetramethyl-1,3,2-dioxaborolan-2-yl)benzonitrile. LCMS-ESI⁺ (m/z): [M+H]⁺ calcd for $C_{17}H_{24}BN_2O_4S$: 363.2; found: 363.1

Step 2: Preparation of 2-(3-(methylsulfonyl)azetidin-1-yl)-5-(4-((4-(4-(oxetan-3-yl)piperazin-1-yl)phenyl)amino)-1,3,5-triazin-2-yl)benzonitrile A mixture of 4-chloro-N-(4-(4-(oxetan-3-yl)piperazin-1-yl)phenyl)-1,3,5-triazin-2-amine (0.12 g, 0.35 mmol), 2-(3-(methylsulfonyl)azetidin-1-yl)-5-(4,4,5,5-tetramethyl-1,3,2-dioxaborolan-2-yl)benzonitrile (0.16 g, 0.43 mmol), and tetrakis(triphenylphosphine)palladium(0) (0.030 g, 7.5 mol %) in 1,2-dimethoxyethane (DME, 3 mL) was treated with 2M aqueous sodium carbonate solution (0.78 mL). The mixture was irradiated for 1 hour in a microwave reactor at 130° C. The crude mixture was purified by flash chromatography on silica gel, followed by precipitation with isopropanol, to provide 2-(3-(methylsulfonyl)azetidin-1-yl)-5-(4-((4-(4-(oxetan-3-yl)piperazin-1-yl)phenyl)amino)-1,3,5-triazin-2-yl)benzonitrile. LCMS-ESI⁺ (m/z): [M+H]⁺ calcd for $C_{27}H_{31}N_8O_3S$: 547.2; found: 547.3

Example 273

2-((1-(methylsulfonyl)azetidin-3-yl)oxy)-5-(4-((4-(4-(oxetan-3-yl)piperazin-1-yl)phenyl)amino)-1,3,5-triazin-2-yl)benzonitrile

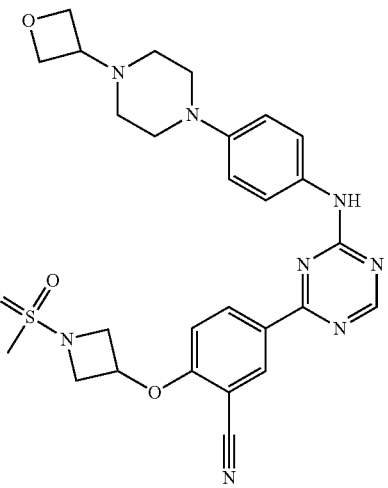

Step 1: Preparation of tert-butyl 3-(4-bromo-2-cyanophenoxy)azetidine-1-carboxylate Sodium hydride (60% dispersion in mineral oil, 0.69 g, 17 mmol) was added in a single portion to a solution of tert-butyl 3-hydroxyazetidine-1-carboxylate (Sigma Aldrich, 3.0 g, 17 mmol) in N,N-dimethylformamide (30 mL) at room temperature. Stirring was continued for about 30 minutes at room temperature before the addition of 5-bromo-2-fluorobenzonitrile 3.3 g, 17 mmol) in a single portion. The mixture was stirred overnight at 50° C. The reaction was quenched by the addition of water and ice. The resulting off-white solid was collected by Büchner filtration, washed with isopropanol, and dried over phosphorus pentoxide to provide tert-butyl 3-(4-bromo-2-cyanophenoxy)azetidine-1-carboxylate. LCMS-ESI⁺ (m/z): [M−isobutylene+H]⁺ calcd for $C_{11}H_{10}BrN_2O_3$: 297.0; found: 296.9

Step 2: Preparation of tert-butyl 3-(2-cyano-4-(4,4,5,5-tetramethyl-1,3,2-dioxaborolan-2-yl)phenoxy)azetidine-1-carboxylate A mixture of tert-butyl 3-(4-bromo-2-cyanophenoxy)azetidine-1-carboxylate (0.50 g, 1.4 mmol), bis(pinacolato)diboron (0.72 g, 2.8 mmol), potassium acetate (0.42 g, 4.2 mmol), and [1,1'-bis(diphenylphosphino)ferrocene]dichloropalladium(II) complex with dichloromethane (110 mg, 10 mol %) in 1,4-dioxane (10 mL) was heated overnight at 90° C. The reaction mixture was filtered through a pad of Celite diatomaceous earth, and the filtrate was concentrated to dryness under reduced pressure. The crude tert-butyl 3-(2-cyano-4-(4,4,5,5-tetramethyl-1,3,2-dioxaborolan-2-yl)phenoxy)azetidine-1-carboxylate was carried forward without further purification. LCMS-ESI⁺ (m/z): [M−isobutylene+H]⁺ calcd for $C_{17}H_{22}BN_2O_5$: 345.2; found: 345.0

Step 3: Preparation of tert-butyl 3-(2-cyano-4-(4-((4-(4-(oxetan-3-yl)piperazin-1-yl)phenyl)amino)-1,3,5-triazin-2-yl)phenoxy)azetidine-1-carboxylate A mixture of 4-chloro-N-(4-(4-(oxetan-3-yl)piperazin-1-yl)phenyl)-1,3,5-triazin-2-amine (0.33 g, 0.94 mmol), crude tert-butyl 3-(2-cyano-4-(4,4,5,5-tetramethyl-1,3,2-dioxaborolan-2-yl)phenoxy)azetidine-1-carboxylate (assumed 1.4 mmol), and tetrakis(triphenylphosphine)palladium(0) (0.081 g, 7.5 mol %) in 1,2-dimethoxyethane (DME, 8 mL)

was treated with 2M aqueous sodium carbonate solution (2.1 mL). The mixture was irradiated for 1 hour in a microwave reactor at 130° C. The crude biphasic mixture was filtered through a short pad of Celite diatomaceous earth, eluting with ethyl acetate and water. The aqueous phase was extracted three times with ethyl acetate. The combined extracts were washed once with saturated aqueous sodium chloride solution, dried over anhydrous magnesium sulfate, filtered, concentrated to dryness under reduced pressure to provide the crude tert-butyl 3-(2-cyano-4-(4-((4-(4-(oxetan-3-yl)piperazin-1-yl)phenyl)amino)-1,3,5-triazin-2-yl)phenoxy)azetidine-1-carboxylate, which was carried on without further purification. LCMS-ESI$^+$ (m/z): [M+H]$^+$ calcd for $C_{31}H_{37}N_8O_4$: 585.3; found: 585.2

Step 4: Preparation of 2-(azetidin-3-yloxy)-5-(4-((4-(4-(oxetan-3-yl)piperazin-1-yl)phenyl)amino)-1,3,5-triazin-2-yl)benzonitrile Crude tert-butyl 3-(2-cyano-4-(4-((4-(4-(oxetan-3-yl)piperazin-1-yl)phenyl)amino)-1,3,5-triazin-2-yl)phenoxy)azetidine-1-carboxylate was taken up in dichloromethane (10 mL) and treated with trifluoroacetic acid (2 mL). The mixture was concentrated under reduced pressure and purified by flash chromatography on silica gel to provide 2-(azetidin-3-yloxy)-5-(4-((4-(4-(oxetan-3-yl)piperazin-1-yl)phenyl)amino)-1,3,5-triazin-2-yl)benzonitrile. LCMS-ESI$^+$ (m/z): [M+H]$^+$ calcd for $C_{26}H_{29}N_8O_2$: 485.2; found: 485.3

Step 5: Preparation of 2-((1-(methylsulfonyl)azetidin-3-yl)oxy)-5-(4-((4-(4-(oxetan-3-yl)piperazin-1-yl)phenyl)amino)-1,3,5-triazin-2-yl)benzonitrile A solution of 2-(azetidin-3-yloxy)-5-(4-((4-(4-(oxetan-3-yl)piperazin-1-yl)phenyl)amino)-1,3,5-triazin-2-yl)benzonitrile (56 mg, 0.12 mmol) in N,N-dimethylformamide (2 mL) was treated successively with N,N-diisopropylethylamine (50 µL, 0.29 mmol) and methanesulfonyl chloride 18 µL, 0.23 mmol). The mixture was refrigerated overnight, then concentrated under reduced pressure. The residue was purified by flash chromatography on silica gel to provide 2-((1-(methylsulfonyl)azetidin-3-yl)oxy)-5-(4-((4-(4-(oxetan-3-yl)piperazin-1-yl)phenyl)amino)-1,3,5-triazin-2-yl)benzonitrile. LCMS-ESI$^+$ (m/z): [M+H]$^+$ calcd for $C_{27}H_{31}N_8O_4S$: 563.2; found: 563.3

Example 274

2-((1-(2-hydroxyacetyl)azetidin-3-yl)oxy)-5-(4-((4-(4-(oxetan-3-yl)piperazin-1-yl)phenyl)amino)-1,3,5-triazin-2-yl)benzonitrile

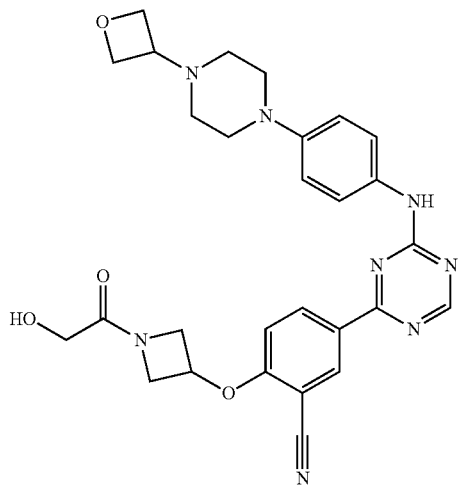 [SMILES: N#Cc1cc(-c2ncnc(Nc3ccc(N4CCN(C5COC5)CC4)cc3)n2)ccc1OC1CN(C(=O)CO)C1]

A mixture of 2-(azetidin-3-yloxy)-5-(4-((4-(4-(oxetan-3-yl)piperazin-1-yl)phenyl)amino)-1,3,5-triazin-2-yl)benzonitrile (56 mg, 0.12 mmol) and glycolic acid (13 mg, 0.17 mmol) in N,N-dimethylformamide (2 mL) was treated successively with N,N-diisopropylethylamine (50 µL, 0.29 mmol) and N-[(dimethylamino)-1H-1,2,3-triazolo-[4,5-b]pyridin-1-ylmethylene]-N-methylmethanaminiumhexafluorophosphate N-oxide (HATU, 66 mg, 0.17 mmol). After standing overnight at room temperature, the mixture was purified by flash chromatography on silica gel to provide 2-((1-(2-hydroxyacetyl)azetidin-3-yl)oxy)-5-(4-((4-(4-(oxetan-3-yl)piperazin-1-yl)phenyl)amino)-1,3,5-triazin-2-yl)benzonitrile. LCMS-ESI$^+$ (m/z): [M+H]$^+$ calcd for $C_{28}H_{31}N_8O_4$: 543.2; found: 543.4

Example 275

5-(4-((2,2-difluorobenzo[d][1,3]dioxol-5-yl)amino)-1,3,5-triazin-2-yl)-2-((tetrahydro-2H-pyran-4-yl)oxy)benzonitrile

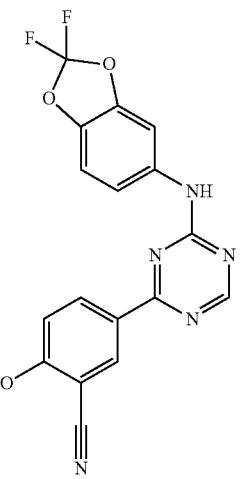

A suspension of 5-(4-chloro-1,3,5-triazin-2-yl)-2-((tetrahydro-2H-pyran-4-yl)oxy)benzonitrile (93 mg, 0.29 mmol) and 5-amino-2,2-difluorobenzodioxole (Combi-Blocks, 61 mg, 0.35 mmol) in acetonitrile (3 mL) was treated with N,N-diisopropylethylamine (0.15 mL, 0.88 mmol). The mixture was heated in a microwave reactor for 30 minutes at 90° C. The precipitated solid was collected by filtration, washed with acetonitrile, and dried under vacuum to provide 5-(4-((2,2-difluorobenzo[d][1,3]dioxol-5-yl)amino)-1,3,5-triazin-2-yl)-2-((tetrahydro-2H-pyran-4-yl)oxy)benzonitrile. LCMS-ESI$^+$ (m/z): [M+H]$^+$ calcd for $C_{22}H_{18}F_2N_5O_4$: 454.1; found: 454.1

Example 276

1-(2-cyano-4-(4-((4-(4-(oxetan-3-yl)piperazin-1-yl)phenyl)amino)-1,3,5-triazin-2-yl)phenyl)azetidin-3-yl methanesulfonate

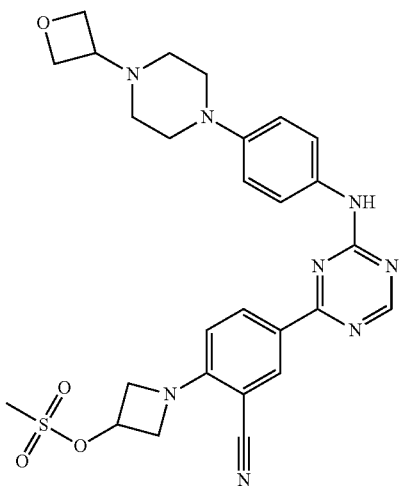 [SMILES: CS(=O)(=O)OC1CN(c2ccc(-c3ncnc(Nc4ccc(N5CCN(C6COC6)CC5)cc4)n3)cc2C#N)C1]

Step 1: Preparation of 2-(3-hydroxyazetidin-1-yl)-5-(4,4,5,5-tetramethyl-1,3,2-dioxaborolan-2-yl)benzonitrile 2-Fluoro-5-(4,4,5,5-tetramethyl[1,3,2]dioxaborolan-2-yl)benzonitrile (2.0 g, 8.1 mmol), potassium carbonate (2.2 g 16 mmol), and 3-hydroxyazetidine hydrochloride (0.89 g, 8.1 mmol) were taken up as a suspension in N,N-dimethylacetamide (20 mL) and heated on at 120° C. overnight. After the mixture had cooled to room temperature it was filtered, and the filtrate was concentrated under reduced pressure. The residue was purified by flash chromatography on silica gel to provide 2-(3-hydroxyazetidin-1-yl)-5-(4,4,5,5-tetramethyl-1,3,2-dioxaborolan-2-yl)benzonitrile. LCMS-ESI$^+$ (m/z): [M+H]$^+$ calcd for $C_{16}H_{22}BN_2O_3$: 301.2; found: 301.1

Step 2: Preparation of 2-(3-hydroxyazetidin-1-yl)-5-(4-((4-(4-(oxetan-3-yl)piperazin-1-yl)phenyl)amino)-1,3,5-triazin-2-yl)benzonitrile A mixture of 4-chloro-N-(4-(4-(oxetan-3-yl)piperazin-1-yl)phenyl)-1,3,5-triazin-2-amine (0.24 g, 0.69 mmol), 2-(3-hydroxyazetidin-1-yl)-5-(4,4,5,5-tetramethyl-1,3,2-dioxaborolan-2-yl)benzonitrile (0.23 g, 0.76 mmol), and [1,1'-bis(diphenylphosphino)ferrocene]dichloropalladium(II) (0.051 g, 10 mol %) in 1,2-dimethoxyethane (DME, 8 mL) was treated with 2 M aqueous sodium carbonate solution (1.6 mL). The mixture was purified by flash chromatography on silica gel to provide 2-(3-hydroxyazetidin-1-yl)-5-(4-((4-(4-(oxetan-3-yl)piperazin-1-yl)phenyl)amino)-1,3,5-triazin-2-yl)benzonitrile. LCMS-ESI$^+$ (m/z): [M+H]$^+$ calcd for $C_{26}H_{29}N_8O_2$: 485.2; found: 485.3

Step 3: Preparation of 1-(2-cyano-4-(4-((4-(4-(oxetan-3-yl)piperazin-1-yl)phenyl)amino)-1,3,5-triazin-2-yl)phenyl)azetidin-3-yl methanesulfonate 2-(3-hydroxyazetidin-1-yl)-5-(4-((4-(4-(oxetan-3-yl)piperazin-1-yl)phenyl)amino)-1,3,5-triazin-2-yl)benzonitrile (60 mg, 0.12 mmol) was taken up as a suspension in dichloromethane. The suspension was treated with N,N-diisopropylethylamine (25 µL, 0.15 mmol) and cooled in an ice-water bath. Methanesulfonyl chloride (11 µL, 0.14 mmol) was added and the mixture was allowed to regain room temperature. After 5 minutes of stirring at room temperature, the mixture cooled in an ice-water bath and treated with the original stoichiometries of N,N-diisopropylethylamine and methanesulfonyl chloride. After one hour of stirring at room temperature, the mixture was purified by flash chromatography on silica gel to provide 1-(2-cyano-4-(4-((4-(4-(oxetan-3-yl)piperazin-1-yl)phenyl)amino)-1,3,5-triazin-2-yl)phenyl)azetidin-3-yl methanesulfonate. LCMS-ESI$^+$ (m/z): [M+H]$^+$ calcd for $C_{27}H_{31}N_8O_4S$: 563.2; found: 563.3 $^1$H NMR (400 MHz, DMSO-d$_6$) δ 10.04 (d, J=18.6 Hz, 1H), 8.71 (s, 1H), 8.54-8.32 (m, 2H), 7.61 (m, 2H), 7.00 (m, 2H), 6.81 (d, J=9.0 Hz, 1H), 5.50 (m, 1H), 4.79-4.67 (m, 2H), 4.61 (t, J=6.5 Hz, 2H), 4.52 (t, J=6.0 Hz, 2H), 4.43-4.37 (m, 2H), 3.57-3.44 (m, 1H), 3.36 (s, 3H), 3.18 (m, 4H), 2.45 (m, 4H).

Example 277

5-(4-((2-oxo-2,3-dihydrobenzo[d]oxazol-5-yl)amino)-1,3,5-triazin-2-yl)-2-((tetrahydro-2H-pyran-4-yl)oxy)benzonitrile

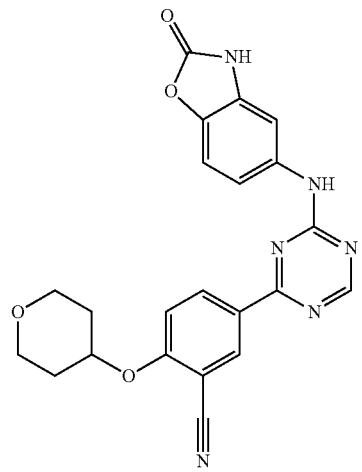 [SMILES: N#Cc1cc(-c2ncnc(Nc3ccc4oc(=O)[nH]c4c3)n2)ccc1OC1CCOCC1]

A suspension of 5-(4-chloro-1,3,5-triazin-2-yl)-2-((tetrahydro-2H-pyran-4-yl)oxy)benzonitrile (93 mg, 0.29 mmol) and 5-amino-1,3-benzoxazol-2(3H)-one (Enamine, 53 mg, 0.35 mmol) in acetonitrile (3 mL) was treated with N,N-diisopropylethylamine (0.15 mL, 0.88 mmol). The mixture was heated in a microwave reactor for 20 minutes at 80° C. The mixture was purified by flash chromatography on silica gel to provide 5-(4-((2-oxo-2,3-dihydrobenzo[d]oxazol-5-yl)amino)-1,3,5-triazin-2-yl)-2-((tetrahydro-2H-pyran-4-yl)oxy)benzonitrile.

LCMS-ESI$^+$ (m/z): [M+H]$^+$ calcd for $C_{22}H_{19}N_6O_4$: 431.1; found: 431.1

$^1$H NMR (400 MHz, DMSO-d$_6$) δ 11.70 (s, 1H), 10.41 (s, 1H), 8.86 (s, 1H), 8.62 (m, 2H), 7.69 (bs, 1H), 7.59 (m, 1H), 7.41 (bs, 1H), 7.31 (m, 1H), 4.99 (m, 1H), 3.92 (m, 2H), 3.60 (ddd, J=11.6, 8.5, 3.1 Hz, 2H), 2.09 (m, 2H), 1.74 (m, 2H).

Example 278

5-(4-((3,3-dimethyl-2-oxoindolin-5-yl)amino)-1,3,5-triazin-2-yl)-2-((tetrahydro-2H-pyran-4-yl)oxy)benzonitrile

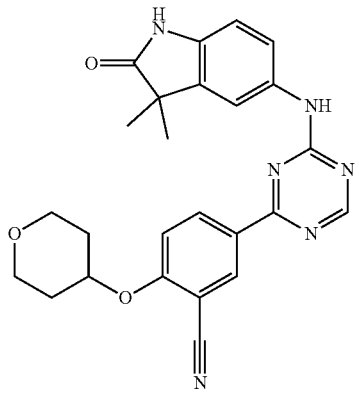 [SMILES: CC1(C)C(=O)Nc2ccc(Nc3ncnc(-c4ccc(OC5CCOCC5)c(C#N)c4)n3)cc21]

A suspension of 5-(4-chloro-1,3,5-triazin-2-yl)-2-((tetrahydro-2H-pyran-4-yl)oxy)benzonitrile (93 mg, 0.29 mmol) and 5-amino-3,3dimethylindolin-2-one (Princeton BioMolecular Research, 62 mg, 0.35 mmol) in acetonitrile (3 mL) was treated with N,N-diisopropylethylamine (0.15 mL, 0.88 mmol). The mixture was heated in a microwave reactor for 20 minutes at 80° C. The mixture was purified by flash chromatography on silica gel to provide 5-(4-((3,3-dimethyl-2-oxoindolin-5-yl)amino)-1,3,5-triazin-2-yl)-2-((tetrahydro-2H-pyran-4-yl)oxy)benzonitrile. LCMS-ESI$^+$ (m/z): [M+H]$^+$ calcd for $C_{25}H_{25}N_6O_3$: 457.2; found: 457.2 $^1$H NMR (400 MHz, DMSO-d$_6$) δ 10.37 (s, 1H), 10.26 (m, 1H), 8.79 (s, 1H), 8.57 (m, 2H), 7.85 (s, 1H), 7.71-7.52 (m, 1H), 7.33 (m, 1H), 6.90 (d, J=8.3 Hz, 1H), 4.99 (m, 1H), 3.90 (m, 2H), 3.59 (ddd, J=11.7, 8.5, 3.2 Hz, 2H), 2.09 (m, 2H), 1.73 (m, 2H), 1.33 (m, 6H).

Example 279

2-(1,4-dioxaspiro[4.5]decan-8-yloxy)-5-(4-((4-(4-(oxetan-3-yl)piperazin-1-yl)phenyl)amino)-1,3,5-triazin-2-yl)benzonitrile

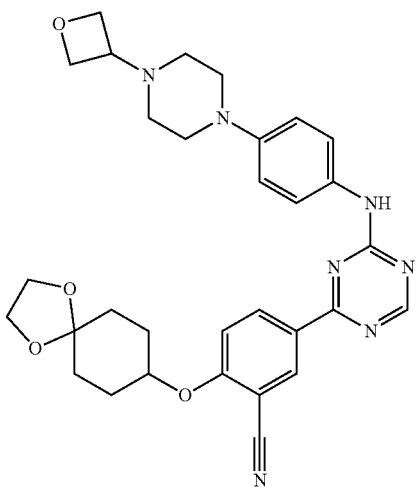 [SMILES: N#Cc1cc(-c2ncnc(Nc3ccc(N4CCN(C5COC5)CC4)cc3)n2)ccc1OC1CCC2(CC1)OCCO2]

Potassium tert-butoxide (0.12 g, 1.0 mmol) was added to a solution of 4-hydroxycyclohexanone ethylene ketal (0.16 g, 1.0 mmol) in 2-methyltetrahydrofuran (5 mL). The resulting suspension was stirred at room temperature for 30 minutes before the addition of 2-fluoro-5-(4-((4-(4-(oxetan-3-yl)piperazin-1-yl)phenyl)amino)-1,3,5-triazin-2-yl)benzonitrile (0.15 g, 0.35 mmol). The mixture was heated at 60° C. overnight, then purified by flash chromatography on silica gel to provide 2-(1,4-dioxaspiro[4.5]decan-8-yloxy)-5-(4-((4-(4-(oxetan-3-yl)piperazin-1-yl)phenyl)amino)-1,3,5-triazin-2-yl)benzonitrile. LCMS-ESI$^+$ (m/z): [M+H]$^+$ calcd for $C_{31}H_{36}N_7O_4$: 570.3; found: 570.4 $^1$H NMR (400 MHz, DMSO-d$_6$) δ 10.15 (d, J=20.9 Hz, 1H), 8.77 (d, J=2.6 Hz, 1H), 8.68-8.52 (m, 2H), 7.74-7.53 (m, 3H), 7.00 (m, 2H), 4.91 (m, 1H), 4.61 (t, J=6.5 Hz, 2H), 4.52 (t, J=6.0 Hz, 2H), 3.94 (m, 4H), 3.49 (p, J=6.2 Hz, 1H), 3.18 (m, 4H), 2.46 (m, 4H), 2.05-1.76 (m, 6H), 1.75-1.59 (m, 2H).

Example 280

2-((3-fluorooxetan-3-yl)methyoxy)-5-(4-((4-(4-(oxetan-3-yl)piperazin-1-yl)phenyl)amino)-1,3,5-triazin-2-yl)benzonitrile

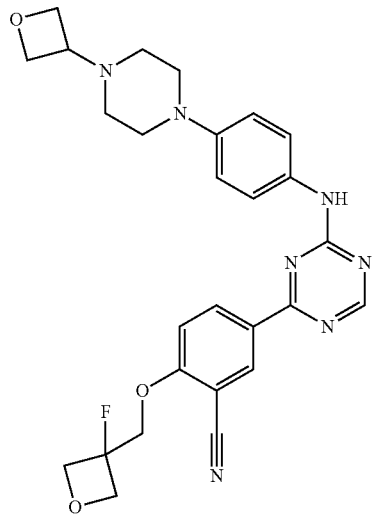 [SMILES: N#Cc1cc(-c2ncnc(Nc3ccc(N4CCN(C5COC5)CC4)cc3)n2)ccc1OCC1(F)COC1]

Potassium tert-butoxide (0.08 g, 0.70 mmol) was added to a solution of 3-fluoro-3-oxetanemethanol (Synnovator, 0.07 g, 0.70 mmol) in 2-methyltetrahydrofuran (5 mL). The resulting suspension was stirred at room temperature for 30 minutes before the addition of 2-fluoro-5-(4-((4-(4-(oxetan-3-yl)piperazin-1-yl)phenyl)amino)-1,3,5-triazin-2-yl)benzonitrile (0.10 g, 0.23 mmol). The mixture was heated at 60° C. overnight and then purified by flash chromatography on silica gel to provide 2-((3-fluorooxetan-3-yl)methoxy)-5-(4-((4-(4-(oxetan-3-yl)piperazin-1-yl)phenyl)amino)-1,3,5-triazin-2-yl)benzonitrile. LCMS-ESI$^+$ (m/z): [M+H]$^+$ calcd for $C_{27}H_{29}FN_7O_3$: 518.2; found: 518.3 $^1$H NMR (400 MHz, DMSO-d$_6$) δ 10.17 (s, 1H), 8.78 (s, 1H), 8.70-8.50 (m, 2H), 7.63-7.54 (m, 3H), 7.01 (m, 2H), 4.88-4.70 (m, 6H), 4.61 (t, J=6.5 Hz, 2H), 4.52 (t, J=6.0 Hz, 2H), 3.49 (m, 1H), 3.18 (m, 4H), 2.45 (m, 4H).

Example 281

(S)-2-((1-(2-hydroxypropanoyl)piperidin-4-yl)oxy)-5-(4-((3-methoxy-4-(4-(oxetan-3-yl)piperazin-1-yl)phenyl)amino)-1,3,5-triazin-2-yl)benzonitrile

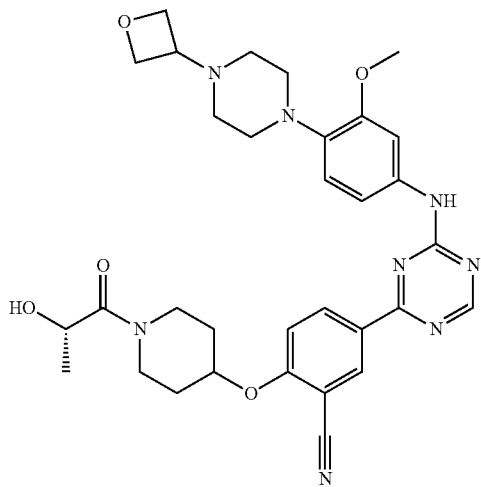 [SMILES: COc1cc(Nc2ncnc(-c3ccc(OC4CCN(C(=O)[C@H](C)O)CC4)c(C#N)c3)n2)ccc1N1CCN(C2COC2)CC1]

Step 1: Preparation of tert-butyl 4-(2-cyano-4-(4-((3-methoxy-4-(4-(oxetan-3-yl)piperazin-1-yl)phenyl)amino)-1,3,5-triazin-2-yl)phenoxy)piperidine-1-carboxylate A mixture of 4-chloro-N-(3-methoxy-4-(4-(oxetan-3-yl)piperazin-1-yl)phenyl)-1,3,5-triazin-2-amine (0.11 g, 0.28 mmol), tert-butyl 4-(2-cyano-4-(4,4,5,5-tetramethyl-1,3,2-dioxaborolan-2-yl)phenoxy)piperidine-1-carboxylate (0.13 g, 0.31 mmol), and tetrakis(triphenylphosphine)palladium (0) (0.025 g, 7.5 mol %) in 1,2-dimethoxyethane (DME, 3 mL) was treated with 2M aqueous sodium carbonate solution (0.64 mL). The mixture was irradiated for 1 hour in a microwave reactor at 130° C. The layers of the biphasic mixture were separated. The aqueous phase was extracted three times with ethyl acetate. The combined extracts were dried over anhydrous magnesium sulfate, filtered, and concentrated to dryness under reduced pressure to provide crude tert-butyl 4-(2-cyano-4-(4-((3-methoxy-4-(4-(oxetan-3-yl)piperazin-1-yl)phenyl)amino)-1,3,5-triazin-2-yl)phenoxy)piperidine-1-carboxylate, which was carried on without further purification. LCMS-ESI+ (m/z): [M+H]+ calcd for $C_{34}H_{43}N_8O_5$: 643.3; found: 643.2

Step 2: Preparation of 5-(4-((3-methoxy-4-(4-(oxetan-3-yl)piperazin-1-yl)phenyl)amino)-1,3,5-triazin-2-yl)-2-(piperidin-4-yloxy)benzonitrile tert-butyl 4-(2-cyano-4-(4-((3-methoxy-4-(4-(oxetan-3-yl)piperazin-1-yl)phenyl)amino)-1,3,5-triazin-2-yl)phenoxy)piperidine-1-carboxylate (assumed 0.28 mmol) was taken up in dichloromethane (5 mL) and treated with trifluoroacetic acid (1 mL). The mixture was concentrated under reduced pressure and purified by flash chromatography on silica gel to provide 5-(4-((3-methoxy-4-(4-(oxetan-3-yl)piperazin-1-yl)phenyl)amino)-1,3,5-triazin-2-yl)-2-(piperidin-4-yloxy)benzonitrile. LCMS-ESI+ (m/z): [M+H]+ calcd for $C_{29}H_{35}N_8O_3$: 543.3; found: 543.3

Step 3: Preparation of (S)-2-((1-(2-hydroxypropanoyl)piperidin-4-yl)oxy)-5-(4-((3-methoxy-4-(4-(oxetan-3-yl)piperazin-1-yl)phenyl)amino)-1,3,5-triazin-2-yl)benzonitrile 5-(4-((3-methoxy-4-(4-(oxetan-3-yl)piperazin-1-yl)phenyl)amino)-1,3,5-triazin-2-yl)-2-(piperidin-4-yloxy)benzonitrile (0.15 g, 0.28 mmol) and L-(−)-lactic acid (Sigma Aldrich, 38 mg, 0.43 mmol) were taken up in N,N-dimethylformamide (3 mL). The mixture was treated successively with N,N-diisopropylethylamine (150 μL, 0.85 mmol) and N-[(dimethylamino)-1H-1,2,3-triazolo-[4,5-b]pyridin-1-ylmethylene]-N-methylmethanaminiumhexafluorophosphate N-oxide (HATU, 160 mg, 0.43 mmol). The mixture remained at room temperature overnight and was then purified by prep HPLC (5-85% acetonitrile in water, 0.1% trifluoroacetic acid buffer) to provide (S)-2-((1-(2-hydroxypropanoyl)piperidin-4-yl)oxy)-5-(4-((3-methoxy-4-(4-(oxetan-3-yl)piperazin-1-yl)phenyl)amino)-1,3,5-triazin-2-yl)benzonitrile. LCMS-ESI+ (m/z): [M+H]+ calcd for $C_{32}H_{39}N_8O_5$: 615.3; found: 615.4 1H NMR (400 MHz, DMSO-$d_6$) δ 10.35 (m, 1H), 8.84 (s, 1H), 8.65-8.62 (m, 2H), 7.76 (bs, 1H), 7.66-7.58 (m, 1H), 7.65-7.18 (br, 1H), 7.02 (d, J=8.6 Hz, 1H), 5.06 (m, 1H), 4.88-4.75 (m, 3H), 4.50 (m, 2H), 3.93-3.77 (m, 4H), 3.65-3.40 (m, 4H), 3.30-2.90 (m, 3H), 2.13-1.96 (m, 2H), 1.84-1.64 (m, 2H), 1.24 (d, J=6.5 Hz, 3H).

Example 282

(S)-5-(4-((4-(4-(oxetan-3-yl)piperazin-1-yl)phenyl)amino)-1,3,5-triazin-2-yl)-2-(1-(tetrahydro-2H-pyran-4-yl)ethoxy)benzonitrile

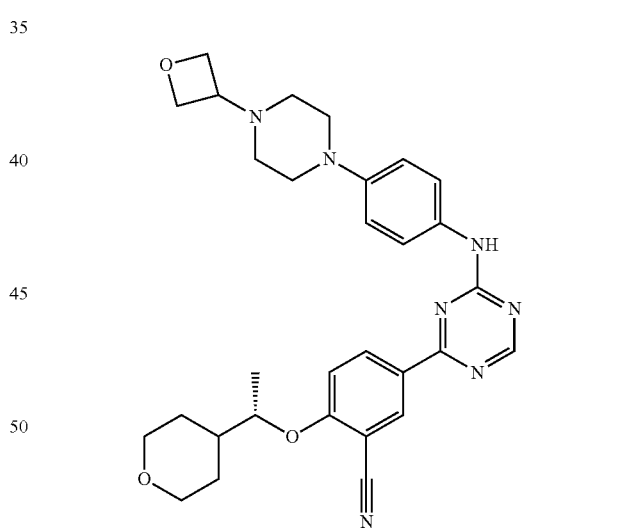

Potassium tert-butoxide (0.10 g, 0.90 mmol) was added to a solution of (1S)-1-(oxan-4-yl)ethan-1-ol (Enamine, 0.12 g, 0.90 mmol) in 2-methyltetrahydrofuran (5 mL). The resulting suspension was stirred at room temperature for 30 minutes before the addition of 2-fluoro-5-(4-((4-(4-(oxetan-3-yl)piperazin-1-yl)phenyl)amino)-1,3,5-triazin-2-yl)benzonitrile (0.13 g, 0.30 mmol). The mixture was heated at 60° C. overnight and then purified by flash chromatography on silica gel to provide (S)-5-(4-((4-(4-(oxetan-3-yl)piperazin-1-yl)phenyl)amino)-1,3,5-triazin-2-yl)-2-(1-(tetrahydro-2H-pyran-4-yl)ethoxy)benzonitrile. LCMS-ESI+ (m/z): [M+H]+ calcd for $C_{30}H_{36}N_7O_3$: 542.3; found: 542.4 1H NMR (400

MHz, DMSO-d$_6$) δ 10.15 (d, J=20.5 Hz, 1H), 8.77 (s, 1H), 8.67-8.48 (m, 2H), 7.61 (m, 2H), 7.53 (d, J=9.2 Hz, 1H), 7.00 (m, 2H), 4.66 (m, 1H), 4.61 (t, J=6.5 Hz, 2H), 4.51 (t, J=6.0 Hz, 2H), 3.95 (m, 2H), 3.49 (p, J=6.5 Hz, 1H), 3.36 (m, 2H), 3.18 (m 4H), 2.44 (m, 4H), 2.02-1.86 (m, 1H), 1.78 (d, J=12.9 Hz, 1H), 1.62 (d, J=12.8 Hz, 1H), 1.53-1.38 (m, 2H), 1.35 (d, J=6.1 Hz, 3H).

Example 283

(R)-5-(4-((4-(4-(oxetan-3-yl)piperazin-1-yl)phenyl)amino)-1,3,5-triazin-2-yl)-2-(1-(tetrahydro-2H-pyran-4-yl)ethoxy)benzonitrile

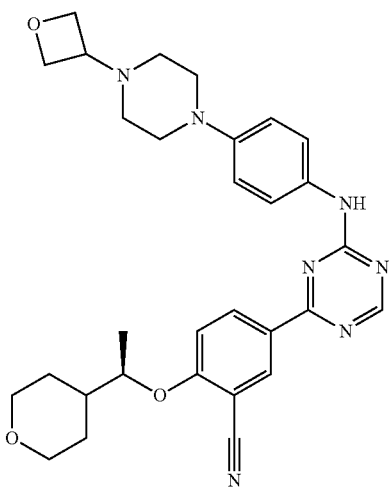 [SMILES: C[C@@H](Oc1ccc(-c2ncnc(Nc3ccc(N4CCN(C5COC5)CC4)cc3)n2)cc1C#N)C1CCOCC1]

Potassium tert-butoxide (0.10 g, 0.90 mmol) was added to a solution of (1R)-1-(oxan-4-yl)ethan-1-ol (Enamine, 0.12 g, 0.90 mmol) in 2-methyltetrahydrofuran (5 mL). The resulting suspension was stirred at room temperature for 30 minutes before the addition of 2-fluoro-5-(4-((4-(4-(oxetan-3-yl)piperazin-1-yl)phenyl)amino)-1,3,5-triazin-2-yl)benzonitrile (0.13 g, 0.30 mmol). The mixture was heated at 60° C. overnight and then purified by flash chromatography on silica gel to provide (R)-5-(4-((4-(4-(oxetan-3-yl)piperazin-1-yl)phenyl)amino)-1,3,5-triazin-2-yl)-2-(1-(tetrahydro-2H-pyran-4-yl)ethoxy)benzonitrile. LCMS-ESI$^+$ (m/z): [M+H]$^+$ calcd for C$_{30}$H$_{36}$N$_7$O$_3$: 542.3; found: 542.4 $^1$H NMR (400 MHz, DMSO-d$_6$) δ 10.15 (m, 1H), 8.77 (s, 1H), 8.66-8.50 (m, 2H), 7.61 (m, 2H), 7.53 (d, J=9.2 Hz, 1H), 7.01 (s, 2H), 4.66 (m, 1H), 4.61 (t, J=6.5 Hz, 2H), 4.52 (t, J=6.1 Hz, 2H), 3.95 (m, 2H), 3.49 (p, J=6.3 Hz, 1H), 3.35 (m, 2H), 3.21 (m, 4H), 2.45 (m, 4H), 1.94 (m, 1H), 1.78 (m, 1H), 1.52 (m, 1H), 1.44 (m, 2H), 1.35 (d, J=6.1 Hz, 3H).

Example 284

2-((4-methyl-1,2,3-thiadiazol-5-yl)methoxy)-5-(4-((4-(4-(oxetan-3-yl)piperazin-1-yl)phenyl)amino)-1,3,5-triazin-2-yl)benzonitrile

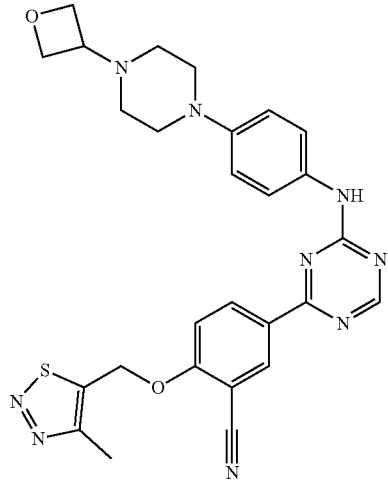 [SMILES: Cc1nnsc1COc1ccc(-c2ncnc(Nc3ccc(N4CCN(C5COC5)CC4)cc3)n2)cc1C#N]

Potassium tert-butoxide (0.10 g, 0.90 mmol) was added to a solution of 4-methyl-1,2,3-thiadiazole-5-methanol (Astatech, 0.12 g, 0.90 mmol) in 2-methyltetrahydrofuran (5 mL). The resulting suspension was stirred at room temperature for 30 minutes before the addition of 2-fluoro-5-(4-((4-(4-(oxetan-3-yl)piperazin-1-yl)phenyl)amino)-1,3,5-triazin-2-yl)benzonitrile (0.13 g, 0.30 mmol). The mixture was heated at 60° C. overnight and then purified by flash chromatography on silica gel to provide 2-((4-methyl-1,2,3-thiadiazol-5-yl)methoxy)-5-(4-((4-(4-(oxetan-3-yl)piperazin-1-yl)phenyl)amino)-1,3,5-triazin-2-yl)benzonitrile. LCMS-ESI$^+$ (m/z): [M+H]$^+$ calcd for C$_{27}$H$_{28}$N$_9$O$_2$S: 542.2; found: 542.2

Example 285

5-(4-((4-(4-(oxetan-3-yl)piperazin-1-yl)phenyl)amino)-1,3,5-triazin-2-yl)-2-((tetrahydro-2H-pyran-4-yl)methoxy)benzonitrile

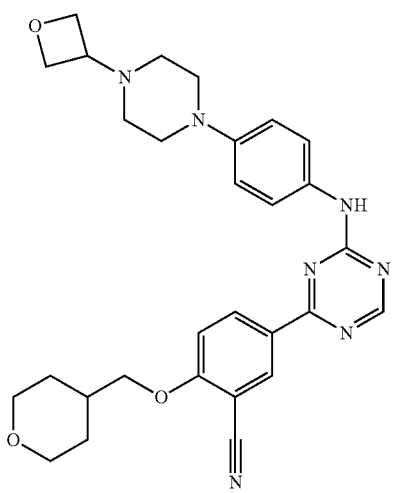 [SMILES: N#Cc1cc(-c2ncnc(Nc3ccc(N4CCN(C5COC5)CC4)cc3)n2)ccc1OCC1CCOCC1]

Potassium tert-butoxide (0.10 g, 0.90 mmol) was added to a solution of tetrahydropyran-4-methanol (0.10 g, 0.90 mmol) in 2-methyltetrahydrofuran (4 mL). The resulting suspension was stirred at room temperature for 30 minutes before the addition of 2-fluoro-5-(4-((4-(4-(oxetan-3-yl)piperazin-1-yl)phenyl)amino)-1,3,5-triazin-2-yl)benzonitrile (0.13 g, 0.30 mmol). The mixture was heated at 70° C. overnight and then purified by flash chromatography on silica gel to provide 5-(4-((4-(4-(oxetan-3-yl)piperazin-1-yl)phenyl)amino)-1,3,5-triazin-2-yl)-2-((tetrahydro-2H-pyran-4-yl)methoxy)benzonitrile. LCMS-ESI$^+$ (m/z): [M+H]$^+$ calcd for $C_{29}H_{34}N_7O_3$: 528.3; found: 528.4 $^1$H NMR (400 MHz, DMSO-d$_6$) δ 10.15 (m, 1H), 8.77 (s, 1H), 8.68-8.51 (m, 2H), 7.61 (m, 2H), 7.49 (d, J=9.0 Hz, 1H), 7.00 (m, 2H), 4.61 (t, J=6.5 Hz, 2H), 4.52 (t, J=6.0 Hz, 2H), 4.16 (d, J=6.4 Hz, 2H), 4.00-3.87 (m, 2H), 3.47 (p J=6.4 Hz, 1H), 3.38 (m, 2H), 3.18 (m, 4H), 2.43 (m, 4H), 2.12 (m, 1H), 1.73 (m, 2H), 1.44 (m, 2H).

Example 286

(S)-2-(2-cyano-4-(4-((4-(4-(oxetan-3-yl)piperazin-1-yl)phenyl)amino)-1,3,5-triazin-2-yl)phenoxy)-3-methylbutanamide

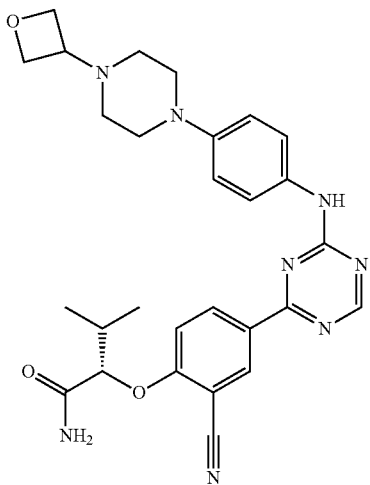 [SMILES: CC(C)[C@H](Oc1ccc(-c2ncnc(Nc3ccc(N4CCN(C5COC5)CC4)cc3)n2)cc1C#N)C(N)=O]

Step 1: Preparation of (S)-methyl 2-(4-bromo-2-cyanophenoxy)-3-methylbutanoate

A solution of 5-bromo-2-hydroxybenzonitrile (1.2 g, 6.1 mmol) was in 2-methyltetrandrofuran (10 mL) was cooled in an ice-water bath while stirring under an atmosphere of Argon. Triphenylphosphine (1.7 g, 6.4 mmol) was added in a single portion. To the stirred mixture was added dropwise via syringe (R)-methyl 2-hydroxy-3-methylbutanoate (BOC Sciences, 0.85 g, 6.4 mmol) followed by diisopropyl azodicarboxylate (1.9 g, 9.2 mmol). The mixture was stirred overnight under an Argon atmosphere, gradually regaining room temperature. The mixture was concentrated under reduced pressure and then purified by flash chromatography on silica gel to provide (S)-methyl 2-(4-bromo-2-cyanophenoxy)-3-methylbutanoate. LCMS-ESI$^+$ (m/z): [M+H]$^+$ calcd for $C_{13}H_{15}BrNO_3$: 312.0; found: 311.8

Step 2: Preparation of (S)-2-(4-bromo-2-cyanophenoxy)-3-methylbutanamide (S)-methyl 2-(4-bromo-2-cyanophenoxy)-3-methylbutanoate (1.7 g, 5.3 mmol) was taken up in 2-methyltetrahydrofuran/methanol/water (2:2:1, 25 mL). The mixture was cooled in an ice-water bath while lithium hydroxide monohydrate (0.33 g, 7.9 mmol) was added in a single portion. After two hours of stirring, the mixture was removed from bath and acidified to ~pH 2 with 10% aqueous citric acid solution. The mixture was extracted three times with ethyl acetate. The combined extracts were washed with saturated aqueous sodium chloride solution that was made acidic by the addition of <5% of 10% aqueous hydrochloric acid solution. The combined organic extracts were dried over anhydrous magnesium sulfate, filtered, and concentrated to provide the putative intermediate (S)-2-(4-bromo-2-cyanophenoxy)-3-methylbutanoic acid, of which a portion thereof (0.71 g, 2.4 mmol) was taken up in N,N-dimethylformamide (10 mL), cooled in an ice-water bath, and treated successively with N,N-diisopropylethylamine (1.0 mL, 6.0 mmol) and N-[(dimethylamino)-1H-1,2,3-triazolo-[4,5-b]pyridin-1-ylmethylene]-N-methylmethanaminiumhexafluorophosphate N-oxide (HATU, 1.4 g, 3.6 mmol). After 20 minutes of stirring in the bath, the mixture was treated with concentrated ammonium hydroxide solution (28%, 1.3 mL, 9.5 mmol). The mixture was allowed to continue stirring overnight, gradually regaining room temperature. The mixture was quenched by the addition of saturated aqueous sodium bicarbonate solution and was made homogeneous by the addition of water and ethyl acetate. The aqueous phase was extracted three times with ethyl acetate. The combined extracts were washed once with saturated aqueous sodium bicarbonate solution and saturated aqueous sodium chloride solution and then dried over anhydrous magnesium sulfate, filtered, and concentrated under reduced pressure. The residue was purified by flash chromatography on silica gel to provide (S)-2-(4-bromo-2-cyanophenoxy)-3-methylbutanamide.

LCMS-ESI$^+$ (m/z): [M+H]$^+$ calcd for $C_{12}H_{14}BrN_2O_2$: 297.0; found: 297.0

Step 3: Preparation of (S)-2-(2-cyano-4-(4,4,5,5-tetramethyl-1,3,2-dioxaborolan-2-yl)phenoxy)-3-methylbutanamide A mixture of (S)-2-(4-bromo-2-cyanophenoxy)-3-methylbutanamide (0.16 g, 0.55 mmol), bis(pinacolato)diboron (0.28 g, 1.1 mmol), potassium acetate (0.16 g, 1.6 mmol), and [1,1'-bis(diphenylphosphino)ferrocene]dichloropalladium(II) complex with dichloromethane (45 mg, 10 mol %) in 1,4-dioxane (3 mL) was heated for 4 hours at 95° C. The reaction mixture was filtered through a pad of Celite diatomaceous earth, and the filtrate was concentrated to dryness under reduced pressure. The crude (S)-2-(2-cyano-4-(4,4,5,5-tetramethyl-1,3,2-dioxaborolan-2-yl)phenoxy)-3-methylbutanamide was carried forward without further purification. LCMS-ESI$^+$ (m/z): [M+H]$^+$ calcd for $C_{18}H_{26}BN_2O_4$: 345.2; found: 345.1

Step 4: Preparation of (S)-2-(2-cyano-4-(4-((4-(4-(oxetan-3-yl)piperazin-1-yl)phenyl)amino)-1,3,5-triazin-2-yl)phenoxy)-3-methylbutanamide A mixture of 4-chloro-N-(4-(4-(oxetan-3-yl)piperazin-1-yl)phenyl)-1,3,5-triazin-2-amine (0.16 g, 0.36 mmol), crude (S)-2-(2-cyano-4-(4,4,5,5-tetramethyl-1,3,2-dioxaborolan-2-yl)phenoxy)-3-methylbutanamide (0.54 mmol assumed), and tetrakis(triphenylphosphine)palladium(0) (0.031 g, 7.5 mol %) in 1,2-dimethoxyethane (DME, 3 mL) was treated saturated aqueous sodium hydrogen carbonate solution (1.6 mL). The mixture was irradiated for 1 hour in a microwave reactor at 120° C. The crude mixture was purified by flash chromatography on silica gel to provide (S)-2-(2-cyano-4-(4-((4-(4-(oxetan-3-yl)piperazin-1-yl)phenyl)amino)-1,3,5- triazin-2-yl)phenoxy)-3-methylbutanamide. LCMS-ESI⁺ (m/z): [M+H]⁺ calcd for $C_{28}H_{33}N_8O_3$: 529.3; found: 529.3

Example 287

5-(4-((6-(3-hydroxyazetidin-1-yl)pyridin-3-yl)amino)-1,3,5-triazin-2-yl)-2-((tetrahydro-2H-pyran-4-yl)oxy)benzonitrile

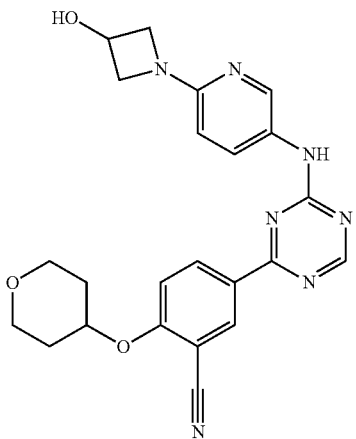 [SMILES: N#Cc1cc(-c2ncnc(Nc3ccc(N4CC(O)C4)nc3)n2)ccc1OC1CCOCC1]

Step 1: Preparation of 1-(5-nitropyridin-2-yl)azetidin-3-ol

A mixture of 2-chloro-5-nitropyridine (2.0 g, 13 mmol) and 3-hydroxyazetidine hydrochloride (1.5 g, 13 mmol) in N,N-dimethylformamide (8 mL) was cooled in an ice-water bath while triethylamine (3.8 mL, 28 mmol) was added dropwise. At the end of the addition, the mixture was removed from the bath was allowed to stir over the weekend at room temperature. The Slurry was partitioned between ethyl acetate and saturated aqueous sodium hydrogen carbonate solution. The aqueous phase was extracted three times with ethyl acetate. The combined extracts were washed once with saturated aqueous sodium chloride solution. The brine wash was back-extracted three times with ethyl acetate. The combined extracts were dried over anhydrous magnesium sulfate, filtered, and concentrated to provide a crude solid, which was triturated with toluene, collected by filtration, and dried under house vacuum to provide 1-(5-nitropyridin-2-yl)azetidin-3-ol. LCMS-ESI⁺ (m/z): [M+H]⁺ calcd for $C_8H_{10}N_3O_3$: 196.1; found: 196.0

Step 2: Preparation of 1-(5-aminopyridin-2-yl)azetidin-3-ol

A solution of 1-(5-nitropyridin-2-yl)azetidin-3-ol (0.20 g, 1.0 mmol) in ethanol (20 mL) was degassed before the addition of 10% palladium on carbon (25 mg). The suspension was shaken overnight under 55 psi of hydrogen gas. The suspension was filtered through a pad of Celite diatomaceous earth, and the filtrate was concentrated under reduced pressure to provide 1-(5-aminopyridin-2-yl)azetidin-3-ol. LCMS-ESI⁺ (m/z): [M+H]⁺ calcd for $C_8H_{12}N_3O$: 166.1; found: 166.0

Step 3: Preparation of 5-(4-((6-(3-hydroxyazetidin-1-yl)pyridin-3-yl)amino)-1,3,5-triazin-2-yl)-2-((tetrahydro-2H-pyran-4-yl)oxy)benzonitrile A suspension of 5-(4-chloro-1,3,5-triazin-2-yl)-2-((tetrahydro-2H-pyran-4-yl)oxy)benzonitrile (0.13 g, 0.40 mmol) 1-(5-aminopyridin-2-yl)azetidin-3-ol (0.17 g, 1.0 mmol) in acetonitrile (5 mL) was treated with N,N-diisopropylethylamine (0.20 mL, 1.2 mmol). The mixture was heated for 20 minutes at 100° C. and was purified by flash chromatography on silica gel to provide 5-(4-((6-(3-hydroxyazetidin-1-yl)pyridin-3-yl)amino)-1,3,5-triazin-2-yl)-2-((tetrahydro-2H-pyran-4-yl)oxy)benzonitrile. LCMS-ESI⁺ (m/z): [M+H]⁺ calcd for $C_{23}H_{24}N_7O_3$: 446.2; found: 446.2

¹H NMR (400 MHz, DMSO-d₆) δ 10.10 (m, 1H), 8.76 (s, 1H), 8.65-8.49 (m, 2H), 8.47-8.28 (m, 1H), 7.84 (t, J=9.3 Hz, 1H), 7.60 (d, J=9.3 Hz, 1H), 6.49 (dd, J=17.1, 8.8 Hz, 1H), 5.67 (d, J=6.5 Hz, 1H), 4.96 (m, 1H), 4.61 (m, 1H), 4.19 (m, 2H), 3.90 (m, 2H), 3.71 (m, 2H), 3.59 (t, J=10.0 Hz, 2H), 2.09 (m, 2H), 1.72 (m, 2H).

Example 288

2-(((3R,4S)-1-(2,2-difluoroacetyl)-3-fluoropiperidin-4-yl)oxy)-5-(4-((4-(4-(oxetan-3-yl)piperazin-1-yl)phenyl)amino)-1,3,5-triazin-2-yl)benzonitrile

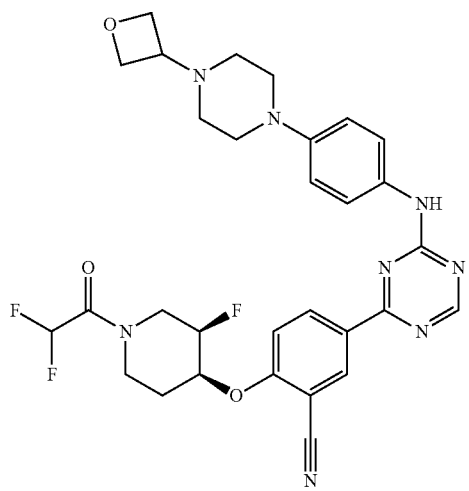 [SMILES: N#Cc1cc(-c2ncnc(Nc3ccc(N4CCN(C5COC5)CC4)cc3)n2)ccc1O[C@H]1CCN(C(=O)C(F)F)C[C@H]1F]

Step 1: Preparation of (3R,4S)-tert-butyl 4-(2-cyano-4-(4-((4-(4-(oxetan-3-yl)piperazin-1-yl)phenyl)amino)-1,3,5-triazin-2-yl)phenoxy)-3-fluoropiperidine-1-carboxylate Potassium tert-butoxide (0.066 g, 0.58 mmol) was added to a solution of (3R,4S)-tert-butyl 3-fluoro-4-hydroxypiperidine-1-carboxylate (PharmaBlock, 0.13 g, 0.58 mmol) in 2-methyltetrahydrofuran (5 mL), cooled in an ice-water bath. The resulting suspension was stirred at 0° C. for 30 minutes before the addition of 2-fluoro-5-(4-((4-(4-(oxetan-3-yl)piperazin-1-yl)phenyl)amino)-1,3,5-triazin-2-yl)benzonitrile (0.18 g, 0.42 mmol). The mixture was heated at 72° C. overnight and then concentrated under reduced pressure to provide crude (3R,4S)-tert-butyl 4-(2-cyano-4-(4-((4-(4-(oxetan-3-yl)piperazin-1-yl)phenyl)amino)-1,3,5-triazin-2-yl)phenoxy)-3-fluoropiperidine-1-carboxylate, which was carried forward without further purification. LCMS-ESI⁺ (m/z): [M+H]⁺ calcd for $C_{33}H_{40}FN_8O_4$: 631.3; found: 631.2

Step 2: Preparation of 2-(((3R,4S)-3-fluoropiperidin-4-yl)oxy)-5-(4-((4-(4-(oxetan-3-yl)piperazin-1-yl)phenyl)amino)-1,3,5-triazin-2-yl)benzonitrile Crude (3R,4S)-tert-butyl 4-(2-cyano-4-(4-((4-(4-(oxetan-3-yl)piperazin-1-yl)phenyl)amino)-1,3,5-triazin-2-yl)phenoxy)-3-fluoropiperidine-1-carboxylate (assumed 0.42 mmol) was taken up in dichloromethane (5 mL) and treated with trifluoroacetic acid (1.3 mL, 17 mmol). After the passage of one hour, the mixture was concentrated under reduced pressure and the residue was purified by flash chromatography (silica gel) to provide 2-(((3R,4S)-3-fluoropiperidin-4-yl)oxy)-5-(4-((4-(4-(oxetan-3-yl)piperazin-1-yl)phenyl)amino)-1,3,5-triazin-2-yl)benzonitrile.

LCMS-ESI⁺ (m/z): [M+H]⁺ calcd for $C_{28}H_{32}FN_8O_2$: 531.3; found: 531.2

Step 3: Preparation of 2-(((3R,4S)-1-(2,2-difluoroacetyl)-3-fluoropiperidin-4-yl)oxy)-5-(4-((4-(4-(oxetan-3-yl)piperazin-1-yl)phenyl)amino)-1,3,5-triazin-2-yl)benzonitrile, trifluoroacetic acid salt 2-(((3R,4S)-3-fluoropiperidin-4-yl)oxy)-5-(4-((4-(4-(oxetan-3-yl)piperazin-1-yl)phenyl)amino)-1,3,5-triazin-2-yl)benzonitrile (74 mg, 0.14 mmol) and difluoroacetic acid (13 μL, 0.21 mmol) were taken up as suspension in dichloromethane (3 mL). The mixture was treated with successively with N,N-diisopropylethylamine (49 μL, 0.28 mmol) and HATU (80 mg, 0.21 mmol). The suspension was stirred for approximately 30 minutes and was purified first by flash chromatography (silica gel) and then by prep HPLC (5-70% acetonitrile in water, 0.1% trifluoroacetic acid buffer) to provide 2-(((3R,4S)-1-(2,2-difluoroacetyl)-3-fluoropiperidin-4-yl)oxy)-5-(4-((4-(4-(oxetan-3-yl)piperazin-1-yl)phenyl)amino)-1,3,5-triazin-2-yl)benzonitrile, trifluoroacetic acid salt. LCMS-ESI⁺ (m/z): [M+H]⁺ calcd for $C_{30}H_{32}F_3N_8O_3$: 609.3; found: 609.4 ¹H NMR (400 MHz, DMSO-d₆) δ 10.82 (bs, 1H), 10.25 (d, J=22.9 Hz, 1H), 8.81 (s, 1H), 8.63 (dd, J=9.0, 2.2 Hz, 1H), 8.58 (bs, 1H), 7.69 (d, J=9.2 Hz, 2H), 7.65 (m, 1H), 7.11 (m, 2H), 6.84 (td, J=52.5, 23.1 Hz, 1H), 5.23 (m, 1.5H), 5.19 (m, 1H), 5.10 (m, 0.5H), 4.82 (m, 4H), 4.59-4.39 (m, 1H), 4.26-4.09 (m, 1H), 3.93 (m 1H) 3.82-3.24 (m, 2H) 3.13 (s, 4H), 2.24-1.82 (m, 2H).

Example 289

2-(((3R,4S)-1-acetyl-3-fluoropiperidin-4-yl)oxy)-5-(4-((4-(4-(oxetan-3-yl)piperazin-1-yl)phenyl)amino)-1,3,5-triazin-2-yl)benzonitrile

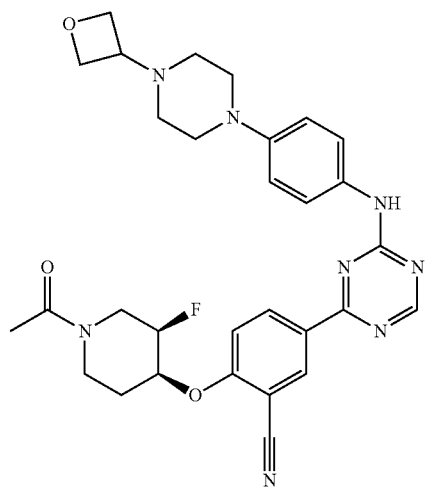 [SMILES: CC(=O)N1CC[C@H](Oc2ccc(-c3ncnc(Nc4ccc(N5CCN(C6COC6)CC5)cc4)n3)cc2C#N)[C@H](F)C1]

2-(((3R,4S)-3-fluoropiperidin-4-yl)oxy)-5-(4-((4-(4-(oxetan-3-yl)piperazin-1-yl)phenyl)amino)-1,3,5-triazin-2-yl)benzonitrile (74 mg, 0.14 mmol) was taken up as suspension in dichloromethane (3 mL) and treated successively with N,N-diisopropylethylamine (51 μL, 0.28 mmol) and acetyl chloride (15 μL, 0.21 mmol). The mixture turned homogeneous, and after approximately 90 minutes, it was concentrated to dryness under reduced pressure. The residue was taken up in pyridine (5 mL) and treated with concentrated ammonium hydroxide solution (28%, 2 mL). The mixture was stirred for 10 minutes at 60° C. and then concentrated to dryness under reduced pressure. The residue was purified by flash chromatography (silica gel) to provide 2-(((3R,4S)-1-acetyl-3-fluoropiperidin-4-yl)oxy)-5-(4-((4-(4-(oxetan-3-yl)piperazin-1-yl)phenyl)amino)-1,3,5-triazin-2-yl)benzonitrile. LCMS-ESI⁺ (m/z): [M+H]⁺ calcd for $C_{30}H_{34}FN_8O_3$: 573.3; found: 573.4 ¹H NMR (400 MHz, DMSO-d₆) δ 10.18 (d, J=24.9 Hz, 1H), 8.79 (s, 1H), 8.60 (m, 2H), 7.68 (d, J=9.2 Hz, 1H), 7.60 (m, 1H), 7.01 (m, 3H), 5.23-4.94 (m, 2H), 4.62 (t, J=6.6 Hz, 2H), 4.52 (m, 2H), 4.37 (m, 0.5H), 4.19 (m, 0.5H), 4.09 (m, 0.5H), 3.81 (m, 0.5H), 3.61 (dd, J=30.6, 14.5 Hz, 0.5H), 3.53-3.45 (m, 1H), 3.18 (s, 4H), 3.09 (m, 0.5H), 2.46 (m, 4H), 2.11 (s, 1.5H), 2.08 (s, 1.5H), 2.06-1.94 (m, 2H), 1.91-1.77 (m, 1H).

Example 290

(3R,4S)-methyl 4-(2-cyano-4-(4-((4-(4-(oxetan-3-yl)piperazin-1-yl)phenyl)amino)-1,3,5-triazin-2-yl)phenoxy)-3-fluoropiperidine-1-carboxylate

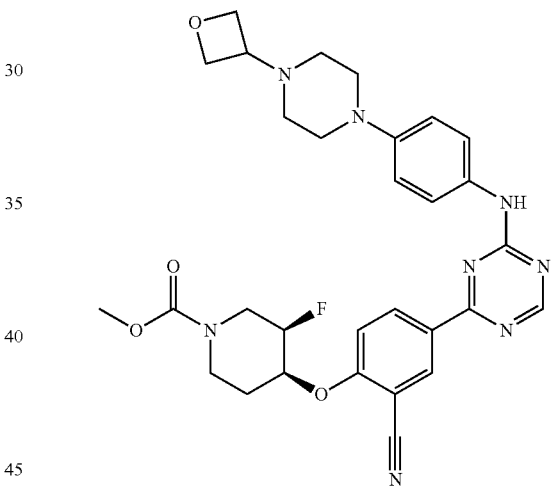

2-(((3R,4S)-3-fluoropiperidin-4-yl)oxy)-5-(4-((4-(4-(oxetan-3-yl)piperazin-1-yl)phenyl)amino)-1,3,5-triazin-2-yl)benzonitrile (74 mg, 0.14 mmol) was taken up as suspension in dichloromethane (2 mL) and treated successively with N,N-diisopropylethylamine (49 μL, 0.28 mmol) and methyl chloroformate (16 μL, 0.21 mmol). The mixture turned homogeneous, and after approximately 5 minutes, it was concentrated to dryness under reduced pressure. The residue was purified by flash chromatography (silica gel) to provide (3R,4S)-methyl 4-(2-cyano-4-(4-((4-(4-(oxetan-3-yl)piperazin-1-yl)phenyl)amino)-1,3,5-triazin-2-yl)phenoxy)-3-fluoropiperidine-1-carboxylate.\ LCMS-ESI⁺ (m/z): [M+H]⁺ calcd for $C_{30}H_{34}FN_8O_4$: 589.3; found: 589.4 ¹H NMR (400 MHz, DMSO-d₆) δ 10.17 (d, J=24.9 Hz, 1H), 8.78 (s, 1H), 8.71-8.52 (m, 2H), 7.66 (d, J=9.2 Hz, 1H), 7.61 (m, 2H), 7.02 (m, 2H), 5.14 (m, 1H), 5.10-4.98 (m, 1H), 4.61 (t, J=6.5 Hz, 2H), 4.52 (t, J=6.5 Hz, 2H), 4.16 (m, 1H), 3.94 (m, 1H). 3.67 (s, 3H), 3.55-3.43 (m, 2H), 3.18 (m, 4H), 2.46 (m, 4H), 2.10-1.83 (m, 2H).

Example 291

2-(((1S,2R)-2-aminocyclohexyl)oxy)-5-(4-((4-(4-(oxetan-3-yl)piperazin-1-yl)phenyl)amino)-1,3,5-triazin-2-yl)benzonitrile

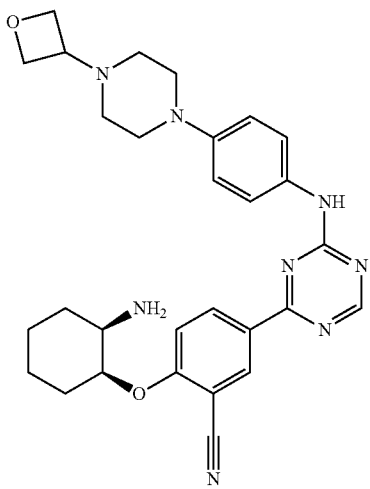 [SMILES: N#Cc1cc(-c2ncnc(Nc3ccc(N4CCN(C5COC5)CC4)cc3)n2)ccc1O[C@H]1CCCC[C@H]1N]

Step 1: Preparation of tert-butyl ((1R,2S)-2-(4-bromo-2-cyanophenoxy)cyclohexyl)carbamate A mixture of 5-bromo-2-hydroxybenzonitrile (1.0 g, 5.1 mmol) and triphenylphosphine (1.3 g, 5.1 mmol) in 2-methyltetrahydrofuran (20 mL) was cooled in an ice-water bath while stirring under an atmosphere of Argon. To the stirred mixture was added dropwise via syringe tert-butyl N-[(1R, 2R)-2-hydroxycyclohexyl]carbamate (PharmaBlock, 1.0 g, 4.6 mmol, as a solution in 5 mL 2-MeTHF), followed by diethyl azodicarboxylate (40% in toluene, 2.7 mL, 5.1 mmol). The mixture was stirred overnight under an Ar atmosphere while gradually regaining room temperature. The mixture was concentrated under reduced pressure and purified by flash chromatography (silica gel) to provide tert-butyl ((1R,2S)-2-(4-bromo-2-cyanophenoxy)cyclohexyl)carbamate. LCMS-ESI$^+$ (m/z): [M−isobutylene+H]$^+$ calcd for $C_{14}H_{16}BrN_2O_3$: 339.0; found: 338.9

Step 2: Preparation of tert-butyl ((1R,2S)-2-(2-cyano-4-(4,4,5,5-tetramethyl-1,3,2-dioxaborolan-2-yl)phenoxy)cyclohexyl)carbamate A mixture of tert-butyl ((1R,2S)-2-(4-bromo-2-cyanophenoxy)cyclohexyl)carbamate (0.13 g, 0.32 mmol), bis(pinacolato)diboron (0.16 g, 0.64 mmol), potassium acetate (0.10 g, 0.96 mmol), and [1,1'-bis(diphenylphosphino)ferrocene]dichloropalladium(II) complex with dichloromethane (25 mg, 10 mol %) in 1,4-dioxane (2 mL) was heated for 90 minutes at 95° C. The reaction mixture was filtered through a pad of Celite diatomaceous earth, and the filtrate was concentrated to dryness under reduced pressure. The crude tert-butyl ((1R,2S)-2-(2-cyano-4-(4,4,5,5-tetramethyl-1,3,2-dioxaborolan-2-yl)phenoxy)cyclohexyl)carbamate was carried forward without further purification. LCMS-ESI$^+$ (m/z): [M−isobutylene+H]$^+$ calcd for $C_{20}H_{28}BN_2O_5$: 387.2; found: 387.0

Step 3: Preparation of tert-butyl ((1R,2S)-2-(2-cyano-4-(4-((4-(4-(oxetan-3-yl)piperazin-1-yl)phenyl)amino)-1,3,5-triazin-2-yl)phenoxy)cyclohexyl)carbamate A mixture of 4-chloro-N-(4-(4-(oxetan-3-yl)piperazin-1-yl)phenyl)-1,3,5-triazin-2-amine (0.14 g, 0.42 mmol), crude tert-butyl ((1R,2S)-2-(2-cyano-4-(4,4,5,5-tetramethyl-1,3,2-dioxaborolan-2-yl)phenoxy)cyclohexyl)carbamate (0.32 mmol assumed), and tetrakis(triphenylphosphine)palladium (0) (0.028 g, 7.5 mol %) in 1,2-dimethoxyethane (DME, 3 mL) was treated with 2 M aqueous sodium carbonate solution (0.72 mL). The mixture was irradiated for 75 minutes in a microwave reactor at 120° C. Additional quantities of 4-chloro-N-(4-(4-(oxetan-3-yl)piperazin-1-yl)phenyl)-1,3,5-triazin-2-amine (75 mg) and palladium catalyst (25 mg) were added. The mixture was again irradiated for 75 minutes at 130° C. An additional portion of 4-chloro-N-(4-(4-(oxetan-3-yl)piperazin-1-yl)phenyl)-1,3,5-triazin-2-amine (75 mg) was added, and the mixture was again heated for 75 minutes at 130° C. After cooling, the biphasic mixture was separated. The aqueous phase was extracted five times with ethyl acetate. The combined extracts were concentrated to dryness under reduced pressure and purified by flash chromatography on silica gel to provide tert-butyl ((1R,2S)-2-(2-cyano-4-(4-((4-(4-(oxetan-3-yl)piperazin-1-yl)phenyl)amino)-1,3,5-triazin-2-yl)phenoxy)cyclohexyl)carbamate. LCMS-ESI$^+$ (m/z): [M+H]$^+$ calcd for $C_{34}H_{43}N_8O_4$: 627.3; found: 627.2

Step 4: Preparation of 2-(((1S,2R)-2-aminocyclohexyl)oxy)-5-(4-((4-(4-(oxetan-3-yl)piperazin-1-yl)phenyl)amino)-1,3,5-triazin-2-yl)benzonitrile tert-butyl ((1R,2S)-2-(2-cyano-4-(4-((4-(4-(oxetan-3-yl)piperazin-1-yl)phenyl)amino)-1,3,5-triazin-2-yl)phenoxy)cyclohexyl)carbamate (86 mg, 0.14 mmol) was taken up in dichloromethane (6 mL) and treated with trifluoroacetic acid (0.42 mL, 5.5 mmol). After standing for 2 hours at room temperature, the acidic mixture was basified with 1:1 1 M aqueous sodium hydroxide solution/saturated aqueous sodium chloride solution. The aqueous phase was extracted three times with dichloromethane. The combined extracts were dried over anhydrous magnesium sulfate, filtered, and concentrated to provide 2-(((1S,2R)-2-aminocyclohexyl)oxy)-5-(4-((4-(4-(oxetan-3-yl)piperazin-1-yl)phenyl)amino)-1,3,5-triazin-2-yl)benzonitrile.

LCMS-ESI$^+$ (m/z): [M+H]$^+$ calcd for $C_{29}H_{35}N_8O_2$: 527.3; found: 527.3

Example 292 rac-2-(((1S,2R)-2-fluorocyclohexyl)oxy)-5-(4-((4-(piperidin-4-yl)phenyl)amino)-1,3,5-triazin-2-yl)benzonitrile

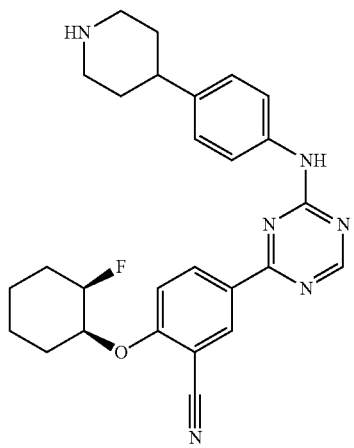 [SMILES: N#Cc1cc(-c2ncnc(Nc3ccc(C4CCNCC4)cc3)n2)ccc1O[C@H]1CCCC[C@H]1F]

Step 1: Preparation of rac-5-bromo-2-(((1S,2R)-2-fluorocyclohexyl)oxy)benzonitrile A mixture of 5-bromo-2-hydroxybenzonitrile (0.60 g, 3.0 mmol) and triphenylphosphine (0.95 g, 3.6 mmol) in 2-methyltetrahydrofuran (15 mL) was cooled in an ice-water bath while stirring under an atmosphere of Argon. To the stirred mixture was added dropwise via syringe trans-2-fluoro-1-cyclohexanol (0.43 g, 3.6 mmol), followed by diethyl azodicarboxylate (40% solution in toluene, 2.1 mL, 4.5 mmol). The mixture was stirred overnight under an Argon atmosphere, gradually regaining room temperature. The mixture was purified by flash chromatography on silica gel to provide rac-5-bromo-2-(((1S,2R)-2-fluorocyclohexyl)oxy)benzonitrile. $^1$H NMR (400 MHz, DMSO-d$_6$) δ 8.04 (d, J=2.5 Hz, 1H), 7.85 (dd, J=9.1, 2.6 Hz, 1H), 7.38 (d, J=9.1 Hz, 1H), 4.96 (m, 1H), 4.87 (m, 1H), 2.01 (m, 1H), 1.87 (m, 2H), 1.75 (m, 1H), 1.63 (m, 2H), 1.45 (m, 2H).

Step 2: Preparation of rac-2-(((1S,2R)-2-fluorocyclohexyl)oxy)-5-(4,4,5,5-tetramethyl-1,3,2-dioxaborolan-2-yl)benzonitrile A mixture of rac-5-bromo-2-(((1S,2R)-2-fluorocyclohexyl)oxy)benzonitrile. (0.31 g, 1.0 mmol), bis(pinacolato)diboron (0.53 g, 2.1 mmol), potassium acetate (0.30 g, 3.1 mmol), and [1,1'-bis(diphenylphosphino)ferrocene]dichloropalladium(II) complex with dichloromethane (76 mg, 10 mol %) in 1,4-dioxane (6 mL) was heated for 4 hours at 95° C. The reaction mixture was filtered through a pad of Celite diatomaceous earth, and the filtrate was concentrated to dryness under reduced pressure. The crude rac-2-(((1S,2R)-2-fluorocyclohexyl)oxy)-5-(4,4,5,5-tetramethyl-1,3,2-dioxaborolan-2-yl)benzonitrile was carried forward without further purification. LCMS-ESI$^+$ (m/z): [M+OH+H]$^+$ calcd for C$_{19}$H$_{27}$BFNO$_4$: 363.2; found: 363.1

Step 3: Preparation of tert-butyl 4-(4-((4-chloro-1,3,5-triazin-2-yl)amino)phenyl)piperidine-1-carboxylate To a solution of 2,4-dichloro-1,3,5-triazine (0.60 g, 4.0 mmol) in N,N-dimethylformamide (DMF, 8 mL) at 0° C. were added sequentially N,N-diisopropylethylamine (DIEA, 0.73 mL, 4.2 mmol) and tert-butyl 4-(4-aminophenyl)piperidine-1-carboxylate (1.0 g, 3.6 mmol). The mixture was stirred at 0° C. for 30 minutes and then allowed to warm to room temperature. The mixture was diluted with ethyl acetate and water and filtered through a pad of Celite diatomaceous earth. The aqueous phase was extracted twice with ethyl acetate. The combined extracts were dried over anhydrous magnesium sulfate, filtered, and concentrated under reduced pressure. The residue was purified by flash chromatography (silica gel) to provide tert-butyl 4-(4-((4-chloro-1,3,5-triazin-2-yl)amino)phenyl)piperidine-1-carboxylate. LCMS-ESI$^+$ (m/z): [M+H]$^+$ calcd for C$_{19}$H$_{25}$ClN$_5$O$_2$: 390.2; found: 389.8

Step 4: Preparation of rac-tert-butyl 4-(4-((4-(3-cyano-4-(((1S,2R)-2-fluorocyclohexyl)oxy)phenyl)-1,3,5-triazin-2-yl)amino)phenyl)piperidine-1-carboxylate A mixture of tert-butyl 4-(4-((4-chloro-1,3,5-triazin-2-yl)amino)phenyl)piperidine-1-carboxylate (0.16 g, 0.40 mmol), crude rac-2-(((1S,2R)-2-fluorocyclohexyl)oxy)-5-(4,4,5,5-tetramethyl-1,3,2-dioxaborolan-2-yl)benzonitrile (0.52 mmol assumed), and tetrakis(triphenylphosphine)palladium(0) (0.035 g, 7.5 mol %) in 1,2-dimethoxyethane (DME, 3 mL) was treated with 2 M aqueous sodium carbonate solution (0.90 mL). The mixture was irradiated for 75 minutes in a microwave reactor at 130° C. After cooling, the biphasic mixture was separated. The aqueous phase was extracted five times with ethyl acetate. The combined extracts were concentrated to dryness under reduced pressure and purified by flash chromatography on silica gel to provide rac-tert-butyl 4-(4-((4-(3-cyano-4-(((1S,2R)-2-fluorocyclohexyl)oxy)phenyl)-1,3,5-triazin-2-yl)amino)phenyl)piperidine-1-carboxylate. LCMS-ESI$^+$ (m/z): [M+H]$^+$ calcd for C$_{32}$H$_{38}$FN$_6$O$_3$: 573.3; found: 573.3

Step 5: Preparation of rac-2-(((1S,2R)-2-fluorocyclohexyl)oxy)-5-(4-((4-(piperidin-4-yl)phenyl)amino)-1,3,5-triazin-2-yl)benzonitrile rac-tert-butyl 4-(4-((4-(3-cyano-4-(((1S,2R)-2-fluorocyclohexyl)oxy)phenyl)-1,3,5-triazin-2-yl)amino)phenyl)piperidine-1-carboxylate (0.15 g, 0.25 mmol) was taken up in dichloromethane (6 mL) and treated with trifluoroacetic acid (0.78 mL, 10 mmol). After completion of the deprotection, the mixture was concentrated under reduced pressure. The residue was partitioned between dichloromethane and 0.5 M aqueous sodium hydroxide solution. The aqueous phase was extracted three times with dichloromethane. The combined extracts were dried over anhydrous magnesium sulfate, filtered, and concentrated to provide rac-2-(((1 S,2R)-2-fluorocyclohexyl)oxy)-5-(4-((4-(piperidin-4-yl)phenyl)amino)-1,3,5-triazin-2-yl)benzonitrile.

LCMS-ESI$^+$ (m/z): [M+H]$^+$ calcd for C$_{27}$H$_{30}$N$_6$O$_3$: 473.2; found: 473.4 $^1$H NMR (400 MHz, DMSO-d$_6$) δ 10.31 (bs, 1H), 8.83 (s, 1H), 8.68-8.55 (m, 2H), 7.71 (m, 2H), 7.61 (d, J=9.4 Hz, 1H), 7.27 (d, J=8.0 Hz, 2H), 5.13-4.84 (m, 2H), 3.38 (br, 4H), 3.07 (d, J=11.7 Hz, 2H), 2.63 (m, 2H), 2.06 (m, 1H), 1.93 (m, 1H), 1.88-1.62 (m, 4H), 1.62-1.41 (m, 4H).

Example 293

2-(((3R,4S)-3-fluoro-1-((S)-2-hydroxypropanoyl)piperidin-4-yl)oxy)-5-(4-((4-(tetrahydro-2H-pyran-4-yl)phenyl)amino)-1,3,5-triazin-2-yl)benzonitrile

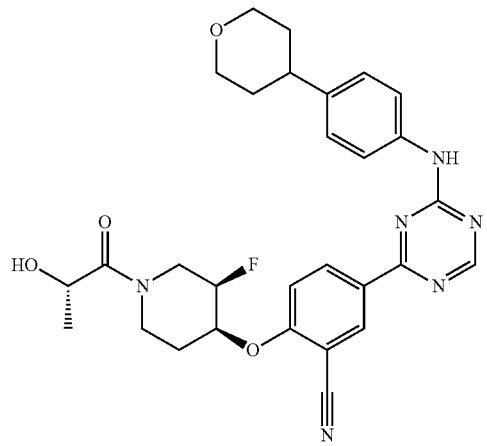 [SMILES: C[C@H](O)C(=O)N1CC[C@H](Oc2ccc(-c3ncnc(Nc4ccc(C5CCOCC5)cc4)n3)cc2C#N)[C@H](F)C1]

Step 1: Preparation of 4-chloro-N-(4-(tetrahydro-2H-pyran-4-yl)phenyl)-1,3,5-triazin-2-amine To a solution of 2,4-dichloro-1,3,5-triazine (0.93 g, 6.2 mmol) in N,N-dimethylformamide (DMF, 10 mL) at 0° C. were added sequentially N,N-diisopropylethylamine (DIEA, 1.1 mL, 6.5 mmol) and a solution of 4-(oxan-4-yl)aniline (Combi-Blocks, 1.0 g, 5.6 mmol) in DMF (5 mL). The mixture was stirred at 0° C. for 30 minutes and then allowed to warm to room temperature overnight. The mixture was diluted with first with toluene and half-saturated aqueous sodium hydrogen carbonate solution and then with ethyl acetate and water. The mixture was filtered through a pad of Celite diatomaceous earth. The aqueous phase was extracted thrice with ethyl acetate. The combined extracts were dried over anhydrous magnesium sulfate, filtered, and concentrated under reduced pressure. The residue was purified by flash chromatography (silica gel) to provide 4-chloro-N-(4-(tetrahydro-2H-pyran-4-yl)phenyl)-1,3,5-triazin-2-amine. LCMS-ESI$^+$ (m/z): [M+H]$^+$ calcd for $C_{14}H_{16}ClN_4O$: 291.1; found: 291.2

Step 2: Preparation of (3R,4S)-tert-butyl 4-(4-bromo-2-cyanophenoxy)-3-fluoropiperidine-1-carboxylate A solution (3R,4S)-tert-butyl 3-fluoro-4-hydroxypiperidine-1-carboxylate (PharmaBlock, 0.60 g, 2.8 mmol) in N,N-dimethylformamide (10 mL) was treated with sodium hydride (60% dispersion in mineral oil, 0.11 g, 2.8 mmol) in a single portion at room temperature. After the mixture was stirred for 30 minutes at room temperature, 5-bromo-2-fluorobenzonitrile (0.50 g, 2.5 mmol) was added in a single portion at room temperature. The mixture was stirred overnight with heating at 50° C. The mixture was quenched with glacial acetic acid and purified by flash chromatography on silica gel to provide (3R,4S)-tert-butyl 4-(4-bromo-2-cyanophenoxy)-3-fluoropiperidine-1-carboxylate. LCMS-ESI$^+$ (m/z): [M−isobutylene+H]$^+$ calcd for $C_{13}H_{13}BrFN_2O_3$: 343.0; found: 342.9

Step 3: Preparation of (3R,4S)-tert-butyl 4-(2-cyano-4-(4,4,5,5-tetramethyl-1,3,2-dioxaborolan-2-yl)phenoxy)-3-fluoropiperidine-1-carboxylate A mixture of (3R,4S)-tert-butyl 4-(4-bromo-2-cyanophenoxy)-3-fluoropiperidine-1-carboxylate (0.27 g, 0.67 mmol), bis(pinacolato)diboron (0.34 g, 1.3 mmol), potassium acetate (0.20 g, 2.0 mmol), and [1,1'-bis(diphenylphosphino)ferrocene]dichloropalladium(II) complex with dichloromethane (67 mg, 10 mol %) in 1,4-dioxane (3 mL) was heated overnight at 90° C. The reaction mixture was filtered through a pad of Celite diatomaceous earth, and the filtrate was concentrated to dryness under reduced pressure. The crude (3R,4S)-tert-butyl 4-(2-cyano-4-(4,4,5,5-tetramethyl-1,3,2-dioxaborolan-2-yl)phenoxy)-3-fluoropiperidine-1-carboxylate was carried forward without further purification. LCMS-ESI$^+$ (m/z): [M+H]$^+$ calcd for $C_{23}H_{33}BFN_2O_5$: 447.2; found: 446.8

Step 4: Preparation of (3R,4S)-tert-butyl 4-(2-cyano-4-(4-((4-(tetrahydro-2H-pyran-4-yl)phenyl)amino)-1,3,5-triazin-2-yl)phenoxy)-3-fluoropiperidine-1-carboxylate A mixture of 4-chloro-N-(4-(tetrahydro-2H-pyran-4-yl)phenyl)-1,3,5-triazin-2-amine (0.15 g, 0.51 mmol), (3R,4S)-tert-butyl 4-(2-cyano-4-(4,4,5,5-tetramethyl-1,3,2-dioxaborolan-2-yl)phenoxy)-3-fluoropiperidine-1-carboxylate (0.66 mmol assumed), and tetrakis(triphenylphosphine)palladium(0) (0.044 g, 7.5 mol %) in 1,2-dimethoxyethane (DME, 3 mL) was treated with 2 M aqueous sodium carbonate solution (1.1 mL). The mixture was irradiated for 75 minutes in a microwave reactor at 130° C. After cooling, the biphasic mixture was separated. The aqueous phase was extracted five times with ethyl acetate. The combined extracts were concentrated to dryness under reduced pressure to provide crude (3R,4S)-tert-butyl 4-(2-cyano-4-(4-((4-(tetrahydro-2H-pyran-4-yl)phenyl)amino)-1,3,5-triazin-2-yl)phenoxy)-3-fluoropiperidine-1-carboxylate, which was carried forward without further purification.

LCMS-ESI$^+$ (m/z): [M+H]$^+$ calcd for $C_{31}H_{36}FN_6O_4$: 575.3; found: 575.1

Step 5: Preparation of 2-(((3R,4S)-3-fluoropiperidin-4-yl)oxy)-5-(4-((4-(tetrahydro-2H-pyran-4-yl)phenyl)amino)-1,3,5-triazin-2-yl)benzonitrile Crude (3R,4S)-tert-butyl 4-(2-cyano-4-(4-((4-(tetrahydro-2H-pyran-4-yl)phenyl)amino)-1,3,5-triazin-2-yl)phenoxy)-3-fluoropiperidine-1-carboxylate (0.51 mmol assumed) was taken up in dichloromethane (6 mL) and treated with trifluoroacetic acid (1.6 mL, 20 mmol). After the completion of the deprotection, the mixture was concentrated under reduced pressure. The residue was purified by flash chromatography (silica gel) to provide 2-(((3R,4S)-3-fluoropiperidin-4-yl)oxy)-5-(4-((4-(tetrahydro-2H-pyran-4-yl)phenyl)amino)-1,3,5-triazin-2-yl)benzonitrile. LCMS-ESI$^+$ (m/z): [M+H]$^+$ calcd for $C_{26}H_{28}FN_6O_2$: 475.2; found: 475.2

Step 6: Preparation of 2-(((3R,4S)-3-fluoro-1-((S)-2-hydroxypropanoyl)piperidin-4-yl)oxy)-5-(4-((4-(tetrahydro-2H-pyran-4-yl)phenyl)amino)-1,3,5-triazin-2-yl)benzonitrile 2-(((3R,4S)-3-fluoropiperidin-4-yl)oxy)-5-(4-((4-(tetrahydro-2H-pyran-4-yl)phenyl)amino)-1,3,5-triazin-2-yl)benzonitrile (73 mg, 0.15 mmol) and L-(−)-lactic acid (Sigma Aldrich, 21 mg, 0.23 mmol) were taken up in N,N-dimethylformamide (1 mL). The mixture was treated successively with N,N-diisopropylethylamine (80 μL, 0.46 mmol) and N-[(dimethylamino)-1H-1,2,3-triazolo-[4,5-b]pyridin-1-ylmethylene]-N-methylmethanaminiumhexafluorophosphate N-oxide (HATU, 88 mg, 0.23 mmol). The mixture remained at room temperature for one hour and was then purified by prep HPLC (5-85% acetonitrile in water, 0.1% trifluoroacetic acid buffer) to provide 2-(((3R,4S)-3-fluoro-1-((S)-2-hydroxypropanoyl)piperidin-4-yl)oxy)-5-(4-((4-(tetrahydro-2H-pyran-4-yl)phenyl)amino)-1,3,5-triazin-2-yl)benzonitrile. LCMS-ESI$^+$ (m/z): [M+H]$^+$ calcd for $C_{29}H_{32}FN_6O_4$: 547.2; found: 547.3 $^1$H NMR (400 MHz, DMSO-d$_6$) δ 10.32 (bs, 1H), 8.84 (s, 1H), 8.64 (dd, J=9.2, 1.9 Hz, 2H), 7.84-7.64 (m. 3H), 7.31 (m, 2H), 5.27-4.98 (m, 2H), 4.51 (m, 2H), 4.31-4.06 (m, 1H), 3.99 (m, 2H), 3.69 (dd, J=28.6, 14.2 Hz, 0.5H), 3.56-3.31 (m, 3H), 3.20 (m, 0.5H), 2.79 (m, 1H), 2.02 (m, 1H), 1.89 (m, 1H), 1.72 (m, 4H), 1.25 (m, 3H).

Example 294

5-(4-((1-(tert-butyl)-1H-pyrazol-4-yl)amino)-1,3,5-triazin-2-yl)-2-(((3R,4S)-3-fluoro-1-((S)-2-hydroxypropanoyl)piperidin-4-yl)oxy)benzonitrile

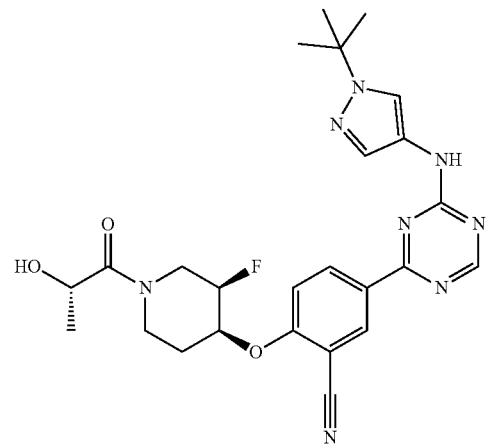 [SMILES: C[C@H](O)C(=O)N1CC[C@H](Oc2ccc(-c3ncnc(Nc4cnn(C(C)(C)C)c4)n3)cc2C#N)[C@H](F)C1]

Step 1: Preparation of N-(1-(tert-butyl)-1H-pyrazol-4-yl)-4-chloro-1,3,5-triazin-2-amine To a solution of 2,4-dichloro-1,3,5-triazine (1.2 g, 7.9 mmol) in N,N-dimethylformamide (DMF, 10 mL) at 0° C. were added sequentially N,N-diisopropylethylamine (DIEA, 1.4 mL, 8.3 mmol) and a solution of 1-(tert-butyl)-1H-pyrazol-4-amine (Matrix Scientific, 1.0 g, 7.2 mmol) in DMF (15 mL). The mixture was allowed to warm to room temperature. The mixture was diluted with ethyl acetate and water. The aqueous phase basified with saturated aqueous sodium hydrogen carbonate solution and then was extracted thrice with ethyl acetate. The combined extracts were dried over anhydrous magnesium sulfate, filtered, and concentrated under reduced pressure. The residue was purified by flash chromatography (silica gel) to provide N-(1-(tert-butyl)-1H-pyrazol-4-yl)-4-chloro-1,3,5-triazin-2-amine. LCMS-ESI$^+$ (m/z): [M+H]$^+$ calcd for $C_{10}H_{14}ClN_6$: 253.1; found: 252.9

Step 2: Preparation of (3R,4S)-tert-butyl 4-(4-(4-((1-(tert-butyl)-1H-pyrazol-4-yl)amino)-1,3,5-triazin-2-yl)-2-cyanophenoxy)-3-fluoropiperidine-1-carboxylate A mixture of N-(1-(tert-butyl)-1H-pyrazol-4-yl)-4-chloro-1,3,5-triazin-2-amine (0.11 g, 0.42 mmol), crude (3R,4S)-tert-butyl 4-(2-cyano-4-(4,4,5,5-tetramethyl-1,3,2-dioxaborolan-2-yl)phenoxy)-3-fluoropiperidine-1-carboxylate (0.52 mmol assumed), and tetrakis(triphenylphosphine)palladium(0) (0.036 g, 7.5 mol %) in 1,2-dimethoxyethane (DME, 3 mL) was treated with 2 M aqueous sodium carbonate solution (0.94 mL). The mixture was irradiated for 75 minutes in a microwave reactor at 130° C. After cooling, the biphasic mixture was separated. The aqueous phase was extracted five times with ethyl acetate. The combined extracts were concentrated to dryness under reduced pressure to provide crude (3R,4S)-tert-butyl 4-(4-(4-((1-(tert-butyl)-1H-pyrazol-4-yl)amino)-1,3,5-triazin-2-yl)-2-cyanophenoxy)-3-fluoropiperidine-1-carboxylate, which was carried forward without further purification. LCMS-ESI$^+$ (m/z): calcd for $C_{27}H_{34}FN_8O_3$: 537.3; found: 537.1

Step 3: Preparation of 5-(4-((1-(tert-butyl)-1H-pyrazol-4-yl)amino)-1,3,5-triazin-2-yl)-2-(((3R,4S)-3-fluoropiperidin-4-yl)oxy)benzonitrile (3R,4S)-tert-butyl 4-(4-(4-((1-(tert-butyl)-1H-pyrazol-4-yl)amino)-1,3,5-triazin-2-yl)-2-cyanophenoxy)-3-fluoropiperidin-1-carboxylate (0.42 mmol assumed) was taken up in dichloromethane (6 mL) and treated with trifluoroacetic acid (1.3 mL, 17 mmol). After the passage of two hours, the mixture was concentrated under reduced pressure. The residue was purified by flash chromatography (silica gel) to provide 5-(4-((1-(tert-butyl)-1H-pyrazol-4-yl)amino)-1,3,5-triazin-2-yl)-2-(((3R,4S)-3-fluoropiperidin-4-yl)oxy)benzonitrile. LCMS-ESI$^+$ (m/z): [M+H]$^+$ calcd for $C_{22}H_{26}FN_8O$: 437.2; found: 437.1

Step 4: Preparation of 5-(4-((1-(tert-butyl)-1H-pyrazol-4-yl)amino)-1,3,5-triazin-2-yl)-2-(((3R,4S)-3-fluoro-1-((S)-2-hydroxypropanoyl)piperidin-4-yl)oxy)benzonitrile 5-(4-((1-(tert-butyl)-1H-pyrazol-4-yl)amino)-1,3,5-triazin-2-yl)-2-(((3R,4S)-3-fluoropiperidin-4-yl)oxy)benzonitrile (87 mg, 0.20 mmol) and L-(−)-lactic acid (Sigma Aldrich, 27 mg, 0.30 mmol) were taken up in N,N-dimethylformamide (1 mL). The mixture was treated successively with N,N-diisopropylethylamine (100 µL, 0.60 mmol) and N-[(dimethylamino)-1H-1,2,3-triazolo-[4,5-b]pyridin-1-ylmethylene]-N-methylmethanaminiumhexafluorophosphate N-oxide (HATU, 110 mg, 0.30 mmol). The mixture remained at room temperature for one hour and then was refrigerated for 2 days. The mixture was purified by prep HPLC (5-85% acetonitrile in water, 0.1% trifluoroacetic acid buffer) to provide 5-(4-((1-(tert-butyl)-1H-pyrazol-4-yl)amino)-1,3,5-triazin-2-yl)-2-(((3R,4S)-3-fluoro-1-((S)-2-hydroxypropanoyl)piperidin-4-yl)oxy)benzonitrile.

LCMS-ESI$^+$ (m/z): [M+H]$^+$ calcd for $C_{25}H_{30}FN_8O_3$: 509.2; found: 509.2 $^1$H NMR (400 MHz, DMSO-d$_6$) δ 10.35 (s, 0.6H), 10.30 (s, 0.4H), 8.86 (s, 0.4H), 8.76 (s, 0.6H), 8.70-8.55 (m, 2H), 8.15 (s, 0.6H), 8.05 (s, 0.4H), 7.72 (s, 0.6H), 7.68 (m, 1H), 7.65 (s, 0.4H), 5.28-4.99 (m, 3H), 4.52 (m, 1H), 4.45 (m, 0.5H), 4.22 (m, 0.5H), 4.12 (m, 0.5H), 4.00 (m, 0.5H), 3.69 (dd, J=28.7, 14.4 Hz, 0.5H), 3.39 (m, 1H), 3.22 (m, 0.5H), 2.01 (m, 1.5H), 1.89 (m, 0.5H), 1.61 (s, 5H), 1.56 (s, 4H), 1.25 (dd, J=6.4, 3.5 Hz, 3H).

Example 295 rac-2-(((1S,2R)-2-fluorocyclohexyl)oxy)-5-(4-((1-(piperidin-4-yl)-1H-pyrazol-4-yl)amino)-1,3,5-triazin-2-yl)benzonitrile

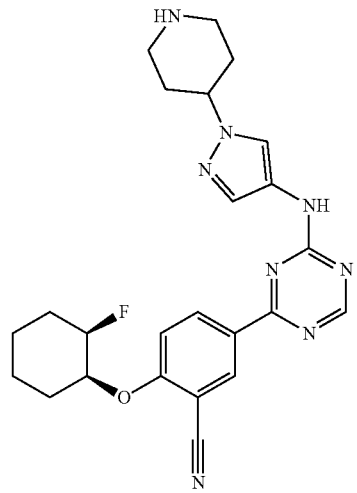 [SMILES: N#Cc1cc(-c2ncnc(Nc3cnn(C4CCNCC4)c3)n2)ccc1O[C@H]1CCCC[C@H]1F]

Step 1: Preparation of tert-butyl 4-(4-((4-chloro-1,3,5-triazin-2-yl)amino)-1H-pyrazol-1-yl)piperidine-1-carboxylate:

To a solution of 2,4-dichloro-1,3,5-triazine (0.62 g, 4.1 mmol) in N,N-dimethylformamide (DMF, 10 mL) at 0° C. were added sequentially N,N-diisopropylethylamine (DIEA, 0.75 mL, 4.3 mmol) and tert-butyl 4-(4-amino-1H-pyrazol-1-yl)piperidine-1-carboxylate (Combi-Blocks, 1.0 g, 3.8 mmol). The mixture was allowed to warm to room temperature. The mixture was diluted with ethyl acetate and water. The aqueous phase basified with saturated aqueous sodium hydrogen carbonate solution and then was extracted thrice with ethyl acetate. The combined extracts were dried over anhydrous magnesium sulfate, filtered, and concentrated under reduced pressure. The residue was purified by flash chromatography (silica gel) to provide tert-butyl 4-(4-((4-chloro-1,3,5-triazin-2-yl)amino)-1H-pyrazol-1-yl)piperidine-1-carboxylate. LCMS-ESI$^+$ (m/z): [M+H]$^+$ calcd for $C_{16}H_{23}ClN_7O_2$: 380.2; found: 379.8

Step 2: Preparation of rac-tert-butyl 4-(4-((4-(3-cyano-4-(((1S,2R)-2-fluorocyclohexyl)oxy)phenyl)-1,3,5-triazin-2-yl)amino)-1H-pyrazol-1-yl)piperidine-1-carboxylate:

A mixture tert-butyl 4-(4-((4-chloro-1,3,5-triazin-2-yl)amino)-1H-pyrazol-1-yl)piperidine-1-carboxylate (0.15 g, 0.40 mmol), crude rac-2-(((1S,2R)-2-fluorocyclohexyl)oxy)-5-(4,4,5,5-tetramethyl-1,3,2-dioxaborolan-2-yl)benzonitrile (0.52 mmol assumed), and tetrakis(triphenylphosphine)palladium(0) (0.035 g, 7.5 mol %) in 1,2-dimethoxyethane (DME, 3 mL) was treated with 2 M aqueous sodium carbonate solution (0.90 mL). The mixture was irradiated for 75 minutes in a microwave reactor at 130° C. After cooling, the biphasic mixture was separated. The aqueous phase was extracted five times with ethyl acetate. The combined extracts were concentrated to dryness under reduced pressure and purified by flash chromatography on silica gel to provide rac-tert-butyl 4-(4-((4-(3-cyano-4-(((1S,2R)-2-fluorocyclohexyl)oxy)phenyl)-1,3,5-triazin-2-yl)amino)-1H-pyrazol-1-yl)piperidine-1-carboxylate. LCMS-ESI$^+$ (m/z): [M+H]$^+$ calcd for $C_{29}H_{36}FN_8O_3$: 563.3; found: 563.2

Step 3: Preparation of rac-2-(((1S,2R)-2-fluorocyclohexyl)oxy)-5-(4-((1-(piperidin-4-yl)-1H-pyrazol-4-yl)amino)-1,3,5-triazin-2-yl)benzonitrile:

rac-tert-butyl 4-(4-((4-(3-cyano-4-(((1S,2R)-2-fluorocyclohexyl)oxy)phenyl)-1,3,5-triazin-2-yl)amino)-1H-pyrazol-1-yl)piperidine-1-carboxylate (0.13 g, 0.24 mmol) was taken up in dichloromethane (6 mL) and treated with trifluoroacetic acid (0.72 mL, 9.4 mmol). After standing overnight at room temperature, the mixture was concentrated under reduced pressure. The residue was purified by flash chromatography (silica gel) to provide rac-2-(((1S,2R)-2-fluorocyclohexyl)oxy)-5-(4-((1-(piperidin-4-yl)-1H-pyrazol-4-yl)amino)-1,3,5-triazin-2-yl)benzonitrile. LCMS-ESI$^+$ (m/z): [M+H]$^+$ calcd for $C_{24}H_{28}FN_8O$: 463.2; found: 463.3 $^1$H NMR (400 MHz, DMSO-d$_6$) δ 10.35 (s, 1H), 8.85 (s, 0.5H), 8.76 (s, 0.5H), 8.68-8.57 (m, 2H), 6.06 (d, J=5.4 Hz, 1H), 7.79 (s, 0.5H), 7.67 (s, 0.5H), 7.64-7.56 (m, 1H), 5.15-4.86 (m, 2H), 4.48 (m, 1H), 3.36 (m, 3H), 2.98 (m, 2H), 2.28-2.00 (m, 5H), 2.00-1.77 (m, 2H), 1.77-1.60 (m, 2H), 1.48 (m, 3H).

Example 296

2-(((3R,4S)-3-fluoro-1-formylpiperidin-4-yl)oxy)-5-(4-((3-fluoro-4-(piperazin-1-yl)phenyl)amino)-1,3,5-triazin-2-yl)benzonitrile

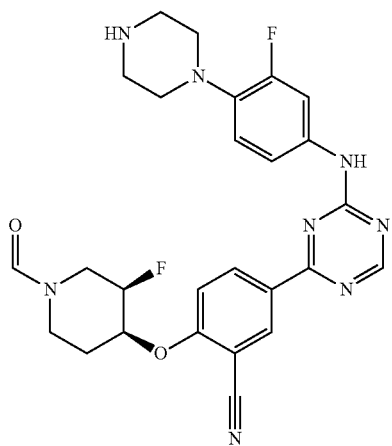 [SMILES: N#Cc1cc(-c2ncnc(Nc3ccc(N4CCNCC4)c(F)c3)n2)ccc1O[C@H]1CCN(C=O)C[C@H]1F]

Step 1: Preparation of tert-butyl 4-(4-((4-chloro-1,3,5-triazin-2-yl)amino)-2-fluorophenyl)piperazine-1-carboxylate:

To a solution of 2,4-dichloro-1,3,5-triazine (0.95 g, 6.3 mmol) in N,N-dimethylformamide (DMF, 10 mL) at 0° C. were added sequentially N,N-diisopropylethylamine (DIEA, 1.2 mL, 6.6 mmol) and a solution of tert-butyl 4-(4-amino-2-fluorophenyl)piperazine-1-carboxylate (1.7 g, 5.8 mmol) in DMF (10 mL). The mixture was allowed to warm to room temperature. The mixture was diluted with ethyl acetate and saturated aqueous sodium hydrogen carbonate solution. The aqueous phase was extracted thrice each with ethyl acetate and dichloromethane. The combined extracts were concentrated under reduced pressure. The residue was purified by flash chromatography (silica gel) to provide tert-butyl 4-(4-((4-chloro-1,3,5-triazin-2-yl)amino)-2-fluorophenyl)piperazine-1-carboxylate. LCMS-ESI$^+$ (m/z): [M+H]$^+$ calcd for $C_{18}H_{23}ClFN_6O_2$: 409.2; found: 408.8

Step 2: Preparation of 5-bromo-2-(((3R,4S)-3-fluoropiperidin-4-yl)oxy)benzonitrile hydrochloride:

A mixture of (3R,4S)-tert-butyl 4-(4-bromo-2-cyanophenoxy)-3-fluoropiperidine-1-carboxylate (1.4 g, 3.4 mmol) in 4 N hydrogen chloride/dioxanes (20 mL) was stirred for 30 minutes at 35-40° C. At the completion of the reaction, as determined by LC analysis, the mixture was concentrated under reduced pressure to provide 5-bromo-2-(((3R,4S)-3-fluoropiperidin-4-yl)oxy)benzonitrile hydrochloride. LCMS-ESI$^+$ (m/z): [M+H]$^+$ calcd for $C_{12}H_{13}BrFN_2O$: 299.0; found: 299.1

Step 3: Preparation of 5-bromo-2-(((3R,4S)-3-fluoro-1-formylpiperidin-4-yl)oxy)benzonitrile:

5-bromo-2-(((3R,4S)-3-fluoropiperidin-4-yl)oxy)benzonitrile hydrochloride (1.1 g, 3.2 mmol) was taken up as a suspension in N,N-dimethylformamide and was treated sequentially with the following reagents: N,N-diisopropylethylamine (2.2 mL, 13 mmol), formic acid (0.14 mL, 3.8 mmol), and N-[(dimethylamino)-1H-1,2,3-triazolo-[4,5-b]pyridin-1-ylmethylene]-N-methylmethanaminiumhexafluorophosphate N-oxide (HATU, 1.5 g, 3.9 mmol). in an effervescent and exothermic reaction. The resulting suspension was swirled manually for about one minute until homogeneous. The mixture was refrigerated for 2 days.

Mixture was diluted with saturated aqueous sodium hydrogen carbonate solution and extracted three times with ethyl acetate. The combined organic extracts were washed once with water and once with saturated aqueous sodium chloride solution and then dried over anhydrous magnesium sulfate, filtered, concentrated to dryness under reduced pressure to provide 5-bromo-2-(((3R,4S)-3-fluoro-1-formylpiperidin-4-yl)oxy)benzonitrile. LCMS-ESI$^+$ (m/z): [M+H]$^+$ calcd for $C_{13}H_{13}BrFN_2O_2$: 327.0; found: 327.1

Step 4: Preparation of 2-(((3R,4S)-3-fluoro-1-formylpiperidin-4-yl)oxy)-5-(4,4,5,5-tetramethyl-1,3,2-dioxaborolan-2-yl)benzonitrile:

A mixture of 5-bromo-2-(((3R,4S)-3-fluoro-1-formylpiperidin-4-yl)oxy)benzonitrile (0.38 g, 1.2 mmol), bis(pinacolato)diboron (0.59 g, 2.3 mmol), potassium acetate (0.34 g, 3.5 mmol), and [1,1'-bis(diphenylphosphino)ferrocene]dichloropalladium(II) complex with dichloromethane (84 mg, 10 mol %) in 1,4-dioxane (6 mL) was heated overnight at 90° C. The reaction mixture was filtered through a pad of Celite diatomaceous earth, and the filtrate was concentrated to dryness under reduced pressure. The crude 2-(((3R,4S)-3-fluoro-1-formylpiperidin-4-yl)oxy)-5-(4,4,5,5-tetramethyl-1,3,2-dioxaborolan-2-yl)benzonitrile was carried forward without further purification. LCMS-ESI$^+$ (m/z): [M+H]$^+$ calcd for $C_{19}H_{25}BFN_2O_4$: 375.2; found: 375.3

Step 5: Preparation of tert-butyl 4-(4-((4-(3-cyano-4-(((3R,4S)-3-fluoro-1-formylpiperidin-4-yl)oxy)phenyl)-1,3,5-triazin-2-yl)amino)-2-fluorophenyl)piperazine-1-carboxylate:

A mixture of tert-butyl 4-(4-((4-chloro-1,3,5-triazin-2-yl)amino)-2-fluorophenyl)piperazine-1-carboxylate (0.31 g, 0.75 mmol), crude 2-(((3R,4S)-3-fluoro-1-formylpiperidin-4-yl)oxy)-5-(4,4,5,5-tetramethyl-1,3,2-dioxaborolan-2-yl)benzonitrile (1.1 mmol assumed), and tetrakis(triphenylphosphine)palladium(0) (0.065 g, 7.5 mol %) in 1,2-dimethoxyethane (DME, 7 mL) was treated with 2 M aqueous sodium carbonate solution (2.5 mL). The mixture was irradiated for 75 minutes in a microwave reactor at 130° C. After cooling, the biphasic mixture was separated. The aqueous phase was extracted five times with ethyl acetate. The combined extracts were concentrated to dryness under reduced pressure to provide crude tert-butyl 4-(4-((4-(3-cyano-4-(((3R,4S)-3-fluoro-1-formylpiperidin-4-yl)oxy)phenyl)-1,3,5-triazin-2-yl)amino)-2-fluorophenyl)piperazine-1-carboxylate, which was carried forward without further purification.

LCMS-ESI$^+$ (m/z): [M+H]$^+$ calcd for $C_{31}H_{34}F_2N_8O_4$: 621.3; found: 620.8

Step 6: Preparation of 2-(((3R,4S)-3-fluoro-1-formylpiperidin-4-yl)oxy)-5-(4-((3-fluoro-4-(piperazin-1-yl)phenyl)amino)-1,3,5-triazin-2-yl)benzonitrile:

Crude tert-butyl 4-(4-((4-(3-cyano-4-(((3R,4S)-3-fluoro-1-formylpiperidin-4-yl)oxy)phenyl)-1,3,5-triazin-2-yl)amino)-2-fluorophenyl)piperazine-1-carboxylate (0.75 mmol assumed) was taken up in dichloromethane (6 mL) and treated with trifluoroacetic acid (2.3 mL, 30 mmol). After standing for two hours at room temperature, the mixture was concentrated under reduced pressure. The residue was purified first by flash chromatography (silica gel) and then by prep HPLC (5-75% acetonitrile in water, 0.1% trifluoroacetic acid buffer). The combined HPLC fractions were basified with 0.5 M sodium hydroxide solution and extracted three times with dichloromethane. The combined organics were dried over anhydrous magnesium sulfate, filtered, concentrated to provide 2-(((3R,4S)-3-fluoro-1-formylpiperidin-4-yl)oxy)-5-(4-((3-fluoro-4-(piperazin-1-yl)phenyl)amino)-1,3,5-triazin-2-yl)benzonitrile. LCMS-ESI$^+$ (m/z): [M+H]$^+$ calcd for $C_{26}H_{27}F_2N_8O_2$: 521.2; found: 521.4 $^1$H NMR (400 MHz, DMSO-d$_6$) δ 10.40 (bs, 1H), 8.86 (bs, 1H), 8.71-8.55 (m, 2H), 8.17 (s, 0.5H), 8.06 (s, 0.5H), 7.78-7.65 (m, 2H), 7.47 (bs, 1H), 7.07 (dd, J=9.3 Hz, 1H), 5.26-5.11 (m, 1.5H), 5.07 (m, 0.5H), 4.36-4.24 (m, 0.5H), 4.17-4.05 (m, 0.5H), 3.97 (m, 0.5H), 3.79 (m, 1H), 3.69-3.52 (m, 0.5H), 3.36 (m, 2H), 3.09 (m, 0.5H), 3.02-2.83 (m, 8H), 2.18-1.90 (m, 1.5H), 1.90-1.75 (m, 0.5H).

Example 297

2-(((3R,4S)-3-fluorotetrahydro-2H-pyran-4-yl)oxy)-5-(4-((4-(4-(oxetan-3-yl)piperazin-1-yl)phenyl)amino)-1,3,5-triazin-2-yl)benzonitrile

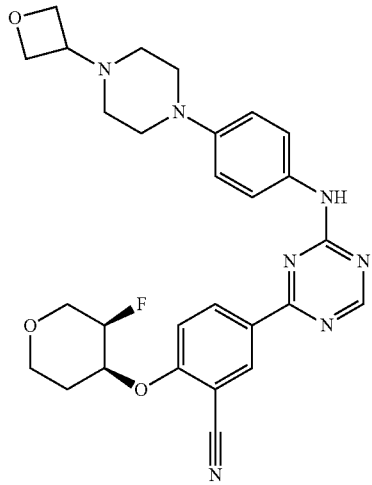 [SMILES: N#Cc1cc(-c2ncnc(Nc3ccc(N4CCN(C5COC5)CC4)cc3)n2)ccc1O[C@H]1CCOC[C@H]1F]

Step 1: Preparation of (3R,4S)-3-fluorotetrahydro-2H-pyran-4-ol:

(R)-3-fluorodihydro-2H-pyran-4(3H)-one was prepared according to Kwiatkowski, P. et al J. Am. Chem. Soc., 2011, 133 (6), 1738-1741.

A stirred solution of (R)-3-fluorodihydro-2H-pyran-4(3H)-one (1.0 g, 8.5 mmol) in tetrahydrofuran (10 mL) was cooled to −78° C. under an Argon atmosphere. L-Selectride solution in tetrahydrofuran (1.0 M, 8.9 mL) was added dropwise and the reaction was stirred for 30 minutes. Methanol (32 μL) and 1 M aqueous sodium hydroxide solution (25 mL) were then added, and the reaction was allowed to warm to 0° C. To the solution was added slowly dropwise 30 wt % hydrogen peroxide solution (4.3 mL), and the reaction was stirred for an additional 30 minutes. The reaction mixture was extracted four times with ethyl acetate. The combined extracts were dried over anhydrous sodium sulfate, decanted, concentrated under reduced pressure. The residue was purified by flash chromatography (silica gel) to provide (3R,4S)-3-fluorotetrahydro-2H-pyran-4-ol. $^1$H NMR (400 MHz, Chloroform-d) δ 4.74-4.49 (m, 1H), 4.04 (dddd, J=12.7, 9.4, 5.0, 1.1 Hz, 1H), 3.97-3.84 (m, 2H), 3.58 (ddd, J=27.0, 12.6, 2.3 Hz, 1H), 3.46 (dddd, J=11.9, 8.6, 3.4, 1.9 Hz, 1H), 2.00-1.79 (m, 2H).

Step 2: Preparation of 2-(((3R,4S)-3-fluorotetrahydro-2H-pyran-4-yl)oxy)-5-(4-((4-(4-(oxetan-3-yl)piperazin-1-yl)phenyl)amino)-1,3,5-triazin-2-yl)benzonitrile Potassium tert-butoxide (0.066 g, 0.58 mmol) was added to a solution of (3R,4S)-3-fluorotetrahydro-2H-pyran-4-ol (0.07 g, 0.59 mmol) in 2-methyltetrahydrofuran (3 mL), cooled in an ice-water bath. The resulting suspension was stirred at room temperature for 5 hours before the addition of 2-fluoro-5-(4-((4-(4-(oxetan-3-yl)piperazin-1-yl)phenyl)amino)-1,3,5-triazin-2-yl)benzonitrile (0.085 g, 0.20 mmol). The mixture was heated at 75° C. overnight and was then purified by flash chromatography (silica gel) to provide 2-(((3R,4S)-3-fluorotetrahydro-2H-pyran-4-yl)oxy)-5-(4-((4-(4-(oxetan-3-yl)piperazin-1-yl)phenyl)amino)-1,3,5-triazin-2-yl)benzonitrile. LCMS-ESI$^+$ (m/z): calcd for $C_{28}H_{31}FN_7O_3$: 532.2; found: 532.3

$^1$H NMR (400 MHz, DMSO-d$_6$) δ 10.17 (d, J=23.9 Hz, 1H), 8.78 (s, 1H), 8.62 (m, 2H), 7.68 (d, J=9.2 Hz, 1H), 7.64 (m, 2H), 7.01 (m, 2H), 5.24-5.01 (m, 1.5H), 4.95 (m, 0.5H), 4.61 (t, J=6.5 Hz, 2H), 4.52 (t, J=6.0 Hz, 2H), 4.05 (m, 1H), 3.98-3.89 (m, 1H), 3.80-3.64 (m, 1H), 3.64-3.55 (m, 1H), 3.50 (m, 1H), 3.18 (m, 4H), 2.45 (m, 4H), 2.14-1.95 (m, 2H).

Example 298

5-(4-((3-fluoro-4-(piperazin-1-yl)phenyl)amino)-1,3,5-triazin-2-yl)-2-(((3R,4S)-3-fluorotetrahydro-2H-pyran-4-yl)oxy)benzonitrile

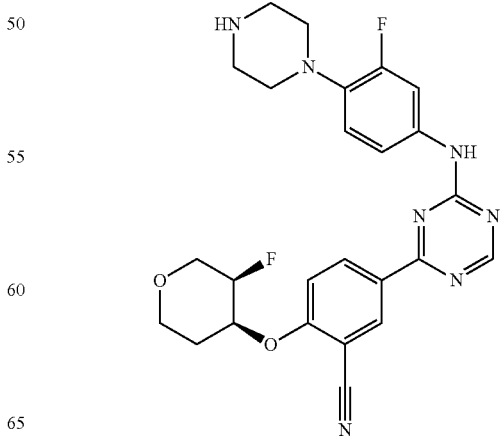

Step 1: Preparation of tert-butyl 4-(4-((4-(3-cyano-4-fluorophenyl)-1,3,5-triazin-2-yl)amino)-2-fluorophenyl)piperazine-1-carboxylate:

A mixture of tert-butyl 4-(4-((4-chloro-1,3,5-triazin-2-yl)amino)-2-fluorophenyl)piperazine-1-carboxylate (0.50 g, 1.2 mmol), 2-fluoro-5-(4,4,5,,5-tetramethyl-1,3,2-dioxaborolan-2-yl)benzonitrile (0.33 g, 1.3 mmol), and tetrakis(triphenylphosphine)palladium(0) (0.11 g, 7.5 mol %) in 1,2-dimethoxyethane (DME, 7 mL) was treated with 2 M aqueous sodium carbonate solution (2.7 mL). The mixture was irradiated for 75 minutes in a microwave reactor at 130° C. After cooling, the biphasic mixture was separated. The aqueous phase was extracted five times with ethyl acetate. The combined extracts were concentrated to dryness under reduced pressure and the residue was purified by flash chromatography (silica gel) to provide tert-butyl 4-(4-((4-(3-cyano-4-fluorophenyl)-1,3,5-triazin-2-yl)amino)-2-fluorophenyl)piperazine-1-carboxylate. LCMS-ESI$^+$ (m/z): [M+H]$^+$ calcd for $C_{25}H_{26}F_2N_7O_2$: 494.2; found: 493.8

Step 2: Preparation of tert-butyl 4-(4-((4-(3-cyano-4-(((3R,4S)-3-fluorotetrahydro-2H-pyran-4-yl)oxy)phenyl)-1,3,5-triazin-2-yl)amino)-2-fluorophenyl)piperazine-1-carboxylate Potassium tert-butoxide (0.11 g, 0.97 mmol) was added to a solution of (3R,4S)-3-fluorotetrahydro-2H-pyran-4-ol (0.12 g, 0.97 mmol) in 2-methyltetrahydrofuran (5 mL), cooled in an ice-water bath. The resulting suspension was stirred at room temperature for 5 hours before the addition of tert-butyl 4-(4-((4-(3-cyano-4-fluorophenyl)-1,3,5-triazin-2-yl)amino)-2-fluorophenyl)piperazine-1-carboxylate (0.24 g, 0.49 mmol). The mixture was concentrated under reduced pressure to provide crude tert-butyl 4-(4-((4-(3-cyano-4-(((3R,4S)-3-fluorotetrahydro-2H-pyran-4-yl)oxy)phenyl)-1,3,5-triazin-2-yl)amino)-2-fluorophenyl)piperazine-1-carboxylate, which was carried forward without further purification.

LCMS-ESI$^+$ (m/z): [M+H]$^+$ calcd for $C_{30}H_{34}F_2N_7O_4$: 594.3; found: 593.9

Step 3: Preparation of 5-(4-((3-fluoro-4-(piperazin-1-yl)phenyl)amino)-1,3,5-triazin-2-yl)-2-(((3R,4S)-3-fluorotetrahydro-2H-pyran-4-yl)oxy)benzonitrile Crude tert-butyl 4-(4-((4-(3-cyano-4-(((3R,4S)-3-fluorotetrahydro-2H-pyran-4-yl)oxy)phenyl)-1,3,5-triazin-2-yl)amino)-2-fluorophenyl)piperazine-1-carboxylate (0.49 mmol assumed) was taken up in dichloromethane (5 mL) and treated with trifluoroacetic acid (1.5 mL, 19 mmol). After standing for one hour at room temperature, the mixture was concentrated under reduced pressure. The residue was purified by flash chromatography (silica gel) to provide 5-(4-((3-fluoro-4-(piperazin-1-yl)phenyl)amino)-1,3,5-triazin-2-yl)-2-(((3R,4S)-3-fluorotetrahydro-2H-pyran-4-yl)oxy)benzonitrile. LCMS-ESI$^+$ (m/z): [M+H]$^+$ calcd for $C_{25}H_{26}F_2N_7O_2$: 494.2; found: 494.3 $^1$H NMR (400 MHz, DMSO-d$_6$) δ 10.45 (bs, 1H), 8.88 (s, 1H), 8.62 (m, 2H), 8.44 (bs, 2H), 7.79 (dd, J=14.9, 2.4 Hz, 1H), 7.69 (d, J=9.2 Hz, 1H), 7.51 (d, J=8.9 Hz, 1H), 7.17 (dd, J=9.4 Hz, 1H), 5.24-5.09 (m, 1H), 5.01 (d, J=49.5 Hz, 1H), 4.12-3.99 (m, 1H), 3.94 (m, 1H), 3.81-3.65 (m, 1H), 3.61 (m, 1H), 3.48-3.13 (m, 8H), 2.05 (m, 2H).

Example 299

5-(4-((3-fluoro-4-(4-formylpiperazin-1-yl)phenyl)amino)-1,3,5-triazin-2-yl)-2-(((3R,4S)-3-fluorotetrahydro-2H-pyran-4-yl)oxy)benzonitrile

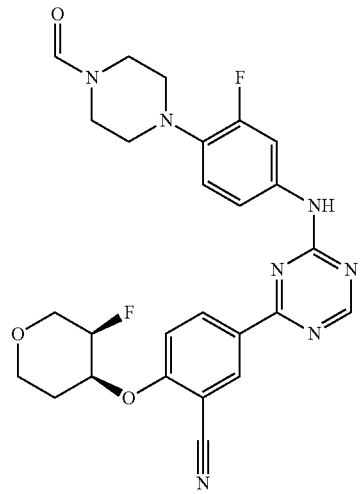 [SMILES: N#Cc1cc(-c2ncnc(Nc3ccc(N4CCN(C=O)CC4)c(F)c3)n2)ccc1O[C@H]1CCOC[C@H]1F]

Formic acid (14 mg, 0.30 mmol) was added to a solution of 5-(4-((3-fluoro-4-(piperazin-1-yl)phenyl)amino)-1,3,5-triazin-2-yl)-2-(((3R,4S)-3-fluorotetrahydro-2H-pyran-4-yl)oxy)benzonitrile (71 mg, 0.14 mmol) in N,N-dimethylformamide (1 mL). The mixture was treated successively with N,N-diisopropylethylamine (100 μL, 0.58 mmol) and N-[(dimethylamino)-1H-1,2,3-triazolo-[4,5-b]pyridin-1-ylmethylene]-N-methylmethanaminiumhexafluorophosphate N-oxide (HATU, 110 mg, 0.29 mmol). The mixture was purified by prep HPLC (5-70% acetonitrile in water, 0.1% trifluoroacetic acid buffer) to provide 5-(4-((3-fluoro-4-(4-formylpiperazin-1-yl)phenyl)amino)-1,3,5-triazin-2-yl)-2-(((3R,4S)-3-fluorotetrahydro-2H-pyran-4-yl)oxy)benzonitrile. LCMS-ESI$^+$ (m/z): [M+H]$^+$ calcd for $C_{26}H_{26}F_2N_7O_3$: 522.2; found: 522.3 $^1$H NMR (400 MHz, DMSO-d$_6$) δ 10.44 (bs, 1H), 8.87 (bs, 1H), 8.61 (m, 2H), 8.12 (s, 1H), 7.77 (dd, J=14.8, 2.4 Hz, 1H), 7.70 (d, J=9.0 Hz, 1H), 7.51 (br, 1H), 7.12 (dd, J=9.3 Hz, 1H), 5.15 (m, 1H), 5.00 (m, 1H), 4.06 (m, 1H), 3.94 (m, 1H), 3.69 (m, 1H), 3.58 (m. 5H), 3.01 (dt, J=24.4. 5.0 Hz, 4H), 2.14-1.96 (m, 2H).

Example 300

2-(((3R,4S)-3-fluorotetrahydro-2H-pyran-4-yl)oxy)-5-(4-((4-(1-methylpiperidin-4-yl)phenyl)amino)-1,3,5-triazin-2-yl)benzonitrile

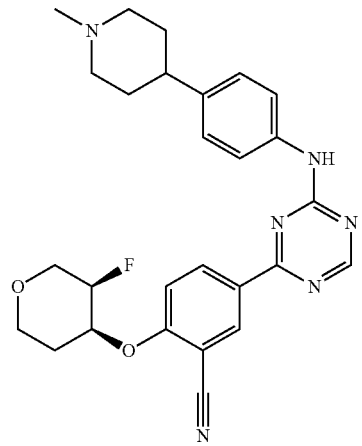 [SMILES: CN1CCC(c2ccc(Nc3ncnc(-c4ccc(O[C@H]5CCOC[C@H]5F)c(C#N)c4)n3)cc2)CC1]

Step 1: Preparation of tert-butyl 4-(4-((4-(3-cyano-4-fluorophenyl)-1,3,5-triazin-2-yl)amino)phenyl)piperidine-1-carboxylate: A mixture of tert-butyl 4-(4-((4-chloro-1,3,5-triazin-2-yl)amino)phenyl)piperidine-1-carboxylate (0.41 g, 1.2 mmol), 2-fluoro-5-(4,4,5,5-tetramethyl-1,3,2-dioxaborolan-2-yl)benzonitrile (0.29 g, 1.2 mmol), and tetrakis(triphenylphosphine)palladium(0) (0.09 g, 7.5 mol %) in 1,2-dimethoxyethane (DME, 7 mL) was treated with 2 M aqueous sodium carbonate solution (2.4 mL). The mixture was irradiated for 75 minutes in a microwave reactor at 130° C. After cooling, the biphasic mixture was separated. The aqueous phase was extracted five times with ethyl acetate. The combined extracts were concentrated to dryness under reduced pressure and the residue was purified by flash chromatography (silica gel) to provide tert-butyl 4-(4-((4-(3-cyano-4-fluorophenyl)-1,3,5-triazin-2-yl)amino)phenyl)piperidine-1-carboxylate. LCMS-ESI⁺ (m/z): [M+H]⁺ calcd for $C_{26}H_{28}FN_6O_2$: 475.2; found: 475.0

Step 2: Preparation of tert-butyl 4-(4-((4-(3-cyano-4-(((3R,4S)-3-fluorotetrahydro-2H-pyran-4-yl)oxy)phenyl)-1,3,5-triazin-2-yl)amino)phenyl)piperidine-1-carboxylate Potassium tert-butoxide (0.14 g, 1.3 mmol) was added to a solution of (3R,4S)-3-fluorotetrahydro-2H-pyran-4-ol (0.15 g, 1.3 mmol) in 2-methyltetrahydrofuran (6 mL), cooled in an ice-water bath. The resulting suspension was stirred in the bath for 10 minutes and then at room temperature for 30 minutes before the addition of tert-butyl 4-(4-((4-(3-cyano-4-fluorophenyl)-1,3,5-triazin-2-yl)amino)phenyl)piperidine-1-carboxylate (0.38 g, 0.80 mmol). The mixture was heated at 75° C. overnight and then concentrated under reduced pressure to provide crude tert-butyl 4-(4-((4-(3-cyano-4-(((3R,4S)-3-fluorotetrahydro-2H-pyran-4-yl)oxy)phenyl)-1,3,5-triazin-2-yl)amino)phenyl)piperidine-1-carboxylate, which was carried forward without further purification. LCMS-ESI⁺ (m/z): [M+H]⁺ calcd for $C_{31}H_{36}FN_6O_4$: 575.3; found: 575.2

Step 3: Preparation of 2-(((3R,4S)-3-fluorotetrahydro-2H-pyran-4-yl)oxy)-5-(4-((4-(piperidin-4-yl)phenyl)amino)-1,3,5-triazin-2-yl)benzonitrile:

A mixture of crude tert-butyl 4-(4-((4-(3-cyano-4-(((3R,4S)-3-fluorotetrahydro-2H-pyran-4-yl)oxy)phenyl)-1,3,5-triazin-2-yl)amino)phenyl)piperidine-1-carboxylate (0.80 mmol assumed) in dichloromethane (8 mL) was treated with trifluoroacetic acid (2.5 mL, 32 mmol). After three hours of standing at room temperature, the mixture was concentrated under reduced pressure and purified by flash chromatography (silica gel) to provide 2-(((3R,4S)-3-fluorotetrahydro-2H-pyran-4-yl)oxy)-5-(4-((4-(piperidin-4-yl)phenyl)amino)-1,3,5-triazin-2-yl)benzonitrile. LCMS-ESI⁺ (m/z): [M+H]⁺ calcd for $C_{26}H_{28}FN_6O_2$: 475.2; found: 475.3

Step 4: Preparation of 2-(((3R,4S)-3-fluorotetrahydro-2H-pyran-4-yl)oxy)-5-(4-((4-(1-methylpiperidin-4-yl)phenyl)amino)-1,3,5-triazin-2-yl)benzonitrile:

A solution of 2-(((3R,4S)-3-fluorotetrahydro-2H-pyran-4-yl)oxy)-5-(4-((4-(piperidin-4-yl)phenyl)amino)-1,3,5-triazin-2-yl)benzonitrile (67 mg, 0.14 mmol) in methanol was treated with 37% formalin solution (42 µL, 0.57 mmol). After five minutes of stirring at room temperature, the mixture was treated with sodium tri(acetoxy)borohydride (0.15 g, 0.71 mmol), and the reaction mixture was stirred overnight at room temperature. The mixture was concentrated to dryness under reduced pressure. The residue was suspended in 1 M aqueous sodium hydroxide solution (~2 mL). After five minutes, the mixture was extracted three times with dichloromethane. The combined organic phases were dried over anhydrous magnesium sulfate, filtered, and evaporated. The residue was purified first by flash chromatography (silica gel) and then by prep HPLC (5-65% acetonitrile in water, 0.1% trifluoroacetic acid buffer). The combined HPLC fractions were basified with 0.5 M sodium hydroxide solution and extracted three times with dichloromethane. The combined organics were dried over anhydrous magnesium sulfate, filtered, concentrated to provide 2-(((3R,4S)-3-fluorotetrahydro-2H-pyran-4-yl)oxy)-5-(4-((4-(1-methylpiperidin-4-yl)phenyl)amino)-1,3,5-triazin-2-yl)benzonitrile. LCMS-ESI⁺ (m/z): [M+H]⁺ calcd for $C_{27}H_{30}FN_6O_2$: 489.2; found: 489.4 ¹H NMR (400 MHz, DMSO-d₆) δ 10.37 (bs, 1H), 8.85 (s, 1H), 8.62 (m, 2H), 7.74 (bs, 2H), 7.70 (d, J=9.4 Hz, 1H), 7.29 (m, 2H), 5.15 (m, 1H), 5.00 (m, 1H), 4.05 (m, 1H), 3.94 (m, 1H), 3.72 (ddd, J=31.5, 12.8, 1.6 Hz, 1H), 3.61 (m, 1H), 3.36 (bs, 2H), 3.25 (m, 2H), 2.66 (m, 1H), 2.57 (bs, 3H), 2.04 (m, 2H), 1.97-1.75 (m, 4H).

Example 301

(S)-2-((1-acetyl-3,3-difluoropiperidin-4-yl)oxy)-5-(4-((4-(piperidin-4-yl)phenyl)amino)-1,3,5-triazin-2-yl)benzonitrile

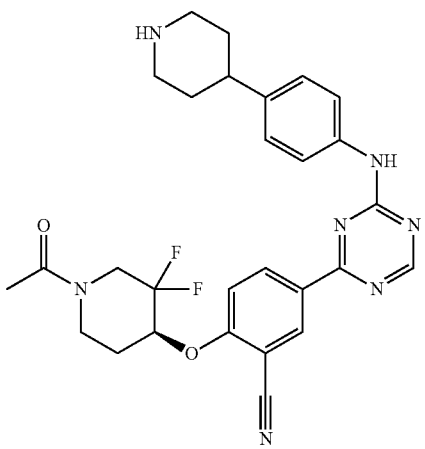 [SMILES: CC(=O)N1CC[C@H](Oc2ccc(-c3ncnc(Nc4ccc(C5CCNCC5)cc4)n3)cc2C#N)C(F)(F)C1]

Step 1: Preparation of (S)-tert-butyl 4-(4-bromo-2-cyanophenoxy)-3,3-difluoropiperidine-1-carboxylate:

Sodium hydride (60% dispersion in mineral oil, 88 mg, 2.2 mmol) was added slowly in a single portion to a stirred solution of (S)-tert-butyl 3,3-difluoro-4-hydroxypiperidine-1-carboxylate (0.52 g, 2.2 mmol) in N,N-dimethylformamide at room temperature. After the passage of 30 minutes, 5-bromo-2-fluorobenzonitrile (0.42 g, 2.1 mmol) was added in a single portion. The mixture was stirred overnight while heating at 60° C. Water was added to the reaction mixture. The resulting aqueous suspension was extracted three times with ethyl acetate. The combined extracts were washed with saturated aqueous sodium chloride solution, dried over anhydrous magnesium sulfate, filtered, and concentrated to dryness under reduced pressure to provide crude (S)-tert-butyl 4-(4-bromo-2-cyanophenoxy)-3,3-difluoropiperidine-1-carboxylate, which was carried forward without further purification. LCMS-ESI⁺ (m/z): [M−Boc+H]⁺ calcd for $C_{12}H_{12}BrF_2N_2O$: 317.0; found: 317.1

Step 2: Preparation of provide (S)-5-bromo-2-((3,3-difluoropiperidin-4-yl)oxy)benzonitrile Crude (S)-tert-butyl 4-(4-bromo-2-cyanophenoxy)-3,3-difluoropiperidine-1-carboxylate (2.1 mmol assumed) was taken up in dichloromethane (8 mL) and treated with trifluoroacetic acid (2 mL). The mixture was allowed to stand at room temperature overnight and was then purified by flash chromatography (silica gel) to provide (S)-5-bromo-2-((3,3-difluoropiperidin-4-yl)oxy)benzonitrile. LCMS-ESI$^+$ (m/z): [M+H]$^+$ calcd for $C_{12}H_{12}BrF_2N_2O$: 317.0; found: 317.2

Step 3: Preparation of (S)-2-((1-acetyl-3,3-difluoropiperidin-4-yl)oxy)-5-bromobenzonitrile To a solution of (S)-5-bromo-2-((3,3-difluoropiperidin-4-yl)oxy)benzonitrile (0.32 g, 1.0 mmol) in dichloromethane (5 mL) was added sequentially N,N-diisopropylethylamine (0.53 mL, 3.0 mmol) and acetyl chloride (0.11 mL, 1.5 mmol, dropwise via syringe). After the passage of 20 minutes, the mixture was washed with 10% aqueous hydrochloric acid solution, followed by saturated aqueous sodium hydrogen carbonate solution. The organics were dried over anhydrous magnesium sulfate, filtered, concentrated to dryness under reduced pressure to give crude (S)-2-((1-acetyl-3,3-difluoropiperidin-4-yl)oxy)-5-bromobenzonitrile, which was carried forward without further purification. LCMS-ESI$^+$ (m/z): [M+H]$^+$ calcd for $C_{14}H_{14}BrF_2N_2O_2$: 359.0; found: 359.1

Step 3: Preparation (S)-2-((1-acetyl-3,3-difluoropiperidin-4-yl)oxy)-5-(4,4,5,5-tetramethyl-1,3,2-dioxaborolan-2-yl)benzonitrile A mixture of crude (S)-2-((1-acetyl-3,3-difluoropiperidin-4-yl)oxy)-5-bromobenzonitrile (0.29 g, 0.82 mmol), bis(pinacolato)diboron (0.41 g, 1.6 mmol), potassium acetate (0.24 g, 2.4 mmol), and [1,1'-bis(diphenylphosphino)ferrocene]dichloropalladium(II) complex with dichloromethane (60 mg, 10 mol %) in 1,4-dioxane (6 mL) was heated overnight at 88° C. The reaction mixture was filtered through a pad of Celite diatomaceous earth, and the filtrate was concentrated to dryness under reduced pressure. The crude (S)-2-((1-acetyl-3,3-difluoropiperidin-4-yl)oxy)-5-(4,4,5,5-tetramethyl-1,3,2-dioxaborolan-2-yl)benzonitrile was carried forward without further purification. LCMS-ESI$^+$ (m/z): [M+H]$^+$ calcd for $C_{20}H_{26}BF_2N_2O_4$: 407.2; found: 407.2

Step 4: Preparation of (S)-tert-butyl 4-(4-((4-(4-((1-acetyl-3,3-difluoropiperidin-4-yl)oxy)-3-cyanophenyl)-1,3,5-triazin-2-yl)amino)phenyl)piperidine-1-carboxylate A mixture of tert-butyl 4-(4-((4-chloro-1,3,5-triazin-2-yl)amino)phenyl)piperidine-1-carboxylate (0.26 g, 0.67 mmol), (S)-2-((1-acetyl-3,3-difluoropiperidin-4-yl)oxy)-5-(4,4,5,5-tetramethyl-1,3,2-dioxaborolan-2-yl)benzonitrile (0.81 mmol assumed), and tetrakis(triphenylphosphine)palladium(0) (0.06 g, 7.5 mol %) in 1,2-dimethoxyethane (DME, 4 mL) was treated with 2 M aqueous sodium carbonate solution (1.5 mL). The mixture was irradiated for 75 minutes in a microwave reactor at 130° C. After cooling, the biphasic mixture was separated. The aqueous phase was extracted five times with ethyl acetate. The combined extracts were concentrated to dryness under reduced pressure and the residue was purified by flash chromatography (silica gel) to provide (S)-tert-butyl 4-(4-((4-(4-((1-acetyl-3,3-difluoropiperidin-4-yl)oxy)-3-cyanophenyl)-1,3,5-triazin-2-yl)amino)phenyl)piperidine-1-carboxylate LCMS-ESI$^+$ (m/z): [M+H]$^+$ calcd for $C_{33}H_{38}F_2N_7O_4$: 634.3; found: 633.8

Step 5: Preparation of (S)-2-((1-acetyl-3,3-difluoropiperidin-4-yl)oxy)-5-(4-((4-(piperidin-4-yl)phenyl)amino)-1,3,5-triazin-2-yl)benzonitrile:

(S)-tert-butyl 4-(4-((4-(4-((1-acetyl-3,3-difluoropiperidin-4-yl)oxy)-3-cyanophenyl)-1,3,5-triazin-2-yl)amino)phenyl)piperidine-1-carboxylate (0.12 g, 0.18 mmol) was taken up in dichloromethane (3 mL) and treated with trifluoroacetic acid (0.78 mL, 10 mmol). The mixture was allowed to stand at room temperature for one hour and was then partitioned between dichloromethane and 0.5 M aqueous sodium hydroxide solution. The aqueous phase was extracted three times with dichloromethane. The combined extracts were dried over anhydrous magnesium sulfate, filtered, and concentrated to provide (S)-2-((1-acetyl-3,3-difluoropiperidin-4-yl)oxy)-5-(4-((4-(piperidin-4-yl)phenyl)amino)-1,3,5-triazin-2-yl)benzonitrile. LCMS-ESI$^+$ (m/z): [M+H]$^+$ calcd for $C_{28}H_{30}F_2N_7O_2$: 534.2; found: 534.4 $^1$H NMR (400 MHz, DMSO-d$_6$) δ 10.35 (bs, 1H), 8.85 (s, 1H), 8.65 (m, 2H), 7.74 (dd, J=9.6, 3.9 Hz, 1H), 7.71 (d, J=4.6 Hz, 2H), 7.28 (m, 2H), 5.41 (ddd, J=12.6, 8.5, 4.1 Hz, 1H), 4.13 (m, 1H), 3.86 (m, 2H), 3.56 (m, 1H), 3.34 (m, 4H), 3.06 (m, 2H), 2.63 (m, 2H), 2.15 (s, 1.5H), 2.12 (s, 1.5H), 1.73 (m, 2H), 1.55 (m, 2H).

Example 302

(S)-2-((1-acetyl-3,3-difluoropiperidin-4-yl)oxy)-5-(4-((4-(1-methylpiperidin-4-yl)phenyl)amino)-1,3,5-triazin-2-yl)benzonitrile

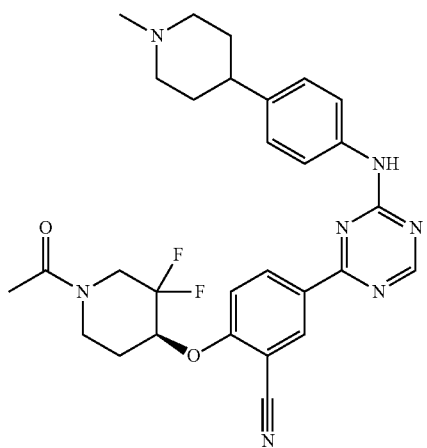 [SMILES: CC(=O)N1CC[C@H](Oc2ccc(-c3ncnc(Nc4ccc(C5CCN(C)CC5)cc4)n3)cc2C#N)C(F)(F)C1]

A solution of (S)-2-((1-acetyl-3,3-difluoropiperidin-4-yl)oxy)-5-(4-((4-(piperidin-4-yl)phenyl)amino)-1,3,5-triazin-2-yl)benzonitrile (50 mg, 0.09 mmol) in methanol (4 mL) was treated with 37% formalin solution (28 μL, 0.38 mmol). After five minutes of stirring at room temperature, the mixture was treated with sodium tri(acetoxy)borohydride (0.10 g, 0.47 mmol), and the reaction mixture was stirred for two hours at room temperature. The mixture was concentrated to dryness under reduced pressure. The residue was suspended in 1 M aqueous sodium hydroxide solution (~2 mL). After five minutes, the mixture was extracted three times with dichloromethane. The combined organic phases were dried over anhydrous magnesium sulfate, filtered, and evaporated to provide (S)-2-((1-acetyl-3,3-difluoropiperidin-4-yl)oxy)-5-(4-((4-(1-methylpiperidin-4-yl)phenyl)amino)-1,3,5-triazin-2-yl)benzonitrile. LCMS-ESI$^+$ (m/z): [M+H]$^+$ calcd for $C_{29}H_{32}F_2N_7O_2$: 548.3; found: 548.4 $^1$H NMR (400 MHz, DMSO-d$_6$) δ 10.34 (m, 1H), 8.85 (s, 1H), 8.65 (m, 2H), 7.73 (m, 3H), 7.29 (d, J=8.1 Hz, 2H), 5.41 (m, 1H), 4.13 (ddt, J=23.9, 11.4, 6.5 Hz, 1H), 4.04-3.68 (m, 2H), 3.66-3.47 (m, 1H), 3.36 (s, 2H), 2.90 (m, 2H), 2.48 (m, 1H), 2.23 (s, 3H), 2.15 (s, 1.5H), 2.12 (s, 1.5H), 2.00 (m, 2H), 1.84-1.61 (m, 4H).

Example 303

(S)-2-((3,3-difluoro-1-formylpiperidin-4-yl)oxy)-5-(4-((3-methyl-4-(piperidin-4-yl)phenyl)amino)-1,3,5-triazin-2-yl)benzonitrile

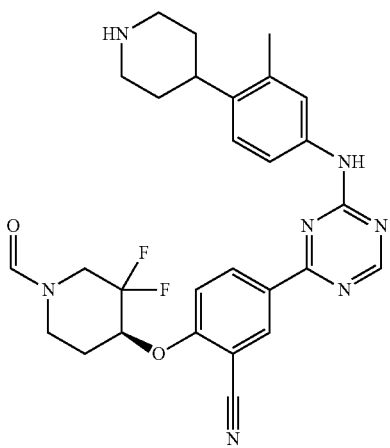 [SMILES: Cc1cc(Nc2ncnc(-c3ccc(O[C@H]4CCN(C=O)CC4(F)F)c(C#N)c3)n2)ccc1C1CCNCC1]

Step 1: Preparation of tert-butyl 4-(2-methyl-4-nitrophenyl)-5,6-dihydropyridine-1(2H)-carboxylate 2-bromo-5-nitrotoluene (5.0 g, 23 mmol), 4-(4,4,5,5-tetramethyl-[1,3,2]dioxaborolan-2-yl)-3,6-dihydro-2H-pyridine-1-carboxylic acid tert-butyl ester (Boron Molecular, 7.5 g, 24 mmol), tetrakis(triphenylphosphine)palladium(0) (1.5 g, 1.3 mmol), sodium carbonate aqueous solution (2M, 32 mL, 65 mmol), and 1,4-dioxane (75 mL) were combined in a sealed tube, and the mixture was heated at 80° C. for 3 days. After cooling to room temperature, the mixture was diluted with ethyl acetate and water and filtered through a pad of Celite diatomaceous earth. The aqueous phase was extracted three times with ethyl acetate. The combined extracts were washed once with a saturated aqueous sodium chloride solution, dried over anhydrous magnesium sulfate, filtered, and concentrated under reduced pressure. The crude residue was purified by flash chromatography (silica gel) to provide tert-butyl 4-(2-methyl-4-nitrophenyl)-5,6-dihydropyridine-1(2H)-carboxylate. LCMS-ESI+ (m/z): [M−tBu+H]+ calcd for $C_{13}H_{15}N_2O_4$: 263.1; found: 263.0

Step 2: Preparation of tert-butyl 4-(4-amino-2-methylphenyl)piperidine-1-carboxylate tert-butyl 4-(2-methyl-4-nitrophenyl)-5,6-dihydropyridine-1(2H)-carboxylate (2.6 g, 8.2 mmol) was taken up methanol (50 mL) in a Parr bottle. After the degassing of the mixture, it was treated with 10% palladium on charcoal (260 mg). The suspension was shaken under 55 psi hydrogen overnight and then filtered through a bed of Celite diatomaceous earth. The filtrate was concentrated under reduced pressure to provide tert-butyl 4-(4-amino-2-methylphenyl)piperidine-1-carboxylate. LCMS-ESI+ (m/z): [M+H]+ calcd for $C_{17}H_{27}N_2O_2$: 291.2; found: 290.6

Step 3: Preparation of tert-butyl 4-(4-((4-chloro-1,3,5-triazin-2-yl)amino)-2-methylphenyl)piperidine-1-carboxylate To a solution of 2,4-dichloro-1,3,5-triazine (1.2 g, 8.0 mmol) in N,N-dimethylformamide (DMF, 15 mL) at 0° C. were added sequentially N,N-diisopropylethylamine (DIEA, 1.5 mL, 8.4 mmol) tert-butyl 4-(4-amino-2-methylphenyl)piperidine-1-carboxylate (1.9 g, 6.5 mmol), followed by a DMF rinsate (15 mL). The mixture was allowed to warm to room temperature. After the passage of two days, the mixture was diluted with ethyl acetate and half-saturated aqueous sodium hydrogen carbonate solution. The mixture was filtered through a pad of Celite diatomaceous earth and then was diluted with more water. The aqueous phase was extracted thrice each with diethyl ether. The combined extracts were washed with water, was filtered again through a pad of Celite diatomaceous earth, and concentrated under reduced pressure. The residue was purified by flash chromatography (silica gel) to provide tert-butyl 4-(4-((4-chloro-1,3,5-triazin-2-yl)amino)-2-methylphenyl)piperidine-1-carboxylate. LCMS-ESI+ (m/z): [M+H]+ calcd for $C_{20}H_{27}ClN_5O_2$: 404.2; found: 404.0

Step 4: Preparation of (S)-5-bromo-2-((3,3-difluoro-1-formylpiperidin-4-yl)oxy)benzonitrile Formic acid (96 µL, 2.5 mmol) was added to a solution (S)-5-bromo-2-((3,3-difluoropiperidin-4-yl)oxy)benzonitrile (0.54 g, 1.7 mmol) in N,N-dimethylformamide (5 mL). Mixture was treated with successively with N,N-diisopropylethylamine (0.89 mL, 5.1 mmol) and N-[(dimethylamino)-1H-1,2,3-triazolo-[4,5-b]pyridin-1-ylmethylene]-N-methylmethanaminiumhexafluorophosphate N-oxide (HATU, 1.3 g, 3.4 mmol). The suspension was shaken vigorously for 1 minute until homogeneous and then left to stir for 4 hours at room temperature. The mixture was concentrated under reduced pressure. The residue was partitioned between ethyl acetate and saturated aqueous sodium hydrogen carbonate solution. The aqueous phase was extracted three times with ethyl acetate. The combined organics were washed with 1:1 saturated aqueous sodium chloride solution/saturated aqueous sodium hydrogen carbonate solution, dried over anhydrous magnesium sulfate, filtered, concentrated to dryness under reduced pressure. The residue was purified by flash chromatography (silica gel) to provide (S)-5-bromo-2-((3,3-difluoro-1-formylpiperidin-4-yl)oxy)benzonitrile. LCMS-ESI+ (m/z): [M+H]+ calcd for $C_{13}H_{12}BrF_2N_2O_2$: 345.0; found: 345.0

Step 5: Preparation of (S)-2-((3,3-difluoro-1-formylpiperidin-4-yl)oxy)-5-(4,4,5,5-tetramethyl-1,3,2-dioxaborolan-2-yl)benzonitrile A mixture of (S)-5-bromo-2-((3,3-difluoro-1-formylpiperidin-4-yl)oxy)benzonitrile (0.17 g, 0.50 mmol), bis(pinacolato)diboron (0.26 g, 1.0 mmol), potassium acetate (0.15 g, 1.5 mmol), and [1,1'-bis(diphenylphosphino)ferrocene] dichloropalladium(II) complex with dichloromethane (37 mg, 10 mol %) in 1,4-dioxane (3 mL) was heated overnight at 85° C. The reaction mixture was filtered through a pad of Celite diatomaceous earth, and the filtrate was concentrated to dryness under reduced pressure. The crude (S)-2-((3,3-difluoro-1-formylpiperidin-4-yl)oxy)-5-(4,4,5,5-tetramethyl-1,3,2-dioxaborolan-2-yl)benzonitrile was carried forward without further purification. LCMS-ESI+ (m/z): [M+H]+ calcd for $C_{19}H_{24}BF_2N_2O_4$: 393.2: found: 393.2

Step 6: Preparation of (S)-tert-butyl 4-(4-((4-(3-cyano-4-((3,3-difluoro-1-formylpiperidin-4-yl)oxy)phenyl)-1,3,5-triazin-2-yl)amino)-2-methylphenyl)piperidine-1-carboxylate A mixture of tert-butyl 4-(4-((4-chloro-1,3,5-triazin-2-yl)amino)-2-methylphenyl)piperidine-1-carboxylate (0.20 g, 0.51 mmol), crude (S)-2-((3,3-difluoro-1-formylpiperidin-4-yl)oxy)-5-(4,4,5,5-tetramethyl-1,3,2-dioxaborolan-2-yl)benzonitrile (0.51 mmol assumed), and tetrakis(triphenylphosphine)palladium(0) (0.04 g, 7.5 mol %) in 1,2-dimethoxyethane (DME, 3 mL) was treated with 2 M aqueous sodium carbonate solution (0.72 mL). The mixture was irradiated for 75 minutes in a microwave reactor at 130° C. After cooling, the biphasic mixture was separated. The aqueous phase was extracted five times with ethyl acetate. The combined extracts were concentrated to dryness under reduced pressure and the residue was purified by flash chromatography (silica gel) to provide (S)-tert-butyl 4-(4-((4-(3-cyano-4-((3,3-difluoro-1-formylpiperidin-4-yl)oxy)phenyl)-1,3,5-triazin-2-yl)amino)-2-methylphenyl)piperidine-1-carboxylate. LCMS-ESI+ (m/z): [M+H]+ calcd for $C_{33}H_{37}F_2N_7O_4$: 634.3; found: 633.8

Step 7: Preparation of (S)-2-((3,3-difluoro-1-formylpiperidin-4-yl)oxy)-5-(4-((3-methyl-4-(piperidin-4-yl)phenyl)amino)-1,3,5-triazin-2-yl)benzonitrile (S)-tert-butyl 4-(4-((4-(3-cyano-4-((3,3-difluoro-1-formylpiperidin-4-yl)oxy)phenyl)-1,3,5-triazin-2-yl)amino)-2-methylphenyl)piperidine-1-carboxylate (0.20 g, 0.31 mmol) was taken up in dichloromethane (4 mL) and treated with trifluoroacetic acid (2.0 mL, 26 mmol). The mixture was allowed to stand overnight at room temperature and was then concentrated to dryness under reduced pressure. The residue was purified by prep HPLC (5-65% acetonitrile in water, 0.1% trifluoroacetic acid buffer). The combined HPLC fractions were basified to pH 10 with 1 M sodium hydroxide solution and extracted five times with dichloromethane. The combined organics were dried over anhydrous magnesium sulfate, filtered, and concentrated to provide (S)-2-((3,3-difluoro-1-formylpiperidin-4-yl)oxy)-5-(4-((3-methyl-4-(piperidin-4-yl)phenyl)amino)-1,3,5-triazin-2-yl)benzonitrile. LCMS-ESI+ (m/z): [M+H]+ calcd for $C_{28}H_{30}F_2N_7O_2$: 534.2; found: 534.3 1H NMR (400 MHz, DMSO-d6) δ 10.29 (br, 1H), 8.84 (s, 1H), 8.65 (d, J=7.4 Hz, 2H), 8.21 (s, 0.5H), 8.14 (s, 0.5H), 7.74 (d, J=9.6 Hz, 1H), 7.70-7.43 (m, 2H), 7.23 (d, J=8.3 Hz, 1H), 5.47 (m, 1H), 4.16-4.00 (m, 1H), 4.00-3.82 (m, 1H), 3.82-3.65 (m, 1H), 3.65-3.43 (m, 1H), 3.35 (bs, 1H), 3.07 (d, J=11.8 Hz, 2H), 2.79 (m, 1H), 2.65 (m, 2H), 2.37(s, 3H), 2.19 (m, 1H), 2.08-1.82 (m, 1H), 1.65 (m, 2H), 1.54 (m, 2H).

Example 304

(S)-2-((3,3-difluoro-1-formylpiperidin-4-yl)oxy)-5-(4-((3-methyl-4-(1-methylpiperidin-4-yl)phenyl)amino)-1,3,5-triazin-2-yl)benzonitrile

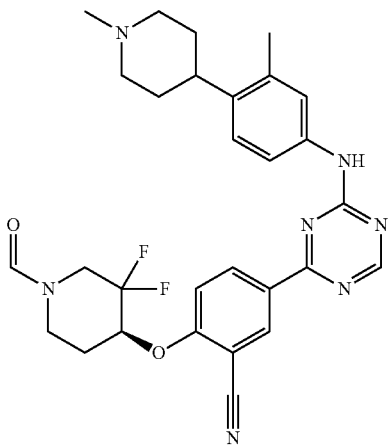 [SMILES: Cc1cc(Nc2ncnc(-c3ccc(O[C@H]4CCN(C=O)CC4(F)F)c(C#N)c3)n2)ccc1C1CCN(C)CC1]

A solution of (S)-2-((3,3-difluoro-1-formylpiperidin-4-yl)oxy)-5-(4-((3-methyl-4-(piperidin-4-yl)phenyl)amino)-1,3,5-triazin-2-yl)benzonitrile (43 mg, 0.08 mmol) in methanol (4 mL) was treated with 37% formalin solution (24 μL, 0.32 mmol). After five minutes of stirring at room temperature, the mixture was treated with sodium tri(acetoxy)borohydride (0.10 g, 0.47 mmol), and the reaction mixture was stirred for 45 minutes at room temperature. The mixture was concentrated to dryness under reduced pressure. The residue was suspended in 1 M aqueous sodium hydroxide solution (~2 mL). After five minutes, the mixture was extracted three times with dichloromethane. The combined organic phases were dried over anhydrous magnesium sulfate, filtered, and evaporated to provide (S)-2-((3,3-difluoro-1-formylpiperidin-4-yl)oxy)-5-(4-((3-methyl-4-(1-methylpiperidin-4-yl)phenyl)amino)-1,3,5-triazin-2-yl)benzonitrile.

LCMS-ESI+ (m/z): [M+H]+ calcd for $C_{29}H_{32}F_2N_7O_2$: 548.3; found: 548.4 1H NMR (400 MHz, DMSO-d6) δ 10.31 (m, 1H), 8.84 (s, 1H), 8.66 (m, 2H), 8.21 (s, 0.5H), 8.14 (s, 0.5H), 7.74 (d, J=9.5 Hz, 1H), 7.71-7.60 (m, 1H), 7.57 (m, 1H), 7.25 (d, J=8.2 Hz, 1H), 5.47 (ddt, J=12.8, 8.1, 4.0 Hz, 1H), 4.15-3.99 (m, 1H), 3.99-3.82 (m, 1H), 3.82-3.65 (m, 1H), 3.53 (m, 1H), 3.36 (s, 1H), 2.95 (d, J=11.2 Hz, 2H), 2.68 (p, J=7.8 Hz, 1H), 2.37 (s, 3H), 2.28 (s, 3H), 2.19-1.98 (m, 3H), 1.71 (m, 4H).

Example 305

2-(((3R,4S)-3-fluoro-1-(2-hydroxyacetyl)piperidin-4-yl)oxy)-5-(4-((4-(1-(oxetan-3-yl)piperidin-4-yl)phenyl)amino)-1,3,5-triazin-2-yl)benzonitrile

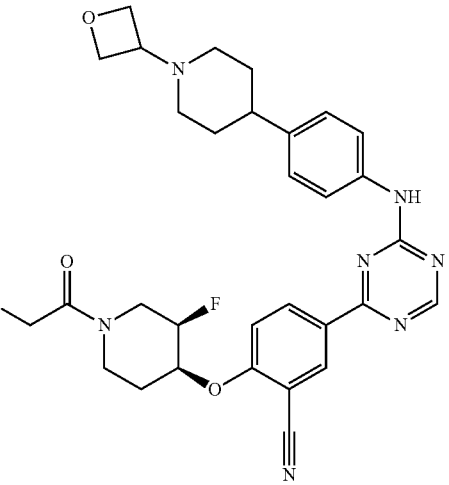

2-(((3R,4S)-3-fluoropiperidin-4-yl)oxy)-5-(4-((4-(1-(oxetan-3-yl)piperidin-4-yl)phenyl)amino)-1,3,5-triazin-2-yl)benzonitrile (100 mg, 0.19 mmol) was dissolved in dichloromethane (2.7 mL), N,N-Diisopropylethylamine (0.07 ml, 0.38 mmol), N-[(dimethylamino)-1H-1,2,3-triazolo-[4,5-b]pyridin-1-ylmethylene]-N-methylmethanaminiumhexafluorophosphate N-oxide (107.98 mg, 0.28 mmol), glycolic acid (28.72 mg, 0.38 mmol) followed and the reaction was allowed to stir for 1 hour at room temperature. The mixture was diluted with dichloromethane and water. The aqueous phase was extracted three times with dichloromethane. The combined extracts were dried over anhydrous sodium sulfate, filtered, and concentrated under reduced pressure. The residue was purified via prep HPLC (0-40% acetonitrile in water, 0.1% trifluoroacetic acid buffer) to provide 2-(((3R,4S)-3-fluoro-1-(2-hydroxyacetyl)piperidin-4-yl)oxy)-5-(4-((4-(1-(oxetan-3-yl)piperidin-4-yl)phenyl)amino)-1,3,5-triazin-2-yl)benzonitrile. LCMS-ESI⁺ (m/z): [M+H]⁺ calcd for $C_{31}H_{34}FN_7O_4$: 587.6; found: 588.3

¹H NMR (400 MHz, DMSO-d₆) δ 10.30 (s, 1H), 8.80 (s, 1H), 8.64-8.54 (d, J=10.8, 2H), 7.65 (dd, J=9.1, 6.0 Hz, 3H), 7.26 (d, J=8.2 Hz, 2H), 5.14-4.90 (m, 2H), 4.68 (q, J=6.2 Hz, 1H), 4.49 (dt, J=29.2, 6.3 Hz, 4H), 4.40-4.30 (m, 1H), 4.24-3.37 (m, 3H), 4.35-3.35 (m, 2H), 3.17 (m, 1H), 2.80 (m, 2H), 1.93-1.56 (m, 8H).

Example 306

2-(((3R,4S)-3-fluoro-1-(2-hydroxyacetyl)piperidin-4-yl)oxy)-5-(4-((4-(4-(tetrahydro-2H-pyran-4-yl)piperazin-1-yl)phenyl)amino)-1,3,5-triazin-2-yl)benzonitrile

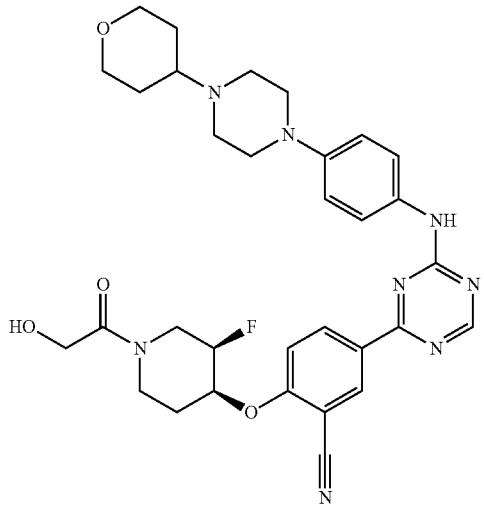 [SMILES: N#Cc1cc(-c2ncnc(Nc3ccc(N4CCN(C5CCOCC5)CC4)cc3)n2)ccc1O[C@H]1CCN(C(=O)CO)C[C@H]1F]

2-(((3R,4S)-3-fluoropiperidin-4-yl)oxy)-5-(4-((4-(4-(tetrahydro-2H-pyran-4-yl)piperazin-1-yl)phenyl)amino)-1,3,5-triazin-2-yl)benzonitrile (100 mg, 0.18 mmol) was dissolved in dichloromethane (2.6 mL), N,N-Diisopropylethylamine (0.06 ml, 0.36 mmol), N-[(dimethylamino)-1H-1,2,3-triazolo-[4,5-b]pyridin-1-yl-methylene]-N-methylmethanaminiumhexafluorophosphate N-oxide (102.36 mg, 0.27 mmol), glycolic acid (27.23 mg, 0.36 mmol) was added and the reaction was allowed to stir for 1 hour at room temperature. The mixture was diluted with dichloromethane and water. The aqueous phase was extracted three times with dichloromethane. The combined extracts were dried over anhydrous sodium sulfate, filtered, and concentrated under reduced pressure. The residue was purified via prep HPLC (0-40% acetonitrile in water, 0.1% trifluoroacetic acid buffer) to provide 2-(((3R,4S)-3-fluoro-1-(2-hydroxyacetyl)piperidin-4-yl)oxy)-5-(4-((4-(4-(tetrahydro-2H-pyran-4-yl)piperazin-1-yl)phenyl)amino)-1,3,5-triazin-2-yl)benzonitrile. LCMS-ESI⁺ (m/z): [M+H]⁺ calcd for $C_{32}H_{37}FN_8O_4$: 616.7; found: 617.2

¹H NMR (400 MHz, DMSO-d₆) δ 10.12 (d, J=17.9 Hz, 1H), 8.74 (s, 1H), 8.57 (d, J=11.3 Hz, 2H), 7.68-7.53 (m, 3H), 6.94 (s, 2H), 5.20-4.93 (m, 2H), 4.67 (q, J=6.2 Hz, 1H), 4.24-4.04 (m, 3H), 3.95-3.83 (m, 3H), 3.72-3.35 (m, 1H), 3.19-3.04 (m, 6H), 2.67-2.52 (m, 4H), 2.51-2.32 (m, 2H), 1.98 (s, 2H), 1.74 (d, J=13.6 Hz, 2H), 1.41 (qd, J=12.2, 4.5 Hz, 2H).

Example 307

2-(((3R,4S)-3-fluoro-1-(2-hydroxyacetyl)piperidin-4-yl)oxy)-5-(4-((3-fluoro-4-(4-(tetrahydro-2H-pyran-4-yl)piperazin-1-yl)phenyl)amino)-1,3,5-triazin-2-yl)benzonitrile

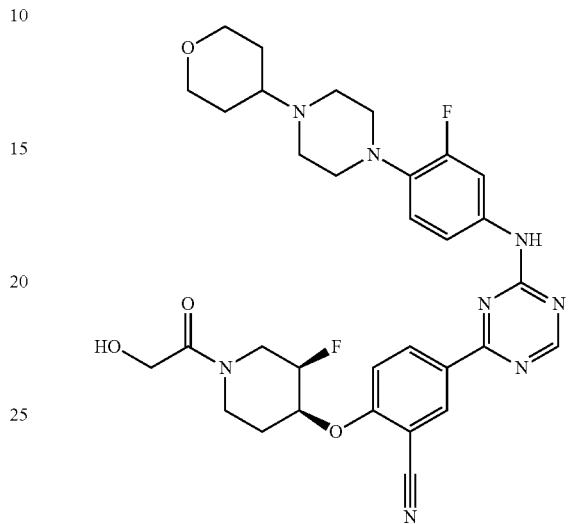

1-(2-fluoro-4-nitrophenyl)piperazine (2000 mg, 8.88 mmol), dihydro-2H-pyran-4(3H)-one (2667.15 mg, 26.64 mmol), sodium cyanoborohydride (1674.15 mg, 26.64 mmol) in methanol (68 ml) followed by zinc chloride (1815.77 mg, 13.32 mmol) was stirred at 48° C. for 4 hours. The reaction was diluted with dichloromethane to make a 25% methanol/dichloromethane solution and the reaction was washed with water. The crude material was dried, filtered, concentrated and purified by flash chromatography (silica gel) to provide 1-(2-fluoro-4-nitrophenyl)-4-(tetrahydro-2H-pyran-4-yl)piperazine. LCMS-ESI⁺ (m/z): [M+H]⁺ calcd for $C_{15}H_{20}FN_3O_3$: 309.3; found: 310.9

1-(2-fluoro-4-nitrophenyl)-4-(tetrahydro-2H-pyran-4-yl)piperazine (2740 mg, 8.86 mmol), palladium (10%, 471.32 mg, 0.44 mmol) on carbon in ethanol (12.6 ml) were combined in a PARR flask and shaken on the hydrogenator for 3 h at 45 PSI. The reaction was filtered over celite and washed down with 25% methanol/dichloromethane, concentrated and provided 3-fluoro-4-(4-(tetrahydro-2H-pyran-4-yl)piperazin-1-yl)aniline. LCMS-ESI⁺ (m/z): [M+H]⁺ calcd for $C_{15}H_{22}FN_3O$: 279.4; found: 279.9

3-fluoro-4-(4-(tetrahydro-2H-pyran-4-yl)piperazin-1-yl)aniline (500 mg, 1.79 mmol), 1-(4-pyridinyl)piperazine (1156.77 mg, 7.09 mmol), potassium carbonate (742.1 mg, 5.37 mmol) dimethylformamide (10 mL) were combined, cooled to 0° C., followed by 2,4-dichloro-1,3,5-triazine (268.42 mg, 1.79 mmol) in dimethylformamide (8 mL) and stirred at 0C. The reaction was stirred for 5 minutes, quenched with water, extracted with ethyl acetate, washed with water, and dried. The reaction extracted with 30% methanol/dichloromethane, washed with water, dried and purified by flash in chromatography (silica gel) to provide 4-chloro-N-(3-fluoro-4-(4-(tetrahydro-2H-pyran-4-yl)piperazin-1-yl)phenyl)-1,3,5-triazin-2-amine. LCMS-ESI⁺ (m/z): [M+H]⁺ calcd for $C_{18}H_{22}ClFN_6O$: 392.9; found: 393.4

A 2-5 mL microwave vial was charged with 4-chloro-N-(3-fluoro-4-(4-(tetrahydro-2H-pyran-4-yl)piperazin-1-yl)phenyl)-1,3,5-triazin-2-amine (100 mg, 0.25 mmol), (3R,4S)-tert-butyl 4-(2-cyano-4-(4,4,5,5-tetramethyl-1,3,2-doxaborolan-2-yl)phenoxy)-3-fluoropiperidine-1-carboxylate (136.33 mg, 0.31 mmol), 2M Sodium carbonate (0.23 ml), and Tetrakis(triphenylphosphine)palladium(0) (17.48 mg, 0.02 mmol) in dimethoxyethane (2.5 mL). The solution was degassed with nitrogen, irridated for 20 minutes at 150° C. The reaction was extracted with 30% methanol/dichloromethane, washed with water, dried, filtered and concentrated. The crude material was then purified by flash chromatography (silica gel) to provide (3R,4S)-tert-butyl 4-(2-cyano-4-(4-((3-fluoro-4-(4-(tetrahydro-2H-pyran-4-yl)piperazin-1-yl)phenyl)amino)-1,3,5-triazin-2-yl)phenoxy)-3-fluoropiperidine-1-carboxylate. LCMS-ESI$^+$ (m/z): [M+H]$^+$ calcd for $C_{35}H_{42}F_2N_8O_4$: 676.8; found: 677.3

(3R,4S)-tert-butyl 4-(2-cyano-4-(4-((3-fluoro-4-(4-(tetrahydro-2H-pyran-4-yl)piperazin-1-yl)phenyl)amino)-1,3,5-triazin-2-yl)phenoxy)-3-fluoropiperidine-1-carboxylate (180 mg, 0.27 mmol) was dissolved in dichloromethane (1.3 ml), trifluoroacetic acid (0.2 ml, 2.66 mmol) was added and the reaction was stirred at room temperature for 1 h. The reaction was cooled to 0° C., neutralized with saturated sodium bicarbonate, washed with water, dried, filtered and concentrated to provide 5-(4-((3-fluoro-4-(4-(tetrahydro-2H-pyran-4-yl)piperazin-1-yl)phenyl)amino)-1,3,5-triazin-2-yl)-2-(((3R,4S)-3-fluoropiperidin-4-yl)oxy)benzonitrile. LCMS-ESI$^+$ (m/z): [M+H]$^+$ calcd for $C_{30}H_{34}F_2N_8O_2$: 576.6; found: 577.1

5-(4-((3-fluoro-4-(4-(tetrahydro-2H-pyran-4-yl)piperazin-1-yl)phenyl)amino)-1,3,5-triazin-2-yl)-2-(((3R,4S)-3-fluoropiperidin-4-yl)oxy)benzonitrile (104.70 mg, 0.18 mmol) was dissolved in dichloromethane (2.5 mL), N,N-Diisopropylethylamine (0.06 ml, 0.36 mmol), N-[(dimethylamino)-1H-1,2,3-triazolo-[4,5-b]pyridin-1-ylmethylene]-N-methylmethanaminiumhexafluorophosphate N-oxide (103.83 mg, 0.27 mmol), glycolic acid (27.62 mg, 0.36 mmol) was added and the reaction was allowed to stir for 2 hours 30 minutes. The mixture was diluted with dichloromethane and water. The aqueous phase was extracted three times with dichloromethane. The combined extracts were dried over anhydrous sodium sulfate, filtered, and concentrated under reduced pressure. The residue was purified via prep HPLC (0-40% acetonitrile in water, 0.1% trifluoroacetic acid buffer) to provide 2-(((3R,4S)-3-fluoro-1-(2-hydroxyacetyl)piperidin-4-yl)oxy)-5-(4-((3-fluoro-4-(4-(tetrahydro-2H-pyran-4-yl)piperazin-1-yl)phenyl)amino)-1,3,5-triazin-2-yl)benzonitrile. LCMS-ESI$^+$ (m/z): [M+H]$^+$ calcd for $C_{32}H_{36}F_2N_8O_4$: 634.7; found: 635.3

$^1$H NMR (400 MHz, DMSO-d$_6$) δ 10.45 (s, 1H), 8.86 (s, 1H), 8.77 (d, J=16.3 Hz, 2H), 7.77-7.56 (m, 2H), 7.43 (s, 1H), 7.04 (t, J=16.4 Hz, 1H), 5.22-4.93 (m, 2H), 4.67 (q, J=6.2 Hz, 1H), 4.45-4.05 (m, 3H), 3.95-3.83 (m, 3H), 3.71-3.44 (m, 2H), 3.39 (s, 1H), 2.91 (s, 4H), 2.72 (s, 4H), 2.45 (s, 1H), 2.07-1.80 (m, 2H), 1.80-1.71 (m, 2H), 1.41 (qd, J=12.2, 4.5 Hz, 2H).

Example 308

2-(((3R,4S)-3-fluoro-1-((S)-2-hydroxypropanoyl)piperidin-4-yl)oxy)-5-(4-((4-(4-(oxetan-3-ylmethyl)piperazin-1-yl)phenyl)amino)-1,3,5-triazin-2-yl)benzonitrile

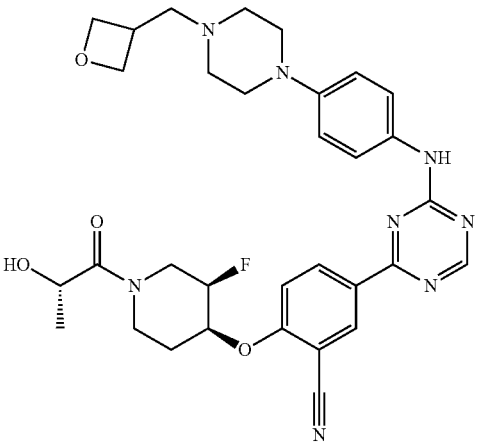 [SMILES: C[C@H](O)C(=O)N1CC[C@H](Oc2ccc(-c3ncnc(Nc4ccc(N5CCN(CC6COC6)CC5)cc4)n3)cc2C#N)[C@H](F)C1]

Oxetane-3-carbaldehyde (977.11 mg, 11.35 mmol) in dichloromethane, 1-(4-nitrophenyl)piperazine (1176.02 mg, 5.67 mmol) in dichloromethane, sodium triacetoxyborohydride (24055.12 mg, 113.5 mmol) were combined and stirred at room temperature for 2 hours. The reaction was concentrated, diluted with dichloromethane, and washed with sodium bicarbonate and stirred for 20 minutes. The organic layer was separated and washed with saturated sodium bicarbonate, dried, filtered, concentrated and purified by flash chromatography (silica gel) to provide 1-(4-nitrophenyl)-4-(oxetan-3-ylmethyl)piperazine.

LCMS-ESI$^+$ (m/z): [M+H]$^+$ calcd for $C_{14}H_{19}N_3O_3$: 277.3; found: 278.1

1-(4-nitrophenyl)-4-(oxetan-3-ylmethyl)piperazine (820 mg, 2.96 mmol), Iron (1155.99 mg, 20.7 mmol), ammonium chloride (1107.15 mg, 20.7 mmol) were combined in water (14.8 mL) and ethanol (14.8 mL), heated to 80° C. for 1 hour. The reaction was extracted with dichloromethane, washed with water, dried, filtered and concentrated to provide 4-(4-(oxetan-3-ylmethyl)piperazin-1-yl)aniline. LCMS-ESI$^+$ (m/z): [M+H]$^+$ calcd for $C_{14}H_{21}N_3O$: 247.3; found: 248.0

4-(4-(oxetan-3-ylmethyl)piperazin-1-yl)aniline (360 mg, 1.46 mmol), potassium carbonate (603.48 mg, 4.37 mmol) in dichloromethane (7.5 mL) were combined, cooled to 0° C., followed by 2,4-dichloro-1,3,5-triazine (218.28 mg, 1.46 mmol) in dichloromethane (7 mL) that was cooled to 0° C. before addition and stirred at 0° C. The reaction monitored at 5 minutes and then was subjected 2 times to 40 mg of more triazine and stirred for 10 minutes after each addition. The reaction was quenched with water, extracted with 30% methanol/dichloromethane and back extracted with water. 4-chloro-N-(4-(4-(oxetan-3-ylmethyl)piperazin-1-yl)phenyl)-1,3,5-triazin-2-amine. LCMS-ESI$^+$ (m/z): [M+H]$^+$ calcd for $C_{17}H_{21}ClN_6O$: 525.2; found: 525.8

A 2-5 mL microwave vial was charged with 4-chloro-N-(4-(4-(oxetan-3-ylmethyl)piperazin-1-yl)phenyl)-1,3,5-triazin-2-amine (100 mg, 0 28 mmol), (3R,4S)-tert-butyl 4-(2-cyano-4-(4,4,5,5-tetramethyl-1,3,2-dioxaborolan-2-yl)phenoxy)-3-fluoropiperidine-1-carboxylate (148.43 mg, 0.33 mmol), 2M sodium carbonate (0.62 ml), Tetrakis(triphenylphosphine)palladium(0) (19.04 mg, 0.02 mmol) in 2.7 mL of dimethoxyethane, blown down with nitrogen gas, irridated for 20 minutes at 150° C. The reaction was extracted with dichloromethane, dried, filtered, concentrated and then purified by flash chromatography (silica gel) to provide (3R,4S)-tert-butyl 4-(2-cyano-4-(4-((4-(4-(oxetan-3-ylmethyl)piperazin-1-yl)phenyl)amino)-1,3,5-triazin-2-yl)phenoxy)-3-fluoropiperidine-1-carboxylate. LCMS-ESI$^+$ (m/z): [M+H]$^+$ calcd for $C_{34}H_{41}FN_8O_4$: 644.7; found: 645.4

(3R,4S)-tert-butyl 4-(2-cyano-4-(4-((4-(4-(tetrahydro-2H-pyran-4-yl)piperazin-1-yl)phenyl)amino)-1,3,5-triazin-2-yl)phenoxy)-3-fluoropiperidine-1-carboxylate (210 mg, 0.32 mmol) was dissolved in dichloromethane (1.5 ml), trifluoroacetic acid (0.25 ml, 3.19 mmol) was added and the reaction was stirred at room temperature for 45 minutes. The reaction cooled to 0° C., neutralized with saturated sodium bicarbonate, diluted with 30% methanol/dichloromethane, washed with water, dried, filtered, and concentrated to provide 2-(((3R,4S)-3-fluoropiperidin-4-yl)oxy)-5-(4-((4-(4-(oxetan-3-ylmethyl)piperazin-1-yl)phenyl)amino)-1,3,5-triazin-2-yl)benzonitrile. LCMS-ESI$^+$ (m/z): [M+H]$^+$ calcd for $C_{29}H_{33}FN_8O_2$: 544.6; found: 545.1

2-(((3R,4S)-3-fluoropiperidin-4-yl)oxy)-5-(4-((4-(1-(oxetan-3-ylmethyl)piperidin-4-yl)phenyl)amino)-1,3,5-triazin-2-yl)benzonitrile (100 mg, 0.18 mmol) was dissolved in dichloromethane (2.6 mL), N,N-Diisopropylethylamine (0.06 ml, 0.37 mmol), N-[(dimethylamino)-1H-1,2,3-triazolo-[4,5-b]pyridin-1-ylmethylene]-N-methylmethanaminiumhexafluorophosphate N-oxide (105.19 mg, 0.28 mmol), (S)-2-hydroxypropanoic acid (33.14 mg, 0.37 mmol) was added and the reaction was allowed to stir for 1 hour at room temperature. The mixture was diluted with dichloromethane and water. The aqueous phase was extracted three times with dichloromethane. The combined extracts were dried over anhydrous sodium sulfate, filtered, and concentrated under reduced pressure. The residue was purified via prep HPLC (0-40% acetonitrile in water, 0.1% trifluoroacetic acid buffer) to provide 2-(((3R,4S)-3-fluoro-1-((S)-2-hydroxypropanoyl)piperidin-4-yl)oxy)-5-(4-((4-(4-(oxetan-3-ylmethyl)piperazin-1-yl)phenyl)amino-1,3,5-triazin-2-yl)benzonitrile.

LCMS-ESI$^+$ (m/z): [M+H]$^+$ calcd for $C_{33}H_{38}FN_7O_4$: 615.7; found: 617.3

$^1$H NMR (400 MHz, DMSO-d$_6$) δ 10.13 (d, J=17.2 Hz, 1H), 8.74 (s, 1H), 8.57 (d, J=12.2 Hz, 2H), 7.68-7.53 (m, 3H), 6.96 (d, J=9.3 Hz, 2H), 5.17-4.94 (m, 3H), 4.66 (dd, J=7.8, 5.8 Hz, 2H), 4.55-4.37 (m, 2H), 4.33-4.02 (m, 2H), 3.96 (d, J=14.1 Hz, 2H), 3.74-3.53 (m, 1H), 3.48-3.33 (m, 1H), 3.31-3.02 (m, 6H), 2.77-2.62 (m, 2H), 1.99 (d, J=10.2 Hz, 1H), 1.84 (s, 1H), 1.30-1.16 (m, 4H).

Example 309

2-(((3R,4S)-3-fluoro-1-((S)-2-hydroxypropanoyl)piperidin-4-yl)oxy)-5-(4-((4-(4-(tetrahydro-2H-pyran-4-yl)piperazin-1-yl)phenyl)amino)-1,3,5-triazin-2-yl)benzonitrile

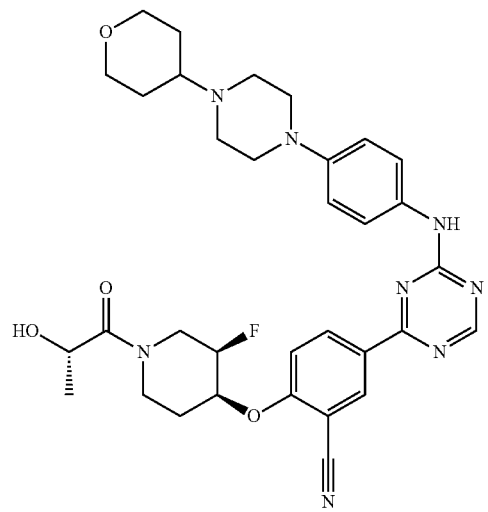 [SMILES: C[C@H](O)C(=O)N1CC[C@H](Oc2ccc(-c3ncnc(Nc4ccc(N5CCN(C6CCOCC6)CC5)cc4)n3)cc2C#N)[C@H](F)C1]

1-(4-nitrophenyl)piperazine (2000 mg, 9.65 mmol), dihydro-2H-pyran-4(3H)-one (2898.7 mg, 28.95 mmol), sodium cyanoborohydride (1819.49 mg, 28.95 mmol) in methanol (74 ml) followed by zinc chloride (1973.41 mg, 14.48 mmol) was stirred at 48° C. for 1 hour. The reaction was diluted with dichloromethane to make a 25% methanol/dichloromethane solution and the reaction was washed with water. The crude material was dried, filtered, concentrated and purified by flash chromatography (silica gel) to provide 1-(4-nitrophenyl)-4-(tetrahydro-2H-pyran-4-yl)piperazine. LCMS-ESI$^+$ (m/z): [M+H]$^+$ calcd for $C_{15}H_{21}N_3O$: 291.4; found: 292.1

1-(4-nitrophenyl)-4-(tetrahydro-2H-pyran-4-yl)piperazine (2810 mg, 9.64 mmol), palladium (10%, 513.21 mg, 0.48 mmol) on carbon in ethanol (14 ml) were combined in a PARR flask and shaken on the hydrogenator for overnight at 45 PSI. The reaction was filtered over celite and washed down with 25% methanol/dichloromethane, concentrated and provided 4-(4-(tetrahydro-2H-pyran-4-yl)piperazin-1-yl)aniline. LCMS-ESI$^+$ (m/z): [M+H]$^+$ calcd for $C_{15}H_{23}N_3O$: 261.4; found: 262.1

4-(4-(tetrahydro-2H-pyran-4-yl)piperazin-1-yl)aniline (1000 mg, 3.83 mmol), 1-(4-pyridinyl)piperazine (1156.77 mg, 7.09 mmol), potassium carbonate (1586.36 mg, 11.48 mmol) in dichloromethane (19 mL) were combined, cooled to 0° C., followed by 2,4-dichloro-1,3,5-triazine (573.79 mg, 3.83 mmol) in DCM (19 mL) and stirred at 0° C. The reaction was subjected to additional solid 2,4-dichloro-1,3,5-triazine (114.76 mg, 0.77 mmol) and stirred for 5 minutes. The reaction was quenched with water, extracted with 30% methanol/dichloromethane, dried, filtered and concentrated to provide 4-chloro-N-(4-(4-(tetrahydro-2H-pyran-4-yl)piperazin-1-yl)phenyl)-1,3,5-triazin-2-amine. LCMS-ESI$^+$ (m/z): [M+H]$^+$ calcd for $C_{18}H_{23}ClN_6O$: 374.9; found: 375.5

343

A 2-5 mL microwave vial was charged with 4-chloro-N-(4-(4-(tetrahydro-2H-pyran-4-yl)piperazin-1-yl)phenyl)-1,3,5-triazin-2-amine (100 mg, 0.27 mmol), (3R,4S)-tert-butyl 4-(2-cyano-4-(4,4,5,5-tetramethyl-1,3,2-dioxaborolan-2-yl)phenoxy)-3-fluoropiperidine-1-carboxylate (142.87 mg, 0.32 mmol), 2M Sodium carbonate (0.6 ml), Tetrakis(triphenylphosphine)palladium(0) (18.32 mg, 0.02 mmol) in 2.63 mL of dimethoxyethane, blown down with nitrogen, irridated for 20 minutes at 150° C. The reaction was extracted with 30% methanol/dichloromethane, dried, filtered, concentrated and purified by flash chromatography (silica gel) to provide 2-(((3R,4S)-3-fluoro-1-((S)-2-hydroxypropanoyl)piperidin-4-yl)oxy)-5-(4-((4-(4-(tetrahydro-2H-pyran-4-yl)piperazin-1-yl)phenyl)amino)-1,3,5-triazin-2-yl)benzonitrile. LCMS-ESI$^+$ (m/z): [M+H]$^+$ calcd for $C_{35}H_{43}FN_8O_4$: 658.8; found: 659.4

(3R,4S)-tert-butyl 4-(2-cyano-4-(4-((4-(4-(tetrahydro-2H-pyran-4-yl)piperazin-1-yl)phenyl)amino)-1,3,5-triazin-2-yl)phenoxy)-3-fluoropiperidine-1-carboxylate (210 mg, 0.32 mmol) was dissolved in dichloromethane (1.5 ml), trifluoroacetic acid (0.25 ml, 3.19 mmol) was added and the reaction was stirred at room temperature for 45 minutes. The reaction cooled to 0° C., neutralized with saturated sodium bicarbonate, diluted with 30% methanol/dichloromethane washed with water, dried, filtered and concentrated to provide 2-(((3R,4S)-3-fluoropiperidin-4-yl)oxy)-5-(4-((4-(4-(tetrahydro-2H-pyran-4-yl)piperazin-1-yl)phenyl)amino)-1,3,5-triazin-2-yl)benzonitrile. LCMS-ESI$^+$ (m/z): [M+H]$^+$ calcd for $C_{30}H_{35}FN_8O_2$: 558.7; found: 559.3

2-(((3R,4S)-3-fluoropiperidin-4-yl)oxy)-5-(4-((4-(4-(tetrahydro-2H-pyran-4-yl)piperazin-1-yl)phenyl)amino)-1,3,5-triazin-2-yl)benzonitrile (100 mg, 0.18 mmol) was dissolved in dichloromethane (2.6 mL), N,N-Diisopropylethylamine (0.06 ml, 0.36 mmol), N-[(dimethylamino)-1H-1,2,3-triazolo-[4,5-b]pyridin-1-ylmethylene]-N-methylmethanaminiumhexafluorophosphate N-oxide (102.36 mg, 0.27 mmol), (S)-2-hydroxypropanoic acid (32.25 mg, 0.36 mmol) was added and the reaction was allowed to stir for 1 hour at room temperature. The mixture was diluted with dichloromethane and water. The aqueous phase was extracted three times with dichloromethane. The combined extracts were dried over anhydrous sodium sulfate, filtered, and concentrated under reduced pressure. The residue was purified via prep HPLC (0-40% acetonitrile in water, 0.1% trifluoroacetic acid buffer) to provide 2-(((3R,4S)-3-fluoro-1-((S)-2-hydroxypropanoyl)piperidin-4-yl)oxy)-5-(4-((4-(4-(tetrahydro-2H-pyran-4-yl)piperazin-1-yl)phenyl)amino)-1,3,5-triazin-2-yl)benzonitrile. LCMS-ESI$^+$ (m/z): [M+H]$^+$ calcd for $C_{33}H_{39}FN_8O_4$: 630.7; found: 631.3

$^1$H NMR (400 MHz, DMSO-d$_6$) δ 10.13 (d, J=17.3 Hz, 1H), 8.74 (s, 1H), 8.67-8.50 (m, 2H), 7.72-7.44 (m, 3H), 6.96 (d, J=9.1 Hz, 2H), 5.20-4.90 (m, 3H), 4.45 (dd, J=7.8, 5.8 Hz, 2H), 3.90 (dt, J=10.3, 6.7 Hz, 2H), 3.72-3.52 (m, 1H), 3.10 (s, 5H), 2.62 (s, 4H), 2.48-2.45 (m, 2H), 2.02-1.78 (m, 2H), 1.75 (d, J=7.4 Hz, 2H), 1.50-1.35 (m, 2H), 1.22 (dd, J=6.5, 3.2 Hz, 3H).

344

Example 310

2-(((3R,4S)-3-fluoro-1-((S)-2-hydroxypropanoyl)piperidin-4-yl)oxy)-5-(4-((3-fluoro-4-(1-(oxetan-3-yl)piperidin-4-yl)phenyl)amino)-1,3,5-triazin-2-yl)benzonitrile

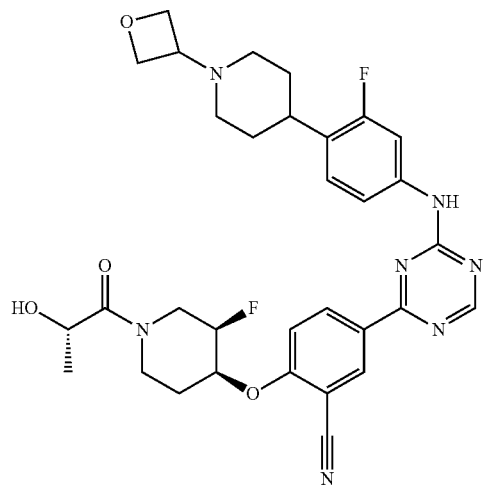 [SMILES: C[C@H](O)C(=O)N1CC[C@H](Oc2ccc(-c3ncnc(Nc4ccc(C5CCN(C6COC6)CC5)c(F)c4)n3)cc2C#N)[C@H](F)C1]

4-(2-fluoro-4-nitrophenyl)piperidine (300 mg, 1.155 mmol), oxetan-3-one (248.8 mg, 3.45 mmol), sodium cyanoborohydride (216.95 mg, 3.45 mmol) in methanol (8.9 ml) followed by zinc chloride (235.3 mg, 1.73 mmol) was stirred at 48C for overnight. The reaction was diluted with dichloromethane to make a 25% methanol/dichloromethane solution, washed with water, dried, filtered, concentrated and purified by flash chromatography (silica gel) to provide 4-(2-fluoro-4-nitrophenyl)-1-(oxetan-3-yl)piperidine. LCMS-ESI$^+$ (m/z): [M+H]$^+$ calcd for $C_{14}H_{17}N_2O_3$: 280.3; found: 281.1

4-(2-fluoro-4-nitrophenyl)-1-(oxetan-3-yl)piperidine (310 mg, 1.11 mmol), palladium (10%, 58.85 mg, 0.06 mmol) on carbon in ethanol (3 ml) were combined in a PARR flask and shaken on the hydrogenator for 2 hours at 45 PSI. The reaction was filtered over celite and washed down with 25% methanol/dichloromethane and concentrated to provide 3-fluoro-4-(1-(oxetan-3-yl)piperidin-4-yl)aniline. LCMS-ESI$^+$ (m/z): [M+H]$^+$ calcd for $C_{14}H_{19}FN_2O$: 250.3; found: 251.1

3-fluoro-4-(1-(oxetan-3-yl)piperidin-4-yl)aniline (276 mg, 1.1 mmol), potassium carbonate (457.17 mg, 3.31 mmol) in dichloromethane (5.5 mL) were combined, cooled to 0° C., followed by 2,4-dichloro-1,3,5-triazine (165.36 mg, 1.1 mmol) in dichloromethane (5.5 mL) that was cooled to 0C before addition and stirred at 0C. The reaction was quenched with water, extracted with 30% methanol/dichloromethane and back extracted with water. The organic layers were combined, dried, filtered, concentrated and purified by flash chromatography (silica gel) to provide 4-chloro-N-(4-(4-(oxetan-3-ylmethyl)piperazin-1-yl)phenyl)-1,3,5-triazin-2-amine LCMS-ESI$^+$ (m/z): [M+H]$^+$ calcd for $C_{17}H_{19}ClFN_5O$: 363.8; found: 364.3

In a 5 ml microwave tube, combined 4-chloro-N-(3-fluoro-4-(1-(oxetan-3-yl)piperidin-4-yl)phenyl)-1,3,5-triazin-2-amine (70 mg, 0.19 mmol), 2-(((3R,4S)-3-fluoro-1-((S)-2-hydroxypropanoyl)piperidin-4-yl)oxy)-5-(4,4,5,5-tetramethyl-1,3,2-dioxaborolan-2-yl)benzonitrile (96.57 mg, 0.23 mmol), dimethoxyethane (2 mL) and 2M Sodium carbonate solution in water (0.43 ml), tetrakis(triphenylphosphine)palladium (22.23 mg, 0.02 mmol) was added, blown down with nitrogen and the vial was sealed. The reaction mixture was heated in microwave at 150° C. for 20 minutes. The mixture was diluted with 30% methanol/dichloromethane and water. The aqueous phase was extracted three times with 30% methanol/dichloromethane. The combined extracts were dried over anhydrous sodium sulfate, filtered, and concentrated under reduced pressure. The residue was purified via prep HPLC (0-70% acetonitrile in water, 0.1% trifluoroacetic acid buffer) to provide 2-(((3R,4S)-3-fluoro-1-((S)-2-hydroxypropanoyl)piperidin-4-yl)oxy)-5-(4-((3-fluoro-4-(1-(oxetan-3-yl)piperidin-4-yl)phenyl)amino)-1,3,5-triazin-2-yl)benzonitrile. LCMS-ESI$^+$(m/z): [M+H]$^+$ calcd for $C_{32}H_{35}FN_7O_4$: 619.7; found: 620.3 $^1$H NMR (400 MHz, DMSO-d$_6$) δ 10.30 (s, 1H), 8.79 (s, 1H), 8.63-8.53 (m, 2H), 7.64 (d, J=9.1 Hz, 2H), 7.25 (d, J=8.1 Hz, 2H), 5.16-4.93 (m, 3H), 4.48 (dt, J=29.7, 6.3 Hz, 4H), 4.25-3.90 (m, 2H), 3.46-3.26 (m, 2H), 3.26-3.11 (m, 1H), 2.78 (s, 3H), 1.98-1.60 (m, 8H), 1.19 (dd, J=6.5, 3.2 Hz, 3H).

Example 311

2-(((3R,4S)-3-fluoro-1-((S)-2-hydroxypropanoyl)piperidin-4-yl)oxy)-5-(4-((4-(1-(oxetan-3-yl)piperidin-4-yl)phenyl)amino)-1,3,5-triazin-2-yl)benzonitrile

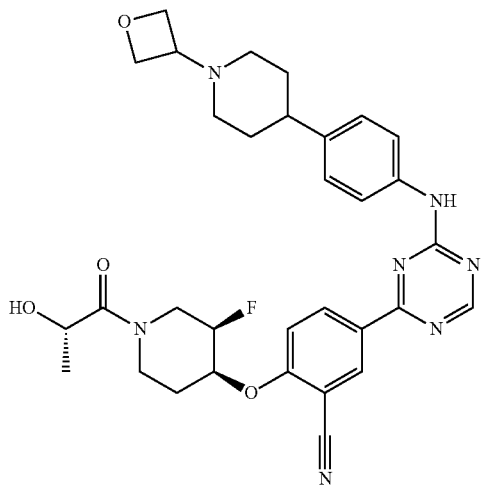

In a 5 ml microwave tube, combined 4-chloro-N-(4-(1-(oxetan-3-yl)piperidin-4-yl)phenyl)-1,3,5-triazin-2-amine (70 mg, 0.2 mmol), 2-(((3R,4S)-3-fluoro-1-((S)-2-hydroxypropanoyl)piperidin-4-yl)oxy)-5-(4,4,5,5-tetramethyl-1,3,2-dioxaborolan-2-yl)benzonitrile (101.6 mg, 0.24 mmol), dimethoxyethane (2 mL) and 2M Sodium carbonate solution in water (0.46 ml), tetrakis(triphenylphosphine)palladium (23.39 mg, 0.02 mmol) was added, blown down with nitrogen and the vial was sealed. The reaction mixture was heated in microwave at 150° C. for 20 minutes. The mixture was diluted with 30% methanol/dichloromethane and water. The aqueous phase was extracted three times with 30% methanol/dichloromethane. The combined extracts were dried over anhydrous sodium sulfate, filtered, and concentrated under reduced pressure. The residue was purified via prep HPLC (0-70% acetonitrile in water, 0.1% trifluoroacetic acid buffer) to provide 2-(((3R,4S)-3-fluoro-1-((S)-2-hydroxypropanoyl)piperidin-4-yl)oxy)-5-(4-((4-(1-(oxetan-3-yl)piperidin-4-yl)phenyl)amino)-1,3,5-triazin-2-yl)benzonitrile. LCMS-ESI$^+$ (m/z): [M+H]$^+$ calcd for $C_{32}H_{36}FN_7O_4$: 601.7; found: 602.2 $^1$H NMR (400 MHz, DMSO-d$_6$) δ 10.30 (s, 1H), 8.79 (s, 1H), 8.63-8.53 (m, 2H), 7.64 (d, J=9.1 Hz, 3H), 7.25 (d, J=8.1 Hz, 2H), 5.16-4.93 (m, 3H), 4.48 (dt, J=29.7, 6.3 Hz, 4H), 4.25-3.90 (m, 2H), 3.46-3.26 (m, 2H), 3.26-3.11 (m, 1H), 2.78 (d, J=10.7 Hz, 2H), 1.98 (s, 2H), 1.84 (t, J=10.6 Hz, 4H), 1.76-1.58 (m, 2H), 1.19 (dd, J=6.5, 3.2 Hz, 3H).

Example 312

2-(((3R,4S)-3-fluoro-1-((S)-2-hydroxypropanoyl)piperidin-4-yl)oxy)-5-(4-((4-(4-(3-methyloxetan-3-yl)piperazin-1-yl)phenyl)amino)-1,3,5-triazin-2-yl)benzonitrile

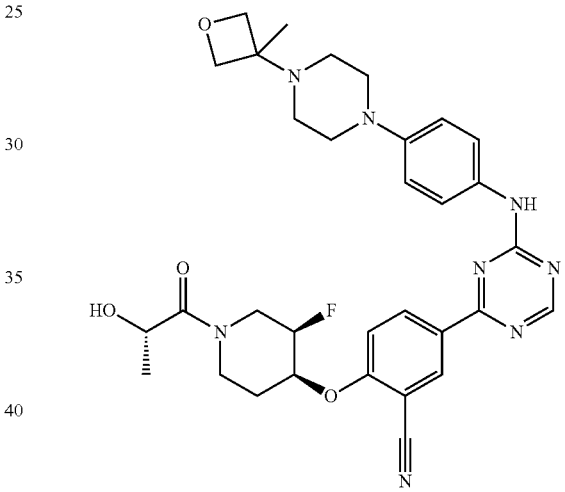

1-fluoro-4-nitrobenzene (0.9 ml, 8.5 mmol), 1-(3-methyloxetan-3-yl)piperazine (1328.64 mg, 8.5 mmol), potassium carbonate (3526.15 mg, 25.51 mmol) in acetonitrile (13 ml) was stirred at 150° C. for 2 overnights. The reaction was diluted with ethyl acetate, washed with water, dried, concentrated and purified by flash chromatography (silica gel) to provide 1-(3-methyloxetan-3-yl)-4-(4-nitrophenyl)piperazine. LCMS-ESI$^+$ (m/z): [M+H]$^+$ calcd for $C_{14}H_{19}N_3O_3$: 277.3; found: 278.0

1-(3-methyloxetan-3-yl)-4-(4-nitrophenyl)piperazine (2030 mg, 7.32 mmol), palladium (10%, 389.5 mg, 0.37 mmol) on carbon in ethanol (11 ml) were combined in a PARR flask and shaken on the hydrogenator for overnight at 45 PSI. The reaction was filtered over celite and washed down with 25% methanol/dichloromethane, concentrated to provide 4-(4-(3-methyloxetan-3-yl)piperazin-1-yl)aniline. LCMS-ESI$^+$ (m/z): [M+H]$^+$ calcd for $C_{14}H_{21}N_3O$: 247.3; found: 248.1

4-(4-(1-methylcyclobutyl)piperazin-1-yl)aniline (800 mg, 3.06 mmol), potassium carbonate (1269.09 mg, 9.18 mmol) in dichloromethane (15.5 mL) were combined, cooled to 0C, followed by 2,4-dichloro-1,3,5-triazine (459.03 mg, 3.06 mmol) in dichloromethane (15.5 mL) that was cooled to 0C before addition and stirred at 0° C. for 5 minutes. The reaction was subjected to an additional 225 mg of 2,4-dichloro-1,3,5-triazine in dichloromethane (5 mL) and stirred for an additional 5 minutes. The reaction was quenched with water, extracted with 30% methanol/dichloromethane, dried, filtered, concentrated and purified by flash chromatography (silica gel) to provide 4-chloro-N-(4-(4-(3-methyloxetan-3-yl)piperazin-1-yl)phenyl)-1,3,5-triazin-2-amine. LCMS-ESI$^+$ (m/z): [M+H]$^+$ calcd for $C_{17}H_{21}ClN_6O$: 360.8; found: 361.4

In a 5 ml microwave tube, combined 4-chloro-N-(4-(4-(3-methyloxetan-3-yl)piperazin-1-yl)phenyl)-1,3,5-triazin-2-amine (70 mg, 0.19 mmol), 2-(((3R,4S)-3-fluoro-1-((S)-2-hydroxypropanoyl)piperidin-4-yl)oxy)-5-(4,4,5,5-tetramethyl-1,3,2-dioxaborolan-2-yl)benzonitrile (97.37 mg, 0.23 mmol), dimethoxyethane (2 ml) and 2M Sodium carbonate solution in water (0.44 ml), tetrakis(triphenylphosphine)palladium (22.42 mg, 0.02 mmol) was added, blown down with nitrogen and the vial was sealed. The reaction mixture was heated in microwave at 150° C. for 20 minutes. The mixture was diluted with 30% methanol/dichloromethane and water. The aqueous phase was extracted three times with 30% methanol/dichloromethane. The combined extracts were dried over anhydrous sodium sulfate, filtered, and concentrated under reduced pressure. The residue was purified via prep HPLC (0-70% acetonitrile in water, 0.1% trifluoroacetic acid buffer) to provide 2-(((3R,4S)-3-fluoro-1-((S)-2-hydroxypropanoyl)piperidin-4-yl)oxy)-5-(4-((4-(4-(3-methyloxetan-3-yl)piperazin-1-yl)phenyl)amino)-1,3,5-triazin-2-yl)benzonitrile. LCMS-ESI$^+$ (m/z): [M+H]$^+$ calcd for $C_{32}H_{37}FN_8O_4$: 616.7; found: 617.2 $^1$H NMR (400 MHz, DMSO-d$_6$) δ 10.14 (d, J=19.3 Hz, 1H), 8.73 (s, 1H), 8.62-8.50 (m, 2H), 7.59 (dd, J=21.7. 8.9 Hz, 3H), 6.96 (d, J=9.2 Hz, 2H), 5.16-4.93 (m, 3H), 4.45 (d, J=5.6 Hz, 2H), 4.53-3.5 (m, 2H), 4.14 (d, J=5.6 Hz, 2H), 3.13 (d, J=6.3 Hz, 4H), 2.43 (d, J=6.3 Hz, 4H), 1.96 (d, J=11.2 Hz, 2H), 1.32-1.14 (m, 7H), 0.91-0.76 (m, 1H).

Example 313

5-(4-((4-(7-oxa-2-azaspiro[3.5]nonan-2-yl)phenyl)amino)-1,3,5-triazin-2-yl)-2-(((3R,4S)-3-fluoro-1-((S)-2-hydroxypropanoyl)piperidin-4-yl)oxy)benzonitrile

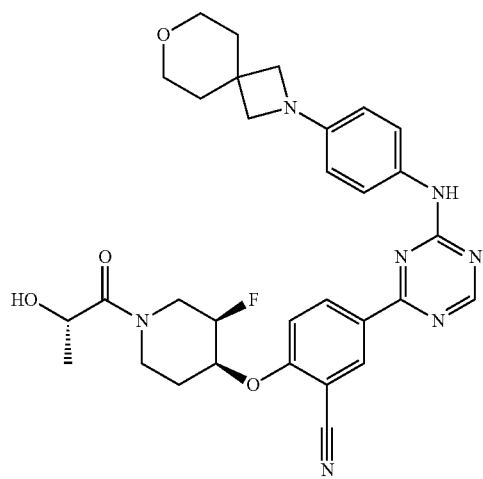 [SMILES: C[C@H](O)C(=O)N1CC[C@H](Oc2ccc(-c3ncnc(Nc4ccc(N5CC6(CCOCC6)C5)cc4)n3)cc2C#N)[C@H](F)C1]

1-fluoro-4-nitrobenzene (0.75 ml, 7.09 mmol), 7-oxa-2-azaspiro[3.5]nonane oxalate salt (1525.19 mg, 7.09 mmol), potassium carbonate (2938.46 mg, 21.26 mmol) in acetonitrile (11 ml) was stirred at 100° C. for 2 overnights. The reaction was diluted with ethyl acetate, washed with water, dried and concentrated. The crude material was washed with ethyl acetate, filtered and dried to provide 2-(4-nitrophenyl)-7-oxa-2-azaspiro[3.5]nonane. LCMS-ESI$^+$ (m/z): [M+H]$^+$ calcd for $C_{13}H_{16}N_2O_3$: 248.3; found: 249.1

2-(4-nitrophenyl)-7-oxa-2-azaspiro[3.5]nonane (1750 mg, 7.05 mmol), palladium (10%, 375.05 mg, 0.35 mmol) on carbon in ethanol (10 ml) were combined in a PARR flask and shaken on the hydrogenator for overnight at 45 PSI. The reaction was filtered over celite and washed down with 25% methanol/dichloromethane, concentrated to provide 4-(7-oxa-2-azaspiro[3.5]nonan-2-yl)aniline. LCMS-ESI$^+$ (m/z): [M+H]$^+$ calcd for $C_{13}H_{18}N_2O$: 218.3; found: 219.3

4-(7-oxa-2-azaspiro[3.5]nonan-2-yl)aniline (800 mg, 3.66 mmol), potassium carbonate (1519.47 mg, 10.99 mmol) in dichloromethane (18 mL) were combined, cooled to 0C, followed by 2,4-dichloro-1,3,5-triazine (549.59 mg, 3.66 mmol) in dichloromethane (18 mL) that was cooled to 0° C. before addition and stirred at 0C for 5 minutes. The reaction was quenched with water, extracted with 30% methanol/dichloromethane, dried, filtered, concentrated and purified by flash chromatography (silica gel) to provide N-(4-(7-oxa-2-azaspiro[3.5]nonan-2-yl)phenyl)-4-chloro-1,3,5-triazin-2-amine. LCMS-ESI$^+$ (m/z): [M+H]$^+$ calcd for $C_{16}H_{18}ClN_5O$: 331.8; found: 332.6

In a 5 ml microwave tube, combined N-(4-(7-oxa-2-azaspiro[3.5]nonan-2-yl)phenyl)-4-chloro-1,3,5-triazin-2-amine (65 mg, 0.2 mmol), 2-(((3R,4S)-3-fluoro-1-((S)-2-hydroxypropanoyl)piperidin-4-yl)oxy)-5-(4,4,5,5-tetramethyl-1,3,2-dioxaborolan-2-yl)benzonitrile (98.33 mg, 0.24 mmol), dimethoxyethane (2 mL) and 2M Sodium carbonate solution in water (0.44 ml), tetrakis(triphenylphosphine)palladium (22.64 mg, 0.02 mmol) was added, blown down with nitrogen and the vial was sealed. The reaction mixture was heated in microwave at 150° C. for 20 minutes. The mixture was diluted with 30% methanol/dichloromethane and water. The aqueous phase was extracted three times with 30% methanol/dichloromethane. The combined extracts were dried over anhydrous sodium sulfate, filtered, and concentrated under reduced pressure. The residue was purified via prep HPLC (0-70% acetonitrile in water, 0.1% trifluoroacetic acid buffer) to provide 5-(4-((4-(7-oxa-2-azaspiro[3.5]nonan-2-yl)phenyl)amino)-1,3,5-triazin-2-yl)-2-(((3R,4S)-3-fluoro-1-((S)-2-hydroxypropanoyl)piperidin-4-yl)oxy)benzonitrile. LCMS-ESI$^+$ (m/z): [M+H]$^+$ calcd for $C_{31}H_{34}FN_7O_4$: 587.6; found: 588.2 $^1$H NMR (400 MHz, DMSO-d$_6$) δ 10.07 (d, J=21.0 Hz, 1H), 8.72 (s, 1H), 8.67-8.45 (m, 2H), 7.64 (d, J=9.1 Hz, 1H), 7.49 (dd, J=17.9, 8.5 Hz, 2H), 6.45 (dd, J=11.5, 8.4 Hz, 2H), 5.24-4.90 (m, 3H), 4.59-4.30 (m, 2H), 4.28-3.86 (m, 1H), 3.71-3.45 (m, 8H), 2.13-1.64 (m, 6H), 1.36-1.10 (m, 3H).

Example 314

4-(4-((4-(3-cyano-4-(((3R,4S)-3-fluoro-1-((S)-2-hydroxypropanoyl)piperidin-4-yl)oxy)phenyl)-1,3,5-triazin-2-yl)amino)phenyl)morpholine-2-carboxamide

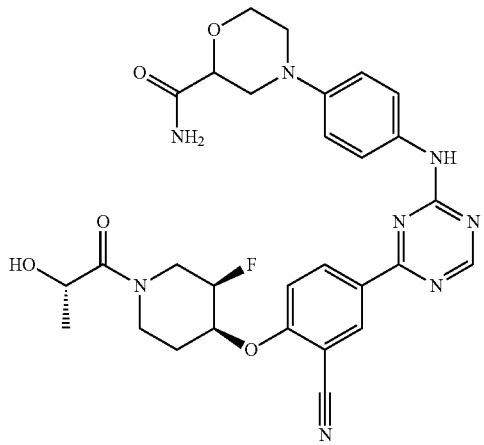

1-fluoro-4-nitrobenzene (0.75 ml, 7.09 mmol), morpholine-2-carboxamide (1535.03 mg, 9.21 mmol), potassium carbonate (4897.44 mg, 35.44 mmol) in N-Methyl-2-pyrrolidone (11 ml) was stirred at 100° C. for 3 overnights. The reaction was diluted with ethyl acetate, washed with water, dried and concentrated. The crude was washed with ethyl acetate, filtered and dried to provide 4-(4-nitrophenyl)morpholine-2-carboxamide. LCMS-ESI$^+$ (m/z): [M+H]$^+$ calcd for $C_{11}H_{13}N_3O_4$: 251.2; found: 252.1

1-(4-nitrophenyl)-4-(tetrahydro-2H-pyran-4-yl)piperazine (2810 mg, 9.64 mmol), palladium (10%, 513.21 mg, 0.48 mmol) on carbon in ethanol (14 ml) were combined in a PARR flask and shaken on the hydrogenator for overnight at 45 PSI. The reaction was filtered over celite and washed down with 25% methanol/dichloromethane, concentrated to provide 4-(4-aminophenyl)tetrahydro-2H-pyran-2-carboxamide.

LCMS-ESI$^+$ (m/z): [M+H]$^+$ calcd for $C_{12}H_{16}N_2O_2$: 220.3; found: 221.1

4-(4-aminophenyl)morpholine-2-carboxamide (500 mg, 2.26 mmol), potassium carbonate (936.96 mg, 6.76 mmol) in dichloromethane (11 mL) were combined, cooled to 0° C., followed by 2,4-dichloro-1,3,5-triazine (338.9 mg, 2.26 mmol) in dichloromethane (11 mL) that was cooled to 0C before addition and stirred at 0C for 5 minutes. The reaction was quenched with water, extracted with 30% methanol/dichloromethane, dried, filtered, concentrated and purified by flash chromatography (silica gel) to provide 4-(4-((4-chloro-1,3,5-triazin-2-yl)amino)phenyl)morpholine-2-carboxamide. LCMS-ESI$^+$ (m/z): [M+H]$^+$ calcd for $C_{14}H_{15}ClN_6O_2$: 334.8; found: 335.4

In a 0.5-2 ml microwave tube, combined 4-(4-((4-chloro-1,3,5-triazin-2-yl)amino)phenyl)morpholine-2-carboxamide (35 mg, 0.1 mmol), 2-(((3R,4S)-3-fluoro-1-((S)-2-hydroxypropanoyl)piperidin-4-yl)oxy)-5-(4,4,5,5-tetramethyl-1,3,2-dioxaborolan-2-yl)benzonitrile (52.48 mg, 0.13 mmol), dimethoxyethane (1 mL) and 2M Sodium carbonate solution in water (0.24 ml), tetrakis(triphenylphosphine)palladium (12.08 mg, 0.01 mmol) was added, blown down with nitrogen and the vial was sealed. The reaction mixture was heated in microwave at 150° C. for 20 minutes. The mixture was diluted with 30% methanol/dichloromethane and water. The aqueous phase was extracted three times with 30% methanol/dichloromethane. The combined extracts were dried over anhydrous sodium sulfate, filtered, and concentrated under reduced pressure. The residue was purified via prep HPLC (0-70% acetonitrile in water, 0.1% trifluoroacetic acid buffer) to provide 4-(4-((4-(3-cyano-4-(((3R,4S)-3-fluoro-1-((S)-2-hydroxypropanoyl)piperidin-4-yl)oxy)phenyl)-1,3,5-triazin-2-yl)amino)phenyl)morpholine-2-carboxamide. LCMS-ESI$^+$ (m/z): [M+H]$^+$ calcd for $C_{29}H_{31}FN_8O_4$: 590.6; found: 591.1 $^1$H NMR (400 MHz, DMSO-d$_6$) δ 10.18 (d, J=18.1 Hz, 1H), 8.75 (s, 1H), 8.57 (d, J=11.2 Hz, 2H), 7.63 (d, J=9.5 Hz, 3H), 7.34 (d, J=22.2 Hz, 2H), 6.99 (d, J=8.5 Hz, 2H), 5.27-4.84 (m, 3H), 4.60-4.30 (m, 1H), 4.24-3.88 (m, 4H), 3.71 (td, J=11.2, 2.8 Hz, 2H), 3.52-3.33 (m, 2H), 2.67 (d, J=33.1 Hz, 2H), 2.04-1.72 (m, 2H), 1.19 (dd, J=6.5, 3.2 Hz, 3H).

Example 315

(R)-4-(4-((4-(3-cyano-4-(((3R,4S)-3-fluoro-1-((S)-2-hydroxypropanoyl)piperidin-4-yl)oxy)phenyl)-1,3,5-triazin-2-yl)amino)phenyl)morpholine-2-carboxamide

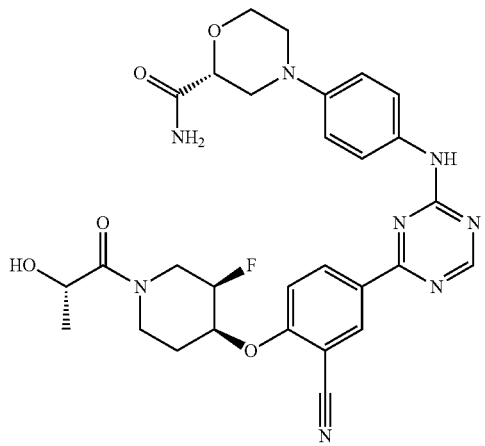 [SMILES: C[C@H](O)C(=O)N1CC[C@H](Oc2ccc(-c3ncnc(Nc4ccc(N5CCO[C@@H](C(N)=O)C5)cc4)n3)cc2C#N)[C@H](F)C1]

4-(4-((4-(3-cyano-4-(((3R,4S)-3-fluoro-1-((S)-2-hydroxypropanoyl)piperidin-4-yl)oxy)phenyl)-1,3,5-triazin-2-yl)amino)phenyl)morpholine-2-carboxamide was subjected to chiral HPLC chromatography (CHIRALCEL OD-H, ACN: methanol (90:10)) to isolate (R)-4-(4-((4-(3-cyano-4-(((3R,4S)-3-fluoro-1-((S)-2-hydroxypropanoyl)piperidin-4-yl)oxy)phenyl)-1,3,5-triazin-2-yl)amino)phenyl)morpholine-2-carboxamide. $^1$H NMR (400 MHz, DMSO-d$_6$) δ 10.16 (d, J=16.3 Hz, 1H), 8.74 (s, 1H), 8.57 (d, J=10.7 Hz, 2H), 7.63 (d, J=9.6 Hz, 3H), 7.31 (d, J=22.7 Hz, 2H), 6.97 (d, J=8.5 Hz, 2H), 5.25-4.89 (m, 3H), 4.61-4.34 (m, 1H), 4.28-3.86 (m, 4H), 3.71 (td, J=11.2, 2.8Hz, 2H), 3.52-3.41 (m, 2H), 2.70 (d, J=33.1 Hz, 2H), 2.04-1.72 (m, 2H), 1.19 (dd, J=6.5, 3.2 Hz, 3H).

Example 316

(S)-4-(4-((4-(3-cyano-4-(((3R,4S)-3-fluoro-1-((S)-2-hydroxypropanoyl)piperidin-4-yl)oxy)phenyl)-1,3,5-triazin-2-yl)amino)phenyl)morpholine-2-carboxamide

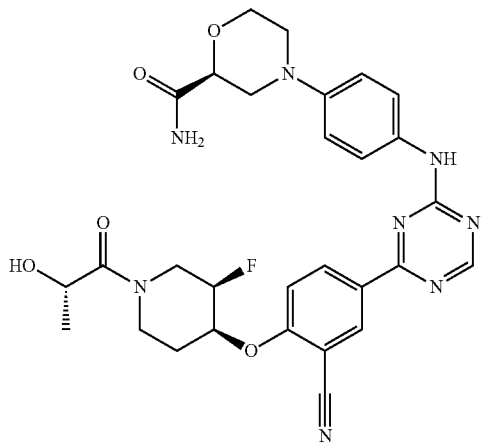 [SMILES: C[C@H](O)C(=O)N1CC[C@H](Oc2ccc(-c3ncnc(Nc4ccc(N5CCO[C@H](C(N)=O)C5)cc4)n3)cc2C#N)[C@H](F)C1]

4-(4-((4-(3-cyano-4-(((3R,4S)-3-fluoro-1-((S)-2-hydroxypropanoyl)piperidin-4-yl)oxy)phenyl)-1,3,5-triazin-2-yl)amino)phenyl)morpholine-2-carboxamide was subjected to chiral HPLC chromatography (CHIRALCEL OD-H, ACN: methanol (90:10)) to isolate (S)-4-(4-((4-(3-cyano-4-(((3R,4S)-3-fluoro-1-((S)-2-hydroxypropanoyl)piperidin-4-yl)oxy)phenyl)-1,3,5-triazin-2-yl)amino)phenyl)morpholine-2-carboxamide.

$^1$H NMR (400 MHz, DMSO-$d_6$) δ 10.16 (d, J=16.5 Hz, 1H), 8.74 (s, 1H), 8.57 (d, J=10.4 Hz, 2H), 7.63 (d, J=9.6 Hz, 3H), 7.32 (d, J=22.5 Hz, 2H), 6.97 (d, J=8.5 Hz, 2H), 5.24-4.93 (m, 3H), 4.59-4.33 (m, 1H), 4.23-3.89 (m, 4H), 3.71 (td, J=11.2,2.8 Hz, 2H), 3.51-3.33 (m, 2H), 2.70 (d, J=33.1 Hz, 2H), 2.04-1.69 (m, 2H), 1.19 (dd, J=6.4, 2.8 Hz, 3H).

Example 317

2-(((3R,4S)-3-fluoro-1-((S)-2-hydroxypropanoyl)piperidin-4-yl)oxy)-5-(4-((4-(tetrahydro-1H-furo[3,4-c]pyrrol-5(3H)-yl)phenyl)amino)-1,3,5-triazin-2-yl)benzonitrile

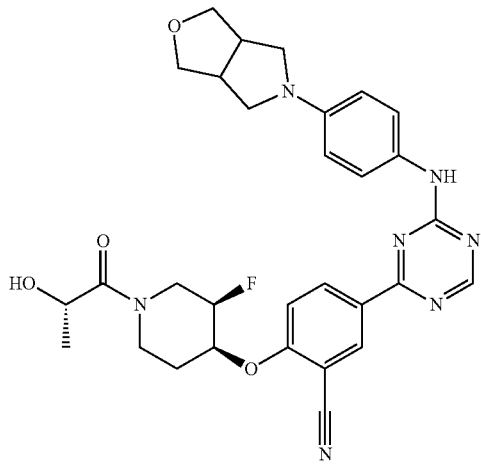 [SMILES: C[C@H](O)C(=O)N1CC[C@H](Oc2ccc(-c3ncnc(Nc4ccc(N5CC6COCC6C5)cc4)n3)cc2C#N)[C@H](F)C1]

1-fluoro-4-nitrobenzene (0.75 ml, 7.09 mmol), hexahydro-1H-furo[3,4-c]pyrrole (1378.49 mg, 9.21 mmol), potassium carbonate (4897.44 mg, 35.44 mmol) in N-Methyl-2-pyrrolidone (11 ml) was stirred at 100° C. for 3 overnights. The reaction was diluted with ethyl acetate, washed with water, dried, concentrated and purified by flash chromatography (silica gel) to provide 5-(4-nitrophenyl)hexahydro-1H-furo[3,4-c]pyrrole LCMS-ESI$^+$ (m/z): [M+H]$^+$ calcd for $C_{12}H_{14}N_2O_3$: 234.3; found: 235.1

5-(4-nitrophenyl)hexahydro-1H-furo[3,4-c]pyrrole (1530 mg, 6.53 mmol), palladium (10%, 347.54 mg, 0.33 mmol) on carbon in ethanol (10 ml) were combined in a PARR flask and shaken on the hydrogenator for 1 hour at 45 PSI. The reaction was filtered over celite and washed down with 25% methanol/dichloromethane, and concentrated to provide 4-(tetrahydro-1H-furo[3,4-c]pyrrol-5(3H)-yl)aniline. LCMS-ESI$^+$ (m/z): [M+H]$^+$ calcd for $C_{12}H_{16}N_2O$: 204.3; found: 205.1

4-(tetrahydro-1H-furo[3,4-c]pyrrol-5(3H)-yl)aniline (500 mg, 2.45 mmol), potassium carbonate (1014.88 mg, 7.34 mmol) in dichloromethane (12 mL) were combined, cooled to 0° C., followed by 2,4-dichloro-1,3,5-triazine (367.08 mg, 2.45 mmol) in dichloromethane (12 mL) and stirred at 0° C. for 5 minutes. The crude material was quenched with water, extracted with 30% methanol/dichloromethane, washed with water, dried, concentrated and purified by flash chromatography (silica gel) to provide 4-chloro-N-(4-(tetrahydro-1H-furo[3,4-c]pyrrol-5(3H)-yl)phenyl)-1,3,5-triazin-2-amine. LCMS-ESI$^+$ (m/z): [M+H]$^+$ calcd for $C_{15}H_{16}ClN_5O$: 317.8; found: 318.5

In a 2-5 ml microwave tube, combined 4-chloro-N-(4-(tetrahydro-1H-furo[3,4-c]pyrrol-5(3H)-yl)phenyl)-1,3,5-triazin-2-amine (70 mg, 0.22 mmol), 2-(((3R,4S)-3-fluoro-1-((S)-2-hydroxypropanoyl)piperidin-4-yl)oxy)-5-(4,4,5,5-tetramethyl-1,3,2-dioxaborolan-2-yl)benzonitrile (110.56 mg, 0.26 mmol), dimethoxyethane (2 mL) and 2M Sodium carbonate solution in water (0.5 ml), tetrakis(triphenylphosphine)palladium (25.46 mg, 0.02 mmol) was added, blown down with nitrogen and the vial was sealed. The reaction mixture was heated in microwave at 150° C. for 20 minutes. The mixture was diluted with 30% methanol/dichloromethane and water. The aqueous phase was extracted three times with 30% methanol/dichloromethane. The combined extracts were dried over anhydrous sodium sulfate, filtered, and concentrated under reduced pressure. The residue was purified via prep HPLC (0-60% acetonitrile in water, 0.1% trifluoroacetic acid buffer) to provide 2-(((3R,4S)-3-fluoro-1-((S)-2-hydroxypropanoyl)piperidin-4-yl)oxy)-5-(4-((4-(tetrahydro-1H-furo[3,4-c]pyrrol-5(3H)-yl)phenyl)amino)-1,3,5-triazin-2-yl)benzonitrile. LCMS-ESI$^+$ (m/z): [M+H]$^+$ calcd for $C_{30}H_{32}FN_7O_4$: 573.6; found: 574.2 $^1$H NMR (400 MHz, DMSO-$d_6$) δ 10.06 (d, J=18.8 Hz, 1H), 8.70 (d, J=2.7 Hz, 1H), 8.64-8.45 (m, 2H), 7.62 (d, J=9.1 Hz, 1H), 7.50 (dd, J=16.4, 8.5 Hz, 2H), 6.64 (dd, J=11.6, 8.5 Hz, 2H), 5.26-4.86 (m, 3H), 4.56-4.32 (m, 2H), 4.25-3.91 (m, 2H), 3.89-3.72 (m, 2H), 3.60-3.48 (m, 2H), 3.25-3.03 (m, 3H), 2.97 (q, J=4.1 Hz, 2H), 1.98-1.83 (m, 2H), 1.19 (dd, J=6.6, 3.3 Hz, 3H).

Example 318

2-(((3R,4S)-3-fluoro-1-(1H-pyrazole-5-carbonyl)piperidin-4-yl)oxy)-5-(4-((4-(1-(oxetan-3-yl)piperidin-4-yl)phenyl)amino)-1,3,5-triazin-2-yl)benzonitrile

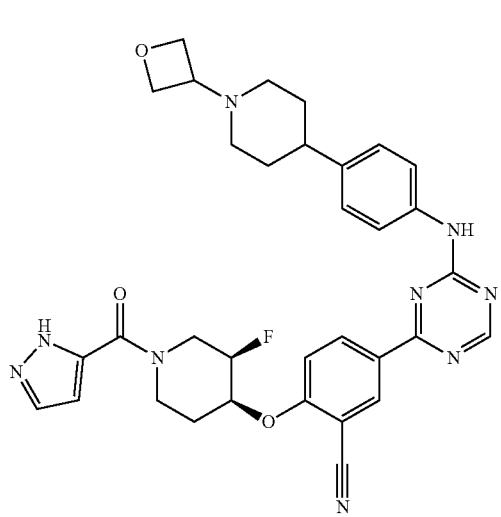 [SMILES: N#Cc1cc(-c2ncnc(Nc3ccc(C4CCN(C5COC5)CC4)cc3)n2)ccc1O[C@H]1CCN(C(=O)c2ccn[nH]2)C[C@H]1F]

2-(((3R,4S)-3-fluoropiperidin-4-yl)oxy)-5-(4-((4-(1-(oxetan-3-yl)piperidin-4-yl)phenyl)amino)-1,3,5-triazin-2-yl)benzonitrile (70 mg, 0.13 mmol) was dissolved in dichloromethane (2 mL), N,N-Diisopropylethylamine (0.05 ml, 0.26 mmol), N-[(dimethylamino)-1H-1,2,3-triazolo-[4,5-b]pyridin-1-ylmethylene]-N-methylmethanaminiumhexafluorophosphate N-oxide (75.58 mg, 0.2 mmol), 1H-pyrazole-5-carboxylic acid (29.63 mg, 0.26 mmol) was added and the reaction was allowed to stir for 1 hour at room temperature. The mixture was diluted with 30% methanol/dichloromethane and water. The aqueous phase was extracted three times with 30% methanol/dichloromethane. The combined extracts were dried over anhydrous sodium sulfate, filtered, and concentrated under reduced pressure. The residue was purified via prep HPLC (0-60% acetonitrile in water, 0.1% trifluoroacetic acid buffer) to provide 2-(((3R,4S)-3-fluoro-1-((S)-2-hydroxypropanoyl)piperidin-4-yl)oxy)-5-(4-((4-(tetrahydro-1H-furo[3,4-c]pyrrol-5(3H)-yl)phenyl)amino)-1,3,5-triazin-2-yl)benzonitrile. LCMS-ESI+ (m/z): [M+H]+ calcd for $C_{33}H_{34}FN_9O_3$: 623.7; found: 624.2 1H NMR (400 MHz, DMSO-$d_6$) δ 13.23 (d, J=2.2 Hz, 1H), 10.32 (s, 1H), 8.79 (s, 1H), 8.66-8.46 (m, 2H), 7.92-7.75 (m, 1H), 7.65 (d, J=9.2 Hz, 3H), 7.25 (d, J=8.3 Hz, 2H), 6.60 (t, J=2.2 Hz, 1H), 5.28-4.83 (m, 3H), 4.53 (t, J=2.2 Hz, 2H), 4.44 (t, J=2.2 Hz, 2H), 4.38-4.19 (m, 1H), 3.68 (m, 2H), 2.80 (d, J=10.8 Hz, 2H), 2.13-1.53 (m, 10H).

Example 319

2-(((3R,4S)-1-(2-(1H-1,2,3-triazol-5-yl)acetyl)-3-fluoropiperidin-4-yl)oxy)-5-(4-((4-(4-(oxetan-3-yl)piperazin-1-yl)phenyl)amino)-1,3,5-triazin-2-yl)benzonitrile

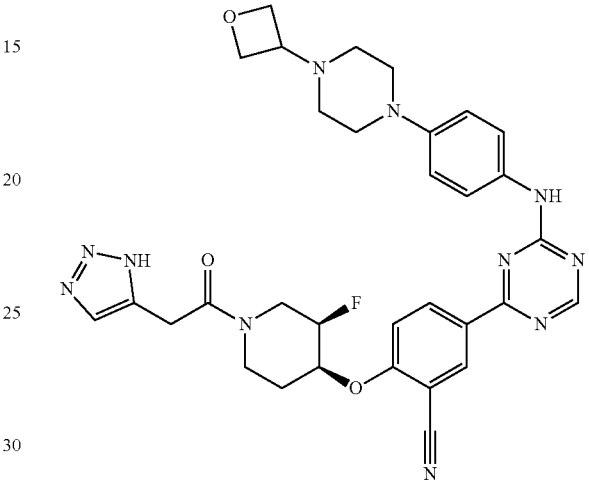

2-(((3R,4S)-3-fluoropiperidin-4-yl)oxy)-5-(4-((4-(4-(oxetan-3-yl)piperazin-1-yl)phenyl)amino)-1,3,5-triazin-2-yl)benzonitrile (50 mg, 0.09 mmol) was dissolved in dichloromethane (1.3 mL), N,N-Diisopropylethylamine (0.03 ml, 0.19 mmol), N-[(dimethylamino)-1H-1,2,3-triazolo-[4,5-b]pyridin-1-ylmethylene]-N-methylmethanaminiumhexafluorophosphate N-oxide (53.89 mg, 0.14 mmol), 2-(1H-1,2,3-triazol-5-yl)acetic acid (23.95 mg, 0.19 mmol) was added and the reaction was allowed to stir for 1 hour at room temperature. According to LCMS, the reaction was complete but allowed to run for 3 hours 30 minutes. The mixture was diluted with 30% methanol/dichloromethane and water. The aqueous phase was extracted three times with 30% methanol/dichloromethane. The combined extracts were dried over anhydrous sodium sulfate, filtered, and concentrated under reduced pressure. The residue was purified via prep HPLC (0-40% acetonitrile in water, 0.1% trifluoroacetic acid buffer) to provide 2-(((3R,4S)-1-(2-(1H-1,2,3-triazol-5-yl)acetyl)-3-fluoropiperidin-4-yl)oxy)-5-(4-((4-(4-(oxetan-3-yl)piperazin-1-yl)phenyl)amino)-1,3,5-triazin-2-yl)benzonitrile. LCMS-ESI+ (m/z): [M+H]+ calcd for $C_{32}H_{34}FN_{11}O_3$: 639.7; found: 640.2 1H NMR (400 MHz, DMSO-$d_6$) δ 10.16 (d, J=18.8 Hz, 1H), 8.75 (s, 1H), 8.57 (d, J=12.5 Hz, 2H), 7.74-7.47 (m, 4H), 6.97 (t, J=9.3 Hz, 2H), 5.06 (d, J=58.3 Hz, 2H), 4.57 (t, J=6.5 Hz, 2H), 4.47 (t, J=6.1 Hz, 2H), 4.39 (s, 1H), 3.94 (d, J=19.8 Hz, 2H), 3.86-3.56 (m, 1H), 3.47-3.38 (m, 2H), 3.14 (m, 5H), 2.41 (dd, J=6.0, 3.7 Hz, 2H), 1.91 (d, J=37.7 Hz, 2H), 1.24 (d, J=3.3 Hz, 1H).

Example 320

2-(((3R,4S)-1-(2-(1H-pyrazol-5-yl)acetyl)-3-fluoropiperidin-4-yl)oxy)-5-(4-((4-(4-(oxetan-3-yl)piperazin-1-yl)phenyl)amino)-1,3,5-triazin-2-yl)benzonitrile

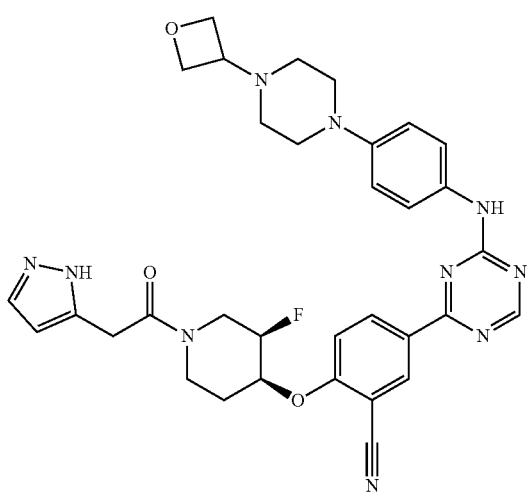 [SMILES: N#Cc1cc(-c2ncnc(Nc3ccc(N4CCN(C5COC5)CC4)cc3)n2)ccc1O[C@H]1CCN(C(=O)Cc2ccn[nH]2)C[C@H]1F]

2-(((3R,4S)-3-fluoropiperidin-4-yl)oxy)-5-(4-((4-(4-(oxetan-3-yl)piperazin-1-yl)phenyl)amino)-1,3,5-triazin-2-yl)benzonitrile (50 mg, 0.09 mmol) was dissolved in dichloromethane (1.3 mL), N,N-Diisopropylethylamine (0.03 ml, 0.19 mmol), N-[(dimethylamino)-1H-1,2,3-triazolo-[4,5-b]pyridin-1-ylmethylene]-N-methylmethanaminiumhexafluorophosphate N-oxide (53.89 mg, 0.14 mmol), 2-(1H-pyrazol-5-yl)acetic acid (23.77 mg, 0.19 mmol) was added and the reaction was allowed to stir for 1 hour at room temperature. The mixture was diluted with 30% methanol/dichloromethane and water. The aqueous phase was extracted three times with 30% methanol/dichloromethane. The combined extracts were dried over anhydrous sodium sulfate, filtered, and concentrated under reduced pressure. The residue was purified via prep HPLC (0-40% acetonitrile in water, 0.1% trifluoroacetic acid buffer) to provide 2-(((3R,4S)-1-(2-(1H-pyrazol-5-yl)acetyl)-3-fluoropiperidin-4-yl)oxy)-5-(4-((4-(4-(oxetan-3-yl)piperazin-1-yl)phenyl)amino)-1,3,5-triazin-2-yl)benzonitrile. LCMS-ESI$^+$ (m/z): [M+H]$^+$ calcd for $C_{33}H_{35}FN_{10}O_3$: 638.7; found: 639.1 $^1$H NMR (400 MHz, DMSO-d$_6$) δ 10.16 (d, J=19.1 Hz, 1H), 8.75 (s, 1H), 8.58 (d, J=12.4 Hz, 2H), 7.76-7.52 (m, 4H), 7.43 (s, 1H), 6.99 (d, J=9.2 Hz, 2H), 6.26 (td, J=2.1, 1.2 Hz, 1H), 5.33-4.89 (m, 4H), 4.57 (t, J=6.5 Hz, 2H), 4.48 (t, J=6.5 Hz, 2H), 4.41 (d, J=27.5 Hz, 1H), 4.23-3.99 (m, 1H), 3.90-3.66 (m, 1H), 3.53-3.38 (m, 2H), 3.22-3.12 (m, 4H), 2.41 (dd, J=6.4, 3.4 Hz, 4H), 1.95 (d, J=49.2 Hz, 2H).

Example 321

2-(((3R,4S)-3-fluoro-1-(3-methyl-1H-pyrazole-5-carbonyl)piperidin-4-yl)oxy)-5-(4-((4-(4-(oxetan-3-yl)piperazin-1-yl)phenyl)amino)-1,3,5-triazin-2-yl)benzonitrile 2-(((3R,4S)-3-fluoropiperidin-4-yl)oxy)-5-(4-((4-(4-(oxetan-3-yl)piperazin-1-yl)phenyl)amino)-1,3,5-triazin-2-yl)benzonitrile (50 mg, 0.09 mmol) was dissolved in dichloromethane (1.3 mL), N,N-Diisopropylethylamine (0.03 ml, 0.19 mmol), N-[(dimethylamino)-1H-1,2,3-triazolo-[4,5-b]pyridin-1-ylmethylene]-N-methylmethanaminiumhexafluorophosphate N-oxide (53.89 mg, 0.14 mmol), 3-methyl-1H-pyrazole-5-carboxylic acid (23.77 mg, 0.19 mmol) was added and the reaction was allowed to stir for 1 hour at room temperature. The reaction was then subjected to 0.5 mL-1 mL of DMF until all of the precipitate went into solution. The reaction was allowed to stir overnight. The reaction was concentrated and then purified via prep HPLC (0-40% acetonitrile in water, 0.1% trifluoroacetic acid buffer) to provide 2-(((3R,4S)-3-fluoro-1-(3-methyl-1H-pyrazole-5-carbonyl)piperidin-4-yl)oxy)-5-(4-((4-(4-(oxetan-3-yl)piperazin-1-yl)phenyl)amino)-1,3,5-triazin-2-yl)benzonitrile. LCMS-ESI$^+$ (m/z): [M+H]$^+$ calcd for $C_{33}H_{35}FN_{10}O_3$: 638.7; found: 639.3

$^1$H NMR (400 MHz, DMSO-d$_6$) δ 12.90 (s, 1H), 10.15 (d, J=18.5 Hz, 1H), 8.74-8.45 (m, 2H), 7.82-7.51 (m, 3H), 6.97 (d, J=9.2 Hz, 2H), 6.33 (s, 1H), 5.24-4.80 (m, 2H), 4.56 (t, J=6.5 Hz, 2H), 4.46 (t, J=6.0 Hz, 2H), 4.35-4.22 (m, 1H), 3.92-3.50 (m, 1H), 3.44 (q, J=6.3 Hz, 1H), 3.13 (t, J=4.9 Hz, 4H), 2.39 (t, J=4.9 Hz, 4H), 2.45 (s, 3H), 2.20-1.85 (m, 2H).

Example 322

2-(((3R,4S)-1-(4-chloro-1H-pyrazole-5-carbonyl)-3-fluoropiperidin-4-yl)oxy)-5-(4-((4-(4-(oxetan-3-yl)piperazin-1-yl)phenyl)amino)-1,3,5-triazin-2-yl)benzonitrile

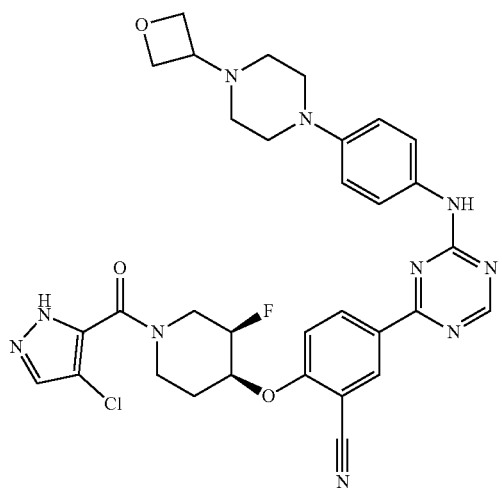 [SMILES: N#Cc1cc(-c2ncnc(Nc3ccc(N4CCN(C5COC5)CC4)cc3)n2)ccc1O[C@H]1CCN(C(=O)c2[nH]ncc2Cl)C[C@H]1F]

2-(((3R,4S)-3-fluoropiperidin-4-yl)oxy)-5-(4-((4-(4-(oxetan-3-yl)piperazin-1-yl)phenyl)amino)-1,3,5-triazin-2-yl)benzonitrile (50 mg, 0.09 mmol) was dissolved in dichloromethane (1.3 mL), N,N-Diisopropylethylamine (0.03 ml, 0.19 mmol), N-[(dimethylamino)-1H-1,2,3-triazolo-[4,5-b]pyridin-1-ylmethylene]-N-methylmethanaminiumhexafluorophosphate N-oxide (53.89 mg, 0.14 mmol), 3-methyl-1H-pyrazole-5-carboxylic acid (23.77 mg, 0.19 mmol) was added and the reaction was allowed to stir for 1 hour at room temperature. The reaction was then subjected to 0.5 mL-1 mL of DMF until all of the precipitate went into solution. The reaction was allowed to stir overnight. The reaction was then subjected to 0.5 mL-1 mL of DMF until all of the precipitate went into solution. The reaction was allowed to stir overnight. The reaction was concentrated and then purified via prep HPLC (0-40% acetonitrile in water, 0.1% trifluoroacetic acid buffer) to provide 2-(((3R,4S)-1-(4-chloro-1H-pyrazole-5-carbonyl)-3-fluoropiperidin-4-yl)oxy)-5-(4-((4-(4-(oxetan-3-yl)piperazin-1-yl)phenyl)amino)-1,3,5-triazin-2-yl)benzonitrile. LCMS-ESI$^+$ (m/z): [M+H]$^+$ calcd for $C_{32}H_{32}ClFN_{10}O_3$: 659.1; found: 659.3

$^1$H NMR (400 MHz, DMSO-d$_6$) δ 10.14 (d, J=6.0 Hz, 1H), 8.73 (s, 1H), 8.56 (d, J=12.7 Hz, 2H), 8.05 (s, 1H), 7.71-7.48 (m, 3H), 6.95 (t, J=9.1 Hz, 2H), 5.33-4.81 (m, 2H), 4.56 (t, J=6.5 Hz, 2H), 4.47 (t, J=6.5 Hz, 2H), 4.41-4.25 (m, 1H), 4.00-3.50 (m, 1H), 3.44 (h, J=6.4 Hz, 2H), 3.14 (m, 5H), 2.44-2.28 (m, 4H), 2.03 (d, J=17.5 Hz, 2H).

Example 323

2-(((3R,4S)-1-(3-amino-4-chloro-1H-pyrazole-5-carbonyl)-3-fluoropiperidin-4-yl)oxy)-5-(4-((4-(4-(oxetan-3-yl)piperazin-1-yl)phenyl)amino)-1,3,5-triazin-2-yl)benzonitrile

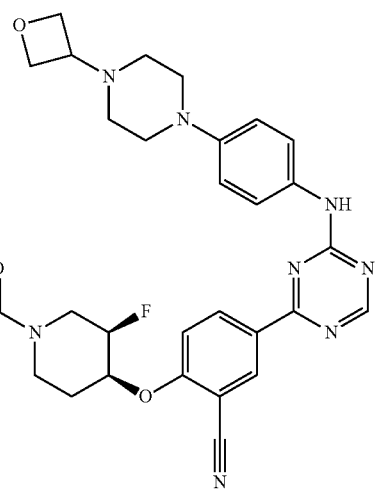

2-(((3R,4S)-3-fluoropiperidin-4-yl)oxy)-5-(4-((4-(4-(oxetan-3-yl)piperazin-1-yl)phenyl)amino)-1,3,5-triazin-2-yl)benzonitrile (50 mg, 0.09 mmol) was dissolved in dichloromethane (1.3 mL), N,N-Diisopropylethylamine (0.2 ml, 1.13 mmol), N-[(dimethylamino)-1H-1,2,3-triazolo-[4,5-b]pyridin-1-ylmethylene]-N-methylmethanaminiumhexafluorophosphate N-oxide (53.89 mg, 0.14 mmol), 3-amino-4-chloro-1H-pyrazole-5-carboxylic acid (30.45 mg, 0.19 mmol) was added and the reaction was allowed to stir for 1 hour at room temperature. The reaction was then subjected to 0.5 mL-1 mL of DMF until all of the precipitate went into solution. The reaction was allowed to stir overnight. The reaction was concentrated and then purified via prep HPLC (0-40% acetonitrile in water, 0.1% trifluoroacetic acid buffer) to provide 2-(((3R,4S)-1-(3-amino-4-chloro-1H-pyrazole-5-carbonyl)-3-fluoropiperidin-4-yl)oxy)-5-(4-((4-(4-(oxetan-3-yl)piperazin-1-yl)phenyl)amino)-1,3,5-triazin-2-yl)benzonitrile. LCMS-ESI$^+$ (m/z): [M+H]$^+$ calcd for $C_{32}H_{33}ClFN_{11}O_3$: 674.1: found: 674.9

$^1$H NMR (400 MHz, DMSO-d$_6$) δ 12.16 (s, 1H), 10.12 (d, J=16.6 Hz, 1H), 8.73 (s, 1H), 8.56 (d, J=10.2 Hz, 2H), 7.79-7.45 (m, 3H), 6.95 (s, 2H) 5.38 (s, 1H), 5.27-4.82 (m, 2H), 4.58 (t, J=6.0 Hz, 2H), 4.46 (t, J=6.0 Hz, 2H), 4.38-4.18 (m, 1H), 4.13-3.90 (m, 1H), 3.80-3.35 (m, 2H), 3.20-3.05 (t, J=4.8 Hz, 4H), 2.40 (t, J=4.8 Hz, 4H), 2.10-1.80 (m, 2H).

Example 324

2-(((3R,4S)-1-(3-chloro-1H-pyrazole-5-carbonyl)-3-fluoropiperidin-4-yl)oxy)-5-(4-((4-(4-(oxetan-3-yl)piperazin-1-yl)phenyl)amino)-1,3,5-triazin-2-yl)benzonitrile

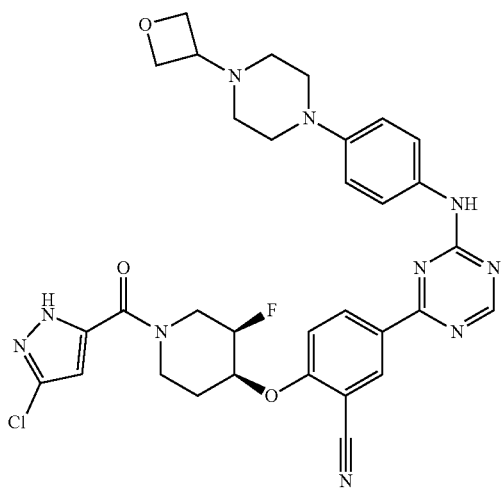 [SMILES: N#Cc1cc(-c2ncnc(Nc3ccc(N4CCN(C5COC5)CC4)cc3)n2)ccc1O[C@H]1CCN(C(=O)c2cc(Cl)n[nH]2)C[C@H]1F]

2-(((3R,4S)-3-fluoropiperidin-4-yl)oxy)-5-(4-((4-(4-(oxetan-3-yl)piperazin-1-yl)phenyl)amino)-1,3,5-triazin-2-yl)benzonitrile (50 mg, 0.09 mmol) was dissolved in dichloromethane (1.3 mL), N,N-Diisopropylethylamine (0.2 ml, 1.13 mmol), N-[(dimethylamino)-1H-1,2,3-triazolo-[4,5-b]pyridin-1-ylmethylene]-N-methylmethanaminiumhexafluorophosphate N-oxide (53.89 mg, 0.14 mmol), 3-chloro-1H-pyrazole-5-carboxylic acid (27.62 mg, 0.19 mmol) was added and the reaction was allowed to stir for 1 hour at room temperature. The reaction was then subjected to 0.5 mL-1 mL of DMF until all of the precipitate went into solution. The reaction was allowed to stir overnight. The reaction was concentrated and then purified via prep HPLC (0-40% acetonitrile in water, 0.1% trifluoroacetic acid buffer) to provide 2-(((3R,4S)-1-(3-chloro-1H-pyrazole-5-carbonyl)-3-fluoropiperidin-4-yl)oxy)-5-(4-((4-(4-(oxetan-3-yl)piperazin-1-yl)phenyl)amino)-1,3,5-triazin-2-yl)benzonitrile. LCMS-ESI$^+$ (m/z): [M+H]$^+$ calcd for $C_{32}H_{33}ClFN_{11}O_3$: 674.1; found: 674.2 $^1$H NMR (400 MHz, DMSO-d$_6$) δ 13.79 (s, 1H), 10.12 (d, J=17.9 Hz, 1H), 8.73 (s, 1H), 8.57 (d, J=10.7 Hz, 2H), 7.73-7.43 (m, 3H), 6.95 (s, 2H), 6.70 (s, 1H), 5.20-5.00 (m, 2H), 4.55 (t, J=6.5 Hz, 2H), 4.46 (t, J=6.1 Hz, 2H), 4.4-4.25 (m, 1H), 3.42 (td, J=11.8, 11.0, 5.5 Hz, 2H), 3.13 (s, 4H), 2.42-2.32 (m, 4H), 2.15-1.80 (m, 2H), 1.22 (d, J=3.4 Hz, 1H).

Example 325

2-(((3R,4S)-3-fluoro-1-(2-hydroxyacetyl)piperidin-4-yl)oxy)-5-(4-((3-methoxy-4-(4-morpholinopiperidin-1-yl)phenyl)amino)-1,3,5-triazin-2-yl)benzonitrile

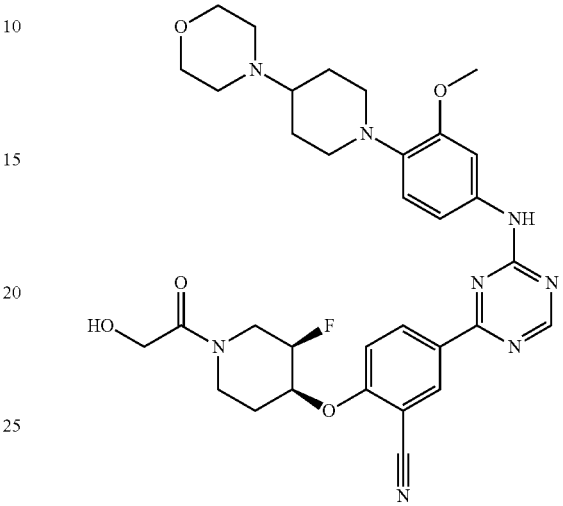

1-fluoro-2-methoxy-4-nitrobenzene (5000 mg, 29.22 mmol), 4-(piperidin-4-yl)morpholine (4974 mg, 29.22 mmol), potassium carbonate (80764 mg, 58.44 mmol) in acetonitrile (45 ml) was stirred at 100° C. for overnight. The reaction was diluted with ethyl acetate, washed with water, dried, concentrated and purified by flash chromatography (silica gel) to provide 4-(1-(2-methoxy-4-nitrophenyl)piperidin-4-yl)morpholine. LCMS-ESI$^+$ (m/z): [M+H]$^+$ calcd for $C_{16}H_{23}N_3O_4$: 321.4; found: 322.0

4-(1-(2-methoxy-4-nitrophenyl)piperidin-4-yl)morpholine (8470 mg, 26.36 mmol), palladium (10%, 4207 mg, 3.953 mmol) on carbon in ethanol (38 ml) were combined in a PARR flask and shaken on the hydrogenator for 1 hour at 45 PSI. The reaction was filtered over celite and washed down with 25% methanol/dichloromethane, and concentrated to provide 3-methoxy-4-(4-morpholinopiperidin-1-yl)aniline. LCMS-ESI$^+$ (m/z): [M+H]$^+$ calcd for $C_{16}H_{25}N_3O_2$: 291.4; found: 292.0

3-methoxy-4-(4-morpholinopiperidin-1-yl)aniline (2000 mg, 6.86 mmol) and potassium carbonate (2845.8 mg, 20.59 mmol) in dichloromethane (34 mL) were combined, cooled to 0° C., followed by 2,4-dichloro-1,3,5-triazine (1029.32 mg, 6.86 mmol) in dichloromethane (34 mL) and the reaction was stirred at 0° C. for 5 minutes. The reaction was filtered, washed with dichloromethane. The filtrate was quenched with water, washed with water and dried to provide 4-chloro-N-(3-methoxy-4-(4-morpholinopiperidin-1-yl)phenyl)-1,3,5-triazin-2-amine.

LCMS-ESI$^+$ (m/z): [M+H]$^+$ calcd for $C_{19}H_{25}ClN_6O_2$: 590.0; found: 591.5

A 10-20 mL microwave vial was charged with (3R,4S)-tert-butyl 4-(2-cyano-4-(4,4,5,5-tetramethyl-1,3,2-dioxaborolan-2-yl)phenoxy)-3-fluoropiperidine-1-carboxylate (496.04 mg, 1.11 mmol), 4-chloro-N-(3-methoxy-4-(4-morpholinopiperidin-1-yl)phenyl)-1,3,5-triazin-2-amine (375 mg, 0.93 mmol), 2M Sodium carbonate (2.08 ml), Palladium-tetrakis(triphenylphosphine (63.62 mg, 0.06 mmol) in 10 mL of dimethoxyethane, blown down with nitrogen, irridated for 20 minutes at 150° C. The reaction was extracted with 30% methanol/dichloromethane, dried, filtered, concentrated and purified by flash chromatography (silica gel) to provide (3R,4S)-tert-butyl 4-(2-cyano-4-(4-((3-methoxy-4-(4-morpholinopiperidin-1-yl)phenyl)amino)-1,3,5-triazin-2-yl)phenoxy)-3-fluoropiperidine-1-carboxylate.

LCMS-ESI+ (m/z): [M+H]+ calcd for $C_{36}H_{45}FN_8O_5$: 688.8; found: 689.4

(3R,4S)-tert-butyl 4-(2-cyano-4-(4-((3-methoxy-4-(4-morpholinopiperidin-1-yl)phenyl)amino)-1,3,5-triazin-2-yl)phenoxy)-3-fluoropiperidine-1-carboxylate (450 mg, 0.65 mmol) was dissolved in dichloromethane (3 ml), trifluoroacetic acid (0.5 ml, 6.53 mmol) was added and the reaction was stirred at room temperature for 1 h and then an additional 0.1 mL of TFA was added and the reaction was stirred for 10 minutes more. The reaction cooled to 0C, neutralized with saturated sodium bicarbonate, washed with water, dried, filtered and concentrated to provide 2-(((3R,4S)-3-fluoropiperidin-4-yl)oxy)-5-(4-((3-methoxy-4-(4-morpholinopiperidin-1-yl)phenyl)amino)-1,3,5-triazin-2-yl)benzonitrile. LCMS-ESI+ (m/z): [M+H]+ calcd for $C_{31}H_{37}FN_8O_3$: 588.7; found: 589.3

2-(((3R,4S)-3-fluoropiperidin-4-yl)oxy)-5-(4-((3-methoxy-4-(4-morpholinopiperidin-1-yl)phenyl)amino)-1,3,5-triazin-2-yl)benzonitrile (50 mg, 0.08 mmol) was dissolved in dimethylformamide (0.5 mL), N,N-Diisopropylethylamine (0.03 ml, 0.17 mmol), N-[(dimethylamino)-1H-1,2,3-triazolo-[4,5-b]pyridin-1-ylmethylene]-N-methylmethanaminiumhexafluorophosphate N-oxide (48.57 mg, 0.13 mmol), 2-hydroxyacetic acid (12.92 mg, 0.17 mmol) was added and the reaction was allowed to stir for 1 hour at room temperature. The reaction was concentrated and then purified via prep HPLC (0-40% acetonitrile in water, 0.1% trifluoroacetic acid buffer) to provide 2-(((3R,4S)-3-fluoro-1-(2-hydroxyacetyl)piperidin-4-yl)oxy)-5-(4-((3-methoxy-4-(4-morpholinopiperidin-1-yl)phenyl)amino)-1,3,5-triazin-2-yl)benzonitrile. LCMS-ESI+ (m/z): [M+H]+ calcd for $C_{33}H_{39}FN_8O_5$: 646.7; found: 647.3

$^1$H NMR (400 MHz, DMSO-$d_6$) δ 10.22 (s, 1H), 8.76 (s, 1H), 8.66-8.50 (m, 2H), 7.74-7.54 (m, 2H), 7.16 (s, 1H), 6.87 (d, J=8.6 Hz, 1H), 5.22-4.90 (m, 2H), 4.66 (s, 1H), 4.42-4.03 (m, 4H), 4.00-3.60 (m, 4H), 3.60-3.50 (m, 5H), 3.42-3.32 (m, 3H), 3.23-3.04 (m, 1H), 2.21 (dd, J=9.2, 5.5 Hz, 2H), 2.06-1.73 (m, 5H), 1.65-1.42 (m, 2H).

Example 326

2-(((3R,4S)-3-fluoro-1-((S)-2-hydroxypropanoyl) piperidin-4-yl)oxy)-5-(4-((3-methoxy-4-(4-morpholinopiperidin-1-yl)phenyl)amino)-1,3,5-triazin-2-yl)benzonitrile

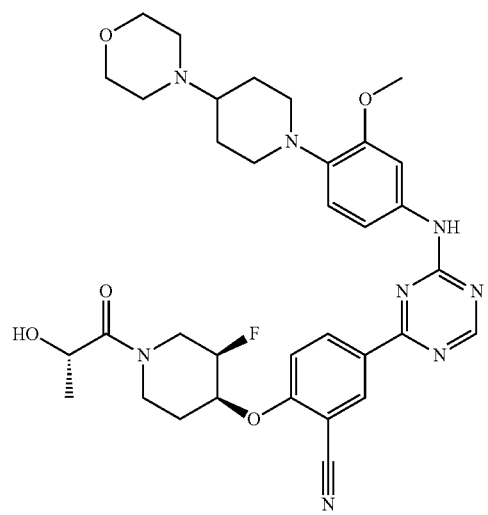 [SMILES: COc1cc(Nc2ncnc(-c3ccc(O[C@H]4CCN(C(=O)[C@H](C)O)C[C@H]4F)c(C#N)c3)n2)ccc1N1CCC(N2CCOCC2)CC1]

2-(((3R,4S)-3-fluoropiperidin-4-yl)oxy)-5-(4-((3-methoxy-4-(4-morpholinopiperidin-1-yl)phenyl)amino)-1,3,5-triazin-2-yl)benzonitrile (50 mg, 0.08 mmol) was dissolved in dimethylformamide (0.5 mL), N,N-Diisopropylethylamine (0.03 ml, 0.17 mmol), N-[(dimethylamino)-1H-1,2,3-triazolo-[4,5-b]pyridin-1-ylmethylene]-N-methylmethanaminiumhexafluorophosphate N-oxide (48.57 mg, 0.13 mmol), (S)-2-hydroxypropanoic acid (15.3 mg, 0.17 mmol) was added and the reaction was allowed to stir for 1 hour at room temperature. The reaction was concentrated and then purified via prep HPLC (0-40% acetonitrile in water, 0.1% trifluoroacetic acid buffer) to provide 2-(((3R,4S)-3-fluoro-1-((S)-2-hydroxypropanoyl) piperidin-4-yl)oxy)-5-(4-((3-methoxy-4-(4-morpholinopiperidin-1-yl)phenyl)amino)-1,3,5-triazin-2-yl)benzonitrile. LCMS-ESI+ (m/z): [M+H]+ calcd for $C_{34}H_{41}FN_8O_5$: 660.7; found: 661.3

$^1$H NMR (400 MHz, DMSO-$d_6$) δ 10.23 (s, 1H), 8.76 (s, 1H), 8.67-8.51 (m, 2H), 7.63 (d, J=9.0 Hz, 2H), 7.16 (d, J=8.6 Hz, 1H), 6.88 (d, J=8.6 Hz, 1H), 5.22-4.90 (m, 3H), 4.58-4.38 (m, 2H), 4.22-3.90 (m, 2H), 3.90-3.75 (m, 4H), 3.6-3.55 (m, 5H), 3.45-3.33 (m, 3H), 3.25-3.05 (m, 1H), 2.20 (d, J=11.7 Hz, 2H), 2.06-1.72 (m, 5H), 1.52 (d, J=11.2 Hz, 2H), 1.19 (dd, J=6.5, 2.7 Hz, 3H).

Example 327

2-(((3R,4S)-1-(2-cyanoacetyl)-3-fluoropiperidin-4-yl)oxy)-5-(4-((3-methoxy-4-(4-morpholinopiperidin-1-yl)phenyl)amino)-1,3,5-triazin-2-yl)benzonitrile

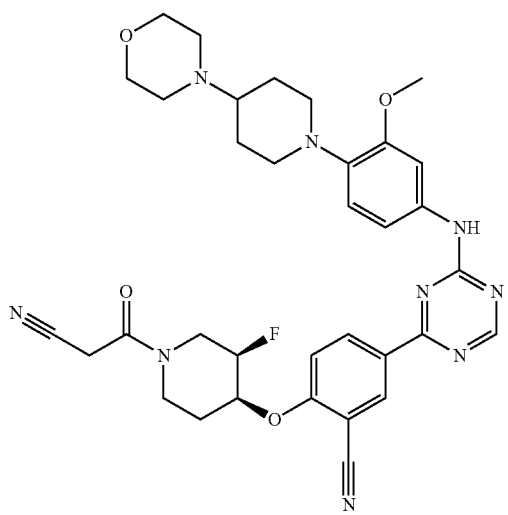 [SMILES: COc1cc(Nc2ncnc(-c3ccc(O[C@H]4CCN(C(=O)CC#N)C[C@H]4F)c(C#N)c3)n2)ccc1N1CCC(N2CCOCC2)CC1]

2-(((3R,4S)-3-fluoropiperidin-4-yl)oxy)-5-(4-((3-methoxy-4-(4-morpholinopiperidin-1-yl)phenyl)amino)-1,3,5-triazin-2-yl)benzonitrile (50 mg, 0.08 mmol) was dissolved in dimethylformamide (0.5 mL), N,N-Diisopropylethylamine (0.03 ml, 0.13 mmol), N-[(dimethylamino)-1H-1,2,3-triazolo-[4,5-b]pyridin-1-yl-methylene]-N-methylmethanaminiumhexafluorophosphate N-oxide (48.57 mg, 0.13 mmol), 2-cyanoacetic acid (14.45 mg, 0.17 mmol) was added and the reaction was allowed to stir for 1 hour at room temperature. The reaction was concentrated and then purified via prep HPLC (0-40% acetonitrile in water, 0.1% trifluoroacetic acid buffer) to provide 2-(((3R,4S)-1-(2-cyanoacetyl)-3-fluoropiperidin-4-yl)oxy)-5-(4-((3-methoxy-4-(4-morpholinopiperidin-1-yl)phenyl)amino)-1,3,5-triazin-2-yl)benzonitrile. LCMS-ESI⁺ (m/z): [M+H]⁺ calcd for $C_{34}H_{38}FN_9O_4$: 655.7; found: 656.3

¹H NMR (400 MHz, DMSO-$d_6$) δ 10.23 (s, 1H), 8.76 (s, 1H), 8.68-8.54 (m, 2H), 7.62 (d, J=9.0 Hz, 2H), 7.40-7.20 (m, 1H), 6.87 (d, J=8.5 Hz, 1H), 5.29-4.92 (m, 2H), 4.40-4.30 (m, 1H), 4.25-3.90 (m, 3H), 3.88-3.70 (m, 4H), 3.70-3.56 (m, 5H), 3.40-3.34 (m, 3H), 2.20 (d, J=11.4 Hz, 2H), 1.97 (d, J=17.1 Hz, 2H), 1.82 (d, J=12.3 Hz, 3H), 1.52 (q, J=11.5 Hz, 3H).

Example 328

3-fluoro-2-(((3R,4S)-3-fluoro-1-((S)-2-hydroxypropanoyl)piperidin-4-yl)oxy)-5-(4-((4-(4-(oxetan-3-yl)piperazin-1-yl)phenyl)amino)-1,3,5-triazin-2-yl)benzonitrile

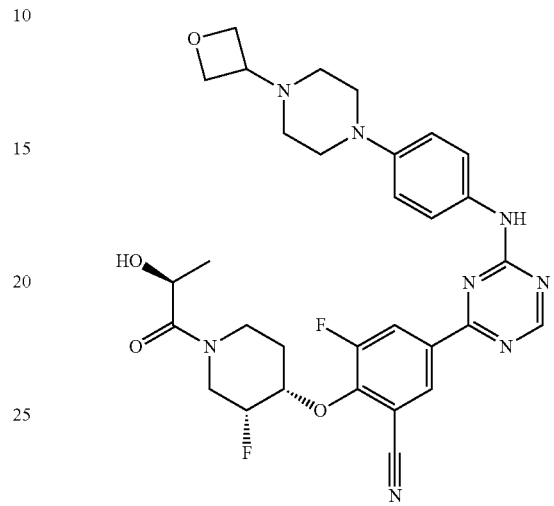

Step 1: Preparation of (3R,4S)-tert-butyl 4-(4-bromo-2-cyano-6-fluorophenoxy)-3-fluoropiperidine-1-carboxylate:

PS-PPh₃ resin (5.34 g, 20.4 mmol 4.4 equiv) was added to a dried 500 mL RBF that was then capped and flushed with nitrogen. The resin was suspended in 75 mL of anhydrous THF. After a period of 2 min, 5-bromo-3-fluoro-2-hydroxybenzonitrile (1 g, 4.63 mmol) dissolved in 38 mL of anhydrous THF was added in a single portion. The resultant suspension was mixed briefly, after which a solution of DEAD was added in a single portion. This mixture was then agitated on an orbital shaker for 30 min, after which a solution of 3R,4R)-tert-butyl 3-fluoro-4-hydroxypiperidine-1-carboxylate (1.27 g, 5.79 mmol) in THF (38 ml) was added in a single portion. The reaction mixture was then stirred 3 h. Then another portion of DEAD was added. The stirring was maintained overnight. The resultant suspension was filtered, and the resin was washed with THF. The filtrate was evaporated in vacuum. Solids were dissolved in DCM and water was added. The organic phase was evaporated under reduced pressure and purified by silica gel column chromatography with EtOAc in hexanes to give the product.

Step 2: Preparation of (3R,4S)-tert-butyl 4-(2-cyano-6-fluoro-4-(4,4,5,5-tetramethyl-1,3,2-dioxaborolan-2-yl)phenoxy)-3-fluoropiperidine-1-carboxylate:

(3R,4S)-tert-butyl 4-(4-bromo-2-cyano-6-fluorophenoxy)-3-fluoropiperidine-1-carboxylate (750 mg, 1.8 mmol), potassium acetate (530 mg, 5.4 mmol), bis(pinacolato)diboron (913 mg, 3.6 mmol), and Pd(dppf)Cl2 (133 mg, 0.18 mmol) were combined in a sealed tube. 1.4-dioxane (25 mL) was added and the mixture was heated at 90° C. overnight. After cooling down, the mixture was filtered through a pad of Celite, eluting with 1,4-dioxane. The filtrate was concentrated to dryness under reduced pressure and the residue was purified by a silica gel column with the ESCO system with 0-5% MeOH in CH2Cl2 to give the product.

Step 3: Preparation of (3R,4S)-tert-butyl 4-(2-cyano-6-fluoro-4-(4-((4-(4-(oxetan-3-yl)piperazin-1-yl)phenyl)amino)-1,3,5-triazin-2-yl)phenoxy)-3-fluoropiperidine-1-carboxylate:

To a mixture of the (3R,4S)-tert-butyl 4-(2-cyano-6-fluoro-4-(4,4,5,5-tetramethyl-1,3,2-dioxaborolan-2-yl)phenoxy)-3-methylpiperidine-1-carboxylate (372 mg, 0.81 mmol), 4-chloro-N-(4-(4-(oxetan-3-yl)piperazin-1-yl)phenyl)-1,3,5-triazin-2-amine (280 mg, 0.81 mmol), and Pd(PPh$_3$)$_4$ (70 mg, 0.061 mmol) in 1,2-DME (4 mL), was added 2M sodium carbonate solution (1.82 mL). The mixture was run under microwave at 130° C. for 75 minutes. Then the reaction mixture was diluted with a mixture of DCM and MeOH (1:1), filtered through a pad of Celite. The biphasic filtrate was concentrated under reduced pressure. Ethanol was added and concentrated. The residue was passed over a silica gel column with 5-15% MeOH in CH$_2$Cl$_2$ to give the product. LCMS-ESI$^+$ (m/z): [M+H]$^+$ calcd for C$_{33}$H$_{38}$F$_2$N$_8$O$_4$: 649.3; found: 649.2

Step 4: Preparation of 3-fluoro-2-(((3R,4S)-3-fluoropiperidin-4-yl)oxy)-5-(4-((4-(4-(oxetan-3-yl)piperazin-1-yl)phenyl)amino)-1,3,5-triazin-2-yl)benzonitrile:

(3R,4S)-tert-butyl 4-(2-cyano-6-fluoro-4-(4-((4-(4-(oxetan-3-yl)piperazin-1-yl)phenyl)amino)-1,3,5-triazin-2-yl)phenoxy)-3-fluoropiperidine-1-carboxylate (414 mg, 0.64 mmol) was taken up in DCM (8 mL) and treated with TFA (2 mL). The reaction mixture was stirred at room temperature overnight. The mixture was concentrated under reduced pressure and the residue was purified by silica gel column eluting 0-20% MeOH in dichloromethane to give the product. LCMS-ESI$^+$ (m/z): calcd for C$_{28}$H$_{30}$F$_2$N$_8$O$_2$: 549.3; found: 549.2

Step 5: Preparation of 3-fluoro-2-(((3R,4S)-3-fluoro-1-((S)-2-hydroxypropanoyl)piperidin-4-yl)oxy)-5-(4-((4-(4-(oxetan-3-yl)piperazin-1-yl)phenyl)amino)-1,3,5-triazin-2-yl)benzonitrile:

To a mixture of 3-fluoro-2-(((3R,4S)-3-fluoropiperidin-4-yl)oxy)-5-(4-((4-(4-(oxetan-3-yl)piperazin-1-yl)phenyl)amino)-1,3,5-triazin-2-yl)benzonitrile (50 mg), (S)-2-hydroxypropanoic acid (16 mg) and TEA (45 mg) in DMF (3 mL) was added HATU (69 mg). The reaction mixture was stirred at room temperature overnight. The mixture was treated with water and extracted with DCM. The organic phase was dried over Na2SO4, concentrated to dryness. The residue was purified by silica gel column chromatography using 5-20% MeOH in CH2Cl2 as eluent to give the title compound. $^1$H NMR (400 MHz, DMSO-d$_6$) δ 10.22 (d, 1H), 8.77 (d, 1H), 8.53-8.24 (m, 2H), 7.55 (t, 2H), 6.95 (d, 2H), 5.02 (m, 2H), 4.90 (d, 2H), 4.56 (t, 2H), 4.46 (t, 3H), 4.24-3.81 (m, 2H), 3.60 (m, 1H), 3.43 (m, 1H), 3.14 (d, 4H), 2.40 (d, 4H), 2.13-1.79 (m, 2H), 1.12 (d, 3H). LCMS-ESI$^+$ (m/z): [M+H]$^+$ calcd for C$_{31}$H$_{34}$F$_2$N$_8$O$_4$: 621.3; found: 621.4

Example 329

3-fluoro-2-(((3R,4S)-3-fluoro-1-(2-hydroxyacetyl)piperidin-4-yl)oxy)-5-(4-((4-(4-(oxetan-3-yl)piperazin-1-yl)phenyl)amino)-1,3,5-triazin-2-yl)benzonitrile

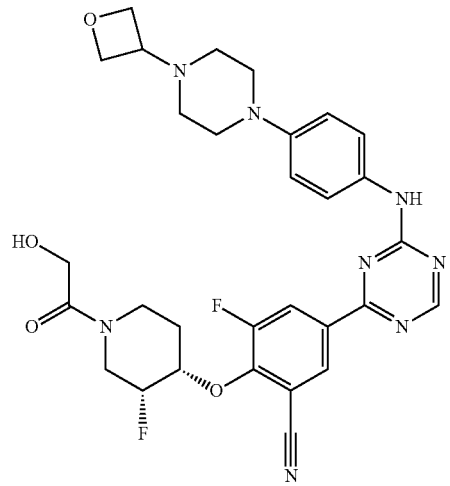 [SMILES: N#Cc1cc(-c2ncnc(Nc3ccc(N4CCN(C5COC5)CC4)cc3)n2)cc(F)c1O[C@H]1CCN(C(=O)CO)C[C@H]1F]

To a mixture of 3-fluoro-2-(((3R,4S)-3-fluoropiperidin-4-yl)oxy)-5-(4-((4-(4-(oxetan-3-yl)piperazin-1-yl)phenyl)amino)-1,3,5-triazin-2-yl)benzonitrile (50 mg, 0.09 mmol), glycolic acid (14 mg, 0.18 mmol) and TEA (45 mg, 0.37 mmol) in DMF (3 mL) was added HATU (69 mg, 0.18 mmol). The reaction mixture was stirred at room temperature overnight. The mixture was treated with water and extracted with DCM. The organic phase was dried over Na2SO4, concentrated to dryness. The residue was purified by silica gel column with ESCO system using 5-20% MeOH in CH2Cl2 as eluent to give the title compound. $^1$H NMR (400 MHz, DMSO-d6) δ 10.22 (d, 1H), 8.77 (d, 1H), 8.53-8.26 (m, 2H), 7.55 (t, 2H), 7.12-6.86 (m, 2H), 5.05 (s, 1H), 4.89 (m, 1H), 4.66 (s, 1H), 4.56 (m, 2H), 4.46 (m, 2H), 4.24-3.99 (m, 3H), 3.93 (m, 1H), 3.67 (d, 1H), 3.52-3.37 (m, 1H), 3.13 (m, 5H), 2.40 (m, 4H), 2.13-1.84 (m, 2H). LCMS-ESI$^+$ (m/z): [M+H]$^+$ calcd for C$_{30}$H$_{32}$F$_2$N$_8$O$_4$: 607.3; found: 607.4

Example 330

2-(((3R,4S)-1-(2-cyanoacetyl)-3-fluoropiperidin-4-yl)oxy)-3-fluoro-5-(4-((4-(4-(oxetan-3-yl)piperazin-1-yl)phenyl)amino)-1,3,5-triazin-2-yl)benzonitrile

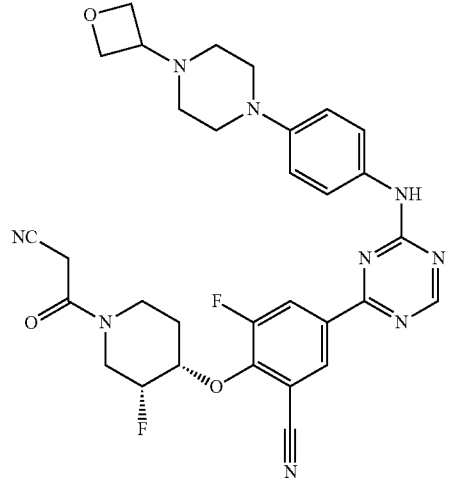 [SMILES: N#CCC(=O)N1CC[C@H](Oc2c(F)cc(-c3ncnc(Nc4ccc(N5CCN(C6COC6)CC5)cc4)n3)cc2C#N)[C@H](F)C1]

3-fluoro-2-(((3R,4S)-3-fluoropiperidin-4-yl)oxy)-5-(4-((4-(4-(oxetan-3-yl)piperazin-1-yl)phenyl)amino)-1,3,5-triazin-2-yl)benzonitrile (35 mg, 0.064 mmol), HATU (48 mg, 0.128 mmol), TEA (32 mg, 0.26 mmol) and 2-cyanoacetic acid (11 mg, 0.128 mmol) were dissolved in DMF(2 mL) and stirred at room temperature for 2 hr. The mixture was diluted with DCM and extracted with water. The organic phase was evaporated and the residue was purified by preparative HPLC. The fractions were taken and extracted with DCM and washed aqueous NaHCO3 solution. The organic phase was dried over Na2SO4, filtered. The filtrate was evaporated under reduced pressure to give the title compound. 1H NMR (400 MHz, DMSO-d6) δ 10.28 (d, 1H), 8.79 (s, 1H), 8.53-8.32 (m, 2H), 7.59 (m, 2H), 7.14-6.92 (m, 2H), 5.07 (d, 1H), 5.01-4.80 (m, 2H), 4.72 (m, 4H), 4.33 (m, 1H), 4.25-3.93 (m, 3H), 3.72-3.52 (m, 2H), 3.27 (m, 2H), 3.01 (m, 4H), 2.25-1.78 (m, 4H). LCMS-ESI$^+$ (m/z): [M+H]$^+$ calcd for $C_{31}H_{31}F_2N_9O_3$: 616.3; found: 616.4

Example 331

3-fluoro-2-(((3R,4S)-3-fluoro-1-(3-hydroxypropanoyl)piperidin-4-yl)oxy)-5-(4-((4-(4-(oxetan-3-yl)piperazin-1-yl)phenyl)amino)-1,3,5-triazin-2-yl)benzonitrile

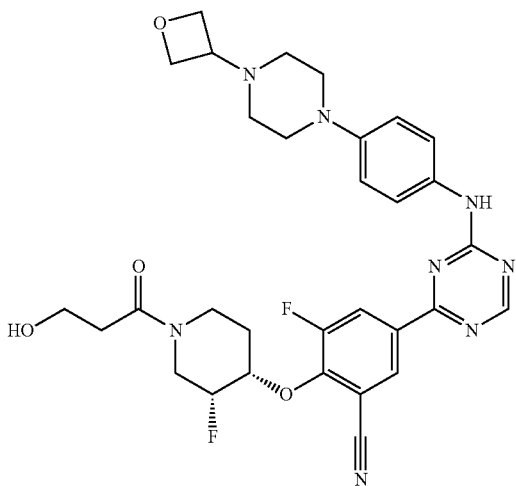 [SMILES: N#Cc1cc(-c2ncnc(Nc3ccc(N4CCN(C5COC5)CC4)cc3)n2)cc(F)c1O[C@H]1CCN(C(=O)CCO)C[C@H]1F]

3-fluoro-2-(((3R,4S)-3-fluoropiperidin-4-yl)oxy)-5-(4-((4-(4-(oxetan-3-yl)piperazin-1-yl)phenyl)amino)-1,3,5-triazin-2-yl)benzonitrile (25 mg, 0.046 mmol), HATU (35 mg, 0.09 mmol), TEA (22 mg, 0.18 mmol) and 3-hydroxypropanoic acid (8 mg, 0.09 mmol) were dissolved in DMF (2 mL) and stirred at room temperature for 2 hr. The mixture was diluted with DCM and extracted with water. The organic phase was evaporated and the residue was purified by preparative HPLC. The fractions were taken and extracted with DCM and washed aqueous NaHCO3 solution. The organic phase was dried over Na2SO4, filtered. The filtrate was evaporated under reduced pressure to give the title compound. $^1$H NMR (400 MHz, DMSO-d$_6$) δ 10.28 (d, 1H), 8.79 (s, 1H), 8.54-8.27 (m, 2H), 7.60 (t, 2H), 7.04 (m, 2H), 5.02 (d, 1H), 4.94-4.81 (m, 2H), 4.73 (m, 4H), 4.36-4.15 (m, 1H), 4.08 (m, 1H), 3.96-3.70 (m, 2H), 3.62 (m, 3H), 3.16-2.85 (m, 4H), 2.48 (m, 6H), 2.16-1.76 (m, 2H). LCMS-ESI$^+$ (m/z): [M+H]$^+$ calcd for $C_{31}H_{34}F_2N_8O_4$: 620.3; found: 621.4

Example 332

5-(4-((4-(2-(pyrrolidin-1-yl)ethoxy)phenyl)amino)-1,3,5-triazin-2-yl)-2-((tetrahydro-2H-pyran-4-yl)oxy)benzonitrile

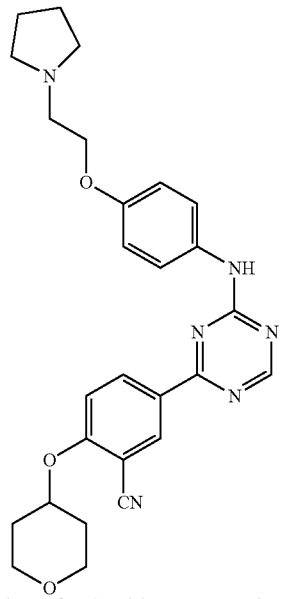 [SMILES: N#Cc1cc(-c2ncnc(Nc3ccc(OCCN4CCCC4)cc3)n2)ccc1OC1CCOCC1]

To a suspension of 5-(4-chloro-1,3,5-triazin-2-yl)-2-((tetrahydro-2H-pyran-4-yl)oxy)benzonitrile (222 mg, 0.70 mmol) in DMF (4 mL) was treated with 4-(2-(pyrrolidin-1-yl)ethoxy)aniline (145 mg, 0.70 mmol) and DIEA (0.18 g, 1.4 mmol) at room temperature. The mixture was stirred at room temperature for 15 min. The mixture was purified by preparative HPLC to give the title compound. 1H NMR (400 MHz, DMSO-d6) δ 9.97 (s, 1H), 8.76 (s, 1H), 8.65-8.40 (m, 1H), 7.67 (d, 2H), 7.54 (d, 1H), 7.03 (d, 2H), 4.93 (m, 1H), 4.29 (m, 2H), 3.94-3.77 (m, 3H), 3.71-3.40 (m, 7H), 3.12 (m, 2H), 2.04 (m, 3H), 1.88 (m, 2H), 1.68 (m, 2H). LCMS-ESI$^+$ (m/z): [M+H]$^+$ calcd for $C_{27}H_{30}N_6O_3$: 487.2; found: 487.3

Example 333

2-(((3R,4S)-3-fluoro-1-((S)-2-oxooxazolidine-4-carbonyl)piperidin-4-yl)oxy)-5-(4-((4-(4-(oxetan-3-yl)piperazin-1-yl)phenyl)amino)-1,3,5-triazin-2-yl)benzonitrile

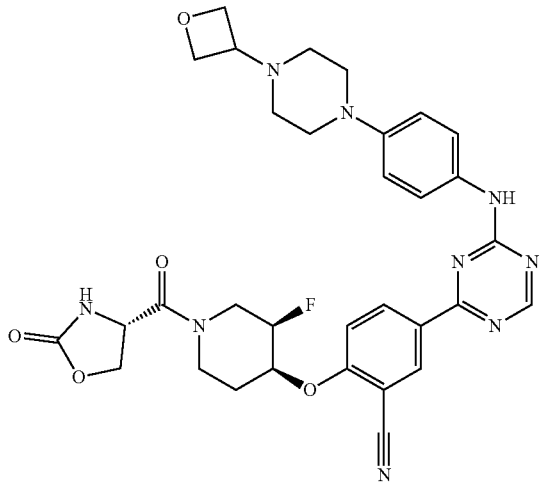 [SMILES: N#Cc1cc(-c2ncnc(Nc3ccc(N4CCN(C5COC5)CC4)cc3)n2)ccc1O[C@H]1CCN(C(=O)[C@@H]2COC(=O)N2)C[C@H]1F]

2-(((3R,4S)-3-fluoropiperidin-4-yl)oxy)-5-(4-((4-(4-(oxetan-3-yl)piperazin-1-yl)phenyl)amino)-1,3,5-triazin-2-yl)benzonitrile ( 82 mg, 0.15 mmol), HATU (117 mg, 0.31 mmol), TEA (76 mg, 0.62 mmol) and (S)-2-oxooxazolidine-4-carboxylic acid (41 mg, 0.31 mmol) were dissolved in DMF (4 mL) and stirred at room temperature for 2 hr. The mixture was diluted with DCM and extracted with water. The organic phase was evaporated and the residue was purified by preparative HPLC. The fractions were taken and extracted with DCM and washed aqueous NaHCO3 solution. The organic phase was dried over Na2SO4, filtered. The filtrate was evaporated under reduced pressure to give the title compound. 1H NMR (400 MHz, DMSO-d6) δ 10.11 (d, 1H), 8.73 (s. 1H), 8.65-8.44 (m, 2H), 7.95 (d, 1H), 7.71-7.42 (m, 3H), 6.95 (m, 2H), 5.22-4.93 (m, 2H), 4.86 (m, 1H), 4.63-4.39 (m, 6H), 4.38-4.12 (m, 2H), 4.04 (m, 1H), 3.44 (m, 1H), 3.13 m, 5H), 2.40 (m, 4H), 1.99 (m, 2H). LCMS-ESI$^+$ (m/z): [M+H]$^+$ calcd for $C_{32}H_{34}FN_9O_5$: 644.3; found: 644.3

Example 334

2-(((3R,4S)-1-(3-amino-1H-1,2,4-triazole-5-carbonyl)-3-fluoropiperidin-4-yl)oxy)-5-(4-((4-(4-(oxetan-3-yl)piperazin-1-yl)phenyl)amino)-1,3,5-triazin-2-yl)benzonitrile

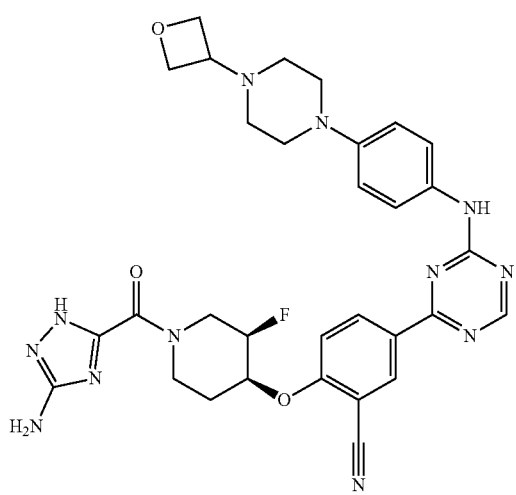 [SMILES: N#Cc1cc(-c2ncnc(Nc3ccc(N4CCN(C5COC5)CC4)cc3)n2)ccc1O[C@H]1CCN(C(=O)c2nc(N)n[nH]2)C[C@H]1F]

2-(((3R,4S)-3-fluoropiperidin-4-yl)oxy)-5-(4-((4-(4-(oxetan-3-yl)piperazin-1-yl)phenyl)amino)-1,3,5-triazin-2-yl)benzonitrile (70 mg, 0.13 mmol), HATU (100 mg, 0.26 mmol), DIEA (52 mg, 0.4 mmol) and 3-amino-1H-1,2,4-triazole-5-carboxylic acid (34 mg, 0.26 mmol) were dissolved in DMF (4 mL) and stirred at room temperature for 2 hr. The mixture was diluted with DCM and extracted with water. The organic phase was dried over Na2SO4 and concentrated. The residue was purified silica gel column with ESCO system with 5-20% MeOH in CH2Cl2 to give the title compound. 1H NMR (400 MHz, DMSO-d6) δ 12.33 (d, J=7.3 Hz, 1H), 10.12 (d, J=22.3 Hz, 1H), 8.81-8.66 (m, 1H), 8.66-8.42 (m, 2H), 7.71-7.34 (m, 3H), 6.95 (t, J=9.2 Hz, 2H), 6.15 (s, 1H), 5.26-4.85 (m, 2H), 4.51 (m , 4H), 4.17 (s, 1H), 3.73 (m, 1H), 3.60 (m, 1H), 3.45 (m, 1H), 3.12 (m, 4H), 2.41 (m, 4H), 2.12-1.79 (m, 2H). LCMS-ESI$^+$ (m/z): [M+H]$^+$ calcd for $C_{31}H_{33}FN_{12}O_3$: 641.3; found: 641.4

Example 335

N-((S)-1-((3R,4S)-4-(2-cyano-4-(4-((4-(4-(oxetan-3-yl)piperazin-1-yl)phenyl)amino)-1,3,5-triazin-2-yl)phenoxy)-3-fluoropiperidin-1-yl)-1-oxopropan-2-yl)acetamide

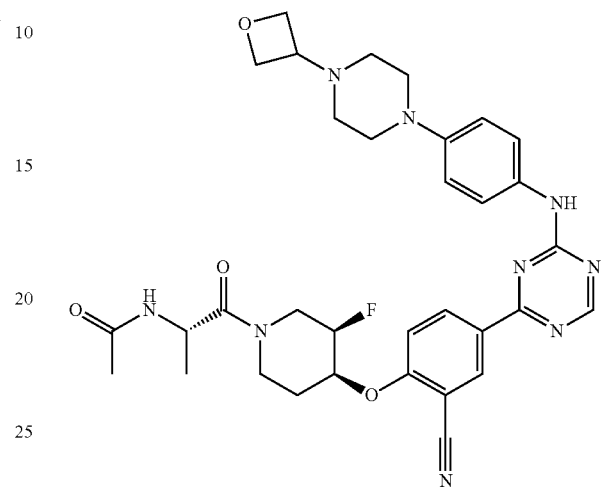

2-(((3R,4S)-3-fluoropiperidin-4-yl)oxy)-5-(4-((4-(4-(oxetan-3-yl)piperazin-1-yl)phenyl)amino)-1,3,5-triazin-2-yl)benzonitrile (60 mg, 0.11 mmol), HATU (86 mg, 0.23 mmol), DIEA (44 mg, 0.34 mmol), and (S)-2-acetamidopropanoic acid (30 mg, 0.23 mmol) were dissolved in DMF (4 mL) and stirred at room temperature overnight. The mixture was diluted with DCM and extracted with water. The organic phase was dried over Na2SO4 and concentrated. The residue was purified by silica gel column chromatography with 5-20% MeOH in CH2Cl2 to give the product. LCMS-ESI$^+$ (m/z): [M+H]$^+$ calcd for $C_{33}H_{38}FN_9O_4$: 644.3; found: 644.3

Example 336

2-(((3R,4S)-3-fluoro-1-(pyrazine-2-carbonyl)piperidin-4-yl)oxy)-5-(4-((4-(4-(oxetan-3-yl)piperazin-1-yl)phenyl)amino)-1,3,5-triazin-2-yl)benzonitrile

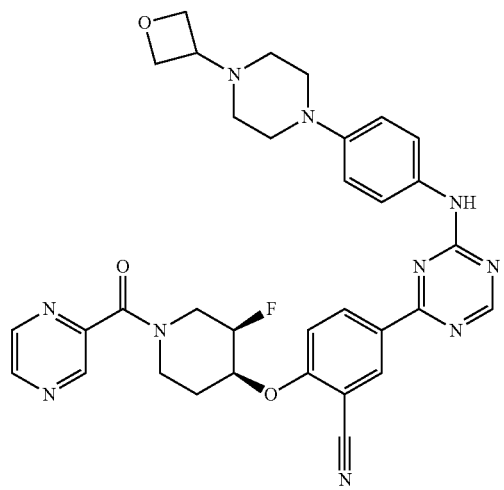 [SMILES: N#Cc1cc(-c2ncnc(Nc3ccc(N4CCN(C5COC5)CC4)cc3)n2)ccc1O[C@H]1CCN(C(=O)c2cnccn2)C[C@H]1F]

2-(((3R,4S)-3-fluoropiperidin-4-yl)oxy)-5-(4-((4-(1-(oxetan-3-yl)piperidin-4-yl)phenyl)amino)-1,3,5-triazin-2-yl)benzonitrile (40 mg, 0.075 mmol) was dissolved in dimethylformamide (5 mL), N,N-diisopropylethylamine (0.04 ml, 0.23 mmol), (1-[Bis(dimethylamino)methylene]-1H-1,2,3-triazolo[4,5-b]pyridinium 3-oxid hexafluorophosphate) (57 mg, 0.15 mmol), pyrazine-2-carboxylic acid (19 mg, 0.15 mmol) was added and the reaction was allowed to stir for 1 hour at room temperature. The mixture was diluted with 20% methanol/dichloromethane and water. The aqueous phase was extracted twice with 20% methanol/dichloromethane. The combined extracts were dried over anhydrous sodium sulfate, filtered, and concentrated under reduced pressure. The residue was purified via normal phase prep HPLC (0-25% methanol/dichloromethane) to provide 2-(((3R,4S)-3-fluoro-1-(pyrazine-2-carbonyl)piperidin-4-yl)oxy)-5-(4-((4-(4-(oxetan-3-yl)piperazin-1-yl)phenyl)amino)-1,3,5-triazin-2-yl)benzonitrile. LCMS-ESI$^+$ (m/z): [M+H]$^+$ calcd for C$_{33}$H$_{33}$FN$_{10}$O$_3$: 636.68; found: 637.17 $^1$H NMR (300 MHz, DMSO-d$_6$) δ 10.15 (d, J=18.2 Hz, 1H), 8.86 (t, J=1.3 Hz, 1H), 8.82-8.65 (m, 3H), 8.65-8.43 (m, 2H), 7.79-7.41 (m, 3H), 6.97 (d, J=8.7 Hz, 2H), 5.37-4.75 (m, 2H), 4.56 (t, J=6.5 Hz, 2H), 4.46 (t, J=6.0 Hz, 2H), 4.37-3.34 (m, 5H), 3.11 (t, J=7.2 Hz, 4H), 2.43 (t, J=23.6 Hz, 4H), 2.27-1.78 (m, 2H).

Example 337

2-(((3R,4S)-3-fluoro-1-(pyrimidine-4-carbonyl)piperidin-4-yl)oxy)-5-(4-((4-(4-(oxetan-3-yl)piperazin-1-yl)phenyl)amino)-1,3,5-triazin-2-yl)benzonitrile

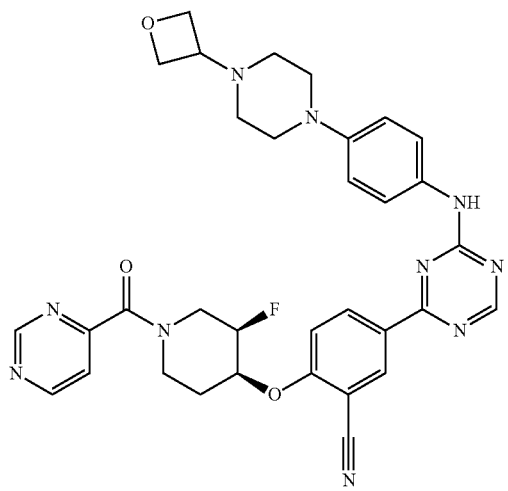

This molecule was synthesized in the same manner as Example 336 except replacing with 4-pyrimidinecarboxilic acid. LCMS-ESI$^+$ (m/z): [M+H]$^+$ calcd for C$_{33}$H$_{33}$FN$_{10}$O$_3$: 636.68; found: 637.22. $^1$H NMR (300 MHz, DMSO-d$_6$) δ 10.14 (d, J=19.8 Hz, 1H), 9.26 (t, J=1.6 Hz, 1H), 8.98 (dd, J=5.1, 2.6 Hz, 1H), 8.73 (s, 1H), 8.55 (dd, J=13.3, 5.0 Hz, 2H), 7.83-7.42 (m, 4H), 6.95 (t, J=8.7 Hz, 2H), 5.35-4.84 (m, 2H), 4.55 (t, J=6.5 Hz, 2H), 4.45 (t, J=6.0 Hz, 2H), 4.39-3.20 (m, 5H), 3.12 (bs, 4H), 2.39 (t, J=4.8 Hz, 4H), 2.24-1.80 (m, 2H).

Example 338

2-(((3R,4S)-3-fluoro-1-(pyridazine-4-carbonyl)piperidin-4-yl)oxy)-5-(4-((4-(4-(oxetan-3-yl)piperazin-1-yl)phenyl)amino)-1,3,5-triazin-2-yl)benzonitrile

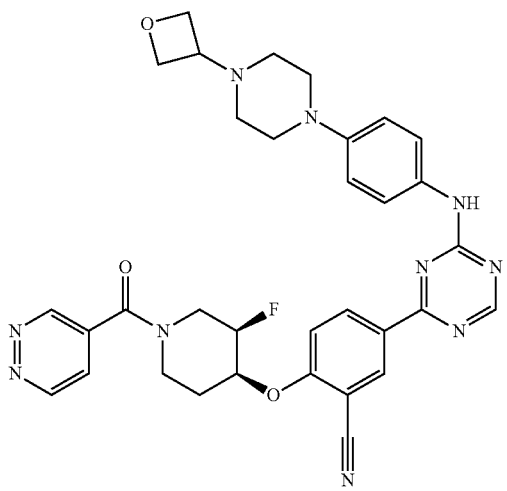

This molecule was synthesized in the same manner Example 336 except replacing with 4-pyridazinecarboxilic acid. LCMS-ESI$^+$ (m/z): [M+H]$^+$ calcd for C$_{33}$H$_{33}$FN$_{10}$O$_3$: 636.68; found: 637.22. $^1$H NMR (300 MHz, DMSO-d$_6$) δ 10.14 (d, J=20.3 Hz, 1H), 9.49-9.15 (m, 2H), 8.73 (s, 1H), 8.68-8.42 (m, 2H), 7.76 (ddd, J=15.9, 5.3, 2.3 Hz, 1H), 7.69-7.42 (m, 3H), 6.95 (t, J=8.7 Hz, 2H), 5.32-4.81 (m, 2H), 4.55 (t, J=6.5 Hz, 2H), 4.45 (t, J=6.0 Hz, 2H), 3.93-3.18 (m, 5H), 3.18-2.95 (m, 4H), 2.39 (t, J=6.1, 4H), 2.04 (m, 2H).

Example 339

2-(((3R,4S)-1-(3-aminopyrazine-2-carbonyl)-3-fluoropiperidin-4-yl)oxy)-5-(4-((4-(4-(oxetan-3-yl)piperazin-1-yl)phenyl)amino)-1,3,5-triazin-2-yl)benzonitrile

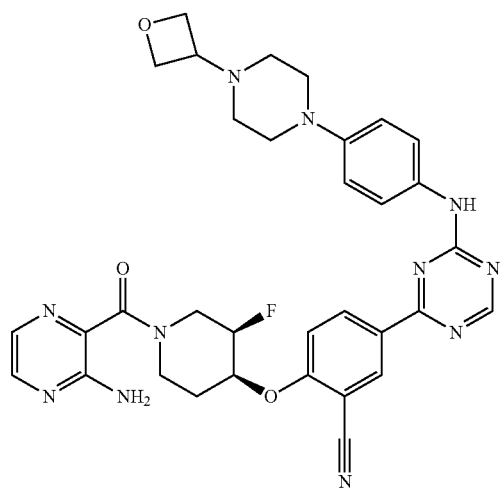 [SMILES: N#Cc1cc(-c2ncnc(Nc3ccc(N4CCN(C5COC5)CC4)cc3)n2)ccc1O[C@H]1CCN(C(=O)c2nccnc2N)C[C@H]1F]

This molecule was synthesized in the same manner as Example 336 except replacing with 3-amino-2-pyrazinecarboxilic acid. LCMS-ESI+ (m/z): [M+H]+ calcd for C33H34FN11O3: 651.69; found: 652.27. 1H NMR (300 MHz, DMSO-d6) δ 10.15 (d, J=18.8 Hz, 1H), 8.83-8.41 (m, 2H), 8.05 (dd, J=2.6, 1.5 Hz, 1H), 7.78 (d, J=2.5 Hz, 1H), 7.70-7.44 (m, 3H), 6.97 (d, J=9.2 Hz, 2H), 6.54 (m, 3H), 5.40-4.72 (m, 2H), 4.56 (t, J=6.5 Hz, 2H), 4.46 (t, J=6.0 Hz, 2H), 4.35-3.52 (m, 2H), 3.52-3.21 (m, 3H), 3.13 (t, J=6.0 Hz, 4H), 2.39 (t, J=4.9 Hz, 4H), 1.94 (m, 2H).

Example 340

2-(((3R,4S)-1-(6-aminopyrazine-2-carbonyl)-3-fluoropiperidin-4-yl)oxy)-5-(4-((4-(4-(oxetan-3-yl)piperazin-1-yl)phenyl)amino)-1,3,5-triazin-2-yl)benzonitrile

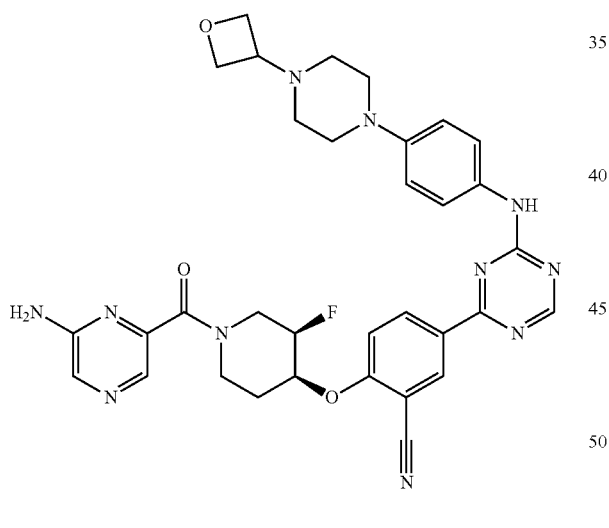

This molecule was synthesized in the same manner as Example 336 except replacing with 6-amino-2-pyrazinecarboxilic acid. LCMS-ESI+ (m/z): [M+H]+ calcd for C33H34FN11O3: 651.69; found: 652.32. 1H NMR (300 MHz, DMSO-d6) δ 10.12 (d, J=18.0 Hz, 1H), 8.72 (s 1H), 8.56 (d, J=10.7 Hz, 2H), 7.91 (s, 1H), 7.80 (d, J=3.0 Hz, 1H), 7.73-7.43 (m, 3H), 6.94 (t, J=7.8 Hz, 2H), 6.69 (s, 2H), 5.32-4.79 (m, 1H), 4.55 (t, J=6.5 Hz, 2H), 4.50 (m, 1H), 4.45 (t, J=6.0 Hz, 2H), 4.34-3.88 (m, 1H), 3.83-3.33 (m, 3H), 3.21-2.98 (m, 4H), 2.47-2.30 (m, 5H), 2.20-1.80 (m, 2H).

Example 341

2-(((3R,4S)-1-(5-aminopyrazine-2-carbonyl)-3-fluoropiperidin-4-yl)oxy)-5-(4-((4-(4-(oxetan-3-yl)piperazin-1-yl)phenyl)amino)-1,3,5-triazin-2-yl)benzonitrile

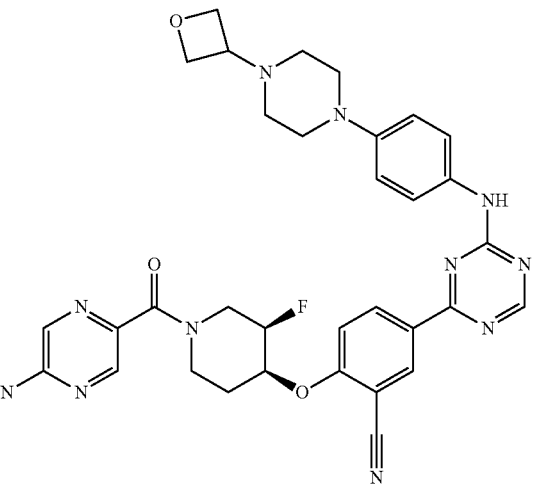

This molecule was synthesized in the same manner as Example 336 except replacing with 5-amino-2-pyrazinecarboxilic acid. LCMS-ESI+ (m/z): [M+H]+ calcd for C33H34FN11O3: 651.69; found: 652.27. 1H NMR (300 MHz, DMSO-d6) δ 10.12 (d, J=16.3 Hz, 1H), 8.73 (s, 1H), 8.56 (d, J=11.0 Hz, 2H), 8.24 (s, 1H), 7.89-7.71 (m, 1H), 7.71-7.41 (m, 3H), 6.97 (bs, 4H), 5.14 (d, J=21.6 Hz, 1H), 4.55 (t, J=6.5 Hz, 2H), 4.46 (t, J=6.0 Hz, 2H), 4.40 (m, 1H), 4.29-3.48 (m, 1H), 3.48-3.36 (m, 3H), 3.21-2.99 (m, 4H), 2.47-2.29 (m, 4H), 2.00 (s, 2H).

Example 342

2-(((3R,4S)-3-fluoro-1-((S)-2-hydroxypropanoyl)piperidin-4-yl)oxy)-5-(4-((4-(3-hydroxy-3-methylazetidin-1-yl)phenyl)amino)-1,3,5-triazin-2-yl)benzonitrile

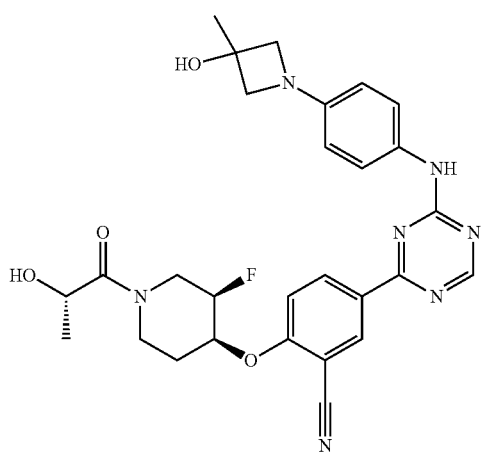 [SMILES: C[C@H](O)C(=O)N1CC[C@H](Oc2ccc(-c3ncnc(Nc4ccc(N5CC(C)(O)C5)cc4)n3)cc2C#N)[C@H](F)C1]

Step 1: 1-(4-((4-chloro-1,3,5-triazin-2-yl)amino)phenyl)-3-methylazetidin-3-ol:

1-(4-aminophenyl)-3-methylazetidin-3-ol (680 mg, 4 mmol) and potassium carbonate (1.581 g, 11 mmol) were charged to a RB-flask under nitrogen and dimethylformamide (15 mL) was added and the suspension was cooled to 0° C. using an ice bath. 2,4-dichloro-1,3,5-triazine (572 mg, 4 mmol) was placed into a 50 mL vial and dissolved in dimethylformamide (5 mL) and cooled to 0° C. for 10 min. The triazine was then added via syringe to the suspension over 2 min and allowed to react at 0° C. for 5 min. Water (100 mL) and 20% methanol/dichloromethane (100 mL) was then added and the organic layer was washed with saturated sodium bicarbonate (1×50 mL) and brine (1×50 mL) and then dried over sodium sulfate and concentrated under reduced pressure. The residue was purified via normal phase prep HPLC (15-85% ethyl acetate/hexanes) to provide 1-(4-((4-chloro-1,3,5-triazin-2-yl)amino)phenyl)-3-methylazetidin-3-ol.

Step 2: (3R,4S)-tert-butyl 4-(2-cyano-4-(4-((4-(3-hydroxy-3-methylazetidin-1-yl)phenyl)amino)-1,3,5-triazin-2-yl)phenoxy)-3-fluoropiperidine-1-carboxylate:

1-(4-((4-chloro-1,3,5-triazin-2-yl)amino)phenyl)-3-methylazetidin-3-ol (89 mg, 0.31 mmol), (3R,4S)-tert-butyl 4-(2-cyano-4-(4,4,5,5-tetramethyl-1,3,2-dioxaborolan-2-yl)phenoxy)-3-fluoropiperidine-1-carboxylate (150 mg, 0.36 mmol), sodium carbonate (129 mg, 1.24 mmol) and Tetrakis(triphenylphosphine)palladium(0) (35 mg, 0.03 mmol) were all placed into a microwave reaction vessel and to that was added dimethoxyethane (3 mL) and water (2 mL) and then placed in a microwave reactor at 150° C. for 20 min. Water (100 mL) and 20% methanol/dichloromethane (100 mL) was then added and the organic layer was washed with saturated sodium bicarbonate (1×50 mL) and brine (1×50 mL) and then dried over sodium sulfate and concentrated under reduced pressure. The residue was purified via normal phase prep HPLC (0-20% methanol/dichloromethane) to provide (3R,4S)-tert-butyl 4-(2-cyano-4-(4-((4-(3-hydroxy-3-methylazetidin-1-yl)phenyl)amino)-1,3,5-triazin-2-yl)phenoxy)-3-fluoropiperidine-1-carboxylate.

Step 3: 2-(((3R,4S)-3-fluoropiperidin-4-yl)oxy)-5-(4-((4-(3-hydroxy-3-methylazetidin-1-yl)phenyl)amino)-1,3,5-triazin-2-yl)benzonitrile:

4-(2-cyano-4-(4-((4-(3-hydroxy-3-methylazetidin-1-yl)phenyl)amino)-1,3,5-triazin-2-yl)phenoxy)-3-fluoropiperidine-1-1-carboxylate (118 mg, 0.21 mmol) was dissolved in dichloromethane (5 mL) and to that was added trifluoroacetic acid (1 mL) and was allowed to react for 1 hr at room temperature. The reaction was then concentrated under reduced pressure and to the residue was added saturated sodium bicarbonate and 20% methanol/dichloromethane and the extracted organic layer was washed with saturated sodium bicarbonate (1×50 mL) and brine (1×50 mL) and then dried over sodium sulfate and concentrated under reduced pressure to provide 2-(((3R,4S)-3-fluoropiperidin-4-yl)oxy)-5-(4-((4-(3-hydroxy-3-methylazetidin-1-yl)phenyl)amino)-1,3,5-triazin-2-yl)benzonitrile which was used directly in the next reaction.

Step 4: 2-(((3R,4S)-3-fluoro-1-((S)-2-hydroxypropanoyl)piperidin-4-yl)oxy)-5-(4-((4-(3-hydroxy-3-methylazetidin-1-yl)phenyl)amino)-1,3,5-triazin-2-yl)benzonitrile:

2-(((3R,4S)-3-fluoropiperidin-4-yl)oxy)-5-(4-((4-(3-hydroxy-3-methylazetidin-1-yl)phenyl)amino)-1,3,5-triazin-2-yl)benzonitrile (76 mg, 0.16 mmol), (1-[Bis(dimethylamino)methylene]-1H-1,2,3-triazolo[4,5-b]pyridinium 3-oxid hexafluorophosphate) (91 mg, 0.24 mmol), L-(+)-lactic acid (29 mg, 0.32 mmol) and N,N-diisopropylethylamine (0.056 mL, 0.32 mmol) were all added to a 100 mL flask and dissolved in dimethylformamide (5 mL) and allowed to react at room temperature for 1 hour. Water (100 mL) and 20% methanol/dichloromethane (100 mL) was then added and the organic layer was washed with saturated sodium bicarbonate (1×50 mL) and brine (1×50 mL) and then dried over sodium sulfate and concentrated under reduced pressure. The residue was purified via normal phase prep HPLC (0-20% methanol/dichloromethane) to provide 2-(((3R,4S)-3-fluoro-1-((S)-2-hydroxypropanoyl)piperidin-4-yl)oxy)-5-(4-((4-(3-hydroxy-3-methylazetidin-1-yl)phenyl)amino)-1,3,5-triazin-2-yl)benzonitrile. LCMS-ESI$^+$ (m/z): [M+H]$^+$ calcd for $C_{28}H_{30}FN_7O_4$: 547.58; found: 548.22. $^1$H NMR (300 MHz, DMSO-d$_6$) δ 10.05 (d, J=20.3 Hz, 1H), 8.72 (s, 1H), 8.63-8.41 (m, 2H), 7.63 (d, J=9.1 Hz, 1H), 7.49 (dd, J=18.0, 8.3 Hz, 2H), 6.46 (t, J=9.8 Hz, 2H), 5.48 (s, 1H), 5.30-4.78 (m, 3H), 4.64-3.84 (m, 3H), 3.84-3.64 (m, 2H), 3.64-3.47 (m, 2H), 3.47-3.03 (m, 2H), 1.90 (m, 2H), 1.46 (s, 3H), 1.34-1.16 (m, 3H).

Example 343

2-(((3R,4S)-3-fluoro-1-(2-hydroxyacetyl)piperidin-4-yl)oxy)-5-(4-((1-methyl-1H-indazol-6-yl)amino)-1,3,5-triazin-2-yl)benzonitrile

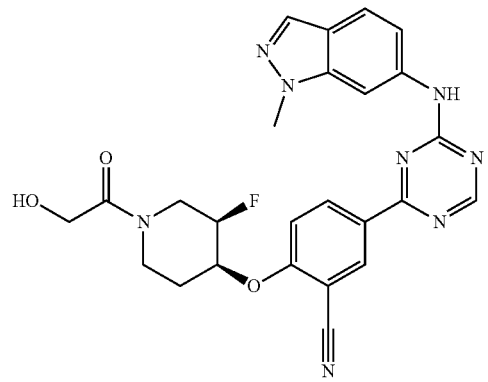 [SMILES: Cn1ncc2ccc(Nc3ncnc(-c4ccc(O[C@H]5CCN(C(=O)CO)C[C@H]5F)c(C#N)c4)n3)cc21]

This molecule was synthesized in the same manner as Example 342 except starting with 1-methyl-1H-indazol-6-amine and substituting glycolic acid for L-(+)-lactic acid. LCMS-ESI$^+$ (m/z): [M+H]$^+$ calcd for $C_{25}H_{23}FN_8O_3$: 502.50; found: 503.07. $^1$H NMR (300 MHz, DMSO-d$_6$) δ 10.61 (s, 1H), 8.88 (s, 1H), 8.75-8.54 (m, 2H), 8.37 (s, 1H), 7.98 (d, J=0.9 Hz, 1H), 7.68 (dd, J=17.7, 8.9 Hz, 2H), 7.32 (d, J=8.7 Hz, 1H), 5.25-4.56 (m, 3H), 4.49-3.78 (m, 6H), 3.77-3.15 (m, 2H), 2.16-1.56 (m, 2H).

Example 344

2-(((3R,4S)-3-fluoro-1-((S)-2-hydroxypropanoyl)piperidin-4-yl)oxy)-5-(4-((1-methyl-1H-indazol-6-yl)amino)-1,3,5-triazin-2-yl)benzonitrile

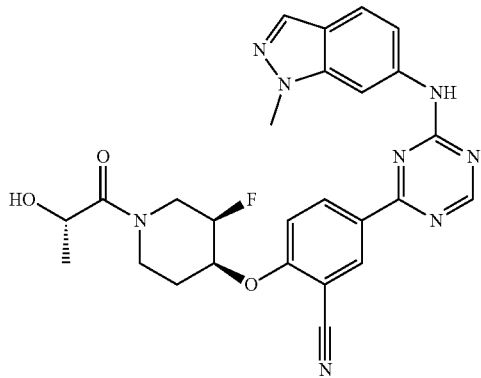 [SMILES: C[C@H](O)C(=O)N1CC[C@H](Oc2ccc(-c3ncnc(Nc4ccc5cnn(C)c5c4)n3)cc2C#N)[C@H](F)C1]

This molecule was synthesized in the same manner as Example 342 except starting with 1-methyl-1H-indazol-6-amine. LCMS-ESI+ (m/z): [M+H]+ calcd for $C_{26}H_{25}FN_8O_3$: 516.53; found: 517.07. $^1$H NMR (300 MHz, DMSO-$d_6$) δ 10.59 (s, 1H), 8.87 (s, 1H), 8.76-8.50 (m, 2H), 8.37 (s, 1H), 7.97 (d, J=0.9 Hz, 1H), 7.80-7.53 (m, 2H), 7.31 (d, J=8.7 Hz, 1H), 5.31-4.82 (m, 3H), 4.59-4.27 (m, 1H), 4.27-3.80 (m, 4H), 3.77-3.03 (m, 2H), 2.13-1.65 (m, 2H), 1.34-1.11 (m, 3H).

Example 345

2-(((3R,4S)-1-(2,4-dimethyl-1H-imidazole-5-carbonyl)-3-fluoropiperidin-4-yl)oxy)-5-(4-((4-(4-(oxetan-3-yl)piperazin-1-yl)phenyl)amino)-1,3,5-triazin-2-yl)benzonitrile

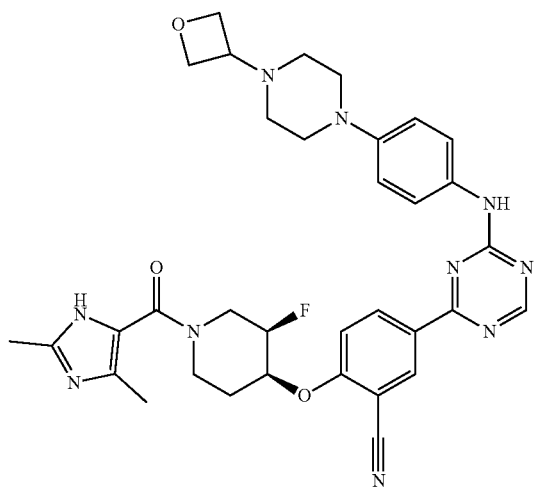 [SMILES: Cc1nc(C)c(C(=O)N2CC[C@H](Oc3ccc(-c4ncnc(Nc5ccc(N6CCN(C7COC7)CC6)cc5)n4)cc3C#N)[C@H](F)C2)[nH]1]

This molecule was synthesized in the same manner as Example 336 except replacing with 2,5-dimethylimidazole-4-carboxilic acid. LCMS-ESI+ (m/z): [M+N]+ calcd for $C_{34}H_{37}FN_{10}O_3$: 652.72; found: 653.22. $^1$H NMR (300 MHz, DMSO-$d_6$) δ 11.94 (s, 1H), 10.14 (d, J=15.9 Hz, 1H), 8.74 (s, 1H), 8.58 (d, J=10.6 Hz, 2H), 7.59 (dd, J=23.5, 10.8 Hz, 3H), 6.97 (s, 2H), 5.30-4.80 (m, 3H), 4.57 (t, J=6.5 Hz, 2H), 4.51 (t, J=6.5 Hz, 2H), 3.58-3.36 (m, 1H), 3.29-3.00 (m, 6H), 2.41 (t, J=4.7 Hz, 4H), 2.31 (s, 3H), 2.23 (s, 3H), 2.05 (m, 3H).

Example 346

5-(4-((1,3-dimethyl-1H-indazol-6-yl)amino)-1,3,5-triazin-2-yl)-2-(((3R,4S)-3-fluoro-1-(2-hydroxyacetyl)piperidin-4-yl)oxy)benzonitrile

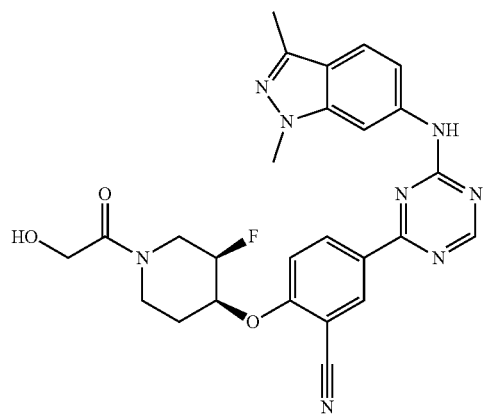 [SMILES: Cc1nn(C)c2cc(Nc3ncnc(-c4ccc(O[C@H]5CCN(C(=O)CO)C[C@H]5F)c(C#N)c4)n3)ccc12]

This molecule was synthesized in the same manner as Example 342 except starting with 1,3-dimethyl-1H-indazol-6-amine and substituting glycolic acid for L-(+)-lactic acid. LCMS-ESI+ (m/z): [M+H]+ calcd for $C_{26}H_{25}FN_8O_3$: 516.53; found: 517.12. $^1$H NMR (300 MHz, DMSO-$d_6$) δ 10.59 (s, 1H), 8.88 (s, 1H), 8.76-8.47 (m, 2H), 8.30 (s, 1H), 7.65 (d, J=8.9 Hz, 2H), 7.28 (d, J=8.7 Hz, 1H), 5.32-4.57 (m, 3H), 4.51-4.00 (m, 3H), 3.95 (d, J=7.6 Hz, 3H), 3.79-2.94 (m, 22H), 2.44 (s, 3H), 1.90 (m, 2H).

Example 347

5-(4-((1,3-dimethyl-1H-indazol-6-yl)amino)-1,3,5-triazin-2-yl)-2-(((3R,4S)-3-fluoro-1-((S)-2-hydroxypropanoyl)piperidin-4-yl)oxy)benzonitrile

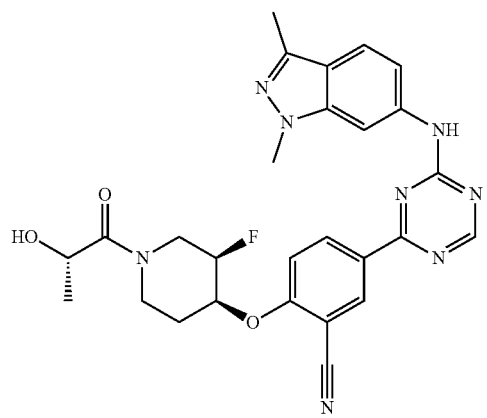 [SMILES: Cc1nn(C)c2cc(Nc3ncnc(-c4ccc(O[C@H]5CCN(C(=O)[C@H](C)O)C[C@H]5F)c(C#N)c4)n3)ccc12]

This molecule was synthesized in the same manner as Example 342 except starting with 1,3-dimethyl-1H-indazol-6-amine. LCMS-ESI⁺ (m/z): [M+H]⁺ calcd for $C_{27}H_{27}FN_8O_3$: 530.55; found: 531.17. ¹H NMR (300 MHz, DMSO-d₆) δ 10.59 (s, 1H), 8.87 (s, 1H), 8.74-8.51 (m, 2H), 8.12 (m, 1H), 7.65 (d, J=8.8 Hz, 2H), 7.28 (d, J=8.6 Hz, 1H), 5.29-4.79 (m, 3H), 4.46 (dt, J=11.0, 6.7 Hz, 1H), 4.25-3.83 (m, 4H), 3.83-2.99 (m, 2H), 2.46 (s, 3H), 1.91 (m, 2H), 1.35-1.09 (m, 3H).

Example 348

2-(((3R,4S)-1-(2,3-dihydroxypropanoyl)-3-fluoropiperidin-4-yl)oxy)-5-(4-((4-(4-(oxetan-3-yl)piperazin-1-yl)phenyl)amino)-1,3,5-triazin-2-yl)benzonitrile

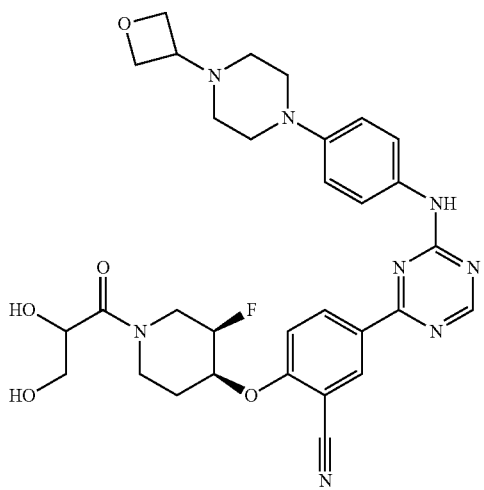 [SMILES: N#Cc1cc(-c2ncnc(Nc3ccc(N4CCN(C5COC5)CC4)cc3)n2)ccc1O[C@H]1CCN(C(=O)C(O)CO)C[C@H]1F]

Step 1: 2-(((3R,4S)-1-(2,2-dimethyl-1,3-dioxolane-4-carbonyl)-3-fluoropiperidin-4-yl)oxy)-5-(4-((4-(4-(oxetan-3-yl)piperazin-1-yl)phenyl)amino)-1,3,5-triazin-2-yl)benzonitrile The title compound was synthesized in the same manner as Example 336 except replacing with 2,2-dimethyl-1,3-dioxolane-4-carboxylic acid.

Step 2: 2-(((3R,4S)-1-(2,3-dihydroxypropanoyl)-3-fluoropiperidin-4-yl)oxy)-5-(4-((4-(4-(oxetan-3-yl)piperazin-1-yl)phenyl)amino)-1,3,5-triazin-2-yl)benzonitrile:

2-(((3R,4S)-1-(2,2-dimethyl-1,3-dioxolane-4-carbonyl)-3-fluoropiperidin-4-yl)oxy)-5-(4-((4-(4-(oxetan-3-yl)piperazin-1-yl)phenyl)amino)-1,3,5-triazin-2-yl)benzonitrile (150 mg, 0.23 mmol) was dissolved in tetrahydrofuran (18 mL) and to that was added HCl (1M, 2.0 mL) and the reaction was allowed to proceed for 18 hours. Following day the sample was concentrated and redissolved in 20% methanol/dichloromethane and basified using saturated sodium bicarbonate (2×50 mL), washed with brine (1×50 mL) and dried over sodium sulfate and concentrated under reduced pressure. The residue was purified via normal phase prep HPLC (0-25% methanol/dichloromethane) to provide 2-(((3R,4S)-1-(2,3-dihydroxypropanoyl)-3-fluoropiperidin-4-yl)oxy)-5-(4-((4-(4-(oxetan-3-yl)piperazin-1-yl)phenyl)amino)-1,3,5-triazin-2-yl)benzonitrile as a racemate. LCMS-ESI⁺ (m/z): [M+H]⁺ calcd for $C_{31}H_{35}FN_8O_5$: 618.66; found: 619.27. ¹H NMR (300 MHz, DMSO-d₆) δ 10.12 (d, J=17.3 Hz, 1H), 8.73 (s, 1H), 8.56 (d, J=10.6 Hz, 2H), 7.58 (dd, J=23.5, 10.4 Hz, 3H), 6.95 (s, 2H), 5.74-4.63 (m, 3H), 4.55 (t, J=6.5 Hz, 2H), 4.46 (t, J=6.0 Hz, 2H), 4.41-3.83 (m, 4H), 3.78-3.34 (m, 3H), 3.13 (m, 4H), 2.40 (m, J=5.0 Hz, 4H), 1.91 (m, 2H).

Example 349

2-(((3R,4S)-3-fluoro-1-(2-hydroxyacetyl)piperidin-4-yl)oxy)-5-(4-((1-isopropyl-1H-pyrazol-4-yl)amino)-1,3,5-triazin-2-yl)benzonitrile

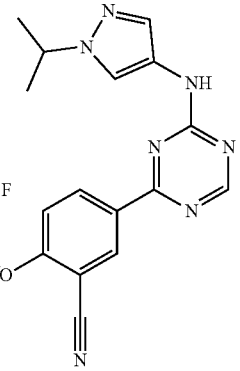

This molecule was synthesized in the same manner as Example Example 342 except starting with 1-isopropyl-1H-pyrazol-4-amine and substituting glycolic acid for L-(+)-lactic acid. LCMS-ESI⁺ (m/z): [M+H]⁺ calcd for $C_{23}H_{25}FN_8O_3$: 480.49; found: 481.18. ¹H NMR (300 MHz, DMSO-d₆) δ 10.28 (d, J=7.8 Hz, 1H), 8.75 (d, J=29.5 Hz, 1H), 8.66-8.44 (m, 2H), 7.99 (dd, J=14.5, 0.7 Hz, 1H), 7.74-7.48 (m, 2H), 5.28-4.84 (m, 2H), 4.50 (dp, J=11.3, 6.6 Hz, 1H), 4.41-3.81 (m, 3H), 3.42 (m, 3H), 2.09-1.70 (m, 2H), 1.42 (dd, J=13.9, 6.6 Hz, 6H).

Example 350

2-(((3R,4S)-3-fluoro-1-((S)-2-hydroxypropanoyl)piperidin-4-yl)oxy)-5-(4-((1-isopropyl-1H-pyrazol-4-yl)amino)-1,3,5-triazin-2-yl)benzonitrile

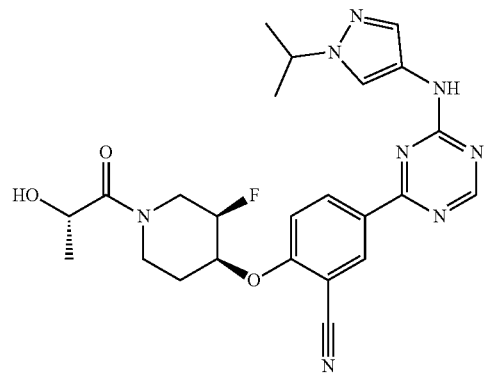 [SMILES: CC(C)n1cc(Nc2ncnc(-c3ccc(O[C@H]4CCN(C(=O)[C@H](C)O)C[C@H]4F)c(C#N)c3)n2)cn1]

This molecule was synthesized in the same manner as Example 342 except starting with 1-isopropyl-1H-pyrazol-4-amine. LCMS-ESI⁺ (m/z): [M+H]⁺ calcd for $C_{24}H_{27}FN_6O_3$: 494.52; found: 495.17. ¹H NMR (300 MHz, DMSO-d₆) δ 10.28 (d, J=7.6 Hz, 1H), 8.75 (d, J=29.5 Hz, 1H), 8.64-8.44 (m, 2H), 7.99 (d, J=14.7 Hz, 1H), 7.79-7.34 (m, 2H), 5.04 (d, J=48.3 Hz, 2H), 4.67-4.25 (m, 2H), 4.25-3.82 (m, 1H), 3.82-2.89 (m, 3H), 2.18-1.65 (m, 2H), 1.42 (dd, J=14.0, 6.7 Hz, 6H), 1.32-1.08 (m, 3H).

Example 351

5-(4-((1-ethyl-1H-pyrazol-4-yl)amino)-1,3,5-triazin-2-yl)-2-(((3R,4S)-3-fluoro-1-((S)-2-hydroxypropanoyl)piperidin-4-yl)oxy)benzonitrile

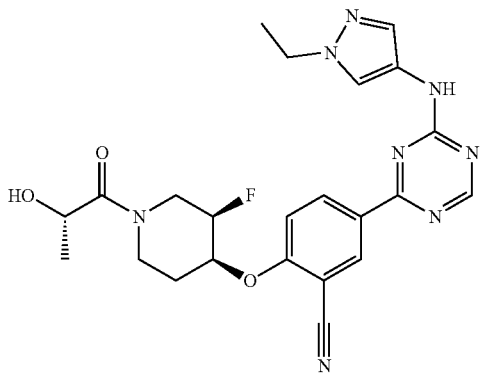 [SMILES: CCn1cc(Nc2ncnc(-c3ccc(O[C@H]4CCN(C(=O)[C@H](C)O)C[C@H]4F)c(C#N)c3)n2)cn1]

This molecule was synthesized in the same manner as Example 342 except starting with 1-ethyl-1H-pyrazol-4-amine. LCMS-ESI$^+$ (m/z): [M+H]$^+$ calcd for $C_{23}H_{25}FN_8O_3$: 480.49; found: 481.18. $^1$H NMR (300 MHz, DMSO-d$_6$) δ 9.58 (s, 1H), 8.63 (d, J=1.1 Hz, 1H), 8.34 (d, J=2.3 Hz, 1H), 8.28 (dd, J=9.0, 2.3 Hz, 1H), 8.03 (s, 1H), 7.75-7.38 (m, 2H), 7.06 (d, J=1.2 Hz, 1H), 5.23-4.79 (m, 3H), 4.64-4.26 (m, 1H), 4.11 (q, J=7.2 Hz, 3H), 3.75-2.98 (m, 2H), 2.12-1.66 (m, 2H), 1.35 (t, J=7.2 Hz, 3H), 1.28-1.12 (m, 3H).

Example 352

5-(4-((1-(2,2-difluoroethyl)-1H-pyrazol-4-yl)amino)-1,3,5-triazin-2-yl)-2-(((3R,4S)-3-fluoro-1-((S)-2-hydroxypropanoyl)piperidin-4-yl)oxy)benzonitrile

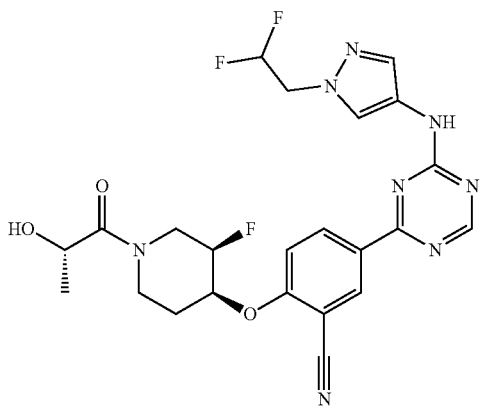 [SMILES: C[C@H](O)C(=O)N1CC[C@H](Oc2ccc(-c3ncnc(Nc4cnn(CC(F)F)c4)n3)cc2C#N)[C@H](F)C1]

This molecule was synthesized in the similar manner as Example 342 except starting with 1-(2,2-difluoroethyl)-1H-pyrazol-4-amine and replacing the boronate for 2-(((3R,4S)-3-fluoro-1-((S)-2-hydroxypropanoyl)piperidin-4-yl)oxy)-5-(4,4,5,5-tetramethyl-1,3,2-dioxaborolan-2-yl)benzonitrile in the microwave Suzuki reaction. LCMS-ESI$^+$ (m/z): [M+H]$^+$ calcd for $C_{23}H_{23}F_3N_8O_3$: 516.48; found: 517.12. $^1$H NMR (300 MHz, DMSO-d$_6$) δ 10.39 (d, J=2.2 Hz, 1H), 8.78 (d, J=30.7 Hz, 1H), 8.67-8.47 (m, 2H), 8.10 (d, J=6.7 Hz, 1H), 7.81-7.53 (m, 2H), 6.70-6.02 (m, 1H), 5.35-4.79 (m, 3H), 4.64 (qd, J=15.0, 3.8 Hz, 2H), 4.52-4.27 (m, 1H), 4.24-2.94 (m, 2H), 1.90 (d, J=42.5 Hz, 2H), 1.19 (dt, J=6.6, 3.2 Hz, 3H).

Example 353

2-(((3R,4S)-3-fluoro-1-((S)-2-hydroxypropanoyl)piperidin-4-yl)oxy)-5-(4-((1-(oxetan-3-yl)-1H-pyrazol-4-yl)amino)-1,3,5-triazin-2-yl)benzonitrile

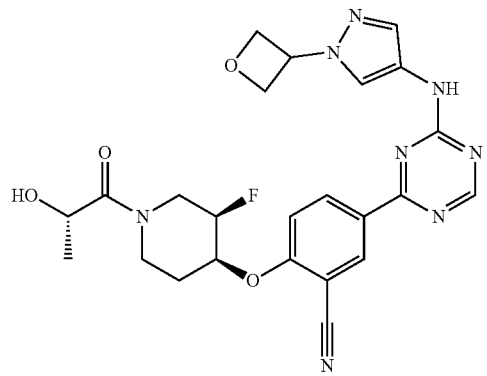 [SMILES: C[C@H](O)C(=O)N1CC[C@H](Oc2ccc(-c3ncnc(Nc4cnn(C5COC5)c4)n3)cc2C#N)[C@H](F)C1]

This molecule was synthesized in the same manner as Example 342 except starting with 1-(oxetan-3-yl)-1H-pyrazol-4-amine and replacing the boronate for 2-(((3R,4S)-3-fluoro-1-((S)-2-hydroxypropanoyl)piperidin-4-yl)oxy)-5-(4,4,5,5-tetramethyl-1,3,2-dioxaborolan-2-yl)benzonitrile in the microwave Suzuki reaction. LCMS-ESI$^+$ (m/z): [M+H]$^+$ calcd for $C_{24}H_{25}FN_8O_4$: 508.50; found: 509.12. $^1$H NMR (300 MHz, DMSO-d$_6$) δ 10.39 (d, J=3.0 Hz, 1H), 8.77 (d, J=29.3 Hz, 1H), 8.69-8.45 (m, 2H), 8.12 (dd, J=4.6, 0.7 Hz, 1H), 7.78 (d, J=37.7 Hz, 1H), 7.62 (d, J=9.1 Hz, 1H), 5.79-5.43 (m, 1H), 5.26-4.96 (m, 3H), 4.89 (tt, J=10.3, 6.7 Hz, 4H), 4.46 (dt, J=11.7, 6.8 Hz, 1H), 4.26-3.78 (m, 1H), 3.77-3.27 (m, 2H), 1.90 (d, J=45.1 Hz, 2H), 1.40-1.04 (m, 3H).

Example 354

2-(((3R,4S)-3-fluoro-1-((S)-2-hydroxypropanoyl)piperidin-4-yl)oxy)-5-(4-((1-(tetrahydro-2H-pyran-4-yl)-1H-pyrazol-4-yl)amino)-1,3,5-triazin-2-yl)benzonitrile

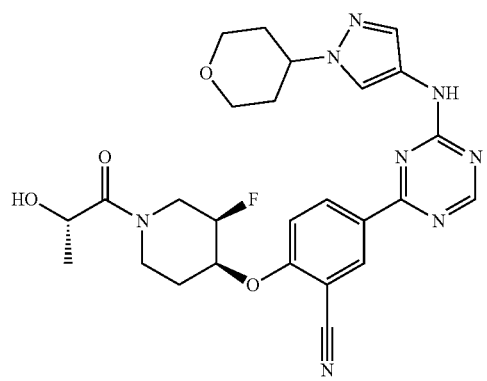 [SMILES: C[C@H](O)C(=O)N1CC[C@H](Oc2ccc(-c3ncnc(Nc4cnn(C5CCOCC5)c4)n3)cc2C#N)[C@H](F)C1]

This molecule was synthesized in the same manner as Example 342 except starting with 1-(tetrahydro-2H-pyran-4-yl)-1H-pyrazol-4-amine and replacing the boronate for 2-(((3R,4S)-3-fluoro-1-((S)-2-hydroxypropanoyl)piperidin-4-yl)oxy)-5-(4,4,5,5-tetramethyl-1,3,2-dioxaborolan-2-yl)benzonitrile in the microwave Suzuki reaction. LCMS-ESI+ (m/z): [M+H]+ calcd for $C_{26}H_{29}FN_8O_4$: 536.56; found: 537.12. $^1$H NMR (300 MHz, DMSO-$d_6$) δ 10.32 (d, J=4.8 Hz, 1H), 8.75 (d, J=27.9 Hz, 1H), 8.67-8.46 (m, 2H), 8.03 (d, J=13.1 Hz, 1H), 7.81-7.50 (m, 2H), 5.33-4.84 (m, 3H), 4.44 (m, 2H), 4.26-3.80 (m, 2H), 3.53-3.15 (m, 5H), 1.96 (m, 6H), 1.19 (dt, J=6.3, 3.4 Hz, 3H).

Example 355

2-(((3R,4S)-3-fluoro-1-((S)-2-hydroxypropanoyl)piperidin-4-yl)oxy)-5-(4-((4-(4-hydroxy-4-methylpiperidin-1-yl)phenyl)amino)-1,3,5-triazin-2-yl)benzonitrile

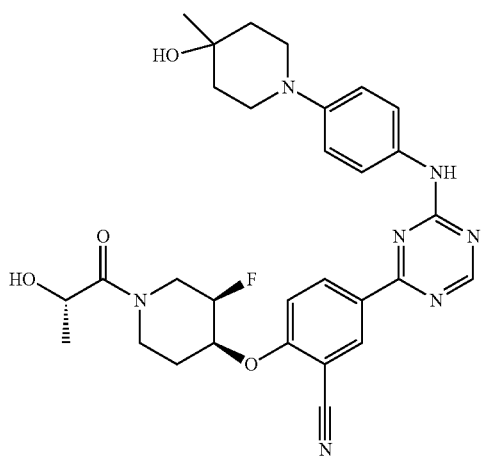 [SMILES: C[C@H](O)C(=O)N1CC[C@H](Oc2ccc(-c3ncnc(Nc4ccc(N5CCC(C)(O)CC5)cc4)n3)cc2C#N)[C@H](F)C1]

This molecule was synthesized in the same manner as Example 342 except starting with 1-(4-aminophenyl)-4-methylpiperidin-4-ol. LCMS-ESI+ (m/z): [M+H]+ calcd for $C_{30}H_{34}FN_7O_4$: 575.63; found: 576.27. $^1$H NMR (300 MHz, DMSO-$d_6$) δ 10.08 (d, J=17.6 Hz, 1H), 8.89-8.38 (m, 3H), 7.58 (dd, J=24.8, 10.4 Hz, 3H), 6.95 (d, J=8.8 Hz, 2H), 5.32-4.71 (m, 3H), 4.45 (d, J=10.0 Hz, 1H), 4.26 (m, 2H), 3.80-3.43 (m, 1H), 3.45-3.22 (m, 5H), 3.11 (ddt, J=11.9, 8.9, 3.9 Hz, 3H), 2.10-1.67 (m, 2H), 1.55 (t, J=5.6 Hz, 3H), 1.38-1.01 (m, 4H).

Example 356

2-(((3R,4S)-3-fluoro-1-(1H-pyrazole-4-carbonyl)piperidin-4-yl)oxy)-5-(4-((4-(4-(oxetan-3-yl)piperazin-1-yl)phenyl)amino)-1,3,5-triazin-2-yl)benzonitrile

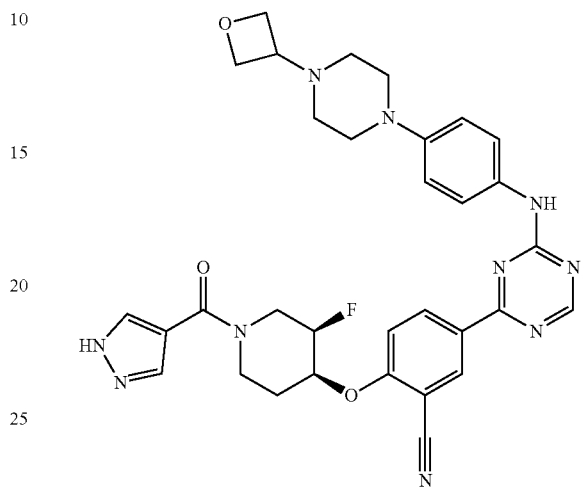

This molecule was synthesized in the same manner as Example 336 except replacing with (1H)-pyrazole-4carboxilic acid. LCMS-ESI+ (m/z): [M+H]+ calcd for $C_{32}H_{33}FN_{10}O_3$: 624.67; found: 625.17. $^1$H NMR (300 MHz, DMSO-$d_6$) δ 13.22 (s, 1H), 10.14 (d, J=18.2 Hz, 1H), 8.73 (s, 1H), 8.57 (d, J=11.1 Hz, 2H), 8.10 (s, 1H), 7.87-7.68 (m, 1H), 7.68-7.42 (m, 3H), 6.95 (t, J=8.9 Hz, 2H), 5.74 (s, 1H), 5.41-4.76 (m, 2H), 4.56 (t, J=6.5 Hz, 2H), 4.46 (t, J=6.0 Hz, 2H), 4.41-3.90 (m, 2H), 3.90-3.35 (m, 2H), 3.23-2.95 (m, 4H), 2.39 (t, J=4.9 Hz, 4H), 2.01 (s, 2H).

Example 357

2-(((3R,4S)-3-fluoro-1-((S)-2-hydroxypropanoyl)piperidin-4-yl)oxy)-5-(4-((4-((R)-3-hydroxypiperidin-1-yl)phenyl)amino)-1,3,5-triazin-2-yl)benzonitrile

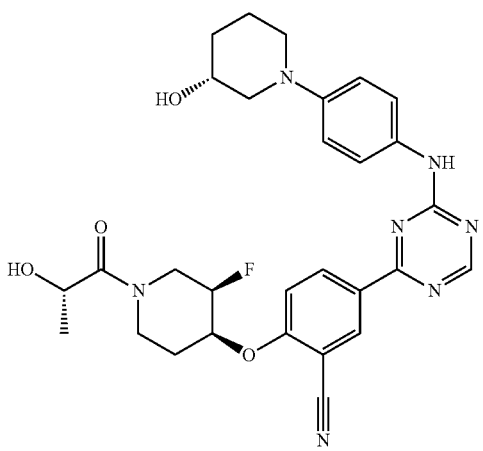 [SMILES: C[C@H](O)C(=O)N1CC[C@H](Oc2ccc(-c3ncnc(Nc4ccc(N5CCC[C@@H](O)C5)cc4)n3)cc2C#N)[C@H](F)C1]

This molecule was synthesized in the same manner as Example Example 342 except starting with (R)-1-(4-aminophenyl)piperidin-3-ol. LCMS-ESI+ (m/z): [M+H]+ calcd for $C_{29}H_{32}FN_7O_4$: 561.25; found: 562.00. ¹H NMR (300 MHz, DMSO-d₆) δ 10.14 (d, J=18.4 Hz, 1H), 8.88-8.37 (m, 2H), 7.77-7.35 (m, 3H), 6.93 (t, J=9.0 Hz, 2H), 5.33-4.89 (m, 3H), 4.83 (d, J=4.4 Hz, 1 H), 4.62-3.78 (m, 3H), 3.75-3.03 (m, 3H), 2.81-2.52 (m, 1H), 2.14-1.38 (m, 5H), 1.24 (dtd, J=15.3, 6.6, 6.1, 2.9 Hz, 6H).

Example 358

2-(((3R,4S)-3-fluoro-1-((S)-2-hydroxypropanoyl) piperdin-4-yl)oxy)-5-(4-((5-fluoro-6-(4-(oxetan-3-yl) piperazin-1-yl)pyridin-3-yl)amino)-1,3,5-triazin-2-yl)benzonitrile

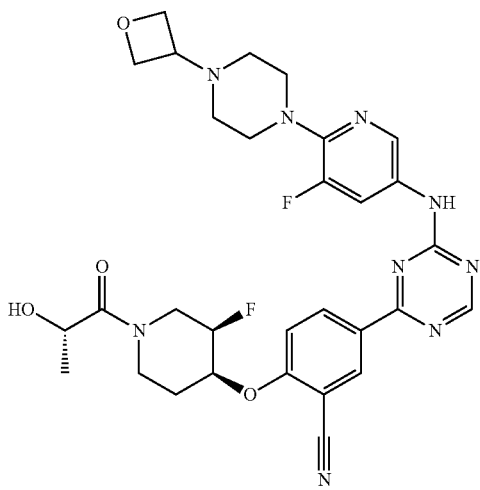 [SMILES: C[C@H](O)C(=O)N1CC[C@H](Oc2ccc(-c3ncnc(Nc4cnc(N5CCN(C6COC6)CC5)c(F)c4)n3)cc2C#N)[C@H](F)C1]

This molecule was synthesized in the same manner as Example 342 starting with 5-fluoro-6-(4-(oxetan-3-yl)piperazin-1-yl)pyridin-3-amine. LCMS-ESI+ (m/z): [M+H]+ calcd for $C_{30}H_{30}F_2N_9O_4$: 621.64; found: 622.82. ¹H NMR (300 MHz, DMSO-d₆) δ 10.43 (s, 1H), 8.82 (s, 1H), 8.56 (s, 1H), 8.39 (s, 1H), 7.99 (dd, J=14.9, 2.2 Hz, 1H), 7.65 (d, J=8.9 Hz, 1H), 5.31-4.80 (m, 3H), 4.54 (t, J=6.5 Hz, 2H), 4.46 (t, J=6.0 Hz, 2H), 4.29-3.00 (m, 8H), 2.45-2.31 (m, 4H), 1.98 (d, J=7.7 Hz, 2H), 1.19 (dt, J=7.6, 3.9 Hz, 3H).

Example 359

2-((1-((S)-2-hydroxypropanoyl)azepan-4-yl)oxy)-5-(4-((4-(4-(oxetan-3-yl)piperazin-1-yl)phenyl)amino)-1,3,5-triazin-2-yl)benzonitrile

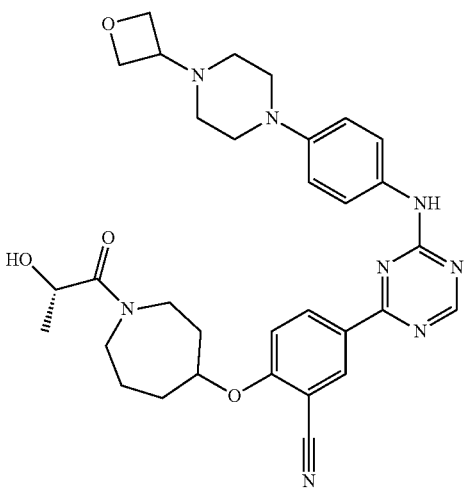 [SMILES: C[C@H](O)C(=O)N1CCCC(Oc2ccc(-c3ncnc(Nc4ccc(N5CCN(C6COC6)CC5)cc4)n3)cc2C#N)CC1]

This molecule was synthesized in the same manner as Example 342 except replacing with 2-(azepan-4-yloxy)-5-(4-((4-(4-(oxetan-3-yl)piperazin-1-yl)phenyl)amino)-1,3,5-triazin-2-yl)benzonitrile. LCMS-ESI+ (m/z): [M+H]+ calcd for $C_{32}H_{38}N_8O_4$: 598.70; found; 599.22. ¹H NMR (300 MHz, DMSO-d₆) δ 10.13 (s, 1H), 8.72 (s, 1H), 8.55 (d, J=9.4 Hz, 2H), 7.73-7.35 (m, 3H), 6.96 (d, J=8.1 Hz, 2H), 5.04-4.73 (m, 2H), 4.55 (t, J=6.5 Hz, 2H), 4.44 (dt, J=13.0, 6.2 Hz, 3H), 3.85-3.35 (m, 5H), 3.12 (d, J=5.5 Hz, 4H), 2.40 (t, J=5.0 Hz, 4H), 1.90 (s, 5H), 1.19 (dd, J=6.5, 2.5 Hz, 3H).

Example 360

5-(4-((1-ethyl-1H-pyrazol-4-yl)amino)-1,3,5-triazin-2-yl)-2-(((3R,4S)-3-fluoro-1-(2-hydroxyacetyl)piperidin-4-yl)oxy)benzonitrile

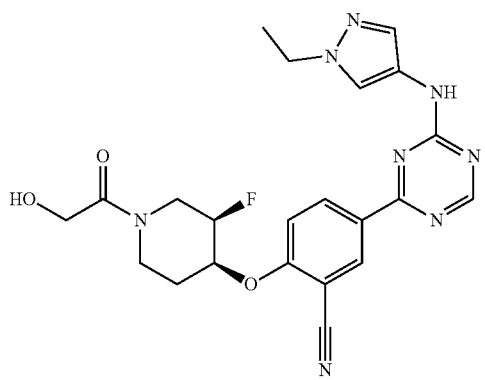 [SMILES: CCn1cc(Nc2ncnc(-c3ccc(O[C@H]4CCN(C(=O)CO)C[C@H]4F)c(C#N)c3)n2)cn1]

This molecule was synthesized in the same manner as Example 342 except starting with 1-ethyl-1H-pyrazol-4-amine and substituting glycolic acid for L-(+)-lactic acid. LCMS-ESI+ (m/z): [M+H]+ calcd for $C_{22}H_{23}FN_8O_3$: 466.47; found: 467.23. ¹H NMR (300 MHz, DMSO-d₆) δ

10.29 (d, J=4.7 Hz, 1H), 8.75 (d, J=28.8 Hz, 1H), 8.66-8.45 (m, 2H), 7.98 (dd, J=8.4, 0.8 Hz, 1H), 7.76-7.45 (m, 2H), 5.04 (d, J=49.5 Hz, 2H), 4.66 (q, J=6.1 Hz, 1H), 4.47-3.82 (m, 4H), 3.79-3.25 (m, 3H), 1.70-2.1 (m, 2H), 1.37 (dt, J=13.3, 7.3 Hz, 3H).

Example 361

5-(4-((1-(2,2-difluoroethyl)-1H-pyrazol-4-yl)amino)-1,3,5-triazin-2-yl)-2-(((3R,4S)-3-fluoro-1-(2-hydroxyacetyl)piperidin-4-yl)oxy)benzonitrile

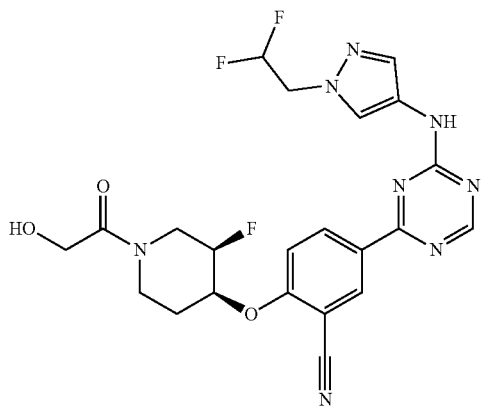 [SMILES: N#Cc1cc(-c2ncnc(Nc3cnn(CC(F)F)c3)n2)ccc1O[C@H]1CCN(C(=O)CO)C[C@H]1F]

This molecule was synthesized in the same manner as Example 342 except starting with 1-(2,2-difluoroethyl)-1H-pyrazol-4-amine and substituting glycolic acid for L-(+)-lactic acid. LCMS-ESI⁺ (m/z): [M+H]⁺ calcd for $C_{22}H_{21}NF_3N_8O_3$: 502.45; found: 503.07. ¹H NMR (300 MHz, DMSO-d₆) δ 10.37 (s, 1H), 8.77 (d, J=30.5 Hz, 1H), 8.68-8.43 (m, 2H), 8.09 (d, J=6.0 Hz, 1H), 7.82-7.51 (m, 2H), 6.72-6.05 (dtt, 1H), 5.04 (d, J=48.7 Hz, 2H), 4.79-4.49 (m, 3H), 4.48-3.80 (m, 4H), 3.79-3.03 (m, 1H), 1.90 (m, 2H).

Example 362

5-(4-((4-(8-oxa-3-azabicyclo[3.2.1]octan-3-yl)phenyl)amino)-1,3,5-triazin-2-yl)-2-(((3R,4S)-3-fluoro-1-((S)-2-hydroxypropanoyl)piperidin-4-yl)oxy)benzonitrile

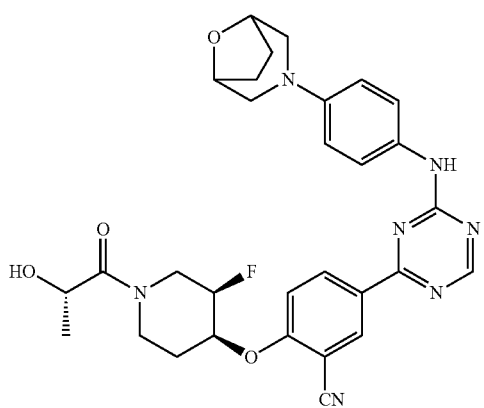 [SMILES: C[C@H](O)C(=O)N1CC[C@H](Oc2ccc(-c3ncnc(Nc4ccc(N5CC6CCC(C5)O6)cc4)n3)cc2C#N)[C@H](F)C1]

Step 1: Preparation of 3-(4-nitrophenyl)-8-oxa-3-azabicyclo[3.2.1]octane

To 4-fluoro nitrobenzene (200 mg, 1.42 mmol) and 8-oxa-3-azabicyclo[3.2.1]octane (320 mg, 2.83 mmol) dissolved in DMSO (6 mL) was added potassium carbonate (294 mg, 2.14 mmol). The reaction mixture was heated at 90° C. for 1 h. After cooling to room temperature, the reaction mixture was diluted with ethyl acetate and washed with water. The organic layer was dried over sodium sulfate, filtered, and concentrated. The residue was purified by flash column chromatography to give 3-(4-nitrophenyl)-8-oxa-3-azabicyclo[3.2.1]octane.

Step 2: Preparation of 4-(8-oxa-3-azabicyclo[3.2.1]octan-3-yl)aniline:

3-(4-nitrophenyl)-8-oxa-3-azabicyclo[3.2.1]octane (242 mg, 1.03 mmol) dissolved in ethanol (4 mL) was treated with ammonium formate (390 mg, 6.19 mmol) and 10% Pd/C (110 mg, 0.103 mmol). The reaction mixture was heated at 60° C. for 30 min. After cooling to room temperature, the reaction mixture was filtered, washed with methanol. The filtrate was concentrated to give 4-(8-oxa-3-azabicyclo[3.2.1]octan-3-yl)aniline.

Step 3: Preparation of N-(4-(8-oxa-3-azabicyclo[3.2.1]octan-3-yl)phenyl)-4-chloro-1,3,5-triazin-2-amine:

4-(8-oxa-3-azabicyclo[3.2.1]octan-3-yl)aniline (100 mg, 0.490 mmol) was dissolved in methanol (2 mL) and cooled to 0° C. Triethyl amine (90 μL, 0.646 mmol) was then added, followed by 2,4-dichloro-1,3,5-triazine (73 mg, 0.487 mmol). The reaction mixture was allowed to warm to room temperature. After 30 min, the reaction mixture was concentrated. The residue was dissolved in dichloromethane and washed with water. The organic layer was dried over sodium sulfate, filtered, and concentrated to give N-(4-(8-oxa-3-azabicyclo[3.2.1]octan-3-yl)phenyl)-4-chloro-1,3,5-triazin-2-amine.

Step 4: Preparation of 5-(4-((4-(8-oxa-3-azabicyclo[3.2.1]octan-3-yl)phenyl)amino)-1,3,5-triazin-2-yl)-2-fluorobenzonitrile:

N-(4-(8-oxa-3-azabicyclo[3.2.1]octan-3-yl)phenyl)-4-chloro-1,3,5-triazin-2-amine (47 mg, 0.148 mmol) was dissolved in dioxane (4 mL) and the reaction mixture was degassed with argon. 2-fluoro-5-(4,4,5,5-tetramethyl-1,3,2-dioxaborolan-2-yl)benzonitrile (37 mg, 0.150 mmol) was then added, followed by [1,1'-Bis(diphenylphosphino)ferrocene]dichloropalladium(II) dichloromethane (12 mg, 0.015 mmol), and 2M sodium carbonate solution (240 μL, 0.480 mmol). The reaction mixture was heated at 90° C. After 30 min, the reaction mixture was cooled to room temperature and concentrated. The residue was dissolved in ethyl acetate and washed with water. The organic layer was dried over sodium sulfate, filtered, and concentrated to give 5-(4-((4-(8-oxa-3-azabicyclo[3.2.1]octan-3-yl)phenyl)amino)-1,3,5-triazin-2-yl)-2-fluorobenzonitrile.

Step 5: Preparation of (3R,4S)-tert-butyl 4-(4-(4-((4-(8-oxa-3-azabicyclo[3.2.1]octan-3-yl)phenyl)amino)-1,3,5-triazin-2-yl)-2-cyanophenoxy)-3-fluoropiperidine-1-carboxylate Tert-butyl 3-fluoro-4-hydroxypiperidine-1-carboxylate (11 mg, 0.050 mmol) dissolved in DMF (2 mL) was cooled to 0° C. and treated with 60% sodium hydride (2 mg, 0.050 mmol). After stirring at 0° C. for 20 min, 5-(4-((4-(8-oxa-3-azabicyclo[3.2.1]octan-3-yl)phenyl)amino)-1,3,5-triazin-2-yl)-2-fluorobenzonitrile (16 mg, 0.040 mmol) dissolved in DMF (500 μL) was added dropwise. The reaction mixture was warmed at 45° C. for 2 h. After cooling to room temperature, the reaction was quenched by addition of water and then extracted with dichloromethane. The organic layer was dried over sodium sulfate, filtered, and concentrated. The residue was purified by flash column chromatography to give (3R,4S)-tert-butyl 4-(4-(4-((4-(8-oxa-3-azabicyclo[3.2.1]octan-3-yl)phenyl)amino)-1,3,5-triazin-2-yl)-2-cyanophenoxy)-3-fluoropiperidine-1-carboxylate.

Step 6: Preparation of 5-(4-((4-(8-oxa-3-azabicyclo[3.2.1]octan-3-yl)phenyl)amino)-1,3,5-triazin-2-yl)-2-(((3R,4S)-3-fluoropiperidin-4-yl)oxy)benzonitrile:

(3R,4S)-tert-butyl 4-(4-(4-((4-(8-oxa-3-azabicyclo[3.2.1]octan-3-yl)phenyl)amino)-1,3,5-triazin-2-yl)-2-cyanophenoxy)-3-fluoropiperidine-1-carboxylate (12 mg, 0.020 mmol) dissolved in DCM (1 mL) was treated with trifluoroacetic acid (40 μL, 0.523 mmol). The reaction mixture was stirred at room temperature for 30 min and then concentrated to give 5-(4-((4-(8-oxa-3-azabicyclo[3.2.1]octan-3-yl)phenyl)amino)-1,3,5-triazin-2-yl)-2-(((3R,4S)-3-fluoropiperidin-4-yl)oxy)benzonitrile.

Step 7: Preparation of 5-(4-((4-(8-oxa-3-azabicyclo[3.2.1]octan-3-yl)phenyl)amino)-1,3,5-triazin-2-yl)-2-(((3R,4S)-3-fluoro-1-((S)-2-hydroxypropanoyl)piperidin-4-yl)oxy)benzonitrile:

5-(4-((4-(8-oxa-3-azabicyclo[3.2.1]octan-3-yl)phenyl)amino)-1,3,5-triazin-2-yl)-2-(((3R,4S)-3-fluoropiperidin-4-yl)oxy)benzonitrile (15 mg, 0.030 mmol) dissolved in DCM (1 mL) was treated with HATU (14 mg, 0.037 mmol), (S)-2-hydroxypropanoic acid (3.5 mg, 0.039 mmol), and N,N-diisopropylethylamine (80 μL, 0.459 mmol). The reaction mixture was stirred at room temperature for 30 min. It was then diluted with dichloromethane and washed with water. The organic layer was dried over sodium sulfate, filtered, and concentrated. The residue was purified by HPLC to give the title compound. $^1$H NMR (400 MHz, domo) δ 10.08 (d, J=24.8 Hz, 1H), 8.72 (s, 1H), 8.56 (s, 1H), 7.62 (d, J=9.2 Hz, 1H), 7.53 (d, J=18.5 Hz, 2H), 6.84 (s, 2H), 5.19-4.93 (m, 2H), 4.97 (s, 1H), 4.43 (d, J=15.3 Hz, 2H), 4.16-3.92 (m, 4H), 3.16 (s, 2H), 2.77 (d, J=11.1 Hz, 2H), 1.97 (s, 2H), 1.82 (s, 4H), 1.19 (dd, J=6.4, 3.8 Hz, 3H). LCMS-ESI$^+$ (m/z): [M+H]$^+$ calcd for C30H32FN7O4: 574.3; found: 574.3.

Example 363

5-(4-((4-(1,4-oxazepan-4-yl)phenyl)amino)-1,3,5-triazin-2-yl)-2-(((3R,4S)-3-fluoro-1-((S)-2-hydroxypropanoyl)piperidin-4-yl)oxy)benzonitrile

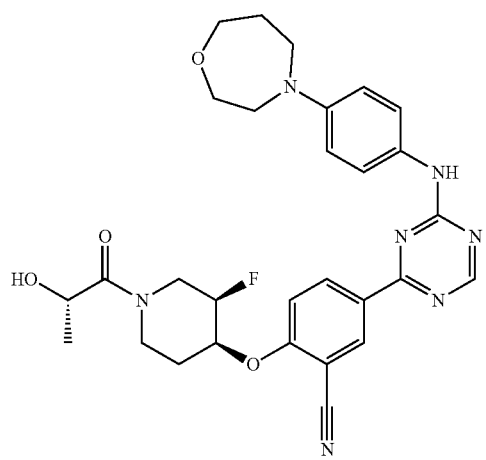 [SMILES: C[C@H](O)C(=O)N1CC[C@H](Oc2ccc(-c3ncnc(Nc4ccc(N5CCCOCC5)cc4)n3)cc2C#N)[C@H](F)C1]

The title compound was synthesized in the same manner as Example 362 using 1,4-oxazepane. $^1$H NMR (400 MHz, DMSO-d6) δ 10.00 (d, J=29.2 Hz, 1H), 8.69 (s, 1H), 8.63-8.46 (m, 2H), 7.61 (d, J=9.1 Hz, 1H), 7.47 (dd, J=31.0, 8.5 Hz, 2H), 6.77 (d, J=11.5 Hz, 2H), 5.03 (d, J=48.0 Hz, 2H), 4.53-4.28 (m, 2H), 4.21-3.87 (m, 7H), 3.71 (s, 2H), 3.55 (s, 6H), 1.93 (d, J=32.7 Hz, 5H), 1.19 (dd, J=6.5, 3.8 Hz, 3H). LCMS-ESI$^+$ (m/z): [M+H]$^+$ calcd for C29H32FN7O4: 562.2; found: 562.2.

Example 364

5-(4-((4-(2-oxa-6-azaspiro[3.3]heptan-6-yl)phenyl)amino)-1,3,5-triazin-2-yl)-2-(((3R,4S)-3-fluoro-1-((S)-2-hydroxypropanoyl)piperidin-4-yl)oxy)benzonitrile

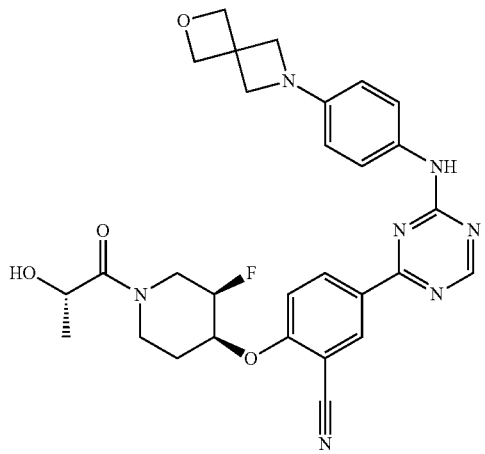 [SMILES: C[C@H](O)C(=O)N1CC[C@H](Oc2ccc(-c3ncnc(Nc4ccc(N5CC6(COC6)C5)cc4)n3)cc2C#N)[C@H](F)C1]

The title compound was synthesized in the same manner as Example 362 using 2-oxa-6-azaspiro[3.3]heptane. $^1$H NMR (400 MHz, DMSO-d6) δ 10.08 (d, J=24.8 Hz, 1H), 8.72 (s, 1H), 8.56 (s, 1H), 7.62 (d, J=9.2 Hz, 1H), 7.53 (d, J=18.5 Hz, 2H), 6.84 (s, 2H), 5.19-4.93 (m, 2H), 4.43 (d, J=15.3 Hz, 2H), 4.26 (m, 2H), 3.16 (s, 2H), 2.77 (d, J=11.1 Hz, 2H), 1.97 (s, 2H), 1.82 (s, 4H), 1.19 (dd, J=6.4, 3.8 Hz, 3H). LCMS-ESI$^+$ (m/z): [M+H]$^+$ calcd for C29H30FN7O4: 560.2; found: 560.1.

Example 365

5-(4-((4-(2-oxa-7-azaspiro[3.5]nonan-7-yl)phenyl)amino)-1,3,5-triazin-2-yl)-2-(((3R,4S)-3-fluoro-1-((S)-2-hydroxypropanoyl)piperidin-4-yl)oxy)benzonitrile

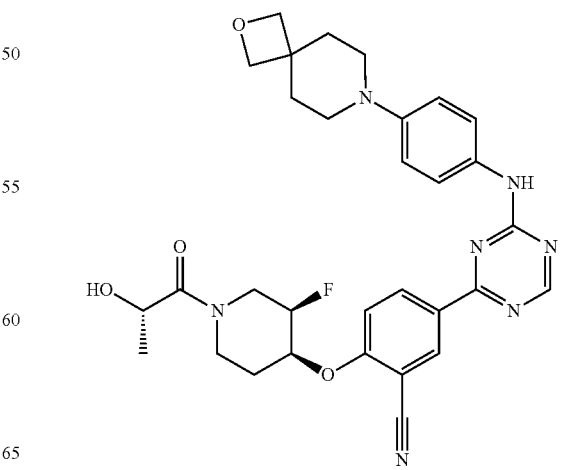

The title compound was synthesized in the same manner as Example 362 using 2-oxa-7-azaspiro[3.5]nonane. ¹H NMR (400 MHz, DMSO-d6) δ 10.23 (s, 1H), 8.76 (s, 1H), 8.67-8.46 (m, 2H), 7.63 (dd, J=12.5, 7.7 Hz, 3H), 7.15 (s, 2H), 5.18-4.87 (m, 3H), 4.53-4.41 (m, 1H), 4.35 (s, 4H), 4.16-4.01 (m, 4H), 3.17 (s, 4H), 1.96 (s, 4H), 1.84 (s, 1H), 1.19 (dd, J=6.5, 3.0 Hz, 3H). LCMS-ESI⁺ (m/z): [M+H]⁺ calcd for C31H34FN7O4: 588.3; found: 588.4.

Example 366

5-(4-((4-(3-oxa-6-azabicyclo[3.1.1]heptan-6-yl)phenyl)amino)-1,3,5-triazin-2-yl)-2-(((3R,4S)-3-fluoro-1-((S)-2-hydroxypropanoyl)piperidin-4-yl)oxy)benzonitrile

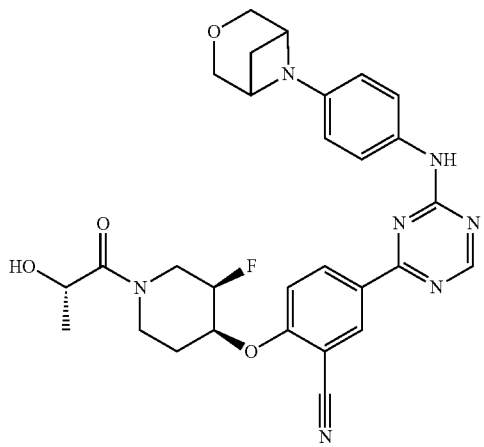 [SMILES: C[C@H](O)C(=O)N1CC[C@H](Oc2ccc(-c3ncnc(Nc4ccc(N5C6COCC5C6)cc4)n3)cc2C#N)[C@H](F)C1]

The title compound was synthesized in the same manner as Example 362 using 2-oxa-7-azaspiro[3.5]nonane. ¹H NMR (400 MHz, DMSO-d6)δ 10.09 (d, J=27.5 Hz, 1H), 8.71 (d, J=12.9 Hz, 1H), 8.56 (q, J=11.0, 10.2, 10.2 Hz, 2H), 7.61 (d, J=9.2 Hz, 1H), 7.56 (d, J=9.4 Hz, 2H), 6.64 (s, 2H), 5.21-4.88 (m, 3H), 4.46 (dq, J=13.4, 6.8, 6.6, 6.6 Hz, 2H), 4.36-4.07 (m, 5H), 3.40-3.07 (m, 3H), 2.66 (d, J=7.3 Hz, 1H), 1.91 (dd, J=54.0, 7.1 Hz, 3H), 1.19 (dd, J=6.4. 4.0 Hz, 3H). LCMS-ESI⁺ (m/z): [M+H]⁺ calcd for C29H30FN7O4: 560.2; found: 560.2.

Example 367

2-(((3R,4S)-3-fluoro-1-((S)-2-hydroxypropanoyl)piperidin-4-yl)oxy)-5-(4-((3-fluoro-4-(4-(oxetan-3-yl)piperazin-1-yl)phenyl)amino)-1,3,5-triazin-2-yl)benzonitrile

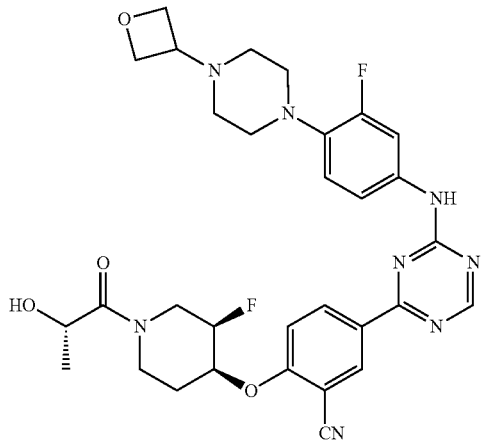 [SMILES: C[C@H](O)C(=O)N1CC[C@H](Oc2ccc(-c3ncnc(Nc4ccc(N5CCN(C6COC6)CC5)c(F)c4)n3)cc2C#N)[C@H](F)C1]

The title compound was synthesized in the same manner as Example 362 using 1-(oxetan-3-yl)piperazine and 1,2-difluoro-4-nitrobenzene instead of 4-fluoro nitrobenzene and 8-oxa-3-azabicyclo[3.2.1]octane. ¹H NMR (400 MHz, DMSO-d6) δ 10.49 (d, J=51.4 Hz, 2H), 8.58 (d, J=7.5 Hz, 3H), 7.82-7.59 (m, 3H), 7.52-7.37 (m, 2H), 7.22-6.93 (m, 3H), 5.21-4.96 (m, 3H), 4.75 (d, J=5.9 Hz, 4H), 4.55-4.29 (m, 3H), 4.24-3.82 (m, 4H), 1.91 (d, J=57.5 Hz, 4H), 1.25-1.15 (m, 3H). LCMS-ESI⁺ (m/z): [M+H]⁺ calcd for C31H34F2N8O4: 621.3; found: 621.4.

Example 368

2-(((3R,4S)-3-fluoro-1-(2-hydroxyacetyl)piperidin-4-yl)oxy)-5-(4-((4-(4-(oxetan-3-yl)piperazin-1-yl)-3-(trifluoromethyl)phenyl)amino)-1,3,5-triazin-2-yl)benzonitrile

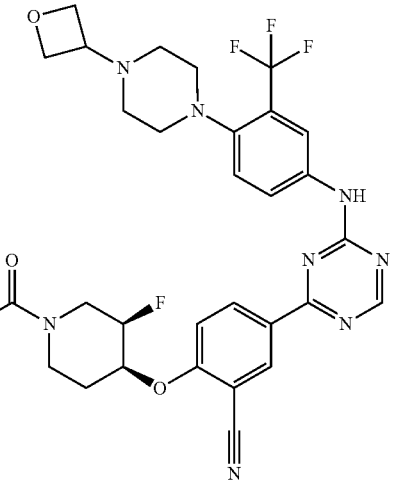

The title compound was synthesized in the same manner as Example 362 using 1-(oxetan-3-yl)piperazine and 1-fluoro-4-nitro-2-(trifluoromethyl)benzene. ¹H NMR (400 MHz, DMSO-d6) δ 10.66 (s, 2H), 8.88 (s, 1H), 8.66-8.47 (m, 2H), 7.93 (s, 2H), 7.63 (t, J=10.1, 10.1 Hz, 2H), 5.19-4.94 (m, 3H), 4.72 (s, 4H), 4.25-4.03 (m, 5H), 3.93 (s, 2H), 3.60 (m, 2H), 3.09 (s, 4H), 1.98 (s, 1H). LCMS-ESI⁺ (m/z): [M+H]⁺ calcd for C31H32F4N8O4: 657.3; found: 657.4.

Example 369

5-((4-(3-cyano-4-(((3R,4S)-3-fluoro-1-((S)-2-hydroxypropanoyl)piperidin-4-yl)oxy)phenyl)-1,3,5-triazin-2-yl)amino)-2-(4-(oxetan-3-yl)piperazin-1-yl)benzonitrile

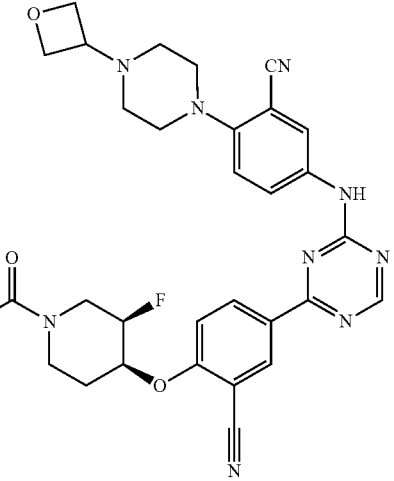

393

The title compound was synthesized in the same manner as Example 362 using 1-(oxetan-3-yl)piperazine and 2-fluoro-5-nitrobenzonitrile. $^1$H NMR (400 MHz, DMSO-d6) δ 10.50 (s, 1H), 8.85 (s, 1H), 8.57 (d, J=8.5 Hz, 2H), 8.13 (s, 1H), 7.93 (s, 1H), 7.63 (d, J=9.3 Hz, 1H), 7.30 (s, 1H), 5.22-4.97 (m, 3H), 4.79-4.39 (m, 6H), 4.04-3.92 (m, 4H), 3.60 (m, 2H), 3.17 (s, 4H), 1.98 (s, 2H), 1.19 (dd, J=6.4, 3.4 Hz, 3H). LCMS-ESI$^+$ (m/z): [M+H]$^+$ calcd for C32H34FN9O4: 628.3; found: 628.4.

Example 370

2-(((3R,4S)-3-fluoro-1-((S)-2-hydroxypropanoyl)piperidin-4-yl)oxy)-5-(4-((4-(4-(oxetan-3-yl)piperazin-1-yl)-3-(trifluoromethyl)phenyl)amino)-1,3,5-triazin-2-yl)benzonitrile

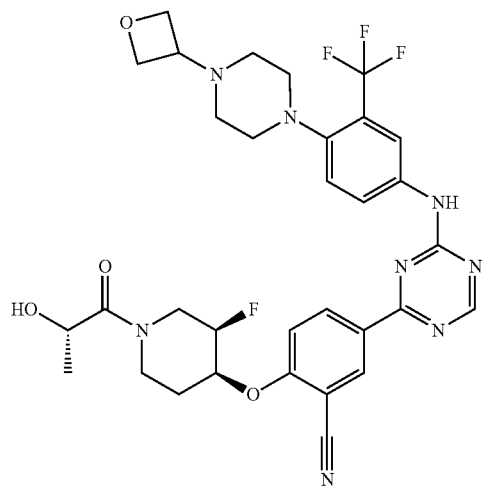 [SMILES: C[C@H](O)C(=O)N1CC[C@H](Oc2ccc(-c3ncnc(Nc4ccc(N5CCN(C6COC6)CC5)c(C(F)(F)F)c4)n3)cc2C#N)[C@H](F)C1]

The title compound was synthesized in the same manner as Example 362 using 1-(oxetan-3-yl)piperazine and 1-fluoro-4-nitro-2-(trifluoromethyl)benzene. $^1$H NMR (400 MHz, DMSO-d6) δ 10.53 (s, 1H), 8.85 (s, 1H), 8.57 (d, J=8.5 Hz, 2H), 8.13 (s, 1H), 7.93 (s, 1H), 7.63 (d, J=9.3 Hz, 1H), 5.22-4.97 (m, 3H), 4.79-4.39 (m, 6H), 4.03 (m, 4H), 3.59 (m, 2H), 3.17 (s, 5H), 1.98 (s, 2H), 1.19 (dd, J=6.4, 3.4 Hz, 3H). LCMS-ESI$^+$ (m/z): [M+H]$^+$ calcd for C32H34F4N8O4: 671.3; found: 671.4.

394

Example 371

5-(4-((3-(difluoromethyl)-4-(4-(oxetan-3-yl)piperazin-1-yl)phenyl)amino)-1,3,5-triazin-2-yl)-2-(((3R,4S)-3-fluoro-1-((S)-2-hydroxypropanoyl)piperidin-4-yl)oxy)benzonitrile

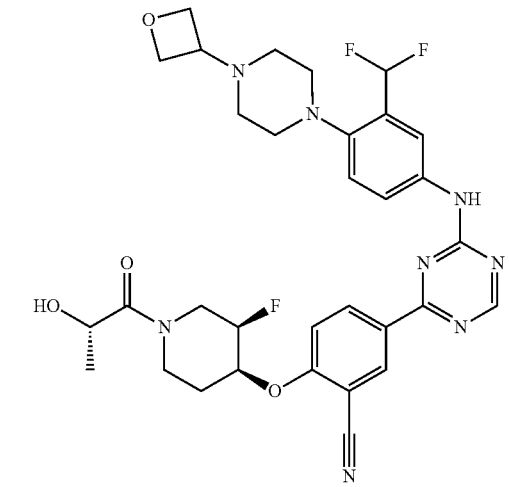 [SMILES: C[C@H](O)C(=O)N1CC[C@H](Oc2ccc(-c3ncnc(Nc4ccc(N5CCN(C6COC6)CC5)c(C(F)F)c4)n3)cc2C#N)[C@H](F)C1]

The title compound was synthesized in the same manner as Example 362 using 1-(oxetan-3-yl)piperazine and 2-(difluoromethyl)-1-fluoro-4-nitrobenzene. $^1$H NMR (400 MHz, DMSO-d6) δ 10.54 (s, 1H), 8.85 (s, 1H), 8.60 (d, J=7.4 Hz, 2H), 7.76 (s, 2H), 7.70-7.52 (m, 2H), 7.42 (d, J=8.7 Hz, 2H), 5.14 (d, J=27.7 Hz, 2H), 4.75 (s, 4H), 4.50-4.22 (m, 4H), 4.22-3.83 (m, 4H), 3.16-2.95 (m, 4H), 2.29 (s, 2H), 1.97 (s, 2H), 1.28-1.14 (m, 3H). LCMS-ESI$^+$ (m/z): [M+H]$^+$ calcd for C32H35F3N8O4: 653.3; found: 653.3.

Example 372

2-(((3R,4S)-3-fluoro-1-((S)-5-oxopyrrolidine-2-carbonyl)piperidin-4-yl)oxy)-5-(4-((3-fluoro-4-(4-(oxetan-3-yl)piperazin-1-yl)phenyl)amino)-1,3,5-triazin-2-yl)benzonitrile

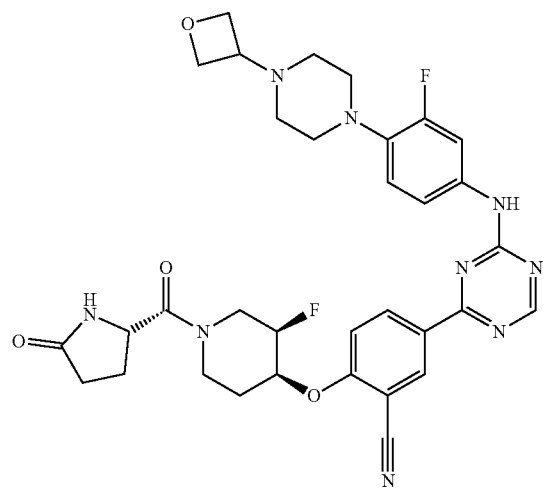

The title compound was synthesized in the same manner as Example 362 using 1-(oxetan-3-yl)piperazine and 1,2-difluoro-4-nitrobenzene. ¹H NMR (400 MHz, DMSO-d6) δ 10.43 (s, 1H), 8.83 (s, 1H), 8.58 (d, J=8.3 Hz, 2H), 7.79-7.61 (m, 3H), 7.47 (s, 1H), 7.15 (t, J=9.4, 9.4 Hz, 1H), 5.07 (d, J=48.9 Hz, 3H), 4.77 (d, J=6.3 Hz, 4H), 4.68-4.30 (m, 4H), 4.04 (m, 2H), 3.08 (s, 5H), 2.21 (s, 2H), 2.09 (t, J=8.2, 8.2 Hz, 2H), 2.00 (s, 4H). LCMS-ESI⁺ (m/z): [M+H]⁺ calcd for C33H35F2N9O4: 660.3; found: 660.4.

Example 373

2-(((3R,4S)-3-fluoro-1-(1H-1,2,3-triazole-5-carbonyl)piperidin-4-yl)oxy)-5-(4-((3-fluoro-4-(4-(oxetan-3-yl)piperazin-1-yl)phenyl)amino)-1,3,5-triazin-2-yl)benzonitrile

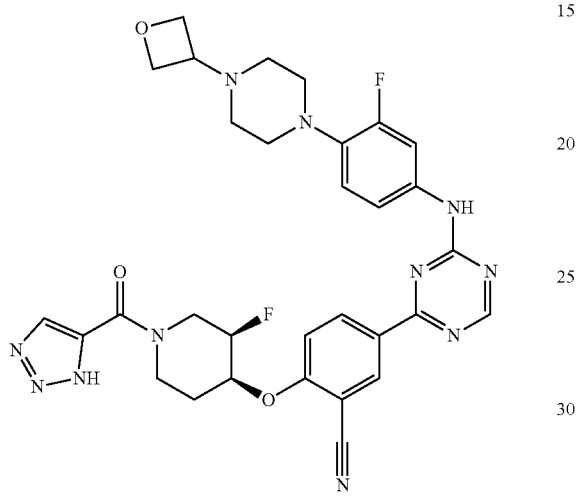

The title compound was synthesized in the same manner as Example 362 using 1-(oxetan-3-yl)piperazine and 1,2-difluoro-4-nitrobenzene. ¹H NMR (400 MHz, DMSO-d6) δ 1H NMR (400 MHz, dmso) δ 10.41 (s, 1H), 8.83 (s, 1H), 8.63-8.51 (m, 3H), 7.75-7.59 (m, 3H), 7.46 (s, 2H), 7.13 (s, 2H), 5.17 (d, J=24.5 Hz, 5H), 4.72 (s, 6H), 4.54 (s, 4H), 3.06 (s, 4H). LCMS-ESI⁺ (m/z): [M+H]⁺ calcd for C31H31F2N11O3: 644.3; found: 644.2.

Example 374

2-(((3R,4S)-3-fluoro-1-((S)-5-oxopyrrolidine-2-carbonyl)piperidin-4-yl)oxy)-5-(4-((2-fluoro-4-(4-(oxetan-3-yl)piperazin-1-yl)phenyl)amino)-1,3,5-triazin-2-yl)benzonitrile

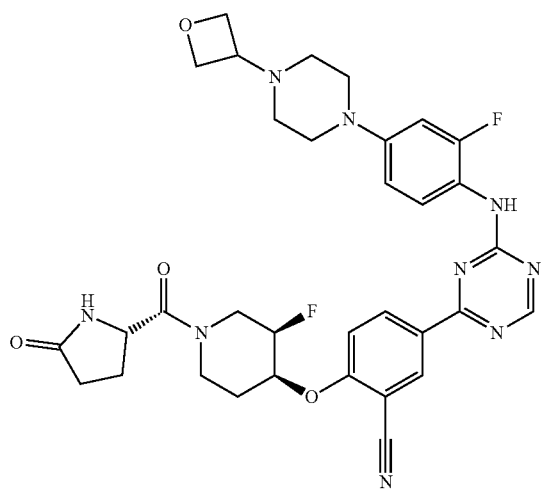

The title compound was synthesized in the same manner as Example 362. ¹H NMR (400 MHz, DMSO-d6) δ 9.32 (s, 1H), 8.76 (s, 1H), 8.52 (s, 2H), 7.72 (d, J=20.5 Hz, 2H), 7.61 (d, J=8.8 Hz, 1H), 7.09 (dd, J=10.4, 2.8 Hz, 1H), 7.06-6.92 (m, 1H), 5.73 (s, 1H), 5.05 (d, J=51.2 Hz, 2H), 4.79-4.66 (m, 4H), 4.59 (ddd, J=13.2, 9.1, 3.9 Hz, 2H), 4.38 (d, J=17.2 Hz, 2H), 3.83 (d, J=14.3 Hz, 2H), 3.32 (dd, J=18.7, 12.1 Hz, 2H), 3.05 (s, 4H), 2.31 (q, J=10.6, 10.6, 10.1 Hz, 2H), 2.16-2.02 (m, 2H), 2.02-1.71 (m, 3H).). LCMS-ESI⁺ (m/z): [M+H]⁺ calcd for C33H35F2N9O4: 660.3; found; 660.3.

Example 375

2-(((3R,4S)-3-fluoro-1-((S)-2-hydroxypropanoyl)piperidin-4-yl)oxy)-5-(4-((2-fluoro-4-(4-(oxetan-3-yl)piperazin-1-yl)phenyl)amino)-1,3,5-triazin-2-yl)benzonitrile

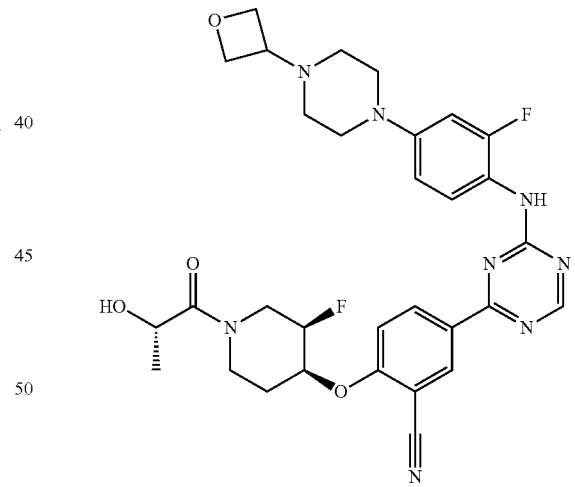

The title compound was synthesized in the same manner as Example 362. ¹H NMR (400 MHz, DMSO-d6) δ 9.32 (s, 1H), 8.76 (s, 1H), 8.52 (s, 2H), 7.76 (s, 1H), 7.60 (d, J=8.9 Hz, 1H), 7.14-6.92 (m, 2H), 5.73 (s, 3H), 5.21-4.94 (m, 3H), 4.72 (m, 4H), 4.58-4.30 (m, 4H), 3.04 (s, 4H), 2.00-1.80 (m, 2H), 1.19 (d, J=6.5 Hz, 4H). LCMS-ESI⁺ (m/z): [M+H]⁺ calcd for C31H34F2N8O4: 621.3; found: 621.3.

Example 376

2-(((3R,4S)-3-fluoro-1-(1-(2-hydroxyethyl)-1H-1,2,3-triazole-4-carbonyl)piperidin-4-yl)oxy)-5-(4-((4-(4-(oxetan-3-yl)piperazin-1-yl)phenyl)amino)-1,3,5-triazin-2-yl)benzonitrile

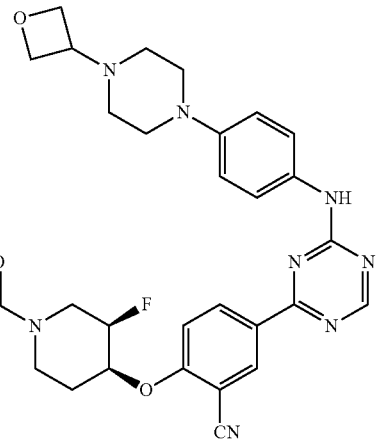

2-(((3R,4S)-3-fluoropiperidin-4-yl)oxy)-5-(4-((4-(4-(oxetan-3-yl)piperazin-1-yl)phenyl)amino)-1,3,5-triazin-2-yl)benzonitrile (38 mg, 0.072 mmol) suspended in DCM (1 mL) was treated with HATU (33 mg, 0.087 mmol), 1-(2-hydroxyethyl)-1H-1,2,3-triazole-4-carboxylic acid (14 mg, 0.089 mmol), and N,N-diisopropylethylamine (60 μL, 0.344 mmol). The reaction mixture was stirred at room temperature for 30 min. It was then diluted with dichloromethane and washed with water. The organic layer was dried over sodium sulfate, filtered, and concentrated. The residue was purified by HPLC to give the title compound. $^1$H NMR (400 MHz, dmso) δ 10.20 (s, 1H), 8.75 (s, 1H), 8.58 (dd, J=9.0, 2.1 Hz, 1H), 8.51 (s, 2H), 7.64 (d, J=9.3 Hz, 3H), 7.04 (s, 2H), 5.15 (s, 3H), 4.75 (d, J=6.0 Hz, 5H), 4.44 (t, J=5.3, 5.3 Hz, 3H), 3.80 (t, J=5.4, 5.4 Hz, 2H), 2.98 (s, 5H), 2.05 (m, 4H). LCMS-ESI$^+$ (m/z): [M+H]$^+$ calcd for C33H36FN11O4: 670.3; found: 670.4.

Example 377

2-(((3R,4S)-1-(2-(4H-1,2,4-triazol-4-yl)acetyl)-3-fluoropiperidin-4-yl)oxy)-5-(4-((4-(4-(oxetan-3-yl)piperazin-1-yl)phenyl)amino)-1,3,5-triazin-2-yl)benzonitrile

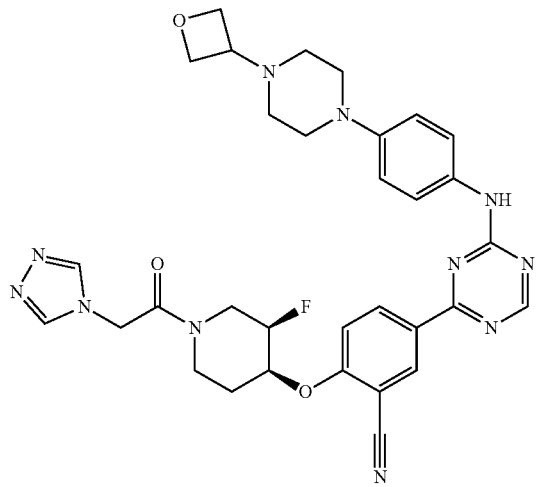 [SMILES: N#Cc1cc(-c2ncnc(Nc3ccc(N4CCN(C5COC5)CC4)cc3)n2)ccc1O[C@H]1CCN(C(=O)Cn2cnnc2)C[C@H]1F]

The title compound was synthesized in the same manner as Example 376 using 2-(4H-1,2,4-triazol-4-yl)acetic acid instead of 1-(2-hydroxyethyl)-1H-1,2,3-triazole-4-carboxylic acid. $^1$H NMR (400 MHz, dmso) δ 10.20 (s, 1H), 8.75 (s, 1H), 8.58 (dd, J=9.0, 2.1 Hz, 1H), 8.51 (s, 2H), 7.64 (d, J=9.3 Hz, 4H), 7.04 (s, 3H), 5.15 (m, 6H), 4.75 (d, J=6.0 Hz, 5H), 4.44 (t, J=5.3, 5.3 Hz, 3H), 3.80 (t, J=5.4, 5.4 Hz, 2H), 2.98 (s, 5H). LCMS-ESI$^+$ (m/z): [M+H]$^+$ calcd for C32H34FN11O3: 640.3; found: 640.3.

Example 378

5-(4-((3-chloro-4-(4-(oxetan-3-yl)piperazin-1-yl)phenyl)amino)-1,3,5-triazin-2-yl)-2-(((3R,4S)-3-fluoro-1-((S)-2-hydroxypropanoyl)piperidin-4-yl)oxy)benzonitrile

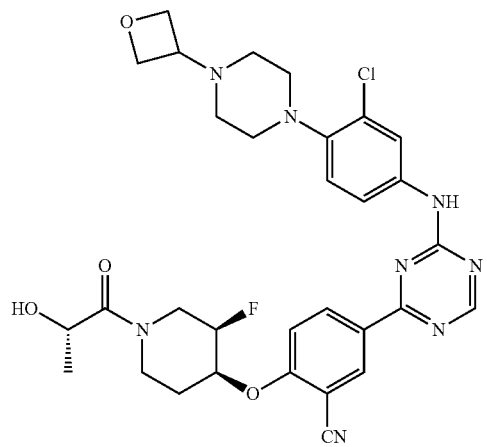 [SMILES: C[C@H](O)C(=O)N1CC[C@H](Oc2ccc(-c3ncnc(Nc4ccc(N5CCN(C6COC6)CC5)c(Cl)c4)n3)cc2C#N)[C@H](F)C1]

The title compound was synthesized in the same manner as Example 362 starting from 1-(oxetan-3-yl)piperazine and 2-chloro-1-fluoro-4-nitrobenzene except the reduction of the nitro group to the aniline was carried out by the following procedure. 1-(2-chloro-4-nitrophenyl)-4-(oxetan-3-yl)piperazine (155 mg, 0.521 mmol) suspended in ethanol (4 mL) was treated with a solution of ammonium chloride (143 mg, 2.673 mmol) in 1.5 mL water followed by iron powder (232 mg, 4.154 mmol). The reaction mixture was heated at 90° C. for 2 h. After cooling to room temperature, the reaction mixture was filtered and the filtrate was concentrated. The residue was dissolved in saturated sodium bicarbonate solution and extracted with ethyl acetate. The organic layer was dried over sodium sulfate, filtered and concentrated to give 3-chloro-4-(4-(oxetan-3-yl)piperazin-1-yl)aniline.

$^1$H NMR (400 MHz, dmso) δ 10.47 (s, 1H), 8.84 (s, 1H), 8.58 (d, J=8.0 Hz, 2H), 8.01 (s, 2H), 7.64 (d, J=9.1 Hz, 2H), 7.26 (s, 2H), 5.13 (d, J=23.9 Hz, 3H), 4.73 (s, 5H), 4.46 (d, J=6.5 Hz, 4H), 1.98 (s, 3H), 1.26 (s, 2H), 1.25-1.16 (m, 4H). LCMS-ESI$^+$ (m/z): [M+H]$^+$ calcd for C31H34ClFN8O4: 637.3; found: 637.4.

Example 379

2-(((3R,4S)-3-fluoro-1-((S)-2-hydroxypropanoyl)piperidin-4-yl)oxy)-5-(4-((6-(4-(oxetan-3-yl)piperazin-1-yl)pyridin-3-yl)amino)-1,3,5,-triazin-2-yl)benzonitrile

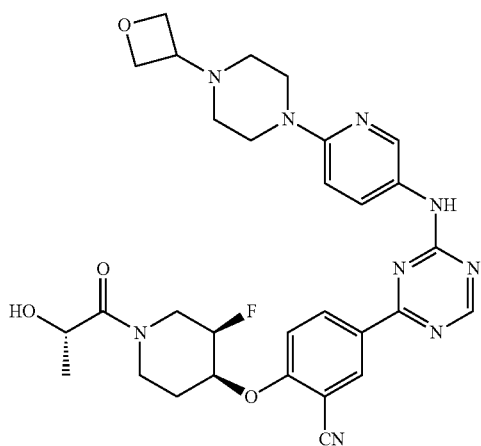 [SMILES: C[C@H](O)C(=O)N1CC[C@H](Oc2ccc(-c3ncnc(Nc4ccc(N5CCN(C6COC6)CC5)nc4)n3)cc2C#N)[C@H](F)C1]

The title compound was synthesized in the same manner as Example 362 starting from 6-(4-(oxetan-3-yl)piperazin-1-yl)pyridin-3-amine. $^1$H NMR (400 MHz, dmso) δ 10.21 (d, J=23.9 Hz, 1H), 8.76 (s, 1H), 8.64-8.45 (m, 2H), 7.94 (m, 2H), 7.62 (d, J=9.2 Hz, 1H), 7.04 (m, 2H), 5.18-4.93 (m, 3H), 4.75 (d, J=6.6 Hz, 4H), 4.54-4.28 (m, 4H), 4.20-3.88 (m, 4H), 1.97 (s, 2H), 1.83 (s, 1H), 1.30-1.12 (m, 3H). LCMS-ESI$^+$ (m/z): [M+H]$^+$ calcd for C30H34FN9O4: 604.3; found: 604.4.

Example 380

Ethyl 3-((4-(3-cyano-4-(((3R,4S)-3-fluoro-1-((S)-2-hydroxypropanoyl)piperidin-4-yl)oxy)phenyl)-1,3,5-triazin-2-yl)amino)benzoate

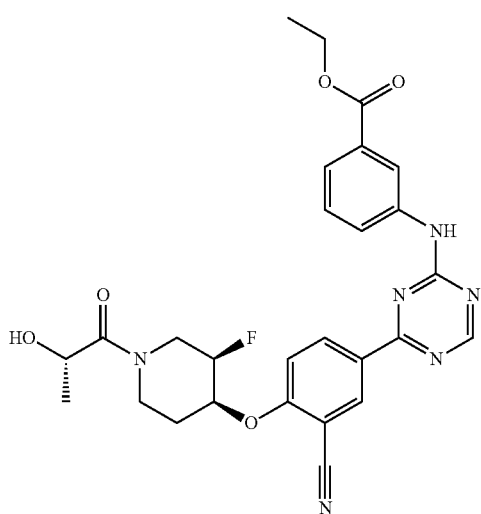 [SMILES: CCOC(=O)c1cccc(Nc2ncnc(-c3ccc(O[C@H]4CCN(C(=O)[C@H](C)O)C[C@H]4F)c(C#N)c3)n2)c1]

The title compound was synthesized in the same manner as Example 362 starting from ethyl 3-aminobenzoate $^1$H NMR (400 MHz, dmso) δ 10.57 (s, 1H), 8.87 (s, 1H), 8.62 (m, 2H), 7.94 (s, 1H), 7.66 (dd, J=22.4, 8.6 Hz, 2H), 7.52 (t, J=7.9, 7.9 Hz, 1H), 5.21-4.97 (m, 3H), 4.47 (dt, J=13.1, 6.4, 6.4 Hz, 2H), 4.35 (q, J=7.2, 7.2, 7.2 Hz, 3H), 4.25-3.87 (m, 4H), 2.01-1.80 (m, 2H), 1.32 (t, J=7.1, 7.1 Hz, 3H), 1.19 (dd, J=6.5, 3.8 Hz, 2H). LCMS-ESI$^+$ (m/z): [M+H]$^+$ calcd for C27H27FN6O5: 535.2; found: 535.1.

Example 381

2-(((3R,4S)-3-fluoro-1-((S)-5-oxopyrrolidine-2-carbonyl)piperidin-4-yl)oxy)-5-(4-((4-((S)-2-methyl-4-(oxetan-3-yl)piperazin-1-yl)phenyl)amino)-1,3,5-triazin-2-yl)benzonitrile

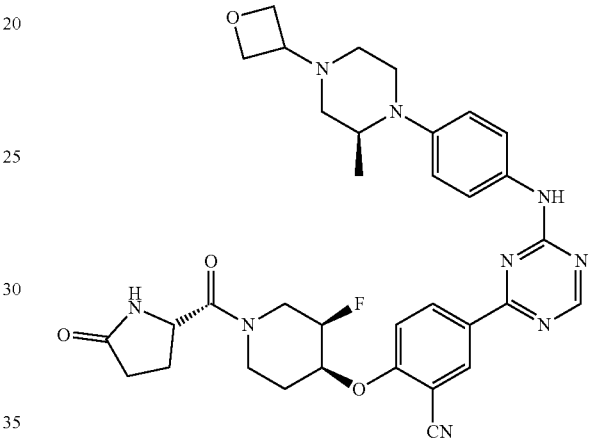

Step 1: (S)-tert-butyl 2-methylpiperazine-1-carboxylate (800 mg, 3.99 mmol) dissolved in 1,2-dichloroethane (20 mL) was treated with 3-oxetanone (200 µL, 3.43 mmol). The reaction mixture was stirred at room temperature for 1 h before sodium triacetoxyborohydride (1.10 g, 5.19 mmol) was added in portions. The reaction mixture was stirred at room temperature for 30 min. It was then diluted with dichloromethane and washed with water. The organic layer was dried over sodium sulfate, filtered and concentrated to give (S)-tert-butyl 2-methyl-4-(oxetan-3-yl)piperazine-1-carboxylate.

Step 2: (S)-tert-butyl 2-methyl-4-(oxetan-3-yl)piperazine-1-carboxylate (1000 mg, 3.90 mmol) dissolved in dichloromethane (15 mL) was treated with trifluoroacetic acid (7.0 mL, 91.5 mmol). The reaction mixture was stirred at room temperature for 1 h and then concentrated. The residue was dissolved in ethyl acetate and washed with saturated sodium bicarbonate solution. The organic layer was dried over sodium sulfate, filtered and concentrated to give (S)-3-methyl-1-(oxetan-3-yl)piperazine.

The title compound was then synthesized in the same manner as Example 362 starting from (S)-3-methyl-1-(oxetan-3-yl)piperazine. $^1$H NMR (400 MHz, dmso) δ 10.26 (s, 1H), 8.81 (s, 1H), 8.24 (s, 1H), 7.81-7.60 (m, 3H), 7.50 (d, J=9.1 Hz, 2H), 6.97 (s, 4H), 4.98 (s, 3H), 4.72 (s, 4H), 4.61-4.37 (m, 3H), 4.35-4.05 (m, 3H), 3.89 (d, J=13.8 Hz, 2H), 2.28 (s, 1H), 2.19-2.02 (m, 2H), 1.91 (d, J=18.4 Hz, 4H), 1.07 (s, 3H). LCMS-ESI$^+$ (m/z): [M+H]$^+$ calcd for C34H38FN9O4: 656.3; found: 656.3.

Example 382

2-(((3R,4S)-3-fluoro-1-((S)-2-hydroxypropanoyl)piperidin-4-yl)oxy)-5-(4-((6-(2-hydroxypropan-2-yl)pyridin-3-yl)amino)-1,3,5-triazin-2-yl)benzonitrile

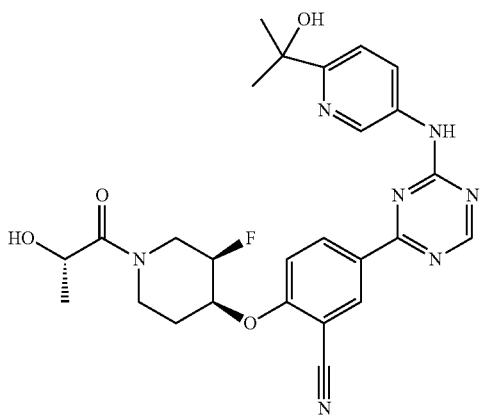 [SMILES: C[C@H](O)C(=O)N1CC[C@H](Oc2ccc(-c3ncnc(Nc4ccc(C(C)(C)O)nc4)n3)cc2C#N)[C@H](F)C1]

Step 1: Preparation of 2-bromo-5-(2,2,5,5-tetramethyl-1,2,5-azadisilolidin-1-yl)pyridine:

6-bromopyridin-3-amine (2.24 g, 12.95 mmol), bis(dimethylaminodimethylsilyl)ethane (5.12 mL, 18.14 mmol) and Zinc Iodide (0.11 g, 0.345 mmol) were applied to a 100 mL sealed tube and the mixture was heated up to 140° C. for overnight. After cooling to room temperature, the mixture was quenched with saturated aqueous amino chloride solution (PH~7) and extracted with ethyl acetate for three times. The combined extracts were washed once with saturated aqueous sodium chloride solution, dried over anhydrous sodium sulfate, filtered, and concentrated under reduced pressure. The crude residue was purified by flash chromatography (silica gel) to provide the desired material as a white solid. $^1$H NMR (300 MHz, DMSO-d$_6$) δ 7.92 (d, J=3.6 Hz, 1H), 7.41 (d, J=8.7 Hz, 1H), 7.22 (dd, J=3.0 Hz, J=8.4 Hz, 1H), 0.84 (S, 4H), 0.22 (t, J=3.6 Hz, 12H).

Step 2: Preparation of 2-(5-aminopyridin-2-yl)propan-2-ol:

2-bromo-5-(2,2,5,5-tetramethyl-1,2,5-azadisilolidin-1-yl)pyridine (635 mg, 2 mmol) was dissolved in Tetrahydrofuran (12 mL) and cooled to −78° C. nBuLi solution (1.6M in hexane, 1.9 mL) was added drop wise and the resulting bright yellow solution was stirred at −78° C. for 1 h. Then acetone (0.5 mL, 6.8 mmol) was added and the reaction mixture was stirred at −78° C. for another 1 h. After that time, water (5.5 mL) was added and dry-ice bath was removed. The reaction mixture was allowed to warm up to room temperature, followed by addition of 1M HCl solution (4 mL), and stir for 15 minutes. Reaction mixture was quenched with saturated sodium bicarbonate solution (PH~8) and extracted with dichloromethane for three times. The combined extracts were washed once with saturated aqueous sodium chloride solution, dried over anhydrous sodium sulfate, filtered, and concentrated under reduced pressure. The crude residue was purified by flash chromatography (silica gel) to provide the desired material as light green oil: LCMS-ESI$^+$ (m/z): [M+H]$^+$ calcd for C$_8$H$_{13}$N$_2$O: 153.2; found: 153.1.

Step 3: Preparation of 2-(5-((4-chloro-1,3,5-triazin-2-yl)amino)pyridin-2-yl)propan-2-ol:

To a solution of 2,4-dichloro-1,3,5-triazine in N,N-dimethylformamide (1mL) at 0° C., 2-(5-aminopyridin-2-yl)propan-2-ol (50 mg) in N,N-dimethylformamide (1 mL) was added drop wise and the reaction mixture was stirred at 0° C. for 1 h. After this time, the reaction was quenched with saturated sodium bicarbonate solution (PH~8) and extracted with dichloromethane for three times. The combined extracts were washed once with saturated aqueous sodium chloride solution, dried over anhydrous sodium sulfate, filtered, and concentrated under reduced pressure to give the desired material. Use as crude for next step. LCMS-ESI$^+$ (m/z): [M+H]+ calcd for C$_{11}$H$_{13}$ClN$_5$O: 266.7; found: 266.1.

Step 4: Preparation of (3R,4S)-tert-butyl 4-(4-bromo-2-cyanophenoxy)-3-fluoropiperidine-1-carboxylate:

(3R,4S)-tert-butyl 3-fluoro-4-hydroxypiperidine-1-carboxylate (3.6 g, 16.4 mmol) was dissolved in N,N-Dimethylacetamide (40 mL) and sodium hydrides was added in a single portion and stirred at room temperature for 30 minutes. A solution of 5-bromo-2-fluorobenzonitrile (3.0 g, 15.1 mmol) in N,N-Dimethylacetamide (14mL) was added to the above reaction mixture drop wise. N,N-dimethylformamide (40 mL) was added to make all material into solution. The reaction mixture was stirred at room temperature for 30 minutes and was quenched with saturated sodium bicarbonate solution (PH~8), extracted with dichloromethane for three times. The combined extracts were washed once with saturated aqueous sodium chloride solution, dried over anhydrous sodium sulfate, filtered, and concentrated under reduced pressure. The crude residue was purified by flash chromatography (silica gel) to provide the desired material as light yellow solid. $^1$H NMR (300 MHz, DMSO-d$_6$) δ 8.02 (d, J=2.7 Hz, 1H), 7.85 (dd, J=9.0, 2.4 Hz, 1H), 7.39 (d, J=8.7 Hz, 1H), 4.99 (m, 2H), 4.04 (m, 1H), 3.78 (m, 1H), 3.30 (m, 2H), 1.85 (m, 2H), 1.31 (s, 9H).

Step 5: Preparation of 5-bromo-2-(((3R,4S)-3-fluoropiperidin-4-yl)oxy)benzonitrile:

(3R,4S)-tert-butyl 4-(4-bromo-2-cyanophenoxy)-3-fluoropiperidine-1-carboxylate (1.03 g, 2.58 mmol) was dissolved in dichloromethane (25 mL), trifluoroacetic acid (4.8 mL, 62.4 mmol) was added drop wise and the reaction mixture was stirred at room temperature for 30 minutes. After this time, the reaction was quenched with saturated sodium bicarbonate solution (PH~8), extracted with dichloromethane for three times. The combined extracts were washed once with saturated aqueous sodium chloride solution, dried over anhydrous sodium sulfate, filtered, and concentrated under reduced pressure. The crude was used for next step. LCMS-ESI$^+$ (m/z): [M+H]+ calcd for C$_{12}$H$_{13}$BrFN$_2$O: 300.1; found: 300.2.

Step 6: Preparation of 5-bromo-2-(((3R,4S)-3-fluoro-1-((S)-2-hydroxypropanoyl)piperidin-4-yl)oxy)benzonitrile:

5-bromo-2-(((3R,4S)-3-fluoropiperidin-4-yl)oxy)benzonitrile (824 mg, 2.76 mmol) and L-(+)-Lactic acid (248 mg, 2.76 mmol) were taken up as suspension in N,N-dimethylformamide (20 mL). The mixture was treated successively with N,N-diisopropylethylamine (1.44 mL, 8.26 mmol) and N-[(dimethylamino)-1H-1,2,3-triazolo-[4,5-b]pyridin-1-ylmethylene]-N-methylmethanaminiumhexafluorophosphate N-oxide (HATU, 1.57 g, 4.1 mmol). The mixture was stirred for 2 hours at room temperature and then purified by flash chromatography (silica gel) to provide the desired material. LCMS-ESI+ (m/z): [M+H]+ calcd for C$_{15}$H$_{17}$BrFN$_2$O$_3$: 372.2; found: 372.6.

Step 7: Preparation of 2-(((3R,4S)-3-fluoro-1-((S)-2-hydroxypropanoyl)piperidin-4-yl)oxy)-5-(4,4,5,5-tetramethyl-1,3,2-dioxaborolan-2-yl)benzonitrile:

To 5-bromo-2-(((3R,4S)-3-fluoro-1-((S)-2-hydroxypropanoyl)piperidin-4-yl)oxy)benzonitrile (0.596 g, 1.6 mmol) in 1,4-Dioxane (9 mL) was added bis(pinacolato)diboron (0.61 g, 2.4 mmol), Potassium acetate (0.47 g, 4.8 mmol), and Pd(dppf)Cl$_2$ (0.13 g, 0.16 mmol). The reaction was heated to 110° C. for 1 h. The reaction mixture was filtered through a pad of Celite diatomaceous earth. The filtrate was concentrated to dryness under reduced pressure. The crude residue was purified by flash chromatography (silica gel) to provide the desired material. LCMS-ESI+ (m/z): [M+H]+ calcd for $C_{21}H_{29}BFN_2O_5$: 419.2; found: 419.1.

Step 8: Preparation of 2-(((3R,4S)-3-fluoro-1-((S)-2-hydroxypropanoyl)piperidin-4-yl)oxy)-5-(4-((6-(2-hydroxypropan-2-yl)pyridin-3-yl)amino)-1,3,5-triazin-2-yl)benzonitrile:

A suspension of 2-(5-((4-chloro-1,3,5-triazin-2-yl)amino)pyridin-2-yl)propan-2-ol (90 mg, 0.34 mmol) and 2-(((3R,4S)-3-fluoro-1-((S)-2-hydroxypropanoyl)piperidin-4-yl)oxy)-5-(4,4,5,5-tetramethyl-1,3,2-dioxaborolan-2-yl)benzonitrile (198 mg, 0.47 mmol) in 1,2-Dimethoxyethane (4 mL) was treated with 2M sodium carbonate solution (0.67 mL, 1.36 mmol) and Tetrakis(triphenylphosphine)palladium (39 mg, 0.034 mmol). The mixture was heated in a microwave reactor for 30 minutes at 130° C. The cooled reaction mixture was quenched with water and extracted with dichloromethane for three times. The combined extracts were washed once with saturated aqueous sodium chloride solution, dried over anhydrous sodium sulfate, filtered, and concentrated under reduced pressure. The crude residue was purified by flash chromatography (silica gel) to give the desired product as off-white solid. LCMS-ESI+ (m/z): [M+H]+ calcd for $C_{26}H_{29}FN_7O_4$: 522.5; found: 522.2. 1H NMR (300 MHz, DMSO-d6) δ 10.46 (s, 1H), 8.83 (s, 1H), 8.89-8.70 (br, 1H), 8.59 (m, 2H), 8.13 (m, 2H), 7.66 (m, 1H), 5.18 (m, 4H), 4.51 (m, 3H), 3.71 (m, 1H), 3.28 (m, 1H), 1.99 (m, 2H), 1.43 (s, 6H), 1.20 (dd, J=6.3, 2.4 Hz, 3H).

Example 383

2-(((3R,4S)-3-fluoro-1-((S)-2-hydroxypropanoyl)piperidin-4-yl)oxy)-5-(4-((4-((R)-3-(hydroxymethyl)morpholino)phenyl)amino)-1,3,5-triazin-2-yl)benzonitrile

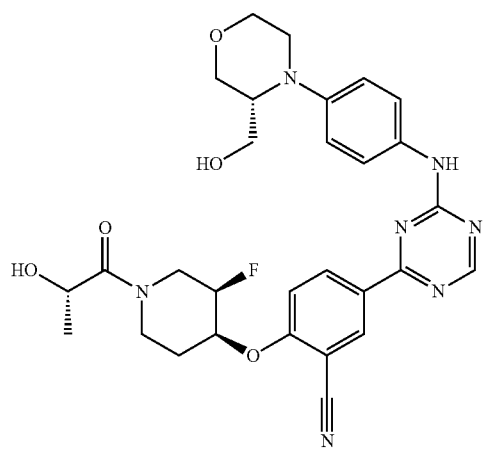 [SMILES: C[C@H](O)C(=O)N1CC[C@H](Oc2ccc(-c3ncnc(Nc4ccc(N5CCOC[C@H]5CO)cc4)n3)cc2C#N)[C@H](F)C1]

Step 1: Preparation of (R)-(4-(4-nitrophenyl)morpholin-3-yl)methanol:

A mixture of 4-Fluoronitrobenzene (0.69 mL, 6.5 mmol), (R)-morpholin-3-ylmethanol hydrochloride (1.99 g, 13 mmol), and potassium carbonate (3.64 g, 26 mmol) in N,N-dimethylformamide (15 mL) was stirred at 100° C. for 15 hours. After cooling to room temperature, the mixture was partitioned between ethyl acetate and water. The mixture was extracted three times with ethyl acetate The combined extracts were washed once with saturated aqueous sodium chloride solution, dried over anhydrous sodium sulfate, filtered, and concentrated under reduced pressure. The crude residue was purified by flash chromatography (silica gel) to provide the desired material. LCMS-ESI+ (m/z): [M+H]+ calcd for $C_{11}H_{15}N_2O_4$: 239.2; found: 239.1.

Step 2: Preparation of (R)-(4-(4-aminophenyl)morpholin-3-yl)methanol: In a Parr bottle, A mixture of (R)-(4-(4-nitrophenyl)morpholin-3-yl)methanol (0.77 g, 3 mmol) in ethanol (40 mL.) was treated with 10% palladium on charcoal (150 mg). The bottle was placed on Parr-shaker under an atmosphere of hydrogen gas at 35-40 PSI and shake for 30 minutes. The catalyst was removed by filtration through a pad of Celite diatomaceous earth. The filtrate was concentrated to dryness under reduced pressure to provide the desired material. LCMS-ESI+ (m/z): [M+H]+ calcd for $C_{11}H_{17}N_2O_2$: 209.2; found: 209.1.

Step 3: Preparation of (R)-(4-(4-((4-chloro-1,3,5-triazin-2-yl)amino)phenyl)morpholin-3-yl)methanol:

To a solution of 2,4-dichloro-1,3,5-triazine (252 mg, 1.68 mmol) in dichloromethane (6 mL) at 0° C., (R)-(4-(4-aminophenyl)morpholin-3-yl)methanol (350 mg, 1.68 mmol) in dichloromethane (10 mL) was added drop wise, followed by N,N-Diisopropylethylamine (0.44 mL, 2.6 mmol). The reaction mixture was stirred at 0° C. for 20 minutes. After this time, the reaction was quenched with saturated sodium bicarbonate solution (PH~8) and extracted with dichloromethane for three times. The combined extracts were washed once with saturated aqueous sodium chloride solution, dried over anhydrous sodium sulfate, filtered, and concentrated under reduced pressure to give the desired material. Use as crude for next step. LCMS-ESI+ (m/z): [M+H]+ calcd for $C_{14}H_{17}ClN_5O_2$: 322.7; found: 322.1.

Step 4: Preparation of 2-(((3R,4S)-3-fluoro-1-((S)-2-hydroxypropanoyl)piperidin-4-yl)oxy)-5-(4-((4-((R)-3-(hydroxymethyl)morpholino)phenyl)amino)-1,3,5-triazin-2-yl)benzonitrile:

A suspension of (R)-(4-(4-((4-chloro-1,3,5-triazin-2-yl)amino)phenyl)morpholin-3-yl)methanol (65 mg, 0.20 mmol) and 2-(((3R,4S)-3-fluoro-1-((S)-2-hydroxypropanoyl)piperidin-4-yl)oxy)-5-(4,4,5,5-tetramethyl-1,3,2-dioxaborolan-2-yl)benzonitrile (101 mg, 0.24 mmol) in 1,2-Dimethoxyethane (3 mL) was treated with 2M sodium carbonate solution (0.40 mL, 0.81 mmol) and Tetrakis(triphenylphosphine)palladium (23 mg, 0.02 mmol). The mixture was heated in a microwave reactor for 30 minutes at 130° C. The cooled reaction mixture was quenched with water and extracted with dichloromethane for three times. The combined extracts were washed once with saturated aqueous sodium chloride solution, dried over anhydrous sodium sulfate, filtered, and concentrated under reduced pressure. The crude residue was purified by flash chromatography (silica gel) to give the desired product as yellow solid. LCMS-ESI+ (m/z): [M+H]+ calcd for $C_{29}H_{33}FN_7O_5$: 578.6; found: 578.2. 1H NMR (300 MHz, DMSO-d6) δ 10.15 (m, 1H), 8.63 (s, 1H), 8.51 (m, 2H), 7.58 (m, 3H), 6.95

(m, 2H), 5.12 (m, 3H), 4.68 (s, 1H), 4.50 (m, 5H), 3.70 (m, 4H), 3.45 (m, 1H), 3.23 (m, 4H), 1.99 (m, 2H), 1.20 (dd, J=6.3, 3.0 Hz, 3H).

Example 384

2-(((3R,4S)-3-fluoro-1-(2-hydroxyacetyl)piperidin-4-yl)oxy)-5-(4-((4-((R)-3-(hydroxymethyl)morpholino)phenyl)amino)-1,3,5-triazin-2-yl)benzonitrile

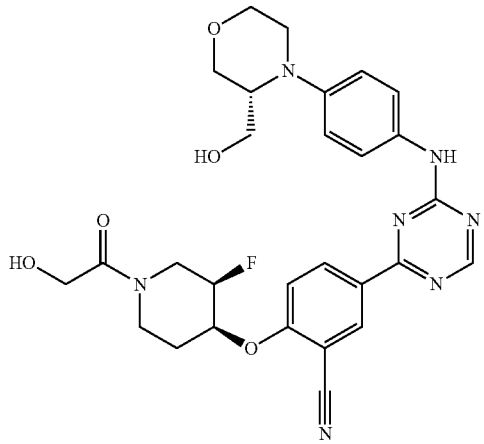 [SMILES: N#Cc1cc(-c2ncnc(Nc3ccc(N4CCOC[C@H]4CO)cc3)n2)ccc1O[C@H]1CCN(C(=O)CO)C[C@H]1F]

Step 1: Preparation of 5-bromo-2-(((3R,4S)-3-fluoro-1-(2-hydroxyacetyl)piperidin-4-yl)oxy)benzonitrile:

5-bromo-2-(((3R,4S)-3-fluoropiperidin-4-yl)oxy)benzonitrile (772 mg, 2.58 mmol) and Glycolic acid (392 mg, 5.16 mmol) were taken up as suspension in N,N-dimethylformamide (20 mL). The mixture was treated successively with N,N-diisopropylethylamine (1.35 mL, 7.75 mmol) and N-[(dimethylamino)-1H-1,2,3-triazolo-[4,5-b]pyridin-1-yl-methylene]-N-methylmethanaminiumhexafluorophosphate N-oxide (HATU, 1.96 g, 5.16 mmol). The mixture was stirred for 2 hours at room temperature and then purified by flash chromatography (silica gel) to provide the desired material. LCMS-ESI+ (m/z): [M+H]+ calcd for $C_{14}H_{15}BrFN_2O_3$: 358.1; found: 358.0.

Step 2: Preparation of 2-(((3R,4S)-3-fluoro-1-(2-hydroxyacetyl)piperidin-4-yl)oxy)-5-(4,4,5,5-tetramethyl-1,3,2-dioxaborolan-2-yl)benzonitrile:

To 5-bromo-2-(((3R,4S)-3-fluoro-1-(2-hydroxyacetyl)piperidin-4-yl)oxy)benzonitrile (0.76 g, 2.1 mmol) in 1,4-Dioxane (15 mL) was added bis(pinacolato)diboron (0.81 g, 3.2 mmol), Potassium acetate (0.63 g, 6.4 mmol), and Pd(dppf)Cl₂ (0.17 g, 0.2 mmol). The reaction was heated to 110° C. for 1 h. The reaction mixture was filtered through a pad of Celite diatomaceous earth. The filtrate was concentrated to dryness under reduced pressure. The crude residue was purified by flash chromatography (silica gel) to provide the desired material. LCMS-ESI+ (m/z): [M+H]+ calcd for $C_{20}H_{27}BFN_2O_5$: 405.2; found: 405.1.

Step 3: A suspension of (R)-(4-(4-((4-chloro-1,3,5-triazin-2-yl)amino)phenyl)morpholin-3-yl)methanol (65 mg, 0.20 mmol) and 2-(((3R,4S)-3-fluoro-1-(2-hydroxyacetyl)piperidin-4-yl)oxy)-5-(4,4,5,5-tetramethyl-1,3,2-dioxaborolan-2-yl)benzonitrile (91 mg, 0.23 mmol) in 1,2-Dimethoxyethane (3 mL) was treated with 2M sodium carbonate solution (0.40 mL, 0.81 mmol) and Tetrakis(triphenylphosphine)palladium (23 mg, 0.02 mmol). The mixture was heated in a microwave reactor for 30 minutes at 130° C. The cooled reaction mixture was quenched with water and extracted with dichloromethane for three times. The combined extracts were washed once with saturated aqueous sodium chloride solution, dried over anhydrous sodium sulfate, filtered, and concentrated under reduced pressure. The crude residue was purified by flash chromatography (silica gel) to give the desired product as yellow solid. LCMS-ESI+ (m/z): [M+H]+ calcd for $C_{28}H_{31}FN_7O_5$: 564.6; found: 564.6. 1H NMR (300 MHz, DMSO-d6) δ 10.13 (m, 1H), 8.72 (s, 1H), 8.58 (m, 2H), 7.64 (m, 3H), 6.89 (m, 2H), 5.12 (m, 2H), 4.68 (m, 2H), 4.35 (m, 6H), 3.70 (m, 5H), 3.23 (m, 4H), 2.02 (m, 2H).

Example 385

5-(4-((3,3-dimethyl-2-oxoindolin-6-yl)amino)-1,3,5-triazin-2-yl)-2-(((3R,4S)-3-fluoro-1-((S)-2-hydroxypropanoyl)piperidin-4-yl)oxy)benzonitrile

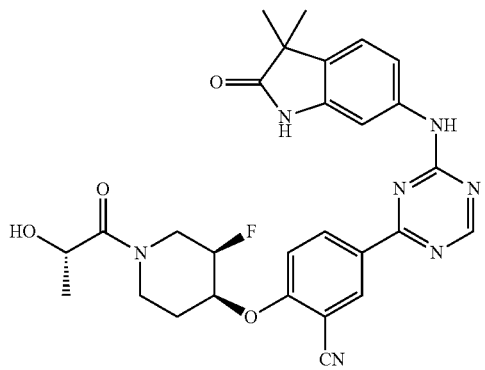 [SMILES: C[C@H](O)C(=O)N1CC[C@H](Oc2ccc(-c3ncnc(Nc4ccc5c(c4)NC(=O)C5(C)C)n3)cc2C#N)[C@H](F)C1]

Step 1: Preparation of 6-((4-chloro-1,3,5-triazin-2-yl)amino)-3,3-dimethylindolin-2-one:

To a solution of 2,4-dichloro-1,3,5-triazine (300 mg, 2 mmol) in dichloromethane (15 mL) at 0° C., (R)-(4-(4-aminophenyl)morpholin-3-yl)methanol (352 mg, 2 mmol) in dichloromethane (5 mL) was added drop wise, followed by N,N-Diisopropylethylamine (0.52 mL, 3 mmol). The reaction mixture was stirred at 0° C. for 20 minutes. After this time, the reaction was quenched with saturated sodium bicarbonate solution (PH~8) and extracted with dichloromethane for three times. The combined extracts were washed once with saturated sodium chloride solution, dried over anhydrous sodium sulfate, filtered, and concentrated under reduced pressure to give the desired material. Use as crude for next step. LCMS-ESI+ (m/z): [M+H]+ calcd for $C_{13}H_{13}ClN_5O$: 290.7; found: 290.1.

Step 2: Preparation of 5-(4-((3,3-dimethyl-2-oxoindolin-6-yl)amino)-1,3,5-triazin-2-yl)-2-(((3R,4S)-3-fluoro-1-((S)-2-hydroxypropanoyl)piperidin-4-yl)oxy)benzonitrile:

A suspension of 6-((4-chloro-1,3,5-triazin-2-yl)amino)-3,3-dimethylindolin-2-one (59 mg, 0.20 mmol) and 2-(((3R,4S)-3-fluoro-1-((S)-2-hydroxypropanoyl)piperidin-4-yl)oxy)-5-(4,4,5,5-tetramethyl-1,3,2-dioxaborolan-2-yl)benzonitrile (103 mg, 0.24 mmol) in 1,2-Dimethoxyethane (3 mL) was treated with 2M sodium carbonate solution (0.41 mL, 0.82 mmol) and Tetrakis(triphenylphosphine)palladium (24 mg, 0.02 mmol). The mixture was heated in a microwave reactor for 30 minutes at 130° C. The cooled reaction mixture was quenched with water and extracted with dichloromethane for three times. The combined extracts were washed once with saturated aqueous sodium chloride solution, dried over anhydrous sodium sulfate, filtered, and concentrated under reduced pressure. The crude residue was purified by flash chromatography (silica gel) to give the desired product as white solid. LCMS-ESI+ (m/z): [M+H]+ calcd for $C_{28}H_{29}FN_7O_4$: 546.6; found: 546.2. 1H NMR (300 MHz, DMSO-d6) δ 10.34 (m, 2H), 8.81 (.s, 1H), 8.61 (d, J=6.9 Hz, 2H), 7.64 (d, J=9.0 Hz, 1H), 7.45 (s, 1H), 7.25 (m, 2H), 5.16 (m, 3H), 4.48 (m, 2H), 3.70 (m, 1H), 3.38 (m, 1H), 3.29 (m, 1H), 1.98 (m, 2H), 1.24 (m, 9H).

Example 386

2-(((3R,4S)-3-fluoro-1-((S)-2-hydroxypropanoyl)piperidin-4-yl)oxy)-5-(4-((2-(2-hydroxypropan-2-yl)pyridin-4-yl)amino)-1,3,5-triazin-2-yl)benzonitrile

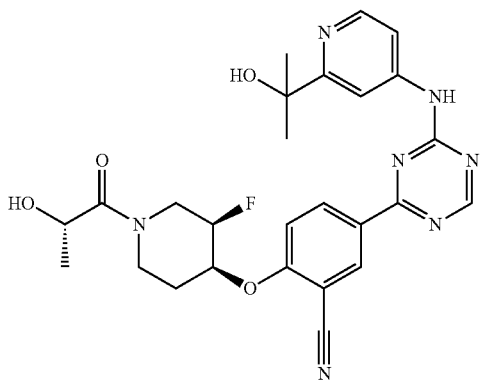 [SMILES: C[C@H](O)C(=O)N1CC[C@H](Oc2ccc(-c3ncnc(Nc4ccnc(C(C)(C)O)c4)n3)cc2C#N)[C@H](F)C1]

Step 1: Preparation of 2-(4-((4-chloro-1,3,5-triazin-2-yl)amino)pyridin-2-yl)propan-2-ol:

To a solution of 2,4-dichloro-1,3,5-triazine (390 mg, 2.6 mmol) in N,N-dimethylformamide (3 mL) at room temperature, 2-(4-aminopyridin-2-yl)propan-2-ol (304 mg, 2 mmol) in N,N-dimethylformamide (3 mL) was added drop wise and the reaction mixture was heated at 50° C. for 30 minutes. After this time, the reaction was cooled and quenched with saturated sodium bicarbonate solution (PH~8) and extracted with dichloromethane for three times. The combined extracts were washed once with saturated aqueous sodium chloride solution, dried over anhydrous sodium sulfate, filtered, and concentrated under reduced pressure. The crude residue was purified by flash chromatography (silica gel) to give the desired material. LCMS-ESI+ (m/z): [M+H]+ calcd for $C_{11}H_{13}ClN_5O$: 266.7; found: 266.1.

Step 2: Preparation of 2-(((3R,4S)-3-fluoro-1-((S)-2-hydroxypropanoyl)piperidin-4-yl)oxy)-5-(4-((2-(2-hydroxypropan-2-yl)pyridin-4-yl)amino)-1,3,5-triazin-2-yl)benzonitrile:

A suspension of 2-(4-((4-chloro-1,3,5-triazin-2-yl)amino)pyridin-2-yl)propan-2-ol (80 mg, 0.30 mmol) and 2-(((3R,4S)-3-fluoro-1-((S)-2-hydroxypropanoyl)piperidin-4-yl)oxy)-5-(4,4,5,5-tetramethyl-1,3,2-dioxaborolan-2-yl)benzonitrile (132 mg, 0.32 mmol) in 1,2-Dimethoxyethane (4 mL) was treated with 2M sodium carbonate solution (0.60 mL, 1.2 mmol) and Tetrakis(triphenylphosphine)palladium (35 mg, 0.030 mmol). The mixture was heated in a microwave reactor for 30 minutes at 130° C. The cooled reaction mixture was quenched with water and extracted with dichloromethane for three times. The combined extracts were washed once with saturated aqueous sodium chloride solution, dried over anhydrous sodium sulfate, filtered, and concentrated under reduced pressure. The crude residue was purified by flash chromatography (silica gel) to give the desired product as off-white solid. LCMS-ESI+ (m/z): [M+H]+ calcd for $C_{26}H_{29}FN_7O_4$: 522.7; found: 523.0. 1H NMR (300 MHz, DMSO-d6) δ 10.72 (s, 1H), 8.94 (s, 1H), 8.68 (m, 2H), 8.39 (d, J=5.4 Hz, 1H), 8.25 (br, 1H), 7.65 (m, 2H), 5.21 (m, 4H), 4.51 (m, 3H), 3.71 (m, 1H), 3.28 (m, 1H), 2.0 (m, 2H), 1.45 (m, 6H), 1.21 (dd, J=6.3, 3.0 Hz, 3H).

Example 387

2-(((3R,4S)-3-fluoro-1-((S)-2-hydroxypropanoyl)piperidin-4-yl)oxy)-5-(4-((4-((S)-3-(hydroxymethyl)morpholino)phenyl)amino)-1,3,5-triazin-2-yl)benzonitrile

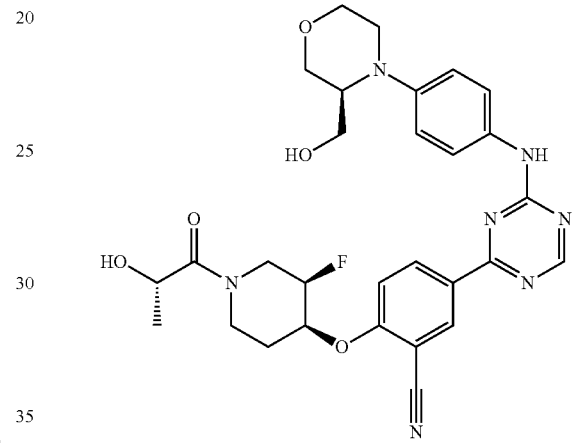

Step 1: Preparation of (S)-(4-(4-nitrophenyl)morpholin-3-yl)methanol:

This compound was prepared by the same procedure as Example 383, step 1, using (S)-morpholin-3-ylmethanol (1.00 g, 8.56 mmol), fluoronitrobenzene (0.45 ml, 4.26 mmol), and potassium carbonate (1.76 g, 15.8 mmol) in N,N-dimethylformamide (14 mL). LCMS-ESI+ (m/z): [M+H]+ calcd for $C_{11}H_{15}N_2O_4$: 239.2; found: 239.1.

Step 2: Preparation of (S)-(4-(4-aminophenyl)morpholin-3-yl)methanol:

This compound was prepared by the same procedure as Example 383, step 2, using (S)-(4-(4-nitrophenyl)morpholin-3-yl)methanol (300 mg, 1.26 mmol), 10% palladium on charcoal (50 mg) in ethanol (30 mL). LCMS-ESI+ (m/z): [M+H]+ calcd for $C_{11}H_{17}N_2O_2$: 209.2; found: 209.1.

Step 3: Preparation of (S)-(4-(4-((4-chloro-1,3,5-triazin-2-yl)amino)phenyl)morpholin-3-yl)methanol:

This compound was prepared by the same procedure as Example 383, step 3, using (S)-(4-(4-aminophenyl)morpholin-3-yl)methanol (230 mg, 1.1 mmol), 2,4-dichloro-1,3,5-triazine (165 mg, 1.1 mmol) and N,N-Diisopropylethylamine (0.29 mL, 2.0 mmol) in dichloromethane (10 mL). LCMS-ESI+ (m/z): [M+H]+ calcd for $C_{14}H_{17}ClN_5O_2$: 322.7; found: 322.1.

Step 4: Preparation of 2-(((3R,4S)-3-fluoro-1-((S)-2-hydroxypropanoyl)piperidin-4-yl)oxy)-5-(4-((4-((S)-3-(hydroxymethyl)morpholino)phenyl)amino)-1,3,5-triazin-2-yl)-benzonitrile:

This compound was prepared by the same procedure as Example 383, step 4, using (S)-(4-(4-((4-chloro-1,3,5-triazin-2-yl)amino)phenyl)morpholin-3-yl)methanol (354 mg, 0.88 mmol), 2-(((3R,4S)-3-fluoro-1-((S)-2-hydroxypropanoyl)piperidin-4-yl)oxy)-5-(4,4,5,5-tetramethyl-1,3,2-dioxaborolan-2-yl)benzonitrile (368 mg, 0.88 mmol), 2M sodium carbonate solution (1.76 mL, 3.52 mmol) and Tetrakis(triphenylphosphine)palladium (102 mg, 0.088 mmol) in 1,2-Dimethoxyethane (9 mL). LCMS-ESI+ (m/z): [M+H]+ calcd for $C_{29}H_{33}FN_7O_5$: 578.6; found: 578.2. 1H NMR (300 MHz, DMSO-d6) δ 10.19 (m, 1H), 8.73 (s, 1H), 8.54 (m, 2H), 7.64 (m, 3H), 6.90 (m, 2H), 5.07 (m, 3H), 4.70 (m, 2H), 4.04 (m, 3H), 3.57 (m, 4H), 3.22 (m, 6H), 1.99 (m, 2H), 1.20 (dd, J=6.3, 3.3 Hz, 3H).

Example 388

2-(((3R,4S)-3-fluoro-1-(2-hydroxyacetyl)piperidin-4-yl)oxy)-5-(4-((6-(2-hydroxypropan-2-yl)pyridin-3-yl)amino)-1,3,5-triazin-2-yl)benzonitrile

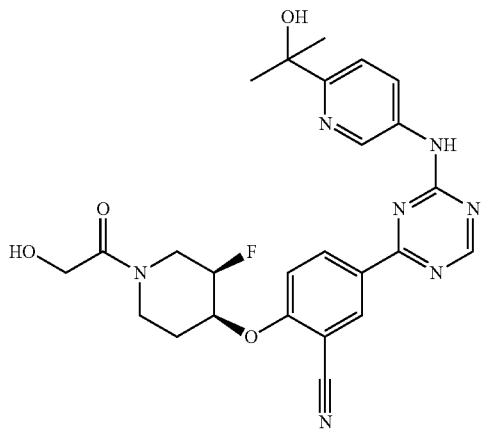 [SMILES: CC(C)(O)c1ccc(Nc2ncnc(-c3ccc(O[C@H]4CCN(C(=O)CO)C[C@H]4F)c(C#N)c3)n2)cn1]

A suspension of 2-(5-((4-chloro-1,3,5-triazin-2-yl)amino)pyridin-2-yl)propan-2-ol (100 mg, 0.38 mmol) and 2-(((3R,4S)-3-fluoro-1-(2-hydroxyacetyl)piperidin-4-yl)oxy)-5-(4,4,5,5-tetramethyl-1,3,2-dioxaborolan-2-yl)benzonitrile (167 mg, 0.41 mmol) in 1,2-Dimethoxyethane (4 mL) was treated with 2M sodium carbonate solution (0.75 mL, 1.50 mmol) and Tetrakis(triphenylphosphine)palladium (43 mg, 0.038 mmol). The mixture was heated in a microwave reactor for 30 minutes at 130° C. The cooled reaction mixture was quenched with water and extracted with dichloromethane for three times. The combined extracts were washed once with saturated aqueous sodium chloride solution, dried over anhydrous sodium sulfate, filtered, and concentrated under reduced pressure. The crude residue was purified by flash chromatography (silica gel) to give the desired product. LCMS-ESI+ (m/z): [M+H]+ calcd for $C_{25}H_{27}FN_7O_4$: 508.5; found: 508.2. 1H NMR (300 MHz, DMSO-d6) δ 10.47 (s, 1H), 8.83 (m, 2H), 8.59 (d, J=7.8 Hz, 2H), 8.10 (m, 1H), 7.67 (d, J=9.3 Hz, 2H), 5.19 (m, 4H), 4.42 (m, 3H), 3.87 (m, 1H), 3.30 (m, 2H), 1.99 (m, 2H), 1.52 (m, 6H).

Example 389

2-(((3R,4S)-3-fluoro-1-((S)-2-hydroxypropanoyl)piperidin-4-yl)oxy)-5-(4-((3-methoxy-4-(4-(oxetan-3-yl)piperazin-1-yl)phenyl)amino)-1,3,5-triazin-2-yl)benzonitrile

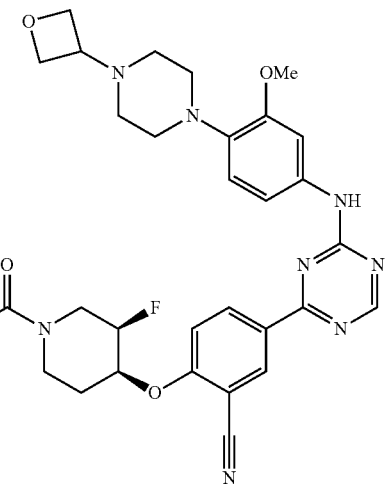

Step 1: Preparation of 4-chloro-N-(3-methoxy-4-(4-(oxetan-3-yl)piperazin-1-yl)phenyl)-1,3,5-triazin-2-amine:

To a solution of 2,4-dichloro-1,3,5-triazine (150 mg, 1 mmol) in dichloromethane (4 mL) at 0° C., 3-methoxy-4-(4-(oxetan-3-yl)piperazin-1-yl)aniline (263 mg, 1 mmol) in dichloromethane (6 mL) was added drop wise, followed by N,N-Diisopropylethylamine (0.26 mL, 1.5 mmol). The reaction mixture was stirred at 0° C. for 10 minutes, then at room temperature for 1.5 hr. After this time, the reaction was quenched with saturated sodium bicarbonate solution (PH~8) and extracted with dichloromethane for three times. The combined extracts were washed once with saturated aqueous sodium chloride solution, dried over anhydrous sodium sulfate, filtered, and concentrated under reduced pressure to give the desired material. Use as crude for next step. LCMS-ESI+ (m/z): [M+H]+ calcd for $C_{17}H_{22}ClN_6O_2$: 377.7; found: 377.1.

Step 2: Preparation of 2-(((3R,4S)-3-fluoro-1-((S)-2-hydroxypropanoyl)piperidin-4-yl)oxy)-5-(4-((3-methoxy-4-(4-(oxetan-3-yl)piperazin-1-yl)phenyl)amino)-1,3,5-triazin-2-yl)benzonitrile:

A suspension of 4-chloro-N-(3-methoxy-4-(4-(oxetan-3-yl)piperazin-1-yl)phenyl)-1,3,5-triazin-2-amine (73 mg, 0.194 mmol) and 2-(((3R,4S)-3-fluoro-1-((S)-2-hydroxypropanoyl)piperidin-4-yl)oxy)-5-(4,4,5,5-tetramethyl-1,3,2-dioxaborolan-2-yl)benzonitrile (97 mg, 0.233 mmol) in 1,2-Dimethoxyethane (2 mL) was treated with 2M sodium carbonate solution (0.39 mL, 0.78 mmol) and Tetrakis(triphenylphosphine)palladium (22 mg, 0.019 mmol). The mixture was heated in a microwave reactor for 25 minutes at 135° C. The cooled reaction mixture was quenched with water and extracted with dichloromethane for three times.

The combined extracts were washed once with saturated aqueous sodium chloride solution, dried over anhydrous sodium sulfate, filtered, and concentrated under reduced pressure. The crude residue was purified by flash chromatography (silica gel) to give the desired product. LCMS-ESI+ (m/z): [M+H]+ calcd for $C_{32}H_{38}FN_8O_5$: 633.7; found: 633.9. 1H NMR (300 MHz, DMSO-d6) δ 10.23 (m, 1H), 8.77 (s, 1H), 8.61 (m, 2H), 7.65 (d, J=9.3 Hz, 2H), 7.37 (m, 1H), 6.90 (m, 1H), 5.18 (m, 3H), 4.56 (m, 2H), 4.47 (m, 3H), 4.41 (m, 2H), 3.84 (m, 3H), 3.47 (m, 1H), 3.31 (m, 1H), 2.96 (br, 4H), 2.39 (br, 4H), 1.99 (m, 2H), 1.20 (dd, J=6.3, 2.7 Hz, 3H).

Example 390

2-(((3R,4S)-1-(3-aminoisonicotinoyl)-3-fluoropiperidin-4-yl)oxy)-5-(4-((4-(4-(oxetan-3-yl)piperazin-1-yl)phenyl)amino)-1,3,5-triazin-2-yl)benzonitrile

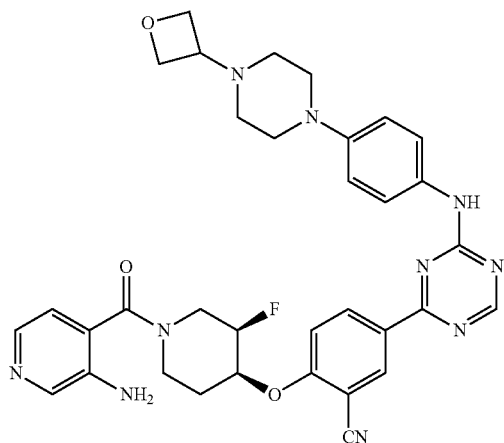 [SMILES: N#Cc1cc(-c2ncnc(Nc3ccc(N4CCN(C5COC5)CC4)cc3)n2)ccc1O[C@H]1CCN(C(=O)c2ccncc2N)C[C@H]1F]

2-(((3R,4S)-3-fluoropiperidin-4-yl)oxy)-5-(4-((4-(4-(oxetan-3-yl)piperazin-1-yl)phenyl)amino)-1,3,5-triazin-2-yl)benzonitrile (50 mg, 0.094 mmol) and 3-aminoisonicotinic acid (26 mg, 0.19 mmol) were taken up as suspension in dichloromethane (1 mL) and N,N-dimethylformamide (1 mL). The mixture was treated successively with N,N-diisopropylethylamine (0.05 mL, 0.28 mmol) and N-[(dimethylamino)-1H-1,2,3-triazolo-[4,5-b]pyridin-1-ylmethylene]-N-methylmethanaminiumhexafluorophosphate N-oxide (HATU, 72 mg, 0.19 mmol). The mixture was stirred for 25 minutes at room temperature and then purified by flash chromatography (silica gel) to provide 2-(((3R,4S)-1-(3-aminoisonicotinoyl)-3-fluoropiperidin-4-yl)oxy)-5-(4-((4-(4-(oxetan-3-yl)piperazin-1-yl)phenyl)amino)-1,3,5-triazin-2-yl)benzonitrile. LCMS-ESI+ (m/z): [M+H]+ calcd for $C_{34}H_{36}FN_{10}O_3$: 651.7; found: 651.3.

Example 391

2-(((3R,4S)-1-(4-amino-1H-pyrazole-5-carbonyl)-3-fluoropiperidin-4-yl)oxy)-5-(4-((4-(4-(oxetan-3-yl)piperazin-1-yl)phenyl)amino)-1,3,5-triazin-2-yl)benzonitrile

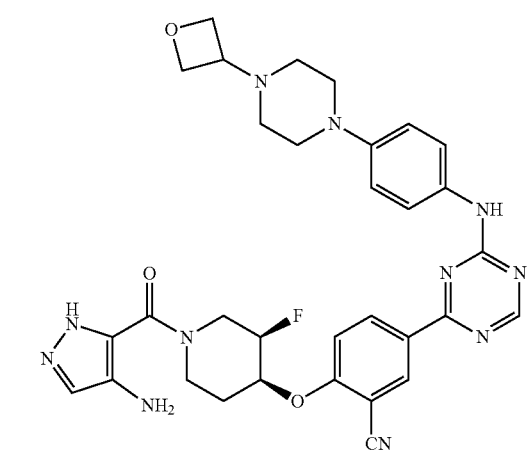 [SMILES: N#Cc1cc(-c2ncnc(Nc3ccc(N4CCN(C5COC5)CC4)cc3)n2)ccc1O[C@H]1CCN(C(=O)c2[nH]ncc2N)C[C@H]1F]

2-(((3R,4S)-3-fluoropiperidin-4-yl)oxy)-5-(4-((4-(4-(oxetan-3-yl)piperazin-1-yl)phenyl)amino)-1,3,5-triazin-2-yl)benzonitrile (50 mg, 0.094 mmol) and 4-amino-1H-pyrazole-5-carboxylic acid (24 mg, 0.19 mmol) were taken up as suspension in dichloromethane (1 mL) and N,N-dimethylformamide (1mL). The mixture was treated successively with N,N-diisopropylethylamine (0.05 mL, 0.28 mmol) and N-[(dimethylamino)-1H-1,2,3-triazolo-[4,5-b]pyridin-1-ylmethylene]-N-methylmethanaminiumhexafluorophosphate N-oxide (HATU, 72 mg, 0.19 mmol). The mixture was stirred for 4 hr at room temperature and then purified by flash chromatography (silica gel) to provide 2-(((3R,4S)-1-(3-aminoisonicotinoyl)-3-fluoropiperidin-4-yl)oxy)-5-(4-((4-(4-(oxetan-3-yl)piperazin-1-yl)phenyl)amino)-1,3,5-triazin-2-yl)benzonitrile. LCMS-ESI+ (m/z): [M+H]+ calcd for $C_{32}H_{35}FN_{11}O_3$: 640.7; found: 640.1. 1H NMR (300 MHz, DMSO-d6) δ 12.6 (s, 1H), 10.18 (m, 1H), 8.73 (s, 1H), 8.59 (m, 2H), 7.66 (m, 3H), 7.14 (s, 1H), 6.99 (m, 2H), 5.15 (m, 3H), 4.60 (m, 4H), 4.47 (m, 2H), 4.43-3.60 (br, 1H), 3.45 (m, 1H), 3.31 (m, 1H), 3.14 (m, 4H), 2.92 (br, 1H), 2.41 (m, 4H), 2.01 (m, 2H).

Example 392

2-(((3R,4S)-3-fluoro-1-(2-hydroxyacetyl)piperidin-4-yl)oxy)-5-(4-((3-methoxy-4-(4-(oxetan-3-yl)piperazin-1-yl)phenyl)amino)-1,3,5-triazin-2-yl)benzonitrile

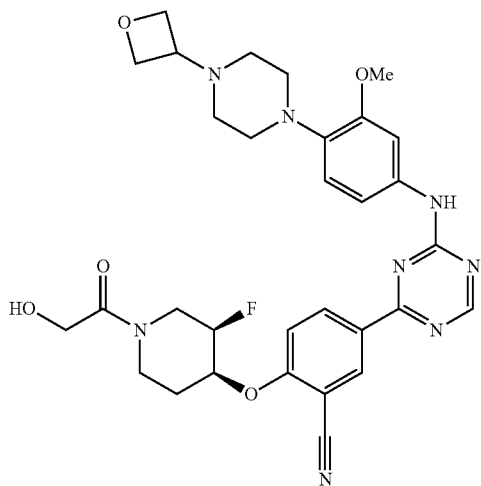 [SMILES: COc1cc(Nc2ncnc(-c3ccc(O[C@H]4CCN(C(=O)CO)C[C@H]4F)c(C#N)c3)n2)ccc1N1CCN(C2COC2)CC1]

A suspension of 4-chloro-N-(3-methoxy-4-(4-(oxetan-3-yl)piperazin-1-yl)phenyl)-1,3,5-triazin-2-amine (73 mg, 0.194 mmol) and 2-(((3R,4S)-3-fluoro-1-(2-hydroxyacetyl)piperidin-4-yl)oxy)-5-(4,4,5,5-tetramethyl-1,3,2-dioxaborolan-2-yl)benzonitrile (86 mg, 0.213 mmol) in 1,2-Dimethoxyethane (2 mL) was treated with 2M sodium carbonate solution (0.39 mL, 0.78 mmol) and Tetrakis(triphenylphosphine)palladium (22 mg, 0.019 mmol). The mixture was heated in a microwave reactor for 20 minutes at 135° C. The cooled reaction mixture was quenched with water and extracted with dichloromethane for three times. The combined extracts were washed once with saturated aqueous sodium chloride solution, dried over anhydrous sodium sulfate, filtered, and concentrated under reduced pressure. The crude residue was purified by flash chromatography (silica gel) to give the desired. LCMS-ESI$^+$ (m/z): [M+H]$^+$ calcd for $C_{31}H_{36}FN_8O_5$: 619.7; found: 619.2. 1H NMR (300 MHz, DMSO-d6) δ 10.24 (m, 1H), 8.77 (s, 1H), 8.61 (m, 2H), 7.64 (d, J=8.7 Hz, 2H), 7.38-7.15 (br, 1H), 6.90 (m, 1H), 5.12 (m, 2H), 4.67 (m, 1H), 4.56 (m, 2H), 4.47 (m, 2H), 3.84 (m, 3H), 4.41-4.00 (m, 2H), 4.00-3.50 (m, 4H), 3.47 (m, 1H), 3.28-3.10 (br, 1H), 2.96 (br, 4H), 2.85-2.50 (br, 1H), 2.39 (br, 1H), 1.99 (m, 2H).

Example 393

5-(4-((3-(difluoromethoxy)-4-(4-(oxetan-3-yl)piperazin-1-yl)phenyl)amino)-1,3,5-triazin-2-yl)-2-(((3R,4S)-3-fluoro-1-(2-hydroxyacetyl)piperidin-4-yl)oxy)benzonitrile

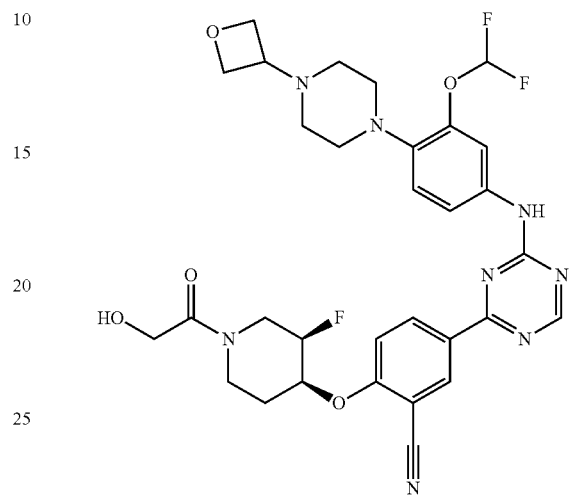

Step 1: Preparation of 1-(2-(difluoromethoxy)-4-nitrophenyl)-4-(oxetan-3-yl)piperazine:

A mixture of 2-(difluoromethoxy)-1-fluoro-4-nitrobenzene (1 g, 4.83 mmol), 1-(oxetan-3-yl)piperazine (1.43 g, 10 mmol), and potassium carbonate (2.66 g, 19 mmol) in N,N-dimethylformamide (30 mL) was stirred at 100° C. for 2 hours. After cooling to room temperature, the mixture was quenched with water and sonicated. The resulting solid was filtered and dried under vacuum to provide the desired material. LCMS-ESI$^+$ (m/z): [M+H]$^+$ calcd for $C_{14}H_{18}F_2N_3O_4$: 330.3; found: 330.5.

Step 2: Preparation of 3-(difluoromethoxy)-4-(4-(oxetan-3-yl)piperazin-1-yl)aniline:

In a Parr bottle, A mixture of 1-(2-(difluoromethoxy)-4-nitrophenyl)-4-(oxetan-3-yl)piperazine (1.76 g, 4.8 mmol) in ethanol (60 mL) and ethyl acetate (25 mL) was treated with 10% palladium on charcoal (170 mg). The bottle was placed on Parr-shaker under an atmosphere of hydrogen gas at 35-40 PSI and shake for 40 minutes. The catalyst was removed by filtration through a pad of Celite diatomaceous earth. The filtrate was concentrated to dryness under reduced pressure to provide the desired material. LCMS-ESI$^+$ (m/z): [M+H]$^+$ calcd for $C_{14}H_{20}F_2N_3O_2$: 300.3; found: 300.1.

Step 3: Preparation of 4-chloro-N-(3-(difluoromethoxy)-4-(4-(oxetan-3-yl)piperazin-1-yl)phenyl)-1,3,5-triazin-2-amine:

To a solution of 2,4-dichloro-1,3,5-triazine (300 mg, 2 mmol) in dichloromethane (10 mL) at 0° C., 3-(difluoromethoxy)-4-(4-(oxetan-3-yl)piperazin-1-yl)aniline (623 mg, 2 mmol) in dichloromethane (5 mL) was added drop wise, followed by N,N-Diisopropylethylamine (0.52 mL, 3 mmol). The reaction mixture was stirred at 0° C. for 1 hr. After this time, the reaction was quenched with saturated sodium bicarbonate solution (PH~8) and extracted with dichloromethane for three times. The combined extracts were washed once with saturated aqueous sodium chloride solution, dried over anhydrous sodium sulfate, filtered, and concentrated under reduced pressure to give the desired material. Use as crude for next step. LCMS-ESI+ (m/z): [M+H]+ calcd for $C_{17}H_{20}ClF_2N_6O_2$: 413.8; found: 413.6.

Step 4: Preparation of 5-(4-((3-(difluoromethoxy)-4-(4-(oxetan-3-yl)piperazin-1-yl)phenyl)amino)-1,3,5-triazin-2-yl)-2-(((3R,4S)-3-fluoro-1-(2-hydroxyacetyl)piperidin-4-yl)oxy)benzonitrile:

A suspension of 4-chloro-N-(3-(difluoromethoxy)-4-(4-(oxetan-3-yl)piperazin-1-yl)phenyl)-1,3,5-triazin-2-amine (93 mg, 0.194 mmol) and 2-(((3R,4S)-3-fluoro-1-(2-hydroxyacetyl)piperidin-4-yl)oxy)-5-(4,4,5,5-tetramethyl-1,3,2-dioxaborolan-2-yl)benzonitrile (86 mg, 0.213 mmol) in 1,2-Dimethoxyethane (2 mL) was treated with 2M sodium carbonate solution (0.39 mL, 0.78 mmol) and Tetrakis(triphenylphosphine)palladium (23 mg, 0.02 mmol). The mixture was heated in a microwave reactor for 20 minutes at 135° C. The cooled reaction mixture was quenched with water and extracted with dichloromethane for three times. The combined extracts were washed once with saturated aqueous sodium chloride solution, dried over anhydrous sodium sulfate, filtered, and concentrated under reduced pressure. The crude residue was purified by flash chromatography (silica gel) to give the desired product. LCMS-ESI+ (m/z): [M+H]+ calcd for $C_{31}H_{34}F_3N_8O_5$: 655.6; found: 655.3. 1H NMR (300 MHz, DMSO-d6) δ 10.40 (m, 1H), 8.81 (s, 1H), 8.59 (m, 2H), 7.83-7.25 (m, 3H), 7.12 (d, J=8.7 Hz, 1H), 5.12 (m, 2H), 4.67 (m, 1H), 4.57 (m, 2H), 4.46 (m, 2H), 4.40-3.53 (m, 3H), 3.47 (m, 1H), 3.28 (m, 1H), 2.98 (m, 4H), 2.40 (m, 4H), 1.98 (m, 2H).

Example 394

2-(((3R,4S)-3-fluoro-1-(2-hydroxyacetyl)piperidin-4-yl)oxy)-5-(4-((3-methyl-4-(4-(oxetan-3-yl)piperazin-1-yl)phenyl)amino)-1,3,5-triazin-2-yl)benzonitrile

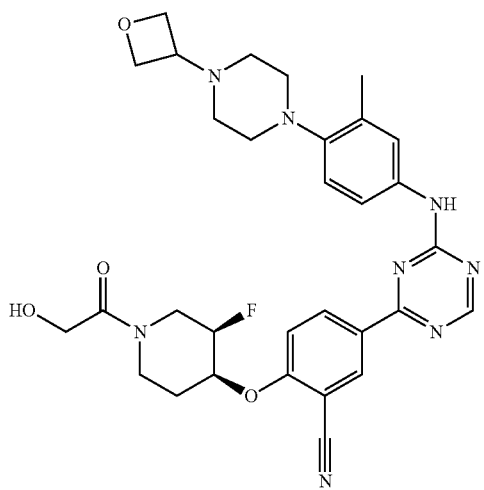 [SMILES: Cc1cc(Nc2ncnc(-c3ccc(O[C@H]4CCN(C(=O)CO)C[C@H]4F)c(C#N)c3)n2)ccc1N1CCN(C2COC2)CC1]

Step 1: Preparation of 1-(2-methyl-4-nitrophenyl)-4-(oxetan-3-yl)piperazine:

A mixture of 1-fluoro-2-methyl-4-nitrobenzene (1.16 mL, 10 mmol), 1-(oxetan-3-yl)piperazine (1.42 g, 10 mmol), and potassium carbonate (5.5 g, 40 mmol) in N,N-dimethylformamide (60 mL) was stirred at 100° C. for overnight. After cooling to room temperature, the mixture was partitioned between ethyl acetate and water. The mixture was extracted three times with ethyl acetate. The combined extracts were washed once with saturated aqueous sodium chloride solution, dried over anhydrous sodium sulfate, filtered, and concentrated under reduced pressure. The crude residue was purified by flash chromatography (silica gel) to provide the desired material. LCMS-ESI+ (m/z): [M+H]+ calcd for $C_{14}H_{20}N_3O_3$: 278.3; found: 278.6.

Step 2: Preparation of 3-methyl-4-(4-(oxetan-3-yl)piperazin-1-yl)aniline:

In a Parr bottle, A mixture of 1-(2-methyl-4-nitrophenyl)-4-(oxetan-3-yl)piperazine (2 g, 7.2 mmol) in ethanol (60 mL) and ethyl acetate (20 mL) was treated with 10% palladium on charcoal (260 mg). The bottle was placed on Parr-shaker under an atmosphere of hydrogen gas at 35-40 PSI and shake for 40 minutes. The catalyst was removed by filtration through a pad of Celite diatomaceous earth. The filtrate was concentrated to dryness under reduced pressure to provide the desired material. LCMS-ESI+ (m/z): [M+H]+ calcd for $C_{14}H_{22}N_3O$: 248.3; found: 248.1.

Step 3: Preparation of 4-chloro-N-(3-methyl-4-(4-(oxetan-3-yl)piperazin-1-yl)phenyl)-1,3,5-triazin-2-amine:

To a solution of 2,4-dichloro-1,3,5-triazine (300 mg, 2 mmol) in dichloromethane (10 mL) at 0° C., 3-methyl-4-(4-(oxetan-3-yl)piperazin-1-yl)aniline (515 mg, 2 mmol) in dichloromethane (4 mL) was added drop wise, followed by N,N-Diisopropylethylamine (0.52 mL, 3 mmol). The reaction mixture was stirred at 0° C. for 30 minutes. After this time, the reaction was quenched with saturated sodium bicarbonate solution (pH~8) and extracted with dichloromethane for three times. The combined extracts were washed once with saturated aqueous sodium chloride solution, dried over anhydrous sodium sulfate, filtered, and concentrated under reduced pressure to give the desired material. Use as crude for next step. LCMS-ESI+ (m/z): [M+H]+ calcd for $C_{17}H_{22}Cl N_6O$: 361.8; found: 361.6.

Step 4: Preparation of 2-(((3R,4S)-3-fluoro-1-(2-hydroxyacetyl)piperidin-4-yl)oxy)-5-(4-((3-methyl-4-(4-(oxetan-3-yl)piperazin-1-yl)phenyl)amino)-1,3,5-triazin-2-yl)benzonitrile:

A suspension of 4-chloro-N-(3-methyl-4-(4-(oxetan-3-yl)piperazin-1-yl)phenyl)-1,3,5-triazin-2-amine (77 mg, 0.194 mmol) and 2-(((3R,4S)-3-fluoro-1-(2-hydroxyacetyl)piperidin-4-yl)oxy)-5-(4,4,5,5-tetramethyl-1,3,2-dioxaborolan-2-yl)benzonitrile (86 mg, 0.213 mmol) in 1,2-Dimethoxyethane (2 mL) was treated with 2M sodium carbonate solution (0.39 mL, 0.78 mmol) and Tetrakis(triphenylphosphine)palladium (23 mg, 0.02 mmol). The mixture was heated in a microwave reactor for 20 minutes at 135° C. The cooled reaction mixture was quenched with water and extracted with dichloromethane for three times. The combined extracts were washed once with saturated aqueous sodium chloride solution, dried over anhydrous sodium sulfate, filtered, and concentrated under reduced pressure. The crude residue was purified by flash chromatography (silica gel) to give the desired product. LCMS-ESI+ (m/z): [M+H]+ calcd for $C_{31}H_{36}FN_8O_4$: 603.6; found: 603.3. 1H NMR (300 MHz, DMSO-d6) δ 10.21 (m, 1H), 8.76 (s, 1H), 8.57 (m, 2H), 7.64 (m, 3H), 7.06 (d, J=8.4 Hz, 1H), 5.13 (m, 2H), 4.67 (m, 1H), 4.56 (m, 2H), 4.48 (m, 2H), 4.40-3.81 (m, 3H), 3.91 (m, 1H), 3.21 (m, 1H), 2.84 (m, 4H), 2.41 (m, 4H), 2.25 (s, 3H),1.96 (m, 2H), 1.21 (s, 1H).

Example 395

5-(4-((3-(difluoromethoxy)-4-(4-(oxetan-3-yl)piper-azin-1-yl)phenyl)amino)-1,3,5-triazin-2-yl)-(((3R,4S)-3-fluoro-1-((S)-2-hydroxypropanoyl)piperidin-4-yl)oxy)benzonitrile

Example 396

2-(((3R,4S)-3-fluoro-1-((S)-2-hydroxypropanoyl)piperidin-4-yl)oxy)-5-(4-((3-methyl-4-(4-(oxetan-3-yl)piperazin-1-yl)phenyl)amino)-1,3,5-triazin-2-yl)benzonitrile

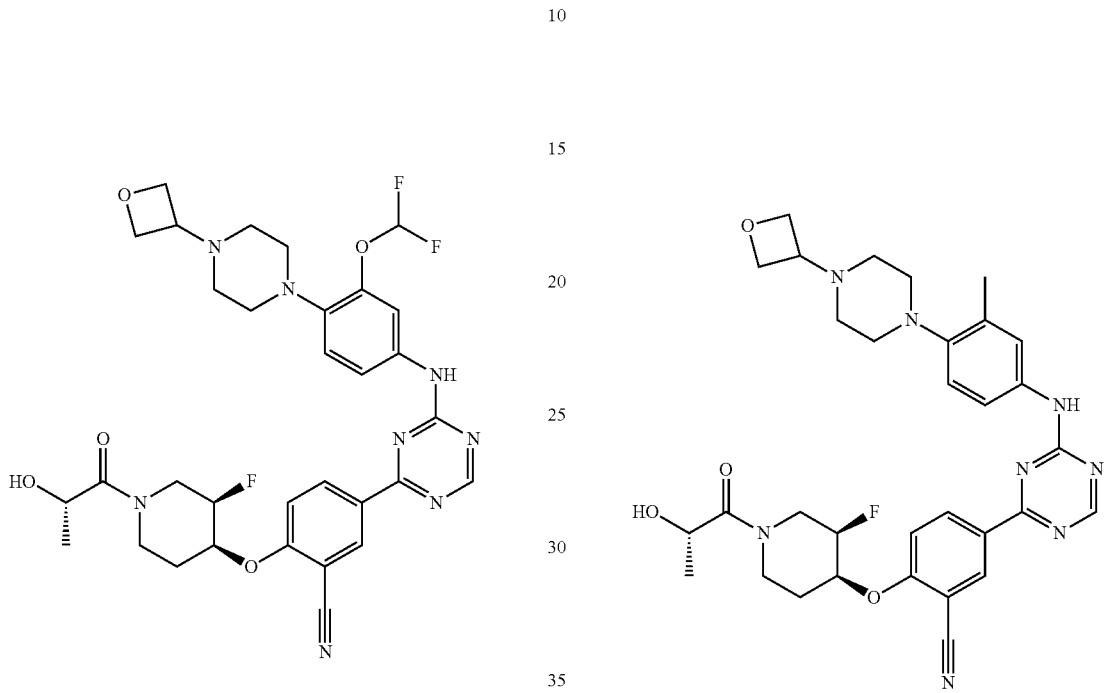

A suspension of 4-chloro-N-(3-(difluoromethoxy)-4-(4-(oxetan-3-yl)piperazin-1-yl)phenyl)-1,3,5-triazin-2-amine (216 mg, 0.45 mmol) and 2-(((3R,4S)-3-fluoro-1-((S)-2-hydroxypropanoyl)piperidin-4-yl)oxy)-5-(4,4,5,5-tetramethyl-1,3,2-dioxaborolan-2-yl)benzonitrile (188 mg, 0.45 mmol) in 1,2-Dimethoxyethane (4.5 mL) was treated with 2M sodium carbonate solution (0.90 mL, 1.8 mmol) and Tetrakis(triphenylphosphine)palladium (52 mg, 0.045 mmol). The mixture was heated in a microwave reactor for 15 minutes at 135° C. The cooled reaction mixture was quenched with water and extracted with dichloromethane for three times. The combined extracts were washed once with saturated aqueous sodium chloride solution, dried over anhydrous sodium sulfate, filtered, and concentrated under reduced pressure. The crude residue was purified by flash chromatography (silica gel) to give the desired product. LCMS-ESI+ (m/z): [M+H]+ calcd for $C_{32}H_{36}F_3N_3O_5$: 669.7; found: 669.4. 1H NMR (300 MHz, DMSO-d6) δ 10.40 (m, 1H), 8.81 (s, 1H), 8.59 (m, 2H), 7.83-7.25 (m, 3H), 7.13 (d, J=8.7 Hz, 1H), 5.12 (m, 3H), 4.57 (m, 2H), 4.47 (m, 3H), 4.40-3.80 (br, 1H), 3.75-3.50 (br, 1H), 3.47 (m, 1H), 3.21 (m, 1H), 2.98 (m, 4H), 2.40 (m, 4H), 1.97 (m, 2H), 1.20 (m, 3H).

A suspension of 4-chloro-N-(3-methyl-4-(4-(oxetan-3-yl)piperazin-1-yl)phenyl)-1,3,5-triazin-2-amine (88 mg, 0.22 mmol) and 2-(((3R,4S)-3-fluoro-1-((S)-2-hydroxypropanoyl)piperidin-4-yl)oxy)-5-(4,4,5,5-tetramethyl-1,3,2-dioxaborolan-2-yl)benzonitrile (93 mg, 0.22 mmol) in 1,2-Dimethoxyethane (2.2 mL) was treated with 2M sodium carbonate solution (0.45 mL, 0.88 mmol) and Tetrakis(triphenylphosphine)palladium (26 mg, 0.022 mmol). The mixture was heated in a microwave reactor for 20 minutes at 135° C. The cooled reaction mixture was quenched with water and extracted with dichloromethane for three times. The combined extracts were washed once with saturated aqueous sodium chloride solution, dried over anhydrous sodium sulfate, filtered, and concentrated under reduced pressure. The crude residue was purified by flash chromatography (silica gel) to give the desired product. LCMS-ESI+ (m/z): [M+H]+ calcd for $C_{32}H_{38}FN_8O_4$: 617.7; found: 617.9. 1H NMR (300 MHz, DMSO-d6) δ 10.21 (m, 1H), 8.76 (s, 1H), 8.58 (m, 2H), 7.65-7.50 (m, 3H), 7.06 (d, J=9.0 Hz, 1H), 5.02 (m, 3H), 4.57 (m, 2H), 4.48 (m, 3H), 4.40-3.80 (br, 1H), 3.75-3.50 (br, 1H), 3.47 (m, 1H), 3.20 (m, 2H), 2.87 (m, 4H), 2.41 (m, 4H), 2.25 (s, 3H), 1.97 (m, 2H), 1.20 (dd, J=6.3, 2.4 Hz, 3H).

Example 397

2-(((3R,4S)-3-fluoro-1-(2-hydroxyacetyl)piperidin-4-yl)oxy)-5-(4-((2-(2-hydroxypropan-2-yl)pyridin-4-yl)amino)-1,3,5-triazin-2-yl)benzonitrile

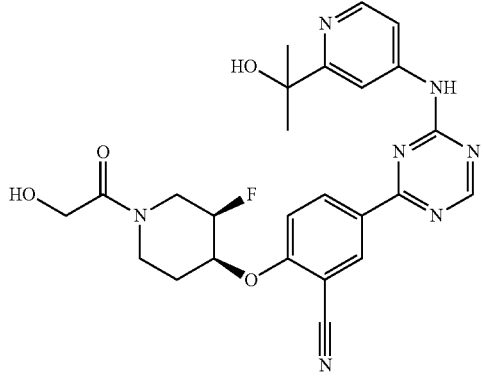 [SMILES: CC(C)(O)c1cc(Nc2ncnc(-c3ccc(O[C@H]4CCN(C(=O)CO)C[C@H]4F)c(C#N)c3)n2)ccn1]

A suspension of 2-(4-((4-chloro-1,3,5-triazin-2-yl)amino)pyridin-2-yl)propan-2-ol (141 mg, 0.53 mmol) and 2-(((3R,4S)-3-fluoro-1-(2-hydroxyacetyl)piperidin-4-yl)oxy)-5-(4,4,5,5-tetramethyl-1,3,2-dioxaborolan-2-yl)benzonitrile (217 mg, 0.54 mmol) in 1,2-Dimethoxyethane (5 mL) was treated with 2M sodium carbonate solution (1.1 mL, 2.1 mmol) and Tetrakis(triphenylphosphine)palladium (61 mg, 0.053 mmol). The mixture was heated in a microwave reactor for 20 minutes at 130° C. The cooled reaction mixture was quenched with water and extracted with dichloromethane for three times. The combined extracts were washed once with saturated aqueous sodium chloride solution, dried over anhydrous sodium sulfate, filtered, and concentrated under reduced pressure. The crude residue was purified by flash chromatography (silica gel) to give the desired product as off-white solid. LCMS-ESI+ (m/z): [M+H]+ calcd for $C_{25}H_{27}FN_7O_4$: 508.5; found: 508.2. 1H NMR (300 MHz, DMSO-d6) δ 10.71 (s, 1H), 8.94 (s, 1H), 8.66 (m, 2H), 8.39 (d, J=5.8 Hz, 1H), 8.25 (br, 1H), 7.65 (m, 2H), 5.19 (m, 3H), 4.68 (m, 1H), 4.39-3.81 (m, 4H), 3.80-3.40 (br, 1H), 3.38 (m, 1H), 3.21 (m, 1H), 1.99 (m, 2H), 1.45 (m, 6H).

Example 398

2-(((3R,4S)-1-((S)-2,3-dihydroxypropanoyl)-3-fluoropiperidin-4-yl)oxy)-5-(4-((4-(((3R,4S)-3-fluoro-1-methylpiperidin-4-yl)oxy)phenyl)amino)-1,3,5-triazin-2-yl)benzonitrile

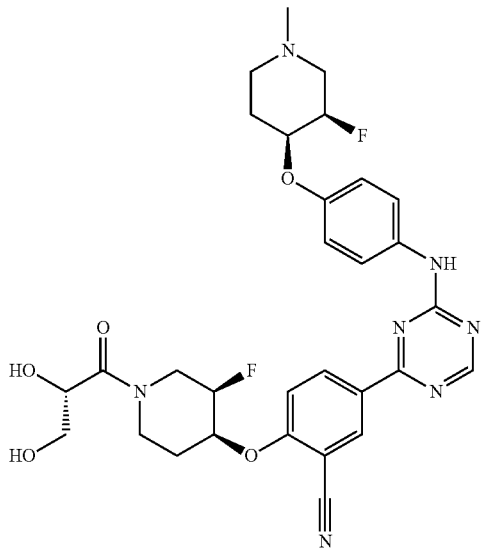 [SMILES: CN1CC[C@H](Oc2ccc(Nc3ncnc(-c4ccc(O[C@H]5CCN(C(=O)[C@@H](O)CO)C[C@H]5F)c(C#N)c4)n3)cc2)[C@H](F)C1]

A solution of 5-(4-((4-(((3R,4S)-3-fluoro-1-methylpiperidin-4-yl)oxy)phenyl)amino)-1,3,5-triazin-2-yl)-2-(((3R,4S)-3-fluoropiperidin-4-yl)oxy)benzonitrile hydrochloride (102 mg, 0.196 mmol) in 1.5 mL DMF was treated with L-glyceric acid (25 mg, 0.23 mmol), DIEA (134 uL, 0.78 mmol) and HATU (89 mg, 0.23 mmol) and stirred for 30 min at rt for 30 min. The reaction mixture was then treated with TFA (92 uL, 1.17 mmol) and diluted with 3 mL MeCN and 4 mL water. Purification by RP-HPLC provided 2-(((3R,4S)-1-((S)-2,3-dihydroxypropanoyl)-3-fluoropiperidin-4-yl)oxy)-5-(4-((4-(((3R,4S)-3-fluoro-1-methylpiperidin-4-yl)oxy)phenyl)amino)-1,3,5-triazin-2-yl)benzonitrile (16 mg) as a yellow solid. $^1$H NMR (400 MHz, DMSO-d6) δ 10.22 (d, J=18.9 Hz, 1H), 9.79 (bs, 1H), 8.73 (s, 1H), 8.62-8.40 (m, 2H), 7.70-7.49 (m, 3H), 7.03 (m, 2H), 5.08 (d, J=29.8 Hz, 3H), 4.92 (s, 1H), 4.80-4.44 (m, 2H), 4.39-4.20 (m, 2H), 4.15-3,82 (m, 2H), 3.61-3.44 (m, 5H), 3.17-3.01 (m, 2H), 2.75 (s, 3H), 2.23-1.72 (m, 4H). ES/MS 610.36 (M+H$^+$).

Example 399

(R)-2-(5-hydroxy-2-oxopiperidin-1-yl)-5-(4-((3-methoxy-4-(4-(oxetan-3-yl)piperazin-1-yl)phenyl)amino)-1,3,5-triazin-2-yl)benzonitrile

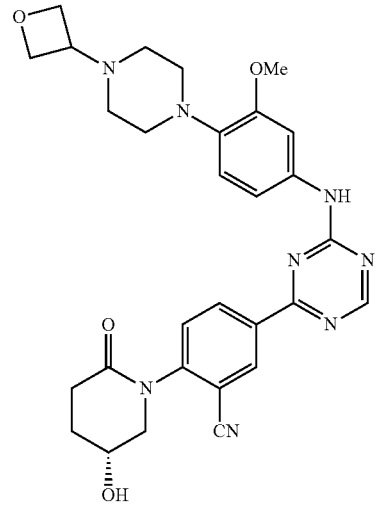 [SMILES: COc1cc(Nc2ncnc(-c3ccc(N4C[C@H](O)CCC4=O)c(C#N)c3)n2)ccc1N1CCN(C2COC2)CC1]

To a solution of 5-hydroxypiperidin-2-one (74.8 mg, 0.650 mmol) in DMF (4 mL) was added potassium t-butoxide (109 mg, 0.975 mmol) at 0° C. The reaction mixture was allowed to stir for 1 hour. To the reaction mixture was added a solution of 2-fluoro-5-(4-((3-methoxy-4-(4-(oxetan-3-yl)piperazin-1-yl)phenyl)amino)-1,3,5-triazin-2-yl)benzonitrile in DMF (2mL) at room temperature. The reaction mixture was brought to 80° C. and heated overnight. The solvent was concentrated under reduced pressure and dissolved in 0.1% TFA in 1:1 H$_2$O:MeCN and purified by preparative HPLC to afford product (R)-2-(5-hydroxy-2-oxopiperidin-1-yl)-5-(4-((3-methoxy-4-(4-(oxetan-3-yl)piperazin-1-yl)phenyl)amino)-1,3,5-triazin-2-yl)benzonitrile.
$^1$H NMR (400 MHz, DMSO-d$_6$) δ 10.36 (s, 1H), 8.83 (s, 1H), 8.64 (d, J=1.8 Hz, 1H), 8.60-8.50 (m, 1H), 7.73 (d, J=8.2 Hz, 1H), 7.49 (s, 1H), 7.18 (s, 1H), 6.97 (s, 1H), 4.76 (d, J=6.4 Hz, 4H), 4.59 (t, J=7.2 Hz, 1H), 4.48 (s, 1H), 3.88

(s, 2H), 3.22-3.13 (m, 2H), 3.09 (s, 2H), 3.03-2.94 (m, 4H), 2.94 (s, 3H), 2.00 (d, J=8.0 Hz, 2H), 1.22 (s, 2H), 0.83 (s, 1H).

LCMS-ESI$^+$ (m/z): [M+H]$^+$ calcd for $C_{29}H_{32}N_5O_4$: 557.6; found: 557.3

Example 400

2-(((3R,4S)-3-fluoro-1-(S)-2-hydroxypropanoyl)piperidin-4-yl)oxy)-5-(4-((4-(((3R,4S)-3-fluoro-1-methylpiperidin-4-yl)oxy)phenyl)amino)-1,3,5-triazin-2-yl)benzonitrile

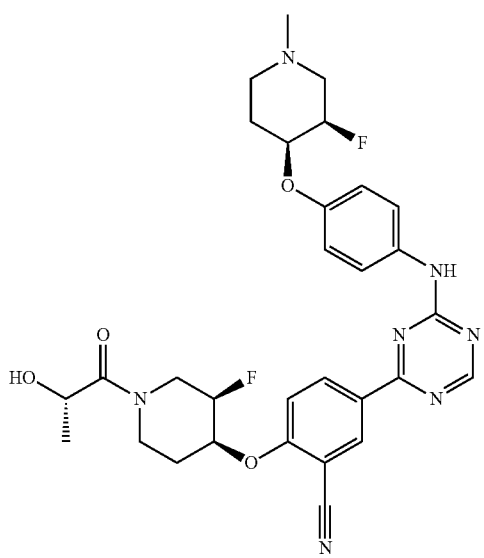 [SMILES: C[C@H](O)C(=O)N1CC[C@H](Oc2ccc(-c3ncnc(Nc4ccc(O[C@H]5CCN(C)C[C@H]5F)cc4)n3)cc2C#N)[C@H](F)C1]

A solution of 5-(4-((4-(((3R,4S)-3-fluoro-1-methylpiperidin-4-yl)oxy)phenyl)amino)-1,3,5-triazin-2-yl)-2-(((3R,4S)-3-fluoropiperidin-4-yl)oxy)benzonitrile hydrochloride (102 mg, 0.196 mmol) in 1.5 mL DMF was treated with L-lactic acid (156 mg, 1.73 mmol), DIEA (134 uL, 0.78 mmol) and HATU (89 mg, 0.23 mmol) and stirred for 30 min at rt for 30 min. The reaction mixture was then treated with TFA (92 uL, 1.17 mmol) and diluted with 3 mL MeCN and 4 mL water. Purification by RP-HPLC provided 2-(((3R,4S)-3-fluoro-1-((S)-2-hydroxypropanoyl)piperidin-4-yl)oxy)-5-(4-((4-(((3R,4S)-3-fluoro-1-methylpiperidin-4-yl)oxy)phenyl)amino)-1,3,5-triazin-2-yl)benzonitrile (32 mg) as a yellow solid. $^1$H NMR (400 MHz, DMSO-d$^6$) 10.24 (d, J=17.7 Hz, 1H), 8.77 (s, 1H), 8.66-8.47 (m, 2H), 7.73-7.57 (m, 4H), 7.06 (s, 3H), 5.20-4.95 (m, 3H), 4.67 (s, 6H), 4.54-4.11 (m, 1H), 4.10-3.87 (m, 1H), 3.69-3.58 (m, 1H), 3.42-3.08 (m, 2H), 2.15-1.78 (m, 4H), 1.19 (t, J=6.6 Hz, 3H). ES/MS 594.4 (M+H$^+$).

Example 401

2-(((3R,4S)-3-fluoro-1-((S)-2-hydroxypropanoyl)piperidin-4-yl)oxy)-5-(4-((4-(((3R,4S)-3-fluoro-1-(oxetan-3-yl)piperidin-4-yl)oxy)phenyl)amino)-1,3,5-triazin-2-yl)benzonitrile A solution of 5-(4-((4-(((3R,4S)-3-fluoro-1-(oxetan-3-yl)piperidin-4-yl)oxy)phenyl)amino)-1,3,5-triazin-2-yl)-2-(((3R,4S)-3-fluoropiperidin-4-yl)oxy)benzonitrile (260 mg, 0.46 mmol) in 4 mL DMF was treated with L-lactic acid (46 mg, 0.51 mmol), HATU (210 mg, 0.55 mmol), and DIEA (158 uL, 0.92 mmol) and stirred for 30 min at rt. The reaction mixture was then treated with TFA (142 uL, 1.84 mmol) and diluted with 3 mL MeCN and 4 mL water. Purification by RP-HPLC provided 2-(((3R,4S)-1-((S)-2,3-dihydroxypropanoyl)-3-fluoropiperidin-4-yl)oxy)-5-(4-((4-(((3R,4S)-3-fluoro-1-methylpiperidin-4-yl)oxy)phenyl)amino)-1,3,5-triazin-2-yl)benzonitrile as a yellow solid. 1H NMR (400 MHz, DMSO-d6) δ 10.24 (d, J=17.6 Hz, 1H), 8.77 (s, 1H), 8.65-8.45 (m, 2H), 7.74-7.52 (m, 4H), 7.06 (s, 2H), 5.35-4.89 (m, 3H), 4.67 (s, 6H), 4.55-4.27 (m, 2H), 4.22-3.87 (m, 2H), 3.63 (dd, J=28.7, 14.6 Hz, 1H), 3.45-3.10 (m, 2H), 2.23-1.74 (m, 4H), 1.20 (dt, J=6.4, 2.4 Hz, 4H). ES/MS 636.6 (M+H$^+$).

Example 402

2-(((3R,4S)-3-fluoro-1-(2-methoxyacetyl)piperidin-4-yl)oxy)-5-(4-((3-fluoro-4-(4-(oxetan-3-yl)piperazin-1-yl)phenyl)amino)-1,3,5-triazin-2-yl)benzonitrile

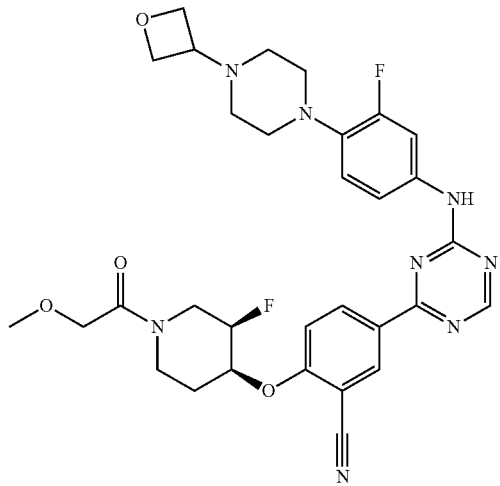

A solution 2-(((3R,4S)-3-fluoropiperidin-4-yl)oxy)-5-(4-((4-(4-(oxetan-3-yl)piperazin-1-yl)phenyl)amino)-1,3,5-triazin-2-yl)benzonitrile (100 mg, 0.18 mmol), 2-methoxyacetic acid (20 mg, 0.22 mmol) in 2 mL DMF was treated with HATU (83 mg, 0.22 mmol) and TEA (76 uL, 0.55 mmol) and stirred at room temperature for 1 h. The reaction was then diluted with water and MeCN and purified by RP-HPLC to provide 2-(((3R,4S)-3-fluoro-1-((2S,4R)-4-fluoro-5-oxopyrrolidine-2-carbonyl)piperidin-4-yl)oxy)-5-(4-((4-(4-(oxetan-3-yl)piperazin-1-yl)phenyl)amino)-1,3,5-triazin-2-yl)benzonitrile as a yellow solid. 1H NMR (400 MHz, DMSO-d6) δ 10.43 (s, 1H), 8.83 (s, 1H), 8.64-8.51 (m, 2H), 7.75 (dd, J=14.8, 2.4 Hz, 1H), 7.64 (d, J=9.4 Hz, 1H), 7.47 (s, 1H), 7.14 (t, J=9.3 Hz, 1H), 5.19-4.91 (m, 3H), 4.76 (d, J=6.4 Hz, 5H), 4.39 (m, 2H), 4.27-3.88 (m, 4H), 3.73 (d, J=13.8 Hz, 1H), 3.66-3.32 (m, 2H), 3.28 (s, 3H), 3.26-2.68 (m, 3H), 1.91 (m, 3H). ES/MS 621.4 (M+H+).

Example 403

2(((3R,4S)-3-fluoro-1-((2S,4R)-4-hydroxy-5-oxopyrrolidine-2-carbonyl)piperidin-4-yl)oxy)-5-(4-((4-(4-(oxetan-3-yl)piperazin-1-yl)phenyl)amino)-1,3,5-triazin-2-yl)benzonitrile

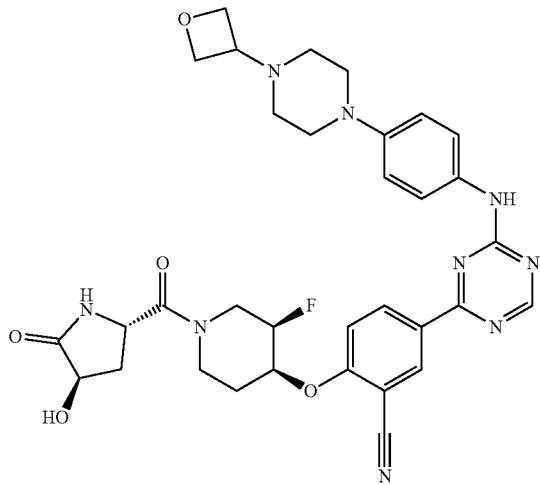 [SMILES: N#Cc1cc(-c2ncnc(Nc3ccc(N4CCN(C5COC5)CC4)cc3)n2)ccc1O[C@H]1CCN(C(=O)[C@@H]2C[C@@H](O)C(=O)N2)C[C@H]1F]

A solution 2-(((3R,4S)-3-fluoropiperidin-4-yl)oxy)-5-(4-((4-(4-(oxetan-3-yl)piperazin-1-yl)phenyl)amino)-1,3,5-triazin-2-yl)benzonitrile (100 mg, 0.19 mmol) and (2S,4R)-4-hydroxy-5-oxopyrrolidine-2-carboxylic acid (33 mg, 0.23 mmol) in 2 mL DMF was treated with HATU (107 mg, 0.28 mmol) and TEA (79 uL, 0.57 mmol) and stirred at room temperature for 1 h. The reaction was then diluted with water and MeCN and purified by RP-HPLC to provide 2-(((3R,4S)-3-fluoro-1-((2S,4R)-4-hydroxy-5-oxopyrrolidine-2-carbonyl)piperidin-4-yl)oxy)-5-(4-((4-(4-(oxetan-3-yl)piperazin-1-yl)phenyl)amino)-1,3,5-triazin-2-yl)benzonitrile as a yellow solid. 1H NMR (400 MHz, DMSO-d6) δ 10.19 (d, J=22.3 Hz, 1H), 8.75 (s, 1H), 8.66-8.44 (m, 2H), 7.90 (d, J=23.2 Hz, 1H), 7.63 (d, J=9.3 Hz, 4H), 7.04 (s, 2H), 5.20-4.95 (m, 3H), 4.76 (m, 5H), 4.65-4.52 (m, 1H), 4.40 (m, 1H), 4.17 (m, 1H), 4.02 (dt, J=17.2, 8.3 Hz, 1H), 3.84 (d, J=14.0 Hz, 1H), 3.69-2.57 (m, 7H), 2.36-1.71 (m, 4H). ES/MS 658.4 (M+H+).

Example 404

2-(((3R,4S)-1-(2-cyanoacetyl)-3-fluoropiperidin-4-yl)oxy)-5-(4-((3-fluoro-4-(4-(oxetan-3-yl)piperazin-1-yl)phenyl)amino)-1,3,5-triazin-2-yl)benzonitrile

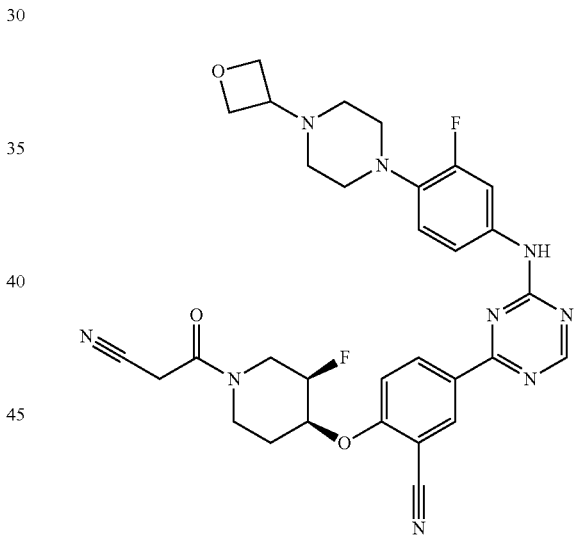

A solution 2-(((3R,4S)-3-fluoropiperidin-4-yl)oxy)-5-(4-((4-(4-(oxetan-3-yl)piperazin-1-yl)phenyl)amino)-1,3,5-triazin-2-yl)benzonitrile (100 mg, 0.18 mmol) 2-cyanoacetic acid (19 mg, 0.22 mmol) in 2 mL DMF was treated with HATU (83 mg, 0.22 mmol) and TEA (76 uL, 0.55 mmol) and stirred at room temperature for 1 h. The reaction was then diluted with water and MeCN and purified by RP-HPLC to provide 2-(((3R,4S)-3-fluoro-1-((2S,4R)-4-fluoro-5-oxopyrrolidine-2-carbonyl)piperidin-4-yl)oxy)-5-(4-((4-(4-(oxetan-3-yl)piperazin-1-yl)phenyl)amino)-1,3,5-triazin-2-yl)benzonitrile as a yellow solid. 1H NMR (400 MHz, DMSO-d6) δ 10.43 (s, 1H), 8.83 (s, 1H), 8.65-8.50 (m, 2H), 7.75 (dd, J=14.8, 2.4 Hz, 1H), 7.69-7.58 (m, 1H), 7.47 (s, 1H), 7.22-7.08 (m, 1H), 5.22-4.92 (m, 2H), 4.76 (d, J=6.7 Hz, 4H), 4.40 (m, 1H), 4.23-3.82 (m, 4H), 3.73-2.64 (m, 9H), 2.09-1.78 (m, 3H). ES/MS 616.4 (M+H+).

Example 405

2-(((3R,4S)-3-fluoro-1-((2S,4R)-4-fluoro-5-oxopyrrolidine-2-carbonyl)piperidin-4-yl)oxy)-5-(4-((4-(4-(oxetan-3-yl)piperazin-1-yl)phenyl)amino)-1,3,5-triazin-2-yl)benzonitrile

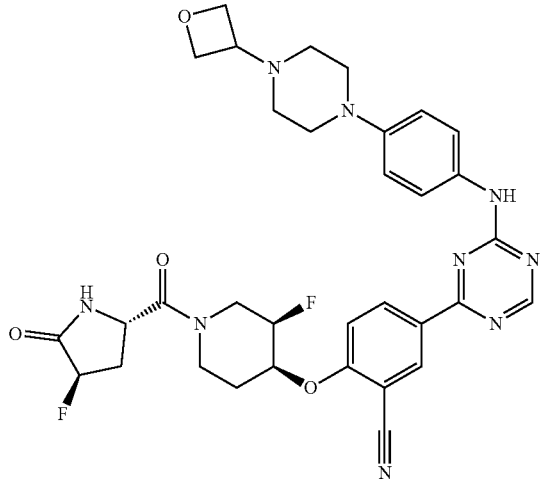 [SMILES: N#Cc1cc(-c2ncnc(Nc3ccc(N4CCN(C5COC5)CC4)cc3)n2)ccc1O[C@H]1CCN(C(=O)[C@@H]2C[C@@H](F)C(=O)N2)C[C@H]1F]

A solution 2-(((3R,4S)-3-fluoropiperidin-4-yl)oxy)-5-(4-((4-(4-(oxetan-3-yl)piperazin-1-yl)phenyl)amino)-1,3,5-triazin-2-yl)benzonitrile (100 mg, 0.19 mmol) and (2S,4R)-4-fluoro-5-oxopyrrolidine-2-carboxylic acid (67 mg, 0.23 mmol) in 2 mL DMF was treated with HATU (107 mg, 0.28 mmol) and TEA (79 uL, 0.57 mmol) and stirred at room temperature for 1 h. The reaction was then diluted with water and MeCN and purified by RP-HPLC to provide 2-(((3R,4S)-3-fluoro-1-((2S,4R)-4-fluoro-5-oxopyrrolidine-2-carbonyl)piperidin-4-yl)oxy)-5-(4-4-((4-(oxetan-3-yl)piperazin-1-yl)phenyl)amino)-1,3,5-triazin-2-yl)benzonitrile as a yellow solid. 1H NMR (400 MHz, DMSO-d6) δ 10.19 (d, J=23.5 Hz, 1H), 8.75 (s, 1H), 8.66-8.39 (m, 3H), 7.63 (dd, J=9.9, 4.7 Hz, 3H), 7.04 (s, 2H), 5.21-4.93 (m, 2H), 4.84-4.65 (m, 6H), 4.41 (d, J=25.5 Hz, 1H), 4.18 (d, J=13.2 Hz, 1H), 3.97-2.64 (m, 10H), 2.44-2.23 (m, 2H), 2.09-1.72 (m, 3H). ES/MS 660.4 (M+H+).

Example 406

2-(((3R,4S)-3-fluoro-1-((2S,4S)-4-fluoro-5-oxopyrrolidine-2-carbonyl)piperidin-4-yl)oxy)-5-(4-((4-(4-(oxetan-3-yl)piperazin-1-yl)phenyl)amino)-1,3,5-triazin-2-yl)benzonitrile

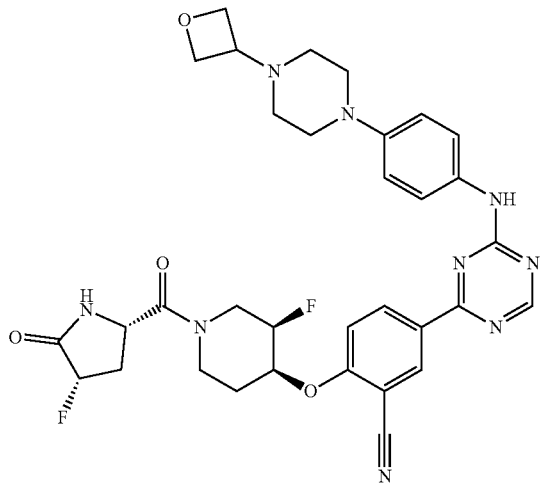 [SMILES: N#Cc1cc(-c2ncnc(Nc3ccc(N4CCN(C5COC5)CC4)cc3)n2)ccc1O[C@H]1CCN(C(=O)[C@@H]2C[C@H](F)C(=O)N2)C[C@H]1F]

A solution 2-(((3R,4S)-3-fluoropiperidin-4-yl)oxy)-5-(4-((4-(4-(oxetan-3-yl)piperazin-1-yl)phenyl)amino)-1,3,5-triazin-2-yl)benzonitrile (100 mg, 0.19 mmol) and (2S,4S)-4-fluoro-5-oxopyrrolidine-2-carboxylic acid (33 mg, 0.23 mmol) in 2 mL DMF was treated with HATU (86 mg, 0.23 mmol) and TEA (39 uL, 0.28 mmol) and stirred at room temperature for 1 h. The reaction was then diluted with water and MeCN and purified by RP-HPLC to provide -(((3R)-3-fluoro-1-((2S,4S)-4-fluoro-5-oxopyrrolidine-2-carbonyl)piperidin-4-yl)oxy)-5-(4-((4-(4-(oxetan-3-yl)piperazin-1-yl)phenyl)amino)-1,3,5-triazin-2-yl)benzonitrile as a yellow solid. 1H NMR (400 MHz, DMSO-d6) δ 10.18 (d, J=24.7 Hz, 1H), 8.75 (s, 1H), 8.65-8.50 (m, 2H), 8.46 (d, J=15.3 Hz, 1H), 7.63 (m, 3H), 7.04 (s, 3H), 5.21-4.94 (m, 3H), 4.76 (d, J=6.4 Hz, 5H), 4.48 (dd, J=64.7, 22.1 Hz, 3H), 4.27-4.03 (m, 1H), 4.02-3.23 (m, 3H), 3.22-2.54 (m, 5H), 2.09-1.71 (m, 4H). ES/MS 660.33 (M+H+).

Example 407

2-(((3R,4S)-3-fluoro-1-((S)-1-methyl-5-oxopyrrolidine-2-carbonyl)piperidin-4-yl)oxy)-5-(4-((4-(4-(oxetan-3-yl)piperazin-1-yl)phenyl)amino)-1,3,5-triazin-2-yl)benzonitrile

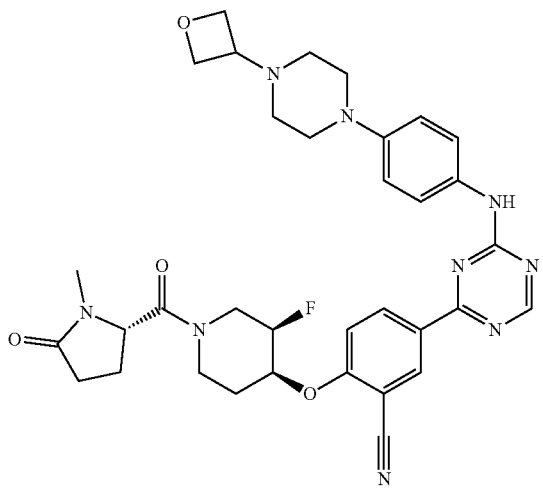 [SMILES: CN1C(=O)CC[C@H]1C(=O)N1CC[C@H](Oc2ccc(-c3ncnc(Nc4ccc(N5CCN(C6COC6)CC5)cc4)n3)cc2C#N)[C@H](F)C1]

A solution 2-(((3R,4S)-3-fluoropiperidin-4-yl)oxy)-5-(4-((4-(4-(oxetan-3-yl)piperazin-1-yl)phenyl)amino)-1,3,5-triazin-2-yl)benzonitrile (100 mg, 0.19 mmol) and (S)-1-methyl-5-oxopyrrolidine-2-carboxylic acid (30 mg, 0.21 mmol) in 3 mL DMF was treated with HATU (83 mg, 0.22 mmol) and TEA (51 uL, 0.37 mmol) and stirred at room temperature for 1 h. The reaction was then diluted with water and MeCN and purified by RP-HPLC to provide 2-(((3R,4S)-3-fluoro-1-((S)-1-methyl-5-oxopyrrolidine-2-carbonyl)piperidin-4-yl)oxy)-5-(4-((4-(4-(oxetan-3-yl)piperazin-1-yl)phenyl)amino)-1,3,5-triazin-2-yl)benzonitrile as a yellow solid. 1H NMR (400 MHz, DMSO-d6) δ 10.19 (d, J=22.0 Hz, 1H), 8.75 (s, 1H), 8.65-8.47 (m, 2H), 7.64 (d, J=9.2 Hz, 3H), 7.05 (s, 2H), 5.22-4.98 (m, 3H), 4.85-4.72 (m, 5H), 4.67 (td, J=9.4, 8.8, 4.8 Hz, 1H), 4.40 (m, 2H), 4.29-4.08 (m, 1H), 4.08-2.70 (m, 6H), 2.61 (m, 3H), 2.35-2.12 (m, 43H), 2.12-1.71 (m, 4H). ES/MS 656.5 (M+H+).

Example 408

2-(((3R,4S)-3-fluoro-1-((S)-1-methyl-5-oxopyrrolidine-2-carbonyl)piperidin-4-yl)oxy)-5-(4-((3-fluoro-4-(4-(oxetan-3-yl)piperazin-1-yl)phenyl)amino)-1,3,5-triazin-2-yl)benzonitrile

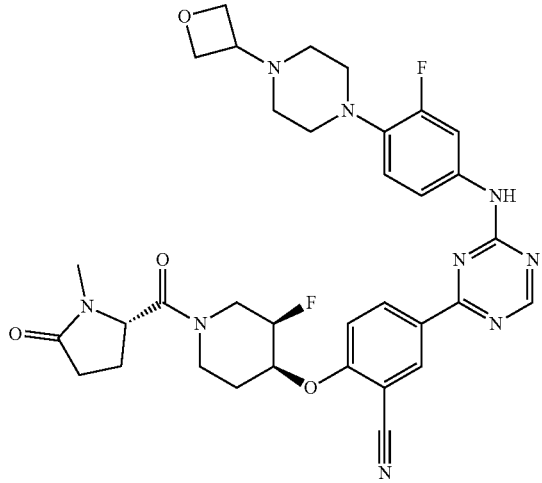 [SMILES: CN1C(=O)CC[C@H]1C(=O)N1CC[C@H](Oc2ccc(-c3ncnc(Nc4ccc(N5CCN(C6COC6)CC5)c(F)c4)n3)cc2C#N)[C@H](F)C1]

A solution 5-(4-((3-fluoro-4-(4-(oxetan-3-yl)piperazin-1-yl)phenyl)amino)-1,3,5-triazin-2-yl)-2-(((3R,4S)-3-fluoropiperidin-4-yl)oxy)benzonitrile (100 mg, 0.19 mmol) and (S)-1-methyl-5-oxopyrrolidine-2-carboxylic acid (29 mg, 0.20 mmol) in 3 mL DMF was treated with HATU (83 mg, 0.22 mmol) and TEA (51 uL, 0.37 mmol) and stirred at room temperature for 1 h. The reaction was then diluted with water and MeCN and purified by RP-HPLC to provide 2-(((3R,4S)-3-fluoro-1-((S)-1-methyl-5-oxopyrrolidine-2-carbonyl)piperidin-4-yl)oxy)-5-(4-((3-fluoro-4-(4-(oxetan-3-yl)piperazin-1-yl)phenyl)amino)-1,3,5-triazin-2-yl)benzonitrile as a yellow solid. 1H NMR (400 MHz, DMSO-d6) δ 10.42 (s, 1H), 8.83 (s, 1H), 8.58 (d, J=8.5 Hz, 2H), 7.75 (dd, J=14.8, 2.4 Hz, 1H), 7.66 (d, J=9.3 Hz, 1H), 7.46 (s, 1H), 7.14 (t, J=9.3 Hz, 1H), 5.22-4.95 (m, 3H), 4.82-4.61 (m, 6H), 4.51-3.68 (m, 5H), 3.68-2.65 (m, 5H), 2.61 (m, 3H), 2.34-2.12 (m, 3H), 2.06-1.70 (m, 4H). ES/MS 677.4 (M+H+).

Example 409

2-(((3R,4S)-1-((S)-2,3-dihydroxypropanoyl)-3-fluoropiperidin-4-yl)oxy)-5-(4-4-((3-fluoro-4-(4-(oxetan-3-yl)piperazin-1-yl)phenyl)amino)-1,3,5-triazin-2-yl)benzonitrile

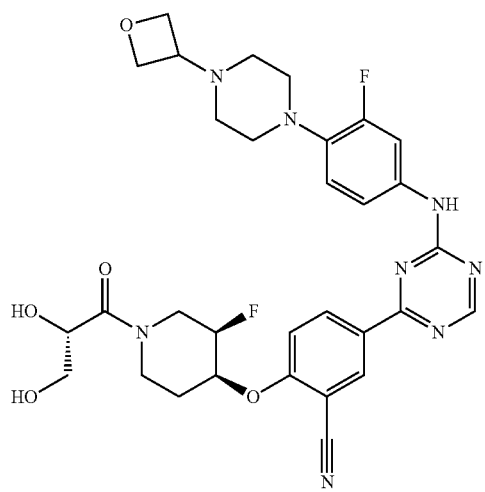

A solution 5-(4-((3-fluoro-4-(4-(oxetan-3-yl)piperazin-1-yl)phenyl)amino)-1,3,5-triazin-2-yl)-2-(((3R,4S)-3-fluoropiperidin-4-yl)oxy)benzonitrile (155 mg, 0.28 mmol) and (S)-glyceric acid (40 mg, 0.31 mmol) in 4 mL DMF was treated with HATU (118 mg, 0.31 mmol) and TEA 118 uL, 0.85 mmol) and stirred at room temperature for 1 h. The reaction was then diluted with water and MeCN and purified by RP-HPLC to provide 2-(((3R)-1-((S)-2,3-dihydroxypropanoyl)-3-fluoropiperidin-4-yl)oxy)-5-(4-((3-fluoro-4-(4-(oxetan-3-yl)piperazin-1-yl)phenyl)amino)-1,3,5-triazin-2-yl)benzonitrile as a yellow solid. 1H NMR (400 MHz, DMSO-d6) δ 10.38 (s, 1H), 8.78 (s, 1H), 8.59-8.44 (m, 2H), 7.70 (dd, J=14.9, 2.4 Hz, 1H), 7.59 (d, J=9.2 Hz, 1H), 7.42 (s, 1H), 7.09 (t, J=9.3 Hz, 1H), 5.19-4.86 (m, 3H), 4.70 (d, J=6.2 Hz, 5H), 4.58-3.80 (m, 5H), 3.80-2.64 (m, 10H), 1.87 (d, J=43.6 Hz, 3H). ES/MS 637.4 (M+H+).

Example 410

2-(((3R,4S)-3-fluoro-1-((2S,4S)-4-hydroxy-5-oxopyrrolidine-2-carbonyl)piperidin-4-yl)oxy)-5-(4-((4-(4-(oxetan-3-yl)piperazin-1-yl)phenyl)amino)-1,3,5-triazin-2-yl)benzonitrile

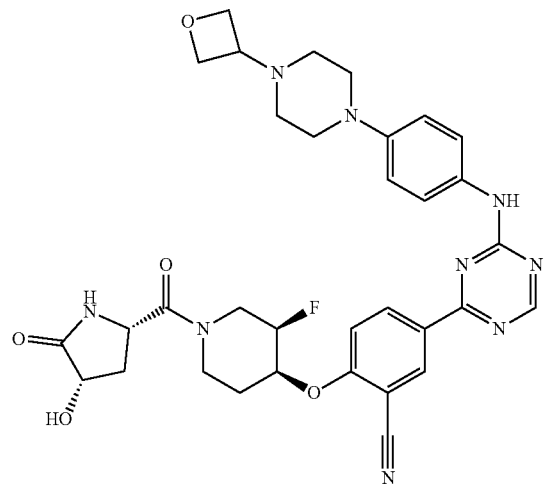 [SMILES: N#Cc1cc(-c2ncnc(Nc3ccc(N4CCN(C5COC5)CC4)cc3)n2)ccc1O[C@H]1CCN(C(=O)[C@@H]2C[C@H](O)C(=O)N2)C[C@H]1F]

A solution 2-(((3R,4S)-3-fluoropiperidin-4-yl)oxy)-5-(4-((4-(4-(oxetan-3-yl)piperazin-1-yl)phenyl)amino)-1,3,5-triazin-2-yl)benzonitrile (150 mg, 0.28 mmol) and (2S,4S)-4-hydroxy-5-oxopyrrolidine-2-carboxylic acid (45 mg, 0.31 mmol) in 2 mL DMF was treated with HATU (129 mg, 0.34 mmol) and TEA (157 uL, 0.11 mmol) and stirred at room temperature for 1 h. The reaction was then diluted with water and MeCN and purified by RP-HPLC to provide 2-(((3R,4S)-3-fluoro-1-((2S,4S)-4-hydroxy-5-oxopyrrolidine-2-carbonyl)piperidin-4-yl)oxy)-5-(4-((4-(4-(oxetan-3-yl)piperazin-1-yl)phenyl)amino)-1,3,5-triazin-2-yl)benzonitrile as a yellow solid. 1H NMR (400 MHz, DMSO-d6) δ 10.14 (d, J=2.4.0 Hz, 1H), 8.70 (s, 1H), 8.62-8.40 (m, 2H), 7.84 (d, J=19.5 Hz, 1H), 7.58 (d, J=9.1 Hz, 2H), 7.00 (s, 3H), 5.02 (m, 3H), 4.71 (d, J=6.4 Hz, 5H), 4.40 (m, 1H), 4.24-3.87 (m, 3H), 3.78 (s, 1H), 3.61-3.21 (m, 4H), 3.19-2.70 (m, 4H), 2.60 (ddd, J=19.7, 15.6, 8.2 Hz, 2H), 1.97 (m, 2H), 1.81-1.45 (m, 1H). ES/MS 658.3 (M+H+).

Example 411

2-(((2S,4S,5R)-5-fluoro-2-methyl-1-((R)-5-oxopyr-rolidine-2-carbonyl)piperidin-4-yl)oxy)-5-(4-((4-(4-(oxetan-3-yl)piperazin-1-yl)phenyl)amino)-1,3,5-triazin-2-yl)benzonitrile

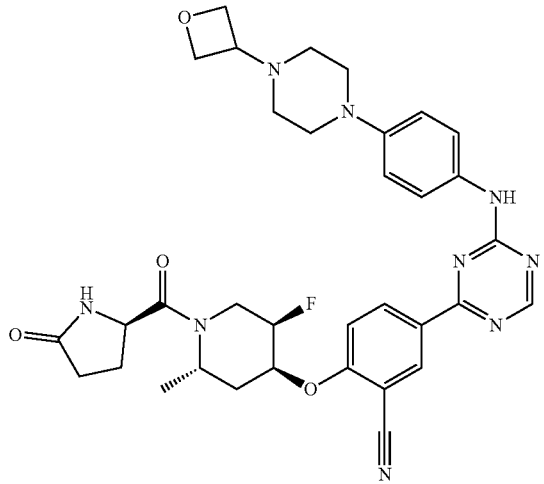 [SMILES: C[C@H]1C[C@H](Oc2ccc(-c3ncnc(Nc4ccc(N5CCN(C6COC6)CC5)cc4)n3)cc2C#N)[C@H](F)CN1C(=O)[C@H]1CCC(=O)N1]

A solution of 2-(((2S,4S,5R)-5-fluoro-2-methylpiperidin-4-yl)oxy)-5-(4-((4-(4-(oxetan-3-yl)piperazin-1-yl)phenyl)amino)-1,3,5-triazin-2-yl)benzonitrile (55 mg, 0.10 mmol) and (R)-5-oxopyrrolidine-2-carboxylic acid (14 mg, 0.11 mmol) in 1 mL DMF was treated with HATU (42 mg, 0.11 mmol) and DIEA (35 uL, 0.20 mmol) and stirred at room temperature overnight. The reaction was then diluted with water and MeCN and purified by RP-HPLC to provide 2-(((2S,5R)-5-fluoro-2-methyl-1-((R)-5-oxopyrrolidine-2-carbonyl)piperidin-4-yl)oxy)-5-(4-((4-(4-(oxetan-3-yl)piperazin-1-yl)phenyl)amino)-1,3,5-triazin-2-yl)benzonitrile as a yellow solid. 1 H NMR (400 MHz, DMSO-d6) δ 10.18 (m, 1H), 8.75 (s, 1H), 8.58 (d, J=9.2 Hz, 2H), 8.52 (m, 1H), 7.72-7.54 (m, 4H), 7.05 (s, 2H), 5.31-5.15 (m, 1H), 5.15-4.90 (m, 2H), 4.76 (d, J=6.5 Hz, 4H), 4.74-4.64 (m, 2H), 4.62-4.27 (m, 2H), 4.27-2.63 (m, 7H), 2.39-1.79 (m, 5H), 1.38-1.20 (m, 3H). ES/MS 656.4 (M+H⁺).

Example 412

2-(((2S,4S,5R)-5-fluoro-1-((R)-2-hydroxypro-panoyl)-2-methylpiperidin-4-yl)oxy)-5-(4-((4-(4-(oxetan-3-yl)piperazin-1-yl)phenyl)amino)-1,3,5-triazin-2-yl)benzonitrile

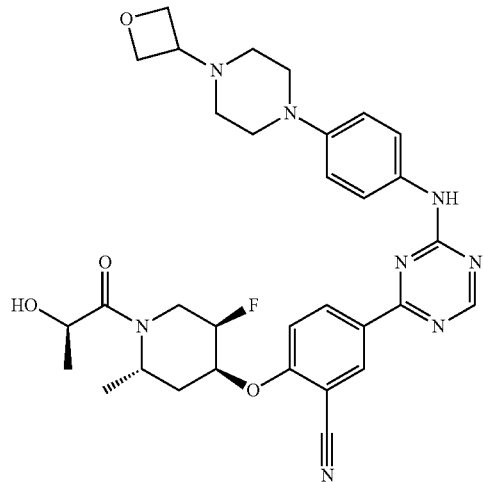 [SMILES: C[C@@H](O)C(=O)N1C[C@@H](F)[C@@H](Oc2ccc(-c3ncnc(Nc4ccc(N5CCN(C6COC6)CC5)cc4)n3)cc2C#N)C[C@@H]1C]

A solution of 2-(((2S,4S,5R)-5-fluoro-2-methylpiperidin-4-yl)oxy)-5-(4-((4-(4-(oxetan-3-yl)piperazin-1-yl)phenyl)amino)-1,3,5-triazin-2-yl)benzonitrile (85 mg, 0.16 mmol) and d-lactic acid (15 mg, 0.17 mmol) in 1 mL DMF was treated with HATU (65 mg, 0.17 mmol) and DIEA (54 uL, 0.31 mmol) and stirred at room temperature for 1 h. The reaction was then diluted with water and MeCN and purified by RP-HPLC to provide 2-(((2S,5R)-5-fluoro-1-((R)-2-hydroxypropanoyl)-2-methylpiperidin-4-yl)oxy)-5-(4-((4-(4-(oxetan-3-yl)piperazin-1-yl)phenyl)amino)-1,3,5-triazin-2-yl)benzonitrile as a yellow solid. 1H NMR (400 MHz, DMSO-d6) δ 10.18 (d, J=24.1 Hz, 1H), 8.75 (s, 1H), 8.67-8.34 (m, 2H), 7.64 (s, 3H), 7.05 (s, 2H), 5.30-4.90 (m, 4H), 4.84-4.65 (m, 5H), 4.60-4.23 (m, 4H), 4.18-2.69 (m, 5H), 2.22-1.85 (m, 3H), 1.35 (d, J=6.8 Hz, 2H), 1.29-1.11 (m, 5H). ES/MS 617.4 (M+H⁺).

Example 413

2-(((3R,4S)-3-fluoro-1-(6-oxo-1,6-dihydropyridine-2-carbonyl)piperidin-4-yl)oxy)-5-(4-((4-(4-(oxetan-3-yl)piperazin-1-yl)phenyl)amino)-1,3,5-triazin-2-yl)benzonitrile

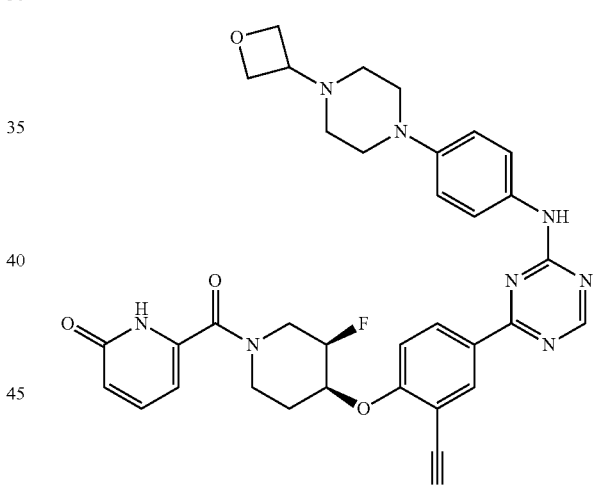

A solution 2-(((3R,4S)-3-fluoropiperidin-4-yl)oxy)-5-(4-((4-(4-(oxetan-3-yl)piperazin-1-yl)phenyl)amino)-1,3,5-triazin-2-yl)benzonitrile (126 mg, 0.24 mmol) and 6-oxo-1,6-dihydropyridine-2-carboxylic acid (36 mg, 0.26 mmol) in 2 mL DMF was treated with HATU (108 mg, 0.29 mmol) and DIEA (60 uL, 0480 mmol) and stirred at room temperature for 1 h. The reaction was then diluted with water and MeCN and purified by RP-HPLC to provide 2-(((3R,4S)-3-fluoro-1-(2-oxoimidazolidine-4-carbonyl)piperidin-4-yl)oxy)-5-(4-((4-(4-(oxetan-3-yl)piperazin-1-yl)phenyl)amino)-1,3,5-triazin-2-yl)benzonitrile as a yellow solid. 1H NMR (400 MHz, DMSO-d6) δ 10.18 (d, J=24.7 Hz, 1H), 8.75 (s, 1H), 8.66-8.44 (m, 3H), 8.29-8.19 (m, 1H), 7.71-7.48 (m, 4H ), 7.00 (m, 4H), 5.27-4.89 (m, 3H), 4.83-4.58 (m, 6H), 4.59-4.11 (m, 2H), 4.04-3.19 (m, 2H), 3.10 (s, 6H), 2.02 (m, 2H). ES/MS 652.4 (M+H⁺).

Example 414

2-(((3R,4S)-3-fluoro-1-(2-oxoimidazolidine-4-carbonyl)piperidin-4-yl)oxy)-5-(4-((4-(4-(oxetan-3-yl)piperazin-1-yl)phenyl)amino)-1,3,5-triazin-2-yl)benzonitrile

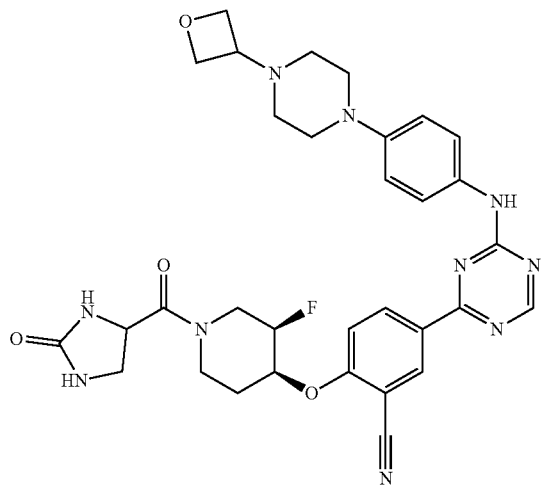 [SMILES: N#Cc1cc(-c2ncnc(Nc3ccc(N4CCN(C5COC5)CC4)cc3)n2)ccc1O[C@H]1CCN(C(=O)C2CNC(=O)N2)C[C@H]1F]

A solution of 2-(((3R,4S)-3-fluoropiperidin-4-yl)oxy)-5-(4-((4-(4-(oxetan-3-yl)piperazin-1-yl)phenyl)amino)-1,3,5-triazin-2-yl)benzonitrile (55 mg, 0.10 mmol) and (±)-2-oxoimidazolidine-4-carboxylic acid (15 mg, 0.11 mmol) in 1 mL DMF was treated with HATU (42 mg, 0.11 mmol) and DIEA (35 uL, 0.20 mmol) and stirred at room temperature for 1 h. The reaction was then diluted with water and MeCN and purified by RP-HPLC to provide 2: 2-(((3R,4S)-3-fluoro-1-(2-oxoimidazolidine-4-carbonyl)piperidin-4-yl)oxy)-5-(4-((4-(4-(oxetan-3-yl)piperazin-1-yl)phenyl)amino)-1,3,5-triazin-2-yl)benzonitrile as a yellow solid. 1H NMR (400 MHz, DMSO-d6) δ 10.18 (d, J=22.2 Hz, 1H), 8.75 (s, 1H), 8.57 (m, 2H), 7.59 (m, 2H), 7.02 (m, 3H), 6.40 (bs, 1H), 6.23 (bs, 1H), 5.24-4.97 (m, 3H), 4.76 (d, J=6.3 Hz, 5H), 4.61 (ddd, J=14.5, 9.7, 4.8 Hz, 1H), 4.38 (m, 2H), 4.24-3.97 (m, 1H), 3.74 (m, 1H), 3.67-3.22 (m, 4H), 3.04 (m, 4H), 1.89 (m, 3H). ES/MS 643.4 (M+H$^+$).

Example 415

2-(((2S,4S,5R)-5-fluoro-1-((S)-2-hydroxypropanoyl)-2-methylpiperidin-4-yl)oxy)-5-(4-((4-(4-(oxetan-3-yl)piperazin-1-yl)phenyl)amino)-1,3,5-triazin-2-yl)benzonitrile

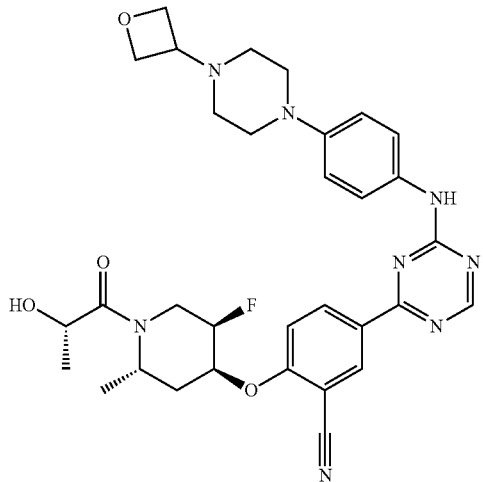 [SMILES: C[C@H](O)C(=O)N1C[C@@H](F)[C@@H](Oc2ccc(-c3ncnc(Nc4ccc(N5CCN(C6COC6)CC5)cc4)n3)cc2C#N)C[C@@H]1C]

A solution of 1-lactic acid (10 mg, 0.11 mmol) in 1 mL DMF was treated with HATU (42 mg, 0.11 mmol), 2-(((2S,4S,5R)-5-fluoro-2-methylpiperidin-4-yl)oxy)-5-(4-((4-(4-(oxetan-3-yl)piperazin-1-yl)phenyl)amino)-1,3,5-triazin-2-yl)benzonitrile (55 mg, 0.10 mmol) and DIEA (35 uL, 0.20 mmol) and stirred at room temperature for 2 h. After 2 h premixed solution of 1-lactic acid (19 mg, 0.22 mmol) and HATU (89 mg, 0.24 mmol) in 1 mL DMF and added and the mixtures stirred for an additional hour. A solution of 252 uL of 2N NaOH in 1 mL MeOH was then added and the mixture stirred for 5 min. 40 mL of TFA was added and the reaction diluted with water and purified by RP-HPLC to provide 2-(((2S,5R)-5-fluoro-1-((S)-2-hydroxypropanoyl)-2-methylpiperidin-4-yl)oxy)-5-(4-((4-(4-(oxetan-3-yl)piperazin-1-yl)phenyl)amino)-1,3,5-triazin-2-yl)benzonitrile as a yellow solid. 1H NMR (400 MHz, DMSO-d6) δ 10.18 (d, J=25.8 Hz, 1H), 8.75 (s, 1H), 8.68-8.45 (m, 2H), 7.65 (d, J=9.3 Hz, 2H), 7.04 (s, 3H), 5.31-5.14 (m, 1H), 5.30-4.84 (m, 2H), 4.84-4.68 (m, 5H), 4.55-4.15 (m, 3H), 4.08-3.57 (m, 3H), 3.52-2.65 (m, 6H), 2.21-1.83 (m, 2H), 1.40-1.15 (m, 5H). ES/MS 617.4 (M+H$^+$).

Example 416

2-(((2S,4S,5R)-5-fluoro-2-methyl-1-((S)-5-oxopyrrolidine-2-carbonyl)piperidin-4-yl)oxy)-5-(4-((4-(4-(oxetan-3-yl)piperazin-1-yl)phenyl)amino)-1,3,5-triazin-2-yl)benzonitrile

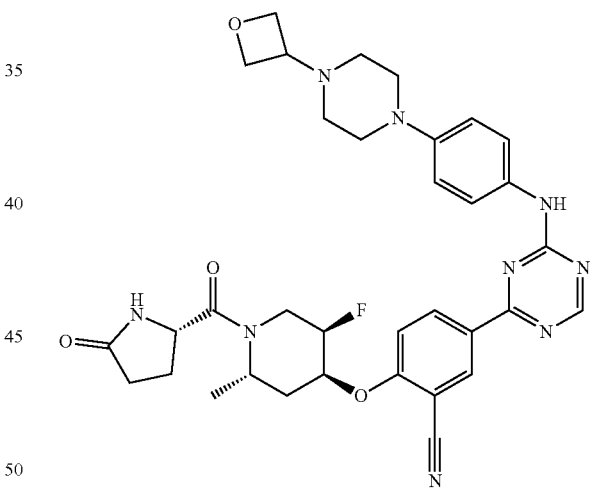

A solution of 2-(((2S,4S,5R)-5-fluoro-2-methylpiperidin-4-yl)oxy)-5-(4-((4-(4-(oxetan-3-yl)piperazin-1-yl)phenyl)amino)-1,3,5-triazin-2-yl)benzonitrile (55 mg, 0.10 mmol) and (S)-5-oxopyrrolidine-2-carboxylic acid (14 mg, 0.11 mmol) in 1 mL DMF was treated with HATU (42 mg, 0.11 mmol) and DIEA (35 uL, 0.20 mmol) and stirred at room temperature overnight. The reaction was then diluted with water and MeCN and purified by RP-HPLC to provide 2-(((2S,5R)-5-fluoro-2-methyl-1-((S)-5-oxopyrrolidine-2-carbonyl)piperidin-4-yl)oxy)-5-(4-((4-(4-(oxetan-3-yl)piperazin-1-yl)phenyl)amino)-1,3,5-triazin-2-yl)benzonitrile as a yellow solid. 1H NMR (400 MHz, DMSO-d6) δ 10.18 (m, 1H), 8.75 (s, 1H), 8.58 (d, J=9.2 Hz, 2H), 8.52 (m, 1H), 7.72-7.54 (m, 4H), 7.05 (s, 2H), 5.31-5.15 (m, 1H), 5.15-4.90 (m, 2H), 4.76 (d, J=6.5 Hz, 4H), 4.74-4.64 (m, 2H), 4.62-4.27 (m, 2H), 4.27-2.63 (m, 8H), 2.39-1.79 (m, 5H), 1.38-1.20 (m, 3H). ES/MS 656.4 (M+H$^+$).

Example 417

2-(((3R,4S)-1-(3-cyanopropanoyl)-3-fluoropiperidin-4-yl)oxy)-5-(4-((4-(4-(oxetan-3-yl)piperazin-1-yl)phenyl)amino)-1,3,5-triazin-2-yl)benzonitrile

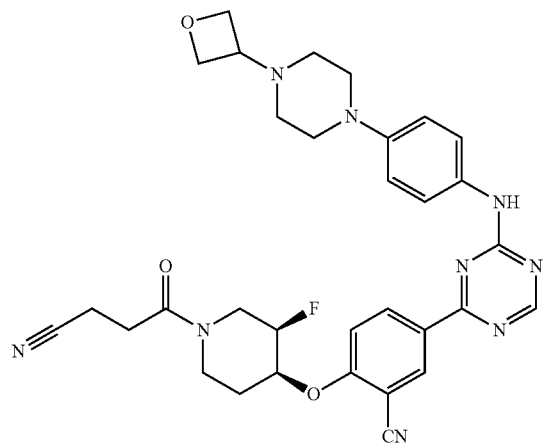 [SMILES: N#CCCC(=O)N1CC[C@H](Oc2ccc(-c3ncnc(Nc4ccc(N5CCN(C6COC6)CC5)cc4)n3)cc2C#N)[C@H](F)C1]

Step-1: To solution of 2,4-dichloro-1,3,5-triazine (2.5 g, 16.67 mmol) in DMF (100 mL) at 0° C. under nitrogen atmosphere was added solution of 4-(4-(oxetan-3-yl)piperazin-1-yl)aniline (3.5 g, 15.1 mmol) in DMF (120 mL) over 5 minutes. The reaction mixture was stirred at 0° C. for 1 h and the solvent concentrated to dryness under reduced pressure. Crude product was added 40% MeOH\DCM and sonicated for 2 minutes to bring solid particles in to solution. The crude product was adsorbed on silica gel and concentrated under reduced pressure. The crude product was purified by flash column chromatography on silica gel [Method, 10-60% B over 15 min (A=DCM, B=20% MeOH/DCM)] to afford product. LCMS-ESI$^+$ (m/z): [M+H]$^+$ calcd for $C_{16}H_{19}ClN_6O$: 347.1 found:347.3.

Step-2. A mixture of 4-chloro-N-(4-(4-(oxetan-3-yl)piperazin-1-yl)phenyl)-1,3,5-triazin-2-amine (1 g, 2.88 mmol), 2-fluoro-5-(4,4,5,5-tetramethyl-1,3,2-dioxaborolan-2-yl)benzonitrile (0.783 g, 3.17 mmol) and Pd(PPh$_3$)$_4$ (0.25 g, 0.21 mmol) was taken up in 1,2-DME (24 mL) in a 100 mL round bottom flask. To well stirred mixture was added solution of sodium carbonate (1.375 g 12.98 mmol) in water (12 mL). The mixture heated at 95° C. for 4 h (500 mg scale was done under microwave irradiation at 120 C for 30 min). The reaction mixture was diluted with 30% MeOH/DCM (50 mL) and filtered through short pad of silica gel and washed with 30% MeOH/DCM (10mL×2). The filtrate was adsorbed on silica gel and concentrated under reduced pressure. The crude product was purified by flash column chromatography on silica gel to afford 2-fluoro-5-(4-((4-(4-(oxetan-3-yl)piperazin-1-yl)phenyl)amino)-1,3,5-triazin-2-yl)benzonitrile LCMS-ESI$^+$ (m/z): [M+H]$^+$ calcd for $C_{23}H_{22}FN_7O$: 432.2; found:432.3. $^1$H NMR (400 MHz, DMSO-d$_6$) δ 10.20 (d, J=21.0 Hz, 1H), 8.77 (s, 1H), 8.65 (d, J=10.8 Hz, 2H), 7.72 (s, 1H), 7.64-7.43 (m, 2H), 6.96 (t, J=10.8 Hz, 2H), 4.55 (t, J=6.5 Hz, 2H), 4.46 (t, J=6.0 Hz, 2H), 3.47-3.40 (m, 1H), 3.13 (d, J=6.6 Hz, 4H), 2.46-2.32 (m, 4H).

Step-3: (3R,4S)-tert-butyl 3-fluoro-4-hydroxypiperidine-1-carboxylate (430 mg, 2.29 mmol) was added Me-THF (20 mL) under argon atmosphere and cooled at 0° C. To well stirred solution was added potassium tert-butoxide at one portion and stirred for 30 minutes. To well stirred solution was added 2-fluoro-5-(4-((4-(4-(oxetan-3-yl)piperazin-1-yl)phenyl)amino)-1,3,5-triazin-2-yl)benzonitrile (900 mg, 2.09 mmol) and warmed to room temperature over 10 min. The reaction was heated at 80° C. overnight. The reaction was quenched with minimum amount of water and diluted with 10% MeOH/DCM to make clear solution. The crude product was adsorbed on silica gel and purified by flash column chromatography on silica gel gel [Method, 0-50% B over 15 min (A=DCM, B=20% MeOH/DCM)] to afford (3R,4S)-tert-butyl 4-(2-cyano-4-(4-((4-(4-(oxetan-3-yl)piperazin-1-yl)phenyl)amino)-1,3,5-triazin-2-yl)phenoxy)-3-fluoropiperidine-1-carboxylate. LCMS-ESI$^+$ (m/z): [M+H]$^+$ calcd for $C_{33}H_{39}FN_8O_4$: 631.3; found: 631.4

Step-4: (3R,4S)-tert-butyl 4-(2-cyano-4-(4-((4-(4-(oxetan-3-yl)piperazin-1-yl)phenyl)amino)-1,3,5-triazin-2-yl)phenoxy)-3-fluoropiperidine-1-carboxylate (90 mg, 0.15 mmol) was dissolved in 20% TFA/DCM (5 mL) and stirred at room temperature for 1 h. The solvent was concentrated under reduced pressure to afford 2-(((3R,4S)-3-fluoropiperidin-4-yl)oxy)-5-(4-((4-(4-(oxetan-3-yl)piperazin-1-yl)phenyl)amino)-1,3,5-triazin-2-yl)benzonitrile. The dried residue was used for next step without purification. LCMS-ESI$^+$ (m/z): [M+H]$^+$ calcd for $C_{28}H_{31}FN_8O_2$: 531.2; found: 531.4

Step-5: To solution of 2-(((3R,4S)-3-fluoropiperidin-4-yl)oxy)-5-(4-((4-(4-(oxetan-3-yl)piperazin-1-yl)phenyl)amino)-1,3,5-triazin-2-yl)benzonitrile (65 mg, 0.12 mmol), 3-cyanopropanoic acid (20 mg, 0.24 mmol), HATU (58 mg, 0.24 mmol) in DMF (3 mL) was added DIPEA (0.26 mL) in a 25 mL round bottom flask and flushed with argon gas. This reaction mixture was stirred at room temperature overnight. The solvent was concentrated and the crude product purified via prep HPLC (5-95% acetonitrile in water, 0.1% trifluoroacetic acid buffer) to isolate 2-(((3R,4S)-1-(3-cyanopropanoyl)-3-fluoropiperidin-4-yl)oxy)-5-(4-((4-(4-(oxetan-3-yl)piperazin-1-yl)phenyl)amino)-1,3,5-triazin-2-yl)benzonitrile. LCMS-ESI$^+$ (m/z): [M+H]$^+$ calcd for $C_{31}H_{36}FN_9O_4$: 612.3: found:612.3 $^1$H NMR (400 MHz, DMSO-d$_6$) δ 10.19 (d, J=20.3 Hz, 1H), 8.75 (s, 1H), 8.63-8.46 (m, 2H), 7.63 (t, J=8.8 Hz, 3H), 7.14-6.90 (m, 2H), 5.24-4.92 (m, 3H), 4.75 (d, J=6.6 Hz, 5H), 4.55-4.26 (m, 2H), 4.25-3.81 (m, 4H), 3.74-3.49 (m, 1H), 3.31 (ddt, J=24.2, 18.0, 12.8 Hz, 2H), 3.19-2.83 (m, 4H), 2.10-1.79 (m, 2H).

Example 418

5-(4-((1-(tert-butyl)-1H-pyrazol-4-yl)amino)-1,3,5-triazin-2-yl)-2-(((3R,4S)-3-fluoro-1-(5-methyl-4H-1,2,4-triazole-3-carbonyl)piperidin-4-yl)oxy)benzonitrile

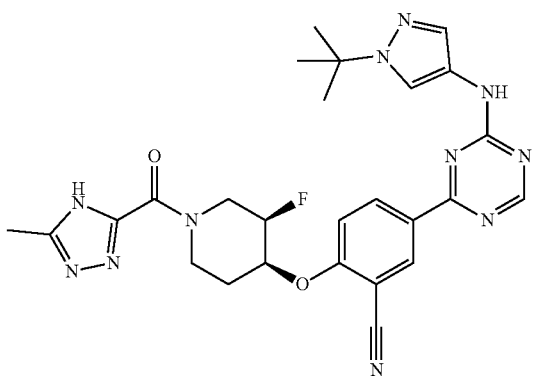 [SMILES: Cc1nnc(C(=O)N2CC[C@H](Oc3ccc(-c4ncnc(Nc5cnn(C(C)(C)C)c5)n4)cc3C#N)[C@H](F)C2)[nH]1]

The title compound was prepared by coupling 5-(4-((1-(tert-butyl)-1H-pyrazol-4-yl)amino)-1,3,5-triazin-2-yl)-2-(((3R,4S)-3-fluoropiperidin-4-yl)oxy)benzonitrile with 5-methyl-4H-1,2,4-triazole-3-carboxylic acid. LCMS-ESI$^+$ (m/z): [M+H]$^+$ calcd for $C_{26}H_{28}FN_{11}O_2$: 546.2: found:546.1 $^1$H NMR (400 MHz, DMSO-d$_6$) δ 10.27 (d, J=21.1 Hz, 1H), 8.75 (d, J=40.2 Hz, 1H), 8.57 (dd, J=7.9, 5.8 Hz, 2H), 8.04 (d, J=39.8 Hz, 1H), 7.71-7.49 (m, 2H), 7.39-7.22 (m, 1H), 7.19-7.06 (m, 1H), 5.29-4.91 (m, 2H), 4.65 (d, J=89.6 Hz, 1H), 4.29 (d, J=13.5 Hz, 1H), 3.92-3.18 (m, 2H), 2.37 (s, 3H), 2.15-1.82 (m, 2H), 1.53 (d, J=18.3 Hz, 9H). LCMS-ESI$^+$ (m/z): [M+H]$^+$ calcd for $C_{26}H_{28}FN_{11}O_2$: 546.2: found: 546.1

Example 419

5-(4-((1-(tert-butyl)-1H-pyrazol-4-yl)amino)-1,3,5-triazin-2-yl)-2-(((3R,4S)-1-((S)-2,3-dihydroxypropanoyl)-3-fluoropiperidin-4-yl)oxy) benzonitrile

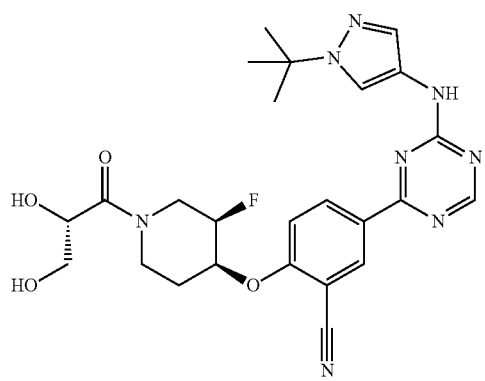 [SMILES: CC(C)(C)n1cc(Nc2ncnc(-c3ccc(O[C@H]4CCN(C(=O)[C@@H](O)CO)C[C@H]4F)c(C#N)c3)n2)cn1]

The title compound was prepared by coupling 5-(4-((1-(tert-butyl)-1H-pyrazol-4-yl)amino)-1,3,5-triazin-2-yl)-2-(((3R,4S)-3-fluoropiperidin-4-yl)oxy)benzonitrile with (S)-2,3-dihydroxypropanoic acid. LCMS-ESI$^+$ (m/z): [M+H]$^+$ calcd for $C_{25}H_{29}FN_8O_4$: 525.2: found:525.1 $^1$H NMR (400 MHz, DMSO-d$_6$) δ 10.27 (d, J=21.3 Hz, 1H), 8.75 (d, J=40.2 Hz, 1H), 8.64-8.49 (m, 2H), 8.04 (d, J=39.6 Hz, 1H), 7.71-7.53 (m, 2H), 5.03 (d, J=55.4 Hz, 3H), 4.48-4.24 (m, 2H), 3.94 (d, J=6.8 Hz, 1H), 3.80-3.18 (m, 5H), 1.92 (d, J=44.0 Hz, 2H), 1.53 (d, J=18.4 Hz, 9H).

Example 420

5-(4-((1-(tert-butyl)-1H-pyrazol-4-yl)amino)-1,3,5-triazin-2-yl)-2-(((3R,4S)-3-fluoro-1-(2-hydroxyacetyl)piperidin-4-yl)oxy)benzonitrile

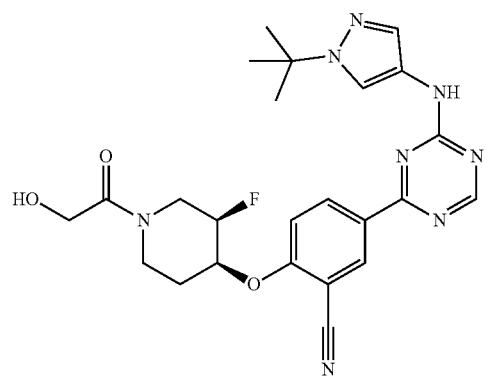 [SMILES: CC(C)(C)n1cc(Nc2ncnc(-c3ccc(O[C@H]4CCN(C(=O)CO)C[C@H]4F)c(C#N)c3)n2)cn1]

The title compound was prepared by coupling 5-(4-((1-(tert-butyl)-1H-pyrazol-4-yl)amino)-1,3,5-triazin-2-yl)-2-(((3R,4S)-3-fluoropiperidin-4-yl)oxy)benzonitrile with 2-hydroxyacetic acid. LCMS-ESI$^+$ (m/z): [M+H]$^+$ calcd for $C_{24}H_{27}FN_8O_3$: 495.2: found:495.1 1H NMR (400 MHz, DMSO-d6) δ 10.27 (d, J=21.7 Hz, 1H), 8.75 (d, J=40.2 Hz, 1H), 8.63-8.48 (m, 2H), 8.04 (d, J=39.0 Hz, 1H), 7.70-7.53 (m, 2H), 5.23-4.92 (m, 2H), 4.66 (s, 1H), 4.42-3.82 (m, 3H), 3.75-3.04 (m, 3H), 2.06-1.75 (m, 2H), 1.53 (d, J=18.2 Hz, 9H).

Example 421

2-((1-methyl-2-oxohexahydropyrimidin-5-yl)oxy)-5-(4-((4-(4-(oxetan-3-yl)piperazin-1-yl)phenyl)amino)-1,3,5-triazin-2-yl)benzonitrile

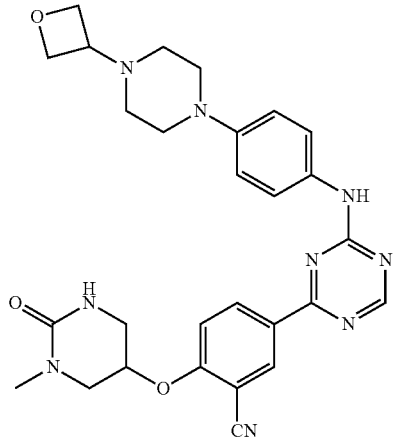 [SMILES: CN1CC(Oc2ccc(-c3ncnc(Nc4ccc(N5CCN(C6COC6)CC5)cc4)n3)cc2C#N)CNC1=O]

To a solution of 5-hydroxy-1-methyltetrahydropyrimidin-2(1H)-one (36 mg, 0.28 mmol) in DMF (4 mL) was added potassium t-butoxide (47 mg, 0.42 mmol) at 0° C. The reaction mixture was allowed to stir for 1 hour. To the reaction mixture was added 2-fluoro-5-(4-((4-(4-(oxetan-3-yl)piperazin-1-yl)phenyl)amino)-1,3,5-triazin-2-yl)benzonitrile (60 mg, 0.14 mmol) at room temperature. The reaction mixture was brought to 80° C. and heated overnight. The solvent was concentrated and the crude product purified via prep HPLC (5-95% acetonitrile in water, 0.1% trifluoroacetic acid buffer) to isolate product 2-((1-methyl-2-oxohexahydropyrimidin-5-yl)oxy)-5-(4-((4-(4-(oxetan-3-yl)piperazin-1-yl)phenyl)amino)-1,3,5-triazin-2-yl)benzonitrile. LCMS-ESI+ (m/z): [M+H]+ calcd for $C_{28}H_{31}N_9O_3$: 542.2: found:542.4

Example 422

2-((1-methyl-6-oxopiperidin-3-yl)oxy)-5-(4-((4-(4-(oxetan-3-yl)piperazin-1-yl)phenyl)amino)-1,3,5-triazin-2-yl)benzonitrile

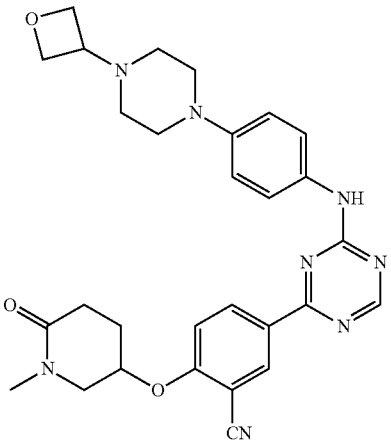 [SMILES: CN1CC(Oc2ccc(-c3ncnc(Nc4ccc(N5CCN(C6COC6)CC5)cc4)n3)cc2C#N)CCC1=O]

The title compound was prepared following the same procedure reported in Example 421 by coupling 2-fluoro-5-(4-((4-(4-(oxetan-3-yl)piperazin-1-yl)phenyl)amino)-1,3,5-triazin-2-yl)benzonitrile with 5-hydroxy-1-methylpiperidin-2-one instead of 5-hydroxy-1-methyltetrahydropyrimidin-2(1H)-one. LCMS-ESI+ (m/z): [M+H]+ calcd for $C_{29}H_{32}N_8O_3$: 541.2: found:541.4

Example 423

2-(((3R,4S)-3-fluoro-1-((R)-3-fluoropyrrolidine-1-carbonyl)piperidin-4-yl)oxy)-5-(4-((4-(4-(oxetan-3-yl)piperazin-1-yl)phenyl)amino)-1,3,5-triazin-2-yl)benzonitrile

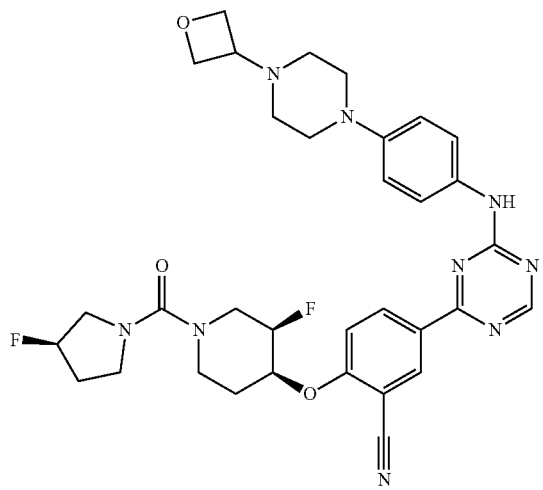 [SMILES: N#Cc1cc(-c2ncnc(Nc3ccc(N4CCN(C5COC5)CC4)cc3)n2)ccc1O[C@H]1CCN(C(=O)N2CC[C@@H](F)C2)C[C@H]1F]

To solution of 2-(((3R,4S)-3-fluoropiperidin-4-yl)oxy)-5-(4-((4-(4-(oxetan-3-yl)piperazin-1-yl)phenyl)amino)-1,3,5-triazin-2-yl)benzonitrile (50 mg, 0.1 mmol) in DMF (3 mL) was activated with DIPE (66 uL) and generated HCl gas was flushed with argon balloon. To stirred solution was added (R)-3-fluoropyrrolidine hydrochloride salt (71 mg, 0.56 mmol) followed by phosgene (15% in Toluene 250 uL) at once and stirred at room temperature for 3 h. Solvent was concentrated and the crude product purified via prep HPLC (5-95% acetonitrile in water, 0.1% trifluoroacetic acid buffer) to isolate 2-(((3R,4S)-3-fluoro-1-((R)-3-fluoropyrrolidine-1-carbonyl)piperidin-4-yl)oxy)-5-(4-((4-(4-(oxetan-3-yl)piperazin-1-yl)phenyl)amino)-1,3,5-triazin-2-yl)benzonitrile. LCMS-ESI+ (m/z): [M+H]+ calcd for $C_{33}H_{37}F_2N_9O_3$: 646.3: found:646.4 $^1$H NMR (400 MHz, DMSO-d$_6$) δ 10.18 (d, J=21.7 Hz, 1H), 8.74 (s, 1H), 8.65-8.43 (m, 2H), 7.60 (d, J=9.2 Hz, 2H), 7.03 (s, 3H), 5.41-4.84 (m, 3H), 4.82-4.57 (m, 5H), 4.42 (s, 1H), 3.93-3.58 (m, 2H), 3.55-3.26 (m, 6H), 3.20-2.86 (m, 7H), 2.12-1.85 (m, 5H).

Example 424

2-(((3R,4S)-3-fluoro-1-(pyrrolidine-1-carbonyl)piperidin-4-yl)oxy)-5-(4-((4-(4-(oxetan-3-yl)piperazin-1-yl)phenyl)amino)-1,3,5-triazin-2-yl)benzonitrile

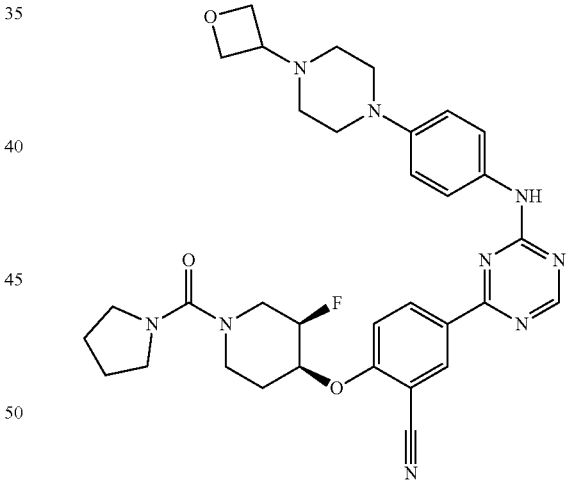

The title compound was prepared following the same procedure reported in Example 423 by coupling 2-(((3R,4S)-3-fluoropiperidin-4-yl)oxy)-5-(4-((4-(4-(oxetan-3-yl)piperazin-1-yl)phenyl)amino)-1,3,5-triazin-2-yl)benzonitrile with pyrrolidine instead of (R)-3-fluoropyrrolidine. LCMS-ESI+ (m/z): [M+H]+ calcd for $C_{33}H_{38}FN_9O_3$: 628.3: found:628.4 $^1$H NMR (400 MHz, DMSO-d$_6$) δ 10.19 (d, J=23.9 Hz, 1H), 8.75 (s, 1H), 8.66-8.42 (m, 2H), 7.64 (d, J=9.2 Hz, 2H), 7.04 (s, 3H), 5.31- 5.01 (m, 4H), 4.75 (d, J=6.6 Hz, 6H), 4.55-4.00 (m, 5H), 3.99-3.62 (m, 2H), 3.59-3.36 (m, 2H), 3.34-2.72 (m, 6H), 2.31-1.68 (m, 4H).

Example 425

2-(((3R,4S)-3-fluoro-1-((R)-3-hydroxypyrrolidine-1-carbonyl)piperidin-4-yl)oxy)-5-(4-((4-(4-(oxetan-3-yl)piperazin-1-yl)phenyl)amino)-1,3,5-triazin-2-yl)benzonitrile

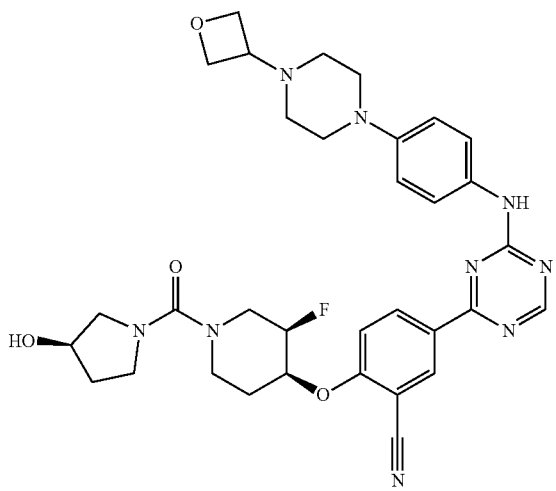 [SMILES: N#Cc1cc(-c2ncnc(Nc3ccc(N4CCN(C5COC5)CC4)cc3)n2)ccc1O[C@H]1CCN(C(=O)N2CC[C@@H](O)C2)C[C@H]1F]

The title compound was prepared following the same procedure reported in Example 423 by coupling 2-(((3R,4S)-3-fluoropiperidin-4-yl)oxy)-5-(4-((4-(4-(oxetan-3-yl)piperazin-1-yl)phenyl)amino)-1,3,5-triazin-2-yl)benzonitrile with (R)-3-pyrrolidin-3-ol instead of (R)-3-fluoropyrrolidine. LCMS-ESI+ (m/z): [M+H]+ calcd for $C_{33}H_{38}FN_9O_4$: 644.3: found:644.4. $^1$H NMR (400 MHz, DMSO-$d_6$) δ 10.23-10.13 (m, 1H), 8.75 (s, 1H), 8.60-8.49 (m, 2H), 7.60 (d, J=10.2 Hz, 3H), 7.04 (s, 2H), 5.23-4.84 (m, 3H), 4.75 (d, J=6.4 Hz, 5H), 4.42 (s, 1H), 4.19 (p, J=4.2 Hz, 1H), 3.89-3.60 (m, 2H), 3.54-3.22 (m, 7H), 3.11 (td, J=12.4, 11.6, 5.4 Hz, 4H), 2.07-1.58 (m, 6H).

Example 426

2-(((3R,4S)-3-fluoro-1-((S)-3-hydroxypyrrolidine-1-carbonyl)piperidin-4-yl)oxy)-5-(4-((4-(4-(oxetan-3-yl)piperazin-1-yl)phenyl)amino)-1,3,5-triazin-2-yl)benzonitrile

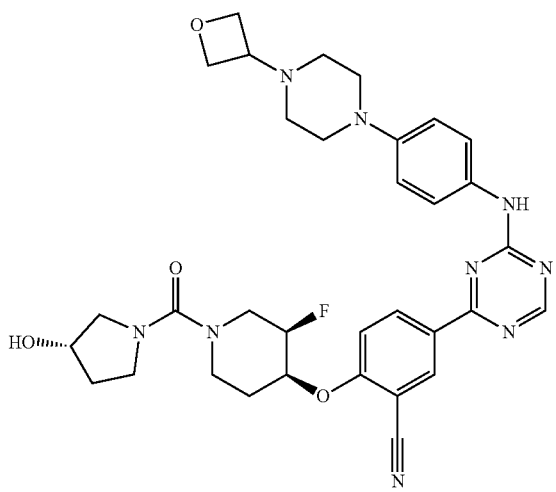 [SMILES: N#Cc1cc(-c2ncnc(Nc3ccc(N4CCN(C5COC5)CC4)cc3)n2)ccc1O[C@H]1CCN(C(=O)N2CC[C@H](O)C2)C[C@H]1F]

The title compound was prepared following the same procedure reported in Example 423 by coupling 2-(((3R,4S)-3-fluoropiperidin-4-yl)oxy)-5-(4-((4-(4-(oxetan-3-yl)piperazin-1-yl)phenyl)amino)-1,3,5-triazin-2-yl)benzonitrile with (S)-pyrrolidin-3-ol instead of (R)-3-fluoropyrrolidine. LCMS-ESI+ (m/z): [M+H]+ calcd for $C_{33}H_{38}FN_9O_4$: 644.3: found:644.4

Example 427

(3R,4S)-4-(2-cyano-4-(4-((4-(4-(oxetan-3-yl)piperazin-1-yl)phenyl)amino)-1,3,5-triazin-2-yl)phenoxy)-3-fluoro-N-(2-methoxyethyl)piperidine-1-carboxamide

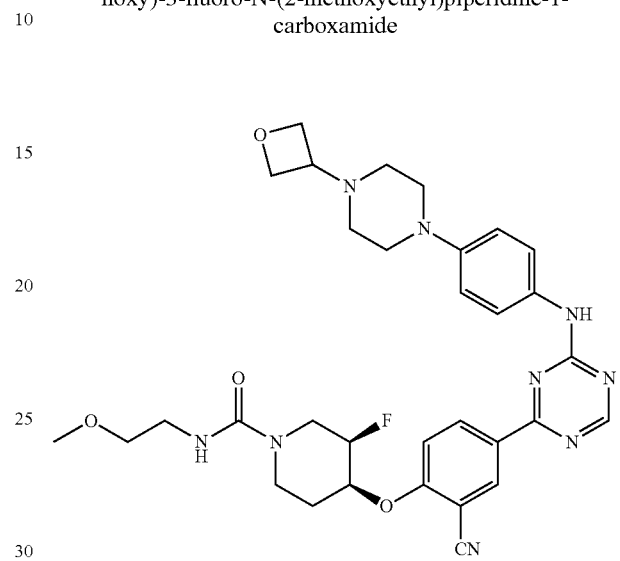

The title compound was prepared following the same procedure reported in Example 423 by coupling 2-(((3R,4S)-3-fluoropiperidin-4-yl)oxy)-5-(4-((4-(4-(oxetan-3-yl)piperazin-1-yl)phenyl)amino)-1,3,5-triazin-2-yl)benzonitrile with 2-methoxyethanamine instead of (R)-3-fluoropyrrolidine. LCMS-ESI+ (m/z): [M+H]+ calcd for $C_{32}H_{38}FN_9O_4$: 632.3: found:632.4

Example 428

(3R,4S)-4-(2-cyano-4-(4-((4-(4-(oxetan-3-yl)piperazin-1-yl)phenyl)amino)-1,3,5-triazin-2-yl)phenoxy)-3-fluoro-N-(2-hydroxyethyl)-N-methylpiperidine-1-carboxamide

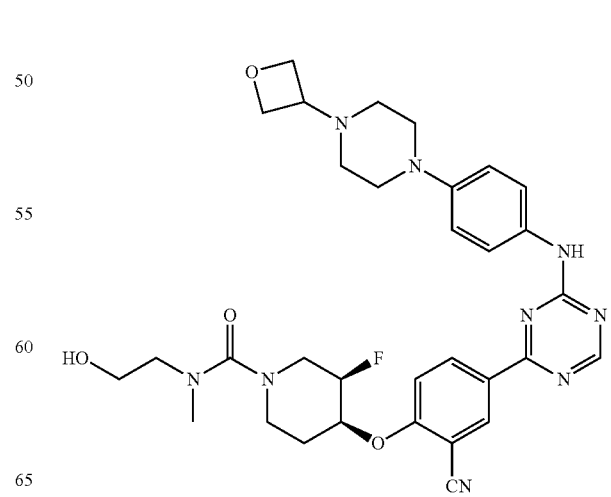

The title compound was prepared following the same procedure reported in Example 423 by coupling 2-(((3R,4S)-3-fluoropiperidin-4-yl)oxy)-5-(4-((4-(4-(oxetan-3-yl)piperazin-1-yl)phenyl)amino)-1,3,5-triazin-2-yl)benzonitrile with 2-(methylamino)ethanol instead of (R)-3-fluoropyrrolidine. LCMS-ESI+ (m/z): [M+H]+ calcd for $C_{32}H_{38}FN_9O_4$: 632.3: found:632.4

Example 429

(3R,4S)-4-(2-cyano-4-(4-((4-(4-(oxetan-3-yl)piperazin-1-yl)phenyl)amino)-1,3,5-triazin-2-yl)phenoxy)-3-fluoro-N-(2-hydroxyethyl)piperidine-1-carboxamide

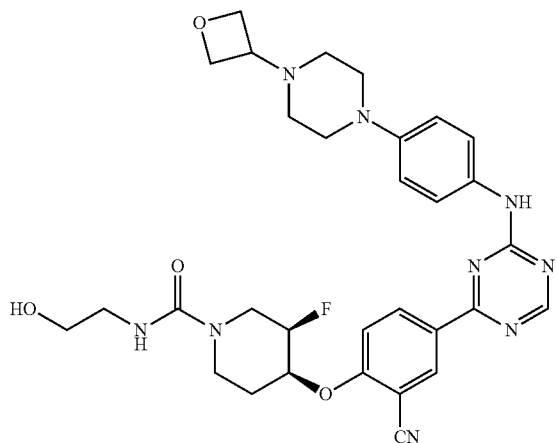 [SMILES: N#Cc1cc(-c2ncnc(Nc3ccc(N4CCN(C5COC5)CC4)cc3)n2)ccc1O[C@H]1CCN(C(=O)NCCO)C[C@H]1F]

The title compound was prepared following the same procedure reported in Example 423 by coupling 2-(((3R,4S)-3-fluoropiperidin-4-yl)oxy)-5-(4-((4-(4-(oxetan-3-yl)piperazin-1-yl)phenyl)amino)-1,3,5-triazin-2-yl)benzonitrile with 2-aminoethanol instead of (R)-3-fluoropyrrolidine. LCMS-ESI+ (m/z): [M+H]+ calcd for $C_{31}H_{36}FN_9O_4$: 618.3: found:618.4 $^1$H NMR (400 MHz, DMSO-$d_6$) δ 10.18 (d, J=22.5 Hz, 1H), 8.75 (s, 1H), 8.65-8.42 (m, 2H), 7.60 (d, J=9.2 Hz, 2H), 7.04 (s, 3H), 6.62 (t, J=5.4 Hz, 1H), 5.18-4.84 (m, 3H), 4.84-4.61 (m, 5H), 4.41 (s, 1H), 3.97 (dt, J=13.3, 6.9 Hz, 1H), 3.80-3.26 (m, 9H), 3.13 (dq, J=36.2, 6.5, 6.0 Hz, 4H), 1.88 (d, J=5.7 Hz, 2H).

Example 430

Cis 2-((3,3-difluoro-1-(2-hydroxyacetyl)-5-methylpiperidin-4-yl)oxy)-5-(4-((4-(4-(oxetan-3-yl)piperazin-1-yl)phenyl)amino)-1,3,5-triazin-2-yl)benzonitrile

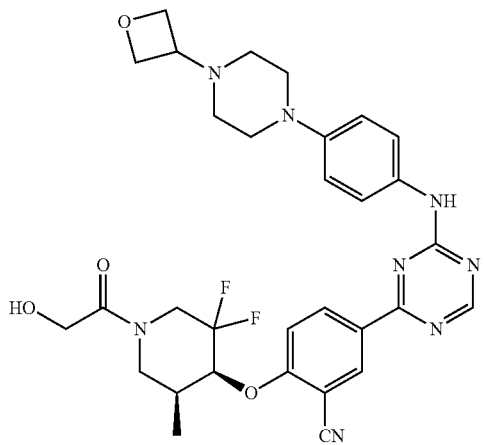 [SMILES: C[C@H]1CN(C(=O)CO)CC(F)(F)[C@H]1Oc1ccc(-c2ncnc(Nc3ccc(N4CCN(C5COC5)CC4)cc3)n2)cc1C#N]

Step1: Synthesis of cis and trans mixture of tert-butyl 4-(2-cyano-4-(4-((4-(4-(oxetan-3-yl)piperazin-1-yl)phenyl)amino)-1,3,5-triazin-2-yl)phenoxy)-3,3-difluoro-5-methylpiperidine-1-carboxylate:

tert-butyl 3,3-difluoro-4-hydroxy-5-methylpiperidine-1-carboxylate (262 mg, 1.04 mmol) was added Me-THF (12 mL) under argon atmosphere and cooled at 0° C. To well stirred solution was added potassium tert-butoxide (117 mg, 1.04 mmol) at one portion and stirred for 30 minutes. To well stirred solution was added 2-fluoro-5-(4-((4-(4-(oxetan-3-yl)piperazin-1-yl)phenyl)amino)-1,3,5-triazin-2-yl)benzonitrile (300 mg, 0.7 mmol) and warmed to room temperature over 5 min and heated at 80° C. overnight. The reaction was quenched with minimum amount of water and diluted with 10% MeOH/DCM to make clear solution. The crude product was adsorbed on silica gel and purified by flash column chromatography on silica gel [Method, 0-50% B over 15 min (A=DCM, B=20% MeOH/DCM)] to afford mixture of 4 isomers. This was subjected for second purification by flash column chromatography on silica gel [Method, 0-40% B over 25 min (A=DCM, B=20% MeOH/DCM)] to isolate the products which was tentatively assigned as cis and trans mixture of enantiomers. Cis and trans isomers: LCMS-ESI+ (m/z): [M+H]+ calcd for $C_{34}H_{40}F_2N_8O_4$: 663.3: found: 663.2. Tentatively assigned mixture of cis enantiomers was subjected for Boc-deprotection followed by coupling with 2-hydroxyacetic acid to afford the title compound. LCMS-ESI+ (m/z): [M+H]+ calcd for $C_{31}H_{36}FN_9O_4$: 621.3: found: 621.3. $^1$H NMR (400 MHz, DMSO-$d_6$) δ 10.21 (d, J=23.5 Hz, 1H), 8.75 (s, 1H), 8.66-8.46 (m, 2H), 7.88-7.45 (m, 3H), 7.04 (s, 2H), 5.30 (s, 1H), 4.74 (s, 5H), 4.50 (s, 1H), 4.17 (dt, J=33.2, 15.9 Hz, 3H), 3.64 (d, J=13.1 Hz, 6H), 3.19-2.72 (m, 5H), 2.23 (d, J=53.3 Hz, 1H), 0.98 (d, J=6.7 Hz, 3H).

Example 431 trans-2-((3,3-difluoro-1-((S)-2-hydroxypropanoyl)-5-methylpiperidin-4-yl)oxy)-5-(4-((4-(4-(oxetan-3-yl)piperazin-1-yl)phenyl)amino)-1,3,5-triazin-2-yl)benzonitrile

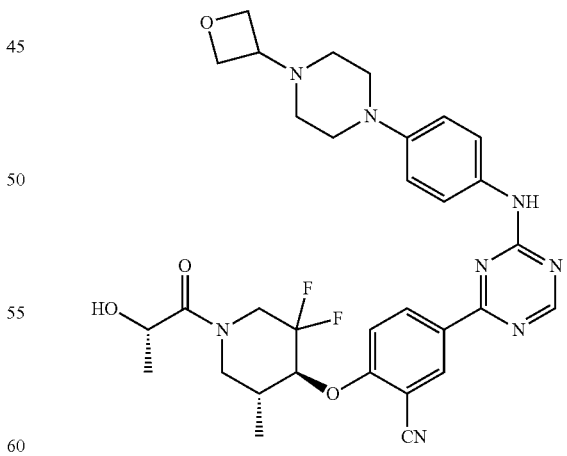

Tentatively assigned mixture of trans isomers from step 1 of Example 430 was subjected for Boc deprotection followed by coupling with (S)-2-hydroxypropanoic acid to afford the title compound. LCMS-ESI+ (m/z): [M+H]+ calcd for $C_{32}H_{36}F_2N_8O_4$: 635.2: found:635.4 $^1$H NMR (400 MHz, DMSO-$d_6$) δ 10.22 (d, J=23.4 Hz, 1H), 8.76 (s, 1H), 8.67-8.45 (m, 2H), 7.62 (d, J=10.0 Hz, 3H), 7.06 (d, J=10.8 Hz, 2H), 5.29-4.90 (m, 2H), 4.75 (d, J=6.3 Hz, 5H), 4.59-4.05 (m, 3H), 3.28-2.67 (m, 6H), 2.07 (d, J=74.5 Hz, 1H), 1.50-1.36 (m, 1H), 1.28-1.13 (m, 3H), 1.00 (d, J=6:1 Hz, 3H).

Example 432 trans-2-((3,3-difluoro-1-(2-hydroxyacetyl)-5-methyl-piperidin-4-yl)oxy)-5-(4-((4-(4-(oxetan-3-yl)piper-azin-1-yl)phenyl)amino)-1,3,5-triazin-2-yl)benzonitrile

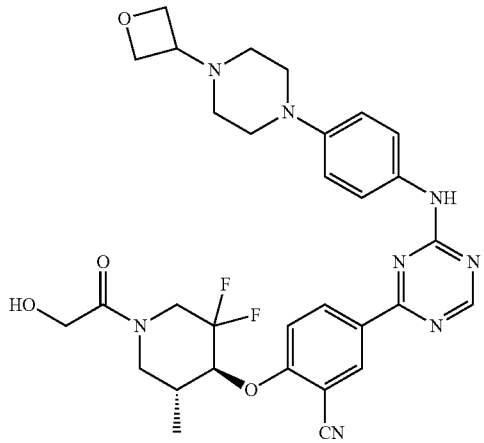 [SMILES: C[C@@H]1CN(C(=O)CO)CC(F)(F)[C@H]1Oc1ccc(-c2ncnc(Nc3ccc(N4CCN(C5COC5)CC4)cc3)n2)cc1C#N]

Tentatively assigned mixture of trans isomers from step 1 of Example 430 was subjected for Boc-deprotection followed by coupling with 2-hydroxyacetic acid to give the title compound. LCMS-ESI⁺ (m/z): [M+H]⁺ calcd for $C_{31}H_{36}FN_9O_4$: 621.3: found:621.3

¹H NMR (400 MHz, DMSO-d₆) δ 10.22 (d, J=25.0 Hz, 1H), 8.76 (s, 1H), 8.75-8.46 (m, 2H), 7.62 (d, J=12.9 Hz, 3H), 7.06 (d, J=10.9 Hz, 2H), 5.35-5.05 (m, 1H), 4.75 (s, 5H), 4.45-4.04 (m, 3H), 3.82 (d, J=13.9 Hz, 1H), 3.54 (s, 7H), 3.28-2.63 (m, 4H), 2.08 (d, J=79.9 Hz, 1H), 0.98 (d, J=6.8 Hz, 3H).

Example 433

2-(((3R,4S)-1-((R)-2-aminopropanoyl)-3-fluoropip-eridin-4-yl)oxy)-5-(4-((4-(4-(oxetan-3-yl)piperazin-1-yl)phenyl)amino)-1,3,5-triazin-2-yl)benzonitrile

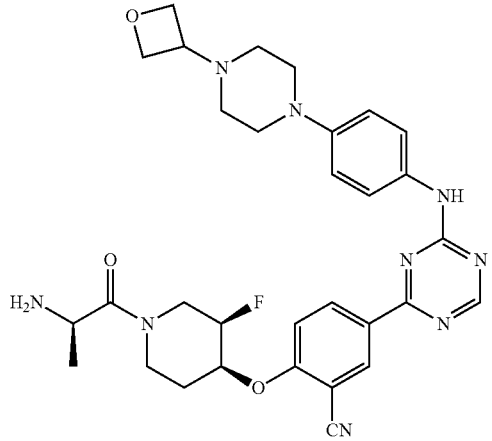 [SMILES: C[C@@H](N)C(=O)N1CC[C@H](Oc2ccc(-c3ncnc(Nc4ccc(N5CCN(C6COC6)CC5)cc4)n3)cc2C#N)[C@H](F)C1]

The title compound was prepared by coupling 2-(((3R,4S)-3-fluoropiperidin-4-yl)oxy)-5-(4-((4-(4-(oxetan-3-yl)piperazin-1-yl)phenyl)amino)-1,3,5-triazin-2-yl)benzonitrile with (R)-2-((tert-butoxycarbonyl)amino)propanoic acid followed by Boc-deprotection. LCMS-ESI⁺ (m/z): [M+H]⁺ calcd for $C_{31}H_{36}FN_9O_3$: 602.3: found:602.4

Example 434

2-(((3R,4S)-1-((R)-2-aminopropanoyl)-3-fluoropip-eridin-4-yl)oxy)-5-(4-((4-(4-(oxetan-3-yl)piperazin-1-yl)phenyl)amino)-1,3,5-triazin-2-yl)benzonitrile

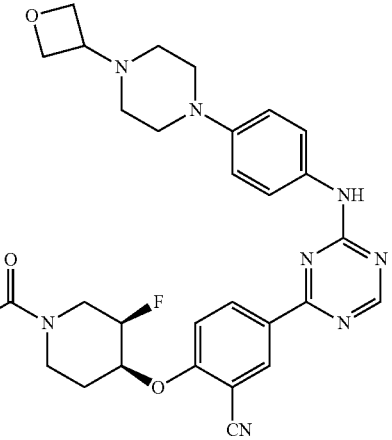

The title compound was prepared by coupling 2-(((3R,4S)-3-fluoropiperidin-4-yl)oxy)-5-(4-((4-(4-(oxetan-3-yl)piperazin-1-yl)phenyl)amino)-1,3,5-triazin-2-yl)benzonitrile with (R)-2-((tert-butoxycarbonyl)amino)propanoic acid followed by Boc-deprotection. LCMS-ESI⁺ (m/z): [M+H]⁺ calcd for $C_{31}H_{36}FN_9O_3$: 602.3: found:602.4. ¹H NMR (400 MHz, DMSO-d₆) δ 10.19 (d, J=26.7 Hz, 1H), 8.76 (s, 1H), 8.67-8.43 (m, 2H), 8.10 (d, J=7.5 Hz, 3H), 7.64 (t, J=8.7 Hz, 2H), 7.04 (s, 2H), 5.28-5.00 (m, 3H), 4.84-4.66 (m, 5H), 4.56-4.30 (m, 3H), 4.19 (dd, J=31.7, 14.4 Hz, 1H), 3.95-3.48 (m, 1H), 3.44-3.22 (m, 2H), 3.15 (s, 5H), 2.13-1.73 (m, 2H), 1.33 (dd, J=14.1, 6.8 Hz, 3H).

Example 435

(R)-5-(4-((4-(4-(oxetan-3-yl)piperazin-1-yl)phenyl) amino)-1,3,5-triazin-2-yl)-2-((1-(5-oxo-2,5-dihydro-1H-1,2,4-triazole-3-carbonyl)pyrrolidin-3-yl)oxy) benzonitrile

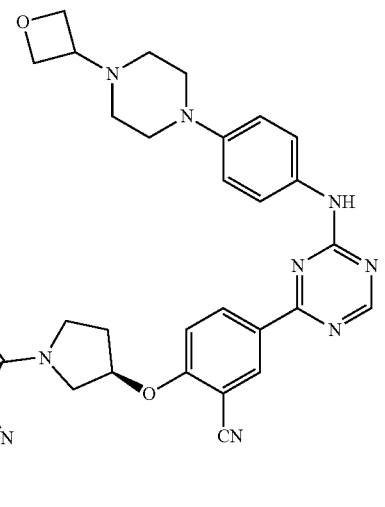

The title compound was prepared by coupling (R)-5-(4-((4-(4-(oxetan-3-yl)piperazin-1-yl)phenyl)amino)-1,3,5-triazin-2-yl)-2-(pyrrolidin-3-yloxy)benzonitrile with 5-oxo-2,5-dihydro-1H-1,2,4-triazole-3-carboxylic acid. LCMS-ESI⁺ (m/z): [M+H]⁺ calcd for $C_{30}H_{31}N_{11}O_4$: 610.3: found:610.4

Example 436

2-(((3R,4S)-3-fluoro-1-((5-oxo-2,5-dihydro-1H-1,2,4-triazol-3-yl)methyl)piperidin-4-yl)oxy)-5-(4-((4-(4-(oxetan-3-yl)piperazin-1-yl)phenyl)amino)-1,3,5-triazin-2-yl)benzonitrile

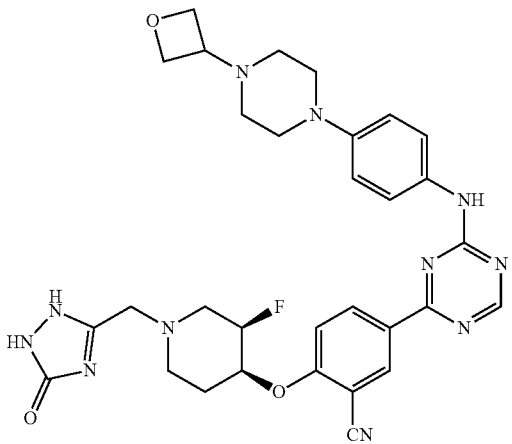 [SMILES: N#Cc1cc(-c2ncnc(Nc3ccc(N4CCN(C5COC5)CC4)cc3)n2)ccc1O[C@H]1CCN(Cc2nc(=O)[nH][nH]2)C[C@H]1F]

2-(((3R,4S)-3-fluoropiperidin-4-yl)oxy)-5-(4-((4-(4-(oxetan-3-yl)piperazin-1-yl)phenyl)amino)-1,3,5-triazin-2-yl)benzonitrile (70 mg, 0.13 mmol) were added 5-(chloromethyl)-1H-1,2,4-triazol-3 (18 mg, 0.13 mmol), IPA (4 mL), and DIPE (0.3 mL) sequentially. The generated HCl gas was flushed with argon balloon and the reaction mixture was heated at 80° C. for 30 minutes. The reaction was cooled to room temperature and the yellow solid was filtered and dried to afford product 2-(((3R,4S)-3-fluoro-1-((5-oxo-2,5-dihydro-1H-1,2,4-triazol-3-yl)methyl)piperidin-4-yl)oxy)-5-(4-((4-(4-(oxetan-3-yl)piperazin-1-yl)phenyl)amino)-1,3,5-triazin-2-yl)benzonitrile. LCMS-ESI⁺ (m/z): [M+H]⁺ calcd for $C_{31}H_{34}FN_{11}O_3$: 628.2: found:628.4

Example 437

2-(((3R,4S)-3-fluoro-1-(5-oxo-2,5-dihydro-1H-1,2,4-triazole-3-carbonyl)piperidin-4-yl)oxy)-5-(4-((4-(4-(oxetan-3-yl)piperazin-1-yl)phenyl)amino)-1,3,5-triazin-2-yl)benzonitrile

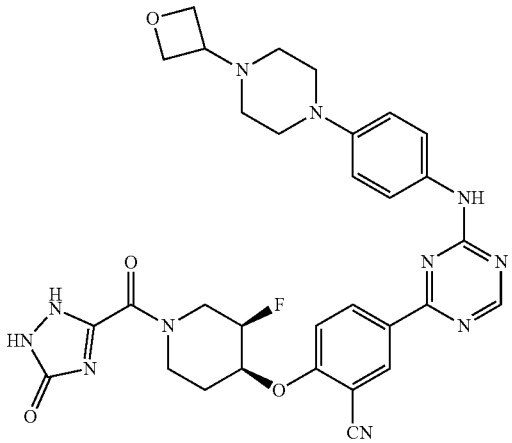 [SMILES: N#Cc1cc(-c2ncnc(Nc3ccc(N4CCN(C5COC5)CC4)cc3)n2)ccc1O[C@H]1CCN(C(=O)c2nc(=O)[nH][nH]2)C[C@H]1F]

The title compound was prepared by coupling 2-(((3R,4S)-3-fluoropiperidin-4-yl)oxy)-5-(4-((4-(4-(oxetan-3-yl)piperazin-1-yl)phenyl)amino)-1,3,5-triazin-2-yl)benzonitrile with 5-oxo-2,5-dihydro-1H-1,2,4-triazole-3-carboxylic acid. LCMS-ESI⁺ (m/z): [M+H]⁺ calcd for $C_{31}H_{32}FN_{11}O_4$: 642.3: found:642.4 ¹H NMR (400 MHz, DMSO-d₆) δ 11.99 (d, J=6.0 Hz, 2H), 10.21 (s, 1H), 10.15 (s, 1H), 8.61-8.50 (m, 2H), 7.63 (d, J=9.2 Hz, 3H), 7.05 (s, 2H), 5.26-4.86 (m, 4H), 4.77 (d, J=6.4 Hz, 5H), 4.65-4.35 (m, 2H), 4.22 (d, J=13.0 Hz, 1H), 3.88 (dd, J=31.2, 14.9 Hz, 1H), 3.53 (td, J=31.9, 13.1 Hz, 2H), 3.24 (s, 1H), 3.13-2.91 (m, 3H), 2.07 (d, J=13.1 Hz, 2H).

Example 438

Trans-2-((1-(2-hydroxyacetyl)-3-(trifluoromethyl)piperidin-4-yl)oxy)-5-(4-((4-(4-(oxetan-3-yl)piperazin-1-yl)phenyl)amino)-1,3,5-triazin-2-yl)benzonitrile

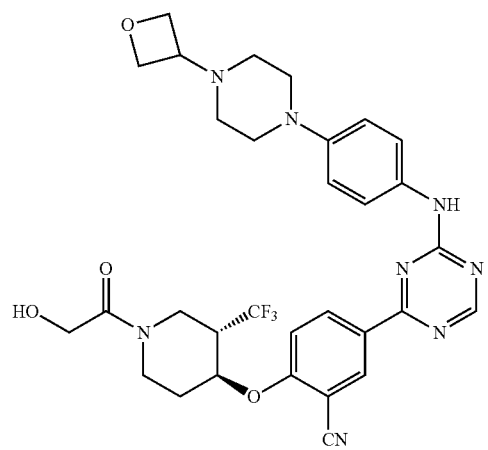 [SMILES: N#Cc1cc(-c2ncnc(Nc3ccc(N4CCN(C5COC5)CC4)cc3)n2)ccc1O[C@H]1CCN(C(=O)CO)C[C@@H]1C(F)(F)F]

Step1: Synthesis of cis and trans mixture of: tert-butyl 4-(2-cyano-4-(4-((4-(4-(oxetan-3-yl)piperazin-1-yl)phenyl)amino)-1,3,5-triazin-2-yl)phenoxy)-3-(trifluoromethyl)piperidine-1-carboxylate: tert-butyl 4-hydroxy-3-(trifluoromethyl)piperidine-1-carboxylate (262 mg, 0.97 mmol) was added Me-THF (12 mL) under argon atmosphere and cooled at 0° C. To well stirred solution was added potassium tert-butoxide (109 mg, 0.97 mmol) at one portion and stirred for 30 minutes. To well stirred solution was added 2-fluoro-5-(4-((4-(4-(oxetan-3-yl)piperazin-1-yl)phenyl)amino)-1,3,5-triazin-2-yl)benzonitrile (300 mg, 0.69 mmol) and warmed to room temperature over 5 min and heated at 80° C. overnight. The reaction was quenched with minimum amount of water and diluted with 10% MeOH/DCM to make clear solution. The crude product was adsorbed on silica gel and purified by flash column chromatography on silica gel [Method, 0-50% B over 15 min (A=DCM, B=20% MeOH/DCM)] to afford mixture of isomers. This was subjected for second purification by flash column chromatography on silica gel [Method, 0-40% B over 25 min (A=DCM, B=20% MeOH/DCM)] to isolate cis and trans isomers (tentatively assigned structures). LCMS-ESI⁺ (m/z): [M+H]⁺ calcd for $C_{34}H_{39}F_3N_8O_4$: 681.3: found:681.2

Step 2: The tentatively assigned trans-isomer mixture from Step 1 was subjected for Boc-deprotection followed by coupling with 2-hydroxyacetic acid to afford the title compound. LCMS-ESI+ (m/z): [M+H]+ calcd for $C_{31}H_{33}F_3N_8O_4$: 639.3: found:639.2
$^1$H NMR (400 MHz, DMSO-d$_6$) δ 10.19 (d, J=19.6 Hz, 1H), 8.75 (s, 1H), 8.66-8.41 (m, 2H), 7.62 (d, J=9.8 Hz, 3H), 7.04 (d, J=8.6 Hz, 2H), 5.38 (d, J=5.0 Hz, 1H), 4.75 (d, J=6.4 Hz, 5H), 4.58-4.30 (m, 2H), 4.29-4.07 (m, 3H), 4.02-3.48 (m, 5H), 3.26 (t, J=13.2 Hz, 2H), 2.97 (d, J=69.7 Hz, 4H), 2.10-1.66 (m, 2H).

Example 439 cis-2-((1-(2-hydroxyacetyl)-3-(trifluoromethyl)piperidin-4-yl)oxy)-5-(4-((4-(4-(oxetan-3-yl)piperazin-1-yl)phenyl)amino)-1,3,5-triazin-2-yl)benzonitrile

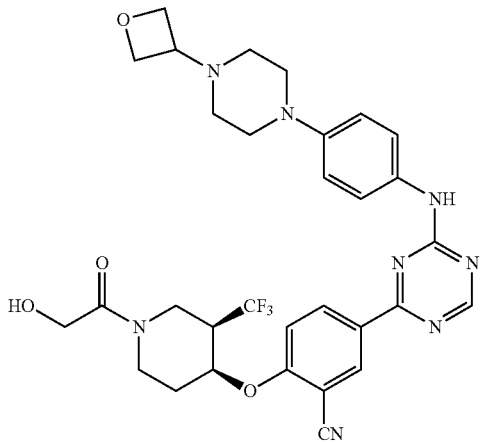 [SMILES: N#Cc1cc(-c2ncnc(Nc3ccc(N4CCN(C5COC5)CC4)cc3)n2)ccc1O[C@H]1CCN(C(=O)CO)C[C@H]1C(F)(F)F]

The tentatively assigned cis-isomer mixture from Step 1 of Example 438 was subjected to Boc-deprotection followed by coupling with 2-hydroxyacetic acid and purification gave the title compound. LCMS-ESI+ (m/z): [M+H]+ calcd for $C_{31}H_{33}F_3N_8O_4$: 639.3: found:639.2. $^1$H NMR (400 MHz, DMSO-d$_6$) δ 10.15 (s, 1H), 8.75 (s, 1H), 8.59 (d, J=9.3 Hz, 1H), 8.54-8.31 (m, 1H), 7.62 (d, J=9.9 Hz, 3H), 7.04 (d, J=11.8 Hz, 2H), 5.39 (s, 1H), 4.74 (s, 5H), 4.50 (s, 1H), 4.16 (d, J=15.9 Hz, 2H), 3.35 (s, 9H), 3.03 (s, 3H), 2.65 (s, 1H), 1.87 (d, J=104.6 Hz, 2H).

Example 440

2-(((4S,5R)-5-fluoro-3,3-dimethylpiperidin-4-yl)oxy)-5-(4-((4-(4-(oxetan-3-yl)piperazin-1-yl)phenyl)amino)-1,3,5-triazin-2-yl)benzonitrile

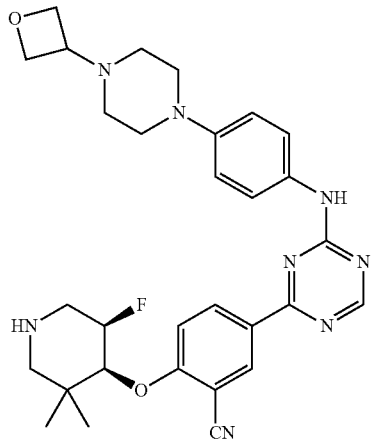 [SMILES: CC1(C)CNC[C@@H](F)[C@H]1Oc1ccc(-c2ncnc(Nc3ccc(N4CCN(C5COC5)CC4)cc3)n2)cc1C#N]

Step 1: Preparation of tert-butyl 4-(2-cyano-4-(4-((4-(4-(oxetan-3-yl)piperazin-1-yl)phenyl)amino)-1,3,5-triazin-2-yl)phenoxy)-5-fluoro-3,3-dimethylpiperidine-1-carboxylate:

tert-butyl 5-fluoro-4-hydroxy-3,3-dimethylpiperidine-1-carboxylate (401 mg, 1.62 mmol) was added Me-THF (16 mL) under argon atmosphere and cooled at 0° C. To well stirred solution was added potassium tert-butoxide (182 mg, 1.62 mmol) at one portion and stirred for 30 minutes. To well stirred solution was added 2-fluoro-5-(4-((4-(4-(oxetan-3-yl)piperazin-1-yl)phenyl)amino)-1,3,5-triazin-2-yl)benzonitrile (500 mg, 1.15 mmol) and warmed to room temperature over 5 min. The reaction was heated at 80° C. overnight. The reaction was quenched with minimum amount of water and diluted with 10% MeOH/DCM to make clear solution. The crude product was adsorbed on silica gel and purified by flash column chromatography on silica gel [Method, 0-50% B over 15 min (A=DCM, B=20% MeOH/DCM)] to afford tert-butyl 4-(2-cyano-4-(4-((4-(4-(oxetan-3-yl)piperazin-1-yl)phenyl)amino)-1,3,5-triazin-2-yl)phenoxy)-5-fluoro-3,3-dimethylpiperidine-1-carboxylate as mixture of cis enantiomers.

Step 2: The mixture of cis enantiomers were separated by chiral separation using chiral column chromatography to afford the two peaks were tentatively assigned as (4S,5R)-tert-butyl 4-(2-cyano-4-(4-((4-(4-(oxetan-3-yl)piperazin-1-yl)phenyl)amino)-1,3,5-triazin-2-yl)phenoxy)-5-fluoro-3,3-dimethylpiperidine-1-carboxylate and (4R,5S)-tert-butyl 4-(2-cyano-4-(4-((4-(4-(oxetan-3-yl)piperazin-1-yl)phenyl)amino)-1,3,5-triazin-2-yl)phenoxy)-5-fluoro-3,3-dimethylpiperidine-1-carboxylate. LCMS-ESI+ (m/z): [M+H]+ calcd for $C_{35}H_{43}FN_8O_4$: 659.3: found:659.2

Step 3: (4S,5R)-tert-butyl 4-(2-cyano-4-(4-((4-(4-(oxetan-3-yl)piperazin-1-yl)phenyl)amino)-1,3,5-triazin-2-yl)phenoxy)-5-fluoro-3,3-dimethylpiperidine-1-carboxylate from step 1 was subjected for Boc-deprotection followed by purification gave the title compound. LCMS-ESI+ (m/z): [M+H]+ calcd for $C_{30}H_{35}FN_8O_2$: 559.3; found:559.2

Example 441

2-(((4S,5R)-5-fluoro-3,3-dimethyl-1-(1-methyl-1H-1,2,3-triazole-4-carbonyl)piperidin-4-yl)oxy)-5-(4-((4-(4-(oxetan-3-yl)piperazin-1-yl)phenyl)amino)-1,3,5-triazin-2-yl)benzonitrile

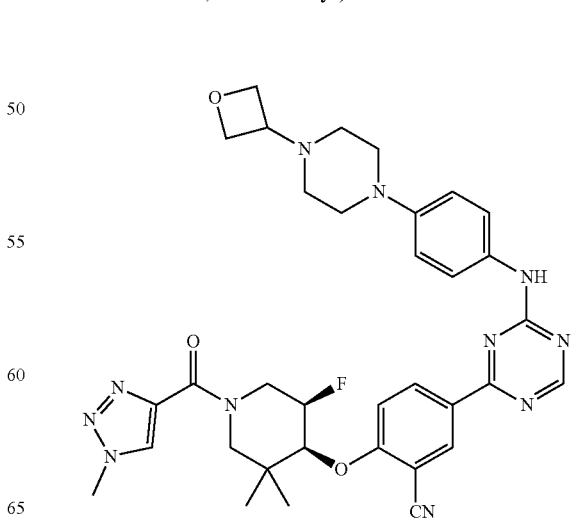

(4S,5R)-tert-butyl 4-(2-cyano-4-(4-((4-(4-(oxetan-3-yl)piperazin-1-yl)phenyl)amino)-1,3,5-triazin-2-yl)phenoxy)-5-fluoro-3,3-dimethylpiperidine-1-carboxylate from Example 440 step 1 was subjected for Boc-deprotection followed by coupling with 1-methyl-1H-1,2,3-triazole-4-carboxylic acid to afford 2-(((4S,5R)-5-fluoro-3,3-dimethyl-1-(1-methyl-1H-1,2,3-triazole-4-carbonyl)piperidin-4-yl)oxy)-5-(4-((4-(4-(oxetan-3-yl)piperazin-1-yl)phenyl)amino)-1,3,5-triazin-2-yl)benzonitrile. LCMS-ESi+ (m/z): [M+H]+ calcd for $C_{34}H_{38}FN_{11}O_3$: 668.3: found:668.2 $^1$H NMR (400 MHz, DMSO-d$_6$) δ 10.20 (d, J=21.1 Hz, 1H), 8.76 (s, 1H), 8.67-8.43 (m, 3H), 7.64 (t, J=12.2 Hz, 3H), 7.05 (s, 2H), 5.30-5.03 (m, 1H), 4.92 (d, J=22.1 Hz, 1H), 4.76 (d, J=6.7 Hz, 5H), 4.52-4.13 (m, 2H), 4.08 (s, 4H), 3.99-3.64 (m, 3H), 3.15 (s, 6H), 1.04 (dd, J=31.0, 17.8 Hz, 6H).

Example 442

2-(((4S,5R)-5-fluoro-3,3-dimethyl-1-(1H-pyrazole-5-carbonyl)piperidin-4-yl)oxy)-5-(4-((4-(4-(oxetan-3-yl)piperazin-1-yl)phenyl)amino)-1,3,5-triazin-2-yl)benzonitrile

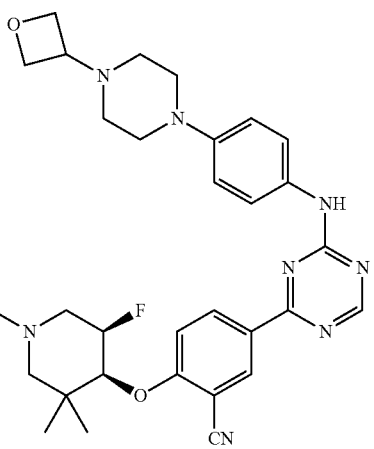

(4S,5R)-tert-butyl 4-(2-cyano-4-(4-((4-(4-(oxetan-3-yl)piperazin-1-yl)phenyl)amino)-1,3,5-triazin-2-yl)phenoxy)-5-fluoro-3,3-dimethylpiperidine-1-carboxylate was subjected for Boc-deprotection followed by coupling with 1H-pyrazole-5-carboxylic acid to afford 2-(((4S,5R)-5-fluoro-3,3-dimethyl-1-(1H-pyrazole-5-carbonyl)piperidin-4-yl)oxy)-5-(4-((4-(4-(oxetan-3-yl)piperazin-1-yl)phenyl)amino)-1,3,5-triazin-2-yl)benzonitrile. LCMS-ESI+ (m/z): [M+H]+ calcd for $C_{34}H_{37}FN_{10}O_3$: 653.3: found:653.2 $^1$H NMR (400 MHz, DMSO-d$_6$) δ 10.19 (d, J=20.7 Hz, 1H), 8.75 (s, 1H), 8.54 (ddd, J=19.7, 8.0, 1.7 Hz, 2H), 7.86-7.70 (m, 1H), 7.71-7.45 (m, 4H), 7.05 (s, 2H), 6.74-6.54 (m, 1H), 5.14 (d, J=47.6 Hz, 1H), 4.92 (d, J=20.9 Hz, 1H), 4.77 (d, J=6.6 Hz, 4H), 4.45 (s, 2H), 4.18 (t, J=15.9 Hz, 1H), 3.92-3.62 (m, 3H), 3.42 (d, J=49.4 Hz, 1H), 3.15 (s, 6H), 1.23-0.81 (m, 6H).

Example 443

2-(((4S,5R)-5-fluoro-1-(3-hydroxypropanoyl)-3,3-dimethylpiperidin-4-yl)oxy)-5-(4-((4-(4-(oxetan-3-yl)piperazin-1-yl)phenyl)amino)-1,3,5-triazin-2-yl)benzonitrile

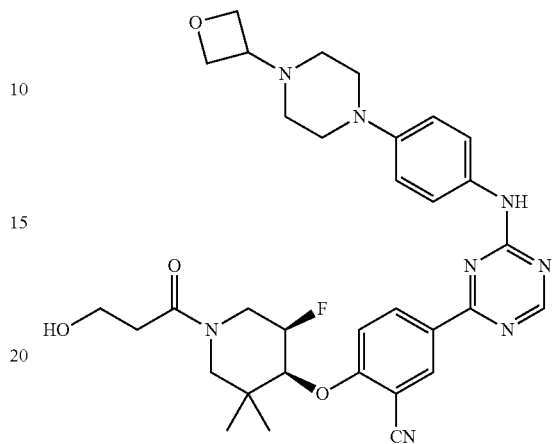

(4S,5R)-tert-butyl 4-(2-cyano-4-(4-((4-(4-(oxetan-3-yl)piperazin-1-yl)phenyl)amino)-1,3,5-triazin-2-yl)phenoxy)-5-fluoro-3,3-dimethylpiperidine-1-carboxylate was subjected for Boc-deprotection followed by coupling with 2-hydroxypropionic acid to afford 2-(((4S,5R)-5-fluoro-1-(3-hydroxypropanoyl)-3,3-dimethylpiperidin-4-yl)oxy)-5-(4-((4-(4-(oxetan-3-yl)piperazin-1-yl)phenyl)amino)-1,3,5-triazin-2-yl)benzonitrile. LCMS-ESI+ (m/z): [M+H]+ calcd for $C_{33}H_{39}FN_8O_4$: 631.3: found:631.2 $^1$H NMR (400 MHz, DMSO-d$_6$) δ 10.19 (d, J=22.0 Hz, 1H), 8.75 (s, 1H), 8.68-8.44 (m, 2H), 7.75-7.49 (m, 3H), 7.05 (d, J=8.4 Hz, 2H), 5.08 (dd, J=48.2, 22.9 Hz, 1H), 4.86 (d, J=21.7 Hz, 1H), 4.75 (d, J=6.2 Hz, 5H), 4.13-3.70 (m, 5H), 3.72-3.46 (m, 3H), 3.30-2.82 (m, 6H), 2.73-2.51 (m, 2H), 1.17-0.84 (m, 6H).

Example 444

2-(((4R,5S)-5-fluoro-3,3-dimethyl-1-((S)-5-oxopyrrolidine-2-carbonyl)piperidin-4-yl)oxy)-5-(4-((4-(4-(oxetan-3-yl)piperazin-1-yl)phenyl)amino)-1,3,5-triazin-2-yl)benzonitrile

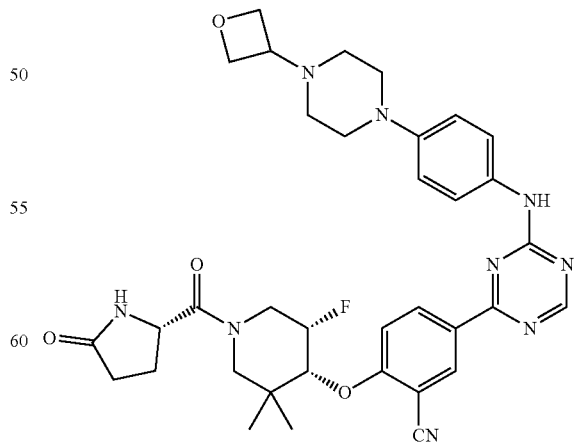

(4R,5S)-tert-butyl 4-(2-cyano-4-(4-((4-(4-(oxetan-3-yl)piperazin-1-yl)phenyl)amino)-1,3,5-triazin-2-yl)phenoxy)-

5-fluoro-3,3-dimethylpiperidine-1-carboxylate was subjected for Boc-deprotection followed by coupling with (S)-5-oxopyrrolidine-2-carboxylic acid to afford 2-(((4R,5S)-5-fluoro-3,3-dimethyl-1-((S)-5-oxopyrrolidine-2-carbonyl)piperidin-4-yl)oxy)-5-(4-((4-(4-(oxetan-3-yl)piperazin-1-yl)phenyl)amino)-1,3,5-triazin-2-yl)benzonitrile. LCMS-ESI⁺ (m/z): [M+H]⁺ calcd for C₃₅H₄₀FN₉O₄: 670.3.3: found: 670.4

Example 445

2-(((4S,5R)-5-fluoro-3,3-dimethyl-1-((S)-5-oxopyrrolidine-2-carbonyl)piperidin-4-yl)oxy)-5-(4-((4-(4-(oxetan-3-yl)piperazin-1-yl)phenyl)amino)-1,3,5-triazin-2-yl)benzonitrile

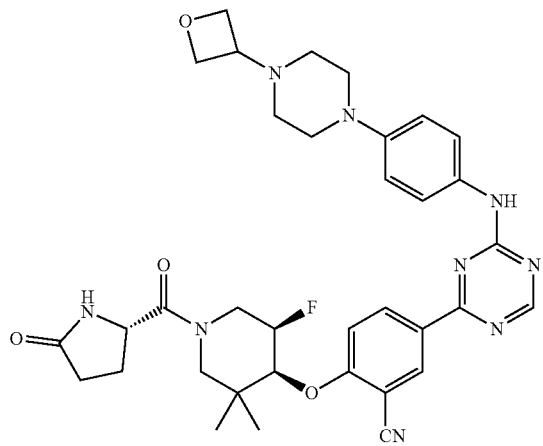 [SMILES: CC1(C)CN(C(=O)[C@@H]2CCC(=O)N2)C[C@@H](F)[C@H]1Oc1ccc(-c2ncnc(Nc3ccc(N4CCN(C5COC5)CC4)cc3)n2)cc1C#N]

(4S,5R)-tert-butyl 4-(2-cyano-4-(4-((4-(4-(oxetan-3-yl)piperazin-1-yl)phenyl)amino)-1,3,5-triazin-2-yl)phenoxy)-5-fluoro-3,3-dimethylpiperidine-1-carboxylate was subjected for Boc-deprotection followed by coupling with (S)-5-oxopyrrolidine-2-carboxylic acid to afford 2-(((4S,5R)-5-fluoro-3,3-dimethyl-1-((S)-5-oxopyrrolidine-2-carbonyl)piperidin-4-yl)oxy)-5-(4-((4-(4-(oxetan-3-yl)piperazin-1-yl)phenyl)amino)-1,3,5-triazin-2-yl)benzonitrile. LCMS-ESI⁺ (m/z): [M+H]⁺ calcd for C₃₅H₄₀FN₉O₄: 670.3: found:670.4
¹H NMR (400 MHz, DMSO-d₆) δ 10.31-10.07 (m, 1H), 8.75 (s, 1H), 8.56 (q, J=12.8, 11.8 Hz, 2H), 7.74 (s, 1H), 7.69-7.48 (m, 3H), 7.04 (s, 2H), 5.12 (dd, J=48.3, 14.4 Hz, 1H), 4.87 (d, J=20.4 Hz, 1H), 4.82-4.69 (m, 5H), 4.63 (ddd, J=21.0, 8.8, 4.1 Hz, 1H), 4.34 (d, J=83.5 Hz, 2H), 4.00-3.34 (m, 4H), 3.15 (s, 5H), 2.34 (ddt, J=16.1, 12.5, 6.6 Hz, 1H), 2.16-2.00 (m, 2H), 2.00-1.76 (m, 1H), 1.19-0.87 (m, 7H).

Example 446

2-((5,5-difluoro-6-oxopiperidin-3-yl)oxy)-5-(4-((4-(4-(oxetan-3-yl)piperazin-1-yl)phenyl)amino)-1,3,5-triazin-2-yl)benzonitrile

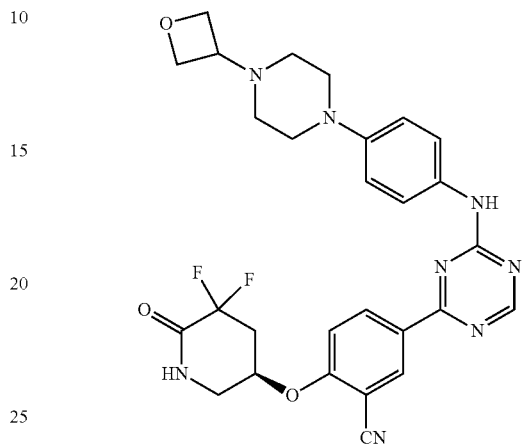

The title compound was prepared by coupling 2-fluoro-5-(4-((4-(4-(oxetan-3-yl)piperazin-1-yl)phenyl)amino)-1,3,5-triazin-2-yl)benzonitrile with 3,3-difluoro-5-hydroxypiperidin-2-one. LCMS-ESI⁺ (m/z): [M+H]⁺ calcd for C₂₈H28F₂N₈O3: 563.2: found:563.3

Example 447

2-((5,5-difluoro-6-oxopiperidin-3-yl)oxy)-5-(4-((4-(4-(oxetan-3-yl)piperazin-1-yl)phenyl)amino)-1,3,5-triazin-2-yl)benzamide

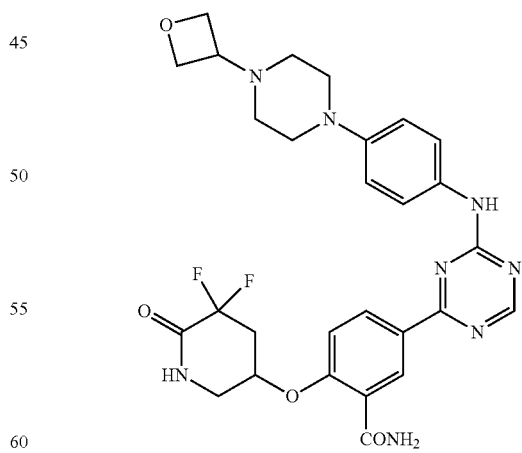

The title compound 2-((5,5-difluoro-6-oxopiperidin-3-yl)oxy)-5-(4-((4-(4-(oxetan-3-yl)piperazin-1-yl)phenyl)amino)-1,3,5-triazin-2-yl)benzamide was isolated as byproduct from example 32. LCMS-ESI⁺ (m/z): [M+H]⁺ calcd for C₂₈H₃₀F₂N₈O₄: 581.2: found:581.2

Example 448

2-(((3R,4S)-3-fluoro-1-(1-(2-hydroxyethyl)-1H-pyrazole-5-carbonyl)piperidin-4-yl)oxy)-5-(4-((4-(4-(oxetan-3-yl)piperazin-1-yl)phenyl)amino)-1,3,5-triazin-2-yl)benzonitrile

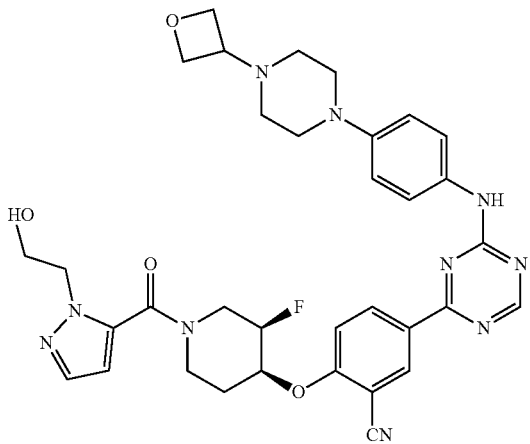 [SMILES: N#Cc1cc(-c2ncnc(Nc3ccc(N4CCN(C5COC5)CC4)cc3)n2)ccc1O[C@H]1CCN(C(=O)c2ccnn2CCO)C[C@H]1F]

The title compound was prepared by coupling 2-(((3R,4S)-3-fluoropiperidin-4-yl)oxy)-5-(4-((4-(4-(oxetan-3-yl)piperazin-1-yl)phenyl)amino)-1,3,5-triazin-2-yl)benzonitrile with 1-(2-hydroxyethyl)-1H-pyrazole-5-carboxylic acid. LCMS-ESI$^+$ (m/z): [M+H]$^+$ calcd for $C_{34}H_{37}FN_{10}O_3$: 669.3: found:669.4

Example 449

2-(((4R,5S)-1-(2-cyanoacetyl)-5-fluoro-3,3-dimethylpiperidin-4-yl)oxy)-5-(4-((4-(4-(oxetan-3-yl)piperazin-1-yl)phenyl)amino)-1,3,5-triazin-2-yl)benzonitrile

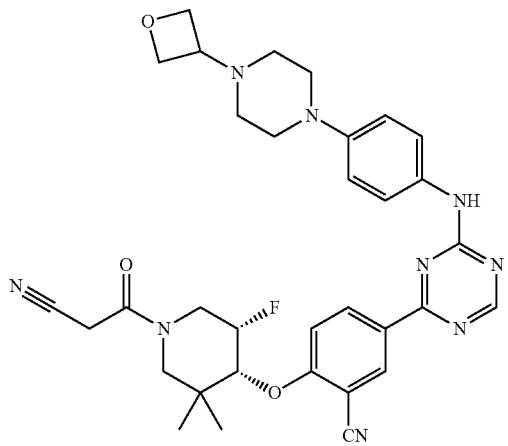 [SMILES: CC1(C)CN(C(=O)CC#N)C[C@H](F)[C@@H]1Oc1ccc(-c2ncnc(Nc3ccc(N4CCN(C5COC5)CC4)cc3)n2)cc1C#N]

(4R,5S)-tert-butyl 4-(2-cyano-4-(4-((4-(4-(oxetan-3-yl)piperazin-1-yl)phenyl)amino)-1,3,5-triazin-2-yl)phenoxy)-5-fluoro-3,3-dimethylpiperidine-1-carboxylate was subjected for Boc-deprotection followed by coupling with 2-cyanoacetic acid to afford the title compound after purification. LCMS-ESI$^+$ (m/z): [M+H]$^+$ calcd for $C_{33}H_{36}FN_9O_3$: 626.3: found:626.4

Example 450

2-(((4S,5R)-1-(2-cyanoacetyl)-5-fluoro-3,3-dimethylpiperidin-4-yl)oxy)-5-(4-((4-(4-(oxetan-3-yl)piperazin-1-yl)phenyl)amino)-1,3,5-triazin-2-yl)benzonitrile

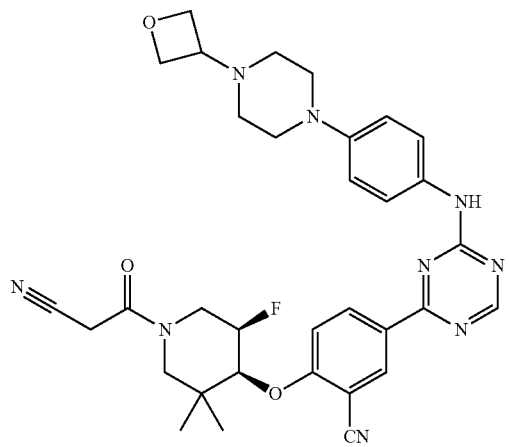 [SMILES: CC1(C)CN(C(=O)CC#N)C[C@@H](F)[C@H]1Oc1ccc(-c2ncnc(Nc3ccc(N4CCN(C5COC5)CC4)cc3)n2)cc1C#N]

(4S,5R)-tert-butyl 4-(2-cyano-4-(4-((4-(4-(oxetan-3-yl)piperazin-1-yl)phenyl)amino)-1,3,5-triazin-2-yl)phenoxy)-5-fluoro-3,3-dimethylpiperidine-1-carboxylate was subjected for Boc-deprotection followed by coupling with 2-cyanoacetic acid, followed by reverse phase purification gave the title compound. LCMS-ESI$^+$ (m/z): [M+H]$^+$ calcd for $C_{33}H_{36}FN_9O_3$: 626.3: found:626.4. $^1$H NMR (400 MHz, DMSO-$d_6$) δ 10.18 (d, J=22.0 Hz, 1H), 8.75 (s, 1H), 8.66-8.43 (m, 2H), 7.73-7.46 (m, 3H), 7.04 (d, J=9.4 Hz, 2H), 5.13 (dd, J=47.1, 18.5 Hz, 1H), 4.99-4.81 (m, 1H), 4.81-4.64 (m, 5H), 4.30-3.95 (m, 3H), 3.86-3.60 (m, 3H), 3.42 (d, J=14.4 Hz, 2H), 3.22-2.88 (m, 5H), 1.15-0.89 (m, 6H).

Example 451

2-(((3R,4S)-3-fluoro-1-(3-methyl-1H-1,2,4-triazole-5-carbonyl)piperidin-4-yl)oxy)-5-(4-((4-(4-(oxetan-3-yl)piperazin-1-yl)phenyl)amino)-1,3,5-triazin-2-yl)benzonitrile

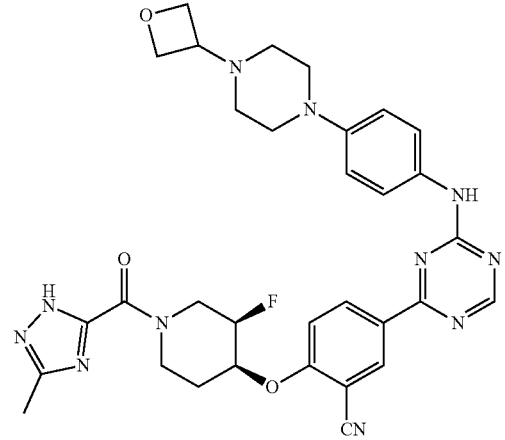 [SMILES: Cc1n[nH]c(C(=O)N2CC[C@H](Oc3ccc(-c4ncnc(Nc5ccc(N6CCN(C7COC7)CC6)cc5)n4)cc3C#N)[C@H](F)C2)n1]

The title compound was prepared by coupling 2-(((3R,4S)-3-fluoropiperidin-4-yl)oxy)-5-(4-((4-(4-(oxetan-3-yl)piperazin-1-yl)phenyl)amino)-1,3,5-triazin-2-yl)benzonitrile with 3-methyl-1H-1,2,4-triazole-5-carboxylic acid. LCMS-ESI+ (m/z): [M+H]+ calcd for $C_{32}H_{34}FN_{11}O_3$: 640.3; found:640.6 $^1$H NMR (400 MHz, DMSO-$d_6$) δ 10.18 (d, J=20.6 Hz, 1H), 8.75 (s, 1H), 8.64-8.46 (m, 2H), 7.61 (t, J=10.3 Hz, 4H), 7.03 (d, J=9.5 Hz, 2H), 5.26-5.02 (m, 3H), 4.75 (d, J=6.4 Hz, 5H), 4.60-4.20 (m, 2H), 3.79 (s, 1H), 3.61-3.20 (m, 3H), 3.19-2.86 (m, 5H), 2.36 (s, 3H), 2.13-1.83 (m, 2H).

Example 452

(S)-2-((3,3-difluoro-1-(3-methyl-1H-1,2,4-triazole-5-carbonyl)piperidin-4-yl)oxy)-5-(4-((4-(4-(oxetan-3-yl)piperazin-1-yl)phenyl)amino)-1,3,5-triazin-2-yl)benzonitrile.

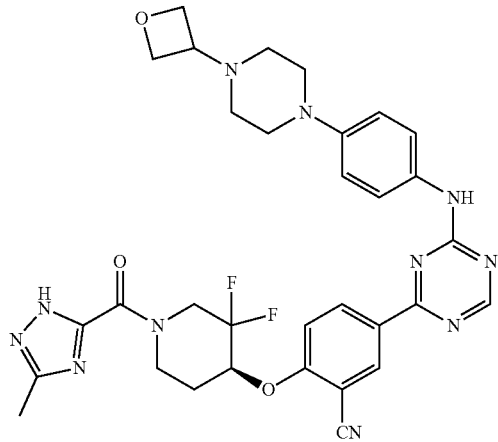 [SMILES: Cc1n[nH]c(C(=O)N2CC[C@H](Oc3ccc(-c4ncnc(Nc5ccc(N6CCN(C7COC7)CC6)cc5)n4)cc3C#N)C(F)(F)C2)n1]

The title compound was prepared by coupling (S)-2-((3,3-difluoropiperidin-4-yl)oxy)-5-(4-((4-(4-(oxetan-3-yl)piperazin-1-yl)phenyl)amino)-1,3,5-triazin-2-yl)benzonitrile with 3-methyl-1H-1,2,4-triazole-5-carboxylic acid. LCMS-ESI+ (m/z): [M+H]+ calcd for $C_{32}H_{33}F_2N_{11}O_3$: 658.3; found:658.4 $^1$H NMR (400 MHz, DMSO-$d_6$) δ 10.20 (d, J=20.6 Hz, 1H), 8.76 (s, 1H), 8.69-8.45 (m, 2H), 7.64 (dd, J=26.0, 11.8 Hz, 4H), 7.04 (s, 2H), 5.43 (d, J=8.8 Hz, 1H), 4.85-4.62 (m, 4H), 4.51-4.18 (m, 2H), 4.13-3.47 (m, 7H), 3.04 (s, 5H), 2.38 (d, J=3.7 Hz, 3H), 2.20 (s, 1H), 1.96 (d, J=20.7 Hz, 1H).

Example 453

5-(4-((1-(difluoromethyl)-1H-pyrazol-4-yl)amino)-1,3,5-triazin-2-yl)-2-(((3R,4S)-3-fluoropiperidin-4-yl)oxy)benzonitrile

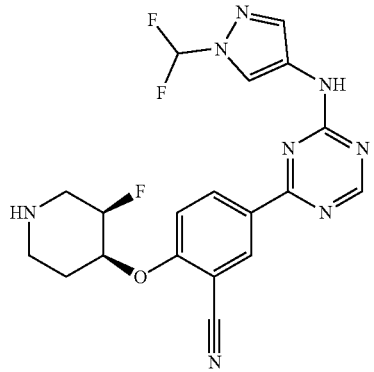 [SMILES: N#Cc1cc(-c2ncnc(Nc3cnn(C(F)F)c3)n2)ccc1O[C@H]1CCNC[C@H]1F]

Step-1: To solution of 2,4-dichloro-1,3,5-triazine (1.46 g, 9.77 mmol) in DMF (9 mL) at 0° C. under nitrogen atmosphere were added DIPEA (2.6 mL), solution of 1-(difluoromethyl)-1H-pyrazol-4-amine (1 g, 7.5 mmol) in DMF (9 mL) at once. The reaction mixture was stirred at 0° C. for 1 h and at room temperature for 2 h. Solvent was concentrated to dryness under reduced pressure. The crude product was dissolved in 10% MeOH\DCM. The crude product was adsorbed on silica gel and solvent was concentrated under reduced pressure. The crude product was purified by flash column chromatography on silica gel [Method, 10-60% B over 15 min (A=DCM, B=20% MeOH/DCM)] to afford product 4-chloro-N-(1-(difluoromethyl)-1H-pyrazol-4-yl)-1,3,5-triazin-2-amine. LCMS-ESI+ (m/z): [M+H]+ calcd for $C_7H_5ClF_2N_6$: 247.0 found:347.2.

Step-2: A mixture of 4-chloro-N-(1-(difluoromethyl)-1H-pyrazol-4-yl)-1,3,5-triazin-2-amine (500 mg, 2.02 mmol), 2-fluoro-5-(4,4,5,5-tetramethyl-1,3,2-dioxaborolan-2-yl)benzonitrile (551 mg, 2.2 mmol) and Pd(PPh$_3$)$_4$ (117 mg, 0.1 mmol) was taken up in 1,2-DME (10 mL) in a 12 mL microwave vial. To this mixture was added solution of sodium carbonate (644 mg 6.08 mmol) in water (5 mL). The mixture heated at 120° C. for 30 minutes. The reaction mixture was diluted with 30% MeOH/DCM (50 mL) and filtered through short pad of silica gel and washed with 30% MeOH/DCM (20 mL×2). The filtrate was adsorbed on silica gel and solvent was concentrated under reduced pressure. The crude product was purified by flash column chromatography on silica gel to afford 5-(4-((1-(difluoromethyl)-1H-pyrazol-4-yl)amino)-1,3,5-triazin-2-yl)-2-fluorobenzonitrile. LCMS-ESI+ (m/z): [M+H]+ calcd for $C_{14}H_8F_3N_7$: 332.1; found:332.2

Step-3: (3R,4S)-tert-butyl 3-fluoro-4-hydroxypiperidine-1-carboxylate (450 mg, 1.36 mmol) was added Me-THF (20 mL) under argon atmosphere and cooled at 0° C. To well stirred solution was added potassium tert-butoxide (213 mg, 1.9 mmol) at one portion and stirred for 30 minutes. To well stirred solution was added 5-(4-((1-(difluoromethyl)-1H-pyrazol-4-yl)amino)-1,3,5-triazin-2-yl)-2-fluorobenzonitrile (450 mg, 1.35 mmol) and warmed to room temperature over 10 min. The reaction was heated at 80° C. overnight. The reaction was quenched with minimum amount of water and diluted with 10% MeOH/DCM to make clear solution. The crude product was adsorbed on silica gel and purified by flash column chromatography on silica gel [Method, 0-50% B over 15 min (A=DCM, B=20% MeOH/DCM)] to afford (3R,4S)-tert-butyl 4-(2-cyano-4-(4-((1-(difluoromethyl)-1H-pyrazol-4-yl)amino)-1,3,5-triazin-2-yl)phenoxy)-3-fluoropiperidine-1-carboxylate. LCMS-ESI+ (m/z): [M+H]+ calcd for $C_{24}H_{25}F_3N_8O_3$: 531.2; found: 631.4

Step-4: (3R,4S)-tert-butyl 4-(2-cyano-4-(4-((4-(4-(oxetan-3-yl)piperazin-1-yl)phenyl)amino)-1,3,5-triazin-2-yl)phenoxy)-3-fluoropiperidine-1-carboxylate (60 mg, 0.11 mmol) was dissolved in 20% TFA/DCM (5 mL) and stirred at room temperature for 1 h. The solvent was concentrated under reduced pressure to afford 5-(4-((1-(difluoromethyl)-1H-pyrazol-4-yl)amino)-1,3,5-triazin-2-yl)-2-(((3R,4S)-3-fluoropiperidin-4-yl)oxy)benzonitrile. LCMS-ESI+ (m/z): [M+H]+ calcd for $C_{19}H_{17}F_3N_8O$: 431.2: found:431.3

Example 454

5-(4-((1-(difluoromethyl)-1H-pyrazol-4-yl)amino)-1,3,5-triazin-2-yl)-2-(((3R,4S)-3-fluoro-1-(2-hydroxyacetyl)piperidin-4-yl)oxy)benzonitrile

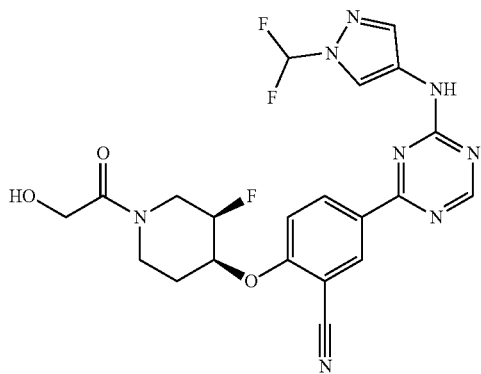 [SMILES: N#Cc1cc(-c2ncnc(Nc3cnn(C(F)F)c3)n2)ccc1O[C@H]1CCN(C(=O)CO)C[C@H]1F]

To solution of 5-(4-((1-(difluoromethyl)-1H-pyrazol-4-yl)amino)-1,3,5-triazin-2-yl)-2-(((3R,4S)-3-fluoropiperidin-4-yl)oxy)benzonitrile (Example 42) (48 mg, 0.11 mmol), 2-hydroxyacetic acid (17 mg, 0.22 mmol), HATU (53 mg, 0.22 mmol) in DMF (4 mL) was added DIPEA (0.24 mL) in a 25 mL round bottom flask and flushed with argon gas. This reaction mixture was stirred at room temperature overnight. Solvent was concentrated and the crude product purified via prep HPLC (5-95% acetonitrile in water, 0.1% trifluoroacetic acid buffer) to isolate 5-(4-((1-(difluoromethyl)-1H-pyrazol-4-yl)amino)-1,3,5-triazin-2-yl)-2-(((3R,4S)-3-fluoro-1-(2-hydroxyacetyl)piperidin-4-yl)oxy)benzonitrile. LCMS-ESI$^+$ (m/z): [M+H]$^+$ calcd for $C_{21}H_{19}F_3N_8O_3$: 489.2: found:489.3. $^1$H NMR (400 MHz, DMSO-d$_6$) δ 10.55 (d, J=6.3 Hz, 1H), 8.83 (d, J=41.4 Hz, 1H), 8.66-8.52 (m, 2H), 8.42 (d, J=2.8 Hz, 1H), 8.03-7.76 (m, 2H), 7.63 (d, J=9.2 Hz, 1H), 5.30-4.85 (m, 2H), 4.41-3.81 (m, 3H), 3.73-3.34 (m, 3H), 3.14 (t, J=11.9 Hz, 1H), 2.07-1.66 (m, 2H).

Example 455

5-(4-((1-(difluoromethyl)-1H-pyrazol-4-yl)amino)-1,3,5-triazin-2-yl)-2-(((3R,4S)-3-fluoro-1-(3-hydroxypropanoyl)piperidin-4-yl)oxy)benzonitrile

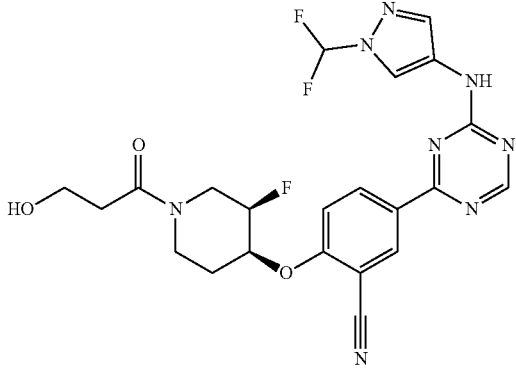 [SMILES: N#Cc1cc(-c2ncnc(Nc3cnn(C(F)F)c3)n2)ccc1O[C@H]1CCN(C(=O)CCO)C[C@H]1F]

The title compound was prepared by coupling 5-(4-((1-(difluoromethyl)-1H-pyrazol-4-yl)amino)-1,3,5-triazin-2-yl)-2-(((3R,4S)-3-fluoropiperidin-4-yl)oxy)benzonitrile with 3-hydroxypropanoic acid. LCMS-ESI$^+$ (m/z): [M+H]$^+$ calcd for $C_{22}H_{21}F_3N_8O_3$: 503.2: found:503.3. $^1$H NMR (400 MHz, DMSO-d$_6$) δ 10.55 (d, J=6.8 Hz, 1H), 8.83 (d, J=41.4 Hz, 1H), 8.66-8.51 (m, 2H), 8.42 (d, J=3.3 Hz, 1H), 8.05-7.56 (m, 3H), 5.26-4.84 (m, 2H), 4.40-3.74 (m, 2H), 3.62 (q, J=9.0, 7.8 Hz, 4H), 3.08 (t, J=11.6 Hz, 1H), 2.56 (dt, J=16.8, 7.4 Hz, 2H), 2.08-1.67 (m, 2H).

Example 456

5-(4-((1-(difluoromethyl)-1H-pyrazol-4-yl)amino)-1,3,5-triazin-2-yl)-2-(((3R,4S)-1-((S)-2,3-dihydroxypropanoyl)-3-fluoropiperidin-4-yl)oxy)benzonitrile

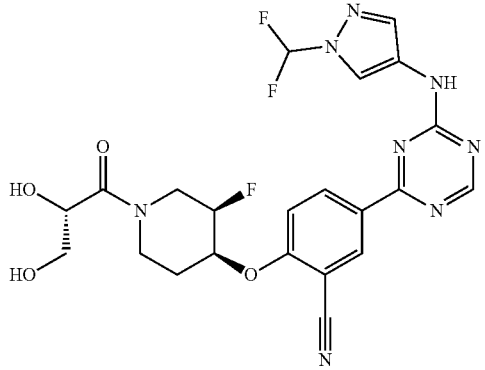 [SMILES: N#Cc1cc(-c2ncnc(Nc3cnn(C(F)F)c3)n2)ccc1O[C@H]1CCN(C(=O)[C@@H](O)CO)C[C@H]1F]

The title compound was prepared by coupling 5-(4-((1-(difluoromethyl)-1H-pyrazol-4-yl)amino)-1,3,5-triazin-2-yl)-2-(((3R,4S)-3-fluoropiperidin-4-yl)oxy)benzonitrile with (S)-2,3-dihydroxypropanoic acid. LCMS-ESI$^+$ (m/z): [M+H]$^+$ calcd for $C_{22}H_{21}F_3N_8O_4$: 519.2: found:519.3 $^1$H NMR (400 MHz, DMSO-d$_6$) δ 10.55 (d, J=7.2 Hz, 1H), 8.84 (d, J=41.5 Hz, 1H), 8.67-8.50 (m, 2H), 8.42 (d, J=3.7 Hz, 1H), 8.07-7.76 (m, 1H), 7.73-7.49 (m, 1H), 7.36-7.03 (m, 1H), 5.27-4.89 (m, 4H), 4.65 (d, J=40.8 Hz, 1H), 4.35 (d, J=34.0 Hz, 2H), 3.93 (s, 1H), 3.82-3.31 (m, 3H), 1.98 (s, 2H).

Example 457

5-(4-((1-(difluoromethyl)-1H-pyrazol-4-yl)amino)-1,3,5-triazin-2-yl)-2-(((3R,4S)-3-fluoro-1-((S)-2-hydroxypropanoyl)piperidin-4-yl)oxy)benzonitrile

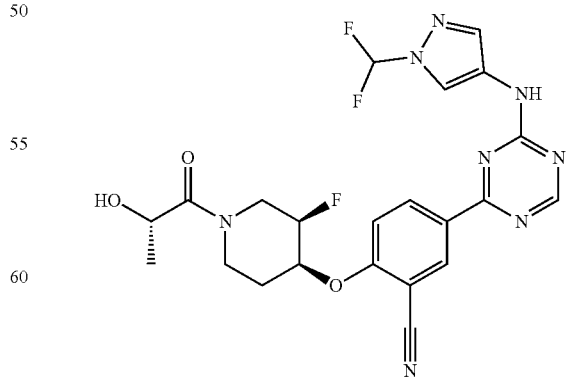

The title compound was prepared by coupling 5-(4-((1-(difluoromethyl)-1H-pyrazol-4-yl)amino)-1,3,5-triazin-2- yl)-2-(((3R,4S)-3-fluoropiperidin-4-yl)oxy)benzonitrile with (S)-2-hydroxypropanoic acid. LCMS-ESI⁺ (m/z): [M+H]⁺ calcd for C₂₂H₂₁F₃N₈O₃: 503.2: found:503.3 ¹H NMR (400 MHz, DMSO-d₆) δ 10.55 (d, J=6.5 Hz, 1H), 8.83 (d, J=41.4 Hz, 1H), 8.64-8.50 (m, 2H), 8.42 (d, J=3.4 Hz, 1H), 8.07-7.75 (m, 2H), 7.72-7.56 (m, 1H), 5.24-4.90 (m, 2H), 4.68-3.82 (m, 4H), 3.77-3.07 (m, 2H), 1.91 (d, J=55.7 Hz, 2H), 1.19 (dd, J=6.5, 4.0 Hz, 3H).

Example 458

5-(4-((1-(tert-butyl)-1H-pyrazol-4-yl)amino)-1,3,5-triazin-2-yl)-2-(((3R,4S)-3-fluoro-1-(3-hydroxypropanoyl)piperidin-4-yl)oxy)benzonitrile

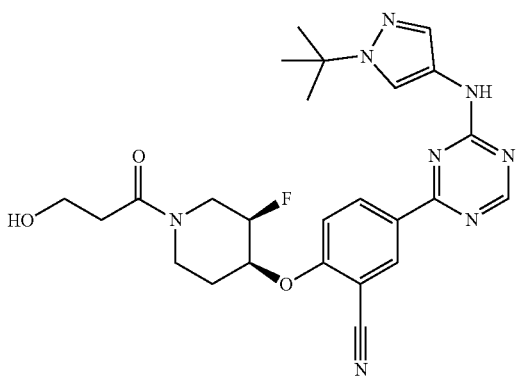 [SMILES: CC(C)(C)n1cc(Nc2ncnc(-c3ccc(O[C@H]4CCN(C(=O)CCO)C[C@H]4F)c(C#N)c3)n2)cn1]

The title compound was prepared by coupling 5-(4-((1-(tert-butyl)-1H-pyrazol-4-yl)amino)-1,3,5-triazin-2-yl)-2-(((3R,4S)-3-fluoropiperidin-4-yl)oxy)benzonitrile with 3-hydroxypropanoic acid. LCMS-ESI⁺ (m/z): [M+H]⁺ calcd for C₂₅H₂₉FN₈O₃: 509.2: found: 509.3 ¹H NMR (400 MHz, DMSO-d₆) δ 10.35-9.98 (m, 1H), 8.75 (d, J=40.3 Hz, 1H), 8.64-8.48 (m, 2H), 8.04 (d, J=39.8 Hz, 1H), 7.74-7.52 (m, 1H), 7.38-7.01 (m, 1H), 5.30-4.86 (m, 2H), 4.40-3.73 (m, 4H), 3.63 (t, J=6.6 Hz, 2H), 3.47-2.94 (m, 1H), 2.77-2.50 (m, 2H), 2.11-1.73 (m, 2H), 1.53 (d, J=18.3 Hz, 9H).

Example 459

5-(4-((1-(tert-butyl)-1H-pyrazol-4-yl)amino)-1,3,5-triazin-2-yl)-2-(((3R,4S)-1-(2-cyanoacetyl)-3-fluoropiperidin-4-yl)oxy)benzonitrile

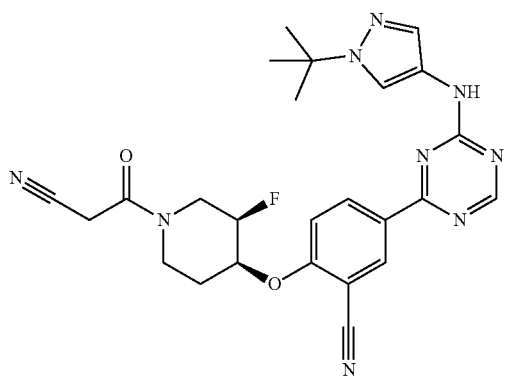 [SMILES: CC(C)(C)n1cc(Nc2ncnc(-c3ccc(O[C@H]4CCN(C(=O)CC#N)C[C@H]4F)c(C#N)c3)n2)cn1]

The title compound was prepared by coupling 5-(4-((1-(tert-butyl)-1H-pyrazol-4-yl)amino)-1,3,5-triazin-2-yl)-2-(((3R,4S)-3-fluoropiperdin-4-yl)oxy)benzonitrile with 2-cyanoacetic acid. LCMS-ESI⁺ (m/z): [M+H]⁺ calcd for C₂₅H₂₆FN₉O₂: 504.2: found: 504.3 ¹H NMR (400 MHz, DMSO-d₆) δ 10.27 (d, J=22.4 Hz, 1H), 8.75 (d, J=40.3 Hz, 1H), 8.62-8.51 (m, 2H), 8.04 (d, J=38.6 Hz, 1H), 7.72-7.55 (m, 2H), 5.26-4.91 (m, 2H), 4.44-3.79 (m, 3H), 3.74-3.14 (m, 3H), 2.09-1.77 (m, 2H), 1.53 (d, J=18.1 Hz, 9H).

Example 460

2-(((S)-3,3-difluoro-1-((S)-2-hydroxypropanoyl)piperidin-4-yl)oxy)-5-(4-((4-((R)-2-(hydroxymethyl)morpholino)phenyl)amino)-1,3,5-triazin-2-yl)benzonitrile

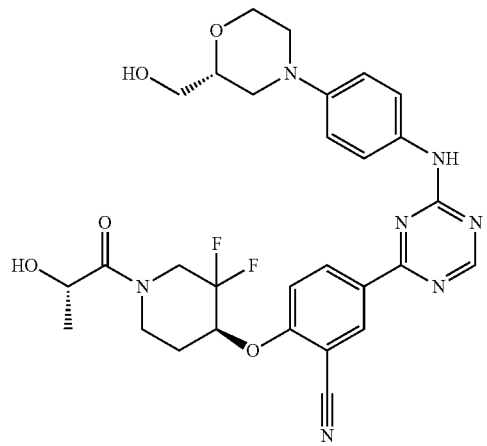 [SMILES: C[C@H](O)C(=O)N1CC[C@H](Oc2ccc(-c3ncnc(Nc4ccc(N5CCO[C@@H](CO)C5)cc4)n3)cc2C#N)C(F)(F)C1]

The title compound was prepared following a similar procedure reported in Example 218 using (R)-(4-(4-aminophenyl)morpholin-2-yl)methanol, (S)-tert-butyl 3,3-difluoro-4-hydroxypiperidine-1-carboxylate and (S)-2-hydroxypropanoic acid. ¹H NMR (400 MHz, DMSO-d₆) δ 10.18 (s, 1H), 8.75 (s, 1H), 8.60 (m, 2H), 7.69-7.59 (m, 3H), 6.99-6.91 (m, 2H), 5.37 (s, 1H), 5.22 (d, J=6.9 Hz, 1H), 4.76 (t, J=5.7 Hz, 1H), 4.57-4.39 (m, 1H), 4.17 (s, 1H), 4.08-3.70 (m, 3H), 3.69-3.36 (m, 4H), 3.04-2.87 (m, 1H), 2.64 (s, 1H), 2.44-2.35 (m, 2H), 2.23-1.68 (m, 3H), 1.20 (d, J=6.3 Hz, 3H). LCMS-ESI⁺ (m/z): [M+H]⁺ calcd. for C₂₉H₃₁F₂N₇O₅: 596.2; found:596.2.

Example 461

2-(((3R,4S)-3-fluoro-1-((S)-2-hydroxy-3-methylbutanoyl)piperidin-4-yl)oxy)-5-(4-((4-(4-(oxetan-3-yl)piperazin-1-yl)phenyl)amino)-1,3,5-triazin-2-yl)benzonitrile

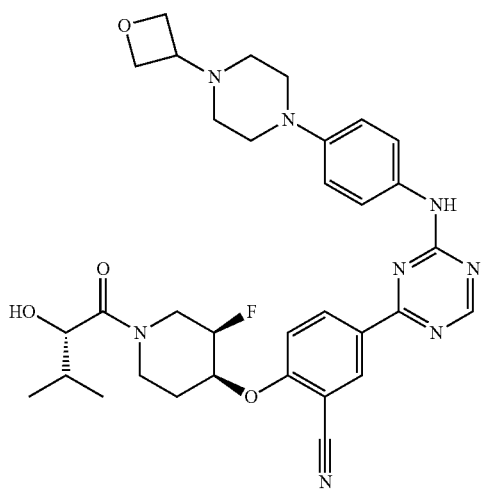 [SMILES: CC(C)[C@H](O)C(=O)N1CC[C@H](Oc2ccc(-c3ncnc(Nc4ccc(N5CCN(C6COC6)CC5)cc4)n3)cc2C#N)[C@H](F)C1]

To a solution of 2-(((3R,4S)-3-fluoropiperidin-4-yl)oxy)-5-(4-((4-(4-(oxetan-3-yl)piperazin-1-yl)phenyl)amino)-1,3,5-triazin-2-yl)benzonitrile (50 mg, 0.09 mmol), (S)-2-hydroxy-3-methylbutanoic acid (14 mg, 0.11 mmol), HATU (72 mg, 0.18 mmol) in 6 ml of DMF, TEA (38 mg, 0.38 mmol) was added. This reaction mixture was stirred at room temperature for 2 hrs. DCM and water were added and organic layer was extracted and evaporated to dryness. Solids were re-dissolved in acetonitrile and then purified via preparative HPLC (5-65% acetonitrile in water, 0.1% trifluoroacteic acid buffer). Fractions containing desired product were collected and DCM and a saturated aqueous solution of NaHCO$_3$ were added. Organics were collected dried over magnesium sulfate and evaporated under reduced pressure to yield 2-(((3R,4S)-3-fluoro-1-((S)-2-hydroxy-3-methylbutanoyl)piperidin-4-yl)oxy)-5-(4-((4-(4-(oxetan-3-yl)piperazin-1-yl)phenyl)amino)-1,3,5-triazin-2-yl)benzonitrile. $^1$H NMR (400 MHz, DMSO-d$_6$) δ 10.13 (s, 1H), 8.73 (s, 1H), 8.67-8.39 (m, 2H), 7.58 (dd, J=26.8, 11.7 Hz, 3H), 6.99-6.88 (m, 2H), 5.23-5.01 (m, 2H), 4.86 (s, 1H), 4.55 (t, J=6.5 Hz, 2H), 4.46 (t, J=6.0 Hz, 3H), 4.06 (dd, J=13.2, 6.0 Hz, 3H), 3.43 (p, J=6.3 Hz, 2H), 3.18-3.09 (m, 4H), 2.40 (t, J=4.9 Hz, 4H), 2.07-1.72 (m, 3H), 0.93-0.78 (m, 6H). LCMS-ESI$^+$ (m/z): [M+H]$^+$ calcd for C$_{33}$H$_{39}$FN$_8$O$_4$ Exact Mass: 631.3 found:631.2.

Example 462

2-(((3R,4S)-3-fluoro-1-((S)-2-hydroxypropanoyl)piperidin-4-yl)oxy)-5-(4-((4-(4-(oxetan-3-yl)-2-oxopiperazin-1-yl)phenyl)amino)-1,3,5-triazin-2-yl)benzonitrile

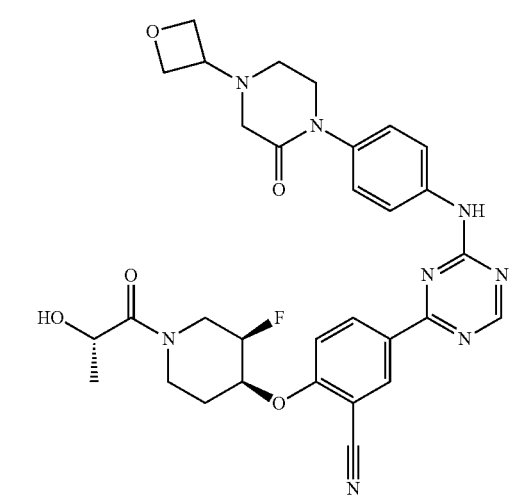 [SMILES: C[C@H](O)C(=O)N1CC[C@H](Oc2ccc(-c3ncnc(Nc4ccc(N5CCN(C6COC6)CC5=O)cc4)n3)cc2C#N)[C@H](F)C1]

To a mixture of tert-butyl 3-oxopiperazine-1-carboxylate (2.0 gr, 9.9 mmol), 1-iodo-4-nitrobenzene (2.2 gr, 8.9 mmol), Cs$_2$CO$_3$ (2.0 gr, 14.9 mmol), 4,5-Bis(diphenylphosphino)-9,9-dimethylxanthene (346 mg, 0.59 mmol) and Pd(OAc)$_2$ (89 mg, 0.4 mmol) in argon atmosphere was added 15 ml of de-gassed 1,4-dioxane. The mixture was stirred in a heating block under argon atmosphere for 2 h at 104° C. Water was added and it was extracted with DCM. Organic layer was dried over Mg$_2$SO$_4$ and evaporated under reduced pressure to dryness to yield tert-butyl 4-(4-nitrophenyl)-3-oxopiperazine-1-carboxylate.

The following steps for the synthesis of the title compound was taken from the procedure reported in Example 241 using the compound tert-butyl 4-(4-nitrophenyl)-3-oxopiperazine-1-carboxylate, shown above, and (S)-2-hydroxypropanoic acid. $^1$H NMR (400 MHz, DMSO-d$_6$) δ 10.42 (s, 1H), 8.80 (s, 1H), 8.68-8.48 (m, 2H), 7.74 (d, J=8.2 Hz, 2H), 7.63 (d, J=9.5 Hz, 1H), 7.32 (d, J=8.2 Hz, 2H), 5.24-4.86 (m, 3H), 4.58 (t, J=6.6 Hz, 2H), 4.53-4.29 (m, 3H), 4.11 (dd, J=35.8, 10.0 Hz, 2H), 3.62 (dt, J=30.6, 5.8 Hz, 3H), 3.13 (d, J=16.7 Hz, 4H), 2.71 (dd, J=6.1, 4.7 Hz, 2H), 2.03-1.92 (m, 2H), 1.19 (dd, J=6.5, 4.3 Hz, 3H). LCMS-ESI$^+$ (m/z): [M+H]$^+$ calcd for C$_{31}$H$_{33}$FN$_8$O$_5$ Exact Mass: 617.3 found:617.2

Example 463

2-(((3R,4S)-3-fluoro-1-(2-hydroxy-2-(1-methyl-1H-pyrazol-4-yl)acetyl)piperidin-4-yl)oxy)-5-(4-((4-(4-(oxetan-3-yl)piperazin-1-yl)phenyl)amino)-1,3,5-triazin-2-yl)benzonitrile

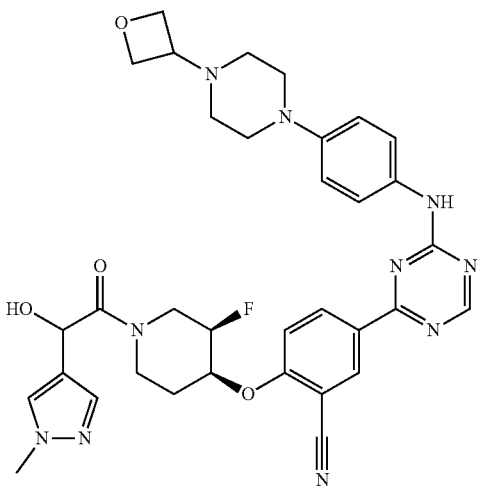 [SMILES: Cn1cc(C(O)C(=O)N2CC[C@H](Oc3ccc(-c4ncnc(Nc5ccc(N6CCN(C7COC7)CC6)cc5)n4)cc3C#N)[C@H](F)C2)cn1]

The title compound was prepared following a similar procedure reported in Example 461 using a racemic mixture of 2-hydroxy-2-(1-methyl-1H-pyrazol-4-yl)acetic acid. LCMS-ESI+ (m/z): [M+H]+ calcd for $C_{34}H_{37}FN_{10}O_4$ Exact Mass: 669.3 found:669.2.

Example 464

2-(((3R,4S)-3-fluoro-1-((R)-2-hydroxypropanoyl)piperidin-4-yl)oxy)-5-(4-((4-(4-(oxetan-3-yl)piperazin-1-yl)phenyl)amino)-1,3,5-triazin-2-yl)benzonitrile

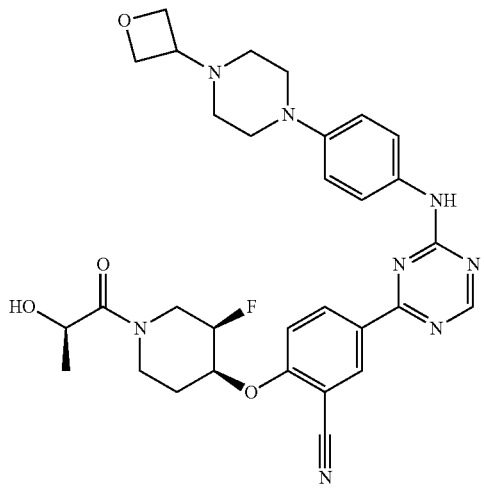 [SMILES: C[C@@H](O)C(=O)N1CC[C@H](Oc2ccc(-c3ncnc(Nc4ccc(N5CCN(C6COC6)CC5)cc4)n3)cc2C#N)[C@H](F)C1]

The title compound was prepared following a similar procedure reported in Example 461 using (R)-2-hydroxypropanoic acid. 1H NMR (400 MHz, DMSO-d6) δ 10.12 (d, J=24.7 Hz, 1H), 8.73 (s, 1H), 8.65-8.47 (m, 2H), 7.59 (dd, J=27.5, 11.0 Hz, 3H), 6.99-6.91 (m, 2H), 5.22-4.86 (m, 3H), 4.55 (t, J=6.5 Hz, 2H), 4.47 (q, J=6.7, 6.1 Hz, 3H), 3.92 (d, J=14.0 Hz, 2H), 3.43 (q, J=6.3 Hz, 2H), 3.20-3.11 (m, 5H), 2.40 (t, J=5.1 Hz, 4H), 1.91 (d, J=59.0 Hz, 2H), 1.27-1.10 (m, 3H). LCMS-ESI+ (m/z): [M+H]+ calcd for $C_{31}H_{35}FN_8O_4$ Exact Mass: 603.3 found:603.2

Example 465

2-(((3R,4S)-3-fluoro-1-((R)-2-hydroxy-3-methylbutanoyl)piperidin-4-yl)oxy)-5-(4-((4-(4-(oxetan-3-yl)piperazin-1-yl)phenyl)amino)-1,3,5-triazin-2-yl)benzonitrile

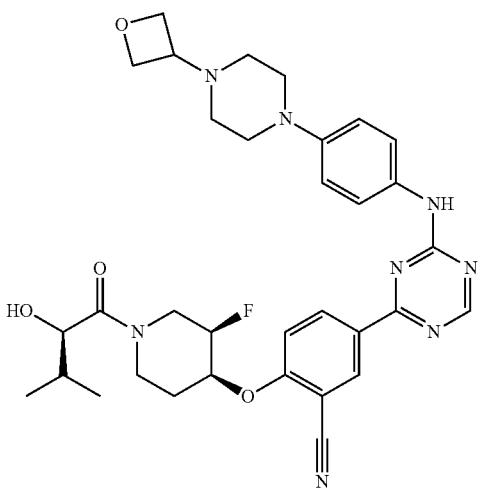 [SMILES: CC(C)[C@@H](O)C(=O)N1CC[C@H](Oc2ccc(-c3ncnc(Nc4ccc(N5CCN(C6COC6)CC5)cc4)n3)cc2C#N)[C@H](F)C1]

The title compound was prepared following a similar procedure reported in Example 461 using (R)-2-hydroxy-3-methylbutanoic acid. LCMS-ESI+ (m/z): [M+H]+ calcd for $C_{33}H_{39}FN_8O_4$ Exact Mass: 631.3 found:631.2

Example 466

2-(((3R,4S)-3-fluoro-1-((S)-5-oxopyrrolidine-2-carbonyl)piperidin-4-yl)oxy)-5-(4-((4-((R)-hexahydropyrazino[2,1-c][1,4]oxazin-8(1H)-yl)phenyl)amino)-1,3,5-triazin-2-yl)benzonitrile

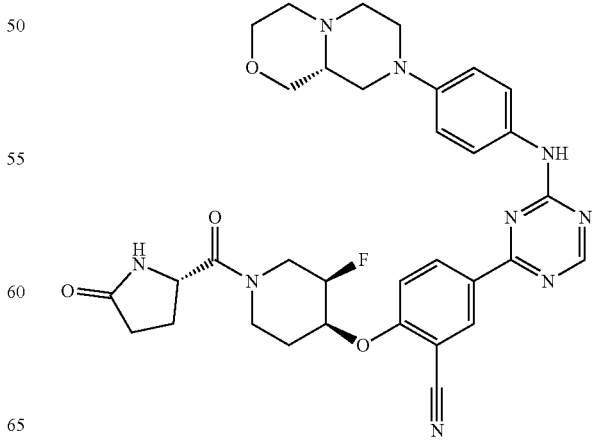

To a stirred solution of 1-fluoro-4-nitrobenzene (1.1 g, 8.0 mmol) in DMSO under a nitrogen atmosphere was added (R)-octahydropyrazino[2,1-c][1,4]oxazine (1.2 g, 9 mmol) followed by TEA (3 ml, 23 mmol). The mixture was stirred at 140° C. for 48 h, and then cooled to room temperature. The mixture was then poured into water and extracted with DCM. The combined organic layers were washed with brine, dried over magnesium sulfate, concentrated in vacuo to obtain (R)-8-(4-nitrophenyl)octahydropyrazino[2,1-c][1,4]oxazine.

The following steps for the synthesis of the title compound was taken from the procedure reported in Example 241 using the compound (R)-8-(4-nitrophenyl)octahydropyrazino[2,1-c][1,4]oxazine, shown above, and (S)-5-oxopyrrolidine-2-carboxylic acid. $^1$H NMR (400 MHz, DMSO-d$_6$) δ 10.14 (s, 1H), 8.74 (s, 1H), 8.65-8.49 (m, 2H), 7.85-7.44 (m, 4H), 6.95 (s, 2H), 5.11 (d, J=23.0 Hz, 2H), 4.61 (ddd, J=15.8, 8.9, 3.8 Hz, 1H), 4.47-4.05 (m, 2H), 3.95-3.67 (m, 3H), 3.67-3.41 (m, 4H), 3.20-2.99 (m, 2H), 2.96-2.60 (m, 4H), 2.41-1.70 (m, 8H). LCMS-ESI$^+$ (m/z): [M+H]$^+$ calcd. for C$_{33}$H$_{36}$FN$_9$O$_4$ Exact Mass: 642.3 found:642.3

Example 467

2-(((3R,4S)-1-(2-cyanoacetyl)-3-fluoropiperidin-4-yl)oxy)-5-(4-((4-((R)-2-(hydroxymethyl)morpholino)phenyl)amino)-1,3,5-triazin-2-yl)benzonitrile The title compound was prepared following a similar procedure reported in Example 218 using (R)-(4-(4-aminophenyl)morpholin-2-yl)methanol, (3R,4S)-tert-butyl 3-fluoro-4-hydroxypiperidine-1-carboxylate and 2-cyanoacetic acid. $^1$H NMR (400 MHz, DMSO-d$_6$) δ 10.17 (s, 1H), 8.74 (s, 1H), 8.57 (d, J=12.2 Hz, 2H), 7.69-7.49 (m, 3H), 6.99-6.82 (m, 2H), 5.24-4.67 (m, 3H), 4.46-3.81 (m, 5H), 3.72-3.36 (m, 8H), 2.41 (d, J=11.9 Hz, 2H), 1.94 (d, J=56.9 Hz, 2H). LCMS-ESI$^+$ (m/z): [M+H]$^+$ calcd for C$_{29}$H$_{29}$FN$_8$O$_4$: 573.2; found:573.2

Example 468

2-(((3R,4S)-3-fluoro-1-((S)-2-hydroxypropanoyl)piperidin-4-yl)oxy)-5-(4-((4-((R)-3-(hydroxymethyl)-4-(oxetan-3-yl)piperazin-1-yl)phenyl)amino)-1,3,5-triazin-2-yl)benzonitrile To a stirred solution of 1-fluoro-4-nitrobenzene (1.1 g, 8.0 mmol) in DMSO under a nitrogen atmosphere was added (R)-tert-butyl 2-(hydroxymethyl)piperazine-1-carboxylate (1.2 g, 9 mmol) followed by DIPEA (3 ml, 23 mmol). The mixture was stirred at 140° C. for 24 h, and then cooled to room temperature. The mixture was then poured into water and extracted with DCM. The combined organic layers were washed with brine, dried over magnesium sulfate, concentrated in vacuo to obtain (R)-tert-butyl 2-(hydroxymethyl)-4-(4-nitrophenyl)piperazine-1-carboxylate.

The following steps for the synthesis of the title compound was taken from the procedure reported in Example 241 using the compound (R)-tert-butyl 2-(hydroxymethyl)-4-(4-nitrophenyl)piperazine-1-carboxylate, shown above, and (S)-2-hydroxypropanoic acid. $^1$H NMR (400 MHz, DMSO-d$_6$) δ 10.17 (s, 1H), 8.74 (s, 1H), 8.56 (d, J=17.2 Hz, 2H), 7.59 (dd, J=28.7, 13.7 Hz, 3H), 6.95 (s, 2H), 5.23-4.87 (m, 3H), 4.63-4.27 (m, 3H), 4.24-3.81 (m, 2H), 3.76-3.39 (m, 4H), 3.18 (dd, J=21.6, 11.1 Hz, 4H), 2.74-2.55 (m, 2H), 2.36-1.72 (m, 7H), 1.23 (s, 3H). LCMS-ESI$^+$ (m/z): [M+H]$^+$ calcd for C$_{32}$H$_{37}$FN$_8$O$_5$ Exact Mass: 633.3 found:633.3

Example 469

2-(((S)-3,3-difluoro-1-((S)-2-hydroxypropanoyl)piperidin-4-yl)oxy)-5-(4-((4-((R)-3-(hydroxymethyl)-4-(oxetan-3-yl)piperazin-1-yl)phenyl)amino)-1,3,5-triazin-2-yl)benzonitrile

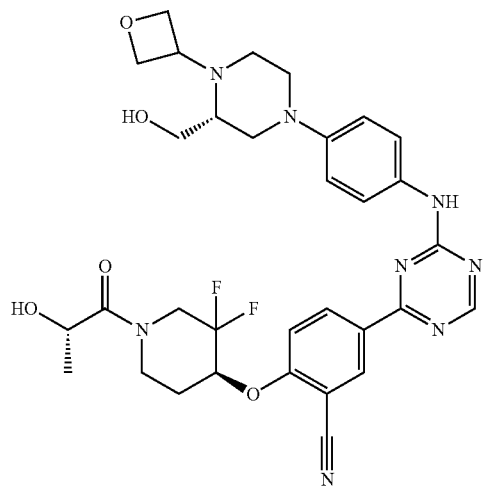 [SMILES: C[C@H](O)C(=O)N1CC[C@H](Oc2ccc(-c3ncnc(Nc4ccc(N5CCN(C6COC6)[C@@H](CO)C5)cc4)n3)cc2C#N)C(F)(F)C1]

The title compound was prepared following a similar procedure reported in Example 468 using (S)-tert-butyl 3,3-difluoro-4-hydroxypiperidine-1-carboxylate. $^1$H NMR (400 MHz, DMSO-$d_6$) δ 10.16 (s, 1H), 8.74 (s, 1H), 8.57 (d, J=20.0 Hz, 2H), 7.61 (dd, J=44.4, 14.6 Hz, 3H), 6.99-6.88 (m, 2H), 5.30 (d, J=55.9 Hz, 2H), 4.70-4.38 (m, 2H), 4.17 (s, 1H), 3.89-3.40 (m, 7H), 3.22-3.04 (m, 3H), 2.68 (d, J=13.4 Hz, 2H), 2.42-1.75 (m, 7H), 1.21 (d, J=6.4 Hz, 3H). LCMS-ESI$^+$ (m/z): [M+H]$^+$ calcd for $C_{32}H_{36}F_2N_8O_5$ Exact Mass: 651.3 found:651.3

Example 470

2-(((3R,4S)-3-fluoro-1-((S)-3-hydroxybutanoyl)piperidin-4-yl)oxy)-5-(4-((4-(4-(oxetan-3-yl)piperazin-1-yl)phenyl)amino)-1,3,5-triazin-2-yl)benzonitrile

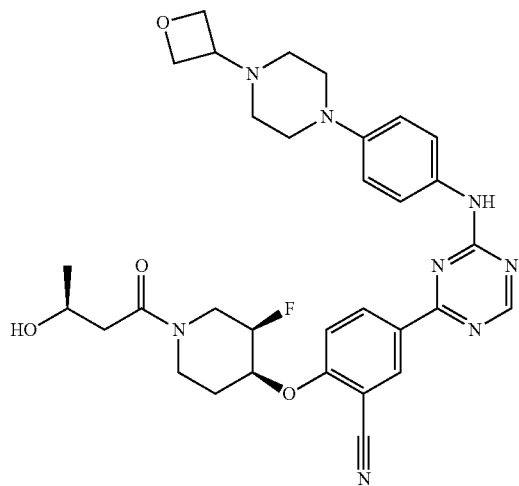 [SMILES: C[C@H](O)CC(=O)N1CC[C@H](Oc2ccc(-c3ncnc(Nc4ccc(N5CCN(C6COC6)CC5)cc4)n3)cc2C#N)[C@H](F)C1]

The title compound was prepared following a similar procedure reported in Example 461 using (S)-3-hydroxybutanoic acid. $^1$H NMR (400 MHz, DMSO-$d_6$) δ 10.11 (s, 1H), 8.70 (s, 1H), 8.63-8.40 (m, 2H), 7.57 (d, J=9.2 Hz, 3H), 7.00 (s, 2H), 5.16-4.82 (m, 3H), 4.71 (d, J=6.3 Hz, 4H), 4.49-4.18 (m, 2H), 3.95 (h, J=6.2 Hz, 3H), 3.1-2.85 (m, 5H), 2.41-2.22 (m, 4H), 2.00-1.62 (m, 4H), 1.04 (t, J=6.3 Hz, 3H). LCMS-ESI$^+$ (m/z): [M+H]$^+$ calcd for $C_{32}H_{37}FN_8O_4$ Exact Mass: 617.3 found:617.3

Example 471

2-(((3R,4S)-3-fluoro-1-((R)-3-hydroxybutanoyl)piperidin-4-yl)oxy)-5-(4-((4-(4-(oxetan-3-yl)piperazin-1-yl)phenyl)amino)-1,3,5-triazin-2-yl)benzonitrile

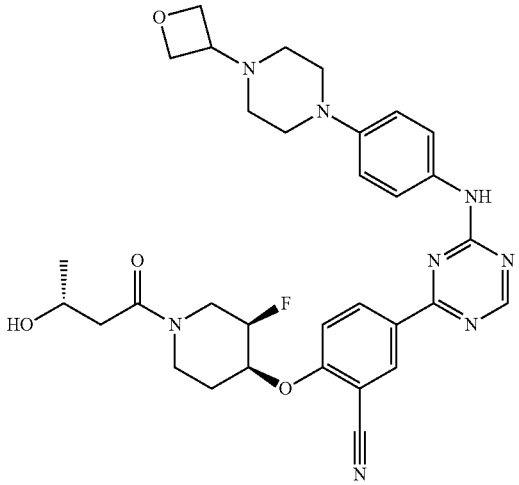 [SMILES: C[C@@H](O)CC(=O)N1CC[C@H](Oc2ccc(-c3ncnc(Nc4ccc(N5CCN(C6COC6)CC5)cc4)n3)cc2C#N)[C@H](F)C1]

The title compound was prepared following a similar procedure reported in Example 461 using (R)-3-hydroxybutanoic acid. $^1$H NMR (400 MHz, DMSO-$d_6$) δ 10.14 (d, J=23.4 Hz, 1H), 8.70 (s, 1H), 8.63-8.41 (m, 2H), 7.57 (d, J=9.1 Hz, 3H), 7.00 (s, 2H), 5.16-4.87 (m, 3H), 4.71 (d, J=6.2 Hz, 4H), 4.34 (d, J=44.5 Hz, 2H), 4.13-3.90 (m, 4H), 3.36-2.78 (m, 7H), 2.67-2.47 (m, 2H), 2.37-2.15 (m, 1H), 2.05-1.59 (m, 2H), 1.08 (dd, J=30.6, 6.2 Hz, 3H). LCMS-ESI$^+$ (m/z): [M+H]$^+$ calcd for $C_{32}H_{37}FN_8O_4$ Exact Mass: 617.3 found:617.3

Example 472

2-(((3R,4S)-3-fluoro-1-(3-hydroxyoxetane-3-carbonyl)piperidin-4-yl)oxy)-5-(4-((4-(4-(oxetan-3-yl)piperazin-1-yl)phenyl)amino)-1,3,5-triazin-2-yl)benzonitrile

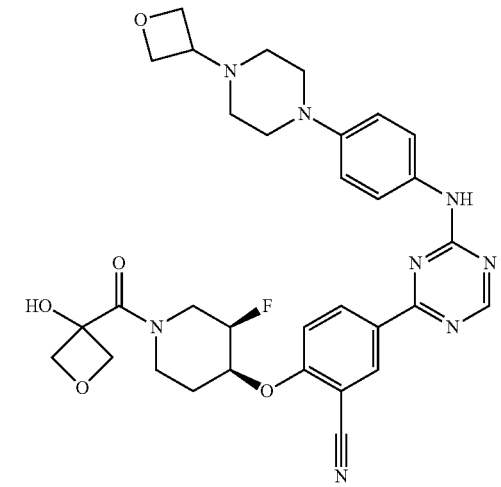 [SMILES: N#Cc1cc(-c2ncnc(Nc3ccc(N4CCN(C5COC5)CC4)cc3)n2)ccc1O[C@H]1CCN(C(=O)C2(O)COC2)C[C@H]1F]

The title compound was prepared following a similar procedure reported in Example 461 using 3-hydroxyoxetane-3-carboxylic acid. $^1$H NMR (400 MHz, DMSO-d$_6$) δ 10.14 (s, 1H), 8.74 (s, 1H), 8.65-8.45 (m, 2H), 7.61 (d, J=9.3 Hz, 3H), 7.11-6.95 (m, 2H), 5.24-4.66 (m, 8H), 4.57-4.24 (m, 4H), 3.88-3.5 (m, 3H), 3.59-2.9 (m, 4H), 3.28-2.92 (s, 5H), 1.96 (d, J=4.7 Hz, 2H). LCMS-ESI$^+$ (m/z): [M+H]$^+$ calcd for C$_{32}$H$_{35}$FN$_8$O$_5$ Exact Mass: 631.3 found:631.3

Example 473

2-(((3R,4S)-3-fluoro-1-(oxazole-5-carbonyl)piperidin-4-yl)oxy)-5-(4-((4-(4-(oxetan-3-yl)piperazin-1-yl)phenyl)amino)-1,3,5-triazin-2-yl)benzonitrile

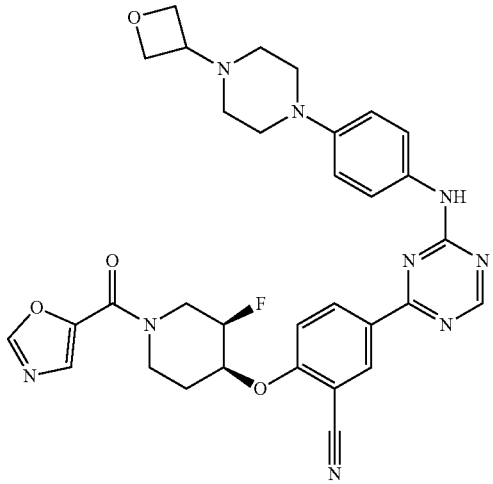 [SMILES: N#Cc1cc(-c2ncnc(Nc3ccc(N4CCN(C5COC5)CC4)cc3)n2)ccc1O[C@H]1CCN(C(=O)c2cnco2)C[C@H]1F]

The title compound was prepared following a similar procedure reported in Example 461 using and oxazole-5-carboxylic acid. $^1$H NMR (400 MHz, DMSO-d$_6$) δ 10.15 (s, 1H), 8.75 (s, 1H), 8.58 (d, J=9.7 Hz, 3H), 7.83-7.51 (m, 4H), 7.11-7.00 (m, 2H), 5.51-5.01 (m, 2H), 4.71-4.32 (m, 7H), 3.92-3.62 (m, 5H), 3.31-2.88 (m, 6H), 2.16-1.79 (m, 1H). LCMS-ESI$^+$ (m/z): [M+H]$^+$ calcd for C$_{32}$H$_{32}$FN$_9$O$_4$ Exact Mass: 626.3 found:626.3

Example 474

2-(3R,4S)-3-fluoro-1-((S)-2-hydroxypropanoyl)piperidin-4-yl)oxy)-5-(4-((2-methoxypyridin-4-yl)amino)-1,3,5-triazin-2-yl)benzonitrile

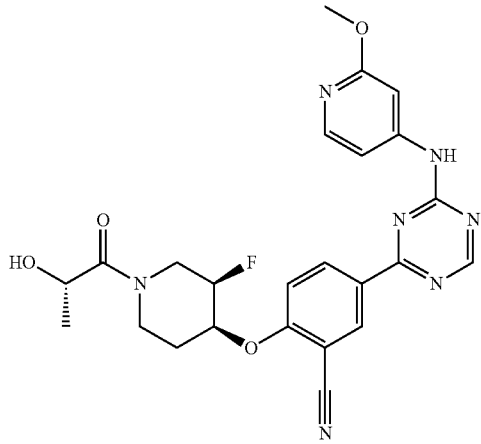 [SMILES: COc1cc(Nc2ncnc(-c3ccc(O[C@H]4CCN(C(=O)[C@H](C)O)C[C@H]4F)c(C#N)c3)n2)ccn1]

The title compound was prepared following a similar procedure reported in Example 218 using 2-methoxypyridin-4-amine, (3R,4S)-tert-butyl 3-fluoro-4-hydroxypiperidine-1-carboxylate and (S)-2-hydroxypropanoic acid. $^1$H NMR (400 MHz, DMSO-d$_6$) δ 10.72 (s, 1H), 8.58 (d, J=9.4 Hz, 3H), 8.03 (s, 1H), 7.66 (d, J=9.0 Hz, 1H), 7.45-7.29 (m, 2H), 5.34-4.80 (m, 3H), 4.52-4.40 (m, 1H), 4.20-4.10 (m, 2H), 3.83 (s, 3H), 3.62 (dd, J=29.4, 14.6 Hz, 1H), 2.12-1.85 (m, 3H), 1.29-1.12 (m, 3H). LCMS-ESI$^+$ (m/z): [M+H]$^+$ calcd for C$_{24}$H$_{24}$FN$_7$O$_4$ Exact Mass: 494.3 found: 494.2

Example 475

2-(((3R,4S)-3-fluoro-1-((S)-morpholine-3-carbonyl)piperidin-4-yl)oxy)-5-(4-((4-(4-(oxetan-3-yl)piperazin-1-yl)phenyl)amino)-1,3,5-triazin-2-yl)benzonitrile

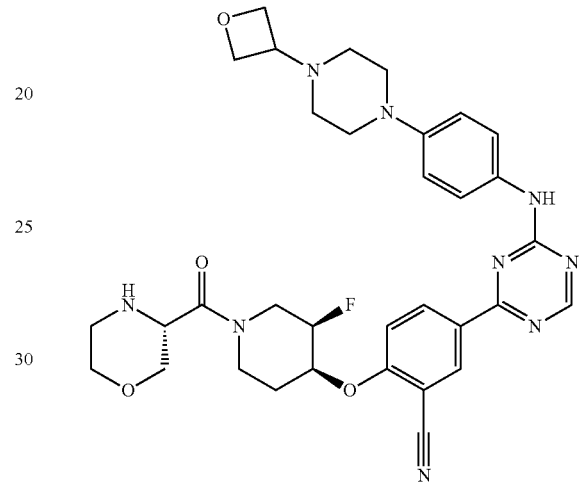

The title compound was prepared following a similar procedure reported in Example 461 using (S)-morpholine-3-carboxylic acid. LCMS-ESI$^+$ (m/z): [M+H]$^+$ calcd for C$_{33}$H$_{38}$FN$_9$O$_4$ Exact Mass: 644.3 found:644.3.

Example 476

2-(((3R,4S)-3-fluoro-1-((S)-2-hydroxypropanoyl)piperidin-4-yl)oxy)-5-(4-((4-(1-methyl-2-oxo-1,2-dihydropyridin-4-yl)phenyl)amino)-1,3,5-triazin-2-yl)benzonitrile

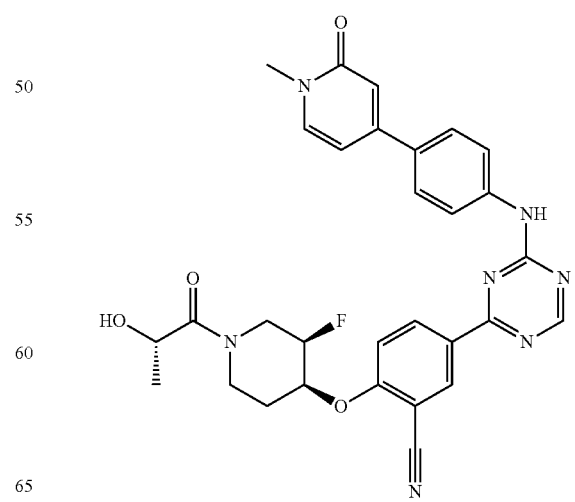

To a mixture of 1-methyl-4-(4,4,5,5-tetramethyl-1,3,2-dioxaborolan-2-yl)pyridin-2(1H)-one (204 mg, 0.87 mmol), potassium carbonate (241 mg, 1.7 mmol), 4,5-Pd(dppf)Cl$_2$CH$_2$Cl$_2$ (80 mg, 0.01 mmol) and 4-bromoaniline (150 mg, 0.87 mmol) in argon atmosphere was added 6 ml of de-gassed mixture of solvents (1,4-dioxane and water 2:1) The mixture was stirred in a heating block under argon atmosphere for 1 h at 104° C. Water was added and it was extracted with DCM. Organic layer was dried over Mg$_2$SO$_4$ and evaporated under reduced pressure to dryness to yield 4-(4-aminophenyl)-1-methylpyridin-2(1H)-one.

The following steps for the synthesis of the title compound was taken from the procedure reported in Example 218 using the compound 4-(4-aminophenyl)-1-methylpyridin-2(1H)-one, shown above, (3R,4S)-tert-butyl 3-fluoro-4-hydroxypiperidine-1-carboxylate and (S)-2-hydroxypropanoic acid. $^1$H NMR (400 MHz, DMSO-d$_6$) δ 10.56 (s, 1H), 8.87 (s, 1H), 8.61 (d, J=7.3 Hz, 2H), 7.90 (d, J=8.7 Hz, 2H), 7.75 (t, J=7.6 Hz, 3H), 7.64 (d, J=9.5 Hz, 1H), 6.68 (d, J=2.1 Hz, 1H), 6.59 (dd, J=7.1, 2.1 Hz, 1H), 5.27-4.89 (m, 3H), 4.56-4.23 (m, 1H), 4.21-3.62 (m, 2H), 3.43 (s, 3H), 3.40-3.09 (m, 1H), 2.09-1.63 (m, 3H), 1.30-1.11 (m, 3H). LCMS-ESI$^+$ (m/z): [M+H]$^+$ calcd for C$_{30}$H$_{28}$FN$_7$O$_4$ Exact Mass: 570.2 found:570.3

Example 477

2-(((3R,4S)-3-fluoro-1-(oxazole-4-carbonyl)piperidin-4-yl)oxy)-5-(4-((4-(4-(oxetan-3-yl)piperazin-1-yl)phenyl)amino)-1,3,5-triazin-2-yl)benzonitrile

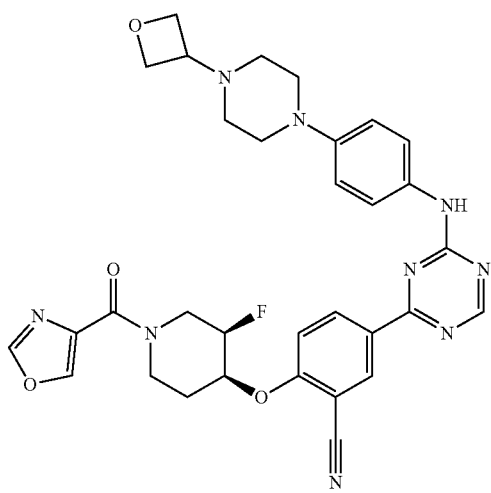 [SMILES: N#Cc1cc(-c2ncnc(Nc3ccc(N4CCN(C5COC5)CC4)cc3)n2)ccc1O[C@H]1CCN(C(=O)c2cocn2)C[C@H]1F]

The title compound was prepared following a similar procedure reported in Example 461 using oxazole-4-carboxylic acid. $^1$H NMR (400 MHz, DMSO-d$_6$) δ 10.15 (s, 1H), 8.76 (s, 1H), 8.68-8.49 (m, 4H), 7.62 (dd, J=34.1, 11.9 Hz, 3H), 7.05-6.82 (m, 2H), 5.33-4.79 (m, 3H), 4.58 (t, J=6.5 Hz, 2H), 4.49 (t, J=6.0 Hz, 3H), 3.57 (s, 1H), 3.46 (p, J=6.2 Hz, 1H), 3.16 (d, J=5.4 Hz, 5H), 2.43 (t, J=4.9 Hz, 4H), 2.17-1.78 (m, 2H). LCMS-ESI$^+$ (m/z): [M+H]$^+$ calcd for C$_{32}$H$_{32}$FN$_9$O$_4$ Exact Mass: 626.3 found:626.3

Example 478

(((3R,4S)-4-(2-cyano-4-(4-((4-(4-(oxetan-3-yl)piperazin-1-yl)phenyl)amino)-1,3,5-triazin-2-yl)phenoxy)-3-fluoro-N-hydroxypiperidine-1-carboxamide

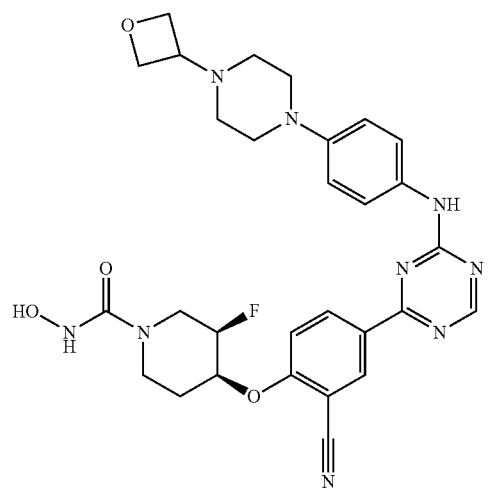 [SMILES: N#Cc1cc(-c2ncnc(Nc3ccc(N4CCN(C5COC5)CC4)cc3)n2)ccc1O[C@H]1CCN(C(=O)NO)C[C@H]1F]

To a stirred solution of 2-(((3R,4S)-3-fluoropiperidin-4-yl)oxy)-5-(4-((4-(4-(oxetan-3-yl)piperazin-1-yl)phenyl)amino)-1,3,5-trazin-2-yl)benzonitrile (96 mg, 0.18 mmol) in THF was added TEA (0.25 ml, 2.0 mmol), O-(tert-butyldimethylsilyl)hydroxylamine (29 mg, 0.19 mmol) followed by triphosgene (48 mg, 0.16 mmol). The mixture was heated at 60° C. for 1 hr, and then cooled to room temperature. The mixture was then poured into water, DCM and a saturated aqueous solution of NaHCO3 and extracted. The combined organic layers were concentrated in vacua to obtain (3R,4S)-N-((tert-butyldimethylsilyl)oxy)-4-(2-cyano-4-(4-((4-(4-(oxetan-3-yl)piperazin-1-yl)phenyl)amino)-1,3,5-triazin-2-yl)phenoxy)-3-fluoropiperidine-1-carboxamide.

(3R,4S)-N-((tert-butyldimethylsilyl)oxy)-4-(2-cyano-4-(4-((4-(4-(oxetan-3-yl)piperazin-1-yl)phenyl)amino)-1,3,5-triazin-2-yl)phenoxy)-3-fluoropiperidine-1-carboxamide was dissolved with a mixture of DCM and TFA and stirred at room temperature for 1 hr. Reaction mixture was evaporated under reduced pressure and solids were purified via preparative HPLC (5-65% acetonitrile in water, 0.1% trifluoroacteic acid buffer). Fractions containing desired product were collected and DCM and a saturated aqueous solution of NaHCO$_3$ were added. Organics were collected dried over magnesium sulfate and evaporated under reduced pressure to yield (3R,4S)-4-(2-cyano-4-(4-((4-(4-(oxetan-3-yl)piperazin-1-yl)phenyl)amino)-1,3,5-triazin-2-yl)phenoxy)-3-fluoro-N-hydroxypiperidine-1-carboxamide. $^1$H NMR (400 MHz, DMSO-d$_6$) δ 10.3-10.2 (m, 1H), 9.18 (s, 1H), 8.75 (s, 1H), 8.57 (d, J=9.4 Hz, 2H), 8.11 (s, 1H), 7.60 (t, J=12.3 Hz, 2H), 6.97 (s, 2H), 5.07 (d, J=22.2 Hz, 3H), 4.58 (t, J=6.5 Hz, 2H), 4.48 (t, J=6.0 Hz, 2H), 4.01 (dt, J=14.1, 7.2 Hz, 1H), 3.72-3.38 (m, 2H), 3.32-3.25 (m, 4H), 2.47-2.36 (m, 5H), 1.91 (d, J=5.8 Hz, 3H). LCMS-ESI$^+$ (m/z): [M+H]$^+$ calcd for C$_{29}$H$_{32}$FN$_9$O$_4$ Exact Mass: 590.3 found:590.2.

Example 479

2-(((S)-1-((S)-2,3-dihydroxypropanoyl)-3,3-difluoropiperidin-4-yl)oxy)-5-(4-((2-methoxypyridin-4-yl)amino)-1,3,5-triazin-2-yl)benzonitrile

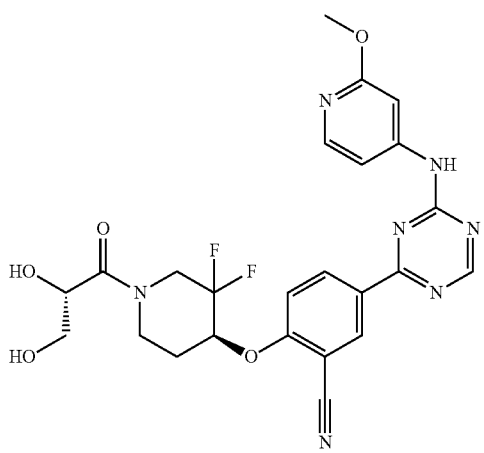 [SMILES: COc1cc(Nc2ncnc(-c3ccc(O[C@H]4CCN(C(=O)[C@@H](O)CO)CC4(F)F)c(C#N)c3)n2)ccn1]

The title compound was prepared following a similar procedure reported in Example 218 using 2-methoxypyridin-4-amine, (S)-tert-butyl 3,3-difluoro-4-hydroxypiperidine-1-carboxylate and (S)-2,3-dihydroxypropanoic acid. $^1$H NMR (400 MHz, DMSO-$d_6$) δ 10.7 (s, 1H), 8.96 (s, 1H), 8.68-8.55 (m, 2H), 8.07 (d, J=5.7 Hz, 1H), 7.78-7.67 (m, 1H), 7.43-7.30 (m, 2H), 5.32 (d, J=68.1 Hz, 2H), 4.75 (s, 1H), 4.29 (d, J=81.4 Hz, 2H), 3.92-3.79 (m, 4H), 3.70-3.41 (m, 3H), 2.08 (d, J=72.2 Hz, 3H). LCMS-ESI$^+$ (m/z): [M+H]$^+$ calcd for $C_{24}H_{23}F_2N_7O_5$ Exact Mass: 528.2 found: 528.1

Example 480

2-(((3R,4S)-3-fluoro-1-(pyridin-2-yl)piperidin-4-yl)oxy)-5-(4-((4-(4-(oxetan-3-yl)piperazin-1-yl)phenyl)amino)-1,3,5-triazin-2-yl)benzonitrile

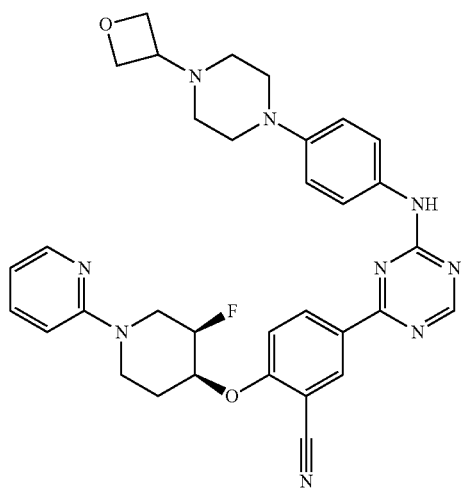 [SMILES: N#Cc1cc(-c2ncnc(Nc3ccc(N4CCN(C5COC5)CC4)cc3)n2)ccc1O[C@H]1CCN(c2ccccn2)C[C@H]1F]

To a solution of 2-(((3R,4S)-3-fluoropiperidin-4-yl)oxy)-5-(4-((4-(4-(oxetan-3-yl)piperazin-1-yl)phenyl)amino)-1,3,5-triazin-2-yl)benzonitrile (50 mg, 0.094 mmol) in 4 ml of DMSO, was added 2-bromopyridine (15 mg, 0.094 mmol), CuI (2 mg, 0.009 mmol), 2-isobutyrylcyclohexanone (16 mg, 0.094 mmol) and K$_2$CO$_3$ (26 mgs, 0.188 mmol). reaction mixture was heated at 60° C. in a heating block for 2 hr. Reaction mixture loaded into a preparative HPLC system (5-65% acetonitrile in water, 0.1% trifluoroacteic acid buffer). Fractions containing desired product were collected and DCM and a saturated aqueous solution of NaHCO$_3$ were added. Organics were collected dried over magnesium sulfate and evaporated under reduced pressure to yield 2-(((3R,4S)-3-fluoro-1-(pyridin-2-yl)piperidin-4-yl)oxy)-5-(4-((4-(4-(oxetan-3-yl)piperazin-1-yl)phenyl)amino)-1,3,5-triazin-2-yl)benzonitrile. LCMS-ESI$^+$ (m/z): [M+H]$^+$ calcd. for $C_{33}H_{34}FN_9O_2$ Exact Mass: 608.3 found: 608.3.

Example 481

2-(((S)-1-acetyl-3,3-difluoropiperidin-4-yl)oxy)-5-(4-((4-(S-methylsulfonimidoyl)phenyl)amino)-1,3,5-triazin-2-yl)benzonitrile

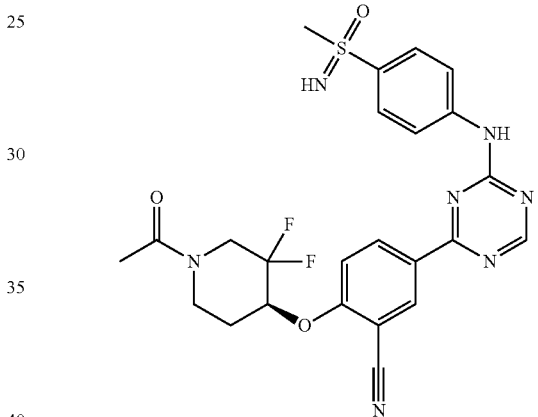

Step 1: Preparation of 4-(N-(tert-butoxycarbonyl)-S-methylsulfonimidoyl)nitrobenzene:

A solution of (R,S)-S-(4-nitrophenyl)-S-methylsulfoximide (Enamine, 0.50 g, 2.5 mmol) in tert-butanol (18 mL) was treated with di-tert-butyl dicarbonate (1.1 g, 5.0 mmol) followed by potassium tert-butoxide (0.56 g, 5.0 mmol). The resulting mixture was heated for 2 days in a sealed vessel on 98° C. heating block. After being allowed to cool to room temperature, the mixture was partitioned between ethyl acetate and water. The pH was adjusted to 3 by the addition of 10% aqueous citric acid solution. The aqueous phase was extracted three times with ethyl acetate. The combined organics were washed once with saturated aqueous sodium chloride solution, dried over anhydrous magnesium sulfate, filtered, and concentrated to provide the desired material. LCMS-ESI$^+$ (m/z): [M+H]$^+$ calcd for $C_{12}H_{17}N_2O_5S$ 301.1; found: 300.6

Step 2: Preparation of 4-(N-(tert-butoxycarbonyl)-S-methylsulfonimidoyl)aniline:

A suspension of 4-(N-(tert-butoxycarbonyl)-S-methylsulfonimidoyl)nitrobenzene (0.75 g, 2.5 mmol) in methanol was added to a stirred suspension of 20% palladium hydroxide on carbon in methanol (15 mL). Ammonium formate (0.78 g, 12 mmol) was added in a single portion. The mixture was heated at 80° C. for 3 hours. After cooling to room temperature, an additional portion of ammonium formate (1 g) was added. The mixture was heated overnight at 90° C. After cooling to room temperature, the mixture was filtered through a pad of Celite diatomaceous earth, and the filtrate was concentrated under reduced pressure. The residue was partitioned between ethyl acetate and water. The aqueous phase was extracted three times with ethyl acetate. The combined extracts were washed with a saturated aqueous solution of sodium chloride, dried over anhydrous magnesium sulfate, and concentrated under reduced pressure to provide the desired material. LCMS-ESI$^+$ (m/z): [M+H]$^+$ calcd for $C_{12}H_{19}N_2O_3S$ 271.1; found: 270.8

Step 3: Preparation of 4-chloro-N-(4-(S-methyl-N-(tert-butoxycarbonyl)sulfonimidoyl)phenyl)-1,3,5-triazin-2-amine To a solution of 2,4-dichloro-1,3,5-triazine (0.38 g, 2.6 mmol) in N,N-dimethylformamide (DMF, 5 mL) at 0° C. were added N,N-diisopropylethylamine (DIEA, 0.46 mL, 2.7 mmol), followed by a solution of 4-(N-(tert-butoxycarbonyl)-S-methylsulfonimidoyl)aniline (0.60 g, 2.2 mmol) in DMF (6 mL). The mixture was stirred at 0° C. for 5 minutes and then allowed to warm to room temperature. The mixture was partitioned between ethyl acetate and half-saturated aqueous sodium hydrogen carbonate solution. The layers were separated and aqueous phase was extracted twice with ethyl acetate. The combined extracts were washed once each with water and saturated aqueous sodium chloride solution, and then dried over anhydrous magnesium sulfate, filtered, and concentrated under reduced pressure. The residue was purified by flash chromatography on silica gel to provide 4-chloro-N-(4-(S-methyl-N-(tert-butoxycarbonyl)sulfonimidoyl)phenyl)-1,3,5-triazin-2-amine. LCMS-ESI$^+$ (m/z): [M+H]$^+$ calcd for $C_{15}H_{19}ClN_5O_3S$ 384.1; found: 383.7

Step 4: Preparation of 2-(((S)-1-acetyl-3,3-difluoropiperidin-4-yl)oxy)-5-(4-((4-(N-(1-tert-butoxylcarbonyl)-S-methylsulfonimidoyl)phenyl)amino)-1,3,5-triazin-2-yl)benzonitrile:

A mixture of crude (S)-2-((1-acetyl-3,3-difluoropiperidin-4-yl)oxy)-5-(4,4,5,5-tetramethyl-1,3,2-dioxaborolan-2-yl)benzonitrile (preparation described in Example 301, 0.84 mmol) was taken up in 1,2-dimethoxyethane (4 mL) and was added to a microwave vial containing 4-chloro-N-(4-(S-methyl-N-(tert-butoxycarbonyl)sulfonimidoyl)phenyl)-1,3,5-triazin-2-amine (0.27 g, 0.71 mmol) and tetrakis(triphenylphosphine)palladium(0) (0.06 g, 7.5 mol %). 2 M aqueous sodium carbonate solution (1.6 mL) was added. The mixture was irradiated in a microwave for 75 minutes at 130° C. The mixture was diluted with ethyl acetate and water. The aqueous phase was extracted with ethyl acetate. The combined extracts were concentrated, and the residue was purified by flash chromatography (silica gel) to provide the desired product. LCMS-ESI$^+$ (m/z): [M–CO$_2$-isobutylene+H]$^+$ calcd for $C_{24}H_{24}F_2N_7O_3S$ 528.2; found: 528.3

Step 5: Preparation of 2-(((S)-1-acetyl-3,3-difluoropiperidin-4-yl)oxy)-5-(4-((4-(S-methylsulfonimidoyl)phenyl)amino)-1,3,5-triazin-2-yl)benzonitrile:

A solution of 2-(((S)-1-acetyl-3,3-difluoropiperidin-4-yl)oxy)-5-(4-((4-(N-(1-tert-butoxylcarbonyl)-S-methylsulfonimidoyl)phenyl)amino)-1,3,5-triazin-2-yl)benzonitrile (85 mg, 0.14 mmol) in dichloromethane (2 mL) was treated with trifluoroacetic acid (0.52 mL, 7 mmol). After standing overnight at room temperature, the mixture was concentrated to dryness under reduced pressure. The residue was purified by preparative HPLC (5-50% acetonitrile in water, 0.1% trifluoroacetic acid buffer) to furnish 2-(((S)-1-acetyl-3,3-difluoropiperidin-4-yl)oxy)-5-(4-((4-(S-methylsulfonimidoyl)phenyl)amino)-1,3,5-triazin-2-yl)benzonitrile.

LCMS-ESI$^+$ (m/z): [M+H]$^+$ calcd for $C_{24}H_{24}F_2N_7O_3S$ 528.2; found: 528.3 $^1$H NMR (400 MHz, DMSO-d$_6$) δ 11.04 (s, 1H), 9.04 (s, 1H), 8.76-8.68 (m, 2H), 8.21 (m, $^2$H), 8.13 (m, 2H), 7.75 (dd, J=9.4, 3.8 Hz, 1H), 5.44 (m, 1H), 4.13 (m, 1H), 4.03-3.75 (m, 2H), 3.73 (s, 3H), 3.57 (m, 1H), 2.29-2.09 (in, 1H), 2.15 (s, 1.5H), 2.12 (s, 1.5H), 2.09-1.82 (m, 1H).

Example 482

2-(((S)-3,3-difluoro-1-formylpiperidin-4-yl)oxy)-5-(4-((4-(S-methylsulfonimidoyl)phenyl)amino)-1,3,5-triazin-2-yl)benzonitrile

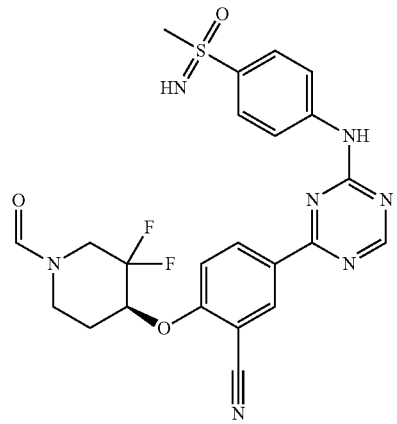 [SMILES: CS(=N)(=O)c1ccc(Nc2ncnc(-c3ccc(O[C@H]4CCN(C=O)CC4(F)F)c(C#N)c3)n2)cc1]

Step 1: Preparation of 2-(((S)-3,3-difluoro-1-formylpiperidin-4-yl)oxy)-5-(4-((4-(N-(1-tert-butoxylcarbonyl)-S-methylsulfonimidoyl)phenyl)amino)-1,3,5-triazin-2-yl)benzonitrile:

A mixture of (S)-2-((3,3-difluoro-1-formylpiperidin-4-yl)oxy)-5-(4,4,5,5-tetramethyl-1,3,2-dioxaborolan-2-yl)benzonitrile (preparation described in Example 303, 0.56 mmol) was taken up in 1,2-dimethoxyethane (3 mL) and was added to a microwave vial containing 4-chloro-N-(4-(S-methyl-N-(tert-butoxycarbonyl)sulfonimidoyl)phenyl)-1,3,5-triazin-2-amine (0.26 g, 0.68 mmol) and tetrakis(triphenylphosphine)palladium(0) (0.05 g, 7.5 mol %). 2 M aqueous sodium carbonate solution (0.8 mL) was added. The mixture was irradiated in a microwave for 75 minutes at 130° C. The mixture was diluted with ethyl acetate and water. The aqueous phase was extracted with ethyl acetate. The combined extracts were concentrated, and the residue was purified by flash chromatography (silica gel) to provide the desired product. LCMS-ESI$^+$ (m/z): [M–CO$_2$-isobutylene+H]$^+$ calcd for $C_{23}H_{22}F_2N_7O_3S$ 514.1; found: 514.3

Step 2: Preparation of 2-(((S)-3,3-difluoro-1-formylpiperidin-4-yl)oxy)-5-(4-((4-(S-methylsulfonimidoyl)phenyl)amino)-1,3,5-triazin-2-yl)benzonitrile:

A solution of 2-(((S)-3,3-difluoro-1-formylpiperidin-4-yl)oxy)-5-(4-((4-(N-(1-tert-butoxylcarbonyl)-S-methylsulfonimidoyl)phenyl)amino)-1,3,5-triazin-2-yl)benzonitrile (195 mg, 0.32 mmol) in dichloromethane (4 mL) was treated with trifluoroacetic acid (2.1 mL, 27 mmol). After standing for three hours at room temperature, the mixture was concentrated to dryness under reduced pressure. The residue was purified by preparative HPLC (5-50% acetonitrile in water, 0.1% trifluoroacetic acid buffer) to furnish 2-(((S)-3,3-difluoro-1-formylpiperidin-4-yl)oxy)-5-(4-((4-(S-methylsulfonimidoyl)phenyl)amino)-1,3,5-triazin-2-yl)benzonitrile. LCMS- ESI+ (m/z): [M+H]+ calcd for $C_{23}H_{22}F_2N_7O_3S$ 514.1; found: 514.3 $^1$H NMR (400 MHz, DMSO-$d_6$) δ 11.01 (s, 1H), 9.03 (s, 1H), 8.79-8.63 (m, 2H), 8.21 (d, J=5.5 Hz, 1H), 8.19-8.08 (m, 4H), 7.80-7.68 (m, 1H), 5.49 (td, J=8.5, 4.0 Hz, 1H), 4.15-3.99 (m, 1H), 3.99-3.66 (m, 2H), 3.63 (s, 3H), 3.61-3.42 (m, 2H), 2.31-2.09 (m, 1H), 2.09-1.82 (m, 1H).

Example 483

2-(((3R,4S)-3-fluoro-1-((S)-2-hydroxypropanoyl) piperidin-4-yl)oxy)-5-(4-((3-methoxy-4-(methylsulfonyl)phenyl)amino)-1,3,5-triazin-2-yl)benzonitrile

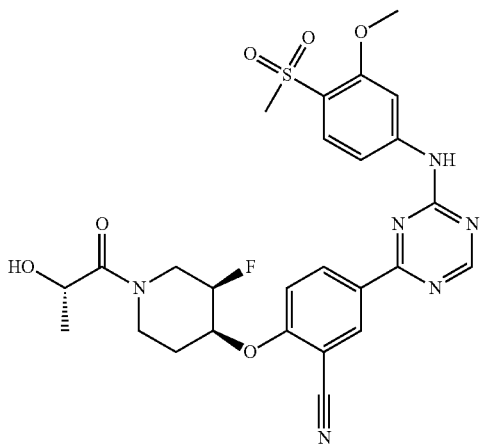 [SMILES: COc1cc(Nc2ncnc(-c3ccc(O[C@H]4CCN(C(=O)[C@H](C)O)C[C@H]4F)c(C#N)c3)n2)ccc1S(C)(=O)=O]

Step 1: Preparation of 4-chloro-N-(3-methoxy-4-(methylsulfonyl)phenyl)-1,3,5-triazin-2-amine:

To a solution of 2,4-dichloro-1,3,5-triazine (0.21 g, 1.4 mmol) in N,N-dimethylformamide (DMF, 3 mL) at 0° C. were added N,N-diisopropylethylamine (DIEA, 0.24 mL, 1.4 mmol), followed by 4-methanesulfonyl-3-methoxyaniline (Combi-Blocks, 0.25 g, 1.2 mmol). The mixture was stirred at 0° C. for 5 minutes and then allowed to warm to room temperature. After three hours of stirring at room temperature, the mixture was partitioned between ethyl acetate and half-saturated aqueous sodium hydrogen carbonate solution. The layers were separated and aqueous phase was extracted twice with ethyl acetate. The combined extracts were washed once each with water and saturated aqueous sodium chloride solution, and then dried over anhydrous magnesium sulfate, filtered, and concentrated under reduced pressure. The residue was triturated with isopropanol to provide the desired material. LCMS-ESI+ (m/z): [M+H]+ calcd for $C_{11}H_{12}ClN_4O_3S$ 315.0; found: 315.9

Step 2: Preparation of (3R,4S)-tert-butyl 4-(2-cyano-4-(4-((3-methoxy-4-(methylsulfonyl)phenyl)amino)-1,3,5-triazin-2-yl)phenoxy)-3-fluoropiperidine-1-carboxylate:

(3R,4S)-tert-butyl 4-(2-cyano-4-(4,4,5,5-tetramethyl-1,3,2-dioxaborolan-2-yl)phenoxy)-3-fluoropiperidine-1-carboxylate (preparation described in Example 293, 0.70 mmol) was taken up in 1,2-dimethoxyethane (3 mL) and was added to a microwave vial containing 4-chloro-N-(3-methoxy-4-(methylsulfonyl)phenyl)-1,3,5-triazin-2-amine (0.20 g, 0.64 mmol) and tetrakis(triphenylphosphine)palladium(0) (0.06 g, 7.5 mol %). 2 M aqueous sodium carbonate solution (0.9 mL) was added. The mixture was irradiated in a microwave for 75 minutes at 130° C. The mixture was diluted with ethyl acetate and water. The aqueous phase was extracted with ethyl acetate. The combined extracts were concentrated, and the residue was purified by flash chromatography (silica gel) to provide the desired product. LCMS-ESI+ (m/z): [M+H]+ calcd for $C_{28}H_{32}FN_6O_6S$ 599.2; found: 599.0

Step 3: Preparation of 2-(((3R,4S)-3-fluoropiperidin-4-yl)oxy)-5-(4-((3-methoxy-4-(methylsulfonyl)phenyl)amino)-1,3,5-triazin-2-yl)benzonitrile hydrochloride:

(3R,4S)-tert-butyl 4-(2-cyano-4-(4-methoxy-4-(methylsulfonyl)phenyl)amino)-1,3,5-triazin-2-yl)phenoxy)-3-fluoropiperidine-1-carboxylate (77 mg, 0.13 mmol) was taken up in 4N HCl/dioxanes (5 mL). The resulting suspension was heated briefly to reflux and then allowed to cool to room temperature. The suspension was homogenized with dichloromethane (3 mL). The mixture was allowed to stand at room temperature for 2 hours before being concentrated under reduced pressure to provide the desired material. LCMS-ESI+ (m/z): [M+H]+ calcd for $C_{23}H_{24}FN_6O_4S$ 499.2; found: 499.3

Step 4: Preparation of 2-(((3R,4S)-3-fluoro-1-((S)-2-hydroxypropanoyl)piperidin-4-yl)oxy)-5-(4-((3-methoxy-4-(methylsulfonyl)phenyl)amino)-1,3,5-triazin-2-yl)benzonitrile:

2-(((3R,4S)-3-fluoropiperidin-4-yl)oxy)-5-(4-((3-methoxy-4-(methylsulfonyl)phenyl)amino)-1,3,5-triazin-2-yl)benzonitrile hydrochloride (0.13 mmol) and L-(+)-lactic acid (Sigma Aldrich, 32 mg, 0.36 mmol) were taken up in N,N-dimethylformamide (2 mL). The mixture was treated successively with N,N-diisopropylethylamine (90 μL, 0.52 mmol) and N-[(dimethylamino)-1H-1,2,3-triazolo-[4,5-b]pyridin-1-ylmethylene]-N-methylmethanaminiumhexafluorophosphate N-oxide (HATU, 98 mg, 0.26 mmol). The mixture remained at room temperature overnight. The mixture was concentrated to dryness under reduced pressure, the residue taken up in pyridine (1.5 mL), and treated with concentrated ammonium hydroxide solution (0.25 mL). The mixture was heated at 50° C. for 3 hours before being concentrated to dryness under reduced pressure. The residue was purified by prep HPLC (5-85% acetonitrile in water, 0.1% trifluoroacetic acid buffer) to provide 2-(((3R,4S)-3-fluoro-1-((S)-2-hydroxypropanoyl)piperidin-4-yl)oxy)-5-(4-((3-methoxy-4-(methylsulfonyl)phenyl)amino)-1,3,5-triazin-2-yl)benzonitrile. LCMS-ESI+ (m/z): [M+H]+ calcd for $C_{26}H_{28}FN_6O_6S$: 571.2; found: 571.1 1H NMR (400 MHz, DMSO-d6) δ 10.82 (s, 1H), 8.99 (s, 1H), 8.71 (d, J=2.2 Hz, 1H), 8.67 (dd, J=9.0, 2.2 Hz, 1H), 7.99 (br, 1H), 7.82 (d, J=8.6 Hz, 1H), 7.70 (d, J=9.1 Hz, 1H), 7.55 (br, 1H), 5.33-4.97 (m, 2H), 4.60-4.35 (m, 2H), 4.27-3.95 (m, 1H), 4.06 (s, 3H), 3.69-3.32 (m, 2H), 3.26 (s, 3H), 3.22 (m, 1H), 2.10-1.83 (m, 2H), 1.25 (dd, J=6.5, 3.9 Hz, 3H).

Example 484

4-(4-(methylsulfonyl)phenyl)-N-(4-(4-(oxetan-3-yl)piperazin-1-yl)phenyl)-1,3,5-triazin-2-amine, trifluoroacetic acid salt

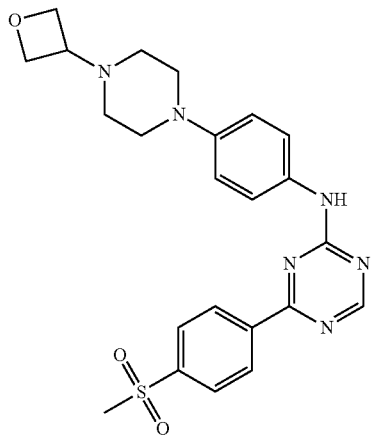 [SMILES: CS(=O)(=O)c1ccc(-c2ncnc(Nc3ccc(N4CCN(C5COC5)CC4)cc3)n2)cc1]

A suspension of crude 4-chloro-N-(4-(4-(oxetan-3-yl)piperazin-1-yl)phenyl)-1,3,5-triazin-2-amine (approximately 0.89 mmol), 4-(methylsulfonyl)phenylboronic acid (Sigma Aldrich, 0.28 g, 1.4 mmol) and tetrakis(triphenylphosphine)palladium(0) (0.08 g, 7.5 mol %) in ethanol/toluene (1:1, 10 mL) was treated with 2 M aqueous sodium carbonate solution. The mixture was irradiated in a microwave reactor for 75 minutes at 130° C. The mixture was diluted with ethyl acetate and water and filtered through a disposable fitted pad of Celite diatomaceous earth. The aqueous phase was extracted four times with ethyl acetate. The combined extracts were washed with saturated aqueous sodium chloride solution, dried over anhydrous magnesium sulfate, filtered, concentrated to dryness under reduced pressure. The residue was purified by prep HPLC (5-80% acetonitrile in water, 0.1% trifluoroacetic acid buffer) to provide the desired product. LCMS-ESI$^+$ (m/z): [M+H]$^+$ calcd for $C_{23}H_{27}N_6O_3S$: 467.2; found: 467.3

Example 485

2-(((3R,4S)-3-fluoro-1-(1-methyl-1H-1,2,3-triazole-4-carbonyl)piperidin-4-yl)oxy]-5-(4-((3-methyl-4-(1-methylpiperidin-4-yl)phenyl)amino)-1,3,5-triazin-2-yl)benzonitrile

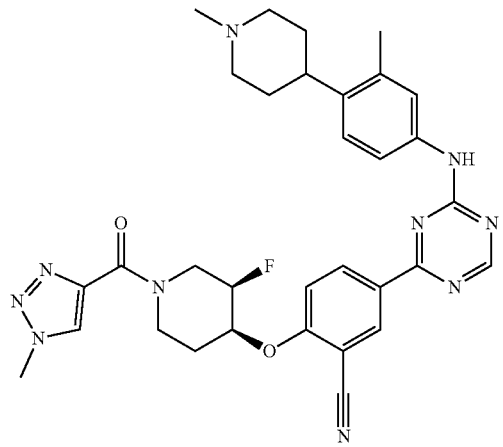 [SMILES: Cc1cc(Nc2ncnc(-c3ccc(O[C@H]4CCN(C(=O)c5cn(C)nn5)C[C@H]4F)c(C#N)c3)n2)ccc1C1CCN(C)CC1]

Step 1: Preparation of 5-bromo-2-(((3R,4S)-3-fluoropiperidin-4-yl)oxy)benzonitrile hydrochloride:

(3R,4S)-tert-butyl 4-(4-bromo-2-cyanophenoxy)-3-fluoropiperidine-1-carboxylate (preparation given in example 382, 0.37 g, 0.93 mmol) was taken up in hydrogen chloride solution (4 M in dioxanes, 9.3 mL, 37 mmol). The mixture was allowed to stand at room temperature overnight and was then concentrated to dryness under reduced pressure to give the desired material. LCMS-ESI$^+$ (m/z): [M+H]$^+$ calcd for $C_{12}H_{13}BrFN_2O$: 299.0; found: 299.1

Step 2: Preparation of 5-bromo-2-(((3R,4S)-3-fluoro-1-(1-methyl-1H-1,2,3-triazole-4-carbonyl)piperidin-4-yl)oxy)benzonitrile:

1-methyl-1H-1,2,3-triazole-4-carboxylic acid (Aurum Pharmtech LLC, 71 mg, 0.56 mmol) was added to a solution of 5-bromo-2-(((3R,4S)-3-fluoropiperidin-4-yl)oxy)benzonitrile hydrochloride in N,N-dimethylformamide (2.5 mL). The mixture was treated with N,N-diisopropylethylamine (0.41 mL, 2.3 mmol) followed by N-[(dimethylamino)-1H-1,2,3-triazolo-[4,5-b]pyridin-1-ylmethylene]-N-methyl-methanaminiumhexafluorophosphate N-oxide (HATU, 0.36 g, 0.93 mmol). The mixture was left to stir overnight at room temperature and then was purified by flash chromatography (silica gel) to provide a semi-solid which was taken up as a suspension in dichloromethane and filtered through a plug of Celite diatomaceous earth. The filtrate was concentrated to dryness under reduced pressure to provide the desired material. LCMS-ESI$^+$ (m/z): [M+H]$^+$ calcd for $C_{16}H_{16}BrFN_5O_2$: 408.0; found: 408.1

Step 3: Preparation of 2-(((3R,4S)-3-fluoro-1-(1-methyl-1H-1,2,3-triazole-4-carbonyl)piperidin-4-yl)oxy)-5-(4,4,5,5-tetramethyl-1,3,2-dioxaborolan-2-yl)benzonitrile:

A mixture of 5-bromo-2-(((3R,4S)-3-fluoro-1-(1-methyl-1H-1,2,3-triazole-4-carbonyl)piperidin-4-yl)oxy)benzonitrile (0.19 g, 0.46 mmol), bis(pinacolato)diboron (0.23 g, 0.92 mmol), potassium acetate (0.14 g, 1.4 mmol), and [1,1'-bis(diphenylphosphino)ferrocene]dichloropalladium(II) (0.03 g, 10 mol %) in 1,4-dioxane (3 mL) was heated in a microwave reactor for 20 minutes at 150° C. The mixture was filtered through a pad of Celite diatomaceous earth and concentrated to dryness under reduced pressure to provide the desired material, which was carried forward without further purification. LCMS-ESI$^+$ (m/z): [M+H]$^+$ calcd for $C_{16}H_{16}BrFN_5O_2$: 408.0; found: 408.1

Step 4: Preparation of tert-butyl 4-(4-((4-(3-cyano-4-(((3R,4S)-3-fluoro-1-(1-methyl-1H-1,2,3-triazole-4-carbonyl)piperidin-4-yl)oxy)phenyl)-1,3,5-triazin-2-yl)amino)-2-methylphenyl)piperidine-1-carboxylate:

A mixture of tert-butyl 4-(4-((4-chloro-1,3,5-triazin-2-yl)amino)-2-methylphenyl)piperidine-1-carboxylate (preparation described in example 303, 0.19 g, 0.46 mmol), crude 2-(((3R,4S)-3-fluoro-1-(1-methyl-1H-1,2,3-triazole-4-carbonyl)piperidin-4-yl)oxy)-5-(4,4,5,5-tetramethyl-1,3,2-dioxaborolan-2-yl)benzonitrile (0.46 mmol assumed), and tetrakis(triphenylphosphine)palladium(0) (0.04 g, 7.5 mol %) in 1,2-dimethoxyethane (DME, 3 mL) was treated with 2 M aqueous sodium carbonate solution (0.65 mL). The mixture was irradiated for 75 minutes in a microwave reactor at 130° C. After cooling, the biphasic mixture was separated. The aqueous phase was extracted three times with ethyl acetate. The combined extracts were dried over anhydrous magnesium sulfate, filtered, and concentrated to dryness under reduced pressure. The residue was purified by flash chromatography (silica gel) to provide tert-butyl 4-(4-((4-(3-cyano-4-(((3R,4S)-3-fluoro-1-(1-methyl-1H-1,2,3-triazole-4-carbonyl)piperidin-4-yl)oxy)phenyl)-1,3,5-triazin-2-yl)

amino)-2-methylphenyl)piperidine-1-carboxylate. LCMS-ESI+ (m/z): [M+H]+ calcd for $C_{36}H_{42}FN_{10}O_4$: 697.3; found: 696.9

Step 5: Preparation of 2-(((3R,4S)-3-fluoro-1-(1-methyl-1H-1,2,3-triazole-4-carbonyl)piperidin-4-yl)oxy)-5-(4-((3-methyl-4-(piperidin-4-yl)phenyl)amino)-1,3,5-triazin-2-yl)benzonitrile:

A solution of tert-butyl 4-(4-((4-(3-cyano-4-(((3R,4S)-3-fluoro-1-(1-methyl-1H-1,2,3-triazole-4-carbonyl)piperidin-4-yl)oxy)phenyl)-1,3,5-triazin-2-yl)amino)-2-methylphenyl)piperidine-1-carboxylate (53 mg, 0.08 mmol) in dichloromethane (2 mL) was treated with trifluoroacetic acid (0.26 mL, 3.4 mmol). After two hours at room temperature, the mixture was added to dilute ammonium hydroxide solution. The basic mixture was extracted five times with dichloromethane. The combined organics were dried over anhydrous magnesium sulfate, filtered, concentrated under reduced pressure to give the desired material. LCMS-ESI+ (m/z): [M+H]+ calcd for $C_{31}H_{34}FN_{10}O_2$: 597.3; found: 597.4

Step 6: Preparation of 2-(((3R,4S)-3-fluoro-1-(1-methyl-1H-1,2,3-triazole-4-carbonyl)piperidin-4-yl)oxy)-5-(4-((3-methyl-4-(1-methylpiperidin-4-yl)phenyl)amino)-1,3,5-triazin-2-yl)benzonitrile, trifluoroacetic acid salt:

A solution of 2-(((3R,4S)-3-fluoro-1-(1-methyl-1H-1,2,3-triazole-4-carbonyl)piperidin-4-yl)oxy)-5-(4-((3-methyl-4-(piperidin-4-yl)phenyl)amino)-1,3,5-triazin-2-yl)benzonitrile (38 mg, 0.06 mmol) in methanol (3 mL) was treated with 37% formalin solution (19 uL, 0.26 mmol). After five minutes, sodium tri(acetoxy)borohydride (67 mg, 0.32 mmol) was added, and the mixture was allowed to stand at room temperature overnight before being treated with 1 M sodium hydroxide solution (0.5 mL). The mixture was concentrated to dryness under reduced pressure and purified by prep HPLC (5-85% acetonitrile in water, 0.1% trifluoroacetic acid buffer) to provide the desired product as a trifluoroacetic acid salt. LCMS-ESI+ (m/z): [M+H]+ calcd for $C_{32}H_{36}FN_{10}O_2$: 611.3; found: 611.4 $^1$H NMR (400 MHz, DMSO-$d_6$) δ 10.29 (s, 1H), 9.37 (s, 1H), 8.82 (s, 1H), 8.66-8.57 (m, 2H), 8.54 (s, 1H), 7.68 (d, J=9.5 Hz, 1H), 7.59 (d, J=8.5 Hz, 1H), 7.16 (d, J=8.4 Hz, 1H), 5.13 (m, 2H), 4.65-4.30 (m, 1H), 4.10 (s, 3H), 3.86 (m, 1H), 3.53 (d, J=11.9 Hz, 3H), 3.31-3.08 (m, 2H), 2.98 (m, 1H), 2.82 (d, J=4.7 Hz, 3H), 2.36 (bs, 4H), 2.18-2.00 (m, 2H), 1.96-1.75 (m, 4H).

Example 486

2-(((3R,4S)-3-fluoro-1-((S)-2-hydroxypropanoyl)piperidin-4-yl)oxy)-5-(4-((3-(2-hydroxypropan-2-yl)phenyl)amino)-1,3,5-triazin-2-yl)benzonitrile

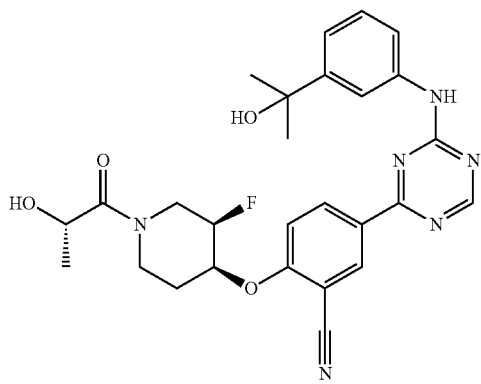 [SMILES: C[C@H](O)C(=O)N1CC[C@H](Oc2ccc(-c3ncnc(Nc4cccc(C(C)(C)O)c4)n3)cc2C#N)[C@H](F)C1]

Step 1: Preparation of 2-(3-((4-chloro-1,3,5-triazin-2-yl)amino)phenyl)propan-2-ol To a solution of 2,4-dichloro-1,3,5-triazine (0.54 g, 3.6 mmol) in N,N-dimethylformamide (DMF, 6 mL) at 0° C. were added N,N-diisopropylethylamine (DIEA, 0.62 mL, 3.6 mmol), followed by a solution 2-(3-aminophenyl)propan-2-ol (Enamine, 0.45 g, 3.0 mmol) in DMF (4 mL, then 2 mL rinsate). The mixture was stirred at 0° C. for 20 minutes and then allowed to warm to room temperature. After four hours, the mixture was partitioned between ethyl acetate and water. The layers were separated, and aqueous phase was extracted three times with ethyl acetate. The combined extracts were washed with saturated aqueous sodium chloride solution, dried over anhydrous magnesium sulfate, filtered, and concentrated under reduced pressure. The residue was purified by flash chromatography on silica gel to provide 2-(3-((4-chloro-1,3,5-triazin-2-yl)amino)phenyl)propan-2-ol. LCMS-ESI+ (m/z): [M+H]+ calcd for $C_{12}H_{14}ClN_4O$ 265.1; found: 265.1

Step 2: Preparation of (3R,4S)-tert-butyl 4-(2-cyano-4-(4-((3-(2-hydroxypropan-2-yl)phenyl)amino)-1,3,5-triazin-2-yl)phenoxy)-3-fluoropiperidine-1-carboxylate (3R,4S)-tert-butyl 4-(2-cyano-4-(4,4,5,5-tetramethyl-1,3,2-dioxaborolan-2-yl)phenoxy)-3-fluoropiperidine-1-carboxylate (preparation described in Example 293, 1.0 mmol) was taken up in 1,2-dimethoxyethane (4 mL) and was added to a microwave vial containing 2-(3-((4-chloro-1,3,5-triazin-2-yl)amino)phenyl)propan-2-ol (0.27 g, 1.0 mmol) and tetrakis(triphenylphosphine)palladium(0) (0.09 g, 7.5 mol %). 2 M aqueous sodium carbonate solution (2.0 mL) was added. The mixture was irradiated in a microwave for 75 minutes at 130° C. The mixture was diluted with ethyl acetate and water. The aqueous phase was extracted with ethyl acetate. The combined extracts were dried over anhydrous magnesium sulfate, filtered, and concentrated under reduced pressure to provide the desired material, which was carried on without further purification. LCMS-ESI+ (m/z): [M+H]+ calcd for $C_{29}H_{34}FN_6O_4$ 549.3; found: 549.1

Step 3: Preparation of 2-(((3R,4S)-3-fluoropiperidin-4-yl)oxy)-5-(4-((3-(2-hydroxypropan-2-yl)phenyl)amino)-1,3,5-triazin-2-yl)benzonitrile A solution of crude (3R,4S)-tert-butyl 4-(2-cyano-4-(4-((3-(2-hydroxypropan-2-yl)phenyl)amino)-1,3,5-triazin-2-yl)phenoxy)-3-fluoropiperidine-1-carboxylate in dichloromethane (10 mL) was added to vigorously stirred 85% aqueous phosphoric acid at room temperature. The mixture was stirred vigorously for 10 minutes. The aqueous phase was diluted with water and cooled in an ice-water bath. 50% w/w aqueous sodium hydroxide solution was added dropwise to ~pH 8. The mixture was extracted three times with dichloromethane. The combined extracts were dried over anhydrous magnesium sulfate, filtered, and concentrated under reduced pressure. The residue was purified by flash chromatography (silica gel) to provide the desired material. LCMS-ESI+ (m/z): [M+H]+ calcd for $C_{24}H_{26}FN_6O_2$ 449.2; found: 449.1

Step 4: Preparation of 2-(((3R,4S)-3-fluoro-1-((S)-2-hydroxypropanoyl)piperidin-4-yl)oxy)-5-(4-((3-(2-hydroxypropan-2-yl)phenyl)amino)-1,3,5-triazin-2-yl)benzonitrile 2-(((3R,4S)-3-fluoropiperidin-4-yl)oxy)-5-(4-((3-(2-hydroxypropan-2-yl)phenyl)amino)-1,3,5-triazin-2-yl)benzonitrile (48 mg, 0.10 mmol) and L-(+)-lactic acid (Sigma Aldrich, 14 mg, 0.16 mmol) were taken up in N,N-dimethylformamide (2 mL). The mixture was treated successively with N,N-diisopropylethylamine (93 µL, 0.54 mmol) and N-[(dimethylamino)-1H-1,2,3-triazolo-[4,5-b]pyridin-1-yl-methylene]-N-methylmethanaminiumhexafluorophosphate N-oxide (HATU, 61 mg, 0.16 mmol). The mixture stirred at room temperature for one hour. The mixture was concentrated to dryness under reduced pressure. The residue was purified by prep HPLC (5-70% acetonitrile in water, 0.1% trifluoroacetic acid buffer) to provide 2-(((3R,4S)-3-fluoro-1-((S)-2-hydroxypropanoyl)piperidin-4-yl)oxy)-5-(4-((3-(2-hydroxypropan-2-yl)phenyl)amino)-1,3,5-triazin-2-yl)benzonitrile. LCMS-ESI$^+$ (m/z): [M+H]$^+$ calcd for $C_{27}H_{30}FN_6O_4$: 521.2; found: 521.1 $^1$H NMR (400 MHz, DMSO-d$_6$) δ 10.36 (s, 1H), 8.86 (s, 1H), 8.67 (m, 2H), 8.13 (bs, 1H), 7.72-7.60 (m, 1H), 7.50 (s, 1H), 7.34 (t, J=7.8 Hz, 1H), 7.26 (d, J=7.8 Hz, 1H), 5.30-4.96 (m, 4H), 4.63-4.34 (m, 1H), 4.25-3.56 (m, 1H), 3.43-3.23 (m, 1H), 2.04 (m, 1H), 1.94-1.80 (m, 1H), 1.52 (s, 6H), 1.35-1.18 (m, 3H).

Example 487

2-(((3R,4S)-3-fluoro-1-((S)-2-hydroxypropanoyl) piperidin-4-yl)oxy)-5-(4-((3-methyl-4-(1-methylpiperidin-4-yl)phenyl)amino)-1,3,5-triazin-2-yl)benzonitrile

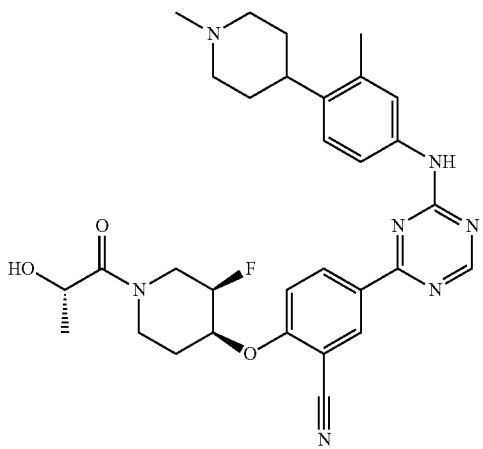 [SMILES: Cc1cc(Nc2ncnc(-c3ccc(O[C@H]4CCN(C(=O)[C@H](C)O)C[C@H]4F)c(C#N)c3)n2)ccc1C1CCN(C)CC1]

Step 1: Preparation of 4-(2-methyl-4-nitrophenyl)-1,2,3,6-tetrahydropyridine hydrochloride:

A solution of tert-butyl 4-(2-methyl-4-nitrophenyl)-5,6-dihydropyridine-1(2H)-carboxylate (preparation described in example 303, 4.8 g, 15 mmol) in toluene (20 mL) was treated dropwise with 4 N hydrogen chloride in dioxanes (20 mL, 80 mmol). After 30 minutes of stirring at room temperature, the resulting precipitate was collected by filtration. The solid was washed with diethyl ether and dried under house vacuum to provide the desired material. LCMS-ESI$^+$ (m/z): [M+H]$^+$ calcd for $C_{12}H_{15}N_2O_2$: 219.1; found: 219.0

Step 2: Preparation of 2-(trimethylsilyl)ethyl 4-(2-methyl-4-nitrophenyl)-5,6-dihydropyridine-1(2H)-carboxylate:

A suspension of 4-(2-methyl-4-nitrophenyl)-1,2,3,6-tetrahydropyridine hydrochloride (3.6 g, 14 mmol) in dichloromethane (60 mL), stirred in an ice-water bath, was treated successively dropwise with N,N-diisopropylethylamine (12 mL, 71 mmol) and a solution of N-[2-(trimethylsilyl)ethoxycarbonyloxy]succinimide (4.4 g, 17 mmol) in dichloromethane (20 mL). The cooling bath was allowed to expire, allowing the mixture to regain room temperature. The mixture was concentrated almost to dryness under reduced pressure. The residue was partitioned between water and ethyl acetate. The aqueous phase was extracted twice with ethyl acetate and once with diethyl ether. The combined extracts were washed twice with water and once with saturated aqueous sodium chloride solution and then were dried over anhydrous magnesium sulfate, filtered, and concentrated under reduced pressure to provide the desired material, which was carried forward without further purification. LCMS-ESI$^+$ (m/z): [M–2CH$_2$+H]$^+$ calcd for $C_{16}H_{23}N_2O_4Si$: 335.1; found: 335.0

Step 3: Preparation of 2-(trimethylsilyl)ethyl 4-(4-amino-2-methylphenyl)piperidine-1-carboxylate:

A solution of crude 2-(trimethylsilyl)ethyl 4-(2-methyl-4-nitrophenyl)-5,6-dihydropyridine-1(2H)-carboxylate (14 mmol assumed) in methanol (75 mL) was degassed before the addition of 10% palladium on carbon (500 mg). The suspension was shaken for four hours under 50 psi of hydrogen. The mixture was filtered through a pad of Celite diatomaceous earth, eluting with methanol. The filtrate was concentrated to dryness under reduced pressure to provide the desired material, which was carried forward without further purification. LCMS-ESI$^+$ (m/z): [M+H]$^+$ calcd for $C_{18}H_{31}N_2O_2Si$: 335.2; found: 334.9

Step 4: Preparation of 2-(trimethylsilyl)ethyl 4-(4-((4-chloro-1,3,5-triazin-2-yl)amino)-2-methylphenyl)piperidine-1-carboxylate:

To a solution of 2,4-dichloro-1,3,5-triazine (2.6 g, 17 mmol) in N,N-dimethylformamide (DMF, 40 mL) at 0° C. were added N,N-diisopropylethylamine (DIEA, 3.1 mL, 18 mmol), followed by a solution of crude 2-(trimethylsilyl) ethyl 4-(4-amino-2-methylphenyl)piperidine-1-carboxylate (14 mmol assumed) in DMF (10 mL then 10 mL rinsate). The mixture was stirred at 0° C. for 20 minutes and then allowed to warm to room temperature. The mixture was partitioned between ethyl acetate and water. The layers were separated and aqueous phase was extracted three times with ethyl acetate. The combined extracts were washed once each with water and saturated aqueous sodium chloride solution, and then dried over anhydrous magnesium sulfate, filtered, and concentrated under reduced pressure. The residue was purified by flash chromatography on silica gel to provide 2-(trimethylsilyl)ethyl 4-(4-((4-chloro-1,3,5-triazin-2-yl) amino)-2-methylphenyl)piperidine-1-carboxylate. LCMS-ESI$^+$ (m/z): [M+H]$^+$ calcd for $C_{21}H_{31}ClN_5O_2Si$ 448.2; found: 447.9

Step 5: Preparation of (3R,4S)-tert-butyl 4-(2-cyano-4-(4-((3-methyl-4-(1-((2-(trimethylsilyl)ethoxy)carbonyl)piperidin-4-yl)phenyl)amino)-1,3,5-triazin-2-yl)phenoxy)-3-fluoropiperidine-1-carboxylate:

(3R,4S)-tert-butyl 4-(2-cyano-4-(4,4,5,5-tetramethyl-1,3,2-dioxaborolan-2-yl)phenoxy)-3-fluoropiperidine-1-carboxylate (preparation described in Example 293, 1.7 mmol) was taken up in 1,2-dimethoxyethane (8 mL) and was added to a microwave vial containing 2-(trimethylsilyl)ethyl 4-(4-((4-chloro-1,3,5-triazin-2-yl)amino)-2-methylphenyl)piperidine-1-carboxylate (0.75 g, 1.7 mmol) and tetrakis(triphenylphosphine)palladium(0) (0.15 g, 7.5 mol %). 2 M aqueous sodium carbonate solution (3.3 mL) was added. The mixture was irradiated in a microwave for 75 minutes at 130° C. The mixture was diluted with ethyl acetate and water. The aqueous phase was extracted with ethyl acetate. The combined extracts were dried over anhydrous magnesium sulfate, filtered, and concentrated under reduced pressure to provide the desired material, which was carried forward without further purification. LCMS-ESI$^+$ (m/z): [M+H]$^+$ calcd for $C_{38}H_{50}FN_7O_5Si$ 732.4; found: 732.2

Step 5: Preparation of (3R,4S)-tert-butyl 4-(2-cyano-4-(4-((3-methyl-4-(piperidin-4-yl)phenyl)amino)-1,3,5-triazin-2-yl)phenoxy)-3-fluoropiperidine-1-carboxylate A solution of crude (3R,4S)-tert-butyl 4-(2-cyano-4-(4-((3-methyl-4-(1-((2-(trimethylsilyl)ethoxy)carbonyl)piperidin-4-yl)phenyl)amino)-1,3,5-triazin-2-yl)phenoxy)-3-fluoropiperidine-1-carboxylate (1.7 mmol assumed) in N,N-dimethylformamide (6 mL) was treated with cesium fluoride (3.0 g, 20 mmol). The mixture was heated at 100° C. for three hours and then was allowed to cool to room temperature. The mixture was filtered through a pad of Celite diatomaceous earth. The filtrate was concentrated under reduced pressure, and the residue was purified by flash chromatography (silica gel) to provide the desired material. LCMS-ESI$^+$ (m/z): [M+H]$^+$ calcd for $C_{32}H_{39}FN_7O_3$ 588.3; found: 588.2

Step 6: Preparation of (3R,4S)-tert-butyl 4-(2-cyano-4-(4-((3-methyl-4-(1-methylpiperidin-4-yl)phenyl)amino)-1,3,5-triazin-2-yl)phenoxy)-3-fluoropiperidine-1-carboxylate:

A solution of (3R,4S)-tert-butyl 4-(2-cyano-4-(4-((3-methyl-4-(1-methylpiperidin-4-yl)phenyl)amino)-1,3,5-triazin-2-yl)phenoxy)-3-fluoropiperidine-1-carboxylate (0.28 g, 0.47 mmol) in methanol (3 mL) was treated with 37% formalin solution (140 uL, 1.9 mmol). After five minutes, sodium tri(acetoxy)borohydride (0.50 g, 2.3 mmol) was added, and the mixture was allowed to stand at room temperature for 20 minutes before being concentrated under reduced pressure. The residue was treated with 1 M sodium hydroxide solution (3 mL) and extracted four times with dichloromethane. The combined extracts were dried over anhydrous magnesium sulfate, filtered, and concentrated under reduced pressure to provide the desired material, which was carried forward without further purification. LCMS-ESI$^+$ (m/z): [M+H]$^+$ calcd for $C_{33}H_{41}FN_7O_3$ 602.3; found: 602.3

Step 7: Preparation of 2-(((3R,4S)-3-fluoropiperidin-4-yl)oxy)-5-(4-((3-methyl-4-(1-methylpiperidin-4-yl)phenyl)amino)-1,3,5-triazin-2-yl)benzonitrile dihydrochloride A solution of (3R,4S)-tert-butyl 4-(2-cyano-4-(4-((3-methyl-4-(1-methylpiperidin-4-yl)phenyl)amino)-1,3,5-triazin-2-yl)phenoxy)-3-fluoropiperidine-1-carboxylate (0.26 g, 0.44 mmol) in dichloromethane (4 mL) was treated with 4 N hydrogen chloride in dioxane (10 mL, 40 mmol). The resulting suspension was allowed to stand overnight at room temperature before being concentrated under reduced pressure to provide the desired material. LCMS-ESI$^+$ (m/z): [M+H]$^+$ calcd for $C_{28}H_{33}FN_7O$ 502.3; found: 502.5

Step 8: Preparation of 2-(((3R,4S)-3-fluoro-1-((S)-2-hydroxypropanoyl)piperidin-4-yl)oxy)-5-(4-((3-methyl-4-(1-methylpiperidin-4-yl)phenyl)amino)-1,3,5-triazin-2-yl)benzonitrile, trifluoroacetic acid salt:

A mixture of 2-(((3R,4S)-3-fluoropiperidin-4-yl)oxy)-5-(4-((3-methyl-4-(1-methylpiperidin-4-yl)phenyl)amino)-1,3,5-triazin-2-yl)benzonitrile dihydrochloride (55 mg, 0.11 mmol) and N,N-diisopropylethylamine (96 μL, 0.55 mmol) in N,N-dimethylformamide (2 mL) was treated successively with L-(+)-lactic acid (Sigma Aldrich, 15 mg, 0.17 mmol) and N-[(dimethylamino)-1H-1,2,3-triazolo-[4,5-b]pyridin-1-ylmethylene]-N-methylmethanaminiumhexafluorophosphate N-oxide (HATU, 63 mg, 0.17 mmol). The mixture stirred at room temperature for one hour. The mixture was concentrated to dryness under reduced pressure. The residue was purified by prep HPLC (5-70% acetonitrile in water, 0.1% trifluoroacetic acid buffer) to provide 2-(((3R,4S)-3-fluoro-1-((S)-2-hydroxypropanoyl)piperidin-4-yl)oxy)-5-(4-((3-methyl-4-(1-methylpiperidin-4-yl)phenyl)amino)-1,3,5-triazin-2-yl)benzonitrile, trifluoroacetic acid salt. LCMS-ESI$^+$ (m/z): [M+H]$^+$ calcd for $C_{31}H_{37}FN_7O_3$: 574.3; found: 574.4 $^1$H NMR (400 MHz, DMSO-d$_6$) δ 10.32 (br, 1H), 9.44 (bs, 1H), 8.81 (s, 1H), 8.67-8.55 (m, 2H), 7.66 (d, J=9.3 Hz, 1H), 7.59 (d, J=8.5 Hz, 1H), 7.16 (d, J=8.4 Hz, 1H), 5.26-4.94 (m, 2H), 4.48 (m, 1H), 4.26-3.91 (m, 2H), 3.64-3.25 (m, 1H), 3.52 (d, J=11.9 Hz, 2H), 3.13 (m, 2H), 2.97 (m, 1H), 2.82 (d, J=4.7 Hz, 3H), 2.36 (bs, 4H), 2.09-1.69 (m, 6H), 1.21 (dd, J=6.4, 4.1 Hz, 3H).

Example 488

2-(((3R,4S)-1-(2-cyanoacetyl)-3-fluoropiperidin-4-yl)oxy)-5-(4-((3-methyl-4-(1-methylpiperidin-4-yl)phenyl)amino)-1,3,5-triazin-2-yl)benzonitrile

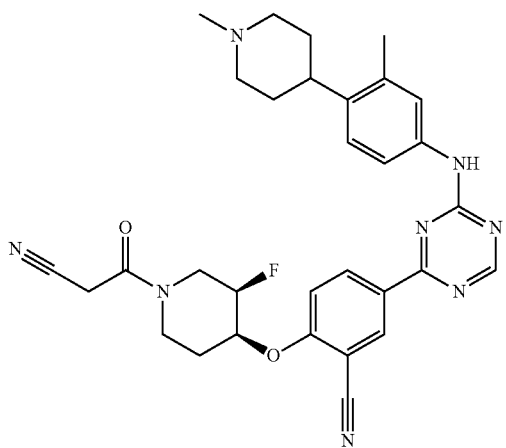 [SMILES: Cc1cc(Nc2ncnc(-c3ccc(O[C@H]4CCN(C(=O)CC#N)C[C@H]4F)c(C#N)c3)n2)ccc1C1CCN(C)CC1]

The title compound was prepared and purified in the manner of Example 487 (2-(((3R,4S)-3-fluoro-1-((S)-2-hydroxypropanoyl)piperidin-4-yl)oxy)-5-(4-((3-methyl-4-(1-methylpiperidin-4-yl)phenyl)amino)-1,3,5-triazin-2-yl)benzonitrile, trifluoroacetic acid salt) by substituting cyanoacetic acid for L-(+)-lactic acid. LCMS-ESI$^+$ (m/z): [M+H]$^+$ calcd for $C_{31}H_{34}FN_8O_2$: 569.3; found: 569.4 $^1$H NMR (400 MHz, DMSO-d$_6$) δ 10.33 (br, 1H), 9.43 (br, 1H), 8.81 (s, 1H), 8.65-8.48 (m, 2H), 7.65 (dd, J=9.6, 1.8 Hz, 1H), 7.58 (d, J=8.5 Hz, 1H), 7.15 (d, J=8.4 Hz, 1H), 5.26-4.93 (m, 2H), 4.37 (dt, J=14.4, 6.9 Hz, 1H), 4.29-3.84 (m, 3H), 3.75-3.58 (m, 1H), 3.54 (m, 2H), 3.48-3.20 (m, 1H), 3.13 (q, J=11.4 Hz, 2H), 3.03-2.89 (m, 1H), 2.82 (d, J=4.7 Hz, 3H), 2.36 (s, 4H), 2.10-1.97 (m, 1H), 1.86 (m, 4H).

Example 489

2-(((3R,4S)-3-1-fluoro-1-(2-methoxyacetyl)piperidin-4-yl)oxy)-5-(4-((3-methyl-4-(1-methylpiperidin-4-yl)phenyl)amino)-1,3,5-triazin-2-yl)benzonitrile

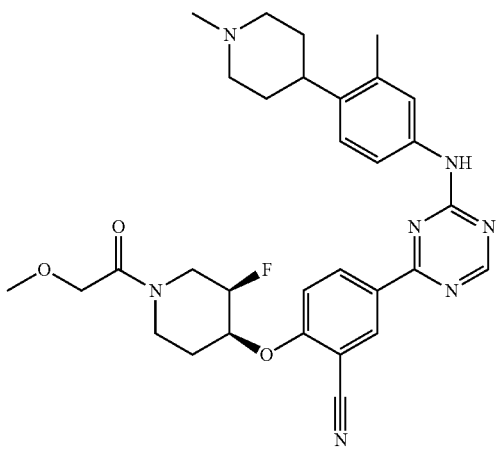 [SMILES: COCC(=O)N1CC[C@H](Oc2ccc(-c3ncnc(Nc4ccc(C5CCN(C)CC5)c(C)c4)n3)cc2C#N)[C@H](F)C1]

The title compound was prepared and purified in the manner of Example 487: (2-(((3R,4S)-3-fluoro-1-((S)-2-hydroxypropanoyl)piperidin-4-yl)oxy)-5-(4-((3-methyl-4-(1-methylpiperidin-4-yl)phenyl)amino)-1,3,5-triazin-2-yl)benzonitrile, trifluoroacetic acid salt) by substituting methoxyacetic acid for L-(+)-lactic acid. LCMS-ESI$^+$ (m/z): [M+H]$^+$ calcd for $C_{31}H_{37}FN_7O_3$: 574.3; found: 574.5 $^1$H NMR (400 MHz, DMSO-d$_6$) δ 10.32 (br, 1H), 9.40 (bs, 1H), 8.81 (s, 1H), 8.68-8.51 (m, 2H), 7.65 (d, J=9.4 Hz, 1H), 7.59 (d, J=8.4 Hz, 1H), 7.15 (d, J=8.4 Hz, 1H), 5.23-4.93 (m, 2H), 4.36 (m, 1H), 4.20 (m, 1H), 4.08 (m, 1H), 3.99 (m, 1H), 3.75 (d, J=14.1 Hz, 1H), 3.52 (d, J=11.7 Hz, 2H), 3.30 (s, 3H), 3.13 (q, J=11.1 Hz, 2H), 2.96 (m, 1H), 2.82 (d, J=4.6 Hz, 3H), 2.36 (br, 4H), 2.10-1.69 (m, 6H).

Example 490

2-(((3R,4S)-3-fluoro-1-(5-methyl-4H-1,2,4-triazole-3-carbonyl)piperidin-4-yl)oxy)-5-(4-((3-methyl-4-(1-methylpiperidin-4-yl)phenyl)amino)-1,3,5-triazin-2-yl)benzonitrile

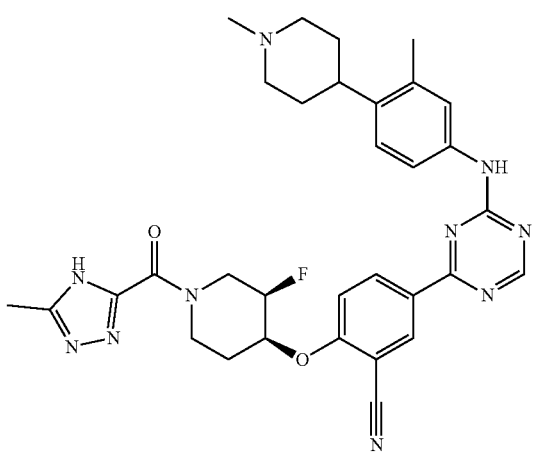 [SMILES: Cc1nnc(C(=O)N2CC[C@H](Oc3ccc(-c4ncnc(Nc5ccc(C6CCN(C)CC6)c(C)c5)n4)cc3C#N)[C@H](F)C2)[nH]1]

The title compound was prepared and purified in the manner of Example 487: (2-(((3R,4S)-3-fluoro-1-((S)-2-hydroxypropanoyl)piperidin-4-yl)oxy)-5-(4-((3-methyl-4-(1-methylpiperidin-4-yl)phenyl)amino)-1,3,5-triazin-2-yl)benzonitrile, trifluoroacetic acid salt) by substituting 5-methyl-1H-1,2,4,-triazole-3-carboxylic acid (Aurum Pharmtech) for L-(−)-lactic acid. LCMS-ESI$^+$ (m/z): [M+H]$^+$ calcd for $C_{32}H_{36}FN_{10}O_2$: 611.3; found: 611.5 $^1$H NMR (400 MHz, DMSO-d$_6$) δ 10.32 (br, 1H), 9.41 (br, 1H), 8.81 (s, 1H), 8.67-8.54 (m, 2H), 7.66 (d, J=9.1 Hz, 1H), 7.59 (d, J=8.9 Hz, 1H), 7.15 (d, J=8.4 Hz, 1H), 5.30-4.93 (m, 2H), 4.55-4.31 (m, 3H), 3.80 (m, 1H), 3.41 (m, 3H), 3.21-2.88 (m, 4H), 2.82 (d, J=4.6 Hz, 3H), 2.44-2.30 (m, 6H), 2.29-2.12 (m, 1H), 2.12-1.61 (m, 4H).

Example 491

3-((2-cyano-4-(4-((4(4-(oxetan-3-yl)piperazin-1-yl)phenyl)amino)-1,3,5-triazin-2-yl)phenoxy)methyl)oxetane-3-carbonitrile

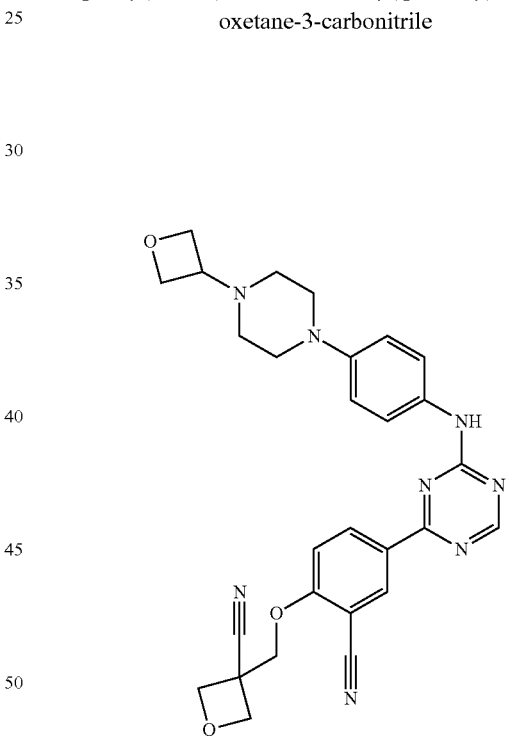

Potassium tert-butoxide (100 mg, 0.88 mmol) was added to a solution of 3-(hydroxymethyl)oxetane-3-carbonitrile (Enamine, 100 mg, 0.88 mmol) in tetrahydrofuran (5 mL). The resulting suspension was stirred at room temperature for 30 minutes before the addition of 2-fluoro-5-(4-((4-(4-(oxetan-3-yl)piperazin-1-yl)phenyl)amino)-1,3,5-triazin-2-yl)benzonitrile (Example 87, 100 mg, 0.23 mmol). The mixture was heated overnight at 60° C. The mixture was purified by flash chromatography (silica gel) to provide the desired product. LCMS-ESI$^+$ (m/z): [M+H]$^+$ calcd for $C_{28}H_{29}N_8O_3$: 525.2; found: 525.3

Example 492

2-(((3R,4S)-3-fluoro-1-(2-methoxyacetyl)piperidin-4-yl)oxy)-5-(4-((4-(1-formylpiperidin-4-yl)-3-methylphenyl)amino)-1,3,5-triazin-2-yl)benzonitrile

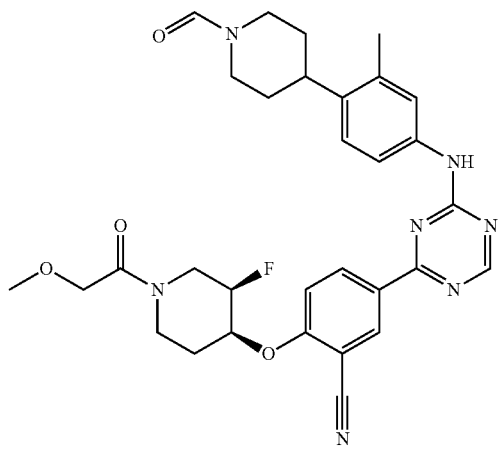 [SMILES: COCC(=O)N1CC[C@H](Oc2ccc(-c3ncnc(Nc4ccc(C5CCN(C=O)CC5)c(C)c4)n3)cc2C#N)[C@H](F)C1]

Step 1: Preparation of 4-(4,4,5,5-tetramethyl-1,3,2-dioxaborolan-2-yl)-1,2,3,6-tetrahydropyridine hydrochloride:

Acetyl chloride (10 mL, 150 mmol) was added to methanol, which was cooled in an ice-water bath. tert-butyl 4-(4,4,5,5-tetramethyl-1,3,2-dioxaborolan-2 -yl)-5,6-dihydropyridine-1(2H)-carboxylate (Advanced ChemBlocks, Inc., 3.0 g, 9.7 mmol) was added to the solution in a single portion. The mixture was removed from the bath and allowed to regain room temperature. Dichloromethane (approximately 20 mL) was added to homogenize the mixture, which was left overnight at room temperature. Concentration under reduced pressure provided the desired material. LCMS-ESI$^+$ (m/z): [M+H]$^+$ calcd for C$_{11}$H$_{21}$BNO$_2$: 210.2; found: 210.1

Step 2: Preparation of 4-(4,4,5,5-tetramethyl-1,3,2-dioxaborolan-2-yl)-5,6-dihydropyridine-1(2H)-carbaldehyde:

To a suspension of 4-(4,4,5,5-tetramethyl-1,3,2-dioxaborolan-2-yl)-1,2,3,6-tetrahydropyridine hydrochloride (2.4 g, 9.7 mmol), 1-ethyl-3-(3-dimethylaminopropyl)carbodiimide hydrochloride (2.5 g, 16 mmol), 4-dimethylaminopyridine (0.59 g, 4.9 mmol) in dichloromethane (80 mL) were added successively N,N-diisopropylethylamine (8.4 mL, 49 mmol) and formic acid (0.92 mL, 24 mmol). The reaction mixture stirred at room temperature overnight. The crude reaction mixture was diluted with dichloromethane and saturated aqueous sodium hydrogen carbonate solution. The aqueous layer was extracted with three times with dichloromethane. The combined extracts were washed with saturated aqueous sodium chloride solution, dried over anhydrous magnesium sulfate, filtered, and concentrated under reduced pressure to provide the desired product. LCMS-ESI$^+$ (m/z): [M+H]$^+$ calcd for C$_{12}$H$_{21}$BNO$_3$: 238.2; found: 238.1

Step 3: Preparation of 4-(2-methyl-4-nitrophenyl)-5,6-dihydropyridine-1(2H)-carbaldehyde:

A mixture of 2-bromo-5-nitrotoluene (0.19 g, 8.8 mmol), crude 4-(4,4,5,5-tetramethyl-1,3,2-dioxaborolan-2-yl)-5,6-dihydropyridine-1(2H)-carbaldehyde (2.3 g, 9.7 mmol), tetrakis(triphenylphosphine)palladium(0) (0.61 g, 6 mol %), 2 M aqueous sodium carbonate solution (13 mL), and 1,4-dioxane (30 mL) was heated at 90° C. for 3 hours. The reaction mixture was allowed to cool to room temperature. The mixture was diluted with ethyl acetate and water. The aqueous phase was extracted three times with ethyl acetate. The combined extracts were dried over anhydrous magnesium sulfate, filtered, and concentrated under reduced pressure. The residue was purified by flash chromatography (silica gel) to provide the desired material. LCMS-ESI$^+$ (m/z): [M+H]$^+$ calcd for C$_{13}$H$_{15}$N$_2$O$_3$: 247.1; found: 246.9

Step 4: Preparation of 4-(4-amino-2-methylphenyl)piperidine-1-carbaldehyde:

A solution of 4-(2-methyl-4-nitrophenyl)-5,6-dihydropyridine-1(2H)-carbaldehyde (2.6 g, 11 mmol) in methanol (25 mL) was degassed and then treated with 10% palladium on carbon (260 mg). The suspension was shaken under 50 psi hydrogen overnight and then filtered through a bed of Celite diatomaceous earth. The filtrate was concentrated to dryness under reduced pressure, and the residue was taken up in methanol (25 mL), degassed, and treated with 10% palladium on carbon (260 mg). The suspension was shaken under 50 psi hydrogen overnight and then filtered through a bed of Celite diatomaceous earth. The filtrate was concentrated to dryness under reduced pressure to provide the desired material. LCMS-ESI$^+$ (m/z): [M+H]$^+$ calcd for C$_{13}$H$_{19}$N$_2$O: 219.1; found: 219.1

Step 5: Preparation of 4-(4-((4-chloro-1,3,5-triazin-2-yl)amino)-2-methylphenyl)piperidine-1-carbaldehyde:

To a solution of 2,4-dichloro-1,3,5-triazine (1.3 g, 8.6 mmol) in N,N-dimethylformamide (DMF, 25 mL) at 0° C. were added N,N-diisopropylethylamine (DIEA, 1.5 mL, 8.6 mmol), followed by a solution of 4-(4-amino-2-methylphenyl)piperidine-1-carbaldehyde (1.7 g, 7.8 mmol) in DMF (5 mL). The mixture was stirred at 0° C. for 5 minutes and then allowed to warm to room temperature. After one hour of stirring, the mixture was partitioned between ethyl acetate and water. The layers were separated and aqueous phase was extracted twice with ethyl acetate. The combined extracts were washed once each with water and saturated aqueous sodium chloride solution, and then dried over anhydrous magnesium sulfate, filtered, and concentrated under reduced pressure. The residue was purified by flash chromatography on silica gel to provide the desired material. LCMS-ESI$^+$ (m/z): [M+H]$^+$ calcd for C$_{16}$H$_{19}$ClN$_5$O 332.1; found: 332.2

Step 6: Preparation of (3R,4S)-tert-butyl 4-(2-cyano-4-(4-((4-(1-formylpiperidin-4-yl)-3-methylphenyl)amino)-1,3,5-triazin-2-yl)phenoxy)-3-fluoropiperidine-1-carboxylate:

A solution of crude (3R,4S)-tert-butyl 4-(2-cyano-4-(4,4,5,5-tetramethyl-1,3,2-dioxaborolan-2-yl)phenoxy)-3-fluoropiperidine-1-carboxylate (preparation described in Example 293, 1.5 mmol) in 1,2-dimethoxyethane (8 mL) was added to a mixture of 4-(4-((4-chloro-1,3,5-triazin-2-yl)amino)-2-methylphenyl)piperidine-1-carbaldehyde (0.65 g, 2.0 mmol), [1,1'-bis(diphenylphosphino)ferrocene]dichloropalladium(II) (0.11 g, 10 mol %), and potassium carbonate (0.85 g, 6.1 mmol). Water (3 mL) was added, and the mixture was heated for 75 minutes at 105° C. After cooling to room temperature, the mixture was diluted with ethyl acetate and saturated aqueous sodium chloride solution and then filtered through a pad of Celite diatomaceous earth. The aqueous phase was extracted three times with ethyl acetate. The combined organic extracts were concentrated under reduced pressure to provide the crude desired material, which was carried forward without further purification.: LCMS-ESI$^+$ (m/z): [M+H]$^+$ calcd for C$_{33}$H$_{39}$FN$_7$O$_4$ 616.3; found: 616.0

Step 7: Preparation of 2-(((3R,4S)-3-fluoropiperidin-4-yl)oxy)-5-(4-((4-(1-formylpiperidin-4-yl)-3-methylphenyl)amino)-1,3,5-triazin-2-yl)benzonitrile A solution of crude (3R,4S)-tert-butyl 4-(2-cyano-4-(4-((4-(1-formylpiperidin-4-yl)-3-methylphenyl)amino)-1,3,5-triazin-2-yl)phenoxy)-3-fluoropiperidine-1-carboxylate (1.5 mmol assumed) in dichloromethane (25 mL) was treated with trifluoroacetic acid (5 mL). The mixture was left at room temperature for 30 minutes before being concentrated to dryness. The residue was purified by flash chromatography (silica gel) to provide the desired material: LCMS-ESI$^+$ (m/z): [M+H]$^+$ calcd for $C_{28}H_{31}FN_7O_2$ 516.2; found: 516.3

Step 8: Preparation of 2-(((3R,4S)-3-fluoro-1-(2-methoxyacetyl)piperidin-4-yl)oxy)-5-(4-((4-(1-formylpiperidin-4-yl)-3-methylphenyl)amino)-1,3,5-triazin-2-yl)benzonitrile:

2-(((3R,4S)-3-fluoropiperidin-4-yl)oxy)-5-(4-((4-(1-formylpiperidin-4-yl)-3-methylphenyl)amino)-1,3,5-triazin-2-yl)benzonitrile (50 mg, 0.10 mmol) and methoxyacetic acid (11 uL, 0.15 mmol) were taken up in N,N-dimethylformamide (2 mL). The mixture was treated successively with N,N-diisopropylethylamine (80 μL, 0.49 mmol) and N-[(dimethylamino)-1H-1,2,3-triazolo-[4,5-b]pyridin-1-ylmethylene]-N-methylmethanaminiumhexafluorophosphate N-oxide (HATU, 55 mg, 0.15 mmol). The mixture remained at room temperature overnight. The mixture was concentrated to dryness under reduced pressure and purified by prep HPLC (5-70% acetonitrile in water, 0.1% trifluoroacetic acid buffer) to provide the desired product. LCMS-ESI$^+$ (m/z): [M+H]$^+$ calcd for $C_{31}H_{35}FN_7O_4$ 588.3; found: 588.4 $^1$H NMR (400 MHz, DMSO-d$_6$) δ 10.25 (m, 1H), 8.80 (s, 1H), 8.64-8.49 (m, 2H), 8.04 (s, 1H), 7.65 (d, J=9.0 Hz, 1H), 7.52 (d, J=8.2 Hz, 1H), 7.19 (d, J=8.4 Hz, 1H), 5.23-4.94 (m, 2H), 4.60 (br, 6H), 4.33 (m, 1H), 4.20 (m, 1H), 4.15-3.91 (m, 1H), 3.78 (m, 2H), 3.65-3.34 (m, 1H), 3.30 (d, J=1.7 Hz, 3H), 3.16 (m, 1H), 2.99 (t, J=12.0 Hz, 1H), 2.71 (td, J=12.9, 3.0 Hz, 1H) 2.36 (s, 3H), 2.09-1.91 (m, 1H), 1.75 (m, 2H).

Example 493

2-(((3R,4S)-3-fluoro-1-((S)-2-hydroxypropanoyl)piperidin-4-yl)oxy)-5-(4-((4-(1-formylpiperidin-4-yl)-3-methylphenyl)amino)-1,3,5-triazin-2-yl)benzonitrile

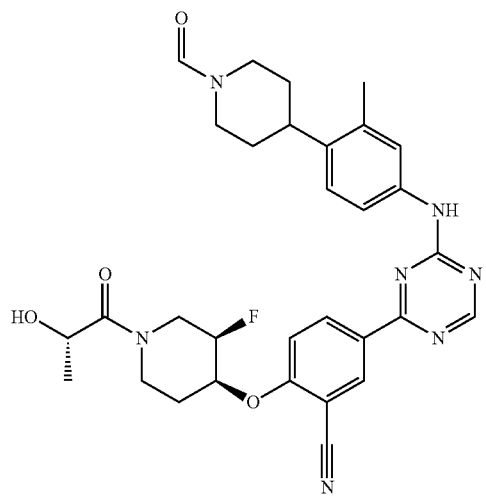 [SMILES: Cc1cc(Nc2ncnc(-c3ccc(O[C@H]4CCN(C(=O)[C@H](C)O)C[C@H]4F)c(C#N)c3)n2)ccc1C1CCN(C=O)CC1]

The title compound was prepared and purified in the manner of Example 492: 2-(((3R,4S)-3-fluoro-1-(2-methoxyacetyl)piperidin-4-yl)oxy)-5-(4-((4-(1-formylpiperidin-4-yl)-3-methylphenyl)amino)-1,3,5-triazin-2-yl)benzonitrile by substituting L-(+)-lactic acid for methoxyacetic acid. LCMS-ESI$^+$ (m/z): [M+H]$^+$ calcd for $C_{31}H_{35}FN_7O_4$: 588.3; found: 588.3 $^1$H NMR (400 MHz, DMSO-d$_6$) δ 10.25 (m, 1H), 8.80 (s, 1H), 8.59 (d, J=9.2 Hz, 2H), 8.04 (s, 1H), 7.65 (d, J=9.0 Hz, 1H), 7.57-7.46 (m, 1H), 7.19 (d, J=8.4 Hz, 1H), 5.41 (br, 6H), 5.25-4.93 (m, 2H), 4.48 (m, 1H), 4.38-4.28 (m, 1H), 4.25-3.90 (m, 1H), 3.87-3.75 (m, 1H), 3.64 (dd, J=29.1, 14.4 Hz, 1H), 3.33 (m, 1H), 3.24-3.11 (m, 1H), 2.99 (t, J=12.1 Hz, 1H), 2.71 (td, J=12.8, 2.9 Hz, 1H), 2.36 (s, 3H), 2.00 (m, 1H), 1.75 (m, 2H), 1.21 (dd, J=6.4, 4.5 Hz, 3H).

Example 494

2-cyano-N-(2-cyano-4-(4-((4-(4-(oxetan-3-yl)piperazin-1-yl)phenyl)amino)-1,3,5-triazin-2-yl)phenyl)acetamide

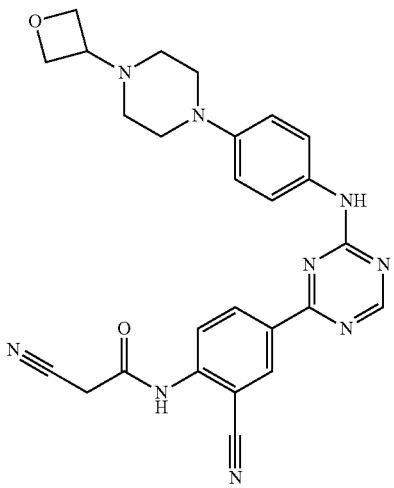 [SMILES: N#CCC(=O)Nc1ccc(-c2ncnc(Nc3ccc(N4CCN(C5COC5)CC4)cc3)n2)cc1C#N]

Step 1: Preparation of 2-amino-5-(4-((4-(4-(oxetan-3-yl)piperazin-1-yl)phenyl)amino)-1,3,5-triazin-2-yl)benzonitrile:

A mixture of 4-chloro-N-(4-(4-(oxetan-3-yl)piperazin-1-yl)phenyl)-1,3,5-triazin-2-amine (1.1 g, 3.1 mmol), 2-amino-5-(4,4,5,5-tetramethyl-1,3,2-dioxaborolan-2-yl)benzonitrile (preparation described in example 37, 0.75 g, 3.1 mmol), [1,1'-bis(diphenylphosphino)ferrocene]dichloropalladium(II) (0.15 g, 7 mol %), and potassium carbonate (1.7 g, 12 mmol) in 1,4-dioxane (15 mL) and water (6 mL) was heated for 30 minutes at 100° C. After cooling, the mixture was purified by flash chromatography (silica gel) to provide the desired product. LCMS-ESI$^+$ (m/z): [M+H]$^+$ calcd for $C_{23}H_{25}N_8O$: 429.2; found: 429.2

Step 2: Preparation of 2-cyano-N-(2-cyano-4-(4-((4-(4-(oxetan-3-yl)piperazin-1-yl)phenyl)amino)-1,3,5-triazin-2-yl)phenyl)acetamide:

A mixture of 2-amino-5-(4-((4-(4-(oxetan-3-yl)piperazin-1-yl)phenyl)amino)-1,3,5-triazin-2-yl)benzonitrile (84 mg, 0.20 mmol) and cyanoacetic acid (36 mg, 0.43 mmol) in pyridine (1 mL) was treated with 1-propanephosphonic anhydride solution (~50% in N,N-dimethylformamide, 0.25 uL) and heated overnight at 80° C. After concentration, the mixture was first purified by flash chromatography (silica gel) and then by preparative HPLC (5-60% acetonitrile in water, 0.1% trifluoroacetic acid buffer) to provide the desired material as a trifluoroacetic acid salt. LCMS-ESI⁺ (m/z): [M+H]⁺ calcd for $C_{26}H_{26}N_9O_2$: 496.2; found: 496.3 ¹H NMR (400 MHz, DMSO-$d_6$) δ 10.83 (s, 1H), 10.28 (d, J=14.7 Hz, 1H), 8.80 (s, 1H), 8.71-8.53 (m, 2H), 7.94 (d, J=8.6 Hz, 1H), 7.75-7.52 (m, 2H), 7.16-7.00 (m, 2H), 4.78 (dd, J=6.5, 3.2 Hz, 4H), 4.46 (bs, 1H), 4.11 (s, 2H), 4.00-2.76 (br, 8H).

Example 495

N-(2-cyano-4-(4-((4-(4-(oxetan-3-yl)piperazin-1-yl)phenyl)amino)-1,3,5-triazin-2-yl)phenyl)propionamide

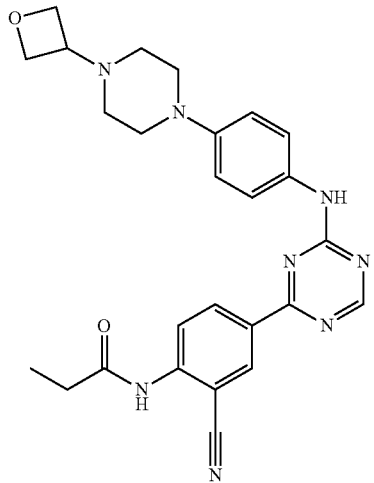 [SMILES: CCC(=O)Nc1ccc(-c2ncnc(Nc3ccc(N4CCN(C5COC5)CC4)cc3)n2)cc1C#N]

The title compound was prepared from 2-amino-5-(4-((4-(4-(oxetan-3-yl)piperazin-1-yl)phenyl)amino)-1,3,5-triazin-2-yl)benzonitrile in the manner of the Example 494 by substituting propionic acid for cyanoacetic acid. It was first purified by flash chromatography (silica gel) and then by preparative HPLC (5-60% acetonitrile in water, 0.1% trifluoroacetic acid buffer) to provide the desired material as a trifluoroacetic acid salt. LCMS-ESI⁺ (m/z): [M+H]⁺ calcd for $C_{26}H_{26}N_9O_2$: 496.2; found: 496.3

Example 496

N-(2-cyano-4-(4-((4-(4-(oxetan-3-yl)piperazin-1-yl)phenyl)amino)-1,3,5-triazin-2-yl)phenyl)-3,3,3-trifluoropropanamide

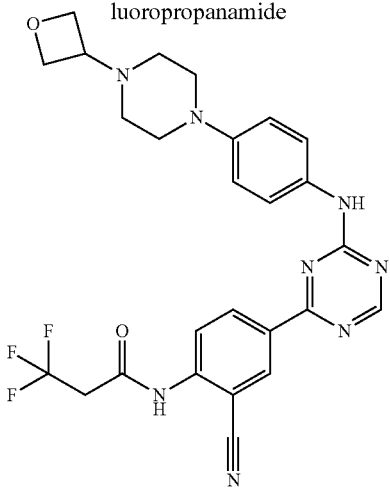

The title compound was prepared from 2-amino-5-(4-((4-(4-(oxetan-3-yl)piperazin-1-yl)phenyl)amino)-1,3,5-triazin-2-yl)benzonitrile in the manner of the Example 494 by substituting 3,3,3-trifluoropropionic acid for cyanoacetic acid. It was first purified by flash chromatography (silica gel) and then by preparative HPLC (5-60% acetonitrile in water, 0.1% trifluoroacetic acid buffer) to provide the desired material as a trifluoroacetic acid salt. LCMS-ESI⁺ (m/z): [M+H]⁺ calcd for $C_{26}H_{26}F_3N_8O_2$: 539.2; found: 496.3 ¹H NMR (400 MHz, DMSO-$d_6$) δ 10.81 (s, 1H), 10.28 (d, J=12.1 Hz, 1H), 8.81 (s, 1H), 8.76-8.53 (m, 2H), 7.93 (s, 1H), 7.75-7.52 (m, 2H), 7.08 (m, 2H), 4.78 (m, 4H), 4.46 (bs, 4H), 3.99 (br, 4H), 3.72 (q, J=11.0 Hz, 2H), 3.06 (br, 4H).

Example 497

2-(((3R,4S)-3-fluoro-1-((S)-2-hydroxypropanoyl)piperidin-4-yl)oxy)-5-(4-((4-(piperazin-1-yl)phenyl)amino)-1,3,5-triazin-2-yl)benzonitrile

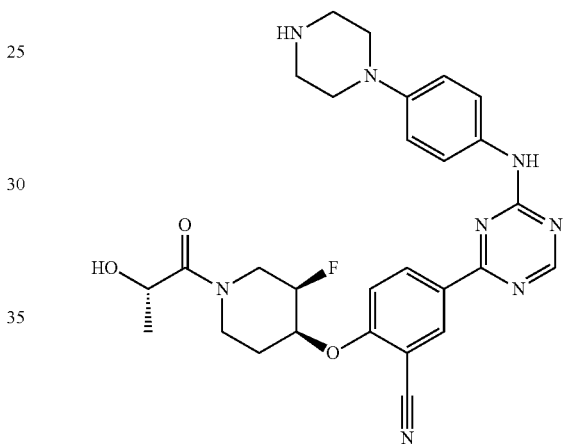

Step 1: tert-butyl 4-(4-((4-chloro-1,3,5-triazin-2-yl)amino)phenyl)piperazine-1-carboxylate:

Tert-butyl 4-(4-aminophenyl)piperazine-1-carboxylate (1260 mg, 4.54 mmol) in 8 mL of DCM was combined with N,N-diisopropylethylamine (3.14 ml, 18.03 mmol) and then cooled to 0° C. 2,4-dichloro-1,3,5-triazine (681.27 mg, 4.54 mmol) in 10 mL of DCM was cooled to 0° C. and then added to the cooled mixture. The reaction then stirred for 5 minutes. The reaction was incomplete. The reaction was subjected to an additional 200 mg of triazine in DCM and stirred for 5 more minutes. According to LCMS, the reaction was complete. The reaction was washed with saturated sodium bicarbonate, extracted with 25% MeOH/DCM, dried, filtered and concentrated to provide tert-butyl 4-(4-((4-chloro-1,3,5-triazin-2-yl)amino)phenyl)piperazine-1-carboxylate.

Step 2: (S)-tert-butyl 4-(4-((4-(3-cyano-4-(((3R,4S)-3-fluoro-1-((S)-2-hydroxypropanoyl)piperidin-4-yl)oxy)phenyl)-1,3,5-triazin-2-yl)amino)phenyl)-3-methylpiperazine-1-carboxylate:

In a microwave tube, tert-butyl 4-(4-((4-chloro-1,3,5-triazin-2-yl)amino)phenyl)piperazine-1-carboxylate (80 mg, 0.2 mmol), 2-(((3R,4S)-3-fluoro-1-((S)-2-hydroxypropanoyl)piperidin-4-yl)oxy)-5-(4,4,5,5-tetramethyl-1,3,2-dioxaborolan-2-yl)benzonitrile (102.73 mg, 0.25 mmol), were combined in DME (2 mL) and 2M Sodium carbonate solution in water (0.46 ml), tetrakis(triphenylphosphine) palladium (23.65 mg, 0.02 mmol) was added, blown down with nitrogen and the vial was sealed, and heated in the microwave at 135° C. for 20 minutes. The reaction was washed with water, extracted with 20% methanol/dichloromethane, dried, filtered and concentrated. The reaction was pushed forward to the next step assuming 100% yield of (S)-tert-butyl 4-(4-((4-(3-cyano-4-(((3R,4S)-3-fluoro-1-((S)-2-hydroxypropanoyl)piperidin-4-yl)oxy)phenyl)-1,3,5-triazin-2-yl)amino)phenyl)-3-methylpiperazine-1-carboxylate.

Step 3: 2-(((3R,4S)-3-fluoro-1-((S)-2-hydroxypropanoyl)piperidin-4-yl)oxy)-5-(4-((4-(piperazin-1-yl)phenyl)amino)-1,3,5-triazin-2-yl)benzonitrile:

In a RBF, (S)-tert-butyl 4-(4-((4-(3-cyano-4-(((3R,4S)-3-fluoro-1-((S)-2-hydroxypropanoyl)piperidin-4-yl)oxy)phenyl)-1,3,5-triazin-2-yl)amino)phenyl)-3-methylpiperazine-1-carboxylate (65 mg, 0.1 mmol) was dissolved in DCM (0.5 ml), trifluoroacetic acid (0.02 ml, 0.2 mmol) was added and the reaction was stirred at rt for 2 h, an additional 2 equivalence of TFA was added and the reaction was stirred for overnight. The reaction cooled to 0° C., neutralized with saturated sodium bicarbonate, washed with water, dried, filtered and concentrated. The residue was purified by reverse phase chromatography to provide 2-(((3R,4S)-3-fluoro-1-((S)-2-hydroxypropanoyl)piperidin-4-yl)oxy)-5-(4-((4-(piperazin-1-yl)phenyl)amino)-1,3,5-triazin-2-yl)benzonitrile (26.3 mg, 24%). LCMS-ESI$^+$ (m/z): [M+H]$^+$ calcd for $C_{25}H_{32}FN_8O_3$: 546.25; found: 547.19. $^1$H NMR (300 MHz, DMSO-d$_6$) δ 10.06 (d, J=16.01 Hz, 1H), 8.73 (s, 1H), 8.55 (d, J=9.05 Hz, 2H), 7.53-6.85 (m, 5H), 6.95 (s, 2H), 5.20-4.90 (m, 3H), 4.50-3.87 (m, 3H), 3.70-3.50 (m, 1H), 3.40-3.30 (m, 1H), 3.0 (s, 4H), 2.80 (s, 4H), 2.0-1.65 (m, 2H), 1.2 (dd, J=9.04, 2.78, 3H).

Example 498

2-(((3R,4S)-3-fluoro-1-((S)-2-hydroxypropanoyl)piperidin-4-yl)oxy)-5-(4-((4-(4-methylpiperazin-1-yl)phenyl)amino)-1,3,5-triazin-2-yl)benzonitrile

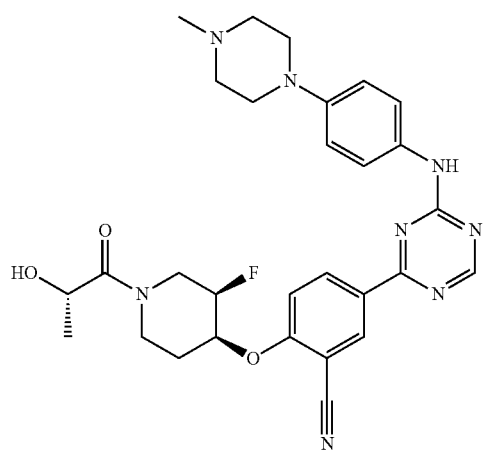 [SMILES: C[C@H](O)C(=O)N1CC[C@H](Oc2ccc(-c3ncnc(Nc4ccc(N5CCN(C)CC5)cc4)n3)cc2C#N)[C@H](F)C1]

2-(((3R,4S)-3-fluoro-1-((S)-2-hydroxypropanoyl)piperidin-4-yl)oxy)-5-(4-((4-(piperazin-1-yl)phenyl)amino)-1,3,5-triazin-2-yl)benzonitrile (22.8 mg, 0.04 mmol) was dissolved in methanol (2 ml), Formaldehyde solution 37%, Formalin (0.01 ml, 0.17 mmol) was added and the reaction was stirred for 5 minutes, followed by the addition of sodium triacetoxyborohydride (44.2 mg, 0.21 mmol). The reaction was allowed to stir at room temperature for 2 hours. The reaction was quenched with 1N NaOH, extracted with 25% methanol/dichloromethane, dried, filtered and concentrated. The crude material was purified by reverse phase to provide 2-(((3R,4S)-3-fluoro-1-((S)-2-hydroxypropanoyl)piperidin-4-yl)oxy)-5-(4-((4-(4-methylpiperazin-1-yl)phenyl)amino)-1,3,5-triazin-2-yl)benzonitrile. LCMS-ESI$^+$ (m/z): [M+H]$^+$ calcd for $C_{29}H_{33}FN_8O_3$: 560.27; found: 561.30. $^1$H NMR (300 MHz, DMSO-d$_6$) δ 10.06 (d, J=16.01 Hz, 1H), 8.73 (s, 1H), 8.55 (d, J=9.05 Hz, 2H), 7.53-6.85 (m, 5H), 6.95 (s, 2H), 5.20-4.90 (m, 3H), 4.50-3.87 (m, 3H), 3.70-3.50 (m, 1H), 3.40-3.30 (m, 1H), 3.15 (s, 4H), 2.45 (m, 4H), 2.20 (s, 1H), 2.0-1.65 (m, 2H), 1.2 (dd, J=9.04, 2.78, 3H).

Example 499

5-(4-((4-((S)-2,4-dimethylpiperazin-1-yl)-3-methoxyphenyl)amino)-1,3,5-triazin-2-yl)-2-(((3R,4S)-3-fluoro-1-((S)-2-hydroxypropanoyl)piperidin-4-yl)oxy)benzonitrile

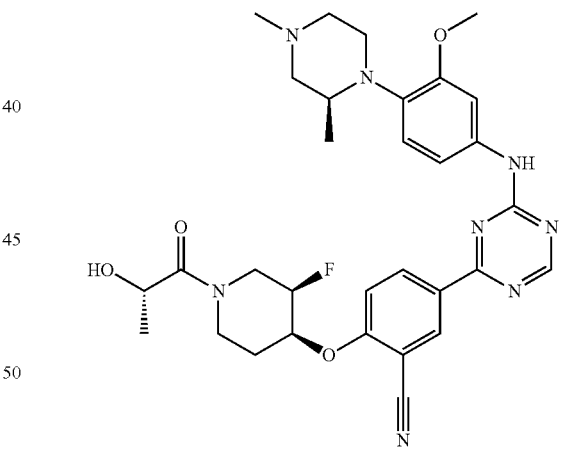

Step 1: (S)-tert-butyl 4-(2-methoxy-4-nitrophenyl)-3-methylpiperazine-1-carboxylate 1-Fluoro-2-methoxy-4-nitrobenzene (2000 mg, 11.69 mmol), (S)-tert-butyl 3-methylpiperazine-1-carboxylate (2340.71 mg, 11.69 mmol), potassium carbonate (4845.75 mg, 35.06 mmol) in NMP (18 ml) was stirred at 100° C. for 3 overnights. The reaction was diluted with EtOAc, washed with water, dried and concentrated. The crude was washed with EtOAc, filtered and dried to provide (S)-tert-butyl 4-(2-methoxy-4-nitrophenyl)-3-methylpiperazine-1-carboxylate.

Step 2: (S)-tert-butyl 4-(4-((4-chloro-1,3,5-triazin-2-yl)amino)-2-methoxyphenyl)-3-methylpiperazine-1-carboxylate:

(S)-tert-butyl 4-(4-amino-2-methoxyphenyl)-3-methylpiperazine-1-carboxylate (1000 mg, 3.11 mmol) in 6 mL of DCM was combined with N,N-Diisopropylethylamine (1.63 ml, 9.33 mmol) and then cooled to 0° C. 2,4-dichloro-1,3,5-triazine (466.58 mg, 3.11 mmol) in 10 mL of DCM was cooled to 0° C. and then added to the cooled mixture. The reaction then stirred for 5 minutes. The reaction was subjected to an additional 150 mg of triazine in DCM and stirred for 5 more minutes. The reaction was washed with saturated sodium bicarbonate, extracted with 25% MeOH/DCM, dried, filtered and concentrated to provide (S)-tert-butyl 4-(4-((4-chloro-1,3,5-triazin-2-yl)amino)-2-methoxyphenyl)-3-methylpiperazine-1-carboxylate.

Step 3: (S)-tert-butyl 4-(4-((4-(3-cyano-4-(((3R,4S)-3-fluoro-1-((S)-2-hydroxypropanoyl)piperidin-4-yl)oxy)phenyl)-1,3,5-triazin-2-yl)amino)-2-methoxyphenyl)-3-methylpiperazine-1-carboxylate:

Tert-butyl 4-(4-((4-chloro-1,3,5-triazin-2-yl)amino)phenyl)piperazine-1-carboxylate (80 mg, 0.2 mmol) and 2-(((3R,4S)-3-fluoro-1-((S)-2-hydroxypropanoyl)piperidin-4-yl)oxy)-5-(4,4,5,5-tetramethyl-1,3,2-dioxaborolan-2-yl)benzonitrile (102.73 mg, 0.25 mmol) were combined in DME (2 mL) and 2M Sodium carbonate solution in water (0.46 ml), tetrakis(triphenylphosphine)palladium (23.65 mg, 0.02 mmol) was added, blown down with nitrogen and the vial was sealed. The reaction mixture was heated in microwave at 135° C. for 20 minutes. The reaction was extracted with 25% MeOH/DCM and water, dried, filtered and concentrated. The crude mixture was purified by flash chromatography on silica gel to provide (S)-tert-butyl 4-(4-((4-(3-cyano-4-(((3R,4S)-3-fluoro-1-((S)-2-hydroxypropanoyl)piperidin-4-yl)oxy)phenyl)-1,3,5-triazin-2-yl)amino)-2-methoxyphenyl)-3-methylpiperazine-1-carboxylate.

Step 4: 5-(4-((4-((S)-2,4-dimethylpiperazin-1-yl)-3-methoxyphenyl)amino)-1,3,5-triazin-2-yl)-2-(((3R,4S)-3-fluoro-1-((S)-2-hydroxypropanoyl)piperidin-4-yl)oxy)benzonitrile:

2-(((3R,4S)-3-fluoro-1-((S)-2-hydroxypropanoyl)piperidin-4-yl)oxy)-5-(4-((3-methoxy-4-((S)-2-methylpiperazin-1-yl)phenyl)amino)-1,3,5-triazin-2-yl)benzonitrile (34.9 mg, 0.06 mmol) was dissolved in methanol (3 ml), Formaldehyde solution 37%, Formalin (0.01 ml, 0.15 mmol) was added and the reaction was stirred for 5 minutes, followed by the addition of sodium triacetoxyborohydride 95% (62.62 mg, 0.3 mmol) and the reaction was allowed to stir at room temperature for 2 h. The reaction was quenched with 1N NaOH, extracted with 25% methanol/dichloromethane, dried, filtered and concentrated. The crude mixture was purified by flash chromatography on silica gel to provide 5-(4-((4-((S)-2,4-dimethylpiperazin-1-yl)-3-methoxyphenyl)amino)-1,3,5-triazin-2-yl)-2-(((3R,4S)-3-fluoro-1-((S)-2-hydroxypropanoyl)piperidin-4-yl)oxy)benzonitrile.
LCMS-ESI$^+$ (m/z): [M+H]$^+$ calcd for $C_{31}H_{37}FN_8O_4$: 604.29; found: 605.19. $^1$H NMR (300 MHz, DMSO-d$_6$) δ 10.11 (m, 1H), 8.73 (s, 1H), 8.55 (m, 2H), 7.64-6.90 (m, 3H), 6.94 (s, 2H), 5.21-4.90 (m, 3H), 4.50-3.92 (m, 3H), 3.75-3.50 (m, 1H), 3.09 (s, 4H), 2.45 (m, 3H), 2.20 (s, 3H), 2.0-1.70 (m, 2H), 1.2 (d, J=6.27, 3H).

Example 500

5-(4-((4-((S)-2,4-dimethylpiperazin-1-yl)phenyl)amino)-1,3,5-triazin-2-yl)-2-(((3R,4S)-3-fluoro-1-(2-hydroxyacetyl)piperidin-4-yl)oxy)benzonitrile

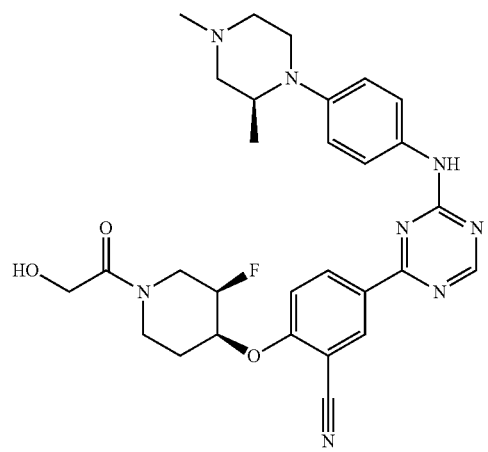 [SMILES: C[C@H]1CN(C)CCN1c1ccc(Nc2ncnc(-c3ccc(O[C@H]4CCN(C(=O)CO)C[C@H]4F)c(C#N)c3)n2)cc1]

This molecule was synthesized in the same manner as Example 499 except starting with (S)-2,4-dimethyl-1-(4-nitrophenyl)piperazine and substituting glycolic acid for L-(+)-lactic acid. LCMS-ESI$^+$ (m/z): [M+H]$^+$ calcd for $C_{28}H_{31}FN_8O_3$: 560.27; found: 561.06. $^1$H NMR (300 MHz, DMSO-d$_6$) δ 10.29 (s, 1H), 8.91 (s, 1H), 8.75-8.73 (m, 2H), 7.82-7.74 (m, 3H), 7.08 (s, 2H), 5.31-5.15 (m, 2H), 4.86-4.82 (m, 1H), 4.54-4.07 (m, 4H), 3.88-3.53 (m, 1H), 3.34-3.25 (m, 2H), 3.20-3.10 (m, 1H), 2.95-2.70 (m, 3H), 2.49-2.37 (m, 3H), 2.31-2.10 (m, 2H), 1.40 (s, 1H), 1.28-1.56 (m, 3H).

Example 501

5-(4-((4-((S)-2,4-dimethylpiperazin-1-yl)phenyl)amino)-1,3,5-triazin-2-yl)-2-(((3R,4S)-3-fluoro-1-((S)-2-hydroxypropanoyl)piperidin-4-yl)oxy)benzonitrile

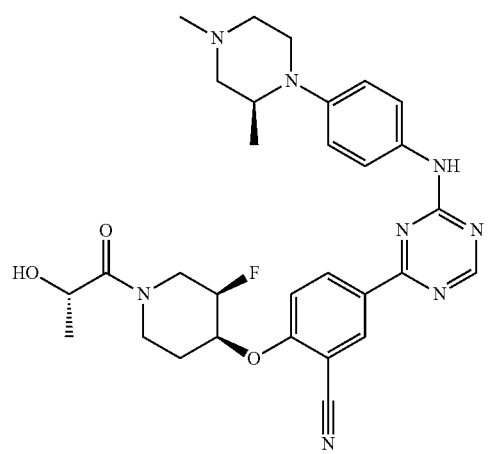 [SMILES: C[C@H](O)C(=O)N1CC[C@H](Oc2ccc(-c3ncnc(Nc4ccc(N5CCN(C)C[C@@H]5C)cc4)n3)cc2C#N)[C@H](F)C1]

This molecule was synthesized in the same manner as Example 499 except starting with (S)-2,4-dimethyl-1-(4-nitrophenyl)piperazine. LCMS-ESI+ (m/z): [M+H]+ calcd for $C_{30}H_{35}FN_8O_3$: 574.28; found: 575.09. $^1$H NMR (300 MHz, DMSO-d$_6$) δ 10.30 (m, 1H), 8.92 (s, 1H), 8.77-8.74 (m, 2H), 7.83-7.75 (m, 3H), 7.09 (s, 2H), 5.31-5.15 (m, 3H), 4.69-4.00 (m, 2H), 3.45-3.33 (m, 1H), 3.20-3.10 (m, 1H), 2.95-2.72 (m, 3H), 2.67-2.38 (m, 1H), 2.38 (s, 3H), 2.31-2.17 (m, 2H), 1.41-1.37 (m, 4H), 1.18-1.16 (m, 1H).

Example 502

5-(4-((1-ethyl-1H-1,2,3-triazol-4-yl)amino)-1,3,5-triazin-2-yl)-2-(((3R,4S)-3-fluoro-1-(2-hydroxyacetyl)piperidin-4-yl)oxy)benzonitrile

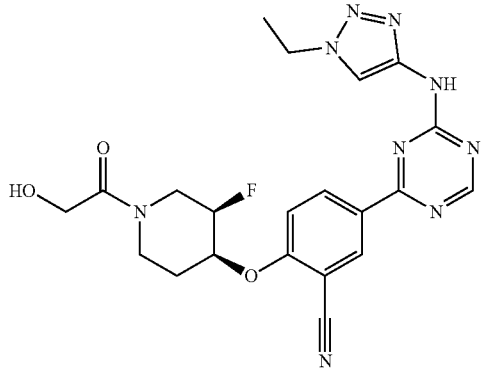

This molecule was synthesized in the same manner as Example 342 except starting with 1-ethyl-1H-1,2,3-triazol-4-amine and substituting glycolic acid for L-(+)-lactic acid. LCMS-ESI+ (m/z): [M+H]+ calcd for $C_{21}H_{22}FN_9O_3$: 467.18; found: 468.18. $^1$H NMR (300 MHz, DMSO-d$_6$) δ 11.06 (s, 1H), 8.84 (d, J=16.7 Hz, 1H), 8.62 (s, 2H), 8.41 (d, J=37.59 Hz, 1H), 7.63 (s, 1H), 5.13-4.97 (m, 2H), 4.71-4.65 (m, 1H), 4.47-4.33 (m, 3H), 4.21-3.92 (m, 3H), 3.70-3.34 (m, 2H), 2.72-2.49 (m, 1H), 2.07-1.82 (m, 2H), 1.51-1.45 (m, 3H).

Example 503

5-(4-((2-ethyl-2H-1,2,3-triazol-4-yl)amino)-1,3,5-triazin-2-yl)-2-(((3R,4S)-3-fluoro-1-(2-hydroxyacetyl)piperidin-4-yl)oxy)benzonitrile

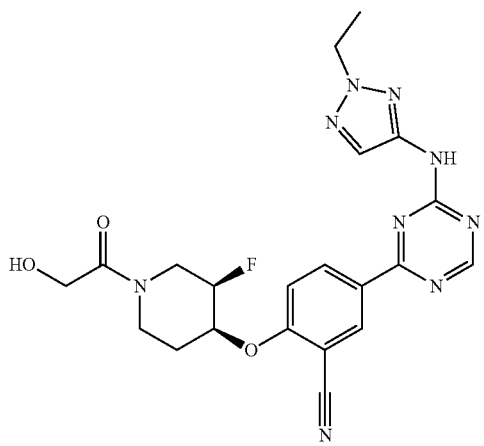 [SMILES: CCn1ncc(Nc2ncnc(-c3ccc(O[C@H]4CCN(C(=O)CO)C[C@H]4F)c(C#N)c3)n2)n1]

This molecule was synthesized in the same manner as Example 342 except starting with 2-ethyl-2H-1,2,3-triazol-4-amine and substituting glycolic acid for L-(+)-lactic acid. LCMS-ESI+ (m/z): [M+H]+ calcd for $C_{21}H_{22}FN_9O_3$: 467.18; found: 468.20. $^1$H NMR (300 MHz, DMSO-d$_6$) δ 11.09 (s, 1H), 8.84 (s, 1H), 8.63-8.59 (m, 2H), 8.15-8.01 (m, 1H), 7.65 (d, J=9.74, 1H), 5.19-4.97 (m, 2H), 4.71-4.64 (m, 1H), 4.40-4.35 (m, 3H), 4.20-3.94 (m, 3H), 3.71-3.86 (m, 1H), 3.33-3.15 (m, 1H), 1.99-1.85 (m, 2H), 1.45 (t, J=m, 3H).

Example 504

2-(((3R,4S)-3-fluoro-1-((S)-tetrahydrofuran-2-carbonyl)piperidin-4-yl)oxy)-5-(4-((4-(4-(oxetan-3-yl)piperazin-1-yl)phenyl)amino)-1,3,5-triazin-2-yl)benzonitrile

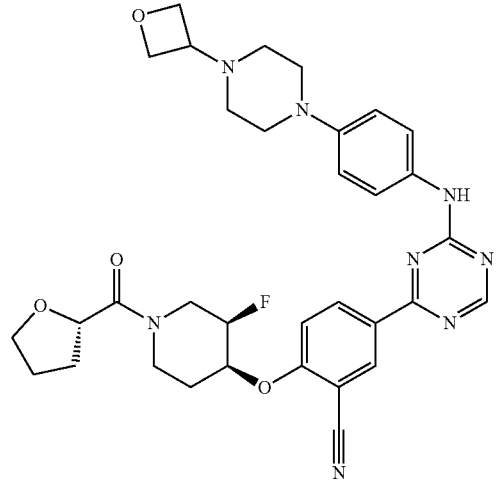 [SMILES: N#Cc1cc(-c2ncnc(Nc3ccc(N4CCN(C5COC5)CC4)cc3)n2)ccc1O[C@H]1CCN(C(=O)[C@@H]2CCCO2)C[C@H]1F]

This molecule was synthesized in the same manner as Example 336 except starting with (S)-tetrahydrofuran-2-carboxylic acid. LCMS-ESI+ (m/z): [M+H]+ calcd for $C_{33}H_{37}FN_8O_4$: 628.29; found: 629.42. $^1$H NMR (300 MHz, DMSO-d$_6$) δ 10.16-10.11 (s, 1H), 8.74 (s, 1H), 8.59-8.56 (m, 2H), 7.64-7.57 (m, 3H), 6.96 (s, 1H), 5.13-4.97 (m, 2H), 4.76-4.67 (m, 1H), 4.57 (dt, J=41.61, 6.45, 4H), 4.20-3.92 (m, 2H), 3.82-3.77 (m, 2H), 3.48-3.30 (m, 2H), 3.14 (s, 5H), 2.41 (s, 4H), 2.13-1.96 (m, 4H), 1.87-1.81 (m, 2H).

Example 505

2-(((3R,4S)-3-fluoro-1-((R)-tetrahydrofuran-2-carbonyl)piperidin-4-yl)oxy)-5-(4-((4-(4-(oxetan-3-yl)piperazin-1-yl)phenyl)amino)-1,3,5-triazin-2-yl)benzonitrile

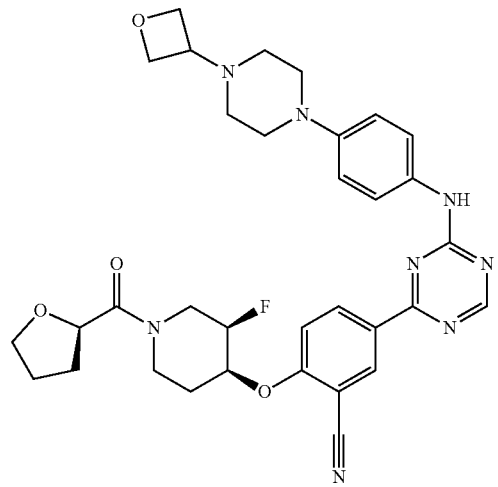 [SMILES: N#Cc1cc(-c2ncnc(Nc3ccc(N4CCN(C5COC5)CC4)cc3)n2)ccc1O[C@H]1CCN(C(=O)[C@H]2CCCO2)C[C@H]1F]

501

This molecule was synthesized in the same manner as Example 336 except starting with (S)-tetrahydrofuran-2-carboxylic acid. LCMS-ESI+ (m/z): [M+H]+ calcd for $C_{33}H_{37}FN_8O_4$: 628.29; found: 629.42. $^1$H NMR (300 MHz, DMSO-$d_6$) δ 10.16-10.11 (s, 1H), 8.74 (s, 1H), 8.59-8.56 (m, 2H), 7.64-7.57 (m, 3H), 6.96 (s, 1H), 5.13-4.97 (m, 2H), 4.76-4.67 (m, 1H), 4.57 (dt, J=41.61, 6.45, 4H), 4.20-3.92 (m, 2H), 3.82-3.77 (m, 2H), 3.48-3.30 (m, 2H), 3.14 (s, 5H), 2.41 (s, 4H), 2.13-1.96 (m, 4H), 1.87-1.81 (m, 2H).

Example 506

2-(((3R,4S)-3-fluoro-1-(2-hydroxyacetyl)piperidin-4-yl)oxy)-5-(4-((1-(2-hydroxyethyl)-1H-pyrazol-4-yl)amino)-1,3,5-triazin-2-yl)benzonitrile

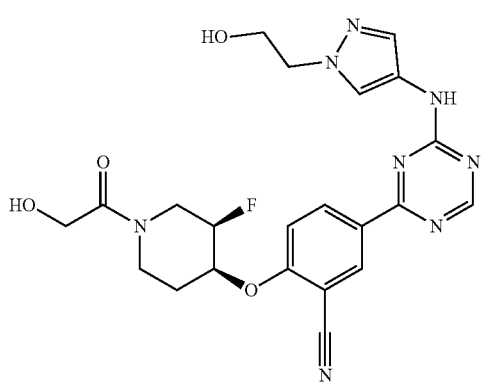 [SMILES: N#Cc1cc(-c2ncnc(Nc3cnn(CCO)c3)n2)ccc1O[C@H]1CCN(C(=O)CO)C[C@H]1F]

This molecule was synthesized in the same manner as Example 342 except starting with 1-(2-((tert-butyldimethylsilyl)oxy)ethyl)-1H-pyrazol-4-amine. Also, with the final step being: 5-(4-((1-(2-((tert-butyldimethylsilyl)oxy)ethyl)-1H-pyrazol-4-yl)amino)-1,3,5-triazin-2-yl)-2-(((3R,4S)-3-fluoro-1-(2-hydroxyacetyl)piperidin-4-yl)oxy)benzonitrile (80 mg, 0.13 mmol) was dissolved in THF (13.4 mL), cooled to 0° C., 1M Tetrabutylammonium fluoride solution 1.0 M in THF in THF (0.16 ml) was added dropwise and the reaction was allowed to stir for 45 minutes. The reaction was quenched with iced water, extracted with DCM. The organic layer was combined, washed, dried and filtered. Solvent was removed by vacuum to provide 2-(((3R,4S)-3-fluoro-1-(2-hydroxyacetyl)piperidin-4-yl)oxy)-5-(4-((1-(2-hydroxyethyl)-1H-pyrazol-4-yl)amino)-1,3,5-triazin-2-yl)benzonitrile. LCMS-ESI+ (m/z): [M+H]+ calcd for $C_{22}H_{23}FN_8O_4$: 482.18; found: 483.23. $^1$H NMR (300 MHz, DMSO-$d_6$) δ 10.32 (s, 1H), 8.81 (s, 1H), 8.71 (s, 1H), 8.65-8.50 (m, 1H), 7.95 (d, J=10.56, 1H), 7.69-7.59 (m, 2H), 5.31-4.68 (m, 4H), 4.36-3.77 (m, 4H), 3.75-3.71 (m, 2H), 3.66-3.78 (m, 1H), 3.15-3.05 (m, 1H), 2.07-1.85 (m, 2H), 1.23 (s, 1H).

Example 507

5-(4-((1H-pyrazol-4-yl)amino)-1,3,5-triazin-2-yl)-2-(((3R,4S)-3-fluoro-1-(2-hydroxyacetyl)piperidin-4-yl)oxy)benzonitrile

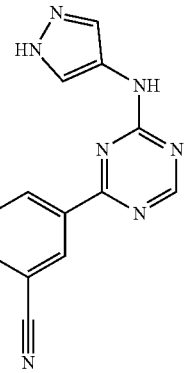

This molecule was synthesized in the same manner as Example 342 except starting with 1-(2-((tert-butyldimethylsilyl)oxy)ethyl)-1H-pyrazol-4-amine. LCMS-ESI+ (m/z): [M+H]+ calcd for $C_{20}H_{19}FN_8O_3$: 438.16; found: 439.23. $^1$H NMR (300 MHz, DMSO-$d_6$) δ 12.75 (s, 1H), 8.81 (d, J=11.21 Hz, 1H), 8.80-8.55 (m, 3H), 8.02-7.61 (m, 3H), 7.69-7.59 (m, 2H), 5.31-4.68 (m, 4H), 4.36-3.77 (m, 4H), 3.75-3.71 (m, 2H), 3.66-3.78 (m, 1H), 3.15-3.05 (m, 1H), 2.07-1.85 (m, 2H), 1.23 (s, 1H).

Example 508

5-(4-((4-((S)-2,4-dimethylpiperazin-1-yl)-3-methoxyphenyl)amino)-1,3,5-triazin-2-yl)-2-(((3R,4S)-3-fluoro-1-(2-hydroxyacetyl)piperidin-4-yl)oxy)benzonitrile

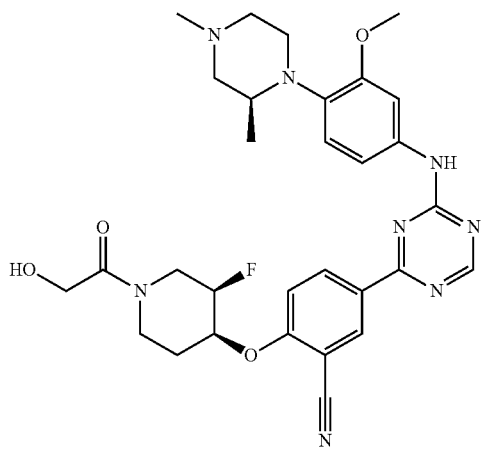 [SMILES: COc1cc(Nc2ncnc(-c3ccc(O[C@H]4CCN(C(=O)CO)C[C@H]4F)c(C#N)c3)n2)ccc1N1CCN(C)C[C@@H]1C]

This molecule was synthesized in the same manner as Example 499 except starting with 1-(2-((tert-butyldimethylsilyl)oxy)ethyl)-1H-pyrazol-4-amine and substituting glycolic acid for L-(+)-lactic acid. LCMS-ESI+ (m/z): [M+H]+ calcd for $C_{30}H_{35}FN_8O_4$: 590.28; found: 591.40. $^1$H NMR (300 MHz, DMSO-$d_6$) δ 10.28 (m, 1H), 8.79 (s, 1H), 8.62-8.57 (m, 2H), 7.64-6.94 (m, 2H), 6.94 (s, 2H), 5.19-4.97 (m, 2H), 4.70-4.64 (m, 1H), 4.45-3.45 (m, 8H), 3.60-3.35 (m, 3H), 3.20-3.0 (m, 2H), 3.09-2.72 (m, 2H), 2.40-3.76 (m, 1H), 2.20 (s, 1H), 1.98-1.70 (m, 2H), 0.83 (d, J=6.45 Hz, 3H).

Example 509

2-(((3R,4S)-1-((S)-2,3-dihydroxypropanoyl)-3-fluoropiperidin-4-yl)oxy)-5-(4-((4-(1-(oxetan-3-yl)piperidin-4-yl)phenyl)amino)-1,3,5-triazin-2-yl)benzonitrile

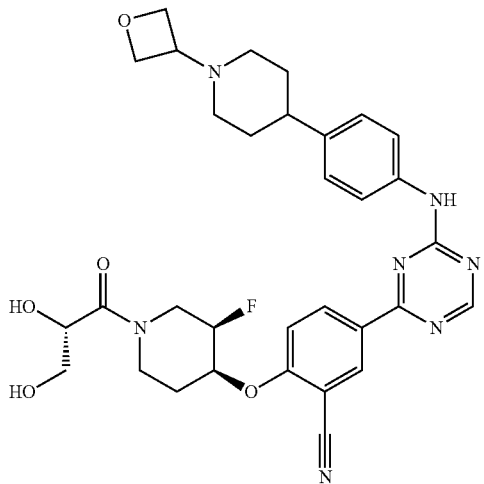

This molecule was synthesized in the same manner as Example 318 except substituting (S)-2,3-dihydroxypropanoic acid for 1H-pyrazole-5-carboxylic acid. LCMS-ESI+ (m/z): [M+H]+ calcd for $C_{32}H_{36}FN_7O_5$: 617.28; found: 618.43. $^1$H NMR (300 MHz, DMSO-d$_6$) δ 10.32 (s, 1H), 8.78 (s, 1H), 8.59 (d, J=7.65 Hz, 2H), 7.66 (t, J=7.65 Hz, 3H), 7.26 (d, J=7.65 Hz, 2H), 5.19-4.98 (m, 2H), 4.83-4.62 (m, 1H), 4.57-4.32 (m, 4H), 4.32-3.85 (m, 2H), 3.80-3.50 (m, 5H), 3.85-3.75 (d, J=10.44 Hz, 2H), 2.16-1.60 (m, 8H), 1.22 (s, 1H).

Example 510

2-(((3R,4S)-1-((S)-2,3-dihydroxypropanoyl)-3-fluoropiperidin-4-yl)oxy)-5-(4-((6-(4-(oxetan-3-yl)piperazin-1-yl)pyridin-3-yl)amino)-1,3,5-triazin-2-yl)benzonitrile

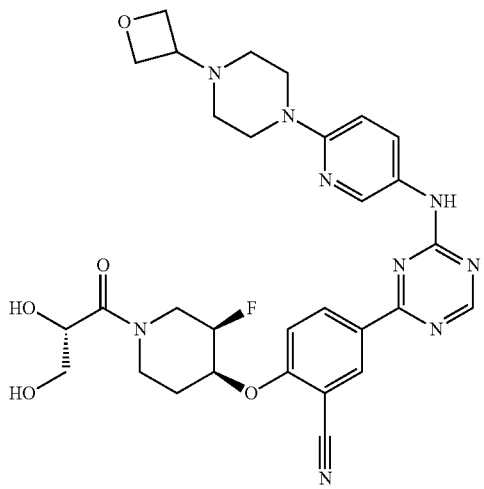

This molecule was synthesized in the same manner as Example 336 except starting with 2-fluoro-5-nitropyridine and substituting (S)-2,3-dihydroxypropanoic acid for pyrazine-2-carboxylic acid. LCMS-ESI+ (m/z): [M+H]+ calcd for $C_{30}H_{34}FN_9O_5$: 619.27; found: 620.37. $^1$H NMR (300 MHz, DMSO-d$_6$) δ 10.13 (m, 1H), 8.74 (s, 1H), 8.60-8.35 (m, 3H), 7.85 (s, 1H), 7.63 (d, J=9.74 Hz, 2H), 5.19-5.16 (m, 2H), 5.00-4.97 (m, 1H), 4.76-4.13 (m, 5H), 3.80-3.30 (m, 9H), 2.45-2.25 (m, 5H), 2.18-1.80 (m, 2H).

Example 511

2-(((3R,4S)-1-((S)-2,3-dihydroxypropanoyl)-3-fluoropiperidin-4-yl)oxy)-5-(4-((5-methoxy-6-(4-(oxetan-3-yl)piperazin-1-yl)pyridin-3-yl)amino)-1,3,5-triazin-2-yl)benzonitrile

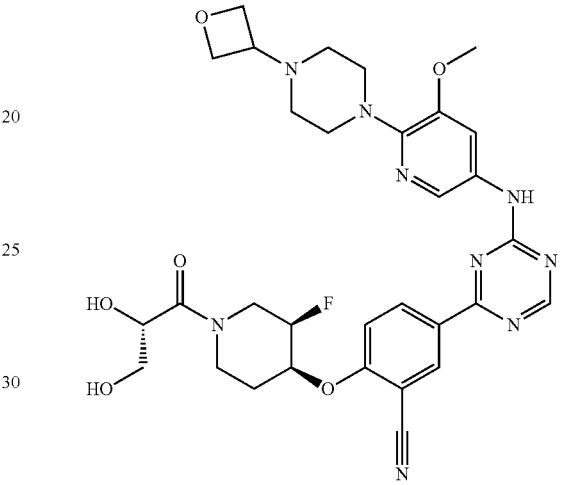

This molecule was synthesized in the same manner as Example 336 except starting with 2-fluoro-3-methoxy-5-nitropyridine and substituting (S)-2,3-dihydroxypropanoic acid for pyrazine-2-carboxylic acid. LCMS-ESI+ (m/z): [M+H]+ calcd for $C_{31}H_{36}FN_9O_6$: 649.28; found 650.38. $^1$H NMR (300 MHz, DMSO-d$_6$) δ 10.28 (m, 1H), 8.80 (s, 1H), 8.60-8.56 (m, 2H), 8.12 (s, 1H), 7.86-7.63 (m, 2H), 5.28-4.98 (m, 3H), 4.80-4.32 (m, 7H), 4.13-3.80 (m, 5H), 3.70-3.36 (m, 4H), 2.38 (s, 4H), 2.18-1.80 (m, 2H).

Example 512

2-(((3R,4S)-1-((S)-2,3-dihydroxypropanoyl)-3-fluoropiperidin-4-yl)oxy)-5-(4-((1-(2-hydroxy-2-methylpropyl)-1H-pyrazol-4-yl)amino)-1,3,5-triazin-2-yl)benzonitrile

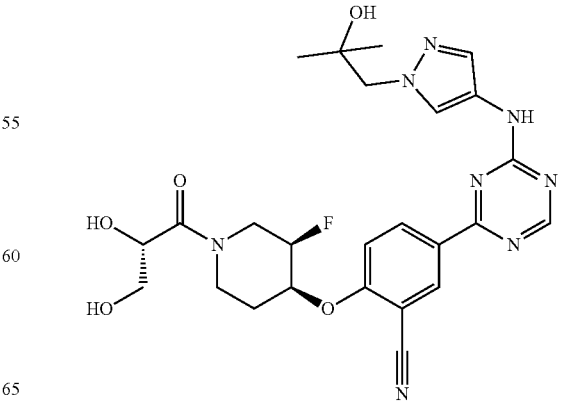

This molecule was synthesized in the same manner as Example 342 except starting with 1-(4-amino-1H-pyrazol-1-yl)-2-methylpropan-2-ol and substituting (S)-2,3-dihydroxypropanoic acid for L-(+)-lactic acid. LCMS-ESI+ (m/z): [M+H]+ calcd for $C_{25}H_{29}FN_8O_5$: 540.22; found: 541.30. $^1$H NMR (300 MHz, DMSO-$d_6$) δ 10.32 (s, 1H), 8.82-8.56 (m, 3H), 8.01 (m, 1H), 7.66-7.58 (m, 2H), 5.19-4.96 (m, 3H), 7.73-7.69 (m, 2H), 4.40-4.32 (m, 1H), 4.20-3.85 (m, 3H), 3.75-3.35 (m, 2H), 2.15-1.70 (m, 2H), 1.08 (d, J=12.89 Hz, 6H).

Example 513

2-(((3R,4S)-1-((S)-2,3-dihydroxypropanoyl)-3-fluoropiperidin-4-yl)oxy)-5-(4-((5-methyl-6-(4-(oxetan-3-yl)piperazin-1-yl)pyridin-3-yl)amino)-1,3,5-triazin-2-yl)benzonitrile

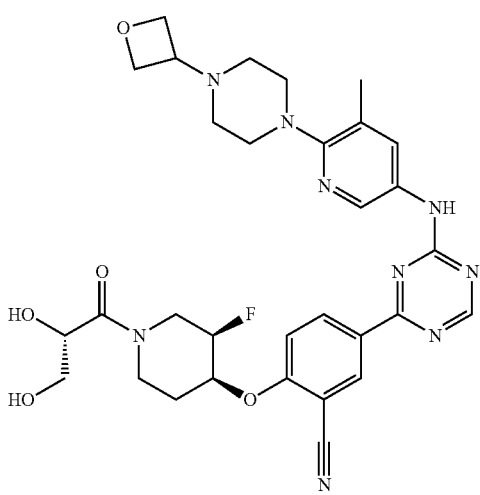 [SMILES: Cc1cc(Nc2ncnc(-c3ccc(O[C@H]4CCN(C(=O)[C@@H](O)CO)C[C@H]4F)c(C#N)c3)n2)cnc1N1CCN(C2COC2)CC1]

This molecule was synthesized in the same manner as Example 336 except starting with 2-fluoro-3-methyl-5-nitropyridine and substituting (S)-2,3-dihydroxypropanoic acid for pyrazine-2-carboxylic acid. LCMS-ESI+ (m/z): [M+H]+ calcd for $C_{31}H_{36}FN_9O_5$: 633.28; found: 634.38. $^1$H NMR (300 MHz, DMSO-$d_6$) δ 10.28 (s, 1H), 8.79 (s, 1H), 8.57-8.36 (m, 3H), 7.89 (s, 1H), 7.65 (d, J=9.38 Hz, 1H), 5.18-4.80 (m, 7H), 4.20-3.35 (m, 3H), 3.06 (s, 5H), 2.42 (s, 5H), 2.26 (s, 5H), 2.16-1.78 (m, 2H).

Example 514

2-(((3R,4S)-3-fluoro-1-((S)-2-hydroxypropanoyl)piperidin-4-yl)oxy)-5-(4-((5-methoxy-6-(4-(oxetan-3-yl)piperazin-1-yl)pyridin-3-yl)amino)-1,3,5-triazin-2-yl)benzonitrile

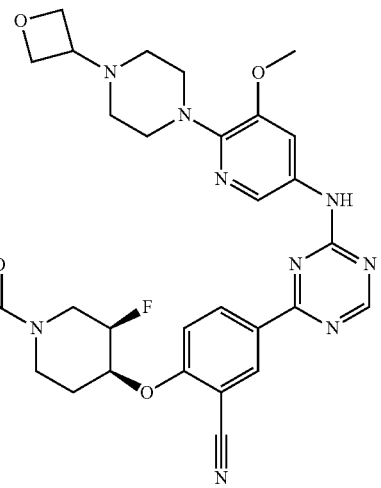

This molecule was synthesized in the same manner as Example 336 except starting with 2-fluoro-3-methoxy-5-nitropyridine and substituting L-(+)-lactic acid for pyrazine-2-carboxylic acid. LCMS-ESI+ (m/z): [M+H]+ calcd for $C_{31}H_{36}FN_9O_5$: 633.28; found: 634.41. $^1$H NMR (300 MHz, DMSO-$d_6$) δ 10.28 (m, 1H), 8.80 (s, 1H), 8.60-8.56 (m, 2H), 8.12 (s, 1H), 7.86-7.63 (m, 2H), 5.28-4.98 (m, 3H), 4.80-4.32 (m, 7H), 4.13-3.80 (m, 5H), 3.70-3.36 (m, 4H), 2.38 (s, 4H), 2.18-1.80 (m, 2H).

Example 515

2-(((3R,4S)-1-((S)-2,3-dihydroxypropanoyl)-3-fluoropiperidin-4-yl)oxy)-5-(4-((4-((S)-2,4-dimethylpiperazin-1-yl)phenyl)amino)-1,3,5-triazin-2-yl)benzonitrile

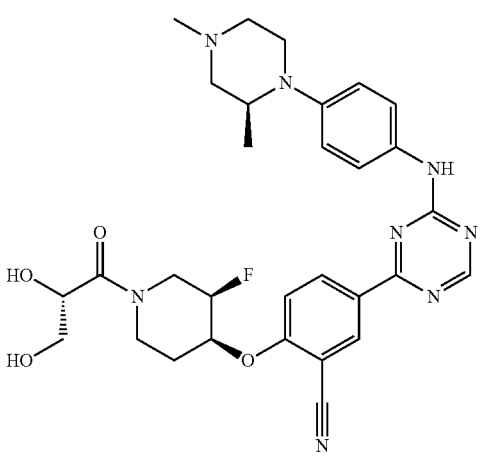 [SMILES: C[C@H]1CN(C)CCN1c1ccc(Nc2ncnc(-c3ccc(O[C@H]4CCN(C(=O)[C@@H](O)CO)C[C@H]4F)c(C#N)c3)n2)cc1]

This molecule was synthesized in the same manner as Example 499 except starting with (S)-2,4-dimethyl-1-(4-nitrophenyl)piperazine and substituting (S)-2,3-dihydroxypropanoic acid for L-(+)-lactic acid. LCMS-ESI+ (m/z): [M+H]+ calcd for $C_{30}H_{35}FN_8O_4$: 590.28; found: 591.36. $^1$H NMR (300 MHz, DMSO-d$_6$) δ 10.11 (m, 1H), 8.74 (s, 1H), 8.59-8.56 (m, 2H), 7.64-7.40 (m, 3H), 6.91 (s, 2H), 5.16-4.87 (m, 3H), 4.75-4.55 (m, 1H), 4.45-3.68 (m, 8H), 3.67-3.35 (m, 4H), 3.25-3.10 (m, 1H), 3.05-2.90 (m, 1H), 2.80-2.70 (m, 1H), 2.60-2.50 (m, 1H), 2.35-2.25 (m, 1H), 2.15-2.05 (m, 1H), 2.03-1.80 (m, 2H), 1.08-0.92 (m, 3H).

Example 516:

5-(4-((3,4-dihydro-2H-pyrido[3,2-b][1,4]oxazin-7-yl)amino)-1,3,5-triazin-2-yl)-2-(((3R,4S)-3-fluoro-1-((S)-2-hydroxypropanoyl)piperidin-4-yl)oxy)benzonitrile

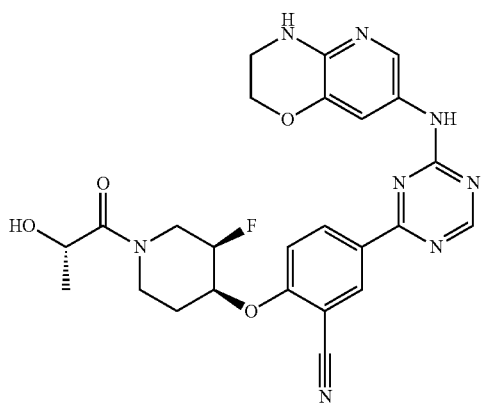 [SMILES: C[C@H](O)C(=O)N1CC[C@H](Oc2ccc(-c3ncnc(Nc4cnc5c(c4)OCCN5)n3)cc2C#N)[C@H](F)C1]

This molecule was synthesized in the same manner as Example 342 except starting with 3,4-dihydro-2H-pyrido[3,2-b][1,4]oxazin-7-amine. LCMS-ESI+ (m/z): [M+H]+ calcd for $C_{26}H_{26}FN_8O_4$: 520.20; found: 521.33. $^1$H NMR (300 MHz, DMSO-d$_6$) δ 10.03 (m, 1H), 8.72 (s, 1H), 8.58-8.50 (m, 2H), 7.96-7.32 (m, 3H), 6.61 (s, 1H), 5.20-4.92 (m, 3H), 4.28-4.55 (m, 1H), 4.22-4.05 (m, 3H), 3.37 (s, 2H), 2.05-1.70 (m, 2H), 1.19 (m, 3H).

Example 517

5-(4-((3,4-dihydro-2H-benzo[b][1,4]oxazin-6-yl)amino)-1,3,5-triazin-2-yl)-2-(((3R, 4S)-3-fluoro-1-((S)-2-hydroxypropanoyl)piperidin-4-yl)oxy)benzonitrile

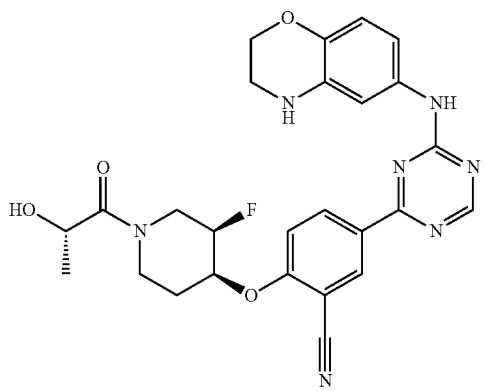 [SMILES: C[C@H](O)C(=O)N1CC[C@H](Oc2ccc(-c3ncnc(Nc4ccc5c(c4)NCCO5)n3)cc2C#N)[C@H](F)C1]

This molecule was synthesized in the same manner as Example 342 except starting with 3,4-dihydro-2H-benzo[b][1,4]oxazin-6-amine. LCMS-ESI+ (m/z): [M+H]+ calcd for $C_{26}H_{26}FN_7O_4$: 519.20; found: 520.33. $^1$H NMR (300 MHz, DMSO-d$_6$) δ 10.01 (s, 1H), 8.72 (s, 1H), 8.59-8.57 (m, 2H), 7.62 (d, J=9.05 Hz, 1H), 7.03 (s, 1H), 6.79 (s, 1H), 6.60 (d, J=9.04 Hz, 1H), 6.00-5.85 (m, 1H), 5.22-4.92 (m, 3), 4.65-4.30 (m, 1H), 4.20-3.90 (m, 4H), 3.30-3.10 (m, 4H), 2.08-1.75 (m, 2H), 1.30-1.15 (m, 3H).

Example 518

5-(4-((4-((R)-1,4-dimethyl-3-oxopiperazin-2-yl)phenyl)amino)-1,3,5-triazin-2-yl)-2-(((3R,4S)-3-fluoro-1-((S)-2-hydroxypropanoyl)piperidin-4-yl)oxy)benzonitrile

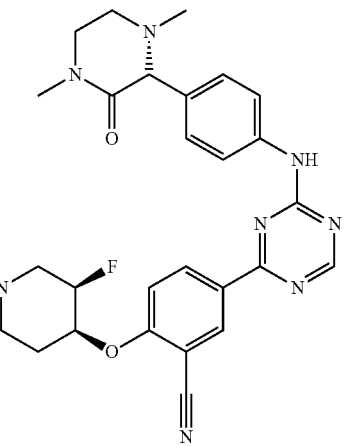

This molecule was synthesized in the same manner as Example 342 except starting with (R)-3-(4-aminophenyl)-1,4-dimethylpiperazin-2-one. LCMS-ESI+ (m/z): [M+H]+ calcd for $C_{30}H_{33}FN_8O_4$: 588.26; found: 589.39. δ10.33 (s, 1H), 8.79 (s, 1H), 8.60-8.57 (m, 2H), 7.65-7.62 (m, 3H), 7.26 (d, J=7.66, 2H), 5.12-4.95 (m, 3H), 4.02-4.30 (m, 1H), 3.65-3.52 (m, 2H), 3.28-3.10 (m, 3H), 3.05-2.95 (m, 1H), 2.82 (s, 3H), 2.60-2.50 (m, 1H), 2.05 (s, 3H), 2.03-1.75 (m, 2H), 1.22-1.70 (m, 3H).

Example 519

2-(((S)-3,3-difluoro-1-((S)-2-oxooxazolidine-4-carbonyl)piperidin-4-yl)oxy)-5-(4-((4-(4-(oxetan-3-yl)piperazin-1-yl)phenyl)amino)-1,3,5-triazin-2-yl)benzonitrile

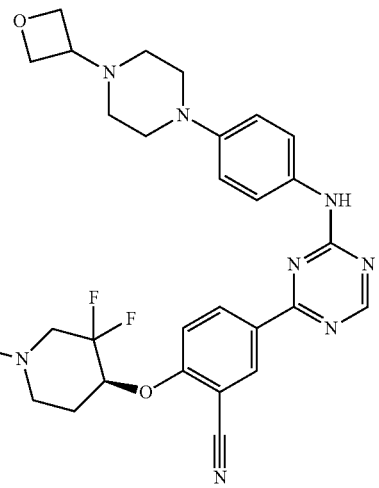

(S)-2-((3,3-difluoropiperidin-4-yl)oxy)-5-(4-((4-(4-(oxetan-3-yl)piperazin-1-yl)phenyl)amino)-1,3,5-triazin-2-yl)benzonitrile (30 mg, 0.055 mmol), HATU (42 mg, 0.11 mmol), DIEA (22 mg, 0.16 mmol) and (S)-2-oxooxazolidine-4-carboxylic acid (15 mg, 0.11 mmol) were dissolved in DMF (1.5 mL) and stirred at room temperature for 2 hr. The mixture was treated with water and extracted with DCM. The organic phase was dried over $Na_2SO_4$, concentrated to dryness. The residue was purified by silica gel column chromatography using 0-15% MeOH in CH2Cl2 as eluent to give the product. $^1$H NMR (400 MHz, DMSO-d6) δ 10.13 (d, 1H), 8.74 (s, 1H), 8.58 (t, 2H), 7.98 (d, 1H), 7.74-7.41 (m, 3H), 6.96 (d, 2H), 5.38 (s, 1H), 4.90 (m, 1H), 4.51 (m, 4H), 4.35-4.02 (m, 2H), 3.96-3.62 (m, 3H), 3.55-3.38 (m, 2H), 3.13 (s, 4H), 2.39 (d, 4H), 2.27-1.72 (m, 2H). LCMS-ESI$^+$ (m/z): [M+H]$^+$ calcd for $C_{32}H_{33}F_2N_9O_5$: 662.26; found: 662.39

Example 520

2-(((S)-3,3-difluoro-1-((R)-2-oxothiazolidine-4-carbonyl)piperidin-4-yl)oxy)-5-(4-((4-(4-(oxetan-3-yl)piperazin-1-yl)phenyl)amino)-1,3,5-triazin-2-yl)benzonitrile

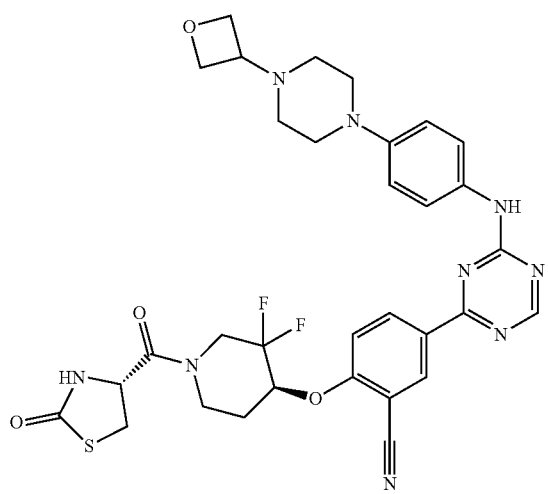

(S)-2-((3,3-difluoropiperidin-4-yl)oxy)-5-(4-((4-(4-(oxetan-3-yl)piperazin-1-yl)phenyl)amino)-1,3,5-triazin-2-yl)benzonitrile (30 mg, 0.065 mmol), HATU (42 mg, 0.11 mmol), DIEA (22 mg, 0.16 mmol) and (R)-2-oxothiazolidine-4-carboxylic acid (16 mg, 0.11 mmol) were dissolved in DMF (1.5 mL) and stirred at room temperature for 2 hr. The mixture was treated with water and extracted with DCM. The organic phase was dried over $Na_2SO_4$, concentrated to dryness. The residue was purified by silica gel column chromatography using 0-15% MeOH in $CH_2Cl_2$ as eluent to give the product. $^1$H NMR (400 MHz, DMSO-d$_6$) δ 10.14 (d, 1H), 8.74 (s, 1H), 8.66-8.49 (m, 2H), 8.22 (d, 1H), 7.67 (t, 1H), 7.63-7.47 (m, 2H), 6.97 (d, 2H), 5.39 (s, 1H), 4.96 (m, 1H), 4.56 (t, 2H), 4.46 (t, 2H), 4.36-3.91 (m, 1H), 3.86-3.65 (m, 3H), 3.63-3.39 (m, 2H), 3.38-3.31 (m, 1H), 3.13 (s, 4H), 2.40 (t, 4H), 2.28-1.75 (m, 2H). LCMS-ESI$^+$ (m/z): [M+H]$^+$ calcd for $C_{32}H_{33}F_2N_9O_4S$: 678.3; found: 678.3

Example 521

2-(((3R,4S)-3-fluoro-1-((S)-2-hydroxypropanoyl)piperidin-4-yl)oxy)-3-methyl-5-(4-((4-(4-(oxetan-3-yl)piperazin-1-yl)phenyl)amino)-1,3,5-triazin-2-yl)benzonitrile

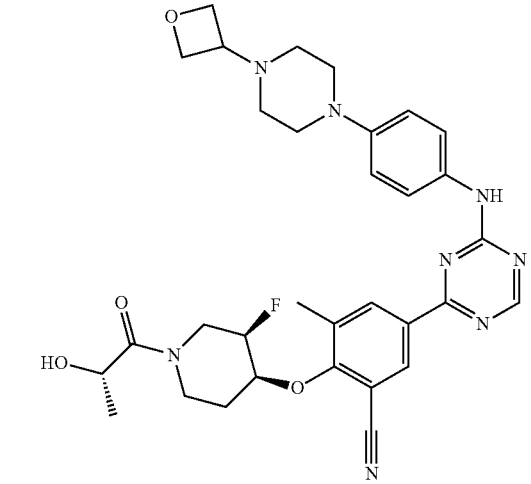

Step 1: Preparation of (3R,4S)-tert-butyl 4-(4-bromo-2-cyano-6-methylphenoxy)-3-fluoropiperidine-1-carboxylate:
PS-PPh$_3$ resin (8.16 g, 31.1 mmol, 4.4 equiv) was added to a dried 500 mL RBF that was then capped and flushed with nitrogen. The resin was suspended in 110 mL of anhydrous THF. After a period of 2 min, 5-bromo-2-hydroxy-3-methylbenzonitrile (1.5 g, 7.07 mmol) dissolved in 60 mL of anhydrous THF was added in a single portion. The resultant suspension was mixed briefly, after which a solution of DEAD (1.97 g, 11.3 mmol) was added in a single portion. This mixture was then stirred for 30 min, after which a solution of (3R,4R)-tert-butyl 3-fluoro-4-hydroxypiperidine-1-carboxylate (1.94 g, 8.84 mmol) in THF (60 mL) was added in a single portion. The reaction mixture was then stirred 3 h. Then another portion of DEAD was added. The stirring was maintained overnight. The resultant suspension was filtered, and the resin was washed with THF. The filtrate was evaporated in vacuum. Solids were dissolved in DCM and water was added. The organic phase was evaporated under reduced pressure and purified by silica gel column chromatography with EtOAc in hexanes to give the product.

Step 2: Preparation of (3R,4S)-tert-butyl 4-(2-cyano-6-methyl-4-(4,4,5,5-tetramethyl-1,3,2-dioxaborolan-2-yl)phenoxy)-3-fluoropiperidine-1-carboxylate:
(3R,4S)-tert-Butyl 4-(4-bromo-2-cyano-6-methylphenoxy)-3-fluoropiperidine-1-carboxylate (1.91 g, 4.62 mmol), potassium acetate (1.36 g, 13.86 mmol), bis(pinacolato)diboron (2.347 g, 9.24 mmol), and Pd(dppf)Cl$_2$ (343 mg, 0.462 mmol) were combined in a sealed tube. 1,4-Dioxane (50 mL) was added and the mixture was heated at 90° C. overnight. After cooling down, the mixture was filtered through a pad of Celite, eluting with 1,4-dioxane. The filtrate was concentrated to dryness under reduced pressure and the residue was purified by a silica gel column with 0-30% EtOAc in hexanes to give the product.

3: Preparation of (3R,4S)-tert-butyl 4-(2-cyano-6-methyl-4-(4-((4-(4-(oxetan-3-yl)piperazin-1-yl)phenyl)amino)-1,3,5-triazin-2-yl)phenoxy)-3-fluoropiperidine-1-carboxylate:

To a mixture of the (3R,4S)-tert-butyl 4-(2-cyano-6-methyl-4-(4,4,5,5-tetramethyl-1,3,2-dioxaborolan-2-yl)phenoxy)-3-fluoropiperidine-1-carboxylate (1.25g, 2.7 mmol), 4-chloro-N-(4-(4-(oxetan-3-yl)piperazin-1-yl)phenyl)-1,3,5-triazin-2-amine (945 mg, 2.7 mmol), and Pd(PPh$_3$)$_4$ (236 mg, 0.204 mmol) in 1,2-DME (12 mL), was added 2M sodium carbonate solution (6.1 mL). The mixture was run under microwave at 130° C. for 75 minutes. Then the reaction mixture was diluted with a mixture of DCM and MeOH (1:1), filtered through a pad of Celite. The biphasic filtrate was concentrated under reduced pressure. Ethanol was added and concentrated. The residue was passed over a silica gel column with 5-15% MeOH in CH$_2$Cl$_2$ to give the product. LCMS-ESI$^+$ (m/z): [M+H]$^+$ calcd for C$_{34}$H$_{41}$FN$_8$O$_4$: 645.3; found: 645.5

Step 4: Preparation of 2-(((3R,4S)-3-fluoropiperidin-4-yl)oxy)-3-methyl-5-(4-((4-(4-(oxetan-3-yl)piperazin-1-yl)phenyl)amino)-1,3,5-triazin-2-yl)benzonitrile:

(3R,4S)-tert-butyl 4-(2-cyano-6-methyl-4-(4-((4-(4-(oxetan-3-yl)piperazin-1-yl)phenyl)amino)-1,3,5-triazin-2-yl)phenoxy)-3-fluoropiperidine-1-carboxylate (670 mg, 1.04 mmol) was taken up in DCM (12 mL) and treated with TFA (3 mL). The reaction mixture was stirred at room temperature overnight. The mixture was concentrated under reduced pressure and the residue was used for next step. LCMS-ESI$^+$ (m/z): [M+H]$^+$ calcd for C$_{29}$H$_{33}$FN$_8$O$_2$: 545.3; found: 545.2

Step 5: 2-(((3R,4S)-3-fluoropiperidin-4-yl)oxy)-3-methyl-5-(4-((4-(4-(oxetan-3-yl)piperazin-1-yl)phenyl)amino)-1,3,5-triazin-2-yl)benzonitrile (128 mg, 0.24 mmol), HATU (179 mg, 0.47 mmol), DIEA (91 mg, 0.71 mmol), and (S)-2-hydroxypropanoic acid (42 mg, 0.47 mmol) were dissolved in DMF (4 mL) and stirred at room temperature for 2 h. The mixture was treated with water and extracted with DCM. The organic phase was dried over Na2SO4, concentrated to dryness. The residue was purified by silica gel column chromatography using 5-20% MeOH in CH$_2$Cl$_2$ as eluent to give the product. $^1$H NMR (400 MHz, DMSO-d$_6$) δ 10.17 (d, 1H), 8.76 (s, 1H), 8.57-8.31 (m, 2H), 7.56 (m, 2H), 7.16-6.83 (m, 3H), 5.74 (s, 1H), 5.10-4.88 (m, 2H), 4.78-4.61 (m, 1H), 4.56 (t, 2H), 4.46 (t, 2H), 4.26 (d, 1H), 4.03 (d, 1H), 3.52-3.38 (m, 1H), 3.24-3.03 (m, 4H), 2.89 (d, 1H), 2.39 (d, 7H), 2.00 (m, 2H), 1.24-1.11 (m, 3H). LCMS-ESI$^+$ (m/z): [M+H]$^+$ calcd for C$_{32}$H$_{37}$FN$_8$O$_4$: 617.3; found: 617.4

Example 522

2-(((3R,4S)-3-fluoro-1-(2-hydroxyacetyl)piperidin-4-yl)oxy)-3-methyl-5-(4-((4-(4-(oxetan-3-yl)piperazin-1-yl)phenyl)amino)-1,3,5-triazin-2-yl)benzonitrile

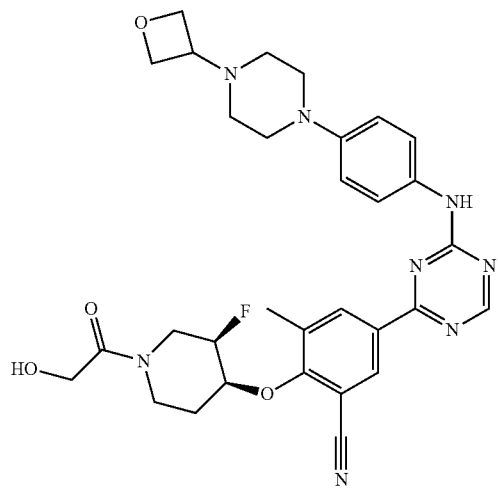

2-(((3R,4S)-3-Fluoropiperidin-4-yl)oxy)-3-methyl-5-(4-((4-(4-(oxetan-3-yl)piperazin-1-yl)phenyl)amino)-1,3,5-triazin-2-yl)benzonitrile (128 mg, 0.24 mmol), HATU (179 mg, 0.47 mmol), DIEA (91 mg, 0.71 mmol), and glycolic acid (36 mg, 0.47 mmol) were dissolved in DMF (4 mL) and stirred at room temperature for 2 h. The mixture was treated with water and extracted with DCM. The organic phase was dried over Na$_2$SO$_4$, concentrated to dryness. The residue was purified by silica gel column chromatography using 5-20% MeOH in CH$_2$Cl$_2$ as eluent to give the product. $^1$H NMR (400 MHz, DMSO-d$_6$) δ 10.17 (d, 1H), 8.75 (s, 1H), 8.58-8.31 (m, 1H), 7.66-7.41 (m, 1H), 6.96 (d, 1H), 5.74 (s, 2H), 4.97 (d, 1H), 4.76-4.60 (m, 2H), 4.56 (m, 2H), 4.46 (t, 2H), 4.28 (d, 1H), 4.21-3.92 (m, 2H), 3.74 (d, 1H), 3.44 (m, 2H), 3.14 (d, 4H), 2.88 (m, 1H), 2.39 (m, 7H), 2.10-1.86 (m, 2H). LCMS-ESI$^+$ (m/z): [M+H]$^+$ calcd for C$_{31}$H$_{35}$FN$_8$O$_4$: 603.3; found: 603.4

Example 523

2-(((3R,4S)-3-fluoro-1-((4S,5R)-5-methyl-2-oxooxazolidine-4-carbonyl)piperidin-4-yl)oxy)-5-(4-((4-(4-(oxetan-3-yl)piperazin-1-yl)phenyl)amino)-1,3,5-triazin-2-yl)benzonitrile

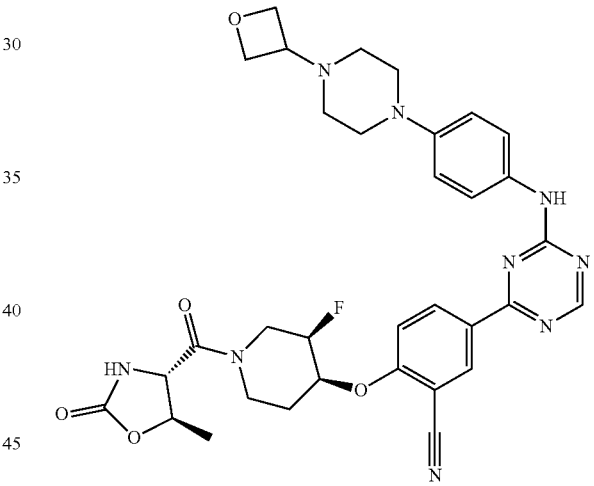

2-(((3R,4S)-3-fluoropiperidin-4-yl)oxy)-5-(4-((4-(4-(oxetan-3-yl)piperazin-1-yl)phenyl)amino)-1,3,5-triazin-2-yl)benzonitrile (131 mg, 0.27 mmol), HATU (188 mg, 1.1 mmol), DIEA (96 mg, 0.74 mmol) and (4S,5R)-5-methyl-2-oxooxazolidine-4-carboxylic acid (72 mg, 0.49 mmol) were dissolved in DMF (4 mL) and stirred at room temperature for 2 hr. The reaction mixture was concentrated to dryness and the residue was purified by silica gel column with 5-20% MeOH in CH$_2$Cl$_2$ to give the product as a yellowish solid. $^1$H NMR (400 MHz, DMSO-d$_6$) δ 10.13 (d, 1H), 8.74 (s, 1H), 8.65-8.48 (m, 2H), 7.90 (d, 1H), 7.69-7.47 (m, 4H), 6.96 (s, 2H), 5.23-4.95 (m, 3H), 4.70-4.34 (m, 4H), 4.31-4.03 (m, 1H), 3.77 (d, 1H), 3.67-3.37 (m, 2H), 3.13 (m, 4H), 2.40 (s, 4H), 2.04-1.81 (m, 2H), 1.36 (m, 3H). LCMS-ESI$^+$ (m/z): [M+H]$^+$ calcd for C$_{33}$H$_{36}$FN$_9$O$_5$: 658.3; found: 658.4

Example 524

2-(((3R,4S)-3-fluoro-1-((4S,5S)-5-methyl-2-oxoox-azolidine-4-carbonyl)piperidin-4-yl)oxy)-5-(4-((4-(4-(oxetan-3-yl)piperazin-1-yl)phenyl)amino)-1,3,5-triazin-2-yl)benzonitrile

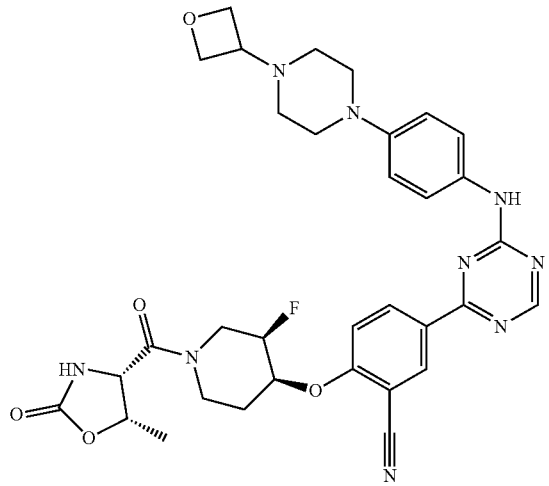 [SMILES: C[C@@H]1OC(=O)N[C@@H]1C(=O)N1CC[C@H](Oc2ccc(-c3ncnc(Nc4ccc(N5CCN(C6COC6)CC5)cc4)n3)cc2C#N)[C@H](F)C1]

2-(((3R,4S)-3-fluoropiperidin-4-yl)oxy)-5-(4-((4-(4-(oxetan-3-yl)piperazin-1-yl)phenyl)amino)-1,3,5-triazin-2-yl)benzonitrile (129 mg, 0.24 mmol), HATU (185 mg, 0.49 mmol), DIEA (94 mg, 0.73 mmol) and (4S,5S)-5-methyl-2-oxooxazolidine-4-carboxylic acid (71 mg, 0.31 mmol) were dissolved in DMF (4 mL) and stirred at room temperature for 2 hr. The mixture was concentrated to dryness and the residue was purified by silica gel column with 5-20 MeOH in $CH_2Cl_2$ to give the product. $^1H$ NMR (400 MHz, DMSO-$d_6$) δ 10.11 (d, 1H), 8.73 (s, 1H), 8.65-8.44 (m, 2H), 7.68-7.48 (m, 4H), 6.95 (s, 2H), 5.23-4.79 (m, 4H), 4.86 (m, m 1H), 4.63-4.39 (m, 4H), 4.38-4.12 (m, 2H), 3.44 (t, 1H), 3.13 (s, 4H), 2.40 (t, 4H), 181-1.99 (m, 2H), 1.22 (m, 3H). LCMS-ESI$^+$ (m/z): [M+H]$^+$ calcd for $C_{33}H_{36}FN_9O_5$: 658.3; found: 658.4

Example 525

2-(((3R,4S)-3-fluoro-1-(2-oxo-2,3-dihydrooxazole-4-carbonyl)piperidin-4-yl)oxy)-5-(4-((4-(4-(oxetan-3-yl)piperazin-1-yl)phenyl)amino)-1,3,5-triazin-2-yl)benzonitrile

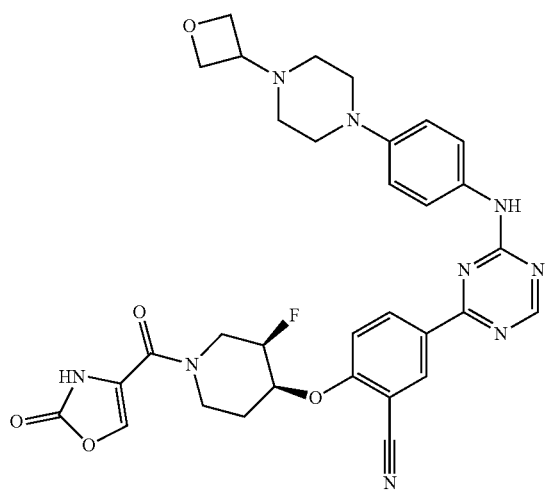 [SMILES: N#Cc1cc(-c2ncnc(Nc3ccc(N4CCN(C5COC5)CC4)cc3)n2)ccc1O[C@H]1CCN(C(=O)c2coc(=O)[nH]2)C[C@H]1F]

3-Fluoro-2-(((3R,4S)-3-fluoropiperidin-4-yl)oxy)-5-(4-((4-(4-(oxetan-3-yl)piperazin-1-yl)phenyl)amino)-1,3,5-triazin-2-yl)benzonitrile (91 mg, 0.172 mmol), HATU (130 mg, 0.34 mmol), DIEA (67 mg, 0.52 mmol) and 2-oxo-2,3-dihydrooxazole-4-carboxylic acid (45 mg, 0.343 mmol) were dissolved in DMF (4 mL) and stirred at room temperature overnight. The mixture was concentrated and the residue was purified by silica gel column with 5-20% MeOH in $CH_2Cl_2$ to give the product. $^1H$ NMR (400 MHz, DMSO-$d_6$) δ 11.19 (s, 1H), 10.12 (d, 1H), 8.82-8.66 (m, 1H), 8.65-8.46 (m, 2H), 7.73-7.61 (m, 2H), 7.57 (t, 3H), 6.95 (s, 2H), 5.03-5.15 (m, 2H), 4.56 (t, 2H), 4.46 (t, 2H), 4.38 (s, 2H), 4.15 (s, 1H), 3.44 (m, 1H), 3.13 (s, 4H), 2.40 (t, 4H), 2.12-1.78 (m, 2H). LCMS-ESI$^+$ (m/z): [M+H]$^+$ calcd for $C_{32}H_{37}FN_9O_5$: 642.3; found: 642.3

Example 526

2-(((3R,4S)-1-(3,4-dimethyl-1H-pyrazole-5-carbonyl)-3-fluoropiperidin-4-yl)oxy)-5-(4-((4-(4-(oxetan-3-yl)piperazin-1-yl)phenyl)amino)-1,3,5-triazin-2-yl)benzonitrile

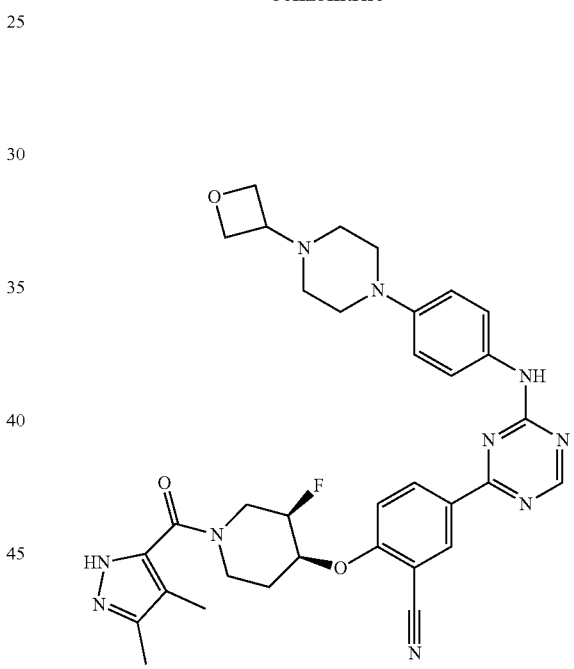

3-Fluoro-2-(((3R,4S)-3-fluoropiperidin-4-yl)oxy)-5-(4-((4-(4-(oxetan-3-yl)piperazin-1-yl)phenyl)amino)-1,3,5-triazin-2-yl)benzonitrile (85 mg, 0.16 mmol), HATU (122 mg, 0.32 mmol), DIEA (62 mg, 0.48 mmol) and 3,4-dimethyl-1H-pyrazole-5-carboxylic acid (45 mg, 0.32 mmol) were dissolved in DMF (4 mL) and stirred at room temperature overnight. The mixture was concentrated and the residue was purified by silica gel column with 5-20% MeOH in $CH_2Cl_2$ to give the product. $^1H$ NMR (400 MHz, DMSO-$d_6$) δ 12.65 (s, 1H), 10.13 (d, 1H), 8.73 (s, 1H), 8.65-8.42 (m, 2H), 7.71-7.40 (m, 4H), 7.07-6.83 (m, 3H), 5.23-4.92 (m, 2H), 4.51 (m, 4H), 4.21 (m, 1H), 3.73 (m, 1H), 3.52-3.39 (m, 1H), 3.13 (s, 4H), 2.40 (s, 4H), 2.15 (s, 3H), 1.95 (m, 5H). LCMS-ESI$^+$ (m/z): [M+H]$^+$ calcd for $C_{34}H_{37}FN_{10}O_3$: 653.3; found: 653.5

Example 527

2-(((3R,4S)-3-fluoro-1-(4-methyl-1H-imidazole-2-carbonyl)piperidin-4-yl)oxy)-5-(4-((4-(4-(oxetan-3-yl)piperazin-1-yl)phenyl)amino)-1,3,5-triazin-2-yl)benzonitrile

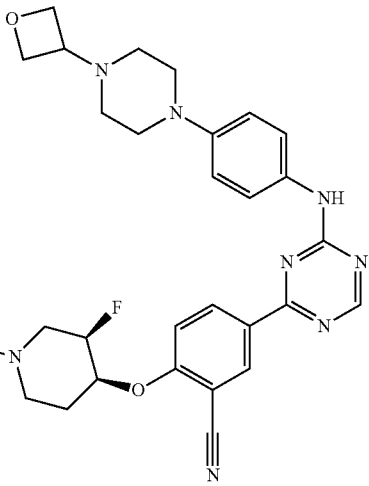

3-Fluoro-2-(((3R,4S)-3-fluoropiperidin-4-yl)oxy)-5-(4-((4-(4-(oxetan-3-yl)piperazin-1-yl)phenyl)amino)-1,3,5-triazin-2-yl)benzonitrile (82 mg, 0.15 mmol), HATU (117 mg, 0.31 mmol), TEA (76 mg, 0.62 mmol) and 4-methyl-1H-imidazole-2-carboxylic acid (41 mg, 0.31 mmol) were dissolved in DMF (4 mL) and stirred at room temperature overnight. The mixture was concentrated and the residue was purified by silica gel column with 5-20% MeOH in $CH_2Cl_2$ to give the product. $^1$H NMR (400 MHz, DMSO-$d_6$) δ 12.63 (m, 1H), 10.12 (d, 1H), 8.83-8.34 (m, 2H), 7.83-7.33 (m, 4H), 6.76 (d, 1H), 5.91-5.55 (m, 1H), 5.37 (s, 1H), 5.08 (m, 3H), 4.51 (m, 4H), 4.30 (d, 1H), 3.79 (m, 1H), 3.43 (m, 1H), 3.13 (s, 4H), 2.40 (t, 4H), 2.15 (s, 3H), 1.65-1.98 (m, 2H). LCMS-ESI$^+$ (m/z): [M+H]$^+$ calcd for $C_{33}H_{35}FN_{10}O_3$: 639.3; found: 639.2

Example 528

2-(((3R,4S)-3-fluoro-1-(4-methyl-1H-pyrazole-5-carbonyl)piperidin-4-yl)oxy)-5-(4-((4-(4-(oxetan-3-yl)piperazin-1-yl)phenyl)amino)-1,3,5-triazin-2-yl)benzonitrile

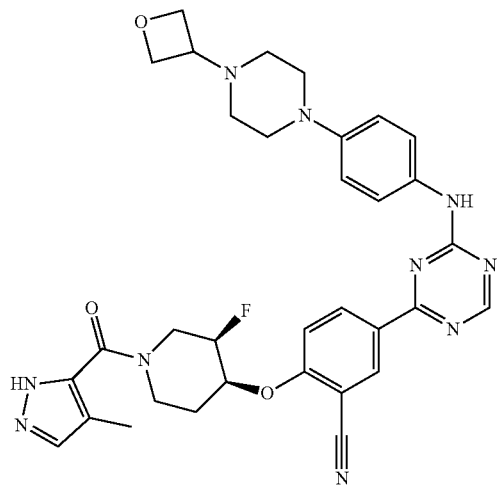 [SMILES: Cc1cn[nH]c1C(=O)N1CC[C@H](Oc2ccc(-c3ncnc(Nc4ccc(N5CCN(C6COC6)CC5)cc4)n3)cc2C#N)[C@H](F)C1]

3-Fluoro-2-(((3R,4S)-3-fluoropiperidin-4-yl)oxy)-5-(4-((4-(4-(oxetan-3-yl)piperazin-1-yl)phenyl)amino)-1,3,5-triazin-2-yl)benzonitrile (82 mg, 0.15 mmol), HATU (117 mg, 0.31 mmol), TEA (76 mg, 0.62 mmol) and 4-methyl-1H-pyrazole-5-carboxylic acid (41 mg, 0.31 mmol) were dissolved in DMF (4 mL) and stirred at room temperature overnight. The mixture was concentrated and the residue was purified by silica gel column with 5-20% MeOH in $CH_2Cl_2$ to give the product. $^1$H NMR (400 MHz, DMSO-$d_6$) δ 12.87 (s, 1H), 10.12 (d, 1H), 8.73 (d, 1H), 8.65-8.42 (m, 2H), 7.58 (m, 4H), 6.95 (s, 2H), 5.30-4.84 (m, 3H), 4.55 (t, 2H), 4.46 (t, 2H), 4.22 (m, 1H), 3.87-3.60 (m, 1H), 3.43 (t, 1H), 3.13 (d, 4H), 2.40 (t, 4H), 2.15-1.82 (m, 5H). LCMS-ESI$^+$ (m/z): [M+H]$^+$ calcd for $C_{33}H_{35}FN_{10}O_3$: 639.3; found: 639.3

Example 529

2-(((3R,4S)-3-fluoro-1-((S)-4-oxoazetidine-2-carbonyl)piperidin-4-yl)oxy)-5-(4-((4-(4-(oxetan-3-yl)piperazin-1-yl)phenyl)amino)-1,3,5-triazin-2-yl)benzonitrile

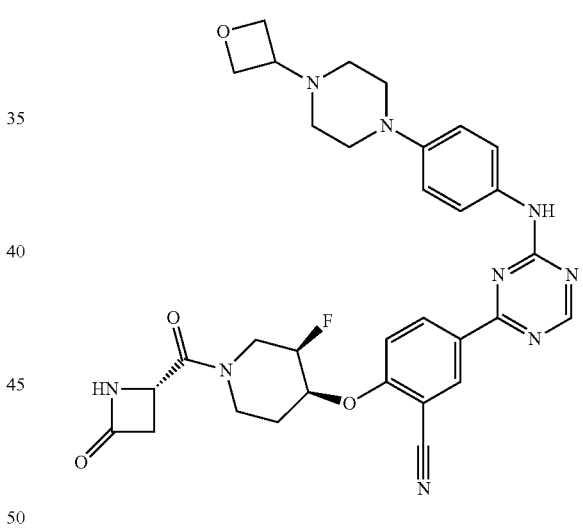

3-Fluoro-2-(((3R,4S)-3-fluoropiperidin-4-yl)oxy)-5-(4-((4-(4-(oxetan-3-yl)piperazin-1-yl)phenyl)amino)-1,3,5-triazin-2-yl)benzonitrile (82 mg, 0.15 mmol), HATU (117 mg, 0.31 mmol), TEA (76 mg, 0.62 mmol) and (S)-4-oxoazetidine-2-carboxylic acid (41 mg, 0.31 mmol) were dissolved in DMF (4 mL) and stirred at room temperature for 2 hr. The mixture was diluted with DCM and extracted with water. The organic phase was concentrated and the residue was purified by silica gel column with 5-20% MeOH in $CH_2Cl_2$ to give the product. $^1$H NMR (400 MHz, DMSO-$d_6$) δ 10.12 (d, 1H), 8.73 (s, 1H), 8.64-8.45 (m, 2H), 8.25 (d, 1H), 7.69-7.43 (m, 4H), 6.95 (t, 2H), 5.21-4.87 (m, 2H), 4.55 (t, 2H), 4.47 (t, 2H), 4.39-4.27 (m, 1H), 4.16 (d, 1H), 3.98 (m, 1H), 3.74-3.38 (m, 2H), 3.13 (s, 4H), 2.92-2.68 (m, 1H), 2.40 (t, 4H), 2.12-1.68 (m, 2H). LCMS-ESI$^+$ (m/z): [M+H]$^+$ calcd for $C_{32}H_{34}FN_9O_4$: 628.3; found: 628.3

Example 530

2-(((3R,4S)-3-fluoro-1-((R)-2-oxothiazolidine-4-carbonyl)piperidin-4-yl)oxy)-5-(4-((4-(4-(oxetan-3-yl)piperazin-1-yl)phenyl)amino)-1,3,5-triazin-2-yl)benzonitrile

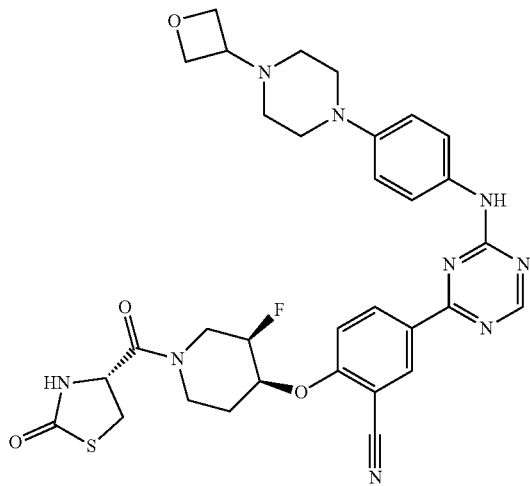 [SMILES: N#Cc1cc(-c2ncnc(Nc3ccc(N4CCN(C5COC5)CC4)cc3)n2)ccc1O[C@H]1CCN(C(=O)[C@@H]2CSC(=O)N2)C[C@H]1F]

3-Fluoro-2-(((3R,4S)-3-fluoropiperidin-4-yl)oxy)-5-(4-((4-(4-(oxetan-3-yl)piperazin-1-yl)phenyl)amino)-1,3,5-triazin-2-yl)benzonitrile (82 mg, 0.15 mmol), HATU (117 mg, 0.31 mmol), TEA (76 mg, 0.62 mmol) and (R)-2-oxothiazolidine-4-carboxylic acid (41 mg, 0.31 mmol) were dissolved in DMF (4 mL) and stirred at room temperature for 2 hr. The mixture was diluted with DCM and extracted with water. The organic phase was concentrated and the residue was purified by silica gel column with 5-20% MeOH in CH$_2$Cl$_2$ to give the product. $^1$H NMR (400 MHz, DMSO-d$_6$) δ 10.12 (d, 1H), 8.73 (s, 1H), 8.64-8.46 (m, 2H), 8.19 (d, 1H), 7.71-7.44 (m, 2H), 6.95 (s, 1H), 5.74 (s, 1H), 5.22-4.96 (m, 1H), 4.92 (m, 1H), 4.55 (m, 2H), 4.46 (m, 2H), 4.15 (t, 1H), 3.84 (d, 1H), 3.77-3.52 (m, 2H), 3.39-3.30 (m, 4H), 3.13 (m, 4H), 2.40 (t, 4H), 1.98-1.83 (m, 2H). LCMS-ESI$^+$ (m/z): [M+H]$^+$ calcd for C$_{32}$H$_{34}$FN$_9$O$_4$S: 660.2; found: 660.3

Example 531

(R)-5-(4-((3-methoxy-4-(4-(oxetan-3-yl)piperazin-1-yl)phenyl)amino)-1,3,5-triazin-2-yl)-2-((6-oxopiperidin-3-yl)oxy)benzonitrile

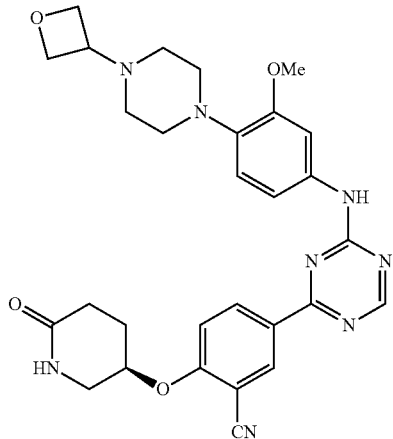 [SMILES: COc1cc(Nc2ncnc(-c3ccc(O[C@@H]4CCC(=O)NC4)c(C#N)c3)n2)ccc1N1CCN(C2COC2)CC1]

Step 1. To solution of 2,4-dichloro-1,3,5-triazine (370 mg, 2.47 mol) in DMF (20 mL) at 0° C. was added solution of 3-methoxy-4-(4-(oxetan-3-yl)piperazin-1-yl)aniline (500 mg, 1.90 mmol) in DMF (20 mL). The reaction mixture was stirred at 0° C. for 30 min. Reaction completed and the solvent was removed under reduced pressure. The crude product was purified by flash column chromatography on silica gel to afford 4-chloro-N-(3-methoxy-4-(4-(oxetan-3-yl)piperazin-1-yl)phenyl)-1,3,5-triazin-2-amine. LCMS-ESI$^+$ (m/z): [M+H]$^+$ calcd for C$_{17}$H$_{21}$ClN$_6$O$_2$: 377.1; found: 377.3.

Step 2. To a solution of 4-chloro-N-(3-methoxy-4-(4-(oxetan-3-yl)piperazin-1-yl)phenyl)-1,3,5-triazin-2-amine (525 mg, 1.39 mmol), 2-fluoro-5-(4,4,5,5-tetramethyl-1,3,2-dioxaborolan-2-yl)benzonitrile, (379 mg, 1.53 mmol), and tetrakis(triphenylphosphine)palladium(0) (80 mg, 0.070 mmol) in DME (9 mL) was added a solution of sodium carbonate (443 mg, 4.18 mmol) in water (5 mL). The mixture was heated at 120° C. for 35 min by microwave. The mixture was diluted with 30% MeOH in CH$_2$Cl$_2$ and filtered through a short pad of silica gel which was washed with 30% MeOH in CH$_2$Cl$_2$. The mixture was adsorbed onto silica gel, and solvent was removed under reduced pressure. The slurry was loaded onto silica gel and purified by flash column chromatography to afford 2-fluoro-5-(4-((3-methoxy-4-(4-(oxetan-3-yl)piperazin-1-yl)phenyl)amino)-1,3,5-triazin-2-yl)benzonitrile. LCMS-ESI$^+$ (m/z): [M+H]$^+$ calcd for C$_{24}$H$_{24}$FN$_7$O$_2$: 462.2; found: 462.3.

Step 3. To a solution of 5-hydroxypiperidin-2-one (74.8 mg, 0.650 mmol) in DMF (4 mL) was added potassium t-butoxide (109 mg, 0.975 mmol) at 0° C. The reaction mixture was allowed to stir for 1 hour. To the reaction mixture was added a solution of 2-fluoro-5-(4-((3-methoxy-4-(4-(oxetan-3-yl)piperazin-1-yl)phenyl)amino)-1,3,5-triazin-2-yl)benzonitrile in DMF (2mL) at room temperature. The reaction mixture was brought to 80° C. and heated overnight. The solvent was concentrated under reduced pressure and dissolved in 0.1% TFA in 1:1 H$_2$O:MeCN and purified by preparative HPLC to afford product (R)-5-(4-((3-methoxy-4-(4-(oxetan-3-yl)piperazin-1-yl)phenyl)amino)-1,3,5-triazin-2-yl)-2-((6-oxopiperidin-3-yl)oxy)benzonitrile. $^1$H NMR (400 MHz, DMSO-d$_6$) δ 10.30 (s, 1H), 8.79 (s, 1H), 8.60 (s, 1H), 8.57 (d, J=2.2 Hz, 1H), 7.71 (s, 1H), 7.58 (d, J=8.9 Hz, 1H), 7.46 (s, 1H), 7.20 (s, 1H), 6.97 (d, J=8.7 Hz, 1H), 5.17-5.07 (m, 2H), 4.76 (d, J=6.5 Hz, 2H), 4.48 (s, 1H), 3.95 (s, 1H), 3.87 (s, 3H), 3.52 (s, 3H), 3.36 (d, J=13.7 Hz, 1H), 3.15 (s, 1H), 2.4-2.17 (m, 5H), 2.10 (d, J=6.9 Hz, 4H).

LCMS-ESI$^+$ (m/z): [M+H]$^+$ calcd for C$_{29}$H$_{32}$N$_8$O$_4$: 557.6; found: 557.7

Example 532

(R)-5-(4-((3-methyl-4-(4-(oxetan-3-yl)piperazin-1-yl)phenyl)amino)-1,3,5-triazin-2-yl)-2-((6-oxopiperidin-3-yl)oxy)benzonitrile

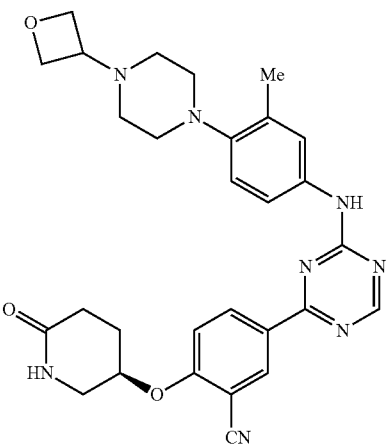 [SMILES: Cc1cc(Nc2ncnc(-c3ccc(O[C@@H]4CCC(=O)NC4)c(C#N)c3)n2)ccc1N1CCN(C2COC2)CC1]

Step 1. To a stirred solution of 1-fluoro-2-methyl-4-nitrobenzene (1.50 g, 9.67 mmol) in DMF (50 mL) in a sealed tube was added 1-(oxetan-3-yl)piperazine (1.65 g, 11.6 mmol) and potassium carbonate (5.35 g, 38.7 mmol) at room temperature. The reaction mixture was brought to 100° C. and heated overnight. The solvent was removed under reduced pressure. The reaction was quenched with water, and extracted with EtOAc (3×50 mL) followed by $CH_2Cl_2$ (2×50 mL) and dried over $Na_2SO_4$. The organic phase was loaded onto silica gel and purified by flash column chromatography to afford 1-(2-methyl-4-nitrophenyl)-4-(oxetan-3-yl)piperazine. LCMS-ESI$^+$ (m/z): [M+H]$^+$ calcd for $C_{14}H_{29}N_3O_3$: 278.1; found: 278.3.

Step 2. To a stirred solution of 1-(2-methyl-4-nitrophenyl)-4-(oxetan-3-yl)piperazine (1.56 g, 5.34 mmol) in EtOH (50 mL) was added 10% Pd/C under a hydrogen atmosphere at room temperature. Reaction mixture was stirred overnight and filtered through a pad of Celite and washed with $CH_2Cl_2$. Solvent was removed under reduced pressure to produce 3-methyl-4-(4-(oxetan-3-yl)piperazin-1-yl)aniline LCMS-ESI$^+$ (m/z): [M+H]$^+$ calcd for $C_{14}H_{21}N_3O$: 248.2; found: 248.4.

Step 3. 4-chloro-N-(3-methyl-4-(4-(oxetan-3-yl)piperazin-1-yl)phenyl)-1,3,5-triazin-2-amine was prepared following the same procedure reported in Example 531 by coupling 3-methyl-4-(4-(oxetan-3-yl)piperazin-1-yl)aniline to 2,4-dichloro-1,3,5-triazine instead of 3-methoxy-4-(4-(oxetan-3-yl)piperazin-1-yl)aniline to afford product. LCMS-ESI$^+$ (m/z): [M+H]$^+$ calcd for $C_{17}H_{21}ClN_6O$: 361.2; found: 361.3.

Step 4. 2-fluoro-5-(4-((3-methyl-4-(4-(oxetan-3-yl)piperazin-1-yl)phenyl)amino)-1,3,5-triazin-2-yl)benzonitrile was prepared following the same procedure reported in Example 531 by coupling 2-fluoro-5-(4,4,5,5-tetramethyl-1,3,2-dioxaborolan-2-yl)benzonitrile with 4-chloro-N-(3-methyl-4-(4-(oxetan-3-yl)piperazin-1-yl)phenyl)-1,3,5-triazin-2-amine instead of 4-chloro-N-(3-methoxy-4-(4-(oxetan-3-yl)piperazin-1-yl)phenyl)-1,3,5-triazin-2-amine to afford product. LCMS-ESI$^+$ (m/z): [M+H]$^+$ calcd for $C_{24}H_{24}FN_7O$: 446.2; found: 446.4.

Step 5. (R)-5-(4-((3-methyl-4-(4-(oxetan-3-yl)piperazin-1-yl)phenyl)amino)-1,3,5-triazin-2-yl)-2-((6-oxopiperidin-3-yl)oxy)benzonitrile was prepared following the same procedure reported in Example 531 by coupling 5-hydroxypiperidin-2-one with 2-fluoro-5-(4-((3-methyl-4-(4-(oxetan-3-yl)piperazin-1-yl)phenyl)amino)-1,3,5-triazin-2-yl)benzonitrile instead of 2-fluoro-5-(4-((3-methoxy-4-(4-(oxetan-3-yl)piperazin-1-yl)phenyl)amino)-1,3,5-triazin-2-yl)benzonitrile to afford product. LCMS-ESI$^+$ (m/z): [M+H]$^+$ calcd for $C_{29}H_{32}N_8O_3$: 541.3; found: 541.4. $^1$H NMR (400 MHz, DMSO-d$_6$) δ 10.26 (s, 1H), 8.78 (s, 1H), 8.58 (d, J=8.6 Hz, 1H), 7.66 (s, 1H), 7.58 (d, J=9.4 Hz, 1H), 7.46 (s, 1H), 7.10 (d, J=8.7 Hz, 1H), 5.12 (s, 1H), 4.83-4.72 (m, 4H), 4.55-4.48 (m, 1H), 3.52 (d, J=14.2 Hz, 2H), 3.20 (s, 1H), 3.11 (s, 1H), 3.01 (s, 1H), 2.87 (s, 1H), 2.71 (s, 1H), 2.41-2.16 (m, 6H), 2.10 (s, 4H), 2.05 (s, 2H).

Example 533

2-(((3R,4S)-3-fluoro-1-(3-hydroxypropanoyl)piperidin-4-yl)oxy)-5-(4-((3-methyl-4-(4-(oxetan-3-yl)piperazin-1-yl)phenyl)amino)-1,3,5-triazin-2-yl)benzonitrile

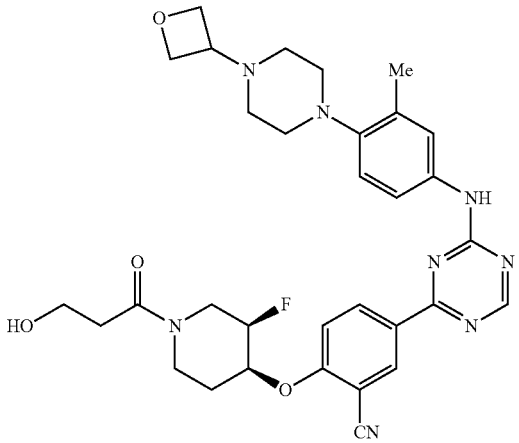 [SMILES: Cc1cc(Nc2ncnc(-c3ccc(O[C@H]4CCN(C(=O)CCO)C[C@H]4F)c(C#N)c3)n2)ccc1N1CCN(C2COC2)CC1]

To a solution of 2-(((3R,4S)-3-fluoropiperidin-4-yl)oxy)-5-(4-((3-methyl-4-(4-(oxetan-3-yl)piperazin-1-yl)phenyl)amino)-1,3,5-triazin-2-yl)benzonitrile (62 mg, 0.113 mmol) in DMF (4 mL) was added 3-hydroxypropanoic acid (61 mg, 1.36 mmol), N,N-diisopropylethylamine (175 mg, 1.36 mmol), 1-[Bis(dimethylamino)methylene]-1H-1,2,3-triazolo[4,5-b]pyridinium 3-oxid hexafluorophosphate, N-[(Dimethylamino)-1H-1,2,3-triazolo-[4,5-b]pyridin-1-yl-methylene]-N-methylmethanaminium hexafluorophosphate N-oxide (79.8 mg, 0.339 mmol) at room temperature and stirred overnight. Solvent was removed under reduced pressure, and crude was dissolved in 0.1% TFA in 1:3 H$_2$O:MeCN and purified by preparative HPLC to afford 2-(((3R,4S)-3-fluoro-1-(3-hydroxypropanoyl)piperidin-4-yl)oxy)-5-(4-((3-methyl-4-(4-(oxetan-3-yl)piperazin-1-yl)phenyl)amino)-1,3,5-triazin-2-yl)benzonitrile LCMS-ESI$^+$ (m/z):

[M+H]+ calcd for $C_{32}H_{32}FN_8O_4$: 617.3; found: 617.5. $^1$H NMR (400 MHz, DMSO-$_6$) δ 10.25 (s, 1H), 8.78 (s, 1H), 8.58 (d, J=8.5 Hz, 2H), 7.59 (dd, J=32.9, 8.7 Hz, 3H), 7.10 (d, J=8.6 Hz, 1H), 5.25-4.88 (m, 2H), 4.89-4.67 (m, 5H), 4.65-4:38 (m, 1H), 4.31 (s, 1H), 4.10 (s, 1H), 3.81 (d, J=13.9 Hz, 1H), 3.70-3.30 (m, 4H), 3.11 (q, J=41.8, 32.0 Hz, 5H), 2.52 (s, 2H), 2.29 (s, 3H), 1.85 (d, J=93.9 Hz, 2H), 1.29-1.11 (m, 2H).

Example 534

2-((2S,4R)-4-hydroxy-2-methylpyrrolidin-1-yl)-5-(4-((3-methyl-4-(4-(oxetan-3-yl)piperazin-1-yl)phenyl)amino)-1,3,5-triazin-2-yl)benzonitrile

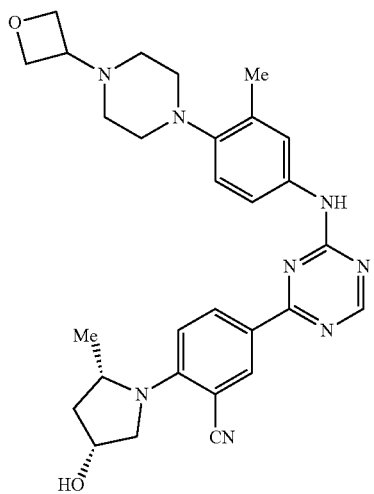 [SMILES: Cc1cc(Nc2ncnc(-c3ccc(N4C[C@H](O)C[C@@H]4C)c(C#N)c3)n2)ccc1N1CCN(C2COC2)CC1]

A solution of 2-fluoro-5-(4-((3-methyl-4-(4-(oxetan-3-yl)piperazin-1-yl)phenyl)amino-1,3,5-triazin-2-yl)benzonitrile (60.0 mg, 0.135 mmol), N,N-diisopropylethylamine (17.4 mg, 0.135 mmol), and (3R,5S)-5-methylpyrrolidin-3-ol (17.0 mg, 0.168 mmol) in i-PrOH (3 mL) was heated by microwave irradiation to 150° C. for 3 hours. Solvent was removed under reduced pressure, and crude was dissolved in 0.1% TFA in 1:3 H$_2$O:MeCN and purified by preparative HPLC to afford 2-((2S,4R)-4-hydroxy-2-methylpyrrolidin-1-yl)-5-(4-((3-methyl-4-(4-(oxetan-3-yl)piperazin-1-yl)phenyl)amino)-1,3,5-triazin-2-yl)benzonitrile. LCMS-ESI+ (m/z): [M+H]+ calcd for $C_{29}H_{34}N_8O_2$: 527.3; found: 527.3.

$^1$H NMR (400 MHz, DMSO-d$_6$) δ 10.10 (s, 1H), 8.69 (s, 1H), 8.45 (s, 1H), 8.32 (dd, J=9.2, 2.2 Hz, 1H), 7.54 (d, J=8.5 Hz, $^2$H), 7.08 (d, J=8.5 Hz, 1H), 7.02 (d, J=9.3 Hz, 1H), 4.83-4.71 (m, 4H), 4.50 (s, 1H), 4.41-4.32 (m, 2H), 4.01 (dd, J=10.9, 4.1 Hz, 1H), 3.95 (s, 1H), 3.15 (s, 8H), 2.29 (s, 3H), 2.13 (dd, J=12.9, 7.0 Hz, 2H), 1.79 (ddd, J=12.6, 8.0, 4.5 Hz, 2H), 1.21 (d, J=6.0 Hz, 3H).

Example 535

2-(((3R,4S)-3-fluoro-1-((S)-5-oxopyrrolidine-2-carbonyl)piperidin-4-yl)oxy)-5-(4-((4-((S)-3-methyl-4-(oxetan-3-yl)piperazin-1-yl)phenyl)amino)-1,3,5-triazin-2-yl)benzonitrile

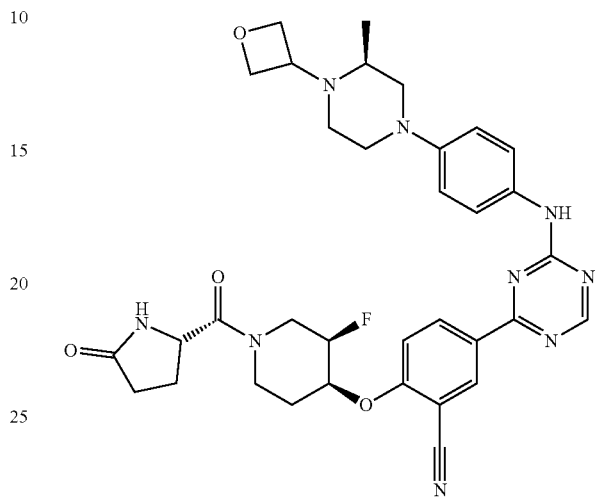

Step 1: Preparation of (S)-tert-butyl 2-methyl-4-(4-nitrophenyl)piperazine-1-carboxylate:

To 4-fluoro nitrobenzene (697 mg, 4.940 mmol) and (S)-tert-butyl 2-methylpiperazine-1-carboxylate (1650 mg, 8.239 mmol) dissolved in DMSO (37 mL) was added potassium carbonate (1050 mg, 7.597 mmol). The reaction mixture was heated at 90° C. for 1 h. After cooling to room temperature, the reaction mixture was diluted with ethyl acetate and washed with water. The organic layer was dried over sodium sulfate, filtered, and concentrated. The residue was purified by flash column chromatography to give (S)-tert-butyl 2-methyl-4-(4-nitrophenyl)piperazine-1-carboxylate.

Step 2: Preparation of (S)-3-methyl-1-(4-nitrophenyl)piperazine:

(S)-tert-butyl 2-methyl-4-(4-nitrophenyl)piperazine-1-carboxylate (500 mg, 1.556 mmol) dissolved in DCM (15 mL) was treated with trifluoroacetic acid (2200 μL, 28.75 mmol). The reaction mixture was stirred at room temperature for 1 h and then concentrated. The residue was dissolved in ethyl acetate and washed with saturated sodium bicarbonate solution. The layers were separated. The organic layer was concentrated to give (S)-3-methyl-1-(4-nitrophenyl)piperazine.

Step 3: Preparation of (S)-2-methyl-4-(4-nitrophenyl)-1-(oxetan-3-yl)piperazine:

(S)-3-methyl-1-(4-nitrophenyl)piperazine (283 mg, 1.279 mmol) dissolved in 1,2-dichloroethane (10 mL) was treated with 3-oxetanone (70 μL, 1.092 mmol). The reaction mixture was stirred at room temperature for 1 h before sodium triacetoxyborohydride (353 mg, 1.666 mmol) was added. The reaction mixture was heated at 55° C. for 2 h. It was then diluted with dichloromethane and washed with water. The organic layer was dried over sodium sulfate, filtered and concentrated to give (S)-2-methyl-4-(4-nitrophenyl)-1-(oxetan-3-yl)piperazine.

Step 4: Preparation of (S)-4-(3-methyl)-4-(oxetan-3-yl)piperazin-1-yl)aniline:

(S)-2-methyl-4-(4-nitrophenyl)-1-(oxetan-3-yl)piperazine (220 mg, 0.793 mmol) dissolved in ethanol (7 mL) was treated with ammonium formate (300 mg, 4.78 mmol) and 10% Pd/C (85 mg, 0.080 mmol). The reaction mixture was heated at 60° C. for 1 h. After cooling to room temperature, the reaction mixture was filtered, washed with methanol. The filtrate was concentrated to give (S)-4-(3-methyl-4-(oxetan-3-yl)piperazin-1-yl)aniline.

Step 5: Preparation of (S)-4-chloro-N-(4-(3-methyl-4-(oxetan-3-yl)piperazin-1-yl)phenyl)-1,3,5-triazin-2-amine:

(S)-4-(3-methyl-4-(oxetan-3-yl)piperazin-1-yl)aniline (184 mg, 0.744 mmol) was dissolved in methanol (6 mL) and cooled to 0° C. Triethyl amine (100 µL, 0.717 mmol) was then added, followed by 2,4-dichloro-1,3,5-triazine (110 mg, 0.733 mmol). The reaction mixture was allowed to warm to room temperature. After 30 min, the reaction mixture was concentrated. The residue was dissolved in dichloromethane and washed with water. The organic layer was dried over sodium sulfate, filtered, and concentrated to give (S)-4-chloro-N-(4-(3-methyl-4-(oxetan-3-yl)piperazin-1-yl)phenyl)-1,3,5-triazin-2-amine.

Step 6: Preparation of (3R,4S)-tert-butyl 4-(2-cyano-4-(4-((4-(S)-3-methyl-4-(oxetan-3-yl)piperazin-1-yl)phenyl)amino)-1,3,5-triazin-2-yl)phenoxy)-3-fluoropiperidine-1-carboxylate:

(S)-4-chloro-N-(4-(3-methyl-4-(oxetan-3-yl)piperazin-1-yl)phenyl)-1,3,5-triazin-2-amine (214 mg, 0.593 mmol) was dissolved in dioxane (5 mL) and the reaction mixture was degassed with argon. (3R,4S)-tert-butyl 4-(2-cyano-4-(4,4,5,5-tetramethyl-1,3,2-dioxaborolan-2-yl)phenoxy)-3-fluoropiperidine-1-carboxylate (270 mg, 0.605 mmol) was then added, followed by [1,1'-Bis(diphenylphosphino)ferrocene]dichloropalladium(II) dichloromethane (45 mg, 0.055 mmol), and 2M sodium carbonate solution (930 µL, 1.860 mmol). The reaction mixture was heated at 90° C. After 3 h, the reaction mixture was cooled to room temperature and concentrated. The residue was dissolved in ethyl acetate and washed with water. The organic layer was dried over sodium sulfate, filtered, and concentrated. The residue was purified by flash column chromatography to give (3R,4S)-tert-butyl 4-(2-cyano-4-(4-((4-((S)-3-methyl-4-(oxetan-3-yl)piperazin-1-yl)phenyl)amino)-1,3,5-triazin-2-yl)phenoxy)-3-fluoropiperidine-1-carboxylate.

Step 7: Preparation of 2-(((3R,4S)-3-fluoropiperidin-4-yl)oxy)-5-(4-((4-((S)-3-methyl-4-(oxetan-3-yl)piperazin-1-yl)phenyl)amino)-1,3,5-triazin-2-yl)benzonitrile:

(3R,4S)-tert-butyl 4-(2-cyano-4-(4-((4-((S)-3-methyl-4-(oxetan-3-yl)piperazin-1-yl)phenyl)amino)-1,3,5-triazin-2-yl)phenoxy)-3-fluoropiperidine-1-carboxylate (290 mg, 0.450 mmol) dissolved in DCM (4 mL) was treated with trifluoroacetic acid (850 µL, 11.11 mmol). The reaction mixture was stirred at room temperature for 30 min and then concentrated. The residue was dissolved in ethyl acetate and washed with saturated sodium bicarbonate solution. The layers were separated. The organic layer was concentrated to give 2-(((3R,4S)-3-fluoropiperidin-4-yl)oxy)-5-(4-((S)-3-methyl-4-(oxetan-3-yl)piperazin-1-yl)phenyl)amino)-1,3,5-triazin-2-yl)benzonitrile.

Step 8: Preparation of 2-(((3R,4S)-3-fluoro-1-((S)-5-oxopyrrolidine-2-carbonyl)piperidin-4-yl)oxy)-5-(4-((4-((S)-3-methyl-4-(oxetan-3-yl)piperazin-1-yl)phenyl)amino)-1,3,5-triazin-2-yl)benzonitrile:

2-(((3R,4S)-3-fluoropiperidin-4-yl)oxy)-5-(4-((4-((S)-3-methyl-4-(oxetan-3-yl)piperazin-1-yl)phenyl)amino)-1,3,5-triazin-2-yl)benzonitrile (90 mg, 0.165 mmol) dissolved in DCM (3 mL) was treated with HATU (75 mg. 0.197 mmol), (S)-5-oxopyrrolidine-2-carboxylic acid (26 mg, 0.201 mmol), and N,N-diisopropylethylamine (100 µL, 0.574 mmol). The reaction mixture was stirred at room temperature for 30 min. It was then diluted with dichloromethane and washed with water. The organic layer was dried over sodium sulfate, filtered, and concentrated. The residue was purified by HPLC to give the title compound. $^1$H NMR (400 MHz, DMSO-d6) δ 10.18 (d, J=23.4 Hz, 1H), 8.75 (s, 1H), 8.62-8.48 (m, 2H), 7.73 (d, J=20.9 Hz, 1H), 7.63 (d, J=9.1 Hz, 3H), 7.04 (s, 2H), 5.19-5.06 (m, 2H), 5.01 (t, J=6.6 Hz, 1H), 4.94-4.73 (m, 3H), 4.73-4.54 (m, 3H), 4.39 (m, 1H), 4.25-4.06 (m, 2H), 3.84 (m, 2H), 3.32 (m, 1H), 3.14-2.94 (m, 2H), 2.79 (s, 1H), 2.31 (m, 1H), 2.17-2.04 (m, 2H), 1.98 (m, 1H), 1.95-1.74 (m, 1H), 1.18 (d, J=6.5 Hz, 3H). LCMS-ESI$^+$ (m/z): [M+H]$^+$ calcd for C34H38FN9O4: 656.3; found: 656.2.

Example 536

2-(((3R,4S)-3-fluoro-1-((S)-5-oxopyrrolidine-2-carbonyl)piperidin-4-yl)oxy)-5-(4-((3-methyl-4-(4-(oxetan-3-yl)piperazin-1-yl)phenyl)amino)-1,3,5-triazin-2-yl)benzonitrile

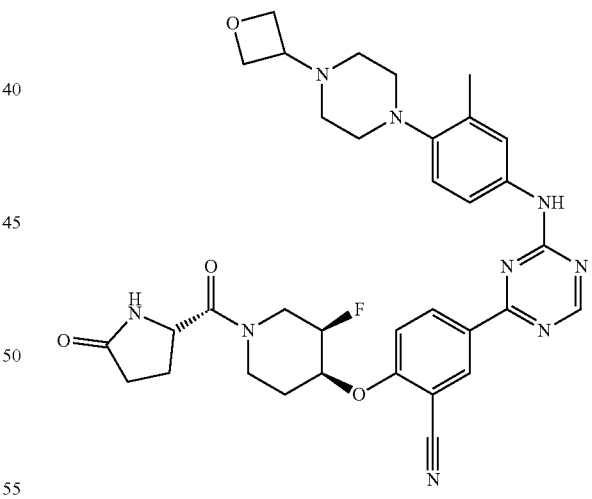

The title compound was synthesized in the same manner as Example 535 using 1-(oxetan-3-yl)piperazine and 1-fluoro-2-methyl-4-nitrobenzene. $^1$H NMR (400 MHz, DMSO-d6) δ 10.26 (s, 1H), 8.78 (s, 1H), 8.62-8.54 (m, 2H), 7.71 (s, 1H), 7.69-7.61 (m, 1H), 7.55 (d, J=8.0 Hz, 1H), 7.10 (d, J=8.6 Hz, 1H), 5.20-5.06 (m, 2H), 5.01 (s, 1H), 4.60 (ddd, J=14.1, 8.7, 3.8 Hz, 1H), 4.49 (s, 1H), 4.38, (m, 1H), 4.13 (m, 1H), 3.84 (m, 1H), 2.30 (m, 2H), 2.09 (m, 3H), 2.00 (m, 2H), 1.86 (m, 3H). LCMS-ESI$^+$ (m/z): [M+H]$^+$ calcd for C34H38FN9O4: 656.3; found: 656.3.

Example 537

N-(5-((4-(3-cyano-4-(((3R,4S)-3-fluoro-1-((S)-5-oxopyrrolidine-2-carbonyl)piperidin-4-yl)oxy)phenyl)-1,3,5-triazin-2-yl)amino)pyridin-2-yl)acetamide

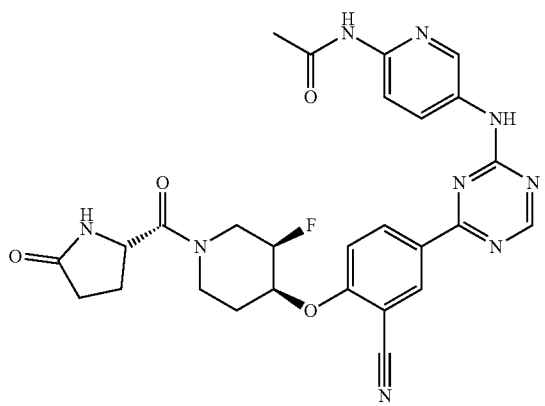

The title compound was synthesized in the same manner as Example 535 using N-(5-aminopyridin-2-yl)acetamide. $^1$H NMR (400 MHz, DMSO-d6) δ 10.47 (s, 1H), 10.42 (s, 1H), 8.82 (s, 1H), 8.65-8.52 (m, 3H), 8.10 (s, 2H), 7.76-7.62 (m, 2H), 5.10 (d, J=23.8 Hz, 2H), 5.01 (s, 1H), 4.60 (s, 2H), 4.38 (s, 1H), 4.19 (d, J=14.5 Hz, 2H), 3.84 (d, J=14.7 Hz, 1H), 2.31 (t, J=15.2 Hz, 3H), 2.10 (s, 1H), 2.08 (d, J=3.9 Hz, 5H), 1.99 (s, 3H). LCMS-ESI$^+$ (m/z): [M+H]$^+$ calcd for C27H26FN9O4: 560.2; found: 560.2.

Example 538

5-(4-((6-ethoxypyridin-3-yl)amino)-1,3,5-triazin-2-yl)-2-(((3R,4S)-3-fluoro-1-((S)-5-oxopyrrolidine-2-carbonyl)piperidin-4-yl)oxy)benzonitrile

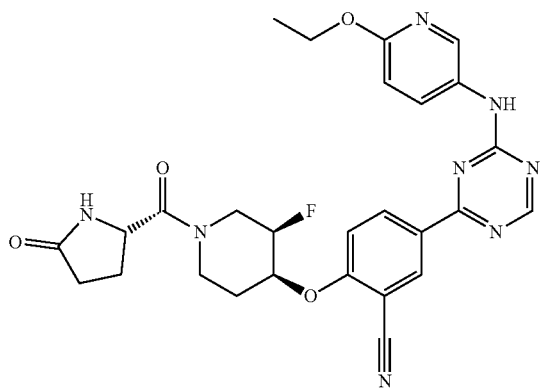

The title compound was synthesized in the same manner as Example 535 using 6-ethoxypyridin-3-amine. $^1$H NMR (400 MHz, DMSO-d6) δ 10.26 (d, J=16.3 Hz, 1H), 8.78 (s, 1H), 8.63-8.35 (m, 3H), 7.98 (dd, J=8.9, 2.8 Hz, 1H), 7.72 (d, J=21.4 Hz, 1H), 7.64 (d, J=9.1 Hz, 1H), 6.83 (s, 1H), 5.10 (m, 2H), 5.00 (m, 1H), 4.65-4.54 (m, 1H), 4.39 (s, 1H), 4.28 (d, J=7.2 Hz, 2H), 4.11 (s, 1H), 3.32 (m, 1H), 3.05 (m, 1H), 2.30 (m, 1H), 2.09 (m, 2H), 1.99 (m, 1H), 1.31 (t, J=7.0 Hz, 3H). LCMS-ESI$^+$ (m/z): [M+H]$^+$ calcd for C27H27FN8O4: 547.2; found: 547.1.

Example 539

2-(((3R,4S)-3-fluoro-1-((S)-2-hydroxypropanoyl)piperidin-4-yl)oxy)-5-(4-((3-(morpholinomethyl)phenyl)amino)-1,3,5-triazin-2-yl)benzonitrile

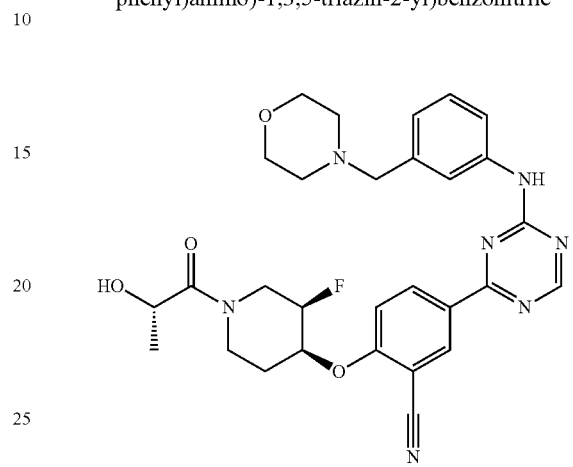

The title compound was synthesized in the same manner as Example 535 using 3-(morpholinomethyl)aniline. $^1$H NMR (400 MHz, DMSO-d6) δ 10.53 (s, 1H), 9.89 (s, 1H), 8.86 (s, 1H), 8.64-8.56 (m, 2H), 7.92 (s, 1H), 7.79 (s, 1H), 7.63 (d, J=9.0 Hz, 1H), 7.49 (t, J=7.8 Hz, 1H), 7.24 (d, J=7.5 Hz, 1H), 5.21-4.93 (m, 3H), 4.46 (m, 1H), 4.37 (m, 3H), 3.96 (m, 3H), 3.62 (m, 1H), 3.16 (m, 3H), 1.97 (m, 2H), 1.84 (m, 1H), 1.20 (m, 3H), 1.07-1.01 (m, 1H). LCMS-ESI$^+$ (m/z): [M+H]$^+$ calcd for C29H32FN7O4: 562.3; found: 562.3.

Example 540

N-(5-((4-(3-cyano-4-(((3R,4S)-3-1H-fluoro-1-((S)-2-hydroxypropanoyl)piperidin-4-yl)oxy)phenyl)-1,3,5-triazin-2-yl)amino)pyridin-2-yl)acetamide

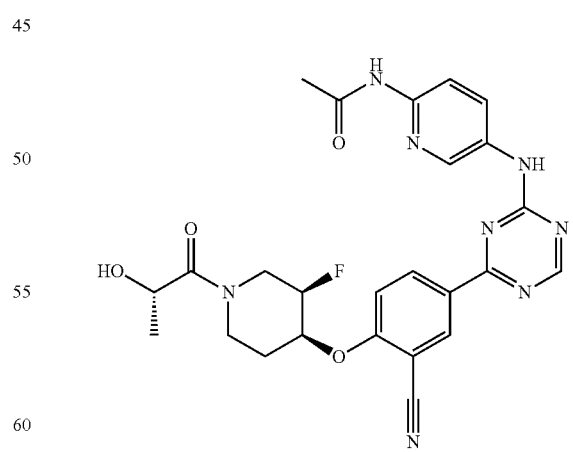

The title compound was synthesized in the same manner as Example 535. $^1$H NMR (400 MHz, DMSO-d6) δ 10.48 (s, 1H), 10.40 (s, 1H), 8.77 (s, 1H), 8.59 (s, 1H), 8.53 (d, J=9.6 Hz, 2H), 8.07 (d, J=23.9 Hz, 2H), 7.59 (m, 2H), 7.33-7.27 (m, 1H), 5.07 (m, 2H), 4.93 (s, 1H), 3.89 (m, 1H), 3.10 (m, 1H), 2.03 (s, 3H), 1.93 (m, 2H), 1.25 (m, 1H), 1.14 (m, 3H). LCMS-ESI⁺ (m/z): [M+H]³⁰ calcd for C25H25FN8O4: 521.2; found: 521.3.

Example 541

5-(4-((6-ethoxypyridin-3-yl)amino)-1,3,5-triazin-2-yl)-2-(((3R,4S)-3-fluoro-1-((S)-2-hydroxypropanoyl)piperidin-4-yl)oxy)benzonitrile

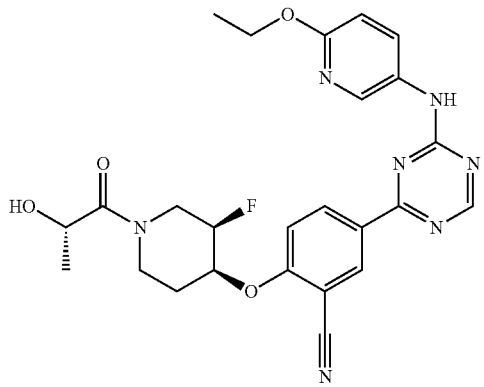 [SMILES: CCOc1ccc(Nc2ncnc(-c3ccc(O[C@H]4CCN(C(=O)[C@H](C)O)C[C@H]4F)c(C#N)c3)n2)cn1]

The title compound was synthesized in the same manner as Example 535. ¹H NMR (400 MHz, DMSO-d6) δ 10.28 (d, J=18.7 Hz, 1H), 8.78 (s, 1H), 8.56 (d, J=31.4 Hz, 3H), 7.98 (dd, J=8.9, 2.8 Hz, 1H), 7.63 (d, J=9.4 Hz, 1H), 6.84 (s, 1H), 5.17-4.94 (m, 3H), 4.28 (s, 2H), 4.15 (m, 1H), 3.35 (m, 1H), 1.98 (m, 2H), 1.81 (s, 1H), 1.36-1.25 (m, 5H), 1.19 (t, J=5.5 Hz, 3H). LCMS-ESI⁺ (m/z): [M+H]⁺ calcd for C25H26FN7O4: 508.2; found: 508.2.

Example 542

2-(((3R,4S)-3-fluoro-1-((S)-5-oxopyrrolidine-2-carbonyl)piperidin-4-yl)oxy)-5-(4-((4-((R)-3-methyl-4-(oxetan-3-yl)piperazin-1-yl)phenyl)amino)-1,3,5-triazin-2-yl)benzonitrile

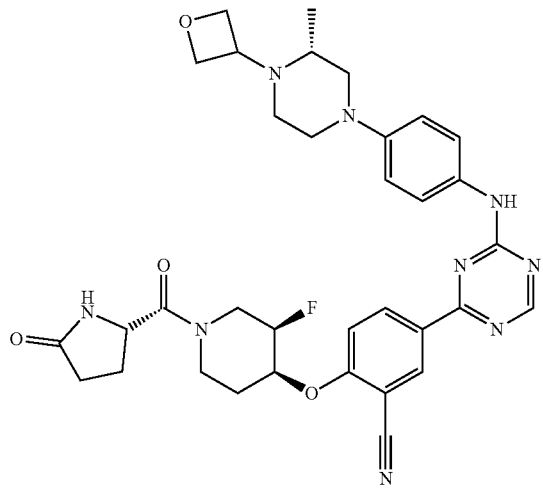

The title compound was synthesized in the same manner as Example 535 using (R)-2-methyl-1-(oxetan-3-yl)piperazine and 4-fluoroaniline. ¹H NMR (400 MHz, DMSO-d6) δ 10.18 (d, J=22.9 Hz, 1H), 8.75 (s, 1H), 8.61-8.50 (m, 2H), 7.73 (d, J=20.8 Hz, 1H), 7.63 (d, J=9.1 Hz, 3H), 7.04 (s, 2H), 5.11 (m, 2H), 5.01 (m, 1H), 4.84 (m, 2H), 4.76 (m, 1H), 4.73-4.54 (m, 4H), 4.43 (m, 1H), 4.19 (m, 2H), 3.40-3.27 (m, 2H), 3.04 (m, 2H), 2.36-2.25 (m, 1H), 2.15-2.06 (m, 2H), 1.99 (m, 2H), 1.91 (m, 1H), 1.19 (m, 3H). LCMS-ESI⁺ (m/z): [M+H]⁺ calcd for C34H38FN9O4: 656.3; found: 656.4.

Example 543

2-(((3R,4S)-3-fluoro-1-((S)-2-hydroxypropanoyl)piperidin-4-yl)oxy)-5-(4-((6-((2-methoxyethyl)amino)pyridin-3-yl)amino)-1,3,5-triazin-2-yl)benzonitrile

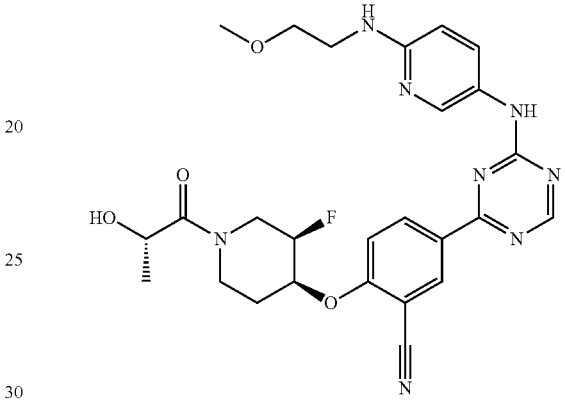

The title compound was synthesized in the same manner as Example 535 using N-(2-methoxyethyl)-5-nitropyridin-2-amine. ¹H NMR (400 MHz, DMSO-d6) δ 10.35 (s, 1H), 8.82 (s, 1H), 8.63-8.49 (m, 2H), 8.32 (d, J=2.4 Hz, 1H), 8.00 (s, 1H), 7.61 (s, 7.03 (d, J=9.3 Hz, 1H), 5.20-4.94 (m, 3H), 4.53-4.41 (m, 1H), 4.35 (m, 1H), 3.93 (m, 2H), 3.56-3.45 (m, 4H), 3.29 (s, 3H), 3.18 (m, 1H), 1.97 (m, 2H), 1.82 (m, 1H), 1.19 (m, 3H). LCMS-ESI⁺ (m/z): [M+H]⁺ calcd for C26H29FN8O4: 537.2; found: 537.3.

Example 544

2-(((3R,4S)-3-fluoro-1-((S)-5-oxopyrrolidine-2-carbonyl)piperidin-4-yl)oxy)-5-(4-((3-methoxy-4-(4-(oxetan-3-yl)piperazin-1-yl)phenyl)amino)-1,3,5-triazin-2-yl)benzonitrile

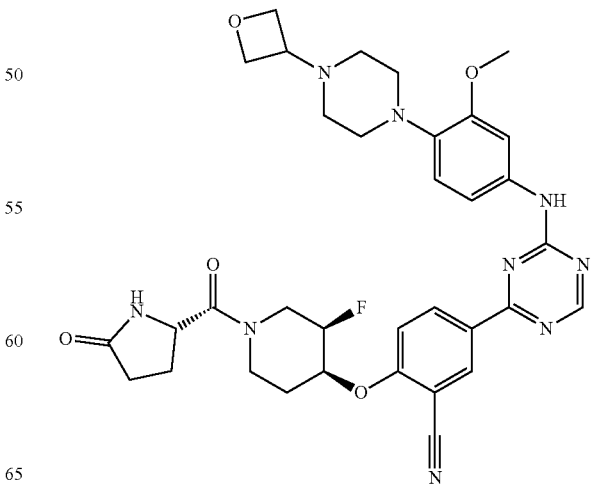

The title compound was synthesized in the same manner as Example 535 starting with 1-fluoro-2-methoxy-4-nitrobenzene and 1-(oxetan-3-yl)piperazine. $^1$H NMR (400 MHz, DMSO-d6) δ 10.29 (s, 1H), 8.79 (s, 1H), 8.62-8.56 (m, 2H), 8.27 (s, 2H), 7.77-7.61 (m, 2H), 6.96 (d, J=8.6 Hz, 1H), 5.13 (s, 2H), 4.74 (m, 4H), 4.59 (m, 2H), 4.37 (s, 2H), 4:17 (s, 3H), 3.60 (m, 7H), 3.32 (m, 4H), 3.22-3.03 (m, 4H), 2.09 (m, 2H). LCMS-ESI$^+$ (m/z): [M+H]$^+$ calcd for C34H38FN9O5: 672.3; found: 672.4.

Example 545

2-(((3R,4S)-3-fluoro-1-((S)-2-hydroxypropanoyl) piperidin-4-yl)oxy)-5-(4-(isoindolin-5-ylamino)-1,3,5-triazin-2-yl)benzonitrile

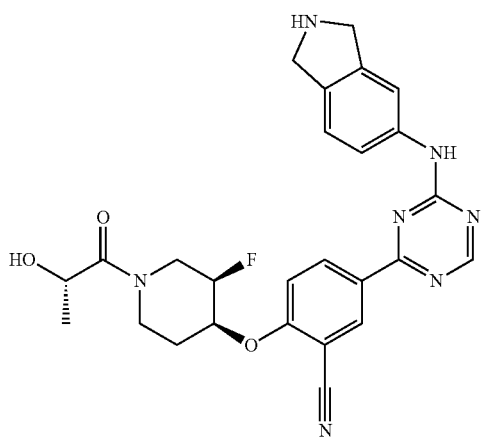 [SMILES: C[C@H](O)C(=O)N1CC[C@H](Oc2ccc(-c3ncnc(Nc4ccc5c(c4)CNC5)n3)cc2C#N)[C@H](F)C1]

Step 1: Preparation of tert-butyl 5-((4-chloro-1,3,5-triazin-2-yl)amino)isoindoline-2-carboxylate:

Tert-butyl 5-aminoisoindoline-2-carboxylate (220 mg, 0.939 mmol) was dissolved in methanol (6 mL) and cooled to 0° C. Triethyl amine (160 µL, 1.148 mmol) was then added, followed by 2,4-dichloro-1,3,5-triazine (138 mg, 0.920 mmol). The reaction mixture was allowed to warm to room temperature. After 30 min, the reaction mixture was concentrated. The residue was dissolved in dichloromethane and washed with water. The organic layer was dried over sodium sulfate, filtered, and concentrated to give tert-butyl 5-((4-chloro-1,3,5-triazin-2-yl)amino)isoindoline-2-carboxylate.

Step 2: Preparation of 2-(((3R,4S)-3-fluoropiperidin-4-yl) oxy)-5-(4,4,5,5-tetramethyl-1,3,2-dioxaborolan-2-yl)benzonitrile:

(3R,4S)-tert-butyl 4-(2-cyano-4-(4,4,5,5-tetramethyl-1,3,2-dioxaborolan-2-yl)phenoxy)-3-fluoropiperidine-1-carboxylate (307 mg, 0.688 mmol) dissolved in DCM (7 mL) was treated with trifluoroacetic acid (1300 µL, 16.99 mmol). The reaction mixture was stirred at room temperature for 1 h and then concentrated. The residue was dissolved in ethyl acetate and washed with saturated sodium bicarbonate solution. The layers were separated. The organic layer was concentrated to give 2-(((3R,4S)-3 -fluoropiperidin-4-yl) oxy)-5-(4,4,5,5-tetramethyl-1,3,2-dioxaborolan-2-yl)benzonitrile.

Step 3: Preparation of 2-(((3R,4S)-3-fluoro-1-((S)-2-hydroxypropanoyl)piperidin-4-yl)oxy)-5-(4,4,5,5-tetramethyl-1,3,2-dioxaborolan-2-yl)benzonitrile:

2-(((3R,4S)-3-fluoropiperidin-4-yl)oxy)-5-(4,4,5,5-tetramethyl-1,3,2-dioxaborolan-2-yl)benzonitrile (190 mg, 0.549 mmol) dissolved in DCM (5 mL) was treated with HATU (244 mg. 0.642 mmol), (S)-2-hydroxypropanoic acid (64 mg, 0.710 mmol), and N,N-diisopropylethylamine (260 µL, 1.493 mmol). The reaction mixture was stirred at room temperature for 30 min. It was then diluted with dichloromethane and washed with water. The organic layer was dried over sodium sulfate, filtered, and concentrated. The residue was purified by flash column chromatography to give 2-(((3R,4S)-3-fluoro-1-((S)-2-hydroxypropanoyl)piperidin-4-yl)oxy)-5-(4,4,5,5-tetramethyl-1,3,2-dioxaborolan-2-yl)benzonitrile.

Step 4: Preparation of tert-butyl 5-((4-(3-cyano-4-(((3R,4S)-3-fluoro-1-((S)-2-hydroxypropanoyl)piperidin-4-yl) oxy)phenyl)-1,3,5-triazin-2-yl)amino)isoindoline-2-carboxylate:

Tert-butyl 5-((4-chloro-1,3,5-triazin-2-yl)amino)isoindoline-2-carboxylate (65 mg, 0.187 mmol) was dissolved in dioxane (2 mL) and the reaction mixture was degassed with argon. 2-(((3R,4S)-3-fluoro-1-((S)-2-hydroxypropanoyl)piperidin-4-yl)oxy)-5-(4,4,5,5-tetramethyl-1,3,2-dioxaborolan-2-yl)benzonitrile (76 mg, 0.182 mmol) was then added, followed by [1,1'-Bis(diphenylphosphino)ferrocene]dichloropalladium(II) dichloromethane (14 mg, 0.017 mmol), and 2M sodium carbonate solution (290 µL, 0.580 mmol). The reaction mixture was heated at 90° C. After 30 min, the reaction mixture was cooled to room temperature and concentrated. The residue was dissolved in ethyl acetate and washed with water. The organic layer was dried over sodium sulfate, filtered, and concentrated. The residue was purified by flash column chromatography to give tert-butyl 5-((4-(3-cyano-4-(((3R,4S)-3-fluoro-1-((S)-2-hydroxypropanoyl)piperidin-4-yl)oxy)phenyl)-1,3,5-triazin-2-yl)amino)isoindoline-2-carboxylate.

Step 5: Preparation of 2-(((3R,4S)-3-fluoro-1-((S)-2-hydroxypropanoyl)piperidin-4-yl)oxy)-5-(4-(isoindolin-5-ylamino)-1,3,5-triazin-2-yl)benzonitrile:

Tert-butyl 5-((4-(3-cyano-4-(((3R,4S)-3-fluoro-1-((S)-2-hydroxypropanoyl)piperidin-4-yl)oxy)phenyl)-1,3,5-triazin-2-yl)amino)isoindoline-2-carboxylate (31 mg, 0.051 mmol) dissolved in DCM (1 mL) was treated with trifluoroacetic acid (100 µL, 1.307 mmol). The reaction mixture was stirred at room temperature for 1 h and then concentrated. The residue was purified by HPLC to give the title compound. $^1$H NMR (400 MHz, DMSO-d6) δ 10.50 (s, 1H), 9.32 (s, 1H), 8.84 (s, 1H), 8.59 (d, J=7.6 Hz, 1H), 7.86 (s, 1H), 7.68 (s, 1H), 7.62 (d, J=9.4 Hz, 1H), 7.40 (d, J=8.2 Hz, 1H), 6.49 (s, 2H), 5.10 (s, 2H), 4.97 (s, 2H), 4.51 (d, J=23.2 Hz, 4H), 1.98 (s, 3H), 1.25-1.17 (m, 3H). LCMS-ESI$^+$ (m/z): [M+H]$^+$ calcd for C26H26FN7O3: 504.2; found: 504.3.

Example 546

2-(((3R,4S)-3-fluoro-1-(2-methoxyacetyl)piperidin-4-yl)oxy)-5-(4-((4-(4-(oxetan-3-yl)piperazin-1-yl)phenyl)amino)-1,3,5-triazin-2-yl)benzonitrile

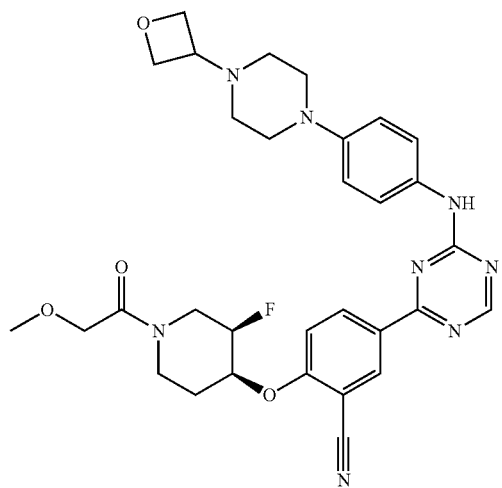 [SMILES: COCC(=O)N1CC[C@H](Oc2ccc(-c3ncnc(Nc4ccc(N5CCN(C6COC6)CC5)cc4)n3)cc2C#N)[C@H](F)C1]

The title compound was synthesized in the same manner as Example 535 using 2-methoxyacetic acid. $^1$H NMR (400 MHz, DMSO-d6) δ 10.18 (d, J=21.4 Hz, 1H), 8.75 (s, 1H), 8.62-8.49 (m, 2H), 7.61 (d, J=9.2 Hz, 3H), 7.04 (s, 2H), 5.18-5.05 (m, 2H), 4.97 (m, 1H), 4.75 (m, 4H), 4.33 (m, 2H), 4.18 (m, 2H), 4.14-3.95 (m, 5H), 3.73 (m, 2H), 3.28 (s, 3H), 3.13 (m, 2H), 1.97 (m, 2H), 1.83 (m, 1H). LCMS-ESI$^+$ (m/z): [M+H]$^+$ calcd for C31H35FN8O4: 603.3; found: 603.4.

Example 547

2-(((3R,4S)-3-fluoro-1-((S)-2-methoxypropanoyl)piperidin-4-yl)oxy)-5-(4-((4-(4-(oxetan-3-yl)piperazin-1-yl)phenyl)amino)-1,3,5-triazin-2-yl)benzonitrile

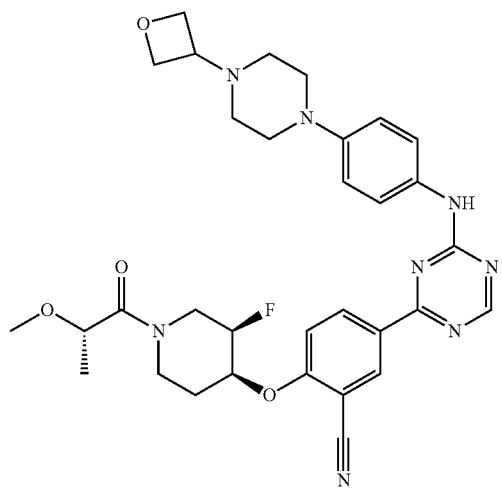 [SMILES: CO[C@@H](C)C(=O)N1CC[C@H](Oc2ccc(-c3ncnc(Nc4ccc(N5CCN(C6COC6)CC5)cc4)n3)cc2C#N)[C@H](F)C1]

The title compound was synthesized in the same manner as Example 535 using (S)-2-methoxypropanoic acid. $^1$H NMR (400 MHz, DMSO-d6) δ 10.19 (d, J=22.4 Hz, 1H), 8.75 (s, 1H), 8.62-8.50 (m, 2H), 7.62 (m, 3H), 7.05 (m, 2H), 5.11 (m, 2H), 4.99 (m, 1H), 4.77 (d, J=6.4 Hz, 4H), 4.44 (m, 2H), 4.34-4.13 (m, 4H), 3.41-3.25 (m, 2H), 3.20 (s, 3H), 3.09 (m, 2H), 1.99 (m, 2H), 1.92 (m, 1H), 1.22 (m, 3H). LCMS-ESI$^+$ (m/z): [M+H]$^+$ calcd for C32H37FN8O4: 617.3; found: 617.4.

Example 548

2-(((3R,4S)-3-fluoro-1-((S)-5-oxopyrrolidine-3-carbonyl)piperidin-4-yl)oxy)-5-(4-((4-(4-(oxetan-3-yl)piperazin-1-yl)phenyl)amino)-1,3,5-triazin-2-yl)benzonitrile

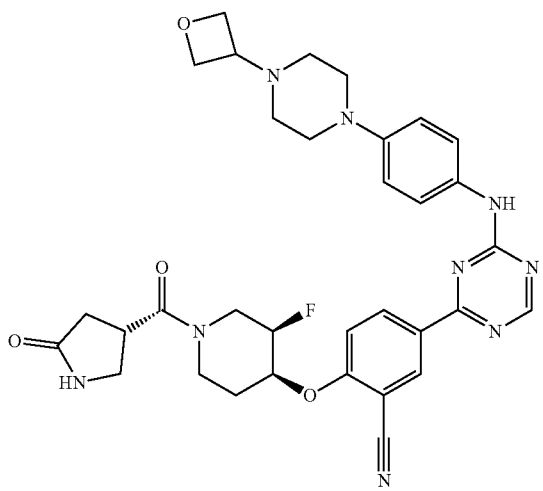

The title compound was synthesized in the same manner as Example 535 using (S)-5-oxopyrrolidine-3-carboxylic acid. $^1$H NMR (400 MHz, DMSO-d6) δ 10.13 (d, J=23.5 Hz, 1H), 8.70 (s, 1H), 8.57-8.43 (m, 2H), 7.56 (dd, J=14.8, 7.9 Hz, 4H), 6.99 (m, 2H), 5.05 (m, 2H), 4.93 (m, 1H), 4.70 (m, 4H), 4.36 (m, 1H), 4.15 (m, 1H), 3.78 (m, 2H), 3.68-3.51 (m, 2H), 3.21 (m, 4H), 2.62 (m, 1H), 2.33-2.24 (m, 3H), 1.92 (m, 2H), 1.72 (m, 1H). LCMS-ESI$^+$ (m/z): [M+H]$^+$ calcd for C33H36FN9O4: 642.3; found: 642.4.

Example 549

2-(((3R,4S)-3-fluoro-1-(2-(methylsulfonyl)acetyl)piperidin-4-yl)oxy)-5-(4-((4-(4-(oxetan-3-yl)piperazin-1-yl)phenyl)amino)-1,3,5-triazin-2-yl)benzonitrile

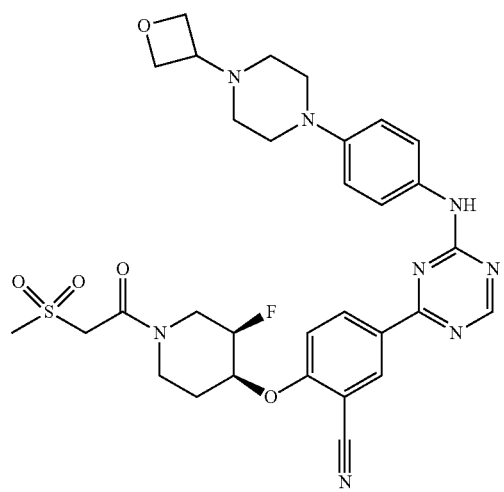 [SMILES: CS(=O)(=O)CC(=O)N1CC[C@H](Oc2ccc(-c3ncnc(Nc4ccc(N5CCN(C6COC6)CC5)cc4)n3)cc2C#N)[C@H](F)C1]

533

The title compound was synthesized in the same manner as Example 535 using 2-(methylsulfonyl)acetic acid. $^1$H NMR (400 MHz, DMSO-d6) δ 10.19 (d, J=21.8 Hz, 1H), 8.75 (s, 1H), 8.63-8.49 (m, 2H), 7.62 (d, J=9.6 Hz, 3H), 7.05 (s, 2H), 5.13 (m, 3H), 4.98 (m, 1H), 4.76 (d, J=6.2 Hz, 4H), 4.56 (s, 1H), 4.38 (m, 2H), 4.18-4.09 (m, 1H), 3.94 (m, 4H), 3.10 (d, J=10.5 Hz, 3H), 2.04-1.93 (m, 2H), 1.89 (m, 1H). LCMS-ESI$^+$ (m/z): [M+H]$^+$ calcd for C31H35FN8O5S: 651.2; found: 651.4.

Example 550

2-(((3R,4S)-3-fluoro-1-(3-hydroxycyclobutanecarbonyl)piperidin-4-yl)oxy)-5-(4-((4-(4-(oxetan-3-yl)piperazin-1-yl)phenyl)amino)-1,3,5-triazin-2-yl)benzonitrile

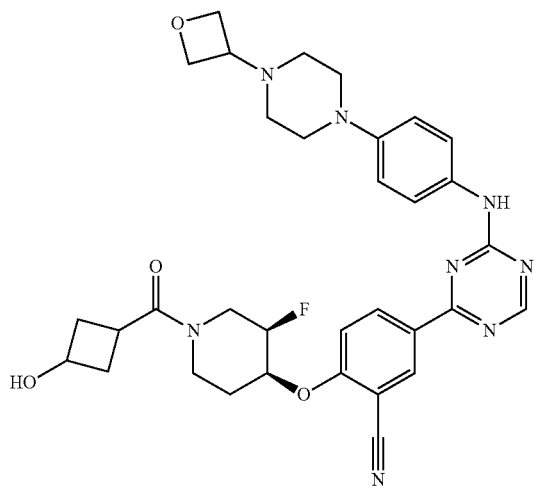 [SMILES: N#Cc1cc(-c2ncnc(Nc3ccc(N4CCN(C5COC5)CC4)cc3)n2)ccc1O[C@H]1CCN(C(=O)C2CC(O)C2)C[C@H]1F]

The title compound was synthesized in the same manner as Example 535 using 3-hydroxycyclobutanecarboxylic acid. $^1$H NMR (400 MHz, DMSO-d6) δ 10.15 (d, J=29.2 Hz, 1H), 8.74 (s, 1H), 8.63-8.46 (m, 2H), 7.61 (d, J=9.1 Hz, 3H), 7.03 (m, 2H), 5.06 (m, 2H), 4.94 (m, 1H), 4.73 (m, 4H), 4.34 (m, 1H), 4.17-4.08 (m, 3H), 3.97 (m, 1H), 3.02 (m, 2H), 2.79 (m, 1H), 2.35 (m, 2H), 2.05 (m, 1H), 1.94 (m, 2H), 1.77 (m, 1H). LCMS-ESI$^+$ (m/z): [M+H]$^+$ calcd for C33H37FN8O4: 629.3; found: 629.4.

Example 551

2-(((3R,4S)-3-fluoro-1-(2-oxopyrrolidine-3-carbonyl)piperidin-4-yl)oxy)-5-(4-((4-(4-(oxetan-3-yl)piperazin-1-yl)phenyl)amino)-1,3,5-triazin-2-yl)benzonitrile

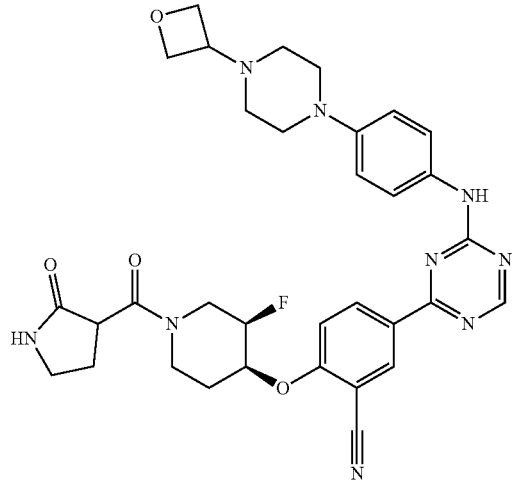 [SMILES: N#Cc1cc(-c2ncnc(Nc3ccc(N4CCN(C5COC5)CC4)cc3)n2)ccc1O[C@H]1CCN(C(=O)C2CCNC2=O)C[C@H]1F]

The title compound was synthesized in the same manner as Example 535 using 2-oxopyrrolidine-3-carboxylic acid. $^1$H NMR (400 MHz, DMSO-d6) δ 10.18 (d, J=21.8 Hz, 1H), 8.76 (s, 1H), 8.60-8.53 (m, 2H), 7.83-7.80 (m, 1H), 7.63-7.54 (m, 3H), 7.05 (m, 2H), 5.15 (m, 2H), 5.10 (m, 1H), 4.93 (m, 1H), 4.75 (m, 5H), 4.39 (m, 3H), 4.09-3.89 (m, 4H), 3.50 (m, 2H), 3.32-3.14 (m, 2H), 2.40 (m, 1H), 2.08 (m, 2H), 1.95 (m, 1H). LCMS-ESI$^+$ (m/z): [M+H]$^+$ calcd for C33H36FN9O4: 642.3; found: 642.7.

Example 552

2-(((3R,4S)-3-fluoro-1-((R)-5-oxopyrrolidine-3-carbonyl)piperidin-4-yl)oxy)-5-(4-((4-(4-(oxetan-3-yl)piperazin-1-yl)phenyl)amino)-1,3,5-triazin-2-yl)benzonitrile

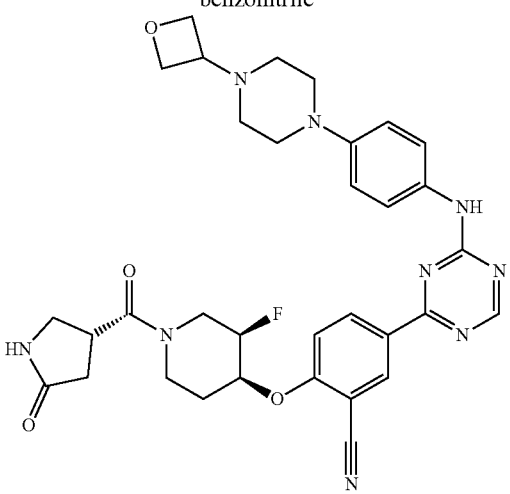

The title compound was synthesized in the same manner as Example 535 using (R)-5-oxopyrrolidine-3-carboxylic acid. $^1$H NMR (400 MHz, DMSO-d6) δ 10.18 (d, J=23.0 Hz, 1H), 8.75 (s, 1H), 8.61-8.49 (m, 2H), 7.68-7.54 (m, 4H), 7.04 (s, 2H), 5.10 (m, 2H), 4.98 (m, 1H), 4.76 (m, 4H), 4.44 (m, 2H), 4.20 (m, 2H), 3.84 (m, 3H), 3.72-3.58 (m, 3H), 3.57-3.27 (m, 4H), 2.36 (m, 2H), 1.99 (m, 2H), 1.79 (m, 1H). LCMS-ESI$^+$ (m/z): [M+H]$^+$ calcd for C33H36FN9O4: 642.3; found: 642.4.

Example 553

2-(((3R,4S)-3-fluoro-1-(3-hydroxy-3-methylbutanoyl)piperidin-4-yl)oxy)-5-(4-((4-(4-(oxetan-3-yl)piperazin-1-yl)phenyl)amino)-1,3,5-triazin-2-yl)benzonitrile

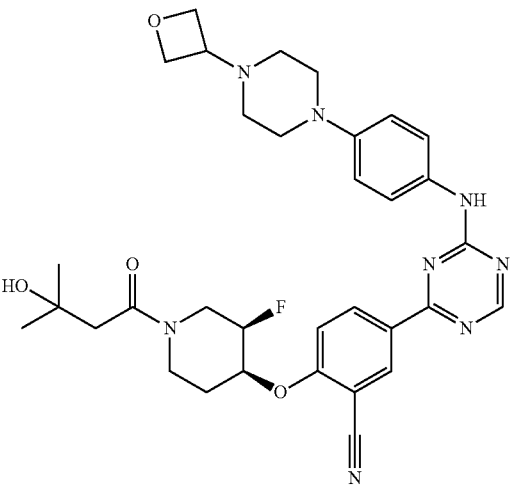 [SMILES: CC(C)(O)CC(=O)N1CC[C@H](Oc2ccc(-c3ncnc(Nc4ccc(N5CCN(C6COC6)CC5)cc4)n3)cc2C#N)[C@H](F)C1]

535

The title compound was synthesized in the same manner as Example 535 using 3-hydroxy-3-methylbutanoic acid. ¹H NMR (400 MHz, DMSO-d6) δ 10.18 (d, J=22.1 Hz, 1H), 8.75 (s, 1H), 8.58-8.52 (m, 2H), 7.62 (m, 3H), 7.05 (m, 2H), 5.16 (m, 3H), 4.99 (m, 1H), 4.76 (m, 4H), 4.41 (m, 2H), 4.15 (m, 2H), 3.97-3.73 (m, 4H), 3.51-3.27 (m, 3H), 2.63 (m, 1H), 2.02-1.92 (m, 2H), 1.81 (m, 1H), 1.16 (s, 6H), 1.11 (m, 1H). LCMS-ESI⁺ (m/z): [M+H]⁺ calcd for C33H39FN8O4: 631.3; found: 631.4.

Example 554

5-(4-((4-(1H-imidazol-1-yl)phenyl)amino)-1,3,5-triazin-2-yl)-2-(((3R,4S)-3-fluoro-1-((S)-2-hydroxy-propanoyl)piperidin-4-yl)oxy)benzonitrile

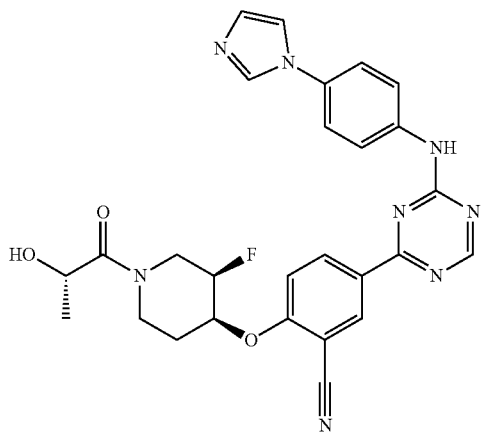 [SMILES: C[C@H](O)C(=O)N1CC[C@H](Oc2ccc(-c3ncnc(Nc4ccc(-n5ccnc5)cc4)n3)cc2C#N)[C@H](F)C1]

The title compound was synthesized in the same manner as Example 535 starting with 4-(1H-imidazol-1-yl)aniline. ¹H NMR (400 MHz, DMSO-d6) δ 10.65 (s, 1H), 9.49 (s, 1H), 8.89 (s, 1H), 8.61 (m, 1H), 8.20 (s, 1H), 8.00 (d, J=8.7 Hz, 2H), 7.83 (m, 3H), 7.64 (d, J=9.3 Hz, 1H), 5.17 (m, 2H), 4.98 (s, 1H), 4.51-4.42 (m, 1H), 4.36 (m, 1H), 4.16 (m, 1H), 4.05 (m, 1H), 3.94 (m, 1H), 2.03-1.92 (m, 2H), 1.83 (m, 1H), 1.19 (m, 3H). LCMS-ESI⁺ (m/z): [M+H]⁺ calcd for C27H25FN8O3: 529.2; found: 529.3.

Example 555

2-(((3R,4S)-1-((S)-2,3-dihydroxypropanoyl)-3-fluoropiperidin-4-yl)oxy)-5-(4-((4-morpholinophenyl)amino)-1,3,5-triazin-2-yl)benzonitrile

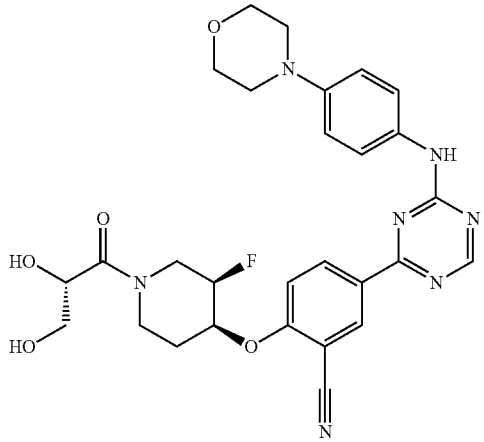 [SMILES: N#Cc1cc(-c2ncnc(Nc3ccc(N4CCOCC4)cc3)n2)ccc1O[C@H]1CCN(C(=O)[C@@H](O)CO)C[C@H]1F]

536

The title compound was synthesized in the same manner as Example 535 using (S)-2,3-dihydroxypropanoic acid. ¹H NMR (400 MHz, DMSO-d6) δ 10.14 (d, J=20.3 Hz, 1H), 8.74 (s, 1H), 8.56 (m, 2H), 7.63-7.58 (m, 3H), 6.97 (m, 2H), 5.09 (m, 2H), 4.97 (m, 1H), 4.38 (m, 2H), 4.12 (m, 1H), 3.93 (m, 1H), 3.75-3.72 (m, 4H), 3.59 (m, 1H), 3.56-3.48 (m, 1H), 3.48-3.40 (m, 2H), 3.08 (m, 2H), 1.97 (m, 3H). LCMS-ESI⁺ (m/z): [M+H]⁺ calcd for C28H30FN7O5: 564.2; found: 564.3.

Example 556

2-(((3R,4S)-1-((S)-2,3-dihydroxypropanoyl)-3-fluoropiperidin-4-yl)oxy)-5-(4-((2-fluoro-4-morpholinophenyl)amino)-1,3,5-triazin-2-yl)benzonitrile

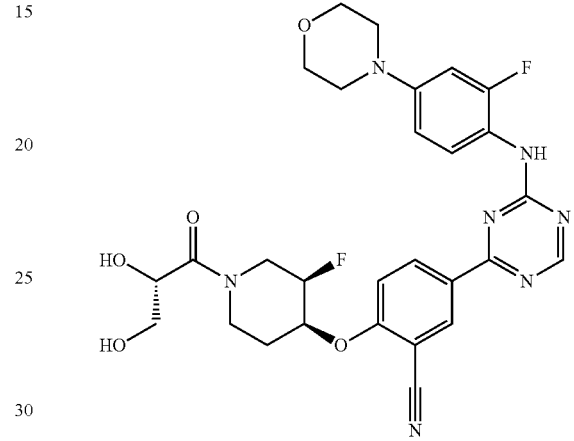

The title compound was synthesized in the same manner as Example 535 starting with 4-(3-fluoro-4-nitrophenyl)morpholine. ¹H NMR (400 MHz, DMSO-d6) δ 9.79 (d, J=27.4 Hz, 1H), 8.72 (m, 1H), 8.58 (s, 1H), 8.39 (s, 1H), 7.59 (m, 1H), 7.31 (m, 1H), 6.87 (m, 1H), 6.78 (m, 1H), 5.08 (m, 2H), 4.96 (s, 1H), 4.39 (m, 2H), 4.12 (m, 1H), 3.92 (m, 1H), 3.74-3.72 (m, 4H), 3.59 (m, 1H), 3.51 (m, 1H), 3.44 (m, 2H), 3.31 (m, 2H), 1.96 (m, 3H). LCMS-ESI⁺ (m/z): [M+H]⁺ calcd for C28H29F2N7O5: 582.2; found: 582.3.

Example 557

2-(((3R,4S)-3-fluoro-1-(2-hydroxy-3-methoxypropanoyl)piperidin-4-yl)oxy)-5-(4-((4-(4-(oxetan-3-yl)piperazin-1-yl)phenyl)amino)-1,3,5-triazin-2-yl)benzonitrile

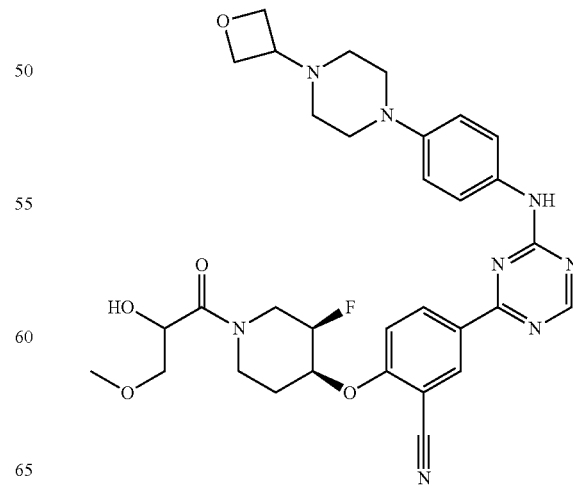

The title compound was synthesized in the same manner as Example 535 using 2-hydroxy-3-methoxypropanoic acid. 1H NMR (400 MHz, DMSO-d6) δ 10.18 (d, J=22.3 Hz, 1H), 8.75 (s, 1H), 8.62-8.49 (m, 2H), 7.61 (m, 3H), 7.04 (s, 2H), 5.13 (m, 2H), 4.95 (s, 1H), 4.76 (m, 4H), 4.51 (m, 2H), 4.45 (m, 2H), 4.14 (m, 2H), 3.96 (m, 2H), 3.56-3.36 (m, 6H), 1.98 (m, 2H), 1.85 (m, 1H). LCMS-ESI+ (m/z): [M+H]+ calcd for C32H37FN8O5: 633.3; found: 633.4.

Example 558

2-(((3R,4S)-1-(2-cyanoacetyl)-3-fluoropiperidin-4-yl)oxy)-5-(4-((3-methoxy-4-(4-(oxetan-3-yl)piperazin-1-yl)phenyl)amino)-1,3,5-triazin-2-yl)benzonitrile

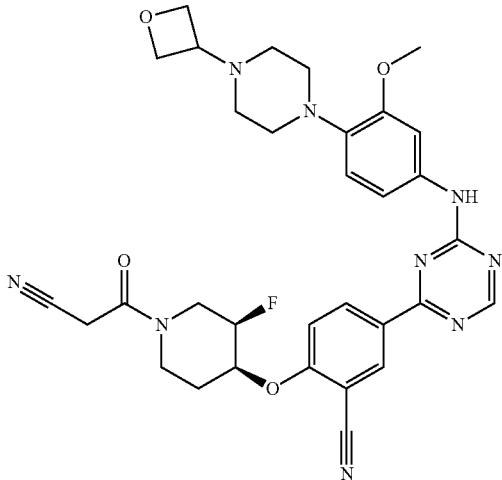 [SMILES: COc1cc(Nc2ncnc(-c3ccc(O[C@H]4CCN(C(=O)CC#N)C[C@H]4F)c(C#N)c3)n2)ccc1N1CCN(C2COC2)CC1]

Step 1: Preparation of (3R,4S)-tert-butyl 4-(2-cyano-4-(4-((3-methoxy-4-(4-(oxetan-3-yl)piperazin-1-yl)phenyl)amino)-1,3,5-triazin-2-yl)phenoxy)-3-fluoropiperidine-1-carboxylate:

A suspension of 4-chloro-N-(3-methoxy-4-(4-(oxetan-3-yl)piperazin-1-yl)phenyl)-1,3,5-triazin-2-amine (170 mg, 0.406 mmol) and (3R,4S)-tert-butyl 4-(2-cyano-4-(4,4,5,5-tetramethyl-1,3,2-dioxaborolan-2-yl)phenoxy)-3-fluoropiperidine-1-carboxylate (190 mg, 0.426 mmol) in 1,2-Dimethoxyethane (4 mL) was treated with 2M sodium carbonate solution (0.82 mL, 1.62 mmol) and Tetrakis(triphenylphosphine)palladium (47 mg, 0.04 mmol). The mixture was heated in a microwave reactor for 20 minutes at 135° C. The cooled reaction mixture was quenched with water and extracted with dichloromethane for three times. The combined extracts were washed once with saturated aqueous sodium chloride solution, dried over anhydrous sodium sulfate, filtered, and concentrated under reduced pressure. The crude residue was purified by flash chromatography (silica gel) to give the desired product as yellow solid. LCMS-ESI+ (m/z): [M+H]+ calcd for C34H42FN8O5: 661.7; found: 661.4.

Step 2: Preparation of 2-(((3R,4S)-3-fluoropiperidin-4-yl)oxy)-5-(4-((3-methoxy-4-(4-(oxetan-3-yl)piperazin-1-yl)phenyl)amino)-1,3,5-triazin-2-yl)benzonitrile:

(3R,4S)-tert-butyl 4-(2-cyano-4-(4-((3-methoxy-4-(4-(oxetan-3-yl)piperazin-1-yl)phenyl)amino)-1,3,5-triazin-2-yl)phenoxy)-3-fluoropiperidine-1-carboxylate (52.3 mg, 0.08 mmol) was taken up in dichloromethane (1 mL) and treated with trifluoroacetic acid (0.12 mL, 1.64 mmol). After 30 minutes, the mixture was quenched with saturated sodium bicarbonate (PH ~8) and extracted with dichloromethane for three times. The combined extracts were washed once with saturated aqueous sodium chloride solution, dried over anhydrous sodium sulfate, filtered, and concentrated under reduced pressure. The crude was used for next step. LCMS-ESI+ (m/z): [M+H]+ calcd for C29H34FN8O3: 561.6; found: 561.2.

Step 3: Preparation of 2-(((3R,4S)-1-(2-cyanoacetyl)-3-fluoropiperidin-4-yl)oxy)-5-(4-((3-methoxy-4-(4-(oxetan-3-yl)piperazin-1-yl)phenyl)amino)-1,3,5-triazin-2-yl)benzonitrile:

2-(((3R,4S)-3-fluoropiperidin-4-yl)oxy)-5-(4-((3-methoxy-4-(4-(oxetan-3-yl)piperazin-1-yl)phenyl)amino)-1,3,5-triazin-2-yl)benzonitrile (40 mg, 0.071 mmol) and 2-cyanoacetic acid (13.8 mg, 0.16 mmol) were taken up as suspension in dichloromethane (1 mL). The mixture was treated successively with N,N-diisopropylethylamine (0.03 mL, 0.17 mmol) and N-[(dimethylamino)-1H-1,2,3-triazolo-[4,5-b]pyridin-1-ylmethylene]-N-methylmethanaminiumhexafluorophosphate N-oxide (HATU, 47 mg, 0.12 mmol). The mixture was stirred for 2 hour at room temperature and then purified by reverse phase chromatography (C18) to provide the desired product as yellow solid. LCMS-ESI+ (m/z): [M+H]+ calcd for C32H35FN9O4: 628.7; found: 628.3. 1H NMR (300 MHz, DMSO-d6) δ 10.24 (s, 1H), 8.78 (s, 1H), 8.61 (m, 2H), 7.64 (d, J=9.0 Hz, 2H), 7.29 (br, 1H), 6.90 (d, J=8.1 Hz, 1H), 5.13 (m, 2H), 4.56 (m, 2H), 4.52 (m, 2H), 4.35 (m, 1H), 4.17-3.95 (br, 3H), 3.84 (m, 3H), 3.61 (m, 1H), 3.47 (m, 1H), 2.96 (m, 4H), 2.39 (m, 4H), 2.01 (m, 2H), 1.21 (s, 1H).

Example 559

2-(((3R,4S)-1-(2-amino-1H-imidazole-5-carbonyl)-3-fluoropiperidin-4-yl)oxy)-5-(4-((4-(4-(oxetan-3-yl)piperazin-1-yl)phenyl)amino)-1,3,5-triazin-2-yl)benzonitrile

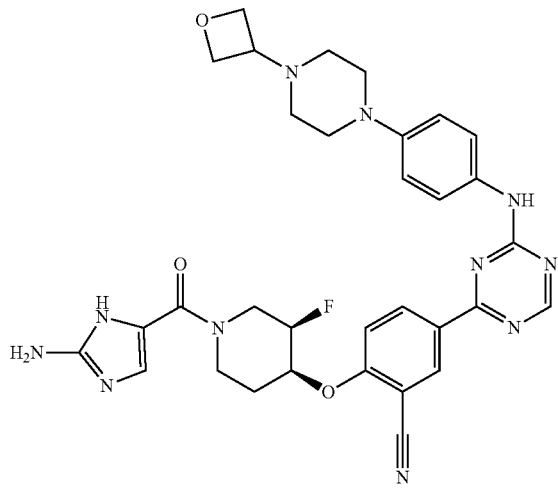 [SMILES: N#Cc1cc(-c2ncnc(Nc3ccc(N4CCN(C5COC5)CC4)cc3)n2)ccc1O[C@H]1CCN(C(=O)c2cnc(N)[nH]2)C[C@H]1F]

2-(((3R,4S)-3-fluoropiperidin-4-yl)oxy)-5-(4-((4-(4-(oxetan-3-yl)piperazin-1-yl)phenyl)amino)-1,3,5-triazin-2-yl)benzonitrile (50 mg, 0.094 mmol) and 2-amino-1H-imidazole-5-carboxylic acid (23.95 mg, 0.19 mmol) were taken up as suspension in N,N-dimethylformamide (3mL). The mixture was treated successively with N,N-diisopropylethylamine (0.05 mL, 0.28 mmol) and N-[(dimethylamino)-1H-1,2,3-triazolo-[4,5-b]pyridin-1-ylmethylene]-N-methylmethanaminiumhexafluorophosphate N-oxide (HATU, 72 mg, 0.19 mmol). The mixture was stirred for 2 hr at room temperature. Another portion of 2-amino-1H-imidazole-5-carboxylic acid (10.7 mg, 0.08 mmol), N,N-diisopropylethylamine (0.05 mL, 0.28 mmol) and N-[(dimethylamino)-1H-1,2,3-triazolo-[4,5-b]pyridin-1-ylmethylene]-N-methylmethanaminiumhexafluorophosphate N-oxide (HATU, 68 mg, 0.18 mmol) were added and the reaction mixture was stirred at room temperature for overnight. After that time, the reaction mixture was quenched with water and extracted with dichloromethane for three times. The combined extracts were washed once with saturated aqueous sodium chloride solution, dried over anhydrous sodium sulfate, filtered, and concentrated under reduced pressure. The crude residue was purified by flash chromatography (silica gel), and by reverse column (C18) to give the desired product as bright yellow solid. LCMS-ESI+ (m/z): [M+H]+ calcd for $C_{32}H_{35}FN_{11}O_3$: 640.7; found: 640.3. 1H NMR (300 MHz, DMSO-d6) δ 10.28 (S, 1H), 10.15 (m, 1H), 8.73 (s, 1H), 8.58 (d, J=8.7 Hz, 2H), 7.64 (m, 3H), 7.06 (m, 3H), 5.40 (s, 1H), 5.10 (m, 2H), 4.57 (m, 2H), 4.48 (m, 7H), 3.45 (m, 1H), 3.13 (m, 4H), 2.40 (m, 4H), 1.96 (br, 2H), 1.43 (m, 1H), 1.21 (s, 2H), 0.82 (m, 1H).

Example 560

(S)-2-((3,3-difluoro-1-(2-hydroxyacetyl)piperidin-4-yl)oxy)-5-(4-((3-methoxy-4-(4-(oxetan-3-yl)piperazin-1-yl)phenyl)amino)-1,3,5-triazin-2-yl)benzonitrile

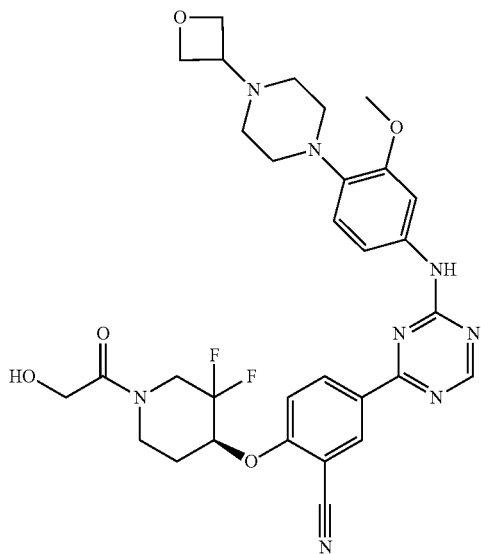 [SMILES: COc1cc(Nc2ncnc(-c3ccc(O[C@H]4CCN(C(=O)CO)CC4(F)F)c(C#N)c3)n2)ccc1N1CCN(C2COC2)CC1]

Step 1: Preparation of (S)-tert-butyl 4-(2-cyano-4-(4-((3-methoxy-4-(4-(oxetan-3-yl)piperazin-1-yl)phenyl)amino)-1,3,5-triazin-2-yl)phenoxy)-3,3-difluoropiperidine-1-carboxylate:

A suspension of 4-chloro-N-(3-methoxy-4-(4-(oxetan-3-yl)piperazin-1-yl)phenyl)-1,3,5-triazin-2-amine (336 mg, 0.802 mmol) and (S)-tert-butyl 4-(2-cyano-4-(4,4,5,5-tetramethyl-1,3,2-dioxaborolan-2-yl)phenoxy)-3,3-difluoropiperidine-1-carboxylate (373 mg, 0.802 mmol) in 1,2-Dimethoxyethane (8 mL) was treated with 2M sodium carbonate solution (1.61 mL, 3.2 mmol) and Tetrakis(triphenylphosphine)palladium (93 mg, 0.08 mmol). The mixture was heated in a microwave reactor for 15 minutes at 145° C. The cooled reaction mixture was quenched with water and extracted with dichloromethane for three times. The combined extracts were washed once with saturated aqueous sodium chloride solution, dried over anhydrous sodium sulfate, filtered, and concentrated under reduced pressure. The crude residue was purified by flash chromatography (silica gel) to give the desired product as yellow solid. LCMS-ESI+ (m/z): [M+H]+ calcd for $C_{34}H_{41}F_2N_8O_5$: 679.7; found: 679.8.

Step 2: Preparation of (S)-2-((3,3-difluoropiperidin-4-yl)oxy)-5-(4-((3-methoxy-4-(4-(oxetan-3-yl)piperazin-1-yl)phenyl)amino)-1,3,5-triazin-2-yl)benzonitrile:

(S)-tert-butyl 4-(2-cyano-4-(4-((3-methoxy-4-(4-(oxetan-3-yl)piperazin-1-yl)phenyl)amino)-1,3,5-triazin-2-yl)phenoxy)-3,3-difluoropiperidine-1-carboxylate (110 mg, 0.162 mmol) was taken up in dichloromethane (2 mL) and treated with trifluoroacetic acid (0.248 mL, 3.24 mmol). After 40 minutes, the mixture was quenched with saturated sodium bicarbonate (PH ~8) and extracted with dichloromethane for three times. The combined extracts were washed once with saturated aqueous sodium chloride solution, dried over anhydrous sodium sulfate, filtered, and concentrated under reduced pressure. The resulting yellow oil was used for next step. LCMS-ESI+ (m/z): [M+H]+ calcd for $C_{29}H_{33}F_2N_8O_3$ 579.6; found: 579.3.

Step 3: Preparation of (S)-2-((3,3-difluoro-1-(2-hydroxyacetyl)piperidin-4-yl)oxy)-5-(4-((3-methoxy-4-(4-(oxetan-3-yl)piperazin-1-yl)phenyl)amino)-1,3,5-triazin-2-yl)benzonitrile:

(S)-2-((3,3-difluoropiperidin-4-yl)oxy)-5-(4-((3-methoxy-4-(4-(oxetan-3-yl)piperazin-1-yl)phenyl)amino)-1,3,5-triazin-2-yl)benzonitrile (47 mg, 0.08 mmol) and Glycolic acid (12.3 mg, 0.16 mmol) were taken up as suspension in dichloromethane (1 mL). The mixture was treated successively with N,N-diisopropylethylamine (0.04 mL, 0.24 mmol) and N-[(dimethylamino)-1H-1,2,3-triazolo-[4,5-b]pyridin-1-ylmethylene]-N-methylmethanaminiumhexafluorophosphate N-oxide (HATU, 46 mg, 0.12 mmol). The mixture was stirred for 2 hour at room temperature and then purified by reverse phase chromatography (C18) to provide the desired product as yellow solid. LCMS-ESI+ (m/z): [M+H]+ calcd for $C_{31}H_{35}F_2N_8O_5$: 637.7; found: 637.2. 1H NMR (300 MHz, DMSO-d6) δ 10.26 (br, 1H), 8.78 (s, 1H), 8.62 (m, 2H), 7.68-7.10 (br, 3H), 6.90 (m, 1H), 5.48-4.80 (br, 1H), 4.54 (m, 2H), 4.45 (m, 2H), 4.20-3.90 (br, 3H), 3.84-3.55 (br, 5H), 3.45 (m, 1H), 2.96 (m, 4H), 2.39 (m, 4H), 2.01 (m, 2H).

Example 561

2-(((S)-3,3-difluoro-1-((S)-2-hydroxypropanoyl)piperidin-4-yl)oxy)-5-(4-((3-methoxy-4-(4-(oxetan-3-yl)piperazin-1-yl)phenyl)amino)-1,3,5-triazin-2-yl)benzonitrile

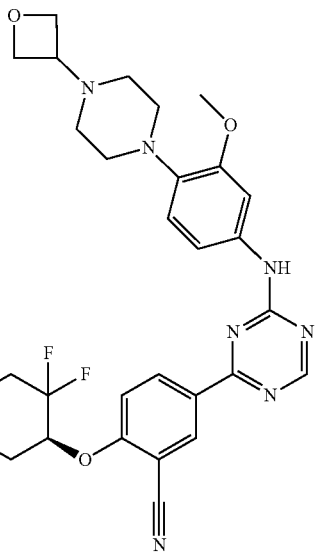

(S)-2-((3,3-difluoropiperidin-4-yl)oxy)-5-(4-((3-methoxy-4-(4-(oxetan-3-yl)piperazin-1-yl)phenyl)amino)-1,3,5-triazin-2-yl)benzonitrile (47 mg, 0.08 mmol) and L-lactic acid (14.6 mg, 0.16 mmol) were taken up as suspension in dichloromethane (1 mL). The mixture was treated successively with N,N-diisopropylethylamine (0.04 mL, 0.24 mmol) and N-[(dimethylamino)-1H-1,2,3-triazolo-[4,5-b]pyridin-1-ylmethylene]-N-methylmethanaminiumhexafluorophosphate N-oxide (HATU, 46 mg, 0.12 mmol). The mixture was stirred for 2 hour at room temperature and then purified by reverse phase chromatography (C18) to provide the desired product as yellow solid. LCMS-ESI+ (m/z): [M+H]+ calcd for $C_{32}H_{37}F_2N_8O_5$: 651.7; found: 651.3. 1H NMR (300 MHz, DMSO-d6) δ 10.26 (br, 1H), 8.78 (s, 1H), 8.62 (m, 2H), 7.68-7.10 (br, 3H), 6.90 (m, 1H), 5.38 (br, 1H), 5.23 (d, J=7.2 Hz, 1H), 4.54 (m, 2H), 4.54 (m, 3H), 4.20-3.45 (br, 7H), 3.47 (m, 1H), 2.96 (m, 4H), 2.39 (m, 4H), 2.14 (m, 2H), 1.21 (m, 3H).

Example 562

2-(((3R,4S)-3-fluoro-1-(3-hydroxypropanoyl)piperidin-4-yl)oxy)-5-(4-((3-methoxy-4-(4-(oxetan-3-yl)piperazin-1-yl)phenyl)amino)-1,3,5-triazin-2-yl)benzonitrile

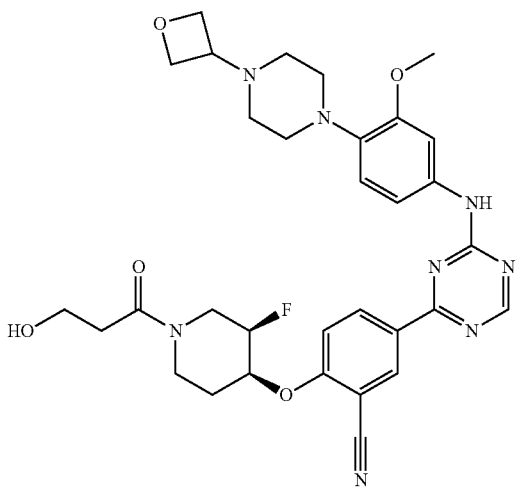 [SMILES: COc1cc(Nc2ncnc(-c3ccc(O[C@H]4CCN(C(=O)CCO)C[C@H]4F)c(C#N)c3)n2)ccc1N1CCN(C2COC2)CC1]

2-(((3R,4S)-3-fluoropiperidin-4-yl)oxy)-5-(4-((3-methoxy-4-(4-(oxetan-3-yl)piperazin-1-yl)phenyl)amino)-1,3,5-triazin-2-yl)benzonitrile (40 mg, 0.071 mmol) and 3-hydroxypropanoic acid (30% in water, 42.85 mg, 0.14 mmol) in were taken up as suspension in N,N-dimethylformamide (1 mL). The mixture was treated successively with N,N-diisopropylethylamine (0.04 mL, 0.21 mmol) and N-[(dimethylamino)-1H-1,2,3-triazolo-[4,5-b]pyridin-1-ylmethylene]-N-methylmethanaminiumhexafluorophosphate N-oxide (HATU, 41 mg, 0.11 mmol). The mixture was stirred for 2 hour at room temperature and then purified by reverse phase chromatography (C18) to provide the desired product as yellow solid. LCMS-ESI+ (m/z): [M+H]+ calcd $C_{32}H_{38}FN_8O_5$: 633.7; found: 633.3. 1H NMR (300 MHz, DMSO-d6) δ 10.26 (br, 1H), 8.78 (s, 1H), 8.62 (m, 2H), 7.65 (d, J=9.3 Hz, 2H), 7.49-7.17 (br, 1H), 6.91 (d, J=9.3 Hz, 1H), 5.14 (m, 2H), 4.57 (m, 3H), 4.44 (m, 2H), 4.20-4.10 (br, 1H), 3.85 (m, 3H), 3.67 (m, 2H), 3.48 (m, 1H), 3.10 (m, 1H), 2.97 (m, 4H), 2.57 (m, 1H), 2.40 (m, 4H), 1.97 (m, 2 H), 1.23 (m, 2H), 0.86 (m, 1H).

Example 563

2-(((3R,4S)-3-fluoro-1-(2-hydroxyacetyl)piperidin-4-yl)oxy)-5-(4-((4-methylthiazol-5-yl)amino)-1,3,5-triazin-2-yl)benzonitrile

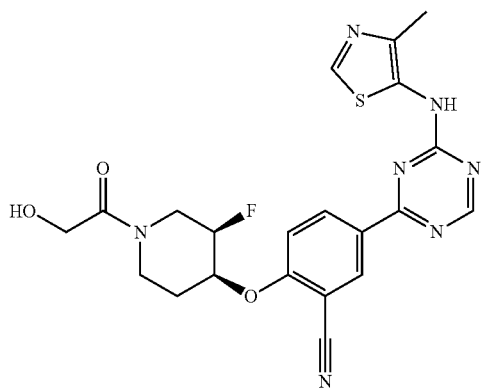 [SMILES: Cc1ncsc1Nc1ncnc(-c2ccc(O[C@H]3CCN(C(=O)CO)C[C@H]3F)c(C#N)c2)n1]

Step 1: Preparation of N-(4-chloro-1,3,5-triazin-2-yl)-4-methylthiazol-5-amine:

To a solution of 2,4-dichloro-1,3,5-triazine (165 mg, 1.1 mmol) in dichloromethane (6 mL) at 0° C., 4-methylthiazol-5-amine HCl salt (187.09 mg, 1 mmol) in dichloromethane (2 mL+2 mL wash) was added, followed by N,N-Diisopropylethylamine (0.61 mL, 3.5 mmol). The reaction mixture was stirred at 0° C. for 15 minutes. After this time, the reaction was quenched with saturated sodium bicarbonate solution (PH~8) and extracted with dichloromethane for three times. The combined extracts were washed once with saturated aqueous sodium chloride solution, dried over anhydrous sodium sulfate, filtered, and concentrated under reduced pressure. The crude residue was purified by flash chromatography (silica gel) to give the desired product as yellow solid. LCMS-ESI+ (m/z): [M+H]+ calcd for $C_7H_7ClN_5S$: 228.7; found: 228.0. 1H NMR (300 MHz, DMSO-d6) δ 10.94 (s, 1H), 8.80 (d, J=6 Hz, 1H), 8.66 (s, 1H), 2.31 (s, 3H).

Step 2: Preparation of 2-(((3R,4S)-3-fluoro-1-(2-hydroxyacetyl)piperidin-4-yl)oxy)-5-(4-((4-methylthiazol-5-yl)amino)-1,3,5-triazin-2-yl)benzonitrile:

A suspension of N-(4-chloro-1,3,5-triazin-2-yl)-4-methylthiazol-5-amine (90 mg, 0.395 mmol) and 2-(((3R,4S)-3-fluoro-1-(2-hydroxyacetyl)piperidin-4-yl)oxy)-5-(4,4,5,5-tetramethyl-1,3,2-dioxaborolan-2-yl)benzonitrile (176 mg, 0.435 mmol) in 1,2-Dimethoxyethane (2 mL) was treated with 2M sodium carbonate solution (2 mL, 4.0 mmol) and Tetrakis(triphenylphosphine)palladium (38 mg, 0.033 mmol). The mixture was heated at 125° C. for 1 h. The cooled reaction mixture was quenched with water and extracted with dichloromethane for three times. The combined extracts were washed once with saturated aqueous sodium chloride solution, dried over anhydrous sodium sulfate, filtered, and concentrated under reduced pressure. The crude residue was purified by flash chromatography (silica gel) to give the desired product as yellow solid. LCMS-ESI+ (m/z): [M+H]+ calcd for $C_{21}H_{21}FN_7O_3S$: 470.5; found: 470.1. 1H NMR (300 MHz, DMSO-d6) δ 10.78 (br, 1H), 8.86 (m, 2H), 8.64 (m, 2H), 8.10 (m, 1H), 5.14 (m, 2H), 4.69 (m, 1H), 4.41-3.85 (br, 3H), 3.78-3.20 (m, 1H), 3.08 (m, 1H), 2.40 (m, 3H), 1.98 (m, 2H), 1.22 (m, 1H).

Example 564

2-(((3R,4S)-3-fluoro-1-((S)-2-hydroxypropanoyl)piperidin-4-yl)oxy)-5-(4-((3-(hydroxymethyl)-1-methyl-1H-pyrazol-4-yl)amino)-1,3,5-triazin-2-yl)benzonitrile

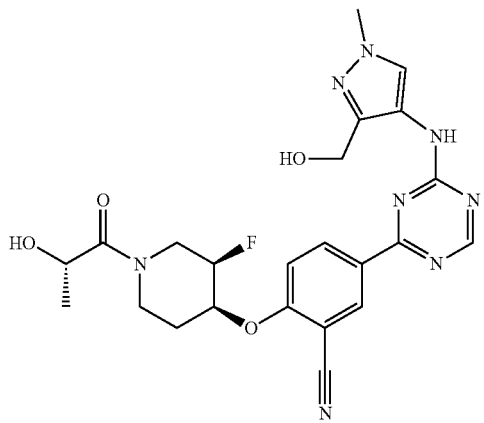 [SMILES: C[C@H](O)C(=O)N1CC[C@H](Oc2ccc(-c3ncnc(Nc4cn(C)nc4CO)n3)cc2C#N)[C@H](F)C1]

Step 1: Preparation of methyl 4-((4-chloro-1,3,5-triazin-2-yl)amino)-1-methyl-1H-pyrazole-3-carboxylate:

To a solution of 2,4-dichloro-1,3,5-triazine (667 mg, 4.45 mmol) in dichloromethane (30 mL) at 0° C., methyl 4-amino-1-methyl-1H-pyrazole-3-carboxylate (0.62 g, 4 mmol) in dichloromethane (5 mL+5 mL wash) was added, followed by N,N-Diisopropylethylamine (1.05 mL, 6 mmol). The reaction mixture was stirred at 0° C. for 2 h. After this time, the reaction was quenched with saturated sodium bicarbonate solution (PH~8) and extracted with dichloromethane for three times. The combined extracts were washed once with saturated aqueous sodium chloride solution, dried over anhydrous sodium sulfate, filtered, and concentrated under reduced pressure. The crude residue was purified by flash chromatography (silica gel) to give the desired product as white solid. LCMS-ESI+ (m/z): [M+H]+ calcd for $C_9H_{10}ClN_6O_2$: 269.7; found: 269.0.

Step 2: Preparation of (3R,4S)-tert-butyl 4-(2-cyano-4-(4-((3-(methoxycarbonyl)-1-methyl-1H-pyrazol-4-yl)amino)-1,3,5-triazin-2-yl)phenoxy)-3-fluoropiperidine-1-carboxylate:

A suspension of methyl 4-((4-chloro-1,3,5-triazin-2-yl)amino)-1-methyl-1H-pyrazole-3-carboxylate (166 mg, 0.62 mmol) and (3R,4S)-tert-butyl 4-(2-cyano-4-(4,4,5,5-tetramethyl-1,3,2-dioxaborolan-2-yl)phenoxy)-3-fluoropiperidine-1-carboxylate (279 mg, 0.63 mmol) in 1,2-Dimethoxyethane (6 mL) was treated with 2M sodium carbonate solution (2.4 mL, 4.8 mmol) and Tetrakis(triphenylphosphine)palladium (75 mg, 0.065 mmol). The mixture was heated in at 115° C. for 30 minutes. The cooled reaction mixture was quenched with water and extracted with dichloromethane for three times. The combined extracts were washed once with saturated aqueous sodium chloride solution, dried over anhydrous sodium sulfate, filtered, and concentrated under reduced pressure. The crude residue was purified by flash chromatography (silica gel) to give the desired product as yellow solid. LCMS-ESI+ (m/z): [M+H]+ calcd for $C_{26}H_{30}FN_8O_5$: 553.6; found: 553.2.

Step 3: Preparation of methyl 4-((4-(3-cyano-4-(((3R,4S)-3-fluoropiperidin-4-yl)oxy)phenyl)-1,3,5-triazin-2-yl)amino)-1-methyl-1H-pyrazole-3-carboxylate:

(3R,4S)-tert-butyl 4-(2-cyano-4-(4-((3-(methoxycarbonyl)-1-methyl-1H-pyrazol-4-yl)amino)-1,3,5-triazin-2-yl)phenoxy)-3-fluoropiperidine-1-carboxylate (330 mg, 0.597 mmol) was taken up in dichloromethane (12 mL) and treated with trifluoroacetic acid (1.2 mL, 15.68 mmol). After 30 minutes, the mixture was quenched with saturated sodium bicarbonate (PH ~8) and extracted with dichloromethane for three times. The combined extracts were washed once with saturated aqueous sodium chloride solution, dried over anhydrous sodium sulfate, filtered, and concentrated under reduced pressure. The crude was used for next step. LCMS-ESI+ (m/z): [M+H]+ calcd for $C_{21}H_{22}FN_8O_3$: 453.4; found: 453.2.

Step 4: Preparation of 2-(((3R,4S)-3-fluoropiperidin-4-yl)oxy)-5-(4-((3-(hydroxymethyl)-1-methyl-1H-pyrazol-4-yl)amino)-1,3,5-triazin-2-yl)benzonitrile:

methyl 4-((4-(3-cyano-4-(((3R,4S)-3-fluoropiperidin-4-yl)oxy)phenyl)-1,3,5-triazin-2-yl)amino)-1-methyl-1H-pyrazole-3-carboxylate (250 mg, 0.47 mmol) was dissolved in THF (7 mL) and the reaction mixture was cooled to 0° C. Lithium Aluminum Hydride (1M solution in THF, 1.57 m, 1.57 mmol) was added drop wise. The reaction mixture was stirred at 0° C. for 1 h and was monitored with LC_MS for completion. Then the mixture was quenched with 0.2 mL H₂O, 0.2 mL 1N NaOH and 0.2 mL water sequentially and stirred at room temperature for 1 h. Small amount of sodium sulfate and Celite were added and filtered. The filtrate was evaporated and purified by flash chromatography (silica gel) to give the desired product as white solid. LCMS-ESI+ (m/z): [M+H]+ calcd for $C_{20}H_{22}FN_8O_2$: 425.4; found: 425.2.

Step 5: Preparation of 2-(((3R,4S)-3-fluoro-1-((S)-2-hydroxypropanoyl)piperidin-4-yl)oxy)-5-(4-((3-(hydroxymethyl)-1-methyl-1H-pyrazol-4-yl)amino)-1,3,5-triazin-2-yl)benzonitrile:

2-(((3R,4S)-3-fluoropiperidin-4-yl)oxy)-5-(4-((3-(hydroxymethyl)-1-methyl-1H-pyrazol-4-yl)amino)-1,3,5-triazin-2-yl)benzonitrile (52 mg, 0.12 mmol) and L-lactic acid (22.1 mg, 0.24 mmol) were taken up as suspension in N,N-dimethylformamide (1.5 mL). The mixture was treated successively with N,N-diisopropylethylamine (0.07 mL, 0.40 mmol) and N-[(dimethylamino)-1H-1,2,3-triazolo-[4,5-b]pyridin-1-ylmethylene]-N-methylmethanaminium-hexafluorophosphate N-oxide (HATU, 73 mg, 0.19 mmol). The mixture was stirred for 1 hour at room temperature and then purified by reverse phase chromatography (C18) to provide the desired product as pale yellow solid. LCMS-ESI+ (m/z): [M+H]+ calcd for $C_{23}H_{26}FN_8O_4$: 497.5; found: 497.2. 1H NMR (300 MHz, DMSO-d6) δ 9.59 (d, J=20.7 Hz, 1H), 8.77 (d, J=12.3 Hz, 1H), 8.62 (m, 2H), 8.06 (d, J=29.1 Hz, 1H), 7.64 (m, 1H), 5.12 (m, 4H), 4.49 (m, 4H), 4.29-3.90 (br, 1H), 3.85 (d, J=16.5 Hz, 3H), 3.75-3.32 (br, 1H), 3.25 (m, 1H), 1.99 (br, 2H), 1.22 (m, 3H).

Example 565

2-(((3R,4S)-3-fluoro-1-((S)-2-hydroxypropanoyl)piperidin-4-yl)oxy)-5-(4-((5-(hydroxymethyl)-1-methyl-1H-pyrazol-4-yl)amino)-1,3,5-triazin-2-yl)benzonitrile

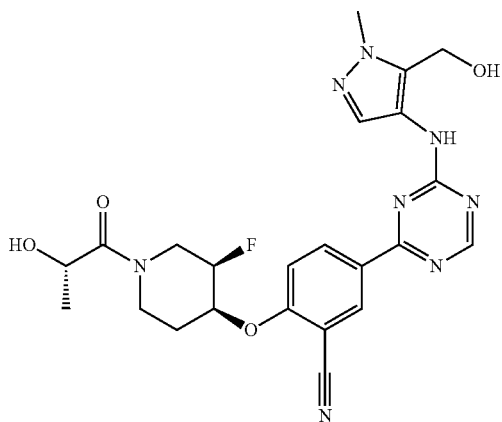 [SMILES: C[C@H](O)C(=O)N1CC[C@H](Oc2ccc(-c3ncnc(Nc4cnn(C)c4CO)n3)cc2C#N)[C@H](F)C1]

Step 1: Preparation of methyl 4((4-chloro-1,3,5-triazin-2-yl)amino)-1-methyl-1H-pyrazole-5-carboxylate:

To a solution of 2,4-dichloro-1,3,5-triazine (665 mg, 4.43 mmol) in dichloromethane (30 mL) at 0° C., methyl 4-amino-1-methyl-1H-pyrazole-5-carboxylate (0.62 g, 4 mmol) in dichloromethane (5 mL+5 mL wash) was added, followed by N,N-Diisopropylethylamine (1.05 mL, 6 mmol). The reaction mixture was stirred at 0° C. for 30 minutes. After this time, the reaction was quenched with saturated sodium bicarbonate solution (PH~8) and extracted with dichloromethane for three times. The combined extracts were washed once with saturated aqueous sodium chloride solution, dried over anhydrous sodium sulfate, filtered, and concentrated under reduced pressure. The crude residue was purified by flash chromatography (silica gel) to give the desired product as white solid. LCMS-ESI+ (m/z): [M+H]+ calcd for $C_9H_{10}ClN_6O_2$: 269.7; found: 269.1.

Step 2: Preparation of (3R,4S)-tert-butyl 4-(2-cyano-4-(4-((5-(methoxycarbonyl)-1-methyl-1H-pyrazol-4-yl)amino)-1,3,5-triazin-2-yl)phenoxy)-3-fluoropiperidine-1-carboxylate:

A suspension of methyl 4-((4-chloro-1,3,5-triazin-2-yl)amino)-1-methyl-1H-pyrazole-5-carboxylate (135 mg, 0.50 mmol) and (3R,4S)-tert-butyl 4-(2-cyano-4-(4,4,5,5-tetramethyl-1,3,2-dioxaborolan-2-yl)phenoxy)-3-fluoropiperidine-1-carboxylate (225 mg, 0.54 mmol) in 1,2-Dimethoxyethane (5 mL) was treated with 2M sodium carbonate solution (2 mL, 4 mmol) and Tetrakis(triphenylphosphine)palladium (60 mg, 0.052 mmol). The mixture was heated in at 115° C. for 40 minutes. The cooled reaction mixture was quenched with water and extracted with dichloromethane for three times. The combined extracts were washed once with saturated aqueous sodium chloride solution, dried over anhydrous sodium sulfate, filtered, and concentrated under reduced pressure. The crude residue was purified by flash chromatography (silica gel) to give the desired product as yellow solid. LCMS-ESI+ (m/z): [M+H]+ calcd for $C_{26}H_{30}FN_8O_5$: 553.6; found: 553.3.

Step 3: Preparation of methyl 4-((4-(3-cyano-4-(((3R,4S)-3-fluoropiperidin-4-yl)oxy)phenyl)-1,3,5-triazin-2-yl)amino)-1-methyl-1H-pyrazole-5-carboxylate:

(3R,4S)-tert-butyl 4-(2-cyano-4-(4-((5-(methoxycarbonyl)-1-methyl-1H-pyrazol-4-yl)amino)-1,3,5-triazin-2-yl)phenoxy)-3-fluoropiperidine-1-carboxylate (100 mg, 0.181 mmol) was taken up in dichloromethane (3 mL) and treated with trifluoroacetic acid (0.35 mL, 4.58 mmol). After 60 minutes, the mixture was quenched with saturated sodium bicarbonate (PH ~8) and extracted with dichloromethane for three times. The combined extracts were washed once with saturated aqueous sodium chloride solution, dried over anhydrous sodium sulfate, filtered, and concentrated under reduced pressure. The crude was used for next step. LCMS-ESI+ (m/z): [M+H]+ calcd for $C_{21}H_{22}FN_8O_3$ 453.4; found: 453.3.

Step 4: Preparation of 2-(((3R,4S)-3-fluoropiperidin-4-yl)oxy)-5-(4-((5-(hydroxymethyl)-1-methyl-1H-pyrazol-4-yl)amino)-1,3,5-triazin-2-yl)benzonitrile:

methyl 4-((4-(3-cyano-4-(((3R,4S)-3-fluoropiperidin-4-yl)oxy)phenyl)-1,3,5-triazin-2-yl)amino)-1-methyl-1H-pyrazole-5-carboxylate (81.9 mg, 0.181 mmol) was dissolved in THF (2 mL) and the reaction mixture was cooled to 0° C. Lithium Aluminum Hydride (1M solution in THF, 0.54 m, 0.54 mmol) was added drop wise. The reaction mixture was stirred at 0° C. for 20 minutes. Then the mixture was quenched with 0.2 mL water, 0.2 mL 1N NaOH and 0.2 mL water sequentially and stirred at room temperature for 1 h. Small amount of sodium sulfate and Celite were added and filtered. The filtrate was evaporated and purified by flash chromatography (silica gel) to give the desired product as white solid. LCMS-ESI+ (m/z): [M+H]+ calcd for $C_{20}H_{22}FN_8O_2$: 425.4; found: 425.2.

Step 5: Preparation of 2-(((3R,4S)-3-fluoro-1-((S)-2-hydroxypropanoyl)piperidin-4-yl)oxy)-5-(4-((5-(hydroxymethyl)-1-methyl-1H-pyrazol-4-yl)amino)-1,3,5-triazin-2-yl)benzonitrile:

2-(((3R,4S)-3-fluoropiperidin-4-yl)oxy)-5-(4-((5-(hydroxymethyl)-1-methyl-1H-pyrazol-4-yl)amino)-1,3,5-triazin-2-yl)benzonitrile (25.2 mg, 0.06 mmol) and L-lactic acid (15 mg, 0.167 mmol) were taken up as suspension in N,N-dimethylformamide (0.5 mL). The mixture was treated successively with N,N-diisopropylethylamine (0.03 mL, 0.18 mmol) and N-[(dimethylamino)-1H-1,2,3-triazolo-[4,5-b]pyridin-1-ylmethylene]-N-methylmethanaminium-hexafluorophosphate N-oxide (HATU, 34 mg, 0.09 mmol). The mixture was stirred for 1 hour at room temperature and then purified by reverse phase chromatography (C18) to provide the desired product as pale yellow solid. LCMS-ESI+ (m/z): [M+H]+ calcd for $C_{23}H_{26}FN_8O_4$: 497.5; found: 497.3. 1H NMR (300 MHz, DMSO-d6) δ 9.76 (d, J=34.2 Hz, 1H), 8.72 (m, 1H), 8.60 (m, 2H), 7.75 (m, 2H), 5.12 (m, 4H), 4.56 (m, 4H), 4.17-3.93 (br, 1H), 3.84 (m, 3H), 3.70-3.45 (br, 1H), 3.26 (m, 1H), 1.99 (br, 2H), 1.21 (m, 3H).

Example 566

5-(4-((1,5-dimethyl-1H-pyrazol-4-yl)amino)-1,3,5-triazin-2-yl)-2-(((3R,4S)-3-fluoro-1-((S)-2-hydroxypropanoyl)piperidin-4-yl)oxy)benzonitrile

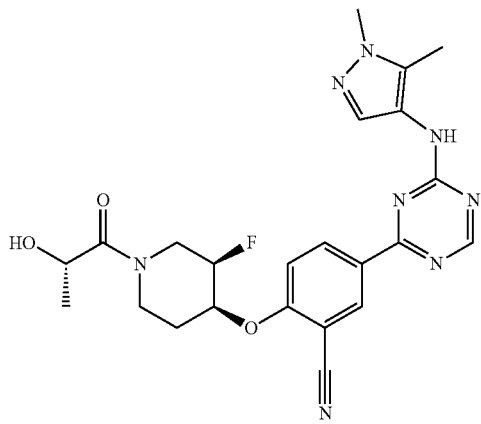 [SMILES: Cc1c(Nc2ncnc(-c3ccc(O[C@H]4CCN(C(=O)[C@H](C)O)C[C@H]4F)c(C#N)c3)n2)cnn1C]

Step 1: Preparation of 4-chloro-N-(1,5-dimethyl-1H-pyrazol-4-yl)-1,3,5-triazin-2-amine:

To a solution of 2,4-dichloro-1,3,5-triazine (363 mg, 2.42 mmol) in dichloromethane (10 mL) at 0° C., 1,5-dimethyl-1H-pyrazol-4-amine, diHCl salt (412.5 mg, 2.24 mmol) was added, followed by N,N-Diisopropylethylamine (1.34 mL, 7.7 mmol). The reaction mixture was stirred at 0° C. for 60 minutes. After this time, the reaction was quenched with saturated sodium bicarbonate solution (PH~8) and extracted with dichloromethane for three times. The combined extracts were washed once with saturated aqueous sodium chloride solution, dried over anhydrous sodium sulfate, filtered, and concentrated under reduced pressure. The crude residue was purified by flash chromatography (silica gel) to give the desired product as white solid. LCMS-ESI+ (m/z): [M+H]+ calcd for $C_{18}H_{10}ClN_6$: 225.7; found: 225.1.

Step 2: Preparation of (3R,4S)-tert-butyl 4-(2-cyano-4-(4-((1,5-dimethyl-1H-pyrazol-4-yl)amino)-1,3,5-triazin-2-yl)phenoxy)-3-fluoropiperidine-1-carboxylate:

A suspension of methyl 4-chloro-N-(1,5-dimethyl-1H-pyrazol-4-yl)-1,3,5-triazin-2-amine (112 mg, 0.50 mmol) and (3R,4S)-tert-butyl 4-(2-cyano-4-(4,4,5,5-tetramethyl-1,3,2-dioxaborolan-2-yl)phenoxy)-3-fluoropiperidine-1-carboxylate (234 mg, 0.525 mmol) in 1,2-Dimethoxyethane (5 mL) was treated with 2M sodium carbonate solution (1.99 mL, 3.98 mmol) and Tetrakis(triphenylphosphine)palladium (58 mg, 0.05 mmol). The mixture was heated in at 115° C. for 30 minutes. The cooled reaction mixture was quenched with water and extracted with dichloromethane for three times. The combined extracts were washed once with saturated sodium chloride solution, dried over anhydrous sodium sulfate, filtered, and concentrated under reduced pressure. The crude residue was purified by flash chromatography (silica gel) to give the desired product as yellow solid. LCMS-ESI+ (m/z): [M+H]+ calcd for $C_{25}H_{30}FN_8O$: 509.6; found: 509.4.

Step 3: Preparation of 5-(4-(((1,5-dimethyl-1H-pyrazol-4-yl)amino)-1,3,5-triazin-2-yl)-2-(((3R,4S)-3-fluoropiperidin-4-yl)oxy)benzonitrile:

(3R,4S)-tert-butyl 4-(2-cyano-4-(4-((1,5-dimethyl-1H-pyrazol-4-yl)amino)-1,3,5-triazin-2-yl)phenoxy)-3-fluoropiperidine-1-carboxylate (100 mg, 0.197 mmol) was taken up in dichloromethane (2mL) and treated with trifluoroacetic acid (0.38 mL, 4.97 mmol). After 60 minutes, the mixture was quenched with saturated sodium bicarbonate (PH ~8) and extracted with dichloromethane for three times. The combined extracts were washed once with saturated aqueous sodium chloride solution, dried over anhydrous sodium sulfate, filtered, and concentrated under reduced pressure. The crude was used for next step. LCMS-ESI+ (m/z): [M+H] calcd for $C_{20}H_{22}FN_8O$ 409.4; found: 409.3.

Step 4: Preparation of 5-(4-((1,5-dimethyl-1H-pyrazol-4-yl)amino)-1,3,5-triazin-2-yl)-2-(((3R,4S)-3-fluoro-1-((S)-2-hydroxypropanoyl)piperidin-4-yl)oxy)benzonitrile:

5-((4-((1,5-dimethyl-1H-pyrazol-4-yl)amino)-1,3,5-triazin-2-yl)-2-(((3R,4S)-3-fluoropiperidin-4-yl)oxy)benzonitrile (80.5 mg, 0.197 mmol) and L-lactic acid (35.5 mg, 0.394 mmol) were taken up as suspension in N,N-dimethylformamide (2 mL). The mixture was treated successively with N,N-diisopropylethylamine (0.11 mL, 0.632 mmol) and N-[(dimethylamino)-1H-1,2,3-triazolo-[4,5-b]pyridin-1-ylmethylene]-N-methylmethanaminiumhexafluorophosphate N-oxide (HATU, 112.4 mg, 0.296 mmol). The mixture was stirred for 1 hour at room temperature and then purified by reverse phase chromatography (C18) to provide the desired product as pale yellow solid. LCMS-ESI+ (m/z): [M+H]+ calcd for $C_{23}H_{26}FN_8O$: 481.5; found: 481.3. 1H NMR (300 MHz, DMSO-d6) δ 9.73 (d, J=47.4 Hz, 1H), 8.70 (d, J=9.3 Hz, 1H), 8.59 (d, J=34.2 Hz, 1H), 8.57 (m, 1H), 7.65 (m, 2H), 5.13 (m, 3H), 4.55-3.90 (br, 3H), 3.74 (d, J=6.9 Hz, 3H), 3.70-3.40 (br, 1H), 3.30 (m, 1H), 2.21 (d, J=12.9 Hz, 3H), 1.98 (br, 2H), 1.23 (m, 3H).

Example 567

2-(((3R,4S)-1-((S)-2,3-dihydroxypropanoyl)-3-fluoropiperidin-4-yl)oxy)-5-(4-((1,5-dimethyl-1H-pyrazol-4-yl)amino)-1,3,5-triazin-2-yl)benzonitrile

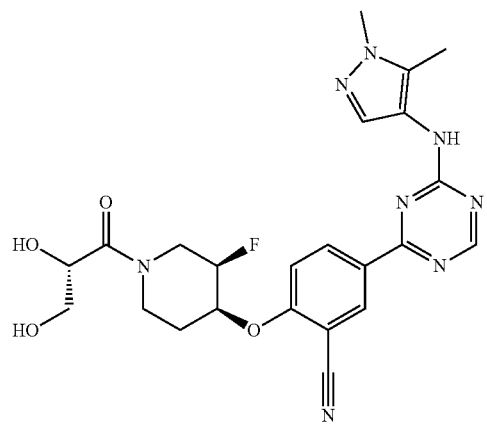 [SMILES: Cc1c(Nc2ncnc(-c3ccc(O[C@H]4CCN(C(=O)[C@@H](O)CO)C[C@H]4F)c(C#N)c3)n2)cnn1C]

5-(4-((1,5-dimethyl-1H-pyrazol-4-yl)amino)-1,3,5-triazin-2-yl)-2-(((3R,4S)-3-fluoropiperidin-4-yl)oxy)benzonitrile (70 mg, 0.171 mmol) and (R)-2,3-dihydroxypropanoic acid (36 mg, 0.34 mmol) were taken up as suspension in N,N-dimethylformamide (2 mL). The mixture was treated successively with N,N-diisopropylethylamine (0.10 mL, 0.574 mmol) and N-[(dimethylamino)-1H-1,2,3-triazolo-[4,5-b]pyridin-1-ylmethylene]-N-methylmethanaminium-hexafluorophosphate N-oxide (HATU, 97.8 mg, 0.257 mmol). The mixture was stirred for 1 hour at room temperature and then purified by reverse phase chromatography (C18) to provide the desired product as pale yellow solid. LCMS-ESI+ (m/z): [M+H]+ calcd for $C_{23}H_{26}FN_8O_4$: 497.5; found: 497.3. 1H NMR (300 MHz, DMSO-d6) δ 9.74 (d, J=47.4 Hz, 1H), 8.70 (d, J=9.3 Hz, 1H), 8.59 (m, 2H), 7.65 (m, 2H), 5.11-3.90 (br, 5H), 3.74 (d, J=6.9 Hz, 3H), 3.70-3.35 (br, 2H), 3.25-3.00 (br, 1H), 2.40-2.20 (br, 1H), 2.21 (d, J=12.3 Hz, 3H), 1.98 (br, 2H), 1.23 (s, 1H).

Example 568

5-(4-((1-ethyl-3-methyl-1H-pyrazol-4-yl)amino)-1,3,5-triazin-2-yl)-2-(((3R,4S)-3-fluoro-1-((S)-2-hydroxypropanoyl)piperidin-4-yl)oxy)benzonitrile

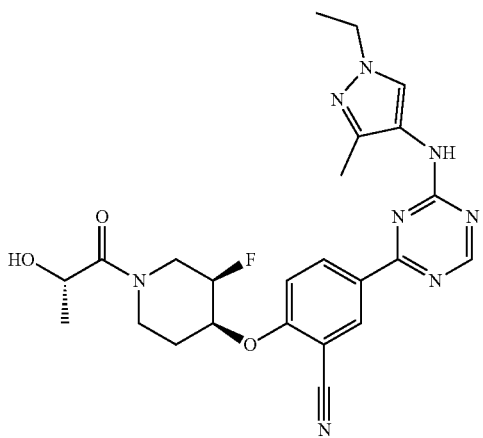 [SMILES: CCn1cc(Nc2ncnc(-c3ccc(O[C@H]4CCN(C(=O)[C@H](C)O)C[C@H]4F)c(C#N)c3)n2)c(C)n1]

Step 1: Preparation of 4-chloro-N-(1-ethyl-3-methyl-1H-pyrazol-4-yl)-1,3,5-triazin-2-amine:

To a solution of 2,4-dichloro-1,3,5-triazine (330 mg, 2.2 mmol) in dichloromethane (15 mL) at 0° C., 1-ethyl-3-methyl-1H-pyrazol-4-amine (250.34 mg, 2 mmol) was added, followed by N,N-Diisopropylethylamine (0.523 mL, 3 mmol). The reaction mixture was stirred at 0° C. for 40 minutes. After this time, the reaction was quenched with saturated sodium bicarbonate solution (PH~8) and extracted with dichloromethane for three times. The combined extracts were washed once with saturated aqueous sodium chloride solution, dried over anhydrous sodium sulfate, filtered, and concentrated under reduced pressure. The crude residue was purified by flash chromatography (silica gel) to give the desired product as red solid. LCMS-ESI+ (m/z): [M+H]+ calcd for $C_9H_{12}ClN_6$: 239.7; found: 239.1.

Step 2: Preparation of (3R,4S)-tert-butyl 4-(2-cyano-4-(4-((1-ethyl-3-methyl-1H-pyrazol-4-yl)amino)-1,3,5-triazin-2-yl)phenoxy)-3-fluoropiperidine-1-carboxylate:

A suspension of 4-chloro-N-(1-ethyl-3-methyl-1H-pyrazol-4-yl)-1,3,5-triazin-2-amine (119 mg, 0.50 mmol) and (3R,4S)-tert-butyl 4-(2-cyano-4-((4,4,5,5-tetramethyl-1,3,2-dioxaborolan-2-yl)phenoxy)-3-fluoropiperidine-1-carboxylate (245.5 mg, 0.55 mmol) in 1,2-Dimethoxyethane (4 mL) was treated with 2M sodium carbonate solution (1.99 mL, 3.98 mmol) and Tetrakis(triphenylphosphine)palladium (58 mg, 0.05 mmol). The mixture was heated in at 115° C. for 30 minutes. The cooled reaction mixture was quenched with water and extracted with dichloromethane for three times. The combined extracts were washed once with saturated aqueous sodium chloride solution, dried over anhydrous sodium sulfate, filtered, and concentrated under reduced pressure. The crude residue was purified by flash chromatography (silica gel) to give the desired product as white solid. LCMS-ESI+ (m/z): [M+H]+ calcd for $C_{26}H_{32}FN_8O_3$: 523.6; found: 523.4.

Step 3: Preparation of 5-(4-((1-ethyl-3-methyl-1H-pyrazol-4-yl)amino)-1,3,5-triazin-2-yl)-2-(((3R,4S)-3-fluoropiperidin-4-yl)oxy)benzonitrile:

(3R,4S)-tert-butyl 4-(2-cyano-4-(4-((1-ethyl-3-methyl-1H-pyrazol-4-yl)amino)-1,3,5-triazin-2-yl)phenoxy)-3-fluoropiperidine-1-carboxylate (256.5 mg, 0.49 mmol) was taken up in dichloromethane (5 mL) and treated with trifluoroacetic acid (0.8 mL, 10.5 mmol). After 20 minutes, the mixture was quenched with saturated sodium bicarbonate (PH ~8) and extracted with dichloromethane for three times. The combined extracts were washed once with saturated aqueous sodium chloride solution, dried over anhydrous sodium sulfate, filtered, and concentrated under reduced pressure. The crude was used for next step. LCMS-ESI+ (m/z): [M+H]+ calcd for $C_{21}H_{24}FN_8O$ 423.5; found: 423.3.

Step 4: Preparation of 5-(4-((1-ethyl-3-methyl-1H-pyrazol-4-yl)amino)-1,3,5-triazin-2-yl)-2-(((3R,4S)-3-fluoro-1-((S)-2-hydroxypropanoyl)piperidin-4-yl)oxy)benzonitrile:

5-(4-(((1-ethyl-3-methyl-1H-pyrazol-4-yl)amino)-1,3,5-triazin-2-yl)-2-(((3R,4S)-3-fluoropiperidin-4-yl)oxy)benzonitrile (85 mg, 0.2 mmol) and L-lactic acid (36.3 mg, 0.42 mmol) were taken up as suspension in N,N-dimethylformamide (2 mL). The mixture was treated successively with N,N-diisopropylethylamine (0.104 mL, 0.597 mmol) and N-[(dimethylamino)-1H-1,2,3-triazolo-[4,5-b]pyridin-1-yl-methylene]-N-methylmethanaminiumhexafluorophosphate N-oxide (HATU, 114.8 mg, 0.30 mmol). The mixture was stirred for 45 minutes at room temperature and then purified by reverse phase chromatography (C18) to provide the desired product as pale yellow solid. LCMS-ESI+ (m/z): [M+H]+ calcd for $C_{24}H_{28}FN_8O_3$:495.5; found: 495.3. 1H NMR (300 MHz, DMSO-d6) δ 9.75 (d, J=38.1 Hz, 1H), 8.72 (d, J=3.0 Hz, 1H), 8.62 (m, 2H), 7.98 (d, J=35.1 Hz, 1H), 7.64 (m, 1H), 5.12-4.13 (br, 5H), 4.20-3.40 (br, 4H), 3.28 (m, 1H), 2.13 (d, J=2.4 Hz, 3H), 1.98 (br, 2H), 1.41 (m, 3H), 1.21 (m, 3H).

Example 569

5-(4-((1-ethyl-3-methyl-1H-pyrazol-4-yl)amino)-1,3,5-triazin-2-yl)-2-(((3R,4S)-3-fluoro-1-(2-hydroxyacetyl)piperidin-4-yl)oxy)benzonitrile

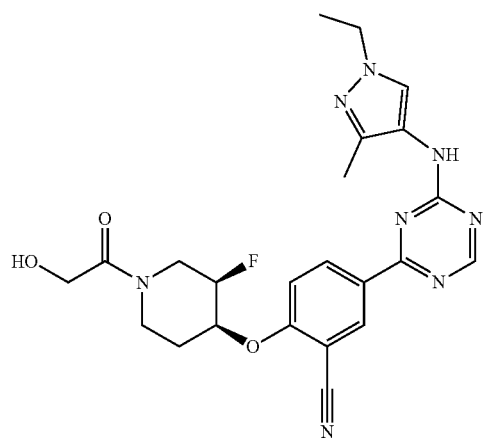 [SMILES: CCn1cc(Nc2ncnc(-c3ccc(O[C@H]4CCN(C(=O)CO)C[C@H]4F)c(C#N)c3)n2)c(C)n1]

5-(4-(((1-ethyl-3-methyl-1H-pyrazol-4-yl)amino)-1,3,5-triazin-2-yl)-2-(((3R,4S)-3-fluoropiperidin-4-yl)oxy)benzonitrile (85 mg, 0.2 mmol) and Glycolic acid (30.6 mg, 0.4 mmol) were taken up as suspension in N,N-dimethylformamide (2 mL). The mixture was treated successively with N,N-diisopropylethylamine (0.104 mL, 0.597 mmol) and N-[(dimethylamino)-1H-1,2,3-triazolo-[4,5-b]pyridin-1-yl-methylene]-N-methylmethanaminiumhexafluorophosphate N-oxide (HATU, 114.8 mg, 0.30 mmol). The mixture was stirred for 60 minutes at room temperature and then purified by reverse phase chromatography (C18) to provide the desired product as pale yellow solid. LCMS-ESI+ (m/z): [M+H]+ calcd for $C_{23}H_{26}FN_8O_3$: 481.5; found: 481.6. 1H NMR (300 MHz, DMSO-d6) δ 9.75 (d, J=38.1 Hz, 1H), 8.72 (d, J=3.0 Hz, 1H), 8.61 (m, 2H), 7.98 (d, J=35.1 Hz, 1H), 7.64 (m, 1H), 5.13-4.25 (br, 3H), 4.15-3.40 (br, 6H), 3.20 (br, 1H), 2.13 (d, J=1.8 Hz, 3H), 1.98 (br, 2H), 1.41 (m, 3H).

Example 570

2-(((3R,4S)-3-fluoro-1-((S)-2-hydroxypropanoyl)piperidin-4-yl)oxy)-5-(4-((2-methylthiazol-5-yl)amino)-1,3,5-triazin-2-yl)benzonitrile

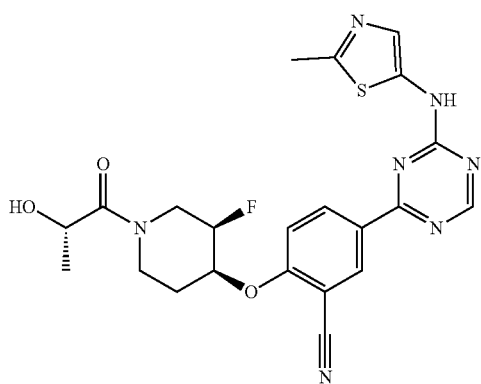 [SMILES: Cc1ncc(Nc2ncnc(-c3ccc(O[C@H]4CCN(C(=O)[C@H](C)O)C[C@H]4F)c(C#N)c3)n2)s1]

Step 1: Preparation of N-(4-chloro-1,3,5-triazin-2-yl)-2-methylthiazol-5-amine:

To a solution of 2,4-dichloro-1,3,5-triazine (333 mg, 2.2 mmol) in dichloromethane (15 mL) at 0° C., 2-methylthiazol-5-amine (230 mg, 2.01 mmol) was added, followed by N,N-Diisopropylethylamine (0.53 mL, 3.02 mmol). The reaction mixture was stirred at 0° C. for 15 minutes. After this time, the reaction was quenched with saturated sodium bicarbonate solution (PH~8) and extracted with dichloromethane for three times. The combined extracts were washed once with saturated aqueous sodium chloride solution, dried over anhydrous sodium sulfate, filtered, and concentrated under reduced pressure. The crude residue was purified by flash chromatography (silica gel) to give the desired product as yellow solid. LCMS-ESI+ (m/z): [M+H]+ calcd for $C_7H_7ClN_5S$: 228.7; found: 228.5.

Step 2: Preparation of 2-(((3R,4S)-3-fluoro-1-((S)-2-hydroxypropanoyl)piperidin-4-yl)oxy)-5-(4-((2-methylthiazol-5-yl)amino)-1,3,5-triazin-2-yl)benzonitrile:

A suspension of N-(4-chloro-1,3,5-triazin-2-yl)-2-methylthiazol-5-amine (228 mg, 1.0 mmol) and 2-(((3R,4S)-3-fluoro-1-((S)-2-hydroxypropanoyl)piperidin-4-yl)oxy)-5-(4,4,5,5-tetramethyl-1,3,2-dioxaborolan-2-yl)benzonitrile (460 mg, 1.1 mmol) in 1,2-Dimethoxyethane (10 mL) was treated with 2M sodium carbonate solution (3.8 mL, 7.6 mmol) and Tetrakis(triphenylphosphine)palladium (115.7 mg, 0.1 mmol). The mixture was heated at 125° C. for 45 minutes. The cooled reaction mixture was quenched with water and extracted with dichloromethane for three times. The combined extracts were washed once with saturated aqueous sodium chloride solution, dried over anhydrous sodium sulfate, filtered, and concentrated under reduced pressure. The crude residue was purified by flash chromatography (silica gel), then reverse phase (C18) to give the desired product as yellow solid. LCMS-ESI+ (m/z): [M+H]+ calcd for $C_{22}H_{23}FN_7O_3S$: 484.5; found: 484.6. 1H NMR (300 MHz, DMSO-d6) δ 11.47 (br, 1H), 8.88 (m, 1H), 8.71 (m, 2H), 7.72 (m, 1H), 7.42 (S, 1H), 5.13 (m, 3H), 4.48-3.90 (br, 3H), 3.80-3.45 (br, 1H), 3.15 (m, 1H), 2.61 (m, 3H), 1.99 (br, 2H), 1.22 (m, 3H).

Example 571

5-(4-((2,4-dimethylthiazol-5-yl)amino)-1,3,5-triazin-2-yl)-2-(((3R,4S)-3-fluoro-1-((S)-2-hydroxypropanoyl)piperidin-4-yl)oxy)benzonitrile

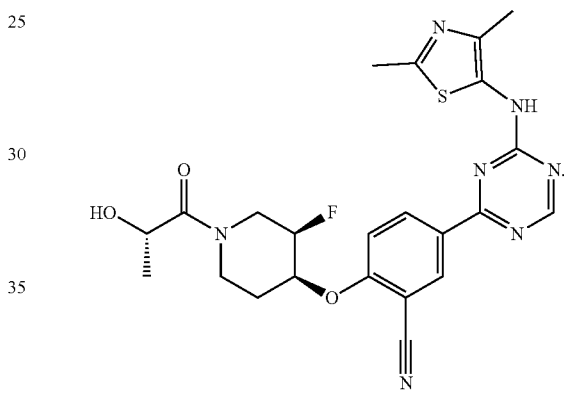

Step 1: Preparation N-(4-chloro-1,3,5-triazin-2-yl)-2,4-dimethylthiazol-5-amine:

To a solution of 2,4-dichloro-1,3,5-triazine (0.825 mg, 5.5 mmol) in dichloromethane (50 mL) at 0° C., 2,4-dimethylthiazol-5-amine (0.64 g, 5 mmol) was added, followed by N,N-Diisopropylethylamine (1.31 mL, 17.5 mmol). The reaction mixture was stirred at 0° C. for 20 minutes. After this time, the reaction was quenched with saturated sodium bicarbonate solution (PH~8) and extracted with dichloromethane for three times. The combined extracts were washed once with saturated aqueous sodium chloride solution, dried over anhydrous sodium sulfate, filtered, and concentrated under reduced pressure. The crude residue was purified by flash chromatography (silica gel) to give the desired product as red solid. LCMS-ESI+ (m/z): [M+H]+ calcd for $C_8H_9ClN_5S$: 242.7; found: 242.3.

Step 2: Preparation of (3R,4S)-tert-butyl 4-(2-cyano-4-(4-((2,4-dimethylthiazol-5-yl)amino)-1,3,5-triazin-2-yl)phenoxy)-3-fluoropiperidine-1-carboxylate:

A suspension of N-(4-chloro-1,3,5-triazin-2-yl)-2,4-dimethylthiazol-5-amine (144 mg, 0.596 mmol) and (3R,4S)-tert-butyl 4-(2-cyano-4-(4,4,5,5-tetramethyl-1,3,2-dioxaborolan-2-yl)phenoxy)-3-fluoropiperidine-1-carboxylate (269.9 mg, 0.605 mmol) in 1,2-Dimethoxyethane (6 mL) was treated with 2M sodium carbonate solution (1.2 mL, 2.4 mmol) and Tetrakis(triphenylphosphine)palladium (72 mg, 0.062 mmol). The mixture was heated in at 125° C. for 40 minutes. The cooled reaction mixture was quenched with water and extracted with dichloromethane for three times. The combined extracts were washed once with saturated aqueous sodium chloride solution, dried over anhydrous sodium sulfate, filtered, and concentrated under reduced pressure. The crude residue was purified by flash chromatography (silica gel) to give the desired product as white solid. LCMS-ESI+ (m/z): [M+H]+ calcd for $C_{25}H_{29}FN_7O_3S$: 526.6; found: 526.3.

Step 3: Preparation of 5-(4-((2,4-dimethylthiazol-5-yl)amino)-1,3,5-triazin-2-yl)-2-(((3R,4S)-3-fluoropiperidin-4-yl)oxy)benzonitrile:

(3R,4S)-tert-butyl 4-(2-cyano-4-(4-((2,4-dimethylthiazol-5-yl)amino)-1,3,5-triazin-2-yl)phenoxy)-3-fluoropiperidine-1-carboxylate (60 mg, 0.108 mmol) was taken up in dichloromethane (1.5 mL) and treated with trifluoroacetic acid (0.175 mL, 2.29 mmol). After 20 minutes, the mixture was quenched with saturated sodium bicarbonate (PH ~8) and extracted with dichloromethane for three times. The combined extracts were washed once with saturated aqueous sodium chloride solution, dried over anhydrous sodium sulfate, filtered, and concentrated under reduced pressure. The crude was used for next step. LCMS-ESI+ (m/z): [M+H]+ calcd for $C_{20}H_{21}FN_7OS$ 426.5; found: 426.3.

Step 4: Preparation of 5-(4-((2,4-dimethylthiazol-5-yl)amino)-1,3,5-triazin-2-yl)-2-(((3R,4S)-3-fluoro-1-((S)-2-hydroxypropanoyl)piperidin-4-yl)oxy)benzonitrile:

5-(4-((2,4-dimethylthiazol-5-yl)amino)-1,3,5-triazin-2-yl)-2-(((3R,4S)-3-fluoropiperidin-4-yl)oxy)benzonitrile (40 mg, 0.094 mmol) and L-lactic acid (18 mg, 0.2 mmol) were taken up as suspension in N,N-dimethylformamide (1 mL). The mixture was treated successively with N,N-diisopropylethylamine (0.052 mL, 0.3 mmol) and N-[(dimethylamino)-1H-1,2,3-triazolo-[4,5-b]pyridin-1-ylmethylene]-N-methylmethanaminiumhexafluorophosphate N-oxide (HATU, 57 mg, 0.15 mmol). The mixture was stirred for 60 minutes at room temperature and then purified by reverse phase chromatography (C18) to provide the desired product as pale yellow solid. LCMS-ESI+ (m/z): [M+H]+ calcd for $C_{23}H_{25}FN_7O_3S$: 498.6; found: 498.3. 1H NMR (300 MHz, DMSO-d6) δ 10.59 (br, 1H), 8.81 (m, 1H), 8.59 (m, 2H), 7.66 (m, 1H), 5.12 (m, 3H), 4.47-3.50 (br, 2H), 3.37 (m, 1H), 3.15 (m, 1H), 2.57 (m, 3H), 2.27 (m, 3H), 1.98 (br, 2H), 1.21 (m, 4H).

Example 572

2-(((3R,4S)-3-fluoro-1-((S)-2-hydroxypropanoyl)piperidin-4-yl)oxy)-5-(4-((4-(hydroxymethyl)thiazol-5-yl)amino)-1,3,5-triazin-2-yl)benzonitrile

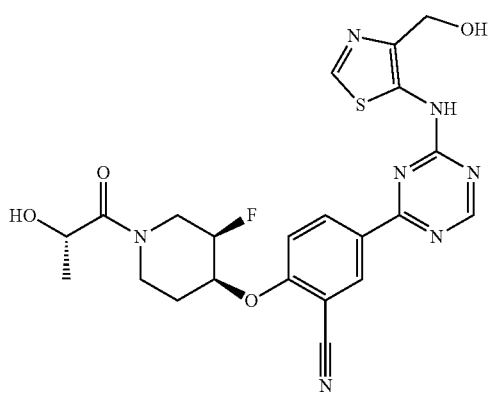 [SMILES: C[C@H](O)C(=O)N1CC[C@H](Oc2ccc(-c3ncnc(Nc4scnc4CO)n3)cc2C#N)[C@H](F)C1]

Step 1: Preparation of ethyl 5-((4-chloro-1,3,5-triazin-2-yl)amino)thiazole-4-carboxylate:

To a solution of 2,4-dichloro-1,3,5-triazine (330.5 mg, 2.2 mmol) in dichloromethane (15 mL) at 0° C., ethyl 5-aminothiazole-4-carboxylate (345 mg, 2 mmol) was added, followed by N,N-Diisopropylethylamine (0.523 mL, 3 mmol). The reaction mixture was stirred at 0° C. for 30 minutes. Then more 2,4-dichloro-1,3,5-triazine (300 mg, 2 mmol) was added and the reaction mixture was stirred at room temperature overnight. After this time, the reaction was quenched with saturated sodium bicarbonate solution (PH~8) and extracted with dichloromethane for three times. The combined extracts were washed once with saturated aqueous sodium chloride solution, dried over anhydrous sodium sulfate, filtered, and concentrated under reduced pressure. The crude residue was purified by flash chromatography (silica gel) to give the desired product as white solid. LCMS-ESI+ (m/z): [M+H]+ calcd for C9H9ClN5O2S: 286.7; found: 286.1.

Step 2: Preparation of ethyl 5-((4-(4-(((3R,4S)-1-(tert-butoxycarbonyl)-3-fluoropiperidin-4-yl)oxy)-3-cyanophenyl)-1,3,5-triazin-2-yl)amino)thiazole-4-carboxylate:

A suspension of ethyl 5-((4-chloro-1,3,5-triazin-2-yl)amino)thiazole-4-carboxylate (308.6 mg, 1.08 mmol) and (3R,4S)-tert-butyl 4-(2-cyano-4-(4,4,5,5-tetramethyl-1,3,2-dioxaborolan-2-yl)phenoxy)-3-fluoropiperidine-1-carboxylate (495 mg, 1.1 mmol) in 1,2-Dimethoxyethane (11 mL) was treated with 2M sodium carbonate solution (2.2 mL, 4.4 mmol) and Tetrakis(triphenylphosphine)palladium (132 mg, 0.114 mmol). The mixture was heated in at 125° C. for 40 minutes. The cooled reaction mixture was quenched with water and extracted with dichloromethane for three times. The combined extracts were washed once with saturated aqueous sodium chloride solution, dried over anhydrous sodium sulfate, filtered, and concentrated under reduced pressure. The crude residue was purified by flash chromatography (silica gel) to give the desired product as yellow solid. LCMS-ESI+ (m/z): [M+H]+ calcd for C26H29FN7O5S: 570.6; found: 570.3.

Step 3: Preparation of (3R,4S)-tert-butyl 4-(2-cyano-4-(4-((4-(hydroxymethyl)thiazol-5-yl(amino)-1,3,5-triazin-2-yl)phenoxy)-3-fluoropiperidine-1-carboxylate:

ethyl 5-((4-(4-(((3R,4S)-1-(tert-butoxycarbonyl)-3-fluoropiperidin-4-yl)oxy)-3-cyanophenyl)-1,3,5-triazin-2-yl)amino)thiazole-4-carboxylate (310 mg, 0.19 mmol) was dissolved in THF (8 mL) and the reaction mixture was cooled to 0° C. Lithium Aluminum Hydride (1M solution in THF, 1.67 mL, 1.67 mmol) was added drop wise. The reaction mixture was stirred at 0° C. for 20 minutes. Then the mixture was quenched with 0.3 mL water, 0.2 mL 1N NaOH and 0.3 mL water sequentially and stirred at room temperature for 1 h. Small amount of sodium sulfate and Celite were added and filtered. The filtrate was evaporated and purified by flash chromatography (silica gel) to give the desired product as white solid. LCMS-ESI+ (m/z): [M+H]+ calcd for C24H26FN7O4S: 528.6; found: 528.3.

Step 4: Preparation of 2-(((3R,4S)-3-fluoropiperidin-4-yl)oxy)-5-(4-((4-(hydroxymethyl)thiazol-5-yl)amino)-1,3,5-triazin-2-yl)benzonitrile:

(3R,4S)-tert-butyl 4-(2-cyano-4-(4-((4-(hydroxymethyl)thiazol-5-yl)amino)-1,3,5-triazin-2-yl)phenoxy)-3-fluoropiperidine-1-carboxylate (50 mg, 0.095 mmol) was taken up in dichloromethane 1 mL) and treated with trifluoroacetic acid (0.145 mL, 1.90 mmol). After 20 minutes, the mixture was quenched with saturated sodium bicarbonate (PH~8) and extracted with dichloromethane for three times. The combined extracts were washed once with saturated aqueous sodium chloride solution, dried over anhydrous sodium sulfate, filtered, and concentrated under reduced pressure. The crude was used for next step. LCMS-ESI+ (m/z): [M+H]+ calcd for C19H19FN7O2S 428.5; found: 428.2.

Step 5: Preparation of 2-(((3R,4S)-3-fluoro-1-((S)-2-hydroxypropanoyl)piperidin-4-yl)oxy)-5-(4-((4-(hydroxymethyl)thiazol-5-yl)amino)-1,3,5-triazin-2-yl)benzonitrile:

Preparation of 2-(((3R,4S)-3-fluoropiperidin-4-yl)oxy)-5-(4-((4-(hydroxymethyl)thiazol-5-yl)amino)-1,3,5-triazin-2-yl)benzonitrile (30 mg, 0.07 mmol) and L-lactic acid (17 mg, 0.189 mmol) were taken up as suspension in N,N-dimethylformamide (1 mL). The mixture was treated successively with N,N-diisopropylethylamine (0.05 mL, 0.28 mmol) and N-[(dimethylamino)-1H-1,2,3-triazolo-[4,5-b]pyridin-1-ylmethylene]-N-methylmethanaminiumhexafluorophosphate N-oxide (HATU, 54 mg, 0.142 mmol). The mixture was stirred for 2 hour at room temperature and then purified by reverse phase chromatography (C18) to provide the desired product as pale yellow solid. LCMS-ESI+ (m/z): [M+H]+ calcd for $C_{22}H_{23}FN_7O_4S$: 500.5; found: 500.3. 1H NMR (300 MHz, DMSO-d6) δ 10.71 (br, 1H), 8.87 (m, 4H), 7.68 (m, 1H), 5.11 (m, 4H), 4.70 (m, 2H), 4.43-3.90 (br, 3H), 3.51 (br, 1H), 3.15 (m, 1H), 1.99 (br, 2H), 1.21 (m, 3H).

Example 573

2-(((3R,4S)-3-fluoro-1-((S)-2-hydroxypropanoyl)piperidin-4-yl)oxy)-5-(4-((4-(4-((S)-2-hydroxypropyl)piperazin-1-yl)phenyl)amino)-1,3,5-triazin-2-yl)benzonitrile

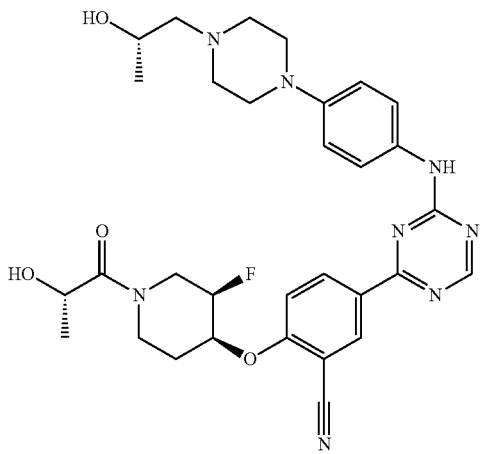 [SMILES: C[C@H](O)CN1CCN(c2ccc(Nc3ncnc(-c4ccc(O[C@H]5CCN(C(=O)[C@H](C)O)C[C@H]5F)c(C#N)c4)n3)cc2)CC1]

Step 1: (S)-1-(4-(4-nitrophenyl)piperazin-1-yl)propan-2-ol: 1-(4-nitrophenyl)piperazine (1.0 g, 4.83 mmol) was charged into a 20 mL pressure vessel and was suspended in 5 mL DMF and to that was added (S)-2-methyloxirane (5 mL, 71.4 mmol, 14.8 equivs) and the reaction was sealed and heated at 100° C. for six hours. LCMS showed complete conversion and the reaction was cooled to room temperature, followed by concentration on a rotary evaporator. The crude was dissolved in 10% methanol/dichloromethane and washed 1×100 mL saturated sodium bicarbonate, 1×100 mL brine and dried over sodium sulfate. The crude was filtered, concentrated on a rotary evaporator and flashed on an ISCO purification system using a gradient of 0-20% methanol/dichloromethane. (S)-1-(4-(4-nitrophenyl)piperazin-1-yl)propan-2-ol was isolated as a colorless syrup, (977 mg, 76%).

Step 2: (S)-1-(4-(4-aminophenyl)piperazin-1-yl)propan-2-ol: (S)-1-(4-(4-nitrophenyl)piperazin-1-yl)propan-2-ol (600 mg, 2.26 mmol) was dissolved in 100 mL of 1:1 ethyl acetate and ethanol and to that was added 100 mg of wet palladium on carbon and then placed into a Parr vessel and hydrogenated with 60 psi hydrogen pressure for six hours. LCMS showed complete reduction and the vessel was removed and the reaction solution was filtered through a pad of Celite® and then concentrated on a rotary evaporator. The sample solidified under vacuum to yield (S)-1-(4-(4-aminophenyl)piperazin-1-yl)propan-2-ol as a light yellow crystalline solid (505 mg, 95%).

Step 3: (S)-1-(4-(4-((4-chloro-1,3,5-triazin-2-yl)amino)phenyl)piperazin-1-yl)propan-2-ol:

To a 250 round-bottomed flask was charged (S)-1-(4-(4-aminophenyl)piperazin-1-yl)propan-2-ol (300 mg, 1.27 mmol), 2,4-dichloro-1,3,5-triazine (191 mg, 1.27 mmol) and potassium carbonate (3.0 equivs, 3.82 mmol, 528 mg) and to that was added 5 mL dimethylacetamide precooled to 0° C. After 15 min LCMS showed the reaction to be complete and 100 mL water was added to the reaction and the crude was extracted into 100 mL 5% methanol/dichloromethane. The sample was washed 1×100 mL saturated sodium bicarbonate, 1×100 mL brine and dried over sodium sulfate. The crude solution was filtered, concentrated on a rotary evaporator and flashed on an ISCO system using a gradient of 0-20% methanol/dichloromethane. The desired product (S)-1-(4-(4-((4-chloro-1,3,5-triazin-2-yl)amino)phenyl)piperazin-1-yl)propan-2-ol was recovered as a light yellow solid (252 mg, 57%).

Step 4: (3R,4S)-tert-butyl 4-(2-cyano-4-(4-((4-(4-((S)-2-hydroxypropyl)piperazin-1-yl)phenyl)amino)-1,3,5-triazin-2-yl)phenoxy)-3-fluoropiperidine-1-carboxylate:

(S)-1-(4-(4-((4-chloro-1,3,5-triazin-2-yl)amino)phenyl)piperazin-1-yl)propan-2-ol (355 mg, 1.02 mmol), (3R,4S)-tert-butyl 4-(2-cyano-4-(4,4,5,5-tetramethyl-1,3,2-dioxaborolan-2-yl)phenoxy)-3-fluoropiperidine-1-carboxylate (1.1 equiv, 500 mg, 1.21 mmol) and tetrakis-triphenylphosphine-palladium[0] (0.1%, 118 mg) were added to a round-bottomed flask and to that was added 20 mL dimethoxyethane and 10 mL 2N sodium carbonate and the reaction was allowed to proceed at 125° C. for 1 hr. LCMS showed reaction complete and after cooling to room temperature the crude solution was transferred to a separatory funnel and to that was added 100 mL water and 100 mL 10% methanol/dichloromethane. The crude sample was extracted into the organic layer which was then dried over sodium sulfate, filtered and concentrated on a rotary evaporator and flashed on an ISCO using a gradient of 0-25% methanol/dichloromethane. The desired product (3R,4S)-tert-butyl 4-(2-cyano-4-(4-((4-(4-((S)-2-hydroxypropyl)piperazin-1-yl)phenyl)amino)-1,3,5-triazin-2-yl)phenoxy)-3-fluoropiperidine-1-carboxylate was obtained as an off-white foam (440 mg, 68%).

Step 5: 2-(((3R,4S)-3-fluoropiperidin-4-yl)oxy)-5-(4-((4-(4-((S)-2-hydroxypropyl)piperazin-1-yl)phenyl)amino)-1,3,5-triazin-2-yl)benzonitrile:

(3R,4S)-tert-butyl 4-(2-cyano-4-(4-((4-(4-((S)-2-hydroxypropyl)piperazin-1-yl)phenyl)amino)-1,3,5-triazin-2-yl)phenoxy)-3-fluoropiperidine-1-carboxylate (82 mg, 0.13 mmol) was dissolved in 9.0 mL dichloromethane and to that was added 1.0 mL trifluoroacetic acid and the sample was stirred at room temperature for two hours. LCMS showed complete deprotection of the Boc-group and all solvent was removed. The crude was dissolved in 100 mL 10% methanol/dichloromethane and free-based by washing 2×100 mL saturated sodium bicarbonate, 1×100mL brine and dried over sodium sulfate. The sample was filtered, concentrated on a rotary evaporator and dried on high vacuum to yield the desired product 2-(((3R,4S)-3-fluoropiperidin-4-yl)oxy)-5-(4-((4-(4-((S)-2-hydroxypropyl)piperazin-1-yl)phenyl)amino)-1,3,5-triazin-2-yl)benzonitrile as an off-white solid (69 mg, 80%).

Step 6: 2-(((3R,4S)-3-fluoropiperidin-4-yl)oxy)-5-(4-((4-(4-((S)-2-hydroxypropyl)piperazin-1-yl)phenyl)amino)-1,3,5-triazin-2-yl)benzonitrile (50 mg, 0.094 mmol) was dissolved in 5 mL dimethylformamide and to that was added (S)-lactic acid (188 uL of a 1M solution in dimethylformamide, 2 equivs), 1-[bis(dimethylamino)methylene]-1H-1,2,3-triazolo[4,5-b]pyridinium 3-oxid hexafluorophosphate (HATU, 2 equivs, 0.188 mmol, 71 mg) and diisopropylethylamine (DIEA, 3 equivs, 0.28 mmol, 49 uL) and allowed to react at room temperature for two hours. LCMS showed completion and 100 mL of water and 100 mL of 10% methanol/dichloromethane were added and the crude was extracted into organic. The organic layer was dried over sodium sulfate, concentrated on a rotary evaporator and flashed on an ISCO 0-25% methanol/dichloromethane yielding the desired target 2-(((3R,4S)-3-fluoro-1-((S)-2-hydroxypropanoyl)piperidin-4-yl)oxy)-5-(4-((4-(4-((S)-2-hydroxypropyl)piperazin-1-yl)phenyl)amino)-1,3,5-triazin-2-yl)benzonitrile as a light yellow solid. $^1$H NMR (300 MHz, DMSO-$d_6$) δ 10.13 (d, J=16.6 Hz, 1H), 8.74 (s, 1H), 8.57 (d, J=10.7 Hz, 2H), 7.79-7.37 (m, 3H), 6.95 (s, 2H), 5.33-4.78 (m, 3H), 4.61-3.45 (m, 5H), 3.45-3.21 (m, 12H), 3.11 (bs, 4H), 2.53 (bs, 4H), 2.34 (m, 2H), 2.07-1.67 (m, 2H), 1.44-1.13 (m, 3H), 1.06 (d, J=6.1 Hz, 3H). LCMS-ESI$^+$ (m/z): [M+H]$^+$ calcd for $C_{31}H_{37}FN_8O_4$: 604.3; found: 605.5.

Example 574

2-(((3R,4S)-1-((S)-2,3-dihydroxypropanoyl)-3-fluoropiperidin-4-yl)oxy)-5-(4-((1-isopropyl-1H-pyrazol-4-yl)amino)-1,3,5-triazin-2-yl)benzonitrile

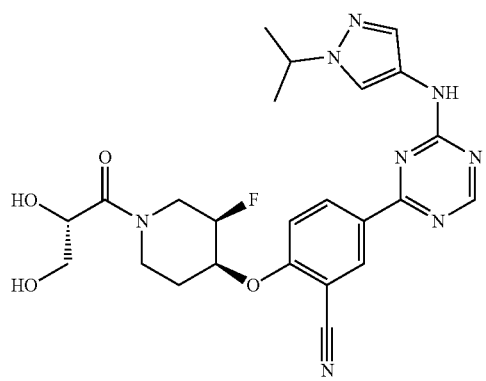 [SMILES: CC(C)n1cc(Nc2ncnc(-c3ccc(O[C@H]4CCN(C(=O)[C@@H](O)CO)C[C@H]4F)c(C#N)c3)n2)cn1]

2-(((3R,4S)-3-fluoropiperidin-4-yl)oxy)-5-(4-((1-isopropyl-1H-pyrazol-4-yl)amino)-1,3,5-triazin-2-yl)benzonitrile (44 mg, 0.104 mmol, 1 equiv) was dissolved in 5 mL dimethylformamide and to that was added diisopropylethylamine (DIEA, 3 equivs, 0.312 mmol, 54 uL), (S)-2,3-dihydroxypropanoic acid (2 equivs, 22 mg, 0.208 mmol) and (1-[bis(dimethylamino)methylene]-1H-1,2,3-triazolo[4,5-b]pyridinium 3-oxid hexafluorophosphate) (HATU, 2 equivs, 0.208 mmol, 79 mg) and the reaction was allowed to proceed for two hours. After which time LCMS showed complete consumption of the free piperidine and the reaction was quenched by the addition of 100 mL water. The crude was extracted into 100 mL of 10% methanol/dichloromethane and was then dried over sodium sulfate. The crude solution was then filtered, concentrated on a rotary evaporator and then flashed on silica gel employing an ISCO purification system using a gradient of 0-30% methanol/dichloromethane. The desired 2-(((3R,4S)-1-((S)-2,3-dihydroxypropanoyl)-3-fluoropiperidin-4-yl)oxy)-5-(4-((1-isopropyl-1H-pyrazol-4-yl)amino)-1,3,5-triazin-2-yl)benzonitrile was recovered as a light yellow solid. $^1$H NMR (300 MHz, DMSO-$d_6$) δ 10.31 (d, J=7.3 Hz, 1H), 9.02-8.44 (m, 3H), 8.01 (d, J=14.6 Hz, 1H), 7.81-7.40 (m, 2H), 5.34-4.84 (m, 3H), 4.87-3.85 (m, 4H), 3.75-3.34 (m, 3H), 2.51 (bs, 2H), 2.00 (bs, 2H), 1.44 (m, 6H). LCMS-ESI$^+$ (m/z): [M+H]$^+$ calcd for $C_{24}H_{27}FN_8O_4$: 510.2; found: 511.2.

Example 575

2-(((3R,4S)-1-((S)-2,3-dihydroxypropanoyl)-3-fluoropiperidin-4-yl)oxy)-5-((4-((3-methyl-4-(4-(oxetan-3-yl)piperazin-1-yl)phenyl)amino)-1,3,5-triazin-2-yl)benzonitrile

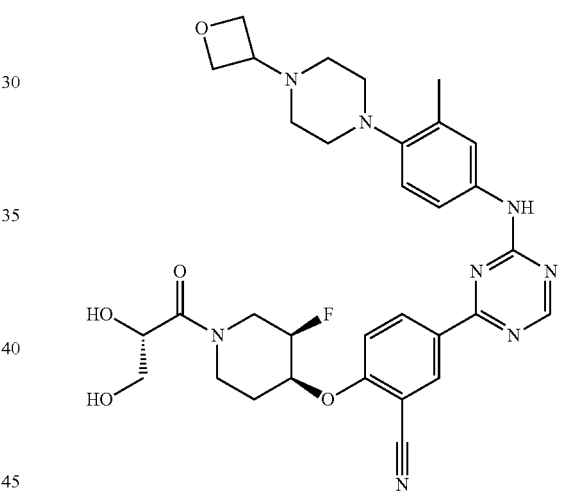

Step 1: 2-(((3R,4S)-1-(2,2-dimethyl-1,3-dioxolane-4-carbonyl)-3-fluoropiperidin-4-yl)oxy)-5-(4-((3-methyl-4-(4-(oxetan-3-yl)piperazin-1-yl)phenyl)amino)-1,3,5-triazin-2-yl)benzonitrile:

2-(((3R,4S)-3-fluoropiperidin-4-yl)oxy)-5-(4-((3-methyl-4-(4-(oxetan-3-yl)piperazin-1-yl)phenyl)amino)-1,3,5-triazin-2-yl)benzonitrile (100 mg, 0.184 mmol, 1 equiv) was dissolved in 5 mL dimethylformamide and to that was added racemic 2,2-dimethyl-1,3-dioxolane-4-carboxylic acid (2 equivs, 54 mg, 0.367 mmol), diisopropylethylamine (DIEA, 3 equivs, 96 uL, 0.551 mmol) and (1-[bis(dimethylamino)methylene]-1H-1,2,3-triazolo[4,5-b]pyridinium 3-oxid hexafluorophosphate) (HATU, 2 equivs, 140 mg, 0.367 mmol) and the reaction allowed to proceed for two hours. LCMS showed reaction complete and 100 mL water was then added to quench the reaction. The crude was extracted into 100 mL of 10% methanol/dichloromethane and then dried over sodium sulfate. The crude solution was then filtered, concentrated on a rotary evaporator and then flashed on silica gel employing an ISCO purification system using a gradient of 0-15% methanol/dichloromethane yielding 84 mg of the racemic ketal (68%) as a light yellow solid.

Step 2: 2-(((3R,4S)-1-(2,2-dimethyl-1,3-dioxolane-4-carbonyl)-3-fluoropiperidin-4-yl)oxy)-5-(4-((3-methyl-4-(4-(oxetan-3-yl)piperazin-1-yl)phenyl)amino)-1,3,5-triazin-2-yl)benzonitrile (84 mg, 0.125 mmol) was dissolved in 9.0 mL dichloromethane and to that was added 1 mL trifluoroacetic acid and allowed to react for two hours at room temperature. LCMS confirmed the complete deprotection of the ketal and all solvent was removed on a rotary evaporator. The crude was then dissolved in 10% methanol/dichloromethane and was washed with 100 mL saturated sodium bicarbonate and then dried on sodium sulfate. The sample was then filtered, concentrated and purified on silica gel employing an ISCO purification system using a gradient of 0-30% methanol/dichloromethane. The desired racemic diol 2-(((3R,4S)-1-(2,3-dihydroxypropanoyl)-3-fluoropiperidin-4-yl)oxy)-5-(4-((3-methyl-4-(4-(oxetan-3-yl)piperazin-1-yl)phenyl)amino)-1,3,5-triazin-2-yl)benzonitrile (71 mg, 90%) was recovered as a light yellow solid. $^1$H NMR (300 MHz, DMSO-$d_6$) δ 10.21 (s, 1H), 8.78 (s, 1H), 8.58 (d, J=8.2 Hz, 2H), 7.81-7.34 (m, 3H), 7.06 (d, J=8.6 Hz, 1H), 5.36-4.65 (m, 4H), 4.57 (t, J=6.5 Hz, 2H), 4.47 (t, J=6.1 Hz, 3H), 4.05 (d, J=59.3 Hz, 2H), 3.87-3.38 (m, 3H), 3.37-3.09 (m, 2H), 2.86 (bs, 4H), 2.50-2.34 (bs, 3H), 2.27 (bs, 4H), 1.99 (s, 2H). LCMS-ESI$^+$ (m/z): [M+H]$^+$ calcd for $C_{32}H_{37}FN_8O_5$: 632.3; found: 633.4.

Step 3: The above compound from Step 2, 2-(((3R,4S)-1-(2,3-dihydroxypropanoyl)-3-fluoropiperidin-4-yl)oxy)-5-(4-((3-methyl-4-(4-(oxetan-3-yl)piperazin-1-yl)phenyl)amino)-1,3,5-triazin-2-yl)benzonitrile was dissolved in (methanol) and purified on chiral column (Chiralpak IC) using gradient (MTBE:MeOH, 90:10) to the title compound as light yellow solid (later eluting isomer) $^1$H NMR (300 MHz, DMSO-$d_6$) δ 10.20 (s, 1H), 8.77 (s, 1H), 8.58 (d, J=8.2 Hz, 2H), 7.82-7.30 (m, 3H), 7.05 (d, J=8.6 Hz, 1H), 5.31-4.85 (m, 3H), 4.80-4.77 (m, 5H), 4.08 (q, J=5.3 Hz, 1H), 3.96 (d, J=13.2 Hz, 1H), 3.86-3.21 (m, 4H), 2.85 (bs, 4H), 2.42 (bs, 4H), 2.26 (s, 3H), 1.98 (s, 2H). LCMS-ESI$^+$ (m/z): [M+H]$^+$ calcd for $C_{32}H_{37}FN_8O_5$: 632.3; found: 633.0.

Example 576

2-(((3R,4S)-1-((R)-2,3-dihydroxypropanoyl)-3-fluoropiperidin-4-yl)oxy)-5-(4-((3-methyl-4-(4-(oxetan-3-yl)piperazin-1-yl)phenyl)amino)-1,3,5-triazin-2-yl)benzonitrile

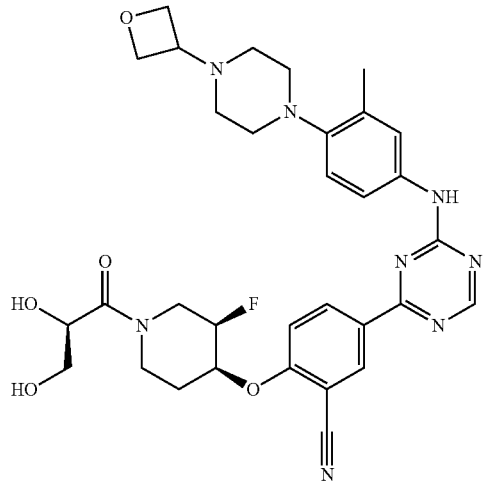 [SMILES: Cc1cc(Nc2ncnc(-c3ccc(O[C@H]4CCN(C(=O)[C@H](O)CO)C[C@H]4F)c(C#N)c3)n2)ccc1N1CCN(C2COC2)CC1]

The compound from Example 575, 2-(((3R,4S)-1-(2,3-dihydroxypropanoyl)-3-fluoropiperidin-4-yl)oxy)-5-(4-((3-methyl-4-(4-(oxetan-3-yl)piperazin-1-yl)phenyl)amino)-1,3,5-triazin-2-yl)benzonitrile was dissolved in methanol and purified on chiral column (Chiralpak IC) using gradient (MTBE:MeOH, 90:10) to yield the title compound (first eluting (R)-enantiomer) as light yellow solid. $^1$H NMR (300 MHz, DMSO-$d_6$) δ 10.18 (d, J=16.6 Hz, 1H), 8.77 (s, 1H), 8.58 (d, J=7.8 Hz, 2H), 7.84-7.31 (m, 3H), 7.05 (d, J=8.6 Hz, 1H), 5.30-4.66 (m, 3H), 4.56 (t, J=6.5 Hz, 2H), 4.51-3.86 (m, 4H), 3.48 (p, J=6.2, 5.6 Hz, 2H), 3.20 (dd, J=22.3, 8.0 Hz, 1H), 2.84 (d, J=4.9 Hz, 4H), 2.49-2.32 (m, 4H), 2.26 (s, 3H), 2.13-1.71 (m, 2H). LCMS-ESI$^+$ (m/z): [M+H]$^+$ calcd for $C_{32}H_{37}FN_8O_5$: 632.3; found: 633.0.

Example 577

2-(((S)-1-((S)-2,3-dihydroxypropanoyl)-3,3-difluoropiperidin-4-yl)oxy)-5-(4-((3-methoxy-4-(4-(oxetan-3-yl)piperazin-1-yl)phenyl)amino)-1,3,5-triazin-2-yl)benzonitrile

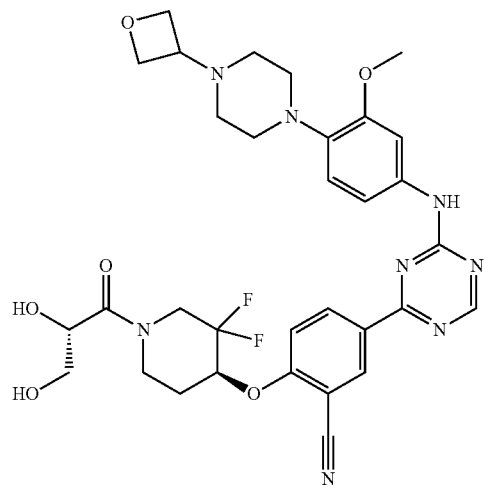 [SMILES: COc1cc(Nc2ncnc(-c3ccc(O[C@H]4CCN(C(=O)[C@@H](O)CO)CC4(F)F)c(C#N)c3)n2)ccc1N1CCN(C2COC2)CC1]

(S)-2-((3,3-difluoropiperidin-4-yl)oxy)-5-(4-((3-methoxy-4-(4-(oxetan-3-yl)piperazin-1-yl)phenyl)amino)-1,3,5-triazin-2-yl)benzonitrile (88 mg, 0.152 mmol, 1 equiv) was dissolved in 5 mL dimethylformamide and to that was added diisopropylethylamine (DIEA, 3 equivs, 0.456 mmol, 79 uL), (S)-2,3-dihydroxypropanoic acid (2 equivs, 32 mg, 0.304 mmol) and (1-[bis(dimethylamino)methylene]-1H-1,2,3-triazolo[4,5-b]pyridinium 3-oxid hexafluorophosphate) (HATU, 2 equivs, 0.304 mmol, 116 mg) and the reaction was allowed to proceed for two hours. After which time LCMS showed complete consumption of the free piperidine and the reaction was quenched by the addition of 100 mL water. The crude was extracted into 100 mL of 10% methanol/dichloromethane and was then dried over sodium sulfate. The crude solution was then filtered, concentrated on a rotary evaporator and then flashed on silica gel employing an ISCO purification system using a gradient of 0-30% methanol/dichloromethane. The desired 2-(((S)-1-((S)-2,3-dihydroxypropanoyl)-3,3-difluoropiperidin-4-yl)oxy)-5-(4-((3-methoxy-4-(4-(oxetan-3-yl)piperazin-1-yl)phenyl)amino)-1,3,5-triazin-2-yl)benzonitrile was recovered as a light yellow solid. ¹H NMR (300 MHz, DMSO-d₆) δ 10.24 (d, J=23.5 Hz, 1H), 8.79 (s, 1H), 8.62 (d, J=8.1 Hz, 2H), 7.69 (d, J=9.2 Hz, 1H), 7.29 (d, J=56.8 Hz, 2H), 6.91 (d, J=8.5 Hz, 1H), 5.57-5.06 (m, 2H), 4.79 (d, J=15.4 Hz, 1H), 4.67-3.98 (m, 6H), 3.86 (s, 3H), 3.72-3.41 (m, 5H), 2.99 (s, 4H), 2.72-2.29 (m, 4H), 2.18 (s, 1H), 1.41-1.09 (m, 1H). LCMS-ESI⁺ (m/z): [M+]⁺ calcd for $C_{32}H_{36}F_2N_8O_6$: 666.3; found: 667.2.

Example 578

2-(((3R,4S)-1-((S)-2,3-dihydroxypropanoyl)-3-fluoropiperidin-4-yl)oxy)-5-(4-((3-methoxy-4-(4-(oxetan-3-yl)piperazin-1-yl)phenyl)amino)-1,3,5-triazin-2-yl)benzonitrile

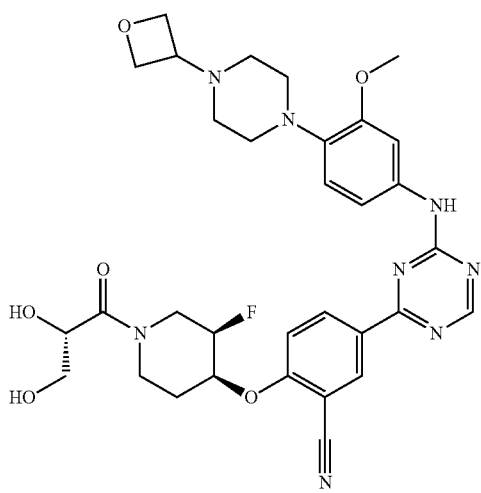 [SMILES: COc1cc(Nc2ncnc(-c3ccc(O[C@H]4CCN(C(=O)[C@@H](O)CO)C[C@H]4F)c(C#N)c3)n2)ccc1N1CCN(C2COC2)CC1]

Step 1: 2-(((3R,4S)-1-(2,3-dihydroxypropanoyl)-3-fluoropiperidin-4-yl)oxy)-5-(4-((3-methoxy-4-(4-(oxetan-3-yl)piperazin-1-yl)phenyl)amino)-1,3,5-triazin-2-yl)benzonitrile was prepared following very similar procedure to Example 575. ¹H NMR (300 MHz, DMSO-d₆) δ 10.21 (d, J=24.2 Hz, 1H), 8.78 (s, 1H), 8.69-8.48 (m, 2H), 7.64 (d, J=9.0 Hz, 2H), 7.20 (s, 1H), 6.90 (d, J=8.5 Hz, 1H), 5.32-5.02 (m, 2H), 5.02-4.66 (m, 2H), 4.55 (t, J=6.5 Hz, 2H), 4.50-4.23 (m, 3H), 3.85 (s, 2H), 3.45 (m, 4H), 2.97 (bs, 4H), 2.40 (bs, 4H), 1.95 (m, 2H). LCMS-ESI⁺ (m/z): [M+H]⁺ calcd for $C_{30}H_{35}FN_8O_4$: 648.3; found: 649.7.

Step 2: The racemic mixture was then separated by chiral column Chromatography to give the title compound. ¹H NMR (300 MHz, DMSO-d₆) δ 10.22 (d, J=24.6 Hz, 1H), 8.78 (s, 1H), 8.70-8.45 (m, 2H), 7.64 (d, J=9.0 Hz, 1H), 7.29 (d, J=54.8 Hz, 2H), 6.90 (d, J=8.5 Hz, 1H), 5.36-4.86 (m, 3H), 4.81-4.22 (m, 7H), 4.22-3.68 (m, 3H), 3.68-3.35 (m, 3H), 3.31 (m, 2H), 2.97 (s, 4H), 2.40 (s, 4H), 1.94 (d, J=25.2 Hz, 2H). LCMS-ESI⁺ (m/z): [M+H]⁺ calcd for $C_{32}H_{37}FN_8O_8$: 648.3; found: 649.5.

Example 579

2-(((3R,4S)-1-((R)-2,3-dihydroxypropanoyl)-3-fluoropiperidin-4-yl)oxy)-5-(4-((3-methoxy-4-(4-(oxetan-3-yl)piperazin-1-yl)phenyl)amino)-1,3,5-triazin-2-yl)benzonitrile

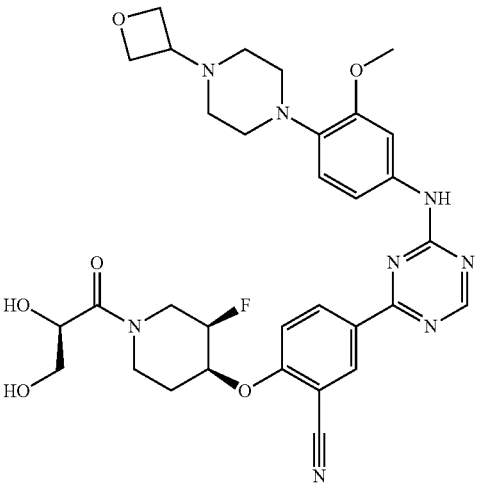 [SMILES: COc1cc(Nc2ncnc(-c3ccc(O[C@H]4CCN(C(=O)[C@H](O)CO)C[C@H]4F)c(C#N)c3)n2)ccc1N1CCN(C2COC2)CC1]

The racemic compound from Example 578 (step 1), was dissolved in (methanol) and purified on chiral column (Chiralpak IC) using gradient (MTBE:MeOH, 90:10) to yield the title compound as light yellow solid ¹H NMR (300 MHz, DMSO-d₆) δ 10.22 (d, J=23.3 Hz, 1H), 8.78 (s, 1H), 8.69-8.45 (m, 2H), 7.64 (d, J=9.0 Hz, 1H), 7.29 (d, J=55.9 Hz, 2H), 6.90 (d, J=8.6 Hz, 1H), 5.31-4.64 (m, 4H), 4.55 (t, J=6.5 Hz, 2H), 4.49-3.63 (m, 7H), 3.63-3.37 (m, 2H), 3.31 (m, 1H), 2.98 (s, 4H), 2.44 (d, J=23.1 Hz, 4H), 1.94 (d, J=25.6 Hz, 2H). LCMS-ESI⁺ (m/z): [M+H]⁺ calcd for $C_{32}H_{37}FN_8O_8$: 648.3; found: 649.5.

Example 580

2-(((4S)-1-(2,3-dihydroxypropanoyl)-3,3-difluoropiperidin-4-yl)oxy)-5-(4-((4-(4-(oxetan-3-yl)piperazin-1-yl)phenyl)amino)-1,3,5-triazin-2-yl)benzonitrile

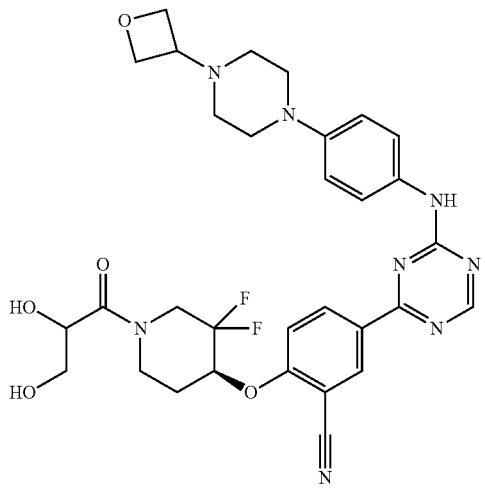 [SMILES: N#Cc1cc(-c2ncnc(Nc3ccc(N4CCN(C5COC5)CC4)cc3)n2)ccc1O[C@H]1CCN(C(=O)C(O)CO)CC1(F)F]

The title compound was synthesized in the same manner as Example 575. ¹H NMR (300 MHz, DMSO-d₆) δ 10.15 (d, J=16.3 Hz, 1H), 8.75 (s, 1H), 8.69-8.45 (m, 2H), 7.78-7.39 (m, 3H), 6.96 (s, 2H), 5.37 (m, 1H), 5.22 (d, J=7.1 Hz, 1H), 4.75 (m, 1H), 4.56 (t, J=6.5 Hz, 2H), 4.50-4.31 (m, 3H), 3.85 (m, 1H), 3.73-3.36 (m, 2H), 3.14 (s, 4H), 2.48-2.31 (bs, 4H), 2.13 (m, 2H). LCMS-ESI⁺ (m/z): [M+H]⁺ calcd for $C_{31}H_{34}F_7N_8O_5$: 636.3; found: 637.0.

Example 581

2-(((S)-1-((S)-2,3-dihydroxypropanoyl)-3,3-difluoropiperidin-4-yl)oxy)-5-(4-((4-(4-(oxetan-3-yl)piperazin-1-yl)phenyl)amino)-1,3,5-triazin-2-yl)benzonitrile

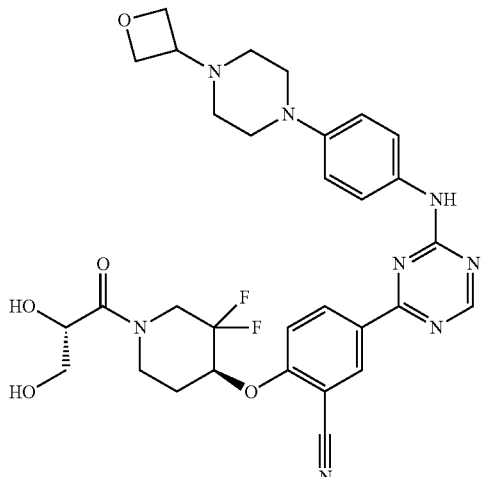

Racemic Example 580 was dissolved in (MeOH) and purified on chiral column (Chiralpak IC) using gradient (MTBE:MeOH, 90:10) to yield the tile compound (second eluting isomer) as light yellow solids. ¹H NMR (300 MHz, DMSO-d₆) δ 10.16 (s, 1H), 8.76 (s, 1H), 8.68-8.44 (m, 2H), 7.82-7.43 (m, 3H), 6.97 (s, 2H), 5.32 (d, J=35.4 Hz, 2H), 4.76 (s, 1H), 4.57 (t, J=6.5 Hz, 2H), 4.48 (t, J=6.1 Hz, 2H), 4.41 (bs, 1H), 4.18 (s, 1H), 3.85 (s, 1H), 3.71-3.37 (m, 3H), 3.15 (s, 4H), 2.41 (t, J=5.0 Hz, 4H), 2.22 (d, J=31.7 Hz, 2H). LCMS-ESI⁺ (m/z): [M+H]⁺ calcd for $C_{31}H_{34}F_2N_8O_5$: 636.3; found: 637.0.

Example 582

2-(((S)-1-((R)-2,3-dihydroxypropanoyl)-3,3-difluoropiperidin-4-yl)oxy)-5-(4-((4-(4-(oxetan-3-yl)piperazin-1-yl)phenyl)amino)-1,3,5-triazin-2-yl)benzonitrile

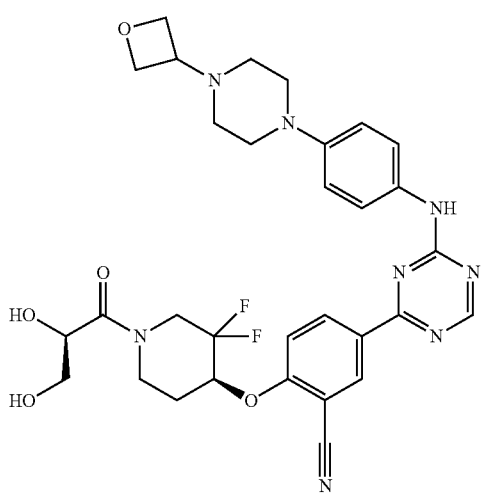 [SMILES: N#Cc1cc(-c2ncnc(Nc3ccc(N4CCN(C5COC5)CC4)cc3)n2)ccc1O[C@H]1CCN(C(=O)[C@H](O)CO)CC1(F)F]

Racemic Example 580 was dissolved in (MeOH) and purified on chiral column (Chiralpak IC) using gradient (MTBE:MeOH, 90:10) to yield the tile compound (first eluting isomer) as light yellow solids ¹H NMR (300 MHz, DMSO-d₆) δ 10.16 (d, J=16.2 Hz, 1H), 8.76 (s, 1H), 8.60 (d, J=10.2 Hz, 2H), 7.79-7.39 (m, 3H), 6.97 (s, 2H), 5.38 (s, 1H), 5.23 (d, J=7.1 Hz, 1H), 4.77 (s, 1H), 4.57 (t, J=6.5 Hz, 2H), 4.48 (t, J=6.0 Hz, 2H), 4.40 (d, J=6.3 Hz, 1H), 4.32-3.77 (m, 1H), 3.77-3.38 (m, 4H), 3.26-3.00 (m, 4H), 2.41 (t, J=5.0 Hz, 4H), 2.02 (d, J=84.1 Hz, 2H). LCMS-ESI⁺ (m/z): [M+H]⁺ calcd for $C_{31}H_{34}F_2N_8O_5$: 636.3; found: 637.0.

Example 583

2-(((3R,4S)-3-fluoro-1-((S)-2-hydroxypropanoyl)piperidin-4-yl)oxy)-5-(4-((4-(4-(2-hydroxyethyl)piperazin-1-yl)phenyl)amino)-1,3,5-triazin-2-yl)benzonitrile

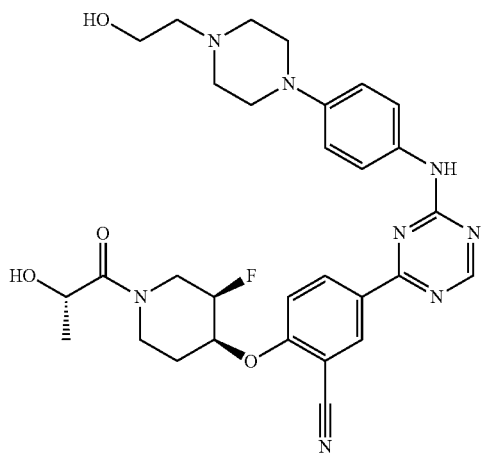 [SMILES: C[C@H](O)C(=O)N1CC[C@H](Oc2ccc(-c3ncnc(Nc4ccc(N5CCN(CCO)CC5)cc4)n3)cc2C#N)[C@H](F)C1]

2-(((3R,4S)-3-fluoropiperidin-4-yl)oxy)-5-(4-((4-(4-(2-hydroxyethyl)piperazin-1-yl)phenyl)amino)-1,3,5-triazin-2-yl)benzonitrile (50mg, 0.096 mmol, 1 equiv) was charged to a 100 mL round-bottomed flask and then dissolved in 5 mL dimethylformamide. To that solution was added diisopropylethylamine (DIEA, 3 equivs, 50 uL, 0.289 mmol), (S)-lactic acid (2 equivs, 193 uL of a 1M solution in dimethylformamide) and (1-[bis(dimethylamino)methylene]-1H-1,2,3-triazolo[4,5-b]pyridinium 3-oxid hexafluorophosphate) (HATU, 2 equivs, 223 mg, 0.193 mmol) and allowed to react for two hours. LCMS confirmed completion of the reaction and 100 mL 10% methanol/dichloromethane and 100 mL water were then added and the crude sample was extracted into the organic layer. The organic layer was then dried over sodium sulfate, filtered, concentrated on a rotary evaporator and flash chromatographed on silica gel employing an ISCO system and using a gradient of 0-25% methanol/dichloromethane. The desired 2-(((3R,4S)-3-fluoro-1-((S)-2-hydroxypropanoyl)piperidin-4-yl)oxy)-5-(4-((4-(4-(2-hydroxyethyl)piperazin-1-yl)phenyl)amino)-1,3,5-triazin-2-yl)benzonitrile was obtained (25mg, 44%) as a light yellow solid.
¹H NMR (300 MHz, DMSO-d₆) δ 10.12 (d, J=16.8 Hz, 1H), 8.74 (s, 1H), 8.57 (d, J=11.3 Hz, 2H), 7.77-7.40 (m, 3H), 6.95 (s, 2H), 5.98-4.88 (m, 3H), 4.62-4.28 (m, 1H), 4.28-3.83 (m, 2H), 3.53 (q, J=6.0 Hz, 2H), 3.32 (m, 3H), 3.09 (d, J=5.9 Hz, 4H), 2.56 (t, J=5.0 Hz, 4H), 2.43 (t, J=6.2 Hz, 2H), 2.14-1.63 (m, 2H), 1.20 (dd, J=6.7, 2.8 Hz, 3H). LCMS-ESI⁺ (m/z): [M+H]⁺ calcd for $C_{30}H_{35}FN_8O_4$: 590.3; found: 590.8.

Example 584

2-(((3R,4S)-1-((S)-2,3-dihydroxypropanoyl)-3-fluoropiperidin-4-yl)oxy)-5-(4-((4-(4-(oxetan-3-yl)piperazin-1-yl)phenyl)amino)-1,3,5-triazin-2-yl)benzonitrile

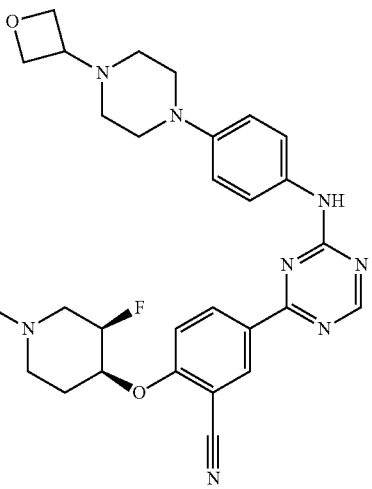

Racemic 2-(((3R,4S)-1-(2,3-dihydroxypropanoyl)-3-fluoropiperidin-4-yl)oxy)-5-(4-((4-(4-(oxetan-3-yl)piperazin-1-yl)phenyl)amino)-1,3,5-triazin-2-yl)benzonitrile was prepared in similar manner to Example 575 and then was purified on a chiral column (Chiralpak IC) using gradient (MTBE:MeOH, 90:10) to afford the title compound. ¹H NMR (300 MHz, DMSO-d₆) δ 10.13 (d, J=17.0 Hz, 1H), 8.74 (s, 1H), 8.57 (d, J=11.0 Hz, 2H), 7.81-7.40 (m, 3H), 6.96 (s, 2H), 5.80-5.29 (m, 1H), 5.29-4.66 (m, 3H), 4.57 (t, J=6.5 Hz, 3H), 4.51-3.86 (m, 5H), 3.87-3.35 (m, 3H), 3.14 (s, 4H), 2.50-2.30 (m, 4H), 1.99 (s, 2H). LCMS-ESI⁺ (m/z): [M+H]⁺ calcd for $C_{31}H_{35}FN_8O_5$: 618.3; found: 619.3.

Example 585

2-(((3R,4S)-1-((R)-2,3-dihydroxypropanoyl)-3-fluoropiperidin-4-yl)oxy)-5-(4-((4-(4-(oxetan-3-yl)piperazin-1-yl)phenyl)amino)-1,3,5-triazin-2-yl)benzonitrile

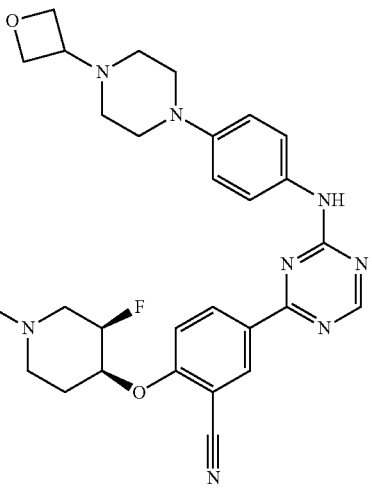

Racemic 2-(((3R,4S)-1-(2,3-dihydroxypropanoyl)-3-fluoropiperidin-4-yl)oxy)-5-(4-((4-(4-(oxetan-3-yl)piperazin-1-yl)phenyl)amino)-1,3,5-triazin-2-yl)benzonitrile was prepared in similar manner to Example 575 and then was purified on a chiral column (Chiralpak IC) using gradient (MTBE:MeOH, 90:10) to afford the title compound.

¹H NMR (300 MHz, DMSO-d₆) δ 10.13 (d, J=16.9 Hz, 1H), 8.74 (s, 1H), 8.57 (d, J=10.4 Hz, 2H), 7.78-7.37 (m, 3H), 6.96 (s, 2H), 5.33-4.64 (m, 4H), 4.56 (t, J=6.5 Hz, 2H), 4.50-3.83 (m, 4H), 3.82-3.35 (m, 4H), 3.26-3.02 (m, 4H), 2.50-2.29 (m, 4H), 2.17-1.70 (m, 2H). LCMS-ESI⁺ (m/z): [M+H]⁺ calcd for $C_{31}H_{35}FN_8O_5$: 618.3; found: 619.3.

Example 586

2-(((3R,4S)-1-(2-cyanopropanoyl)-3-fluoropiperidin-4-yl)oxy)-5-(4-((4-(4-(oxetan-3-yl)piperazin-1-yl)phenyl)amino)-1,3,5-triazin-2-yl)benzonitrile

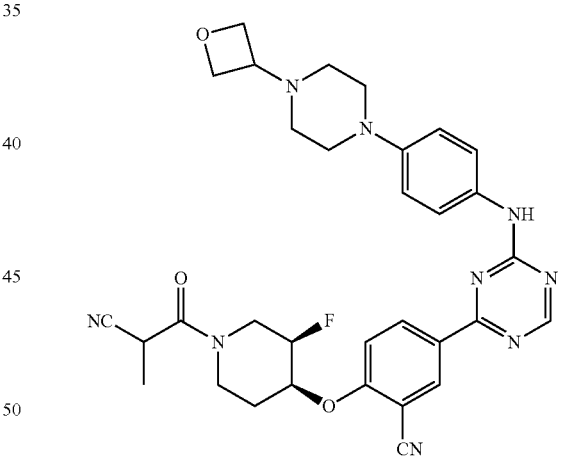

To a solution of 2-(((3R,4S)-3-fluoropiperidin-4-yl)oxy)-5-(4-((4-(4-(oxetan-3-yl)piperazin-1-yl)phenyl)amino)-1,3,5-triazin-2-yl)benzonitrile (35 mgs, 0.07 mmol) in DMF (1.0 mL) was added 2-cyanopropanoic acid (13 mgs, 0.13 mmol), HATU (50 mgs, 0.13 mmol) and DIPEA (0.02 mL, 0.13 mmol). The above reaction mixture was stirred at room temperature for 2 h, evaporated under reduced pressure and purified via preparative HPLC (5-65% acetonitrile in water, 0.1% trifluoroacteic acid buffer) to yield the title compound. LCMS-ESI⁺ (m/z): [M+H]⁺ calcd for $C_{32}H_{34}FN_9O_3$: 612.3; found: 612.3.

Example 587

2-(((3R,4S)-1-(1-cyanocyclopropanecarbonyl)-3-fluoropiperidin-4-yl)oxy)-5-(4-((4-(4-(oxetan-3-yl)piperazin-1-yl)phenyl)amino)-1,3,5-triazin-2-yl)benzonitrile

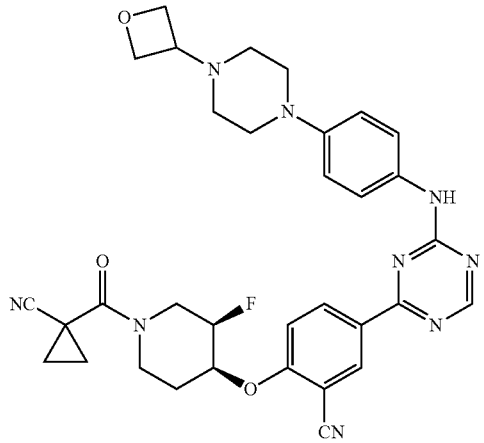 [SMILES: N#Cc1cc(-c2ncnc(Nc3ccc(N4CCN(C5COC5)CC4)cc3)n2)ccc1O[C@H]1CCN(C(=O)C2(C#N)CC2)C[C@H]1F]

The title compound was synthesized in the same manner as Example 586. LCMS-ESI+ (m/z): [M+H]+ calcd for C33H34FN9O3: 624.2; found: 624.3.

Example 588

2-(((3R,4S)-3-fluoro-1-((2S,4S)-4-hydroxypyrrolidine-2-carbonyl)piperidin-4-yl)oxy)-5-(4-((4-(4-(oxetan-3-yl)piperazin-1-yl)phenyl)amino)-1,3,5-triazin-2-yl)benzonitrile

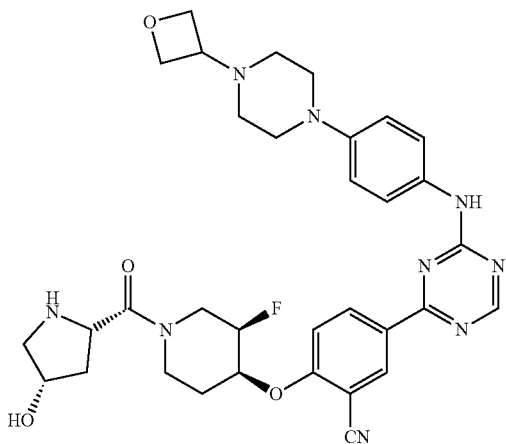

The title compound was synthesized in the same manner as Example 586. LCMS-ESI+ (m/z): [M+H]+ calcd for C33H38FN9O4: 644.3; found: 644.1.

Example 589

2-(((3R,4S)-3-fluoro-1-((2S,4R)-4-hydroxypyrrolidine-2-carbonyl)piperidin-4-yl)oxy)-5-(4-((4-(4-(oxetan-3-yl)piperazin-1-yl)phenyl)amino)-1,3,5-triazin-2-yl)benzonitrile

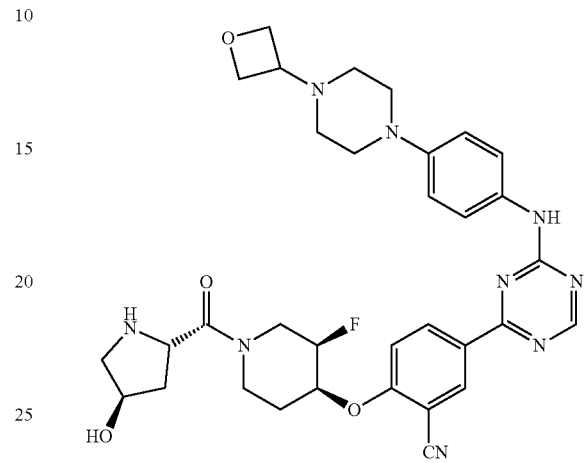

The title compound was synthesized in the same manner as Example 586. LCMS-ESI+ (m/z): [M+H]+ calcd for C33H38FN9O4: 644.3; found: 644.1.

Example 590

3-(((S)-1-((S)-2-hydroxypropanoyl)pyrrolidin-3-yl)methoxy)-5-(4-((4-(4-(oxetan-3-yl)piperazin-1-yl)phenyl)amino)-1,3,5-triazin-2-yl)benzonitrile

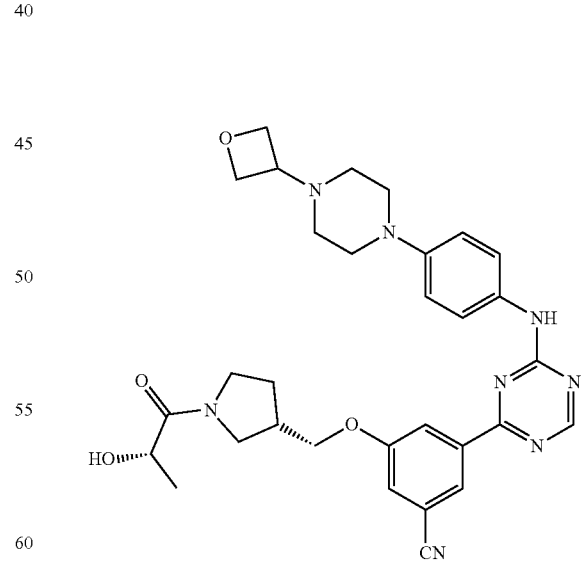

The title compound was synthesized in the same manner as Example 134 using (S)-tert-butyl 3-(hydroxymethyl)pyrrolidine-1-carboxylate instead of tert-butyl 4-hydroxypiperidine-1-carboxylate. LCMS-ESI+ (m/z): [M+H]+ calcd for C31H36N8O4: 585.4; found: 585.2.

Example 591

(S)-3-((1-(2-hydroxyacetyl)pyrrolidin-3-yl)methoxy)-5-(4-((4-(4-(oxetan-3-yl)piperazin-1-yl)phenyl)amino)-1,3,5-triazin-2-yl)benzonitrile

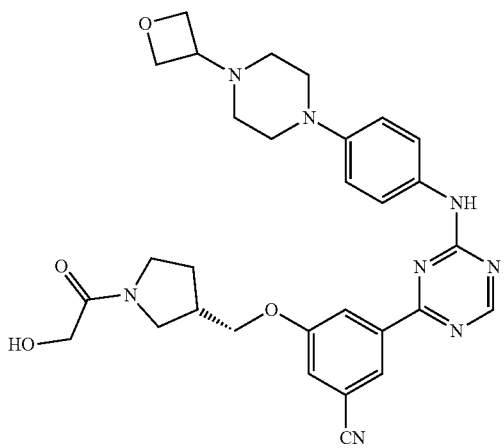

The title compound was synthesized in the same manner as Example 134 using using (S)-tert-butyl 3-(hydroxymethyl)pyrrolidine-1-carboxylate instead of tert-butyl 4-hydroxypiperidine-1-carboxylate and using Glycolic acid instead of (S)-2-hydroxypropanoic acid. LCMS-ESI⁺ (m/z): [M+H]⁺ calcd for C30H34N8O4: 571.3; found: 571.1.

Examples 592-610

The following examples were prepared using general procedure described below: A solution of corresponding alcohol (3 equiv) in THF (3 mL) was stirred in an ice-water bath under an atmosphere of Argon. Potassium tert-butoxide (1.0 M, 3 equiv) was added in a single portion and the mixture was stirred at 0° C. for 30 minutes, and then 2-fluoro-5-(4-((4-(4-(oxetan-3-yl)piperazin-1-yl)phenyl)amino)-1,3,5-triazin-2-yl)benzonitrile was added (1 equiv). The mixture was stirred for 2 hr at rt After the mixture cooled to room temperature, water was added, and mixture evaporated under reduced pressure. Solids were purified via preparative HPLC (5-65% acetonitrile in water, 0.1% trifluoroacetic acid buffer) to yield the final product.

| Example | Structure | Formula-Parent | M calcd | M + H found |
|---|---|---|---|---|
| 592 | 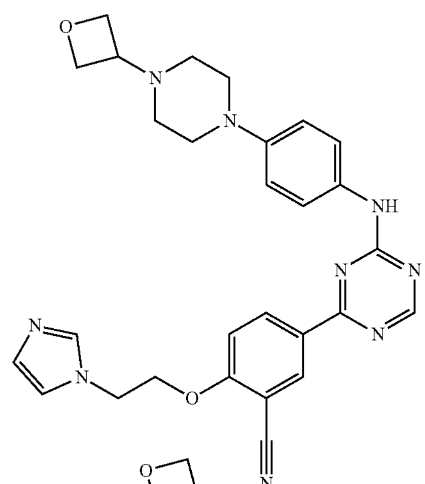 | C28H29N9O2 | 523.6 | 524.3 |
| 593 | 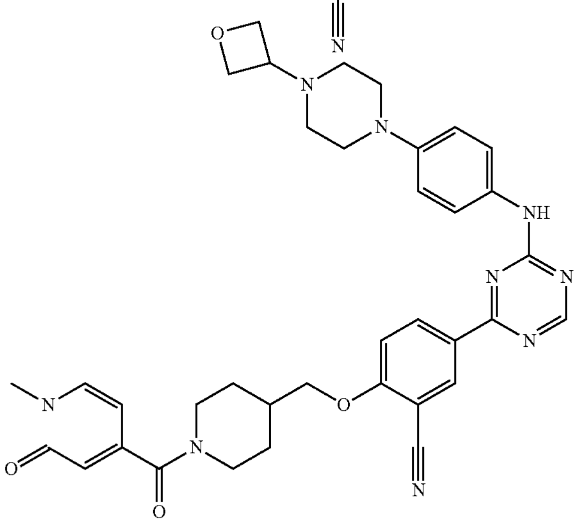 | C36H39N9O4 | 661.8 | 662.5 |

| Example | Structure | Formula-Parent | M calcd | M + H found |
|---|---|---|---|---|
| 594 | 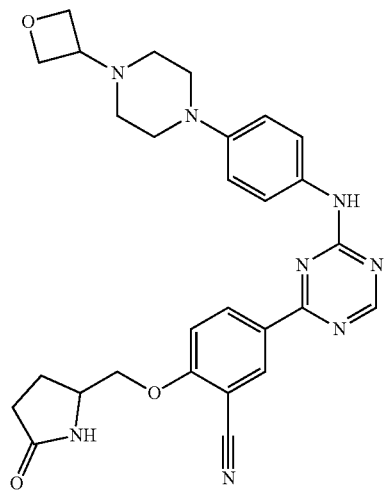 [SMILES: N#Cc1cc(-c2ncnc(Nc3ccc(N4CCN(C5COC5)CC4)cc3)n2)ccc1OCC1CCC(=O)N1] | C28H30N8O3 | 526.6 | 527.2 |
| 595 | 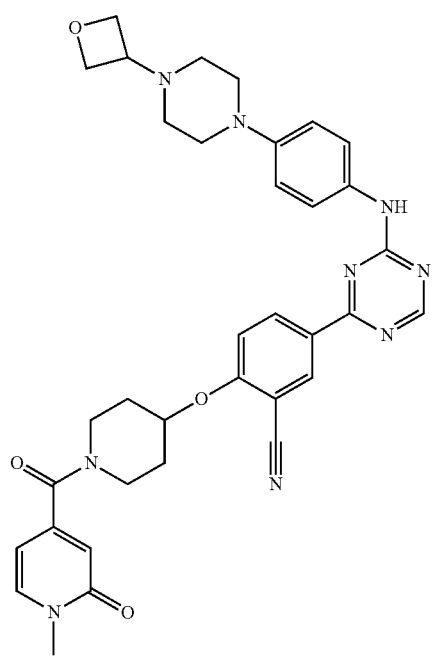 [SMILES: Cn1ccc(C(=O)N2CCC(Oc3ccc(-c4ncnc(Nc5ccc(N6CCN(C7COC7)CC6)cc5)n4)cc3C#N)CC2)cc1=O] | C35H37N9O4 | 647.7 | 648.3 |

-continued

| Example | Structure | Formula-Parent | M calcd | M + H found |
|---|---|---|---|---|
| 596 | 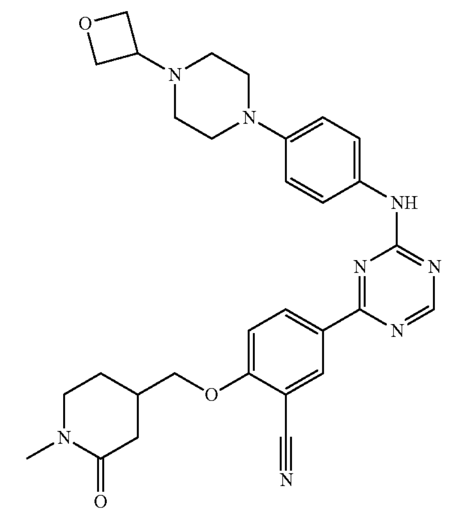 [SMILES: CN1CCC(COc2ccc(-c3ncnc(Nc4ccc(N5CCN(C6COC6)CC5)cc4)n3)cc2C#N)CC1=O] | C30H34N8O3 | 554.6 | 555.4 |
| 597 | 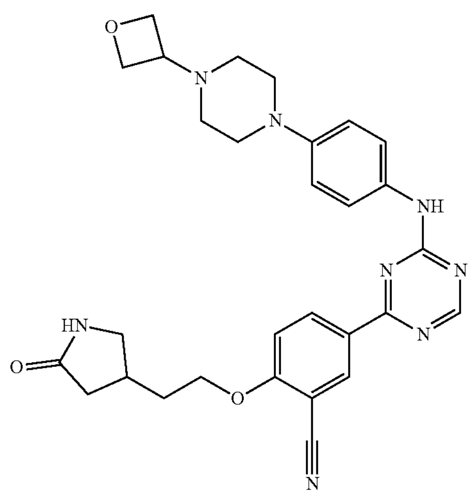 [SMILES: N#Cc1cc(-c2ncnc(Nc3ccc(N4CCN(C5COC5)CC4)cc3)n2)ccc1OCCC1CNC(=O)C1] | C29H32N8O3 | 540.6 | 541.3 |
| 598 | 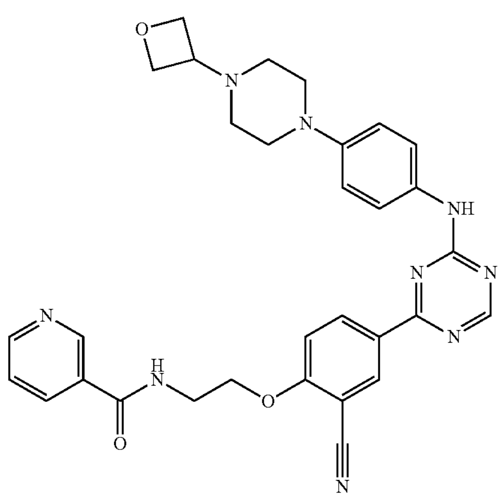 [SMILES: N#Cc1cc(-c2ncnc(Nc3ccc(N4CCN(C5COC5)CC4)cc3)n2)ccc1OCCNC(=O)c1cccnc1] | C31H31N9O3 | 577.6 | 578.3 |

| Example | Structure | Formula-Parent | M calcd | M + H found |
|---|---|---|---|---|
| 599 | 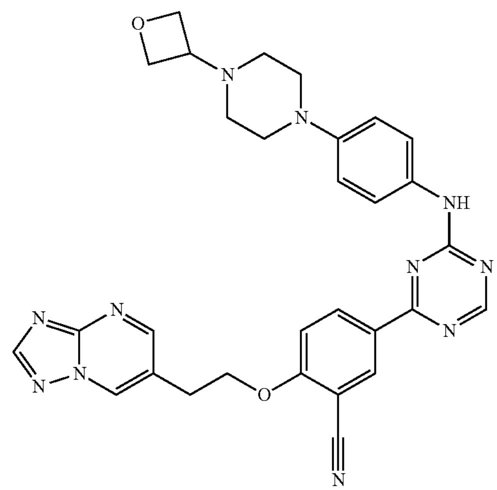 [SMILES: N#Cc1cc(-c2ncnc(Nc3ccc(N4CCN(C5COC5)CC4)cc3)n2)ccc1OCCc1cnc2ncnn2c1] | C30H29N11O2 | 575.6 | 576.2 |
| 600 | 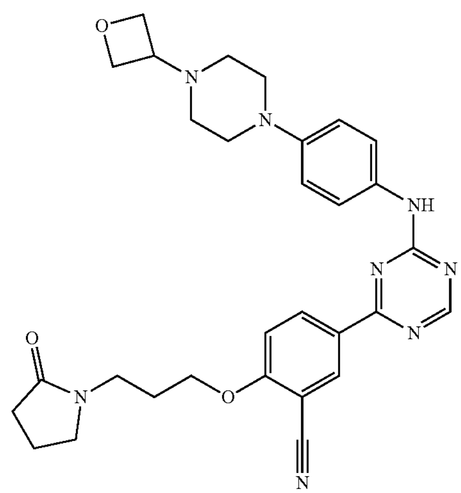 [SMILES: N#Cc1cc(-c2ncnc(Nc3ccc(N4CCN(C5COC5)CC4)cc3)n2)ccc1OCCCN1CCCC1=O] | C30H34N8O3 | 554.6 | 555.4 |
| 601 | 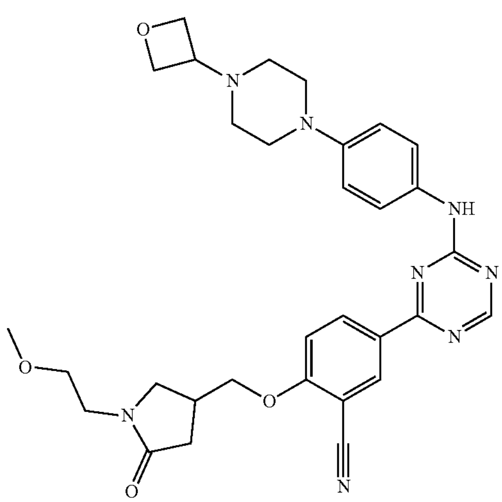 [SMILES: COCCN1CC(COc2ccc(-c3ncnc(Nc4ccc(N5CCN(C6COC6)CC5)cc4)n3)cc2C#N)CC1=O] | C31H36N8O4 | 584.7 | 585.4 |

-continued

| Example | Structure | Formula-Parent | M calcd | M + H found |
|---------|-----------|----------------|---------|-------------|
| 602 | 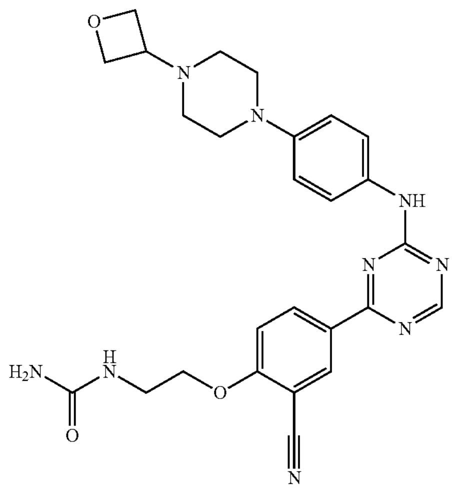 [SMILES: N#Cc1cc(-c2ncnc(Nc3ccc(N4CCN(C5COC5)CC4)cc3)n2)ccc1OCCNC(N)=O] | C26H29N9O3 | 515.6 | 516.3 |
| 603 | 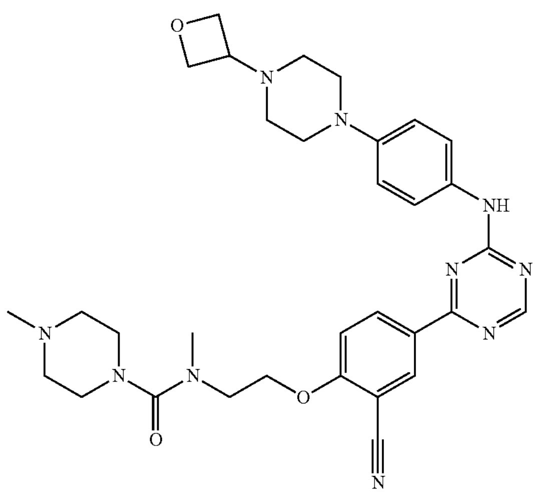 [SMILES: CN1CCN(C(=O)N(C)CCOc2ccc(-c3ncnc(Nc4ccc(N5CCN(C6COC6)CC5)cc4)n3)cc2C#N)CC1] | C32H40N10O3 | 612.7 | 613.3 |
| 604 | 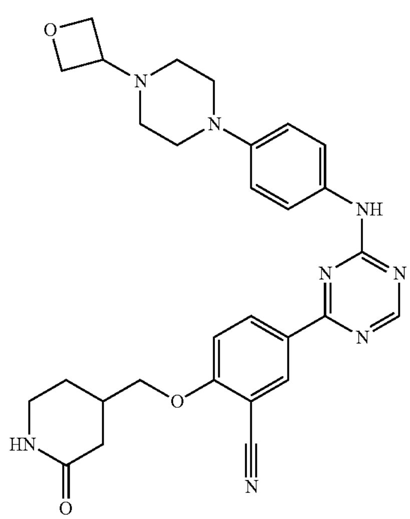 [SMILES: N#Cc1cc(-c2ncnc(Nc3ccc(N4CCN(C5COC5)CC4)cc3)n2)ccc1OCC1CCNC(=O)C1] | C29H32N8O3 | 540.6 | 541.3 |

-continued

| Example | Structure | Formula-Parent | M calcd | M + H found |
|---|---|---|---|---|
| 605 | 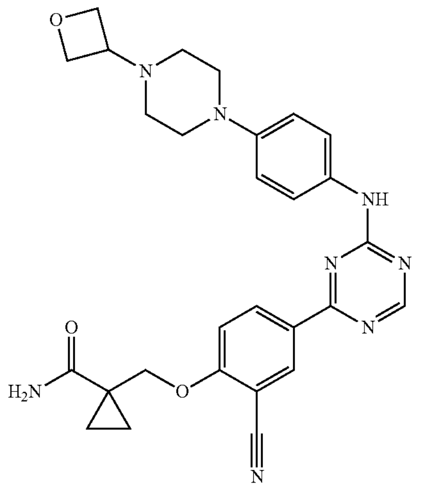 [SMILES: N#Cc1cc(-c2ncnc(Nc3ccc(N4CCN(C5COC5)CC4)cc3)n2)ccc1OCC1(C(N)=O)CC1] | C28H30N8O3 | 526.6 | 527.3 |
| 606 | 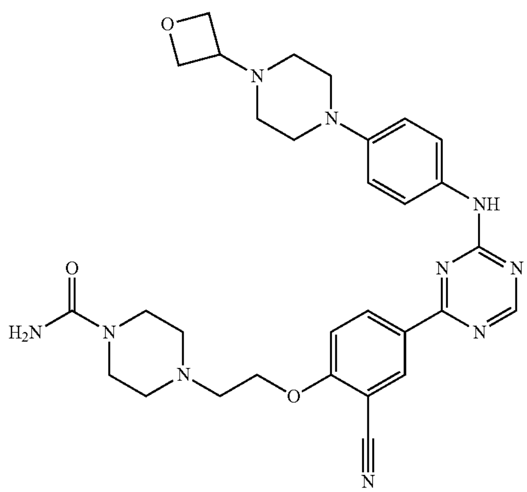 [SMILES: N#Cc1cc(-c2ncnc(Nc3ccc(N4CCN(C5COC5)CC4)cc3)n2)ccc1OCCN1CCN(C(N)=O)CC1] | C30H36N10O3 | 584.7 | 585.3 |
| 607 | 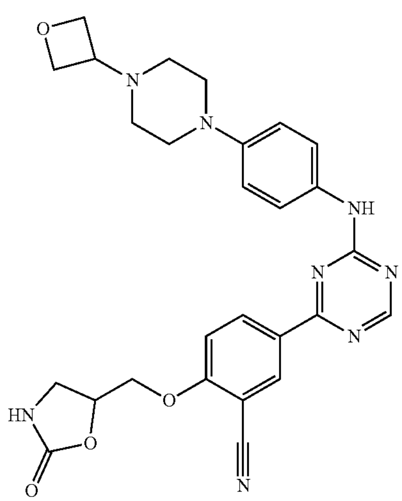 [SMILES: N#Cc1cc(-c2ncnc(Nc3ccc(N4CCN(C5COC5)CC4)cc3)n2)ccc1OCC1CNC(=O)O1] | C27H28N8O4 | 528.6 | 529.3 |

-continued

| Example | Structure | Formula-Parent | M calcd | M + H found |
|---------|-----------|----------------|---------|-------------|
| 608 | 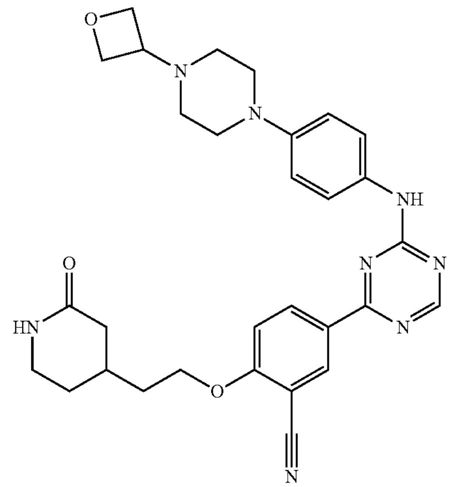 [SMILES: N#Cc1cc(-c2ncnc(Nc3ccc(N4CCN(C5COC5)CC4)cc3)n2)ccc1OCCC1CCNC(=O)C1] | C29H33N9O3 | 555.6 | 556.3 |
| 609 | 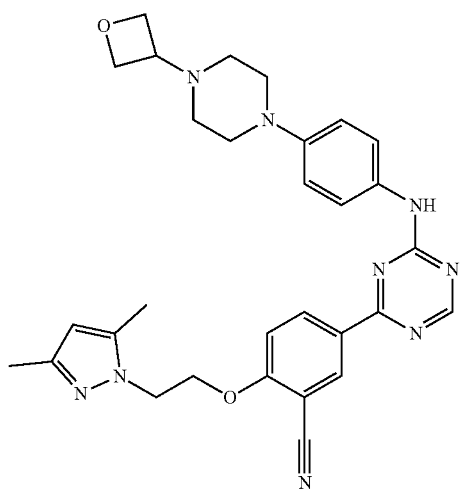 [SMILES: Cc1cc(C)n(CCOc2ccc(-c3ncnc(Nc4ccc(N5CCN(C6COC6)CC5)cc4)n3)cc2C#N)n1] | C30H33N9O2 | 551.6 | 552.3 |
| 610 | 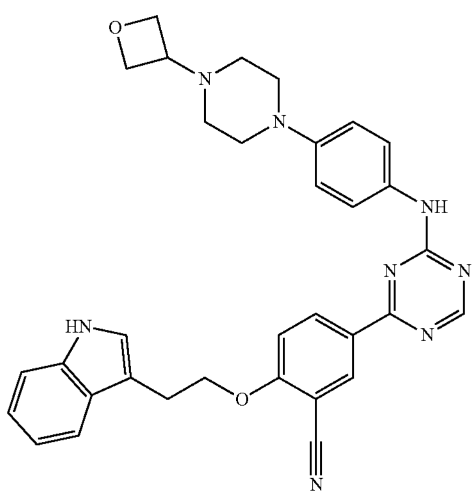 [SMILES: N#Cc1cc(-c2ncnc(Nc3ccc(N4CCN(C5COC5)CC4)cc3)n2)ccc1OCCc1c[nH]c2ccccc12] | C33H32N8O2 | 572.7 | 573.3 |

Example 611

2-(((3R,4S)-3-fluoro-1-(pyridin-3-yl)piperidin-4-yl)oxy)-5-(4-((4-(4-(oxetan-3-yl)piperazin-1-yl)phenyl)amino)-1,3,5-triazin-2-yl)benzonitrile

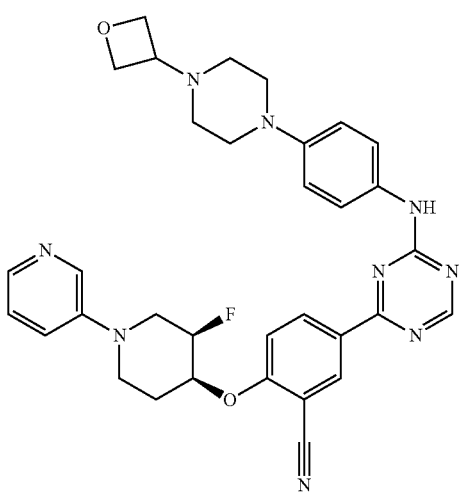 [SMILES: N#Cc1cc(-c2ncnc(Nc3ccc(N4CCN(C5COC5)CC4)cc3)n2)ccc1O[C@H]1CCN(c2cccnc2)C[C@H]1F]

The title compound was prepared following a similar procedure reported in Example 480 using 3-bromopyridine. LCMS-ESI$^+$ (m/z): [M+H]$^+$ calcd. for $C_{33}H_{34}FN_9O_2$ Exact Mass: 608.3 found: 608.3.

Example 612

2-(((3R,4S)-3-fluoro-1-(3-methyl-1,2,4-oxadiazole-5-carbonyl)piperidin-4-yl)oxy)-5-(4-((4-(4-(oxetan-3-yl)piperazin-1-yl)phenyl)amino)-1,3,5-triazin-2-yl)benzonitrile

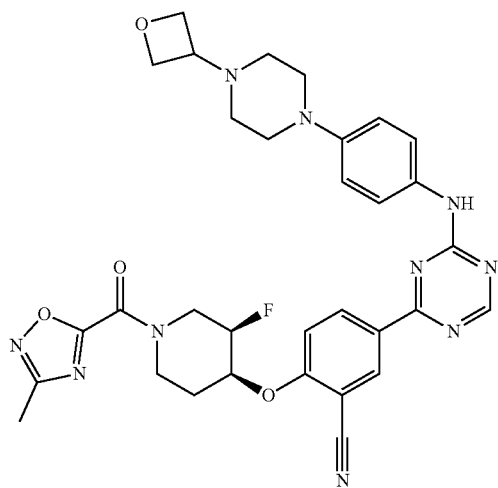 [SMILES: Cc1noc(C(=O)N2CC[C@H](Oc3ccc(-c4ncnc(Nc5ccc(N6CCN(C7COC7)CC6)cc5)n4)cc3C#N)[C@H](F)C2)n1]

The title compound was prepared following a similar procedure reported in Example 461 using 3-methyl-1,2,4-oxadiazole-5-carboxylic acid. $^1$H NMR (400 MHz, DMSO-d$_6$) δ 10.10 (s, 1H), 8.73 (s, 1H), 8.66-8.45 (m, 2H), 7.68-7.61 (m, 1H), 7.61-7.48 (m, 2H), 6.99-6.92 (m, 2H), 5.32-5.15 (m, 2H), 4.55 (t, J=6.5 Hz, 2H), 4.46 (t, J=6.0 Hz, 2H), 4.31 (d, J=14.1 Hz, 1H), 4.13-3.69 (m, 1H), 3.65-3.38 (m, 2H), 3.19-3.10 (m, 4H), 2.44 (d, J=2.4 Hz, 3H), 2.40 (t, J=4.9 Hz, 4H), 2.04 (ddd, J=55.6, 30.8, 12.6 Hz, 2H). LCMS-ESI$^+$ (m/z): [M+H]$^+$ calcd for $C_{32}H_{33}FN_{10}O_4$ Exact Mass: 641.3 found: 641.3

Example 613

2-(((3R,4S)-3-fluoro-1-((S)-2-hydroxypropanoyl)piperidin-4-yl)amino)-5-(4-((4-(4-(oxetan-3-yl)piperazin-1-yl)phenyl)amino)-1,3,5-triazin-2-yl)benzonitrile

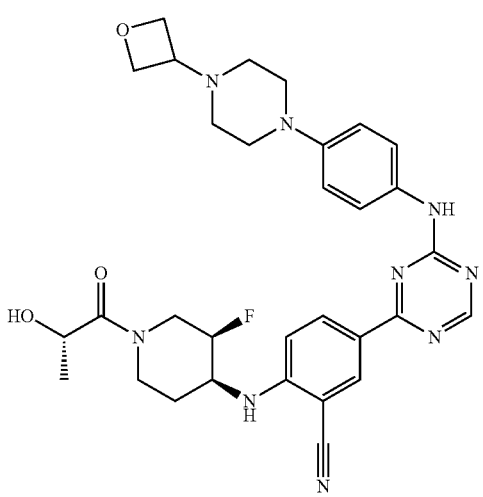 [SMILES: C[C@H](O)C(=O)N1CC[C@H](Nc2ccc(-c3ncnc(Nc4ccc(N5CCN(C6COC6)CC5)cc4)n3)cc2C#N)[C@H](F)C1]

A solution of a 2-fluoro-5-(4-((4-(4-(oxetan-3-yl)piperazin-1-yl)phenyl)amino)-1,3,5-triazin-2-yl)benzonitrile (500 mg, 1.16 mmol), DIPEA (0.26 gr, 2.3 mmol) in DMSO was stirred in a heating block at 120° C. for 24 h. After the mixture cooled to room temperature, water was added, and formed solids were filtered out, washed with diethyl-ether to yield (3R,4S)-tert-butyl 4-((2-cyano-4-(4-((4-(4-(oxetan-3-yl)piperazin-1-yl)phenyl)amino)-1,3,5-triazin-2-yl)phenyl)amino)-3-fluoropiperidine-1-carboxylate.

Oily material from previous step was dissolved with DCM and TFA. Reaction mixture was stirred at room temperature for 1 hr. Reaction mixture was evaporated under reduced pressure and solids were suspended in a saturated aqueous solution of NaHCO$_3$ and extracted with DCM. Organic phase was collected dried over magnesium sulfate and evaporated under reduced pressure to yield 2-(((3R,4S)-3-fluoropiperidin-4-yl)amino)-5-(4-((4-(4-(oxetan-3-yl)piperazin-1-yl)phenyl)amino)-1,3,5-triazin-2-yl)benzonitrile.

To a solution of 2-(((3R,4S)-3-fluoropiperidin-4-yl)amino)-5-(4-((4-(4-(oxetan-3-yl)piperazin-1-yl)phenyl)amino)-1,3,5-triazin-2-yl)benzonitrile (30 mg, 0.05 mmol), (S)-2-hydroxypropanoic acid (5 mg, 0.05 mmol), HATU (43 mgs, 0.11 mmol) in DMF (3 mL) was added TEA (23 mg, 0.23 mmol) in a 100 ml rbf. This reaction mixture was stirred at room temperature for 1 hr. Water was added and desired product was extracted with DCM. Organic layer was dried over Mg$_2$SO$_4$ and evaporated under reduced pressure to dryness. Solids re-dissolved in acetonitrile and purified via preparative HPLC (5-65% acetonitrile in water, 0.1% trifluoroacteic acid buffer) to yield 2-(((3R,4S)-3-fluoro-1-((S)-2-hydroxypropanoyl)piperidin-4-yl)amino)-5-(4-((4-(4-(oxetan-3-yl)piperazin-1-yl)phenyl)amino)-1,3,5-triazin- 2-yl)benzonitrile. LCMS-ESI⁺ (m/z): [M+H]⁺ calcd for C₃₁H₃₆FN₉O₃: 602.3; found: 602.3

Example 614

2-(((3R,4S)-3-fluoro-1-(3-hydroxyazetidine-3-carbonyl)piperidin-4-yl)oxy)-5-(4-((4-(4-(oxetan-3-yl)piperazin-1-yl)phenyl)amino)-1,3,5-triazin-2-yl)benzonitrile

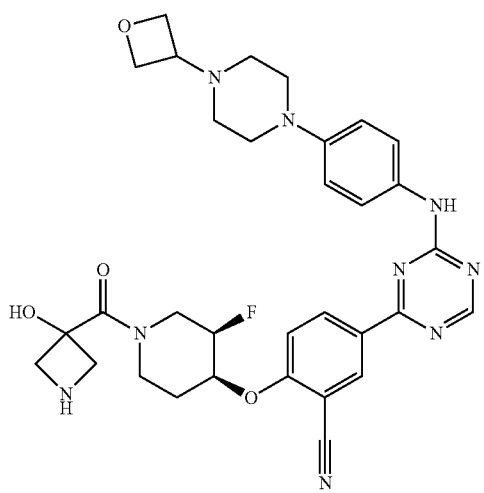 [SMILES: N#Cc1cc(-c2ncnc(Nc3ccc(N4CCN(C5COC5)CC4)cc3)n2)ccc1O[C@H]1CCN(C(=O)C2(O)CNC2)C[C@H]1F]

To a solution of 2-(((3R,4S)-3-fluoropiperidin-4-yl)oxy)-5-(4-((4-(4-(oxetan-3-yl)piperazin-1-yl)phenyl)amino)-1,3,5-triazin-2-yl)benzonitrile (190 mg, 0.36 mmol), 1-(tert-butoxycarbonyl)-3-hydroxyazetidine-3-carboxylic acid (86 mg, 0.39 mmol), HATU (204 mg, 0.54 mmol) in 4 ml of DMF, TEA (54 mg, 0.54 mmol) was added. This reaction mixture was stirred at room temperature for 2 hrs. Water was added to induce precipitation. Solids filtered out to obtain tert-butyl 3-((3R,4S)-4-(2-cyano-4-(4-((4-(4-(oxetan-3-yl)piperazin-1-yl)phenyl)amino)-1,3,5-triazin-2-yl)phenoxy)-3-fluoropiperidine-1-carbonyl)-3-hydroxyazetidine-1-carboxylate.

Solids from previous step were dissolved with DCM and TFA. Reaction mixture was stirred at room temperature for 1 hr. Reaction mixture was evaporated under reduced pressure. Solids re-dissolved in acetonitrile and purified via preparative HPLC (5-65% acetonitrile in water, 0.1% trifluoroacteic acid buffer) to yield 2-(((3R,4S)-3-fluoro-1-(3-hydroxyazetidine-3-carbonyl)piperidin-4-yl)oxy)-5-(4-((4-(4-(oxetan-3-yl)piperazin-1-yl)phenyl)amino)-1,3,5-triazin-2-yl)benzonitrile. LCMS-ESI⁺ (m/z): [M+H]⁺ calcd for C₃₂H₃₆FN₉O₄: 630.3; found: 630.3

Example 615

2-(((3R,4S)-3-fluoro-1-((S)-2-hydroxypropanoyl)piperidin-4-yl)oxy)-5-(4-((4-((R)-pyrrolidin-2-yl)phenyl)amino)-1,3,5-triazin-2-yl)benzonitrile

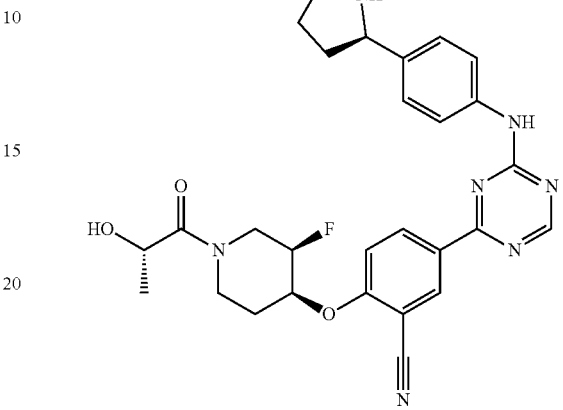

To a solution of N-Boc-pyrrolidine (500 mg, 2.9 mmol) and (−)-sparteine (684 mg, 2.9 mmol) in MTBE (12 ml) at −78° C. was added s-BuLi (1.4M in cyclohexane, 1.2 ml, 2.9 mmol) drop-wise keeping the temperature below −68° C. The resulting solution was aged for 3 h at −74° C. A solution of ZnCl₂ (1.9 M in ether, 238 mg, 1.75 mmol) was added drop-wise to the reaction mixture with rapid stirring keeping the temperature below −68° C. The resulting light suspension was Aged at −74° C. for 30 min and then warmed to 20° C. The resulting homogeneous solution was aged for 30 minutes at 20° C. and then was charged with aryl-bromide (416 mg, 2.4 mmol) followed by Pf(OAc)₂ (12 mg, 0.12 mmol) and ᵗBu₂P-HBF₄ (29 mg, 0.14 mmol) in one portion. The mixture was aged overnight at room temperature. The resulting mixture was filtered over celite and washed with MTBE. The filtrate was washed with 1M HCl solution and then twice with water. The organic layer was dried over Mg₂SO₄ and evaporated under reduced pressure to yield (R)-tert-butyl 2-(4-aminophenyl)pyrrolidine-1-carboxylate.

To a solution of 2,4-dichloro-1,3,5-triazine (228 mg, 1.5 mmol) in DMF at 0° C. (flushed with Argon) was added a solution of (R)-tert-butyl 2-(4-aminophenyl)pyrrolidine-1-carboxylate (400 mg, 1.5 mmol) in DMF over 15 min and stirred in an ice-bath for 1 h. Water was added to the reaction mixture and product was extracted with DCM. Organic layer was dried over Mg₂SO₄ and evaporated to dryness to yield (R)-tert-butyl 2-(4-((4-chloro-1,3,5-triazin-2-yl)amino)phenyl)pyrrolidine-1-carboxylate.

To (R)-tert-butyl 2-(4-((4-chloro-1,3,5-triazin-2-yl)amino)phenyl)pyrrolidine-1-carboxylate (455 mg, 1.2 mmol), 2-(((3R,4S)-3-fluoro-1-((S)-2-hydroxypropanoyl)piperidin-4-yl)oxy)-5-(4,4,5,5-tetramethyl-1,3,2-dioxaborolan-2-yl)benzonitrile (556 mg, 1.3 mmol), Pd(dppf)Cl₂CH₂Cl₂ (111 mg, 0.15 mmol) and potassium carbonate (334 mg, 2.4 mmol) mixture in argon atmosphere was added a mixture of de-gassed solvents (1,4-dioxane and water 2:1). The mixture was heated under argon atmosphere at 104° C. for 60 min in a heating block. After cooling at room temperature, water was added and product was extracted with DCM. Organic layer was dried over Mg$_2$SO$_4$ and evaporated to dryness to yield (R)-tert-butyl 2-(4-((4-(3-cyano-4-(((3R,4S)-3-fluoro-1-((S)-2-hydroxypropanoyl)piperidin-4-yl)oxy)phenyl)-1,3,5-triazin-2-yl)amino)phenyl)pyrrolidine-1-carboxylate.

(R)-tert-butyl 2-(4-((4-(3-cyano-4-(((3R,4S)-3-fluoro-1-((S)-2-hydroxypropanoyl)piperidin-4-yl)oxy)phenyl)-1,3,5-triazin-2-yl)amino)phenyl)pyrrolidine-1-carboxylate was dissolved with DCM and TFA. Reaction mixture was stirred at room temperature for 1 hr. Reaction mixture was evaporated under reduced pressure and solids were suspended in a saturated aqueous solution of NaHCO$_3$ and extracted with DCM. Organic phase was collected dried over magnesium sulfate and evaporated under reduced pressure. Solids re-dissolved in acetonitrile and purified via preparative HPLC (5-65% acetonitrile in water, 0.1% trifluoroacteic acid buffer) to yield 2-(((3R,4S)-3-fluoro-1-((S)-2-hydroxypropanoyl)piperidin-4-yl)oxy)-5-(4-((4-((R)-pyrrolidin-2-yl)phenyl)amino)-1,3,5-triazin-2-yl)benzonitrile. $^1$H NMR (400 MHz, DMSO-d$_6$) δ 9.31 (s, 1H), 8.85 (s, 1H), 8.66-8.52 (m, 2H), 7.83 (d, J=8.2 Hz, 2H), 7.63 (d, J=9.2 Hz, 1H), 7.49 (d, J=8.2 Hz, 2H), 6.51 (s, 1H), 5.38-4.92 (m, 3H), 4.61-4.29 (m, 3H), 4.23-3.84 (m, 2H), 3.12-3.22 (m, 1H), 2.42-2.29 (m, 2H), 2.15-1.76 (m, 6H), 1.19 (dd, J=6.6, 3.7 Hz, 3H). LCMS-ESI$^+$ (m/z): [M+H]$^+$ calcd for C$_{28}$H$_{30}$FN$_7$O$_3$: 532.3; found: 532.3

Example 616

2-(((3R,4S)-3-fluoro-1-((S)-2-hydroxypropanoyl)piperidin-4-yl)oxy)-5-(4-((4-((R)-1-(oxetan-3-yl)pyrrolidin-2-yl)phenyl)amino)-1,3,5-triazin-2-yl)benzonitrile

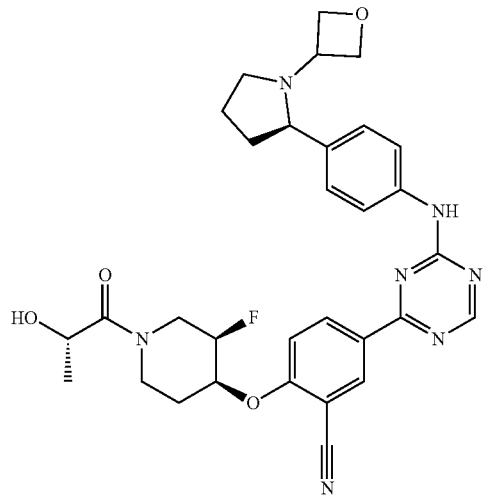 [SMILES: C[C@H](O)C(=O)N1CC[C@H](Oc2ccc(-c3ncnc(Nc4ccc([C@H]5CCCN5C5COC5)cc4)n3)cc2C#N)[C@H](F)C1]

To a mixture of 2-(((3R,4S)-3-fluoro-1-((S)-2-hydroxypropanoyl)piperidin-4-yl)oxy)-5-(4-((4-((R)-pyrrolidin-2-yl)phenyl)amino)-1,3,5-triazin-2-yl)benzonitrile (30 mg, 0.05 mmol), zinc chloride (10 mg, 0.07 mmol), oxetan-3-one (40 mg, 0.05 mmol) in methanol was added NaBH$_3$CN (9 mg, 0.07 mmol). The mixture was stirred at 75° C. for 2 hours. Reaction mixture was diluted with 1N HCl in water and stirred at room temperature for 30 min. To reaction mixture a saturated aqueous solution of NaHCO$_3$ and DCM were added. Organic phase was collected dried over magnesium sulfate and evaporated under reduced pressure. Solids re-dissolved in acetonitrile and purified via preparative HPLC (5-65% acetonitrile in water, 0.1% trifluoroacteic acid buffer) to yield 2-(((3R,4S)-3-fluoro-1-((S)-2-hydroxypropanoyl)piperidin-4-yl)oxy)-5-(4-((4-((R)-1-(oxetan-3-yl)pyrrolidin-2-yl)phenyl)amino)-1,3,5-triazin-2-yl)benzonitrile. $^1$H NMR (400 MHz, DMSO-d$_6$) δ 10.51 (s, 1H), 8.82 (s, 1H), 8.56 (d, J=7.2 Hz, 2H), 7.82 (s, 2H), 7.59 (d, J=9.4 Hz, 1H), 7.50 (s, 2H), 4.99 (d, J=50.4 Hz, 3H), 4.74-4.49 (m, 3H), 4.45-4.22 (m, 4H), 4.16-3.78 (m, 3H), 3.22-3.10 (m, 3H), 2.42-2.05 (m, 6H), 1.14 (dd, J=6.6, 3.9 Hz, 3H). LCMS-ESI$^+$ (m/z): [M+H]$^+$ calcd for C$_{31}$H$_{34}$FN$_7$O$_4$: 588.3; found: 588.3.

Example 617

2-(((3R,4S)-3-fluoro-1-((R)-2-hydroxy-3-methoxypropanoyl)piperidin-4-yl)oxy)-5-(4-((4-(4-(oxetan-3-yl)piperazin-1-yl)phenyl)amino)-1,3,5-triazin-2-yl)benzonitrile

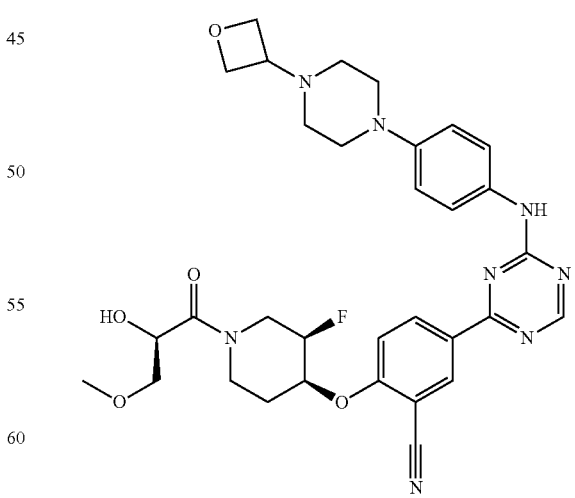

The title compound was separated from Example 557 via chiral HPLC. LCMS-ESI$^+$ (m/z): [M+H]$^+$ calcd for C32H37FN8O5: 633.3; found: 633.4.

Example 618

2-(((3R,4S)-3-fluoro-1-((S)-2-hydroxy-3-methoxy-propanoyl)piperidin-4-yl)oxy)-5-(4-((4-(4-(oxetan-3-yl)piperazin-1-yl)phenyl)amino)-1,3,5-triazin-2-yl)benzonitrile

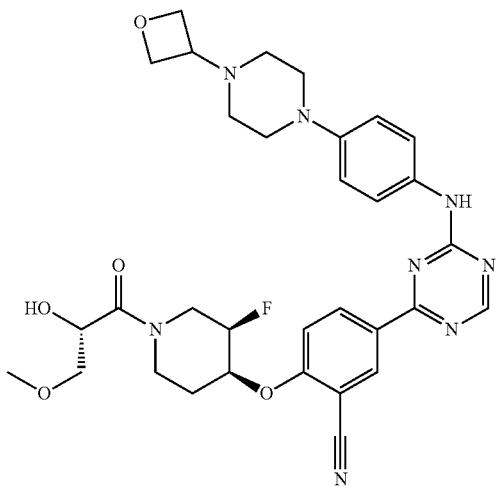

The title compound was separated from Example 557 via chiral HPLC. $^1$H NMR (400 MHz, DMSO-d6) δ 10.08 (d, J=24.5 Hz, 1H), 8.68 (s, 1H), 8.49 (m, 3H), 7.56 (m, 3H), 6.91 (m, 3H), 5.26 (m, 1H), 5.04 (m, 3H), 4.41 (m, 4H), 3.91 (m, 2H), 3.42 (m, 6H), 3.07 (m, 6H), 2.35 (m, 4H). LCMS-ESI$^+$ (m/z): [M+H]$^+$ calcd for C32H37FN8O5: 633.3; found: 633.4.

Example 619

2-(((3R,4S)-3-fluoro-1-((S)-2-hydroxypropanoyl)piperidin-4-yl)oxy)-5-(4-((4-((R)-hexahydropyrazino[2,1-c][1,4]oxazin-8(1H)-yl)phenyl)amino)-1,3,5-triazin-2-yl)benzonitrile

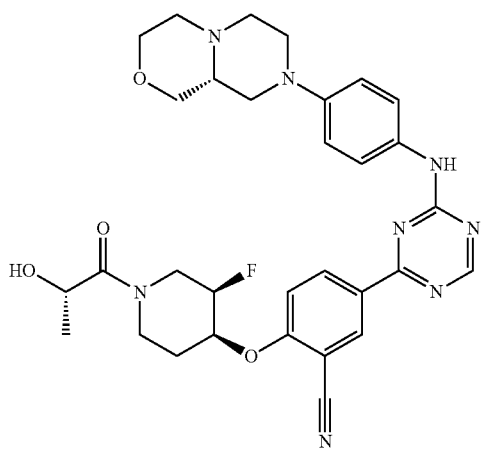 [SMILES: C[C@H](O)C(=O)N1CC[C@H](Oc2ccc(-c3ncnc(Nc4ccc(N5CCN6CCOC[C@H]6C5)cc4)n3)cc2C#N)[C@H](F)C1]

The title compound was synthesized in the same manner as Example 535 starting with (R)-octahydropyrazino[2,1-c][1,4]oxazine. $^1$H NMR (400 MHz, DMSO-d6) δ 10.19 (d, J=24.9 Hz, 1H), 8.75 (s, 1H), 8.64-8.47 (m, 2H), 7.62 (m, 3H), 7.03 (s, 2H), 5.12 (m, 2H), 4.97 (s, 1H), 4.47 (dt, J=13.3, 6.5 Hz, 2H), 4.39 (m, 2H), 4.23-4.12 (m, 2H), 4.05 (m, 3H), 3.74 (m, 2H), 3.59-3.12 (m, 6H), 2.99 (m, 1H), 1.97 (s, 2H), 1.19 (m, 3H). LCMS-ESI$^+$ (m/z): [M+H]$^+$ calcd for C31H35FN8O4: 603.3; found: 603.4.

Biological Assays:
TBK1 and IKKε

Enzymatic activity of IKKε and TBK1 was measured using a homogeneous time resolved fluorescence resonance energy transfer (TR-FRET) assay that monitors enzyme dependent phosphorylation of a biotinylated serine/threonine peptide substrate. An increase in the amount of phopshorylated peptide results in an increase in TR-FRET signal. TBK1 and IKKε were expressed and purified as full length recombinant proteins. Detection reagents for the assay were purchased from Cisbio. TBK1 and IKKε enzymes were assayed under initial rate conditions in the presence of 2× Km ATP (40-80 μM) and 1 μM peptide, hepes (pH 7), 0.1 mM orthovanadate, 0.02% NaN3, 0.01% BSA, 10 mM MgCl2, 0.01% (v/v) tritonX, 1 mM dithiothreitol, 0.5% (v/v) DMSO at the following concentrations for each enzyme: TBK1 at 2.5 nM and IKKε at 0.3 nM. After an assay reaction time of 240 minutes at 25° C., reactions were terminated with EDTA.

Amount of phosphorylated peptide was determined by the addition of 125 nM streptavidin XL665 and europium cryptate labeled anti-phospho monoclonal antibody and the resulting TR-FRET signal was recorded on an Envision plate reader (Ex: 340 nm; Em: 615/665 nm; 100 μs delay and 200 μs read window). Data was normalized based on a positive (1 μM Staurosporine) and negative (DMSO) controls and IC50 values calculated from the fit of the dose—response curves to a four-parameter equation. All IC50 values represent geometric mean values of a minimum of four determinations. These assays generally produced results within 3-fold of the reported mean.

hJAK2:

Enzymatic activity of hJAK2 was measured using a LANCE homogeneous time resolved fluorescence resonance energy transfer (TR-FRET) assay that monitors enzyme dependent phosphorylation of a biotinylated serine/threonine peptide substrate (PTK). An increase in the amount of phopshorylated peptide results in an increase in TR-FRET signal. hJAK2 was expressed and purified as full length recombinant proteins. Detection reagents for the assay were purchased from PerkinElmer. hJAK2 enzyme was assayed under initial rate conditions in the presence of 2×Km ATP (30 μM) and 1 μM peptide, 50 mM Tris-Cl (pH 7.5), 10 mM MgCl2, 1mM dithiothreitol, 0.01% BSA, 0.05% (v/v) DMSO at the following concentration of enzyme: hJAK2 at 0.3 nM. After an assay reaction time of 40 minutes at 25° C., reactions were terminated with EDTA and LANCE Detection Buffer.

Amount of phosphorylated peptide was determined by the addition of 20 nM SA-APC and 1 nM europium cryptate labeled anti-phospho PTK monoclonal antibody PY66 and the resulting TR-FRET signal was recorded on an Envision plate reader (Ex: 340 nm; Em: 615/665 nm; 100 μs delay and 200 μs read window). Data was normalized based on a positive (1 μM Staurosporine) and negative (DMSO) controls and IC50 values calculated from the fit of the dose—response curves to a four-parameter equation. All IC50 values represent geometric mean values of a minimum of four determinations. These assays generally produced results within 3-fold of the reported mean.

Results:
Table 1 below depicts IKKε-IC50 (nM), TBK1-IC50 (nM) and JAK2 (nM) values for the compounds described herein.

TABLE 1

| Ex. | Structure | TBK1 IC50 | IKKe IC50 | JAK2 IC50 | Name |
|---|---|---|---|---|---|
| 1 | 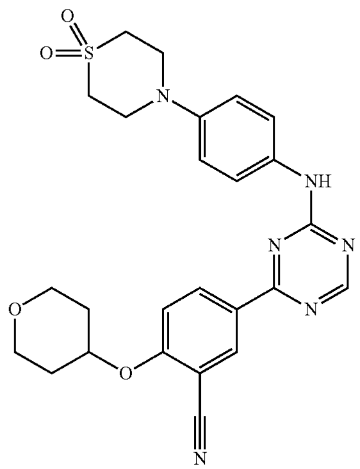 [SMILES: N#Cc1cc(-c2ncnc(Nc3ccc(N4CCS(=O)(=O)CC4)cc3)n2)ccc1OC1CCOCC1] | 2 | 6 | 360 | 5-[4-[4-(1,1-dioxo-1,4-thiazinan-4-yl)anilino]-1,3,5-triazin-2-yl]-2-(oxan-4-yloxy)benzonitrile |
| 2 | 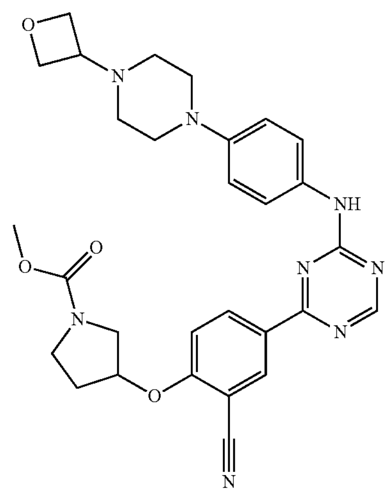 [SMILES: COC(=O)N1CCC(Oc2ccc(-c3ncnc(Nc4ccc(N5CCN(C6COC6)CC5)cc4)n3)cc2C#N)C1] | 37 | 148 | 660 | methyl (3R)-3-[2-cyano-4-[4-[4-(oxetan-3-yl)piperazin-1-yl]anilino]-1,3,5-triazin-2-yl]phenoxy]pyrrolidine-1-carboxylate |
| 3 | 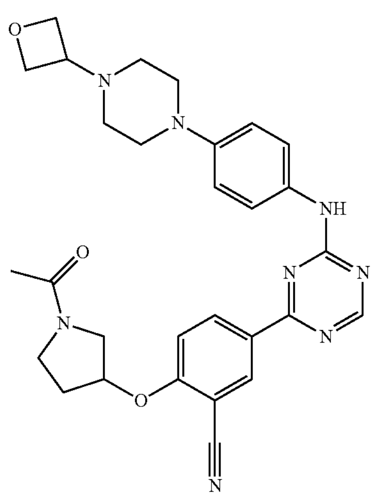 [SMILES: CC(=O)N1CCC(Oc2ccc(-c3ncnc(Nc4ccc(N5CCN(C6COC6)CC5)cc4)n3)cc2C#N)C1] | 20 | 99 | 724 | 2-[(3R)-1-acetylpyrrolidin-3-yl]oxy-5-[4-[4-[4-(oxetan-3-yl)piperazin-1-yl]anilino]-1,3,5-triazin-2-yl]benzonitrile |

TABLE 1-continued

| Ex. | Structure | TBK1 IC50 | IKKe IC50 | JAK2 IC50 | Name |
|---|---|---|---|---|---|
| 4 | 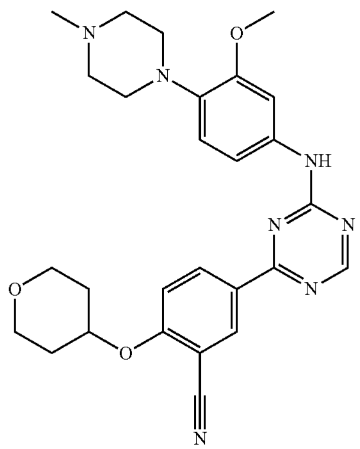 [SMILES: COc1cc(Nc2ncnc(-c3ccc(OC4CCOCC4)c(C#N)c3)n2)ccc1N1CCN(C)CC1] | 1 | 1 | 53 | 5-[4-[3-methoxy-4-(4-methylpiperazin-1-yl)anilino]-1,3,5-triazin-2-yl]-2-(oxan-4-yloxy)benzonitrile |
| 5 | 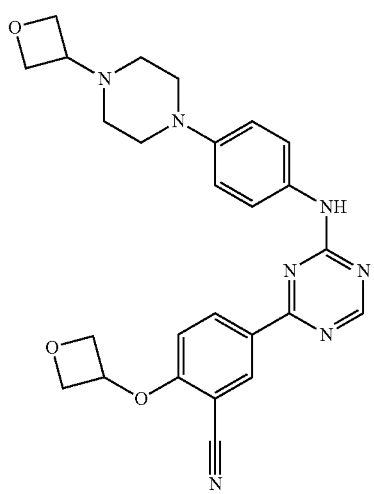 [SMILES: N#Cc1cc(-c2ncnc(Nc3ccc(N4CCN(C5COC5)CC4)cc3)n2)ccc1OC1COC1] | 35 | 101 | 269 | 2-(oxetan-3-yloxy)-5-[4-[4-[4-(oxetan-3-yl)piperazin-1-yl]anilino]-1,3,5-triazin-2-yl]benzonitrile |
| 6 | 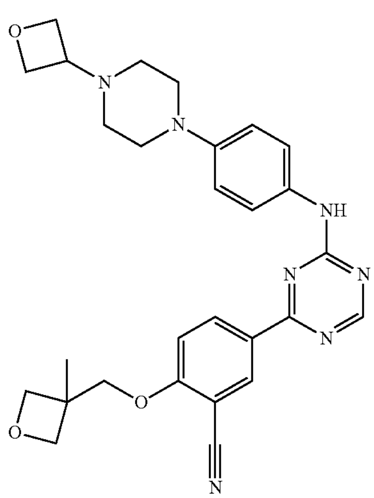 [SMILES: CC1(COc2ccc(-c3ncnc(Nc4ccc(N5CCN(C6COC6)CC5)cc4)n3)cc2C#N)COC1] | 7 | 20 | 178 | 2-[(3-methyloxetan-3-yl)methoxy]-5-[4-[4-[4-(oxetan-3-yl)piperazin-1-yl]anilino]-1,3,5-triazin-2-yl]benzonitrile |

TABLE 1-continued

| Ex. | Structure | TBK1 IC50 | IKKe IC50 | JAK2 IC50 | Name |
|---|---|---|---|---|---|
| 7 | 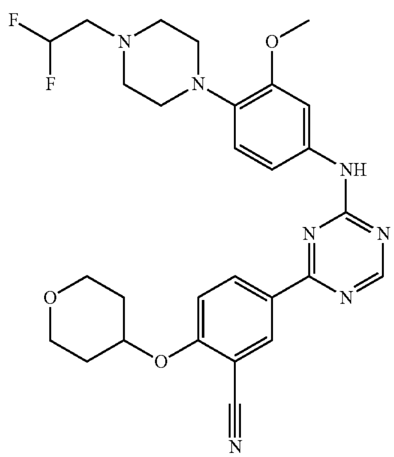 [SMILES: COc1cc(Nc2ncnc(-c3ccc(OC4CCOCC4)c(C#N)c3)n2)ccc1N1CCN(CC(F)F)CC1] | 1 | 3 | 225 | 5-[4-[4-[4-(2,2-difluoroethyl)piperazin-1-yl]-3-methoxyanilino]-1,3,5-triazin-2-yl]-2-(oxan-4-yloxy)benzonitrile |
| 8 | 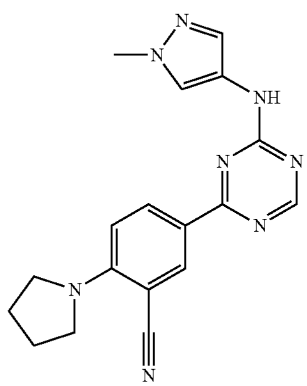 [SMILES: Cn1cc(Nc2ncnc(-c3ccc(N4CCCC4)c(C#N)c3)n2)cn1] | 7 | 19 | 278 | 5-[4-[(1-methylpyrazol-4-yl)amino]-1,3,5-triazin-2-yl]-2-pyrrolidin-1-ylbenzonitrile |
| 9 | 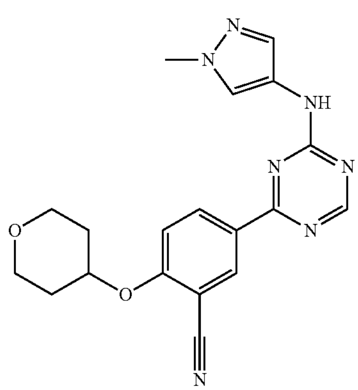 [SMILES: Cn1cc(Nc2ncnc(-c3ccc(OC4CCOCC4)c(C#N)c3)n2)cn1] | 3 | 7 | 363 | 5-[4-[(1-methylpyrazol-4-yl)amino]-1,3,5-triazin-2-yl]-2-(oxan-4-yloxy)benzonitrile |

TABLE 1-continued

| Ex. | Structure | TBK1 IC50 | IKKe IC50 | JAK2 IC50 | Name |
|---|---|---|---|---|---|
| 10 | 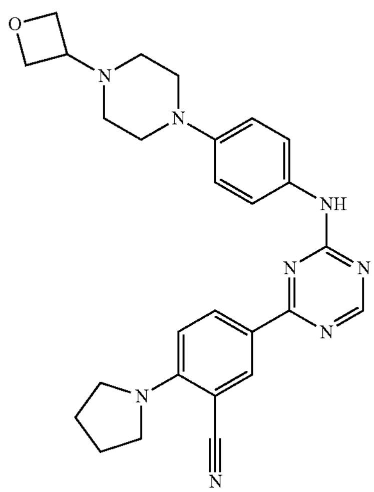 [SMILES: N#Cc1cc(-c2ncnc(Nc3ccc(N4CCN(C5COC5)CC4)cc3)n2)ccc1N1CCCC1] | 5 | 15 | 336 | 5-[4-[4-[4-(oxetan-3-yl)piperazin-1-yl]anilino]-1,3,5-triazin-2-yl]-2-pyrrolidin-1-ylbenzonitrile |
| 11 | 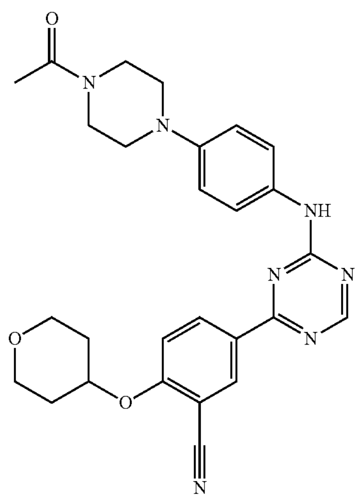 [SMILES: CC(=O)N1CCN(c2ccc(Nc3ncnc(-c4ccc(OC5CCOCC5)c(C#N)c4)n3)cc2)CC1] | 1 | 4 | 224 | 5-[4-[4-(4-acetyl-piperazin-1-yl)anilino]-1,3,5-triazin-2-yl]-2-(oxan-4-yloxy)benzonitrile |
| 12 | 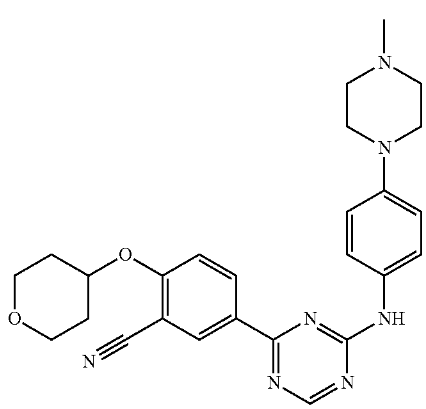 [SMILES: CN1CCN(c2ccc(Nc3ncnc(-c4ccc(OC5CCOCC5)c(C#N)c4)n3)cc2)CC1] | 1 | 1 | 162 | 5-[4-[4-(4-methylpiperazin-1-yl)anilino]-1,3,5-triazin-2-yl]-2-(oxan-4-yloxy)benzonitrile |

TABLE 1-continued

| Ex. | Structure | TBK1 IC50 | IKKe IC50 | JAK2 IC50 | Name |
|---|---|---|---|---|---|
| 13 | 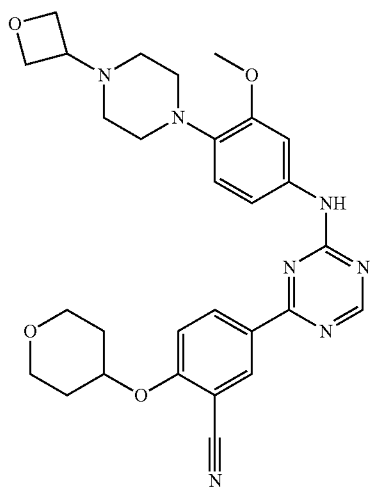 | 1 | 2 | 127 | 5-[4-[3-methoxy-4-[4-(oxetan-3-yl)piperazin-1-yl]anilino]-1,3,5-triazin-2-yl]-2-(oxan-4-yloxy)benzonitrile |
| 14 | 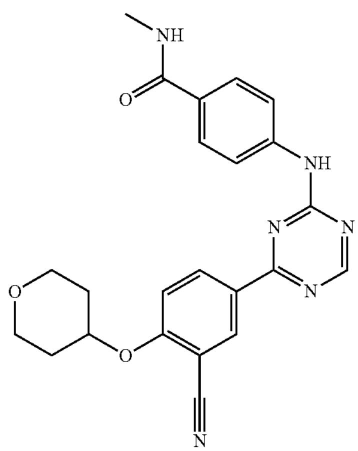 [SMILES: CNC(=O)c1ccc(Nc2ncnc(-c3ccc(OC4CCOCC4)c(C#N)c3)n2)cc1] | 4 | 21 | 856 | 4-[[4-[3-cyano-4-(oxan-4-yloxy)phenyl]-1,3,5-triazin-2-yl]amino]-N-methylbenzamide |
| 15 | 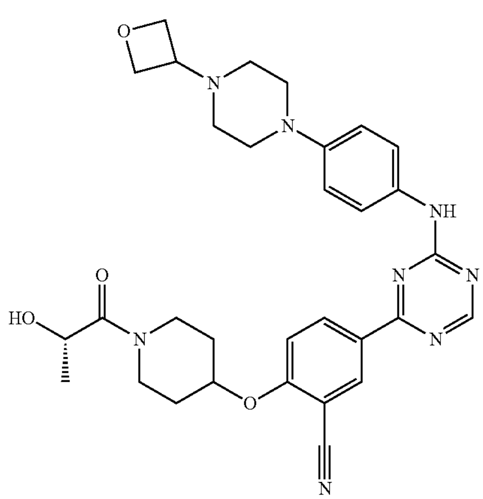 [SMILES: C[C@H](O)C(=O)N1CCC(Oc2ccc(-c3ncnc(Nc4ccc(N5CCN(C6COC6)CC5)cc4)n3)cc2C#N)CC1] | 5 | 14 | >1000 | 2-[1-[(2S)-2-hydroxypropanoyl]piperidin-4-yl]oxy-5-[4-[4-(oxetan-3-yl)piperazin-1-yl]anilino]-1,3,5-triazin-2-yl]benzonitrile |

TABLE 1-continued

| Ex. | Structure | TBK1 IC50 | IKKe IC50 | JAK2 IC50 | Name |
|---|---|---|---|---|---|
| 16 | 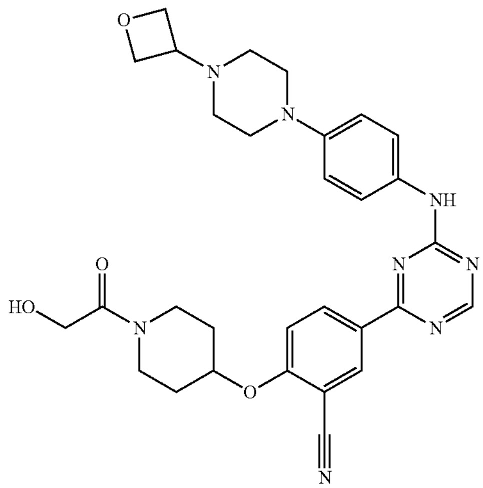 [SMILES: N#Cc1cc(-c2ncnc(Nc3ccc(N4CCN(C5COC5)CC4)cc3)n2)ccc1OC1CCN(C(=O)CO)CC1] | 1 | 4 | 603 | 2-[1-(2-hydroxyacetyl)piperidin-4-yl)oxy-5-[4-[4-(oxetan-3-yl)piperazin-1-yl]anilino]-1,3,5-triazin-2-yl]benzonitrile |
| 17 | 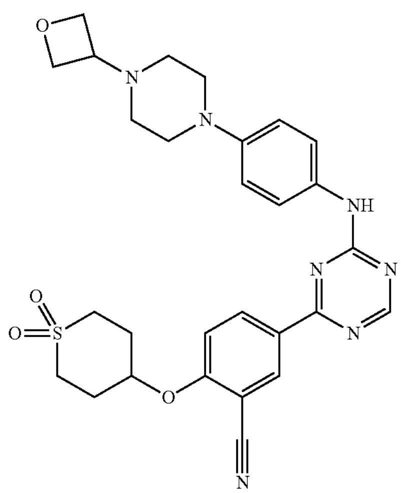 [SMILES: N#Cc1cc(-c2ncnc(Nc3ccc(N4CCN(C5COC5)CC4)cc3)n2)ccc1OC1CCS(=O)(=O)CC1] | 9 | 54 | 540 | 2-(1,1-dioxothian-4-yl)oxy-5-[4-[4-(oxetan-3-yl)piperazin-1-yl]anilino]-1,3,5-triazin-2-yl]benzonitrile |
| 18 | 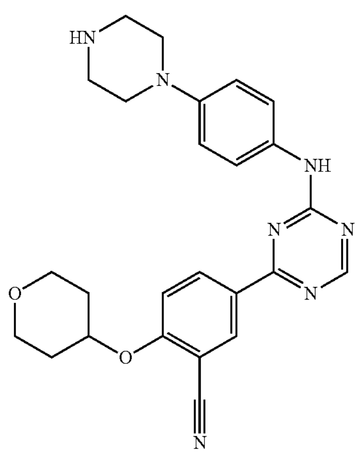 | 1 | 1 | 271 | 2-(oxan-4-yloxy)-5-[4-(4-piperazin-1-ylanilino)-1,3,5-triazin-2-yl]benzonitrile |

TABLE 1-continued

| Ex. | Structure | TBK1 IC50 | IKKe IC50 | JAK2 IC50 | Name |
|---|---|---|---|---|---|
| 19 | 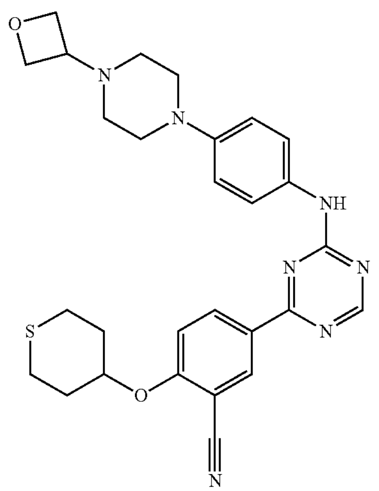 | 1 | 4 | >1000 | 5-[4-[4-[4-(oxetan-3-yl)piperazin-1-yl]anilino]-1,3,5-triazin-2-yl]-2-(thian-4-yloxy)benzonitrile |
| 20 | 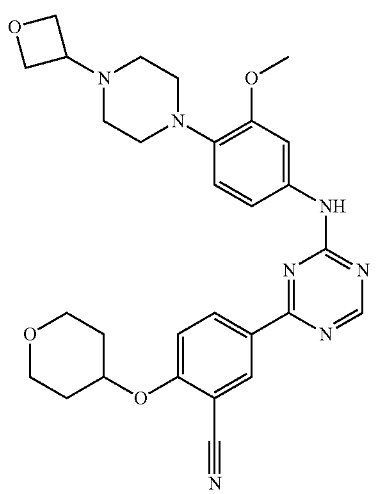 [SMILES: COc1cc(Nc2ncnc(-c3ccc(OC4CCOCC4)c(C#N)c3)n2)ccc1N1CCN(C2COC2)CC1] | 2 | 2 | >1000 | 5-[4-[3-methoxy-4-[1-(oxetan-3-yl)piperidin-4-yl]anilino]-1,3,5-triazin-2-yl]-2-(oxan-4-yloxy)benzonitrile |
| 21 | 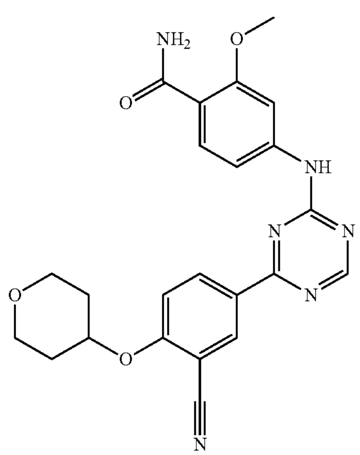 [SMILES: COc1cc(Nc2ncnc(-c3ccc(OC4CCOCC4)c(C#N)c3)n2)ccc1C(N)=O] | 4 | 6 | >1000 | 4-[[4-[3-cyano-4-(oxan-4-yloxy)pheny]-1,3,5-triazin-2-yl]amino]-2-methoxybenzamide |

TABLE 1-continued

| Ex. | Structure | TBK1 IC50 | IKKe IC50 | JAK2 IC50 | Name |
|---|---|---|---|---|---|
| 22 | 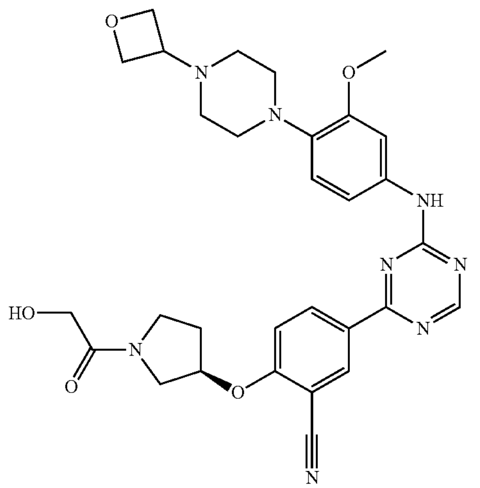 [SMILES: COc1cc(Nc2ncnc(-c3ccc(O[C@@H]4CCN(C(=O)CO)C4)c(C#N)c3)n2)ccc1N1CCN(C2COC2)CC1] | 3 | 8 | 128 | 2-[(3R)-1-(2-hydroxyacetyl)pyrrolidin-3-yl]oxy-5-[4-[3-methoxy-4-[4-(oxetan-3-yl)piperazin-1-yl]anilino]-1,3,5-triazin-2-yl]benzonitrile |
| 23 | 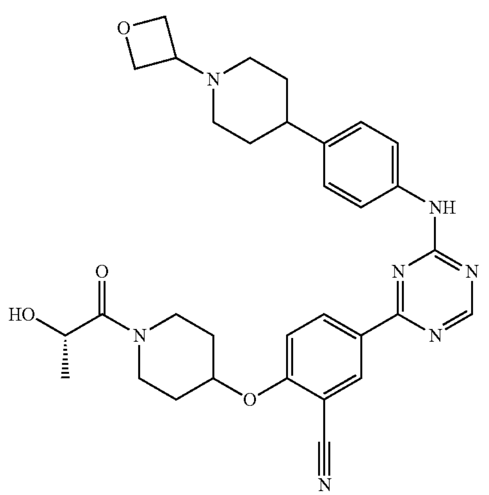 [SMILES: C[C@H](O)C(=O)N1CCC(Oc2ccc(-c3ncnc(Nc4ccc(C5CCN(C6COC6)CC5)cc4)n3)cc2C#N)CC1] | 6 | 10 | >1000 | 2-[1-[(2S)-2-hydroxypropanoyl]piperidin-4-yl]oxy-5-[4-[4-[1-(oxetan-3-yl)pipendin-4-yl]anilino]-1,3,5-triazin-2-yl]benzonitrile |
| 24 | 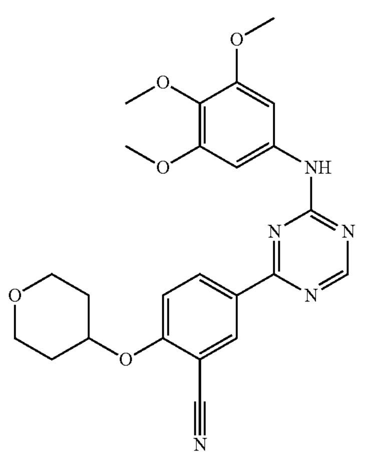 [SMILES: COc1cc(Nc2ncnc(-c3ccc(OC4CCOCC4)c(C#N)c3)n2)cc(OC)c1OC] | 1 | 2 | 602 | 2-(oxan-4-yloxy)-5-[4-(3,4,5-trimethoxyanilino)-1,3,5-triazin-2-yl]benzonitrile |

TABLE 1-continued

| Ex. | Structure | TBK1 IC50 | IKKe IC50 | JAK2 IC50 | Name |
|---|---|---|---|---|---|
| 25 | 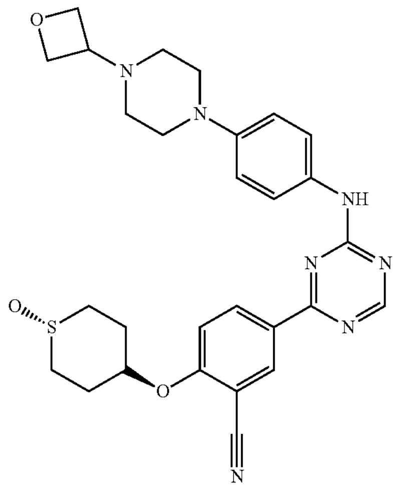 | 21 | 73 | >1000 | 5-[4-[4-[4-(oxetan-3-yl)piperazin-1-yl]anilino]-1,3,5-triazin-2-yl]-2-(1-oxidothian-1-ium-4-yl)oxybenzonitrile |
| 26 | 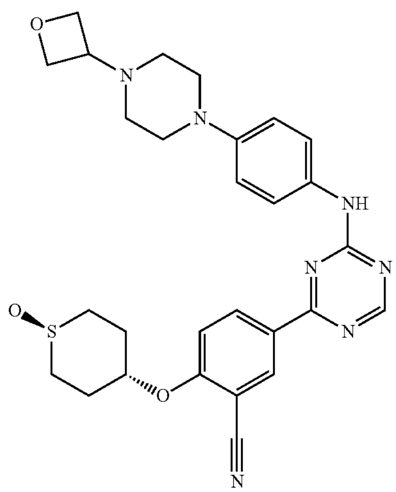 | 6 | 23 | 407 | 5-[4-[4-[4-(oxetan-3-yl)piperazin-1-yl]anilino]-1,3,5-triazin-2-yl]-2-(1-oxidothian-1-ium-4-yl)oxybenzonitrile |
| 27 | 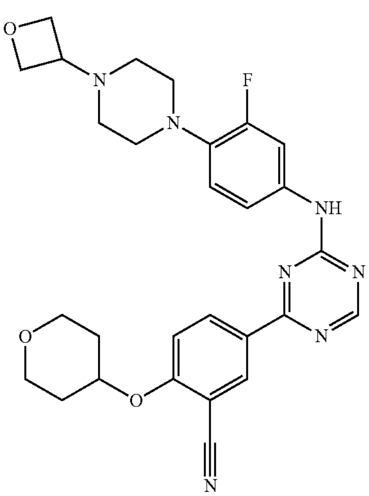 | 2 | 7 | 988 | 5-[4-[3-fluoro-4-[4-(oxetan-3-yl)piperazin-1-yl]anilino]-1,3,5-triazin-2-yl]-2-(oxan-4-yloxy)benzonitrile |

TABLE 1-continued
| Ex. | Structure | TBK1 IC50 | IKKe IC50 | JAK2 IC50 | Name |
|---|---|---|---|---|---|
| 28 | 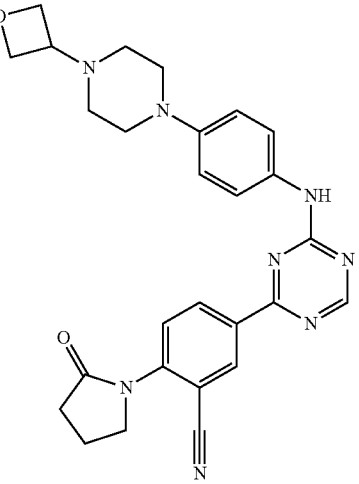 | 225 | 529 | 583 | 5-[4-[4-[4-(oxetan-3-yl)piperazin-1-yl]anilino]-1,3,5-triazin-2-yl]-2-(2-oxopyrrolidin-1-yl)benzonitrile |
| 29 | 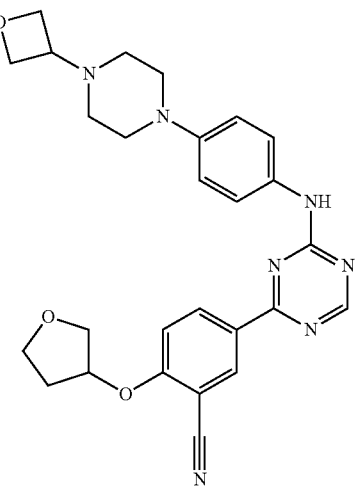 | 5 | 32 | 546 | 5-[4-[4-[4-(oxetan-3-yl)piperazin-1-yl]anilino]-1,3,5-triazin-2-yl]-2-[(3R)-oxolan-3-yl]oxybenzonitrile |
| 30 | 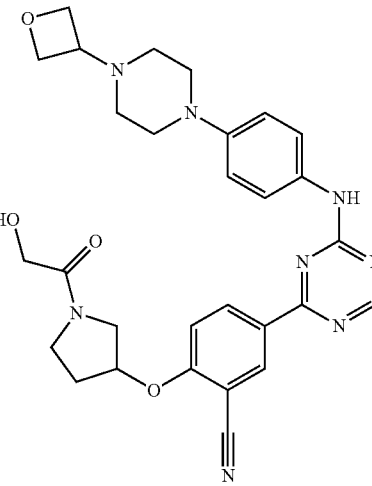 | 3 | 14 | 387 | 2-[(3R)-1-(2-hydroxyacetyl)pyrrolidin-3-yl]oxy-5-[4-[4-[4-(oxetan-3-yl)piperazin-1-yl]anilino]-1,3,5-triazin-2-yl]benzonitrile |

TABLE 1-continued

| Ex. | Structure | TBK1 IC50 | IKKe IC50 | JAK2 IC50 | Name |
|---|---|---|---|---|---|
| 31 | 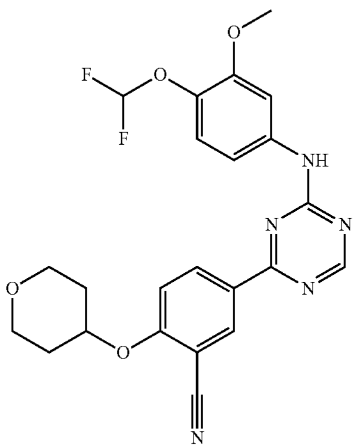 [SMILES: COc1cc(Nc2ncnc(-c3ccc(OC4CCOCC4)c(C#N)c3)n2)ccc1OC(F)F] | 9 | 20 | >1000 | 5-[4-[4-(difluoro-methoxy)-3-methoxyanilino]-1,3,5-triazin-2-yl]-2-(oxan-4-yloxy)benzonitrile |
| 32 | 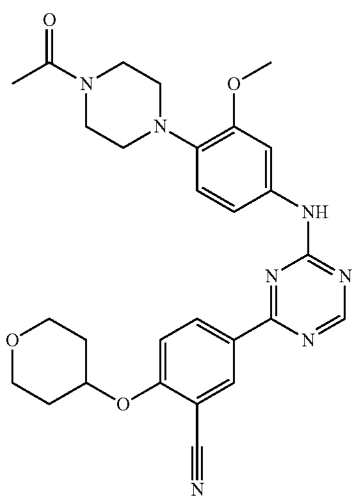 [SMILES: COc1cc(Nc2ncnc(-c3ccc(OC4CCOCC4)c(C#N)c3)n2)ccc1N1CCN(C(C)=O)CC1] | 1 | 2 | 68 | 5-[4-[4-(4-acetylpiperazin-1-yl)-3-methoxyanilino]-1,3,5-triazin-2-yl]-2-(oxan-4-yloxy)benzonitrile |
| 33 | 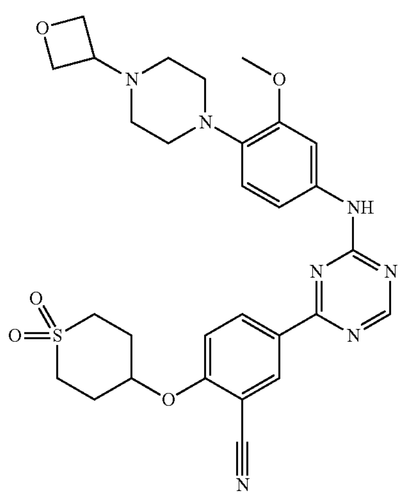 [SMILES: COc1cc(Nc2ncnc(-c3ccc(OC4CCS(=O)(=O)CC4)c(C#N)c3)n2)ccc1N1CCN(C2COC2)CC1] | 4 | 18 | 59 | 2-(1,1-dioxothian-4-yl)oxy-5-[4-[3-methoxy-4-[4-(oxetan-3-yl)piperazin-1-yl]anilino]-1,3,5-triazin-2-yl]benzonitrile |

TABLE 1-continued

| Ex. | Structure | TBK1 IC50 | IKKe IC50 | JAK2 IC50 | Name |
| --- | --- | --- | --- | --- | --- |
| 34 | 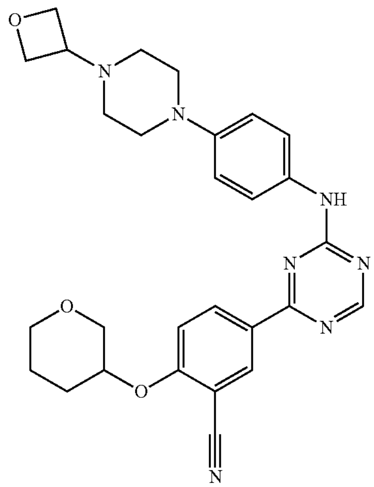 | 12 | 45 | >1000 | 2-(oxan-3-yloxy)-5-[4-[4-(oxetan-3-yl)piperazin-1-yl]anilino]-1,3,5-triazin-2-yl]benzonitrile |
| 35 | 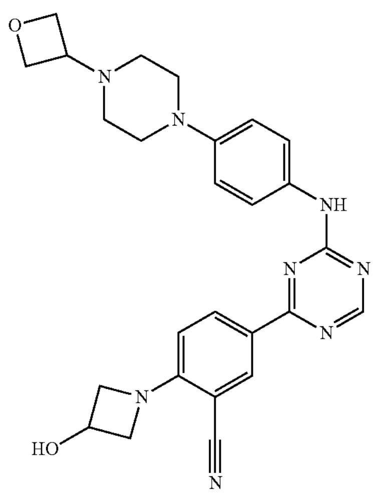 | 7 | 29 | 166 | 2-(3-hydroxyazetidin-1-yl)-5-[4-[4-(oxetan-3-yl)piperazin-1-yl]anilino]-1,3,5-triazin-2-yl]benzonitrile |
| 36 | 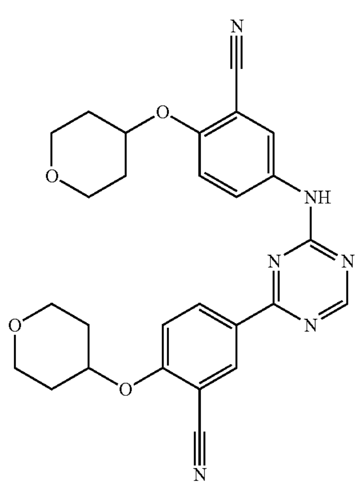 [SMILES: N#Cc1cc(Nc2ncnc(-c3ccc(OC4CCOCC4)c(C#N)c3)n2)ccc1OC1CCOCC1] | 10 | 12 | >1000 | 5-[4-[3-cyano-4-(oxan-4-yloxy)anilino]-1,3,5-triazin-2-yl]-2-(oxan-4-yloxy)benzonitrile |

TABLE 1-continued
| Ex. | Structure | TBK1 IC50 | IKKe IC50 | JAK2 IC50 | Name |
|---|---|---|---|---|---|
| 37 | 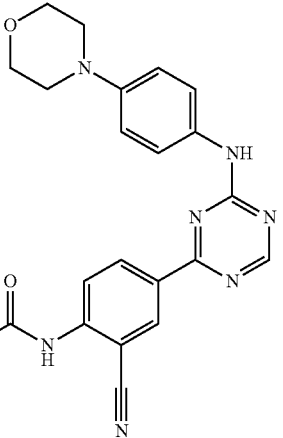 | 203 | 305 | 326 | (2S)-N-[2-cyano-4-[4-(4-morpholin-4-ylanilino)-1,3,5-triazin-2-yl]phenyl]pyrrolidine-2-carboxamide |
| 38 | 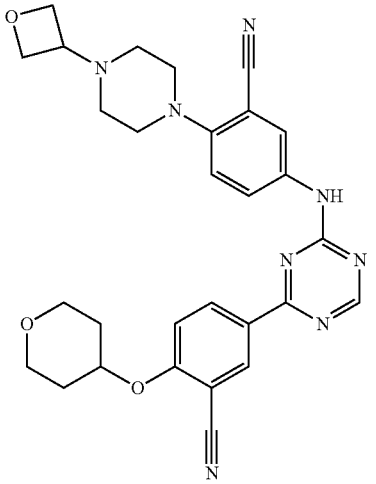 [SMILES: N#Cc1cc(-c2ncnc(Nc3ccc(N4CCN(C5COC5)CC4)c(C#N)c3)n2)ccc1OC1CCOCC1] | 3 | 6 | >1000 | 5-[4-[3-cyano-4-[4-(oxetan-3-yl)piperazin-1-yl]anilino]-1,3,5-triazin-2-yl]-2-(oxan-4-yloxy)benzonitrile |
| 39 | 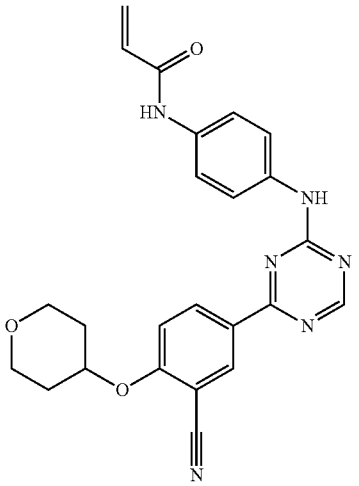 [SMILES: C=CC(=O)Nc1ccc(Nc2ncnc(-c3ccc(OC4CCOCC4)c(C#N)c3)n2)cc1] | 6 | 35 | >1000 | N-[4-[[4-[3-cyano-4-(oxan-4-yloxy)phenyl]-1,3,5-triazin-2-yl]amino]phenyl]prop-2-enamide |

TABLE 1-continued

| Ex. | Structure | TBK1 IC50 | IKKe IC50 | JAK2 IC50 | Name |
|---|---|---|---|---|---|
| 40 | 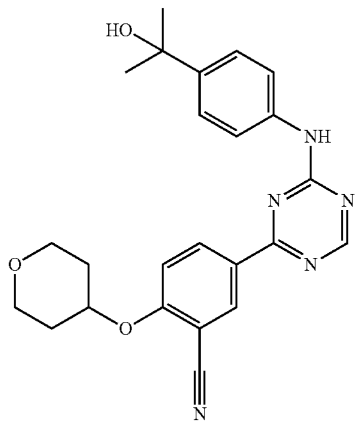 [SMILES: CC(C)(O)c1ccc(Nc2ncnc(-c3ccc(OC4CCOCC4)c(C#N)c3)n2)cc1] | 6 | 23 | >1000 | 5-[4-[4-(2-hydroxy-propan-2-yl)anilino]-1,3,5-triazin-2-yl]-2-(oxan-4-yloxy)benzonitrile |
| 41 | 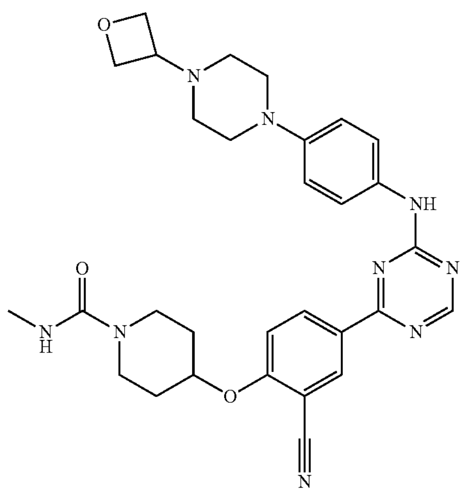 [SMILES: CNC(=O)N1CCC(Oc2ccc(-c3ncnc(Nc4ccc(N5CCN(C6COC6)CC5)cc4)n3)cc2C#N)CC1] | 35 | 110 | >1000 | 4-[2-cyano-4-[4-[4-[4-(oxetan-3-yl)piperazin-1-yl]anilino]-1,3,5-triazin-2-yl]phenoxy]-N-methylpiperidine-1-carboxamide |
| 42 | 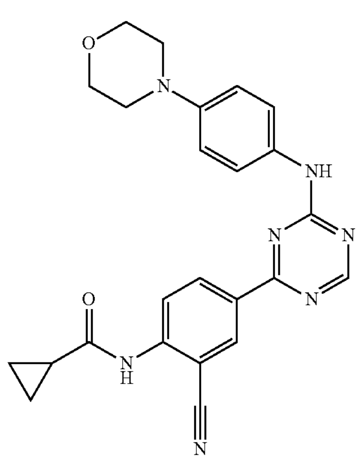 [SMILES: N#Cc1cc(-c2ncnc(Nc3ccc(N4CCOCC4)cc3)n2)ccc1NC(=O)C1CC1] | 35 | 71 | 24 | N-[2-cyano-4-[4-(4-morpholin-4-ylanilino)-1,3,5-triazin-2-yl]phenyl]cyclopropanecarboxamide |

TABLE 1-continued

| Ex. | Structure | TBK1 IC50 | IKKe IC50 | JAK2 IC50 | Name |
|---|---|---|---|---|---|
| 43 | 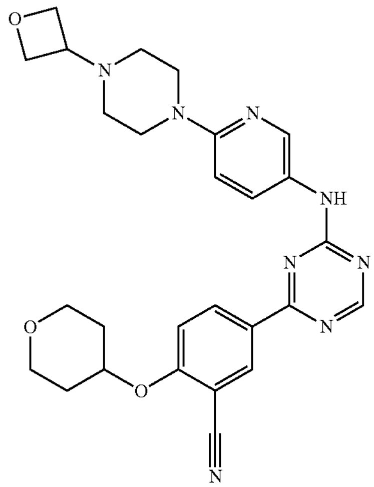 | 7 | 15 | >1000 | 2-(oxan-4-yloxy)-5-[4-[[6-[4-(oxetan-3-yl)piperazin-1-yl]pyridin-3-yl]amino]-1,3,5-triazin-2-yl]benzonitrile |
| 44 | 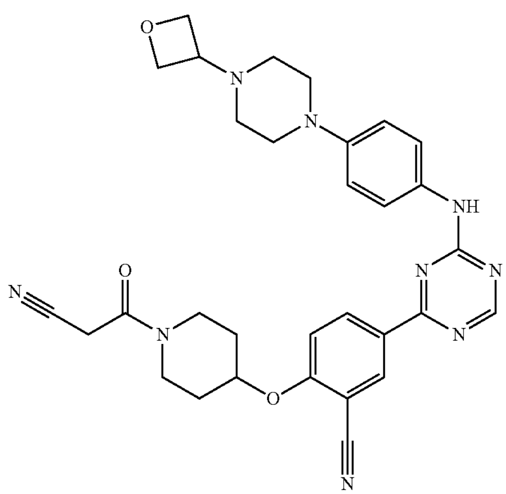 [SMILES: N#CCC(=O)N1CCC(Oc2ccc(-c3ncnc(Nc4ccc(N5CCN(C6COC6)CC5)cc4)n3)cc2C#N)CC1] | 9 | 26 | 444 | 2-[1-(2-cyanoacetyl)piperdin-4-yl]oxy-5-[4-[4-(oxetan-3-yl]piperazin-1-yl]anilino]-1,3,5-triazin-2-yl]benzonitrile |
| 45 | 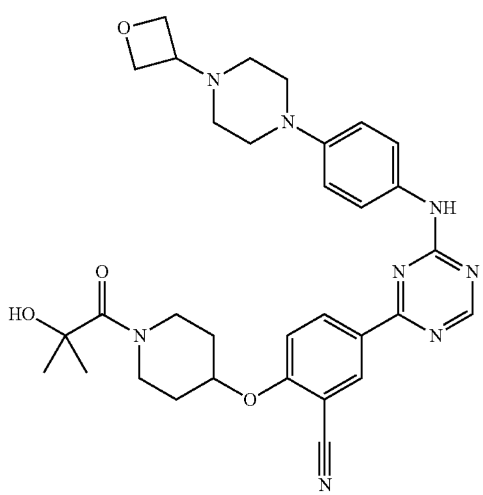 [SMILES: CC(C)(O)C(=O)N1CCC(Oc2ccc(-c3ncnc(Nc4ccc(N5CCN(C6COC6)CC5)cc4)n3)cc2C#N)CC1] | 202 | 243 | >1000 | 2-[1-(2-hydroxy-2-methylpropanoyl)piperidin-4-yl]oxy-5-[4-[4-(oxetan-3-yl)piperazin-1-yl]anilino]-1,3,5-triazin-2-yl]benzonitrile |

TABLE 1-continued

| Ex. | Structure | TBK1 IC50 | IKKe IC50 | JAK2 IC50 | Name |
|---|---|---|---|---|---|
| 46 | 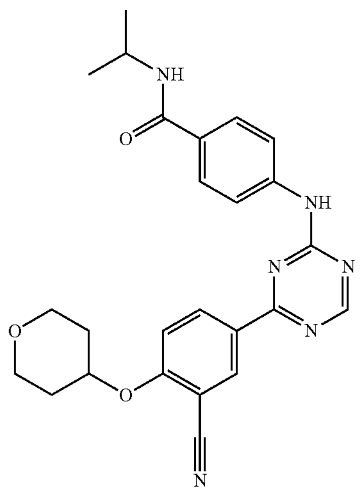 [SMILES: CC(C)NC(=O)c1ccc(Nc2ncnc(-c3ccc(OC4CCOCC4)c(C#N)c3)n2)cc1] | 3 | 9 | 670 | 4-[[4-[3-cyano-4-(oxan-4-yloxy)phenyl]-1,3,5-triazin-2-yl]amino]-N-propan-2-ylbenzamide |
| 47 | 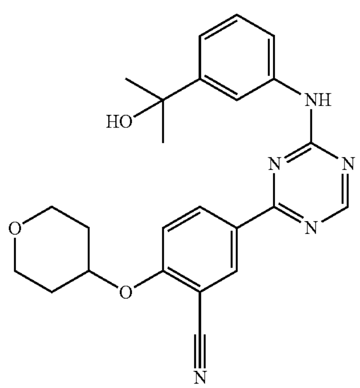 [SMILES: CC(C)(O)c1cccc(Nc2ncnc(-c3ccc(OC4CCOCC4)c(C#N)c3)n2)c1] | 2 | 14 | 811 | 5-[4-[3-(2-hydroxypropan-2-yl)anilino]-1,3,5-triazin-2-yl]-2-(oxan-4-yloxy)benzonitrile |
| 48 | 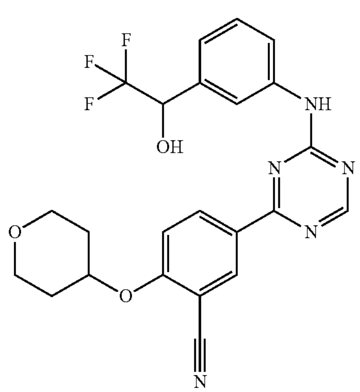 [SMILES: N#Cc1cc(-c2ncnc(Nc3cccc(C(O)C(F)(F)F)c3)n2)ccc1OC1CCOCC1] | 3 | 31 | >1000 | 2-(oxan-4-yloxy)-5-[4-[3-(2,2,2-trifluoro-1-hydroxyethyl)anilino]-1,3,5-triazin-2-yl]benzonitrile |

TABLE 1-continued

| Ex. | Structure | TBK1 IC50 | IKKe IC50 | JAK2 IC50 | Name |
|---|---|---|---|---|---|
| 49 | 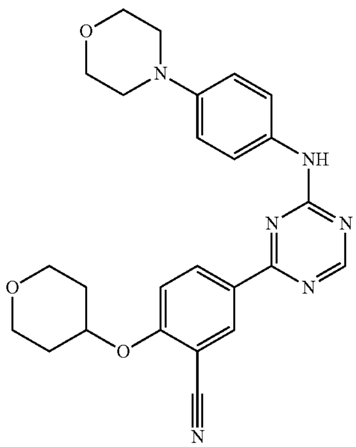 | 2 | 7 | 436 | 5-[4-(4-morpholin-4-ylanilino)-1,3,5-triazin-2-yl]-2-(oxan-4-yloxy)benzonitrile |
| 50 | 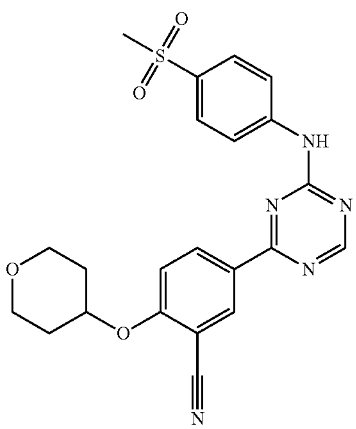 [SMILES: CS(=O)(=O)c1ccc(Nc2ncnc(-c3ccc(OC4CCOCC4)c(C#N)c3)n2)cc1] | 5 | *nd | >1000 | 5-[4-(4-methylsulfonyl-anilino)-1,3,5-triazin-2-yl]-2-(oxan-4-yloxy)benzonitrile |
| 51 | 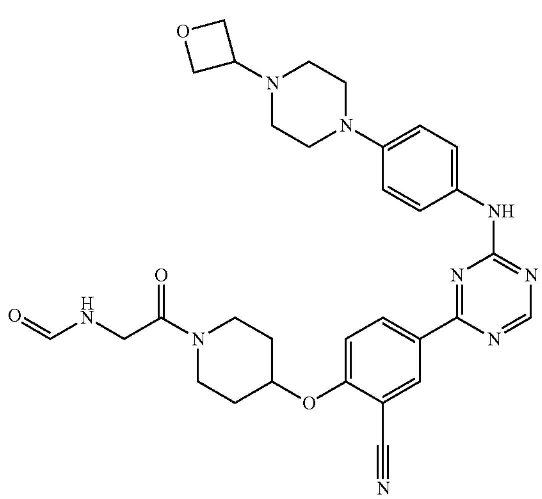 [SMILES: N#Cc1cc(-c2ncnc(Nc3ccc(N4CCN(C5COC5)CC4)cc3)n2)ccc1OC1CCN(C(=O)CNC=O)CC1] | 26 | 79 | 408 | N-[2-[4-[2-cyano-4-[4-[4-[4-(oxetan-3-yl)piperazin-1-yl]anilino]-1,3,5-triazin-2-yl]phenoxy]pipendin-1-yl]-2-oxoethyl]formamide |

TABLE 1-continued

| Ex. | Structure | TBK1 IC50 | IKKe IC50 | JAK2 IC50 | Name |
|---|---|---|---|---|---|
| 52 | 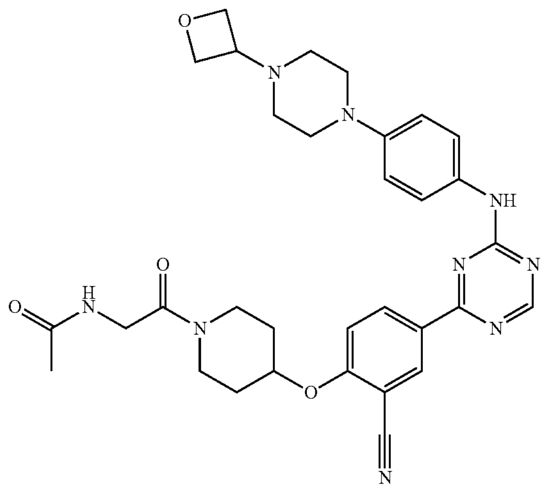 [SMILES: CC(=O)NCC(=O)N1CCC(Oc2ccc(-c3ncnc(Nc4ccc(N5CCN(C6COC6)CC5)cc4)n3)cc2C#N)CC1] | 65 | 223 | 491 | N-[2-[4-[2-cyano-4-[4-[4-(oxetan-3-yl)piperazin-1-yl]anilino]-1,3,5-triazin-2-yl]phenoxy]piperidin-1-yl]-2-oxoethyl]acetamide |
| 53 | 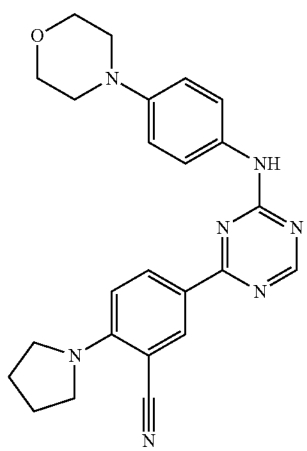 [SMILES: N#Cc1cc(-c2ncnc(Nc3ccc(N4CCOCC4)cc3)n2)ccc1N1CCCC1] | 5 | 18 | 261 | 5-[4-(4-morpholin-4-ylanilino)-1,3,5-triazin-2-yl]-2-pyrrolidin-1-ylbenzonitrile |
| 54 | 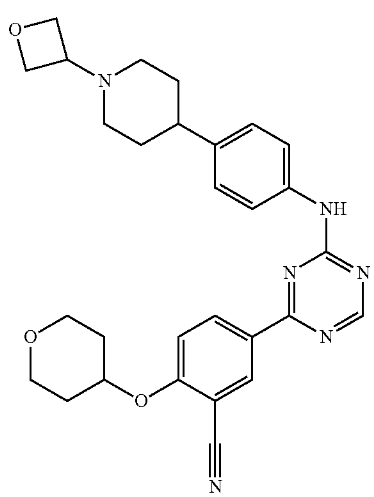 | 2 | 4 | >1000 | 2-(oxan-4-yloxy)-5-[4-[4-[1-(oxetan-3-yl)piperidin-4-yl]anilino]-1,3,5-triazin-2-yl]benzonitrile |

TABLE 1-continued

| Ex. | Structure | TBK1 IC50 | IKKe IC50 | JAK2 IC50 | Name |
|---|---|---|---|---|---|
| 55 | 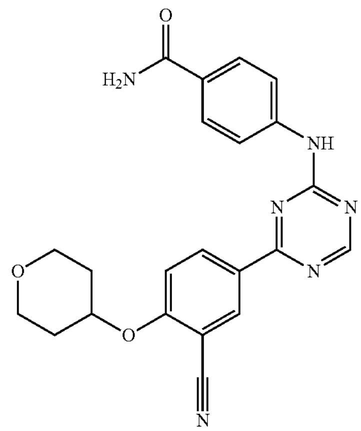 [SMILES: N#Cc1cc(-c2ncnc(Nc3ccc(C(N)=O)cc3)n2)ccc1OC1CCOCC1] | 2 | 5 | >1000 | 4-[[4-[3-cyano-4-(oxan-4-yloxy)phenyl]-1,3,5-triazin-2-yl]amino]benzamide |
| 56 | 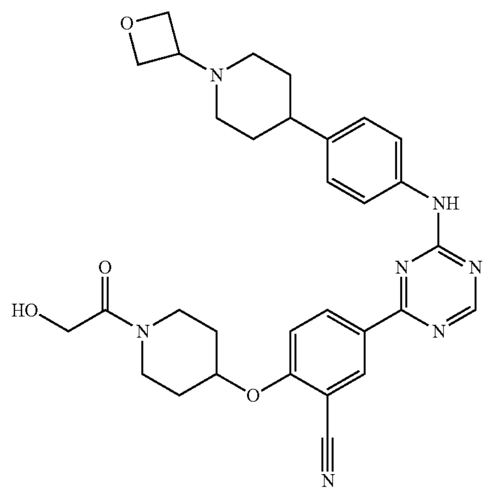 [SMILES: N#Cc1cc(-c2ncnc(Nc3ccc(C4CCN(C5COC5)CC4)cc3)n2)ccc1OC1CCN(C(=O)CO)CC1] | 2 | 3 | >1000 | 2-[1-(2-hydroxyacetyl)piperidin-4-yl]oxy-5-[4-[1-(oxetan-3-yl)piperidin-4-yl]anilino]-1,3,5-triazin-2-yl]benzonitrile |
| 57 | 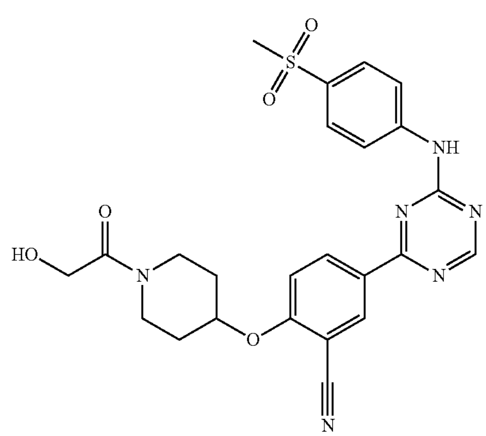 [SMILES: CS(=O)(=O)c1ccc(Nc2ncnc(-c3ccc(OC4CCN(C(=O)CO)CC4)c(C#N)c3)n2)cc1] | 5 | 8 | >1000 | 2-[1-(2-hydroxyacetyl)piperidin-4-yl]oxy-5-[4-(4-methylsulfonyl-anilino)-1,3,5-triazin-2-yl]benzonitrile |

TABLE 1-continued

| Ex. | Structure | TBK1 IC50 | IKKe IC50 | JAK2 IC50 | Name |
|---|---|---|---|---|---|
| 58 | 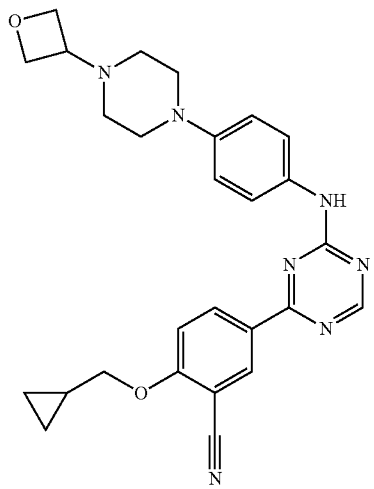 [SMILES: N#Cc1cc(-c2ncnc(Nc3ccc(N4CCN(C5COC5)CC4)cc3)n2)ccc1OCC1CC1] | 2 | 4 | 455 | 2-(cyclopropyl-methoxy)-5-[4-[4-[4-(oxetan-3-yl)piperazin-1-yl]anilino]-1,3,5-triazin-2-yl]benzonitrile |
| 59 | 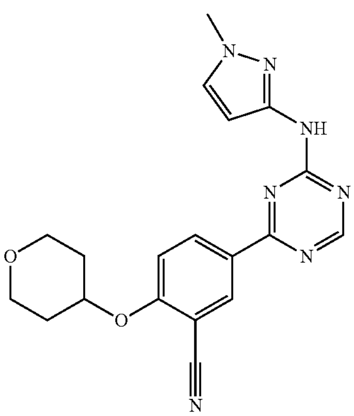 [SMILES: Cn1ccc(Nc2ncnc(-c3ccc(OC4CCOCC4)c(C#N)c3)n2)n1] | 55 | 83 | >1000 | 5-[4-[(1-methyl-pyrazol-3-yl)amino]-1,3,5-triazin-2-yl]-2-(oxan-4-yloxy)benzonitrile |
| 60 | 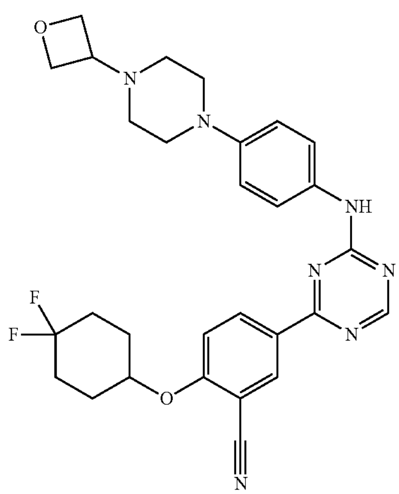 [SMILES: N#Cc1cc(-c2ncnc(Nc3ccc(N4CCN(C5COC5)CC4)cc3)n2)ccc1OC1CCC(F)(F)CC1] | 3 | 7 | 655 | 2-(4,4-difluorocyclohexyl)oxy-5-[4-[4-[4-(oxetan-3-yl)piperazin-1-yl]anilino]-1,3,5-triazin-2-yl]benzonitrile |

TABLE 1-continued

| Ex. | Structure | TBK1 IC50 | IKKe IC50 | JAK2 IC50 | Name |
|---|---|---|---|---|---|
| 61 | 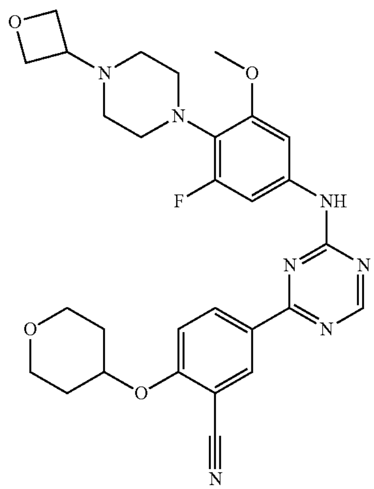 [SMILES: COc1cc(Nc2ncnc(-c3ccc(OC4CCOCC4)c(C#N)c3)n2)cc(F)c1N1CCN(C2COC2)CC1] | 2 | 7 | 671 | 5-[4-[3-fluoro-5-methoxy-4-[4-(oxetan-3-yl)piperazin-1-yl]anilino]-1,3,5-triazin-2-yl]-2-(oxan-4-yloxy)benzonitrile |
| 62 | 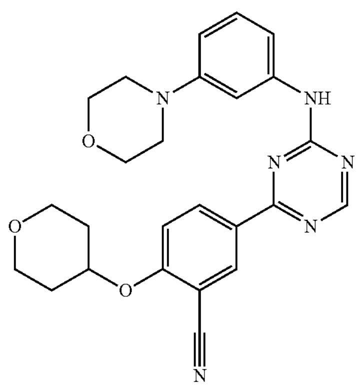 [SMILES: N#Cc1cc(-c2ncnc(Nc3cccc(N4CCOCC4)c3)n2)ccc1OC1CCOCC1] | 5 | 3 | >1000 | 5-[4-[3-(4-methyl-piperazin-1-yl)anilino]-1,3,5-triazin-2-yl]-2-(oxan-4-yloxy)benzonitrile |
| 63 | 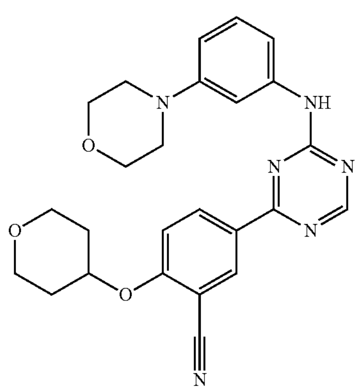 [SMILES: N#Cc1cc(-c2ncnc(Nc3cccc(N4CCOCC4)c3)n2)ccc1OC1CCOCC1] | 4 | 8 | 938 | 5-[4-(3-morpholin-4-ylanilino)-1,3,5-triazin-2-yl]-2-(oxan-4-yloxy)benzonitrile |

TABLE 1-continued

| Ex. | Structure | TBK1 IC50 | IKKe IC50 | JAK2 IC50 | Name |
| --- | --- | --- | --- | --- | --- |
| 64 | 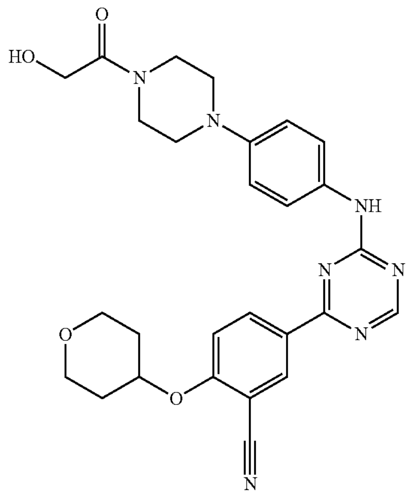 [SMILES: N#Cc1cc(-c2ncnc(Nc3ccc(N4CCN(C(=O)CO)CC4)cc3)n2)ccc1OC1CCOCC1] | 1 | 5 | 347 | 5-[4-[4-[4-(2-hydroxyacetyl)piperazin-1-yl]anilino]-1,3,5-triazin-2-yl]-2-(oxan-4-yloxy)benzonitrile |
| 65 | 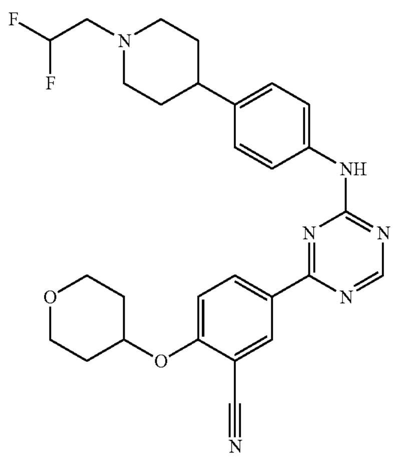 [SMILES: N#Cc1cc(-c2ncnc(Nc3ccc(C4CCN(CC(F)F)CC4)cc3)n2)ccc1OC1CCOCC1] | 4 | 11 | >1000 | 5-[4-[4-[1-(2,2-difluoroethyl)piperidin-4-yl]anilino]-1,3,5-triazin-2-yl]-2-(oxan-4-yloxy)benzonitrile |
| 66 | 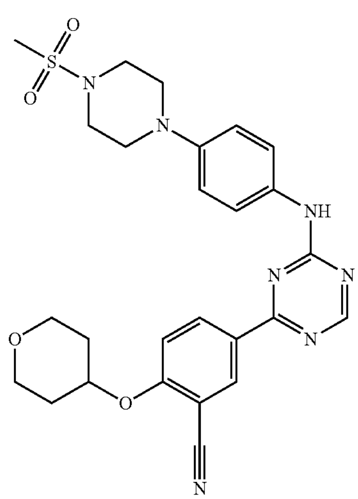 [SMILES: CS(=O)(=O)N1CCN(c2ccc(Nc3ncnc(-c4ccc(OC5CCOCC5)c(C#N)c4)n3)cc2)CC1] | 2 | 5 | 345 | 5-[4-[4-(4-methylsulfonyl-piperazin-1-yl)anilino]-1,3,5-triazin-2-yl]-2-(oxan-4-yloxy)benzonitrile |

TABLE 1-continued

| Ex. | Structure | TBK1 IC50 | IKKe IC50 | JAK2 IC50 | Name |
|---|---|---|---|---|---|
| 67 | 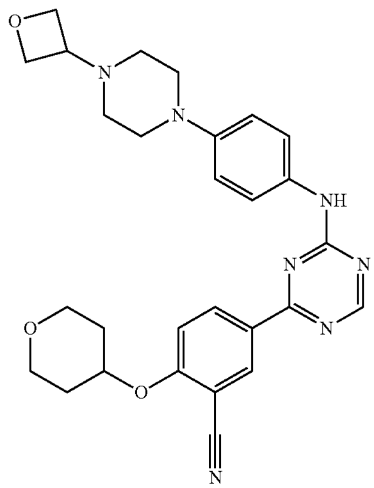 | 2 | 6 | 802 | 2-(oxan-4-yloxy)-5-[4-[4-[4-(oxetan-3-yl)piperazin-1-yl]anilino]-1,3,5-triazin-2-yl]benzonitrile |
| 68 | 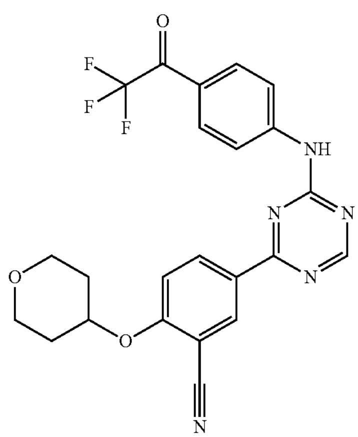 [SMILES: N#Cc1cc(-c2ncnc(Nc3ccc(C(=O)C(F)(F)F)cc3)n2)ccc1OC1CCOCC1] | 2 | 11 | 415 | 2-(oxan-4-yloxy)-5-[4-[4-(2,2,2-trifluoroacetyl)anilino]-1,3,5-triazin-2-yl]benzonitrile |
| 69 | 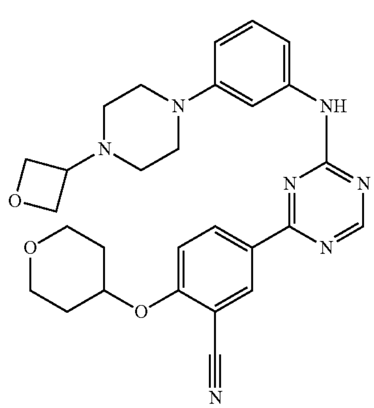 [SMILES: N#Cc1cc(-c2ncnc(Nc3cccc(N4CCN(C5COC5)CC4)c3)n2)ccc1OC1CCOCC1] | 6 | 4 | >1000 | 2-(oxan-4-yloxy)-5-[4-[3-[4-(oxetan-3-yl)piperazin-1-yl]anilino]-1,3,5-triazin-2-yl]benzonitrile |

TABLE 1-continued

| Ex. | Structure | TBK1 IC50 | IKKe IC50 | JAK2 IC50 | Name |
|---|---|---|---|---|---|
| 70 | 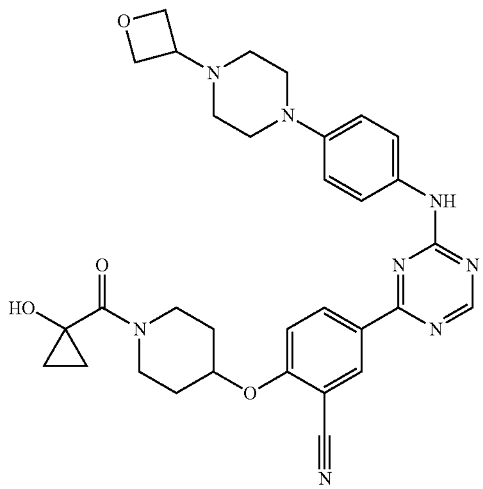 | 28 | 70 | 918 | 2-[1-(1-hydroxycyclopropane-carbonyl)piperidin-4-yl]oxy-5-[4-[4-(oxetan-3-yl)piperazin-1-yl]anilino]-1,3,5-triazin-2-yl]benzonitrile |
| 71 | 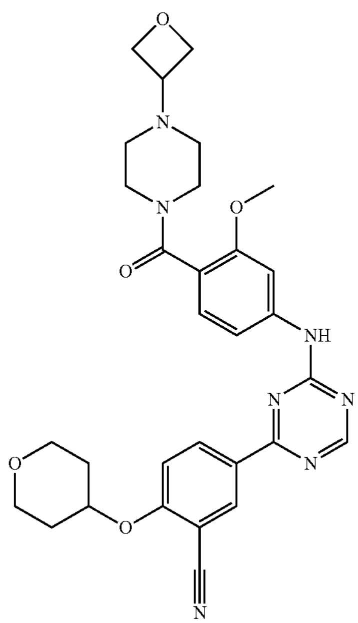 [SMILES: COc1cc(Nc2ncnc(-c3ccc(OC4CCOCC4)c(C#N)c3)n2)ccc1C(=O)N1CCN(C2COC2)CC1] | 2 | 10 | >1000 | 5-[4-[3-methoxy-4-[4-(oxetan-3-yl)piperazine-1-carbonyl]anilino]-1,3,5-triazin-2-yl]-2-(oxan-4-yloxy)benzonitrile |
| 72 | 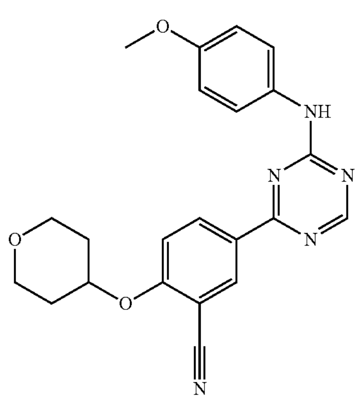 [SMILES: COc1ccc(Nc2ncnc(-c3ccc(OC4CCOCC4)c(C#N)c3)n2)cc1] | 5 | 21 | >1000 | 5-[4-(4-methoxy-anilino)-1,3,5-triazin-2-yl]-2-(oxan-4-yloxy)benzonitrile |

TABLE 1-continued

| Ex. | Structure | TBK1 IC50 | IKKe IC50 | JAK2 IC50 | Name |
|---|---|---|---|---|---|
| 73 | 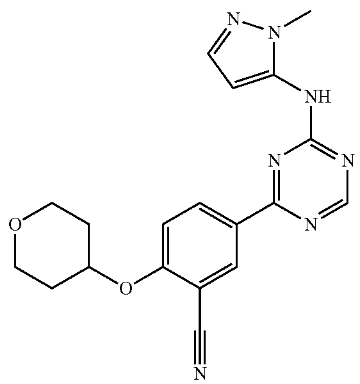 [SMILES: Cn1nccc1Nc1ncnc(-c2ccc(OC3CCOCC3)c(C#N)c2)n1] | 90 | 202 | >1000 | 5-[4-[(2-methyl-pyrazol-3-yl)amino]-1,3,5-triazin-2-yl]-2-(oxan-4-yloxy)benzonitrile |
| 74 | 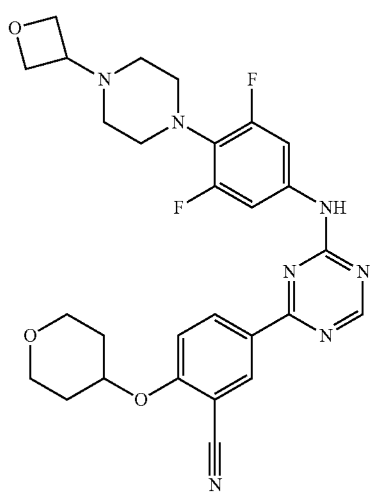 | 3 | 12 | >1000 | 5-[4-[3,5-difluoro-4-[4-(oxetan-3-yl)piperazin-1-yl]anilino]-1,3,5-triazin-2-yl]-2-(oxan-4-yloxy)benzonitrile |
| 75 | 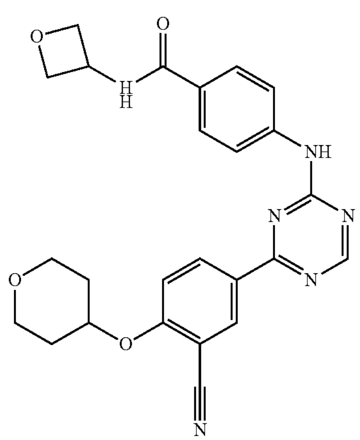 | 3 | 12 | 899 | 4-[[4-[3-cyano-4-(oxan-4-yloxy)phenyl]-1,3,5-triazin-2-yl]amino]-N-(oxetan-3-yl)benzamide |

TABLE 1-continued

| Ex. | Structure | TBK1 IC50 | IKKe IC50 | JAK2 IC50 | Name |
|---|---|---|---|---|---|
| 76 | 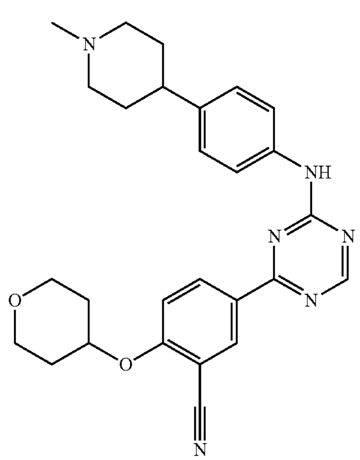 [SMILES: CN1CCC(c2ccc(Nc3ncnc(-c4ccc(OC5CCOCC5)c(C#N)c4)n3)cc2)CC1] | 1 | 3 | 575 | 5-[4-[4-(1-methyl-piperidin-4-yl)anilino]-1,3,5-triazin-2-yl]-2-(oxan-4-yloxy)benzonitrile |
| 77 | 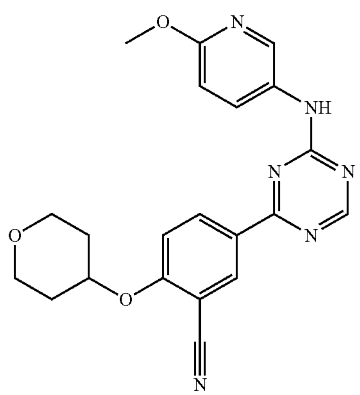 [SMILES: COc1ccc(Nc2ncnc(-c3ccc(OC4CCOCC4)c(C#N)c3)n2)cn1] | 21 | 55 | >1000 | 5-[4-(6-methoxy-pyridin-3-yl)amino]-1,3,5-triazin-2-yl]-2-(oxan-4-yloxy)benzonitrile |
| 78 | 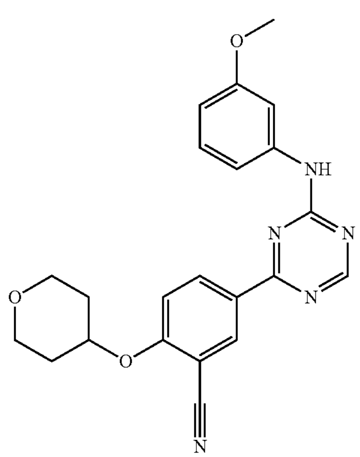 [SMILES: COc1cccc(Nc2ncnc(-c3ccc(OC4CCOCC4)c(C#N)c3)n2)c1] | 6 | 17 | >1000 | 5-[4-(3-methoxyanilino)-1,3,5-triazin-2-yl]-2-(oxan-4-yloxy)benzonitrile |

TABLE 1-continued
| Ex. | Structure | TBK1 IC50 | IKKe IC50 | JAK2 IC50 | Name |
|---|---|---|---|---|---|
| 79 | 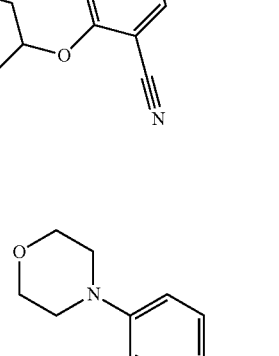 | 8 | 19 | >1000 | 5-(4-anilino-1,3,5-triazin-2-yl)-2-(oxan-4-yloxy)benzonitrile |
| 80 | 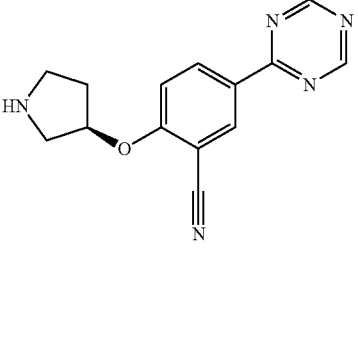 | 19 | 37 | 389 | 5-[4-(4-morpholin-4-ylanilino)-1,3,5-triazin-2-yl]-2-[(3R)-pyrrolidin-3-yl]oxybenzonitrile |
| 81 | 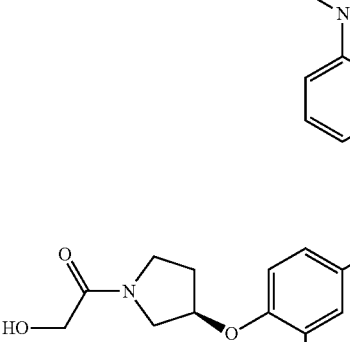 | 27 | *nd | 290 | 2-[(3R)-1-(2-hydroxyacetyl)pyrrolidin-3-yl]oxy-5-[4-(3-morpholin-4-ylanilino)-1,3,5-triazin-2-yl]benzonitrile |

TABLE 1-continued

| Ex. | Structure | TBK1 IC50 | IKKe IC50 | JAK2 IC50 | Name |
|---|---|---|---|---|---|
| 82 | | | 94 | 53 | 641 | 5-[4-(3-morpholin-4-ylanilino)-1,3,5-triazin-2-yl]-2-[(3R)-pyrrolidin-3-yl]oxybenzonitrile |
| 83 | 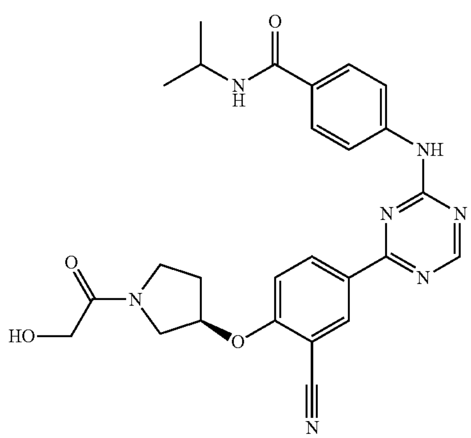 [SMILES: CC(C)NC(=O)c1ccc(Nc2ncnc(-c3ccc(O[C@@H]4CCN(C(=O)CO)C4)c(C#N)c3)n2)cc1] | 8 | 14 | 604 | 4-[[4-[3-cyano-4-[(3R)-1-(2-hydroxyacetyl)pyrrolidin-3-yl]oxyphenyl]-1,3,5-triazin-2-yl]amino]-N-propan-2-ylbenzamide |
| 84 | 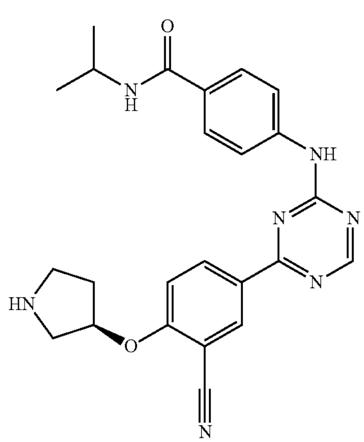 [SMILES: CC(C)NC(=O)c1ccc(Nc2ncnc(-c3ccc(O[C@@H]4CCNC4)c(C#N)c3)n2)cc1] | 72 | 166 | 805 | 4-[[4-3-cyano-4-[(3R)-pyrrolidin-3-yl]oxyphenyl]-1,3,5-triazin-9-yl]amino]-N-propan-2-ylbenzamide |

TABLE 1-continued

| Ex. | Structure | TBK1 IC50 | IKKe IC50 | JAK2 IC50 | Name |
|---|---|---|---|---|---|
| 85 | 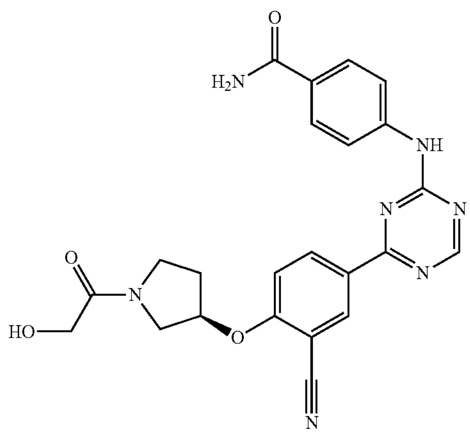 [SMILES: N#Cc1cc(-c2ncnc(Nc3ccc(C(N)=O)cc3)n2)ccc1O[C@@H]1CCN(C(=O)CO)C1] | 13 | 26 | 678 | 4-[[4-[3-cyano-4-[(3R)-1-(2-hydroxyacetyl)pyrrolidin-3-yl]oxyphenyl]-1,3,5-triazin-2-yl]amino]benzamide |
| 86 | 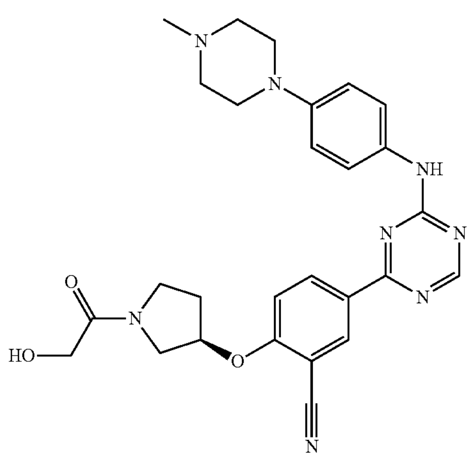 [SMILES: CN1CCN(c2ccc(Nc3ncnc(-c4ccc(O[C@@H]5CCN(C(=O)CO)C5)c(C#N)c4)n3)cc2)CC1] | 8 | 4 | 459 | 2-[(3R)-1-(2-hydroxyacetyl)pyrrolidin-3-yl]oxy-5-[4-[4-(4-methylpiperazin-1-yl)anilino]-1,3,5-triazin-2-yl]benzonitrile |
| 87 | 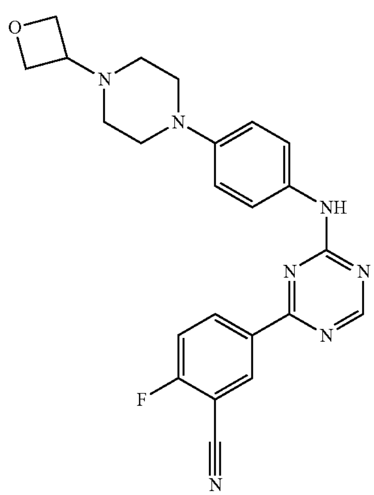 [SMILES: N#Cc1cc(-c2ncnc(Nc3ccc(N4CCN(C5COC5)CC4)cc3)n2)ccc1F] | 853 | >1000 | >1000 | 2-fluoro-5-[4-[4-[4-(oxetan-3-yl)piperazin-1-yl]anilino]-1,3,5-triazin-2-yl]benzonitrile |

TABLE 1-continued

| Ex. | Structure | TBK1 IC50 | IKKe IC50 | JAK2 IC50 | Name |
|---|---|---|---|---|---|
| 88 | 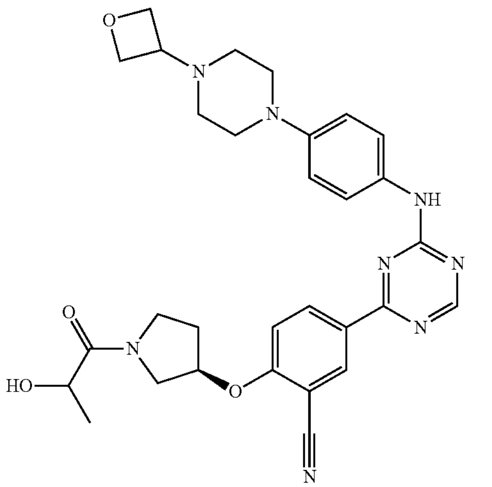 [SMILES: CC(O)C(=O)N1CC[C@@H](Oc2ccc(-c3ncnc(Nc4ccc(N5CCN(C6COC6)CC5)cc4)n3)cc2C#N)C1] | 26 | 91 | 488 | 2-[(3R)-1-[(2S)-2-hydroxypropanoyl]pyrrolidin-3-yl]oxy-5-[4-[4-(oxetan-3-yl)piperazin-1-yl]anilino]-1,3,5-triazin-2-yl]benzonitrile |
| 89 | 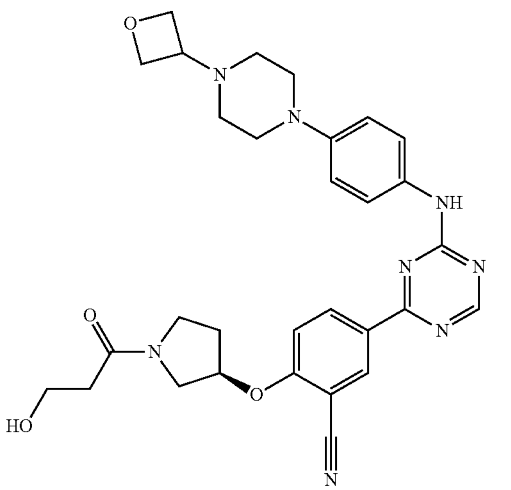 [SMILES: N#Cc1cc(-c2ncnc(Nc3ccc(N4CCN(C5COC5)CC4)cc3)n2)ccc1O[C@@H]1CCN(C(=O)CCO)C1] | 16 | 52 | 359 | 2-[(3R)-1-(3-hydroxypropanoyl)pyrrolidin-3-yl]oxy-5-[4-[4-(oxetan-3-yl)piperazin-1-yl]anilino]-1,3,5-triazin-2-yl]benzonitrile |
| 90 | 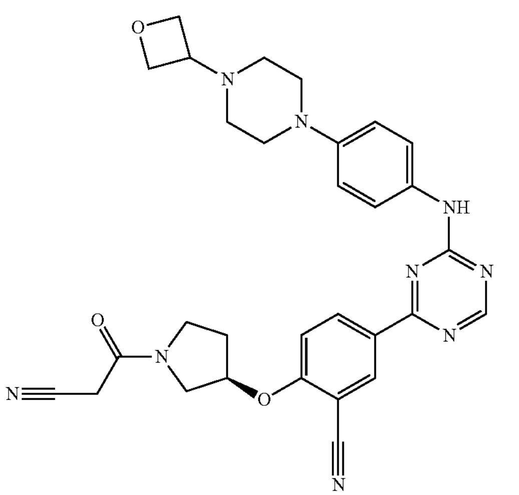 [SMILES: N#CCC(=O)N1CC[C@@H](Oc2ccc(-c3ncnc(Nc4ccc(N5CCN(C6COC6)CC5)cc4)n3)cc2C#N)C1] | 7 | 37 | 292 | 2-[(3R)-1-(2-cyanoacetyl)pyrrolidin-3-yl]oxy-5-[4-[4-(oxetan-3-yl)piperazin-1-yl]anilino]-1,3,5-triazin-2-yl]benzonitrile |

TABLE 1-continued

| Ex. | Structure | TBK1 IC50 | IKKe IC50 | JAK2 IC50 | Name |
|---|---|---|---|---|---|
| 91 | 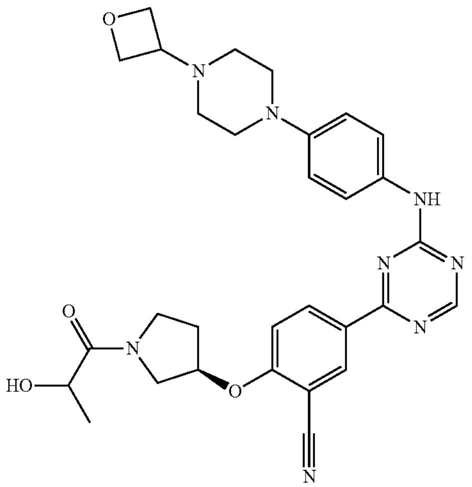 [SMILES: CC(O)C(=O)N1CC[C@@H](Oc2ccc(-c3ncnc(Nc4ccc(N5CCN(C6COC6)CC5)cc4)n3)cc2C#N)C1] | 145 | 607 | 693 | 2-[(3R)-1-[(2S)-2-hydroxypropanoyl]pyrrolidin-3-yl]oxy-5-[4-[4-(oxetan-3-yl)piperazin-1-yl]anilino]-1,3,5-triazin-2-yl]benzonitrile |
| 92 | 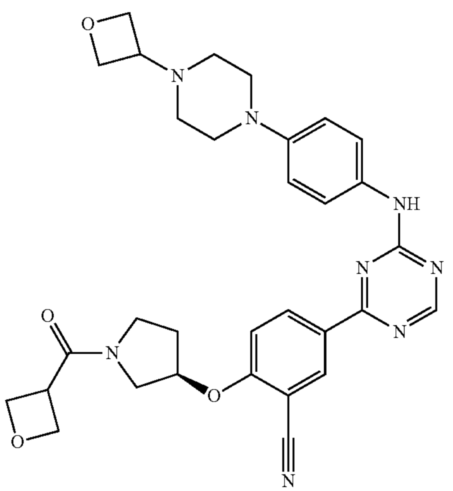 [SMILES: N#Cc1cc(-c2ncnc(Nc3ccc(N4CCN(C5COC5)CC4)cc3)n2)ccc1O[C@@H]1CCN(C(=O)C2COC2)C1] | 45 | 197 | >1000 | 2-[(3R)-1-(oxetane-3-carbonyl)pyrrolidin-3-yl]oxy-5-[4-[4-(oxetan-3-yl)piperazin-1-yl]anilino]-1,3,5-triazin-2-yl]benzonitrile |
| 93 | 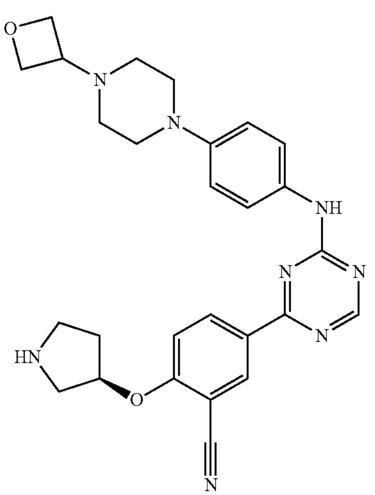 [SMILES: N#Cc1cc(-c2ncnc(Nc3ccc(N4CCN(C5COC5)CC4)cc3)n2)ccc1O[C@@H]1CCNC1] | 30 | 120 | 961 | 5-[4-[4-[4-(oxetan-3-yl)piperazin-1-yl]anilino]-1,3,5-triazin-2-yl]-2-[(3R)-pyrrolidin-3-yl]oxybenzonitrile |

TABLE 1-continued

| Ex. | Structure | TBK1 IC50 | IKKe IC50 | JAK2 IC50 | Name |
|---|---|---|---|---|---|
| 94 | 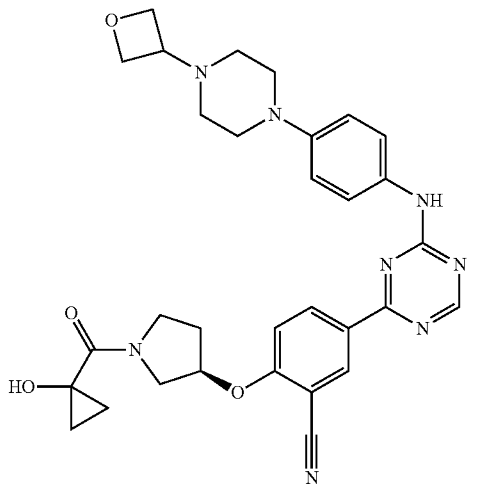 [SMILES: N#Cc1cc(-c2ncnc(Nc3ccc(N4CCN(C5COC5)CC4)cc3)n2)ccc1O[C@@H]1CCN(C(=O)C2(O)CC2)C1] | 173 | 367 | >1000 | 2-[(3R)-1-(1-hydroxycyclopropane-carbonyl)pyrrolidin-3-yl]oxy-5-[4-[4-[4-(oxetan-3-yl)piperazin-1-yl]anilino]-1,3,5-triazin-2-yl]benzonitrile |
| 95 | 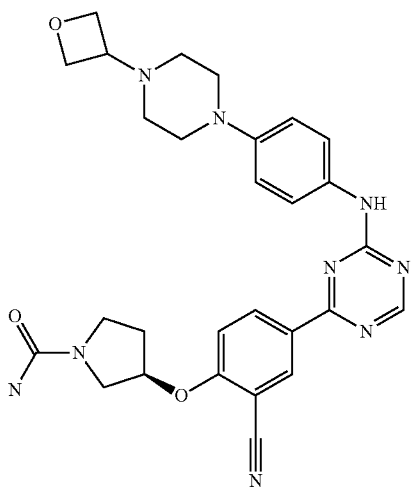 [SMILES: N#Cc1cc(-c2ncnc(Nc3ccc(N4CCN(C5COC5)CC4)cc3)n2)ccc1O[C@@H]1CCN(C(N)=O)C1] | 7 | 21 | 377 | 2-[(3R)-1-formylpyrrolidin-3-yl]oxy-5-[4-[4-[4-(oxetan-3-yl)piperazin-1-yl]anilino]-1,3,5-triazin-2-yl]benzonitrile |
| 96 | 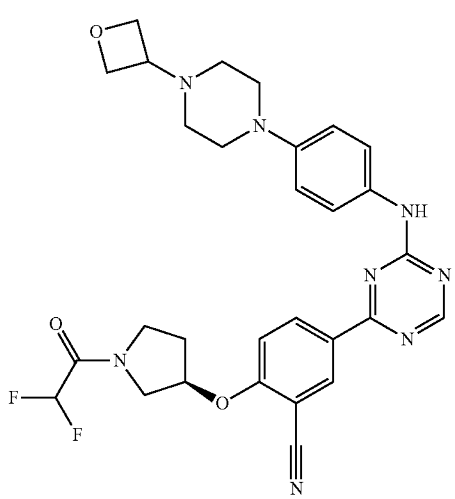 [SMILES: N#Cc1cc(-c2ncnc(Nc3ccc(N4CCN(C5COC5)CC4)cc3)n2)ccc1O[C@@H]1CCN(C(=O)C(F)F)C1] | 21 | 91 | 560 | 2-[(3R)-1-(2,2-difluoroacetyl)pyrrolidin-3-yl]oxy-5-[4-[4-[4-(oxetan-3-yl)piperazin-1-yl]anilino]-1,3,5-triazin-2-yl]benzonitrile |

TABLE 1-continued

| Ex. | Structure | TBK1 IC50 | IKKe IC50 | JAK2 IC50 | Name |
|---|---|---|---|---|---|
| 97 | 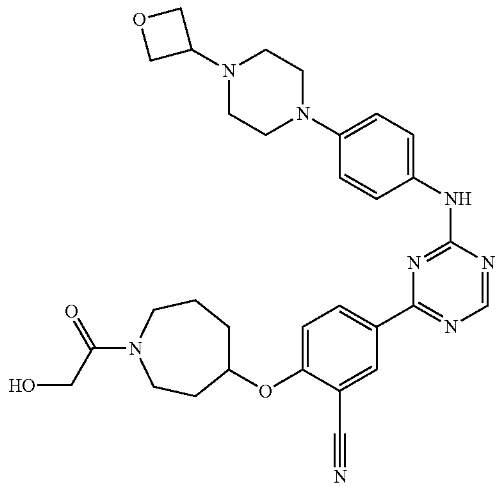 [SMILES: N#Cc1cc(-c2ncnc(Nc3ccc(N4CCN(C5COC5)CC4)cc3)n2)ccc1OC1CCCN(C(=O)CO)CC1] | 11 | 22 | 241 | 2-[1-(2-hydroxyacetyl)azepan-4-yl]oxy-5-[4-[4-[4-(oxetan-3-yl)piperazin-1-yl]anilino]-1,3,5-triazin-2-yl]benzonitrile |
| 98 | 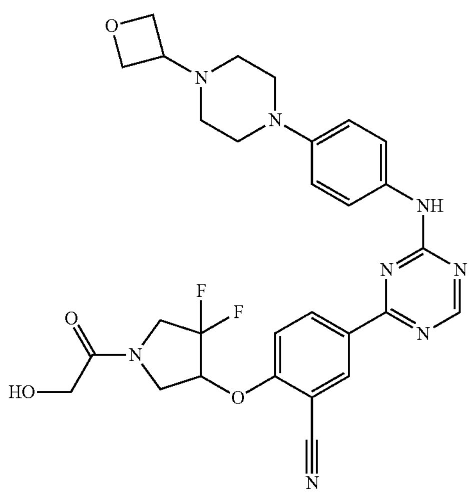 [SMILES: N#Cc1cc(-c2ncnc(Nc3ccc(N4CCN(C5COC5)CC4)cc3)n2)ccc1OC1CN(C(=O)CO)CC1(F)F] | 5 | 14 | 119 | 2-[4,4-difluoro-1-(2-hydroxyacetyl)pyrrolidin-3-yl]oxy-5-[4-[4-[4-(oxetan-3-yl)piperazin-1-yl]anilino]-1,3,5-triazin-2-yl]benzonitrile |
| 99 | 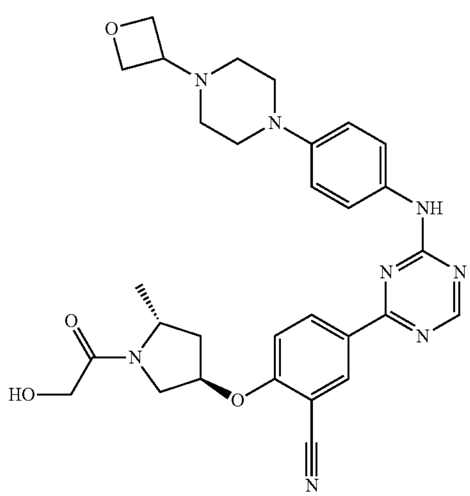 [SMILES: C[C@@H]1C[C@@H](Oc2ccc(-c3ncnc(Nc4ccc(N5CCN(C6COC6)CC5)cc4)n3)cc2C#N)CN1C(=O)CO] | 77 | 193 | 440 | 2-[(3R,5R)-1-(2-hydroxyacetyl)-5-methylpyrrolidin-3-yl]oxy-5-[4-[4-[4-(oxetan-3-yl)piperazin-1-yl]anilino]-1,3,5-triazin-2-yl]benzonitrile |

TABLE 1-continued

| Ex. | Structure | TBK1 IC50 | IKKe IC50 | JAK2 IC50 | Name |
|---|---|---|---|---|---|
| 100 | 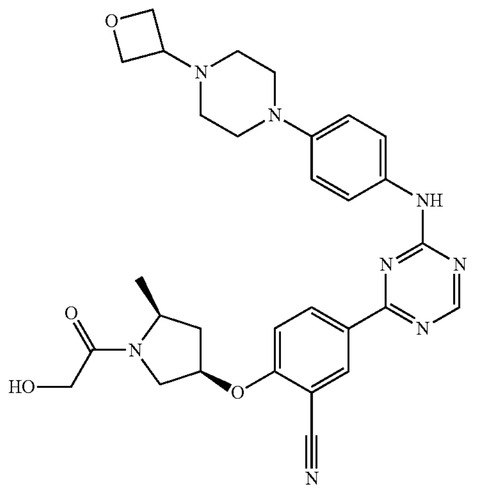 [SMILES: C[C@H]1C[C@@H](Oc2ccc(-c3ncnc(Nc4ccc(N5CCN(C6COC6)CC5)cc4)n3)cc2C#N)CN1C(=O)CO] | 121 | 249 | 525 | 2-[(3R,5S)-1-(2-hydroxyacetyl)-5-methylpyrrolidin-3-yl]oxy-5-[4-[4-[4-(oxetan-3-yl)piperazin-1-yl]anilino]-1,3,5-triazin-2-yl]benzonitrile |
| 101 | 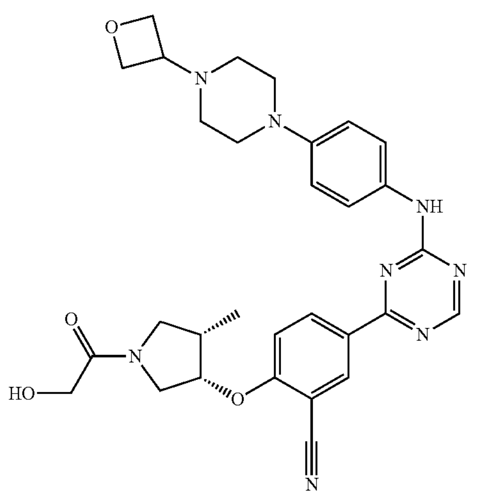 [SMILES: C[C@H]1CN(C(=O)CO)C[C@H]1Oc1ccc(-c2ncnc(Nc3ccc(N4CCN(C5COC5)CC4)cc3)n2)cc1C#N] | 14 | 26 | 638 | 2-[(3R,4S)-4-fluoro-1-(2-hydroxyacetyl)pyrrolidin-3-yl]oxy-5-[4-[4-[4-(oxetan-3-yl)piperazin-1-yl]anilino]-1,3,5-triazin-2-yl]benzonitrile |
| 102 | 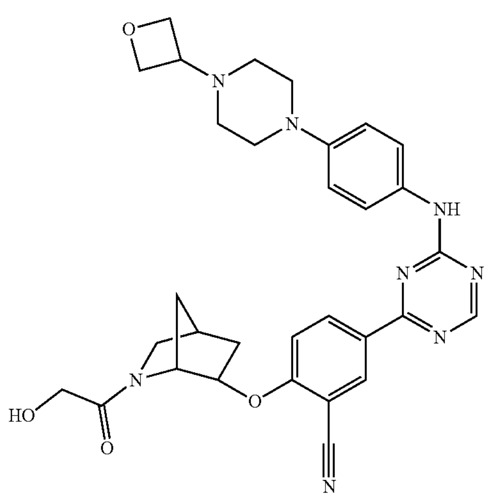 [SMILES: N#Cc1cc(-c2ncnc(Nc3ccc(N4CCN(C5COC5)CC4)cc3)n2)ccc1OC1CC2CC1N(C(=O)CO)C2] | 11 | 24 | 380 | 2-[[3-(2-hydroxyacetyl)-3-azabicyclo[2.2.1]heptan-5-yl]oxy]-5-[4-[4-[4-(oxetan-3-yl)piperazin-1-yl]anilino]-1,3,5-triazin-2-yl]benzonitrile |

TABLE 1-continued

| Ex. | Structure | TBK1 IC50 | IKKe IC50 | JAK2 IC50 | Name |
|---|---|---|---|---|---|
| 103 | 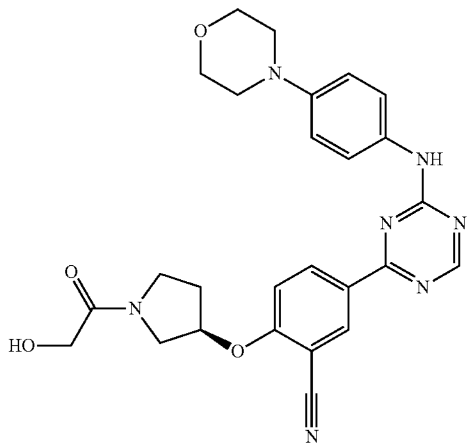 [SMILES: N#Cc1cc(-c2ncnc(Nc3ccc(N4CCOCC4)cc3)n2)ccc1O[C@@H]1CCN(C(=O)CO)C1] | 6 | 10 | 260 | 2-[(3R)-1-(2-hydroxyacetyl)pyrrolidin-3-yl]oxy-5-[4-(4-morpholin-4-ylanilino)-1,3,5-triazin-2-yl]benzonitrile |
| 104 | 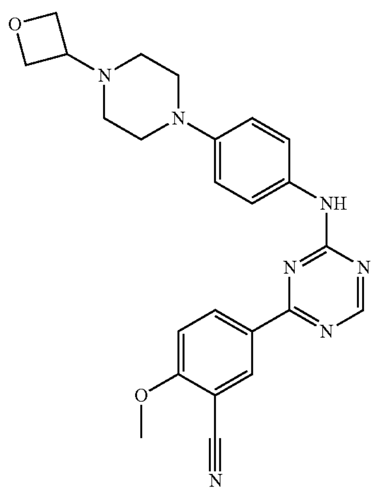 [SMILES: COc1ccc(-c2ncnc(Nc3ccc(N4CCN(C5COC5)CC4)cc3)n2)cc1C#N] | 42 | 215 | 328 | 2-methoxy-5-[4-[4-[4-(oxetan-3-yl)piperazin-1-yl]anilino]-1,3,5-triazin-2-yl]benzonitrile |
| 105 | 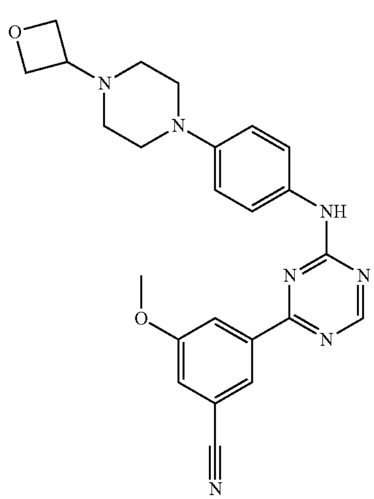 [SMILES: COc1cc(C#N)cc(-c2ncnc(Nc3ccc(N4CCN(C5COC5)CC4)cc3)n2)c1] | 79 | >1000 | 212 | 3-methoxy-5-[4-[4-[4-(oxetan-3-yl)piperazin-1-yl]anilino]-1,3,5-triazin-2-yl]benzonitrile |

TABLE 1-continued

| Ex. | Structure | TBK1 IC50 | IKKe IC50 | JAK2 IC50 | Name |
|---|---|---|---|---|---|
| 106 | 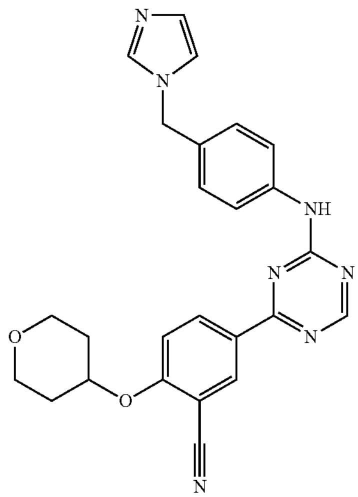 [SMILES: N#Cc1cc(-c2ncnc(Nc3ccc(Cn4ccnc4)cc3)n2)ccc1OC1CCOCC1] | 5 | 4 | >1000 | 5-[4-[4-(imidazol-1-ylmethyl)anilino]-1,3,5-triazin-2-yl]-2-(oxan-4-yloxy)benzonitrile |
| 107 | 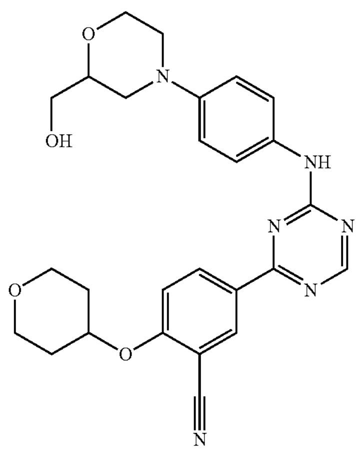 [SMILES: N#Cc1cc(-c2ncnc(Nc3ccc(N4CCOC(CO)C4)cc3)n2)ccc1OC1CCOCC1] | 2 | 3 | 258 | 5-[4-[4-[(2R)-2-(hydroxymethyl)morpholin-4-yl]anilino]-1,3,5-triazin-2-yl]-2-(oxan-4-yloxy)benzonitrile |
| 108 | 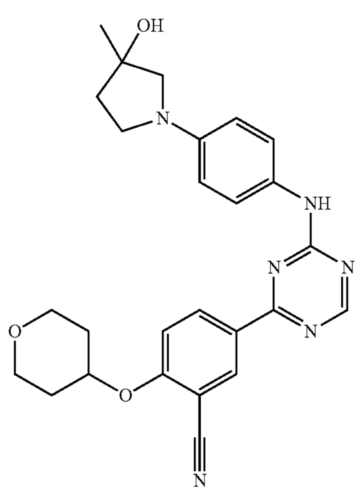 [SMILES: CC1(O)CCN(c2ccc(Nc3ncnc(-c4ccc(OC5CCOCC5)c(C#N)c4)n3)cc2)C1] | 3 | 6 | >1000 | 5-[4-[4-(3-hydroxy-3-methylpyrrolidin-1-yl)anilino]-1,3,5-triazin-2-yl]-2-(oxan-4-yloxy)benzonitrile |

TABLE 1-continued

| Ex. | Structure | TBK1 IC50 | IKKe IC50 | JAK2 IC50 | Name |
|---|---|---|---|---|---|
| 109 | 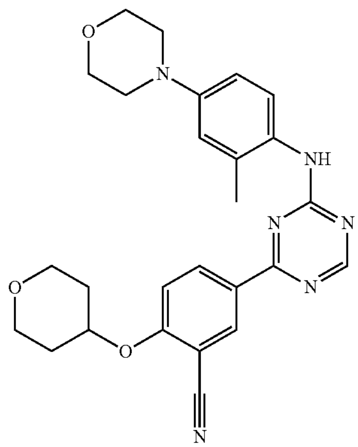 [SMILES: Cc1cc(N2CCOCC2)ccc1Nc1ncnc(-c2ccc(OC3CCOCC3)c(C#N)c2)n1] | 76 | 161 | >1000 | 5-[4-(2-methyl-4-morpholin-4-ylanilino)-1,3,5-triazin-2-yl-7-(oxan-4-yloxy)benzonitrile |
| 110 | 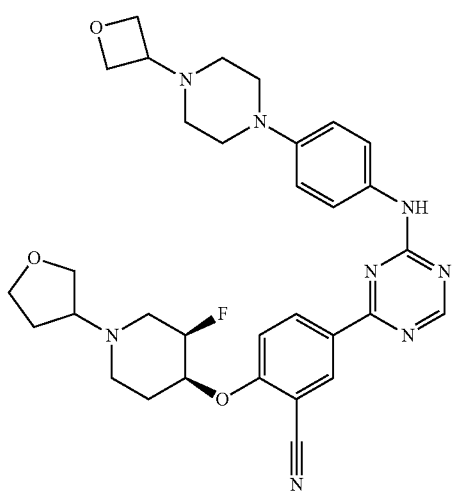 [SMILES: N#Cc1cc(-c2ncnc(Nc3ccc(N4CCN(C5COC5)CC4)cc3)n2)ccc1O[C@H]1CCN(C2CCOC2)C[C@H]1F] | 243 | 330 | 740 | 2-(((3R,4S)-3-fluoro-1-(tetrahydrofuran-3-yl)piperidin-4-yl)oxy)-5-(4-((4-(4-(oxetan-3-yl)piperazin-1-yl)phenyl)amino)-1,3,5-triazin-2-yl)benzonitrile |
| 111 | 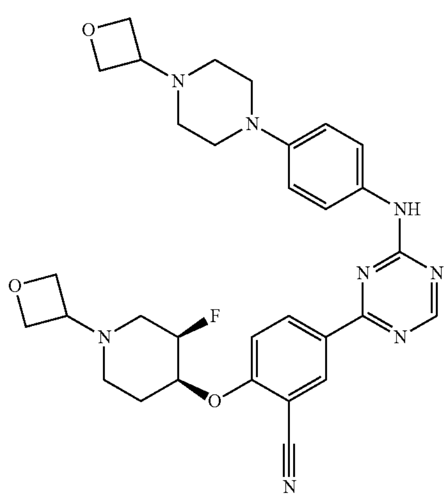 [SMILES: N#Cc1cc(-c2ncnc(Nc3ccc(N4CCN(C5COC5)CC4)cc3)n2)ccc1O[C@H]1CCN(C2COC2)C[C@H]1F] | 146 | 328 | 602 | 2-(((3R,4S)-3-fluoro-1-(oxetan-3-yl)piperidin-4-yl)oxy)-5-(4-((4-(4-(oxetan-3-yl)piperazin-1-yl)phenyl)amino)-1,3,5-triazin-2-yl)benzonitrile |

TABLE 1-continued

| Ex. | Structure | TBK1 IC50 | IKKe IC50 | JAK2 IC50 | Name |
|---|---|---|---|---|---|
| 112 | 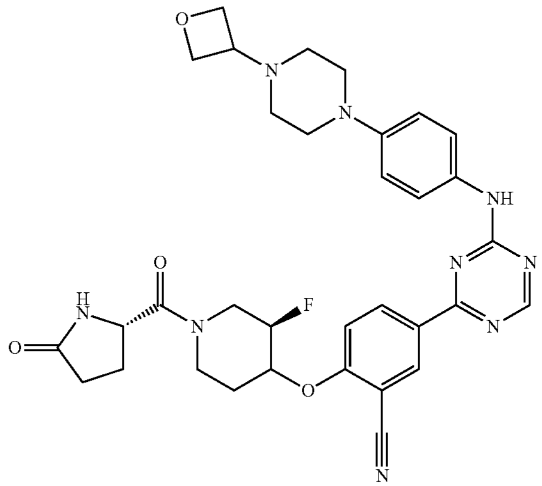 [SMILES: N#Cc1cc(-c2ncnc(Nc3ccc(N4CCN(C5COC5)CC4)cc3)n2)ccc1OC1CCN(C(=O)[C@@H]2CCC(=O)N2)C[C@H]1F] | 4 | 4 | 375 | 2-(((3R)-3-fluoro-1-((S)-5-oxopyrrolidine-2-carbonyl)piperidin-4-yl)oxy)-5-(4-((4-(4-(oxetan-3-yl)piperazin-1-yl)phenyl)amino)-1,3,5-triazin-2-yl)benzonitrile |
| 113 | 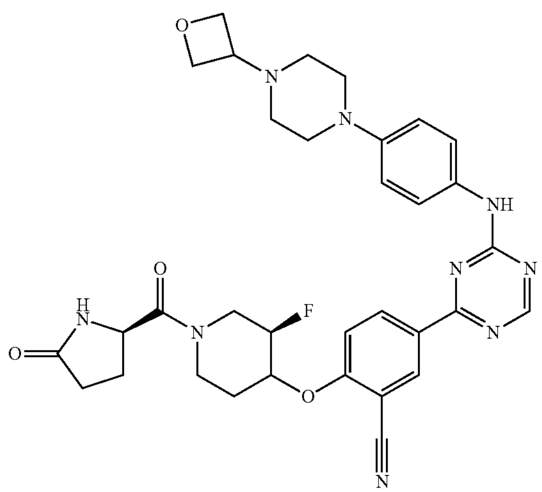 [SMILES: N#Cc1cc(-c2ncnc(Nc3ccc(N4CCN(C5COC5)CC4)cc3)n2)ccc1OC1CCN(C(=O)[C@H]2CCC(=O)N2)C[C@H]1F] | 64 | 100 | 292 | 2-(((3R)-3-fluoro-1-((R)-5-oxopyrrolidine-2-carbonyl)piperidin-4-yl)oxy)-5-(4-((4-(4-(oxetan-3-yl)piperazin-1-yl)phenyl)amino)-1,3,5-triazin-2-yl)benzonitrile |
| 114 | 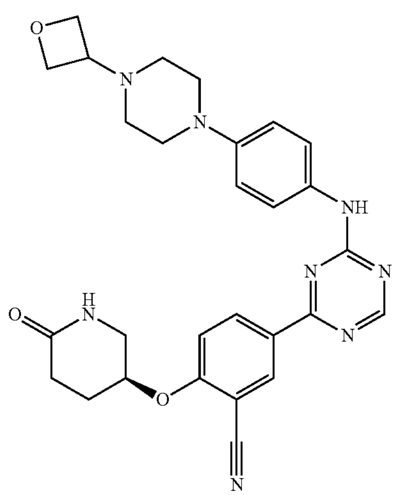 [SMILES: N#Cc1cc(-c2ncnc(Nc3ccc(N4CCN(C5COC5)CC4)cc3)n2)ccc1O[C@H]1CCC(=O)NC1] | 20 | 56 | 175 | (S)-5-(4-((4-(4-(oxetan-3-yl)piperazin-1-yl)phenyl)amino)-1,3,5-triazin-2-yl)-2-((6-oxopiperidin-3-yl)oxy)benzonitrile |

TABLE 1-continued

| Ex. | Structure | TBK1 IC50 | IKKe IC50 | JAK2 IC50 | Name |
|---|---|---|---|---|---|
| 115 | 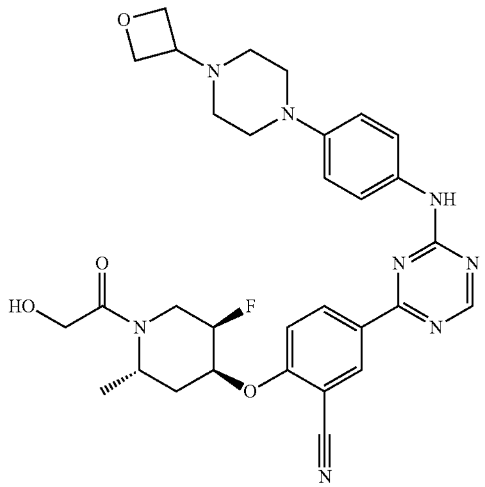 [SMILES: C[C@H]1C[C@H](Oc2ccc(-c3ncnc(Nc4ccc(N5CCN(C6COC6)CC5)cc4)n3)cc2C#N)[C@H](F)CN1C(=O)CO] | 12 | 21 | 1000 | 2-(((2S,4S,5R)-5-fluoro-1-(2-hydroxyacetyl)-2-methylpiperidin-4-yl)oxy)-5-(4-((4-(4-(oxetan-3-yl)piperazin-1-yl)phenyl)amino)-1,3,5-triazin-2-yl)benzonitrile |
| 116 | 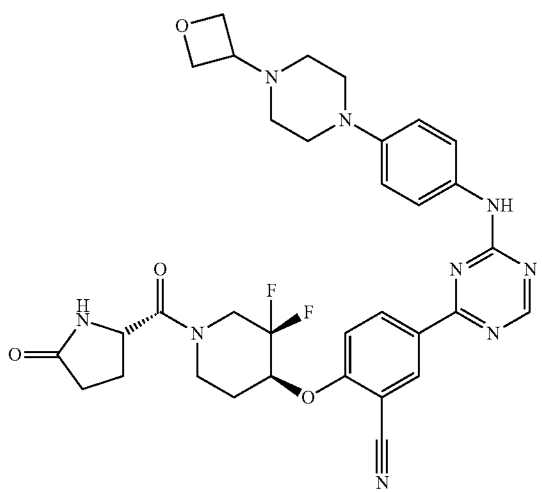 | 2 | 1 | 146 | 2-(((S)-3,3-difluoro-1-((S)-5-oxopyrrolidine-2-carbonyl)piperidin-4-yl)oxy)-5-(4-((4-(4-(oxetan-3-yl)piperazin-1-yl)phenyl)amino)-1,3,5-triazin-2-yl)benzonitrile |
| 117 | 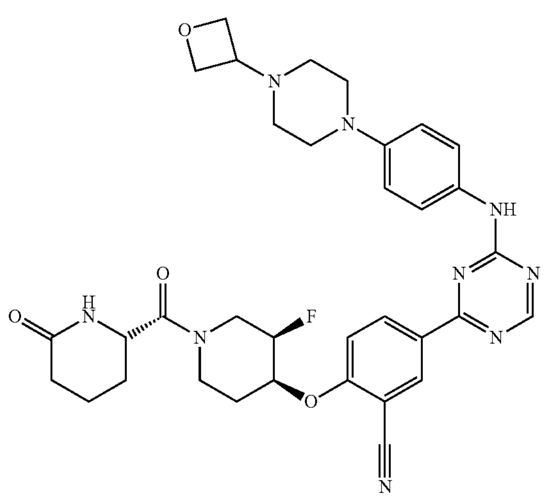 | 3 | 4 | 342 | 2-(((3R,4S)-3-fluoro-1-((S)-6-oxopiperidine-2-carbonyl)piperidin-4-yl)oxy)-5-(4-((4-(4-(oxetan-3-yl)piperazin-1-yl)phenyl)amino)-1,3,5-triazin-2-yl)benzonitrile |

TABLE 1-continued

| Ex. | Structure | TBK1 IC50 | IKKe IC50 | JAK2 IC50 | Name |
|---|---|---|---|---|---|
| 118 | 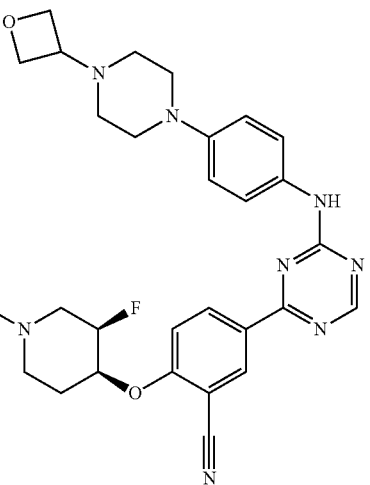 | 7 | 11 | 284 | 2-(((3R,4S)-1-(1,1-dioxidoisothiazolidine-3-carbonyl)-3-fluoropiperidin-4-yl)oxy)-5-(4-((4-(4-(oxetan-3-yl)piperazin-1-yl)phenyl)amino)-1,3,5-triazin-2-yl)benzonitrile |
| 119 | 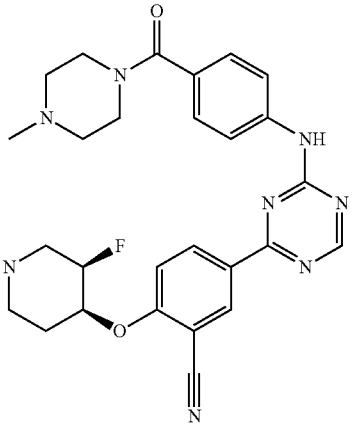 | 6 | 2 | 338 | 2-(((3R,4S)-3-fluoro-1-(2-hydroxyacetyl)piperidin-4-yl)oxy)-5-(4-((4-(4-methylpiperazine-1-carbonyl)phenyl)amino)-1,3,5-triazin-2-yl)benzonitrile |
| 120 | 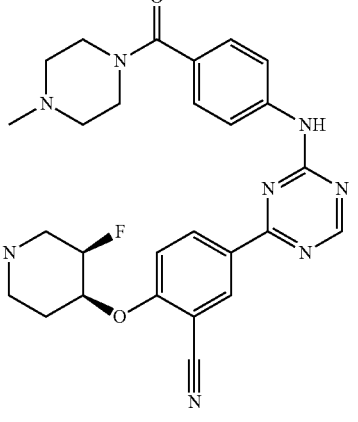 | 4 | 2 | 674 | 2-(((3R,4S)-3-fluoro-1-((S)-2-hydroxypropanoyl)piperidin-4-yl)oxy)-5-(4-((4-(4-methylpiperazine-1-carbonyl)phenyl)amino)-1,3,5-triazin-2-yl)benzonitrile |

TABLE 1-continued

| Ex. | Structure | TBK1 IC50 | IKKe IC50 | JAK2 IC50 | Name |
|---|---|---|---|---|---|
| 121 | 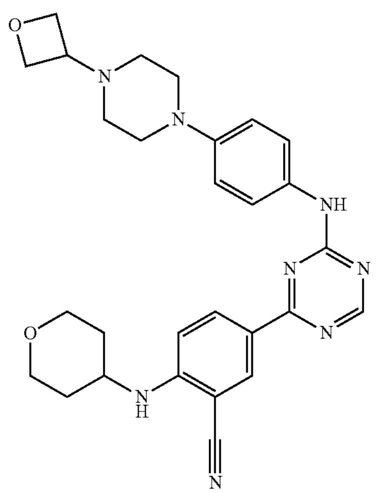 [SMILES: N#Cc1cc(-c2ncnc(Nc3ccc(N4CCN(C5COC5)CC4)cc3)n2)ccc1NC1CCOCC1] | 11 | 47 | 32 | 5-(4-((4-(4-(oxetan-3-yl)piperazin-1-yl)phenyl)amino)-1,3,5-triazin-2-yl)-2-((tetrahydro-2H-pyran-4-yl)amino)benzonitrile |
| 122 | 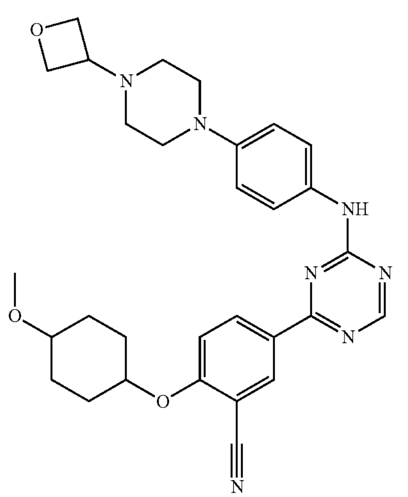 [SMILES: COC1CCC(Oc2ccc(-c3ncnc(Nc4ccc(N5CCN(C6COC6)CC5)cc4)n3)cc2C#N)CC1] | 15 | 15 | 402 | 2-((4-methoxycyclohexyl)oxy)-5-(4-((4-(4-(oxetan-3-yl)piperazin-1-yl)phenyl)amino)-1,3,5-triazin-2-yl)benzonitrile |
| 123 | Chiral | 31 | 132 | 546 | 2-(((3R,4S)-3-fluoro-1-((S)-3-hydroxy-2-methylpropanoyl)piperidin-4-yl)oxy)-5-(4-((4-(4-(oxetan-3-yl)piperazin-1-yl)phenyl)amino)-1,3,5-triazin-2-yl)benzonitrile |

TABLE 1-continued

| Ex. | Structure | TBK1 IC50 | IKKe IC50 | JAK2 IC50 | Name |
|---|---|---|---|---|---|
| 124 | 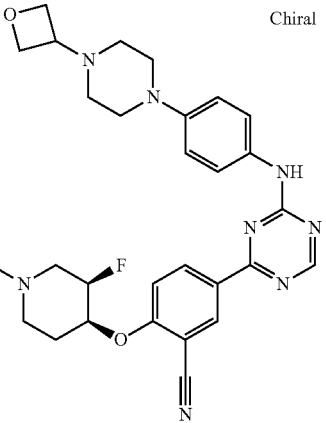 Chiral | 15 | 54 | 676 | 2-(((3R,4S)-3-fluoro-1-((R)-3-hydroxy-2-methylpropanoyl)piperidin-4-yl)oxy)-5-(4-((4-(4-(oxetan-3-yl)piperazin-1-yl)phenyl)amino)-1,3,5-triazin-2-yl)benzonitrile |
| 125 | 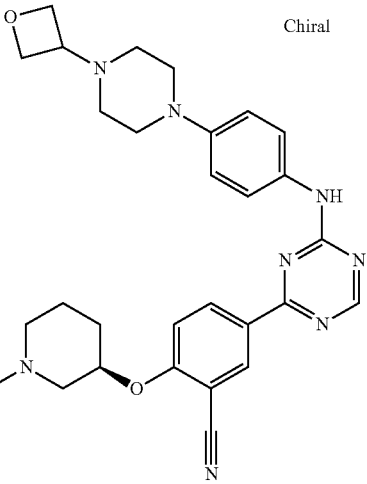 Chiral | 31 | 86 | 952 | (R)-2-((1-(2-hydroxyacetyl)piperidin-3-yl)oxy)-5-(4-((4-(4-(oxetan-3-yl)piperazin-1-yl)phenyl)amino)-1,3,5-triazin-2-yl)benzonitrile |
| 126 | 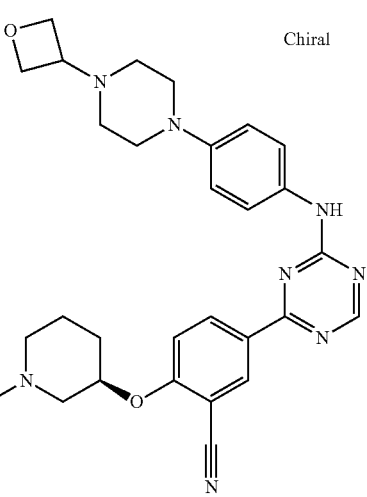 Chiral | 56 | 111 | 1000 | 2-(((R)-1-((S)-2-hydroxypropanoyl)piperidin-3-yl)oxy)-5-(4-((4-(4-(oxetan-3-yl)piperazin-1-yl)phenyl)amino)-1,3,5-triazin-2-yl)benzonitrile |

TABLE 1-continued

| Ex. | Structure | TBK1 IC50 | IKKe IC50 | JAK2 IC50 | Name |
|---|---|---|---|---|---|
| 127 | 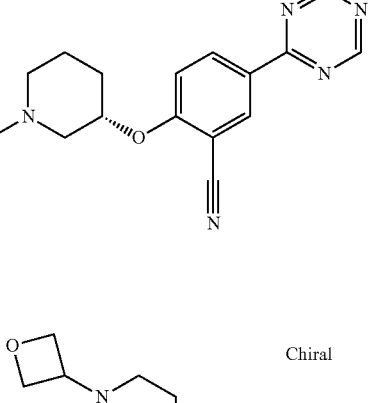 Chiral | 180 | 562 | 394 | (S)-2-((1-(2-hydroxyacetyl)piperidin-3-yl)oxy)-5-(4-((4-(4-(oxetan-3-yl)piperazin-1-yl)phenyl)amino)-1,3,5-triazin-2-yl)benzonitrile |
| 128 | 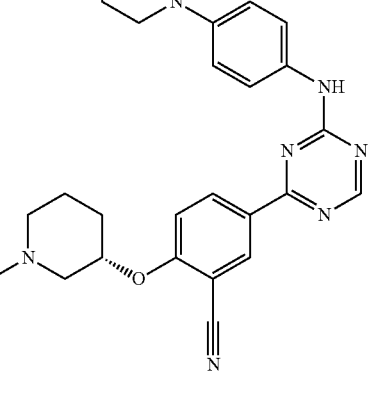 Chiral | 37 | 177 | 632 | 2-(((S)-1-((S)-2-hydroxypropanoyl)piperidin-3-yl)oxy)-5-(4-((4-(4-(oxetan-3-yl)piperazin-1-yl)phenyl)amino)-1,3,5-triazin-2-yl)benzonitrile |
| 129 | 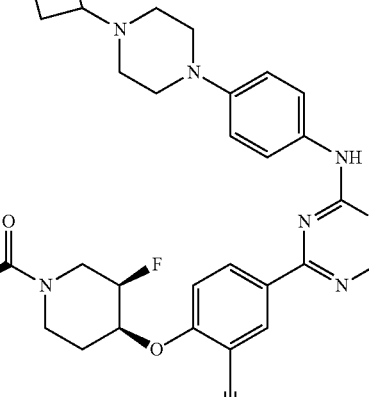 Chiral | 334 | 619 | 1000 | 2-(((3R,4S)-3-fluoro-1-((R)-piperidine-2-carbonyl)piperidin-4-yl)oxy)-5-(4-((4-(4-(oxetan-3-yl)piperazin-1-yl)phenyl)amino)-1,3,5-triazin-2-yl)benzonitrile |

TABLE 1-continued

| Ex. | Structure | TBK1 IC50 | IKKe IC50 | JAK2 IC50 | Name |
|---|---|---|---|---|---|
| 130 | 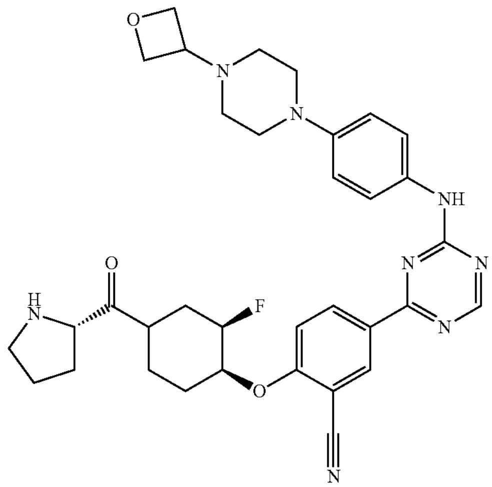 [SMILES: N#Cc1cc(-c2ncnc(Nc3ccc(N4CCN(C5COC5)CC4)cc3)n2)ccc1O[C@H]1CCC(C(=O)[C@@H]2CCCN2)C[C@H]1F] | 29 | 73 | 1000 | 2-(((3R,4S)-3-fluoro-1-((R)-pyrrolidine-2-carbonyl)piperidin-4-yl)oxy)-5-(4-((4-(4-(oxetan-3-yl)piperazin-1-yl)phenyl)amino)-1,3,5-triazin-2-yl)benzonitrile |
| 131 | Chiral | 101 | 175 | 1000 | 2-(((3R,4S)-3-fluoro-1-((S)-piperidine-2-carbonyl)piperidin-4-yl)oxy)-5-(4-((4-(4-(oxetan-3-yl)piperazin-1-yl)phenyl)amino)-1,3,5-triazin-2-yl)benzonitrile |
| 132 | 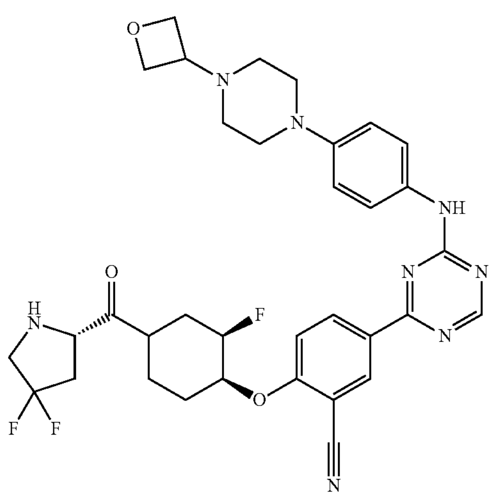 [SMILES: N#Cc1cc(-c2ncnc(Nc3ccc(N4CCN(C5COC5)CC4)cc3)n2)ccc1O[C@H]1CCC(C(=O)[C@@H]2CC(F)(F)CN2)C[C@H]1F] | 25 | 51 | 1000 | 2-(((3R,4S)-1-((R)-4,4-difluoropyrrolidine-2-carbonyl)-3-fluoropiperidin-4-yl)oxy)-5-(4-((4-(4-(oxetan-3-yl)piperazin-1-yl)phenyl)amino)-1,3,5-triazin-2-yl)benzonitrile |

TABLE 1-continued

| Ex. | Structure | TBK1 IC50 | IKKe IC50 | JAK2 IC50 | Name |
|---|---|---|---|---|---|
| 133 | 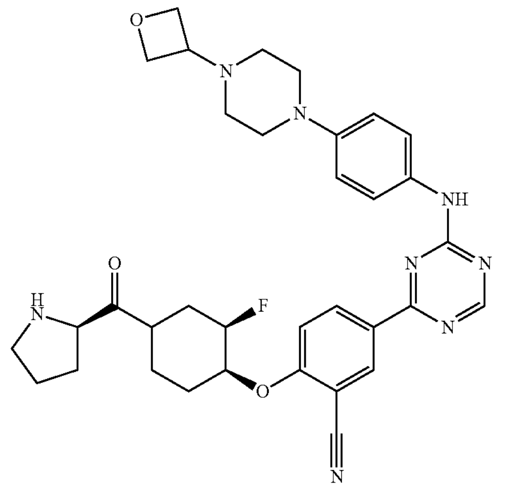 [SMILES: N#Cc1cc(-c2ncnc(Nc3ccc(N4CCN(C5COC5)CC4)cc3)n2)ccc1O[C@H]1CCC(C(=O)[C@H]2CCCN2)C[C@H]1F] | 483 | 1000 | 1000 | 2-(((3R,4S)-3-fluoro-1-((S)-pyrrolidine-2-carbonyl)piperidin-4-yl)oxy)-5-(4-((4-(4-(oxetan-3-yl)piperazin-1-yl)phenyl)amino)-1,3,5-triazin-2-yl)benzonitrile |
| 134 | Chiral | 520 | 1000 | 371 | (S)-3-((1-(2-hydroxypropanoyl)piperidin-4-yl)oxy)-5-(4-((4-(4-(oxetan-3-yl)piperazin-1-yl)phenyl)amino)-1,3,5-triazin-2-yl)benzonitrile |
| 135 | 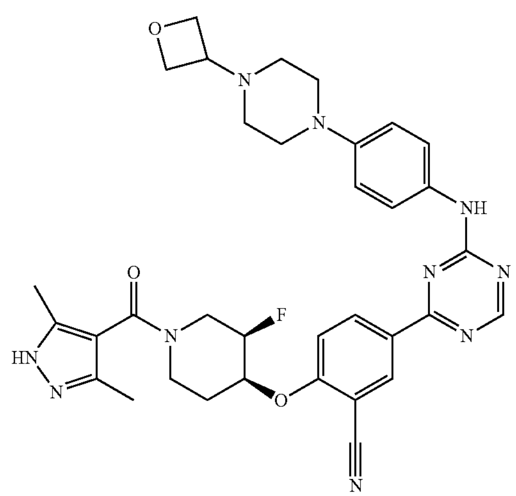 [SMILES: Cc1n[nH]c(C)c1C(=O)N1CC[C@H](Oc2ccc(-c3ncnc(Nc4ccc(N5CCN(C6COC6)CC5)cc4)n3)cc2C#N)[C@H](F)C1] | 7 | 7 | 212 | 2-(((3R,4S)-1-(3,5-dimethyl-1H-pyrazole-4-carbonyl)-3-fluoropiperidin-4-yl)oxy)-5-(4-((4-(4-(oxetan-3-yl)piperazin-1-yl)phenyl)amino)-1,3,5-triazin-2-yl)benzonitrile |

TABLE 1-continued

| Ex. | Structure | TBK1 IC50 | IKKe IC50 | JAK2 IC50 | Name |
|---|---|---|---|---|---|
| 136 | 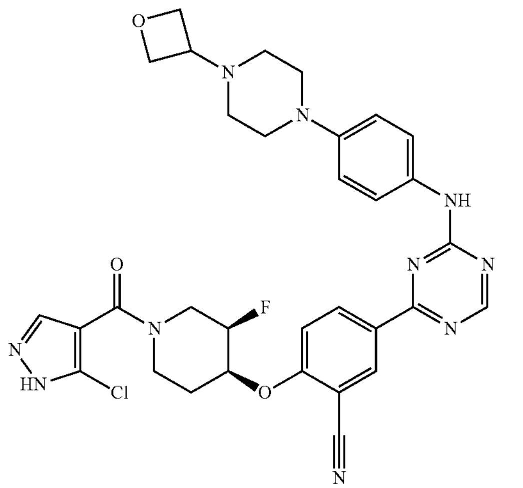 [SMILES: N#Cc1cc(-c2ncnc(Nc3ccc(N4CCN(C5COC5)CC4)cc3)n2)ccc1O[C@H]1CCN(C(=O)c2cn[nH]c2Cl)C[C@H]1F] | 46 | 73 | 167 | 2-(((3R,4S)-1-(5-chloro-1H-pyrazole-4-carbonyl)-3-fluoropiperidin-4-yl)oxy)-5-(4-((4-(4-(oxetan-3-yl)piperazin-1-yl)phenyl)amino)-1,3,5-triazin-2-yl)benzonitrile |
| 137 | 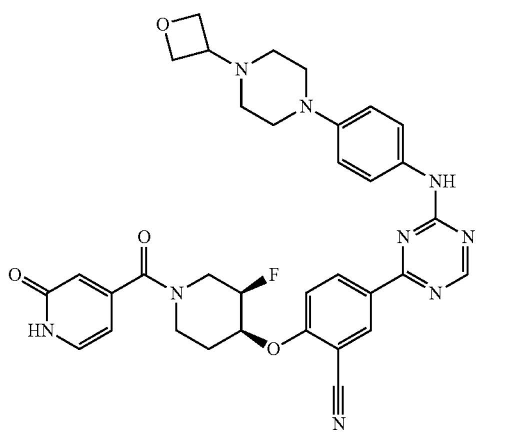 [SMILES: N#Cc1cc(-c2ncnc(Nc3ccc(N4CCN(C5COC5)CC4)cc3)n2)ccc1O[C@H]1CCN(C(=O)c2cc[nH]c(=O)c2)C[C@H]1F] | 19 | 32 | 207 | 2-(((3R,4S)-3-fluoro-1-(2-oxo-1,2-dihydropyridine-4-carbonyl)piperidin-4-yl)oxy)-5-(4-((4-(4-(oxetan-3-yl)piperazin-1-yl)phenyl)amino)-1,3,5-triazin-2-yl)benzonitrile |
| 138 | 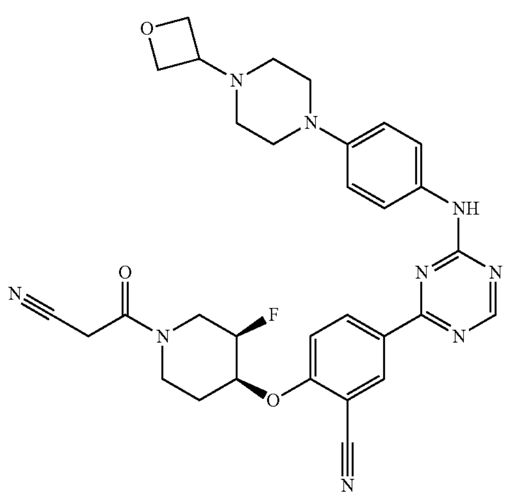 [SMILES: N#CCC(=O)N1CC[C@H](Oc2ccc(-c3ncnc(Nc4ccc(N5CCN(C6COC6)CC5)cc4)n3)cc2C#N)[C@H](F)C1] | 2 | 2 | 146 | 2-(((3R,4S)-1-(2-cyanoacetyl)-3-fluoropiperidin-4-yl)oxy)-5-(4-((4-(4-(oxetan-3-yl)piperazin-1-yl)phenyl)amino)-1,3,5-triazin-2-yl)benzonitrile |

TABLE 1-continued

| Ex. | Structure | TBK1 IC50 | IKKe IC50 | JAK2 IC50 | Name |
|---|---|---|---|---|---|
| 139 | 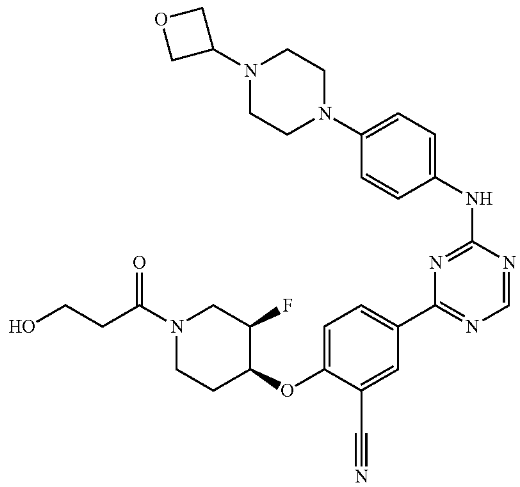 [SMILES: N#Cc1cc(-c2ncnc(Nc3ccc(N4CCN(C5COC5)CC4)cc3)n2)ccc1O[C@H]1CCN(C(=O)CCO)C[C@H]1F] | 4 | 7 | 408 | 2-(((3R,4S)-3-fluoro-1-(3-hydroxypropanoyl)piperidin-4-yl)oxy)-5-(4-((4-(4-(oxetan-3-yl)piperazin-1-yl)phenyl)amino)-1,3,5-triazin-2-yl)benzonitrile |
| 140 | 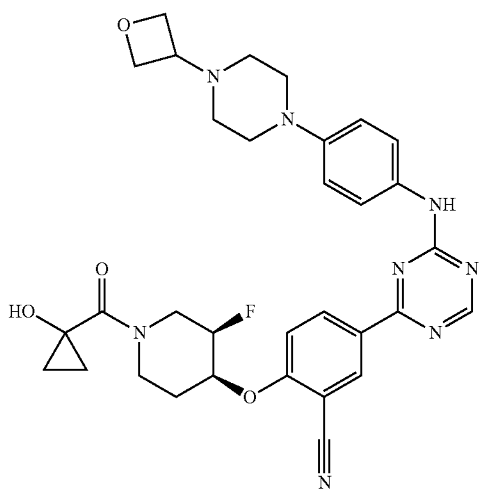 [SMILES: N#Cc1cc(-c2ncnc(Nc3ccc(N4CCN(C5COC5)CC4)cc3)n2)ccc1O[C@H]1CCN(C(=O)C2(O)CC2)C[C@H]1F] | 6 | 10 | 341 | 2-(((3R,4S)-3-fluoro-1-(1-hydroxycyclopropane-carbonyl)piperidin-4-yl)oxy)-5-(4-((4-(4-(oxetan-3-yl)piperazin-1-yl)phenyl)amino)-1,3,5-triazin-2-yl)benzonitrile |
| 141 | 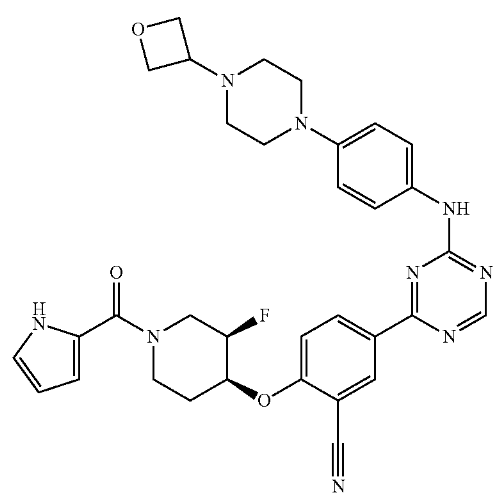 [SMILES: N#Cc1cc(-c2ncnc(Nc3ccc(N4CCN(C5COC5)CC4)cc3)n2)ccc1O[C@H]1CCN(C(=O)c2ccc[nH]2)C[C@H]1F] | 3 | 2 | 356 | 2-(((3R,4S)-3-fluoro-1-(1H-pyrrole-2-carbonyl)piperidin-4-yl)oxy)-5-(4-((4-(4-(oxetan-3-yl)piperazin-1-yl)phenyl)amino)-1,3,5-triazin-2-yl)benzonitrile |

TABLE 1-continued

| Ex. | Structure | TBK1 IC50 | IKKe IC50 | JAK2 IC50 | Name |
|---|---|---|---|---|---|
| 142 | 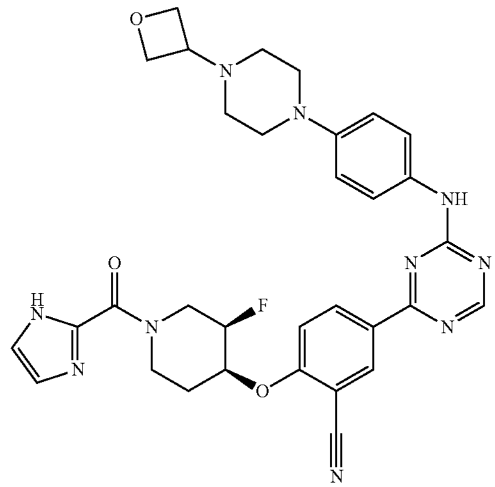 [SMILES: N#Cc1cc(-c2ncnc(Nc3ccc(N4CCN(C5COC5)CC4)cc3)n2)ccc1O[C@H]1CCN(C(=O)c2ncc[nH]2)C[C@H]1F] | 3 | 4 | 174 | 2-(((3R,4S)-3-fluoro-1-(1H-imidazole-2-carbonyl)piperidin-4-yl)oxy)-5-(4-((4-(4-(oxetan-3-yl)piperazin-1-yl)phenyl)amino)-1,3,5-triazin-2-yl)benzonitrile |
| 143 | 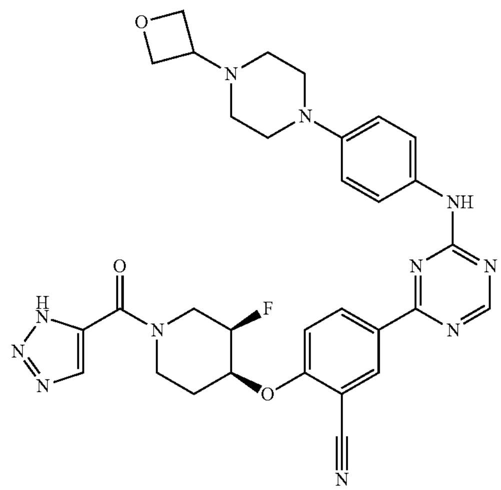 [SMILES: N#Cc1cc(-c2ncnc(Nc3ccc(N4CCN(C5COC5)CC4)cc3)n2)ccc1O[C@H]1CCN(C(=O)c2cnn[nH]2)C[C@H]1F] | 2 | 1 | 84 | 2-(((3R,4S)-3-fluoro-1-(1H-1,2,3-triazole-5-carbonyl)piperidin-4-yl)oxy)-5-(4-((4-(4-(oxetan-3-yl)piperazin-1-yl)phenyl)amino)-1,3,5-triazin-2-yl)benzonitrile |
| 144 | 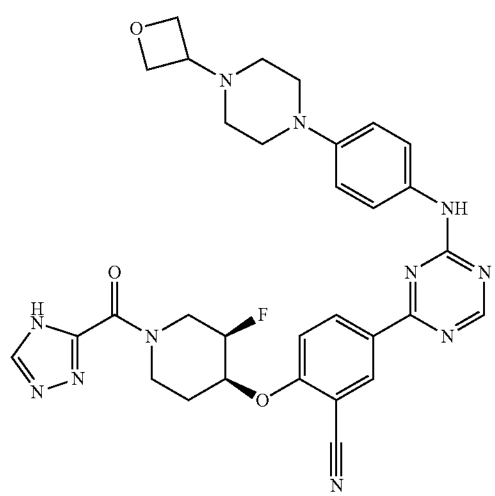 [SMILES: N#Cc1cc(-c2ncnc(Nc3ccc(N4CCN(C5COC5)CC4)cc3)n2)ccc1O[C@H]1CCN(C(=O)c2cnc[nH]2)C[C@H]1F] | 2 | 1 | 104 | 2-(3R,4S)-3-fluoro-1-(4H-1,2,4-triazole-3-carbonyl)piperidin-4-yl)oxy)-5-(4-((4-(4-(oxetan-3-yl)piperazin-1-yl)phenyl)amino)-1,3,5-triazin-2-yl)benzonitrile |

TABLE 1-continued

| Ex. | Structure | TBK1 IC50 | IKKe IC50 | JAK2 IC50 | Name |
|---|---|---|---|---|---|
| 145 | 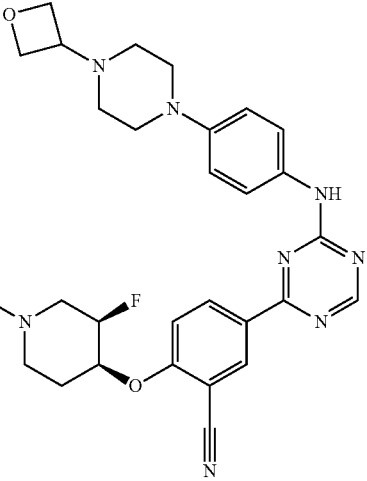 | 2 | 1 | 219 | 2-(((3R,4S)-3-fluoro-1-(1H-pyrazole-5-carbonyl)piperidin-4-yl)oxy)-5-(4-((4-(4-(oxetan-3-yl)piperazin-1-yl)phenyl)amino)-1,3,5-triazin-2-yl)benzonitrile |
| 146 | 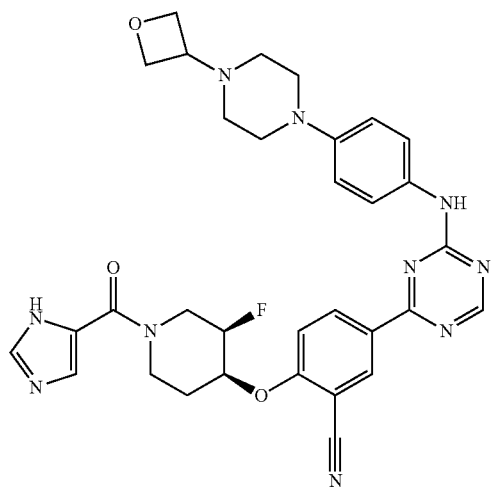 | 3 | 1 | 156 | 2-(((3R,4S)-3-fluoro-1-(1H-imidazole-5-carbonyl)piperidin-4-yl)oxy)-5-(4-((4-(4-(oxetan-3-yl)piperazin-1-yl)phenyl)amino)-1,3,5-triazin-2-yl)benzonitrile |
| 147 | 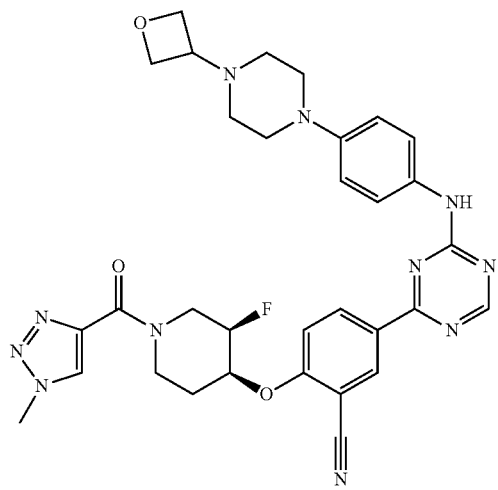 [SMILES: Cn1cc(C(=O)N2CC[C@H](Oc3ccc(-c4ncnc(Nc5ccc(N6CCN(C7COC7)CC6)cc5)n4)cc3C#N)[C@H](F)C2)nn1] | 3 | 1 | 184 | 2-(((3R,4S)-3-fluoro-1-(1-methyl-1H-1,2,3-triazole-4-carbonyl)piperidin-4-yl)oxy)-5-(4-((4-(4-(oxetan-3-yl)piperazin-1-yl)phenyl)amino)-1,3,5-triazin-2-yl)benzonitrile |

TABLE 1-continued

| Ex. | Structure | TBK1 IC50 | IKKe IC50 | JAK2 IC50 | Name |
|---|---|---|---|---|---|
| 148 | 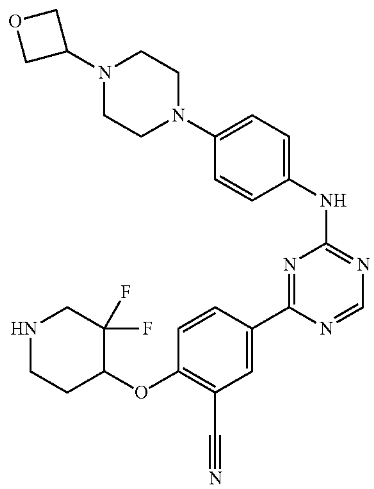 [SMILES: N#Cc1cc(-c2ncnc(Nc3ccc(N4CCN(C5COC5)CC4)cc3)n2)ccc1OC1CCNCC1(F)F] | 3 | 23 | 242 | 2-((3,3-difluoropiperidin-4-yl)oxy)-5-(4-((4-(4-(oxetan-3-yl)piperazin-1-yl)phenyl)amino)-1,3,5-triazin-2-yl)benzonitrile |
| 149 | 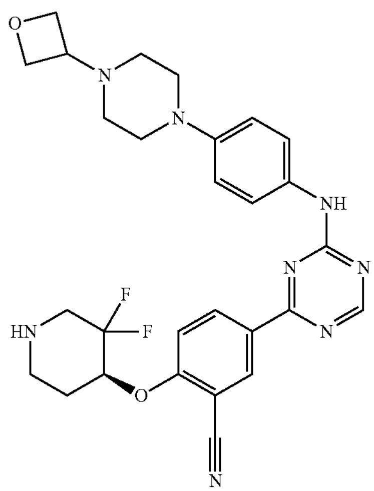 [SMILES: N#Cc1cc(-c2ncnc(Nc3ccc(N4CCN(C5COC5)CC4)cc3)n2)ccc1O[C@H]1CCNCC1(F)F] | 49 | 229 | 330 | (S)-2-((3,3-difluoropiperidin-4-yl)oxy)-5-(4-((4-(4-(oxetan-3-yl)piperazin-1-yl)phenyl)amino)-1,3,5-triazin-2-yl)benzonitrile |
| 150 | 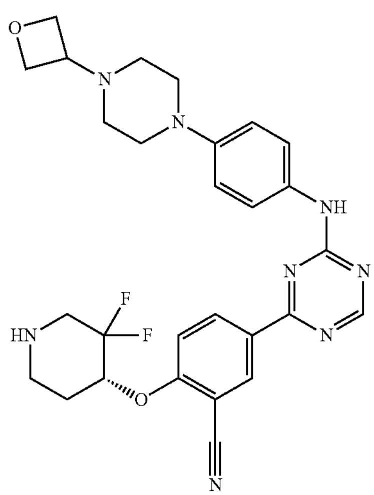 [SMILES: N#Cc1cc(-c2ncnc(Nc3ccc(N4CCN(C5COC5)CC4)cc3)n2)ccc1O[C@@H]1CCNCC1(F)F] | 2 | 14 | 270 | (R)-2-((3,3-difluoropiperidin-4-yl)oxy)-5-(4-((4-(4-(oxetan-3-yl)piperazin-1-yl)phenyl)amino)-1,3,5-triazin-2-yl)benzonitrile |

TABLE 1-continued

| Ex. | Structure | TBK1 IC50 | IKKe IC50 | JAK2 IC50 | Name |
|---|---|---|---|---|---|
| 151 | 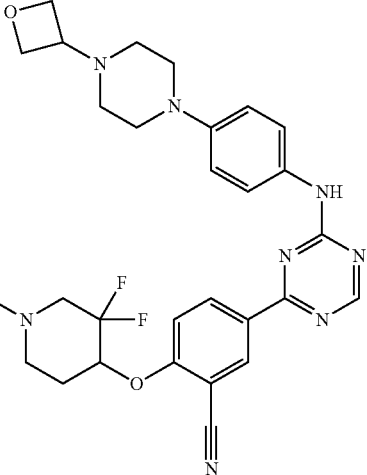 | 1 | 1 | 122 | 2-((3,3-difluoro-1-(2-hydroxyacetyl)piperidin-4-yl)oxy)-5-(4-((4-(4-(oxetan-3-yl)piperazin-1-yl)phenyl)amino)-1,3,5-triazin-2-yl)benzonitrile. |
| 152 | 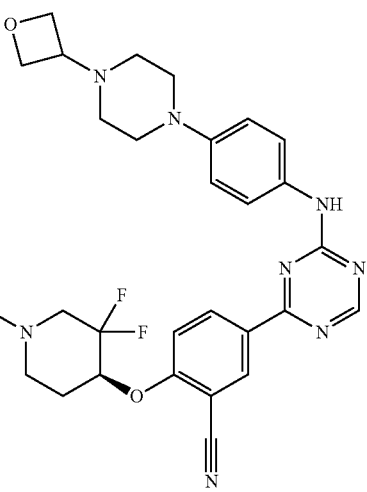 | 8 | 14 | 75 | (S)-2-((3,3-difluoro-1-(2-hydroxyacetyl)piperidin-4-yl)oxy)-5-(4-((4-(4-(oxetan-3-yl)piperazin-1-yl)phenyl)amino)-1,3,5-triazin-2-yl)benzonitrile |
| 153 | 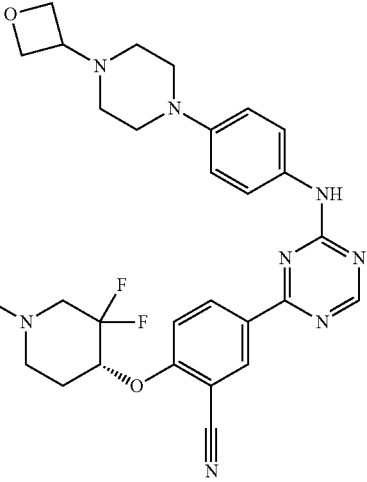 | 1 | 1 | 56 | (R)-2-((3,3-difluoro-1-(2-hydroxyacetyl)piperidin-4-yl)oxy)-5-(4-((4-(4-(oxetan-3-yl)piperazin-1-yl)phenyl)amino)-1,3,5-triazin-2-yl)benzonitrile |

TABLE 1-continued

| Ex. | Structure | TBK1 IC50 | IKKe IC50 | JAK2 IC50 | Name |
|---|---|---|---|---|---|
| 154 | 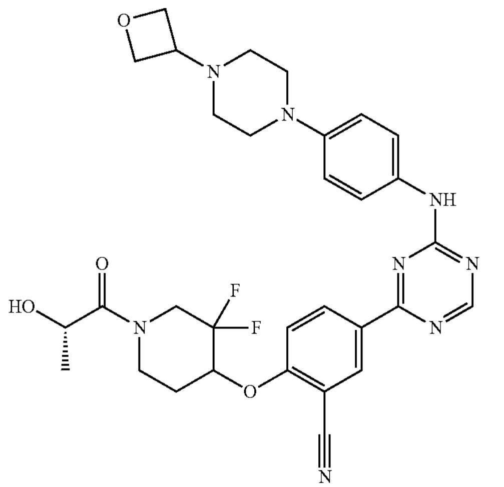 | 1 | 3 | 168 | 2-((3,3-difluoro-1-((S)-2-hydroxypropanoyl)piperidin-4-yl)oxy)-5-(4-((4-(4-(oxetan-3-yl)piperazin-1-yl)phenyl)amino)-1,3,5-triazin-2-yl)benzonitrile |
| 155 | 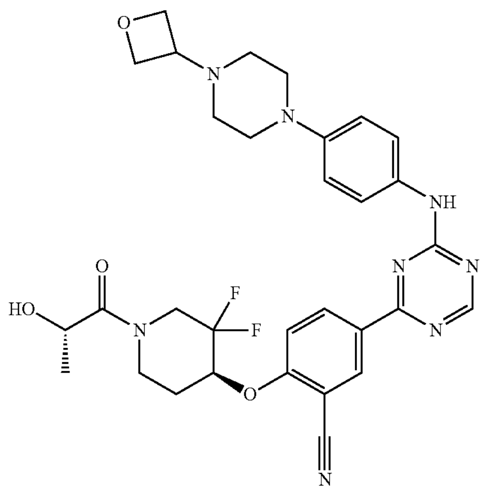 [SMILES: C[C@H](O)C(=O)N1CC[C@H](Oc2ccc(-c3ncnc(Nc4ccc(N5CCN(C6COC6)CC5)cc4)n3)cc2C#N)C(F)(F)C1] | 0 | 1 | 198 | 2-(((S)-3,3-difluoro-1-((S)-2-hydroxypropanoyl)piperidin-4-yl)oxy)-5-(4-((4-(4-(oxetan-3-yl)piperazin-1-yl)phenyl)amino)-1,3,5-triazin-2-yl)benzonitrile |
| 156 | 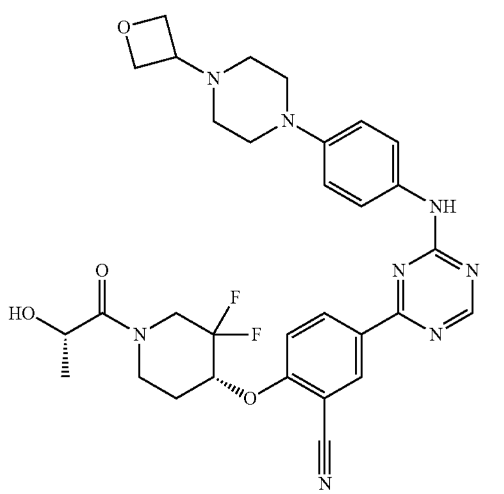 [SMILES: C[C@H](O)C(=O)N1CC[C@@H](Oc2ccc(-c3ncnc(Nc4ccc(N5CCN(C6COC6)CC5)cc4)n3)cc2C#N)C(F)(F)C1] | 16 | 23 | 196 | 2-(((R)-3,3-difluoro-1-((S)-2-hydroxypropanoyl)piperidin-4-yl)oxy)-5-(4-((4-(4-(oxetan-3-yl)piperazin-1-yl)phenyl)amino)-1,3,5-triazin-2-yl)benzonitrile |

TABLE 1-continued

| Ex. | Structure | TBK1 IC50 | IKKe IC50 | JAK2 IC50 | Name |
|---|---|---|---|---|---|
| 157 | 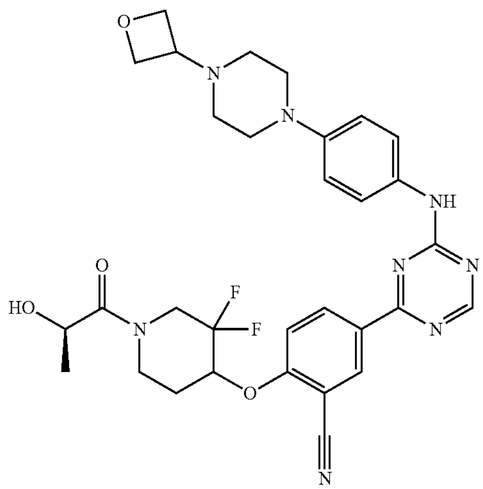 [SMILES: C[C@@H](O)C(=O)N1CCC(Oc2ccc(-c3ncnc(Nc4ccc(N5CCN(C6COC6)CC5)cc4)n3)cc2C#N)C(F)(F)C1] | 3 | 14 | 188 | 2-((3,3-difluoro-1-((R)-2-hydroxypropanoyl)piperidin-4-yl)oxy)-5-(4-((4-(4-(oxetan-3-yl)piperazin-1-yl)phenyl)amino)-1,3,5-triazin-2-yl)benzonitrile |
| 158 | 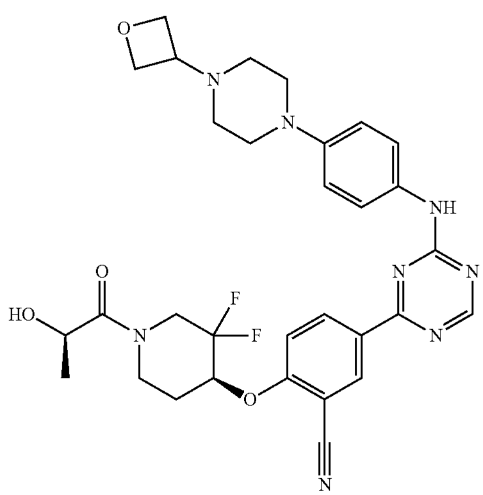 [SMILES: C[C@@H](O)C(=O)N1CC[C@H](Oc2ccc(-c3ncnc(Nc4ccc(N5CCN(C6COC6)CC5)cc4)n3)cc2C#N)C(F)(F)C1] | 1 | 3 | 171 | 2-(((S)-3,3-difluoro-1-((R)-2-hydroxypropanoyl)piperidin-4-yl)oxy)-5-(4-((4-(4-(oxetan-3-yl)piperazin-1-yl)phenyl)amino)-1,3,5-triazin-2-yl)benzonitrile |
| 159 | 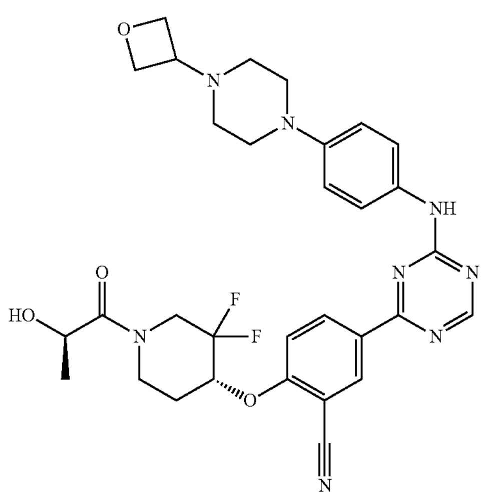 | 79 | 209 | 207 | 2-(((R)-3,3-difluoro-1-((R)-2-hydroxypropanoyl)piperidin-4-yl)oxy)-5-(4-((4-(4-(oxetan-3-yl)piperazin-1-yl)phenyl)amino)-1,3,5-triazin-2-yl)benzonitrile |

TABLE 1-continued

| Ex. | Structure | TBK1 IC50 | IKKe IC50 | JAK2 IC50 | Name |
|---|---|---|---|---|---|
| 160 | 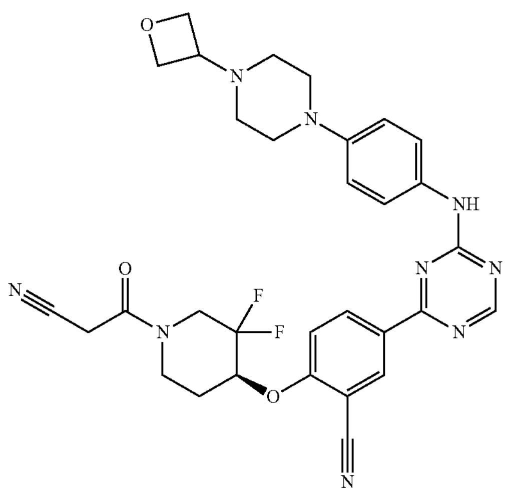 [SMILES: N#CCC(=O)N1CC[C@H](Oc2ccc(-c3ncnc(Nc4ccc(N5CCN(C6COC6)CC5)cc4)n3)cc2C#N)C(F)(F)C1] | 3 | 2 | 93 | (S)-2-((1-(2-cyanoacetyl)-3,3-difluoropiperidin-4-yl)oxy)-5-(4-((4-(4-(oxetan-3-yl)piperazin-1-yl)phenyl)amino)-1,3,5-triazin-2-yl)benzonitrile |
| 161 | 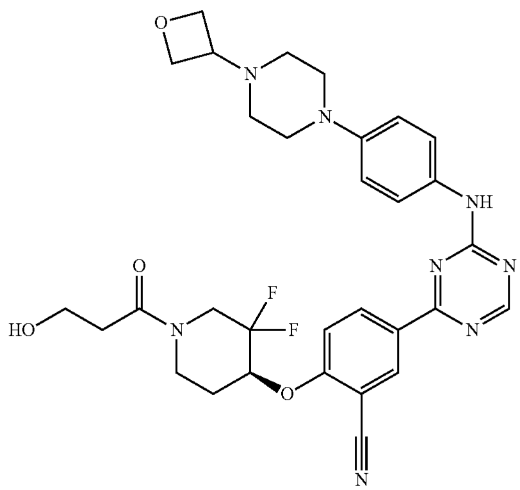 [SMILES: N#Cc1cc(-c2ncnc(Nc3ccc(N4CCN(C5COC5)CC4)cc3)n2)ccc1O[C@H]1CCN(C(=O)CCO)CC1(F)F] | 2 | 2 | 173 | (S)-2-((3,3-difluoro-1-(3-hydroxypropanoyl)piperidin-4-yl)oxy)-5-(4-((4-(4-(oxetan-3-yl)piperazin-1-yl)phenyl)amino)-1,3,5-triazin-2-yl)benzonitrile |
| 162 | 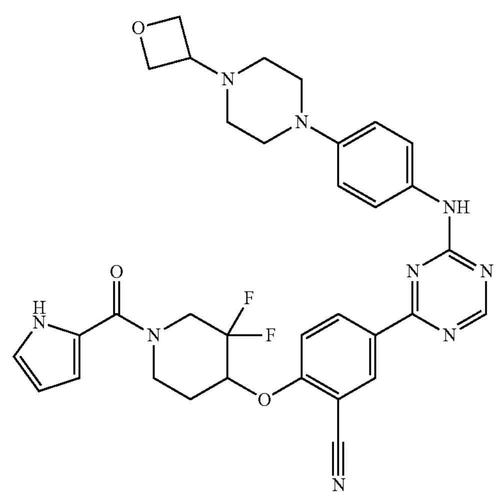 [SMILES: N#Cc1cc(-c2ncnc(Nc3ccc(N4CCN(C5COC5)CC4)cc3)n2)ccc1OC1CCN(C(=O)c2ncc[nH]2)CC1(F)F] | 5 | 4 | 583 | 2-((3,3-difluoro-1-(1H-pyrrole-2-carbonyl)piperidin-4-yl)oxy)-5-(4-((4-(4-(oxetan-3-yl)piperazin-1-yl)phenyl)amino)-1,3,5-triazin-2-yl)benzonitrile |

TABLE 1-continued

| Ex. | Structure | TBK1 IC50 | IKKe IC50 | JAK2 IC50 | Name |
|---|---|---|---|---|---|
| 163 | 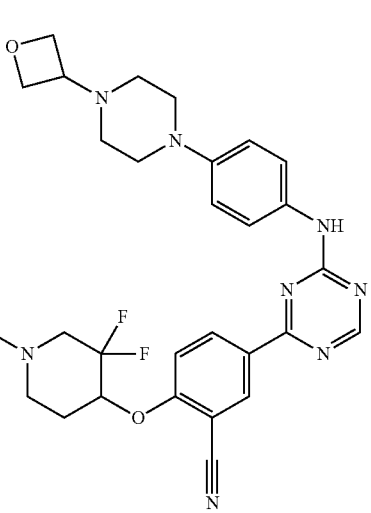 | 6 | 6 | 248 | 2-((3,3-difluoro-1-(1H-imidazole-2-carbonyl)pipendin-4-yl)oxy)-5-(4-((4-(4-(oxetan-3-yl)piperazin-1-yl)phenyl)amino)-1,3,5-triazin-2-yl)benzonitrile |
| 164 | 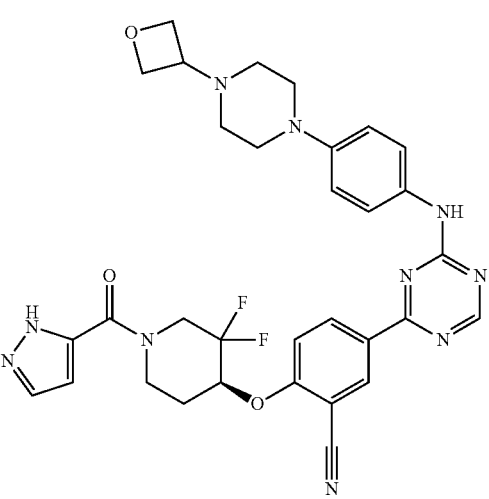 [SMILES: N#Cc1cc(-c2ncnc(Nc3ccc(N4CCN(C5COC5)CC4)cc3)n2)ccc1O[C@H]1CCN(C(=O)c2ccn[nH]2)CC1(F)F] | 3 | 1 | 155 | (S)-2-((3,3-difluoro-1-(1H-pyrazole-5-carbonyl)piperidin-4-yl)oxy)-5-(4-((4-(4-(oxetan-3-yl)piperazin-1-yl)phenyl)amino)-1,3,5-triazin-2-yl)benzonitrile |
| 165 | 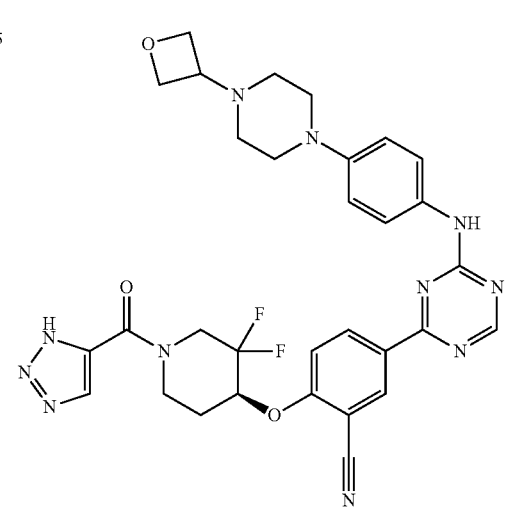 | 2 | 1 | 83 | (S)-2-((3,3-difluoro-1-(1H-1,2,3-triazole-5-carbonyl)piperidin-4-yl)oxy)-5-(4-((4-(4-(oxetan-3-yl)piperazin-1-yl)phenyl)amino)-1,3,5-triazin-2-yl)benzonitrile |

TABLE 1-continued

| Ex. | Structure | TBK1 IC50 | IKKe IC50 | JAK2 IC50 | Name |
|---|---|---|---|---|---|
| 166 | 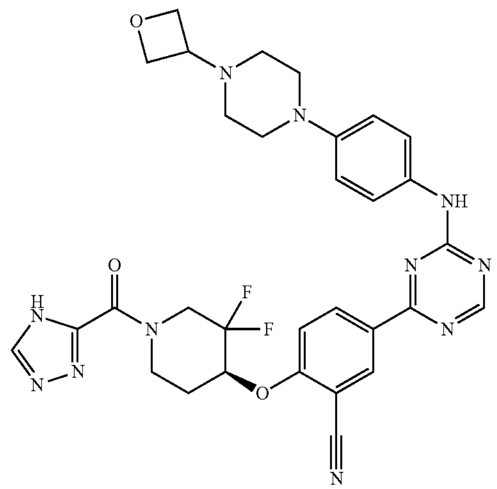 | 2 | 0 | 53 | (S)-2-((3,3-difluoro-1-(4H-1,2,4-triazole-3-carbonyl)piperidin-4-yl)oxy)-5-(4-((4-(4-(oxetan-3-yl)piperazin-1-yl)phenyl)amino)-1,3,5-triazin-2-yl)benzonitrile |
| 167 | 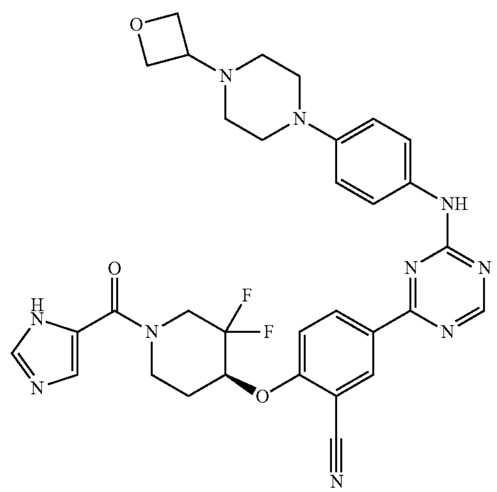 [SMILES: N#Cc1cc(-c2ncnc(Nc3ccc(N4CCN(C5COC5)CC4)cc3)n2)ccc1O[C@H]1CCN(C(=O)c2cnc[nH]2)CC1(F)F] | 3 | 1 | 104 | (S)-2-((3,3-difluoro-1-(1H-imidazole-5-carbonyl)piperidin-4-yl)oxy)-5-(4-((4-(4-(oxetan-3-yl)piperazin-1-yl)phenyl)amino)-1,3,5-triazin-2-yl)benzonitrile |
| 168 | 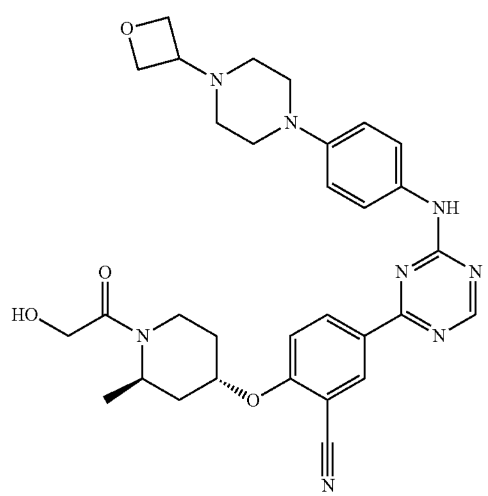 [SMILES: C[C@@H]1C[C@@H](Oc2ccc(-c3ncnc(Nc4ccc(N5CCN(C6COC6)CC5)cc4)n3)cc2C#N)CCN1C(=O)CO] | 15 | 61 | 877 | 2-(((2R,4S)-1-(2-hydroxyacetyl)-2-methylpiperidin-4-yl)oxy)-5-(4-((4-(4-(oxetan-3-yl)piperazin-1-yl)phenyl)amino)-1,3,5-triazin-2-yl)benzonitrile. |

TABLE 1-continued

| Ex. | Structure | TBK1 IC50 | IKKe IC50 | JAK2 IC50 | Name |
|---|---|---|---|---|---|
| 169 | 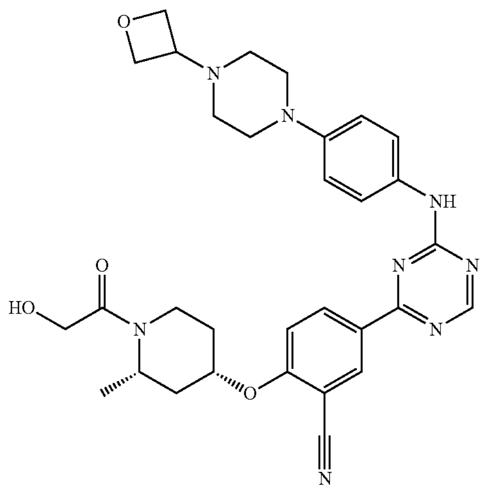 [SMILES: C[C@H]1C[C@@H](Oc2ccc(-c3ncnc(Nc4ccc(N5CCN(C6COC6)CC5)cc4)n3)cc2C#N)CCN1C(=O)CO] | 2 | 5 | 230 | 2-(((2S,4S)-1-(2-hydroxyacetyl)-2-methylpiperidin-4-yl)oxy)-5-(4-((4-(4-(oxetan-3-yl)piperazin-1-yl)phenyl)amino)-1,3,5-triazin-2-yl)benzonitrile. |
| 170 | 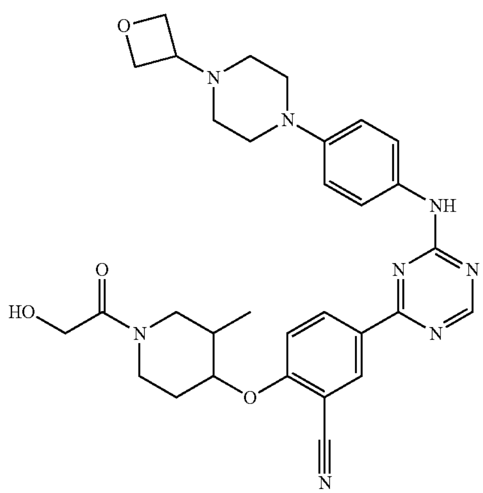 [SMILES: CC1CN(C(=O)CO)CCC1Oc1ccc(-c2ncnc(Nc3ccc(N4CCN(C5COC5)CC4)cc3)n2)cc1C#N] | 3 | 8 | 255 | 2-((1-(2-hydroxyacetyl)-3-methylpiperidin-4-yl)oxy)-5-(4-((4-(4-(oxetan-3-yl)piperazin-1-yl)phenyl)amino)-1,3,5-triazin-2-yl)benzonitrile |
| 171 | 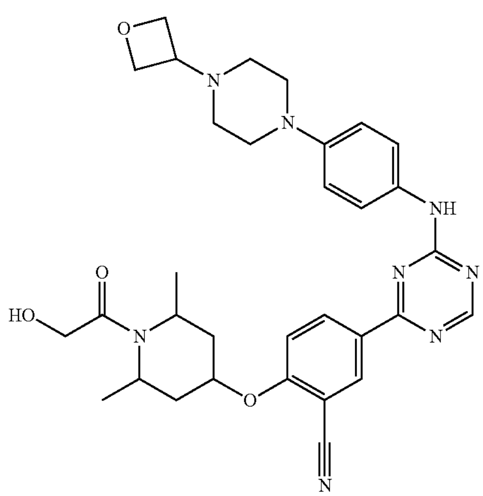 [SMILES: CC1CC(Oc2ccc(-c3ncnc(Nc4ccc(N5CCN(C6COC6)CC5)cc4)n3)cc2C#N)CC(C)N1C(=O)CO] | 2 | 9 | 463 | 2-((1-(2-hydroxyacetyl)-2,6-dimethylpiperidin-4-yl)oxy)-5-(4-((4-(4-(oxetan-3-yl)piperazin-1-yl)phenyl)amino)-1,3,5-triazin-2-yl)benzonitrile |

TABLE 1-continued

| Ex. | Structure | TBK1 IC50 | IKKe IC50 | JAK2 IC50 | Name |
|---|---|---|---|---|---|
| 172 | 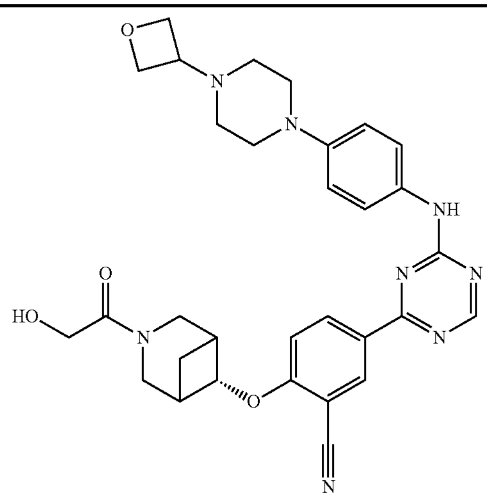 | 72 | 676 | 1000 | 2-((3-(2-hydroxyacetyl)-3-azabicyclo[3.1.1]heptan-6-yl)oxy)-5-(4-((4-(4-(oxetan-3-yl)piperazin-1-yl)phenyl)amino)-1,3,5-triazin-2-yl)benzonitrile |
| 173 | 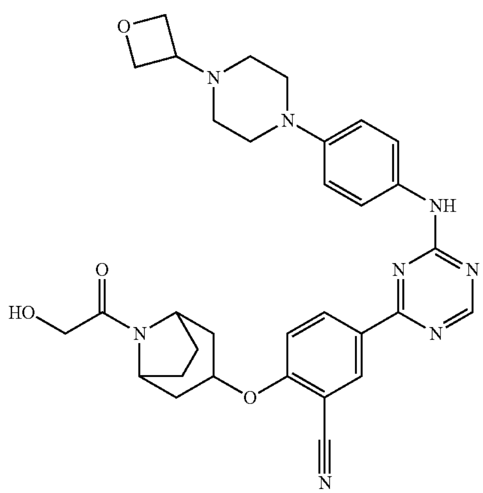 [SMILES: N#Cc1cc(-c2ncnc(Nc3ccc(N4CCN(C5COC5)CC4)cc3)n2)ccc1OC1CC2CCC(C1)N2C(=O)CO] | 92 | 218 | 265 | 2-((8-(2-hydroxyacetyl)-8-azabicyclo[3.2.1]octan-3-yl)oxy)-5-(4-((4-(4-(oxetan-3-yl)piperazin-1-yl)phenyl)amino)-1,3,5-triazin-2-yl)benzonitrile |
| 174 | 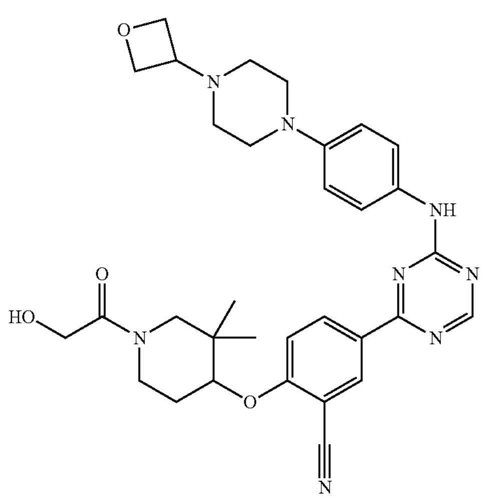 [SMILES: CC1(C)CN(C(=O)CO)CCC1Oc1ccc(-c2ncnc(Nc3ccc(N4CCN(C5COC5)CC4)cc3)n2)cc1C#N] | 4 | 4 | 160 | 2-((1-(2-hydroxyacetyl)-3,3-dimethylpiperidin-4-yl)oxy)-5-(4-((4-(4-(oxetan-3-yl)piperazin-1-yl)phenyl)amino)-1,3,5-triazin-2-yl)benzonitrile |

TABLE 1-continued

| Ex. | Structure | TBK1 IC50 | IKKe IC50 | JAK2 IC50 | Name |
|---|---|---|---|---|---|
| 175 | 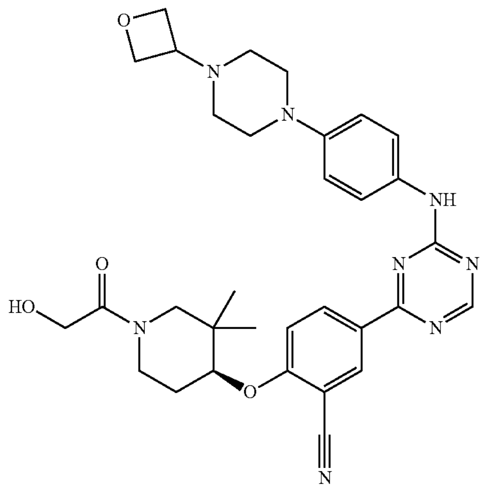 [SMILES: CC1(C)CN(C(=O)CO)CC[C@@H]1Oc1ccc(-c2ncnc(Nc3ccc(N4CCN(C5COC5)CC4)cc3)n2)cc1C#N] | 4 | 5 | 397 | (S)-2-((1-(2-hydroxyacetyl)-3,3-dimethylpiperidin-4-yl)oxy)-5-(4-((4-(4-(oxetan-3-yl)piperazin-1-yl)phenyl)amino)-1,3,5-triazin-2-yl)benzonitrile |
| 176 | 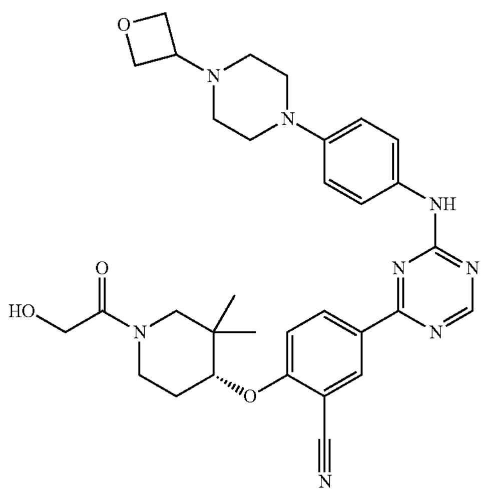 [SMILES: CC1(C)CN(C(=O)CO)CC[C@H]1Oc1ccc(-c2ncnc(Nc3ccc(N4CCN(C5COC5)CC4)cc3)n2)cc1C#N] | 3 | 3 | 133 | (R)-2-((1-(2-hydroxyacetyl)-3,3-dimethylpiperidin-4-yl)oxy)-5-(4-((4-(4-(oxetan-3-yl)piperazin-1-yl)phenyl)amino)-1,3,5-triazin-2-yl)benzonitrile |
| 177 | 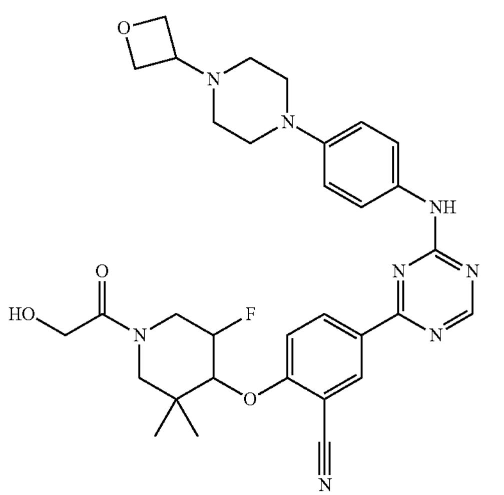 [SMILES: CC1(C)CN(C(=O)CO)CC(F)C1Oc1ccc(-c2ncnc(Nc3ccc(N4CCN(C5COC5)CC4)cc3)n2)cc1C#N] | 6 | 3 | 117 | 2-((5-fluoro-1-(2-hydroxyacetyl)-3,3-dimethylpiperidin-4-yl)oxy)-5-(4-((4-(4-(oxetan-3-yl)piperazin-1-yl)phenyl)amino)-1,3,5-triazin-2-yl)benzonitrile |

TABLE 1-continued

| Ex. | Structure | TBK1 IC50 | IKKe IC50 | JAK2 IC50 | Name |
|---|---|---|---|---|---|
| 178 | 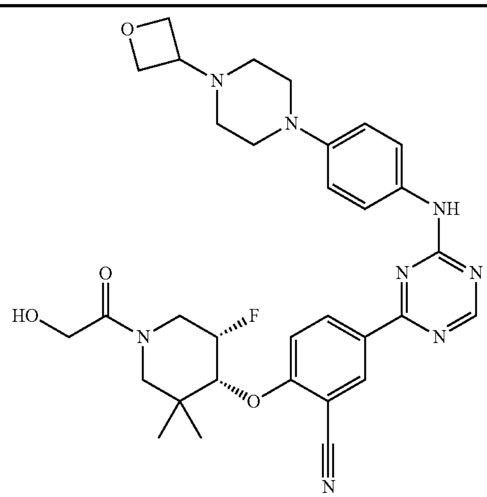 | 2 | 1 | 49 | 2-(((4R,5S)-5-fluoro-1-(2-hydroxyacetyl)-3,3-dimethylpiperidin-4-yl)oxy)-5-(4-((4-(4-(oxetan-3-yl)piperazin-1-yl)phenyl)amino)-1,3,5-triazin-2-yl)benzonitrile |
| 179 | 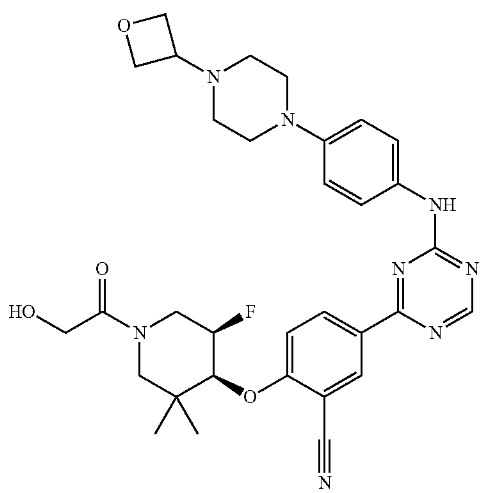 [SMILES: CC1(C)CN(C(=O)CO)C[C@@H](F)[C@H]1Oc1ccc(-c2ncnc(Nc3ccc(N4CCN(C5COC5)CC4)cc3)n2)cc1C#N] | 8 | 13 | 234 | 2-(((4S,5R)-5-fluoro-1-(2-hydroxyacetyl)-3,3-dimethylpiperidin-4-yl)oxy)-5-(4-((4-(4-(oxetan-3-yl)piperazin-1-yl)phenyl)amino)-1,3,5-triazin-2-yl)benzonitrile |
| 180 | 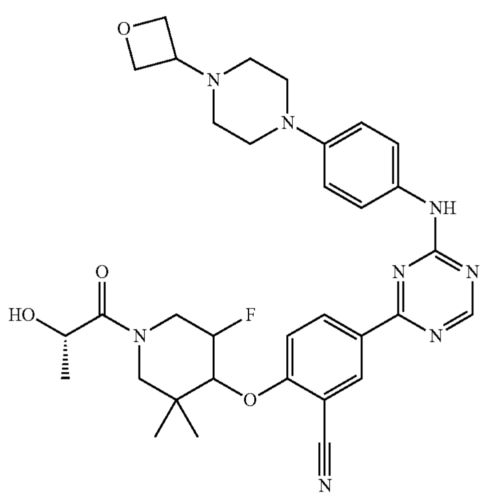 [SMILES: C[C@H](O)C(=O)N1CC(F)C(Oc2ccc(-c3ncnc(Nc4ccc(N5CCN(C6COC6)CC5)cc4)n3)cc2C#N)C(C)(C)C1] | 11 | 17 | 317 | 2-((5-fluoro-1-((S)-2-hydroxypropanoyl)-3,3-dimethylpiperidin-4-yl)oxy)-5-(4-((4-(4-(oxetan-3-yl)piperazin-1-yl)phenyl)amino)-1,3,5-triazin-2-yl)benzonitrile |

TABLE 1-continued

| Ex. | Structure | TBK1 IC50 | IKKe IC50 | JAK2 IC50 | Name |
|---|---|---|---|---|---|
| 181 | 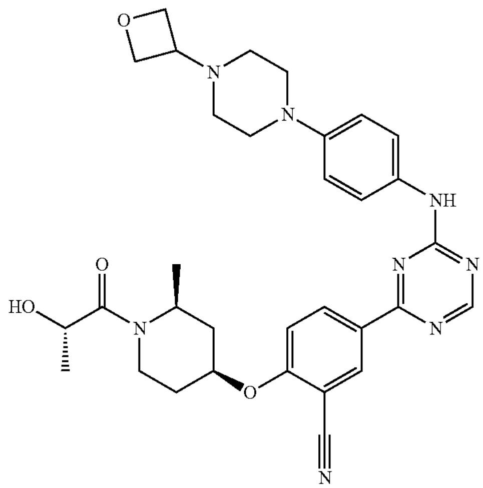 [SMILES: C[C@H](O)C(=O)N1CC[C@H](Oc2ccc(-c3ncnc(Nc4ccc(N5CCN(C6COC6)CC5)cc4)n3)cc2C#N)C[C@@H]1C] | 10 | 20 | 432 | 2-(((2S,4S)-1-((S)-2-hydroxypropanoyl)-2-methylpiperidin-4-yl)oxy)-5-(4-((4-(4-(oxetan-3-yl)piperazin-1-yl)phenyl)amino)-1,3,5-triazin-2-yl)benzonitrile |
| 182 | 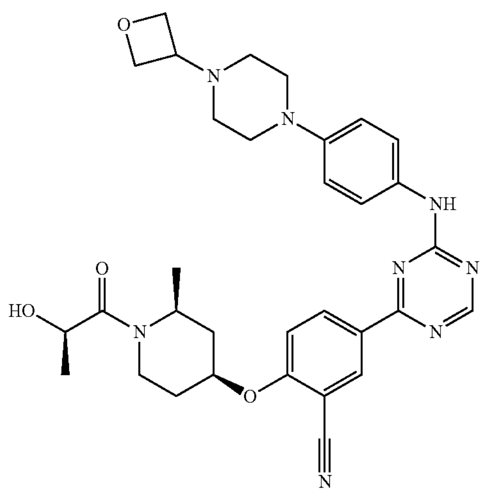 [SMILES: C[C@@H](O)C(=O)N1CC[C@H](Oc2ccc(-c3ncnc(Nc4ccc(N5CCN(C6COC6)CC5)cc4)n3)cc2C#N)C[C@@H]1C] | 32 | 95 | 491 | 2-(((2S,4S)-1-((R)-2-hydroxypropanoyl)-2-methylpiperidin-4-yl)oxy)-5-(4-((4-(4-(oxetan-3-yl)piperazin-1-yl)phenyl)amino)-1,3,5-triazin-2-yl)benzonitrile |
| 183 | 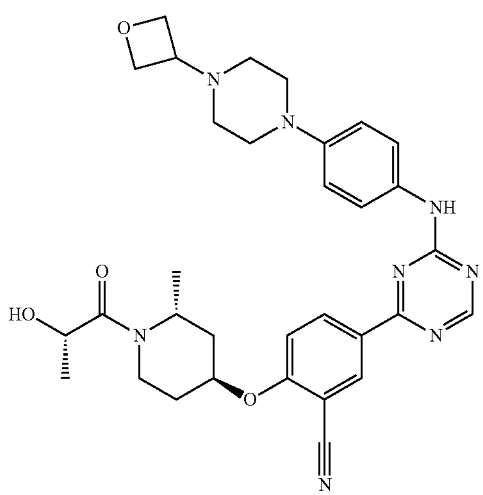 [SMILES: C[C@H](O)C(=O)N1CC[C@H](Oc2ccc(-c3ncnc(Nc4ccc(N5CCN(C6COC6)CC5)cc4)n3)cc2C#N)C[C@H]1C] | 50 | 120 | 593 | 2-(((2R,4S)-1-((S)-2-hydroxypropanoyl)-2-methylpiperidin-4-yl)oxy)-5-(4-((4-(4-(oxetan-3-yl)piperazin-1-yl)phenyl)amino)-1,3,5-triazin-2-yl)benzonitrile |

TABLE 1-continued

| Ex. | Structure | TBK1 IC50 | IKKe IC50 | JAK2 IC50 | Name |
|---|---|---|---|---|---|
| 184 | 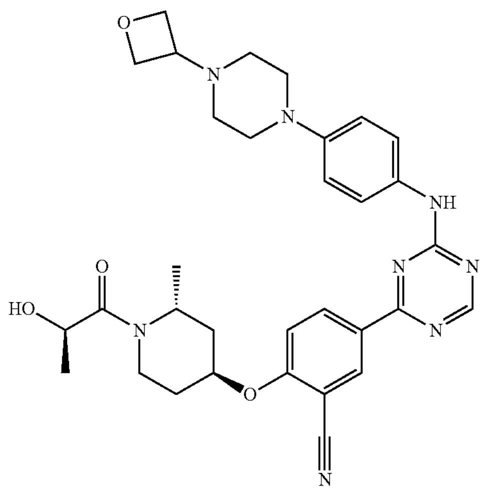 [SMILES: C[C@@H]1C[C@@H](Oc2ccc(-c3ncnc(Nc4ccc(N5CCN(C6COC6)CC5)cc4)n3)cc2C#N)CCN1C(=O)[C@@H](C)O] | 103 | 277 | 1000 | 2-(((2R,4S)-1-((R)-2-hydroxypropanoyl)-2-methylpiperidin-4-yl)oxy)-5-(4-((4-(4-(oxetan-3-yl)piperazin-1-yl)phenyl)amino)-1,3,5-triazin-2-yl)benzonitrile |
| 185 | 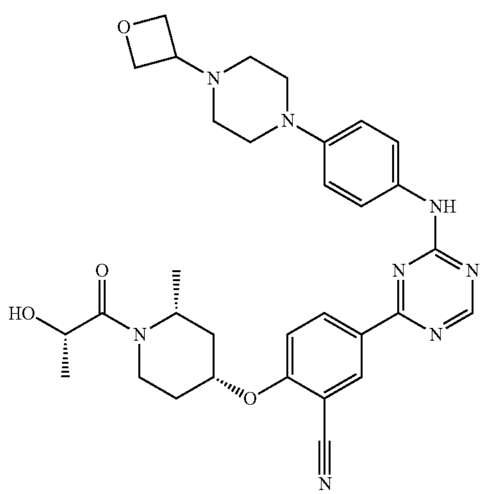 [SMILES: C[C@H](O)C(=O)N1CC[C@@H](Oc2ccc(-c3ncnc(Nc4ccc(N5CCN(C6COC6)CC5)cc4)n3)cc2C#N)C[C@H]1C] | 94 | 190 | 1000 | 2-(((2R,4R)-1-((S)-2-hydroxypropanoyl)-2-methylpiperidin-4-yl)oxy)-5-(4-((4-(4-(oxetan-3-yl)piperazin-1-yl)phenyl)amino)-1,3,5-triazin-2-yl)benzonitrile |
| 186 | 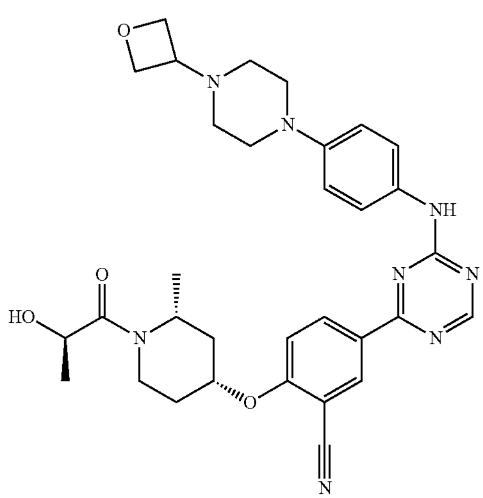 [SMILES: C[C@@H]1C[C@H](Oc2ccc(-c3ncnc(Nc4ccc(N5CCN(C6COC6)CC5)cc4)n3)cc2C#N)CCN1C(=O)[C@@H](C)O] | 128 | 312 | 1000 | 2-(((2R,4R)-1-((R)-2-hydroxypropanoyl)-2-methylpiperidin-4-yl)oxy)-5-(4-((4-(4-(oxetan-3-yl)piperazin-1-yl)phenyl)amino)-1,3,5-triazin-2-yl)benzonitrile |

TABLE 1-continued

| Ex. | Structure | TBK1 IC50 | IKKe IC50 | JAK2 IC50 | Name |
|---|---|---|---|---|---|
| 187 | 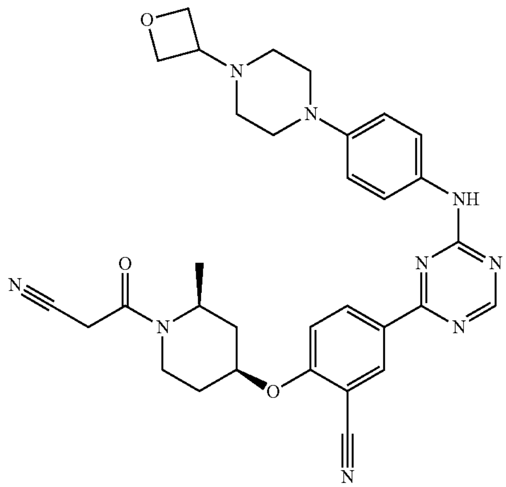 [SMILES: C[C@H]1C[C@@H](Oc2ccc(-c3ncnc(Nc4ccc(N5CCN(C6COC6)CC5)cc4)n3)cc2C#N)CCN1C(=O)CC#N] | 5 | 13 | 183 | 2-(((2S,4S)-1-(2-cyanoacetyl)-2-methylpiperidin-4-yl)oxy)-5-(4-((4-(4-(oxetan-3-yl)piperazin-1-yl)phenyl)amino)-1,3,5-triazin-2-yl)benzonitrile |
| 188 | 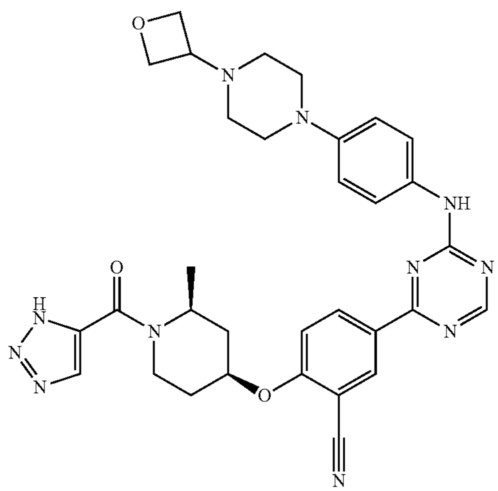 [SMILES: C[C@H]1C[C@@H](Oc2ccc(-c3ncnc(Nc4ccc(N5CCN(C6COC6)CC5)cc4)n3)cc2C#N)CCN1C(=O)c1cnn[nH]1] | 5 | 5 | 224 | 2-(((2S,4S)-2-methyl-1-(1H-1,2,3-triazole-5-carbonyl)piperidin-4-yl)oxy)-5-(4-((4-(4-(oxetan-3-yl)piperazin-1-yl)phenyl)amino)-1,3,5-triazin-2-yl)benzonitrile |
| 189 | 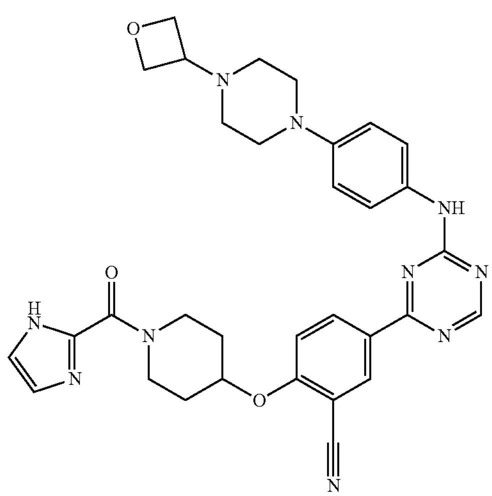 [SMILES: N#Cc1cc(-c2ncnc(Nc3ccc(N4CCN(C5COC5)CC4)cc3)n2)ccc1OC1CCN(C(=O)c2ncc[nH]2)CC1] | 5 | 19 | 289 | 2-((1-(1H-imidazole-2-carbonyl)piperidin-4-yl)oxy)-5-(4-((4-(4-(oxetan-3-yl)piperazin-1-yl)phenyl)amino)-1,3,5-triazin-2-yl)benzonitrile |

TABLE 1-continued

| Ex. | Structure | TBK1 IC50 | IKKe IC50 | JAK2 IC50 | Name |
|---|---|---|---|---|---|
| 190 | 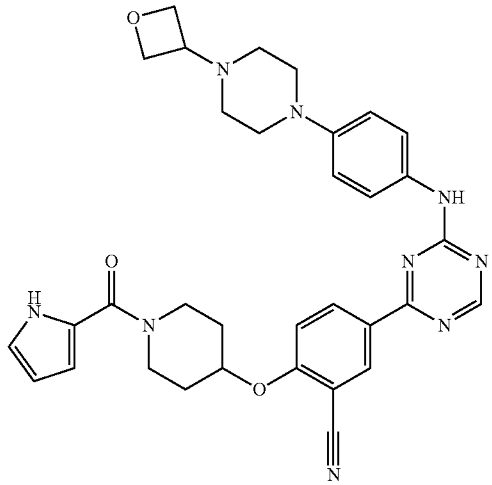 [SMILES: N#Cc1cc(-c2ncnc(Nc3ccc(N4CCN(C5COC5)CC4)cc3)n2)ccc1OC1CCN(C(=O)c2ccc[nH]2)CC1] | 3 | 15 | 1000 | 2-((1-(1H-pyrrole-2-carbonyl)piperidin-4-yl)oxy)-5-(4-((4-(4-(oxetan-3-yl)piperazin-1-yl)phenyl)amino)-1,3,5-triazin-2-yl)benzonitrile |
| 191 | 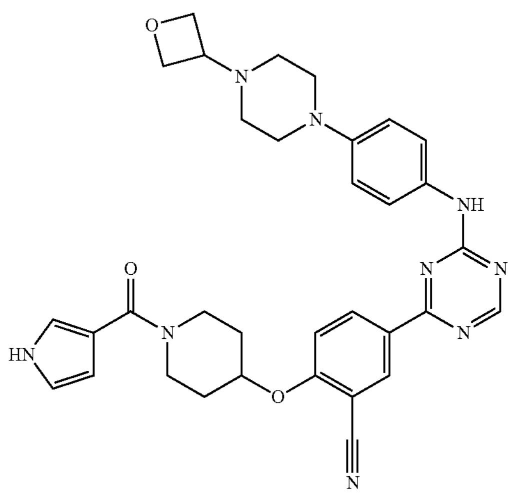 [SMILES: N#Cc1cc(-c2ncnc(Nc3ccc(N4CCN(C5COC5)CC4)cc3)n2)ccc1OC1CCN(C(=O)c2cc[nH]c2)CC1] | 67 | 226 | 1000 | 2-((1-(1H-pyrrole-3-carbonyl)piperidin-4-yl)oxy)-5-(4-((4-(4-(oxetan-3-yl)piperazin-1-yl)phenyl)amino)-1,3,5-triazin-2-yl)benzonitrile |
| 192 | 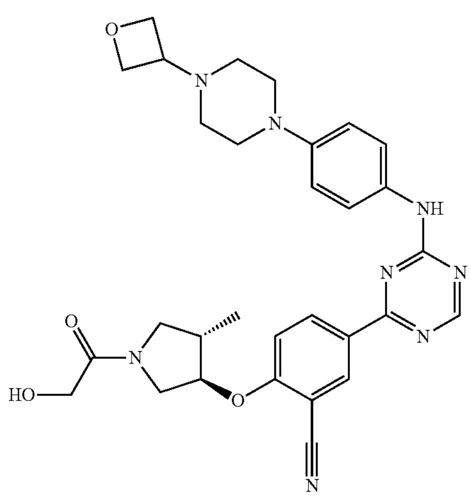 [SMILES: C[C@H]1CN(C(=O)CO)C[C@@H]1Oc1ccc(-c2ncnc(Nc3ccc(N4CCN(C5COC5)CC4)cc3)n2)cc1C#N] | 8 | 30 | 1000 | 2-(((3R,4S)-1-(2-hydroxyacetyl)-4-methylpyrrolidin-3-yl)oxy)-5-(4-((4-(4-(oxetan-3-yl)piperazin-1-yl)phenyl)amino)-1,3,5-triazin-2-yl)benzonitrile |

TABLE 1-continued
| Ex. | Structure | TBK1 IC50 | IKKe IC50 | JAK2 IC50 | Name |
|---|---|---|---|---|---|
| 193 | 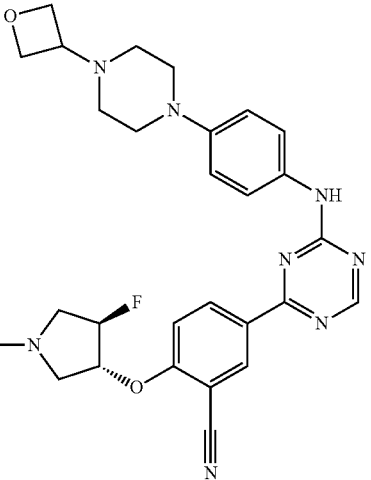 | 14 | 48 | 1000 | 2-(((3R,4R)-4-fluoro-1-(2-hydroxyacetyl)pyrrolidin-3-yl)oxy)-5-(4-((4-(4-(oxetan-3-yl)piperazin-1-yl)phenyl)amino)-1,3,5-triazin-2-yl)benzonitrile. |
| 194 | 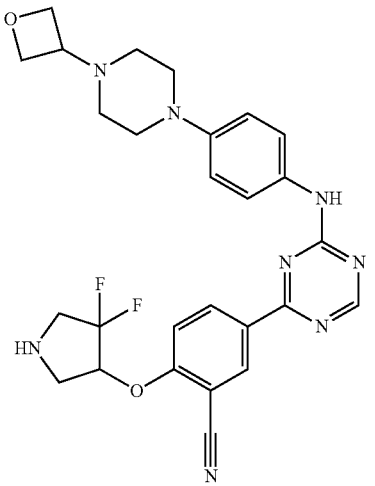 [SMILES: N#Cc1cc(-c2ncnc(Nc3ccc(N4CCN(C5COC5)CC4)cc3)n2)ccc1OC1CNCC1(F)F] | 6 | 29 | 308 | 2-((4,4-difluoropyrrolidin-3-yl)oxy)-5-(4-((4-(4-(oxetan-3-yl)piperazin-1-yl)phenyl)amino)-1,3,5-triazin-2-yl)benzonitrile |
| 195 | 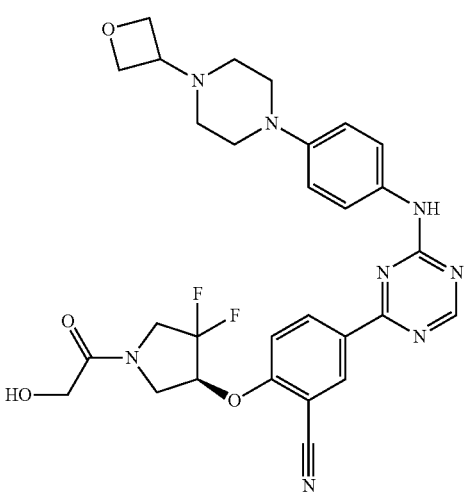 [SMILES: N#Cc1cc(-c2ncnc(Nc3ccc(N4CCN(C5COC5)CC4)cc3)n2)ccc1O[C@H]1CN(C(=O)CO)CC1(F)F] | 2 | 10 | 90 | (S)-2-((4,4-difluoro-1-(2-hydroxyacetyl)pyrrolidin-3-yl)oxy)-5-(4-((4-(4-(oxetan-3-yl)piperazin-1-yl)phenyl)amino)-1,3,5-triazin-2-yl)benzonitrile |

TABLE 1-continued

| Ex. | Structure | TBK1 IC50 | IKKe IC50 | JAK2 IC50 | Name |
|---|---|---|---|---|---|
| 196 | 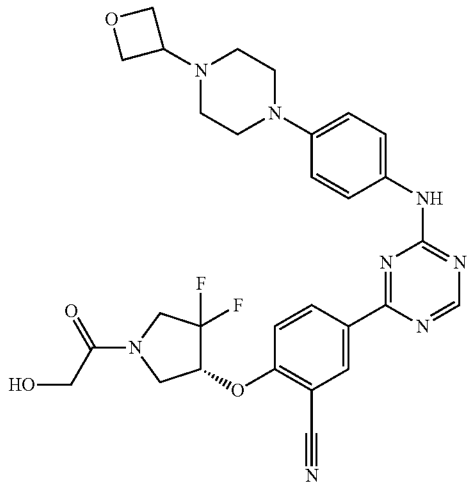 [SMILES: N#Cc1cc(-c2ncnc(Nc3ccc(N4CCN(C5COC5)CC4)cc3)n2)ccc1O[C@@H]1CN(C(=O)CO)CC1(F)F] | 114 | 391 | 118 | (R)-2-((4,4-difluoro-1-(2-hydroxyacetyl)pyrrolidin-3-yl)oxy)-5-(4-((4-(4-(oxetan-3-yl)piperazin-1-yl)phenyl)amino)-1,3,5-triazin-2-yl)benzonitrile |
| 197 | 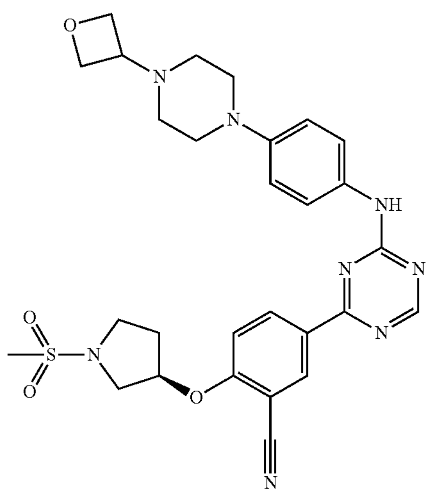 [SMILES: CS(=O)(=O)N1CC[C@@H](Oc2ccc(-c3ncnc(Nc4ccc(N5CCN(C6COC6)CC5)cc4)n3)cc2C#N)C1] | 26 | 79 | 173 | (R)-2-((1-(methylsulfonyl)pyrrolidin-3-yl)oxy)-5-(4-((4-(4-(oxetan-3-yl)piperazin-1-yl)phenyl)amino)-1,3,5-triazin-2-yl)benzonitrile |
| 198 | 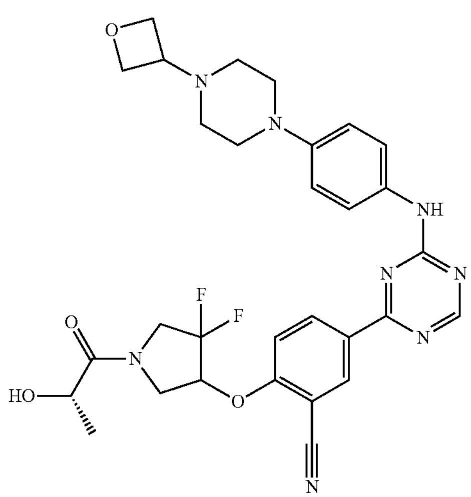 [SMILES: C[C@H](O)C(=O)N1CC(Oc2ccc(-c3ncnc(Nc4ccc(N5CCN(C6COC6)CC5)cc4)n3)cc2C#N)C(F)(F)C1] | 10 | 68 | 265 | 2-((4,4-difluoro-1-((S)-2-hydroxypropanoyl)pyrrolidin-3-yl)oxy)-5-(4-((4-(4-(oxetan-3-yl)piperazin-1-yl)phenyl)amino)-1,3,5-triazin-2-yl)benzonitrile |

TABLE 1-continued

| Ex. | Structure | TBK1 IC50 | IKKe IC50 | JAK2 IC50 | Name |
|---|---|---|---|---|---|
| 199 | 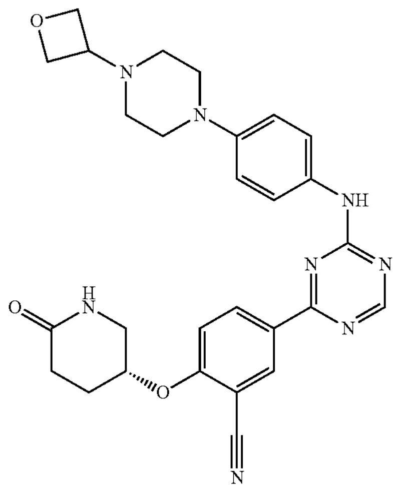 [SMILES: N#Cc1cc(-c2ncnc(Nc3ccc(N4CCN(C5COC5)CC4)cc3)n2)ccc1O[C@@H]1CCC(=O)NC1] | 4 | 6 | 200 | (R)-5-(4-((4-(4-(oxetan-3-yl)piperazin-1-yl)phenyl)amino)-1,3,5-triazin-2-yl)-2-((6-oxopiperidin-3-yl)oxy)benzonitrile |
| 200 | 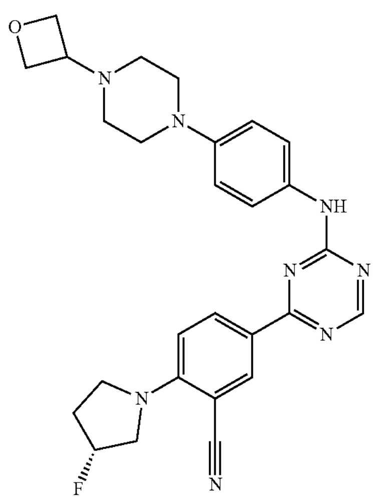 [SMILES: N#Cc1cc(-c2ncnc(Nc3ccc(N4CCN(C5COC5)CC4)cc3)n2)ccc1N1CC[C@@H](F)C1] | 3 | 7 | 109 | (R)-2-(3-fluoro-pyrrolidin-1-yl)-5-(4-((4-(4-(oxetan-3-yl)piperazin-1-yl)phenyl)amino)-1,3,5-triazin-2-yl)benzonitrile |
| 201 | 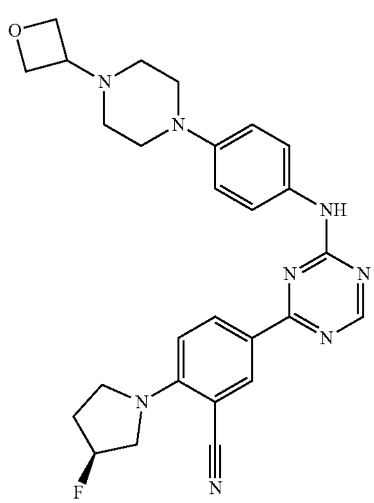 [SMILES: N#Cc1cc(-c2ncnc(Nc3ccc(N4CCN(C5COC5)CC4)cc3)n2)ccc1N1CC[C@H](F)C1] | 1 | 5 | 69 | (S)-2-(3-fluoro-pyrrolidin-1-yl)-5-(4-((4-(4-(oxetan-3-yl)piperazin-1-yl)phenyl)amino)-1,3,5-triazin-2-yl)benzonitrile |

TABLE 1-continued

| Ex. | Structure | TBK1 IC50 | IKKe IC50 | JAK2 IC50 | Name |
|---|---|---|---|---|---|
| 202 | 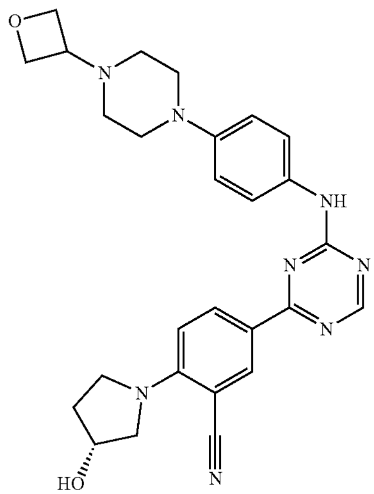 [SMILES: N#Cc1cc(-c2ncnc(Nc3ccc(N4CCN(C5COC5)CC4)cc3)n2)ccc1N1CC[C@@H](O)C1] | 3 | 13 | 192 | (R)-2-(3-hydroxy-pyrrolidin-1-yl)-5-(4-((4-(4-(oxetan-3-yl)piperazin-1-yl)phenyl)amino)-1,3,5-triazin-2-yl)benzonitrile |
| 203 | 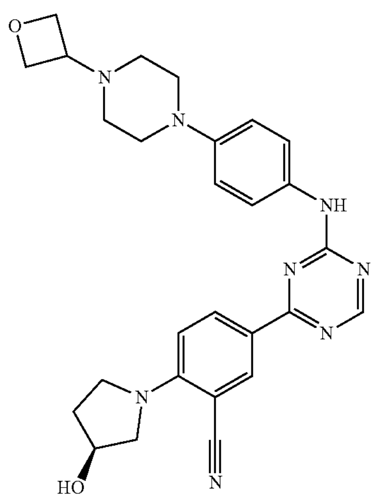 [SMILES: N#Cc1cc(-c2ncnc(Nc3ccc(N4CCN(C5COC5)CC4)cc3)n2)ccc1N1CC[C@H](O)C1] | 7 | 27 | 315 | (S)-2-(3-hydroxy-pyrrolidin-1-yl)-5-(4-((4-(4-oxetan-3-yl)piperazin-1-yl)phenyl)amino)-1,3,5-triazin-2-yl)benzonitrile |
| 204 | 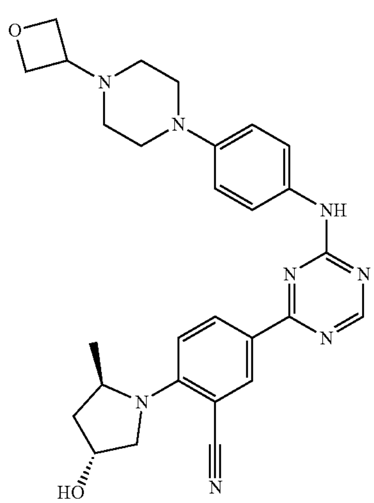 [SMILES: C[C@@H]1C[C@@H](O)CN1c1ccc(-c2ncnc(Nc3ccc(N4CCN(C5COC5)CC4)cc3)n2)cc1C#N] | 1 | 18 | 47 | 2-((2R,4R)-4-hydroxy-2-methylpyrrolidin-1-yl)-5-(4-((4-(4-(oxetan-3-yl)piperazin-1-yl)phenyl)amino)-1,3,5-triazin-2-yl)benzonitrile |

TABLE 1-continued

| Ex. | Structure | TBK1 IC50 | IKKe IC50 | JAK2 IC50 | Name |
|---|---|---|---|---|---|
| 205 | 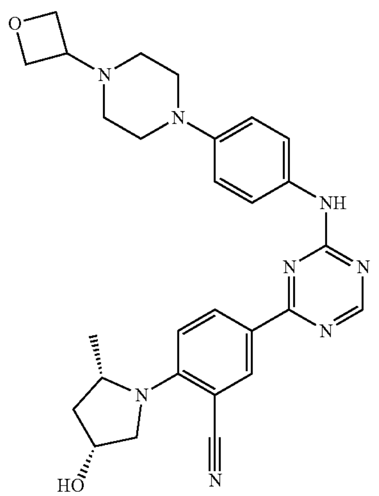 [SMILES: C[C@H]1C[C@@H](O)CN1c1ccc(-c2ncnc(Nc3ccc(N4CCN(C5COC5)CC4)cc3)n2)cc1C#N] | 1 | 17 | 51 | 2-((2S,4R)-4-hydroxy-2-methylpyrrolidin-1-yl)-5-(4-((4-(4-(oxetan-3-yl)piperazin-1-yl)phenyl)amino)-1,3,5-triazin-2-yl)benzonitrile |
| 206 | 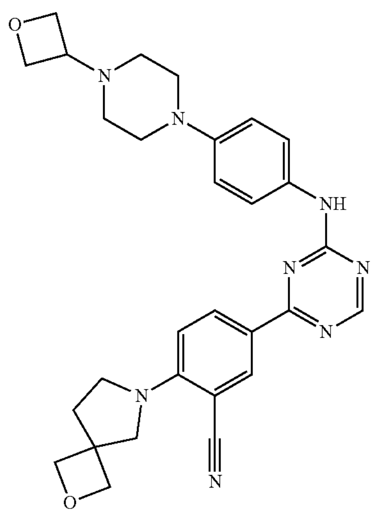 [SMILES: N#Cc1cc(-c2ncnc(Nc3ccc(N4CCN(C5COC5)CC4)cc3)n2)ccc1N1CCC2(COC2)C1] | 12 | 20 | 236 | 5-(4-((4-(4-(oxetan-3-yl)piperazin-1-yl)phenyl)amino)-1,3,5-triazin-2-yl)-2-(2-oxa-6-azaspiro[3.4]octan-6-yl)benzonitrile |
| 207 | 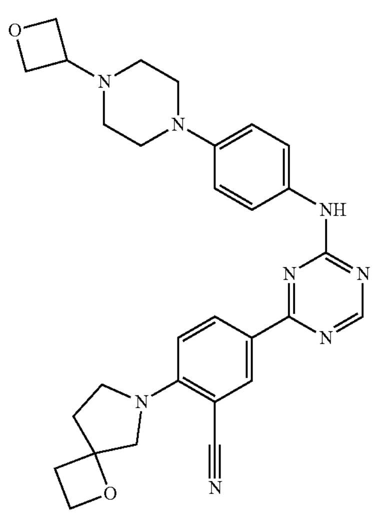 [SMILES: N#Cc1cc(-c2ncnc(Nc3ccc(N4CCN(C5COC5)CC4)cc3)n2)ccc1N1CCC2(CCO2)C1] | 38 | 128 | 258 | 5-(4-((4-(4-(oxetan-3-yl)piperazin-1-yl)phenyl)amino)-1,3,5-triazin-2-yl)-2-(1-oxa-6-azaspiro[3.4]octan-6-yl)benzonitrile |

TABLE 1-continued

| Ex. | Structure | TBK1 IC50 | IKKe IC50 | JAK2 IC50 | Name |
|---|---|---|---|---|---|
| 208 | 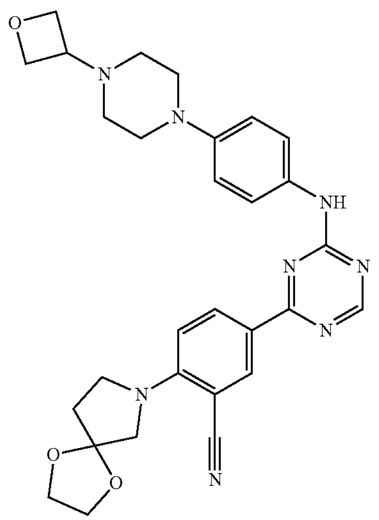 [SMILES: N#Cc1cc(-c2ncnc(Nc3ccc(N4CCN(C5COC5)CC4)cc3)n2)ccc1N1CCC2(C1)OCCO2] | 64 | 283 | 330 | 5-(4-((4-(4-(oxetan-3-yl)piperazin-1-yl)phenyl)amino)-1,3,5-triazin-2-yl)-2-(1,4-dioxa-7-azaspiro[4.4]nonan-7-yl)benzonitrile |
| 209 | 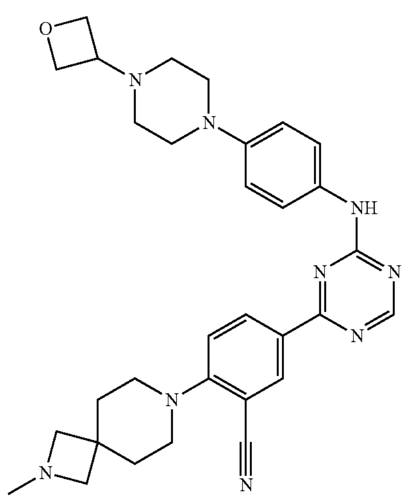 [SMILES: CN1CC2(CCN(c3ccc(-c4ncnc(Nc5ccc(N6CCN(C7COC7)CC6)cc5)n4)cc3C#N)CC2)C1] | 49 | 213 | 307 | 2-(2-methyl-2,7-diazaspiro[3.5]nonan-7-yl)-5-(4-((4-(4-(oxetan-3-yl)piperazin-1-yl)phenyl)amino)-1,3,5-triazin-2-yl)benzonitrile |
| 210 | 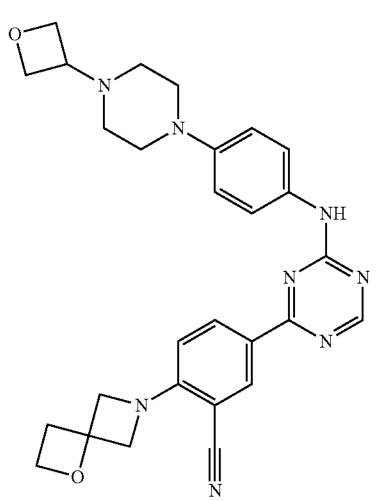 [SMILES: N#Cc1cc(-c2ncnc(Nc3ccc(N4CCN(C5COC5)CC4)cc3)n2)ccc1N1CC2(CCO2)C1] | 26 | 71 | 354 | 5-(4-((4-(4-(oxetan-3-yl)piperazin-1-yl)phenyl)amino)-1,3,5-triazin-2-yl)-2-(1-oxa-6-azaspiro[3.3]heptan-6-yl)benzonitrile |

TABLE 1-continued

| Ex. | Structure | TBK1 IC50 | IKKe IC50 | JAK2 IC50 | Name |
|---|---|---|---|---|---|
| 211 | 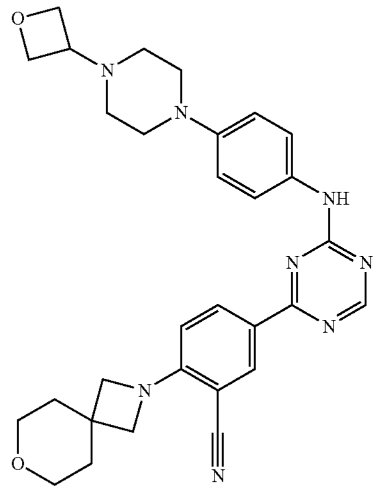 [SMILES: N#Cc1cc(-c2ncnc(Nc3ccc(N4CCN(C5COC5)CC4)cc3)n2)ccc1N1CC2(CCOCC2)C1] | 6 | 22 | 170 | 5-(4-((4-(4-(oxetan-3-yl)piperazin-1-yl)phenyl)amino)-1,3,5-triazin-2-yl)-2-(7-oxa-2-azaspiro[3.5]nonan-2-yl)benzonitrile |
| 212 | 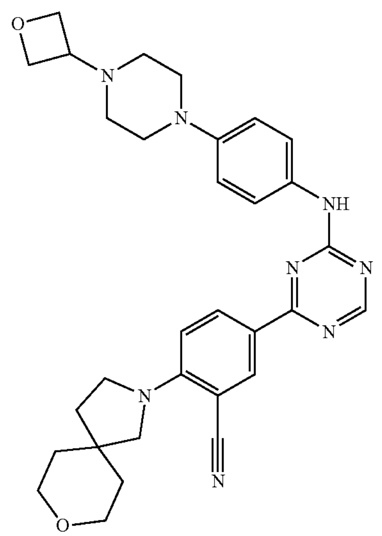 [SMILES: N#Cc1cc(-c2ncnc(Nc3ccc(N4CCN(C5COC5)CC4)cc3)n2)ccc1N1CCC2(CCOCC2)C1] | 29 | 63 | 137 | 5-(4-((4-(4-(oxetan-3-yl)piperazin-1-yl)phenyl)amino)-1,3,5-triazin-2-yl)-2-(8-oxa-2-azaspiro[4.5]decan-2-yl)benzonitrile |
| 213 | 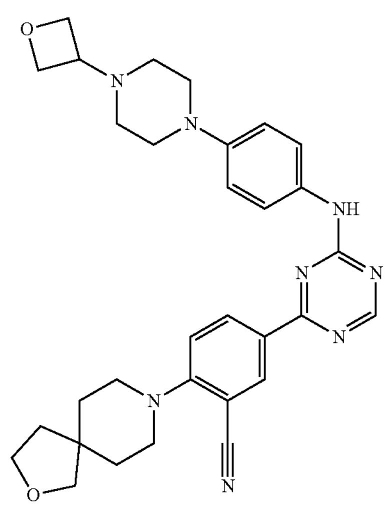 [SMILES: N#Cc1cc(-c2ncnc(Nc3ccc(N4CCN(C5COC5)CC4)cc3)n2)ccc1N1CCC2(CCOC2)CC1] | 3 | 14 | 1000 | 5-(4-((4-(4-(oxetan-3-yl)piperazin-1-yl)phenyl)amino)-1,3,5-triazin-2-yl)-2-(2-oxa-8-azaspiro[4.5]decan-8-yl)benzonitrile |

TABLE 1-continued

| Ex. | Structure | | TBK1 IC50 | IKKe IC50 | JAK2 IC50 | Name |
|---|---|---|---|---|---|---|
| 214 | 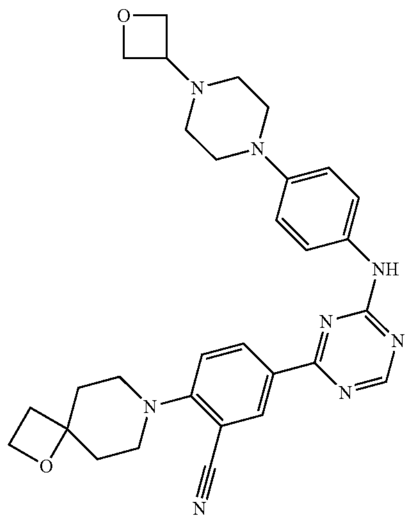 [SMILES: N#Cc1cc(-c2ncnc(Nc3ccc(N4CCN(C5COC5)CC4)cc3)n2)ccc1N1CCC2(CCO2)CC1] | | 12 | 43 | 301 | 5-(4-((4-(4-(oxetan-3-yl)piperazin-1-yl)phenyl)amino)-1,3,5-triazin-2-yl)-2-(1-oxa-7-azaspiro[3.5]nonan-7-yl)benzonitrile |
| 215 | 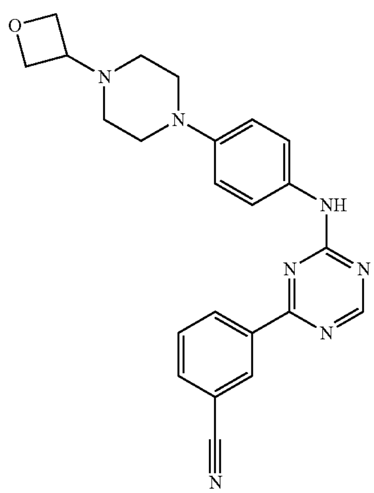 [SMILES: N#Cc1cccc(-c2ncnc(Nc3ccc(N4CCN(C5COC5)CC4)cc3)n2)c1] | | 1000 | 1000 | 657 | 3-(4-((4-(4-(oxetan-3-yl)piperazin-1-yl)phenyl)amino)-1,3,5-triazin-2-yl)benzonitrile |
| 216 | 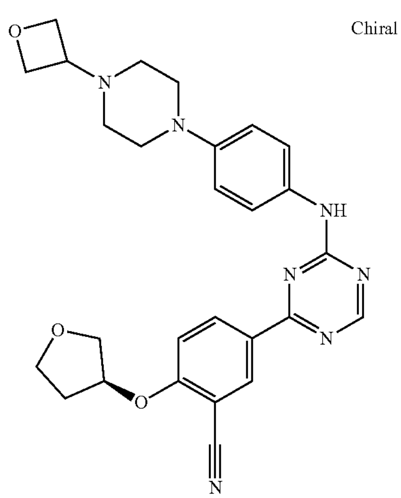 [SMILES: N#Cc1cc(-c2ncnc(Nc3ccc(N4CCN(C5COC5)CC4)cc3)n2)ccc1O[C@H]1CCOC1] | Chiral | 13 | 42 | 281 | (S)-5-(4-((4-(4-(oxetan-3-yl)piperazin-1-yl)phenyl)amino)-1,3,5-triazin-2-yl)-2-((tetrahydrofuran-3-yl)oxy)benzonitrile |

TABLE 1-continued

| Ex. | Structure | TBK1 IC50 | IKKe IC50 | JAK2 IC50 | Name |
|---|---|---|---|---|---|
| 217 | 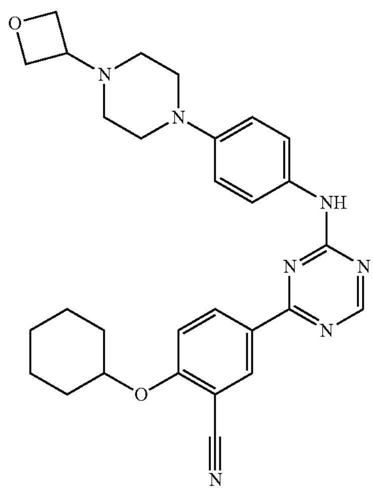 [SMILES: N#Cc1cc(-c2ncnc(Nc3ccc(N4CCN(C5COC5)CC4)cc3)n2)ccc1OC1CCCCC1] | 4 | 14 | 980 | 2-(cyclohexyloxy)-5-(4-((4-(4-(oxetan-3-yl)piperazin-1-yl)phenyl)amino)-1,3,5-triazin-2-yl)benzonitrile |
| 218 | 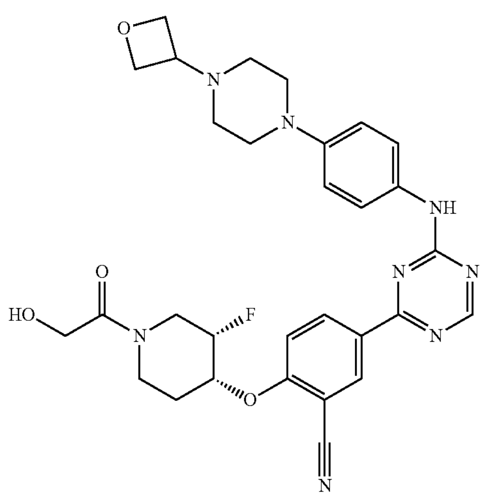 [SMILES: N#Cc1cc(-c2ncnc(Nc3ccc(N4CCN(C5COC5)CC4)cc3)n2)ccc1O[C@@H]1CCN(C(=O)CO)C[C@@H]1F] | 1 | 3 | 174 | 2-((cis-3-fluoro-1-(2-hydroxyacetyl)piperidin-4-yl)oxy)-5-(4-((4-(4-(oxetan-3-yl)piperazin-1-yl)phenyl)amino)-1,3,5-triazin-2-yl)benzonitrile |
| 219 | Chiral | 44 | 126 | 626 | (R)-2-((1-(2-hydroxypropanoyl)piperidin-4-yl)oxy)-5-(4-((4-(4-(oxetan-3-yl)piperazin-1-yl)phenyl)amino)-1,3,5-triazin-2-yl)benzonitrile |

TABLE 1-continued

| Ex. | Structure | | TBK1 IC50 | IKKe IC50 | JAK2 IC50 | Name |
|---|---|---|---|---|---|---|
| 220 | 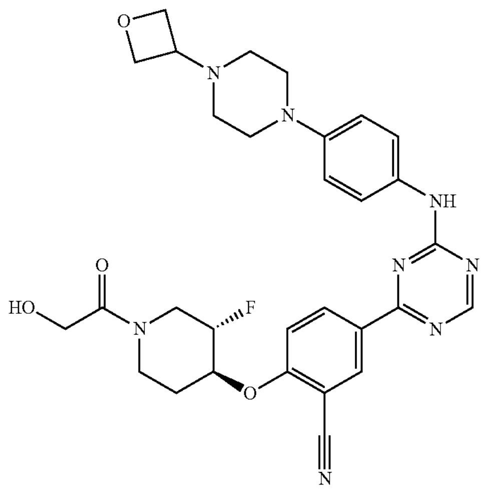 [SMILES: N#Cc1cc(-c2ncnc(Nc3ccc(N4CCN(C5COC5)CC4)cc3)n2)ccc1O[C@H]1CCN(C(=O)CO)C[C@@H]1F] | | 2 | 6 | 256 | 2-((trans-3-fluoro-1-(2-hydroxyacetyl)piperidin-4-yl)oxy)-5-(4-((4-(4-(oxetan-3-yl)piperazin-1-yl)phenyl)amino)-1,3,5-triazin-2-yl)benzonitrile |
| 221 | 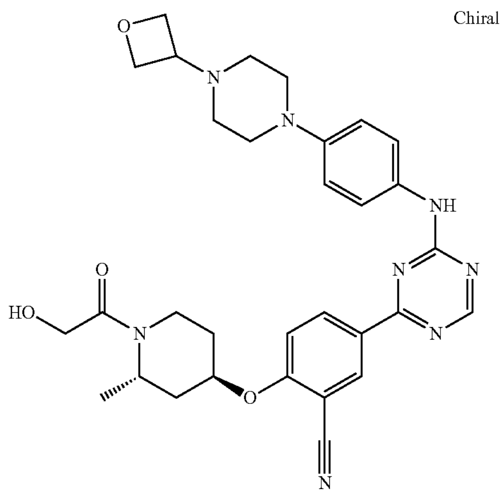 [SMILES: C[C@H]1C[C@H](Oc2ccc(-c3ncnc(Nc4ccc(N5CCN(C6COC6)CC5)cc4)n3)cc2C#N)CCN1C(=O)CO] | Chiral | 18 | 68 | 488 | 2-(((2S,4R)-1-(2-hydroxyacetyl)-2-methylpiperidin-4-yl)oxy)-5-(4-((4-(4-(oxetan-3-yl)piperazin-1-yl)phenyl)amino)-1,3,5-triazin-2-yl)benzonitrile |
| 222 | 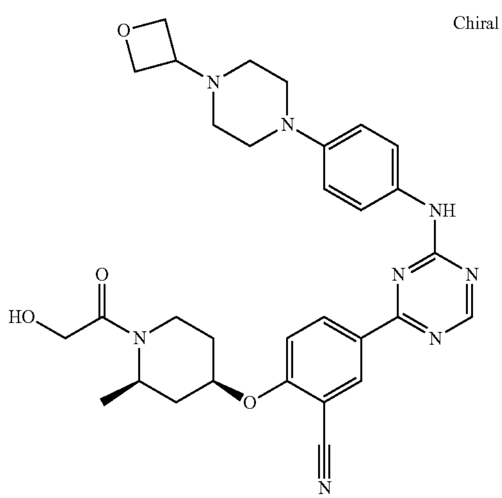 [SMILES: C[C@@H]1C[C@H](Oc2ccc(-c3ncnc(Nc4ccc(N5CCN(C6COC6)CC5)cc4)n3)cc2C#N)CCN1C(=O)CO] | Chiral | 21 | 60 | 182 | 2-(((2R,4R)-1-(2-hydroxyacetyl)-2-methylpiperidin-4-yl)oxy)-5-(4-((4-(4-(oxetan-3-yl)piperazin-1-yl)phenyl)amino)-1,3,5-triazin-2-yl)benzonitrile |

TABLE 1-continued

| Ex. | Structure | | TBK1 IC50 | IKKe IC50 | JAK2 IC50 | Name |
|---|---|---|---|---|---|---|
| 223 | 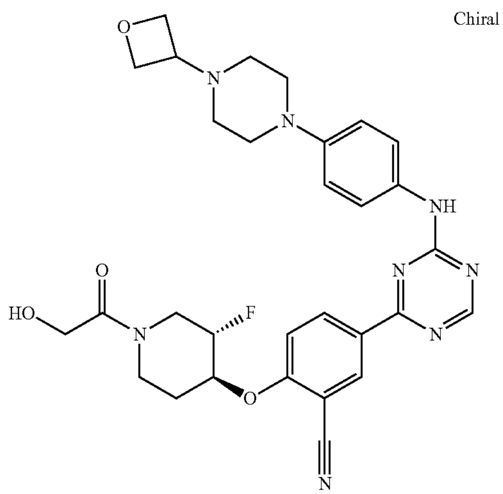 [SMILES: N#Cc1cc(-c2ncnc(Nc3ccc(N4CCN(C5COC5)CC4)cc3)n2)ccc1O[C@H]1CCN(C(=O)CO)C[C@@H]1F] | Chiral | 2 | 7 | 222 | 2-(((3S,4S)-3-fluoro-1-(2-hydroxyacetyl)piperidin-4-yl)oxy)-5-(4-((4-(4-(oxetan-3-yl)piperazin-1-yl)phenyl)amino)-1,3,5-triazin-2-yl)benzonitrile |
| 224 | 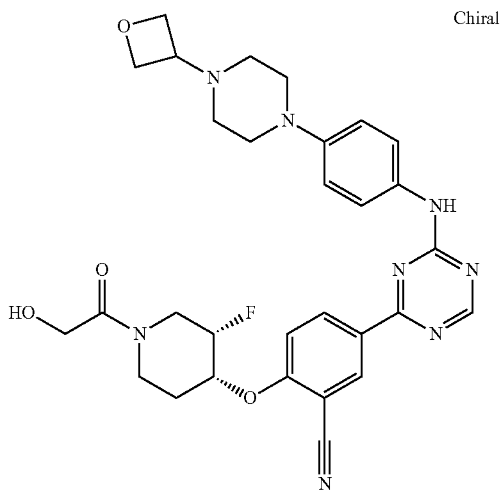 [SMILES: N#Cc1cc(-c2ncnc(Nc3ccc(N4CCN(C5COC5)CC4)cc3)n2)ccc1O[C@@H]1CCN(C(=O)CO)C[C@@H]1F] | Chiral | 9 | 23 | 189 | 2-(((3S,4R)-3-fluoro-1-(2-hydroxyacetyl)piperidin-4-yl)oxy)-5-(4-((4-(4-(oxetan-3-yl)piperazin-1-yl)phenyl)amino)-1,3,5-triazin-2-yl)benzonitrile |
| 225 | 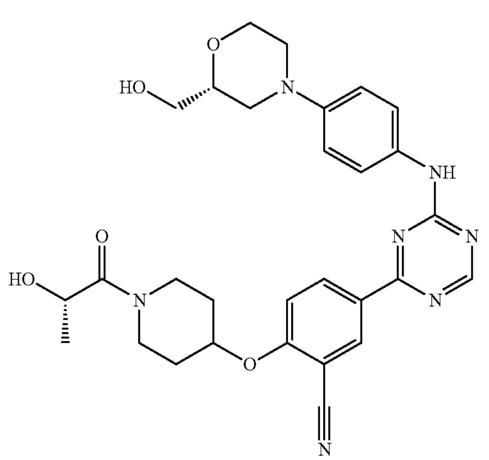 | Chiral | 8 | 22 | 1000 | 5-(4-((4-((R)-2-(hydroxymethyl)morpholino)phenyl)amino)-1,3,5-triazin-2-yl)-2-((1-((S)-2-hydroxypropanoyl)piperidin-4-yl)oxy)benzonitrile |

TABLE 1-continued

| Ex. | Structure | TBK1 IC50 | IKKe IC50 | JAK2 IC50 | Name |
|---|---|---|---|---|---|
| 226 | 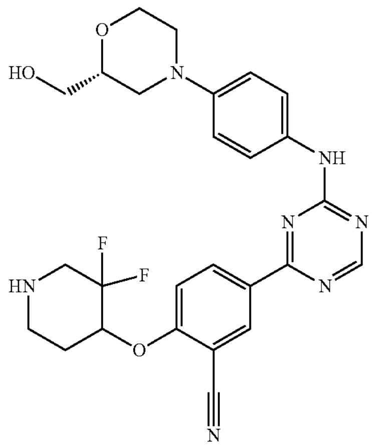 [SMILES: N#Cc1cc(-c2ncnc(Nc3ccc(N4CCO[C@@H](CO)C4)cc3)n2)ccc1OC1CCNCC1(F)F] | 5 | 29 | 311 | 2-((3,3-difluoro-piperidin-4-yl)oxy)-5-(4-((4-((R)-2-(hydroxymethyl)rnorpholino)phenyl)amino)-1,3,5-triazin-2-yl)benzonitrile |
| 227 | Chiral | 2 | 4 | 333 | (R)-2-((1-(2-hydroxyacetyl)piperidin-4-yl)oxy)-5-(4-((4-(2-(hydroxymethyl)morpholino)phenyl)amino)-1,3,5-triazin-2-yl)benzonitrile |
| 228 | 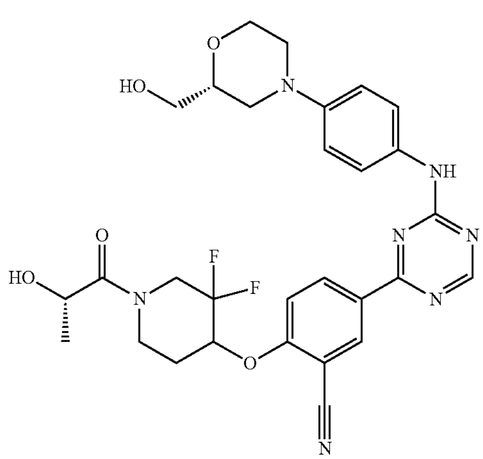 [SMILES: C[C@H](O)C(=O)N1CCC(Oc2ccc(-c3ncnc(Nc4ccc(N5CCO[C@@H](CO)C5)cc4)n3)cc2C#N)C(F)(F)C1] | 1 | 2 | 206 | 2-((3,3-difluoro-1-((S)-2-hydroxypropanoyl)piperidin-4-yl)oxy)-5-(4-((4-((R)-2-(hydroxymethyl)morpholino)phenyl)amino)-1,3,5-triazin-2-yl)benzonitrile |

TABLE 1-continued

| Ex. | Structure | TBK1 IC50 | IKKe IC50 | JAK2 IC50 | Name |
|---|---|---|---|---|---|
| 229 | 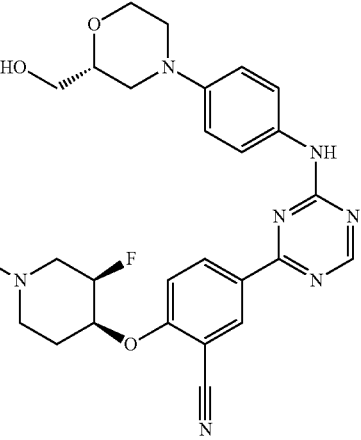 Chiral | 1 | 0 | 189 | 2-(((3R,4S)-3-fluoro-1-(2-hydroxyacetyl)piperidin-4-yl)oxy)-5-(4-((4-((R)-2-(hydroxymethyl)morpholino)phenyl)amino)-1,3,5-triazin-2-yl)benzonitrile |
| 230 | 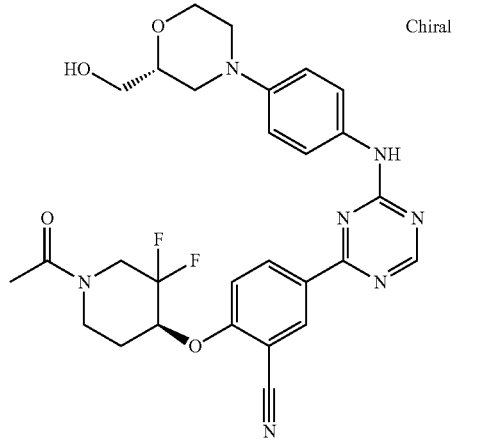 [SMILES: CC(=O)N1CC[C@H](Oc2ccc(-c3ncnc(Nc4ccc(N5CCO[C@@H](CO)C5)cc4)n3)cc2C#N)C(F)(F)C1 ; "Chiral"] Chiral | 4 | 2 | 233 | 2-(((S)-1-acetyl-3,3-difluoropiperidin-4-yl)oxy)-5-(4-((4-((R)-2-(hydroxymethyl)morpholino)phenyl)amino)-1,3,5-triazin-2-yl)benzonitrile |
| 231 | 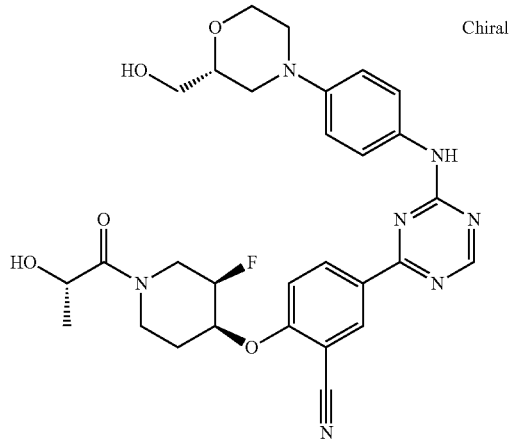 [SMILES: C[C@H](O)C(=O)N1CC[C@H](Oc2ccc(-c3ncnc(Nc4ccc(N5CCO[C@@H](CO)C5)cc4)n3)cc2C#N)[C@H](F)C1 ; "Chiral"] Chiral | 3 | 1 | 486 | 2-(((3R,4S)-3-fluoro-1-((S)-2-hydroxypropanoyl)piperidin-4-yl)oxy)-5-(4-((4-((R)-2-(hydroxymethyl)morpholino)phenyl)amino)-1,3,5-triazin-2-yl)benzonitrile |

TABLE 1-continued

| Ex. | Structure | TBK1 IC50 | IKKe IC50 | JAK2 IC50 | Name |
|---|---|---|---|---|---|
| 232 | 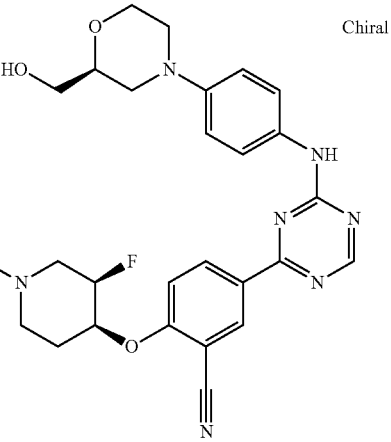 | 2 | 1 | 128 | 2-(((3R,4S)-3-fluoro-1-(2-hydroxyacetyl)piperidin-4-yl)oxy)-5-(4-((4-((S)-2-(hydroxymethyl)morpholino)phenyl)amino)-1,3,5-triazin-2-yl)benzonitrile |
| 233 | 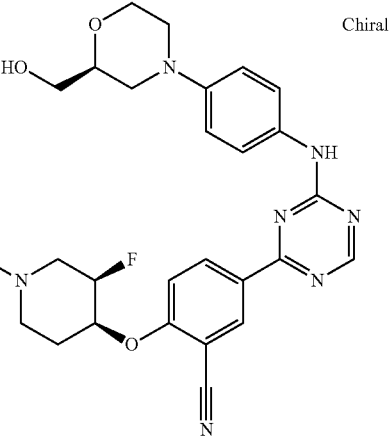 | 2 | 1 | 333 | 2-(((3R,4S)-3-fluoro-1-((S)-2-hydroxypropanoyl)piperidin-4-yl)oxy)-5-(4-((4-((S)-2-(hydroxymethyl)morpholino)phenyl)amino)-1,3,5-triazin-2-yl)benzonitrile |
| 234 | 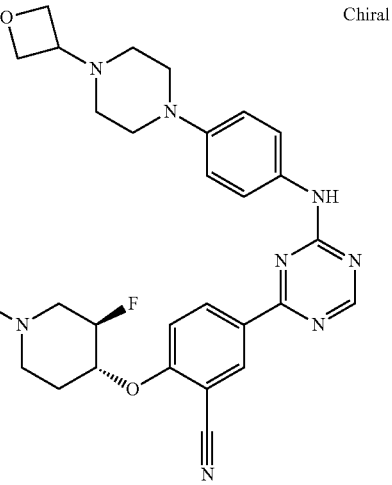 | 4 | 15 | 669 | 2-(((3R,4R)-3-fluoro-1-((S)-2-hydroxypropanoyl)piperidin-4-yl)oxy)-5-(4-((4-(4-(oxetan-3-yl)piperazin-1-yl)phenyl)amino)-1,3,5-triazin-2-yl)benzonitrile |

TABLE 1-continued

| Ex. | Structure | TBK1 IC50 | IKKe IC50 | JAK2 IC50 | Name |
|---|---|---|---|---|---|
| 235 | 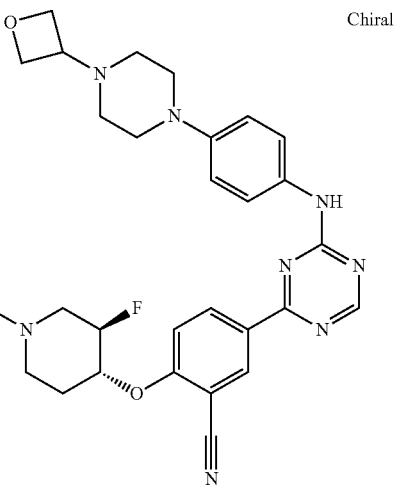 Chiral | 2 | 5 | 317 | 2-(((3R,4R)-3-fluoro-1-(2-hydroxyacetyl)piperidin-4-yl)oxy)-5-(4-((4-(4-(oxetan-3-yl)piperazin-1-yl)phenyl)amino)-1,3,5-triazin-2-yl)benzonitrile |
| 236 | 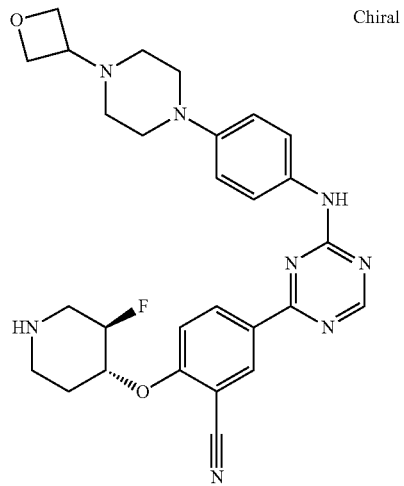 [SMILES: N#Cc1cc(-c2ncnc(Nc3ccc(N4CCN(C5COC5)CC4)cc3)n2)ccc1O[C@@H]1CCNC[C@H]1F ; "Chiral"] Chiral | 58 | 233 | 723 | 2-(((3R,4R)-3-fluoropiperidin-4-yl)oxy)-5-(4-((4-(4-(oxetan-3-yl)piperazin-1-yl)phenyl)amino)-1,3,5-triazin-2-yl)benzonitrile |
| 237 | 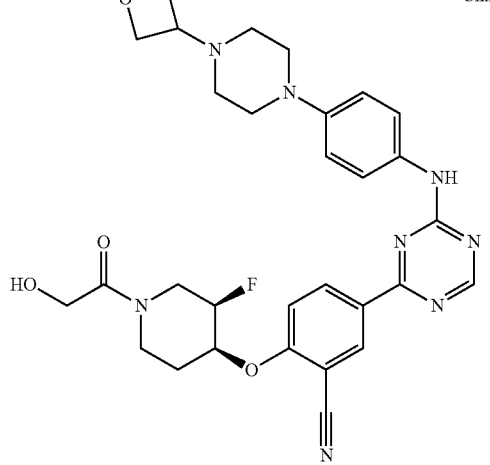 Chiral | 1 | 1 | 120 | 2-(((3R,4S)-3-fluoro-1-(2-hydroxyacetyl)piperidin-4-yl)oxy)-5-(4-((4-(4-(oxetan-3-yl)piperazin-1-yl)phenyl)amino)-1,3,5-triazin-2-yl)benzonitrile |

TABLE 1-continued

| Ex. | Structure | | TBK1 IC50 | IKKe IC50 | JAK2 IC50 | Name |
|---|---|---|---|---|---|---|
| 238 | 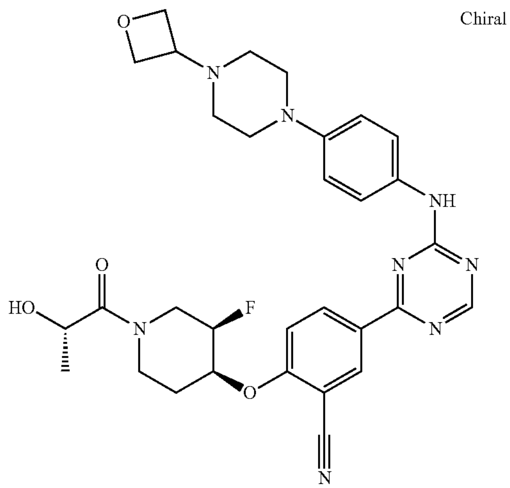 [SMILES: C[C@H](O)C(=O)N1CC[C@H](Oc2ccc(-c3ncnc(Nc4ccc(N5CCN(C6COC6)CC5)cc4)n3)cc2C#N)[C@H](F)C1 ; "Chiral"] | Chiral | 2 | 2 | 445 | 2-(((3R,4S)-3-fluoro-1-((S)-2-hydroxypropanoyl)piperidin-4-yl)oxy)-5-(4-((4-(4-(oxetan-3-yl)piperazin-1-yl)phenyl)amino)-1,3,5-triazin-2-yl)benzonitrile |
| 239 | 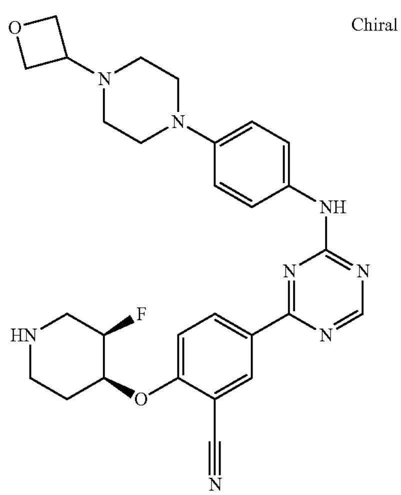 [SMILES: N#Cc1cc(-c2ncnc(Nc3ccc(N4CCN(C5COC5)CC4)cc3)n2)ccc1O[C@H]1CCNC[C@H]1F ; "Chiral"] | Chiral | 8 | 59 | 409 | 2-(((3R,4S)-3-fluoropiperidin-4-yl)oxy)-5-(4-((4-(4-(oxetan-3-yl)piperazin-1-yl)phenyl)amino)-1,3,5-triazin-2-yl)benzonitrile |
| 240 | 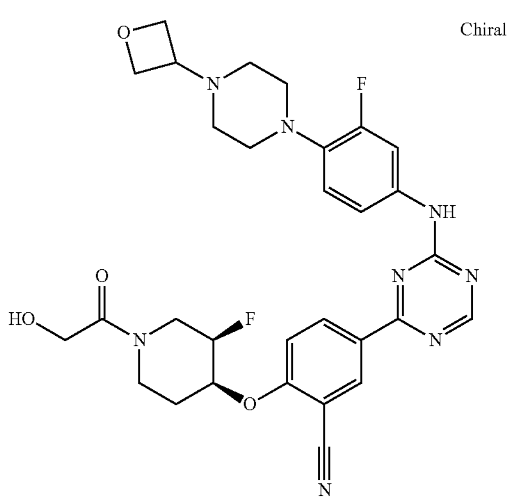 [SMILES: N#Cc1cc(-c2ncnc(Nc3ccc(N4CCN(C5COC5)CC4)c(F)c3)n2)ccc1O[C@H]1CCN(C(=O)CO)C[C@H]1F ; "Chiral"] | Chiral | 1 | 1 | 199 | 2-(((3R,4S)-3-fluoro-1-(2-hydroxyacetyl)piperidin-4-yl)oxy)-5-(4-((3-fluoro-4-(4-(oxetan-3-yl)piperazin-1-yl)phenyl)amino)-1,3,5-triazin-2-yl)benzonitrile |

TABLE 1-continued

| Ex. | Structure | | TBK1 IC50 | IKKe IC50 | JAK2 IC50 | Name |
|---|---|---|---|---|---|---|
| 241 | (structure) | Chiral | 2 | 1 | 120 | 2-(((3R,4S)-3-fluoro-1-(2-hydroxyacetyl)piperidin-4-yl)oxy)-5-(4-((4-((S)-3-methyl-4-(oxetan-3-yl)piperazin-1-yl)phenyl)amino)-1,3,5-triazin-2-yl)benzonitrile |
| 242 | (structure) | Chiral | 2 | 1 | 249 | 2-(((3R,4S)-3-fluoro-1-(2-hydroxyacetyl)piperidin-4-yl)oxy)-5-(4-((4-((R)-2-methyl-4-(oxetan-3-yl)piperazin-1-yl)phenyl)amino)-1,3,5-triazin-2-yl)benzonitrile |
| 243 | (structure) | Chiral | 2 | 1 | 130 | 2-(((3R,4S)-3-fluoro-1-(2-hydroxyacetyl)piperidin-4-yl)oxy)-5-(4-((4-((R)-3-methyl-4-(oxetan-3-yl)piperazin-1-yl)phenyl)amino)-1,3,5-triazin-2-yl)benzonitrile |

TABLE 1-continued

| Ex. | Structure | | TBK1 IC50 | IKKe IC50 | JAK2 IC50 | Name |
|---|---|---|---|---|---|---|
| 244 | 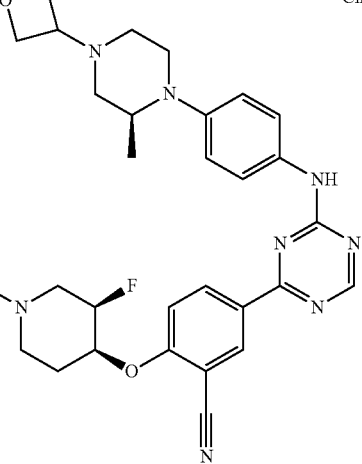 | Chiral | 3 | 1 | 191 | 2-(((3R,4S)-3-fluoro-1-(2-hydroxyacetyl)piperidin-4-yl)oxy)-5-(4-((4-((S)-2-methyl-4-(oxetan-3-yl)piperazin-1-yl)phenyl)amino)-1,3,5-triazin-2-yl)benzonitrile |
| 245 | 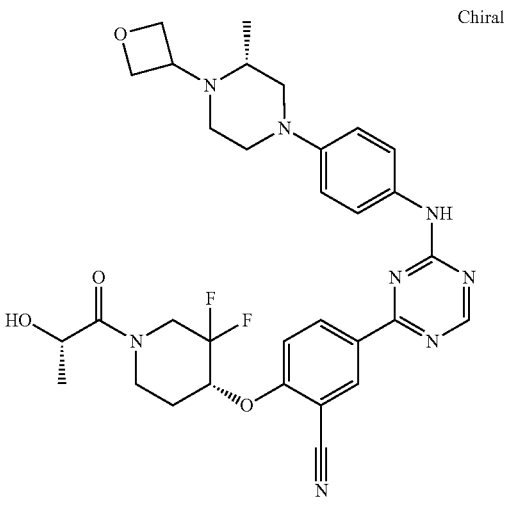 [SMILES: C[C@H](O)C(=O)N1CC[C@@H](Oc2ccc(-c3ncnc(Nc4ccc(N5CCN(C6COC6)[C@H](C)C5)cc4)n3)cc2C#N)C(F)(F)C1] | Chiral | 17 | 26 | 228 | 2-(((R)-3,3-difluoro-1-((S)-2-hydroxypropanoyl)piperidin-4-yl)-oxy)5-(4-((4-((R)-3-methyl-4-(oxetan-3-yl)piperazin-1-yl)phenyl)amino)-1,3,5-triazin-2-yl)benzonitrile |
| 246 | 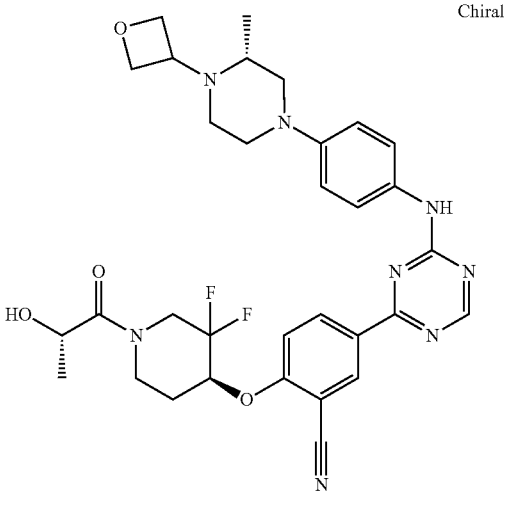 [SMILES: C[C@H](O)C(=O)N1CC[C@H](Oc2ccc(-c3ncnc(Nc4ccc(N5CCN(C6COC6)[C@H](C)C5)cc4)n3)cc2C#N)C(F)(F)C1] | Chiral | 2 | 1 | 181 | 2-(((S)-3,3-difluoro-1-((S)-2-hydroxypropanoyl)piperidin-4-yl)oxy)-5-(4-((4-((R)-3-methyl-4-(oxetan-3-yl)piperazin-1-yl)phenyl)amino)-1,3,5-triazin-2-yl)benzonitrile |

TABLE 1-continued

| Ex. | Structure | TBK1 IC50 | IKKe IC50 | JAK2 IC50 | Name |
|---|---|---|---|---|---|
| 247 | Chiral | 233 | 397 | 333 | 2-(((R)-3,3-difluoro-1-((R)-2-hydroxypropanoyl)piperidin-4-yl)oxy)-5-(4-((4-((R)-3-methyl-4-(oxetan-3-yl)piperazin-1-yl)phenyl)amino)-1,3,5-triazin-2-yl)benzonitrile |
| 248 | Chiral | 3 | 3 | 187 | 2-(((S)-3,3-difluoro-1-((R)-2-hydroxypropanoyl)piperidin-4-yl)oxy)-5-(4-((4-((R)-3-methyl-4-(oxetan-3-yl)piperazin-1-yl)phenyl)amino)-1,3,5-triazin-2-yl)benzonitrile |
| 249 | Chiral | 3 | 2 | 389 | 2-(((3R,4S)-3-fluoro-1-((S)-2-hydroxypropanoyl)piperidin-4-yl)oxy)-5-(4-((4-((S)-2-methyl-4-(oxetan-3-yl)piperazin-1-yl)phenyl)amino)-1,3,5-triazin-2-yl)benzonitrile |

TABLE 1-continued

| Ex. | Structure | | TBK1 IC50 | IKKe IC50 | JAK2 IC50 | Name |
|---|---|---|---|---|---|---|
| 250 | 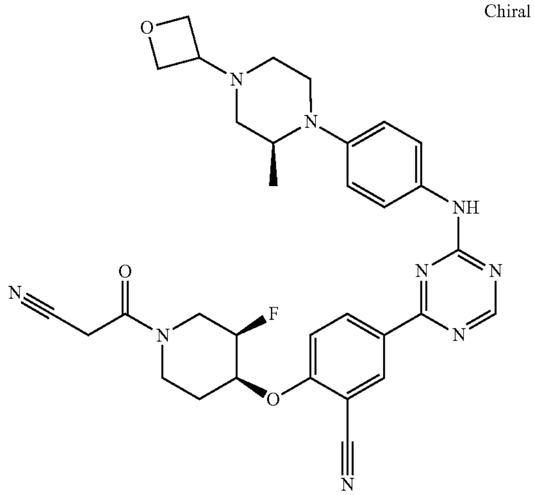 [SMILES: C[C@H]1CN(C2COC2)CCN1c1ccc(Nc2ncnc(-c3ccc(O[C@H]4CCN(C(=O)CC#N)C[C@H]4F)c(C#N)c3)n2)cc1] | Chiral | 3 | 5 | 127 | 2-(((3R,4S)-1-(2-cyanoacetyl)-3-fluoropiperidin-4-yl)oxy)-5-(4-((4-((S)-2-methyl-4-(oxetan-3-yl)piperazin-1-yl)phenyl)amino)-1,3,5-triazin-2-yl)benzonitrile |
| 251 | 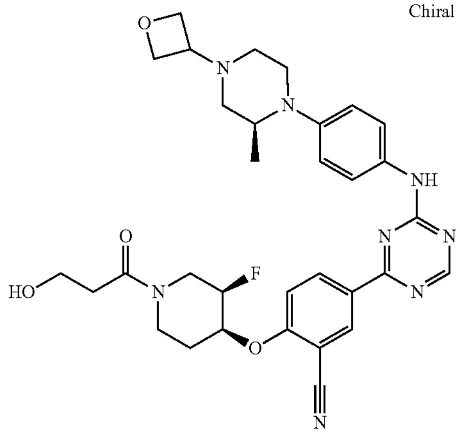 [SMILES: C[C@H]1CN(C2COC2)CCN1c1ccc(Nc2ncnc(-c3ccc(O[C@H]4CCN(C(=O)CCO)C[C@H]4F)c(C#N)c3)n2)cc1] | Chiral | 5 | 14 | 369 | 2-(((3R,4S)-3-fluoro-1-(3-hydroxypropanoyl)piperidin-4-yl)oxy)-5-(4-((4-((S)-2-methyl-4-(oxetan-3-yl)piperazin-1-yl)phenyl)amino)-1,3,5-triazin-2-yl)benzonitrile |
| 252 | 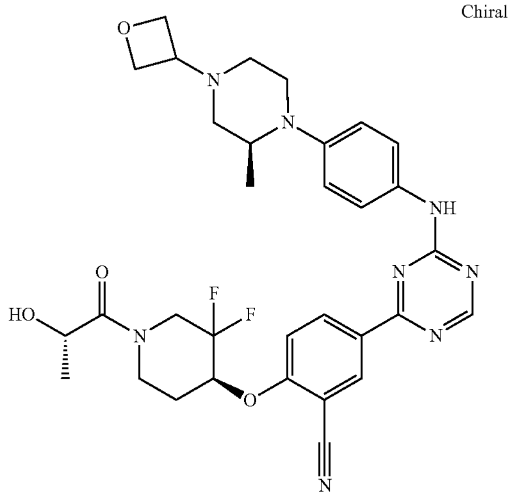 [SMILES: C[C@H](O)C(=O)N1CC[C@H](Oc2ccc(-c3ncnc(Nc4ccc(N5CCN(C6COC6)C[C@@H]5C)cc4)n3)cc2C#N)C(F)(F)C1] | Chiral | 3 | 1 | 213 | 2-(((S)-3,3-difluoro-1-((S)-2-hydroxypropanoyl)piperidin-4-yl)oxy)-5-(4-((4-((S)-2-methyl-4-(oxetan-3-yl)piperazin-1-yl)phenyl)amino)-1,3,5-triazin-2-yl)benzonitrile |

TABLE 1-continued

| Ex. | Structure | TBK1 IC50 | IKKe IC50 | JAK2 IC50 | Name |
|---|---|---|---|---|---|
| 253 | Chiral | 3 | 2 | 61 | 2-(((S)-1-(2-cyanoacetyl)-3,3-difluoropiperidin-4-yl)oxy)-5-(4-((4-((S)-2-methyl-4-(oxetan-3-yl)piperazin-1-yl)phenyl)amino)-1,3,5-triazin-2-yl)benzonitrile |
| 254 | Chiral | 3 | 5 | 151 | 2-(((S)-3,3-difluoro-1-(3-hydroxypropanoyl)piperidin-4-yl)oxy)-5-(4-((4-((S)-2-methyl-4-(oxetan-3-yl)piperazin-1-yl)phenyl)amino)-1,3,5-triazin-2-yl)benzonitrile |
| 255 | Chiral | 4 | 2 | 227 | 2-(((3R,4S)-3-fluoro-1-(1H-1,2,3-triazole-5-carbonyl)piperidin-4-yl)oxy)-5-(4-((4-((S)-2-methyl-4-(oxetan-3-yl)piperazin-1-yl)phenyl)amino)-1,3,5-triazin-2-yl)benzonitrile |

TABLE 1-continued

| Ex. | Structure | | TBK1 IC50 | IKKe IC50 | JAK2 IC50 | Name |
|---|---|---|---|---|---|---|
| 256 | 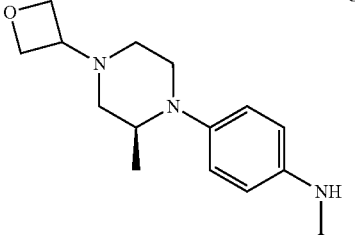 | Chiral | 3 | 1 | 144 | 2-(((3R,4S)-3-fluoro-1-(1H-imidazole-5-carbonyl)piperidin-4-yl)oxy)-5-(4-((4-((S)-2-methyl-4-(oxetan-3-yl)piperazin-1-yl)phenyl)amino)-1,3,5-triazin-2-yl)benzonitrile |
| 257 | 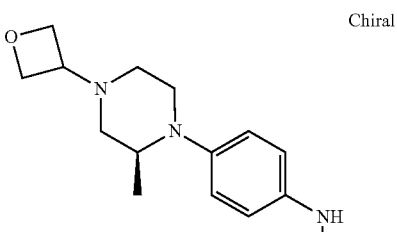 | Chiral | 2 | 1 | 270 | 2-(((3R,4S)-3-fluoro-1-(1H-pyrazole-5-carbonyl)piperidin-4-yl)oxy)-5-(4-((4-((S)-2-methyl-4-(oxetan-3-yl)piperazin-1-yl)phenyl)amino)-1,3,5-triazin-2-yl)benzonitrile |
| 258 | 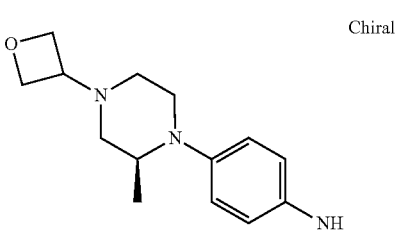 | Chiral | 3 | 1 | 98 | 2-(((S)-3,3-difluoro-1-(1H-1,2,3-triazole-5-carbonyl)piperidin-4-yl)oxy)-5-(4-((4-((S)-2-methyl-4-(oxetan-3-yl(piperazin-1-yl)phenyl)amino)-1,3,5-triazin-2-yl)benzonitrile |

TABLE 1-continued

| Ex. | Structure | | TBK1 IC50 | IKKe IC50 | JAK2 IC50 | Name |
|---|---|---|---|---|---|---|
| 259 | 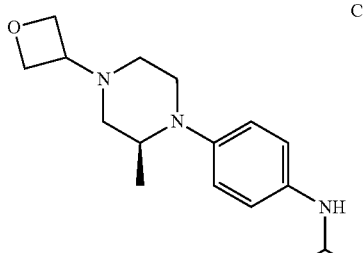 | Chiral | 3 | 1 | 66 | 2-(((S)-3,3-difluoro-1-(1H-imidazole-5-carbonyl)piperidin-4-yl)oxy)-5-(4-((4-((S)-2-methyl-4-(oxetan-3-yl)piperazin-1-yl)phenyl)amino)-1,3,5-triazin-2-yl)benzonitrile |
| 260 | 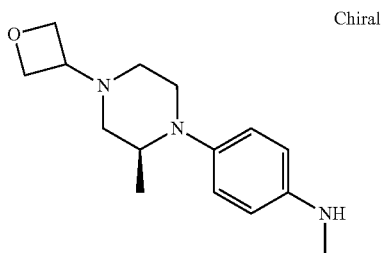 | Chiral | 2 | 0 | 42 | 2-(((S)-3,3-difluoro-1-(4H-1,2,4-triazole-3-carbonyl)piperidin-4-yl)oxy)-5-(4-((4-((S)-2-methyl-4-(oxetan-3-yl)piperazin-1-yl)phenyl)amino)-1,3,5-triazin-2-yl)benzonitrile |
| 261 | 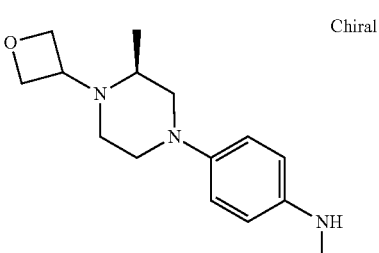 | Chiral | 1 | 0 | 46 | 2-(((S)-3,3-difluoro-1-(2-hydroxyacetyl)piperidin-4-yl)oxy)-5-(4-((4-((S)-3-methyl-4-(oxetan-3-yl)piperazin-1-yl)phenyl)amino)-1,3,5-triazin-2-yl)benzonitrile |

TABLE 1-continued

| Ex. | Structure | TBK1 IC50 | IKKe IC50 | JAK2 IC50 | Name |
|---|---|---|---|---|---|
| 262 | 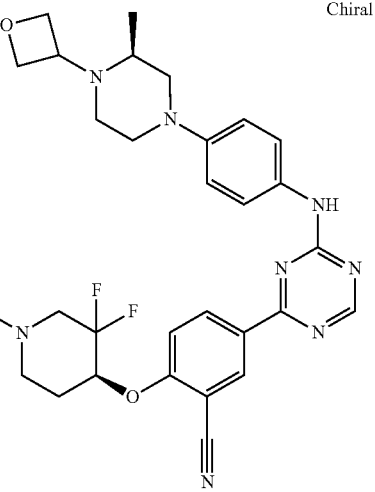 Chiral | 2 | 1 | 156 | 2-(((S)-3,3-difluoro-1-((S)-2-hydroxypropanoyl)piperidin-4-yl)oxy)-5-(4-((4-((S)-3-methyl-4-(oxetan-3-yl)piperazin-1-yl)phenyl)amino)-1,3,5-triazin-2-yl)benzonitrile |
| 263 | 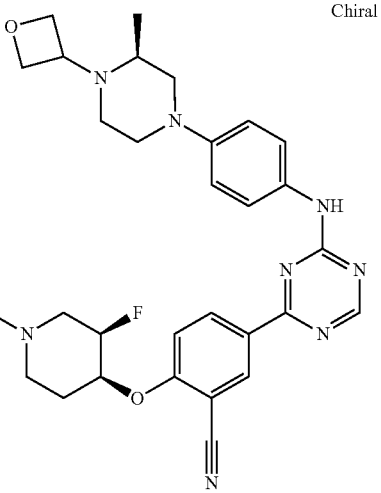 Chiral | 3 | 3 | 158 | 2-(((3R,4S)-3-fluoro-1-(1H-1,2,3-triazole-5-carbonyl)piperidin-4-yl)oxy)-5-(4-((4-((S)-3-methyl-4-(oxetan-3-yl)piperazin-1-yl)phenyl)amino)-1,3,5-triazin-2-yl)benzonitrile |
| 264 | 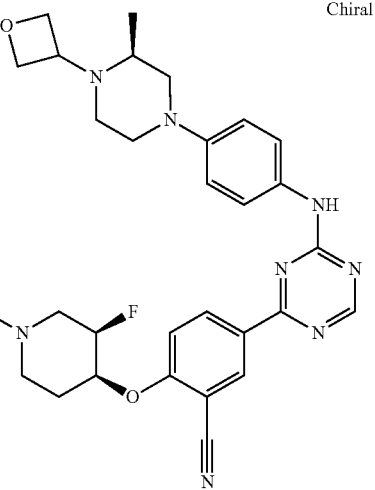 Chiral | 2 | 1 | 296 | 2-(((3R,4S)-3-fluoro-1-((S)-2-hydroxypropanoyl)piperidin-4-yl)oxy)-5-(4-((4-((S)-3-methyl-4-(oxetan-3-yl)piperazin-1-yl)phenyl)amino)-1,3,5-triazin-2-yl)benzonitrile |

TABLE 1-continued

| Ex. | Structure | | TBK1 IC50 | IKKe IC50 | JAK2 IC50 | Name |
|---|---|---|---|---|---|---|
| 265 | 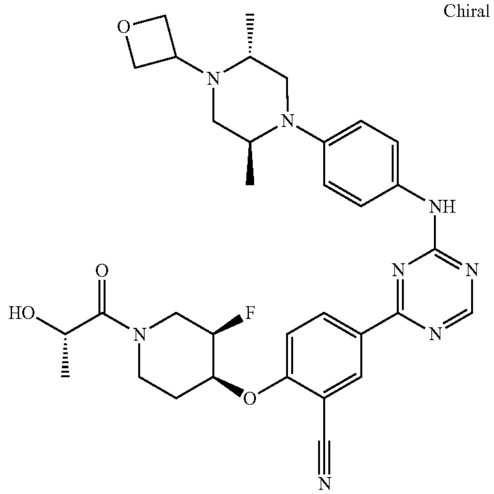 [SMILES: C[C@H](O)C(=O)N1CC[C@H](Oc2ccc(-c3ncnc(Nc4ccc(N5C[C@@H](C)N(C6COC6)C[C@@H]5C)cc4)n3)cc2C#N)[C@H](F)C1] | Chiral | 5 | 4 | 426 | 5-(4-((4-((2S,5R)-2,5-dimethyl-4-(oxetan-3-yl)piperazin-1-yl)phenyl)amino)-1,3,5-triazin-2-yl)-2-(((3R,4S)-3-fluoro-1-((S)-2-hydroxypropanoyl)piperidin-4-yl)oxy)benzonitrile |
| 266 | 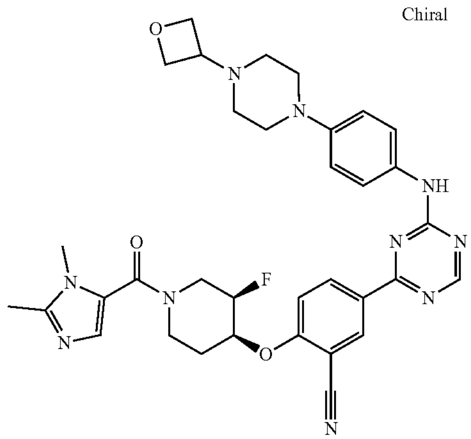 [SMILES: Cc1ncc(C(=O)N2CC[C@H](Oc3ccc(-c4ncnc(Nc5ccc(N6CCN(C7COC7)CC6)cc5)n4)cc3C#N)[C@H](F)C2)n1C] | Chiral | 82 | 83 | 387 | 2-(((3R,4S)-1-(1,2-dimethyl-1H-imidazole-5-carbonyl)-3-fluoropiperidin-4-yl)oxy)-5-(4-((4-(4-(oxetan-3-yl)piperazin-1-yl)phenyl)amino)-1,3,5-triazin-7-yl)benzonitrile |
| 267 | 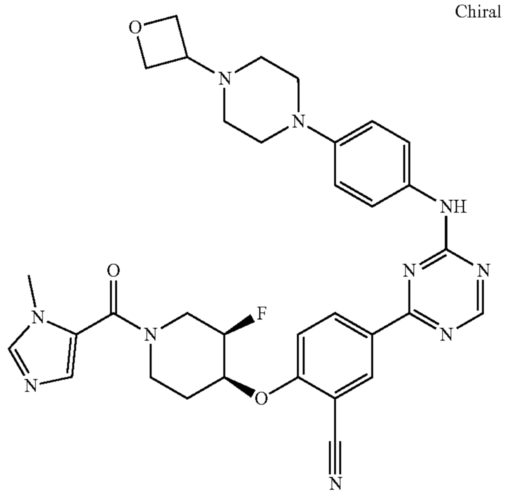 [SMILES: Cn1cncc1C(=O)N1CC[C@H](Oc2ccc(-c3ncnc(Nc4ccc(N5CCN(C6COC6)CC5)cc4)n3)cc2C#N)[C@H](F)C1] | Chiral | 120 | 264 | 404 | 2-((((3R,4S)-3-fluoro-1-(1-methyl-1H-imidazole-5-carbonyl)piperidin-4-yl)oxy)-5-(4-((4-(4-(oxetan-3-yl)piperazin-1-yl)phenyl)amino)-1,3,5-triazin-2-yl)benzonitrile |

TABLE 1-continued
| Ex. | Structure | TBK1 IC50 | IKKe IC50 | JAK2 IC50 | Name |
|---|---|---|---|---|---|
| 268 | 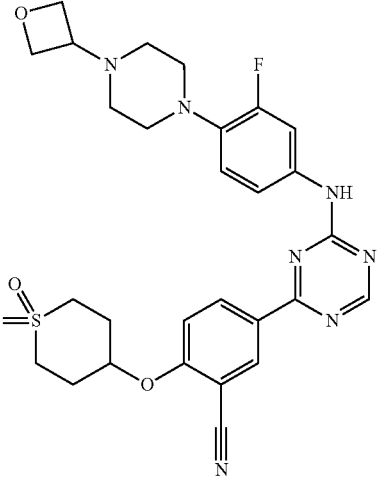 | 12 | 69 | 527 | 2-((1,1-dioxido-tetrahydro-2H-thiopyran-4-yl)oxy)-5-(4-((3-fluoro-4-(4-(oxetan-3-yl)piperazin-1-yl)phenyl)amino)-1,3,5-triazin-2-yl)benzonitrile |
| 269 | 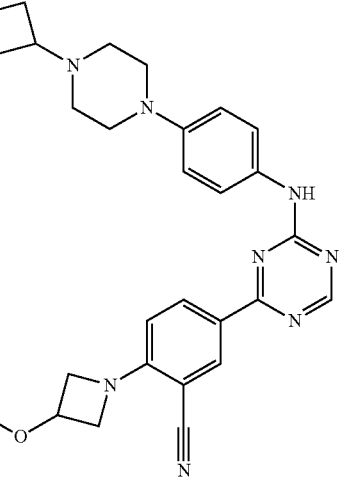 | 13 | 25 | 219 | 2-(3-methoxyazetidin-1-yl)-5-(4-((4-(4-(oxetan-3-yl)piperazin-1-yl)phenyl)amino)-1,3,5-triazin-2-yl)benzonitrile |
| 270 | 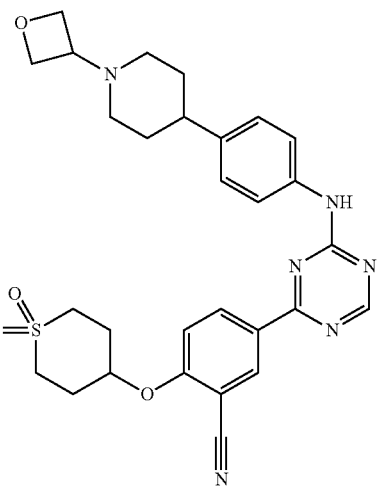 | 12 | 43 | 804 | 2-((1,1-dioxido-tetrahydro-2H-thiopyran-4-yl)oxy)-5-(4-((4-(1-(oxetan-3-yl)piperidin-4-yl)phenyl)amino)-1,3,5-triazin-2-yl)benzonitrile |

TABLE 1-continued

| Ex. | Structure | TBK1 IC50 | IKKe IC50 | JAK2 IC50 | Name |
|---|---|---|---|---|---|
| 271 | 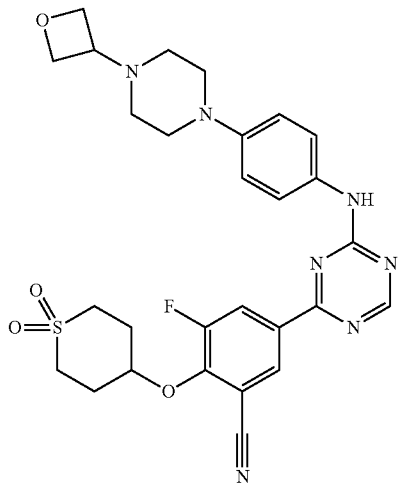 [SMILES: N#Cc1cc(-c2ncnc(Nc3ccc(N4CCN(C5COC5)CC4)cc3)n2)cc(F)c1OC1CCS(=O)(=O)CC1] | 18 | 110 | 1000 | 2-((1,1-dioxido-tetrahydro-2H-thiopyran-4-yl)oxy)-3-fluoro-5-(4-((4-(4-(oxetan-3-yl)piperazin-1-yl)phenyl)amino)-1,3,5-triazin-2-yl)benzonitrile |
| 272 | 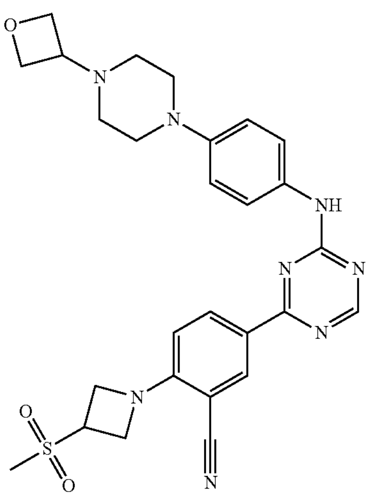 [SMILES: CS(=O)(=O)C1CN(c2ccc(-c3ncnc(Nc4ccc(N5CCN(C6COC6)CC5)cc4)n3)cc2C#N)C1] | 28 | 53 | 68 | 2-(3-(methylsulfonyl)azetidin-1-yl)-5-(4-((4-(4-(oxetan-3-yl)piperazin-1-yl)phenyl)amino)-1,3,5-triazin-2-yl)benzonitrile |
| 273 | 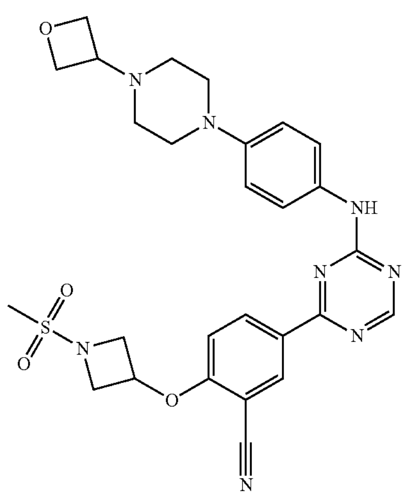 [SMILES: CS(=O)(=O)N1CC(Oc2ccc(-c3ncnc(Nc4ccc(N5CCN(C6COC6)CC5)cc4)n3)cc2C#N)C1] | 139 | 285 | 133 | 2-((1-(methylsulfonyl)azetidin-3-yl)oxy)-5-(4-((4-(4-(oxetan-3-yl)piperazin-1-yl)phenyl)amino)-1,3,5-triazin-2-yl)benzonitrile |

TABLE 1-continued

| Ex. | Structure | TBK1 IC50 | IKKe IC50 | JAK2 IC50 | Name |
|---|---|---|---|---|---|
| 274 | 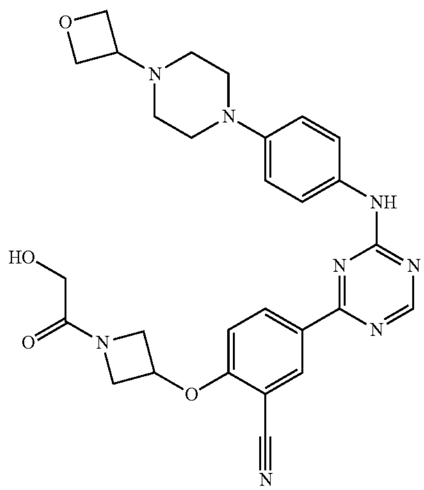 [SMILES: N#Cc1cc(-c2ncnc(Nc3ccc(N4CCN(C5COC5)CC4)cc3)n2)ccc1OC1CN(C(=O)CO)C1] | 47 | 1000 | 1000 | 2-((1-(2-hydroxyacetyl)azetidin-3-yl)oxy)-5-(4-((4-(4-(oxetan-3-yl)piperazin-1-yl)phenyl)amino)-1,3,5-triazin-2-yl)benzonitrile |
| 275 | 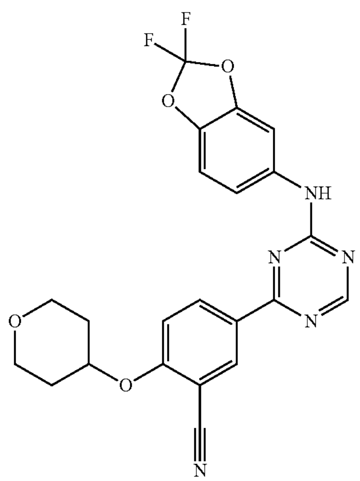 [SMILES: N#Cc1cc(-c2ncnc(Nc3ccc4c(c3)OC(F)(F)O4)n2)ccc1OC1CCOCC1] | 115 | 1000 | 1000 | 5-(4-((2,2-difluorobenzo[d][1,3]dioxol-5-yl)amino)-1,3,5-triazin-2-yl)-2-((tetrahydro-2H-pyran-4-yl)oxy)benzonitrile |
| 276 | 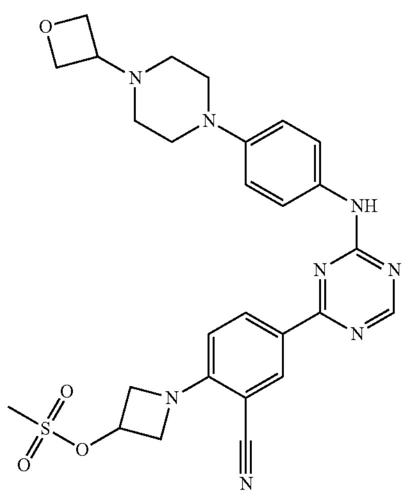 [SMILES: CS(=O)(=O)OC1CN(c2ccc(-c3ncnc(Nc4ccc(N5CCN(C6COC6)CC5)cc4)n3)cc2C#N)C1] | 23 | 38 | 52 | 1-(2-cyano-4-(4-((4-(4-(oxetan-3-yl)piperazin-1-yl)phenyl)amino)-1,3,5-triazin-2-yl)phenyl)azetidin-3-yl methanesulfonate |

TABLE 1-continued

| Ex. | Structure | TBK1 IC50 | IKKe IC50 | JAK2 IC50 | Name |
|---|---|---|---|---|---|
| 277 | 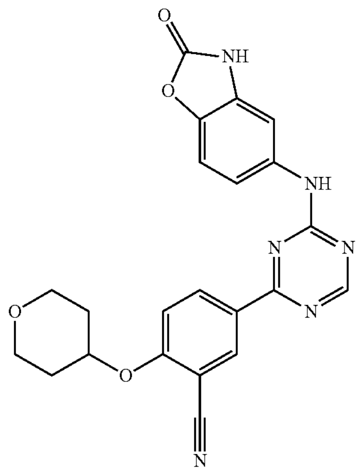 [SMILES: N#Cc1cc(-c2ncnc(Nc3ccc4oc(=O)[nH]c4c3)n2)ccc1OC1CCOCC1] | 18 | 47 | 1000 | 5-(4-((2-oxo-2,3-dihydrobenzo[d]oxazol-5-yl)amino)-1,3,5-triazin-2-yl)-2-((tetrahydro-2H-pyran-4-yl)oxy)benzonitrile |
| 278 | 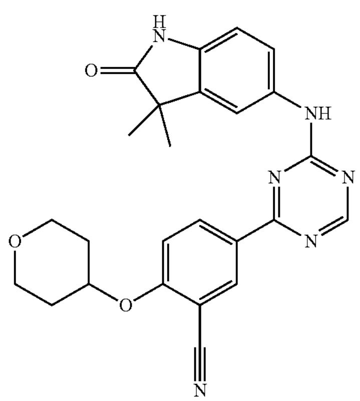 [SMILES: CC1(C)C(=O)Nc2ccc(Nc3ncnc(-c4ccc(OC5CCOCC5)c(C#N)c4)n3)cc21] | 4 | 9 | 541 | 5-(4-((3,3-dimethyl-2-oxoindolin-5-yl)amino)-1,3,5-triazin-2-yl)-2-((tetrahydro-2H-pyran-4-yl)oxy)benzonitrile |
| 279 | 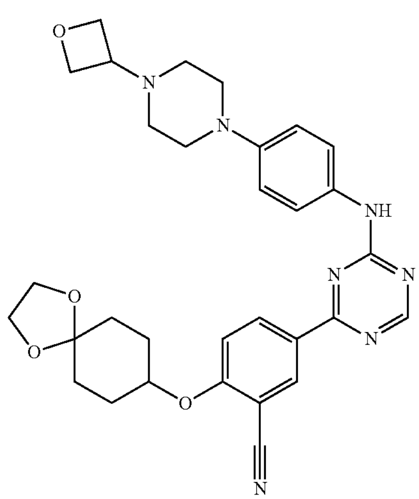 [SMILES: N#Cc1cc(-c2ncnc(Nc3ccc(N4CCN(C5COC5)CC4)cc3)n2)ccc1OC1CCC2(CC1)OCCO2] | 27 | 75 | 1000 | 2-(1,4-dioxaspiro[4.5]decan-8-yloxy)-5-(4-((4-(4-(oxetan-3-yl)piperazin-1-yl)phenyl)amino)-1,3,5-triazin-2-yl)benzonitrile |

TABLE 1-continued

| Ex. | Structure | TBK1 IC50 | IKKe IC50 | JAK2 IC50 | Name |
|---|---|---|---|---|---|
| 280 | 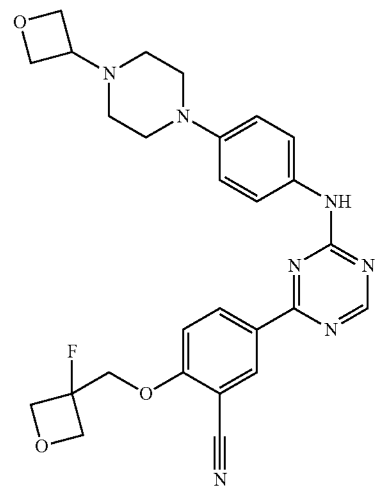 [SMILES: N#Cc1cc(-c2ncnc(Nc3ccc(N4CCN(C5COC5)CC4)cc3)n2)ccc1OCC1(F)COC1] | 4 | 10 | 110 | 2-((3-fluorooxetan-3-yl)methoxy)-5-(4-((4-(4-(oxetan-3-yl)piperazin-1-yl)phenyl)amino)-1,3,5-triazin-2-yl)benzonitrile |
| 281 | Chiral | 2 | 8 | 185 | (S)-2-((1-(2-hydroxypropanoyl)piperidin-4-yl)oxy)-5-(4-((3-methoxy-4-(4-(oxetan-3-yl)piperazin-1-yl)phenyl)amino)-1,3,5-triazin-2-yl)benzonitrile |
| 282 | Chiral | 14 | 16 | 219 | (S)-5-(4-((4-(4-(oxetan-3-yl)piperazin-1-yl)phenyl)amino)-1,3,5-triazin-2-yl)-2-(1-(tetrahydro-2H-pyran-4-yl)ethoxy)benzonitrile |

TABLE 1-continued

| Ex. | Structure | TBK1 IC50 | IKKe IC50 | JAK2 IC50 | Name |
|---|---|---|---|---|---|
| 283 | Chiral | 22 | 115 | 450 | (R)-5-(4-((4-(4-(oxetan-3-yl)piperazin-1-yl)phenyl)amino)-1,3,5-triazin-2-yl)-2-(1-(tetrahydro-2H-pyran-4-yl)ethoxy)benzonitrile |
| 284 | 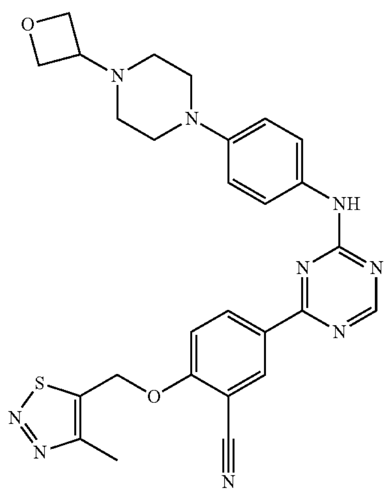 [SMILES: Cc1nnsc1COc1ccc(-c2ncnc(Nc3ccc(N4CCN(C5COC5)CC4)cc3)n2)cc1C#N] | 475 | 1000 | 605 | 2-((4-methyl-1,2,3-thiadiazol-5-yl)methoxy)-5-(4-((4-(4-(oxetan-3-yl)piperazin-1-yl)phenyl)amino)-1,3,5-triazin-2-yl)benzonitrile |
| 285 | 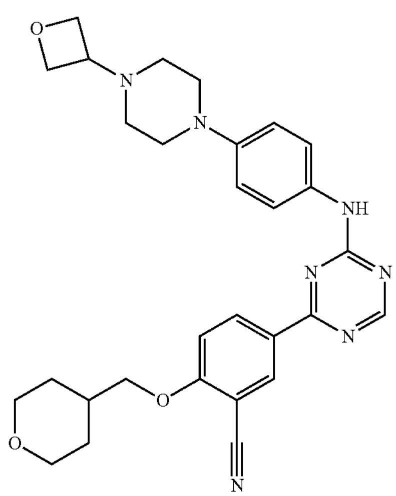 [SMILES: N#Cc1cc(-c2ncnc(Nc3ccc(N4CCN(C5COC5)CC4)cc3)n2)ccc1OCC1CCOCC1] | 4 | 8 | 313 | 5-(4-((4-(4-(oxetan-3-yl)piperazin-1-yl)phenyl)amino)-1,3,5-triazin-2-yl)-2-((tetrahydro-2H-pyran-4-yl)methoxy)benzonitrile |

TABLE 1-continued
| Ex. | Structure | TBK1 IC50 | IKKe IC50 | JAK2 IC50 | Name |
|---|---|---|---|---|---|
| 286 | 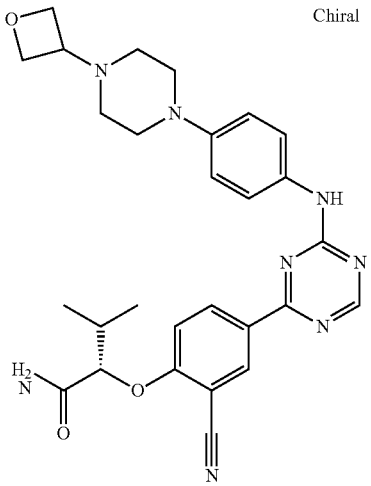 [SMILES: CC(C)[C@H](Oc1ccc(-c2ncnc(Nc3ccc(N4CCN(C5COC5)CC4)cc3)n2)cc1C#N)C(N)=O] Chiral | 94 | 237 | 1000 | (S)-2-(2-cyano-4-(4-((4-(4-(oxetan-3-yl)piperazin-1-yl)phenyl)amino)-1,3,5-triazin-2-yl)phenoxy)-3-methylbutanamide |
| 287 | 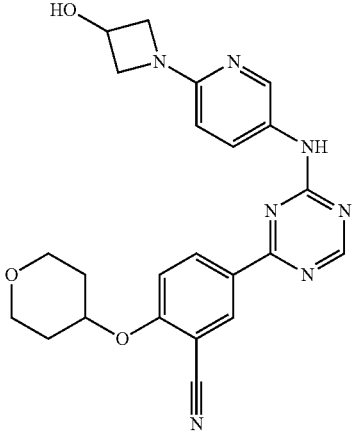 [SMILES: N#Cc1cc(-c2ncnc(Nc3ccc(N4CC(O)C4)nc3)n2)ccc1OC1CCOCC1] | 15 | 20 | 1000 | 5-(4-((6-(3-hydroxyazetidin-1-yl)pyridin-3-yl)amino)-1,3,5-triazin-2-yl)-2-((tetrahydro-2H-pyran-4-yl)oxy)benzonitrile |
| 288 | 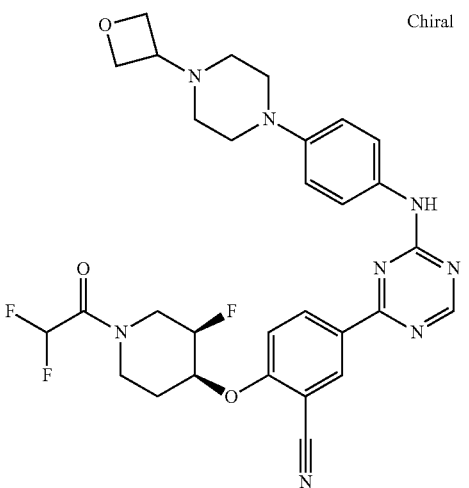 [SMILES: N#Cc1cc(-c2ncnc(Nc3ccc(N4CCN(C5COC5)CC4)cc3)n2)ccc1O[C@H]1CCN(C(=O)C(F)F)C[C@H]1F] Chiral | 3 | 2 | 316 | 2-(((3R,4S)-1-(2,2-difluoroacetyl)-3-fluoropiperidin-4-yl)oxy)-5-(4-((4-(4-(oxetan-3-yl)piperazin-1-yl)phenyl)amino)-1,3,5-triazin-2-yl)benzonitrile |

TABLE 1-continued

| Ex. | Structure | TBK1 IC50 | IKKe IC50 | JAK2 IC50 | Name |
|---|---|---|---|---|---|
| 289 | Chiral | 4 | 5 | 444 | 2-(((3R,4S)-1-acetyl-3-fluoropiperidin-4-yl)oxy)-5-(4-((4-(4-(oxetan-3-yl)piperazin-1-yl)phenyl)amino)-1,3,5-triazin-2-yl)benzonitrile |
| 290 | Chiral | 13 | 32 | 680 | (3R,4S)-methyl 4-(2-cyano-4-(4-((4-(4-(oxetan-3-yl)piperazin-1-yl)phenyl)amino)-1,3,5-triazin-2-yl)phenoxy)-3-fluoropiperidine-1-carboxylate |
| 291 | Chiral | 266 | 603 | 474 | 2-(((1S,2R)-2-aminocyclohexyl)oxy)-5-(4-((4-(4-(oxetan-3-yl)piperazin-1-yl)phenyl)amino)-1,3,5-triazin-2-yl)benzonitrile |

TABLE 1-continued
| Ex. | Structure | TBK1 IC50 | IKKe IC50 | JAK2 IC50 | Name |
|---|---|---|---|---|---|
| 292 | 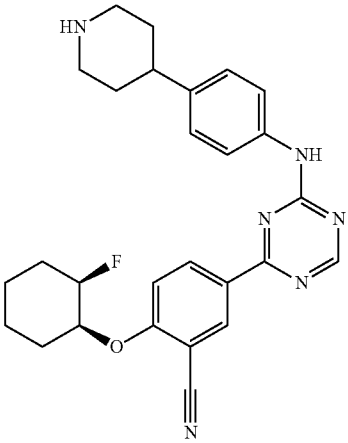 [SMILES: N#Cc1cc(-c2ncnc(Nc3ccc(C4CCNCC4)cc3)n2)ccc1O[C@H]1CCCC[C@H]1F] | 6 | 2 | 415 | rac-2-(((1S,2R)-2-fluorocyclohexyl)oxy)-5-(4-((4-(piperidin-4-yl)phenyl)amino)-1,3,5-triazin-2-yl)benzonitrile |
| 293 | 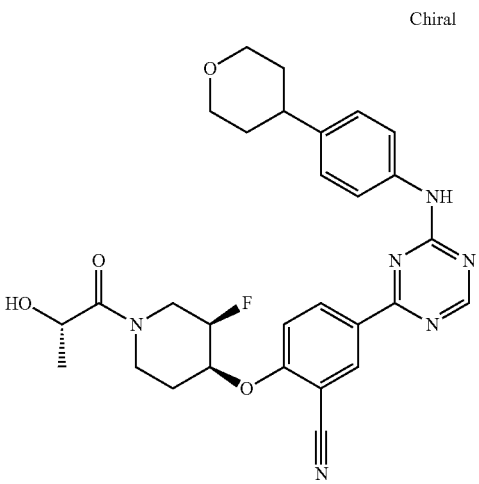 [SMILES: C[C@H](O)C(=O)N1CC[C@H](Oc2ccc(-c3ncnc(Nc4ccc(C5CCOCC5)cc4)n3)cc2C#N)[C@H](F)C1] Chiral | 3 | 2 | 1000 | 2-(((3R,4S)-3-fluoro-1-((S)-2-hydroxypropanoyl)piperidin-4-yl)oxy)-5-(4-((4-(tetrahydro-2H-pyran-4-yl)phenyl)amino)-1,3,5-triazin-2-yl)benzonitrile |
| 294 | 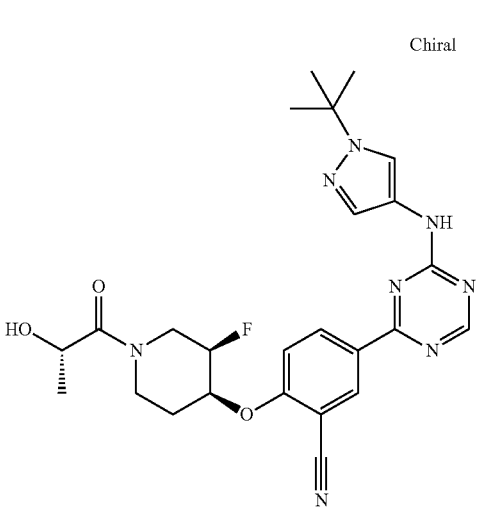 [SMILES: C[C@H](O)C(=O)N1CC[C@H](Oc2ccc(-c3ncnc(Nc4cnn(C(C)(C)C)c4)n3)cc2C#N)[C@H](F)C1] Chiral | 4 | 5 | 228 | 5-(4-((1-(tert-butyl)-1H-pyrazol-4-yl)amino)-1,3,5-triazin-2-yl)-2-(((3R,4S)-3-fluoro-1-((S)-2-hydroxypropanoyl)piperidin-4-yl)oxy)benzonitrile |

TABLE 1-continued

| Ex. | Structure | TBK1 IC50 | IKKe IC50 | JAK2 IC50 | Name |
|---|---|---|---|---|---|
| 295 | 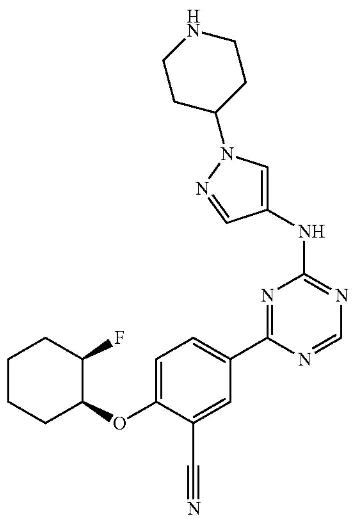 [SMILES: N#Cc1cc(-c2ncnc(Nc3cnn(C4CCNCC4)c3)n2)ccc1O[C@H]1CCCC[C@H]1F] | 24 | 6 | 154 | rac-2-(((1S,2R)-2-fluorocyclohexyl)oxy)-5-(4-((1-(piperidin-4-yl)-1H-pyrazol-4-yl)amino)-1,3,5-triazin-2-yl)benzonitrile |
| 296 | Chiral | 3 | 1 | 274 | 2-(((3R,4S)-3-fluoro-1-formylpiperidin-4-yl)oxy)-5-(4-((3-fluoro-4-(piperazin-1-yl)phenyl)amino)-1,3,5-triazin-2-yl)benzonitrile |
| 297 | Chiral | 2 | 4 | 397 | 2-(((3R,4S)-3-fluorotetrahydro-2H-pyran-4-yl)oxy)-5-(4-((4-(4-(oxetan-3-yl)piperazin-1-yl)phenyl)amino)-1,3,5-triazin-2-yl)benzonitrile |

TABLE 1-continued

| Ex. | Structure | TBK1 IC50 | IKKe IC50 | JAK2 IC50 | Name |
|---|---|---|---|---|---|
| 298 | Chiral | 4 | 1 | 373 | 5-(4-((3-fluoro-4-(piperazin-1-yl)phenyl)amino)-1,3,5-triazin-2-yl)-2-(((3R,4S)-3-fluorotetrahydro-2H-pyran-4-yl)oxy)benzonitrile |
| 299 | Chiral | 4 | 8 | 401 | 5-(4-((3-fluoro-4-(4-formylpiperazin-1-yl)phenyl)amino)-1,3,5-triazin-2-yl)-2-(((3R,4S)-3-fluorotetrahydro-2H-pyran-4-yl)oxy)benzonitrile |
| 300 | Chiral | 4 | 3 | 453 | 2-(((3R,4S)-3-fluorotetrahydro-2H-pyran-4-yl)oxy)-5-(4-((4-(1-methylpiperidin-4-yl)phenyl)amino)-1,3,5-triazin-2-yl)benzonitrile |

TABLE 1-continued

| Ex. | Structure | TBK1 IC50 | IKKe IC50 | JAK2 IC50 | Name |
|---|---|---|---|---|---|
| 301 | Chiral | 3 | 0 | 308 | (S)-2-((1-acetyl-3,3-difluoropiperidin-4-yl)oxy)-5-(4-((4-(piperidin-4-yl)phenyl)amino)-1,3,5-triazin-2-yl)benzonitrile |
| 302 | Chiral | 2 | 0 | 174 | (S)-2-((1-acetyl-3,3-difluoropiperidin-4-yl)oxy)-5-(4-((4-(1-methylpiperidin-4-yl)phenyl)amino)-1,3,5-triazin-2-yl)benzonitrile |
| 303 | Chiral | 1 | 0 | 290 | (S)-2-((3,3-difluoro-1-formylpiperidin-4-yl)oxy)-5-(4-((3-methyl-4-(piperidin-4-yl)phenyl)amino)-1,3,5-triazin-2-yl)benzonitrile |

TABLE 1-continued

| Ex. | Structure | TBK1 IC50 | IKKe IC50 | JAK2 IC50 | Name |
|---|---|---|---|---|---|
| 304 | Chiral | 2 | 0 | 1000 | (S)-2-((3,3-difluoro-1-formylpiperidin-4-yl)oxy)-5-(4-((3-methyl-4-(1-methylpiperidin-4-yl)phenyl)amino)-1,3,5-triazin-2-yl)benzonitrile |
| 305 | 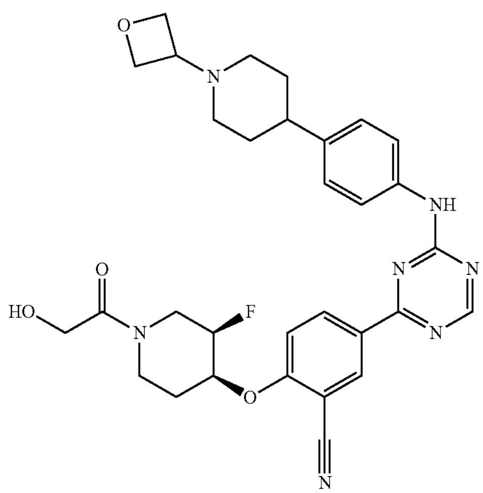 [SMILES: N#Cc1cc(-c2ncnc(Nc3ccc(C4CCN(C5COC5)CC4)cc3)n2)ccc1O[C@H]1CCN(C(=O)CO)C[C@H]1F] | 2 | 0 | 292 | 2-(((3R,4S)-3-fluoro-1-(2-hydroxyacetyl)piperidin-4-yl)oxy)-5-(4-((4-(1-(oxetan-3-yl)piperidin-4-yl)phenyl)amino)-1,3,5-triazin-2-yl)benzonitrile |
| 306 | 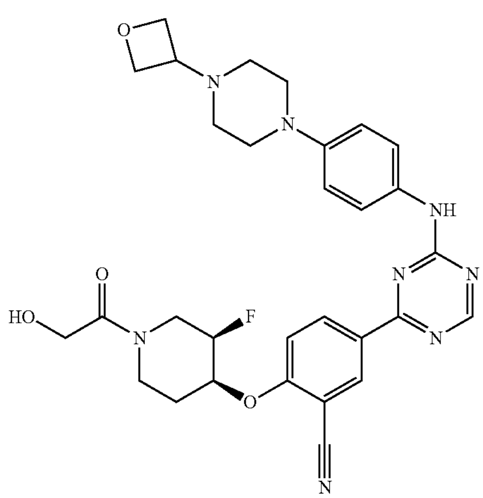 [SMILES: N#Cc1cc(-c2ncnc(Nc3ccc(N4CCN(C5COC5)CC4)cc3)n2)ccc1O[C@H]1CCN(C(=O)CO)C[C@H]1F] | 2 | 0 | 146 | 2-(((3R,4S)-3-fluoro-1-(2-hydroxyacetyl)piperidin-4-yl(oxy)-5-(4-((4-(4-(tetrahydro-2H-pyran-4-yl)piperazin-1-yl)phenyl)amino)-1,3,5-triazin-2-yl)benzonitrile |

TABLE 1-continued

| Ex. | Structure | TBK1 IC50 | IKKe IC50 | JAK2 IC50 | Name |
|---|---|---|---|---|---|
| 307 | 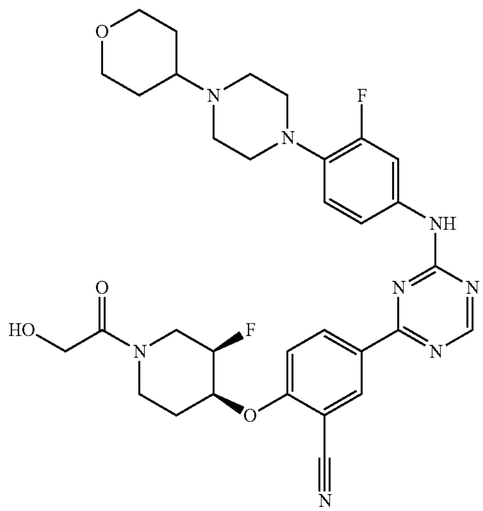 [SMILES: N#Cc1cc(-c2ncnc(Nc3ccc(N4CCN(C5CCOCC5)CC4)c(F)c3)n2)ccc1O[C@H]1CCN(C(=O)CO)C[C@H]1F] | 3 | 1 | 268 | 2-(((3R,4S)-3-fluoro-1-(2-hydroxyacetyl)piperidin-4-yl)oxy)-5-(4-((3-fluoro-4-(4-(tetrahydro-2H-pyran-4-yl)piperazin-1-yl)phenyl)amino)-1,3,5-triazin-2-yl)benzonitrile |
| 308 | 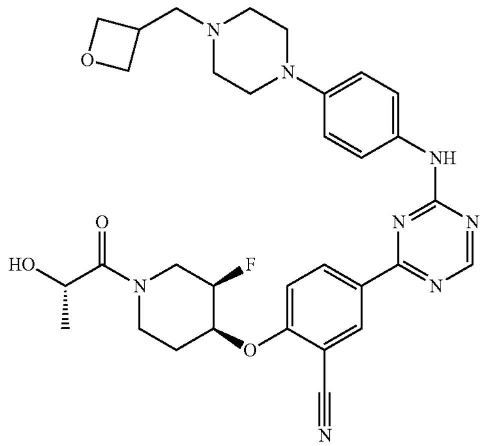 [SMILES: C[C@H](O)C(=O)N1CC[C@H](Oc2ccc(-c3ncnc(Nc4ccc(N5CCN(CC6COC6)CC5)cc4)n3)cc2C#N)[C@H](F)C1] | 2 | 1 | 475 | 2-(((3R,4S)-3-fluoro-1-((S)-2-hydroxypropanoyl)piperidin-4-yl)oxy)-5-(4-((4-(4-(oxetan-3-ylmethyl)piperazin-1-yl)phenyl)amino)-1,3,5-triazin-2-yl)benzonitrile |
| 309 | 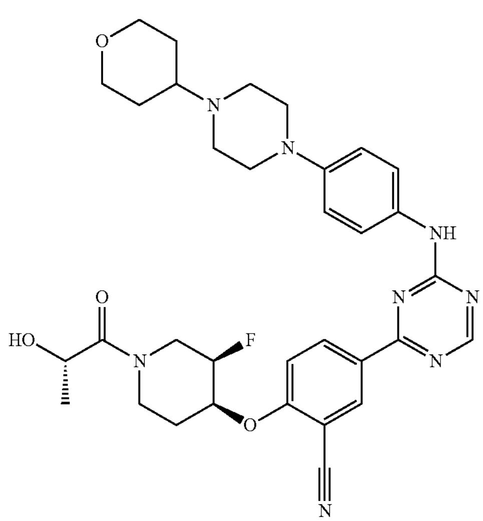 [SMILES: C[C@H](O)C(=O)N1CC[C@H](Oc2ccc(-c3ncnc(Nc4ccc(N5CCN(C6CCOCC6)CC5)cc4)n3)cc2C#N)[C@H](F)C1] | 2 | 1 | 423 | 2-(((3R,4S)-3-fluoro-1-((S)-2-hydroxypropanoyl)piperidin-4-yl)oxy)-5-(4-((4-(4-(tetrahydro-2H-pyran-4-yl)piperazin-1-yl)phenyl)amino)-1,3,5-triazin-2-yl)benzonitrile |

TABLE 1-continued

| Ex. | Structure | TBK1 IC50 | IKKe IC50 | JAK2 IC50 | Name |
|---|---|---|---|---|---|
| 310 | 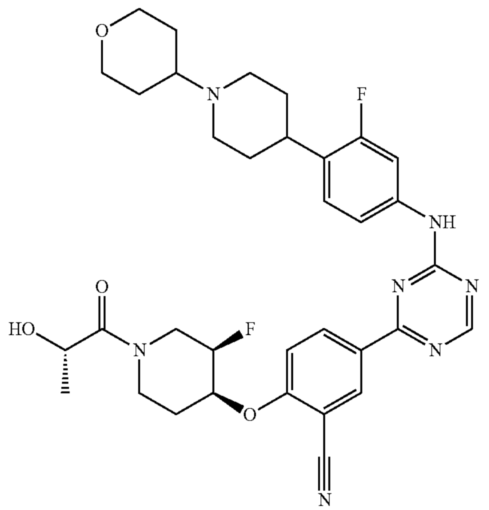 [SMILES: C[C@H](O)C(=O)N1CC[C@H](Oc2ccc(-c3ncnc(Nc4ccc(C5CCN(C6CCOCC6)CC5)c(F)c4)n3)cc2C#N)[C@H](F)C1] | 4 | 2 | 1000 | 2-(((3R,4S)-3-fluoro-1-((S)-2-hydroxypropanoyl)piperidin-4-yl)oxy)-5-(4-((3-fluoro-4-(1-(oxetan-3-yl)piperidin-4-yl)phenyl)amino)-1,3,5-triazin-2-yl)benzonitrile |
| 311 | 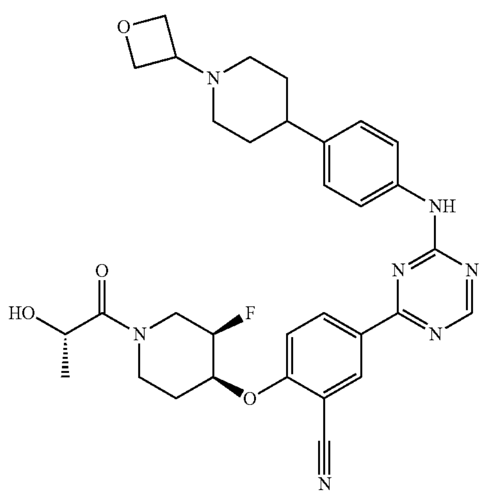 [SMILES: C[C@H](O)C(=O)N1CC[C@H](Oc2ccc(-c3ncnc(Nc4ccc(C5CCN(C6COC6)CC5)cc4)n3)cc2C#N)[C@H](F)C1] | 3 | 1 | 1000 | 2-(((3R,4S)-3-fluoro-1-((S)-2-hydroxypropanoyl)piperidin-4-yl)oxy)-5-(4-((4-(1-(oxetan-3-yl)piperidin-4-yl)phenyl)amino)-1,3,5-triazin-2-yl)benzonitrile |
| 312 | 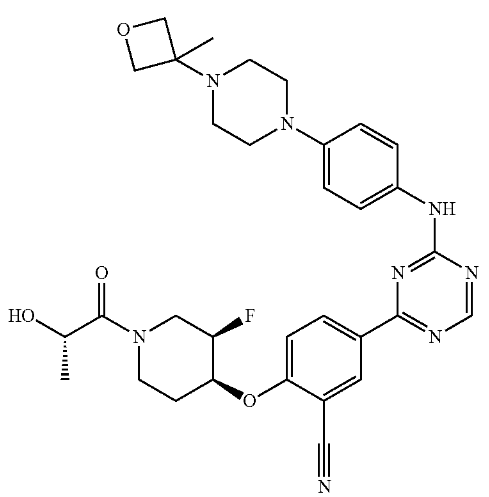 [SMILES: C[C@H](O)C(=O)N1CC[C@H](Oc2ccc(-c3ncnc(Nc4ccc(N5CCN(C6(C)COC6)CC5)cc4)n3)cc2C#N)[C@H](F)C1] | 3 | 3 | 636 | 2-(((3R,4S)-3-fluoro-1-((S)-2-hydroxypropanoyl)piperidin-4-yl)oxy)-5-(4-((4-(4-(3-methyloxetan-3-yl)piperazin-1-yl)phenyl)amino)-1,3,5-triazin-2-yl)benzonitrile |

| Ex. | Structure | TBK1 IC50 | IKKe IC50 | JAK2 IC50 | Name |
|---|---|---|---|---|---|
| 313 | 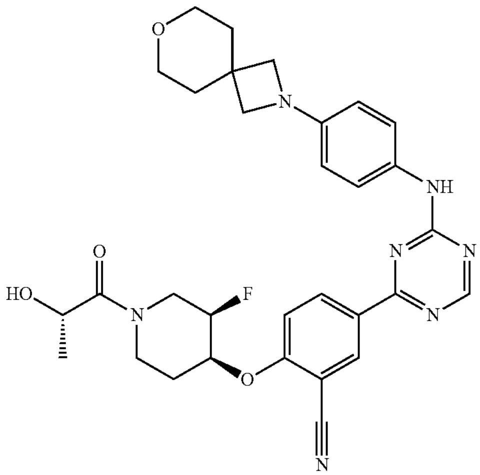 [SMILES: C[C@H](O)C(=O)N1CC[C@H](Oc2ccc(-c3ncnc(Nc4ccc(N5CC6(CCOCC6)C5)cc4)n3)cc2C#N)[C@H](F)C1] | 4 | 2 | 375 | 5-(4-((4-(7-oxa-2-azaspiro[3.5]nonan-2-yl)phenyl)amino)-1,3,5-triazin-2-yl)-2-(((3R,4S)-3-fluoro-1-((S)-2-hydroxypropanoyl)piperidin-4-yl)oxy)benzonitrile |
| 314 | 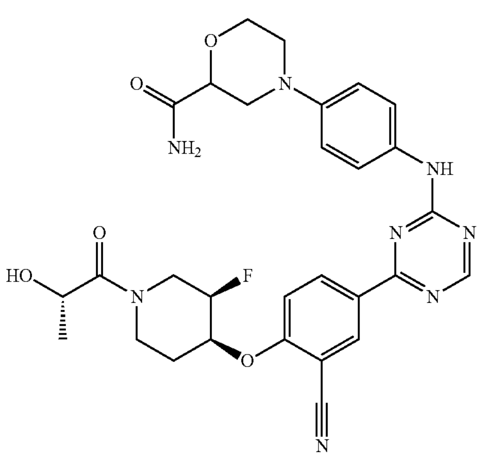 [SMILES: C[C@H](O)C(=O)N1CC[C@H](Oc2ccc(-c3ncnc(Nc4ccc(N5CCOC(C(N)=O)C5)cc4)n3)cc2C#N)[C@H](F)C1] | 3 | 1 | 609 | 4-(4-((4-(3-cyano-4-(((3R,4S)-3-fluoro-1-((S)-2-hydroxypropanoyl)piperidin-4-yl)oxy)phenyl)-1,3,5-triazin-2-yl)amino)phenyl)morpholine-2-carboxamide |
| 315 | 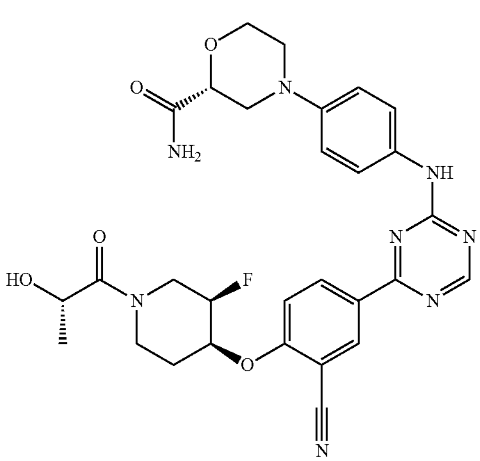 [SMILES: C[C@H](O)C(=O)N1CC[C@H](Oc2ccc(-c3ncnc(Nc4ccc(N5CCO[C@@H](C(N)=O)C5)cc4)n3)cc2C#N)[C@H](F)C1] | 9 | 3 | 564 | (R)-4-(4-((4-(3-cyano-4-(((3R,4S)-3-fluoro-1-((S)-2-hydroxypropanoyl)piperidin-4-yl)oxy)phenyl)-1,3,5-triazin-2-yl)amino)phenyl)morpholine-2-carboxamide |

TABLE 1-continued

| Ex. | Structure | TBK1 IC50 | IKKe IC50 | JAK2 IC50 | Name |
|---|---|---|---|---|---|
| 316 | 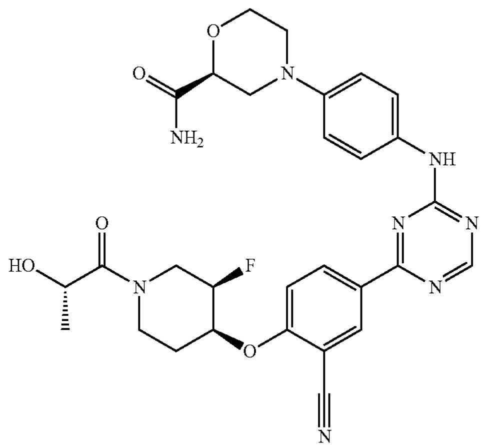 [SMILES: C[C@H](O)C(=O)N1CC[C@H](Oc2ccc(-c3ncnc(Nc4ccc(N5CCO[C@H](C(N)=O)C5)cc4)n3)cc2C#N)[C@H](F)C1] | 3 | 2 | 347 | (S)-4-(4-((4-(3-cyano-4-(((3R,4S)-3-fluoro-1-((S)-2-hydroxypropanoyl)piperidin-4-yl)oxy)phenyl)-1,3,5-triazin-2-yl)amino)phenyl)morpholine-2-carboxamide |
| 317 | 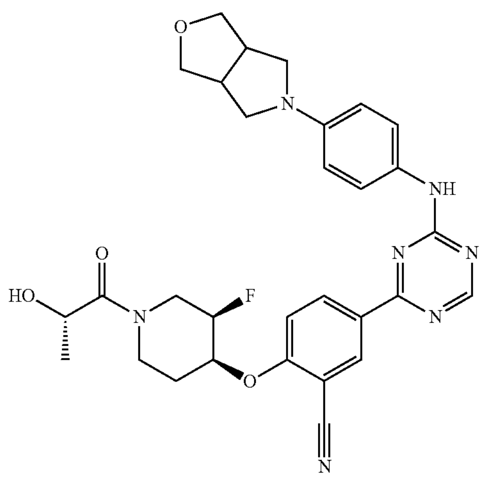 [SMILES: C[C@H](O)C(=O)N1CC[C@H](Oc2ccc(-c3ncnc(Nc4ccc(N5CC6COCC6C5)cc4)n3)cc2C#N)[C@H](F)C1] | 2 | 1 | 1000 | 2-(((3R,4S)-3-fluoro-1-((S)-2-hydroxypropanoyl)piperidin-4-yl)oxy)-5-(4-((4-(tetrahydro-1H-furo[3,4-c]pyrrol-5(3H)-yl)phenyl)amino)-1,3,5-triazin-2-yl)benzonitrile |
| 318 | 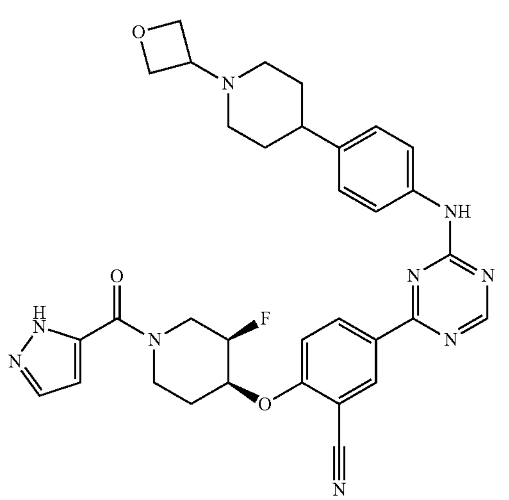 [SMILES: N#Cc1cc(-c2ncnc(Nc3ccc(C4CCN(C5COC5)CC4)cc3)n2)ccc1O[C@H]1CCN(C(=O)c2ccn[nH]2)C[C@H]1F] | 2 | 1 | 1000 | 2-(((3R,4S)-3-fluoro-1-(1H-pyrazole-5-carbonyl)piperidin-4-yl)oxy)-5-(4-((4-(1-(oxetan-3-yl)piperidin-4-yl)phenyl)amino)-1,3,5-triazin-2-yl)benzonitrile |

TABLE 1-continued

| Ex. | Structure | TBK1 IC50 | IKKe IC50 | JAK2 IC50 | Name |
|---|---|---|---|---|---|
| 319 | 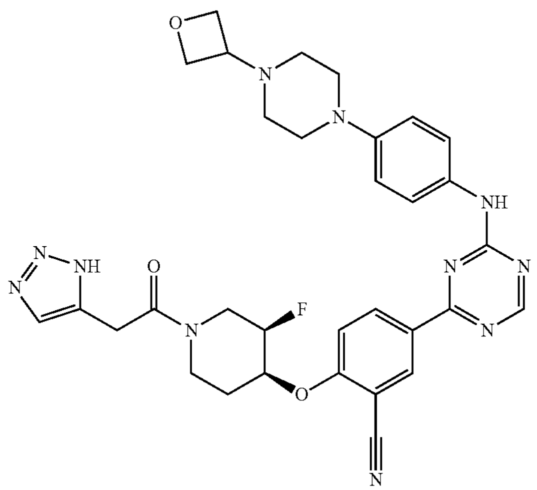 [SMILES: N#Cc1cc(-c2ncnc(Nc3ccc(N4CCN(C5COC5)CC4)cc3)n2)ccc1O[C@H]1CCN(C(=O)Cc2cnn[nH]2)C[C@H]1F] | 4 | 7 | 102 | 2-(((3R,4S)-1-(2-(1H-1,2,3-triazol-5-yl)acetyl)-3-fluoropiperidin-4-yl)oxy)-5-(4-((4-(4-(oxetan-3-yl)piperazin-1-yl)phenyl)amino)-1,3,5-triazin-2-yl)benzonitrile |
| 320 | 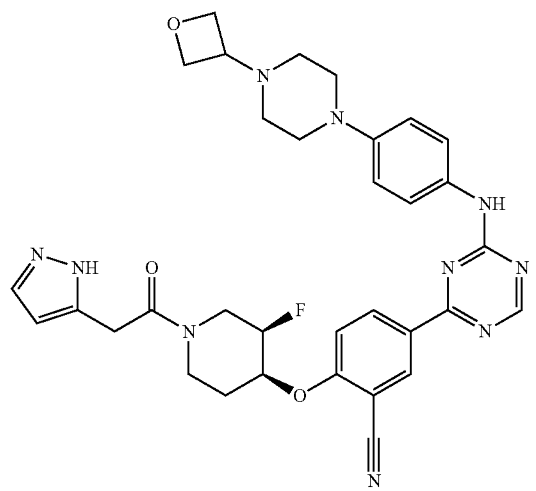 [SMILES: N#Cc1cc(-c2ncnc(Nc3ccc(N4CCN(C5COC5)CC4)cc3)n2)ccc1O[C@H]1CCN(C(=O)Cc2ccn[nH]2)C[C@H]1F] | 14 | 40 | 127 | 2-(((3R,4S)-1-(2-(1H-pyrazol-5-yl)acetyl)-3-fluoropiperidin-4-yl)oxy)-5-(4-((4-(4-(oxetan-3-yl)piperazin-1-yl)phenyl)amino)-1,3,5-triazin-2-yl)benzonitrile |
| 321 | 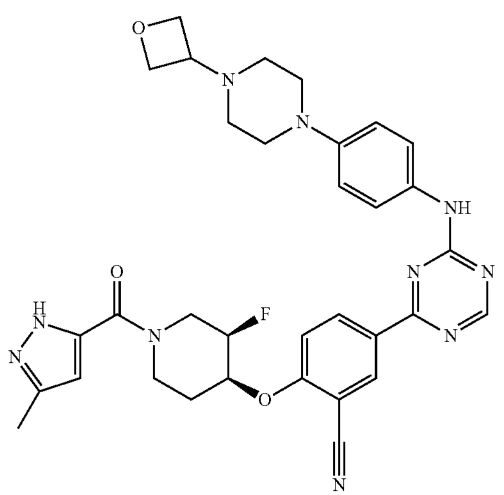 [SMILES: Cc1cc(C(=O)N2CC[C@H](Oc3ccc(-c4ncnc(Nc5ccc(N6CCN(C7COC7)CC6)cc5)n4)cc3C#N)[C@H](F)C2)[nH]n1] | 3 | 2 | 164 | 2-(((3R,4S)-3-fluoro-1-(3-methyl-1H-pyrazole-5-carbonyl)piperidin-4-yl)oxy)-5-((4-(4-(oxetan-3-yl)piperazin-1-yl)phenyl)amino)-1,3,5-triazin-2-yl)benzonitrile |

TABLE 1-continued

| Ex. | Structure | TBK1 IC50 | IKKe IC50 | JAK2 IC50 | Name |
|---|---|---|---|---|---|
| 322 | 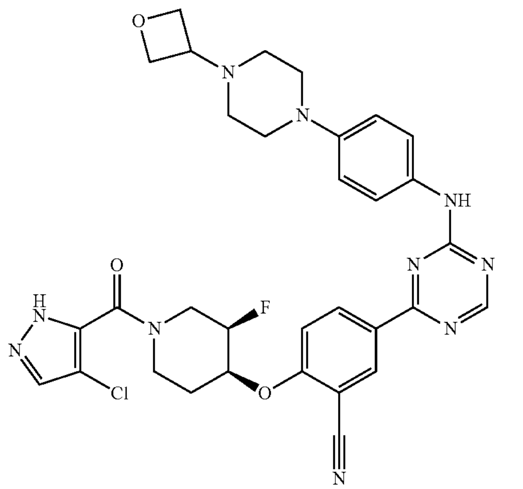 [SMILES: N#Cc1cc(-c2ncnc(Nc3ccc(N4CCN(C5COC5)CC4)cc3)n2)ccc1O[C@H]1CCN(C(=O)c2[nH]ncc2Cl)C[C@H]1F] | 5 | 8 | 192 | 2-(((3R,4S)-1-(4-chloro-1H-pyrazole-5-carbonyl)-3-fluoropiperidin-4-yl)oxy)-5-(4-((4-(4-(oxetan-3-yl)piperazin-1-yl)phenyl)amino)-1,3,5-triazin-2-yl)benzonitrile |
| 323 | 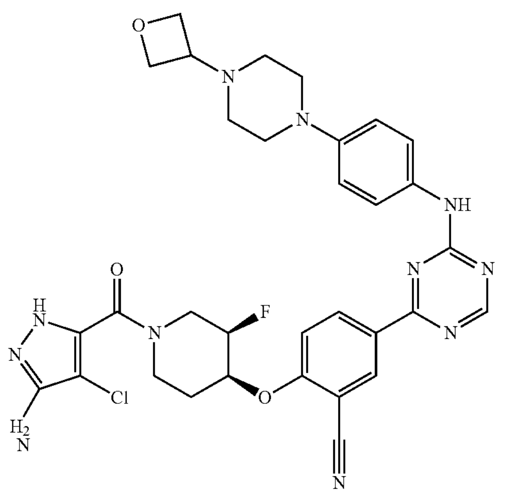 [SMILES: N#Cc1cc(-c2ncnc(Nc3ccc(N4CCN(C5COC5)CC4)cc3)n2)ccc1O[C@H]1CCN(C(=O)c2[nH]nc(N)c2Cl)C[C@H]1F] | 3 | 3 | 75 | 2-(((3R,4S)-1-(3-amino-4-chloro-1H-pyrazole-5-carbonyl)-3-fluoropiperidin-4-yl)oxy)-5-(4-((4-(4-(oxetan-3-yl)piperazin-1-yl)phenyl)amino)-1,3,5-triazin-2-yl)benzonitrile |
| 324 | 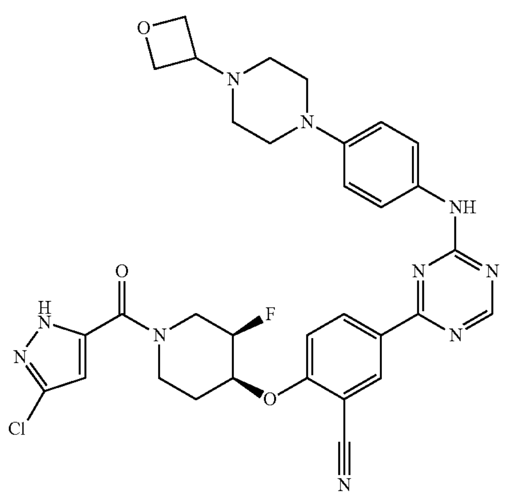 [SMILES: N#Cc1cc(-c2ncnc(Nc3ccc(N4CCN(C5COC5)CC4)cc3)n2)ccc1O[C@H]1CCN(C(=O)c2cc(Cl)n[nH]2)C[C@H]1F] | 4 | 4 | 237 | 2-(((3R,4S)-1-(3-chloro-1H-pyrazole-5-carbonyl)-3-fluoropiperidin-4-yl)oxy)-5-(4-((4-(4-(oxetan-3-yl)piperazin-1-yl)phenyl)amino)-1,3,5-triazin-2-yl)benzonitrile |

TABLE 1-continued

| Ex. | Structure | TBK1 IC50 | IKKe IC50 | JAK2 IC50 | Name |
|---|---|---|---|---|---|
| 325 | 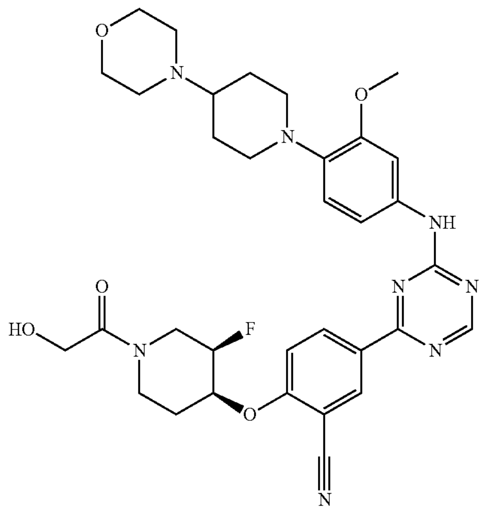 [SMILES: COc1cc(Nc2ncnc(-c3ccc(O[C@H]4CCN(C(=O)CO)C[C@H]4F)c(C#N)c3)n2)ccc1N1CCC(N2CCOCC2)CC1] | 2 | 0 | 28 | 2-(((3R,4S)-3-fluoro-1-(2-hydroxyacetyl)piperidin-4-yl)oxy)-5-(4-((3-methoxy-4-(4-morpholinopiperidin-1-yl)phenyl)amino)-1,3,5-triazin-2-yl)benzonitrile |
| 326 | 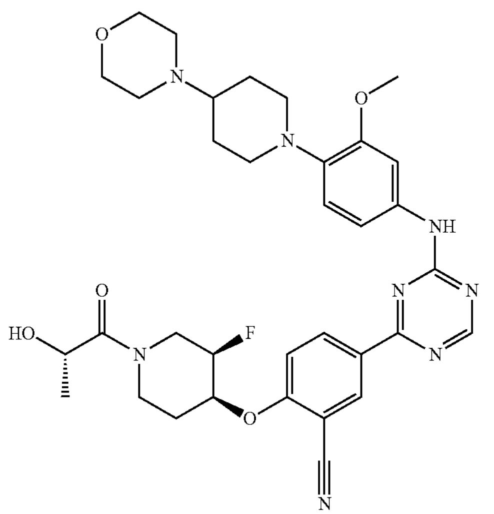 [SMILES: COc1cc(Nc2ncnc(-c3ccc(O[C@H]4CCN(C(=O)[C@H](C)O)C[C@H]4F)c(C#N)c3)n2)ccc1N1CCC(N2CCOCC2)CC1] | 2 | 1 | 72 | 2-(((3R,4S)-3-fluoro-1-((S)-2-hydroxypropanoyl)piperidin-4-yl)oxy)-5-(4-((3-methoxy-4-(4-morpholinopiperidin-1-yl)phenyl)amino)-1,3,5-triazin-2-yl)benzonitrile |
| 327 | 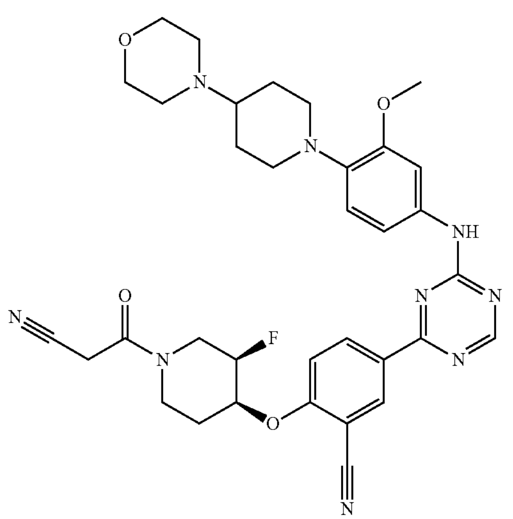 [SMILES: COc1cc(Nc2ncnc(-c3ccc(O[C@H]4CCN(C(=O)CC#N)C[C@H]4F)c(C#N)c3)n2)ccc1N1CCC(N2CCOCC2)CC1] | 4 | 2 | 62 | 2-(((3R,4S)-1-(2-cyanoacetyl)-3-fluoropiperidin-4-yl)oxy)-5-(4-((3-methoxy-4-(4-morpholinopiperidin-1-yl)phenyl)amino)-1,3,5-triazin-2-yl)benzonitrile |

TABLE 1-continued

| Ex. | Structure | TBK1 IC50 | IKKe IC50 | JAK2 IC50 | Name |
|---|---|---|---|---|---|
| 328 | 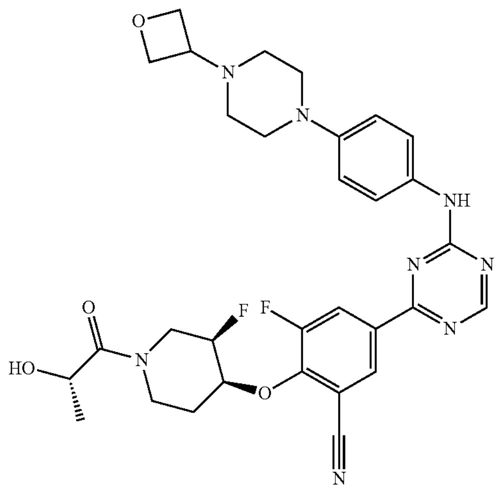 | 4 | 4 | 1000 | 3-fluoro-2-(((3R,4S)-3-fluoro-1-((S)-2-hydroxypropanoyl)piperidin-4-yl)oxy)-5-(4-((4-(4-(oxetan-3-yl)piperazin-1-yl)phenyl)amino)-1,3,5-triazin-2-yl)benzonitrile |
| 329 | 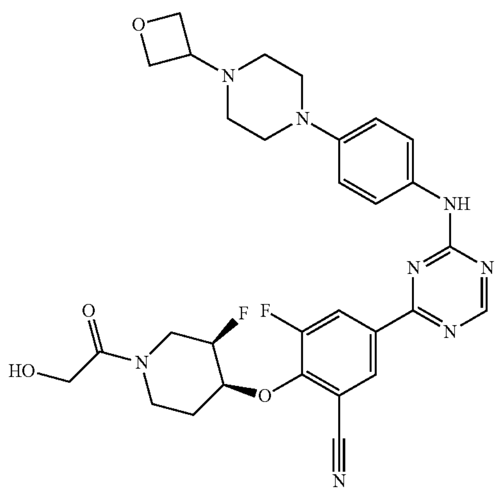 | 4 | 3 | 648 | 3-fluoro-2-(((3R,4S)-3-fluoro-1-(2-hydroxyacetyl)piperidin-4-yl)oxy)-5-(4-((4-(4-(oxetan-3-yl)piperazin-1-yl)phenyl)amino)-1,3,5-triazin-2-yl)benzonitrile |
| 330 | 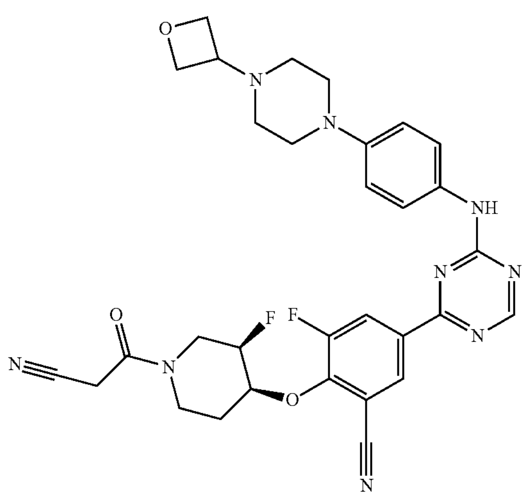 [SMILES: N#CCC(=O)N1CC[C@H](Oc2c(F)cc(-c3ncnc(Nc4ccc(N5CCN(C6COC6)CC5)cc4)n3)cc2C#N)[C@H](F)C1] | 4 | 6 | 941 | 2-(((3R,4S)-1-(2-cyanoacetyl)-3-fluoropiperidin-4-yl)oxy)-3-fluoro-5-(4-((4-(4-(oxetan-3-yl)piperazin-1-yl)phenyl)amino)-1,3,5-triazin-2-yl)benzonitrile |

TABLE 1-continued

| Ex. | Structure | TBK1 IC50 | IKKe IC50 | JAK2 IC50 | Name |
|---|---|---|---|---|---|
| 331 | 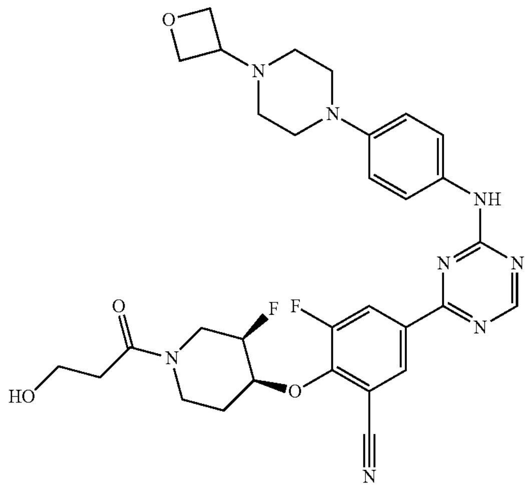 [SMILES: N#Cc1cc(-c2ncnc(Nc3ccc(N4CCN(C5COC5)CC4)cc3)n2)cc(F)c1O[C@H]1CCN(C(=O)CCO)C[C@H]1F] | 7 | 14 | 943 | 3-fluoro-2-(((3R,4S)-3-fluoro-1-(3-hydroxypropanoyl)piperidin-4-yl)oxy)-5-(4-((4-(4-(oxetan-3-yl)piperazin-1-yl)phenyl)amino)-1,3,5-triazin-2-yl)benzonitrile |
| 332 | 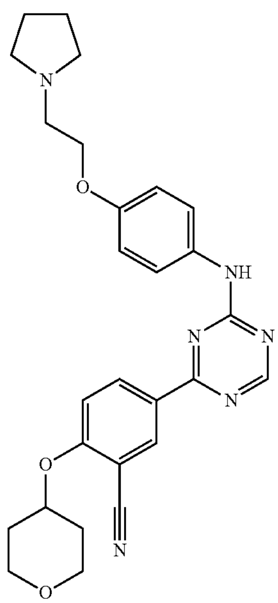 [SMILES: N#Cc1cc(-c2ncnc(Nc3ccc(OCCN4CCCC4)cc3)n2)ccc1OC1CCOCC1] | 10 | 5 | 943 | 5-(4-((4-(2-(pyrrolidin-1-yl)ethoxy)phenyl)amino)-1,3,5-triazin-2-yl)-2-((tetrahydro-2H-pyran-4-yl)oxy)benzonitrile |
| 333 | 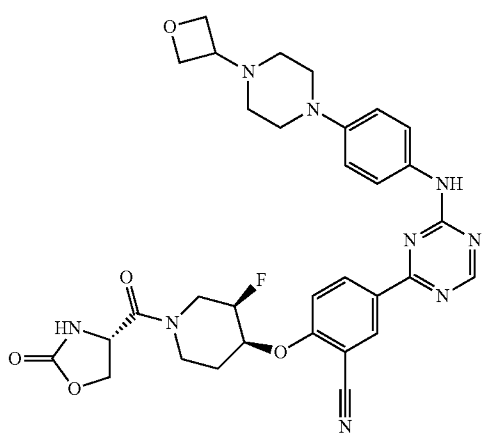 [SMILES: N#Cc1cc(-c2ncnc(Nc3ccc(N4CCN(C5COC5)CC4)cc3)n2)ccc1O[C@H]1CCN(C(=O)[C@@H]2COC(=O)N2)C[C@H]1F] | 2 | 3 | 233 | 2-(((3R,4S)-3-fluoro-1-((S)-2-oxooxazolidine-4-carbonyl)piperidin-4-yl)oxy)-5-(4-((4-(4-(oxetan-3-yl)piperazin-1-yl)phenyl)amino)-1,3,5-triazin-2-yl)benzonitrile |

TABLE 1-continued

| Ex. | Structure | TBK1 IC50 | IKKe IC50 | JAK2 IC50 | Name |
|---|---|---|---|---|---|
| 334 | 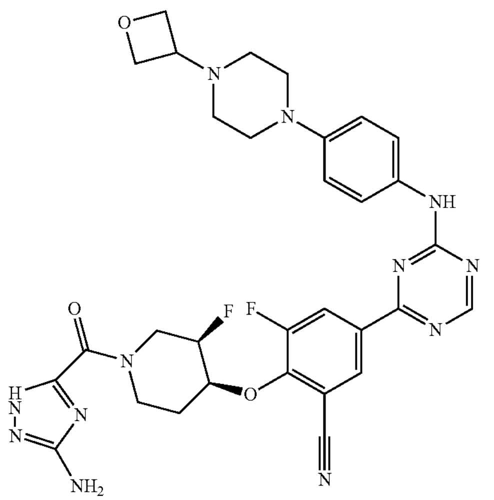 [SMILES: N#Cc1cc(-c2ncnc(Nc3ccc(N4CCN(C5COC5)CC4)cc3)n2)cc(F)c1O[C@H]1CCN(C(=O)c2nc(N)n[nH]2)C[C@H]1F] | 16 | 2 | 80 | 2-(((3R,4S)-1-(3-amino-1H-1,2,4-triazole-5-carbonyl)-3-fluoropiperidin-4-yl)oxy)-5-(4-((4-(4-(oxetan-3-yl)piperazin-1-yl)phenyl)amino)-1,3,5-triazin-2-yl)benzonitrile |
| 335 | 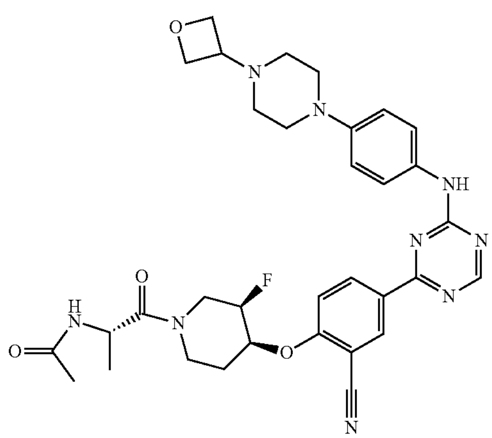 [SMILES: CC(=O)N[C@@H](C)C(=O)N1CC[C@H](Oc2ccc(-c3ncnc(Nc4ccc(N5CCN(C6COC6)CC5)cc4)n3)cc2C#N)[C@H](F)C1] | 508 | 834 | 478 | N-((S)-1-((3R,4S)-4-(2-cyano-4-(4-((4-(4-(oxetan-3-yl)piperazin-1-yl)phenyl)amino)-1,3,5-triazin-2-yl)phenoxy)-3-fluoropiperidin-1-yl)-1-oxopropan-2-yl)acetamide |
| 336 | 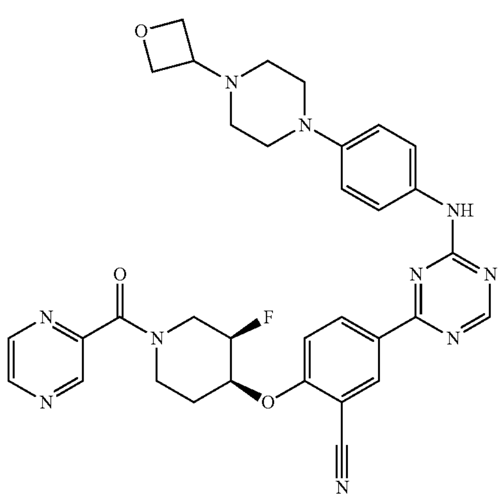 [SMILES: N#Cc1cc(-c2ncnc(Nc3ccc(N4CCN(C5COC5)CC4)cc3)n2)ccc1O[C@H]1CCN(C(=O)c2cnccn2)C[C@H]1F] | 2 | 2 | 882 | 2-(((3R,4S)-3-fluoro-1-(pyrazine-2-carbonyl)piperidin-4-yl)oxy)-5-(4-((4-(4-(oxetan-3-yl)piperazin-1-yl)phenyl)amino)-1,3,5-triazin-2-0benzonitrile |

TABLE 1-continued

| Ex. | Structure | TBK1 IC50 | IKKe IC50 | JAK2 IC50 | Name |
|---|---|---|---|---|---|
| 337 | 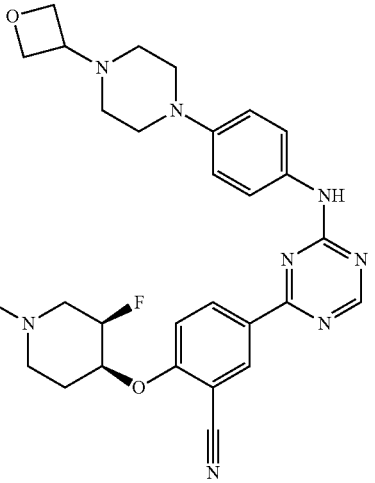 | 4 | 7 | 572 | 2-(((3R,4S)-3-fluoro-1-(pyrimidine-4-carbonyl)piperidin-4-yl)oxy)-5-(4-((4-(4-(oxetan-3-yl)piperazin-1-yl)phenyl)amino)-1,3,5-triazin-2-yl)benzonitrile |
| 338 | 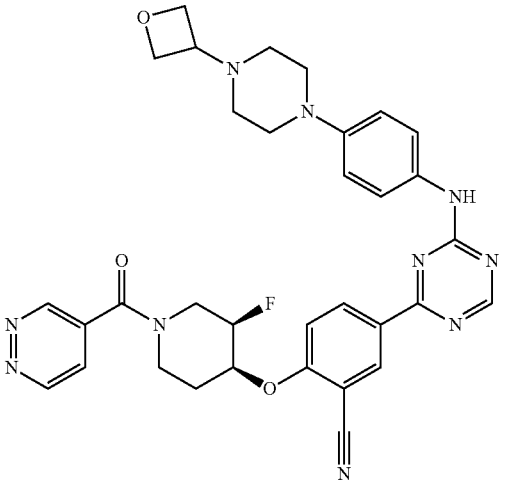 [SMILES: N#Cc1cc(-c2ncnc(Nc3ccc(N4CCN(C5COC5)CC4)cc3)n2)ccc1O[C@H]1CCN(C(=O)c2ccnnc2)C[C@H]1F] | 9 | 18 | 131 | 2-(((3R,4S)-3-fluoro-1-(pyridazine-4-carbonyl)piperidin-4-yl)oxy)-5-(4-((4-(4-(oxetan-3-yl)piperazin-1-yl)phenyl)amino)-1,3,5-triazin-2-yl)benzonitrile |
| 339 | 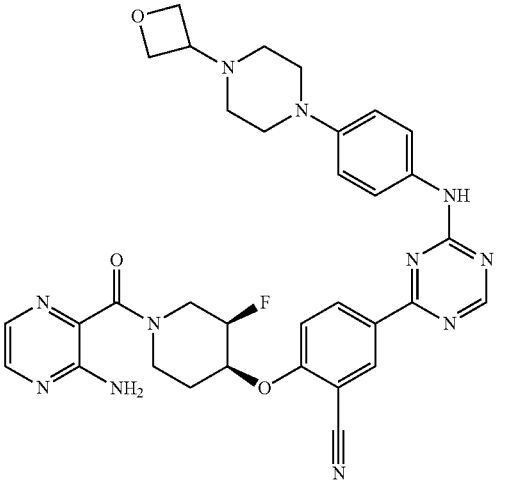 [SMILES: N#Cc1cc(-c2ncnc(Nc3ccc(N4CCN(C5COC5)CC4)cc3)n2)ccc1O[C@H]1CCN(C(=O)c2nccnc2N)C[C@H]1F] | 14 | 58 | 54 | 2-(((3R,4S)-1-(3-aminopyrazine-2-carbonyl)-3-fluoropiperidin-4-yl)oxy)-5-(4-((4-(4-(oxetan-3-yl)piperazin-1-yl)phenyl)amino)-1,3,5-triazin-2-yl)benzonitrile |

TABLE 1-continued

| Ex. | Structure | TBK1 IC50 | IKKe IC50 | JAK2 IC50 | Name |
|---|---|---|---|---|---|
| 340 | 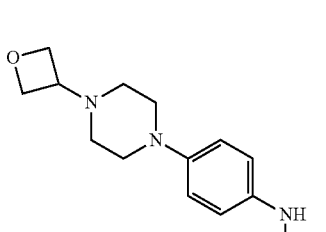 | 4 | 9 | 122 | 2-(((3R,4S)-1-(6-aminopyrazine-2-carbonyl)-3-fluoropiperidin-4-yl)oxy)-5-(4-((4-(4-(oxetan-3-yl)piperazin-1-yl)phenyl)amino)-1,3,5-triazin-2-yl)benzonitrile |
| 341 | 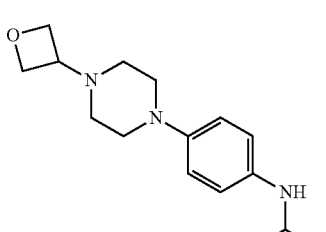 | 2 | 1 | 153 | 2-(((3R,4S)-1-(5-aminopyrazine-2-carbonyl)-3-fluoropiperidin-4-yl)oxy)-5-(4-((4-(4-(oxetan-3-yl)piperazin-1-yl)phenyl)amino)-1,3,5-triazin-2-yl)benzonitrile |
| 342 | 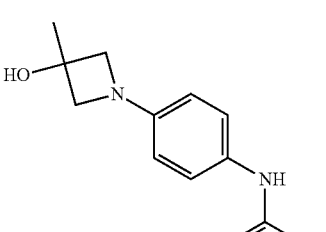 | 2 | 1 | 496 | 2-(((3R,4S)-3-fluoro-1-((S)-2-hydroxypropanoyl)piperidin-4-yl)oxy)-5-(4-((4-(3-hydroxy-3-methylazetidin-1-yl)phenyl)amino)-1,3,5-triazin-2-yl)benzonitrile |

TABLE 1-continued

| Ex. | Structure | TBK1 IC50 | IKKe IC50 | JAK2 IC50 | Name |
|---|---|---|---|---|---|
| 343 | 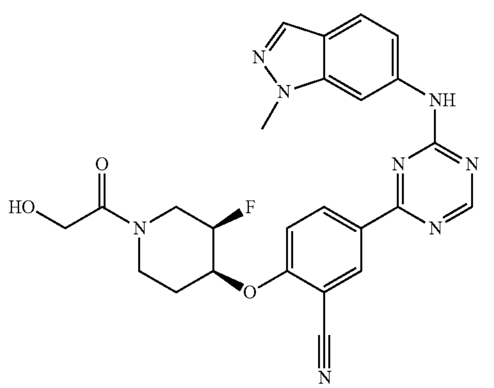 [SMILES: Cn1ncc2ccc(Nc3ncnc(-c4ccc(O[C@H]5CCN(C(=O)CO)C[C@H]5F)c(C#N)c4)n3)cc21] | 4 | 2 | 258 | 2-(((3R,4S)-3-fluoro-1-(2-hydroxyacetyl)piperidin-4-yl)oxy)-5-(4-((1-methyl-1H-insazol-6-yl)amino)-1,3,5-triazin-2-yl)benzonitrile |
| 344 | 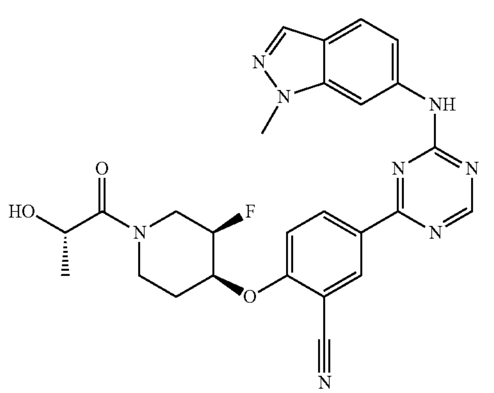 [SMILES: C[C@H](O)C(=O)N1CC[C@H](Oc2ccc(-c3ncnc(Nc4ccc5cnn(C)c5c4)n3)cc2C#N)[C@H](F)C1] | 7 | 5 | 707 | 2-(((3R,4S)-3-fluoro-1-((S)-2-hydroxypropanoyl)piperidin-4-yl)oxy)-5-(4-((1-methyl-1H-indazol-6-yl)amino)-1,3,5-triazin-2-yl)benzonitrile |
| 345 | 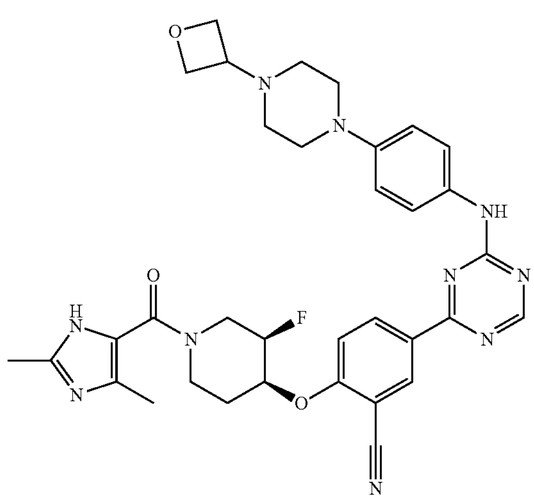 [SMILES: Cc1nc(C)c(C(=O)N2CC[C@H](Oc3ccc(-c4ncnc(Nc5ccc(N6CCN(C7COC7)CC6)cc5)n4)cc3C#N)[C@H](F)C2)[nH]1] | 10 | 12 | 213 | 2-(((3R,4S)-1-(2,4-dimethyl-1H-imidazole-5-carbonyl)-3-fluoropiperidin-4-yl)oxy)-5-(4-((4-(4-(oxetan-3-yl)piperazin-1-yl)phenyl)amino)-1,3,5-triazin-2-yl)benzonitrile |

TABLE 1-continued

| Ex. | Structure | TBK1 IC50 | IKKe IC50 | JAK2 IC50 | Name |
|---|---|---|---|---|---|
| 346 | 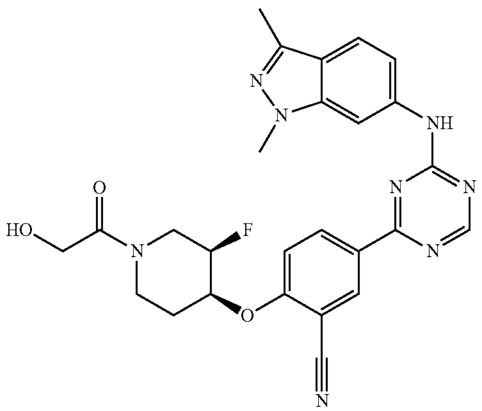 [SMILES: Cc1nn(C)c2cc(Nc3ncnc(-c4ccc(O[C@H]5CCN(C(=O)CO)C[C@H]5F)c(C#N)c4)n3)ccc12] | 3 | 1 | 511 | 5-(4-((1,3-dimethyl-1H-indazol-6-yl)amino)-1,3,5-triazin-2-yl)-2-(((3R,4S)-3-fluro-1-2-hydroxyacetyl)piperidin-4-yl)oxy)benzonitrile |
| 347 | 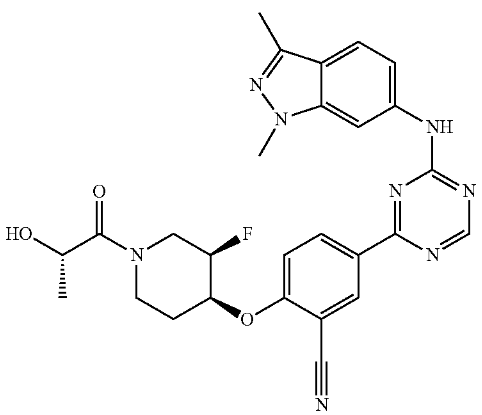 [SMILES: Cc1nn(C)c2cc(Nc3ncnc(-c4ccc(O[C@H]5CCN(C(=O)[C@H](C)O)C[C@H]5F)c(C#N)c4)n3)ccc12] | 4 | 5 | 1000 | 5-(4-((1,3-dimethyl-1H-indazol-6-yl)amino)-1,3,5-triazin-2-yl)-2-(((3R,4S)-3-fluoro-1-((S)-2-hydroxypropanoyl)piperidin-4-yl)oxy)benzonitrile |
| 348 | 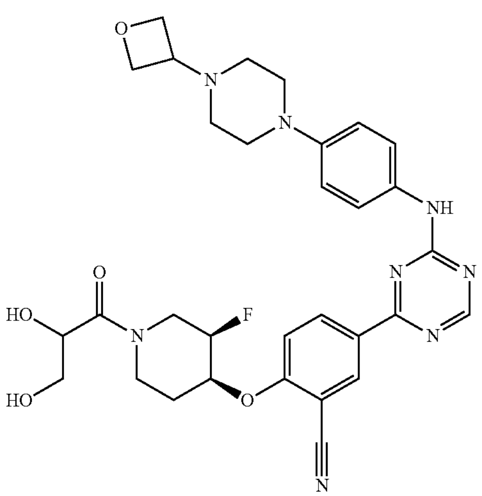 [SMILES: N#Cc1cc(-c2ncnc(Nc3ccc(N4CCN(C5COC5)CC4)cc3)n2)ccc1O[C@H]1CCN(C(=O)C(O)CO)C[C@H]1F] | 4 | 3 | 162 | 2-(((3R,4S)-1-(2,3-dihydroxypropanoyl)-3-fluoropiperidin-4-yl)oxy)-5-(4-((4-(4-(oxetan-3-yl)piperazin-1-yl)phenyl)amino)-1,3,5-triazin-2-yl)benzonitrile |

TABLE 1-continued

| Ex. | Structure | TBK1 IC50 | IKKe IC50 | JAK2 IC50 | Name |
|---|---|---|---|---|---|
| 349 | 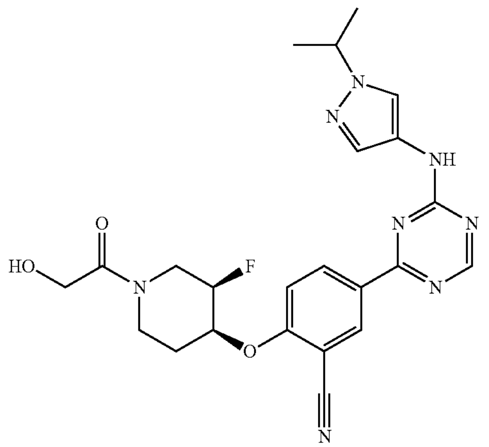 [SMILES: CC(C)n1cc(Nc2ncnc(-c3ccc(O[C@H]4CCN(C(=O)CO)C[C@H]4F)c(C#N)c3)n2)cn1] | 2 | 2 | 98 | 2-(((3R,4S)-3-fluoro-1-(2-hydroxyacetyl)piperidin-4-yl)oxy)-5-(4-((1-isopropyl-1H-pyrazol-4-yl)amino)-1,3,5-triazin-2-yl)benzonitrile |
| 350 | 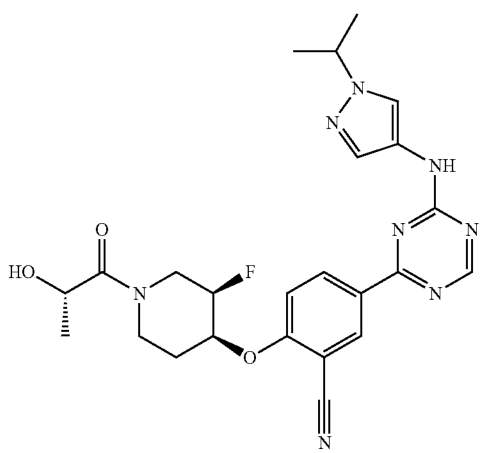 [SMILES: CC(C)n1cc(Nc2ncnc(-c3ccc(O[C@H]4CCN(C(=O)[C@H](C)O)C[C@H]4F)c(C#N)c3)n2)cn1] | 3 | 5 | 231 | 2-(((3R,4S)-3-fluoro-1-((S)-2-hydroxypropanoyl)piperidin-4-yl)oxy)-5-(4-((1-isopropyl-1H-pyrazol-4-yl)amino)-1,3,5-triazin-2-yl)benzonitrile |
| 351 | 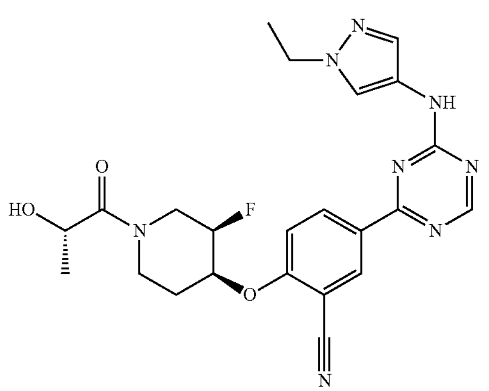 [SMILES: CCn1cc(Nc2ncnc(-c3ccc(O[C@H]4CCN(C(=O)[C@H](C)O)C[C@H]4F)c(C#N)c3)n2)cn1] | 6 | 9 | 662 | 5-(4-((1-ethyl-1H-pyrazol-4-yl)amino)-1,3,5-triazin-2-yl)-2-(((3R,4S)-3-fluoro-1-((S)-2-hydroxypropanoyl)piperidin-4-yl)oxy)benzonitrile |

TABLE 1-continued

| Ex. | Structure | TBK1 IC50 | IKKe IC50 | JAK2 IC50 | Name |
|---|---|---|---|---|---|
| 352 | 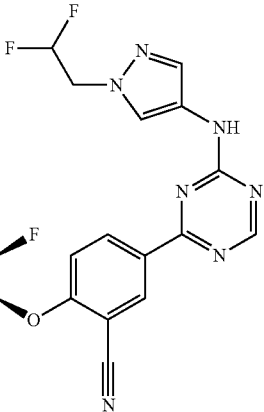 | 4 | 4 | 1000 | 5-(4-((1-(2,2-difluoroethyl)-1H-pyrazol-4-yl)amino)-1,3,5-triazin-2-yl)-2-(((3R,4S)-3-fluoro-1-((S)-2-hydroxypropanoyl)piperidin-4-yl)oxy)benzonitrile |
| 353 | 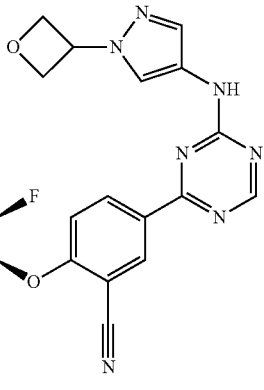 | 7 | 10 | 944 | 2-(((3R,4S)-3-fluoro-1-((S)-2-hydroxypropanoyl)piperidin-4-yl)oxy)-5-(4-((1-(oxetan-3-yl)-1H-pyrazol-4-yl)amino)-1,3,5-triazin-2-yl)benzonitrile |
| 354 | 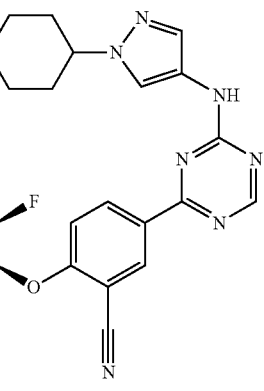 | 6 | 5 | 309 | 2-(((3R,4S)-3-fluoro-1-((S)-2-hydroxypropanoyl)piperidin-4-yl)oxy)-5-(4-((1-(tetrahydro-2H-pyran-4-yl)-1H-pyrazol-4-yl)amino)-1,3,5-triazin-2-yl)benzonitrile |

TABLE 1-continued

| Ex. | Structure | TBK1 IC50 | IKKe IC50 | JAK2 IC50 | Name |
|---|---|---|---|---|---|
| 355 | 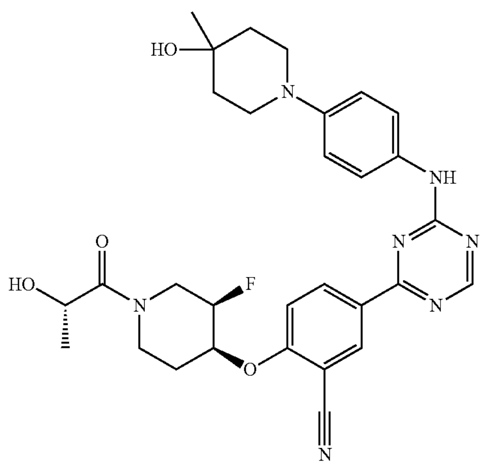 [SMILES: C[C@H](O)C(=O)N1CC[C@H](Oc2ccc(-c3ncnc(Nc4ccc(N5CCC(C)(O)CC5)cc4)n3)cc2C#N)[C@H](F)C1] | 4 | 2 | 474 | 2-(((3R,4S)-3-fluoro-1-((S)-2-hydroxypropanoyl)piperidin-4-yl)oxy)-5-(4-((4-(4-hydroxy-4-methylpiperidin-1-yl)phenyl)amino)-1,3,5-triazin-2-yl)benzonitrile |
| 356 | 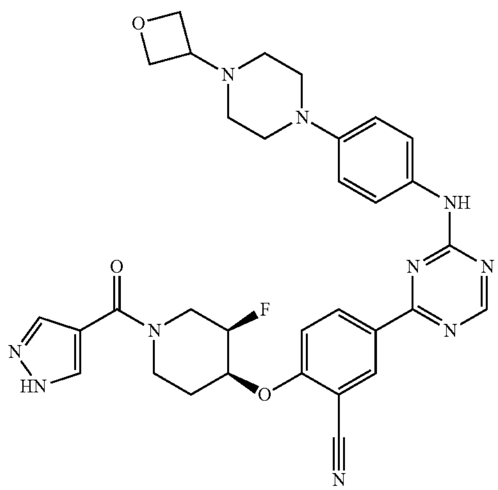 [SMILES: N#Cc1cc(-c2ncnc(Nc3ccc(N4CCN(C5COC5)CC4)cc3)n2)ccc1O[C@H]1CCN(C(=O)c2cn[nH]c2)C[C@H]1F] | 2 | 3 | 550 | 2-(((3R,4S)-3-fluoro-1-(1H-pyrazole-4-carbonyl)piperidin-4-yl)oxy)-5-(4-((4-(4-(oxetan-3-yl)piperazin-1-yl)phenyl)amino)-1,3,5-triazin-2-yl)benzonitrile |
| 357 | 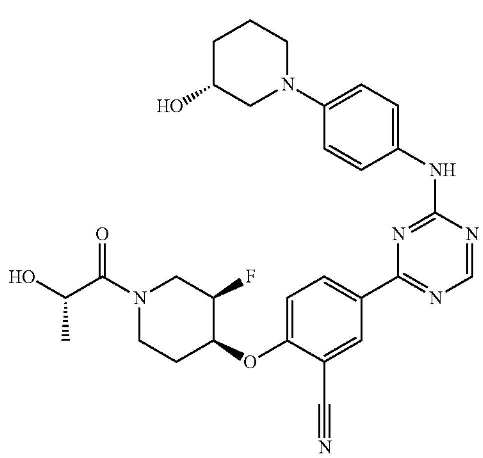 [SMILES: C[C@H](O)C(=O)N1CC[C@H](Oc2ccc(-c3ncnc(Nc4ccc(N5CCC[C@@H](O)C5)cc4)n3)cc2C#N)[C@H](F)C1] | 4 | 2 | 511 | 2-(((3R,4S)-3-fluoro-1-((S)-2-hydroxypropanoyl)piperidin-4-yl)oxy)-5-(4-((4-((R)-3-hydroxypiperidin-1-yl)phenyl)amino)-1,3,5-triazin-2-yl)benzonitrile |

TABLE 1-continued

| Ex. | Structure | TBK1 IC50 | IKKe IC50 | JAK2 IC50 | Name |
|---|---|---|---|---|---|
| 358 | 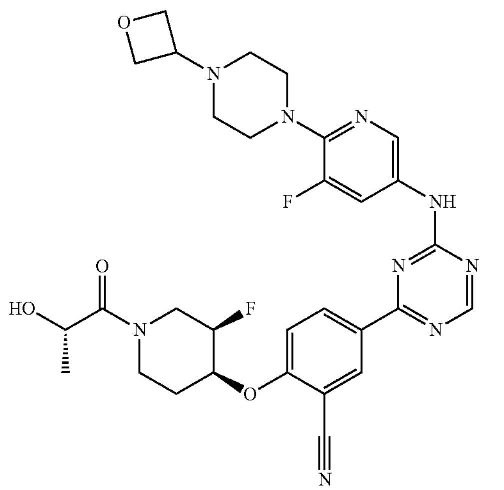 [SMILES: C[C@H](O)C(=O)N1CC[C@H](Oc2ccc(-c3ncnc(Nc4cnc(N5CCN(C6COC6)CC5)c(F)c4)n3)cc2C#N)[C@H](F)C1] | 6 | 11 | 1000 | 2-(((3R,4S)-3-fluoro-1-((S)-2-hydroxypropanoyl)piperidin-4-yl)oxy)-5-(4-((5-fluoro-6-(4-(oxetan-3-yl)piperazin-1-yl)pyridin-3-yl)amino)-1,3,5-triazin-2-yl)benzonitrile |
| 359 | 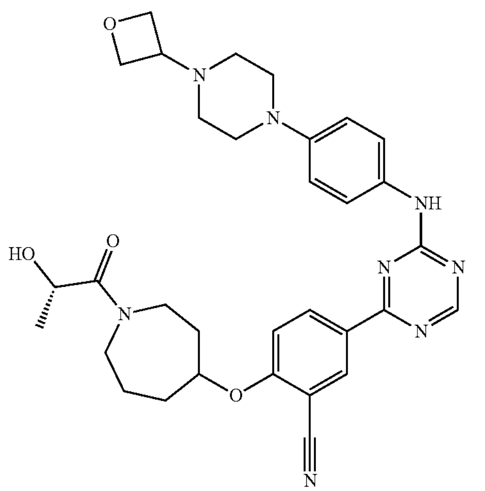 [SMILES: C[C@H](O)C(=O)N1CCCC(Oc2ccc(-c3ncnc(Nc4ccc(N5CCN(C6COC6)CC5)cc4)n3)cc2C#N)CC1] | 17 | 37 | 995 | 2-((1-((S)-2-hydroxypropanoyl)azepan-4-yl)oxy)-5-(4-((4-(4-(oxetan-3-yl)piperazin-1-yl)phenyl)amino)-1,3,5-triazin-2-yl)benzonitrile |
| 360 | 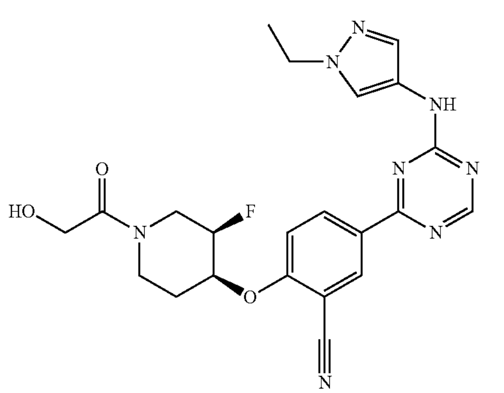 [SMILES: CCn1cc(Nc2ncnc(-c3ccc(O[C@H]4CCN(C(=O)CO)C[C@H]4F)c(C#N)c3)n2)cn1] | 3 | 2 | 185 | 5-(4-((1-ethyl-1H-pyrazol-4-yl)amino)-1,3,5-triazin-2-yl)-2-(((3R,4S)-3-fluoro-1-(2-hydroxyacetyl)piperidin-4-yl)oxy)benzonitrile |

TABLE 1-continued

| Ex. | Structure | TBK1 IC50 | IKKe IC50 | JAK2 IC50 | Name |
|---|---|---|---|---|---|
| 361 | 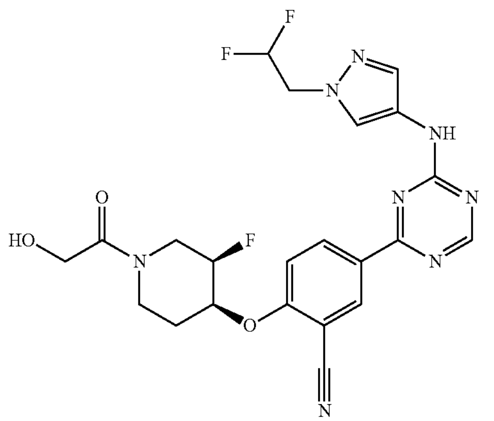 [SMILES: N#Cc1cc(-c2ncnc(Nc3cnn(CC(F)F)c3)n2)ccc1O[C@H]1CCN(C(=O)CO)C[C@H]1F] | 2 | 1 | 317 | 5-(4-((1-(2,2-difluoroethyl)-1H-pyrazol-4-yl)amino)-1,3,5-triazin-2-yl)-2-(((3R,4S)-3-fluoro-1-(2-hydroxyacetyl)piperidin-4-yl)oxy)benzonitrile |
| 362 | 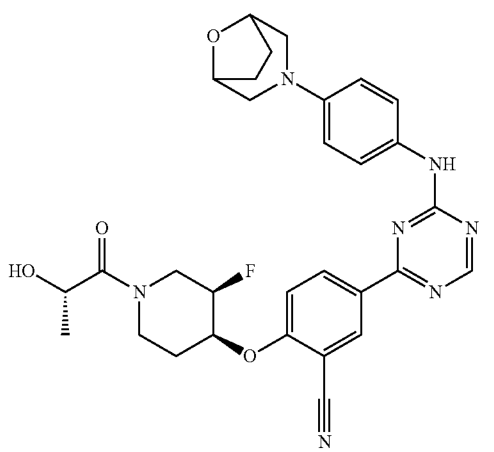 [SMILES: C[C@H](O)C(=O)N1CC[C@H](Oc2ccc(-c3ncnc(Nc4ccc(N5CC6CCC(C5)O6)cc4)n3)cc2C#N)[C@H](F)C1] | 2 | 2 | 747 | 5-(4-((4-(8-oxa-3-azabicyclo[3.2.1]octan-3-yl)phenyl)amino)-1,3,5-triazin-2-yl)-2-(((3R,4S)-3-fluoro-1-((S)-2-hydroxypropanoyl)piperidin-4-yl)oxy)benzonitrile |
| 363 | 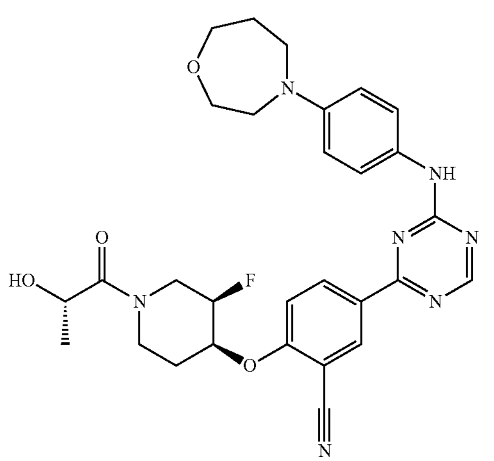 [SMILES: C[C@H](O)C(=O)N1CC[C@H](Oc2ccc(-c3ncnc(Nc4ccc(N5CCCOCC5)cc4)n3)cc2C#N)[C@H](F)C1] | 3 | 1 | 665 | 5-(4-((4-(1,4-oxazepan-4-yl)phenyl)amino)-1,3,5-triazin-2-yl)-2-(((3R,4S)-3-fluoro-1-((S)-2-hydroxypropanoyl)piperidin-4-yl)oxy)benzonitrile |

TABLE 1-continued

| Ex. | Structure | TBK1 IC50 | IKKe IC50 | JAK2 IC50 | Name |
|---|---|---|---|---|---|
| 364 | 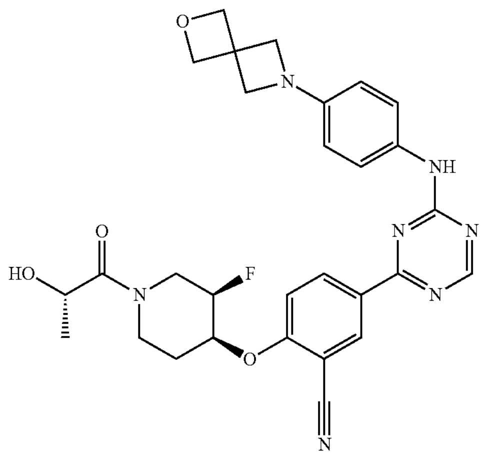 [SMILES: C[C@H](O)C(=O)N1CC[C@H](Oc2ccc(-c3ncnc(Nc4ccc(N5CC6(COC6)C5)cc4)n3)cc2C#N)[C@H](F)C1] | 5 | 4 | 634 | 5-(4-((4-(2-oxa-6-azaspiro[3.3]heptan-6-yl)phenyl)amino)-1,3,5-triazin-2-yl)-2-(((3R,4S)-3-fluoro-1-((S)-2-hydroxypropanoyl)piperidin-4-yl)oxy)benzonitrile |
| 365 | 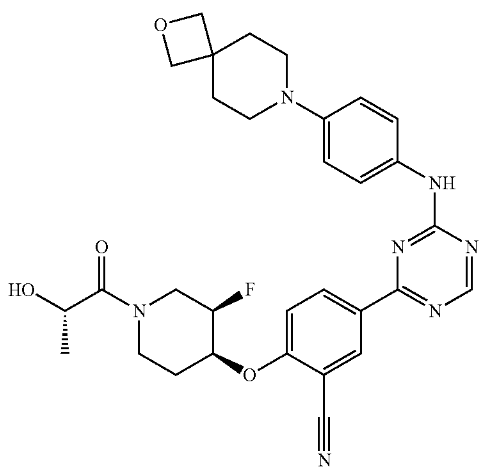 [SMILES: C[C@H](O)C(=O)N1CC[C@H](Oc2ccc(-c3ncnc(Nc4ccc(N5CCC6(CC5)COC6)cc4)n3)cc2C#N)[C@H](F)C1] | 4 | 2 | 474 | 5-(4-((4-(2-oxa-7-azaspiro[3.5]nonan-7-yl)phenyl)amino)-1,3,5-triazin-2-yl)-2-(((3R,4S)-3-fluoro-1-((S)-2-hydroxypropanoyl)piperidin-4-yl)oxy)benzonitrile |
| 366 | 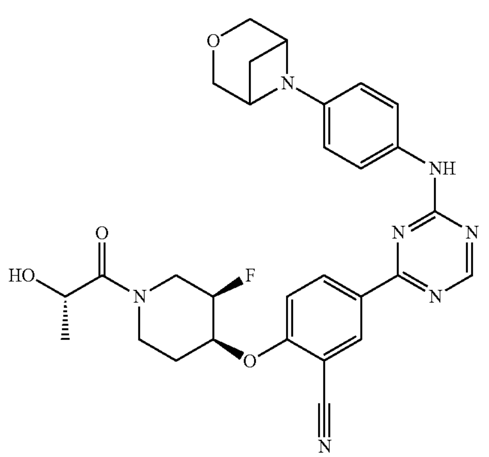 [SMILES: C[C@H](O)C(=O)N1CC[C@H](Oc2ccc(-c3ncnc(Nc4ccc(N5C6COCC5C6)cc4)n3)cc2C#N)[C@H](F)C1] | 3 | 2 | 531 | 5-(4-((4-(3-oxa-6-azabicyclo[3.1.1]heptan-6-yl)phenyl)amino)-1,3,5-triazin-2-yl)-2-(((3R,4S)-3-fluoro-1-((S)-2-hydroxypropanoyl)piperidin-4-yl)oxy)benzonitrile |

TABLE 1-continued

| Ex. | Structure | TBK1 IC50 | IKKe IC50 | JAK2 IC50 | Name |
|---|---|---|---|---|---|
| 367 | 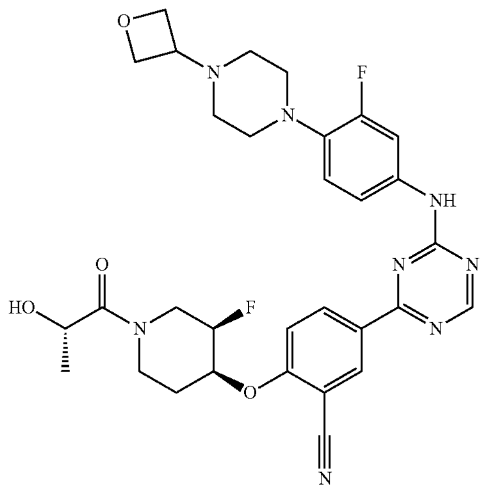 [SMILES: C[C@H](O)C(=O)N1CC[C@H](Oc2ccc(-c3ncnc(Nc4ccc(N5CCN(C6COC6)CC5)c(F)c4)n3)cc2C#N)[C@H](F)C1] | 3 | 2 | 1000 | 2-(((3R,4S)-3-fluoro-1-((S)-2-hydroxypropanoyl)piperidin-4-yl)oxy)-5-(4-((3-fluoro-4-(4-(oxetan-3-yl)piperazin-1-yl)phenyl)amino)-1,3,5-triazin-2-yl)benzonitrile |
| 368 | 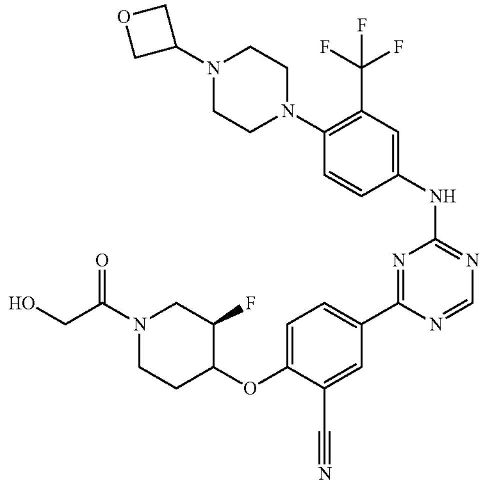 [SMILES: N#Cc1cc(-c2ncnc(Nc3ccc(N4CCN(C5COC5)CC4)c(C(F)(F)F)c3)n2)ccc1OC1CCN(C(=O)CO)C[C@H]1F] | 3 | 2 | 225 | 2-(((3R,4S)-3-fluoro-1-(2-hydroxyacetyl)piperidin-4-yl)oxy)-5-(4-((4-(4-(oxetan-3-yl)piperazin-1-yl)-3-(trifluoromethyl)phenyl)amino)-1,3,5-triazin-2-yl)benzonitrile |
| 369 | 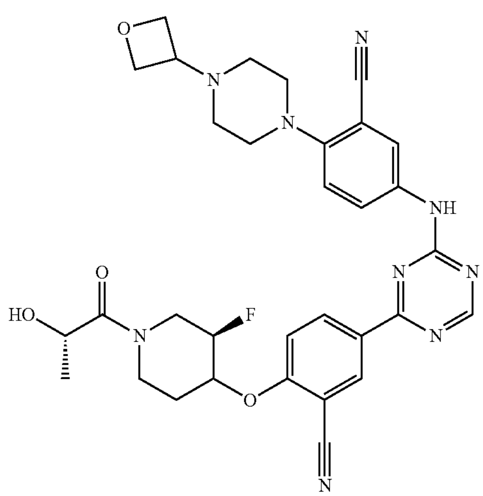 [SMILES: C[C@H](O)C(=O)N1CCC(Oc2ccc(-c3ncnc(Nc4ccc(N5CCN(C6COC6)CC5)c(C#N)c4)n3)cc2C#N)[C@H](F)C1] | 3 | 3 | 718 | 5-((4-(3-cyano-4-(((3R,4S)-3-fluoro-1-((S)-2-hydroxypropanoyl)piperidin-4-yl)oxy)phenyl)-1,3,5-triazin-2-yl)amino)-2-(4-(oxetan-3-yl)piperazin-1-yl)benzonitrile |

TABLE 1-continued

| Ex. | Structure | TBK1 IC50 | IKKe IC50 | JAK2 IC50 | Name |
|---|---|---|---|---|---|
| 370 | 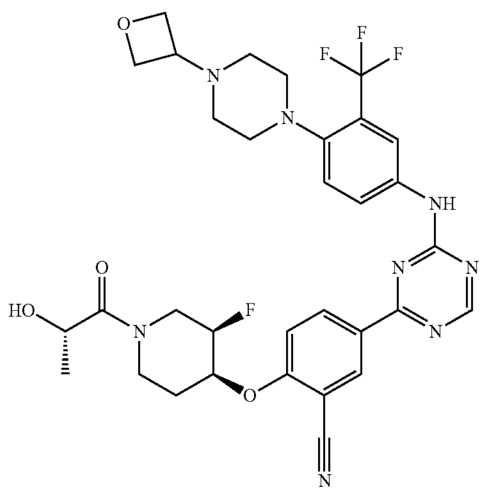 [SMILES: C[C@H](O)C(=O)N1CC[C@H](Oc2ccc(-c3ncnc(Nc4ccc(N5CCN(C6COC6)CC5)c(C(F)(F)F)c4)n3)cc2C#N)[C@H](F)C1] | 5 | 8 | 875 | 2-(((3R,4S)-3-fluoro-1-((S)-2-hydroxypropanoyl)piperidin-4-yl)oxy)-5-(4-((4-(4-(oxetan-3-yl)piperazin-1-(trifluoromethyl)phenyl)amino)-1,3,5-triazin-2-yl)benzonitrile |
| 371 | 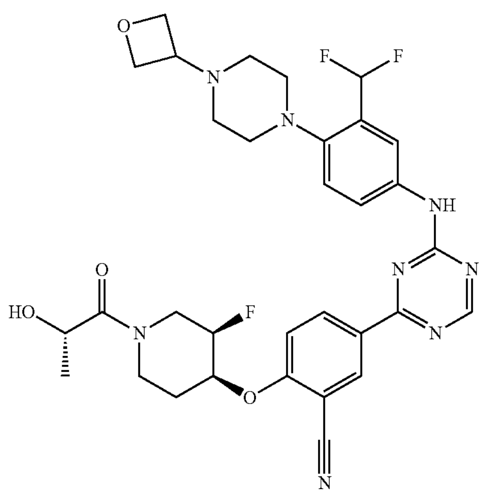 [SMILES: C[C@H](O)C(=O)N1CC[C@H](Oc2ccc(-c3ncnc(Nc4ccc(N5CCN(C6COC6)CC5)c(C(F)F)c4)n3)cc2C#N)[C@H](F)C1] | 2 | 1 | 989 | 5-(4-((3-(difluoromethyl)-4-(oxetan-3-yl)piperazin-1-yl)phenyl)amino)-1,3,5-thazin-2-yl)-2-(((3R,4S)-3-fluoro-1-((S)-2-hydroxypropanoyl)piperidin-4-yl)oxy)benzonitrile |
| 372 | 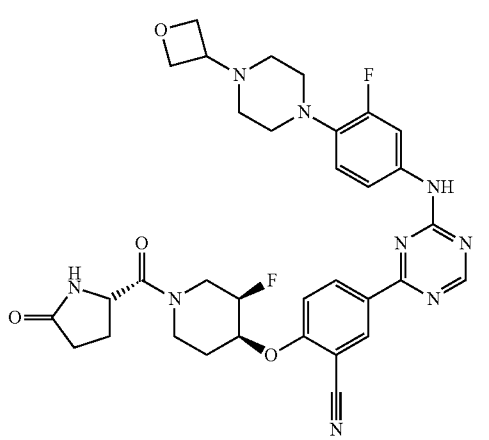 | 4 | 5 | 305 | 2-(((3R,4S)-3-fluoro-1-((S)-5-oxopyrrolidine-2-carbonyl)piperidin-4-yl)oxy)-5-(4-((3-fluoro-4-(4-(oxetan-3-yl)piperazin-1-yl)phenyl)amino)-1,3,5-triazin-2-yl)benzonitrile |

TABLE 1-continued

| Ex. | Structure | TBK1 IC50 | IKKe IC50 | JAK2 IC50 | Name |
|---|---|---|---|---|---|
| 373 | 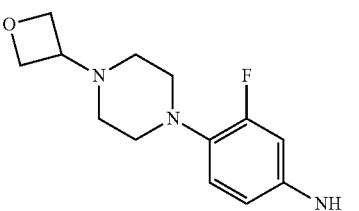 | 2 | 1 | 146 | 2-(((3R,4S)-3-fluoro-1-(1H-1,2,3-triazole-5-carbonyl)piperidin-4-yl)oxy)-5-(4-((3-fluoro-4-(4-(oxetan-3-yl)piperazin-1-yl)phenyl)amino)-1,3,5-triazin-2-yl)benzonitrile |
| 374 | 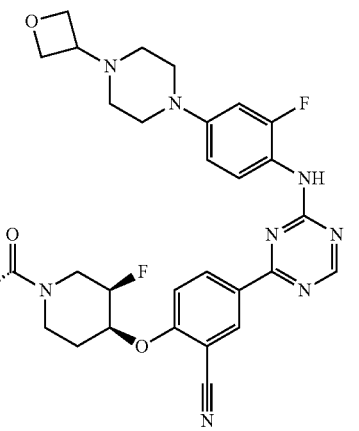 | 1000 | 1000 | 1000 | 2-(((3R,4S)-3-fluoro-1-((S)-5-oxopyrrolidine-2-carbonyl)piperidin-4-yl)oxy)-5-(4-((2-fluoro-4-(4-(oxetan-3-yl)piperazin-1-yl)phenyl)amino)-1,3,5-triazin-2-yl)benzonitrile |
| 375 | 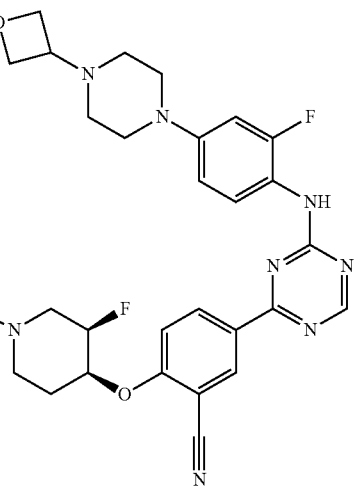 | 1000 | 1000 | 1000 | 2-(((3R,4S)-3-fluoro-1-((S)-2-hydroxypropanoyl)piperidin-4-yl)oxy)-5-(4-((2-fluoro-4-(4-(oxetan-3-yl)piperazin-1-yl)phenyl)amino)-1,3,5-triazin-2-yl)benzonitrile |

TABLE 1-continued

| Ex. | Structure | TBK1 IC50 | IKKe IC50 | JAK2 IC50 | Name |
|---|---|---|---|---|---|
| 376 | 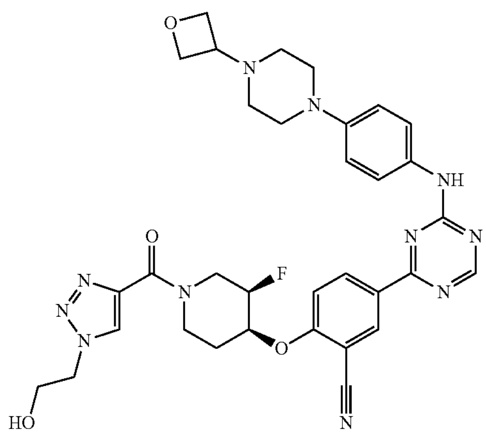 [SMILES: N#Cc1cc(-c2ncnc(Nc3ccc(N4CCN(C5COC5)CC4)cc3)n2)ccc1O[C@H]1CCN(C(=O)c2cn(CCO)nn2)C[C@H]1F] | 5 | 3 | 127 | 2-(((3R,4S)-3-fluoro-1-(1-(2-hydroxyethyl)-1H-1,2,3-triazole-4-carbonyl)piperidin-4-yl)oxy)-5-(4-((4-(4-(oxetan-3-yl)piperazin-1-yl)phenyl)amino)-1,3,5-triazin-2-yl)benzonitrile |
| 377 | 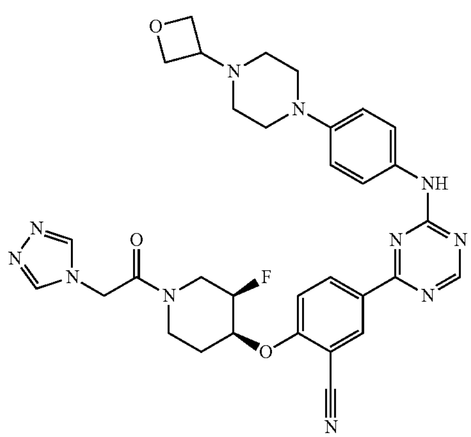 [SMILES: N#Cc1cc(-c2ncnc(Nc3ccc(N4CCN(C5COC5)CC4)cc3)n2)ccc1O[C@H]1CCN(C(=O)Cn2cnnc2)C[C@H]1F] | 37 | 129 | 87 | 2-(((3R,4S)-1-(2-(4H-1,2,4-triazol-4-yl)acetyl)-3-fluoropiperidin-4-yl)oxy)-5-(4-((4-(4-(oxetan-3-yl)piperazin-1-yl)phenyl)amino)-1,3,5-triazin-2-yl)benzonitrile |
| 378 | 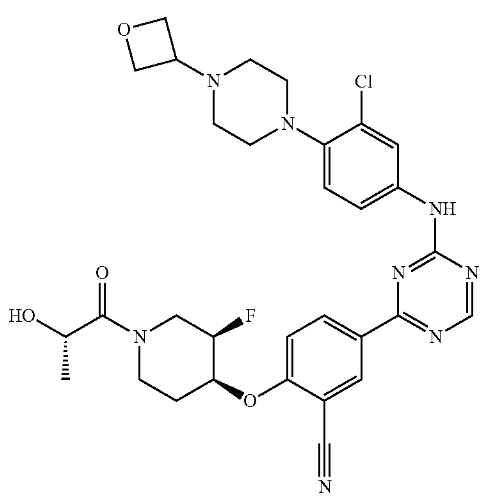 [SMILES: C[C@H](O)C(=O)N1CC[C@H](Oc2ccc(-c3ncnc(Nc4ccc(N5CCN(C6COC6)CC5)c(Cl)c4)n3)cc2C#N)[C@H](F)C1] | 2 | 2 | 173 | 5-(4-((3-chloro-4-(4-(oxetan-3-yl)piperazin-1-yl)phenyl)amino)-1,3,5-triazin-2-yl)-2-(((3R,4S)-3-fluoro-1-((S)-2-hydroxypropanoyl)piperidin-4-yl)oxy)benzonitrile |

TABLE 1-continued

| Ex. | Structure | TBK1 IC50 | IKKe IC50 | JAK2 IC50 | Name |
|---|---|---|---|---|---|
| 379 | 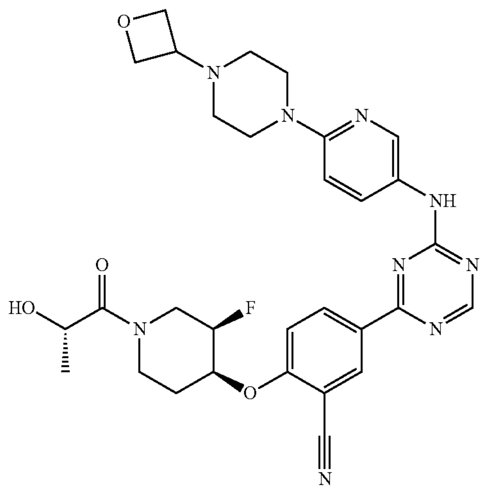 [SMILES: C[C@H](O)C(=O)N1CC[C@H](Oc2ccc(-c3ncnc(Nc4ccc(N5CCN(C6COC6)CC5)nc4)n3)cc2C#N)[C@H](F)C1] | 5 | 3 | 1000 | 2-(((3R,4S)-3-fluoro-1-((S)-2-hydroxypropanoyl)piperidin-4-yl)oxy)-5-(4-((6-(4-(oxetan-3-yl)piperazin-1-yl)pyridin-3-yl)amino)-1,3,5-triazin-2-yl)benzonitrile |
| 380 | 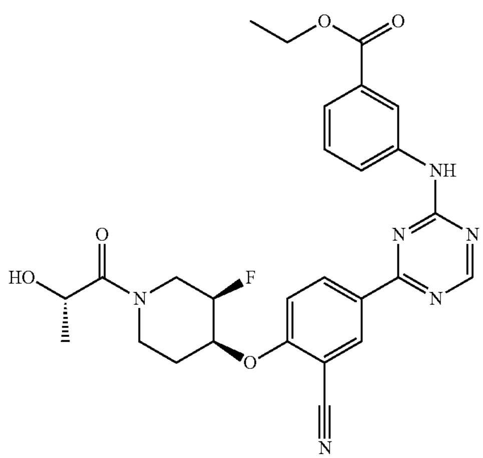 [SMILES: CCOC(=O)c1cccc(Nc2ncnc(-c3ccc(O[C@H]4CCN(C(=O)[C@H](C)O)C[C@H]4F)c(C#N)c3)n2)c1] | 6 | 8 | 891 | Ethyl 3-((4-(3-cyano-4-(((3R,4S)-3-fluoro-1-((S)-2-hydroxypropanoyl)piperidin-4-yl)oxy)phenyl)-1,3,5-triazin-2-yl)amino)benzoate |
| 381 | 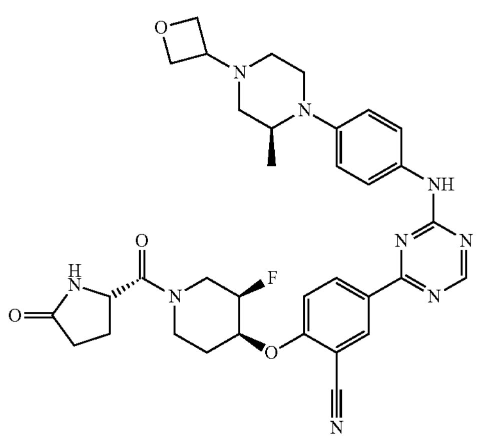 | 1000 | 1000 | 1000 | 2-(((3R,4S)-3-fluoro-1-((S)-5-oxopyrrolidine-2-carbonyl)piperidin-4-yl)oxy)-5-(4-((4-((S)-2-methyl-4-(oxetan-3-yl)piperazin-1-yl)phenyl)amino)-1,3,5-triazin-2-yl)benzonitrile |

TABLE 1-continued

| Ex. | Structure | TBK1 IC50 | IKKe IC50 | JAK2 IC50 | Name |
|---|---|---|---|---|---|
| 382 | 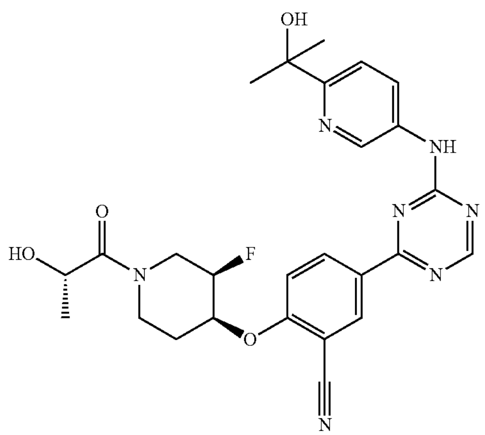 [SMILES: C[C@H](O)C(=O)N1CC[C@H](Oc2ccc(-c3ncnc(Nc4ccc(C(C)(C)O)nc4)n3)cc2C#N)[C@H](F)C1] | 3 | 3 | 1000 | 2-(((3R,4S)-3-fluoro-1-((S)-2-hydroxypropanoyl)piperidin-4-yl)oxy)-5-(4-((6-(2-hydroxypropan-2-yl)pyridin-3-yl)amino)-1,3,5-triazin-2-yl)benzonitrile |
| 383 | 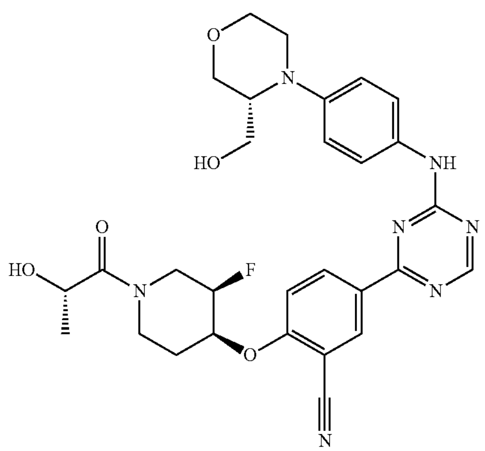 [SMILES: C[C@H](O)C(=O)N1CC[C@H](Oc2ccc(-c3ncnc(Nc4ccc(N5CCOC[C@H]5CO)cc4)n3)cc2C#N)[C@H](F)C1] | 2 | 1 | 568 | 2-(((3R,4S)-3-fluoro-1-((S)-2-hydroxypropanoyl)piperidin-4-yl)oxy)-5-(4-((4-((R)-3-(hydroxymethyl)morpholino)phenyl)amino)-1,3,5-triazin-2-yl)benzonitrile |
| 384 | 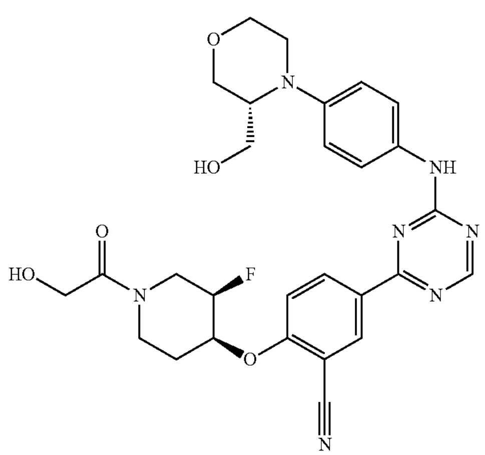 [SMILES: N#Cc1cc(-c2ncnc(Nc3ccc(N4CCOC[C@H]4CO)cc3)n2)ccc1O[C@H]1CCN(C(=O)CO)C[C@H]1F] | 2 | 1 | 189 | 2-(((3R,4S)-3-fluoro-1-(2-hydroxyacetyl)piperidin-4-yl)oxy)-5-(4-((4-((R)-3-(hydroxymethyl)morpholino)phenyl)amino)-1,3,5-triazin-2-yl)benzonitrile |

TABLE 1-continued

| Ex. | Structure | TBK1 IC50 | IKKe IC50 | JAK2 IC50 | Name |
|---|---|---|---|---|---|
| 385 | 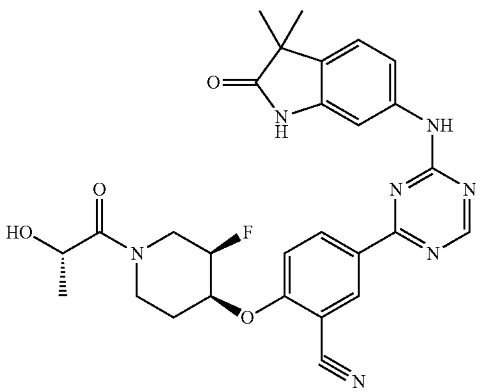 [SMILES: C[C@H](O)C(=O)N1CC[C@H](Oc2ccc(-c3ncnc(Nc4ccc5c(c4)NC(=O)C5(C)C)n3)cc2C#N)[C@H](F)C1] | 2 | 3 | 888 | 5-(4-((3,3-dimethyl-2-oxoindolin-6-yl)amino)-1,3,5-triazin-2-yl)-2-(((3R,4S)-3-fluoro-1-((S)-2-hydroxypropanoyl)piperidin-4-yl)oxy)benzonitrile |
| 386 | 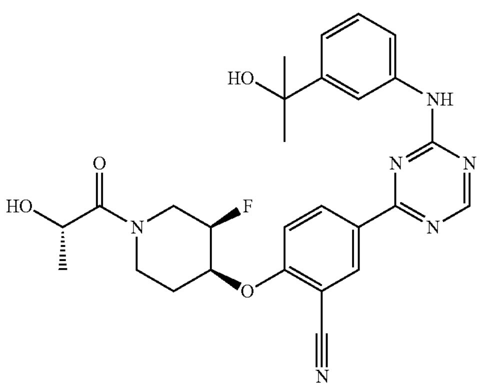 [SMILES: C[C@H](O)C(=O)N1CC[C@H](Oc2ccc(-c3ncnc(Nc4cccc(C(C)(C)O)c4)n3)cc2C#N)[C@H](F)C1] | 4 | 6 | 1000 | 2-(((3R,4S)-3-fluoro-1-((S)-2-hydroxypropanoyl)piperidin-4-yl)oxy)-5-(4-((2-(2-hydroxypropan-2-yl)pyridin-4-yl)amino)-1,3,5-triazin-2-yl)benzonitrile |
| 387 | 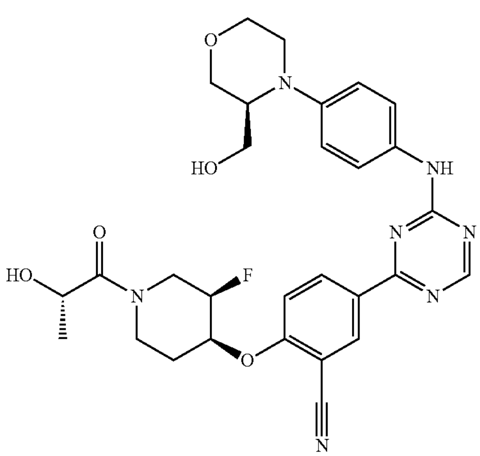 [SMILES: C[C@H](O)C(=O)N1CC[C@H](Oc2ccc(-c3ncnc(Nc4ccc(N5CCOC[C@@H]5CO)cc4)n3)cc2C#N)[C@H](F)C1] | 3 | 2 | 638 | 2-(((3R,4S)-3-fluoro-1-(S)-2-hydroxypropanoyl)piperidin-4-yl)oxy)-5-(4-((4-((S)-3-(hydroxymethyl)morpholino)phenyl)amino)-1,3,5-triazin-2-yl)benzonitrile |

TABLE 1-continued

| Ex. | Structure | TBK1 IC50 | IKKe IC50 | JAK2 IC50 | Name |
|---|---|---|---|---|---|
| 388 | 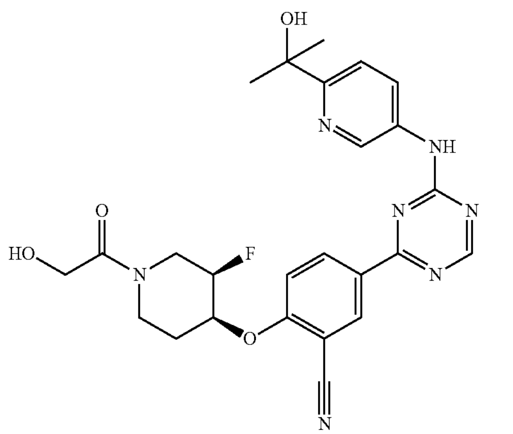 [SMILES: CC(C)(O)c1ccc(Nc2ncnc(-c3ccc(O[C@H]4CCN(C(=O)CO)C[C@H]4F)c(C#N)c3)n2)cn1] | 6 | 4 | 1000 | 2-(((3R,4S)-3-fluoro-1-(2-hydroxyacetyl)piperidin-4-yl)oxy)-5-(4-((6-(2-hydroxypropan-2-yl)pyridin-3-yl)amino)-1,3,5-triazin-2-yl)benzonitrile |
| 389 | 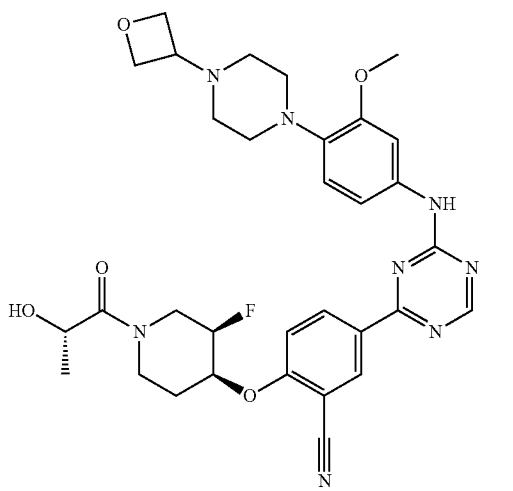 [SMILES: COc1cc(Nc2ncnc(-c3ccc(O[C@H]4CCN(C(=O)[C@H](C)O)C[C@H]4F)c(C#N)c3)n2)ccc1N1CCN(C2COC2)CC1] | 2 | 1 | 55 | 2-(((3R,4S)-3-fluoro-1-((S)-2-hydroxypropanoyl)piperidin-4-yl)oxy)-5-(4-((3-methoxy-4-(4-(oxetan-3-yl)piperazin-1-yl)phenyl)amino)-1,3,5-triazin-2-yl)benzonitrile |
| 390 | 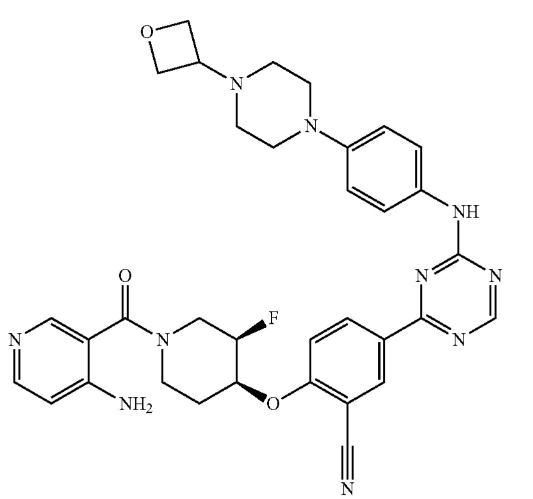 [SMILES: N#Cc1cc(-c2ncnc(Nc3ccc(N4CCN(C5COC5)CC4)cc3)n2)ccc1O[C@H]1CCN(C(=O)c2cnccc2N)C[C@H]1F] | 65 | 165 | 37 | 2-(((3R,4S)-1-(3-aminoisonicotinoyl)-3-fluoropiperidin-4-yl)oxy)-5-(4-((4-(4-(oxetan-3-yl)piperazin-1-yl)phenyl)amino)4,3,5-triazin-2-yl)benzonitrile |

TABLE 1-continued

| Ex. | Structure | TBK1 IC50 | IKKe IC50 | JAK2 IC50 | Name |
|---|---|---|---|---|---|
| 391 | 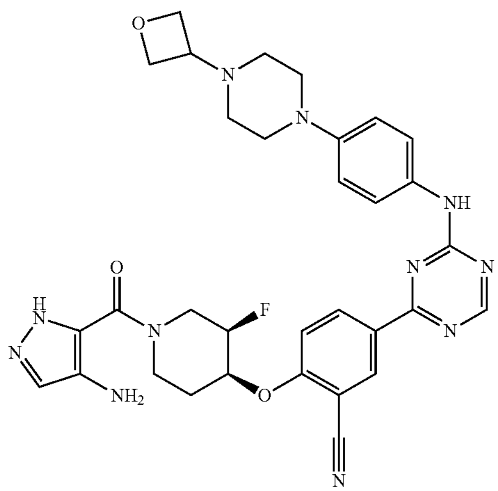 [SMILES: N#Cc1cc(-c2ncnc(Nc3ccc(N4CCN(C5COC5)CC4)cc3)n2)ccc1O[C@H]1CCN(C(=O)c2[nH]ncc2N)C[C@H]1F] | 6 | 9 | 122 | 2-(((3R,4S)-1-(4-amino-1H-pyrazole-5-carbonyl)-3-fluoropiperidin-4-yl)oxy)-5-(4-((4-(oxetan-3-yl)piperazin-1-yl)phenyl)amino)-1,3,5-triazin-2-yl)benzonitrile |
| 392 | 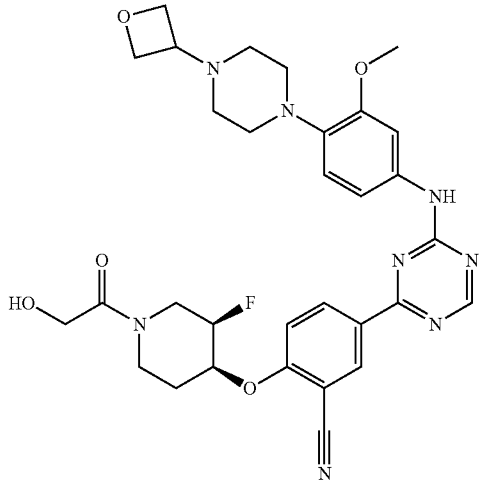 [SMILES: COc1cc(Nc2ncnc(-c3ccc(O[C@H]4CCN(C(=O)CO)C[C@H]4F)c(C#N)c3)n2)ccc1N1CCN(C2COC2)CC1] | 5 | 1 | 26 | 2-(((3R,4S)-3-fluoro-1-(2-hydroxyacetyl)piperidin-4-yl)oxy)-5-(4-((3-methoxy-4-(4-(oxetan-3-yl)piperazin-1-yl)phenyl)amino)-1,3,5-triazin-2-yl)benzonitrile |
| 393 | 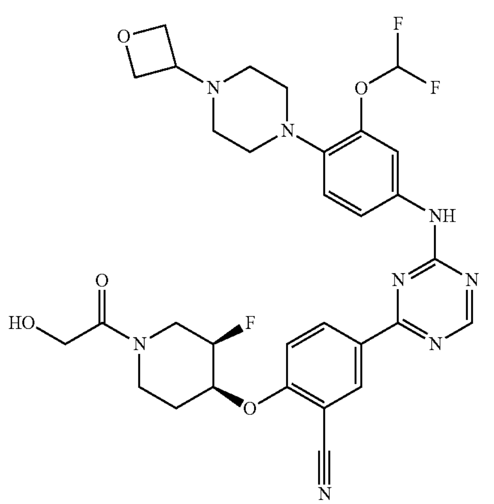 [SMILES: N#Cc1cc(-c2ncnc(Nc3ccc(N4CCN(C5COC5)CC4)c(OC(F)F)c3)n2)ccc1O[C@H]1CCN(C(=O)CO)C[C@H]1F] | 3 | 1 | 29 | 5-(4-((3-difluoromethoxy)-4-(4-(oxetan-3-yl)piperazin-1-yl)phenyl)amino)-1,3,5-triazin-2-yl)-2-(((3R,4S)-3-fluoro-1-(2-hydroxyacetyl)piperidin-4-yl)oxy)benzonitrile |

| Ex. | Structure | TBK1 IC50 | IKKe IC50 | JAK2 IC50 | Name |
|---|---|---|---|---|---|
| 394 | 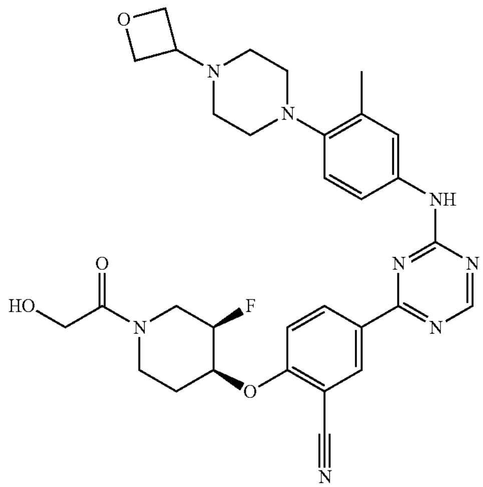 [SMILES: Cc1cc(Nc2ncnc(-c3ccc(O[C@H]4CCN(C(=O)CO)C[C@H]4F)c(C#N)c3)n2)ccc1N1CCN(C2COC2)CC1] | 2 | 1 | 64 | 2-(((3R,4S)-3-fluoro-1-(2-hydroxyacetyl)piperidin-4-yl)oxy)-5-(4-((3-methyl-4-(4-(oxetan-3-yl)piperazin-1-yl)phenyl)amino)-1,3,5-triazin-2-yl)benzonitrile |
| 395 | 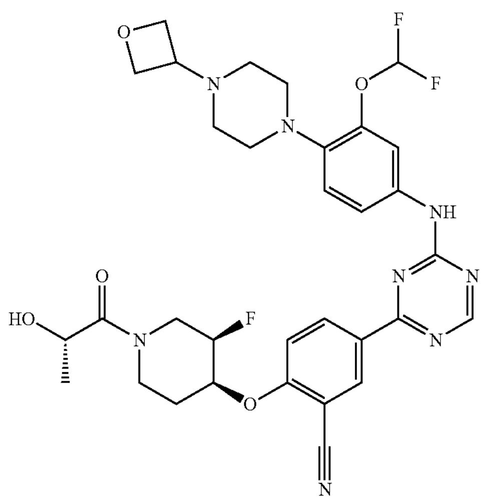 [SMILES: C[C@H](O)C(=O)N1CC[C@H](Oc2ccc(-c3ncnc(Nc4ccc(N5CCN(C6COC6)CC5)c(OC(F)F)c4)n3)cc2C#N)[C@H](F)C1] | 2 | 1 | 119 | 5-(4-((3-(difluoromethoxy)-4-(4-(oxetan-3-yl)piperazin-1-yl)phenyl)amino)-1,3,5-triazin-2-yl)-2-(((3R,4S)-3-fluoro-1-((S)-2-hydroxypropanoyl)piperidin-4-yl)oxy)benzenitrile |
| 396 | 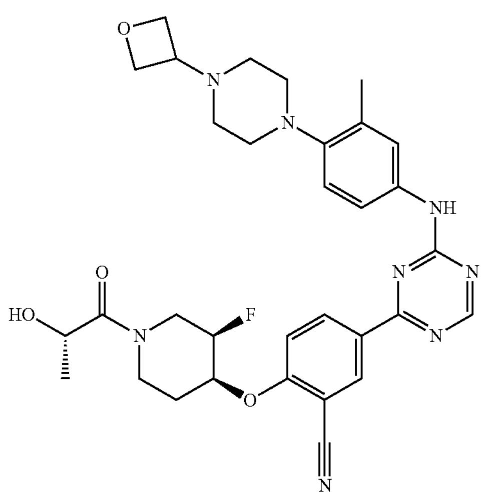 [SMILES: Cc1cc(Nc2ncnc(-c3ccc(O[C@H]4CCN(C(=O)[C@H](C)O)C[C@H]4F)c(C#N)c3)n2)ccc1N1CCN(C2COC2)CC1] | 2 | 1 | 137 | 2-(((3R,4S)-3-fluoro-1-((S)-2-hydroxypropanoyl)piperidin-4-yl)oxy)-5-(4-((3-methyl-4-(4-(oxetan-3-yl)piperazin-1-yl)phenyl)amino)-1,3,5-triazin-2-yl)benzonitrile |

TABLE 1-continued

| Ex. | Structure | TBK1 IC50 | IKKe IC50 | JAK2 IC50 | Name |
|---|---|---|---|---|---|
| 397 | 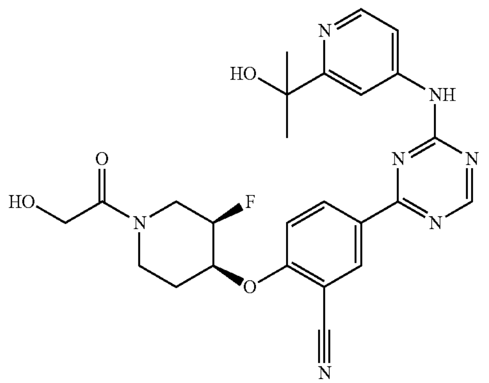 [SMILES: CC(C)(O)c1cc(Nc2ncnc(-c3ccc(O[C@H]4CCN(C(=O)CO)C[C@H]4F)c(C#N)c3)n2)ccn1] | 2 | 2 | 960 | 2-(((3R,4S)-3-fluoro-1-(2-hydroxyacetyl)piperidin-4-yl)oxy)-5-(4-((2-(2-hydroxypropan-2-yl)pyridin-4-yl)amino)-1,3,5-triazin-2-yl)benzonitrile |
| 398 | 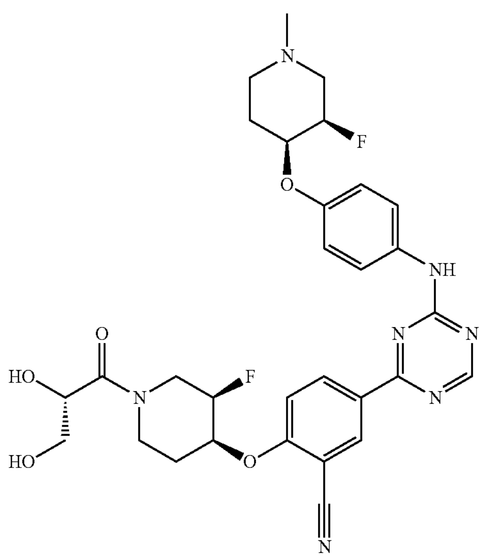 [SMILES: CN1CC[C@H](Oc2ccc(Nc3ncnc(-c4ccc(O[C@H]5CCN(C(=O)[C@@H](O)CO)C[C@H]5F)c(C#N)c4)n3)cc2)[C@H](F)C1] | 3 | 1 | 763 | 2-(((3R,4S)-1-((S)-2,3-dihydroxypropanoyl)-3-fluoropiperidin-4-yl)oxy)-5-(4-((4-(((3R,4S)-3-fluoro-1-methylpiperidin-4-yl)oxy)phenyl)amino)-1,3,5-triazin-2-yl)benzonitrile |
| 399 | 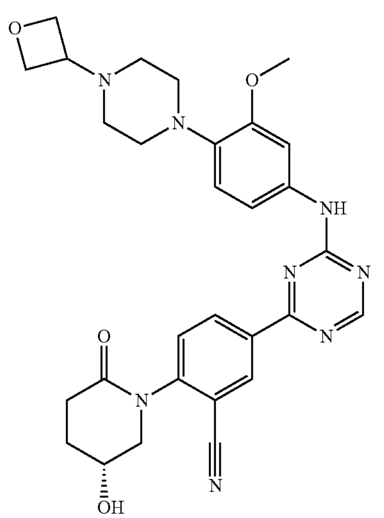 [SMILES: COc1cc(Nc2ncnc(-c3ccc(N4C[C@H](O)CCC4=O)c(C#N)c3)n2)ccc1N1CCN(C2COC2)CC1] | 152 | 270 | 174 | (R)-2-(5-hydroxy-2-oxopiperidin-1-yl)-5-(4-((3-methoxy-4-(4-(oxetan-3-yl)piperazin-1-yl)phenyl)amino)-1,3,5-triazin-2-yl)benzonitrile |

…continued
TABLE 1-continued
| Ex. | Structure | TBK1 IC50 | IKKe IC50 | JAK2 IC50 | Name |
|---|---|---|---|---|---|
| 400 | 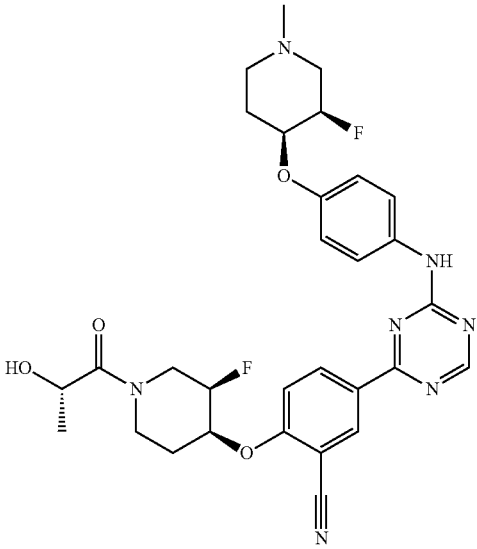 [SMILES: C[C@H](O)C(=O)N1CC[C@H](Oc2ccc(-c3ncnc(Nc4ccc(O[C@H]5CCN(C)C[C@H]5F)cc4)n3)cc2C#N)[C@H](F)C1] | 3 | 1 | 1000 | 2-(((3R,4S)-3-fluoro-1-((S)-2-hydroxypropanoyl)piperidin-4-yl)oxy)-5-(4-((4-(((3R,4S)-3-fluoro-1-methylpiperidin-4-yl)oxy)phenyl)amino)-1,3,5-triazin-2-yl)benzonitrile |
| 401 | 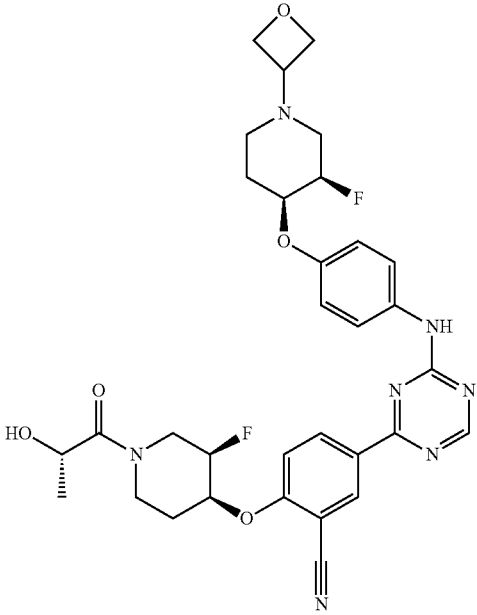 [SMILES: C[C@H](O)C(=O)N1CC[C@H](Oc2ccc(-c3ncnc(Nc4ccc(O[C@H]5CCN(C6COC6)C[C@H]5F)cc4)n3)cc2C#N)[C@H](F)C1] | 3 | 3 | 1000 | 2-(((3R,4S)-3-fluoro-1-((S)-2-hydroxypropanoyl)piperidin-4-yl)oxy)-5-(4-((4-(((3R,4S)-3-fluoro-1-(oxetan-3-yl)piperidin-4-yl)oxy)phenyl)amino)-1,3,5-triazin-2-yl)benzonitrile |

TABLE 1-continued

| Ex. | Structure | TBK1 IC50 | IKKe IC50 | JAK2 IC50 | Name |
|---|---|---|---|---|---|
| 402 | 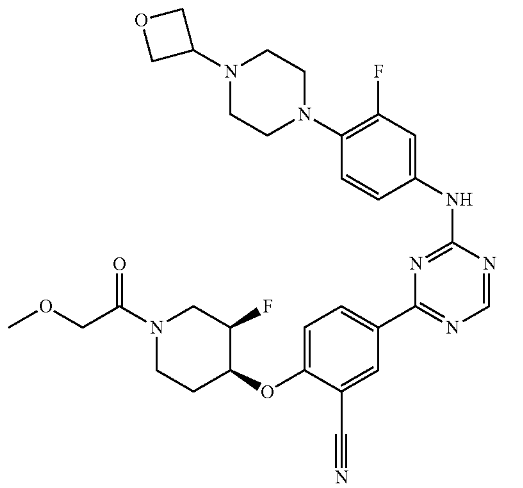 [SMILES: COCC(=O)N1CC[C@H](Oc2ccc(-c3ncnc(Nc4ccc(N5CCN(C6COC6)CC5)c(F)c4)n3)cc2C#N)[C@H](F)C1] | 3 | 3 | 1000 | 2-(((3R,4S)-3-fluoro-1-(2-methoxyacetyl)piperidin-4-yl)oxy)-5-(4-((3-fluoro-4-(oxetan-3-yl)piperazin-1-yl)phenyl)amino)-1,3,5-triazin-2-yl)benzonitrile |
| 403 | 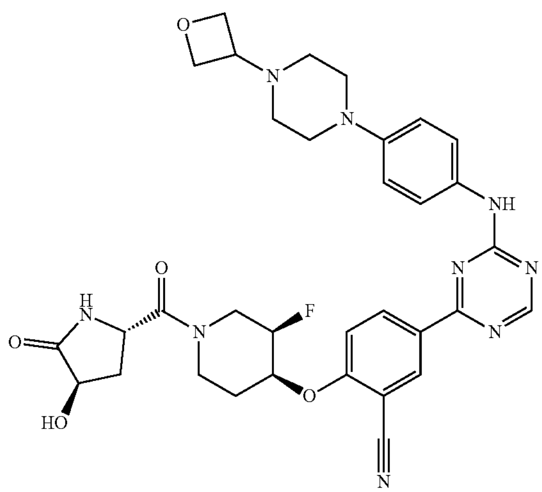 [SMILES: N#Cc1cc(-c2ncnc(Nc3ccc(N4CCN(C5COC5)CC4)cc3)n2)ccc1O[C@H]1CCN(C(=O)[C@@H]2C[C@@H](O)C(=O)N2)C[C@H]1F] | 4 | 6 | 858 | 2-(((3R,43)-3-fluoro-1-((2S,4R)-4-hydroxy-5-oxopyrrolidine-2-carbonyl)piperidin-4-yl)oxy)-5-(4-((4-(4-(oxetan-3-yl)piperazin-1-yl)phenyl)amino)-1,3,5-triazin-2-yl)benzonitrile |
| 404 | 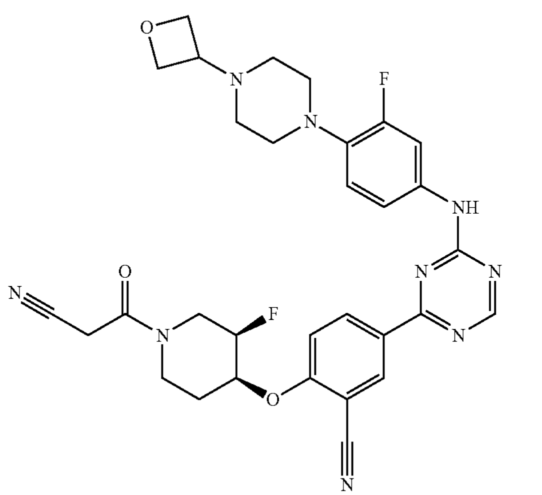 [SMILES: N#CCC(=O)N1CC[C@H](Oc2ccc(-c3ncnc(Nc4ccc(N5CCN(C6COC6)CC5)c(F)c4)n3)cc2C#N)[C@H](F)C1] | | 3 | 457 | 2-(((3R,4S)-1-(2-cyanoacetyl)-3-fluoropiperidin-4-yl)oxy)-5-(4-((3-fluoro-4-(4-(oxetan-3-yl)piperazin-1-yl)phenyl)amino)-1,3,5-triazin-2-yl)benzonitrile |

TABLE 1-continued

| Ex. | Structure | TBK1 IC50 | IKKe IC50 | JAK2 IC50 | Name |
|---|---|---|---|---|---|
| 405 | 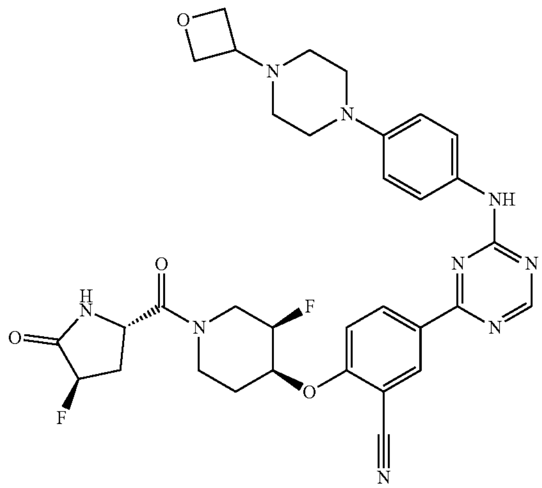 [SMILES: N#Cc1cc(-c2ncnc(Nc3ccc(N4CCN(C5COC5)CC4)cc3)n2)ccc1O[C@H]1CCN(C(=O)[C@@H]2C[C@@H](F)C(=O)N2)C[C@H]1F] | 5 | 10 | 1000 | 2-(((3R,4S)-3-fluoro-1-((2S,4R)-4-fluoro-5-oxopyrrolidine-2-carbonyl)piperidin-4-yl)oxy)-5-(4-((4-(4-(oxetan-3-yl)piperazin-1-yl)phenyl)amino)-1,3,5-triazin-2-yl)benzonitrile |
| 406 | 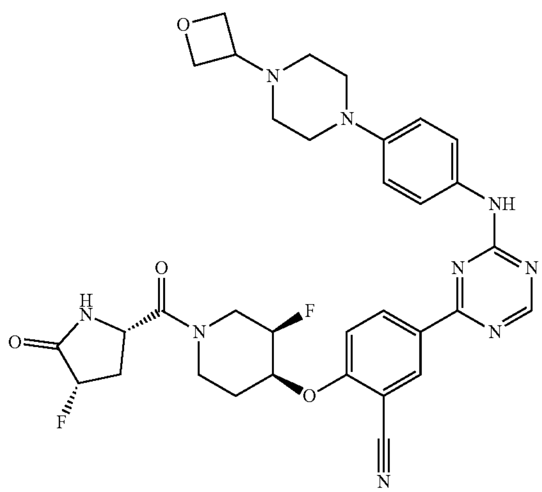 [SMILES: N#Cc1cc(-c2ncnc(Nc3ccc(N4CCN(C5COC5)CC4)cc3)n2)ccc1O[C@H]1CCN(C(=O)[C@@H]2C[C@H](F)C(=O)N2)C[C@H]1F] | 3 | 3 | 1000 | 2-(((3R,4S)-3-fluoro-1-((2S,4S)-4-fluoro-5-oxopyrrolidine-2-carbonyl)piperidin-4-yl)oxy)-5-(4-((4-(4-(oxetan-3-yl)piperazin-1-yl)phenyl)amino)-1,3,5-triazin-2-yl)benzonitrile |
| 407 | 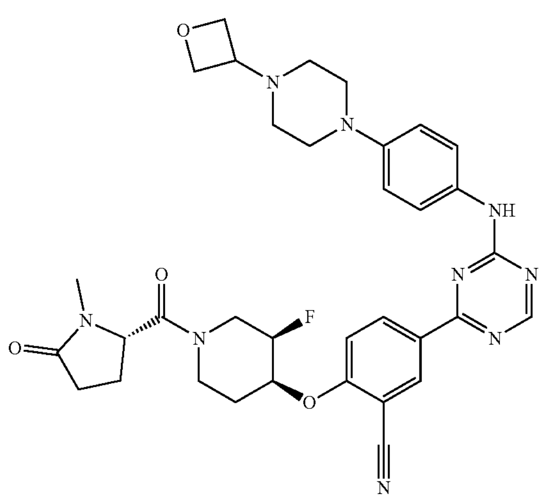 [SMILES: CN1C(=O)CC[C@H]1C(=O)N1CC[C@H](Oc2ccc(-c3ncnc(Nc4ccc(N5CCN(C6COC6)CC5)cc4)n3)cc2C#N)[C@H](F)C1] | 165 | 165 | 1000 | 2-(((3R,4S)-3-fluoro-1-((S)-1-methyl-5-oxopyrrolidine-2-carbonyl)piperidin-4-yl)oxy)-5-(4-((4-(4-(oxetan-3-yl)piperazin-1-yl)phenyl)amino)-1,3,5-triazin-2-yl)benzonitrile |

TABLE 1-continued

| Ex. | Structure | TBK1 IC50 | IKKe IC50 | JAK2 IC50 | Name |
|---|---|---|---|---|---|
| 408 | 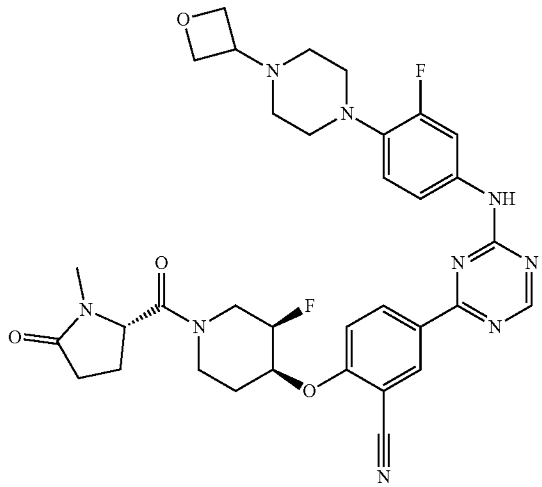 [SMILES: CN1C(=O)CC[C@H]1C(=O)N1CC[C@H](Oc2ccc(-c3ncnc(Nc4ccc(N5CCN(C6COC6)CC5)c(F)c4)n3)cc2C#N)[C@H](F)C1] | 86 | 119 | 1000 | 2-(((3R,4S)-3-fluoro-1-((S)-1-methyl-5-oxopyrrolidine-2-carbonyl)piperidin-4-yl)oxy)-5-(4-((3-fluoro-4-(4-(oxetan-3-yl)piperazin-1-yl)phenyl)amino)-1,3,5-triazin-2-yl)benzonitrile |
| 409 | 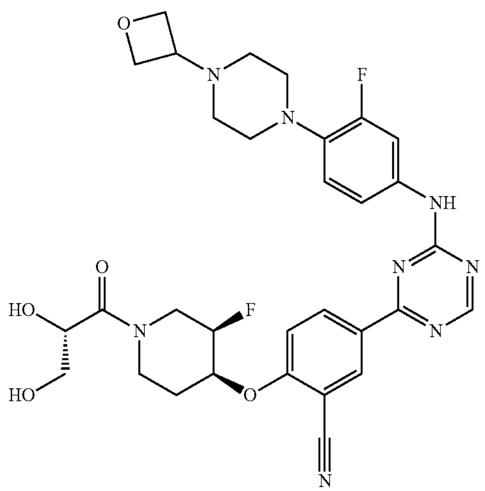 [SMILES: N#Cc1cc(-c2ncnc(Nc3ccc(N4CCN(C5COC5)CC4)c(F)c3)n2)ccc1O[C@H]1CCN(C(=O)[C@@H](O)CO)C[C@H]1F] | 2 | 1 | 327 | 2-(((3R,4S)-1-((S)-2,3-dihydroxypropanoyl)-3-fluoropiperidin-4-yl)oxy)-5-(4-((3-fluoro-4-(4-(oxetan-3-yl)piperazin-1-yl)phenyl)amino)-1,3,5-triazin-2-yl)benzonitrile |
| 410 | 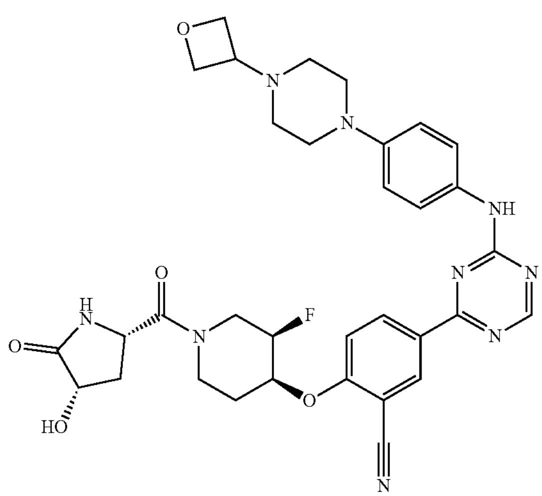 [SMILES: N#Cc1cc(-c2ncnc(Nc3ccc(N4CCN(C5COC5)CC4)cc3)n2)ccc1O[C@H]1CCN(C(=O)[C@@H]2C[C@H](O)C(=O)N2)C[C@H]1F] | 2 | 2 | 450 | 2-(((3R,4S)-3-fluoro-1-((2S,4S)-4-hydroxy-5-oxopyrrolidine-2-carbonyl)piperidin-4-yl)oxy)-5-(4-((4-(4-(oxetan-3-yl)piperazin-1-yl)phenyl)amino)-1,3,5-triazin-2-yl)benzonitrile |

TABLE 1-continued

| Ex. | Structure | TBK1 IC50 | IKKe IC50 | JAK2 IC50 | Name |
|---|---|---|---|---|---|
| 411 | 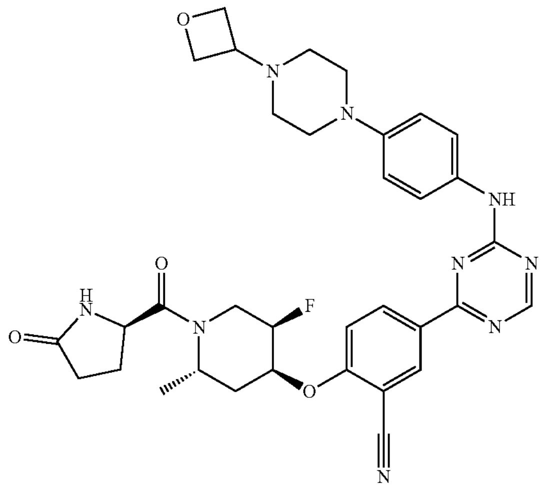 [SMILES: C[C@H]1C[C@H](Oc2ccc(-c3ncnc(Nc4ccc(N5CCN(C6COC6)CC5)cc4)n3)cc2C#N)[C@H](F)CN1C(=O)[C@H]1CCC(=O)N1] | 533 | 1000 | 1000 | 2-(((2S,4S,5R)-5-fluoro-2-methyl-1-((R)-5-oxopyrrolidine-2-carbonyl)piperidin-4-yl)oxy)-5-(4-((4-(4-(oxetan-3-yl)piperazin-1-yl)phenyl)amino)-1,3,5-triazin-2-yl)benzonitrile |
| 412 | 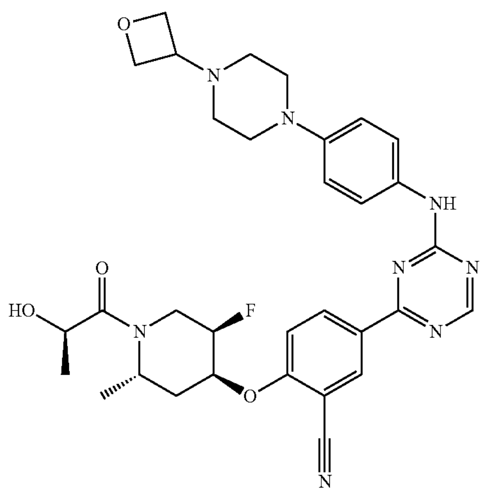 [SMILES: C[C@@H](O)C(=O)N1C[C@@H](F)[C@@H](Oc2ccc(-c3ncnc(Nc4ccc(N5CCN(C6COC6)CC5)cc4)n3)cc2C#N)C[C@@H]1C] | 43 | 202 | 1000 | 2-(((2S,4S,5R)-5-fluoro-1-((R)-2-hydroxypropanoyl)-2-methylpiperidin-4-yl)oxy)-5-(4-((4-(4-(oxetan-3-yl)piperazin-1-yl)phenyl)amino)-1,3,5-triazin-2-yl)benzonitrile |
| 413 | 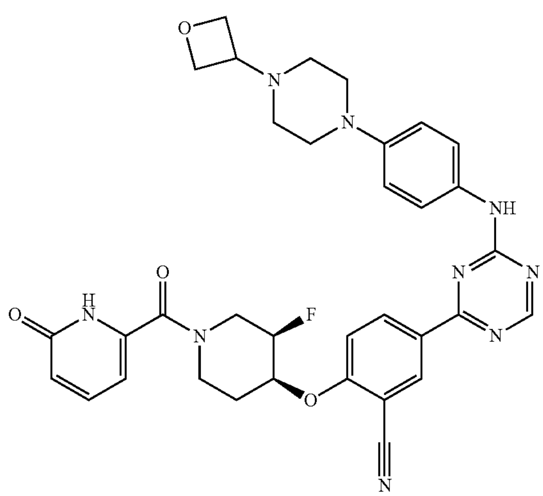 [SMILES: N#Cc1cc(-c2ncnc(Nc3ccc(N4CCN(C5COC5)CC4)cc3)n2)ccc1O[C@H]1CCN(C(=O)c2cccc(=O)[nH]2)C[C@H]1F] | 3 | 2 | 109 | 2-(((3R,4S)-3-fluoro-1-(6-oxo-1,6-dihydropyridine-2-carbonyl)piperidin-4-yl)oxy)-5-(4-((4-(4-(oxetan-3-yl)piperazin-1-yl)phenyl)amino)-1,3,5-triazin-2-yl)benzonitrile |

TABLE 1-continued

| Ex. | Structure | TBK1 IC50 | IKKe IC50 | JAK2 IC50 | Name |
|---|---|---|---|---|---|
| 414 | 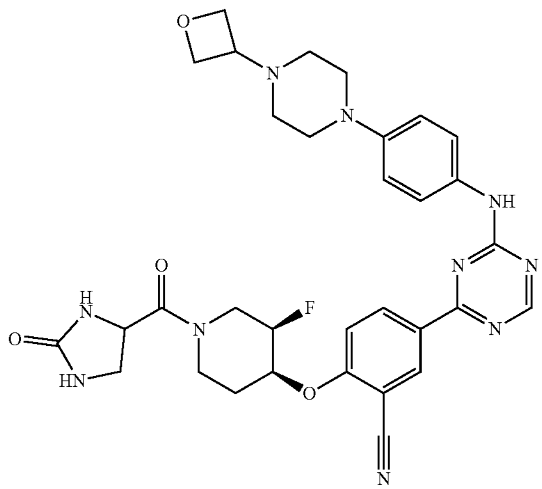 [SMILES: N#Cc1cc(-c2ncnc(Nc3ccc(N4CCN(C5COC5)CC4)cc3)n2)ccc1O[C@H]1CCN(C(=O)C2CNC(=O)N2)C[C@H]1F] | 3 | 3 | 163 | 2-(((3R,4S)-3-fluoro-1-(2-oxoimidazolidine-4-carbonyl)piperidin-4-yl)oxy)-5-(4-((4-(4-(oxetan-3-yl)piperazin-1-yl)phenyl)amino)-1,3,5-triazin-2-yl)benzonitrile |
| 415 | 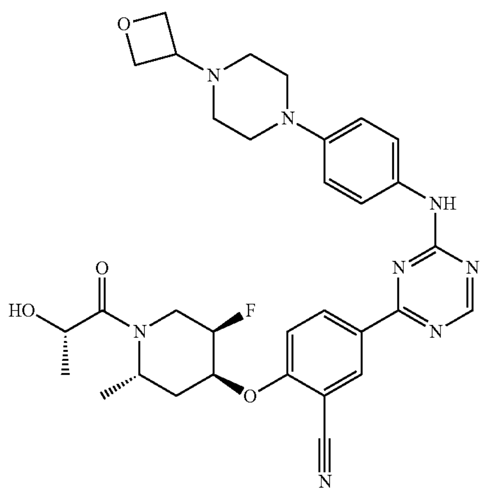 [SMILES: C[C@H](O)C(=O)N1C[C@@H](F)[C@@H](Oc2ccc(-c3ncnc(Nc4ccc(N5CCN(C6COC6)CC5)cc4)n3)cc2C#N)C[C@@H]1C] | 58 | 142 | 1000 | 2-(((2S,4S,5R)-5-fluoro-1-((S)-2-hydroxypropanoyl)-2-methylpiperidin-4-yl)oxy)-5-(4-((4-(4-(oxetan-3-yl)piperazin-1-yl)phenyl)amino)-1,3,5-triazin-2-yl)benzonitrile |
| 416 | 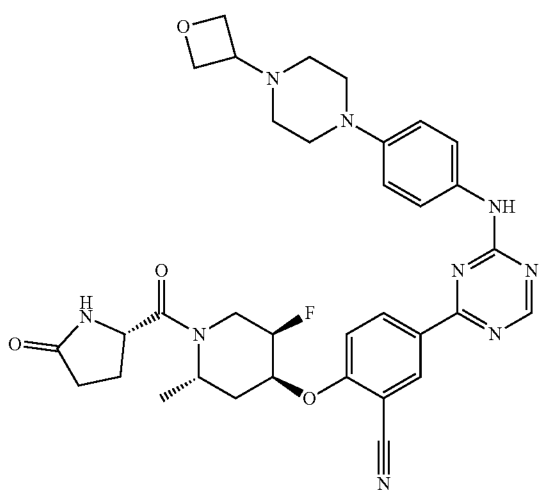 [SMILES: C[C@H]1C[C@H](Oc2ccc(-c3ncnc(Nc4ccc(N5CCN(C6COC6)CC5)cc4)n3)cc2C#N)[C@H](F)CN1C(=O)[C@@H]1CCC(=O)N1] | 64 | 124 | 1000 | 2-(((2S,4S,5R)-5-fluoro-2-methyl-1-((S)-5-oxopyrrolidine-2-carbonyl)piperidin-4-yl)oxy)-5-(4-((4-(4-(oxetan-3-yl)piperazin-1-yl)phenyl)amino)-1,3,5-triazin-2-yl)benzonitrile |

TABLE 1-continued

| Ex. | Structure | TBK1 IC50 | IKKe IC50 | JAK2 IC50 | Name |
|---|---|---|---|---|---|
| 417 | 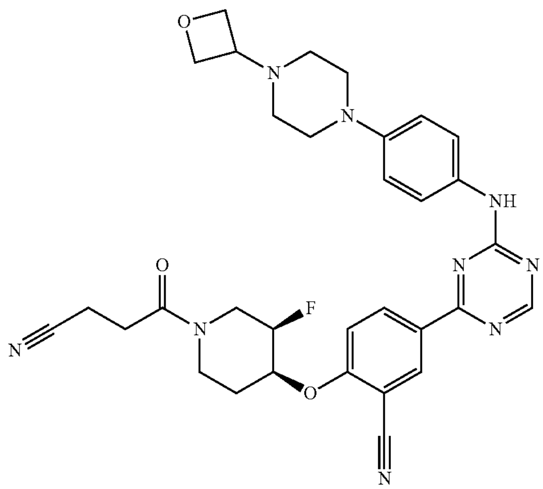 [SMILES: N#CCCC(=O)N1CC[C@H](Oc2ccc(-c3ncnc(Nc4ccc(N5CCN(C6COC6)CC5)cc4)n3)cc2C#N)[C@H](F)C1] | 17 | 79 | 694 | 2-(((3R,4S)-1-(3-cyanopropanoyl)-3-fluoropiperidin-4-yl)oxy)-5-((4-(4-(oxetan-3-yl)piperazin-1-yl)phenyl)amino)-1,3,5-triazin-2-yl)benzonitrile |
| 418 | 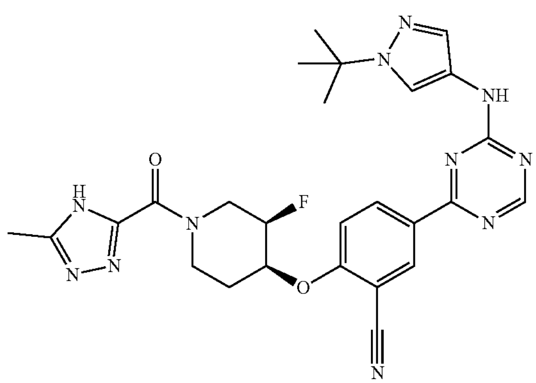 [SMILES: Cc1nnc(C(=O)N2CC[C@H](Oc3ccc(-c4ncnc(Nc5cnn(C(C)(C)C)c5)n4)cc3C#N)[C@H](F)C2)[nH]1] | 4 | 2 | 212 | 5-(4-((1-(tert-butyl)-1H-pyrazol-4-yl)amino)-1,3,5-triazin-2-yl)-2-(((3R,4S)-3-fluoro-1-(5-methyl-4H-1,2,4-triazole-3-carbonyl)piperidin-4-yl)oxy)benzonitrile |
| 419 | 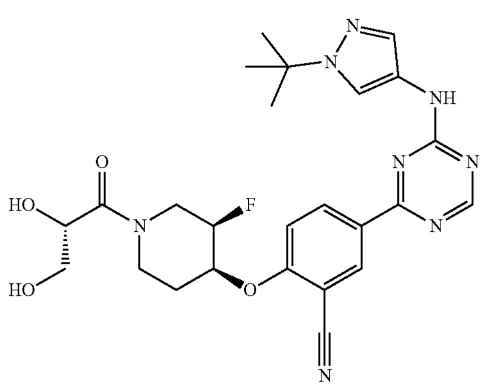 [SMILES: CC(C)(C)n1cc(Nc2ncnc(-c3ccc(O[C@H]4CCN(C(=O)[C@@H](O)CO)C[C@H]4F)c(C#N)c3)n2)cn1] | 2 | 2 | 228 | 5-(4-((1-(tert-butyl)-1H-pyrazol-4-yl)amino)-1,3,5-triazin-2-yl)-2-(((3R,4S)-1-((S)-2,3-dihydroxypropanoyl)-3-fluoropiperidin-4-yl)oxy)benzonitrile |

TABLE 1-continued
| Ex. | Structure | TBK1 IC50 | IKKe IC50 | JAK2 IC50 | Name |
|---|---|---|---|---|---|
| 420 | 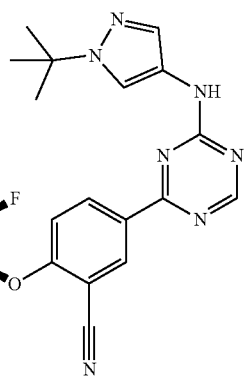 | 2 | 2 | 190 | 5-(4-((1-(tert-butyl)-1H-pyrazol-4-yl)amino)-1,3,5-triazin-2-yl)-2-(((3R,4S)-3-fluoro-1-(2-hydroxyacetyl)piperidin-4-yl)oxy)benzonitrile |
| 421 | 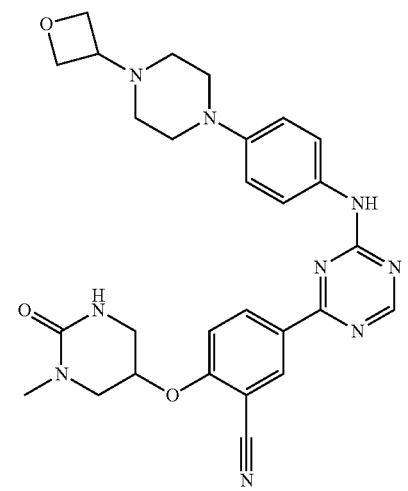 [SMILES: CN1CC(Oc2ccc(-c3ncnc(Nc4ccc(N5CCN(C6COC6)CC5)cc4)n3)cc2C#N)CNC1=O] | 80 | 156 | 60 | 2-((1-methyl-2-oxohexahydropyrimidin-5-yl)oxy)-5-(4-((4-(4-(oxetan-3-yl)piperazin-1-yl)phenyl)amino)-1,3,5-triazin-2-yl)benzonitrile |
| 422 | 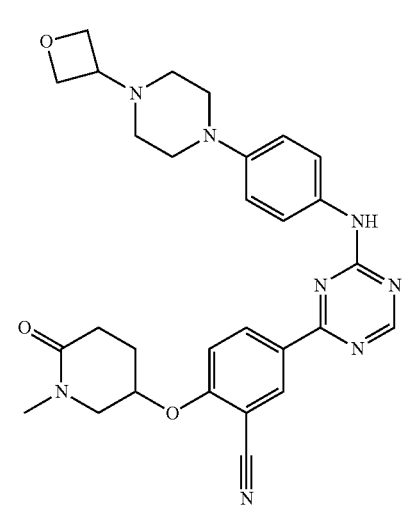 [SMILES: CN1CC(Oc2ccc(-c3ncnc(Nc4ccc(N5CCN(C6COC6)CC5)cc4)n3)cc2C#N)CCC1=O] | 65 | 156 | 849 | 2-((1-methyl-6-oxopiperidin-3-yl)oxy)-5-(4-((4-(4-(oxetan-3-yl)piperazin-1-yl)phenyl)amino)-1,3,5-triazin-2-yl)benzonitrile | ized

TABLE 1-continued

| Ex. | Structure | TBK1 IC50 | IKKe IC50 | JAK2 IC50 | Name |
|---|---|---|---|---|---|
| 423 | 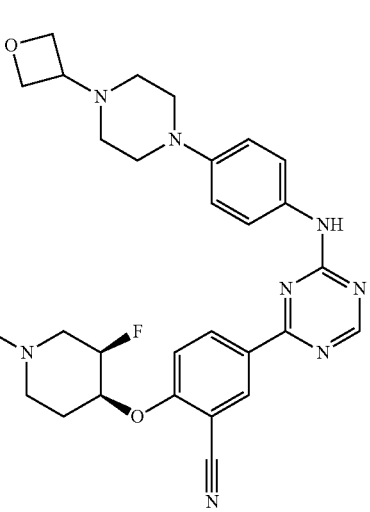 | 16 | 55 | 681 | 2-(((3R,4S)-3-fluoro-1-((R)-3-fluoropyrrolidine-1-carbonyl)piperidin-4-yl)oxy)-5-(4-((4-(4-(oxetan-3-yl)piperazin-1-yl)phenyl)amino)-1,3,5-triazin-2-yl)benzonitrile |
| 424 | 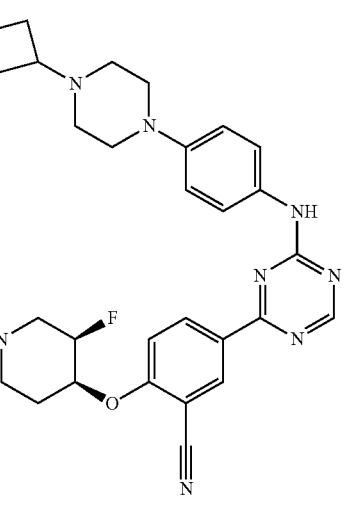 | 6 | 12 | 1000 | 2-(((3R,4S)-3-fluoro-1-(pyrrolidine-1-carbonyl)piperidin-4-yl)oxy)-5-(4-((4-(4-(oxetan-3-yl)piperazin-1-yl)phenyl)amino)-1,3,5-triazin-2-yl)benzonitrile |
| 425 | 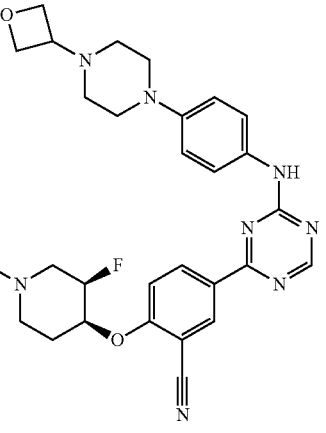 | 7 | 21 | 590 | 2-(((3R,4S)-3-fluoro-1-((R)-3-hydroxypyrrolidine-1-carbonyl)piperidin-4-yl)oxy)-5-((4-(4-(oxetan-3-yl)piperazin-1-yl)phenyl)amino)-1,3,5-triazin-2-yl)benzonitrile |

TABLE 1-continued

| Ex. | Structure | TBK1 IC50 | IKKe IC50 | JAK2 IC50 | Name |
|---|---|---|---|---|---|
| 426 | 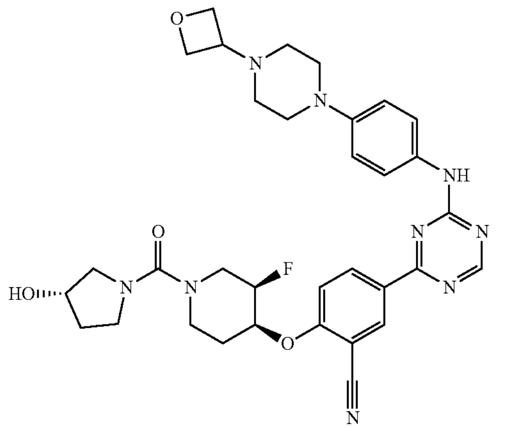 [SMILES: N#Cc1cc(-c2ncnc(Nc3ccc(N4CCN(C5COC5)CC4)cc3)n2)ccc1O[C@H]1CCN(C(=O)N2CC[C@H](O)C2)C[C@H]1F] | 79 | 201 | 1000 | 2-(((3R,4S)-3-fluoro-1-((S)-3-hydroxypyrrolidine-1-carbonyl)piperidin-4-yl)oxy)-5-(4-((4-(4-(oxetan-3-yl)piperazin-1-yl)phenyl)amino)-1,3,5-triazin-2-yl)benzonitrile |
| 427 | 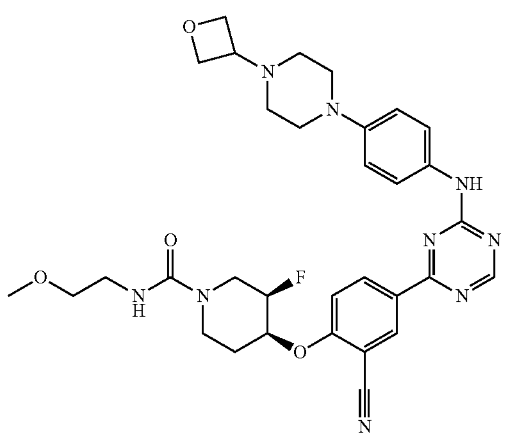 [SMILES: COCCNC(=O)N1CC[C@H](Oc2ccc(-c3ncnc(Nc4ccc(N5CCN(C6COC6)CC5)cc4)n3)cc2C#N)[C@H](F)C1] | 31 | 74 | 1000 | (3R,4S)-4-(2-cyano-4-((4-(4-(oxetan-3-yl)piperazin-1-yl)phenyl)amino)-1,3,5-triazin-2-yl)phenoxy)-3-fluoro-N-(2-methoxyethyl)piperidine-1-carboxamide. |
| 428 | 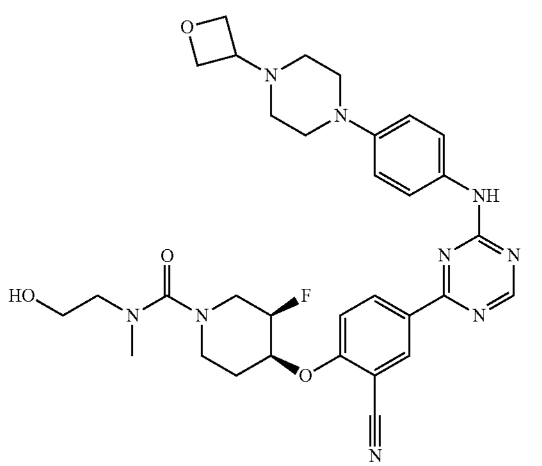 [SMILES: CN(CCO)C(=O)N1CC[C@H](Oc2ccc(-c3ncnc(Nc4ccc(N5CCN(C6COC6)CC5)cc4)n3)cc2C#N)[C@H](F)C1] | 41 | 64 | 1000 | (3R,4S)-4-(2-cyano-4-(4-((4-(4-(oxetan-3-yl)piperazin-1-yl)phenyl)amino)-1,3,5-triazin-2-yl)phenoxy)-3-fluoro-N-(2-hydroxyethyl)-N-methylpiperidine-1-carboxamide |

TABLE 1-continued

| Ex. | Structure | TBK1 IC50 | IKKe IC50 | JAK2 IC50 | Name |
|---|---|---|---|---|---|
| 429 | 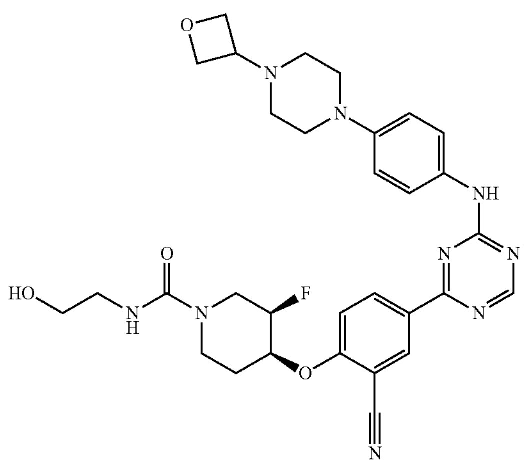 [SMILES: N#Cc1cc(-c2ncnc(Nc3ccc(N4CCN(C5COC5)CC4)cc3)n2)ccc1O[C@H]1CCN(C(=O)NCCO)C[C@H]1F] | 12 | 33 | 601 | (3R,4S)-4-(2-cyano-4-((4-(4-(oxetan-3-yl)piperazin-1-yl)phenyl)amino)-1,3,5-triazin-2-yl)phenoxy)-3-fluoro-N-(2-hydroxyethyl)piperidine-1-carboxamide |
| 430 | 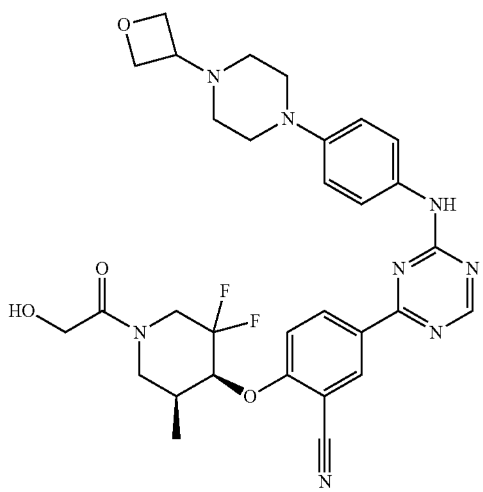 [SMILES: C[C@H]1CN(C(=O)CO)CC(F)(F)[C@H]1Oc1ccc(-c2ncnc(Nc3ccc(N4CCN(C5COC5)CC4)cc3)n2)cc1C#N] | 4 | 2 | 65 | Cis 2-((3,3-difluoro-1-(2-hydroxyacetyl)-5-methylpiperidin-4-yl)oxy)-5-(4-((4-(4-(oxetan-3-yl)piperazin-1-yl)phenyl)amino)-1,3,5-triazin-2-yl)benzonitrile |
| 431 | 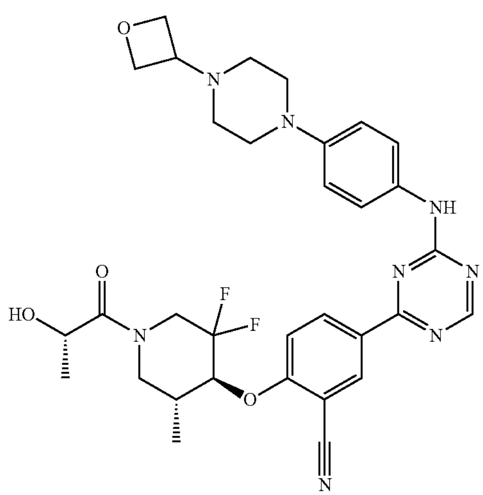 [SMILES: C[C@H](O)C(=O)N1C[C@@H](C)[C@H](Oc2ccc(-c3ncnc(Nc4ccc(N5CCN(C6COC6)CC5)cc4)n3)cc2C#N)C(F)(F)C1] | 11 | 17 | 496 | trans-2-((3,3-difluoro-1-((S)-2-hydroxypropanoyl)-5-methylpiperidin-4-yl)oxy)-5-(4-((4-(4-(oxetan-3-yl)piperazin-1-yl)phenyl)amino)-1,3,5-triazin-2-yl)benzonitrile |

TABLE 1-continued

| Ex. | Structure | TBK1 IC50 | IKKe IC50 | JAK2 IC50 | Name |
|---|---|---|---|---|---|
| 432 | 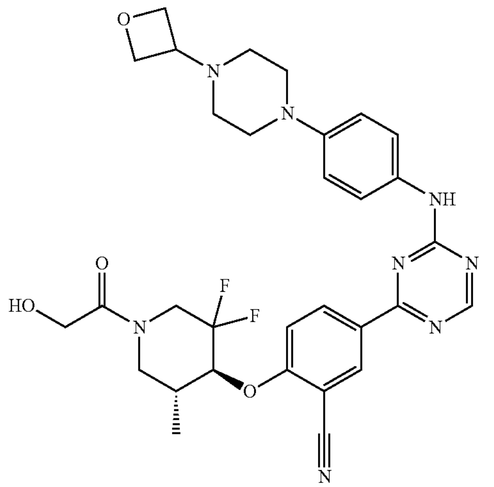 [SMILES: C[C@@H]1CN(C(=O)CO)CC(F)(F)[C@H]1Oc1ccc(-c2ncnc(Nc3ccc(N4CCN(C5COC5)CC4)cc3)n2)cc1C#N] | 5 | 3 | 140 | trans-2-((3,3-difluoro-1-(2-hydroxyacetyl)-5-methylpiperidin-4-yl)oxy)-5-(4-((4-(4-(oxetan-3-yl)piperazin-1-yl)phenyl)amino)-1,3,5-triazin-2-yl)benzonitrile |
| 433 | 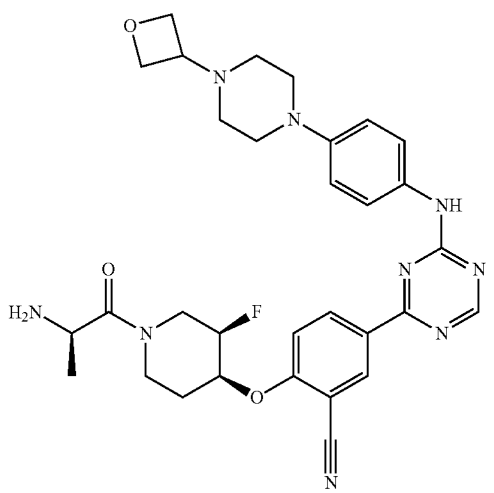 [SMILES: C[C@@H](N)C(=O)N1CC[C@H](Oc2ccc(-c3ncnc(Nc4ccc(N5CCN(C6COC6)CC5)cc4)n3)cc2C#N)[C@H](F)C1] | 76 | 283 | 1000 | 2-(((3R,4S)-1-((R)-2-aminopropanoyl)-3-fluoropiperidin-4-yl)oxy)-5-(4-((4-(4-(oxetan-3-yl)piperazin-1-yl)phenyl)amino)-1,3,5-triazin-2-yl)benzonitrile |
| 434 | 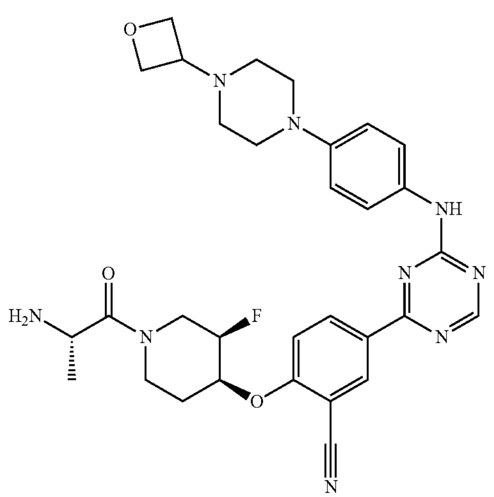 [SMILES: C[C@H](N)C(=O)N1CC[C@H](Oc2ccc(-c3ncnc(Nc4ccc(N5CCN(C6COC6)CC5)cc4)n3)cc2C#N)[C@H](F)C1] | 20 | 42 | 865 | 2-(((3R,4S)-1-((R)-2-aminopropanoyl)-3-fluoropiperidin-4-yl)oxy)-5-(4-((4-(4-(oxetan-3-yl)piperazin-1-yl)phenyl)amino)-1,3,5-triazin-2-yl)benzonitrile |

TABLE 1-continued

| Ex. | Structure | TBK1 IC50 | IKKe IC50 | JAK2 IC50 | Name |
|---|---|---|---|---|---|
| 435 | 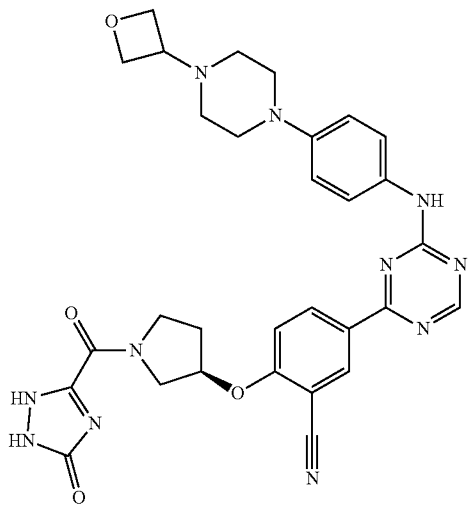 [SMILES: N#Cc1cc(-c2ncnc(Nc3ccc(N4CCN(C5COC5)CC4)cc3)n2)ccc1O[C@@H]1CCN(C(=O)c2nc(=O)[nH][nH]2)C1] | 411 | 292 | 1000 | (R)-5-(4-((4-(4-(oxetan-3-yl)piperazin-1-yl)phenyl)amino)-1,3,5-triazin-2-yl)-2-((1-(5-oxo-2,5-dihydro-1H-1,2,4-triazole-3-carbonyl)pyrrolidin-3-yl)oxy)benzonitrile |
| 436 | 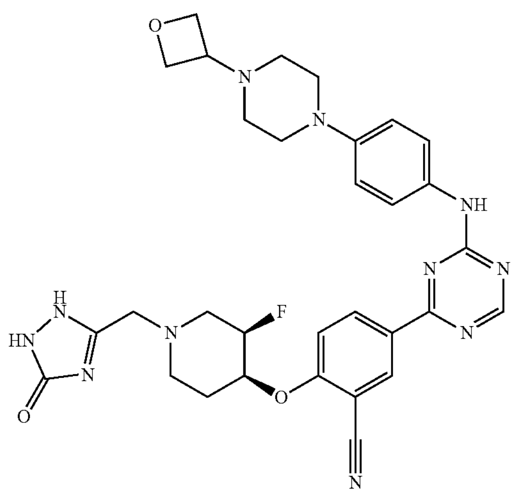 [SMILES: N#Cc1cc(-c2ncnc(Nc3ccc(N4CCN(C5COC5)CC4)cc3)n2)ccc1O[C@H]1CCN(Cc2nc(=O)[nH][nH]2)C[C@H]1F] | 27 | 99 | 156 | 2-(((3R,4S)-3-fluoro-1-((5-oxo-2,5-dihydro-1H-1,2,4-triazol-3-yl)methyl)piperidin-4-yl)oxy)-5-(4-((4-(4-oxetan-3-yl)piperazin-1-yl)phenyl)amino)-1,3,5-triazin-2-yl)benzonitrile |
| 437 | 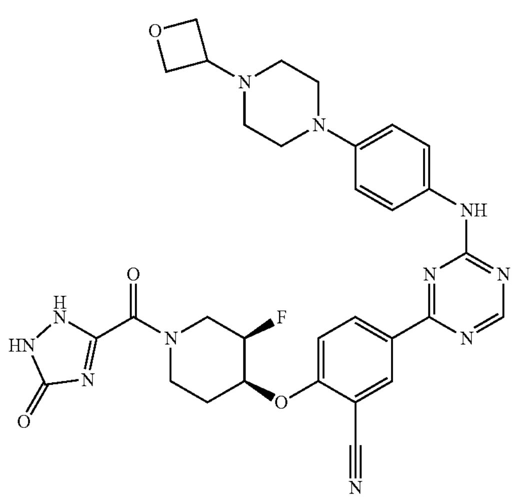 [SMILES: N#Cc1cc(-c2ncnc(Nc3ccc(N4CCN(C5COC5)CC4)cc3)n2)ccc1O[C@H]1CCN(C(=O)c2nc(=O)[nH][nH]2)C[C@H]1F] | 4 | 2 | 111 | 2-(((3R,4S)-3-fluoro-1-(5-oxo-2,5-dihydro-1H-1,2,4-triazole-3-carbonyl)piperidin-4-yl)oxy)-5-(4-((4-(4-(oxetan-3-yl)piperazin-1-yl)phenyl)amino)-1,3,5-triazin-2-yl)benzonitrile |

TABLE 1-continued

| Ex. | Structure | TBK1 IC50 | IKKe IC50 | JAK2 IC50 | Name |
|---|---|---|---|---|---|
| 438 | 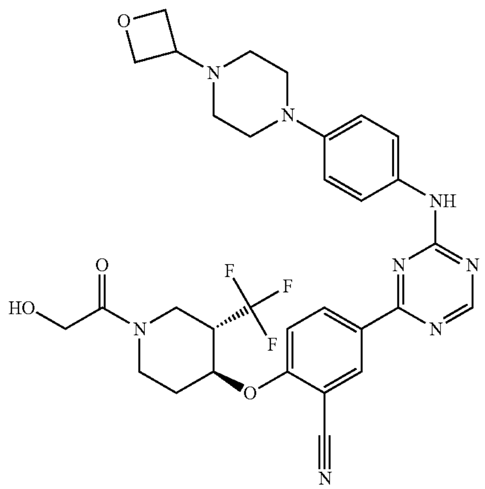 [SMILES: N#Cc1cc(-c2ncnc(Nc3ccc(N4CCN(C5COC5)CC4)cc3)n2)ccc1O[C@H]1CCN(C(=O)CO)C[C@@H]1C(F)(F)F] | 6 | 8 | 15 | Trans-2-((1-(2-hydroxyacetyl)-3-(trifluoromethyl)piperidin-4-yl)oxy)-5-(4-((4-(4-(oxetan-3-yl)piperazin-1-yl)phenyl)amino)-1,3,5-triazin-2-yl)benzonitrile |
| 439 | 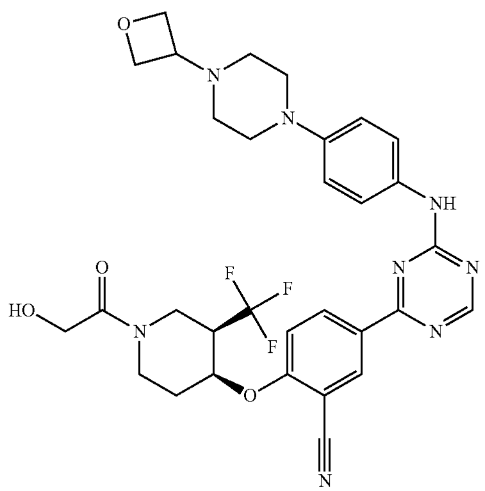 [SMILES: N#Cc1cc(-c2ncnc(Nc3ccc(N4CCN(C5COC5)CC4)cc3)n2)ccc1O[C@H]1CCN(C(=O)CO)C[C@H]1C(F)(F)F] | 9 | 12 | 21 | cis-2-((1-(2-hydroxyacetyl)-3-(trifluoromethyl)piperidin-4-yl)oxy)-5-(4-((4-(4-(oxetan-3-yl)piperazin-1-yl)phenyl)amino)-1,3,5-triazin-2-yl)benzonitrile |
| 440 | 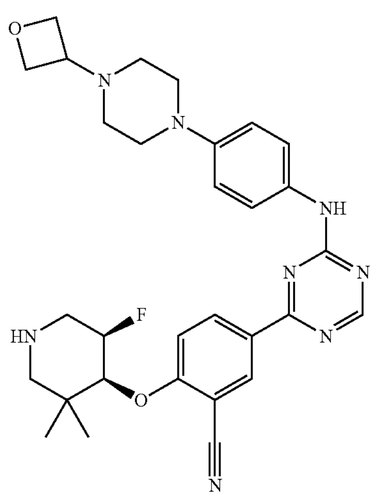 [SMILES: CC1(C)CNC[C@@H](F)[C@H]1Oc1ccc(-c2ncnc(Nc3ccc(N4CCN(C5COC5)CC4)cc3)n2)cc1C#N] | 22 | 51 | 110 | 2-(((4S,5R)-5-fluoro-3,3-dimethylpiperidin-4-yl)oxy)-5-(4-((4-(4-(oxetan-3-yl)piperazin-1-yl)phenyl)amino)-1,3,5-triazin-2-yl)benzonitrile |

TABLE 1-continued

| Ex. | Structure | TBK1 IC50 | IKKe IC50 | JAK2 IC50 | Name |
|---|---|---|---|---|---|
| 441 | 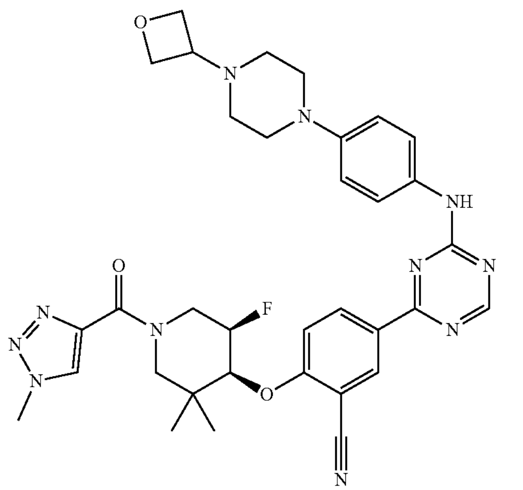 [SMILES: Cn1cc(C(=O)N2C[C@@H](F)[C@@H](Oc3ccc(-c4ncnc(Nc5ccc(N6CCN(C7COC7)CC6)cc5)n4)cc3C#N)C(C)(C)C2)nn1] | 3 | 2 | 88 | 2-(((4S,5R)-5-fluoro-3,3-dimethyl-1-(1-methyl-1H-1,2,3-triazole-4-carbonyl)piperidin-4-yl)oxy)-5-(4-((4-(4-(oxetan-3-yl)piperazin-1-yl)phenyl)amino)-1,3,5-triazin-2-yl)benzonitrile |
| 442 | 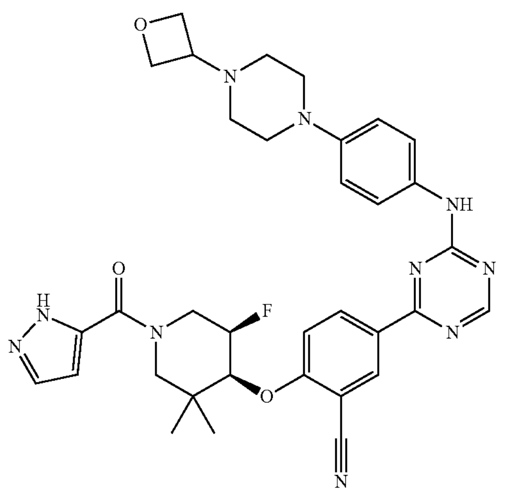 [SMILES: CC1(C)CN(C(=O)c2ccn[nH]2)C[C@@H](F)[C@H]1Oc1ccc(-c2ncnc(Nc3ccc(N4CCN(C5COC5)CC4)cc3)n2)cc1C#N] | 3 | 3 | 125 | 2-(((4S,5R)-5-fluoro-3,3-dimethyl-1-(1H-pyrazole-5-carbonyl)piperidin-4-yl)oxy)-5-(4-((4-(4-(oxetan-3-yl)piperazin-1-yl)phenyl)amino)-1,3,5-triazin-2-yl)benzonitrile |
| 443 | 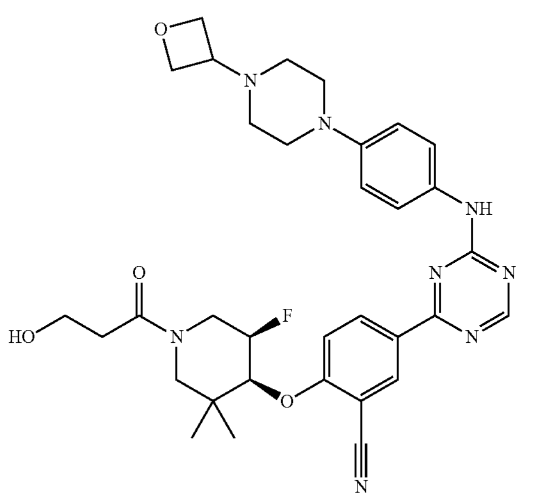 [SMILES: CC1(C)CN(C(=O)CCO)C[C@@H](F)[C@H]1Oc1ccc(-c2ncnc(Nc3ccc(N4CCN(C5COC5)CC4)cc3)n2)cc1C#N] | 3 | 6 | 102 | 2-(((4S,5R)-5-fluoro-1-(3-hydroxypropanoyl)-3,3-dimethylpiperidin-4-yl)oxy)-5-(4-((4-(4-oxetan-3-yl)piperazin-1-yl)phenyl)amino)-1,3,5-triazin-2-yl)benzonitrile |

TABLE 1-continued

| Ex. | Structure | TBK1 IC50 | IKKe IC50 | JAK2 IC50 | Name |
|---|---|---|---|---|---|
| 444 | 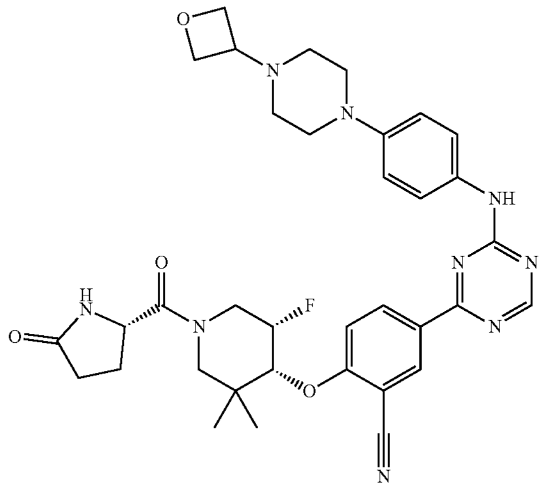 [SMILES: CC1(C)CN(C(=O)[C@@H]2CCC(=O)N2)C[C@H](F)[C@@H]1Oc1ccc(-c2ncnc(Nc3ccc(N4CCN(C5COC5)CC4)cc3)n2)cc1C#N] | 27 | 88 | 476 | 2-(((4R,5S)-5-fluoro-3,3-dimethyl-1-((S)-5-oxopyrrolidine-2-carbonyl)piperidin-4-yl)oxy)-5-(4-((4-(4-(oxetan-3-yl)piperazin-1-yl)phenyl)amino)-1-3,5-triazin-2-yl)benzonitrile |
| 445 | 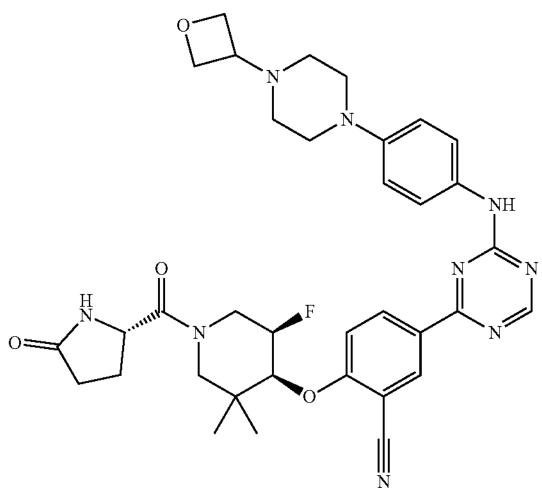 [SMILES: CC1(C)CN(C(=O)[C@@H]2CCC(=O)N2)C[C@@H](F)[C@H]1Oc1ccc(-c2ncnc(Nc3ccc(N4CCN(C5COC5)CC4)cc3)n2)cc1C#N] | 5 | 5 | 90 | 2-(((4S,5R)-5-fluoro-3,3-dimethyl-1-((S)-5-oxopyrrolidine-2-carbonyl)piperidin-4-yl)oxy)-5-(4-((4-(4-(oxetan-3-yl)piperazin-1-yl)phenyl)amino)-1,3,5-triazin-2-yl)benzonitrile |
| 446 | 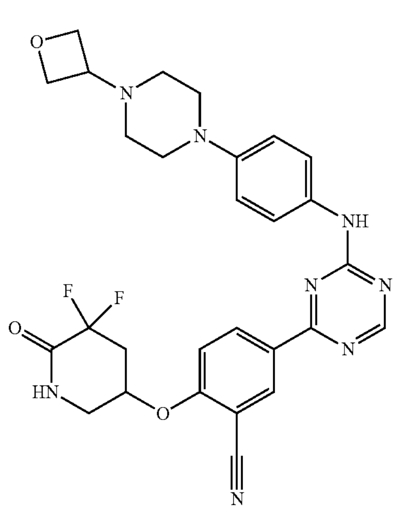 [SMILES: N#Cc1cc(-c2ncnc(Nc3ccc(N4CCN(C5COC5)CC4)cc3)n2)ccc1OC1CNC(=O)C(F)(F)C1] | 48 | 33 | 153 | 2-((5,5-difluoro-6-oxopiperidin-3-yl)oxy)-5-(4-((4-(4-(oxetan-3-yl)piperazin-1-yl)phenyl)amino)-1,3,5-triazin-2-yl)benzonitrile |

TABLE 1-continued

| Ex. | Structure | TBK1 IC50 | IKKe IC50 | JAK2 IC50 | Name |
|---|---|---|---|---|---|
| 447 | 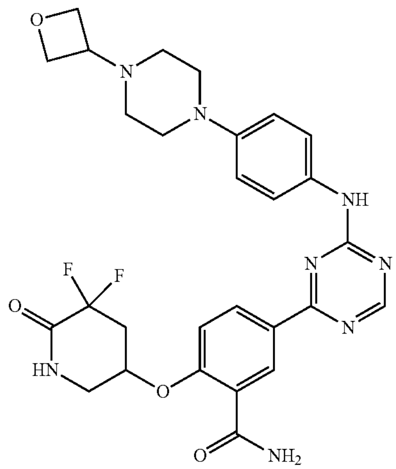 [SMILES: NC(=O)c1cc(-c2ncnc(Nc3ccc(N4CCN(C5COC5)CC4)cc3)n2)ccc1OC1CNC(=O)C(F)(F)C1] | 65 | 197 | 15 | 2-((5,5-difluoro-6-oxopiperidin-3-yl)oxy)-5-(4-((4-(4-(oxetan-3-yl)piperazin-1-yl)phenyl)amino)-1,3,5-triazin-2-yl)benzamide |
| 448 | 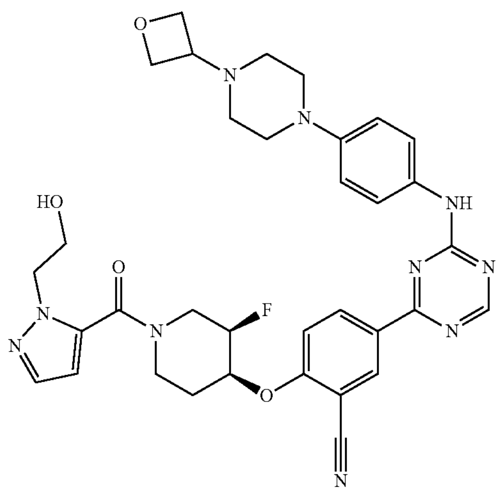 [SMILES: N#Cc1cc(-c2ncnc(Nc3ccc(N4CCN(C5COC5)CC4)cc3)n2)ccc1O[C@H]1CCN(C(=O)c2ccnn2CCO)C[C@H]1F] | 54 | 84 | 213 | 2-(((3R,4S)-3-fluoro-1-(1-(2-hydroxyethyl)-1H-pyrazole-5-carbonyl)piperidin-4-yl)oxy)-5-(4-((4-(4-(oxetan-3-yl)piperazin-1-yl)phenyl)amino)-1,3,5-triazin-2-yl)benzonitrile |
| 449 | 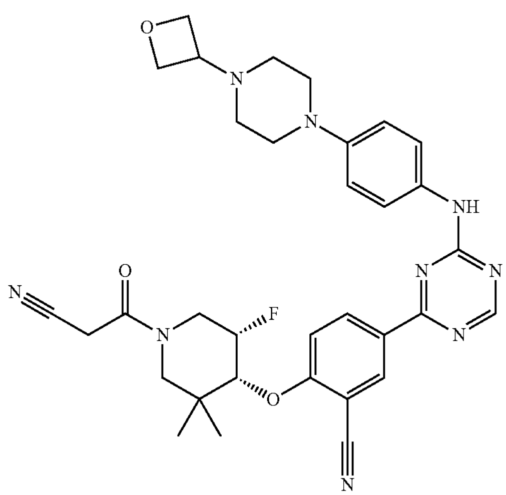 [SMILES: CC1(C)CN(C(=O)CC#N)C[C@H](F)[C@@H]1Oc1ccc(-c2ncnc(Nc3ccc(N4CCN(C5COC5)CC4)cc3)n2)cc1C#N] | 35 | 59 | 443 | 2-(((4R,5S)-1-(2-cyanoacetyl)-5-fluoro-3,3-dimethylpiperidin-4-yl)oxy)-5-(4-((4-(4-(oxetan-3-yl)piperazin-1-yl)phenyl)amino)-1,3,5-triazin-2-yl)benzonitrile |

TABLE 1-continued

| Ex. | Structure | TBK1 IC50 | IKKe IC50 | JAK2 IC50 | Name |
|---|---|---|---|---|---|
| 450 | 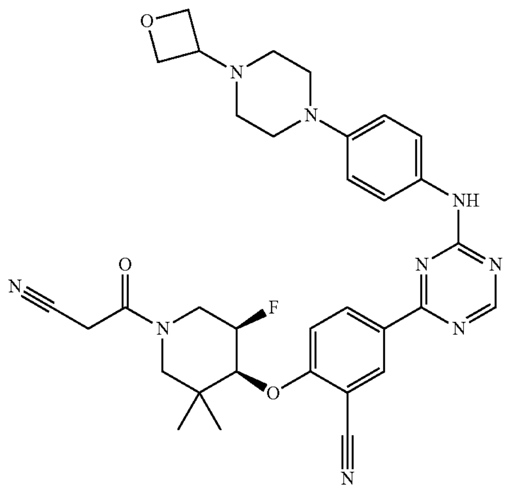 [SMILES: CC1(C)CN(C(=O)CC#N)C[C@@H](F)[C@H]1Oc1ccc(-c2ncnc(Nc3ccc(N4CCN(C5COC5)CC4)cc3)n2)cc1C#N] | 3 | 3 | 48 | 2-(((4S,5R)-1-(2-cyanoacetyl)-5-fluoro-3,3-dimethylpiperidin-4-yl)oxy)-5-(4-((4-(4-(oxetan-3-yl)piperazin-1-yl)phenyl)amino)-1,3,5-triazin-2-yl)benzonitrile |
| 451 | 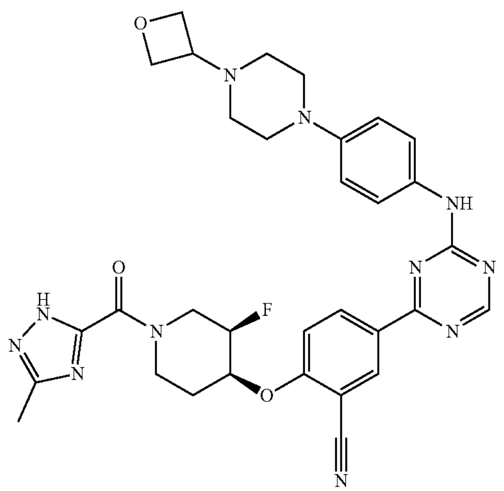 [SMILES: Cc1n[nH]c(C(=O)N2CC[C@H](Oc3ccc(-c4ncnc(Nc5ccc(N6CCN(C7COC7)CC6)cc5)n4)cc3C#N)[C@H](F)C2)n1] | 1 | 1 | 90 | 2-(((3R,4S)-3-fluoro-1-(3-methyl-1H-1,2,4-triazole-5-carbonyl)piperidin-4-yl)oxy)-5-(4-((4-(4-(oxetan-3-yl)piperazin-1-yl)phenyl)amino)-1,3,5-triazin-2-yl)benzonitrile |
| 452 | 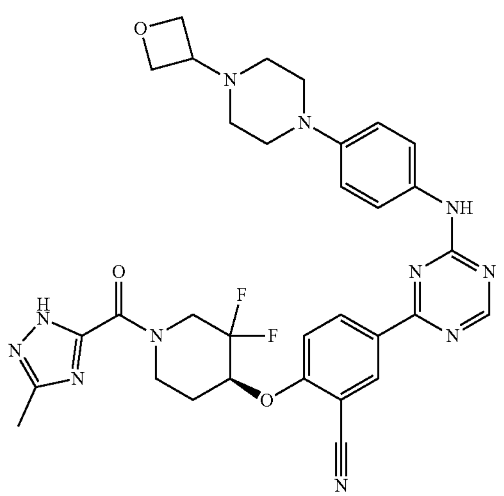 [SMILES: Cc1n[nH]c(C(=O)N2CC[C@H](Oc3ccc(-c4ncnc(Nc5ccc(N6CCN(C7COC7)CC6)cc5)n4)cc3C#N)C(F)(F)C2)n1] | 3 | 1 | 23 | (S)-2-((3,3-difluoro-1-(3-methyl-1H-1,2,4-triazole-5-carbonyl)piperidin-4-yl)oxy)-5-(4-((4-(4-(oxetan-3-yl)piperazin-1-yl)phenyl)amino)-1,3,5-triazin-2-yl)benzonitrile. |

TABLE 1-continued

| Ex. | Structure | TBK1 IC50 | IKKe IC50 | JAK2 IC50 | Name |
|---|---|---|---|---|---|
| 453 | 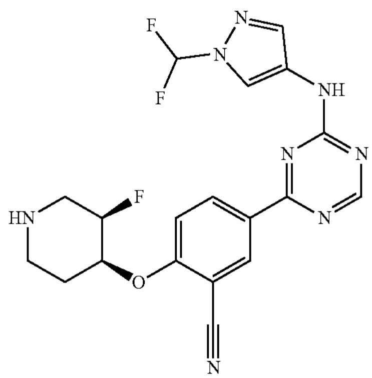 [SMILES: N#Cc1cc(-c2ncnc(Nc3cnn(C(F)F)c3)n2)ccc1O[C@H]1CCNC[C@H]1F] | 359 | 577 | 1000 | 5-(4-((1-(difluoromethyl)-1H-pyrazol-4-yl)amino)-1,3,5-triazin-2-yl)-2-(((3R,4S)-3-fluoropiperidin-4-yl)oxy)benzonitrile |
| 454 | 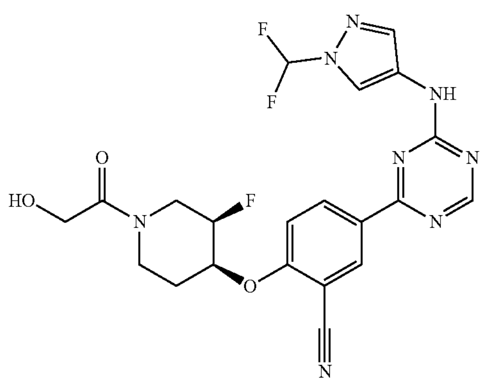 [SMILES: N#Cc1cc(-c2ncnc(Nc3cnn(C(F)F)c3)n2)ccc1O[C@H]1CCN(C(=O)CO)C[C@H]1F] | 5 | 5 | 621 | 5-(4-((1-(difluoromethyl)-1H-pyrazol-4-yl)amino)-1,3,5-triazin-2-yl)-2-(((3R,4S)-3-fluoro-1-(2-hydroxyacetyl)piperidin-4-yl)oxy)benzonitrile |
| 455 | 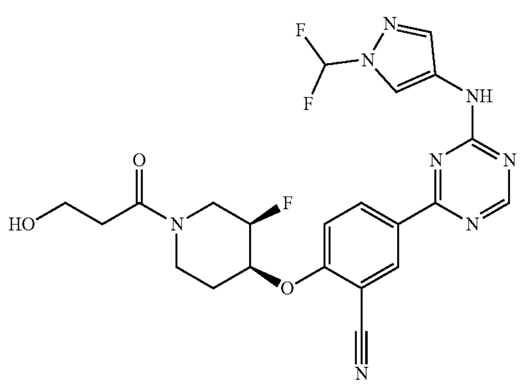 [SMILES: N#Cc1cc(-c2ncnc(Nc3cnn(C(F)F)c3)n2)ccc1O[C@H]1CCN(C(=O)CCO)C[C@H]1F] | 57 | 95 | 1000 | 5-(4-((1-(difluoromethyl)-1H-pyrazol-4-yl)amino)-1,3,5-triazin-2-yl)-2-(((3R,4S)-3-fluoro-1-(3-hydroxypropanoyl)piperidin-4-yl)oxy)benzonitrile |
| 456 | 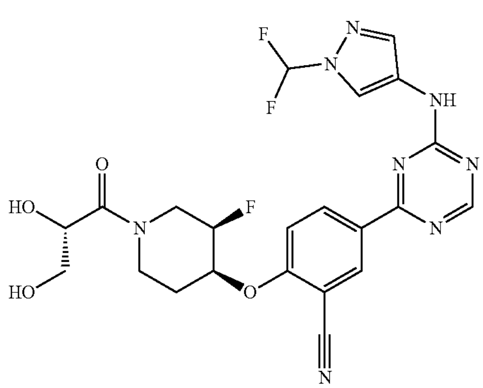 [SMILES: N#Cc1cc(-c2ncnc(Nc3cnn(C(F)F)c3)n2)ccc1O[C@H]1CCN(C(=O)[C@@H](O)CO)C[C@H]1F] | 4 | 7 | 966 | 5-(4-((1-(difluoromethyl)-1H-pyrazol-4-yl)amino)-1,3,5-triazin-2-yl)-2-(((3R,4S)-1-((S)-2,3-dihydroxypropanoyl)-3-fluoropiperidin-4-yl)oxy)benzonitrile |

TABLE 1-continued

| Ex. | Structure | TBK1 IC50 | IKKe IC50 | JAK2 IC50 | Name |
|---|---|---|---|---|---|
| 457 | 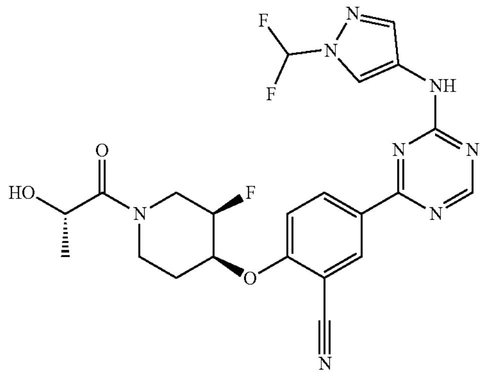 [SMILES: C[C@H](O)C(=O)N1CC[C@H](Oc2ccc(-c3ncnc(Nc4cnn(C(F)F)c4)n3)cc2C#N)[C@H](F)C1] | 13 | 20 | 1000 | 5-(4-((1-(difluoromethyl)-1H-pyrazol-4-yl)amino)-1,3,5-triazin-2-yl)-2-(((3R,4S)-3-fluoro-1-((S)-2-hydroxypropanoyl)piperidin-4-yl)oxy)benzonitrile |
| 458 | 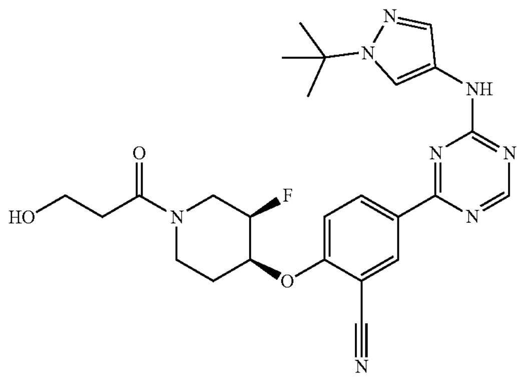 [SMILES: CC(C)(C)n1cc(Nc2ncnc(-c3ccc(O[C@H]4CCN(C(=O)CCO)C[C@H]4F)c(C#N)c3)n2)cn1] | 23 | 61 | 223 | 5-(4-((1-(tert-butyl)-1H-pyrazol-4-yl)amino)-1,3,5-triazin-2-yl)-2-(((3R,4S)-3-fluoro-1-(3-hydroxypropanoyl)piperidin-4-yl)oxy)benzonitrile |
| 459 | 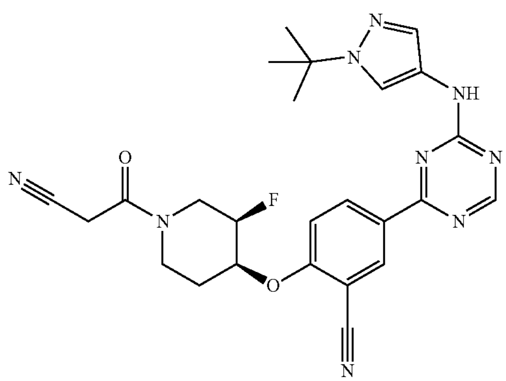 [SMILES: CC(C)(C)n1cc(Nc2ncnc(-c3ccc(O[C@H]4CCN(C(=O)CC#N)C[C@H]4F)c(C#N)c3)n2)cn1] | 11 | 22 | 108 | 5-(4-((1-(tert-butyl)-1H-pyrazol-4-yl)amino)-1,3,5-triazin-2-yl)-2-(((3R,4S)-1-(2-cyanoacetyl)-3-fluoropiperidin-4-yl)oxy)benzonitrile |
| 460 | 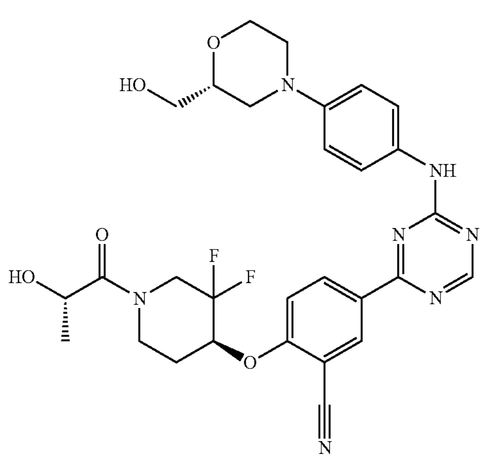 [SMILES: C[C@H](O)C(=O)N1CC[C@H](Oc2ccc(-c3ncnc(Nc4ccc(N5CCO[C@@H](CO)C5)cc4)n3)cc2C#N)C(F)(F)C1] | 2 | 1 | 131 | 2-(((S)-3,3-difluoro-1-((S)-2-hydroxypropanoyl)piperidin-4-yl)oxy)-5-(4-((4-((R)-2-(hydroxymethyl)morpholino)phenyl)amino)-1,3,5-triazin-2-yl)benzonitrile |

TABLE 1-continued

| Ex. | Structure | TBK1 IC50 | IKKe IC50 | JAK2 IC50 | Name |
|---|---|---|---|---|---|
| 461 | 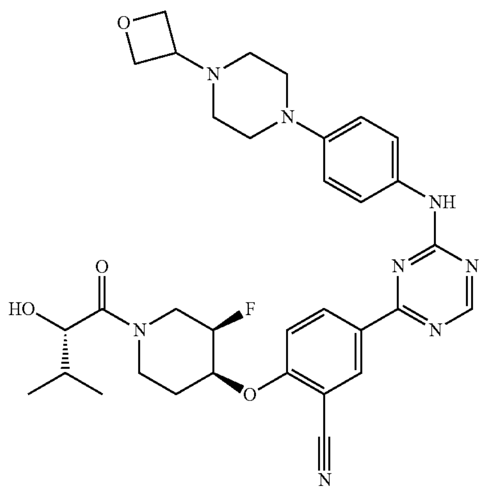 [SMILES: CC(C)[C@H](O)C(=O)N1CC[C@H](Oc2ccc(-c3ncnc(Nc4ccc(N5CCN(C6COC6)CC5)cc4)n3)cc2C#N)[C@H](F)C1] | 16 | 63 | 930 | 2-(((3R,4S)-3-fluoro-1-((S)-2-hydroxy-3-methylbutanoyl)piperidin-4-yl)oxy)-5-(4-((4-(4-(oxetan-3-yl)piperazin-1-yl)phenyl)amino)-1,3,5-triazin-2-yl)benzonitrile |
| 462 | 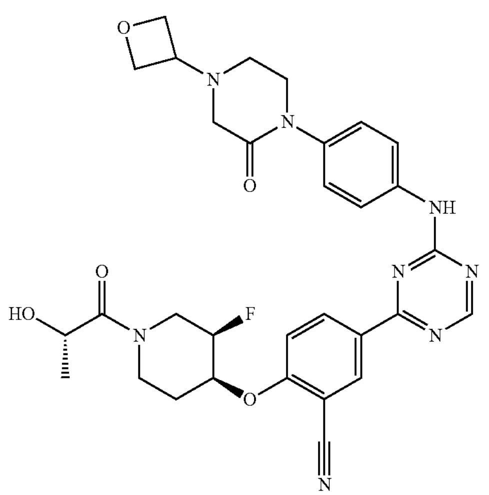 [SMILES: C[C@H](O)C(=O)N1CC[C@H](Oc2ccc(-c3ncnc(Nc4ccc(N5CCN(C6COC6)CC5=O)cc4)n3)cc2C#N)[C@H](F)C1] | 3 | 4 | 1000 | 2-(((3R,4S)-3-fluoro-1-((S)-2-hydroxypropanoyl)piperidin-4-yl)oxy)-5-(4-((4-(4-(oxetan-3-yl)-2-oxopiperazin-1-yl)phenyl)amino)-1,3,5-triazin-2-yl)benzonitrile. |
| 463 | 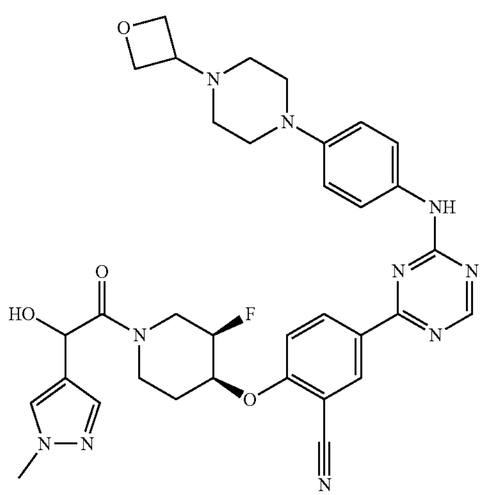 [SMILES: Cn1cc(C(O)C(=O)N2CC[C@H](Oc3ccc(-c4ncnc(Nc5ccc(N6CCN(C7COC7)CC6)cc5)n4)cc3C#N)[C@H](F)C2)cn1] | 30 | 68 | 272 | 2-(((3R,4S)-3-fluoro-1-(2-hydroxy-2-(1-methyl-1H-pyrazol-4-yl)acetyl)piperidin-4-yl)oxy)-5-(4-((4-(4-(oxetan-3-yl)piperazin-1-yl)phenyl)amino)-1,3,5-triazin-2-yl)benzonitrile |

TABLE 1-continued

| Ex. | Structure | TBK1 IC50 | IKKe IC50 | JAK2 IC50 | Name |
|---|---|---|---|---|---|
| 464 | 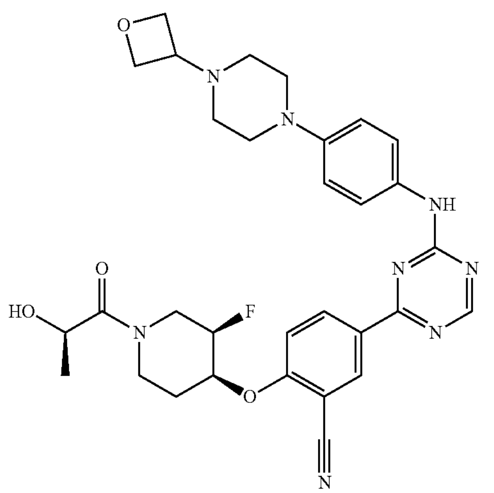 [SMILES: C[C@@H](O)C(=O)N1CC[C@H](Oc2ccc(-c3ncnc(Nc4ccc(N5CCN(C6COC6)CC5)cc4)n3)cc2C#N)[C@H](F)C1] | 8 | 19 | 332 | 2-(((3R,4S)-3-fluoro-1-(((R)-2-hydroxypropanoyl)piperidin-4-yl)oxy)-5-(4-((4-(4-(oxetan-3-yl)piperazin-1-yl)phenyl)amino)-1,3,5-triazin-2-yl)benzonitrile |
| 465 | 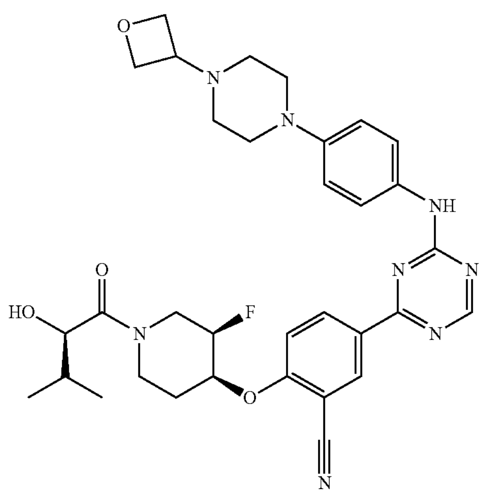 [SMILES: CC(C)[C@@H](O)C(=O)N1CC[C@H](Oc2ccc(-c3ncnc(Nc4ccc(N5CCN(C6COC6)CC5)cc4)n3)cc2C#N)[C@H](F)C1] | 146 | 364 | 706 | 2-(((3R,4S)-3-fluoro-1-((R)-2-hydroxy-3-methylbutanoyl)piperidin-4-yl)oxy)-5-(4-((4-(4-(oxetan-3-yl)piperazin-1-yl)phenyl)amino)-1,3,5-triazin-2-yl)benzonitrile |
| 466 | 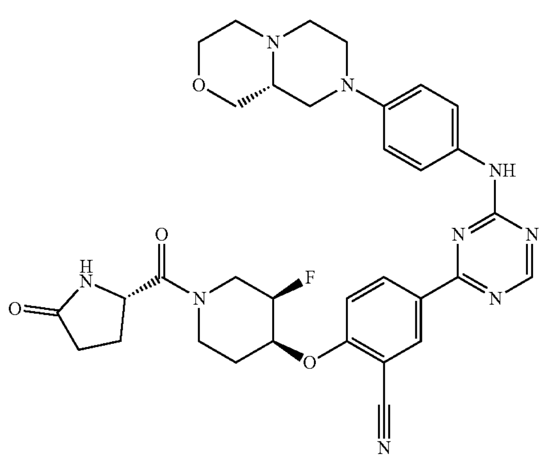 [SMILES: N#Cc1cc(-c2ncnc(Nc3ccc(N4CCN5CCOC[C@H]5C4)cc3)n2)ccc1O[C@H]1CCN(C(=O)[C@@H]2CCC(=O)N2)C[C@H]1F] | 4 | 5 | 422 | 2-(((3R,4S)-3-fluoro-1-((S)-5-oxopyrrolidine-2-carbonyl)piperidin-4-yl)oxy)-5-(4-((4-((R)-hexahydropyrazino[2,1-c][1,4]oxazin-8(1H)-yl)phenyl)amino)-1,3,5-triazin-2-yl)benzonitrile |

TABLE 1-continued

| Ex. | Structure | TBK1 IC50 | IKKe IC50 | JAK2 IC50 | Name |
|---|---|---|---|---|---|
| 467 | 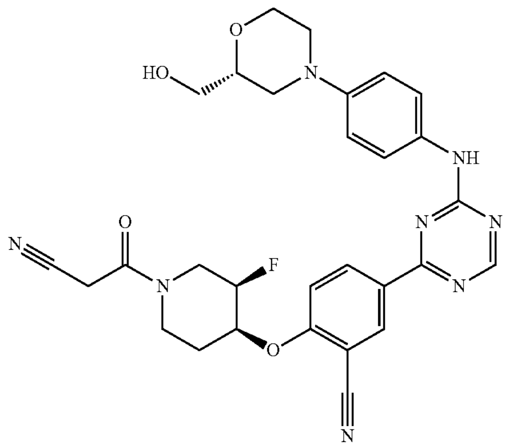 [SMILES: N#CCC(=O)N1CC[C@H](Oc2ccc(-c3ncnc(Nc4ccc(N5CCO[C@@H](CO)C5)cc4)n3)cc2C#N)[C@H](F)C1] | 4 | 4 | 171 | 2-(((3R,4S)-1-(2-cyanoacetyl)-3-fluoropiperidin-4-yl)oxy)-5-(4-((4-((R)-2-(hydroxymethyl)morpholino)phenyl)amino)-1,3,5-triazin-2-yl)benzonitrile |
| 468 | 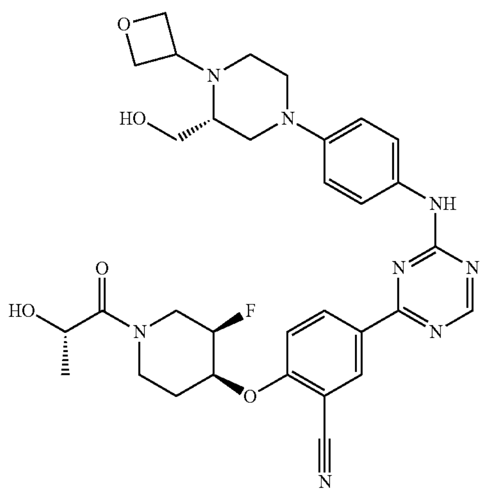 [SMILES: C[C@H](O)C(=O)N1CC[C@H](Oc2ccc(-c3ncnc(Nc4ccc(N5CCN(C6COC6)[C@@H](CO)C5)cc4)n3)cc2C#N)[C@H](F)C1] | 3 | 2 | 486 | 2-(((3R,4S)-3-fluoro-1-((S)-2-hydroxypropanoyl)piperidin-4-yl)oxy)-5-4-((R)-3-(hydroxymethyl)-4-(oxetan-3-yl)piperazin-1-yl)phenyl)amino)-1,3,5-triazin-2-yl)benzonitrile |
| 469 | 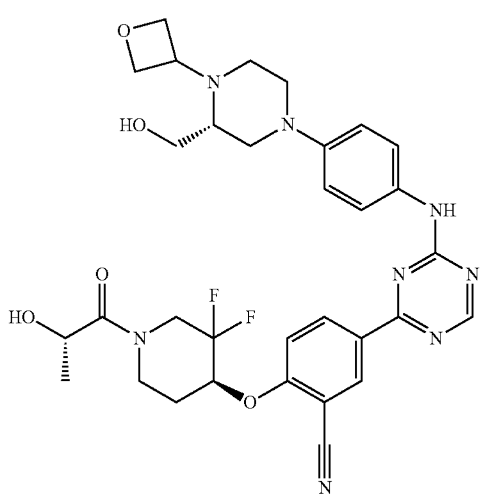 [SMILES: C[C@H](O)C(=O)N1CC[C@H](Oc2ccc(-c3ncnc(Nc4ccc(N5CCN(C6COC6)[C@@H](CO)C5)cc4)n3)cc2C#N)C(F)(F)C1] | 2 | 1 | 197 | 2-(((S)-3,3-difluoro-1-((S)-2-hydroxypropanoyl)piperidin-4-yl)oxy)-5-(4-((4-((R)-3-(hydroxymethyl)-4-(oxetan-3-yl)piperazin-1-yl)phenyl)amino)-1,3,5-triazin-2-yl)benzonitrile |

TABLE 1-continued

| Ex. | Structure | TBK1 IC50 | IKKe IC50 | JAK2 IC50 | Name |
|---|---|---|---|---|---|
| 470 | 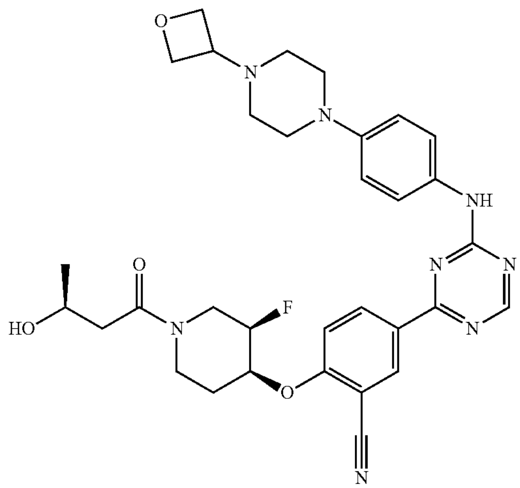 [SMILES: C[C@H](O)CC(=O)N1CC[C@H](Oc2ccc(-c3ncnc(Nc4ccc(N5CCN(C6COC6)CC5)cc4)n3)cc2C#N)[C@H](F)C1] | 12 | 44 | 1000 | 2-(((3R,4S)-3-fluoro-1-((S)-3-hydroxybutanoyl)piperidin-4-yl)oxy)-5-4-((4-(4-(oxetan-3-yl)piperazin-1-yl)phenyl)amino)-1,3,5-triazin-2-yl)benzonitrile |
| 471 | 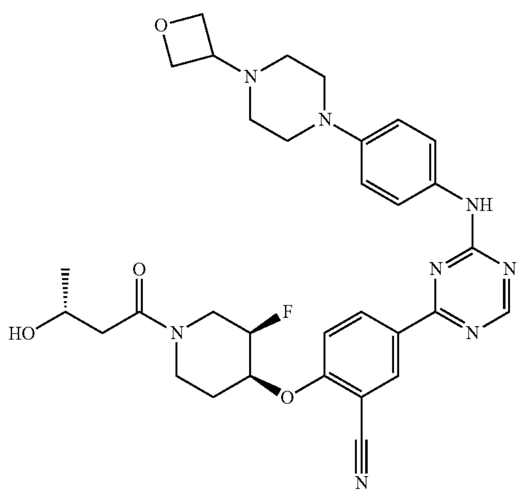 [SMILES: C[C@@H](O)CC(=O)N1CC[C@H](Oc2ccc(-c3ncnc(Nc4ccc(N5CCN(C6COC6)CC5)cc4)n3)cc2C#N)[C@H](F)C1] | 6 | 14 | 702 | 2-(((3R,4S)-3-fluoro-1-((R)-3-hydroxybutanoyl)piperidin-4-yl)oxy)-5-(4-((4-(4-(oxetan-3-yl)piperazin-1-yl)phenyl)amino)-1,3,5-triazin-2-yl)benzonitrile |
| 472 | 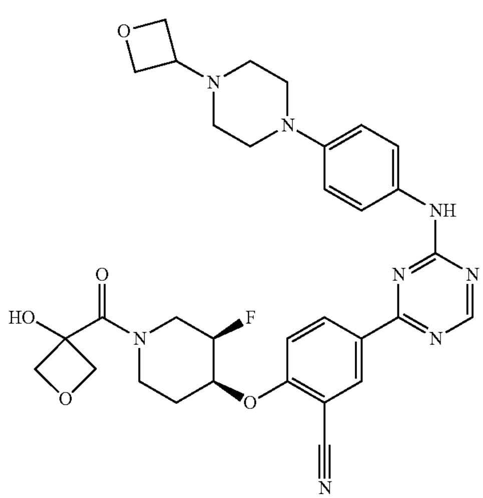 [SMILES: N#Cc1cc(-c2ncnc(Nc3ccc(N4CCN(C5COC5)CC4)cc3)n2)ccc1O[C@H]1CCN(C(=O)C2(O)COC2)C[C@H]1F] | 19 | 43 | 971 | 2-(((3R,4S)-3-fluoro-1-(3-hydroxyoxetane-3-carbonyl)piperidin-4-yl)oxy)-5-(4-((4-(4-(oxetan-3-yl)piperazin-1-yl)phenyl)amino)-1,3,5-triazin-2-yl)benzonitrile |

TABLE 1-continued

| Ex. | Structure | TBK1 IC50 | IKKe IC50 | JAK2 IC50 | Name |
|---|---|---|---|---|---|
| 473 | 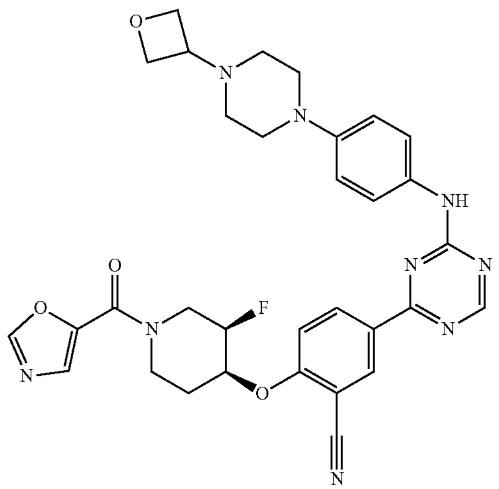 [SMILES: N#Cc1cc(-c2ncnc(Nc3ccc(N4CCN(C5COC5)CC4)cc3)n2)ccc1O[C@H]1CCN(C(=O)c2cnco2)C[C@H]1F] | 3 | 3 | 771 | 2-(((3R,4S)-3-fluoro-1-(oxazole-5-carbonyl)piperidin-4-yl)oxy)-5-(4-((4-(4-(oxetan-3-yl)piperazin-1-yl)phenyl)amino)-1,3,5-triazin-2-yl)benzonitrile |
| 474 | 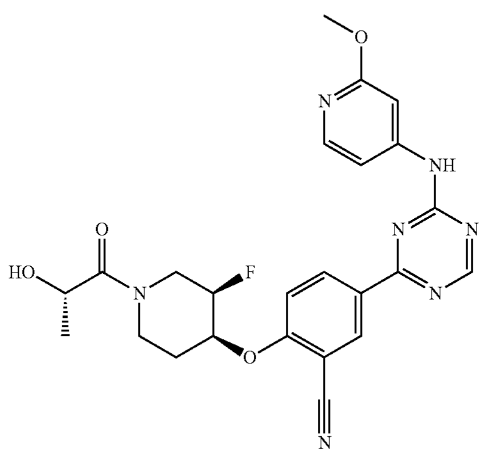 [SMILES: COc1cc(Nc2ncnc(-c3ccc(O[C@H]4CCN(C(=O)[C@H](C)O)C[C@H]4F)c(C#N)c3)n2)ccn1] | 6 | 10 | 1000 | 2-(3R,4S)-3-fluoro-1-((S)-2-hydroxypropanoyl)piperidin-4-yl)oxy)-5-(4-((2-methoxypyridin-4-yl)amino)-1,3,5-triazin-2-yl)benzonitrile |
| 475 | 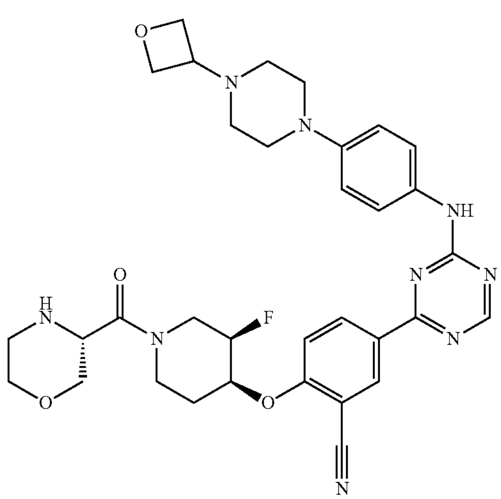 [SMILES: N#Cc1cc(-c2ncnc(Nc3ccc(N4CCN(C5COC5)CC4)cc3)n2)ccc1O[C@H]1CCN(C(=O)[C@@H]2COCCN2)C[C@H]1F] | 23 | 50 | 1000 | 2-(((3R,4S)-3-fluoro-1-((S)-morpholine-3-carbonyl)piperidin-4-yl)oxy)-5-(4-((4-(4-(oxetan-3-yl)piperazin-1-yl)phenyl)amino)-1,3,5-triazin-2-yl)benzonitrile |

TABLE 1-continued

| Ex. | Structure | TBK1 IC50 | IKKe IC50 | JAK2 IC50 | Name |
|---|---|---|---|---|---|
| 476 | 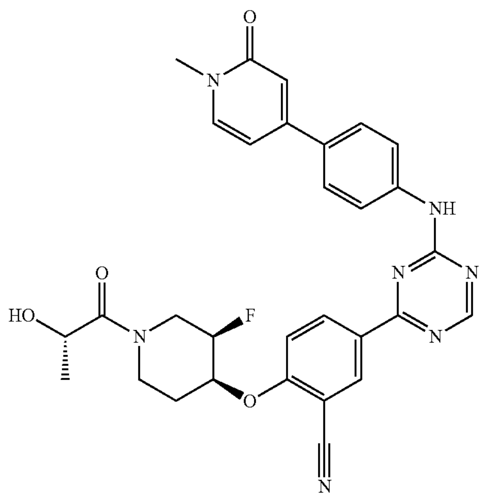 [SMILES: C[C@H](O)C(=O)N1CC[C@H](Oc2ccc(-c3ncnc(Nc4ccc(-c5ccn(C)c(=O)c5)cc4)n3)cc2C#N)[C@H](F)C1] | 3 | 3 | 1000 | 2-(((3R,4S)-3-fluoro-1-((S)-2-hydroxypropanoyl)piperidin-4-yl)oxy)-5-(4-((4-(1-methyl-2-oxo-1,2-dihydropyridin-4-yl)phenyl)amino)-1,3,5-triazin-2-yl)benzonitrile |
| 477 | 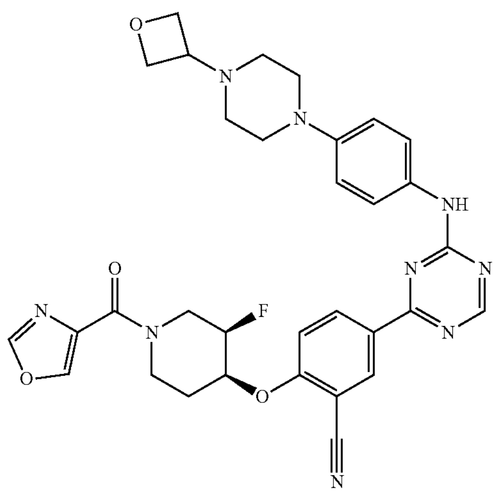 [SMILES: N#Cc1cc(-c2ncnc(Nc3ccc(N4CCN(C5COC5)CC4)cc3)n2)ccc1O[C@H]1CCN(C(=O)c2cocn2)C[C@H]1F] | 3 | 2 | 526 | 2-(((3R,4S)-3-fluoro-1-(oxazole-4-carbonyl)piperidin-4-yl)oxy)-5-(4-((4-(4-(oxetan-3-yl)piperazin-1-yl)phenyl)amino)-1,3,5-triazin-2-yl)benzonitrile |
| 478 | 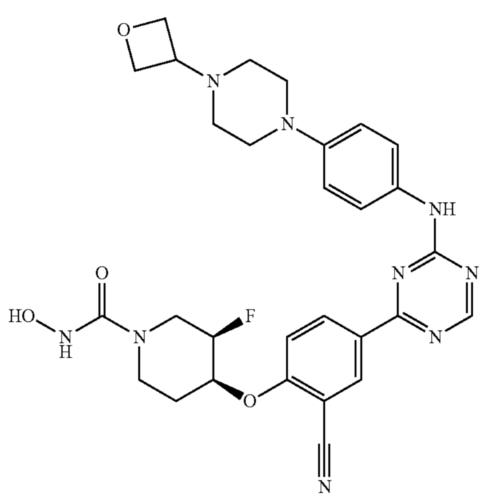 [SMILES: N#Cc1cc(-c2ncnc(Nc3ccc(N4CCN(C5COC5)CC4)cc3)n2)ccc1O[C@H]1CCN(C(=O)NO)C[C@H]1F] | 3 | 1 | 135 | (3R,4S)-4-(2-cyano-4-(4-((4-(4-(oxetan-3-yl)piperazin-1-yl)phenyl)amino)-1,3,5-triazin-2-yl)phenoxy)-3-fluoro-N-hydroxypiperidine-1-carboxamide |

TABLE 1-continued

| Ex. | Structure | TBK1 IC50 | IKKe IC50 | JAK2 IC50 | Name |
|-----|-----------|-----------|-----------|-----------|------|
| 479 | 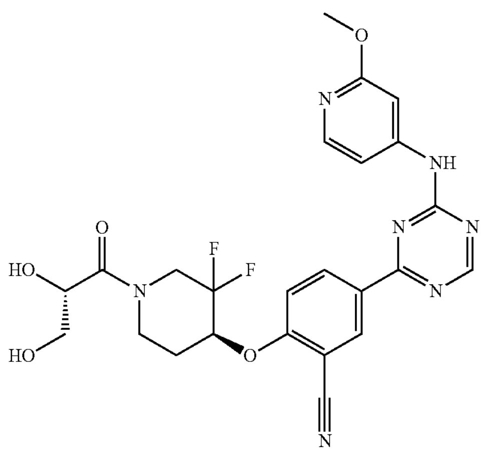 [SMILES: COc1cc(Nc2ncnc(-c3ccc(O[C@H]4CCN(C(=O)[C@@H](O)CO)CC4(F)F)c(C#N)c3)n2)ccn1] | 2 | 1 | 1000 | 2-(((S)-1-((S)-2,3-dihydroxypropanoyl)-3,3-difluoropiperidin-4-yl)oxy)-5-(4-((2-methoxypyridin-4-yl)amino)-1,3,5-triazin-2-yl)benzonitrile |
| 480 | 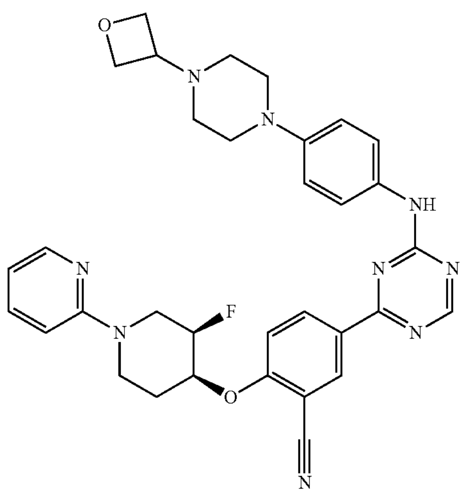 [SMILES: N#Cc1cc(-c2ncnc(Nc3ccc(N4CCN(C5COC5)CC4)cc3)n2)ccc1O[C@H]1CCN(c2ccccn2)C[C@H]1F] | 47 | 180 | 1000 | 2-(((3R,4S)-3-fluoro-1-(pyridin-2-yl)piperidin-4-yl)oxy)-5-(4-((4-(4-(oxetan-3-yl)piperazin-1-yl)phenyl)amino)-1,3,5-triazin-2-yl)benzonitrile. |
| 481 | 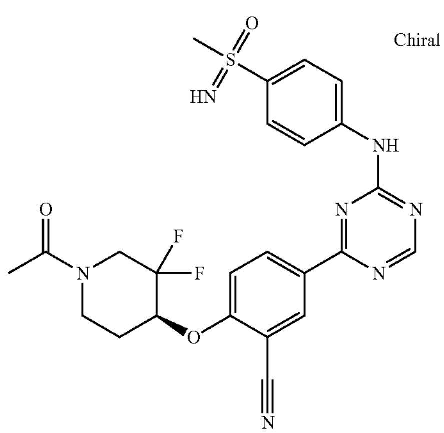 [SMILES: CC(=O)N1CC[C@H](Oc2ccc(-c3ncnc(Nc4ccc(S(C)(=N)=O)cc4)n3)cc2C#N)C(F)(F)C1] | 5 | 5 | 320 | 2-(((S)-1-acetyl-3,3-difluoropipendin-4-yl)oxy)-5-(4-((4-(S-methylsulfonimidoyl)phenyl)amino)-1,3,5-triazin-2-yl)benzonitrile |

TABLE 1-continued

| Ex. | Structure | TBK1 IC50 | IKKe IC50 | JAK2 IC50 | Name |
|---|---|---|---|---|---|
| 482 | 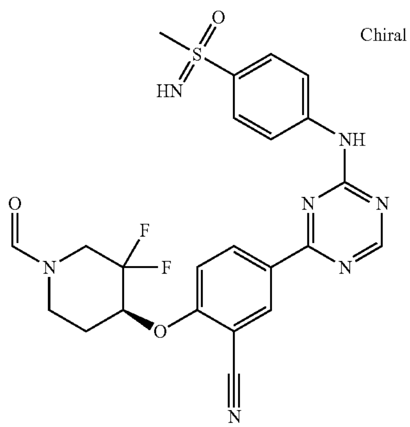 [SMILES: CS(=N)(=O)c1ccc(Nc2ncnc(-c3ccc(O[C@H]4CCN(C=O)CC4(F)F)c(C#N)c3)n2)cc1] | 5 | 7 | 221 | 2-(((S)-3,3-difluoro-1-formylpiperidin-4-yl)oxy)-5-(4-((4-(S-rnethylsulfonimidoyl)phenyl)amino)-1,3,5-triazin-2-yl)benzonitrile |
| 483 | 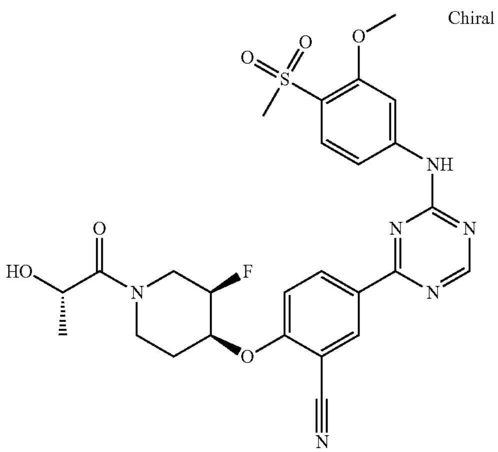 [SMILES: COc1cc(Nc2ncnc(-c3ccc(O[C@H]4CCN(C(=O)[C@H](C)O)C[C@H]4F)c(C#N)c3)n2)ccc1S(C)(=O)=O] | 8 | 6 | 1000 | 2-(((3R,4S)-3-fluoro-1-((S)-2-hydroxypropanoyl)piperidin-4-yl)oxy)-5-(4-((3-methoxy-4-(methylsulfonyl)phenyl)amino)-1,3,5-triazin-2-yl)benzonitrile |
| 484 | 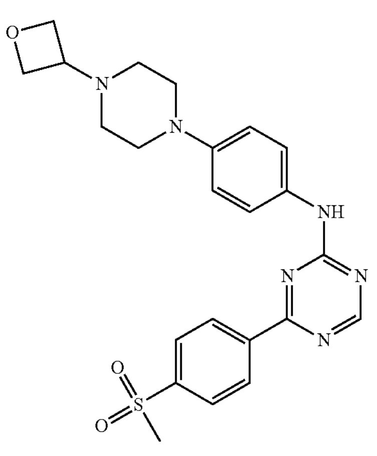 [SMILES: CS(=O)(=O)c1ccc(-c2ncnc(Nc3ccc(N4CCN(C5COC5)CC4)cc3)n2)cc1] | 1000 | 1000 | 837 | 4-(4-(methylsulfonyl)phenyl)-N-(4-(4-(oxetan-3-yl)piperazin-1-yl)phenyl)-1,3,5-triazin-2-amine, trifluoroacetic acid salt |

TABLE 1-continued

| Ex. | Structure | TBK1 IC50 | IKKe IC50 | JAK2 IC50 | Name |
|---|---|---|---|---|---|
| 485 | 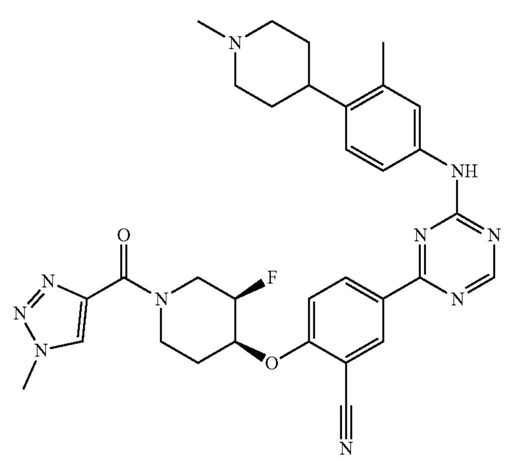 [SMILES: Cc1cc(Nc2ncnc(-c3ccc(O[C@H]4CCN(C(=O)c5cn(C)nn5)C[C@H]4F)c(C#N)c3)n2)ccc1C1CCN(C)CC1] | 3 | 1 | 576 | 2-(((3R,4S)-3-fluoro-1-(1-methyl-1H-1,2,3-triazole-4-carbonyl)piperidin-4-yl)oxy)-5-(4-((3-methyl-4-(1-methylpiperidin-4-yl)phenyl)amino)-1,3,5-triazin-2-yl)benzonitrile |
| 486 | 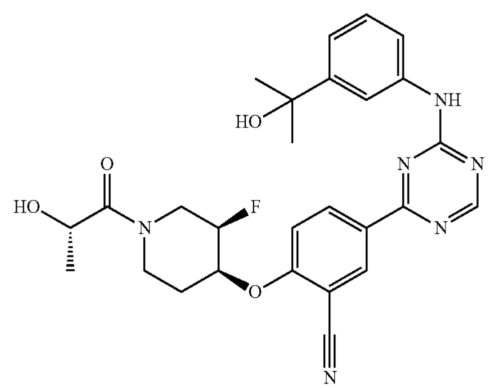 [SMILES: C[C@H](O)C(=O)N1CC[C@H](Oc2ccc(-c3ncnc(Nc4cccc(C(C)(C)O)c4)n3)cc2C#N)[C@H](F)C1] | 3 | 5 | 767 | 2-(((3R,4S)-3-fluoro-1-((S)-2-hydroxypropanoyl)piperidin-4-yl)oxy)-5-(4-((3-(2-hydroxypropan-2-yl)phenyl)amino)-1,3,5-triazin-2-yl)benzonitrile |
| 487 | 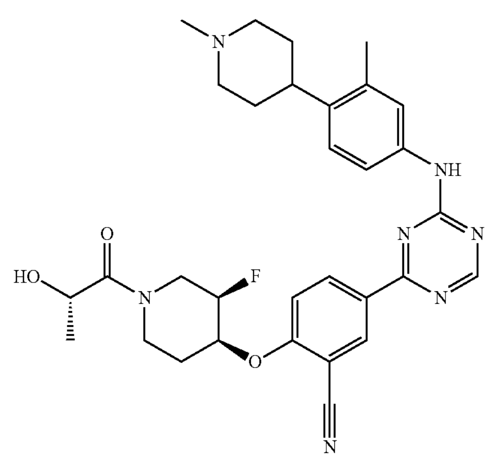 [SMILES: Cc1cc(Nc2ncnc(-c3ccc(O[C@H]4CCN(C(=O)[C@H](C)O)C[C@H]4F)c(C#N)c3)n2)ccc1C1CCN(C)CC1] | 3 | 1 | 324 | 2-(((3R,4S)-3-fluoro-1-((S)-2-hydroxypropanoyl)piperidin-4-yl)oxy)-5-(4-((3-methyl-4-(1-methylpiperidin-4-yl)phenyl)amino)-1,3,5-triazin-2-yl)benzonitrile |

TABLE 1-continued

| Ex. | Structure | TBK1 IC50 | IKKe IC50 | JAK2 IC50 | Name |
|---|---|---|---|---|---|
| 488 | 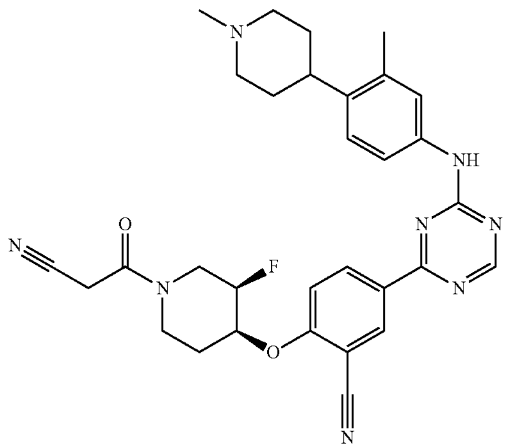 [SMILES: Cc1cc(Nc2ncnc(-c3ccc(O[C@H]4CCN(C(=O)CC#N)C[C@H]4F)c(C#N)c3)n2)ccc1C1CCN(C)CC1] | 4 | 1 | 131 | 2-(((3R,4S)-1-(2-cyanoacetyl)-3-fluoropiperidin-4-yl)oxy)-5-(4-((3-methyl-4-(1-methylpiperidin-4-yl)phenyl)amino)-1,3,5-triazin-2-yl)benzonitrile |
| 489 | 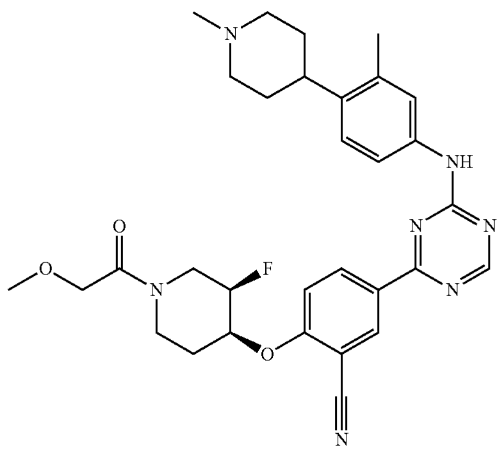 [SMILES: COCC(=O)N1CC[C@H](Oc2ccc(-c3ncnc(Nc4ccc(C5CCN(C)CC5)c(C)c4)n3)cc2C#N)[C@H](F)C1] | 4 | 1 | 183 | 2-(((3R,4S)-3-fluoro-1-(2-methoxyacetyl)piperidin-4-yl)oxy)-5-(4-((3-methyl-4-(1-methylpiperidin-4-yl)phenyl)amino)-1,3,5-triazin-2-yl)benzonitrile |
| 490 | 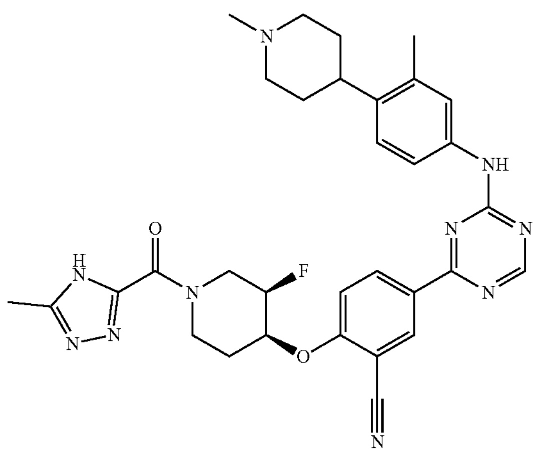 [SMILES: Cc1nnc(C(=O)N2CC[C@H](Oc3ccc(-c4ncnc(Nc5ccc(C6CCN(C)CC6)c(C)c5)n4)cc3C#N)[C@H](F)C2)[nH]1] | 3 | 0 | 78 | 2-(((3R,4S)-3-fluoro-1-(5-methyl-4H-1,2,4-triazole-3-carbonyl)piperidin-4-yl)oxy)-5-(4-((3-methyl-4-(1-methylpiperidin-4-yl)phenyl)amino)-1,3,5-triazin-2-yl)benzonitrile |

TABLE 1-continued

| Ex. | Structure | TBK1 IC50 | IKKe IC50 | JAK2 IC50 | Name |
|---|---|---|---|---|---|
| 491 | 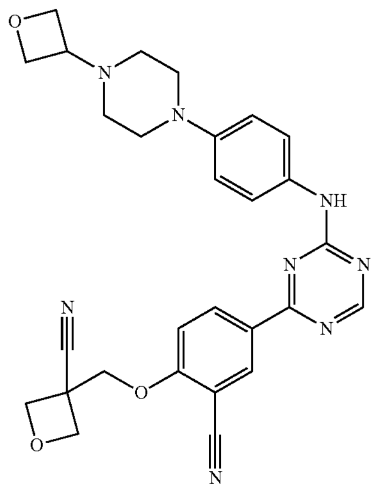 [SMILES: N#Cc1cc(-c2ncnc(Nc3ccc(N4CCN(C5COC5)CC4)cc3)n2)ccc1OCC1(C#N)COC1] | 25 | 33 | 216 | 3-((2-cyano-4-(4-((4-(4-(oxetan-3-yl)piperazin-1-yl)phenyl)amino)-1,3,5-triazin-2-yl)phenoxy)methyl)oxetane-3-carbonitrile |
| 492 | 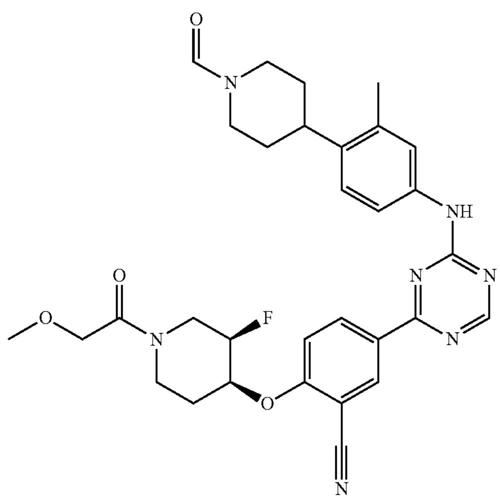 [SMILES: COCC(=O)N1CC[C@H](Oc2ccc(-c3ncnc(Nc4ccc(C5CCN(C=O)CC5)c(C)c4)n3)cc2C#N)[C@H](F)C1] | 2 | 1 | 482 | 2-(((3R,4S)-3-fluoro-1-(2-methoxyacetyl)piperidin-4-yl)oxy)-5-(4-((4-(1-formylpiperidin-4-yl)-3-methylphenyl)amino)-1,3,5-triazin-2-yl)benzonitrile |
| 493 | 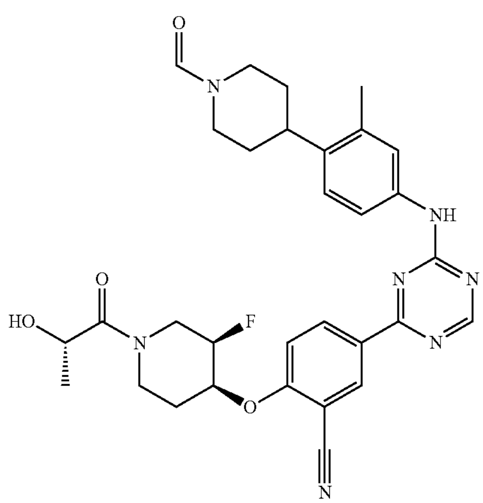 [SMILES: Cc1cc(Nc2ncnc(-c3ccc(O[C@H]4CCN(C(=O)[C@H](C)O)C[C@H]4F)c(C#N)c3)n2)ccc1C1CCN(C=O)CC1] | 2 | 1 | 782 | 2-(((3R,4S)-3-fluoro-1-((S)-2-hydroxypropanoyl)piperidin-4-yl)oxy)-5-(4-((4-(1-formylpiperidin-4-yl)-3-methylphenyl)amino)-1,3,5-triazin-2-yl)benzonitrile |

TABLE 1-continued

| Ex. | Structure | TBK1 IC50 | IKKe IC50 | JAK2 IC50 | Name |
|---|---|---|---|---|---|
| 494 | 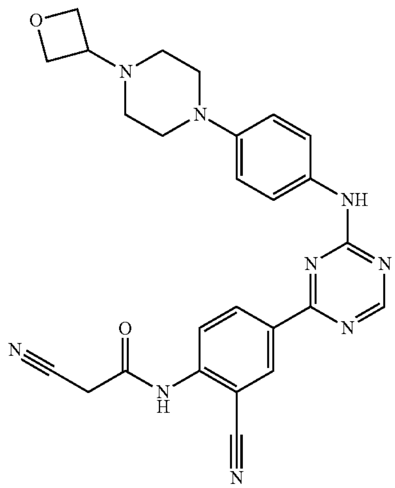 [SMILES: N#CCC(=O)Nc1ccc(-c2ncnc(Nc3ccc(N4CCN(C5COC5)CC4)cc3)n2)cc1C#N] | 19 | 29 | 12 | 2-cyano-N-(2-cyano-4-(4-((4-(4-(oxetan-3-yl)piperazin-1-yl)phenyl)amino)-1,3,5-triazin-2-yl)phenyl)acetamide |
| 495 | 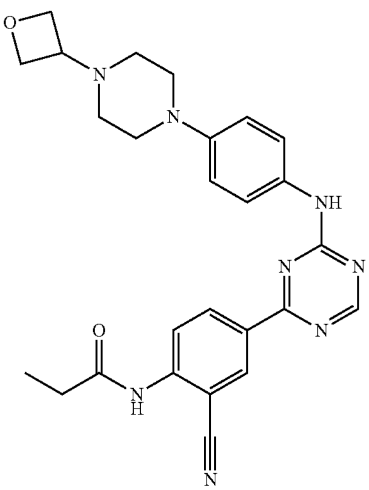 [SMILES: CCC(=O)Nc1ccc(-c2ncnc(Nc3ccc(N4CCN(C5COC5)CC4)cc3)n2)cc1C#N] | 40 | 119 | 109 | N-(2-cyano-4-(4-((4-(4-(oxetan-3-yl)piperazin-1-yl)phenyl)amino)-1,3,5-triazin-2-yl)phenyl)propionamide |
| 496 | 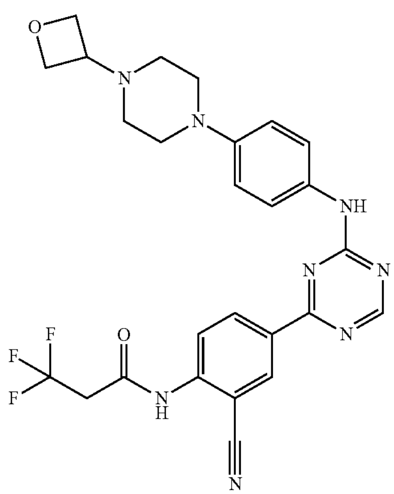 [SMILES: N#Cc1cc(-c2ncnc(Nc3ccc(N4CCN(C5COC5)CC4)cc3)n2)ccc1NC(=O)CC(F)(F)F] | 6 | 8 | 8 | N-(2-cyano-4-(4-((4-(4-(oxetan-3-yl)piperazin-1-yl)phenyl)amino)-1,3,5-triazin-2-yl)phenyl)-3,3,3-trifluoropropanamide |

TABLE 1-continued

| Ex. | Structure | TBK1 IC50 | IKKe IC50 | JAK2 IC50 | Name |
|---|---|---|---|---|---|
| 497 | 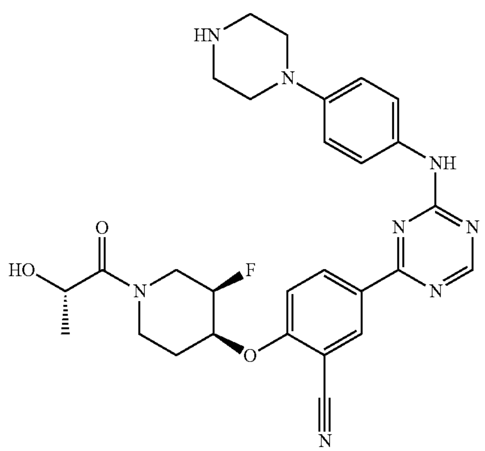 | 1 | 0 | 358 | 2-(((3R,4S)-3-fluoro-1-((S)-2-hydroxypropanoyl)piperidin-4-yl)oxy)-5-(4-((4-(piperazin-1-yl)phenyl)amino)-1,3,5-triazin-2-yl)benzonitrile |
| 498 | 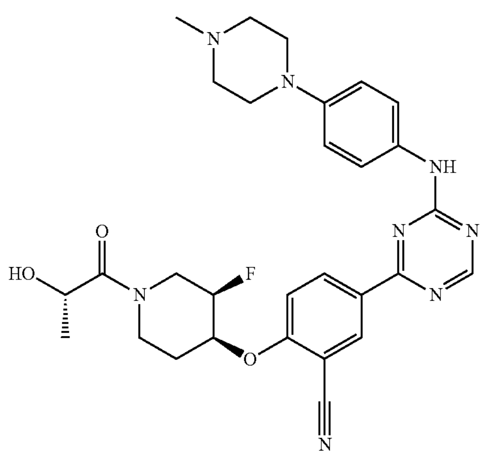 [SMILES: C[C@H](O)C(=O)N1CC[C@H](Oc2ccc(-c3ncnc(Nc4ccc(N5CCN(C)CC5)cc4)n3)cc2C#N)[C@H](F)C1] | 2 | 0 | 389 | 2-(((3R,4S)-3-fluoro-1-((S)-2-hydroxypropanoyl)piperidin-4-yl)oxy)-5-(4-((4-(4-methylpiperazin-1-yl)phenyl)amino)-1,3,5-triazin-2-yl)benzonitrile |
| 499 | 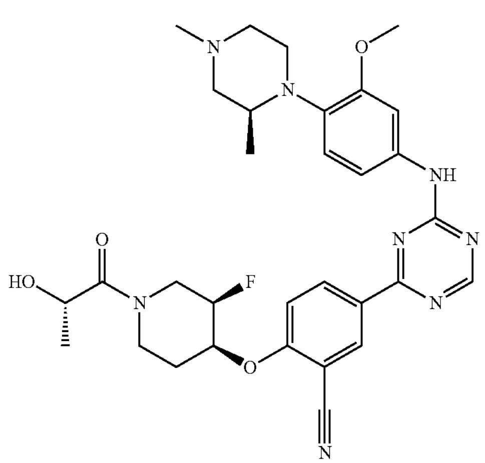 [SMILES: COc1cc(Nc2ncnc(-c3ccc(O[C@H]4CCN(C(=O)[C@H](C)O)C[C@H]4F)c(C#N)c3)n2)ccc1N1CCN(C)C[C@@H]1C] | 2 | 1 | 79 | 5-(4-((4-((S)-2,4-dimethylpiperazin-1-yl)-3-methoxyphenyl)amino)-1,3,5-triazin-2-yl)-2-(((3R,4S)-3-fluoro-1-((S)-2-hydroxypropanoyl)piperidin-4-yl)oxy)benzonitrile |

TABLE 1-continued

| Ex. | Structure | TBK1 IC50 | IKKe IC50 | JAK2 IC50 | Name |
|---|---|---|---|---|---|
| 500 | 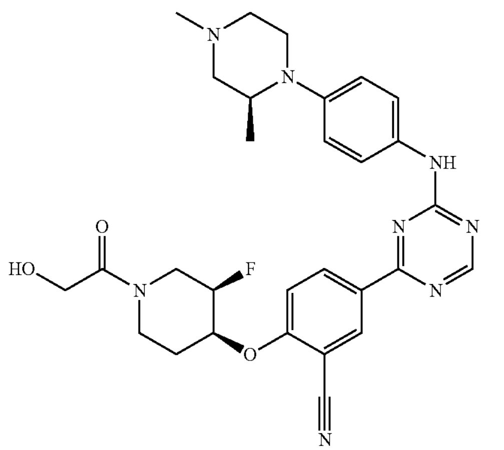 [SMILES: C[C@H]1CN(C)CCN1c1ccc(Nc2ncnc(-c3ccc(O[C@H]4CCN(C(=O)CO)C[C@H]4F)c(C#N)c3)n2)cc1] | 2 | 0 | 182 | 5-(4-((4-((S)-2,4-dimethylpiperazin-1-yl)phenyl)amino)-1,3,5-triazin-2-yl)-2-(((3R,4S)-3-fluoro-1-(2-hydroxyacetyl)piperidin-4-yl)oxy)benzonitrile |
| 501 | 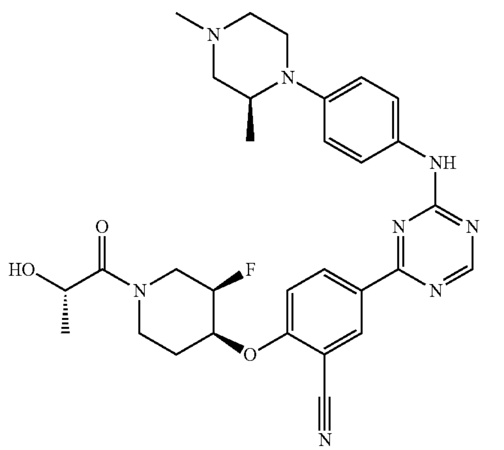 [SMILES: C[C@H](O)C(=O)N1CC[C@H](Oc2ccc(-c3ncnc(Nc4ccc(N5CCN(C)C[C@@H]5C)cc4)n3)cc2C#N)[C@H](F)C1] | 2 | 0 | 457 | 5-(4-((4-((S)-2,4-dimethylpiperazin-1-yl)phenyl)amino)-1,3,5-triazin-2-yl)-2-(((3R,4S)-3-fluoro-1-((S)-2-hydroxypropanoyl)piperidin-4-yl)oxy)benzonitrile |
| 502 | 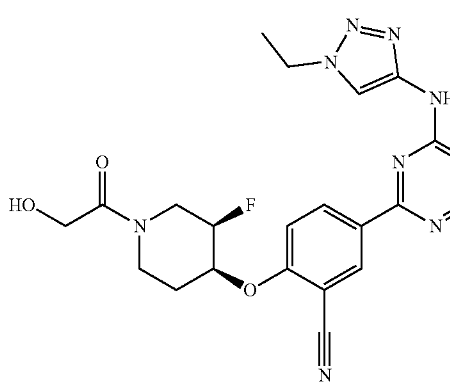 | 28 | 29 | 1000 | 5-(4-((1-ethyl-1H-1,2,3-triazol-4-yl)amino)-1,3,5-triazin-2-yl)-2-(((3R,4S)-3-fluoro-1-(2-hydroxyacetyl)piperidin-4-yl)oxy)benzonitrile |

TABLE 1-continued

| Ex. | Structure | TBK1 IC50 | IKKe IC50 | JAK2 IC50 | Name |
|---|---|---|---|---|---|
| 503 | 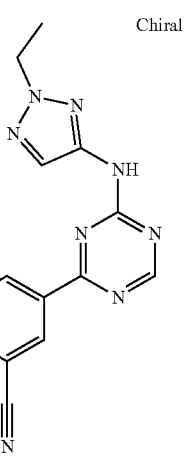 | 7 | 20 | 1000 | 5-(4-((2-ethyl-2H-1,2,3-triazol-4-yl)amino)-1,3,5-triazin-2-yl)-2-(((3R,4S)-3-fluoro-1-(2-hydroxy-acetyl)piperidin-4-yl)oxy)benzonitrile |
| 504 | 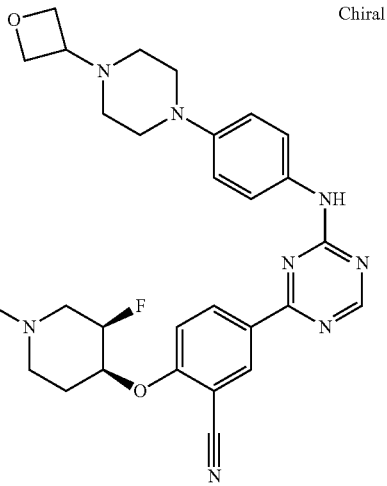 | 4 | 5 | 1000 | 2-(((3R,4S)-3-fluoro-1-((S)-tetrahydrofuran-2-carbonyl)piperidin-4-yl)oxy)-5-(4-((4-(4-(oxetan-3-yl)piperazin-1-yl)phenyl)amino)-1,3,5-triazin-2-yl)benzonitrile |
| 505 | 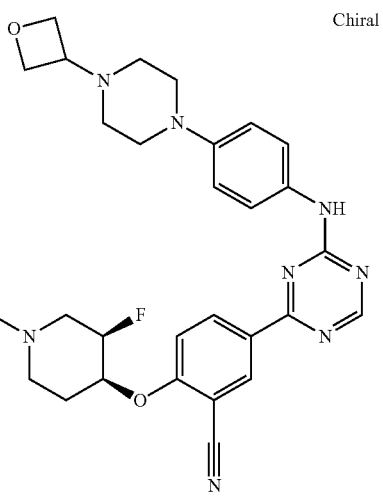 | 12 | 41 | 532 | 2-(((3R,4S)-3-fluoro-1-((R)-tetrahydrofuran-2-carbonyl)piperidin-4-yl)oxy)-5-(4-((4-(4-(oxetan-3-yl)piperazin-1-yl)phenyl)amino)-1,3,5-triazin-2-yl)benzonitrile |

TABLE 1-continued
| Ex. | Structure | TBK1 IC50 | IKKe IC50 | JAK2 IC50 | Name |
|---|---|---|---|---|---|
| 506 | 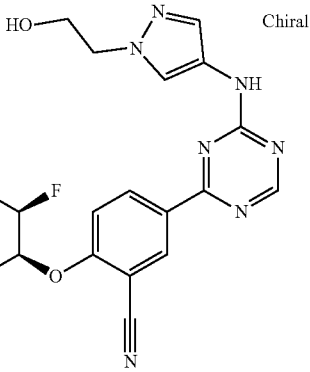 | 3 | 3 | 601 | 2-(((3R,4S)-3-fluoro-1-(2-hydroxyacetyl)piperidin-4-yl)oxy)-5-(4-((1-(2-hydroxyethyl)-1H-pyrazol-4-yl)amino)-1,3,5-triazin-2-yl)benzonitrile |
| 507 | 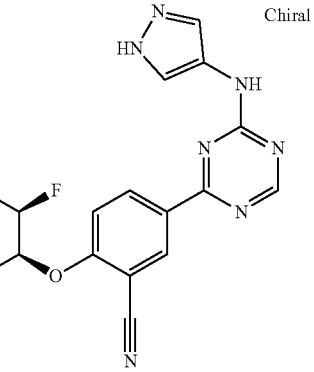 | 3 | 2 | 432 | 5-(4-((1H-pyrazol-4-yl)amino)-1,3,5-triazin-2-yl)-2-(((3R,4S)-3-fluoro-1-(2-hydroxyacetyl)piperidin-4-yl)oxy)benzonitrile |
| 508 | 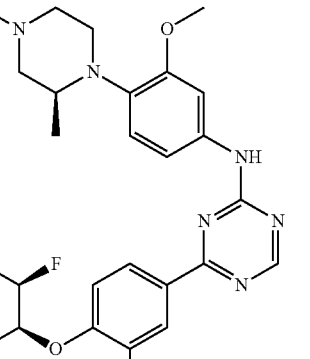 | 2 | 0 | 49 | 5-(4-((4-((S)-2,4-dimethylpiperazin-1-yl)-3-methoxyphenyl)amino)-1,3,5-triazin-2-yl)-2-(((3R,4S)-3-fluoro-1-(2-hydroxyacetyl)piperidin-4-yl)oxy)benzonitrile |

TABLE 1-continued

| Ex. | Structure | TBK1 IC50 | IKKe IC50 | JAK2 IC50 | Name |
|---|---|---|---|---|---|
| 509 | 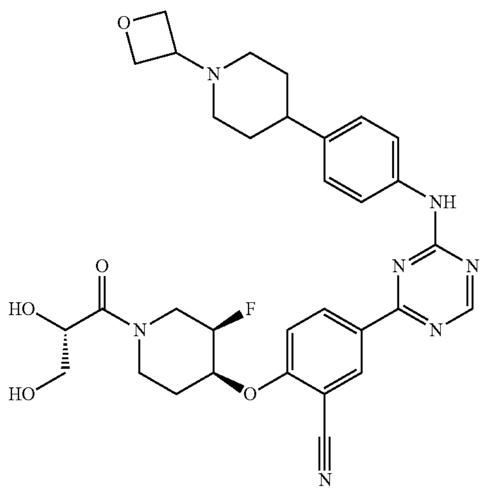 [SMILES: N#Cc1cc(-c2ncnc(Nc3ccc(C4CCN(C5COC5)CC4)cc3)n2)ccc1O[C@H]1CCN(C(=O)[C@@H](O)CO)C[C@H]1F] | 3 | 1 | 699 | 2-(((3R,4S)-1-((S)-2,3-dihydroxypropanoyl)-3-fluoropiperidin-4-yl)oxy)-5-(4-((4-(1-(oxetan-3-yl)piperidin-4-yl)phenyl)amino)-1,3,5-triazin-2-yl)benzonitrile |
| 510 | 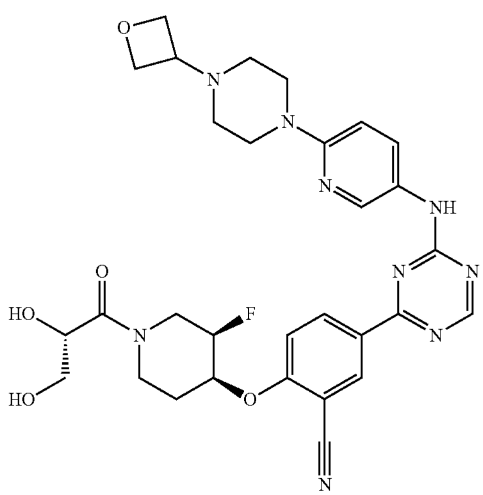 [SMILES: N#Cc1cc(-c2ncnc(Nc3ccc(N4CCN(C5COC5)CC4)nc3)n2)ccc1O[C@H]1CCN(C(=O)[C@@H](O)CO)C[C@H]1F] | 4 | 2 | 1000 | 2-(((3R,4S)-1-((S)-2,3-dihydroxypropanoyl)-3-fluoropiperidin-4-yl)oxy)-5-(4-((6-(4-(oxetan-3-yl)piperazin-1-yl)pyridin-3-yl)amino)-1,3,5-triazin-2-yl)benzonitrile |
| 511 | 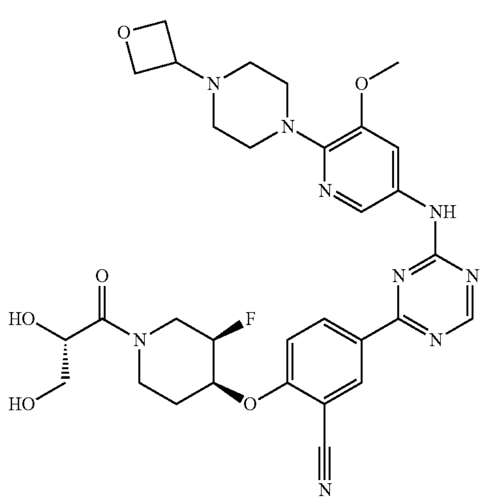 [SMILES: COc1cc(Nc2ncnc(-c3ccc(O[C@H]4CCN(C(=O)[C@@H](O)CO)C[C@H]4F)c(C#N)c3)n2)cnc1N1CCN(C2COC2)CC1] | 4 | 2 | 1000 | 2-(((3R,4S)-1-((S)-2,3-dihydroxypropanoyl)-3-fluoropiperidin-4-yl)oxy)-5-(4-((5-methoxy-6-(4-(oxetan-3-yl)piperazin-1-yl)pyridin-3-yl)amino)-1,3,5-triazin-2-yl)benzonitrile |

TABLE 1-continued

| Ex. | Structure | TBK1 IC50 | IKKe IC50 | JAK2 IC50 | Name |
|---|---|---|---|---|---|
| 512 | 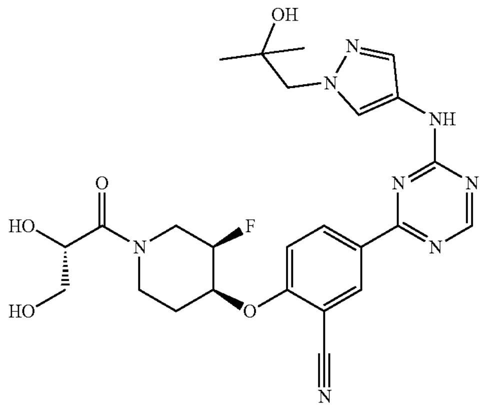 [SMILES: CC(C)(O)Cn1cc(Nc2ncnc(-c3ccc(O[C@H]4CCN(C(=O)[C@@H](O)CO)C[C@H]4F)c(C#N)c3)n2)cn1] | 2 | 2 | 1000 | 2-(((3R,4S)-1-((S)-2,3-dihydroxypropanoyl)-3-fluoropiperidin-4-yl)oxy)-5-(4-((1-(2-hydroxy-2-methylpropyl)-1H-pyrazol-4-yl)amino)-1,3,5-triazin-2-yl)benzonitrile |
| 513 | 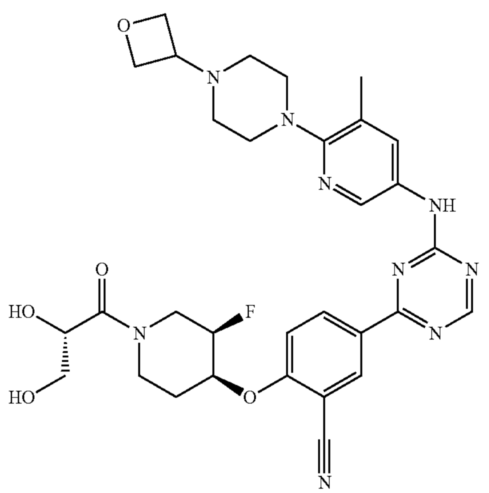 [SMILES: Cc1cc(Nc2ncnc(-c3ccc(O[C@H]4CCN(C(=O)[C@@H](O)CO)C[C@H]4F)c(C#N)c3)n2)cnc1N1CCN(C2COC2)CC1] | 2 | 1 | 517 | 2-(((3R,4S)-1-((S)-2,3-dihydroxypropanoyl)-3-fluoropiperidin-4-yl)oxy)-5-(4-((5-methyl-6-(4-(oxetan-3-yl)piperazin-1-yl)pyridin-3-yl)amino)-1,3,5-triazin-2-yl)benzonitrile |
| 514 | 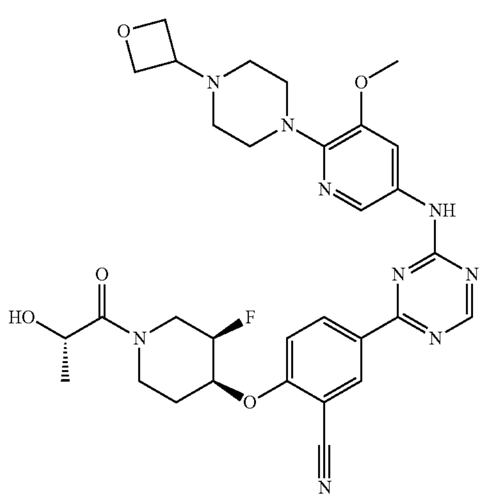 [SMILES: COc1cc(Nc2ncnc(-c3ccc(O[C@H]4CCN(C(=O)[C@H](C)O)C[C@H]4F)c(C#N)c3)n2)cnc1N1CCN(C2COC2)CC1] | 3 | 3 | 1000 | 2-(((3R,4S)-3-fluoro-1-((S)-2-hydroxypropanoyl)piperidin-4-yl)oxy)-5-(4-((5-methoxy-6-(4-(oxetan-3-yl)piperazin-1-yl)pyridin-3-yl)amino)-1,3,5-triazin-2-yl)benzonitrile |

TABLE 1-continued

| Ex. | Structure | TBK1 IC50 | IKKe IC50 | JAK2 IC50 | Name |
|---|---|---|---|---|---|
| 515 | 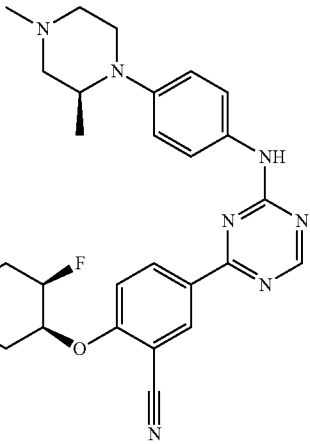 | 2 | 0 | 355 | 2-(((3R,4S)-1-((S)-2,3-dihydroxypropanoyl)-3-fluoropiperidin-4-yl)oxy)-5-(4-((4-((S)-2,4-dimethylpiperazin-1-yl)phenyl)amino)-1,3,5-triazin-2-yl)benzonitrile |
| 516 | 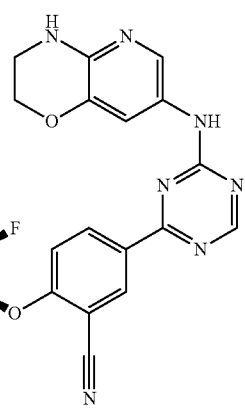 | 6 | 10 | 1000 | 5-(4-((3,4-dihydro-2H-pyrido[3,2-b][1,4]oxazin-7-yl)amino)-1,3,5-triazin-2-yl)-2-(((3R,4S)-3-fluoro-1-((S)-2-hydroxypropanoyl)piperidin-4-yl)oxy)benzonitrile |
| 517 | 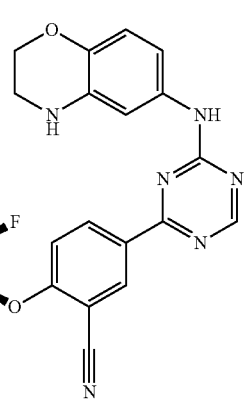 | 2 | 1 | 828 | 5-(4-((3,4-dihydro-2H-benzo[b][1,4]oxazin-6-yl)amino)-1,3,5-triazin-2-yl)-2-(((3R,4S)-3-fluoro-1-((S)-2-hydroxypropanoyl)piperidin-4-yl)oxy)benzonitrile |

TABLE 1-continued

| Ex. | Structure | TBK1 IC50 | IKKe IC50 | JAK2 IC50 | Name |
|---|---|---|---|---|---|
| 518 | 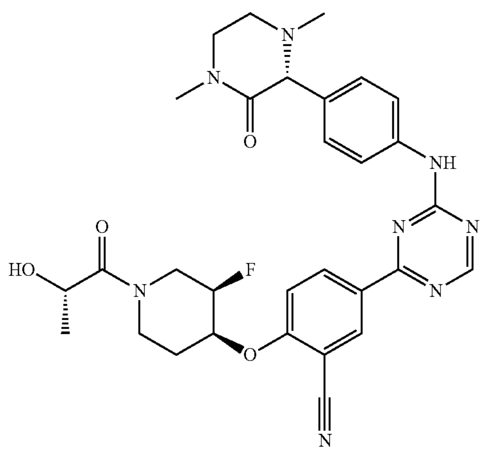 [SMILES: C[C@H](O)C(=O)N1CC[C@H](Oc2ccc(-c3ncnc(Nc4ccc([C@@H]5C(=O)N(C)CCN5C)cc4)n3)cc2C#N)[C@H](F)C1] | 3 | 3 | 1000 | 2-(((3R,4S)-1-((S)-2,3-dihydroxypropanoyl)-3-fluoropiperidin-4-yl)oxy)-5-(4-((4-((R)-1,4-dimethyl-3-oxopiperazin-2-yl)phenyl)amino)-1,3,5-triazin-2-yl)benzonitrile |
| 519 | 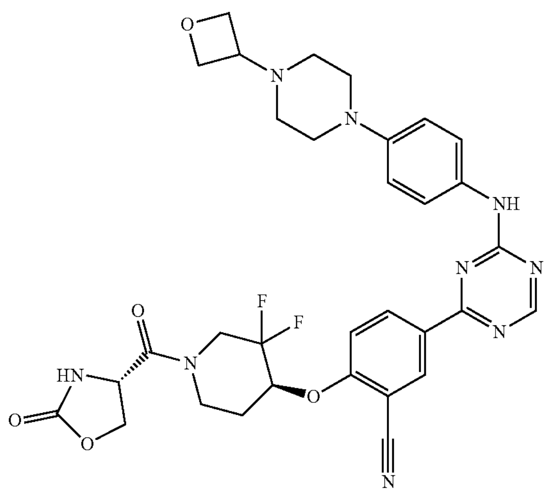 [SMILES: N#Cc1cc(-c2ncnc(Nc3ccc(N4CCN(C5COC5)CC4)cc3)n2)ccc1O[C@H]1CCN(C(=O)[C@@H]2COC(=O)N2)CC1(F)F] | 2 | 1 | 184 | 2-(((S)-3,3-difluoro-1-((S)-2-oxooxazolidine-4-carbonyl)piperidin-4-yl)oxy)-5-(4-((4-(4-(oxetan-3-yl)piperazin-1-yl)phenyl)amino)-1,3,5-triazin-2-yl)benzonitrile |
| 520 | 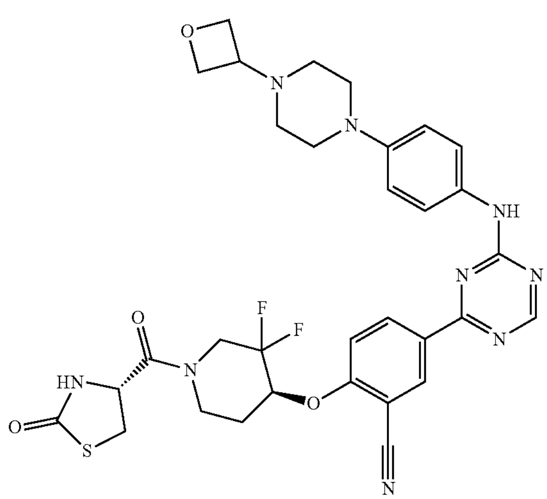 [SMILES: N#Cc1cc(-c2ncnc(Nc3ccc(N4CCN(C5COC5)CC4)cc3)n2)ccc1O[C@H]1CCN(C(=O)[C@@H]2CSC(=O)N2)CC1(F)F] | 2 | 1 | 177 | 2-(((S)-3,3-difluoro-1-((R)-2-oxothiazolidine-4-carbonyl)piperidin-4-yl)oxy)-5-(4-((4-(4-(oxetan-3-yl)piperazin-1-yl)phenyl)amino)-1,3,5-triazin-2-yl)benzonitrile |

TABLE 1-continued

| Ex. | Structure | TBK1 IC50 | IKKe IC50 | JAK2 IC50 | Name |
|---|---|---|---|---|---|
| 521 | 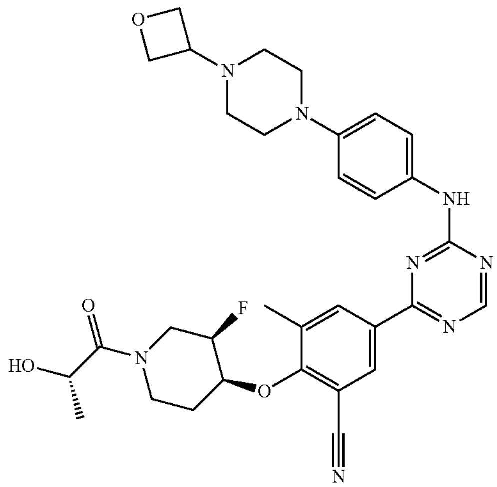 [SMILES: Cc1cc(-c2ncnc(Nc3ccc(N4CCN(C5COC5)CC4)cc3)n2)cc(C#N)c1O[C@H]1CCN(C(=O)[C@H](C)O)C[C@H]1F] | 16 | 39 | 1000 | 521: 2-(((3R,4S)-3-fluoro-1-((S)-2-hydroxypropanoyl)piperidin-4-yl)oxy)-3-methyl-5-(4-((4-(4-(oxetan-3-yl)piperazin-1-yl)phenyl)amino)-1,3,5-triazin-2-yl)benzonitrile |
| 522 | 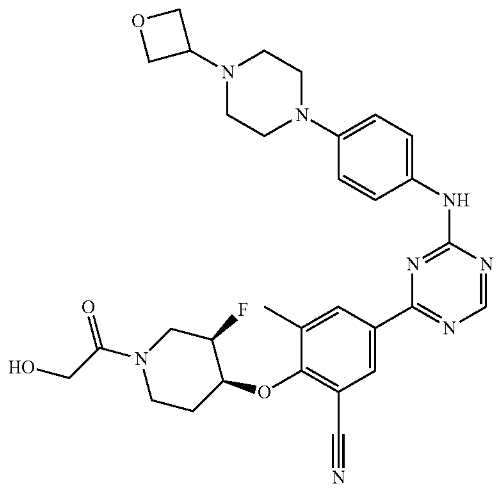 [SMILES: Cc1cc(-c2ncnc(Nc3ccc(N4CCN(C5COC5)CC4)cc3)n2)cc(C#N)c1O[C@H]1CCN(C(=O)CO)C[C@H]1F] | 14 | 28 | 1000 | 2-(((3R,4S)-3-fluoro-1-(2-hydroxyacetyl)piperidin-4-yl)oxy)-3-methyl-5-(4-((4-(4-(oxetan-3-yl)piperazin-1-yl)phenyl)amino)-1,3,5-triazin-2-yl)benzonitrile |
| 523 | 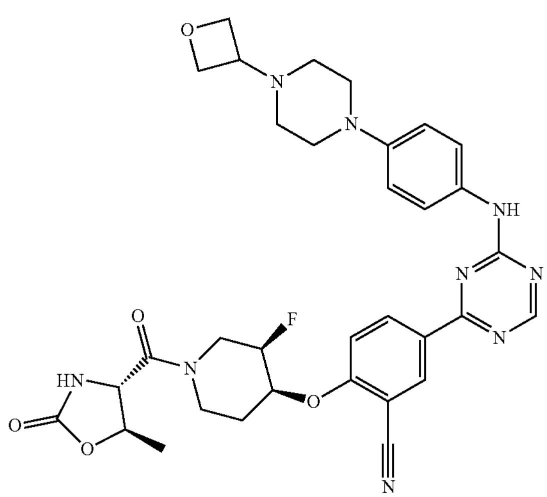 [SMILES: C[C@H]1OC(=O)N[C@@H]1C(=O)N1CC[C@H](Oc2ccc(-c3ncnc(Nc4ccc(N5CCN(C6COC6)CC5)cc4)n3)cc2C#N)[C@H](F)C1] | 10 | 26 | 811 | 2-(((3R,4S)-3-fluoro-1-((4S,5R)-5-methyl-2-oxooxazolidine-4-carbonyl)piperidin-4-yl)oxy)-5-(4-((4-(4-(oxetan-3-yl)piperazin-1-yl)phenyl)amino)-1,3,5-triazin-2-yl)benzonitrile |

TABLE 1-continued

| Ex. | Structure | TBK1 IC50 | IKKe IC50 | JAK2 IC50 | Name |
|---|---|---|---|---|---|
| 524 | 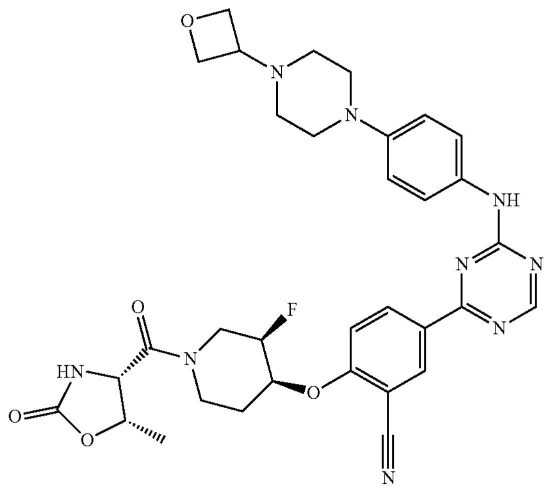 [SMILES: C[C@@H]1OC(=O)N[C@@H]1C(=O)N1CC[C@H](Oc2ccc(-c3ncnc(Nc4ccc(N5CCN(C6COC6)CC5)cc4)n3)cc2C#N)[C@H](F)C1] | 7 | 29 | 959 | 2-(((3R,4S)-3-fluoro-1-((4S,5S)-5-methyl-2-oxooxazolidine-4-carbonyl)piperidin-4-yl)oxy)-5-(4-((4-(4-(oxetan-3-yl)piperazin-1-yl)phenyl)amino)-1,3,5-triazin-2-yl)benzonitrile |
| 525 | 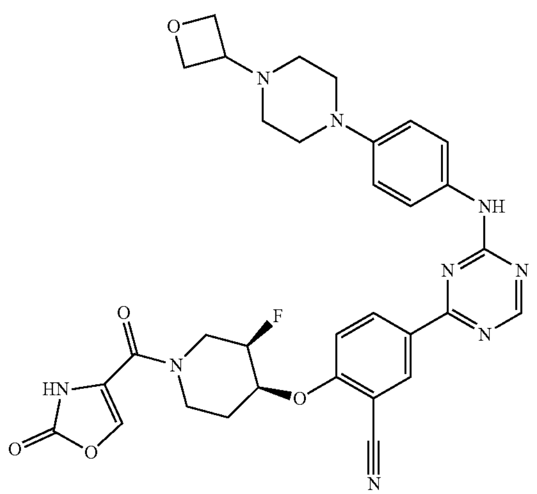 [SMILES: N#Cc1cc(-c2ncnc(Nc3ccc(N4CCN(C5COC5)CC4)cc3)n2)ccc1O[C@H]1CCN(C(=O)c2coc(=O)[nH]2)C[C@H]1F] | 3 | 3 | 390 | 2-(((3R,4S)-3-fluoro-1-(2-oxo-2,3-dihydrooxazole-4-carbonyl)piperidin-4-yl)oxy)-5-(4-((4-(4-(oxetan-3-yl)piperazin-1-yl)phenyl)amino)-1,3,5-triazin-2-yl)benzonitrile |
| 526 | 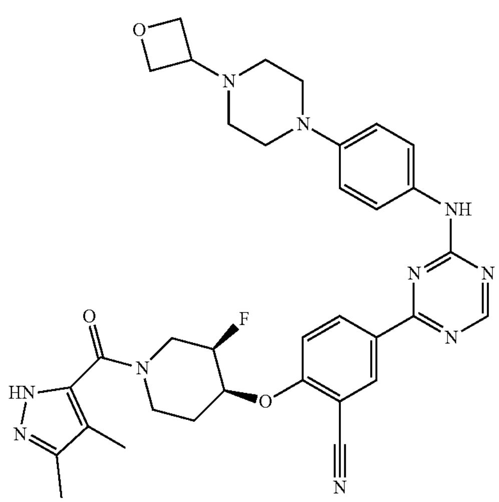 [SMILES: Cc1n[nH]c(C(=O)N2CC[C@H](Oc3ccc(-c4ncnc(Nc5ccc(N6CCN(C7COC7)CC6)cc5)n4)cc3C#N)[C@H](F)C2)c1C] | 9 | 19 | 447 | 2-(((3R,4S)-1-(3,4-dimethyl-1H-pyrazole-5-carbonyl)-3-fluoro-piperidin-4-yl)oxy)-5-(4-((4-(4-(oxetan-3-yl)piperazin-1-yl)phenyl)amino)-1,3,5 triazin-2-yl)benzonitrile |

TABLE 1-continued

| Ex. | Structure | TBK1 IC50 | IKKe IC50 | JAK2 IC50 | Name |
|---|---|---|---|---|---|
| 527 | 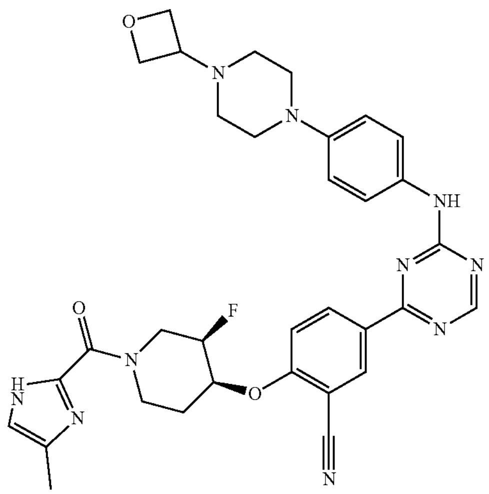 [SMILES: Cc1c[nH]c(C(=O)N2CC[C@H](Oc3ccc(-c4ncnc(Nc5ccc(N6CCN(C7COC7)CC6)cc5)n4)cc3C#N)[C@H](F)C2)n1] | 5 | 8 | 323 | 2-(((3R,4S)-3-fluoro-1-(4-methyl-1H-imidazole-2-carbonyl)piperidin-4-yl)oxy)-5-(4-((4-(4-(oxetan-3-yl)piperazin-1-yl)phenyl)amino)-1,3,5-triazin-2-yl)benzonitrile |
| 528 | 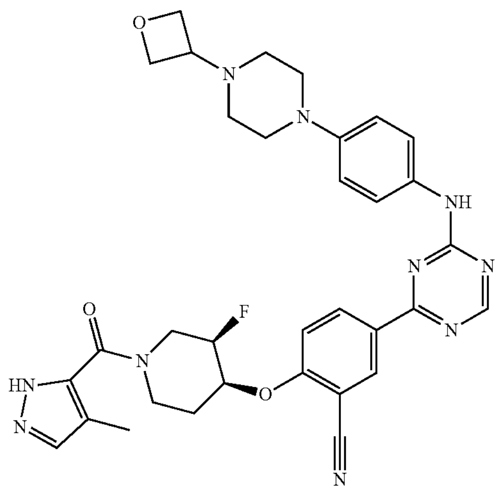 [SMILES: Cc1cn[nH]c1C(=O)N1CC[C@H](Oc2ccc(-c3ncnc(Nc4ccc(N5CCN(C6COC6)CC5)cc4)n3)cc2C#N)[C@H](F)C1] | 8 | 20 | 368 | 2-(((3R,4S)-3-fluoro-1-(4-methyl-1H-pyrazole-5-carbonyl)piperidin-4-yl)oxy)-5-(4-((4-(4-(oxetan-3-yl)piperazin-1-yl)phenyl)amino)-1,3,5-triazin-2-yl)benzonitrile |
| 529 | 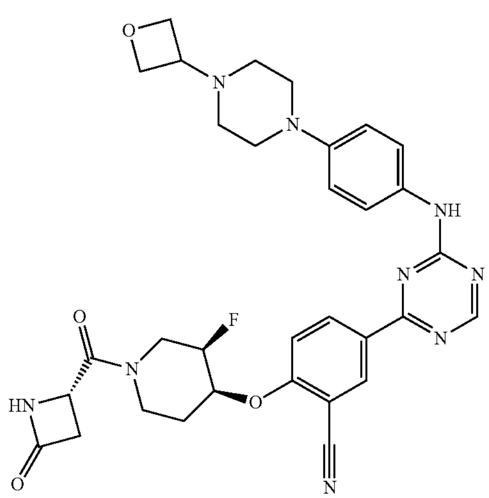 [SMILES: N#Cc1cc(-c2ncnc(Nc3ccc(N4CCN(C5COC5)CC4)cc3)n2)ccc1O[C@H]1CCN(C(=O)[C@@H]2CC(=O)N2)C[C@H]1F] | 3 | 4 | 356 | 2-(((3R,4S)-3-fluoro-1-((S)-4-oxoazetidine-2-carbonyl)piperidin-4-yl)oxy)-5-(4-((4-(4-(oxetan-3-yl)piperazin-1-yl)phenyl)amino)-1,3,5-triazin-2-yl)benzonitrile |

TABLE 1-continued

| Ex. | Structure | TBK1 IC50 | IKKe IC50 | JAK2 IC50 | Name |
|---|---|---|---|---|---|
| 530 | 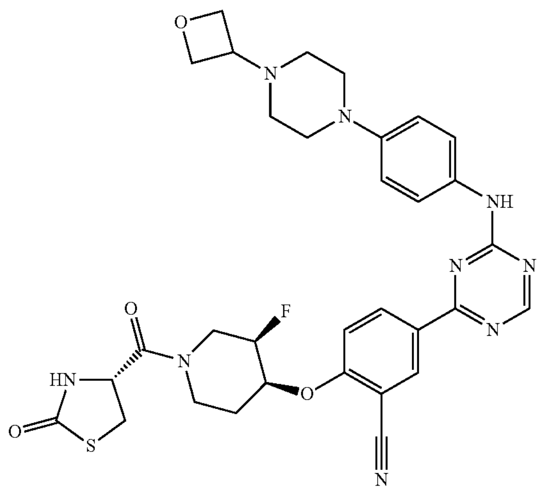 [SMILES: N#Cc1cc(-c2ncnc(Nc3ccc(N4CCN(C5COC5)CC4)cc3)n2)ccc1O[C@H]1CCN(C(=O)[C@@H]2CSC(=O)N2)C[C@H]1F] | 2 | 2 | 289 | 2-(((3R,4S)-3-fluoro-1-((R)-2-oxothiazolidine-4-carbonyl)piperidin-4-yl)oxy)-5-(4-((4-(4-(oxetan-3-yl)piperazin-1-yl)phenyl)amino)4,3,5-triazin-2-yl)benzonitrile |
| 531 | 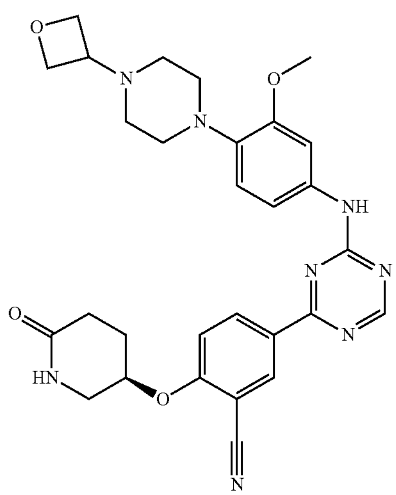 [SMILES: COc1cc(Nc2ncnc(-c3ccc(O[C@@H]4CCC(=O)NC4)c(C#N)c3)n2)ccc1N1CCN(C2COC2)CC1] | 4 | 3 | 55 | (R)-5-(4-((3-methoxy-4-(4-(oxetan-3-yl)piperazin-1-yl)phenyl)amino)-1,3,5-triazin-2-yl)-2-((6-oxopiperidin-3-yl)oxy)benzonitrile |
| 532 | 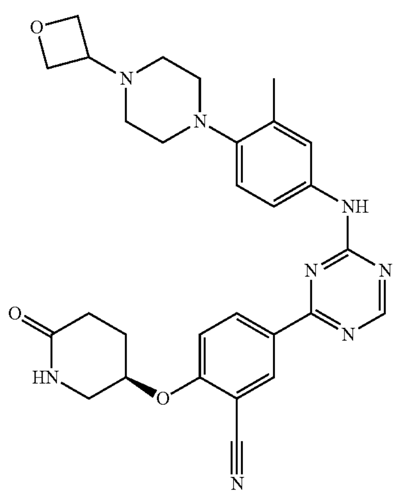 [SMILES: Cc1cc(Nc2ncnc(-c3ccc(O[C@@H]4CCC(=O)NC4)c(C#N)c3)n2)ccc1N1CCN(C2COC2)CC1] | 3 | 2 | 57 | (R)-5-(4-((3-methyl-4-(4-(oxetan-3-yl)piperazin-1-yl)phenyl)amino)-1,3,5-triazin-2-yl)-2-((6-oxopiperidin-3-yl)oxy)benzonitrile |

TABLE 1-continued

| Ex. | Structure | TBK1 IC50 | IKKe IC50 | JAK2 IC50 | Name |
|---|---|---|---|---|---|
| 533 | 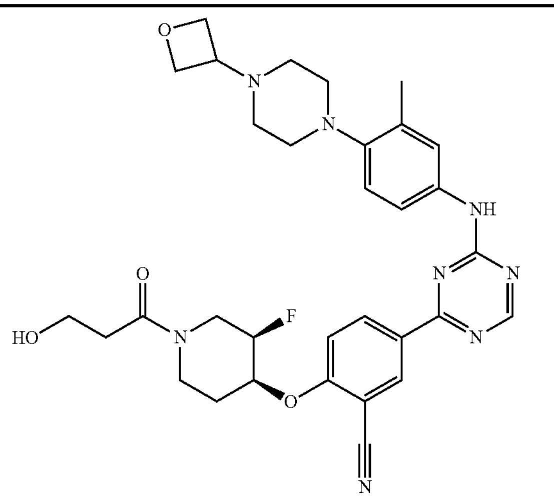 | 4 | 7 | 88 | 2-(((3R,4S)-3-fluoro-1-(3-hydroxypropanoyl)piperidin-4-yl)oxy)-5-(4-((3-methyl-4-(4-(oxetan-3-yl)piperazin-1-yl)phenyl)amino)-1,3,5-triazin-2-yl)benzonitrile |
| 534 | 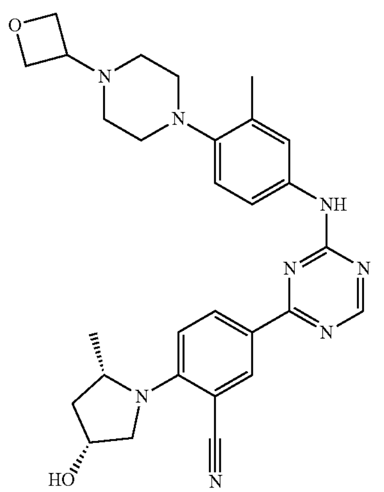 [SMILES: Cc1cc(Nc2ncnc(-c3ccc(N4C[C@H](O)C[C@@H]4C)c(C#N)c3)n2)ccc1N1CCN(C2COC2)CC1] | 4 | 7 | 32 | 2-((2S,4R)-4-hydroxy-2-methylpyrrolidin-1-yl)-5-(4-((3-methyl-4-(oxetan-3-yl)piperazin-1-yl)phenyl)amino)-1,3,5-triazin-2-yl)benzonitrile |
| 535 | 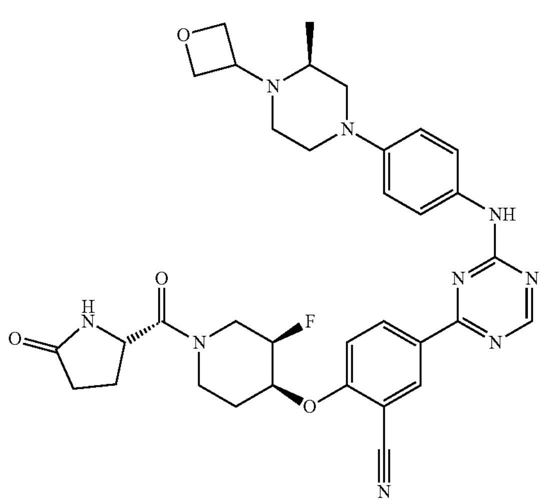 | 3 | 3 | 904 | 2-(((3R,4S)-3-fluoro-1-((S)-5-oxopyrrolidine-2-carbonyl)piperidin-4-yl)oxy)-5-(4-((4-((S)-3-methyl-4-(oxetan-3-yl)piperazin-1-yl)phenyl)amino)-1,3,5-triazin-2-yl)benzonitrile |

TABLE 1-continued

| Ex. | Structure | TBK1 IC50 | IKKe IC50 | JAK2 IC50 | Name |
|---|---|---|---|---|---|
| 536 | 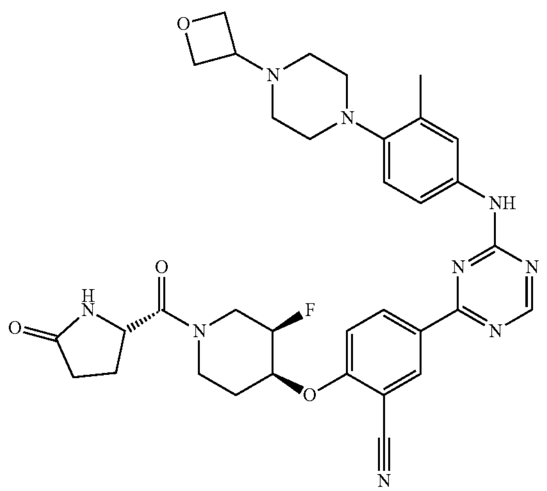 | 2 | 1 | 101 | 2-(((3R,4S)-3-fluoro-1-((S)-5-oxopyrrolidine-2-carbonyl)piperidin-4-yl)oxy)-5-(4-((3-methyl-4-(4-(oxetan-3-yl)piperazin-1-yl)phenyl)amino)-1,3,5-triazin-2-yl)benzonitrile |
| 537 | 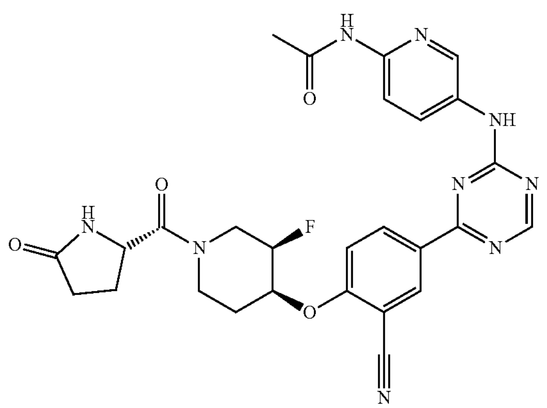 | 8 | 18 | 1000 | N-(5-((4-(3-cyano-4-(((3R,4S)-3-fluoro-1-((S)-5-oxopyrrolidine-2-carbonyl)piperidin-4-yl)oxy)phenyl)-1,3,5-triazin-2-yl)amino)pyridin-2-yl)acetamide |
| 538 | 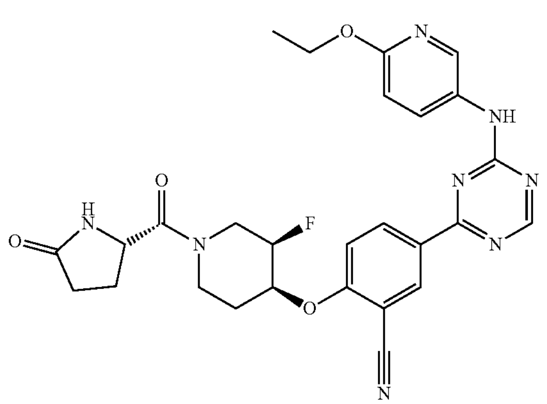 | 7 | 14 | 1000 | 5-(4-((6-ethoxypyridin-3-yl)amino)-1,3,5-triazin-2-yl)-2-(((3R,4S)-3-fluoro-1-((S)-5-oxopyrrolidine-2-carbonyl)piperidin-4-yl)oxy)benzonitrile |

TABLE 1-continued

| Ex. | Structure | TBK1 IC50 | IKKe IC50 | JAK2 IC50 | Name |
|---|---|---|---|---|---|
| 539 | 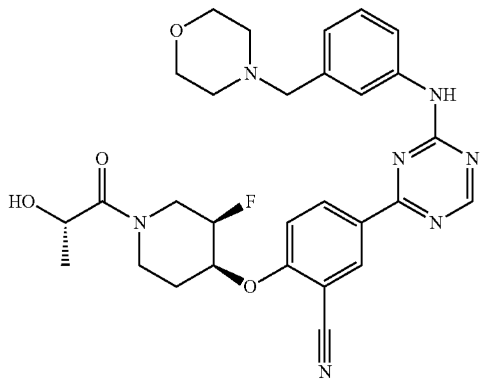 [SMILES: C[C@H](O)C(=O)N1CC[C@H](Oc2ccc(-c3ncnc(Nc4cccc(CN5CCOCC5)c4)n3)cc2C#N)[C@H](F)C1] | 3 | 2 | 519 | 2-(((3R,4S)-3-fluoro-1-((S)-2-hydroxypropanoyl)piperidin-4-yl)oxy)-5-(4-((3-(morpholinomethyl)phenyl)amino)-1,3,5-triazin-2-yl)benzonitrile |
| 540 | 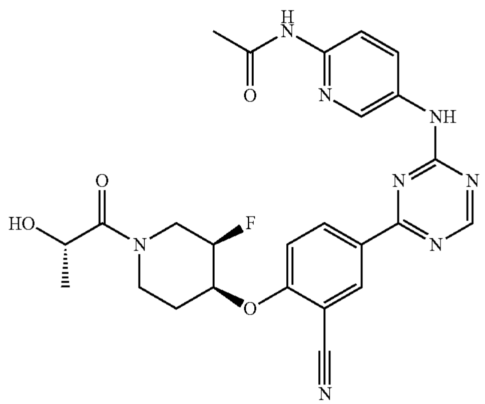 [SMILES: CC(=O)Nc1ccc(Nc2ncnc(-c3ccc(O[C@H]4CCN(C(=O)[C@H](C)O)C[C@H]4F)c(C#N)c3)n2)cn1] | 20 | 21 | 1000 | N-(5-((4-(3-cyano-4-(((3R,4S)-3-fluoro-1-((S)-2-hydroxy-propanoyl)piperidin-4-yl)oxy)phenyl)-1,3,5-triazin-2-yl)amino)pyridin-2-yl)acetamide |
| 541 | 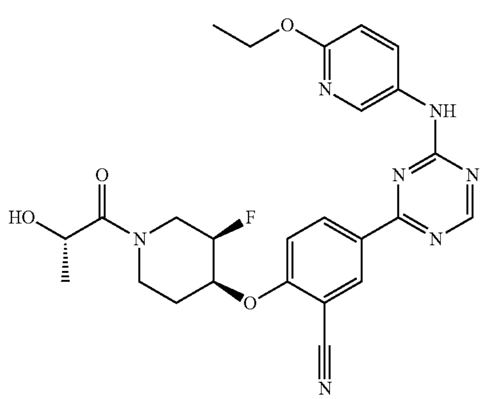 [SMILES: CCOc1ccc(Nc2ncnc(-c3ccc(O[C@H]4CCN(C(=O)[C@H](C)O)C[C@H]4F)c(C#N)c3)n2)cn1] | 15 | 17 | 1000 | 5-(4-((6-ethoxypyridin-3-yl)amino)-1,3,5-triazin-2-yl)-2-(((3R,4S)-3-fluoro-1-((S)-2-hydroxypropanoyl)piperidin-4-yl)oxy)benzonitrile |

TABLE 1-continued

| Ex. | Structure | TBK1 IC50 | IKKe IC50 | JAK2 IC50 | Name |
|---|---|---|---|---|---|
| 542 | 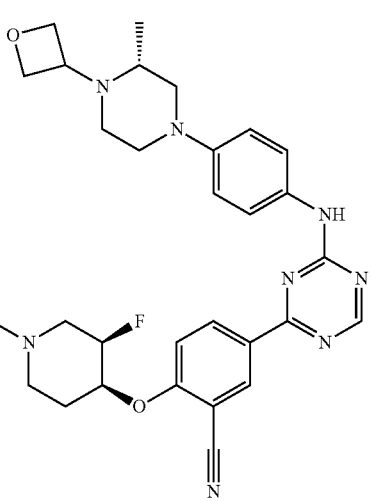 | | 6 | 4 | 363 | 2-(((3R,4S)-3-fluoro-1-((S)-5-oxopyrrolidine-2-carbonyl)piperidin-4-yl)oxy)-5-(4-((4-((R)-3-methyl-4-(oxetan-3-yl)piperazin-1-yl)phenyl)amino)-1,3,5-triazin-2-yl)benzonitrile |
| 543 | 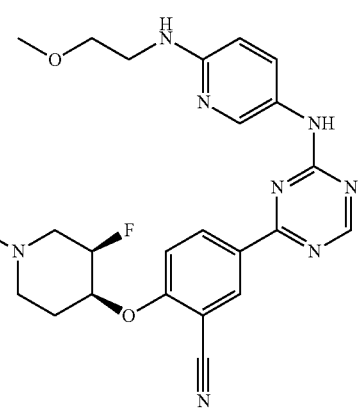 | 12 | 9 | 1000 | 2-(((3R,4S)-3-fluoro-1-((S)-2-hydroxypropanoyl)piperidin-4-yl)oxy)-5-(4-((6-((2-methoxyethyl)amino)pyridin-3-yl)amino)-1,3,5-triazin-2-yl)benzonitrile |
| 544 | 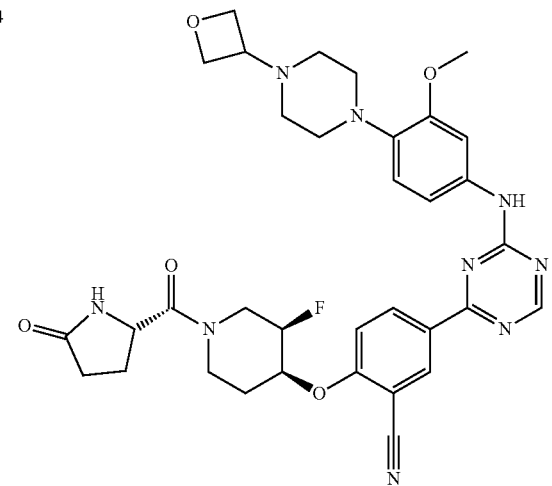 | 2 | 1 | 44 | 2-(((3R,4S)-3-fluoro-1-((S)-5-oxopyrrolidine-2-carbonyl)piperidin-4-yl)oxy)-5-(4-((3-methoxy-4-(4-(oxetan-3-yl)piperazin-1-yl)phenyl)amino)-1,3,5-triazin-2-yl)benzonitrile |

TABLE 1-continued

| Ex. | Structure | TBK1 IC50 | IKKe IC50 | JAK2 IC50 | Name |
|---|---|---|---|---|---|
| 545 | 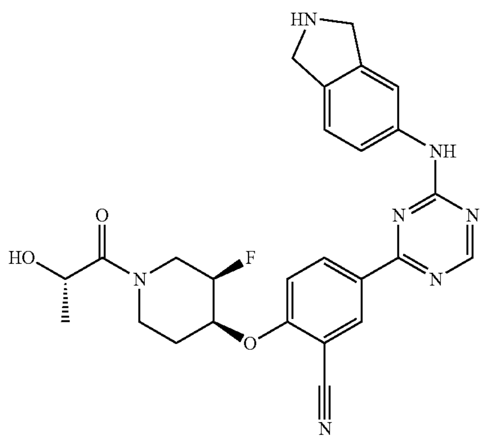 [SMILES: C[C@H](O)C(=O)N1CC[C@H](Oc2ccc(-c3ncnc(Nc4ccc5c(c4)CNC5)n3)cc2C#N)[C@H](F)C1] | 3 | 1 | 659 | 2-(((3R,4S)-3-fluoro-1-((S)-2-hydroxypropanoyl)piperidin-4-yl)oxy)-5-(4-(isoindolin-5-ylamino)-1,3,5-triazin-2-yl)benzonitrile |
| 546 | 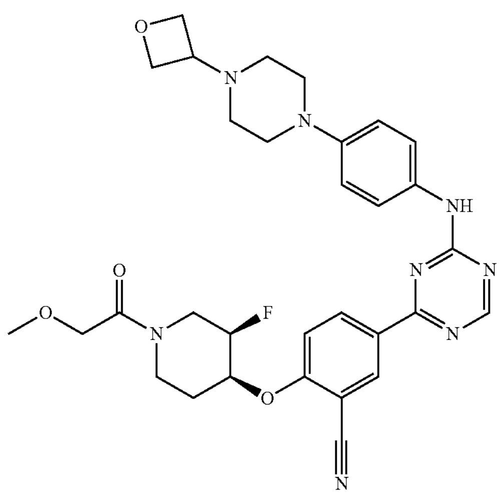 [SMILES: COCC(=O)N1CC[C@H](Oc2ccc(-c3ncnc(Nc4ccc(N5CCN(C6COC6)CC5)cc4)n3)cc2C#N)[C@H](F)C1] | 2 | 2 | 492 | 2-(((3R,4S)-3-fluoro-1-(2-methoxyacetyl)piperidin-4-yl)oxy)-5-(4-((4-(4-(oxetan-3-yl)piperazin-1-yl)phenyl)amino)-1,3,5-triazin-2-yl)benzonitrile |
| 547 | 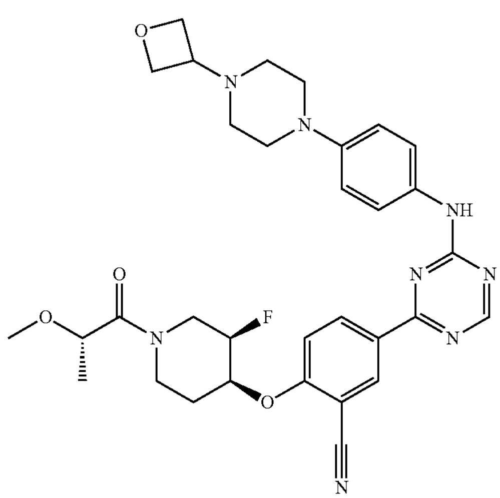 [SMILES: CO[C@@H](C)C(=O)N1CC[C@H](Oc2ccc(-c3ncnc(Nc4ccc(N5CCN(C6COC6)CC5)cc4)n3)cc2C#N)[C@H](F)C1] | 11 | 36 | 1000 | 2-(((3R,4S)-3-fluoro-1-((S)-2-methoxypropanoyl)piperidin-4-yl)oxy)-5-(4-((4-(4-(oxetan-3-yl)piperazin-1-yl)phenyl)amino)-1,3,5-triazin-2-yl)benzonitrile |

TABLE 1-continued

| Ex. | Structure | TBK1 IC50 | IKKe IC50 | JAK2 IC50 | Name |
|---|---|---|---|---|---|
| 548 | 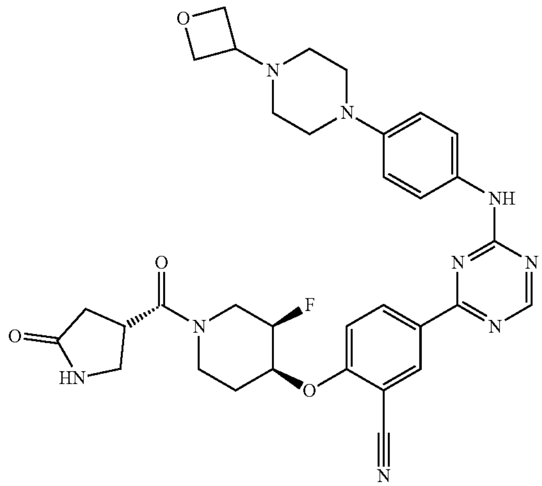 | 21 | 96 | 353 | 2-(((3R,4S)-3-fluoro-1-((S)-5-oxopyrrolidine-3-carbonyl)piperidin-4-yl)oxy)-5-(4-((4-(4-(oxetan-3-yl)piperazin-1-yl)phenyl)amino)-1,3,5-triazin-2-yl)benzonitrile |
| 549 | 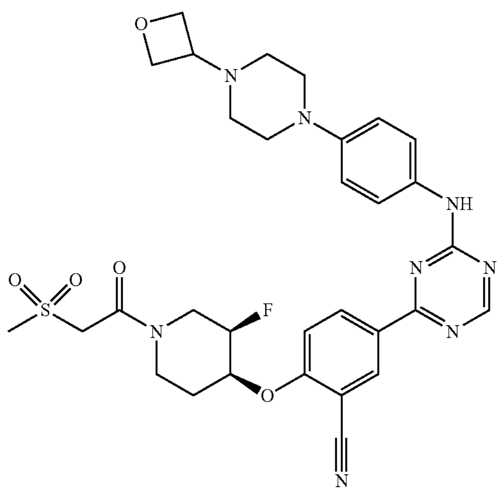 [SMILES: CS(=O)(=O)CC(=O)N1CC[C@H](Oc2ccc(-c3ncnc(Nc4ccc(N5CCN(C6COC6)CC5)cc4)n3)cc2C#N)[C@H](F)C1] | 4 | 11 | 179 | 2-(((3R,4S)-3-fluoro-1-(2-(methylsulfonyl)acetyl)piperidin-4-yl)oxy)-5-(4-((4-(4-(oxetan-3-yl)piperazin-1-yl)phenyl)amino)-1,3,5-triazin-2-yl)benzonitrile |
| 550 | 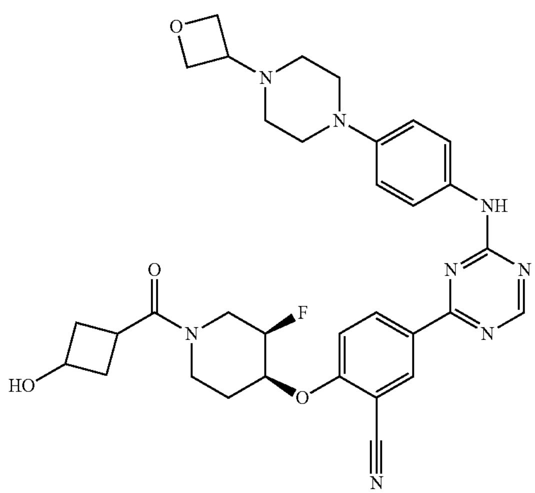 [SMILES: N#Cc1cc(-c2ncnc(Nc3ccc(N4CCN(C5COC5)CC4)cc3)n2)ccc1O[C@H]1CCN(C(=O)C2CC(O)C2)C[C@H]1F] | 11 | 36 | 750 | 2-(((3R,4S)-3-fluoro-1-(3-hydroxycyclobutanecarbonyl)piperidin-4-yl)oxy)-5-((4-(4-(oxetan-3-yl)piperazin-1-yl)phenyl)amino)-1,3,5-triazin-2-yl)benzonitrile |

TABLE 1-continued

| Ex. | Structure | TBK1 IC50 | IKKe IC50 | JAK2 IC50 | Name |
|---|---|---|---|---|---|
| 551 | 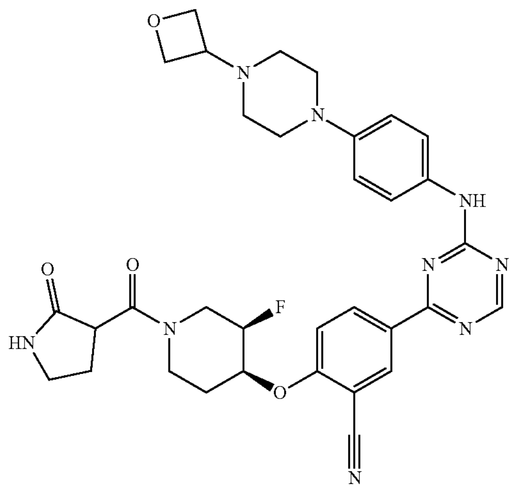 [SMILES: N#Cc1cc(-c2ncnc(Nc3ccc(N4CCN(C5COC5)CC4)cc3)n2)ccc1O[C@H]1CCN(C(=O)C2CCNC2=O)C[C@H]1F] | 16 | 92 | 799 | 2-(((3R,4S)-3-fluoro-1-(2-oxopyrrolidine-3-carbonyl)piperidin-4-yl)oxy)-5-(4-((4-(4-(oxetan-3-yl)piperazin-1-yl)phenyl)amino)-1,3,5-triazin-2-yl)benzonitrile |
| 552 | 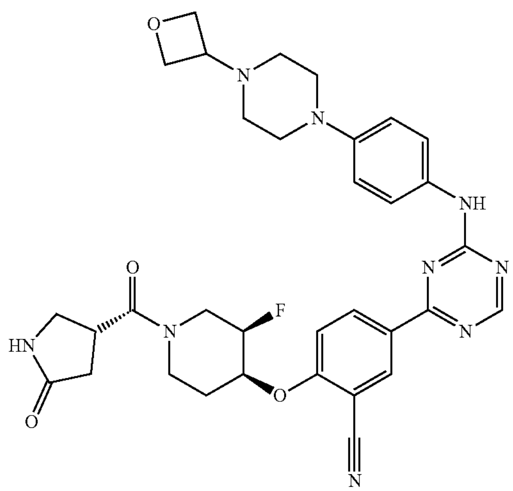 | 28 | 174 | 562 | 2-(((3R,4S)-3-fluoro-1-((R)-5-oxopyrrolidine-3-carbonyl)piperidin-4-yl)oxy)-5-(4-((4-(4-(oxetan-3-yl)piperazin-1-yl)phenyl)amino)-1,3,5-triazin-2-yl)benzonitrile |
| 553 | 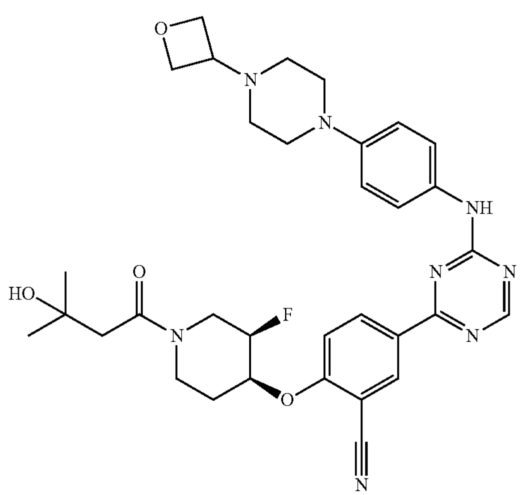 [SMILES: CC(C)(O)CC(=O)N1CC[C@H](Oc2ccc(-c3ncnc(Nc4ccc(N5CCN(C6COC6)CC5)cc4)n3)cc2C#N)[C@H](F)C1] | 38 | 51 | 1000 | 2-(((3R,4S)-3-fluoro-1-(3-hydroxy-3-methylbutanoyl)piperidin-4-yl)oxy)-5-(4-((4-(4-(oxetan-3-yl)piperazin-1-yl(phenyl)amino)-1,3,5-triazin-2-yl)benzonitrile |

TABLE 1-continued

| Ex. | Structure | TBK1 IC50 | IKKe IC50 | JAK2 IC50 | Name |
|---|---|---|---|---|---|
| 554 | 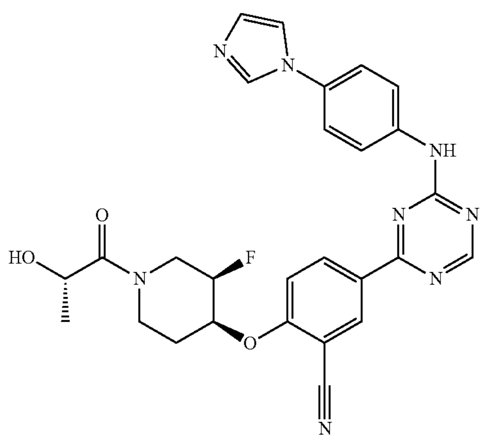 [SMILES: C[C@H](O)C(=O)N1CC[C@H](Oc2ccc(-c3ncnc(Nc4ccc(-n5ccnc5)cc4)n3)cc2C#N)[C@H](F)C1] | 5 | 4 | 1000 | 5-(4-((4-(1H-imidazol-1-yl)phenyl)amino)-1,3,5-triazin-2-yl)-2-(((3R,4S)-3-fluoro-1-((S)-2-hydroxypropanoyl)piperidin-4-yl)oxy)benzonitrile |
| 555 | 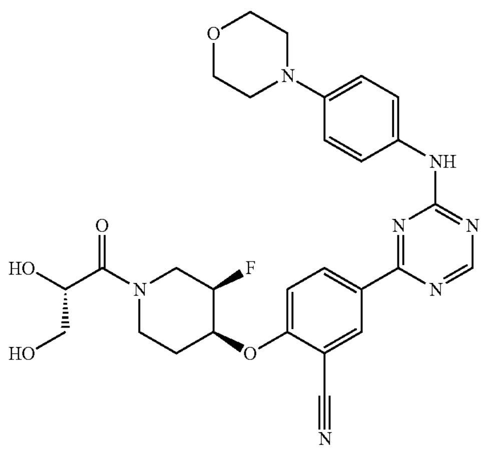 [SMILES: N#Cc1cc(-c2ncnc(Nc3ccc(N4CCOCC4)cc3)n2)ccc1O[C@H]1CCN(C(=O)[C@@H](O)CO)C[C@H]1F] | 4 | 1 | 732 | 2-(((3R,4S)-1-((S)-2,3-dihydroxypropanoyl)-3-fluoropiperidin-4-yl)oxy)-5-(4-((4-morpholinophenyl)amino)-1,3,5-triazin-2-yl)benzonitrile |
| 556 | 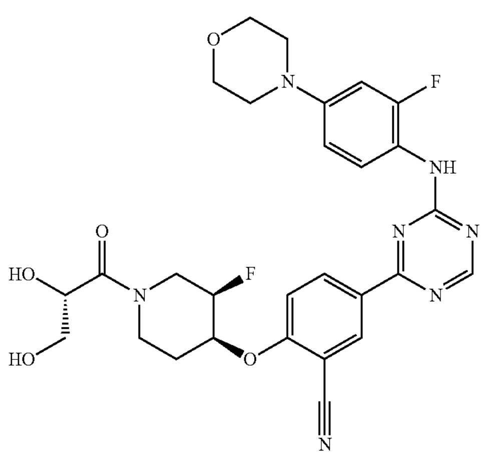 [SMILES: N#Cc1cc(-c2ncnc(Nc3ccc(N4CCOCC4)cc3F)n2)ccc1O[C@H]1CCN(C(=O)[C@@H](O)CO)C[C@H]1F] | 3 | 5 | 1000 | 2-(((3R,4S)-1-((S)-2,3-dihydroxypropanoyl)-3-fluoropiperidin-4-yl)oxy)-5-(4-((2-fluoro-4-morpholinophenyl)amino)-1,3,5-triazin-2-yl)benzonitrile |

TABLE 1-continued

| Ex. | Structure | TBK1 IC50 | IKKe IC50 | JAK2 IC50 | Name |
|---|---|---|---|---|---|
| 557 | 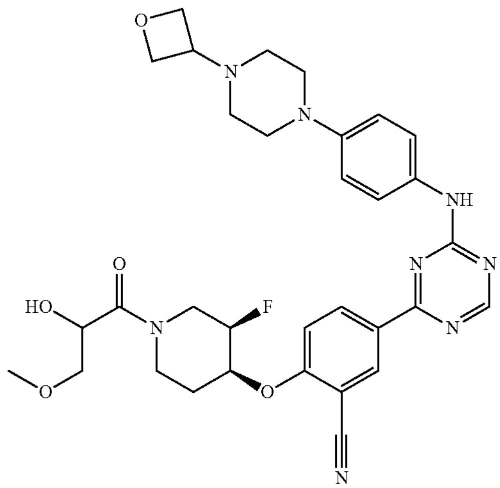 | 6 | 4 | 917 | 2-(((3R,4S)-3-fluoro-1-(2-hydroxy-3-methoxypropanoyl)piperidin-4-yl)oxy)-5-(4-((4-(4-(oxetan-3-yl)piperazin-1-yl)phenyl)amino)-1,3,5-triazin-2-yl)benzonitrile |
| 558 | 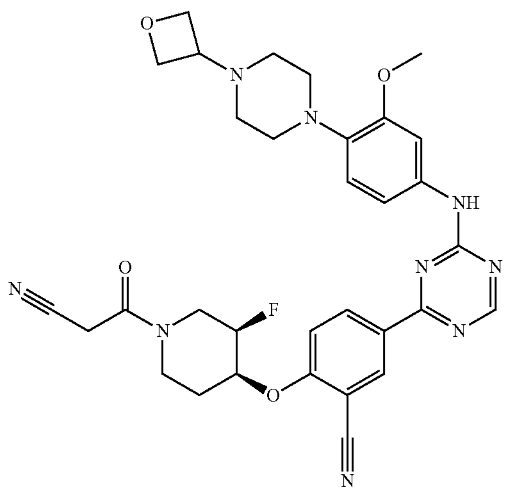 [SMILES: COc1cc(Nc2ncnc(-c3ccc(O[C@H]4CCN(C(=O)CC#N)C[C@H]4F)c(C#N)c3)n2)ccc1N1CCN(C2COC2)CC1] | 2 | 2 | 26 | 2-(((3R,4S)-1-(2-cyanoacetyl)-3-fluoropiperidin-4-yl)oxy)-5-(4-((3-methoxy-4-(4-(oxetan-3-yl)piperazin-1-yl)phenyl)amino)-1,3,5-triazin-2-yl)benzonitrile |
| 559 | 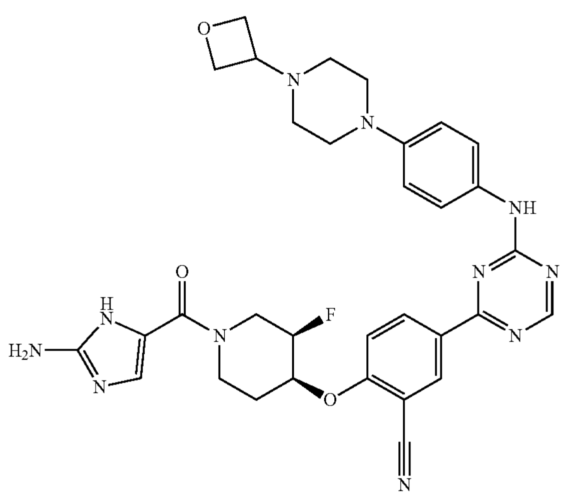 [SMILES: N#Cc1cc(-c2ncnc(Nc3ccc(N4CCN(C5COC5)CC4)cc3)n2)ccc1O[C@H]1CCN(C(=O)c2cnc(N)[nH]2)C[C@H]1F] | 5 | 2 | 83 | 2-(((3R,4S)-1-(2-amino-1H-imidazole-5-carbonyl)-3-fluoropiperidin-4-yl)oxy)-5-4-((4-(4-(oxetan-3-yl)piperazin-1-yl)phenyl)amino)-1,3,5-triazin-2-yl)benzonitrile |

TABLE 1-continued

| Ex. | Structure | TBK1 IC50 | IKKe IC50 | JAK2 IC50 | Name |
|---|---|---|---|---|---|
| 560 | 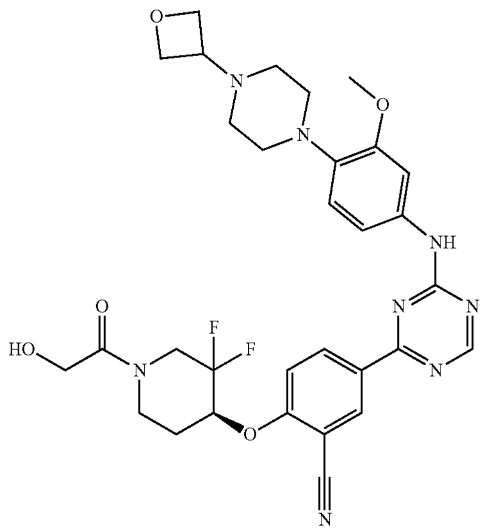 [SMILES: COc1cc(Nc2ncnc(-c3ccc(O[C@H]4CCN(C(=O)CO)CC4(F)F)c(C#N)c3)n2)ccc1N1CCN(C2COC2)CC1] | 2 | 1 | 18 | (S)-2-((3,3-difluoro-1-(2-hydroxyacetyl)piperidn-4-yl)oxy)-5-(4-((3-methoxy-4-(4-(oxetan-3-yl)piperazin-1-yl)phenyl)amino)-1,3,5-triazin-2-yl)benzonitrile |
| 561 | 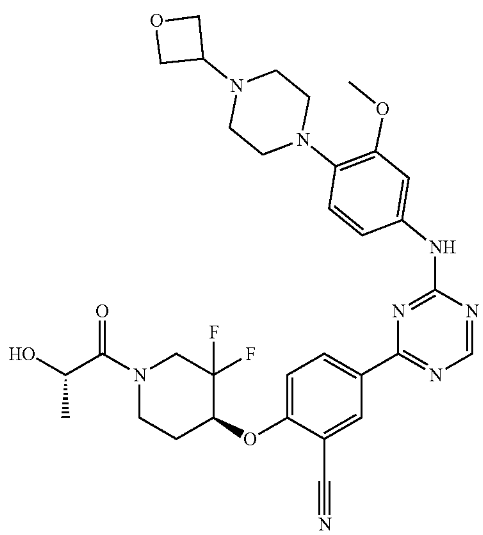 [SMILES: COc1cc(Nc2ncnc(-c3ccc(O[C@H]4CCN(C(=O)[C@H](C)O)CC4(F)F)c(C#N)c3)n2)ccc1N1CCN(C2COC2)CC1] | 2 | 1 | 68 | 2-(((S)-3,3-difluoro-1-((S)-2-hydroxypropanoyl)piperidin-4-yl)oxy)-5-(4-((3-methoxy-4-(4-(oxetan-3-yl)piperazin-1-yl)phenyl)amino)-1,3,5-triazin-2-yl)benzonitrile |
| 562 | 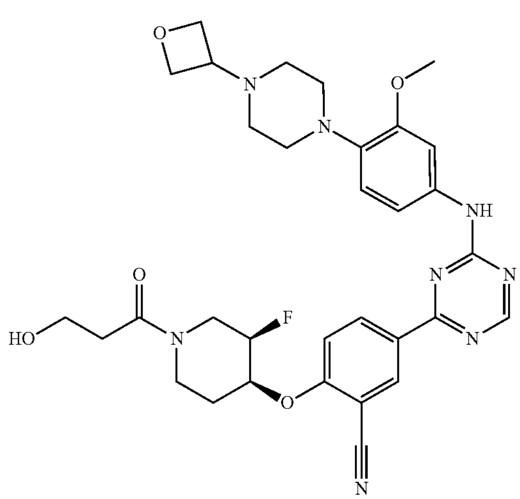 [SMILES: COc1cc(Nc2ncnc(-c3ccc(O[C@H]4CCN(C(=O)CCO)C[C@H]4F)c(C#N)c3)n2)ccc1N1CCN(C2COC2)CC1] | 3 | 6 | 110 | 2-(((3R,4S)-3-fluoro-1-(3-hydroxypropanoyl)piperidin-4-yl)oxy)-5-(4-((3-methoxy-4-(4-(oxetan-3-yl)piperazin-1-yl)phenyl)amino)-1,3,5-triazin-2-yl)benzonitrile |

TABLE 1-continued

| Ex. | Structure | TBK1 IC50 | IKKe IC50 | JAK2 IC50 | Name |
|---|---|---|---|---|---|
| 563 | 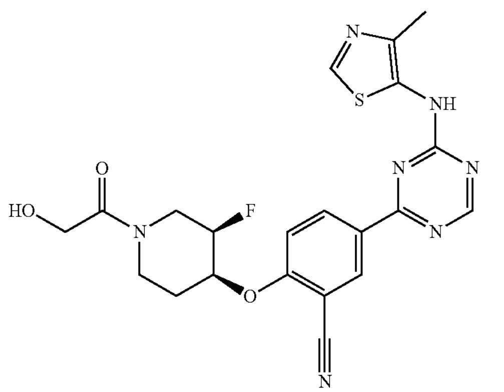 [SMILES: Cc1ncsc1Nc1ncnc(-c2ccc(O[C@H]3CCN(C(=O)CO)C[C@H]3F)c(C#N)c2)n1] | 5 | 3 | 1000 | 2-(((3R,4S)-3-fluoro-1-(2-hydroxyacetyl)piperidin-4-yl)oxy)-5-(4-((4-methylthiazol-5-yl)amino)-1,3,5-triazin-2-yl)benzonitrile |
| 564 | 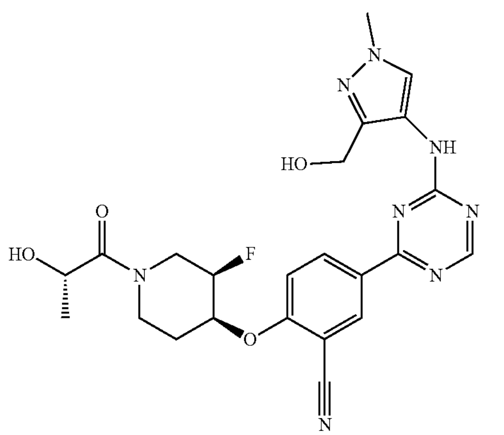 [SMILES: C[C@H](O)C(=O)N1CC[C@H](Oc2ccc(-c3ncnc(Nc4cn(C)nc4CO)n3)cc2C#N)[C@H](F)C1] | 92 | 109 | 1000 | 2-(((3R,4S)-3-fluoro-1-((S)-2-hydroxypropanoyl)piperidin-4-yl)oxy)-5-(4-((3-(hydroxymethyl)-1-methyl-1H-pyrazol-4-yl)amino)-1,3,5-triazin-2-yl)benzonitrile |
| 565 | 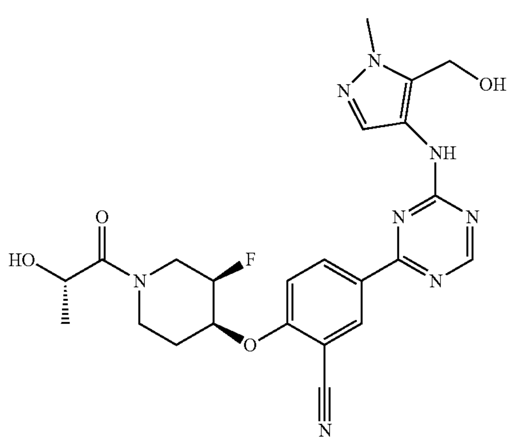 [SMILES: C[C@H](O)C(=O)N1CC[C@H](Oc2ccc(-c3ncnc(Nc4cnn(C)c4CO)n3)cc2C#N)[C@H](F)C1] | 90 | 126 | 1000 | 2-(((3R,4S)-3-fluoro-1-((S)-2-hydroxypropanoyl)piperidin-4-yl)oxy)-5-(4-((5-(hydroxymethyl)-1-methyl-1H-pyrazol-4-yl)amino)-1,3,5-triazin-2-yl)benzonitrile |

TABLE 1-continued

| Ex. | Structure | TBK1 IC50 | IKKe IC50 | JAK2 IC50 | Name |
|---|---|---|---|---|---|
| 566 | 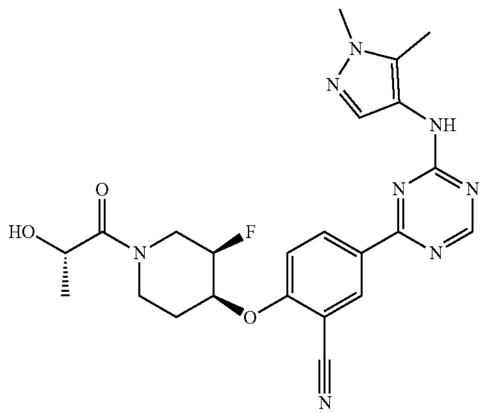 [SMILES: Cc1c(Nc2ncnc(-c3ccc(O[C@H]4CCN(C(=O)[C@H](C)O)C[C@H]4F)c(C#N)c3)n2)cnn1C] | 14 | 33 | 1000 | 5-(4-((1,5-dimethyl-1H-pyrazol-4-yl)amino)-1,3,5-triazin-2-yl)-2-(((3R,4S)-3-fluoro-1-((S)-2-hydroxypropanoyl)piperidin-4-yl)oxy)benzonitrile |
| 567 | 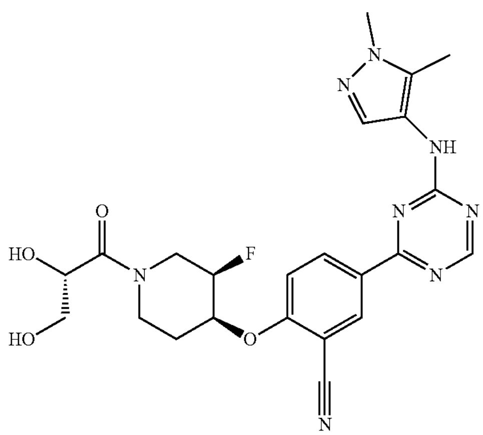 [SMILES: Cc1c(Nc2ncnc(-c3ccc(O[C@H]4CCN(C(=O)[C@@H](O)CO)C[C@H]4F)c(C#N)c3)n2)cnn1C] | 3 | 7 | 1000 | 2-(((3R,4S)-1-((S)-2,3-dihydroxypropanoyl)-3-fluoropiperidin-4-yl)oxy)-5-(4-((1,5-dimethyl-1H-pyrazol-4-yl)amino)-1,3,5-triazin-2-yl)benzonitrile |
| 568 | 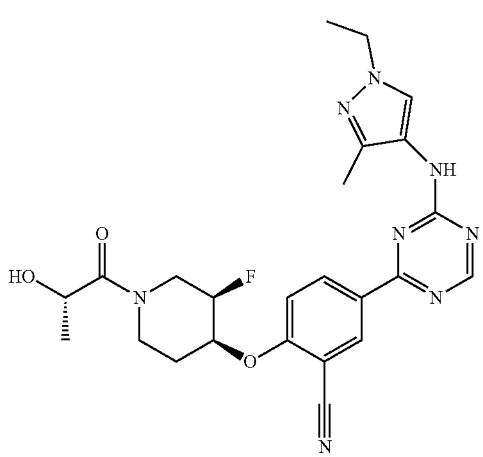 [SMILES: CCn1cc(Nc2ncnc(-c3ccc(O[C@H]4CCN(C(=O)[C@H](C)O)C[C@H]4F)c(C#N)c3)n2)c(C)n1] | 9 | 21 | 1000 | 5-(4-((1-ethyl-3-methyl-1H-pyrazol-4-yl)amino)-1,3,5-triazin-2-yl)-2-(((3R,4S)-3-fluoro-1-((S)-2-hydroxypropanoyl)piperidin-4-yl)oxy)benzonitrile |

TABLE 1-continued

| Ex. | Structure | TBK1 IC50 | IKKe IC50 | JAK2 IC50 | Name |
|---|---|---|---|---|---|
| 569 | 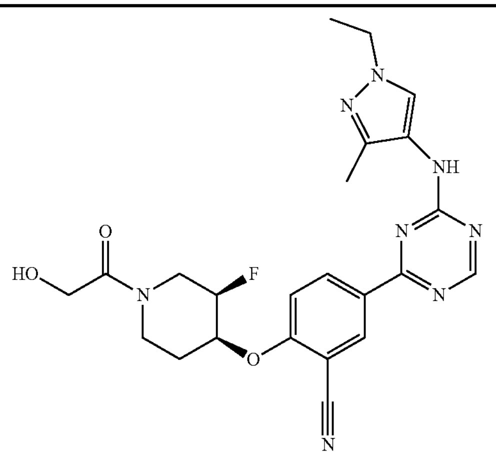 | 4 | 6 | 1000 | 5-(4-((1-ethyl-3-methyl-1H-pyrazol-4-yl)amino)-1,3,5-triazin-2-yl)-2-(((3R,4S)-3-fluoro-1-(2-hydroxyacetyl)piperidin-4-yl)oxy)benzonitrile |
| 570 | 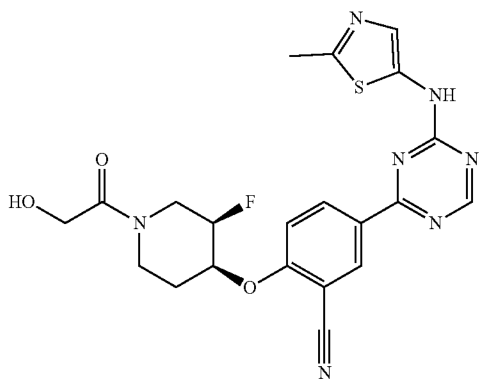 [SMILES: Cc1ncc(Nc2ncnc(-c3ccc(O[C@H]4CCN(C(=O)CO)C[C@H]4F)c(C#N)c3)n2)s1] | 3 | 4 | 1000 | 2-(((3R,4S)-3-fluoro-1-((S)-2-hydroxypropanoyl)piperidin-4-yl)oxy)-5-(4-((2-methylthiazol-5-yl)amino)-1,3,5-triazin-2-yl)benzonitrile |
| 571 | 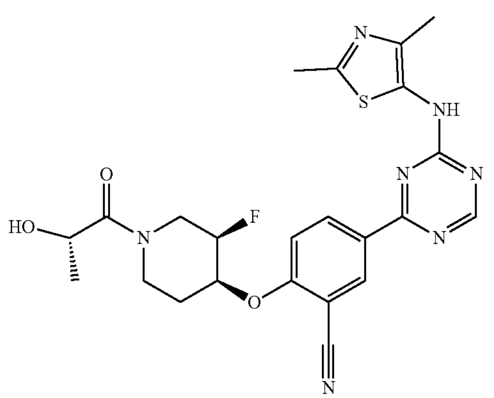 [SMILES: Cc1nc(C)c(Nc2ncnc(-c3ccc(O[C@H]4CCN(C(=O)[C@H](C)O)C[C@H]4F)c(C#N)c3)n2)s1] | 6 | 11 | 1000 | 5-(4-((2,4-dimethylthiazol-5-yl)amino)-1,3,5-triazin-2-yl)-2-(((3R,4S)-3-fluoro-1-((S)-2-hydroxypropanoyl)piperidin-4-yl)oxy)benzonitrile |
| 572 | 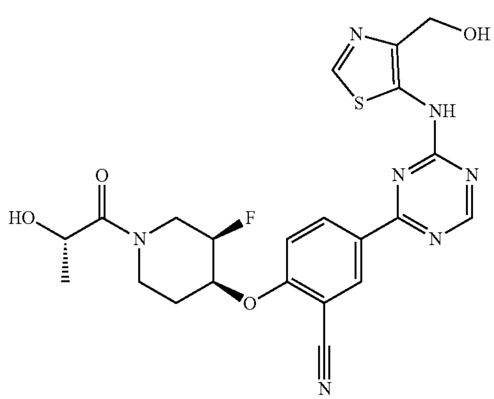 [SMILES: C[C@H](O)C(=O)N1CC[C@H](Oc2ccc(-c3ncnc(Nc4scnc4CO)n3)cc2C#N)[C@H](F)C1] | 36 | 21 | 1000 | 2-(((3R,4S)-3-fluoro-1-((S)-2-hydroxypropanoyl)piperidin-4-yl)oxy)-5-(4-((4-(hydroxymethyl)thiazol-5-yl)amino)-1,3,5-triazin-2-yl)benzonitrile |

TABLE 1-continued

| Ex. | Structure | TBK1 IC50 | IKKe IC50 | JAK2 IC50 | Name |
|---|---|---|---|---|---|
| 573 | 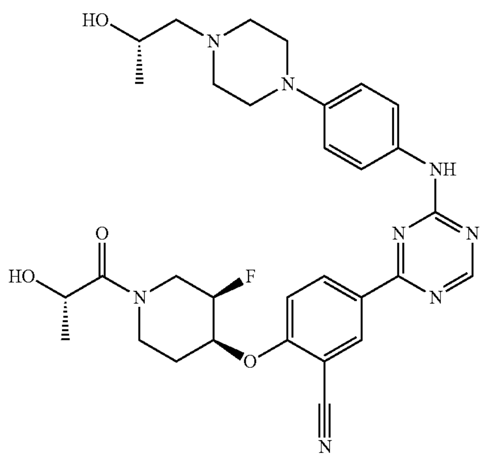 [SMILES: C[C@H](O)CN1CCN(c2ccc(Nc3ncnc(-c4ccc(O[C@H]5CCN(C(=O)[C@H](C)O)C[C@H]5F)c(C#N)c4)n3)cc2)CC1] | 3 | 1 | 969 | 2-(((3R,4S)-3-fluoro-1-((S)-2-hydroxypropanoyl)piperidin-4-yl)oxy)-5-(4-((4-(4-((S)-2-hydroxypropyl)piperazin-1-yl)phenyl)amino)-1,3,5-triazin-2-yl)benzonitrile |
| 574 | 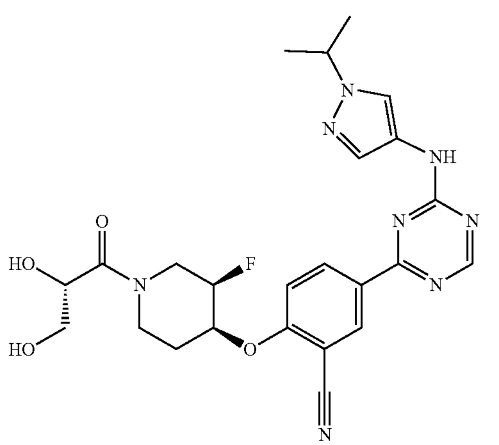 [SMILES: CC(C)n1cc(Nc2ncnc(-c3ccc(O[C@H]4CCN(C(=O)[C@@H](O)CO)C[C@H]4F)c(C#N)c3)n2)cn1] | 2 | 2 | 354 | 2-(((3R,4S)-1-((S)-2,3-dihydroxypropanoyl)-3-fluoropiperidin-4-yl)oxy)-5-(4-((1-isopropyl-1H-pyrazol-4-yl)amino)-1,3,5-triazin-2-yl)benzonitrile |
| 575 | 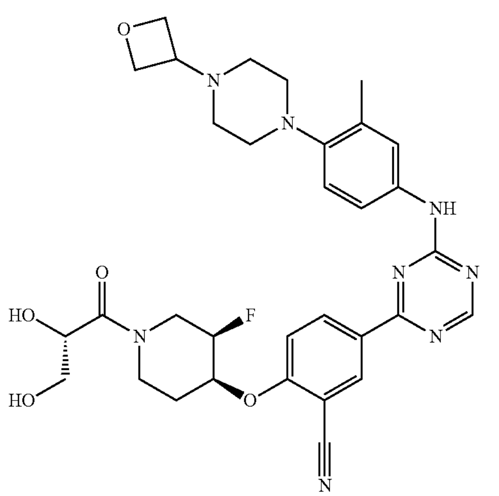 | 2 | 1 | 62 | 2-(((3R,4S)-1-((S)-2,3-dihydroxypropanoyl)-3-fluoropiperidin-4-yl)oxy)-5-(4-((3-methyl-4-(4-(oxetan-3-yl)piperazin-1-yl)phenyl)amino)-1,3,5-triazin-2-yl)benzonitrile |

TABLE 1-continued

| Ex. | Structure | TBK1 IC50 | IKKe IC50 | JAK2 IC50 | Name |
|---|---|---|---|---|---|
| 576 | 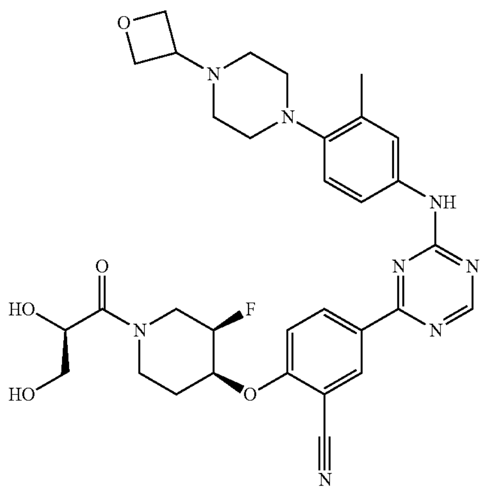 [SMILES: Cc1cc(Nc2ncnc(-c3ccc(O[C@H]4CCN(C(=O)[C@H](O)CO)C[C@H]4F)c(C#N)c3)n2)ccc1N1CCN(C2COC2)CC1] | 2 | 2 | 56 | 2-(((3R,4S)-1-((R)-2,3-dihydroxypropanoyl)-3-fluoropiperidin-4-yl)oxy)-5-(4-((3-methyl-4-(4-(oxetan-3-yl)piperazin-1-yl)phenyl)amino)-1,3,5-triazin-2-yl)benzonitrile |
| 577 | 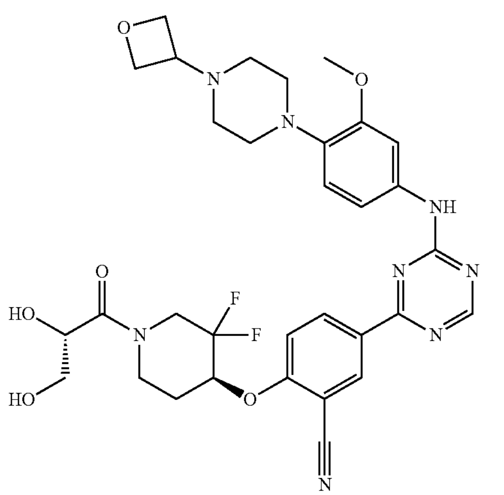 [SMILES: COc1cc(Nc2ncnc(-c3ccc(O[C@H]4CCN(C(=O)[C@@H](O)CO)CC4(F)F)c(C#N)c3)n2)ccc1N1CCN(C2COC2)CC1] | 2 | 1 | 57 | 2-(((S)-1-((S)-2,3-dihydroxypropanoyl)-3,3-difluoropiperidin-4-yl)oxy)-5-(4-((3-methoxy-4-(4-(oxetan-3-yl)piperazin-1-yl)phenyl)amino)-1,3,5-triazin-2-yl)benzonitrile |
| 578 | 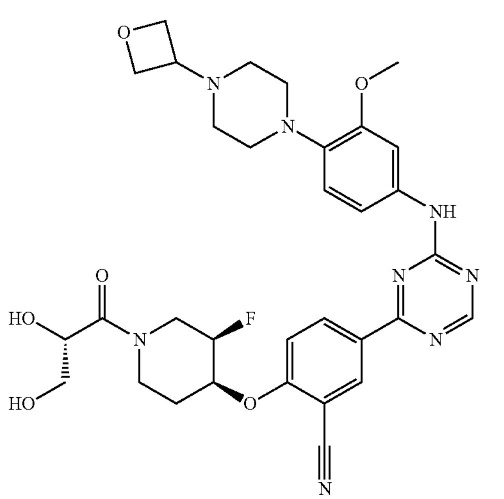 | 2 | 1 | 70 | 2-(((3R,4S)-1-((S)-2,3-dihydroxypropanoyl)-3-fluoropiperidin-4-yl)oxy)-5-(4-((3-methoxy-4-(4-(oxetan-3-yl)piperazin-1-yl)phenyl)amino)-1,3,5-triazin-2-yl)benzonitrile |

TABLE 1-continued

| Ex. | Structure | TBK1 IC50 | IKKe IC50 | JAK2 IC50 | Name |
|---|---|---|---|---|---|
| 579 | 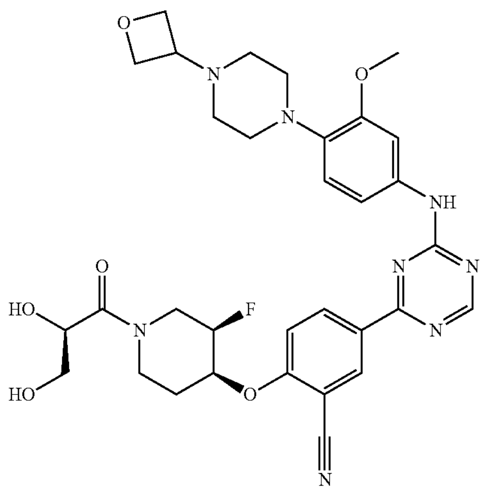 [SMILES: COc1cc(Nc2ncnc(-c3ccc(O[C@H]4CCN(C(=O)[C@H](O)CO)C[C@H]4F)c(C#N)c3)n2)ccc1N1CCN(C2COC2)CC1] | 2 | 2 | 48 | 2-(((3R,4S)-1-((R)-2,3-dihydroxypropanoyl)-3-fluoropiperidin-4-yl)oxy)-5-(4-((3-methoxy-4-(4-(oxetan-3-yl)piperazin-1-yl)phenyl)amino)-1,3,5-triazin-2-yl)benzonitrile |
| 580 | 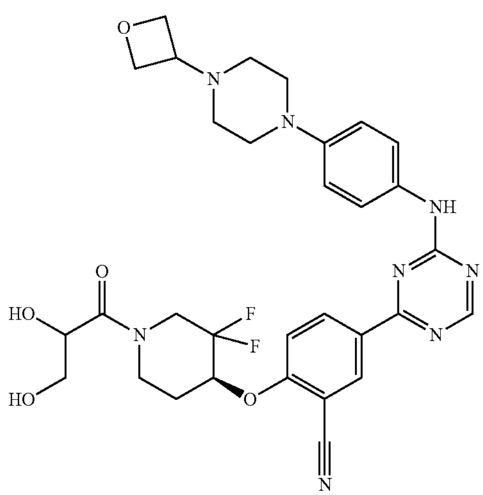 [SMILES: N#Cc1cc(-c2ncnc(Nc3ccc(N4CCN(C5COC5)CC4)cc3)n2)ccc1O[C@H]1CCN(C(=O)C(O)CO)CC1(F)F] | 2 | 1 | 165 | 2-(((4S)-1-(2,3-dihydroxypropanoyl)-3,3-difluoropiperidin-4-yl)oxy)-5-(4-((4-(4-(oxetan-3-yl)piperazin-1-yl)phenyl)amino)-1,3,5-triazin-2-yl)benzonitrile |
| 581 | 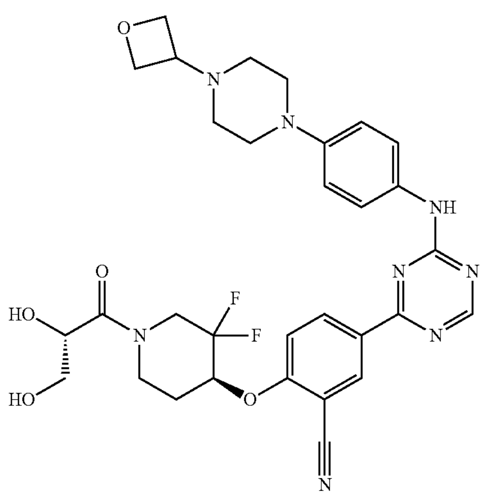 [SMILES: N#Cc1cc(-c2ncnc(Nc3ccc(N4CCN(C5COC5)CC4)cc3)n2)ccc1O[C@H]1CCN(C(=O)[C@@H](O)CO)CC1(F)F] | 2 | 1 | 86 | 2-(((S)-1-((S)-2,3-dihydroxypropanoyl)-3,3-difluoropiperidin-4-yl)oxy)-5-(4-((4-(4-(oxetan-3-yl)piperazin-1-yl)phenyl)amino)-1,3,5-triazin-2-yl)benzonitrile |

TABLE 1-continued

| Ex. | Structure | TBK1 IC50 | IKKe IC50 | JAK2 IC50 | Name |
|---|---|---|---|---|---|
| 582 | 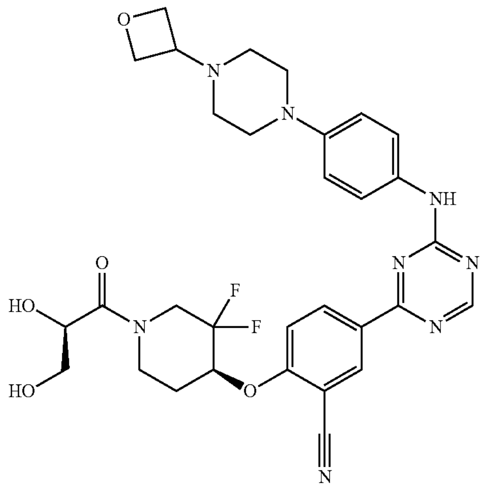 [SMILES: N#Cc1cc(-c2ncnc(Nc3ccc(N4CCN(C5COC5)CC4)cc3)n2)ccc1O[C@H]1CCN(C(=O)[C@H](O)CO)CC1(F)F] | 2 | 1 | 98 | 2-(((S)-1-((R)-2,3-dihydroxypropanoyl)-3,3-difluoropiperidin-4-yl)oxy)-5-(4-((4-(4-(oxetan-3-yl)piperazin-1-yl)phenyl)amino)-1,3,5-triazin-2-yl)benzonitrile |
| 583 | 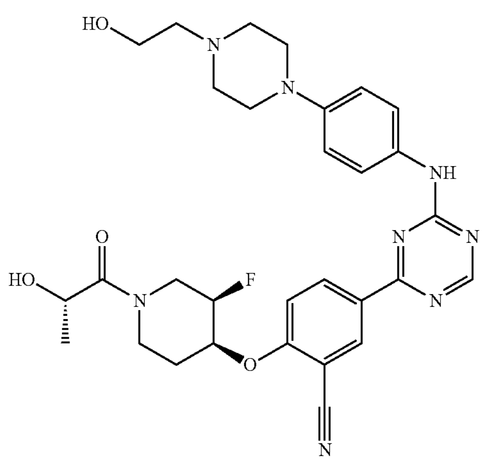 [SMILES: C[C@H](O)C(=O)N1CC[C@H](Oc2ccc(-c3ncnc(Nc4ccc(N5CCN(CCO)CC5)cc4)n3)cc2C#N)[C@H](F)C1] | 2 | 1 | 479 | 2-(((3R,4S)-3-fluoro-1-((S)-2-hydroxypropanoyl)piperidin-4-yl)oxy)-5-(4-((4-(4-(2-hydroxyethyl)piperazin-1-yl)phenyl)amino)-1,3,5-triazin-2-yl)benzonitrile |
| 584 | 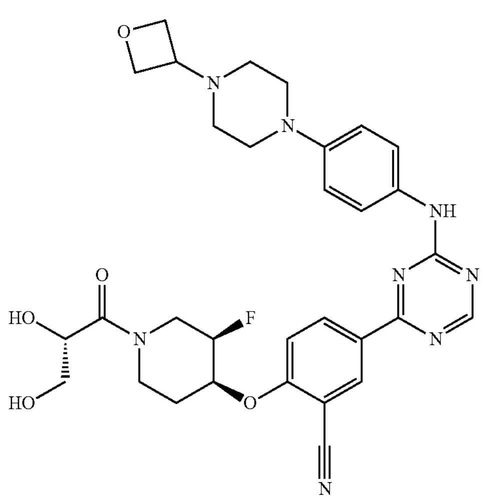 | 2 | 1 | 433 | 2-(((3R,4S)-1-((S)-2,3-dihydroxypropanoyl)-3-fluoropiperidin-4-yl)oxy)-5-(4-((4-(4-(oxetan-3-yl)piperazin-1-yl)phenyl)amino)-1,3,5-triazin-2-yl)benzonitrile |

TABLE 1-continued

| Ex. | Structure | TBK1 IC50 | IKKe IC50 | JAK2 IC50 | Name |
|---|---|---|---|---|---|
| 585 | 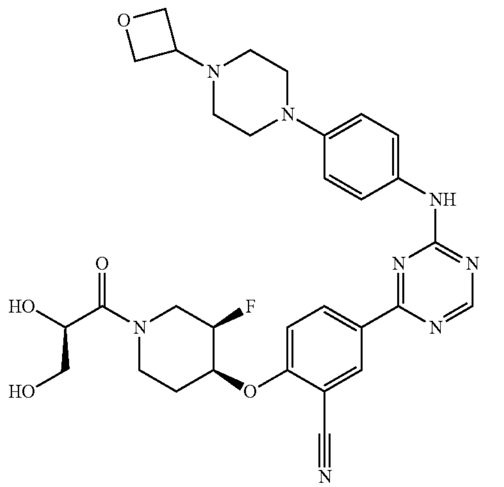 [SMILES: N#Cc1cc(-c2ncnc(Nc3ccc(N4CCN(C5COC5)CC4)cc3)n2)ccc1O[C@H]1CCN(C(=O)[C@H](O)CO)C[C@H]1F] | 2 | 3 | 294 | 2-(((3R,4S)-1-((R)-2,3-dihydroxypropanoyl)-3-fluoropiperidin-4-yl)oxy)-5-(4-((4-(4-(oxetan-3-yl)piperazin-1-yl)phenyl)amino)-1,3,5-triazin-2-yl)benzonitrile |
| 586 | 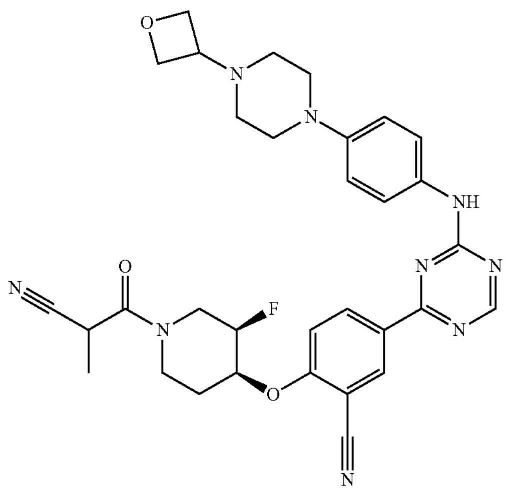 [SMILES: CC(C#N)C(=O)N1CC[C@H](Oc2ccc(-c3ncnc(Nc4ccc(N5CCN(C6COC6)CC5)cc4)n3)cc2C#N)[C@H](F)C1] | 11 | 28 | 212 | 2-(((3R,4S)-1-(2-cyanopropanoyl)-3-fluoropiperidin-4-yl)oxy)-5-(4-((4-(4-(oxetan-3-yl)piperazin-1-yl)phenyl)amino)-1,3,5-triazin-2-yl)benzonitrile |
| 587 | 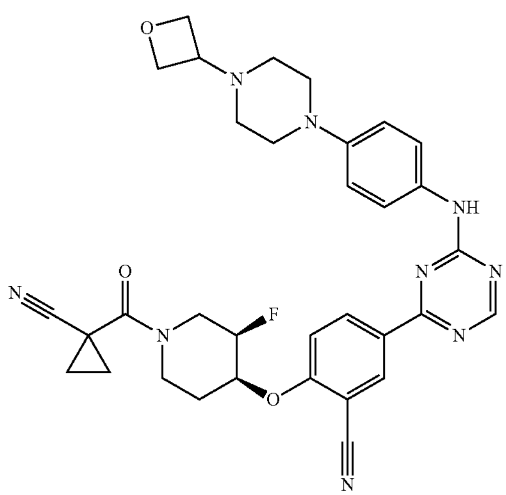 [SMILES: N#Cc1cc(-c2ncnc(Nc3ccc(N4CCN(C5COC5)CC4)cc3)n2)ccc1O[C@H]1CCN(C(=O)C2(C#N)CC2)C[C@H]1F] | 30 | 49 | 235 | 2-(((3R,4S)-1-(1-cyanocyclopropanecarbonyl)-3-fluoropiperidin-4-yl)oxy)-5-(4-((4-(4-(oxetan-3-yl)piperazin-1-yl)phenyl)amino)-1,3,5-triazin-2-yl)benzonitrile |

TABLE 1-continued

| Ex. | Structure | TBK1 IC50 | IKKe IC50 | JAK2 IC50 | Name |
|---|---|---|---|---|---|
| 588 | 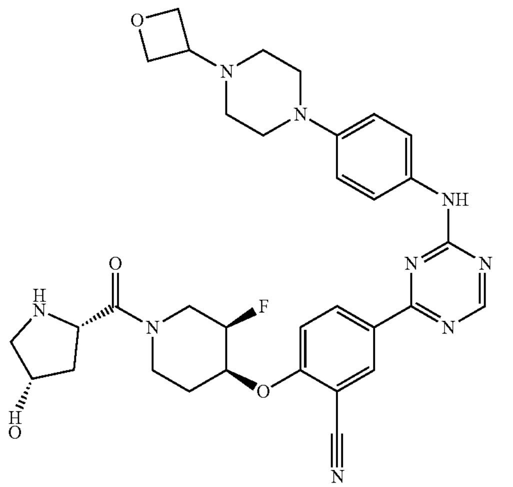 [SMILES: N#Cc1cc(-c2ncnc(Nc3ccc(N4CCN(C5COC5)CC4)cc3)n2)ccc1O[C@H]1CCN(C(=O)[C@@H]2C[C@H](O)CN2)C[C@H]1F] | 18 | 49 | 1000 | 2-(((3R,4S)-3-fluoro-1-((2S,4S)-4-hydroxypyrrolidine-2-carbonyl)piperidin-4-yl)oxy-5-(4-((4-(4-(oxetan-3-yl)piperazin-1-yl)phenyl)amino)-1,3,5-triazin-2-yl)benzonitrile |
| 589 | 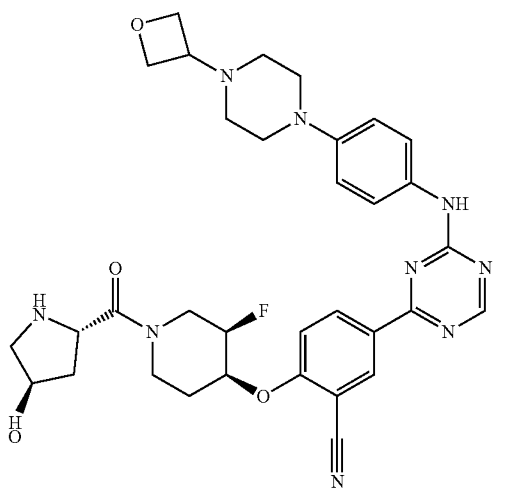 [SMILES: N#Cc1cc(-c2ncnc(Nc3ccc(N4CCN(C5COC5)CC4)cc3)n2)ccc1O[C@H]1CCN(C(=O)[C@@H]2C[C@@H](O)CN2)C[C@H]1F] | 18 | 28 | 855 | 2-(((3R,4S)-3-fluoro-1-((2S,4R)-4-hydroxypyrrolidine-2-carbonyl)piperidin-4-yl)oxy)-5-(4-((4-(4-(oxetan-3-yl)piperazin-1-yl)phenyl)amino)-1,3,5-triazin-2-yl)benzonitrile |
| 590 | 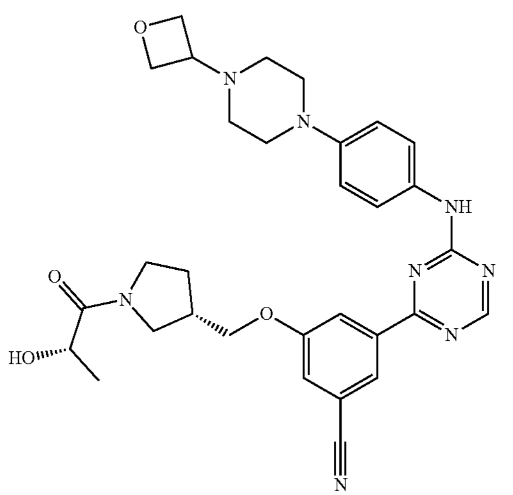 [SMILES: C[C@H](O)C(=O)N1CC[C@H](COc2cc(C#N)cc(-c3ncnc(Nc4ccc(N5CCN(C6COC6)CC5)cc4)n3)c2)C1] | 528 | 1000 | 1000 | 3-(((S)-1-((S)-2-hydroxypropanoyl)pyrrolidin-3-yl)methoxy)-5-(4-((4-(4-(oxetan-3-yl)piperazin-1-yl)phenyl)amino)-1,3,5-triazin-2-yl)benzonitrile |

TABLE 1-continued

| Ex. | Structure | TBK1 IC50 | IKKe IC50 | JAK2 IC50 | Name |
|---|---|---|---|---|---|
| 591 | 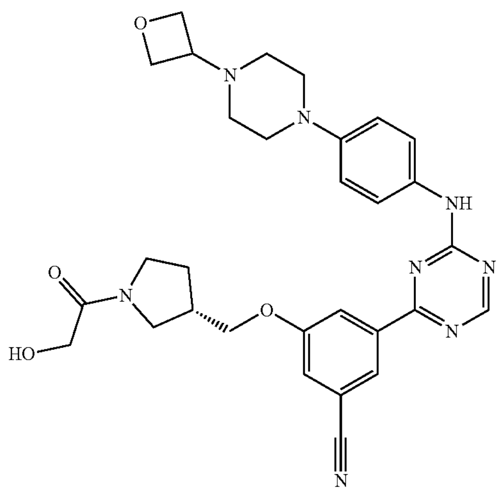 [SMILES: N#Cc1cc(OC[C@H]2CCN(C(=O)CO)C2)cc(-c2ncnc(Nc3ccc(N4CCN(C5COC5)CC4)cc3)n2)c1] | 474 | 1000 | 658 | (S)-3-((1-(2-hydroxy-acetyl)pyrrolidin-3-yl)methoxy)-5-(4-((4-(4-(oxetan-3-yl)piperazin-1-yl)phenyl)amino)-1,3,5-triazin-2-yl)benzonitrile |
| 592 | 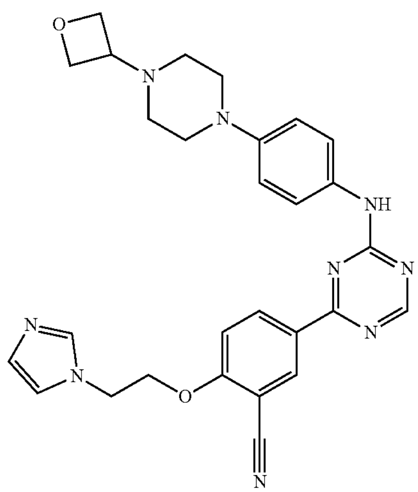 [SMILES: N#Cc1cc(-c2ncnc(Nc3ccc(N4CCN(C5COC5)CC4)cc3)n2)ccc1OCCn1ccnc1] | 21 | 23 | 239 | 2-(2-(1H-imidazol-1-yl)ethoxy)-5-(4-((4-(4-(oxetan-3-yl)piperazin-1-yl)phenyl)amino)-1,3,5-triazin-2-yl)benzonitrile |
| 593 | 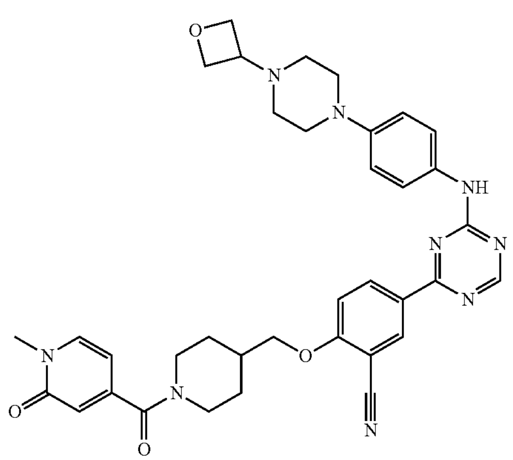 [SMILES: Cn1ccc(C(=O)N2CCC(COc3ccc(-c4ncnc(Nc5ccc(N6CCN(C7COC7)CC6)cc5)n4)cc3C#N)CC2)cc1=O] | 452 | 660 | 1000 | 2-((1-(1-methyl-2-oxo-1,2-dihydropyridine-4-carbonyl)piperidin-4-yl)methoxy)-5-(4-((4-(4-(oxetan-3-yl)piperazin-1-yl)phenyl)amino)-1,3,5-triazin-2-yl)benzonitrile |

TABLE 1-continued
| Ex. | Structure | TBK1 IC50 | IKKe IC50 | JAK2 IC50 | Name |
|---|---|---|---|---|---|
| 594 | 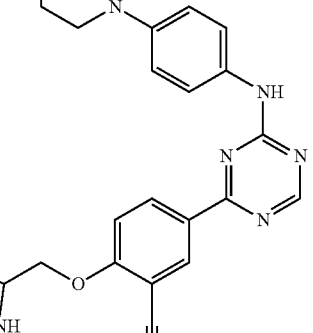 | 169 | 232 | 1000 | 5-(4-((4-(4-(oxetan-3-yl)piperazin-1-yl)phenyl)amino)-1,3,5-triazin-2-yl)-2-((5-oxopyrrolidin-2-yl)methoxy)benzonitrile |
| 595 | 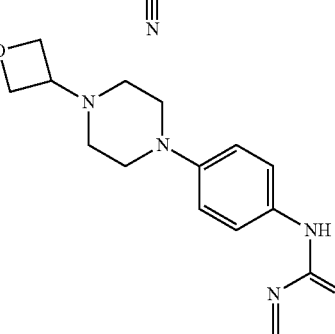 | 69 | 89 | 1000 | 2-((1-(1-methyl-2-oxo-1,2-dihydropyridine-4-carbonyl)piperidin-4-yl)oxy)-5-(4-((4-(4-(oxetan-3-yl)piperazin-1-yl)phenyl)amino)-1,3,5-triazin-2-yl)benzonitrile |
| 596 | 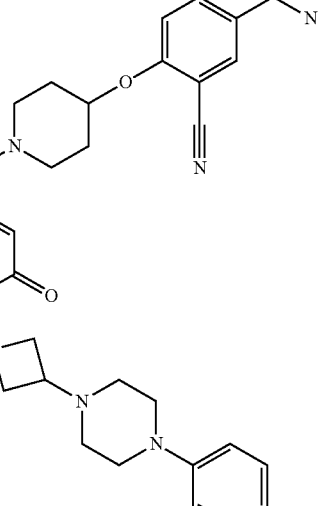 | 264 | 403 | 1000 | 2-((1-methyl-2-oxopiperidin-4-yl)methoxy)-5-(4-((4-(4-(oxetan-3-yl)piperazin-1-yl)phenyl)amino)-1,3,5-triazin-2-yl)benzonitrile |

TABLE 1-continued

| Ex. | Structure | TBK1 IC50 | IKKe IC50 | JAK2 IC50 | Name |
|---|---|---|---|---|---|
| 597 | 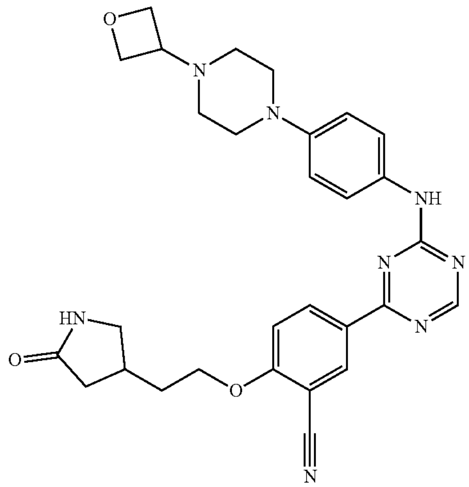 [SMILES: N#Cc1cc(-c2ncnc(Nc3ccc(N4CCN(C5COC5)CC4)cc3)n2)ccc1OCCC1CNC(=O)C1] | 95 | 131 | 1000 | 5-(4-((4-(4-(oxetan-3-yl)piperazin-1-yl)phenyl)amino)-1,3,5-triazin-2-yl)-2-(2-(5-oxopyrrolidin-3-yl)ethoxy)benzonitrile |
| 598 | 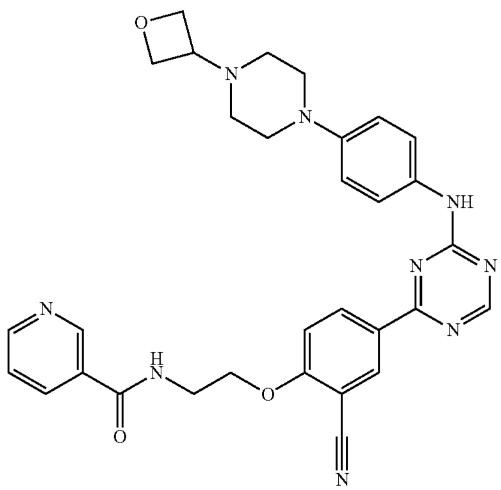 [SMILES: N#Cc1cc(-c2ncnc(Nc3ccc(N4CCN(C5COC5)CC4)cc3)n2)ccc1OCCNC(=O)c1cccnc1] | 267 | 720 | 521 | N-(2-(2-cyano-4-(4-((4-(4-(oxetan-3-yl)piperazin-1-yl)phenyl)amino)-1,3,5-triazin-2-yl)phenoxy)ethyl)nicotinamide |
| 599 | 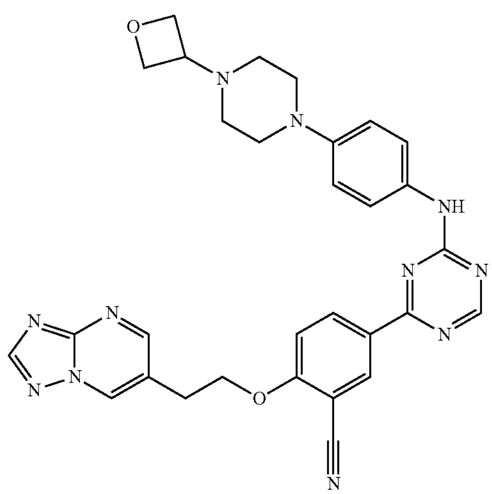 [SMILES: N#Cc1cc(-c2ncnc(Nc3ccc(N4CCN(C5COC5)CC4)cc3)n2)ccc1OCCc1cnc2ncnn2c1] | 37 | 176 | 510 | 2-(2-([1,2,4]triazolo[1,5-a]pyrimidin-6-yl)ethoxy)-5-(4-((4-(4-(oxetan-3-yl)piperazin-1-yl)phenyl)amino)-1,3,5-triazin-2-yl)benznitrile |

TABLE 1-continued

| Ex. | Structure | TBK1 IC50 | IKKe IC50 | JAK2 IC50 | Name |
|---|---|---|---|---|---|
| 600 | 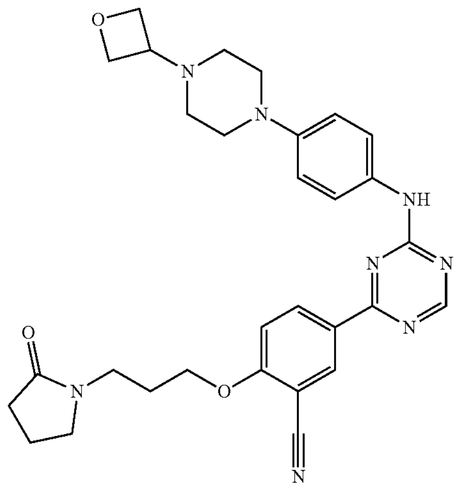 [SMILES: N#Cc1cc(-c2ncnc(Nc3ccc(N4CCN(C5COC5)CC4)cc3)n2)ccc1OCCCN1CCCC1=O] | 517 | 1000 | 1000 | 5-(4-((4-(4-(oxetan-3-yl)piperazin-1-yl)phenyl)amino)-1,3,5-triazin-2-yl)-2-(3-2-oxopyrrolidin-1-yl)propoxy)benzonitrile |
| 601 | 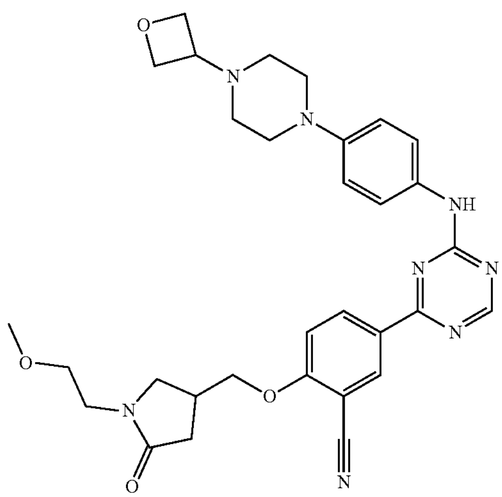 [SMILES: COCCN1CC(COc2ccc(-c3ncnc(Nc4ccc(N5CCN(C6COC6)CC5)cc4)n3)cc2C#N)CC1=O] | 1000 | 1000 | 1000 | 2-((1-(2-methoxyethyl)-5-oxopyrrolidin-3-yl)methoxy)-5-(4-((4-(4-(oxetan-3-yl)piperazin-1-yl)phenyl)amino)-1,3,5-triazin-2-yl)benzonitrile |
| 602 | 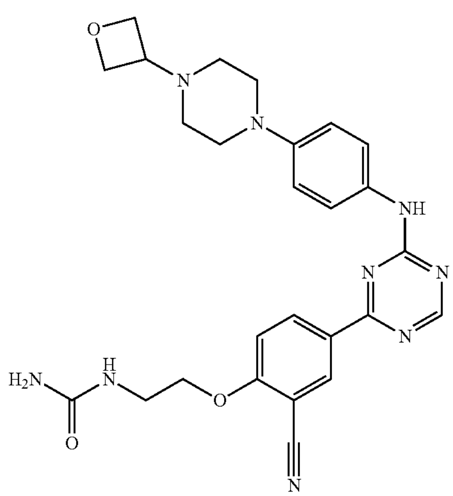 [SMILES: N#Cc1cc(-c2ncnc(Nc3ccc(N4CCN(C5COC5)CC4)cc3)n2)ccc1OCCNC(N)=O] | 126 | 619 | 1000 | 1-(2-(2-cyano-4-(4-((4-(4-(oxetan-3-yl)piperazin-1-yl)phenyl)amino)-1,3,5-triazin-2-yl)phenoxy)ethyl)urea |

TABLE 1-continued

| Ex. | Structure | TBK1 IC50 | IKKe IC50 | JAK2 IC50 | Name |
|---|---|---|---|---|---|
| 603 | 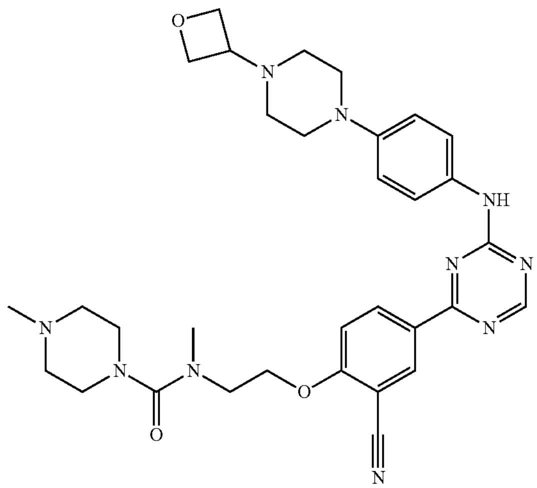 [SMILES: CN1CCN(C(=O)N(C)CCOc2ccc(-c3ncnc(Nc4ccc(N5CCN(C6COC6)CC5)cc4)n3)cc2C#N)CC1] | 466 | 1000 | 1000 | N-(2-(2-cyano-4-(4-((4-(4-(oxetan-3-yl)piperazin-1-yl)phenyl)amino)-1,3,5-triazin-2-yl)phenoxy)ethyl)-N,4-dimethylpiperazine-1-carboxamide |
| 604 | 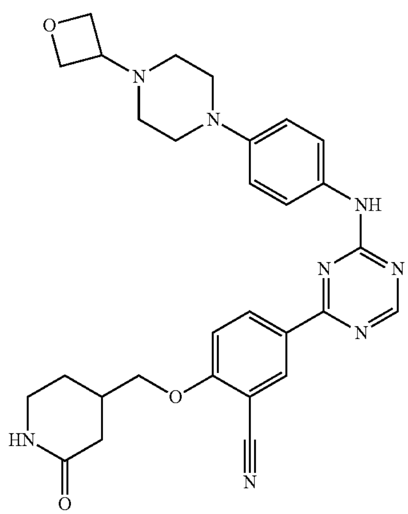 [SMILES: N#Cc1cc(-c2ncnc(Nc3ccc(N4CCN(C5COC5)CC4)cc3)n2)ccc1OCC1CCNC(=O)C1] | 28 | 37 | 950 | 5-(4-((4-(4-(oxetan-3-yl)piperazin-1-yl)phenyl)amino)-1,3,5-triazin-2-yl)-2-((2-oxopiperidin-4-yl)methoxy)benzonitrile |
| 605 | 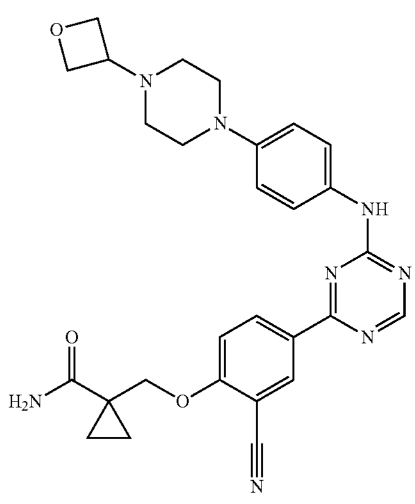 [SMILES: N#Cc1cc(-c2ncnc(Nc3ccc(N4CCN(C5COC5)CC4)cc3)n2)ccc1OCC1(C(N)=O)CC1] | 12 | 20 | 92 | 1-((2-cyano-4-(4-((4-(4-(oxetan-3-yl)piperazin-1-yl)phenyl)amino)-1,3,5-triazin-2-yl)phenoxy)methyl)cyclopropanecarboxamide |

TABLE 1-continued

| Ex. | Structure | TBK1 IC50 | IKKe IC50 | JAK2 IC50 | Name |
|---|---|---|---|---|---|
| 606 | 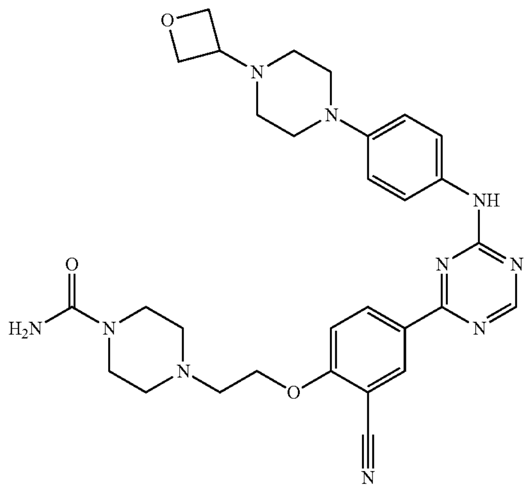 [SMILES: N#Cc1cc(-c2ncnc(Nc3ccc(N4CCN(C5COC5)CC4)cc3)n2)ccc1OCCN1CCN(C(N)=O)CC1] | 503 | 494 | 1000 | 4-(2-(2-cyano-4-(4-((4-(4-(oxetan-3-yl)piperazin-1-yl)phenyl)amino)-1,3,5-triazin-2-yl)phenoxy)ethyl)piperazine-1-carboxamide |
| 607 | 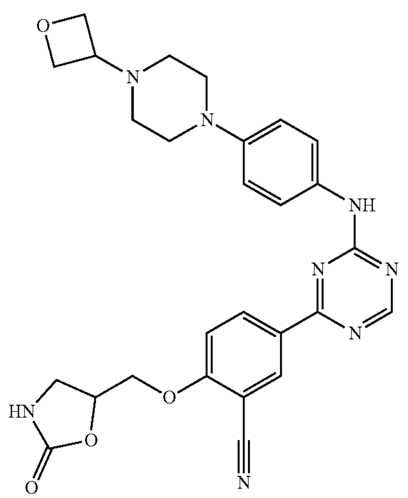 [SMILES: N#Cc1cc(-c2ncnc(Nc3ccc(N4CCN(C5COC5)CC4)cc3)n2)ccc1OCC1CNC(=O)O1] | 21 | 16 | 161 | 5-(4-((4-(4-(oxetan-3-yl)piperazin-1-yl)phenyl)amino)-1,3,5-triazin-2-yl)-2-((2-oxooxazolidin-5-yl)methoxy)benzonitrile |
| 608 | 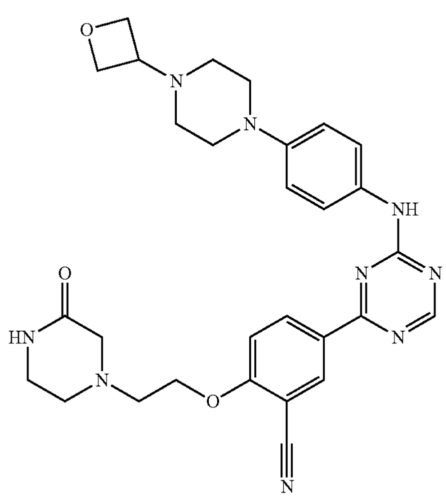 [SMILES: N#Cc1cc(-c2ncnc(Nc3ccc(N4CCN(C5COC5)CC4)cc3)n2)ccc1OCCN1CCNC(=O)C1] | 662 | 1000 | 1000 | 5-(4-((4-(4-(oxetan-3-yl)piperazin-1-yl)phenyl)amino)-1,3,5-triazin-2-yl)-2-(2-(3-oxopiperazin-1-yl)ethoxy)benzonitrile |

TABLE 1-continued

| Ex. | Structure | TBK1 IC50 | IKKe IC50 | JAK2 IC50 | Name |
|---|---|---|---|---|---|
| 609 | 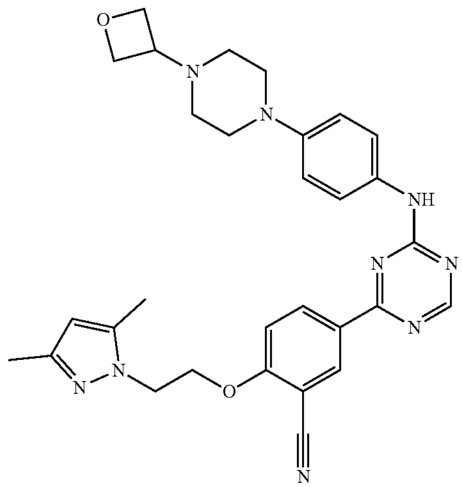 [SMILES: Cc1cc(C)n(CCOc2ccc(-c3ncnc(Nc4ccc(N5CCN(C6COC6)CC5)cc4)n3)cc2C#N)n1] | 1000 | 1000 | 237 | 2-(2-(3,5-dimethyl-1H-pyrazol-1-yl)ethoxy)-5-(4-((4-(4-(oxetan-3-yl)piperazin-1-yl)phenyl)amino)-1,3,5-triazin-2-yl)benzonitrile |
| 610 | 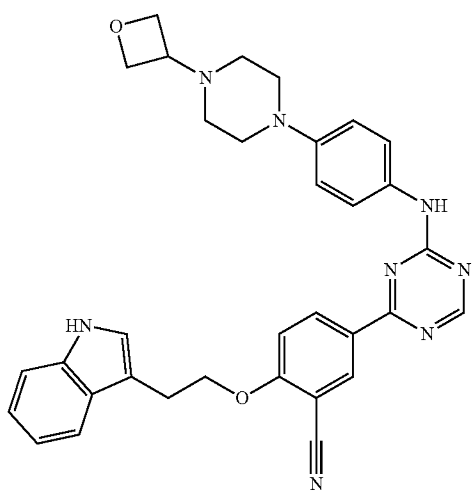 [SMILES: N#Cc1cc(-c2ncnc(Nc3ccc(N4CCN(C5COC5)CC4)cc3)n2)ccc1OCCc1c[nH]c2ccccc12] | 1000 | 1000 | 1000 | 2-(2-(1H-indol-3-yl)ethoxy)-5-(4-((4-(4-(oxetan-3-yl)piperazin-1-yl)phenyl)amino)-1,3,5-triazin-2-yl)benzonitrile |
| 611 | 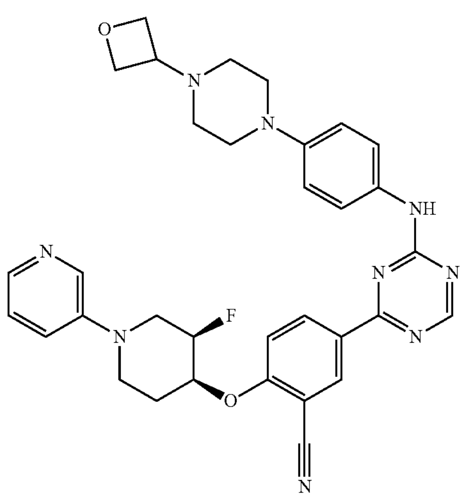 [SMILES: N#Cc1cc(-c2ncnc(Nc3ccc(N4CCN(C5COC5)CC4)cc3)n2)ccc1O[C@H]1CCN(c2cccnc2)C[C@H]1F] | 1000 | 1000 | 1000 | 2-(((3R,4S)-3-fluoro-1-(pyridin-3-yl)piperidin-4-yl)oxy)-5-(4-((4-(4-(oxetan-3-yl)piperazin-1-yl)phenyl)amino)-1,3,5-triazin-2-yl)benzonitrile. |

TABLE 1-continued

| Ex. | Structure | TBK1 IC50 | IKKe IC50 | JAK2 IC50 | Name |
|---|---|---|---|---|---|
| 612 | 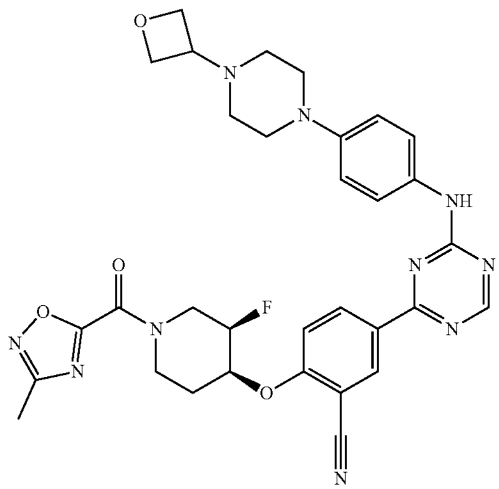 [SMILES: Cc1noc(C(=O)N2CC[C@H](Oc3ccc(-c4ncnc(Nc5ccc(N6CCN(C7COC7)CC6)cc5)n4)cc3C#N)[C@H](F)C2)n1] | 3 | 2 | 607 | 2-(((3R,4S)-3-fluoro-1-(3-methyl-1,2,4-oxadiazole-5-carbonyl)piperidin-4-yl)oxy)-5-(4-((4-(4-(oxetan-3-yl)piperazin-1-yl)phenyl)amino)-1,3,5-triazin-2-yl)benzonitrile |
| 613 | 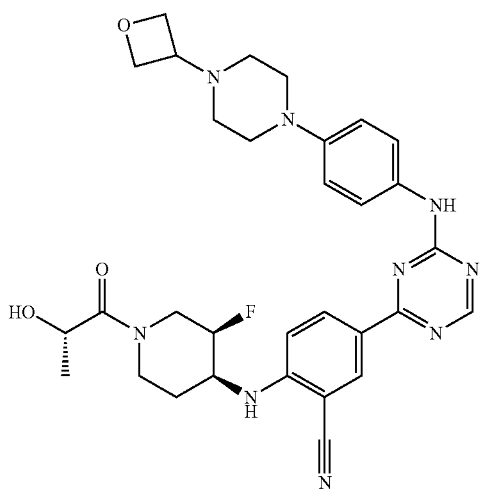 [SMILES: C[C@H](O)C(=O)N1CC[C@H](Nc2ccc(-c3ncnc(Nc4ccc(N5CCN(C6COC6)CC5)cc4)n3)cc2C#N)[C@H](F)C1] | 128 | 175 | 69 | 2-(((3R,4S)-3-fluoro-1-((S)-2-hydroxypropanoyl)piperidin-4-yl)amino)-5-(4-((4-(4-(oxetan-3-yl)piperazin-1-yl)phenyl)amino)-1,3,5-triazin-2-yl)benzonitrile. |
| 614 | 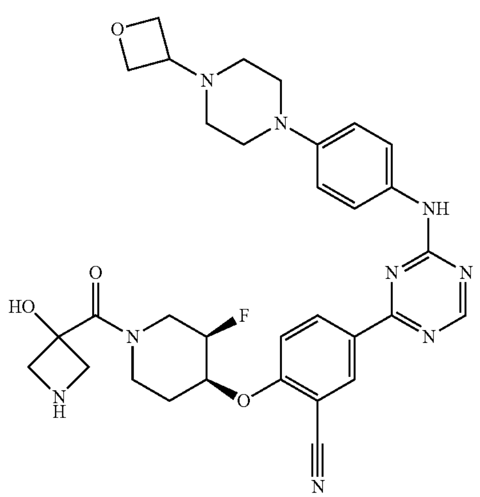 [SMILES: N#Cc1cc(-c2ncnc(Nc3ccc(N4CCN(C5COC5)CC4)cc3)n2)ccc1O[C@H]1CCN(C(=O)C2(O)CNC2)C[C@H]1F] | 25 | 45 | 268 | 2-(((3R,4S)-3-fluoro-1-(3-hydroxyazetidine-3-carbonyl)piperidin-4-yl)oxy)-5-(4-((4-(4-(oxetan-3-yl)piperazin-1-yl)phenyl)amino)-1,3,5-triazin-2-yl)benzonitrile |

TABLE 1-continued

| Ex. | Structure | TBK1 IC50 | IKKe IC50 | JAK2 IC50 | Name |
|---|---|---|---|---|---|
| 615 | 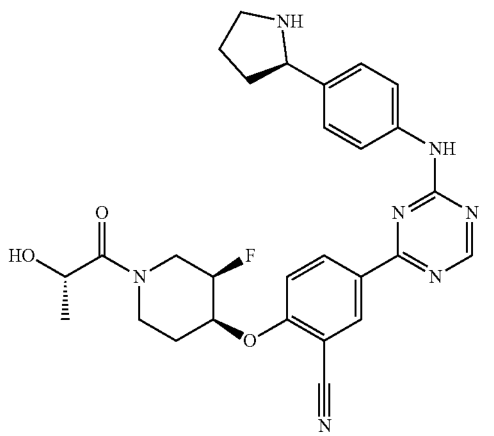 [SMILES: C[C@H](O)C(=O)N1CC[C@H](Oc2ccc(-c3ncnc(Nc4ccc([C@H]5CCCN5)cc4)n3)cc2C#N)[C@H](F)C1] | 4 | 1 | 1000 | 2-(((3R,4S)-3-fluoro-1-((S)-2-hydroxypropanoyl)piperidin-4-yl)oxy)-5-(4-((4-((R)-pyrrolidin-2-yl)phenyl)amino)-1,3,5-triazin-2-yl)benzonitrile |
| 616 | 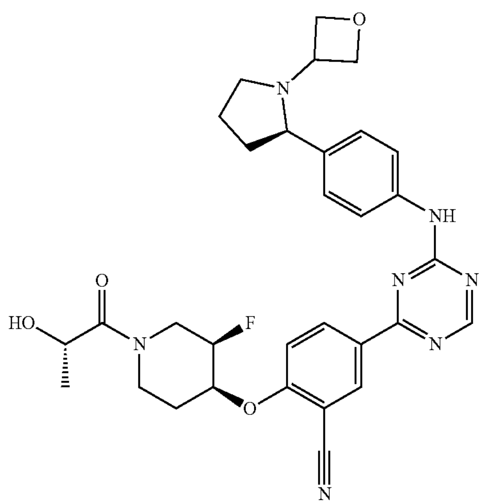 [SMILES: C[C@H](O)C(=O)N1CC[C@H](Oc2ccc(-c3ncnc(Nc4ccc([C@H]5CCCN5C5COC5)cc4)n3)cc2C#N)[C@H](F)C1] | 5 | 4 | 1000 | 2-(((3R,4S)-3-fluoro-1-((S)-2-hydroxypropanoyl)piperidin-4-yl)oxy)-5-(4-((4-((R)-1-(oxetan-3-yl)pyrrolidin-2-yl)phenyl)amino)-1,3,5-triazin-2-yl)benzonitrile |
| 617 | 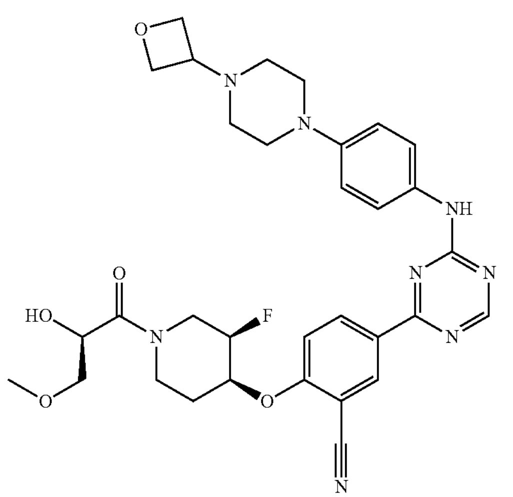 [SMILES: COC[C@@H](O)C(=O)N1CC[C@H](Oc2ccc(-c3ncnc(Nc4ccc(N5CCN(C6COC6)CC5)cc4)n3)cc2C#N)[C@H](F)C1] | 29 | 75 | 226 | 2-(((3R,4S)-3-fluoro-1-((R)-2-hydroxy-3-methoxypropanoyl)piperidin-4-yl)oxy)-5-(4-((4-(4-(oxetan-3-yl)piperazin-1-yl)phenyl)amino)-1,3,5-triazin-2-yl)benzonitrile |

TABLE 1-continued

| Ex. | Structure | TBK1 IC50 | IKKe IC50 | JAK2 IC50 | Name |
|-----|-----------|-----------|-----------|-----------|------|
| 618 | 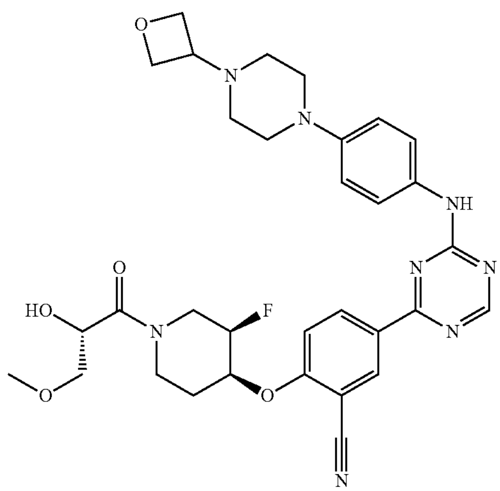 [SMILES: COC[C@H](O)C(=O)N1CC[C@H](Oc2ccc(-c3ncnc(Nc4ccc(N5CCN(C6COC6)CC5)cc4)n3)cc2C#N)[C@H](F)C1] | 2 | 1 | 162 | 2-(((3R,4S)-3-fluoro-1-((S)-2-hydroxy-3-methoxypropanoyl)piperidin-4-yl)oxy)-5-4-((4-(4-(oxetan-3-yl)piperazin-1-yl)phenyl)amino)-1,3,5-triazin-2-yl)benzonitrile |
| 619 | 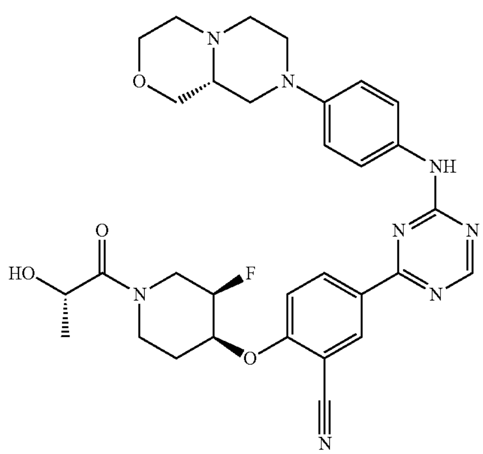 [SMILES: C[C@H](O)C(=O)N1CC[C@H](Oc2ccc(-c3ncnc(Nc4ccc(N5CCN6CCOC[C@H]6C5)cc4)n3)cc2C#N)[C@H](F)C1] | 3 | 3 | 364 | 2-(((3R,4S)-3-fluoro-1-((S)-2-hydroxy-proponyl)piperidin-4-yl)oxy)-5-(4-((4-((R)-hexahydropyrazino[2,1-c][1,4]oxazin-8(1H)-yl)phenyl)amino)-1,3,5-triazin-yl)benzonitrile |

*nd: no data

While the foregoing description describes specific embodiments and aspects, those with ordinary skill in the art will appreciate that various modifications and alternatives can be developed. Accordingly, the particular embodiments and aspects described above are meant to be illustrative only, and not to limit the scope of the invention, which is to be given the full breadth of the appended claims, and any and all equivalents thereof. Each of the foregoing references are hereby incorporated by reference.

The invention claimed is:

1. A method of preparing a compound of formula (I):

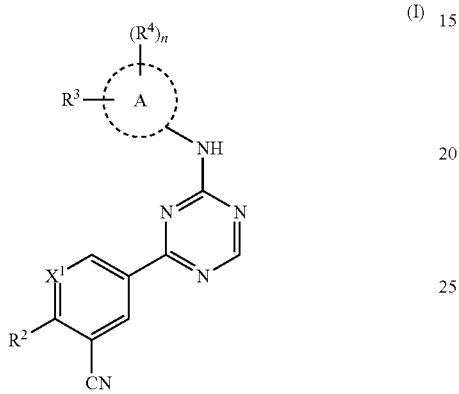

or a pharmaceutically acceptable salt thereof, wherein:
A is $C_{6-10}$ aryl or 5-10 membered heteroaryl;
$X^1$ is $CR^1$ or N;
$R^1$ is selected from the group consisting of H, $C_{1-6}$ alkyl, $C_{1-6}$ haloalkyl, $-NR^aR^b$, halogen, $-CN$, and $-OR^a$;
$R^2$ is selected from the group consisting of H, hydroxyl, $C_{1-6}$ alkyl, $C_{1-6}$ heteroalkyl, $-NR^aR^b$, halogen, $-C(O)R^a$, $-C(O)OR^a$, $-C(O)NR^aR^b$, $-OC(O)NR^aR^b$, $-NR^aC(O)R^b$, $-NR^aC(O)OR^b$, $-S(O)_{0-2}R^c$, $-S(O)_2NR^aR^b$, $-NR^aS(O)_2R^b$, $C_{6-10}$ aryl, $C_{3-10}$ cycloalkyl, 5-10 membered heteroaryl, 3-12 membered heterocyclyl and $-O-R^5$, wherein each $C_{1-6}$ alkyl, $C_{1-6}$ heteroalkyl, $C_{6-10}$ aryl, $C_{3-10}$ cycloalkyl, 5-10 membered heteroaryl and 3-12 membered heterocyclyl is optionally substituted with one to five $R^{20}$ groups;
or $R^1$ and $R^2$ are taken together to form a fused $C_6$ aryl, 5-6 membered heteroaryl, 5-6 membered heterocyclyl or $C_{5-6}$ cycloalkyl, each of which is optionally substituted with one to five $R^{20}$ groups;
$R^3$ is selected from the group consisting of H, $C_{1-6}$ alkyl, $C_{1-6}$ heteroalkyl, $-NR^aR^b$, halogen, $-C(O)R^a$, $-C(O)OR^a$, $-C(O)NR^aR^b$, $-OC(O)NR^aR^b$, $-NR^aC(O)R^b$, $-NR^aC(O)OR^b$, $-S(O)_{0-2}R^c$, $-S(O)(R^c)=NR^b$, $-S(O)_2F$, $-NR^aS(O)_2R^b$, $-N_3$, $-CN$, $-NO_2$, $-OR^a$, $C_{6-10}$ aryl, $C_{3-10}$ cycloalkyl, 5-10 membered heteroaryl and 3-12 membered heterocyclyl, wherein each $C_{1-6}$ alkyl, $C_{1-6}$ heteroalkyl, $C_{6-10}$ aryl, $C_{3-10}$ cycloalkyl, 5-10 membered heteroaryl and 3-12 membered heterocyclyl is optionally substituted with one to five $R^{20}$ groups;
each $R^4$ is independently selected from the group consisting of H, $C_{1-6}$ alkyl, $C_{1-6}$ heteroalkyl, $C_{1-6}$ haloalkyl, $C_{1-6}$ hydroxyalkyl, $C_{2-6}$ alkenyl, $C_{2-6}$ alkynyl, $C_{6-10}$ aryl, $C_{3-10}$ cycloalkyl, 5-10 membered heteroaryl, 3-12 membered heterocyclyl, $-NR^aR^b$, halogen, $-C(O)R^a$, $-C(O)OR^a$, $-C(O)NR^aR^b$, $-OC(O)NR^aR^b$, $-NR^aC(O)R^b$, $-NR^aC(O)OR^b$, $-S(O)_{0-2}R^c$, $-NR^aS(O)_2R^b$, $-N_3$, $-CN$, $-NO_2$ and $-OR^a$, wherein each $C_{1-6}$ alkyl, $C_{1-6}$ heteroalkyl, $C_{6-10}$ aryl, $C_{3-10}$ cycloalkyl, 5-10 membered heteroaryl and 3-12 membered heterocyclyl is optionally substituted with one to five $R^{20}$ groups;
or $R^3$ and one $R^4$ are taken together to form a fused $C_6$ aryl, 5-6 membered heteroaryl, 5-6 membered heterocyclyl or $C_{5-6}$ cycloalkyl, each of which is optionally substituted with one to five $R^{20}$ groups;
$R^5$ is H; or $C_{1-6}$ alkyl, $C_{1-6}$ haloalkyl, $C_{6-10}$ aryl, 5-10 membered heteroaryl, $C_{3-10}$ cycloalkyl, or 3-12 membered heterocyclyl, each of which is optionally substituted with one to five $R^{20}$ groups;
n is 0-2;
each $R^{20}$ is independently $C_{1-6}$ alkyl, $C_{3-10}$ cycloalkyl, $C_{1-6}$ heteroalkyl, 3-12 membered heterocyclyl, $C_{6-10}$ aryl, 5-10 membered heteroaryl, halogen, oxo, $-OR^a$, $-C(O)R^a$, $-C(O)OR^a$, $-C(O)NR^aR^b$, $-OC(O)NR^aR^b$, $-NR^aR^b$, $-NR^aC(O)R^b$, $-NR^aC(O)OR^b$, $-S(O)_{0-2}R^a$, $-S(O)(R^c)=NR^b$, $-NR^aS(O)_2R^b$, $-N_3$, $-CN$, or $-NO_2$, or two $R^{20}$ groups can join together to form a fused, spiro or bridged $C_{3-10}$ cycloalkyl or 3-12 membered heterocyclyl; wherein each $C_{1-6}$ alkyl, $C_{3-10}$ cycloalkyl, $C_{1-6}$ heteroalkyl, 3-12 membered heterocyclyl, $C_{6-10}$ aryl, and 5-10 membered heteroaryl is optionally substituted with one to five halogen, $C_{1-6}$ alkyl, $C_{1-6}$ heteroalkyl, $C_{1-6}$ haloalkyl, oxo, imino, $-OR^a$, $-C(O)R^a$, $-C(O)OR^a$, $-C(O)NR^aR^b$, $-OC(O)NR^aR^b$, $-NR^aR^b$, $-NR^aC(O)R^b$, $-NR^aC(O)OR^b$, $-S(O)_{0-2}R^a$, $-S(O)_2NR^aR^b$, $-NR^aS(O)_2R^b$, $-N_3$, $-CN$, or $-NO_2$;
each $R^{21}$ is independently $C_{1-6}$ alkyl, $C_{3-10}$ cycloalkyl, $C_{1-6}$ heteroalkyl, 3-12 membered heterocyclyl, $C_{6-10}$ aryl, 5-10 membered heteroaryl, hydroxyl, $C_{1-6}$ alkoxy, amino, $-CN$, $-C(O)H$, $-C(O)NH_2$, $-C(O)NH(C_{1-6}$ alkyl), $-C(O)N(C_{1-6}$ alkyl)$_2$, $-COOH$, $-C(O)C_{1-6}$ alkyl, $-C(O)OC_{1-6}$ alkyl, or halogen;
each $R^a$ and each $R^b$ are independently H; or $C_{1-6}$ alkyl, $C_{2-6}$ alkenyl, $C_{3-10}$ cycloalkyl, $C_{1-6}$ heteroalkyl, 3-12 membered heterocyclyl, $C_{6-10}$ aryl, or 5-10 membered heteroaryl, each of which is optionally substituted with one to five $R^{21}$; or $R^a$ and $R^b$ together with the atoms to which they are attached form a 3-12 membered heterocyclyl optionally substituted with one to five $R^{21}$ groups; and
each $R^c$ is independently $C_{1-6}$ alkyl, $C_{2-6}$ alkenyl, $C_{3-10}$ cycloalkyl, $C_{1-6}$ heteroalkyl, 3-12 membered heterocyclyl, $C_{6-10}$ aryl, 5-10 membered heteroaryl, each of which is optionally substituted with one to five $R^{21}$,
said method comprising the steps of:
a) reacting a compound of formula $A(R^3)(R^4)_n$—$NH_2$, wherein A, $R^3$, $R^4$, and n are as defined for the compound of formula (I),
with 2,4-dichloro-1,3,5-triazine to provide a compound of formula (1-1):

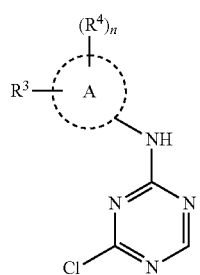

(1-1)

wherein A, $R^3$, $R^4$, and n are as defined for the compound of formula (I);

b) reacting the compound of formula (1-1) with a compound of formula $A^1$-X, wherein X is a boronic ester and $A^1$ is

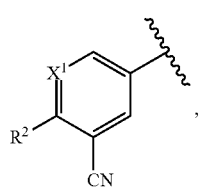

and wherein $X^1$ and $R^2$ are as defined for the compound of formula (I), in the presence of a palladium catalyst to provide the compound of formula (I); and c) optionally converting the compound of formula (I) into a pharmaceutically acceptable salt thereof.

2. The method according to claim 1, wherein the compound of formula (I) is of formula (Ic):

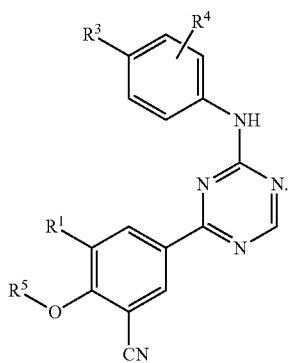

(Ic)

3. The method according to claim 1, wherein $X^1$ is $CR^1$.

4. The method according to claim 1, wherein A is phenyl.

5. The method according to claim 1, wherein $R^3$ is a piperazinyl group optionally substituted with one to five $R^{20}$ groups.

6. The method according to claim 5, wherein the piperazinyl group is substituted with oxetanyl.

7. The method according to claim 1, wherein $R^2$ is —O-$R^5$.

8. The method according to claim 7, wherein $R^5$ is a 5-6 membered heterocyclyl optionally substituted with one to five $R^{20}$ groups.

9. The method according to claim 1, wherein the compound of formula (I) is selected from the group consisting of:

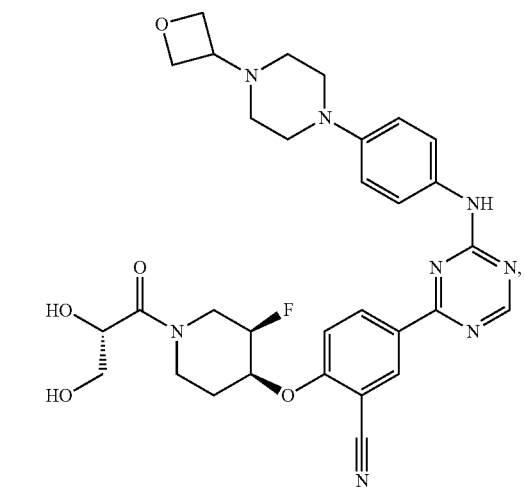

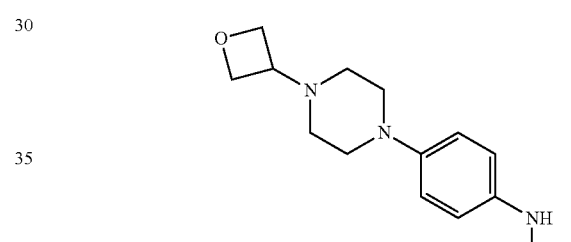

1007
-continued

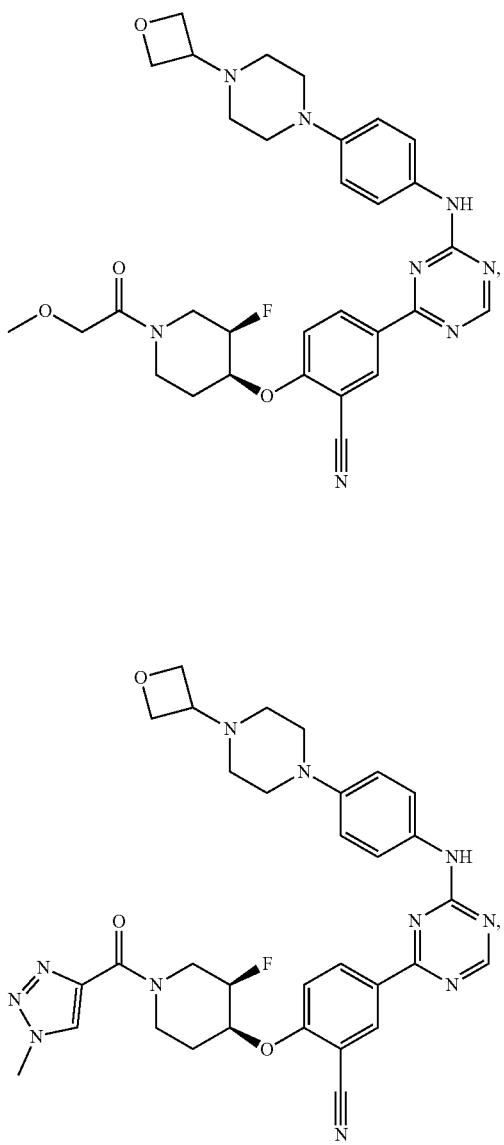

1008
-continued

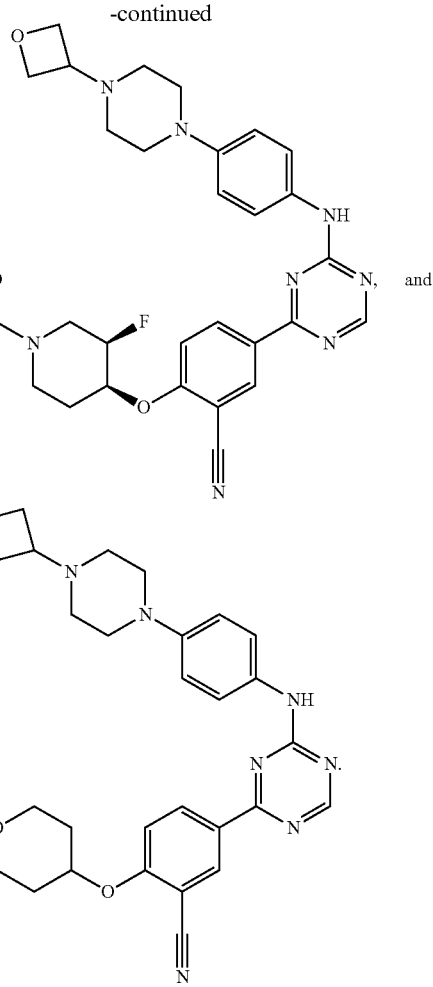

10. The method according to claim 1, wherein step a) is carried out using N,N-dimethylformamide, 1,2-dimethoxyethane, acetonitrile, or a mixture thereof as solvent.

11. The method according to claim 1, wherein step a) is carried out in the presence of a base.

12. The method according to claim 11, wherein the base is N,N-diisopropylethylamine or triethylamine.

13. The method according to claim 1, wherein step b) is carried out using N,N-dimethylformamide, 1,2-dimethoxyethane, or a mixture thereof as solvent.

* * * * *